US009856292B2

(12) United States Patent
Gillman et al.

(10) Patent No.: US 9,856,292 B2
(45) Date of Patent: Jan. 2, 2018

(54) IMMUNOMODULATORS

(71) Applicant: BRISTOL-MYERS SQUIBB COMPANY, Princeton, NJ (US)

(72) Inventors: Kevin W. Gillman, Madison, CT (US); Jason Goodrich, Wallingford, CT (US); Kenneth M. Boy, Durham, CT (US); Yunhui Zhang, Glastonbury, CT (US); Claudio Mapelli, Lawrenceville, NJ (US); Michael A. Poss, Lawrenceville, NJ (US); Paul Michael Scola, Glastonbury, CT (US); David R. Langley, Meriden, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/938,327

(22) Filed: Nov. 11, 2015

(65) Prior Publication Data
US 2016/0137696 A1 May 19, 2016

Related U.S. Application Data

(60) Provisional application No. 62/204,689, filed on Aug. 13, 2015, provisional application No. 62/111,388, filed on Feb. 3, 2015, provisional application No. 62/079,944, filed on Nov. 14, 2014.

(51) Int. Cl.
*C07K 7/08* (2006.01)
*C07K 7/56* (2006.01)
*A61K 38/10* (2006.01)
*A61K 45/06* (2006.01)
*A61K 38/00* (2006.01)

(52) U.S. Cl.
CPC ............... *C07K 7/08* (2013.01); *A61K 38/10* (2013.01); *A61K 45/06* (2013.01); *C07K 7/56* (2013.01); *A61K 38/00* (2013.01)

(58) Field of Classification Search
None
See application file for complete search history.

(56) References Cited

U.S. PATENT DOCUMENTS

| 5,869,451 | A | 2/1999 | Dower et al. | |
|---|---|---|---|---|
| 9,090,668 | B2 | 7/2015 | Suga et al. | |
| 9,308,236 | B2 * | 4/2016 | Miller | A61K 38/10 |
| 9,410,148 | B2 | 8/2016 | Suga et al. | |
| 2014/0018257 | A1 | 1/2014 | Suga et al. | |
| 2016/0158349 | A1 | 6/2016 | Miller et al. | |
| 2016/0272680 | A1 | 9/2016 | Boy et al. | |
| 2016/0340391 | A1 | 11/2016 | Miller et al. | |

FOREIGN PATENT DOCUMENTS

| WO | WO 00/26353 | 5/2000 |
|---|---|---|
| WO | WO 2010/027828 | 3/2010 |
| WO | WO 2011/161699 | 12/2011 |
| WO | WO 2012/168944 | 12/2012 |
| WO | WO 2013/144704 | 10/2013 |
| WO | WO 2013/182240 | 12/2013 |
| WO | WO 2013/183707 | 12/2013 |
| WO | WO 2014/151006 | 9/2014 |
| WO | WO2014/151634 | 9/2014 |
| WO | WO 2015/033303 | 3/2015 |
| WO | WO 2015/044900 | 4/2015 |
| WO | WO2016/039749 | 3/2016 |
| WO | WO2016/057624 | 4/2016 |
| WO | WO2016/100285 | 6/2016 |
| WO | WO2016/100608 | 6/2016 |
| WO | WO2016/126646 | 8/2016 |

OTHER PUBLICATIONS

Barakat "Do We Need Small Molecule Inhibitors for the Immune Checkpoints?"*
Velu et al. "Role of PD-1 co-inhibitory pathway in HIV infection and potential therapeutic options" Retrovirology (2015) 12 pp. 1-17.*
Davu et al. "PD-1 Blockade in Advanced Melanoma in Patients with Hepatitis C and/or HIV" Case Reports in Oncological Medicine vol. 2015, Article ID 737389, pp. 1-5.*
Porichis et al. "Role of PD-1 in HIV Pathogenesis and as Target for Therapy" Curr HIV/AIDS Rep. Mar. 2012 ; 9(1): 81-90, provided as pp. 1-14.*
Zhang et al. "PD-L1 blockade improves survival in experimental sepsis by inhibiting lymphocyte apoptosis and reversing monocyte dysfunction," Critical Care 2010, 14:R220, pp. 1-9.*
Chang et al. "Blockade ofthe negative co-stimulatory molecules PD-1 and CTLA-4 improves survival in primary and secondary fungal sepsis" Critical Care 2013, 17:R85, pp. 1-14.*
Brahmamdam et al. "Delayed administration of anti-PD-1 antibody reverses immune dysfunction and improves survival during sepsis," Journal of Leukocyte Biology, 2010, vol. 88, No. 2 , pp. 233-240.*
Huang et al. "PD-1 expression by macrophages plays a pathologic role in altering microbial clearance and the innate inflammatory response to sepsis," PNAS, 2009, vol. 106, pp. 6303-6308.*
Hotchkiss et al. "Sepsis-induced immunosuppression: from cellular dysfunctions to immunotherapy," Nature, 2013, vol. 13, pp. 862-874.*
Hotchkiss et al. "Parallels between Cancer and Infectious Disease," New England J of Med, 2014, 371;4 pp. 380-383.*
Shin et al. "The evolution of checkpoint blockade as a cancer therapy: what's here, what's next?" Current Opinion in Immunology 2015, 33:23-35.*
Swaika et al. "Current state of anti-PD-L1 and anti-PD-1 agents in cancer therapy," Molecular Immunology 67 (2015) 4-17.*

(Continued)

*Primary Examiner* — Christina Bradley
(74) *Attorney, Agent, or Firm* — Pamela A. Mingo

(57) ABSTRACT

The present disclosure provides compounds which are immunomodulators and thus are useful for the amelioration of various diseases, including cancer and infectious diseases.

32 Claims, No Drawings

(56) References Cited

OTHER PUBLICATIONS

Sunshine et al. "PD-1/PD-L1 inhibitors" Current Opinion in Pharmacology 2015, 23:32-38.*
Momtaz et al. "Immunologic checkpoints in cancer therapy: focus on the programmed death-1 (PD-1) receptor pathway," Pharmacogenomics and Personalized Medicine 2014:7 357-365.*
Hayashi, Y. et al., "In Vitro Selection of Anti-Akt2 Thioether-Macrocyclic Peptides Leading to Isoform-Selective Inhibitors", ACS Chemical Biology, vol. 7, pp. 607-613 (2012).
Morimoto, J. et al., "Discovery of Macrocyclic Peptides Armed with a Mechanism-Based Warhead: Isoform-Selective Inhibition of Human Deacetylase SIRT2", Angewandte Chemie, International Edition, vol. 51, pp. 3423-3427 (2012).
Yamagishi, Y. et al., "Natural Product-Like Macrocyclic N-Methyl-Peptide Inhibitors against a Ubiquitin Ligase Uncovered from a Ribosome-Expressed De Novo Library", Chemistry & Biology, vol. 18, pp. 1562-1570 (2011).

* cited by examiner

IMMUNOMODULATORS

CROSS-REFERENCE TO RELATED APPLICATIONS

This application claims priority to U.S. Provisional Patent Applications U.S. Ser. No. 62/204,689 filed Aug. 13, 2015, U.S. Ser. No. 62/111,388 filed Feb. 3, 2015 and U.S. Ser. No. 62/079,944 filed Nov. 14, 2014 each hereby incorporated by reference in their entireties.

The present disclosure provides novel macrocyclic peptides which inhibit the PD-1/PD-L1 and CD80/PD-L1 protein/protein interaction, and are thus useful for the amelioration of various diseases, including cancer and infectious diseases.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al., Curr. Opin. Immunol., 14:779-782 (2002); Bennett et al., J. Immunol., 170:711-718 (2003)).

The PD-1 protein is a 55 kDa type I transmembrane protein that is part of the Ig gene superfamily (Agata et al., Int. Immunol., 8:765-772 (1996)). PD-1 contains a membrane proximal immunoreceptor tyrosine inhibitory motif (ITIM) and a membrane distal tyrosine-based switch motif (ITSM) (Thomas, M. L., J. Exp. Med., 181:1953-1956 (1995); Vivier, E. et al., Immunol. Today, 18:286-291 (1997)). Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be downregulated upon interaction with cells expressing PD-L1 or PD-L2 (Freeman et al., J. Exp. Med., 192:1027-1034 (2000); Latchman et al., Nat. Immunol., 2:261-268 (2001); Carter et al., Eur. J. Immunol., 32:634-643 (2002)). Both PD-L1 and PD-L2 are B7 protein family members that bind to PD-1, but do not bind to other CD28 family members. The PD-L1 ligand is abundant in a variety of human cancers (Dong et al., Nat. Med., 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., J. Mol. Med., 81:281-287 (2003); Blank et al., Cancer Immunol. Immunother., 54:307-314 (2005); Konishi et al., Clin. Cancer Res., 10:5094-5100 (2004)). Immune suppression can be reversed by inhibiting the local interaction of PD-1 with PD-L1, and the effect is additive when the interaction of PD-1 with PD-L2 is blocked as well (Iwai et al., Proc. Natl. Acad. Sci. USA, 99:12293-12297 (2002); Brown et al., J. Immunol., 170:1257-1266 (2003)).

PD-L1 has also been shown to interact with CD80 (Butte M J et al, Immunity; 27:111-122 (2007)). The interaction PD-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self tolerance (Keir, M. E. et al., Annu. Rev. Immunol., 26:Epub (2008)). Chronic antigen stimulation, such as that which occurs during tumor disease or chronic infections, results in T cells that express elevated levels of PD-1 and are dysfunctional with respect to activity towards the chronic antigen (reviewed in Kim et al., Curr. Opin. Imm. (2010)). This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1 (Brahmer et al., New Engl. J Med. (2012)). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong, H. et al., "B7-H1 pathway and its role in the evasion of tumor immunity", J. Mol. Med., 81(5):281-287 (2003); Dong, H. et al., "Tumor-associated B7-H1 promotes T-cell apoptosis: a potential mechanism of immune evasion", Nat. Med., 8(8):793-800 (2002)).

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection (Barber, D. L. et al., "Restoring function in exhausted CD8 T cells during chronic viral infection", Nature, 439(7077):682-687 (2006)). Humanized mice infected with HIV-1 show enhanced protection against viremia and viral depletion of CD4+ T cells (Palmer et al., J. Immunol. (2013)). Blockade of PD-1/PD-L1 through monoclonal antibodies to PD-L1 can restore in vitro antigen-specific functionality to T cells from HIV patients (Day, Nature (2006); Petrovas, J. Exp. Med. (2006); Trautman, Nature Med. (2006); D'Souza, J. Immunol. (2007); Zhang, Blood (2007); Kaufmann, Nature Imm. (2007); Kasu, J. Immunol. (2010); Porichis, Blood (2011)), HCV patients (Golden-Mason, J. Virol. (2007); Jeung, J. Leuk. Biol. (2007); Urbani, J. Hepatol. (2008); Nakamoto, PLoS Path. (2009); Nakamoto, Gastroenterology (2008)) and HBV patients (Boni, J. Virol. (2007); Fisicaro, Gastro. (2010); Fisicaro et al., Gastroenterology (2012); Boni et al., Gastro. (2012); Penna et al., J. Hep. (2012); Raziorrough, Hepatology (2009); Liang, World J. Gastro. (2010); Zhang, Gastro. (2008)).

Blockade of the PD-L1/CD80 interaction has also been shown to stimulate immunity (Yang J., et al., J Immunol. August 1; 187(3):1113-9 (2011)). Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 (Guignant, et al, Crit. Care (2011)), Cells from septic shock patients with increased levels of PD-1 and PD-L1 exhibit an increased level of T cell apoptosis. Antibodies directed to PD-L1, can reduce the level of Immune cell apoptosis (Zhang et al, Crit. Care (2011)). Furthermore, mice lacking PD-1 expression are more resistant to septic shock symptoms than wildtype mice. Yang J., et al. J Immunol. August 1; 187(3):1113-9 (2011)). Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection (Ha, S. J. et al., "Enhancing therapeutic vaccination by blocking PD-1-mediated inhibitory signals during chronic infection", *J. Exp. Med.*, 205(3):543-555 (2008); Finnefrock, A. C. et al., "PD-1 blockade in rhesus macaques: impact on chronic infection and prophylactic vaccination", *J. Immunol.*, 182(2):980-987 (2009); Song, M.-Y. et al., "Enhancement of vaccine-induced primary and memory CD8+ t-cell responses by soluble PD-1", *J. Immunother.*, 34(3):297-306 (2011)).

The molecules described herein demonstrate the ability to block the interaction of PD-L1 with PD-1, in both biochemical and cell-based experimental systems. These results are consistent with a potential for therapeutic administration to enhance immunity in cancer or chronic infection, including therapeutic vaccine.

The macrocyclic peptides described herein are capable of inhibiting the interaction of PD-L1 with PD-1 and with CD80. These compounds have demonstrated highly efficacious binding to PD-L1, blockade of the interaction of PD-L1 with either PD-1 or CD80, and are capable of promoting enhanced T cell functional activity, thus making them candidates for parenteral, oral, pulmonary, nasal, buccal and sustained release formulations.

In its first embodiment the present disclosure provides a compound of formula (I)

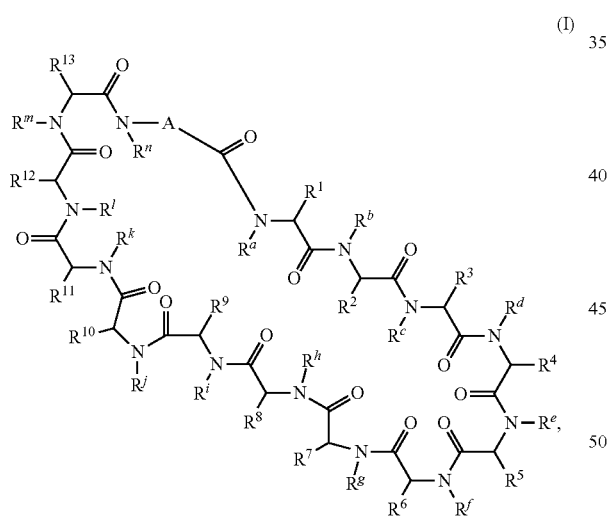

(I)

or a pharmaceutically acceptable salt thereof, wherein:

A is selected from

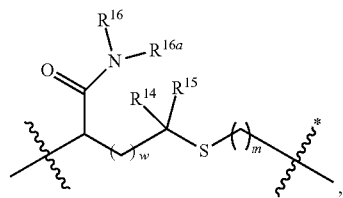

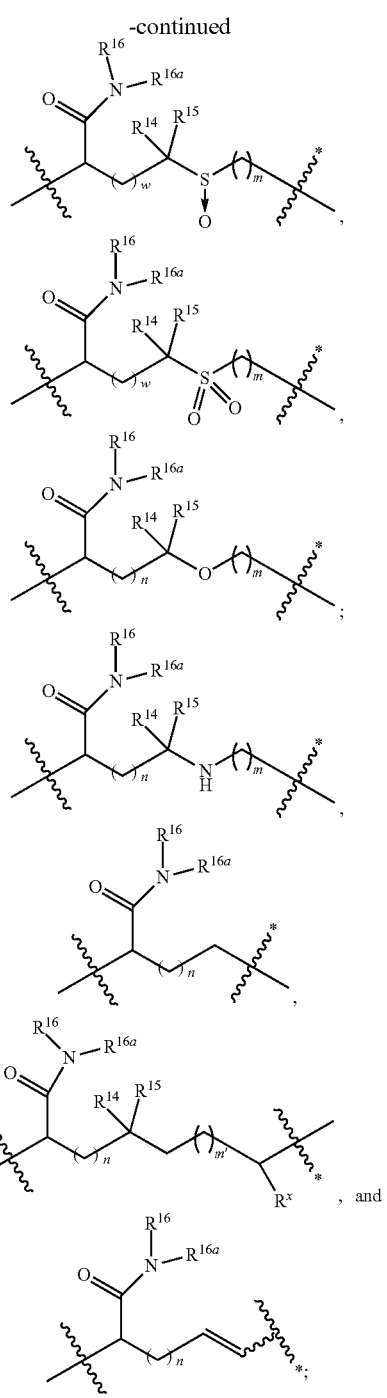

wherein:

⁓* denotes the point of attachment to the carbonyl group and *⁓ denotes the point of attachment to the nitrogen atom;

n is 0 or 1;

m is 1 or 2;

m' is 0 or 1;

w is 0, 1, or 2;

$R^x$ is selected from hydrogen, amino, hydroxy, and methyl;

$R^{14}$ and $R^{15}$ are independently selected from hydrogen and methyl;

$R^{16a}$ is selected from hydrogen and $C_1$-$C_6$ alkyl;

$R^{16}$ is selected from
—$(C(R^{17a})_2)_2$—X—$R^{30}$,
—$C(R^{17a})_2C(O)N(R^{16a})C(R^{17a})_2$—X'—$R^{31}$,
—$C(R^{17a})_2[C(O)N(R^{16a})C(R^{17a})_2]_{w'}$—X—$R^{31}$,
—$(C(R^{17a})(R^{17})C(O)NR^{16a})_{n'}$—H; and
—$(C(R^{17a})(R^{17})C(O)NR^{16a})_{m'}$—$C(R^{17a})(R^{17})$—$CO_2H$;
wherein:
w' is 2 or 3;
n' is 1-6;
m' is 0-5;
X is a chain of between 1 and 172 atoms wherein the atoms are selected from carbon and oxygen and wherein the chain may contain one, two, three, or four groups selected from —NHC(O)NH—, and —C(O)NH-embedded therein; and wherein the chain is optionally substituted with one to six groups independently selected from —$CO_2H$, —C(O)$NH_2$, —$CH_2C(O)NH_2$, and —$(CH_2)CO_2H$;
X' is a chain of between 1 and 172 atoms wherein the atoms are selected from carbon and oxygen and wherein the chain may contain one, two, three, or four groups selected from —NHC(O)NH—, and —C(O)NH-embedded therein; and wherein the chain is optionally substituted with one to six groups independently selected from —$CO_2H$, —C(O)$NH_2$, and —$CH_2CO_2H$, provided that X' is other than unsubstituted PEG;
$R^{30}$ is selected from —$CO_2H$, —C(O)$NR^wR^x$, and —$CH_3$ wherein $R^w$ and $R^x$ are independently selected from hydrogen and $C_1$-$C_6$alkyl, provided that when X is all carbon, $R^{30}$ is other than —$CH_3$;
$R^{31}$ is —$CO_2H$, —C(O)$NR^wR^x$, —$CH_3$, alexa-5-SDP, and biotin;
each $R^{17a}$ is independently selected from hydrogen, $C_1$-$C_6$alkyl, —$CH_2OH$, —$CH_2CO_2H$, —$(CH_2)_2CO_2H$,
each $R^{17}$ is independently selected from hydrogen, —$CH_3$, $(CH_2)_zN_3$, —$(CH_2)_zNH_2$, —X—$R^{31}$, —$(CH_2)_z$$CO_2H$, —$CH_2OH$, $CH_2C\equiv CH$, and —$(CH_2)_z$-triazolyl-X—$R^{35}$, wherein z is 1-6 and $R^{35}$ is selected from —$CO_2H$, —C(O)$NR^wR^x$, $CH_3$, biotin, -2-fluoropyridine, —C(O)—$(CH_2)_2$—C(O)O-vitamin E, —C(O)O-vitamin E; and

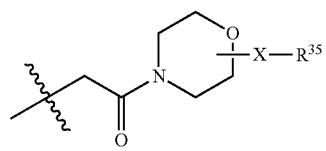

provided at least one $R^{17}$ is other than hydrogen, —$CH_3$, or —$CH_2OH$;
$R^c$, $R^f$, $R^h$, $R^i$, $R^m$, and $R^n$ are hydrogen;
$R^a$, $R^e$, $R^j$, and $R^k$, are each independently selected from hydrogen and methyl;
$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;
$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;
$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and
$R^1$ is methyl or, $R^1$ and $R^{12}$, together with the atoms to which they are attached, form a ring selected from azetidine and pyrollidine, wherein each ring is optionally substituted with one to four independently selected from amino, cyano, methyl, halo, and hydroxy.
In a first aspect of the first embodiment the present disclosure provides a compound of formula (I), or a pharmaceutically acceptable salt thereof, wherein A is

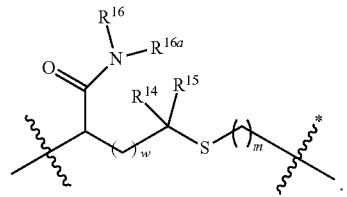

In a second aspect of the first embodiment:
m and w are 1; and
$R^{14}$, $R^{15}$, and $R^{16a}$ are each hydrogen.
In a third aspect of the first embodiment:
$R^{16}$ is —$(C(R^{17a})_2)_2$—X—$R^{30}$.
In a fourth aspect of the first embodiment:
each $R^{17a}$ is hydrogen;
X is a chain of between 8 and 46 atoms wherein the atoms are selected from carbon and oxygen and wherein the chain may contain one, two, or three C(O)NH groups embedded therein; and wherein the chain is optionally substituted with one or two groups independently selected from —$CO_2H$, —C(O)$NH_2$, —$CH_2C(O)NH_2$, and —$CH_2CO_2H$; and
$R^{30}$ is selected from —$CH_3$, —$CO_2H$, and —C(O)$NH_2$; provided that when X is all carbon, $R^{30}$ is other than —$CH_3$.
In a fifth aspect of the first embodiment the present disclosure provides a compound of formula (I), or a pharmaceutically acceptable salt thereof, wherein:
A is

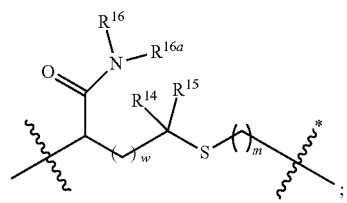

m and w are 1;
$R^{14}$, $R^{15}$, and $R^{16a}$ are each hydrogen; and
$R^{16}$ is $-C(R^{17a})_2C(O)N(R^{16a})C(R^{17a})_2-X'-R^{31}$.

In a sixth aspect of the first embodiment:
each $R^{17a}$ is selected from hydrogen, $-CO_2H$, and $-CH_2CO_2H$;

X' is a chain of between 8 and 48 atoms wherein the atoms are selected from carbon and oxygen and wherein the chain may contain one, two, or three C(O)NH groups embedded therein; and wherein the chain is optionally substituted with one or two groups independently selected from $-CO_2H$, $-C(O)NH_2$, $-CH_2C(O)NH_2$, and $-CH_2CO_2H$; provided that X' is other than unsubstituted PEG; and $R^{30}$ is selected from $-CH_3$, $-CO_2H$, and $-C(O)NH_2$.

In a seventh aspect of the first embodiment the present disclosure provides a compound of formula (I), or a pharmaceutically acceptable salt thereof, wherein:
A is

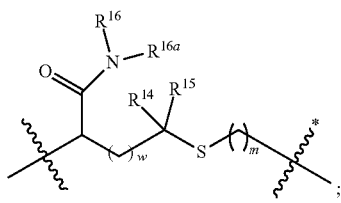

m and w are 1;
$R^{14}$, $R^{15}$, and $R^{16a}$ are each hydrogen; and
$R^{16}$ is $-C(R^{17a})_2[C(O)N(R^{16a})C(R^{17a})_2]_{w'}-X-R^{31}$.

In an eighth aspect of the first embodiment:
each $R^{17a}$ is selected from hydrogen, $-CO_2H$, and $-CH_2CO_2H$;

X is a chain of between 8 and 48 atoms wherein the atoms are selected from carbon and oxygen and wherein the chain may contain one, two, or three C(O)NH groups embedded therein; and wherein the chain is optionally substituted with one or two groups independently selected from $-CO_2H$, $-C(O)NH_2$, $-CH_2C(O)NH_2$, and $-CH_2CO_2H$; and $R^{31}$ is selected from $-CH_3$, $-CO_2H$, and $-C(O)NH_2$.

In a ninth aspect of the first embodiment the present disclosure provides a compound of formula (I), or a pharmaceutically acceptable salt thereof, wherein:
A is

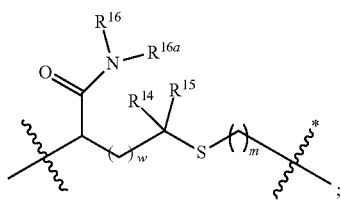

m and w are 1;
$R^{14}$, $R^{15}$, and $R^{16a}$ are each hydrogen; and
$R^{16}$ is $-(C(R^{17a})(R^{17})C(O)NR^{16a})_{n'}-H$.

In a tenth aspect of the first embodiment:
each $R^{17a}$ is hydrogen; and each $R^{17}$ is selected from hydrogen, $-CH_3$, $(CH_2)_zN_3$, $-(CH_2)_zNH_2$, $-X-R^{31}$, $-(CH_2)_zCO_2H$, $-CH_2OH$, $CH_2C\equiv CH$, and $-(CH_2)_z$-triazolyl-$X-R^{35}$; provided at least one $R^{17}$ is other than hydrogen, $-CH_3$, or $-CH_2OH$;

z is 1-4;
$R^{31}$ is selected from $-CH_3$, $-CO_2H$, and $-C(O)NH_2$;

X is a chain of between 7 and 155 atoms wherein the atoms are selected from carbon and oxygen and wherein the chain may contain one, two, or three C(O)NH groups embedded therein; and wherein the chain is optionally substituted with one or two groups independently selected from $-CO_2H$, $-C(O)NH_2$, $-CH_2C(O)NH_2$, and $-CH_2CO_2H$; and $R^{35}$ is selected from $-CO_2H$, $-C(O)NR^wR^x$, $CH_3$, biotin, -2-fluoropyridine, $-C(O)-(CH_2)_2-C(O)O$-vitamin E, and $-C(O)O$-vitamin E.

In an eleventh aspect of the first embodiment the present disclosure provides a compound of formula (I), or a pharmaceutically acceptable salt thereof, wherein:
A is

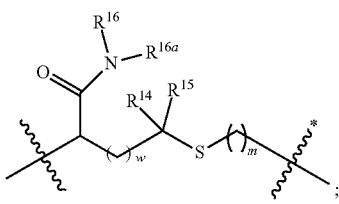

m and w are 1;
$R^{14}$, $R^{15}$, and $R^{16a}$ are each hydrogen; and
$R^{16}$ is $-(CR^{17a})(R^{17})C(O)NR^{16a})_{m'}-C(R^{17a})(R^{17})-CO_2H$.

In a twelfth aspect of the first embodiment:
m' is 1-3;
each $R^{17a}$ is hydrogen;
each $R^{17}$ is selected from hydrogen, $-CH_3$, $(CH_2)_zN_3$, $-(CH_2)_zNH_2$, $-X-R^{31}$, $-(CH_2)_zCO_2H$, $-CH_2OH$, $CH_2C\equiv CH$, $-(CH_2)_z$-triazolyl-$X-R^{35}$, and C(O)O-vitamin E; and

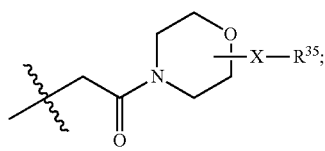

provided at least one $R^{17}$ is other than hydrogen, $-CH_3$, or $-CH_2OH$;

z is 1-4;
$R^{31}$ is selected from $-CH_3$, $-CO_2H$, and $-C(O)NH_2$;

X is a chain of between 20 and 60 atoms wherein the atoms are selected from carbon and oxygen and wherein the chain may contain one, two, or three C(O)NH groups embedded therein; and wherein the chain is optionally substituted with one or two groups independently selected from $-CO_2H$, $-C(O)NH_2$, $-CH_2C(O)NH_2$, and $-CH_2CO_2H$; and $R^{35}$ is selected from —$CO_2H$, —$C(O)NR^wR^x$, $CH_3$, biotin, 2-fluoropyridine, —$C(O)$—$(CH_2)_2$—$C(O)O$-vitamin E, and —$C(O)O$-vitamin E.

In a thirteenth aspect of the first embodiment the present disclosure provides a compound of formula (I), or a pharmaceutically acceptable salt thereof, wherein $R^1$ is phenyl$C_1$-$C_3$alkyl wherein the phenyl part is optionally substituted with hydroxyl, halo, or methoxy; $R^2$ is $C_1$-$C_7$alkyl or, $R^2$ and $R^b$, together with the atoms to which they are attached, form a piperidine ring; $R^3$ is $NR^xR^y(C_1$-$C_7$alkyl), $NR^uR^v$carbonyl$C_1$-$C_3$alkyl, or carboxy$C_1$-$C_3$alkyl; $R^4$ and $R^d$, together with the atoms to which they are attached, form a pyrrolidine ring; $R^5$ is hydroxy$C_1$-$C_3$alkyl, imidazolyl$C_1$-$C_3$alkyl, or $NR^xR^y(C_1$-$C_7$alkyl); $R^6$ is carboxy$C_1$-$C_3$alkyl, $NR^uR^v$carbonyl$C_1$-$C_3$alkyl, $NR^xR^y(C_1$-$C_7$alkyl), or $C_1$-$C_7$alkyl; $R^7$ and $R^g$, together with the atoms to which they are attached, form a pyrrolidine ring optionally substituted with hydroxy; $R^8$ and $R^{10}$ are benzothienyl or indolyl$C_1$-$C_3$alkyl optionally substituted with carboxy$C_1$-$C_3$alkyl; $R^9$ is hydroxy$C_1$-$C_3$alkyl, amino$C_1$-$C_3$alkyl, or $C_1$-$C_7$alkyl, $R^{11}$ is $C_1$-$C_3$alkoxy$C_1$-$C_3$alkyl or $C_1$-$C_7$alkyl; $R^{12}$ is $C_1$-$C_7$alkyl or hydroxy$C_1$-$C_3$alkyl; and $R^{13}$ is $C_1$-$C_7$alkyl, carboxy$C_1$-$C_3$alkyl, or —$(CH_2)_3NHC(NH)NH_2$.

In a fourteenth aspect of the first embodiment the present disclosure provides a compound of formula (I), or a pharmaceutically acceptable salt thereof, wherein:
A is

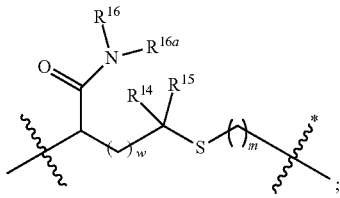

m and w are 1;
$R^{14}$, $R^{15}$, and $R^{16a}$ are each hydrogen;
$R^d$ is methyl or, $R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, hydroxy, and phenyl;
$R^g$ is methyl or, $R^g$ and $R^7$, together with the atoms to which they are attached,
form a ring selected from azetidine, pyrollidine, morpholine, piperidine, piperazine, and tetrahydrothiazole; wherein each ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and
$R^k$ is methyl or, $R^k$ and $R^{11}$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy.

In a second embodiment the present disclosure provides a compound of formula (II)

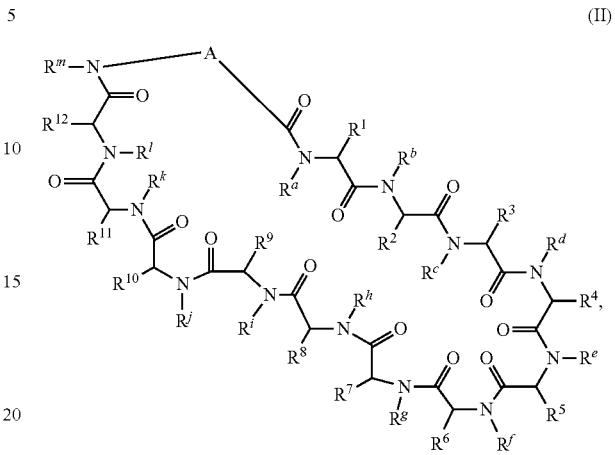

(II)

or a pharmaceutically acceptable salt thereof, wherein:
A is selected from

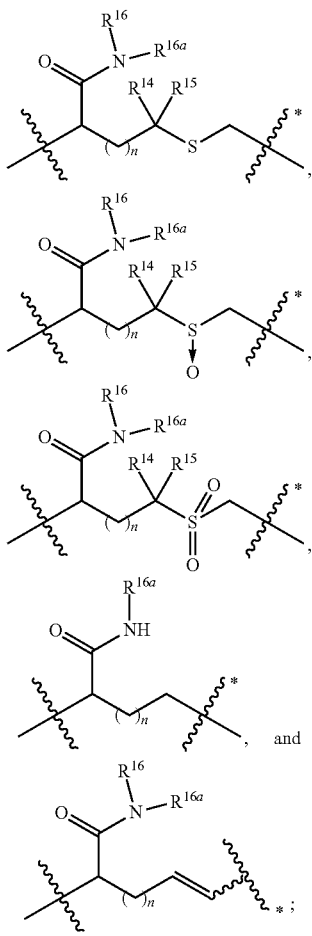

wherein:
n is 0 or 1;
$R^{14}$ and $R^{15}$ are independently selected from hydrogen and methyl;

$R^{16a}$ is selected from hydrogen and $C_1$-$C_6$ alkyl;
$R^{16}$ is selected from
—$(C(R^{17a})_2)_2$—X—$R^{30}$,
—$C(R^{17a})_2C(O)N(R^{16a})C(R^{17a})_2$—X'—$R^{31}$,
—$C(R^{17a})_2[C(O)N(R^{16a})C(R^{17a})_2]_{w'}$—X—$R^{31}$,
—$(C(R^{17a})(R^{17})C(O)NR^{16a})_{n'}$—H; and
—$(CR^{17a})(R^{17})C(O)NR^{16a})_{m'}$—$C(R^{17a})(R^{17})$—$CO_2H$;
wherein:
w' is 2 or 3;
n' is 1-6;
m' is 1-5;
X is a chain of between 1 and 172 atoms wherein the atoms are selected from carbon and oxygen and wherein the chain may contain one, two, three, or four groups selected from —NHC(O)NH—, and —C(O)NH embedded therein; and wherein the chain is optionally substituted with one to six groups independently selected from —$CO_2H$, —C(O)$NH_2$, —$CH_2C(O)NH_2$, and —$CH_2CO_2H$,
X' is a chain of between 1 and 172 atoms wherein the atoms are selected from carbon and oxygen and wherein the chain may contain one, two, three, or four groups selected from —NHC(O)NH—, and —C(O)NH embedded therein; and wherein the chain is optionally substituted with one to six groups independently selected from —$CO_2H$, —C(O)$NH_2$, and —$CH_2CO_2H$, provided that X' is other than unsubstituted PEG;
$R^{30}$ is selected from —$CO_2H$, —$C(O)NR^wR^x$, and —$CH_3$ wherein $R^w$ and $R^x$ are independently selected from hydrogen and $C_1$-$C_6$alkyl, provided that when X is all carbon, $R^{30}$ is other than —$CH_3$;
$R^{31}$ is —$CO_2H$, —$C(O)NR^wR^x$, —$CH_3$, alexa-5-SDP, and biotin;
each $R^{17a}$ is independently selected from hydrogen, $C_1$-$C_6$alkyl, —$CH_2OH$, —$CH_2CO_2H$, —$(CH_2)_2CO_2H$,
each $R^{17}$ is independently selected from hydrogen, —$CH_3$, $(CH_2)_zN_3$, —$(CH_2)_zNH_2$, —X—$R^{31}$, —$(CH_2)_z$$CO_2H$, —$CH_2OH$, $CH_2C\equiv CH$, and —$(CH_2)_z$-triazolyl-X—$R^{35}$, wherein z is 1-6 and $R^{35}$ is selected from —$CO_2H$, —$C(O)NR^wR^x$, $CH_3$, biotin, -2-fluoropyridine, —C(O)—$(CH_2)_2$—C(O)O-vitamin E, —C(O)O-vitamin E, and

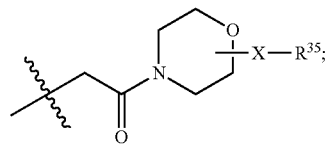

provided at least one $R^{17}$ is other than hydrogen, —$CH_3$, or —$CH_2OH$;
$R^a$, $R^f$, $R^j$, $R^k$, $R^l$, and $R^m$ are hydrogen;
$R^b$ and $R^c$ are methyl;
$R^g$ is selected from hydrogen and methyl;
$R^1$, $R^2$, $R^3$, $R^4$, $R^5$, $R^6$, $R^7$, $R^8$, $R^9$, $R^{10}$, $R^{11}$, and $R^{12}$ are independently selected from a natural amino acid side chain and an unnatural amino acid side chain or form a ring with the corresponding vicinal R group as described below;
$R^d$ is selected from hydrogen and methyl, or, $R^d$ and $R^4$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;
$R^e$ is selected from hydrogen and methyl, or, $R^e$ and $R^5$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;
$R^h$ is selected from hydrogen and methyl, or, $R^h$ and $R^8$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy; and
$R^i$ is selected from hydrogen and methyl, or, $R^i$ and $R^9$, together with the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy.

In a first aspect of the second embodiment the present disclosure provides a compound of formula (II), or a pharmaceutically acceptable salt thereof, wherein
A is

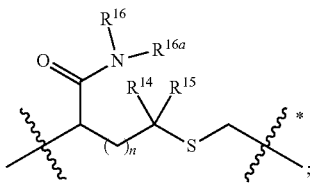

n is 1;
$R^{16}$ is —$(CR^{17a})(R^{17})C(O)NR^{16a})_{m'}$—$C(R^{17a})(R^{17})$—$CO_2H$;
each $R^{16a}$ is hydrogen;
m' is 2, 3, or 4;
each $R^{17a}$ is hydrogen;
each $R^{17}$ is independently selected from hydrogen, —$(CH_2)_zNH_2$, —X—$R^{31}$ and —$CH_2C\equiv CH$,
z is 4;
X is a chain of between 26 and 155 atoms wherein the atoms are selected from carbon and oxygen and wherein the chain may contain one, two, or three C(O)NH groups embedded therein; and wherein the chain is optionally substituted with one or two groups independently selected from —$CO_2H$, —$C(O)NH_2$, —$CH_2C(O)NH_2$, and —$CH_2CO_2H$; and
$R^{31}$ is —$CH_3$, alexa-5-SDP, and biotin.

In a third embodiment the present disclosure provides a method of enhancing, stimulating, and/or increasing the immune response in a subject in need thereof, said method comprising administering to the subject a therapeutically effective amount of a compound of formula (I) or a therapeutically acceptable salt thereof. In a first aspect of the third embodiment the method further comprises administering an additional agent prior to, after, or simultaneously with the compound of formula (I) or a therapeutically acceptable salt thereof. In a second aspect the additional agent is an antimicrobial agent, an antiviral agent, a cytotoxic agent, and/or an immune response modifier.

In a fourth embodiment the present disclosure provides a method of inhibiting growth, proliferation, or metastasis of cancer cells in a subject in need thereof, said method comprising administering to the subject a therapeutically effective amount a compound of formula (I), or a therapeutically acceptable salt thereof. In a first aspect of the fourth embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

In a fifth embodiment the present disclosure provides a method of treating an infectious disease in a subject in need thereof, the method comprising administering to the subject a therapeutically effective amount of a compound of formula (I) or a therapeutically acceptable salt thereof. In a first aspect of the fifth embodiment the infectious disease is caused by a virus. In a second aspect the virus is selected from HIV, Hepatitis A, Hepatitis B, Hepatitis C, herpes viruses, and influenza.

In a sixth embodiment the present disclosure provides a method of treating septic shock in a subject in need thereof, the method comprising administering to the subject a therapeutically effective amount of a compound of formula (I) or a therapeutically acceptable salt thereof.

In a seventh embodiment the present disclosure provides a method of enhancing, stimulating, and/or increasing the immune response in a subject in need thereof, said method comprising administering to the subject a therapeutically effective amount of a compound of formula (II) or a therapeutically acceptable salt thereof. In a first aspect of the seventh embodiment the method further comprises administering an additional agent prior to, after, or simultaneously with the compound of formula (II) or a therapeutically acceptable salt thereof. In a second aspect the additional agent is an antimicrobial agent, an antiviral agent, a cytotoxic agent, and/or an immune response modifier. In a third aspect the additional agent is an HDAC inhibitor. In a fourth embodiment the additional agent is a TLR7 and/or TLR8 agonist.

In an eighth embodiment the present disclosure provides a method of inhibiting growth, proliferation, or metastasis of cancer cells in a subject in need thereof, said method comprising administering to the subject a therapeutically effective amount a compound of formula (II), or a therapeutically acceptable salt thereof. In a first aspect of the eighth embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

In a ninth embodiment the present disclosure provides a method of treating an infectious disease in a subject in need thereof, the method comprising administering to the subject a therapeutically effective amount of a compound of formula (II) or a therapeutically acceptable salt thereof. In a first aspect of the ninth embodiment the infectious disease is caused by a virus. In a second aspect the virus is selected from HIV, Hepatitis A, Hepatitis B, Hepatitis C, herpes viruses, and influenza.

In a tenth embodiment the present disclosure provides a method of treating septic shock in a subject in need thereof, the method comprising administering to the subject a therapeutically effective amount of a compound of formula (II) or a therapeutically acceptable salt thereof.

In another embodiment the present disclosure provides a compound of formula (III)

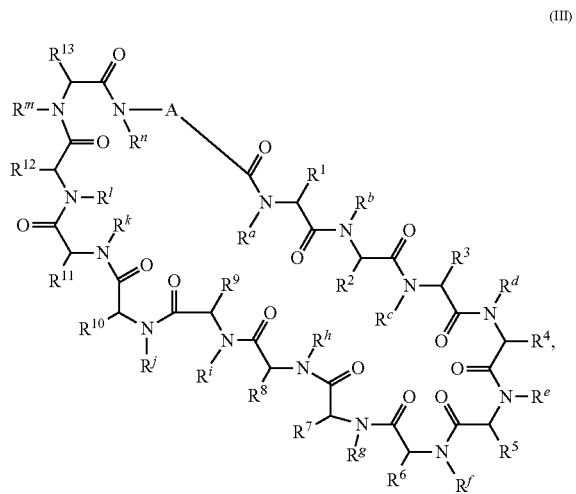

(III)

or a pharmaceutically acceptable salt thereof, wherein:

A is selected from

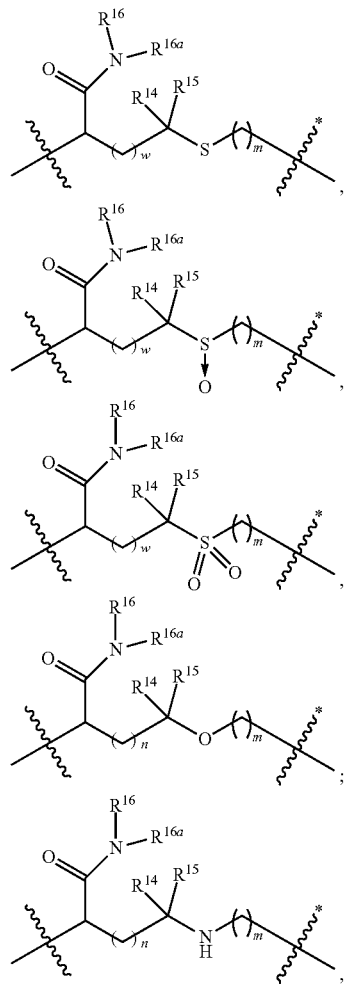

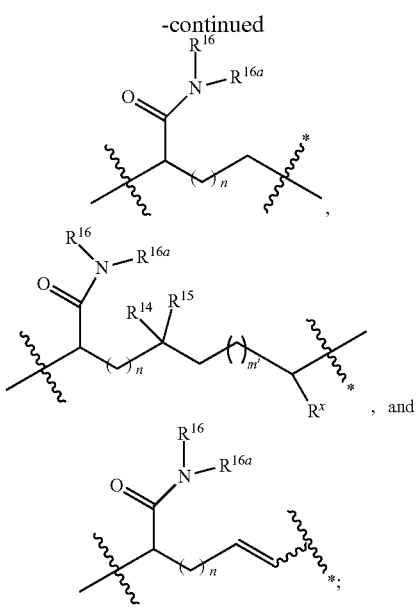
, and wherein:
⁎ denotes the point of attachment to the carbonyl group and ⁎ denotes the point of attachment to the nitrogen atom;
n is 0 or 1;
m is 1 or 2;
w is 0, 1, or 2;
$R^{14}$ and $R^{15}$ are independently selected from hydrogen and methyl;
$R^{16a}$ is selected from hydrogen and $C_1$-$C_6$ alkyl;
$R^{16}$ is selected from
—(C($R^{17a}$)$_2$)$_2$—X—$R^{30}$,
—C($R^{17a}$)$_2$C(O)N($R^{16a}$)C($R^{17a}$)$_2$—X'—$R^{31}$,
—C($R^{17a}$)$_2$[C(O)N($R^{16a}$)C($R^{17a}$)$_2$]$_{w'}$—X—$R^{31}$,
—(C($R^{17a}$)($R^{17}$)C(O)N$R^{16a}$)$_n$—H; and
—(C($R^{17a}$)($R^{17}$)C(O)N$R^{16a}$)$_{m'}$—C($R^{17a}$)($R^{17}$)—$CO_2H$;
wherein:
w' is 2 or 3;
n' is 1-6; (2, 3)
m' is 0-5; (1, 2, 3)
X is a chain of between 1 and 172 atoms wherein the atoms are selected from carbon and oxygen and wherein the chain may contain one, two, three, or four groups selected from —NHC(O)NH—, and —C(O)NH-embedded therein; and wherein the chain is optionally substituted with one to six groups independently selected from —$CO_2H$, —C(O)$NH_2$, —$CH_2$C(O)$NH_2$, and —$CH_2CO_2H$,
X' is a chain of between 1 and 172 atoms wherein the atoms are selected from carbon and oxygen and wherein the chain may contain one, two, three, or four groups selected from —NHC(O)NH—, and —C(O)NH-embedded therein; and wherein the chain is optionally substituted with one to six groups independently selected from —$CO_2H$, —C(O)$NH_2$, and —$CH_2CO_2H$, provided that X' is other than unsubstituted PEG;
$R^{30}$ is selected from —$CO_2H$, —C(O)N$R^wR^x$, and —$CH_3$ wherein $R^w$ and $R^x$ are independently selected from hydrogen and $C_1$-$C_6$alkyl, provided that when X is all carbon, $R^{30}$ is other than —$CH_3$;

$R^{31}$ is —$CO_2H$, —C(O)N$R^wR^x$, —$CH_3$, alexa-5-SDP, and biotin;

each $R^{17a}$ is independently selected from hydrogen, $C_1$-$C_6$alkyl, —$CH_2OH$, —$CH_2CO_2H$, —(CH$_2$)$_2$$CO_2H$, each $R^{17}$ is independently selected from hydrogen, —$CH_3$, (CH$_2$)$_z$$N_3$, —(CH$_2$)$_z$$NH_2$, —X—$R^{31}$, —(CH$_2$)$_z$$CO_2H$, —$CH_2OH$, $CH_2C\equiv CH$, and —(CH$_2$)$_z$-triazolyl-X—$R^{35}$, wherein z is 1-6 and $R^{35}$ is selected from —$CO_2H$, —C(O)N$R^wR^x$, $CH_3$, biotin, -2-fluoropyridine, —C(O)—(CH$_2$)$_2$—C(O)O-vitamin E, and —C(O)O-vitamin E; provided at least one $R^{17}$ is other than hydrogen, —$CH_3$, or —$CH_2OH$;

$R^c$, $R^f$, $R^h$, $R^i$, $R^m$, and $R^n$ are hydrogen;

$R^a$, $R^e$, $R^j$, and $R^k$, are each independently selected from hydrogen and methyl;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;

$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^1$ is methyl or, $R^1$ and $R^{12}$, together with the atoms to which they are attached, form a ring selected from azetidine and pyrollidine, wherein each ring is optionally substituted with one to four independently selected from amino, cyano, methyl, halo, and hydroxy.

In another embodiment the present disclosure provides a compound of formula (IV)

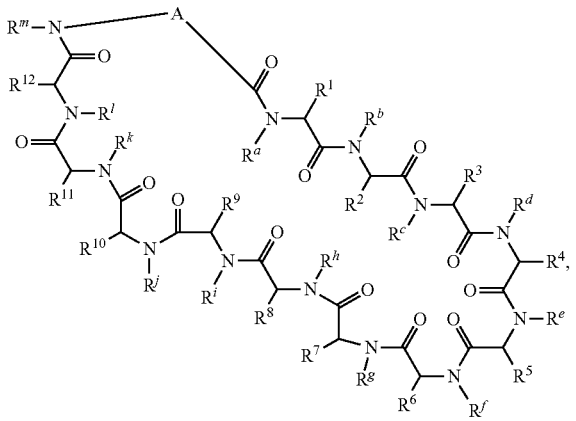

(IV)

or a pharmaceutically acceptable salt thereof, wherein:
A is selected from

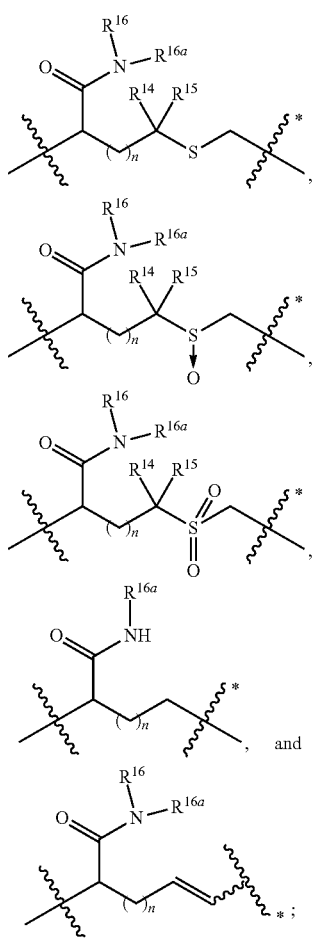

wherein:
n is 0 or 1;
$R^{14}$ and $R^{15}$ are independently selected from hydrogen and methyl;
$R^{16a}$ is selected from hydrogen and $C_1$-$C_6$ alkyl;
$R^{16}$ is selected from
—$C(R^{17a})_2)_2$—X—$R^{30}$,
—$C(R^{17a})_2C(O)N(R^{16a})C(R^{17a})_2$—X'—$R^{31}$,
—$C(R^{17a})_2[C(O)N(R^{16a})C(R^{17a})_2]_{w'}$—X—$R^{31}$,
—$(C(R^{17a})(R^{17})C(O)NR^{16a})_{n'}$—H; and
—$(CR^{17a})(R^{17})C(O)NR^{16a})_{m'}$—$C(R^{17a})(R^{17})$—$CO_2H$;
wherein:
w' is 2 or 3;
n' is 1-6;
m' is 1-5;
X is a chain of between 1 and 172 atoms wherein the atoms are selected from carbon and oxygen and wherein the chain may contain one, two, three, or four groups selected from —NHC(O)NH—, and —C(O)NH embedded therein; and wherein the chain is optionally substituted with one to six groups independently selected from —$CO_2H$, —C(O)$NH_2$, —$CH_2C(O)NH_2$, and —$CH_2CO_2H$,
X' is a chain of between 1 and 172 atoms wherein the atoms are selected from carbon and oxygen and wherein the chain may contain one, two, three, or four groups selected from —NHC(O)NH—, and —C(O)NH embedded therein; and wherein the chain is optionally substituted with one to six groups independently selected from —$CO_2H$, —C(O)$NH_2$, and —$CH_2CO_2H$, provided that X' is other than unsubstituted PEG;
$R^{30}$ is selected from —$CO_2H$, —C(O)$NR^wR^x$, and —$CH_3$ wherein $R^w$ and $R^x$ are independently selected from hydrogen and $C_1$-$C_6$alkyl, provided that when X is all carbon, $R^{30}$ is other than —$CH_3$;
$R^{31}$ is —$CO_2H$, —C(O)$NR^wR^x$, —$CH_3$, alexa-5-SDP, and biotin;
each $R^{17a}$ is independently selected from hydrogen, $C_1$-$C_6$alkyl, —$CH_2OH$, —$CH_2CO_2H$, —$(CH_2)_2CO_2H$,
each $R^{17}$ is independently selected from hydrogen, —$CH_3$, $(CH_2)_zN_3$, —$(CH_2)_zNH_2$, —X—$R^{31}$, —$(CH_2)_z$$CO_2H$, —$CH_2OH$, $CH_2C\equiv CH$, and —$(CH_2)_z$-triazolyl-X—$R^{35}$, wherein z is 1-6 and $R^{35}$ is selected from —$CO_2H$, —C(O)$NR^wR^x$, $CH_3$, biotin, -2-fluoropyridine, —C(O)—$(CH_2)_2$—C(O)O-vitamin E, and —C(O)O-vitamin E; provided at least one $R^{17}$ is other than hydrogen, —$CH_3$, or —$CH_2OH$;
$R^a$, $R^f$, $R^j$, $R^k$, $R^l$, and $R^m$ are hydrogen;
$R^b$ and $R^c$ are methyl;
$R^g$ is selected from hydrogen and methyl;
$R^1$, $R^2$, $R^3$, $R^4$, $R^5$, $R^6$, $R^7$, $R^8$, $R^9$, $R^{10}$, $R^{11}$, and $R^{12}$ are independently selected from a natural amino acid side chain and an unnatural amino acid side chain or form a ring with the corresponding vicinal R group as described below;
$R^d$ is selected from hydrogen and methyl, or, $R^d$ and $R^4$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;
$R^e$ is selected from hydrogen and methyl, or, $R^e$ and $R^5$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;
$R^h$ is selected from hydrogen and methyl, or, $R^h$ and $R^8$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy; and $R^i$ is selected from hydrogen and methyl, or, $R^i$ and $R^9$, together with the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy.

In compounds of formula (I) and (II) where the R side chains are part of a ring that is substituted with methyl, it is understood that the methyl group may be on any substitutable carbon atom in the ring, including the carbon that is part of the macrocyclic parent structure.

The following groups are preferred at each R position. The amino acids may be D- or L-stereochemistry and may be substituted as described elsewhere in the disclosure.

In compounds of formula (I), preferred $R^1$ side chains are: phenylalanine, tyrosine, 3-thien-2-yl, 4-methylphenylalanine, 4-chlorophenylalanine, 3-methoxyphenylalananie, isotryptophan, 3-methylphenylalanine, 1-naphthylalanine, 3,4-difluorophenylalanine, 4-fluorophenylalanine, 3,4-dimethoxyphenylalanine, 3,4-dichlorophenylalanine, 4-difluoromethylphenylalanine, 2-methylphenylalanine, 2-naphthylalanine, tryptophan, 4-pyridinyl, 4-bromophenylalanine, 3-pyridinyl, 4-trifluoromethylphenylalanine, 4-carboxyphenylalanine, 4-methoxyphenylalanine, biphenylalanine, and 3-chlorophenylalanine; and 2,4-diaminobutane.

In compounds of formula (I) where $R^2$ is not part of a ring, preferred $R^2$ side chains are: alanine, serine, and glycine.

In compounds of formula (I), preferred $R^3$ side chains are: asparagine, aspartic acid, glutamic acid, glutamine, serine, ornithine, lysine, histidine, threonine, leucine, alanine, 2,3-diaminopropane, and 2,4-diaminobutane.

In compounds of formula (I) where $R^4$ is not part of a ring, preferred $R^4$ side chains are: valine, alanine, isoleucine, and glycine.

In compounds of formula (I), preferred $R^5$ side chains are: aminomethane, histidine, asparagine, 2,3-diaminopropane, serine, glycine, 2,4-diaminobutane, threonine, alanine, lysine, aspartic acid, alanine, and 3-thiazolylalanine.

In compounds of formula (I), preferred $R^6$ side chains are: leucine, aspartic acid, asparagine, glutamic acid, glutamine, serine, lysine, 3-cyclohexane, threonine, ornithine, 2,4-diaminobutane, alanine, arginine, and ornithine (COCH$_3$).

In compounds of formula (I) where $R^7$ is not part of a ring, preferred $R^7$ side chains are: glycine, 2,4-diaminobutane, serine, lysine, arginine, ornithine, histidine, asparagine, glutamine, alanine, and 2,4-diaminobutane (C(O)cyclobutane).

In compounds of formula (I) preferred $R^8$ side chains are tryptophan and 1,2-benzisothiazolinylalanine.

In compounds of formula (I) preferred $R^9$ side chains are: serine, histidine, lysine, ornithine, 2,4-dibutylamine, threonine, lysine, glycine, glutamic acid, valine, 2,3-diaminopropane, arginine, aspartic acid, and tyrosine.

In compounds of formula (I) preferred $R^{10}$ side chains are: optionally substituted tryptophan, benzisothiazolylalanine, 1-napththylalanine, methionine.

In compounds of formula (I) preferred $R^{11}$ side chains are: norleucine, leucine, asparagine, phenylalanine, methionine, ethoxymethane, alanine, tryptophan, isoleucine, phenylpropane, glutamic acid, hexane, and heptane.

In compounds of formula (I) where $R^{12}$ is not part of a ring, preferred $R^{12}$ side chains are: norleucine, alanine, ethoxymethane, methionine, serine, phenylalanine, methoxyethane, leucine, tryptophan, isoleucine, glutamic acid, hexane, heptane, and glycine.

In compounds of formula (I) preferred $R^{13}$ side chains: arginine, ornithine, alanine, 2,4-diaminobutane, 2,3-diaminopropane, leucine, aspartic acid, glutamic acid, serine, lysine, threonine, cyclopropylmethane, glycine, valine, isoleucine, histidine, and 2-aminobutane.

In accordance with the present disclosure, we have discovered peptides that specifically bind to PD-L1 and are capable of inhibiting the interaction of PD-L1 with PD-1 and CD80. These macrocyclic peptides exhibit in vitro immunomodulatory efficacy thus making them therapeutic candidates for the treatment of various diseases including cancer and infectious diseases.

The terms "specific binding" or "specifically bind" refer to the interaction between a protein and a binding molecule, such as a compound or ligand. The interaction is dependent upon the presence of a particular structure (i.e., an enzyme binding site, an antigenic determinant or epitope) of the protein that is recognized by the binding molecule. For example, if a compound has specific binding for protein binding site "A", the presence of the compound in a reaction containing a protein including binding site A, and a labeled peptide that specifically binds to protein binding site A will reduce the amount of labeled peptide bound to the protein. In contrast, nonspecific binding of a compound to the protein does not result in a concentration-dependent displacement of the labeled peptide from the protein.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

An additional aspect of the subject matter described herein is the use of the disclosed peptides as radiolabeled ligands for development of ligand binding assays or for monitoring of in vivo adsorption, metabolism, distribution, receptor binding or occupancy, or compound disposition. For example, a macrocyclic peptide described herein may be prepared using the radioactive isotope $^{125}$I and the resulting radiolabeled peptide may be used to develop a binding assay or for metabolism studies. Alternatively, and for the same purpose, a macrocyclic peptide described herein may be converted to a radiolabeled form by catalytic tritiation using methods known to those skilled in the art.

The macrocyclic peptides of the present disclosure can also be used as PET imaging agents by adding a radioactive tracer using methods known to those skilled in the art.

Preferred peptides include at least one of the macrocyclic peptides provided herein and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

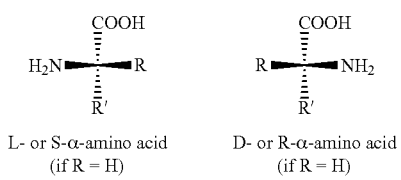

L- or S-α-amino acid (if R = H)   D- or R-α-amino acid (if R = H)

where R and R' are as discussed herein.

Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'" (prime) substituents equal hydrogen, the amino acid is glycine and is not chiral.

The terms "natural amino acid side chain" and "naturally occurring amino acid side chain," as used herein, refer to side chain of any of the naturally occurring amino acids (i.e., alanine, arginine, asparagine, aspartic acid, cysteine, glutamine, glutamic acid, glycine, -histidine, isoleucine, leucine, lysine, methionine, phenylalanine, proline, serine, threonine, tryptophan, tyrosine, and valine) usually in the S-configuration (i.e., the L-amino acid).

The terms "unnatural amino acid side chain" and "non-naturally occurring amino acid side chain," as used herein, refer to a side chain of any naturally occurring amino acid usually in the R-configuration (i.e., the D-amino acid) or to a group other than a naturally occurring amino acid side chain in R- or S-configuration (i.e., the D- or L-amino acid, respectively) selected from:

$C_2$-$C_7$alkenyl, $C_1$-$C_3$alkoxy$C_1$-$C_3$alkyl, $C_1$-$C_6$alkoxycarbonyl$C_1$-$C_3$alkyl, $C_1$-$C_7$alkyl, $C_1$-$C_3$alkylsulfanyl$C_1$-$C_3$alkyl, amido$C_1$-$C_3$alkyl, amino$C_1$-$C_3$alkyl, azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, carboxy$C_1$-$C_3$alkyl, $C_3$-$C_{14}$cycloalkyl$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl;

biphenyl$C_1$-$C_3$alkyl wherein the biphenyl is optionally substituted with a methyl group;

heterorocyclyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —NC(NH$_2$)$_2$, nitro, and —OP(O)(OH)$_2$;

indolyl$C_1$-$C_3$alkyl, wherein the indolyl part is optionally substituted with one group selected from $C_1$-$C_3$alkyl, carboxy$C_1$-$C_3$alkyl, halo, hydroxy, and phenyl, wherein the phenyl is further optionally substituted by one, two, or three groups independently selected from $C_1$-$C_3$alkoxy, $C_1$-$C_3$alkyl, and halo;

$NR^xR^y$($C_1$-$C_7$alkyl), wherein $R^x$ and $R^y$ are independently selected from hydrogen, $C_2$-$C_4$alkenyloxycarbonyl, $C_1$-$C_3$alkyl, $C_1$-$C_3$alkylcarbonyl, $C_3$-$C_{14}$cycloalkylcarbonyl, furanylcarbonyl, and phenylcarbonyl. When the alkyl linker contains more than one carbon an additional $NR^xR^y$ group can be on the chain.

$NR^uR^v$ carbonyl$C_1$-$C_3$alkyl, wherein $R^u$ and $R^v$ are independently selected from hydrogen, $C_1$-$C_3$alkyl, and triphenylmethyl;

phenyl optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —NC(NH$_2$)$_2$, nitro, and —OP(O)(OH)$_2$;

phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkyl sulfonylamino, amido, amino, amino$C_1$-$C_3$alkyl, aminosulfonyl, carboxy, cyano, halo, halo$C_1$-$C_3$alkyl, hydroxy, —NC(NH$_2$)$_2$, nitro, and —OP(O)(OH)$_2$; and phenoxy$C_1$-$C_3$alkyl wherein the phenyl is optionally substituted with a $C_1$-$C_3$alkyl group.

The term "alexa-5-SDP," as used herein, refers to

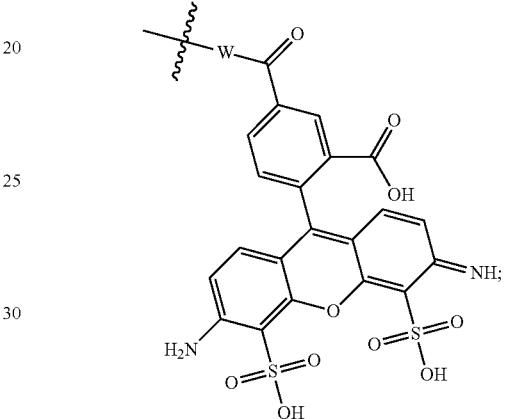

wherein W is O or NH.

The term "$C_2$-$C_4$alkenyl," as used herein, refers to a straight or branched chain group of two to four carbon atoms containing at least one carbon-carbon double bond.

The term "$C_2$-$C_7$alkenyl," as used herein, refers to a straight or branched chain group of two to seven carbon atoms containing at least one carbon-carbon double bond.

The term "$C_2$-$C_4$alkenyloxy," as used herein, refers to a $C_2$-$C_4$alkenyl group attached to the parent molecular moiety through an oxygen atom.

The term "$C_1$-$C_3$alkoxy," as used herein, refers to a $C_1$-$C_3$alkyl group attached to the parent molecular moiety through an oxygen atom.

The term "$C_1$-$C_4$alkoxy," as used herein, refers to a $C_1$-$C_4$alkyl group attached to the parent molecular moiety through an oxygen atom.

The term "$C_1$-$C_6$alkoxy," as used herein, refers to a $C_1$-$C_6$alkyl group attached to the parent molecular moiety through an oxygen atom.

The term "$C_1$-$C_3$alkoxy$C_1$-$C_3$alkyl," as used herein, refers to a $C_1$-$C_3$alkoxy group attached to the parent molecular moiety through a $C_1$-$C_3$alkyl group. The term "$C_1$-$C_6$alkoxycarbonyl," as used herein, refers to a $C_1$-$C_6$alkoxy group attached to the parent molecular moiety through a carbonyl group.

The term "$C_1$-$C_6$alkoxycarbonyl$C_1$-$C_3$alkyl," as used herein, refers to a $C_1$-$C_6$alkoxycarbonyl group attached to the parent molecular moiety through a $C_1$-$C_3$alkyl group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_3$alkylcarbonyl," as used herein, refers to a $C_1$-$C_3$alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl group attached to the parent molecular moiety through a $C_1$-$C_3$alkyl group.

The term "$C_1$-$C_3$alkylsulfonyl," as used herein, refers to a $C_1$-$C_3$alkyl group attached to the parent molecular moiety through a sulfonyl group.

The term "$C_1$-$C_3$alkylsulfonylamino," as used herein, refers to a $C_1$-$C_3$alkylsulfonyl group attached to the parent molecular moiety through an amino group.

The term "amido," as used herein, refers to —C(O)NH$_2$.

The term "amido$C_1$-$C_3$alkyl," as used herein, refers to an amido group attached to the parent molecular moiety through a $C_1$-$C_3$alkyl group.

The term "amino," as used herein, refers to —NH$_2$.

The term "amino$C_1$-$C_3$alkyl," as used herein, refers to an amino group attached to the parent molecular moiety through a $C_1$-$C_3$alkyl group.

The term "aminosulfonyl," as used herein, refers to an amino group attached to the parent molecular moiety through a sulfonyl group.

The term "azaindolyl$C_1$-$C_3$alkyl," as used herein, refers to an azaindolyl group attached to the parent molecular through a $C_1$-$C_3$alkyl group. The azaindolyl group can be attached to the alkyl moiety through any substitutable atom in the group.

The term "benzothiazolyl$C_1$-$C_3$alkyl," as used herein, refers to an benzothiazolyl group attached to the parent molecular through a $C_1$-$C_3$alkyl group. The benzothiazolyl group can be attached to the alkyl moiety through any substitutable atom in the group.

The term "benzothienyl$C_1$-$C_3$alkyl," as used herein, refers to a benzothienyl group attached to the parent molecular through a $C_1$-$C_3$alkyl group. The benzothienyl group can be attached to the alkyl moiety through any substitutable atom in the group.

The term "benzyloxy," as used herein, refers to a benzyl group attached to the parent molecular moiety through an oxygen atom.

The term "benzyloxy$C_1$-$C_3$alkyl," as used herein, refers to a benzyloxy group attached to the parent molecular moiety through a $C_1$-$C_3$alkyl group.

The term "biotin," as used herein, refers to:

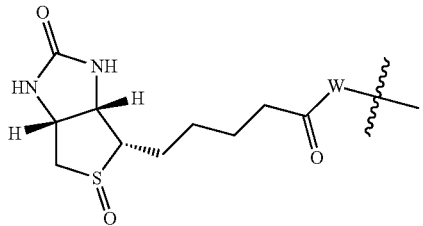

wherein W is O or NH.

The term "biphenyl$C_1$-$C_3$alkyl," as used herein, refers to a biphenyl group attached to the parent molecular moiety through a $C_1$-$C_3$alkyl group. The biphenyl group can be attached to the alkyl moiety through any substitutable atom in the group.

The term "carbonyl," as used herein, refers to —C(O)—.

The term "carboxy," as used herein, refers to —CO$_2$H.

The term "carboxy$C_1$-$C_3$alkyl," as used herein, refers to a carboxy group attached to the parent molecular moiety through a $C_1$-$C_3$alkyl group.

The term "cyano," as used herein, refers to —CN.

The term "$C_3$-$C_{14}$cycloalkyl," as used herein, refers to a saturated monocyclic, bicyclic, or tricyclic hydrocarbon ring system having three to fourteen carbon atoms and zero heteroatoms. The bicyclic and tricyclic rings may be fused, spirocyclic, or bridged. Representative examples of cycloalkyl groups include, but are not limited to, cyclopropyl, cyclopentyl, bicyclo[3.1.1]heptyl, and adamantyl.

The term "$C_3$-$C_{14}$cycloalkyl$C_1$-$C_3$alkyl," as used herein, refers to a $C_3$-$C_{14}$cycloalkyl group attached to the parent molecular moiety through a $C_1$-$C_3$alkyl group.

The term "$C_3$-$C_{14}$cycloalkylcarbonyl," as used herein, refers to a $C_3$-$C_{14}$ cycloalkyl group attached to the parent molecular moiety through a carbonyl group.

The term "furanyl$C_1$-$C_3$alkyl," as used herein, refers to a furanyl group attached to the parent molecular moiety through a $C_1$-$C_3$alkyl group. The furanyl group can be attached to the alkyl moiety through any substitutable atom in the group.

The term "furanylcarbonyl," as used herein, refers to a furanyl group attached to the parent molecular moiety through a carbonyl group.

The terms "halo" and "halogen," as used herein, refer to F, Cl, Br, or I.

The term "halo$C_1$-$C_3$alkyl," as used herein, refers to a $C_1$-$C_3$alkyl group substituted with one, two, or three halogen atoms.

The term "halomethyl," as used herein, refers to a methyl group substituted with one, two, or three halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure are attached to the parent molecular moiety through a carbon atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "hydroxy," as used herein, refers to —OH.

The term "imidazolyl$C_1$-$C_3$alkyl," as used herein, refers to an imidazolyl group attached to the parent molecular moiety through a $C_1$-$C_3$alkyl group. The imidazolyl group can be attached to the alkyl moiety through any substitutable atom in the group.

The term "indolyl$C_1$-$C_3$alkyl," as used herein, refers to an indolyl group attached to the parent molecular moiety through a $C_1$-$C_3$alkyl group. The indolyl group can be attached to the alkyl moiety through any substitutable atom in the group.

The term "naphthylC$_1$-C$_3$alkyl," as used herein, refers to a naphthyl group attached to the parent molecular moiety through a C$_1$-C$_3$alkyl group. The naphthyl group can be attached to the alkyl moiety through any substitutable atom in the group.

The term "nitro," as used herein, refers to —NO$_2$.

The term "NR$^x$R$^y$," as used herein, refers to two groups, R$^a$ and R$^b$, which are attached to the parent molecular moiety through a nitrogen atom. R$^a$ and R$^b$ are independently selected from hydrogen, C$_2$-C$_4$alkenyloxycarbonyl, C$_1$-C$_3$alkylcarbonyl, C$_3$-C$_{14}$cycloalkylcarbonyl, furanylcarbonyl, and phenylcarbonyl.

The term "NR$^x$R$^y$(C$_1$-C$_3$)alkyl," as used herein, refers to an NR$^x$R$^y$ group attached to the parent molecular moiety through a C$_1$-C$_3$alkyl group.

The term "NR$^u$R$^v$," as used herein, refers to two groups, R$^u$ and R$^v$, which are attached to the parent molecular moiety through a nitrogen atom. R$^u$ and R$^v$ are independently selected from hydrogen, C$_1$-C$_3$alkyl, and triphenylmethyl.

The term "NR$^u$R$^v$carbonyl," as used herein, refers to an NR$^u$R$^v$ group attached to the parent molecular moiety through a carbonyl group.

The term "NR$^u$R$^v$ carbonylC$_1$-C$_3$alkyl," as used herein, refers to an NR$^u$R$^v$ carbonyl group attached to the parent molecular moiety through a C$_1$-C$_3$alkyl group.

The term "PEG," as used herein, refers to polyethylene glycol, a polymer of ethylene oxide represented by the formula

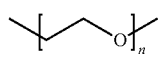

wherein n is between 1 and 57. It should be understood that the PEG group may be attached to the parent molecular moiety through the oxygen atom or the carbon atom.

The tem "phenoxy," as used herein, refers to a phenyl group attached to the parent molecular moiety through an oxygen atom.

The term "phenoxyC$_1$-C$_3$alkyl," as used herein, refers to a phenoxy group attached to the parent molecular moiety through a C$_1$-C$_3$alkyl group.

The term "phenylC$_1$-C$_3$alkyl," as used herein, refers to a phenyl group attached to the parent molecular moiety through a C$_1$-C$_3$alkyl group.

The term "phenylcarbonyl," as used herein, refers to a phenyl group attached to the parent molecular moiety through a carbonyl group.

The term "pyridinylC$_1$-C$_3$alkyl," as used herein, refers to a pyridinyl group attached to the parent molecular moiety through a C$_1$-C$_3$alkyl group. The pyridinyl group can be attached to the alkyl moiety through any substitutable atom in the group.

The term "sulfanyl," as used herein, refers to —S—.

The term "sulfonyl," as used herein, refers to —SO$_2$—.

The term "thiazolylC$_1$-C$_3$alkyl," as used herein, refers to a thiazolyl group attached to the parent molecular moiety through a C$_1$-C$_3$alkyl group. The thiazolyl group can be attached to the alkyl moiety through any substitutable atom in the group.

The term "thienylC$_1$-C$_3$alkyl," as used herein, refers to a thienyl group attached to the parent molecular moiety through a C$_1$-C$_3$alkyl group. The thienyl group can be attached to the alkyl moiety through any substitutable atom in the group.

The term "treating" refers to: (i) preventing a disease, disorder, or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

The term "vitamin E," as used herein refers to:

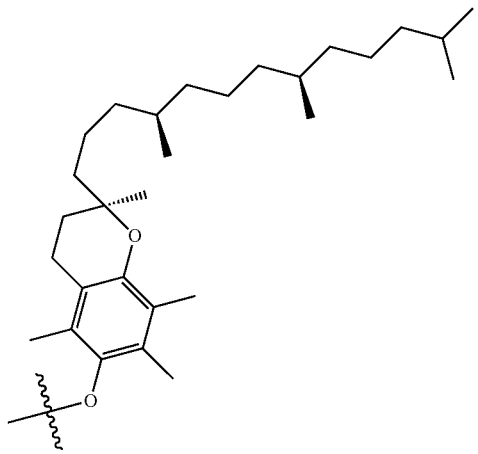 [SMILES: *Oc1c(C)c(C)c2c(c1C)CC[C@@](C)(CCC[C@H](C)CCC[C@H](C)CCCC(C)C)O2]

Binding of the macrocyclic peptides to PD-L1 can be measured, for example, by methods such as homogeneous time-resolved fluorescence (HTRF), Surface Plasmon Resonance (SPR), isothermal titration calorimetry (ITC), nuclear magnetic resonance spectroscopy (NMR), and the like. Further, binding of the macrocyclic peptides to PD-L1 expressed on the surface of cells can be measured as described herein in cellular binding assays.

Administration of a therapeutic agent described herein includes, without limitation, administration of a therapeutically effective amount of therapeutic agent. The term "therapeutically effective amount" as used herein refers, without limitation, to an amount of a therapeutic agent to treat or prevent a condition treatable by administration of a composition of the PD-1/PD-L1 binding inhibitors described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

In another aspect, the disclosure pertains to methods of inhibiting growth of tumor cells in a subject using the macrocyclic peptides of the present disclosure. As demonstrated herein, the macrocyclic peptides of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancement of HIV-specific T cell IFNg secretion. As a result, the macrocyclic peptides of the present disclosure are useful for modifying an immune response, treating diseases such as cancer or infectious disease, stimulating a protective autoimmune response or to stimulate antigen-specific immune responses (e.g., by coadministration of PD-L1 blocking peptides with an antigen of interest).

In order that the present disclosure may be more readily understood, certain terms are first defined. Additional definitions are set forth throughout the detailed description.

The terms "Programmed Death Ligand 1", "Programmed Cell Death Ligand 1", "Protein PD-L1", "PD-L1", "PDL1", "PDCDL1", "hPD-L1", "hPD-LI", "CD274" and "B7-H1" are used interchangeably, and include variants, isoforms, species homologs of human PD-L1, and analogs having at least one common epitope with PD-L1. The complete PD-L1 sequence can be found under GENBANK® Accession No. NP 054862.

The terms "Programmed Death 1", "Programmed Cell Death 1", "Protein PD-1", "PD-1", "PD1", "PDCD1", "hPD-1" and "hPD-I" are used interchangeably, and include variants, isoforms, species homologs of human PD-1, and analogs having at least one common epitope with PD-1. The complete PD-1 sequence can be found under GENBANK® Accession No. U64863.

The terms "cytotoxic T lymphocyte-associated antigen-4", "CTLA-4", "CTLA4", "CTLA-4 antigen" and "CD152" (see, e.g., Murata, *Am. J. Pathol.*, 155:453-460 (1999)) are used interchangeably, and include variants, isoforms, species homologs of human CTLA-4, and analogs having at least one common epitope with CTLA-4 (see, e.g., Balzano, *Int. J. Cancer Suppl.*, 7:28-32 (1992)). The complete CTLA-4 nucleic acid sequence can be found under GENBANK® Accession No. L15006.

The term "immune response" refers to the action of, for example, lymphocytes, antigen presenting cells, phagocytic cells, granulocytes, and soluble macromolecules produced by the above cells or the liver (including macrocyclic peptides, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within one or more than one standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

Competition Assays

The present disclosure is also directed to macrocyclic peptides that are capable of competing with the binding of a reference anti-PD-L1 antibody (MDX-1105) by at least about 20%, at least about 30%, at least about 40%, at least about 50%, at least about 60%, at least about 70%, at least about 80%, at least about 90%, and at least about 100%. Such macrocyclic peptides may share structural homology with one or more macrocyclic peptides disclosed herein, including mutant, conservative substitution, functional substitution, and deletion forms, provided they specific bind to PD-L1. For example, if a macrocyclic peptide binds substantially to the same region of PD-L1 as a reference anti-PD-L1 antibody, the macrocyclic peptide should bind to an epitope of PD-L1 that at least overlaps with the PD-L1 epitope that the anti-PD-L1 monoclonal antibody binds to. The overlapping region can range from one amino acid residue to several hundred amino acid residues. The macrocyclic peptide should then compete with and/or block the binding of the anti-PD-L1 monoclonal antibody to PD-L1 and thereby decrease the binding of the anti-PD-L1 monoclonal antibody to PD-L1, preferably by at least about 50% in a competition assay.

Anti-PD-L1 antibodies that may be used as reference antibodies for competition assay purposes are known in the art. For example, the following representative anti-PD-L1 antibodies may be used: MDX-1105 (BMS); L01X-C (Serono), L1X3 (Serono), MSB-0010718C (Serono), and PD-L1 Probody (CytomX), and the PD-L1 antibodies disclosed in co-owned WO 2007/005874.

Anti-PD-1 antibodies that may be used as reference antibodies for competition assay purposes are known in the art. For example, the following representative anti-PD-1 antibodies may be used: nivolumab (BMS); 17D8, 2D3, 4H1, 4A11, 7D3 and 5F4 each disclosed in co-owned U.S. Pat. No. 8,008,449 (BMS), MK-3475 (Merck, disclosed in U.S. Pat. No. 8,168,757), and the antibodies disclosed in U.S. Pat. No. 7,488,802.

Pharmaceutical Compositions

In another aspect, the present disclosure provides a composition, e.g., a pharmaceutical composition, containing one or a combination of macrocyclic peptides of the present disclosure, formulated together with a pharmaceutically acceptable carrier. Such compositions may include one or a combination of (e.g., two or more different) macrocyclic peptides, or immunoconjugates or bispecific molecules of the disclosure. For example, a pharmaceutical composition of the disclosure can comprise a combination of macrocyclic peptides (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a macrocyclic peptide combined with at least one other anti-inflammatory or immunosuppressant agent. Examples of therapeutic agents that can be used in combination therapy are described in greater detail below in the section on uses of the macrocyclic peptides of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a macrocyclic peptide, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" or "therapeutically acceptable salt" refers to a salt that retains the desired biological activity of the parent compound and does not impart any undesired toxicological effects (see e.g., Berge, S. M. et al., *J. Pharm. Sci.,* 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the macrocyclic peptide, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, twice per day, bi-weekly, tri-weekly, weekly, once every two weeks, once every three weeks, once every four weeks, once a month, once every 3 months or once every three to 6 months. Preferred dosage regimens for a macrocyclic peptide of the disclosure include 1 mg/kg body weight or 3 mg/kg body weight via intravenous administration, with the macrocycle being given using one of the following dosing schedules: (i) every four weeks for six dosages, then every three months; (ii) every three weeks; (iii) 3 mg/kg body weight once followed by 1 mg/kg body weight every three weeks.

In some methods, two or more macrocyclic peptides with different binding specificities are administered simultaneously, in which case the dosage of each compound administered falls within the ranges indicated. The compounds are usually administered on multiple occasions. Intervals between single dosages can be, for example, weekly, monthly, every three months or yearly. Intervals can also be irregular as indicated by measuring blood levels of macrocyclic peptide to the target antigen in the patient. In some methods, dosage is adjusted to achieve a plasma concentration of about 1-1000 .mu.g/ml and in some methods about 25-300 .mu.g/ml.

Alternatively, the macrocyclic peptide can be administered as a sustained release formulation, in which case less frequent administration is required. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a macrocyclic peptide of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth and/or HIV can be evaluated in an animal model system predictive of efficacy in human tumors or viral efficacy. Alternatively, this property of a composition can be evaluated by examining the ability of the compound to inhibit, such inhibition in vitro by assays known to the skilled practitioner. A therapeutically effective amount of a therapeutic compound can decrease tumor size, decrease viral load, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising a macrocyclic peptide and an another immumodulator, as described herein. The kit may also further comprise instructions for use in the treatment of a hyperproliferative disease (such as cancer as described herein) and/or anti-viral disease.

A composition of the present disclosure can be administered via one or more routes of administration using one or more of a variety of methods known in the art. As will be appreciated by the skilled artisan, the route and/or mode of administration will vary depending upon the desired results. Preferred routes of administration for macrocyclic peptides of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a macrocyclic peptide of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the macrocyclic peptides of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522,811, 5,374,548, and 5,399,331. The liposomes may comprise one or more moieties which are selectively transported into specific cells or organs, thus enhance targeted drug delivery (see, e.g., Ranade, V. V., *J. Clin. Pharmacol.*, 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.*, 153:1038 (1988)); macrocyclic peptides (Bloeman, P. G. et al., *FEBS Lett.*, 357:140 (1995); Owais, M. et al., *Antimicrob. Agents Chemother.*, 39:180 (1995)); surfactant protein A receptor (Briscoe et al., *Am. J. Physiol.*, 1233:134 (1995)); p 120 (Schreier et al., *J. Biol. Chem.*, 269:9090 (1994)); see also Keinanen, K. et al., *FEBS Lett.*, 346:123 (1994); Killion, J. J. et al., *Immunomethods* 4:273 (1994).

Uses and Methods of the Disclosure

The macrocyclic peptides, compositions and methods of the present disclosure have numerous in vitro and in vivo utilities involving, for example, detection of PD-L1 or enhancement of immune response by blockade of PD-L1. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the macrocyclic peptide of the disclosure such that the immune response in the subject is modified. Preferably, the response is enhanced, stimulated or up-regulated. In other respects, the macrocyclic peptide may have anti-cyno, anti-mouse, and/or anti-woodchuck binding and therapeutic activity.

As used herein, the term "subject" is intended to include human and non-human animals. Non-human animals includes all vertebrates, e.g., mammals and non-mammals, such as non-human primates, sheep, dogs, cats, cows, horses, chickens, woodchuck, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the macrocyclic peptides can be administered together with an antigen of interest. When macrocyclic peptides to PD-L1 are administered together with another agent, the two can be administered in either order or simultaneously.

The disclosure further provides methods for detecting the presence of human, woodchuck, cyno, and/or mouse PD-L1 antigen in a sample, or measuring the amount of human, woodchuck, cyno, and/or mouse PD-L1 antigen, comprising contacting the sample, and a control sample, with a reference macrocyclic peptide which specifically binds to human, woodchuck, cyno, and/or mouse PD-L1, under conditions that allow for formation of a complex between the macrocycle and human, woodchuck, cyno, and/or mouse PD-L1. The formation of a complex is then detected, wherein a difference complex formation between the sample compared to the control sample is indicative the presence of human, woodchuck, cyno, and/or mouse PD-L1 antigen in the sample.

Given the specific binding of the macrocyclic peptides of the disclosure for PD-L1, compared to CD28, ICOS and CTLA-4, the macrocyclic peptides of the disclosure can be used to specifically detect PD-L1 expression on the surface of cells and, moreover, can be used to purify PD-L1 via immunoaffinity purification.

Cancer

Blockade of PD-1 by macrocyclic peptides can enhance the immune response to cancerous cells in the patient. The ligand for PD-1, PD-L1, is not expressed in normal human cells, but is abundant in a variety of human cancers (Dong et al., *Nat. Med.*, 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med.*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 to PD-L1 and the effect is additive when the interaction of PD-1 to PD-L2 is blocked as well (Iwai et al., *Proc. Natl. Acad. Sci.*, 99:12293-12297 (2002); Brown et al., *J. Immunol.*, 170:1257-1266 (2003)). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present disclosure relates to treatment of a subject in vivo using a macrocyclic peptide such that growth of cancerous tumors is inhibited. A macrocyclic peptide may be used alone to inhibit the growth of cancerous tumors. Alternatively, a macrocyclic peptide may be used in conjunction with other immunogenic agents, standard cancer treatments, or other macrocyclic peptides, as described below.

Accordingly, in one embodiment, the disclosure provides a method of inhibiting growth of tumor cells in a subject, comprising administering to the subject a therapeutically effective amount of a macrocyclic peptide.

Preferred cancers whose growth may be inhibited using the macrocyclic peptides of the disclosure include cancers typically responsive to immunotherapy. Non-limiting examples of preferred cancers for treatment include melanoma (e.g., metastatic malignant melanoma), renal cell carcinoma (e.g., clear cell carcinoma), prostate cancer (e.g., hormone refractory prostate adenocarcinoma and castration-resistant prostate cancer), breast cancer, colorectal cancer and lung cancer (e.g., squamous and non-squamous non-small cell lung cancer). Additionally, the disclosure includes refractory or recurrent malignancies whose growth may be inhibited using the macrocyclic peptides of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, colon cancer, rectal cancer, cancer of the anal region, stomach/gastric cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al., *Int. Immunol.*, 17:133-144 (2005)).

Optionally, macrocyclic peptides to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo, N. et al., Cancer Vaccines, Chapter 61, pp. 3023-3043, in DeVita, V. et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90: 3539-3543 (1993)).

The study of gene expression and large scale gene expression patterns in various tumors has led to the definition of so called tumor specific antigens (Rosenberg, S. A., *Immunity*, 10:281-287 (1999)). In many cases, these tumor specific antigens are differentiated antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R. et al., *Science*, 269:1585-1588 (1995); Tamura, Y. et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al., *Nat. Med.*, 4:328-332 (1998)). DCs may also be transduced by genetic means to express these tumor antigens as well. DCs have also been fused directly to tumor cells for the purposes of immunization (Kugler, A. et al., *Nat. Med.*, 6:332-336 (2000)). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al., *Cancer Res.*, 58:5301-5304 (1998)). An example of such a combination is a macrocyclic peptide in combination with decarbazine for the treatment of melanoma. Another example of such a combination is a macrocyclic peptide in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

PD-L1 blocking macrocyclic peptides can also be used in combination with bispecific macrocyclic peptides that target Fc alpha or Fc gamma receptor-expressing effectors cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). Macrocyclic peptides to each of these entities may be used in combination with anti-PD-L1 to counteract the effects of the immunosuppressive agent and favor tumor immune responses by the host.

Other macrocyclic peptides which may be used to activate host immune responsiveness can be used in combination with anti-PD-L1. These include molecules on the surface of dendritic cells which activate DC function and antigen presentation. Anti-CD40 macrocyclic peptides are able to substitute effectively for T cell helper activity (Ridge, J. et al., *Nature*, 393:474-478 (1998)) and can be used in conjunction with PD-1 antibodies (Ito, N. et al., *Immunobiology*, 201(5):527-540 (2000)). Activating macrocyclic peptides to T cell costimulatory molecules such as CTLA-4 (e.g., U.S. Pat. No. 5,811,097), OX-40 (Weinberg, A. et al., *Immunol.*, 164:2160-2169 (2000)), 4-1BB (Melero, I. et al., *Nat. Med.*, 3:682-685 (1997)), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence of macrocyclic peptides may be expected to increase the frequency and activity of the adoptively transferred T cells.

Infectious Diseases

Other methods of the disclosure are used to treat patients that have been exposed to particular toxins or pathogens. Accordingly, another aspect of the disclosure provides a method of treating an infectious disease in a subject comprising administering to the subject a macrocyclic peptide of the present disclosure such that the subject is treated for the infectious disease.

Similar to its application to tumors as discussed above, PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, and C), Influenza, Herpes, *Giardia*, Malaria (Butler, N. S. et al., *Nature Immunology* 13, 188-195 (2012); Hafalla, J. C. R., et al. *PLOS Pathogens; Feb.* 2, 2012)), *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections treatable by methods of the disclosure include *Candida (albicans, krusei, glabrata, tropicalis*, etc.), *Cryptococcus neoformans, Aspergillus (fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In all of the above methods, PD-L1 blockade can be combined with other forms of immunotherapy such as cytokine treatment (e.g., interferons, agents targeting VEGF activity or VEGF-receptors, GM-CSF, G-CSF, IL-2), or bispecific antibody therapy, which provides for enhanced presentation of tumor antigens (see, e.g., Holliger, *Proc. Natl. Acad. Sci. USA*, 90:6444-6448 (1993); Poljak, *Structure*, 2:1121-1123 (1994)).

Autoimmune Reactions

The macrocyclic peptides may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B16 melanoma in van Elsas et al. supra; depigmentation in Trp-2 vaccinated mice (Overwijk, W. et al., *Proc. Natl. Acad. Sci. USA*, 96:2982-2987 (1999)); autoimmune prostatitis evoked by TRAMP tumor cell vaccines (Hurwitz, A., supra (2000)), melanoma peptide antigen vaccination and vitiligo observed in human clinical trials (Rosenberg, S. A. et al., *J. Immunother. Emphasis Tumor Immunol.*, 19(1):81-84 (1996)).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., *Nature*, 400:173-177 (1999)).

Other self proteins may also be used as targets such as IgE for the treatment of allergy and asthma, and TNF.alpha for rheumatoid arthritis. Finally, antibody responses to various hormones may be induced by the use of the macrocycles disclosed herein. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 macrocycles can be used for induction of therapeutic autoimmune responses to treat patients having an inappropriate accumulation of other self-antigens, such as amyloid deposits, including A.beta. in Alzheimer's disease, cytokines such as TNF.alpha., and IgE.

Vaccines

The macrocyclic peptides may be used to stimulate antigen-specific immune responses by coadministration of an anti-PD-1 macrocycle with an antigen of interest (e.g., a vaccine). Accordingly, in another aspect the disclosure provides a method of enhancing an immune response to an antigen in a subject, comprising administering to the subject: (i) the antigen; and (ii) an anti-PD-1 macrocycle such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the compositions (e.g., macrocyclic peptides, multispecific and bispecific molecules and immunoconjugates) of the disclosure in vivo and in vitro are well known in the art and can be selected by those of ordinary skill. For example, the compositions can be administered by injection (e.g., intravenous or subcutaneous). Suitable dosages of the molecules used will depend on the age and weight of the subject and the concentration and/or formulation of the composition.

As previously described the macrocyclic peptides of the disclosure can be co-administered with one or other more therapeutic agents, e.g., a cytotoxic agent, a radiotoxic agent or an immunosuppressive agent. The peptide can be linked to the agent (as an immunocomplex) or can be administered separate from the agent. In the latter case (separate administration), the peptide can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the macrocyclic peptides of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the peptides.

Also within the scope of the present disclosure are kits comprising the compositions of the disclosure (e.g., macrocyclic peptides, bispecific or multispecific molecules, or immunoconjugates) and instructions for use. The kit can further contain at least one additional reagent, or one or more additional macrocyclic peptides of the disclosure (e.g., a human antibody having a complementary activity which binds to an epitope in PD-L1 antigen distinct from the macrocycle). Kits typically include a label indicating the intended use of the contents of the kit. The term label includes any writing, or recorded material supplied on or with the kit, or which otherwise accompanies the kit.

Combination Therapy

The combination of the macrocyclic peptides of the present disclosure with another PD-L1 antagonist and/or other immunomodulator is useful for enhancement of an immune response against a hyperproliferative disease. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject a macrocyclic peptide of the disclosure such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering a macrocyclic peptide of the present disclosure and a subtherapeutic dose of another immunomodulator to a subject.

Blockade of PD-L1 by macrocyclic peptides can enhance the immune response to cancerous cells in the patient. Cancers whose growth may be inhibited using the macrocyclic peptides of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

In certain embodiments, the combination of therapeutic agents containing at least one macrocyclic peptide discussed herein may be administered concurrently as a single composition in a pharmaceutically acceptable carrier, or concurrently as separate compositions wherein each agent can be administered sequentially. For example, a second immunomodulator and a macrocyclic peptide of the present disclosure can be administered sequentially, such as the second immunomodulator administered first and the macrocyclic peptide second, or the macrocyclic peptide being administered first and the second immunomodulator second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a second immunomodulator and the macrocyclic peptide may be concurrent, the second administration may be sequential with the second immunomodulator first and the macrocyclic peptide second, and the third administration may be sequential with the macrocyclic peptide first and second immunomodulator second, etc. Another representative dosing scheme may involve a first administration that is sequential with the macrocyclic peptide first and the second immunomodulator second, and subsequent administrations may be concurrent.

Optionally, the combination of the macrocyclic peptide and a second immunomodulator can be further combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

A combined PD-L1 macrocyclic peptide and a second immunomodulator can be further combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo et al., Cancer Vaccines, Chapter 61, pp. 3023-3043 in DeVita et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90:3539-3543 (1993)).

The study of gene expression and large scale gene expression patterns in various tumors has led to the definition of so called tumor specific antigens (Rosenberg, *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-L1 macrocyclic peptide and a second immunomodulator may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 macrocyclic peptide blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269:1585-1588 (1995); Tamura et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle et al., *Nat. Med.*, 4:328-332 (1998)). DCs may also be transduced by genetic means to express these tumor antigens as well. DCs have also been fused directly to tumor cells for the purposes of immunization (Kugler et al., *Nat. Med.*, 6:332-336 (2000)). As a method of vaccination, DC immunization may be effectively further combined with a combined anti-PD-L1 macrocyclic peptide and a second immunomodulator to activate more potent anti-tumor responses.

A combined anti-PD-L1 macrocyclic peptide and additional immunomodulator may also be further combined with standard cancer treatments. For example, a combination of a macrocyclic peptide and a second immunomodulator may be effectively combined with chemotherapeutic regimes. In these instances, as is observed with the combination of a macrocyclic peptide and a second immunomodulator, it may be possible to reduce the dose of other chemotherapeutic reagent administered with the combination of the instant disclosure (Mokyr et al., *Cancer Res.,* 58:5301-5304 (1998)). An example of such a combination is a combination of a macrocyclic peptide and a second immunomodulator further in combination with decarbazine for the treatment of melanoma. Another example is a combination of a macrocyclic peptide and a second immunomodulatory agent further in combination with interleukin-2 (IL-2) for the treatment of melanoma. The scientific rationale behind the combined use of PD-L1 macrocyclic peptide and another immunomodulator with chemotherapy is that cell death, which is a consequence of the cytotoxic action of most chemotherapeutic compounds, should result in increased levels of tumor antigen in the antigen presentation pathway. Other combination therapies that may result in synergy with a combined anti-PD-L1 macrocyclic peptide and additional immunomodulator through cell death include radiation, surgery, or hormone deprivation. Each of these protocols creates a source of tumor antigen in the host. Angiogenesis inhibitors may also be combined with a combined PD-L1 and second immunomodulator. Inhibition of angiogenesis leads to tumor cell death, which may also be a source of tumor antigen to be fed into host antigen presentation pathways.

A combination of PD-L1 and another immunomodulator can also be used in combination with bispecific macrocyclic peptides that target Fc.alpha. or Fc.gamma. receptor-expressing effector cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of a combined PD-L1 and a second immunomodulator. Alternatively, antigen may be delivered directly to DCs by the use of bispecific macrocyclic peptides which bind to tumor antigen and a dendritic cell specific cell surface marker.

In another example, a combination of a macrocyclic peptide and a second immunomodulator can be used in conjunction with anti-neoplastic macrocyclic agents, such as RITUXAN® (rituximab), HERCEPTIN® (trastuzumab), BEXXAR® (tositumomab), ZEVALIN® (ibritumomab), CAMPATH® (alemtuzumab), Lymphocide (eprtuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the second immunomodulator target or PD-L1. In an exemplary embodiment, a treatment of a hyperproliferative disease (e.g., a cancer tumor) may include an anti-cancer antibody in combination with a macrocyclic peptide and a second immunomodulator concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-.beta. (Kehrl, J. et al., *J. Exp. Med.,* 163:1037-1050 (1986)), IL-10 (Howard, M. et al., *Immunology Today,* 13:198-200 (1992)), and Fas ligand (Hahne, M. et al., *Science,* 274:1363-1365 (1996)). In another example, antibodies to each of these entities may be further combined with a macrocyclic peptide and another immunomodulator to counteract the effects of immunosuppressive agents and favor anti-tumor immune responses by the host.

Other agents that may be used to activate host immune responsiveness can be further used in combination with a macrocyclic peptide of the present disclosure. These include molecules on the surface of dendritic cells that activate DC function and antigen presentation. Anti-CD40 macrocyclic peptides are able to substitute effectively for T cell helper activity (Ridge, J. et al., *Nature,* 393:474-478 (1998)) and can be used in conjunction with the macrocyclic peptides of the present disclosure, either alone or in combination with an anti-CTLA-4 combination (Ito, N. et al., *Immunobiology,* 201(5):527-540 (2000)). Activating macrocyclic peptides to T cell costimulatory molecules, such as OX-40 (Weinberg, A. et al., *Immunol.,* 164:2160-2169 (2000)), 4-1BB (Melero, I. et al., *Nat. Med.,* 3:682-685 (1997), and ICOS (Hutloff, A. et al., *Nature,* 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A macrocyclic peptide of the present disclosure, either alone or in combination with another immunomodulator, can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science,* 285:546-551 (1999)). These methods may also be used to activate T cell responses to infectious agents such as CMV. Ex vivo activation in the presence a macrocyclic peptide of the present disclosure, either alone or in combination with another innumomodulator, may be expected to increase the frequency and activity of the adoptively transferred T cells.

In certain embodiments, the present disclosure provides a method for altering an adverse event associated with treatment of a hyperproliferative disease with an immunostimulatory agent, comprising administering a macrocyclic peptide of the present disclosure in combination with a subtherapeutic dose of another immunomodulator to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such treatment, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a macrocyclic peptide of the present disclosure, either alone or in combination with another immunomodulator, can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid is budesonide. Budesonide is a locally-acting glucocorticosteroid, which is extensively metabolized, primarily by the liver, following oral administration. ENTOCORT® EC (Astra-Zeneca) is a pH- and time-dependent oral formulation of budesonide developed to optimize drug delivery to the ileum and throughout the colon. ENTOCORT® EC is approved in the U.S. for the treatment of mild to moderate Crohn's disease involving the ileum and/or ascending colon. The usual oral dosage of ENTOCORT® EC for the treatment of Crohn's disease is 6 to 9 mg/day. ENTOCORT® EC is released in the intestines before being absorbed and retained in the gut mucosa. Once it passes through the gut mucosa target tissue, ENTOCORT® EC is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT® EC can result in systemic glucocorticoid effects such as hypercorticism and adrenal suppression. See *Physicians' Desk Reference Supplement*, 58th Edition, 608-610 (2004).

In still further embodiments, a combination PD-L1 and another immunomodulator in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

Dosage and Formulation

A suitable peptide of Formula I, or more specifically a macrocyclic peptide described herein, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraocular, intravenous, or intestinal administration. The compound is formulated according to the route of administration based on acceptable pharmacy practice (Fingl et al., in *The Pharmacological Basis of Therapeutics*, Chapter 1, p. 1 (1975); *Remington's Pharmaceutical Sciences*, 18th Edition, Mack Publishing Co., Easton, Pa. (1990)).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company (1995), a standard reference text in this field.

Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, antioxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

The abbreviations used in the present application, including particularly in the illustrative examples which follow, are well-known to those skilled in the art. Some of the abbreviations used are as follows: HOBt for hydroxybenzotriazole; HOAt for 1-hydroxy-7-azabenzotriazole; DIC for N,N'-diisopropylcarbodiimide; HBTU for O-(benzotriazol-1-yl)-1,1,3,3-tetramethyluronium hexafluorophosphate; BOP for benzotriazol-1-yl-oxy-tris(dimethylamino)phosphonium hexafluorophosphate; PyBOP for (benzotriazol-1-yloxy) tripyrrolidinophosphonium hexafluorophosphate; TIS or TIPS for triisopropylsilane; DMSO for dimethylsulfoxide; MeCN or ACN for acetonitrile; DCM for dichloromethane; min for minutes; NMP for N-methylpyrrolidinone; h for hours; RT for room temperature or retention time (context will dictate); EtOAc for ethyl acetate; FMOC for 9-fluorenylmethyloxycarbonyl; OAc for acetate; MeOH for methanol; TFA for trifluoracetic acid; Et for ethyl; DMAP for 4-(N,N-dimethylamino)pyridine; EDCI for 1-ethyl-3-(3-dimethylaminopropyl)carbodiimide; EtOH for ethanol; DEA for diethylamine; DCC for dicyclohexylcarbodiimide; DMF for N,N-dimethylformamide; EtOAc for ethyl acetate; DIEA for diisopropylethylamine; and HATU for O-(7-azabenzotriazole-1-yl)-1,1,3,3-tetramethyluronium hexafluorophosphate.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Peptide Synthesis

It should be understood that the group —C(O)NH— can be oriented within linkers X and X' in either of the two possible orientations (e.g., as —C(O)NH— or as —NHC(O)—) unless otherwise noted.

The description of the present disclosure herein should be construed in congruity with the laws and principals of chemical bonding. It should be understood that the compounds encompassed by the present disclosure are those that are suitably stable for use as pharmaceutical agent. For example, in compounds of formula (I) while X is a chain of between 1 and 172 atoms wherein the atoms are selected from carbon and oxygen and wherein the chain may contain one, two, three, or four groups selected from —NHC(O)NH—, and —C(O)NH-embedded therein; and wherein the chain is optionally substituted with one to six groups independently selected from —CO$_2$H, —C(O)NH$_2$, —CH$_2$C(O)NH$_2$, and —(CH$_2$)CO$_2$, it should be understood that this does not encompass compounds where multiple heteroatoms are linked to each other (i.e., —O—O— or O—NHC(O)NH—) as these would not be considered to be stable molecules. In another example, X would not encompass compounds wherein two heteroatoms are separated only by one carbon as this would also not be considered to be stable. One of skill in the art will know what compounds would and would not be stable based on the general principles of chemical bonding and stability.

Chemical synthesis of a macrocyclic peptide of the present disclosure can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., *Fmoc Solid Phase Synthesis*, Oxford University Press, Oxford (2000); Barany, G. et al., *The Peptides: Analysis, Synthesis, Biology*, Vol. 2: "Special Methods in Peptide Synthesis, Part A", pp. 3-284, Gross, E. et al., eds., Academic Press, New York (1980); and in Stewart, J. M. et al., *Solid-Phase Peptide Synthesis*, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with Et$_2$O or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

High resolution mass spectrometry (HRMS) analyses were performed on a Fourier Transform Orbitrap mass spectrometer (Exactive, Thermo Fisher Scientific, San Jose, Calif.) using positive or negative electrospray ionization operating at 25,000 resolution (full width at half height maximum, FWHM). The instrument was calibrated daily according to manufacturer's specifications resulting in mass accuracy errors<5 ppm. The operating software, Xcalibur, was used to calculate theoretical mass-to-charge values and to process the obtained data.

Analysis LCMS Condition A:

Column: Waters BEH C18, 2.1×50 mm, 1.7-µm particles; Mobile Phase A: water with 0.05% TFA; Mobile Phase B: Acetonitrile with 0.05% TFA; Temperature: 50° C.; Gradient: 2% B to 98% B over 1 min., then a 0.5 min. hold at 98% B; Flow: 0.8 mL/min; Detection: UV at 220 nm.

Analysis LCMS Condition C:

Column: Waters BEH C18, 2.1×50 mm, 1.7-µm particles; Mobile Phase A: water with 0.2% Formic Acid and 0.01% TFA; Mobile Phase B: Acetonitrile with 0.2% Formic acid an 0.01% TFA; Temperature: 50° C.; Gradient: 2% B to 80% B over 2 min., 80% B to 98% B over 0.1 minute then a 0.5 min. hold at 98% B; Flow: 0.8 mL/min; Detection: UV at 220 nm.

Analysis LCMS Condition D:

Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min., then a 0.75-minute hold at 100% B; Flow: 1.0 mL/min; Detection: UV at 220 nm.

Analysis LCMS Condition E:

Column: Waters BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; temperature: 50° C.; Gradient: 0-100% B over 3 min., then a 0.75-minute hold at 100% B; Flow: 1.11 mL/min; Detection: UV at 220 nm.

Analysis HPLC Condition B:

Column: YMC Pack ODS-AQ 3 um 150×4.6 mm; Mobile Phase A: water with 0.1% TFA; Mobile Phase B: Acetonitrile with 0.1% TFA; Temperature: 40° C.; Gradient: from 10% B to 100% B over 10 to 40 min.; Flow rate: 1 mL/min; Detection: UV at 220 nm.

General Procedures.

Prelude Method A:

All manipulations were performed under automation on a Prelude peptide synthesizer (Protein Technologies). All procedures unless noted were performed in a 10 or 45 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis (dimethylamino)methylene]-1H-1,2,3-triazolo[4,5-b]pyridinium 3-oxid hexafluorophosphate; NMM=N-methylmorpholine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Ile-OH; Fmoc-Leu-OH; Fmoc-Lys(Boc)-OH; Fmoc-Nle-OH; Fmoc-[N-Me]Ala-OH; Fmoc-[N-Me]Nle-OH; Fmoc-Phe-OH; Fmoc-Pro-OH; Fmoc-(D)-cis-Pro(4-OtBu)-OH; Fmoc-(D)-trans-Pro(4-OtBu)-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "Prelude Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:

To a 40 mL polypropylene solid-phase reaction vessel was added Merrifield Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 min. before the solvent was drained through the frit.

Single-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU or HCTU (0.2M in DMF, 5.0 mL, 10 eq), and finally NMM (0.8M in DMF, 2.5 mL, 20 eq). The mixture was periodically agitated for 60 min., then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally NMM (0.8M in DMF, 1.5 mL, 12 eq). The mixture was periodically agitated for 300 min., then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Custom Amino Acids-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 0.5 to 2.5 mL, 1 to 5 eq), then HATU (0.2M in DMF, 0.5 to 2.5 mL, 1 to 5 eq), and finally DIPEA (0.8M in DMF, 0.5 to 1.5 mL, 4 to 12 eq). The mixture was periodically agitated for 60 min. to 600 min., then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Chloroacetic Acid Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

CEM Method A:

All manipulations were performed under automation on a CEM Liberty microwave peptide synthesizer (CEM Corporation). All procedures unless noted were performed in a 30 or 125 mL polypropylene tube fitted with a bottom frit to a CEM Discovery microwave unit. The tube connects to the CEM Liberty synthesizer through both the bottom and the top of the tube. DMF and DCM can be added through the top and bottom of the tube, which washes down the sides of the tube equally. All solutions are removed through the bottom of the tube except while transferring resin from the top. "Periodic bubbling" describes a brief bubbling of $N_2$ gas through the bottom frit. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIEA/DIPEA=diisopropylethylamine; Sieber=Fmoc-aminoxanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "CEM Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed above.

Resin-Swelling Procedure:

To 50 mL polypropylene conical tube was added Merrifield Sieber resin (140 mg, 0.100 mmol). Then DMF (7 mL) was added to the tube followed by DCM (7 mL). The resin was then transferred to the reaction vessel from top of the vessel.

The procedure is repeated additionally two times. DMF (7 mL) was added followed by DCM (7 mL). The resin was allowed to swell with $N_2$ bubbling from the bottom of the reaction vessel for 15 min. before the solvent was drained through the frit.

Standard Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Double-Couple Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by $N_2$ bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by $N_2$ bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Custom Amino Acids-Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid solution (1.25 mL to 5 mL, 2.5 eq to 10 eq) containing HATU (2.5 eq to 10 eq), and finally DIPEA (2M in NMP, 0.5 mL to 1 mL, 20 eq). The mixture was mixed by N2 bubbling for 5 min. to 2 hours at 25° C. to 75° C., then the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

N-methylation on-resin (Turner, R. A.; Hauksson, N. E.; Gipe, J. H.; Lokey, R. S. *Org. Lett.* 2013, 15(19), 5012-5015):

All manipulations were performed manually unless noted. The procedure of "N-methylation on-resin" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale.

The resin was transferred into a 25 mL syringe equipped with a frit. To the resin was added piperidine:DMF (20:80 v/v, 5.0 mL). The mixture was shaken for 3 min. and then the solution was drained through the frit. The resin was washed 3 times with DMF (4.0 mL). To the reaction vessel was added piperidine:DMF (20:80 v/v, 4.0 mL). The mixture was shaken for 3 min. and then the solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

The resin was suspended in DMF (2.0 mL) and ethyl trifluoroacetate (0.119 ml, 1.00 mmol), 1,8-diazabicyclo[5.4.0]undec-7-ene (0.181 ml, 1.20 mmol). The mixture was put on a shaker for 60 min. The solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit. The resin was washed 3 times with dry THF (2.0 mL) to remove any residual water. In an oven dried 4.0 mL vial is added THF (1.0 mL), triphenylphosphine (131 mg, 0.500 mmol) on dry 4 Å molecular sieves (20 mg). The turbid solution is transferred on the resin and isopropyl azodicarboxylate (0.097 mL, 0.5 mmol) is added slowly. The resin is shaken for 15 min. The solution was drained through the frit and the resin was washed with 3 times with dry THF (2.0 mL) to remove any residual water. In an oven dried 4.0 mL vial is added THF (1.0 mL), triphenylphosphine (131 mg, 0.500 mmol) on dry 4 Å molecular sieves (20 mg). The turbid solution is transferred on the resin and diisopropyl azodicarboxylate (0.097 mL, 0.5 mmol) is added slowly. The resin is shaken for 15 min. The solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

The resin was suspended in Ethanol (1.0 mL) and THF (1.0 mL) and sodium borohydride (37.8 mg, 1.000 mmol) was added. The mixture was mixed on a shaker for 30 min. Solution was drained through the frit and the resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

Global Deprotection Method B:

All manipulations were performed manually unless noted. The procedure of "Global Deprotection Method B" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (94:3:3 v:v:w). The resin was removed from the reaction vessel and transferred to a 25 mL syringe equipped with a frit. To the syringe was added the "deprotection solution" (5.0 mL). The mixture was mixed in a shaker for 5 min. The solution was filtered through and diluted in diethyl ether (30 mL). The precipitated solid was centrifuged for 3 min. The supernatant solution was decanted and the solid was re-suspended in diethyl ether (25 mL). The suspension was centrifuged for 3 min. The supernatant was decanted and the remaining solid was suspended diethyl ether (25 mL). The suspension was centrifuged for 3 min. The supernatant was decanted and the remaining solid was dried under high vacuum. The crude peptide was obtained as a white to off-white solid.

Cyclization Method C:

All manipulations were performed manually unless noted. The procedure of "Cyclization Method C" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL: 24 mL), and the solution was then carefully adjusted to pH=8.5-9.0 using aqueous NaOH (1.0 M). The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Preparation of Example 3214

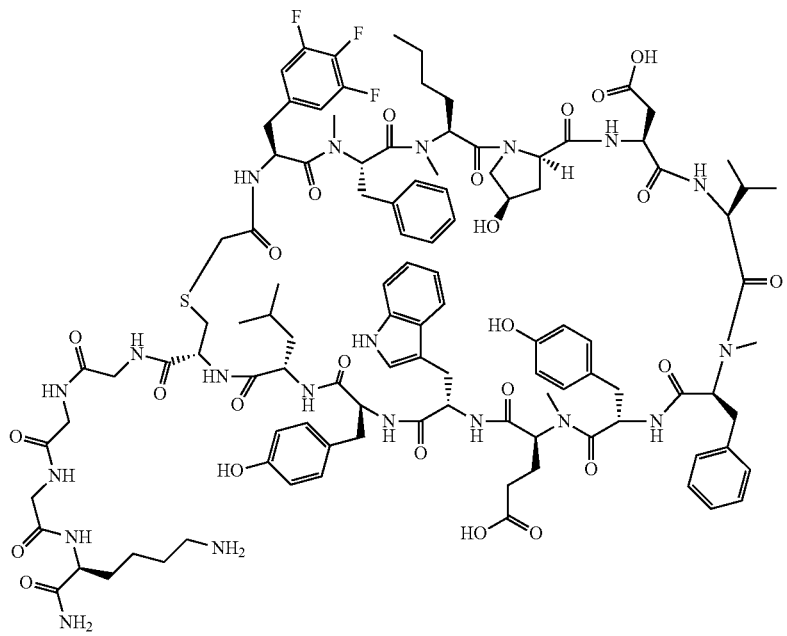

Example 3214

Example 3214 was prepared following the general synthetic sequence described below.

To a 40 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method A: Resin-swelling procedure" was followed;
"Prelude Method A: Single-coupling procedure" was followed with Fmoc-Lys(Boc)-OH;
"Prelude Method A: Single-coupling procedure" was followed with Fmoc-Gly-OH;
"Prelude Method A: Single-coupling procedure" was followed with Fmoc-Gly-OH;
"Prelude Method A: Single-coupling procedure" was followed with Fmoc-Gly-OH;
"Prelude Method A: Single-coupling procedure" was followed with Fmoc-Cys(Trt)-OH;
"Prelude Method A: Single-coupling procedure" was followed with Fmoc-Leu-OH;
"Prelude Method A: Single-coupling procedure" was followed with Fmoc-Tyr(tBu)-OH;
"Prelude Method A: Single-coupling procedure" was followed with Fmoc-Trp(Boc)-OH;
"Prelude Method A: Single-coupling procedure" was followed with Fmoc-[N-Me]Glu(OtBu)-OH;
"Prelude Method A: Secondary amine-coupling procedure" was followed with Fmoc-Tyr(tBu)-OH for 6 h;
"Prelude Method A: Single-coupling procedure" was followed with Fmoc-[N-Me]Phe-OH;
"Prelude Method A: Secondary amine-coupling procedure" was followed with Fmoc-Val-OH for 6 h;
"Prelude Method A: Single-coupling procedure" was followed with Fmoc-Asp(OtBu)-OH;
"Prelude Method A: Single-coupling procedure" was followed with Fmoc-cis-(D)-Pro(4-OH)—OH;
"Prelude Method A: Secondary amine-coupling procedure" was followed with Fmoc-[N-Me]Nle-OH for 6 h;
"Prelude Method A: Secondary amine-coupling procedure" was followed with Fmoc-[N-Me]Phe-OH for 6 h;
"Prelude Method A: Secondary amine-coupling procedure" was followed with Fmoc-Phe(3,4,5-tri-F)—OH for 6 h;
"Prelude Method A: Chloroacetyl chloride coupling procedure A" was followed;
"Global Deprotection Method B" was followed;
"Cyclization Method C" was followed.

The crude material was purified via preparative LC/MS with the following Conditions: Column: Phenomenex Luna 20×250 5 u particles; Mobile Phase A: water with 0.1% TFA; Mobile Phase B: Acetonitrile with 0.1% TFA; Gradient: 35-95% B over 50 min., then a 5-minute hold at 95% B; Flow: 15 mL/min. Fractions containing the desired product were combined and dried via centrifugal evaporation. The yield of the product was 5.3 mg, and its estimated purity by "Analysis HPLC Condition B" was 80% using a gradient of 35% to 80% buffer B in A over 30 min. Analysis LCMS Condition A: Retention time=1.33 min; ESI-MS(+) m/z 1104.1 (M+2H). ESI-HRMS(+) m/z: Calculated: 1103.5019 (M+2H). Found: 1103.5034 (M+2H).

Preparation of Example 3215

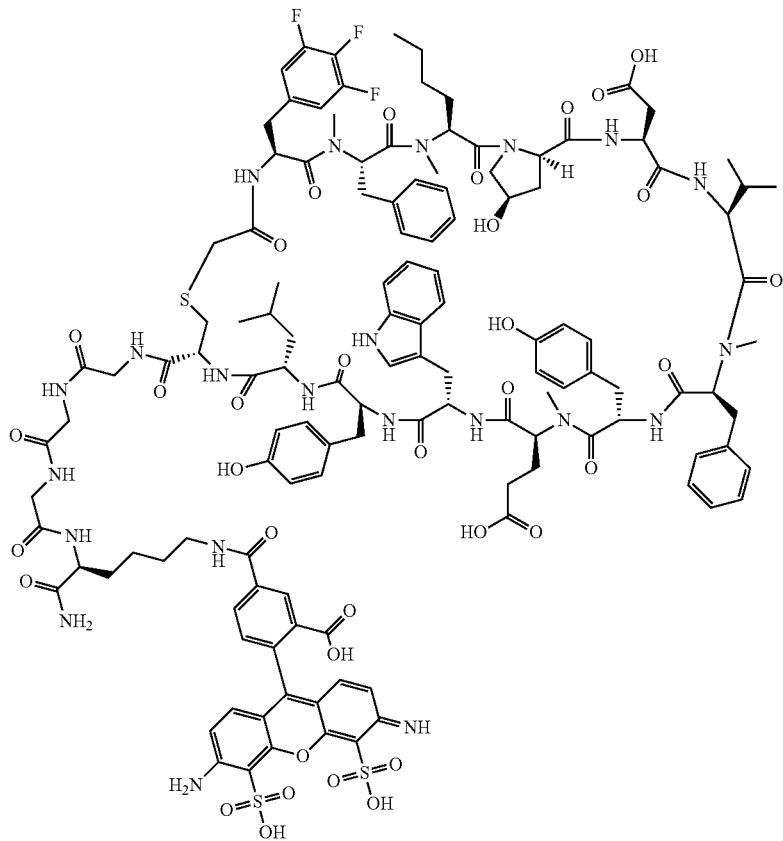

Example 3215

The compound from Example 3214 (4.7 mg, 2.130 µmol) was dissolved in 0.4 mL DMF/ACN (1:1). DIEA (3.72 µl, 0.021 mmol) was added, followed by a 0.9 mL solution of Alexa-5-SDP ester (2.93 mg, 3.5 µmol, Molecular Probes, A30052) in DMF/CH$_3$CN/DMSO (1:1:1). The reaction was stirred at room temperature for 16 h.

The crude material was purified via preparative LC/MS using the following conditions: Column: YMC ODS-AQ 100×10 mm S-5 um 12 nm; Mobile Phase A: water with 0.1% TFA; Mobile Phase B: Acetonitrile with 0.1% TFA; Gradient: 25-75% B over 50 min., then a 5-minute hold at 75% B; Flow: 15 mL/min. Fractions containing the desired product were combined and dried via centrifugal evaporation. The yield of product was 0.75 mg, and its estimated purity by "Analysis HPLC Condition B" was 96% using a gradient of 35% to 65% buffer B over 30 min. Analysis LCMS Condition A: Retention time=1.39 min; ESI-MS(+) m/z 1362.5 (M+2H).

Preparation of Example 3619

Example 3619

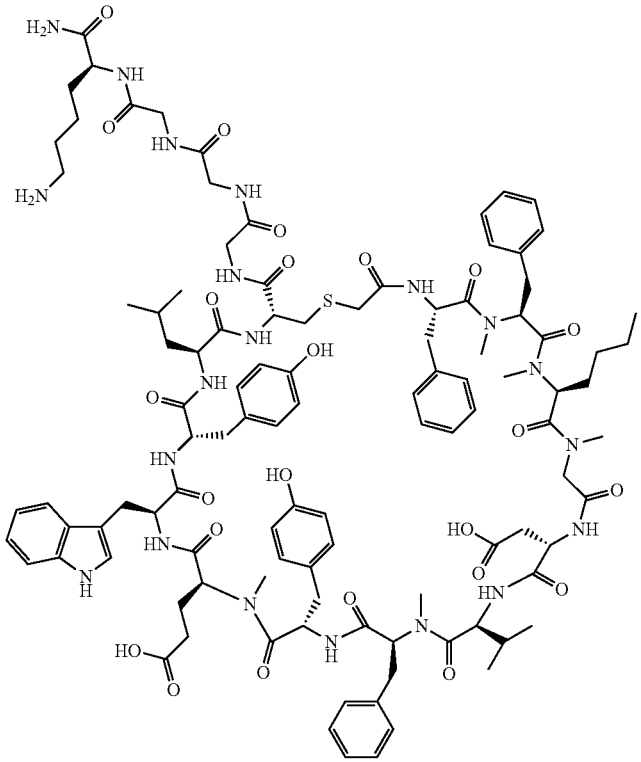

Example 3619 was prepared following the general synthetic sequence described below.

To a 50 mL polypropylene tube was added Sieber resin (350 mg, 0.250 mmol), and the tube was placed on the CEM Liberty microwave peptide synthesizer. The following procedures were then performed sequentially:

"CEM Method A: Resin-swelling procedure" was followed;
"CEM Method A: Standard coupling procedure" was followed with Fmoc-Lys-OH;
"CEM Method A: Standard coupling procedure" was followed with Fmoc-Gly-OH;
"CEM Method A: Standard coupling procedure" was followed with Fmoc-Gly-OH;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Leu-OH;
"CEM Method A: Standard coupling procedure" was followed with Fmoc-Tyr(tBu)-OH;
"CEM Method A: Standard coupling procedure" was followed with Fmoc-Trp(tBu)-OH;
"CEM Method A: Standard coupling procedure" was followed with Fmoc-[N-Me]Glu-OH;
"CEM Method A: Secondary amine-coupling procedure" was followed with Fmoc-Tyr(tBu)-OH;
"CEM Method A: Standard coupling procedure" was followed with Fmoc-[N-Me]Phe-OH;
"CEM Method A: Custom amino acids-coupling procedure" was followed with Fmoc-Val-OH using 10 eq for 10 min at 75° C., followed by 2 hours at room temperature;
"CEM Method A: Standard coupling procedure" was followed with Fmoc-Asp(OtBu)-OH;
"CEM Method A: Standard coupling procedure" was followed with Fmoc-Sar-OH;
"CEM Method A: Custom amino acids-coupling procedure" was followed with Fmoc-[N-Me]Nle-OH using 5 eq for 10 mins;
"CEM Method A: Custom amino acids-coupling procedure" was followed with Fmoc-[N-Me]Phe-OH using 5 eq for 10 mins;
"CEM Method A: Custom amino acids-coupling procedure" was followed with Fmoc-Phe-OH using 5 eq for 10 mins;
"Prelude Method A: Chloroacetyl chloride coupling procedure A" was followed,
"Global Deprotection Method B" was followed and "Cyclization Method C" was followed.

The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation and lyophilization. The yield of product was 12.9 mg, and its estimated purity by LCMS analysis was 98% using "Analysis LCMS conditions A and C". Analysis LCMS Condition A: Retention time=1.29 min; ESI-MS(+) m/z 1056.1 (M+2H). Analysis LCMS Condition C: Retention time=1.33 min; ESI-MS(+) m/z 1055.7 (M+2H).; ESI-HRMS(+) m/z: Calculated: 1056.0077 (M+2H). Found: 1056.0077 (M+2H).

Preparation of Example 3620

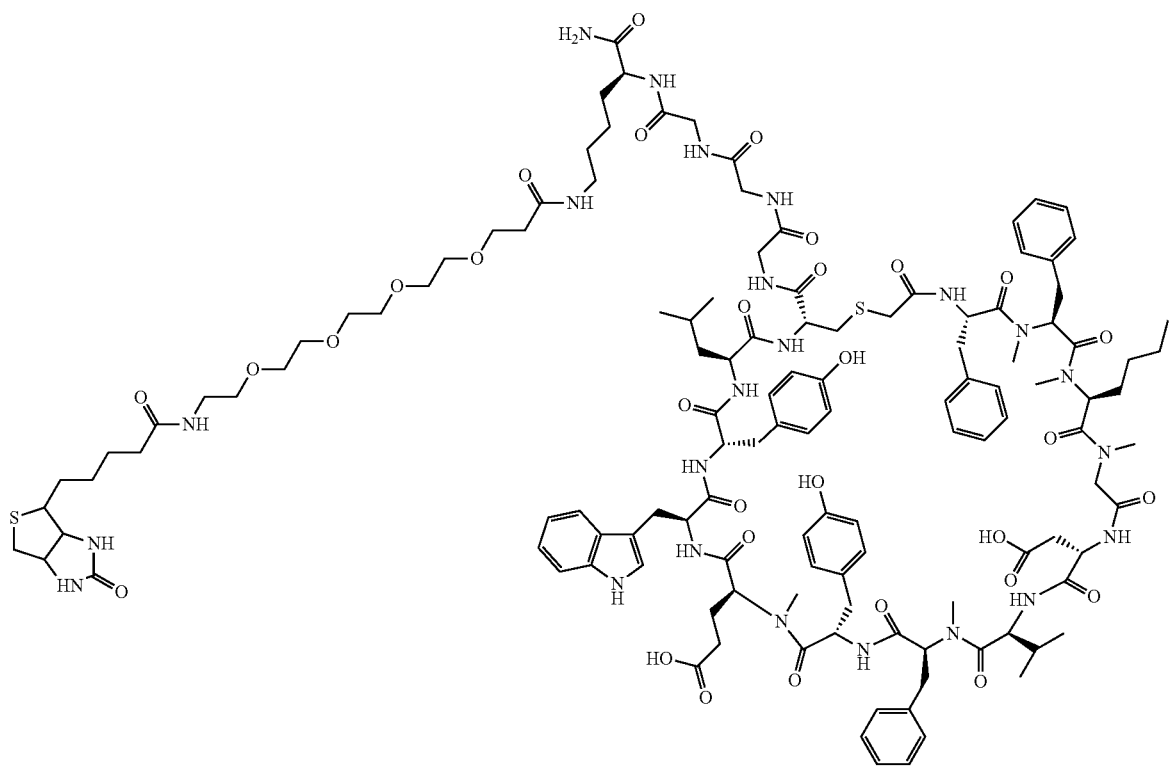

Example 3620

The peptide product from Example 3619 (8.0 mg, 3.79 μmol) was dissolved into 40 μL of DMF and 20 μL of acetonitrile. To this solution was added 2,5-dioxopyrrolidin-1-yl 17-oxo-21-(2-oxohexahydro-1H-thieno[3,4-d]imidazol-4-yl)-4,7,10,13-tetraoxa-16-azahenicosan-1-oate (2.231 mg, 3.79 μmol) and N,N-Diisopropylethylamine (6.60 μl, 0.038 mmol). The solution was stirred for 6 h. The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation and further dried by lyophilization.

The yield of product was 4.4 mg, and its estimated purity by LCMS analysis was 99.5% using "Analysis LCMS conditions A and C". Analysis LCMS Condition A: Retention time=1.34 min; ESI-MS(+) m/z 1292.8 (M+2H). Analysis LCMS Condition C: Retention time=1.56 min; ESI-MS (+) m/z 1292.4 (M+2H); ESI-HRMS(+) m/z: Calculated: 1292.1206 (M+2H). Found: 1292.1219 (M+2H).

Preparation of Example 3621

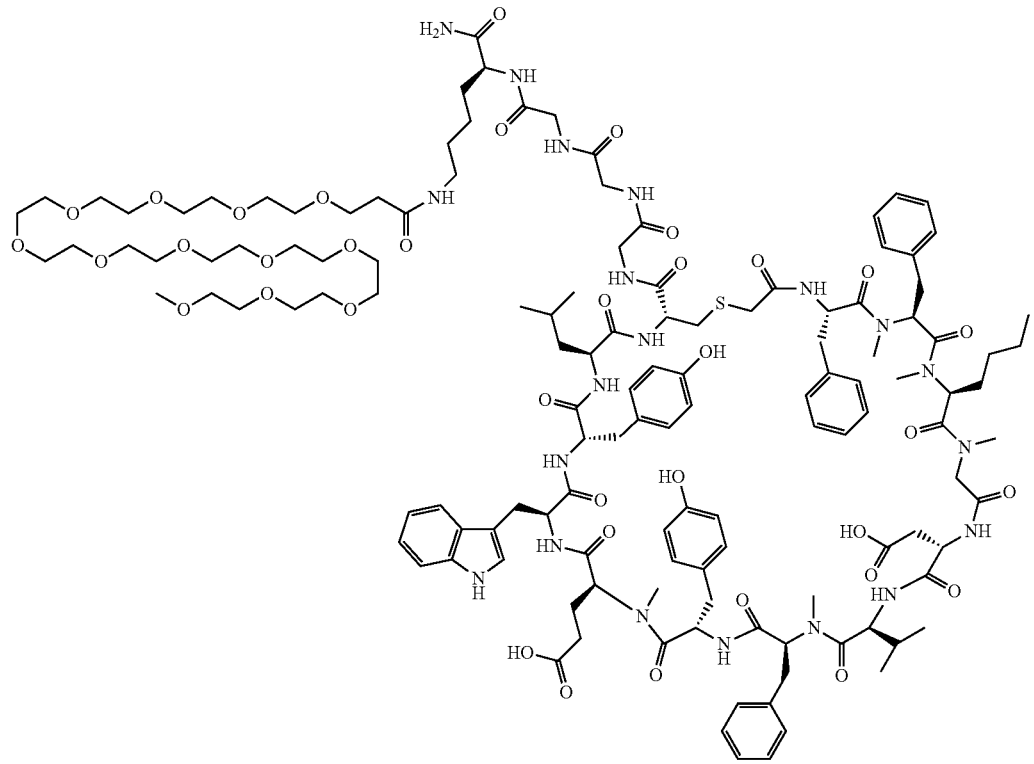

Example 3621

Example 3621 was prepared following the general synthetic sequence described for the preparation of Example 3619, composed of the following procedures: "CEM Method A: Resin-swelling procedure", "CEM Method A: Standard coupling procedure", "CEM Method A: Secondary amine-coupling procedure", "CEM Method A: Custom amino acids-coupling procedure", "Chloroacetic acid coupling procedure A", "Global Deprotection Method B", and "Cyclization Method C". The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation, followed by lyophilization. The peptide (6.0 mg, 2.84 µmol) was dissolved in 100 µL of DMF. To this solution was added 2,5-dioxopyrrolidin-1-yl 2,5,8,11,14,17,20,23,26,29,32,35-dodecaoxaoctatriacontan-38-oate (1.950 mg, 2.84 µmol) and N,N-Diisopropylethylamine (4.95 µl, 0.028 mmol). The solution was stirred for 3 h. The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation, followed by lyophilization. The yield of the product was 4.0 mg, and its estimated purity by LCMS analysis was 98% using "Analysis LCMS conditions A and C". Analysis LCMS Condition A: Retention time=1.34 min; ESI-MS(+) m/z 1341.0 (M+2H). Analysis LCMS Condition C: Retention time=1.62 min; ESI-MS(+) m/z 1341.4 (M+2H).

Preparation of Example 3622

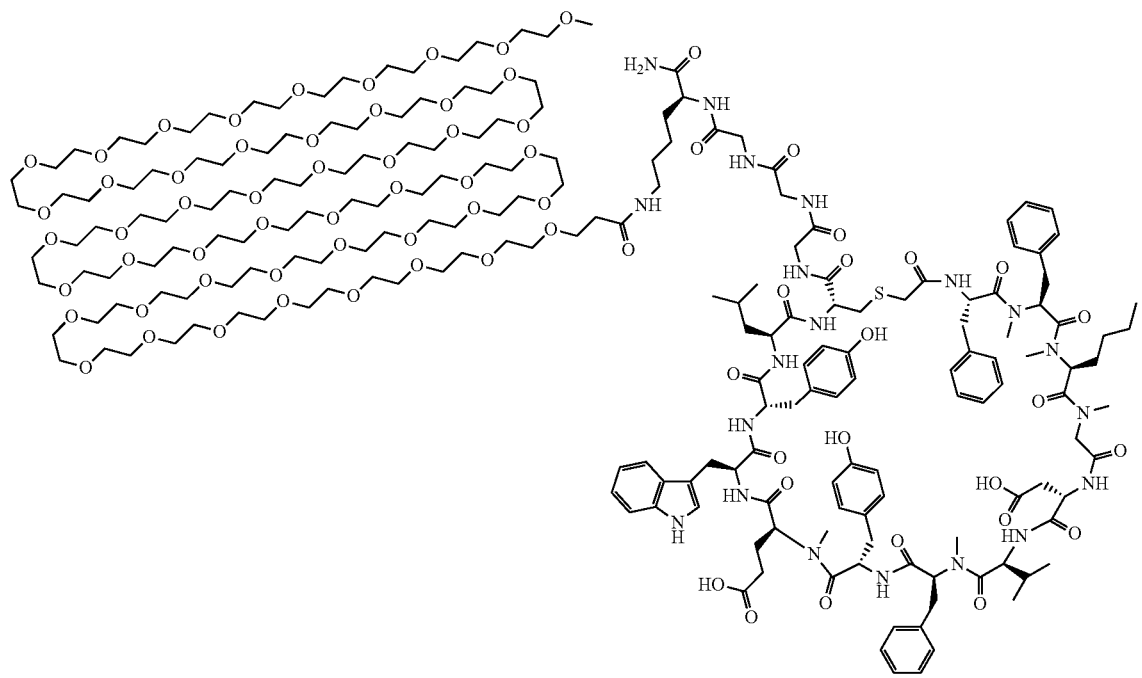

Example 3622

Example 3622 was prepared following the general synthetic sequence described for the preparation of Example 3619, composed of the following procedures: "CEM Method A: Resin-swelling procedure", "CEM Method A: Standard coupling procedure", "CEM Method A: Secondary amine-coupling procedure", "CEM Method A: Custom amino acids-coupling procedure", "Chloroacetic acid coupling procedure A", "Global Deprotection Method B", and "Cyclization Method C". The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation, followed by lyophilization. The peptide (6.0 mg, 2.84 µmol) was dissolved in 100 µL of DMF. To this solution was added 2,5-ioxopyrrolidin-1-yl-2,5,8,11,14,17,20,23,26,29,32,35, 38,41,44,47,50,53,56,59,62,65,68,71,74,77,80,83,86,89,92, 95,98,101,104,107,110,113,116,119,122,125,128,131,134, 137,140,143,146-nonatetracontaoxanonatetracontahectan-149-oate (6.58 mg, 2.84 µmol) and N,N-Diisopropylethylamine (4.95 µl, 0.028 mmol). The solution was stirred for 3 h. The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation, followed by lyophilization. The yield of the product was 3.5 mg, and its estimated purity by LCMS analysis was 96% using "Analysis LCMS conditions A and C". Analysis LCMS Condition A: Retention time=1.39 min; ESI-MS(+) m/z 1078.7 (M+4H). Analysis LCMS Condition C: Retention time=1.63 min; ESI-MS(+) m/z 1078.5 (M+4H).

Preparation of Example 3623

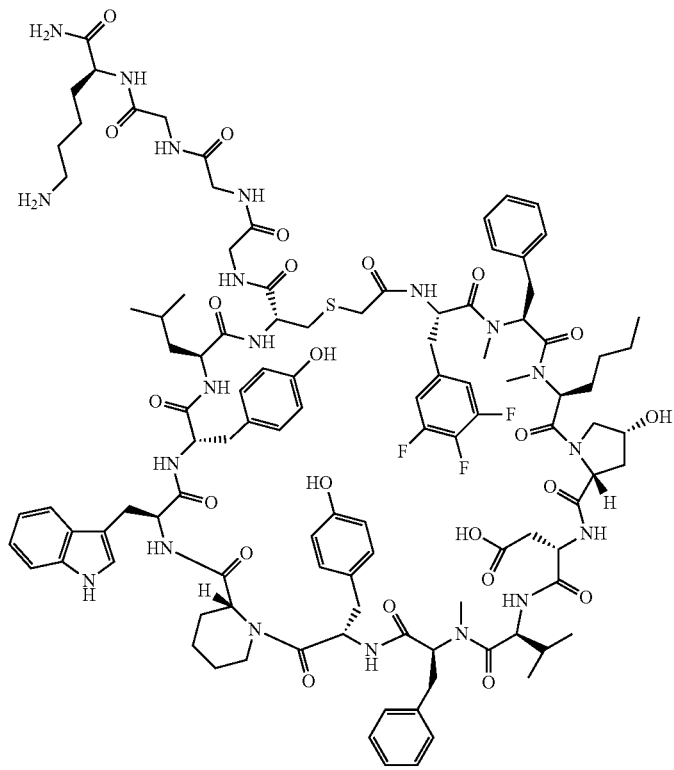

Example 3623

Example 3623 was prepared following the general synthetic sequence described for the preparation of Example 3619, composed of the following procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C". The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation, followed by lyophilization.

The yield of the product was 28 mg, and its estimated purity by LCMS analysis was 98% using "Analysis LCMS conditions D and E". Analysis LCMS Condition D: Retention time=1.69 min; ESI-MS(+) m/z 1088.1 (M+2H). Analysis LCMS Condition E: Retention time=1.80 min; ESI-MS (+) m/z 1088.2 (M+2H). ESI-HRMS(+) m/z: Calculated: 1087.5070 (M+2H). Found: 1087.5062 (M+2H).

Preparation of Example 3624

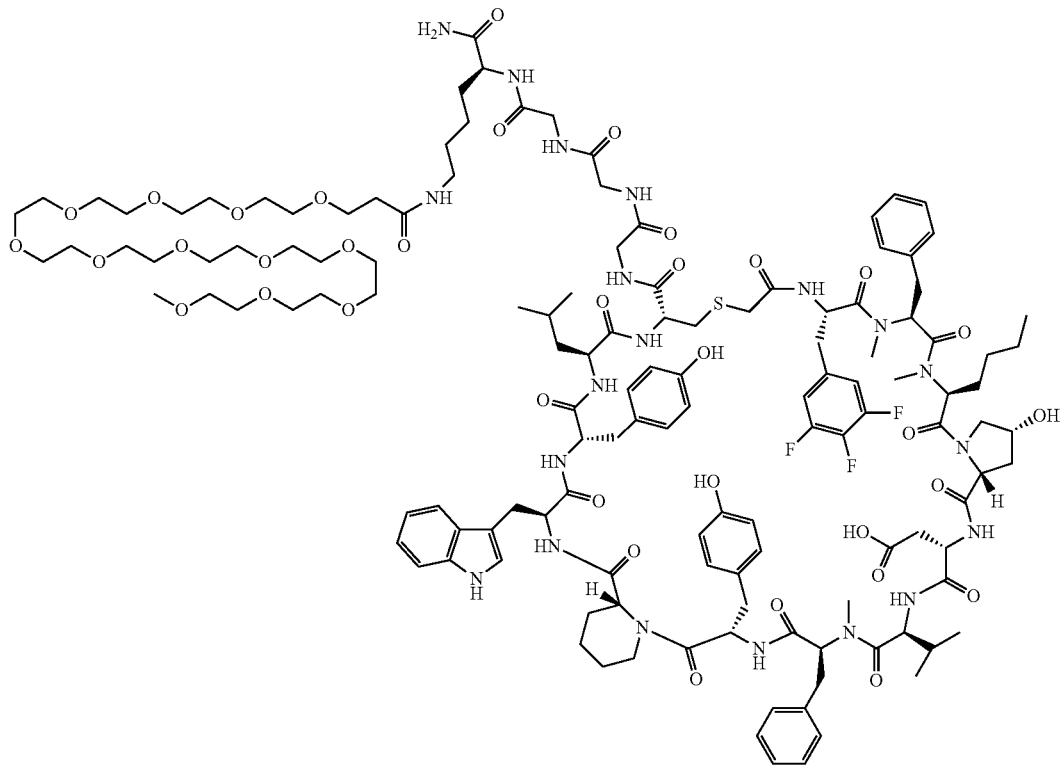

Example 3624

The peptide product from Example 3623 (8.0 mg, 3.68 μmol) was dissolved in 100 μL of DMF. To this solution was added 2,5-dioxopyrrolidin-1-yl 2,5,8,11,14,17,20,23,26,29,32,35-dodecaoxaoctatriacontan-38-oate (2.78 mg, 4.05 μmol) and N,N-Diisopropylethylamine (6.41 μl, 0.037 mmol). The solution was stirred for 3 h. The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of product was 2.5 mg, and its estimated purity by LCMS analysis was 94% using "Analysis LCMS conditions D and E". Analysis LCMS Condition D: Retention time=1.71 min; ESI-MS(+) m/z 1390.2 (M+2H+2H$_2$O); Analysis LCMS Condition E: Retention time=1.89 min; ESI-MS(+) m/z 1372.9 (M+2H); ESI-HRMS(+) m/z: Calculated: 1372.6696 (M+2H). Found: 1372.6729 (M+2H).

Preparation of Example 3625

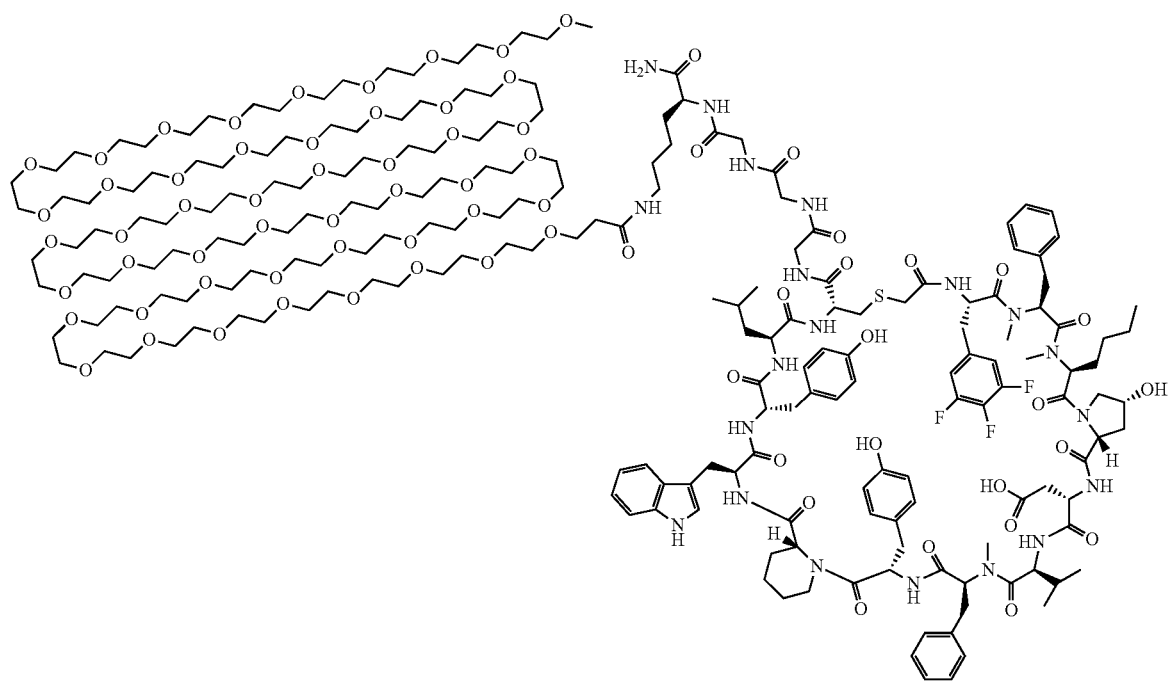

Example 3625

The peptide product from Example 3623 (8.0 mg, 3.68 μmol) was dissolved in 100 μL of DMF. To this solution was added 149-((2,5-dioxopyrrolidin-1-yl)oxy)-149-oxo-2,5,8,11,14,17,20,23,26,29,32,35,38,41,44,47,50,53,56,59,62,65,68,71,74,77,80,83,86,89,92,95,98,101,104,107,110,113,116,119,122,125,128,131,134,137,140,143,146-nonatetracontaoxanonatetracontahectan-56-ium (9.38 mg, 4.05 μmol) and N,N-Diisopropylethylamine (6.41 μl, 0.037 mmol). The solution was stirred for 3 h. The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of product was 3.4 mg, and its estimated purity by LCMS analysis was 91% using "Analysis LCMS conditions D and E". Analysis LCMS Condition D: Retention time=1.76 min; ESI-MS(+) m/z 1112.0 (M+4H+4H$_2$O). Analysis LCMS Condition E: Retention time=1.91 min; ESI-MS(+) m/z 1094.8 (M+4H).

Preparation of Example 3626

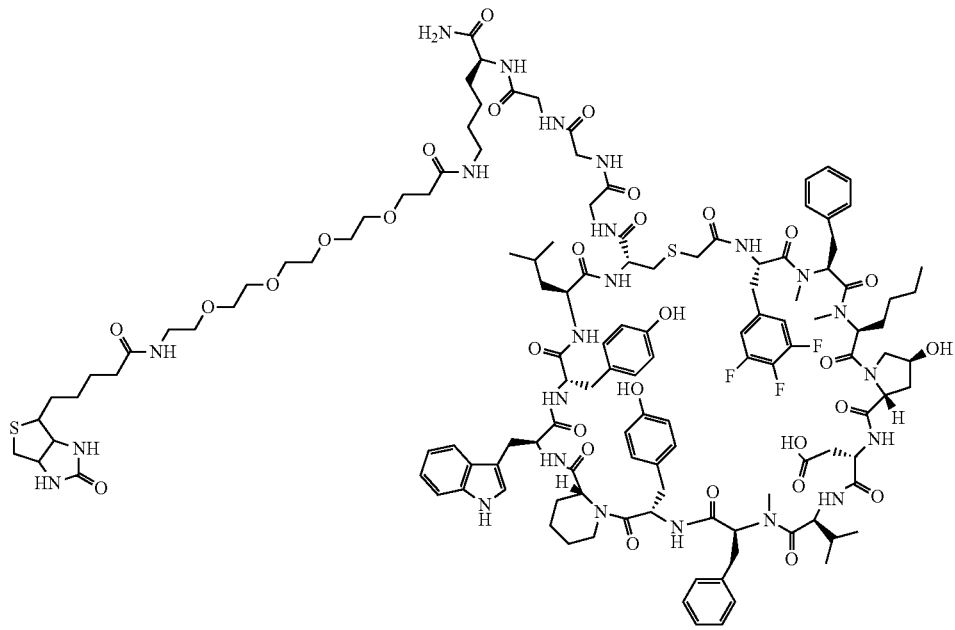

Example 3626

The peptide product from Example 3623 (8.0 mg, 3.68 μmol) was dissolved in 100 μL of DMF. To this solution was added 2,5-dioxopyrrolidin-1-yl 17-oxo-21-(2-oxohexahydro-1H-thieno[3,4-d]imidazol-4-yl)-4,7,10,13-tetraoxa-16-azahenicosan-1-oate (2.382 mg, 4.05 μmol) and N,N-Diisopropylethylamine (6.41 μl, 0.037 mmol). The solution was stirred for 3 h. The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of the product was 2.7 mg, and its estimated purity by LCMS analysis was 92% using "Analysis LCMS conditions D and E". Analysis LCMS Condition D: Retention time=1.65 min; ESI-MS(+) m/z 1323.8 (M+2H). Analysis LCMS Condition E: Retention time=1.81 min; ESI-MS(+) m/z 1324.6 (M+2H). ESI-HRMS(+) m/z: Calculated: 1324.1168 (M+2H). Found: 1324.1180 (M+2H).
Analytical Data:
Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:
Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.
Analysis Condition B:
Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.
Analysis Condition C:
Column: Waters Aquity BEH C18 2.1×50 mm 1.7 Lm particles; Mobile Phase A: water with 0.05% TFA; Mobile Phase B: acetonitrile with 0.05% TFA; Temperature: 40° C.; Gradient: 0% B, 0-100% B over 3 minutes, then a 0.5-minute hold at 100% B; Flow: 0.8 mL/min; Detection: UV at 220 nm.
Analysis Condition D:
Column: Waters Aquity BEH C18 2.1×50 mm 1.7 Lm particles; Mobile Phase A: water with 0.05% TFA; Mobile Phase B: methanol with 0.05% TFA; Temperature: 40° C.; Gradient: 0% B, 0-100% B over 3 minutes, then a 0.5-minute hold at 100% B; Flow: 0.8 mL/min; Detection: UV at 220 nm.
General Procedures.
Prelude Method A:
All manipulations were performed under automation on a Prelude peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; Rink=(2,4-dimethoxyphenyl)(4-alkoxyphenyl)methanamine, where "4-alkoxy" describes the position and type of connectivity to the polystyrene resin. Unless noted otherwise, the resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "Prelude Method A" describe an experiment performed on a 0.100 mmol scale, where the scale is determined by the amount of Rink linker bound to the resin. This scale corresponds to approximately 178 mg of the Rink-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

The resin was washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added DIPEA (0.8M in DMF, 3.0 mL, 24 eq), then chloroacetyl chloride (0.8M in DMF, 1.65 mL, 13.2 eq). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, CH$_2$Cl$_2$ (2.0 mL) was added to top of the vessel and the resulting mixture was periodically agitated for 90 seconds before the solution was drained through the frit. The resulting resin was placed under a N$_2$ stream for 15 minutes.

Symphony Method A:

This collection of procedures is identical that of "Prelude Method A" except as noted. For all procedures a Symphony X peptide synthesizer (Protein Technologies) was used instead of a Prelude peptide synthesizer and all reagents were added through the top of the reaction vessel.

Resin-Swelling Procedure:

This procedure is identical to "Prelude Method A: Resin-swelling procedure".

Single-Coupling Procedure:

This procedure is identical to "Prelude Method A: Single-coupling procedure" except that the concentration of DIPEA solution was 0.4M and 1.0 mL of this solution was delivered to the reaction.

Double-Coupling Procedure:

This procedure is identical to "Prelude Method A: Double-coupling procedure" except that the concentration of DIPEA solution was 0.4M and 1.0 mL of this solution was delivered to the reaction.

Chloroacetyl Chloride Coupling Procedure:

This procedure is identical to "Prelude Method A: Chloroacetyl chloride coupling procedure".

Global Deprotection Method A:

All manipulations were performed manually unless noted. The procedure of "Global Deprotection Method A" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 1-2 h). The mixture was filtered through a 0.2 micron syringe filter and the solids were extracted with the "deprotection solution" (1.0 mL) or TFA (1.0 mL). To a 24 mL test tube charged with the combined filtrates was added Et$_2$O (15 mL). The mixture was vigorously mixed upon which a significant amount of a white solid precipitated. The mixture was centrifuged for 5 minutes, then the solution was decanted away from the solids and discarded. The solids were suspended in Et$_2$O (20 mL); then the mixture was centrifuged for 5 minutes; and the solution was decanted away from the solids and discarded. For a final time, the solids were suspended in Et$_2$O (20 mL); the mixture was centrifuged for 5 minutes; and the solution was decanted away from the solids and discarded to afford the crude peptide as a white to off-white solid.

Cyclization Method A:

All manipulations were performed manually unless noted. The procedure of "Cyclization Method A" describes an experiment performed on a 0.100 mmol scale, where the scale is determined by the amount of Rink linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in MeCN:aq. 0.1M NH$_4$OAc (1:1) to a total volume of 18-22 mL, and the solution was carefully then adjusted to pH=8.5-9.0 using aq NaOH (1.0M). The solution was then allowed to stand without stirring for 12-18 h. The reaction solution was concentrated and the residue was then dissolved in DMSO:MeOH. This solution was subjected to reverse-phase HPLC purification to afford the desired cyclic peptide.

General Synthetic Sequence A:

"General Synthetic Sequence A" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added "Biotin Resin" (see below) (161 mg, 0.050 mmol), and the reaction vessel was placed on the Prelude peptide synthesizer. For the following procedures, the same amounts of reagents described above for a 0.100 mmol scale were used, although in this general synthetic sequence the amount of resin used corresponds to a 0.050 mmol scale. "Prelude Method A: Resin-swelling procedure" was followed. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine. "Prelude Method A: Chloroacetyl chloride coupling procedure" was followed; then "Global Deprotection Method A" was followed; then "Cyclization Method A" was followed.

"Biotin Resin"

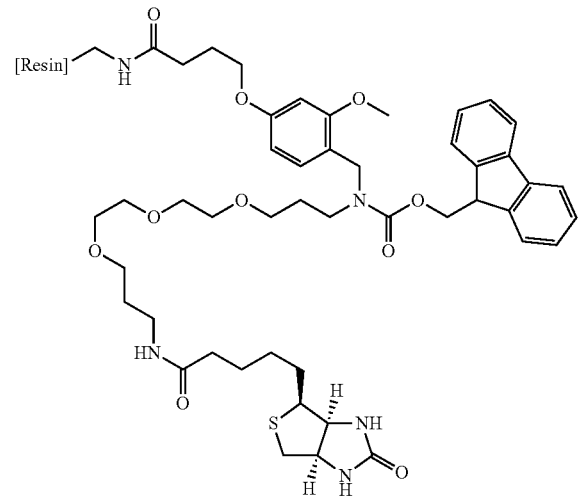

Resin = 0.31 mmol/g loading
1% DVB, 100-200 mesh
Linker = Rink with Biotin-PEG
CAS 1194054-19-7
8550550001 from Novabiochem General Synthetic Sequence B:

"General Synthetic Sequence B" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added Rink-Merrifield resin (178 mg, 0.100 mmol), and the reaction vessel was placed on the Prelude peptide synthesizer. "Prelude Method A: Resin-swelling procedure" was followed. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine. "Prelude Method A: Chloroacetyl chloride coupling procedure" was followed; then "Global Deprotection Method A" was followed; then "Cyclization Method A" was followed.

Preparation of (S)-2-((((9H-fluoren-9-yl)methoxy) carbonyl)(methyl)amino)-3-ethoxypropanoic acid

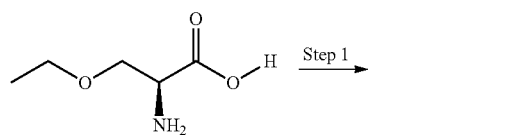

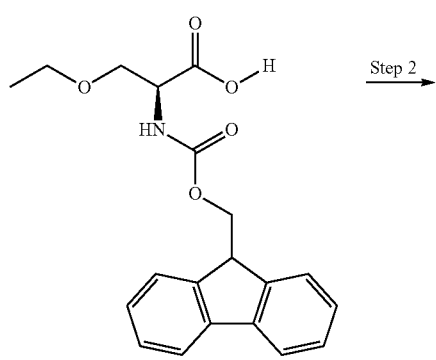

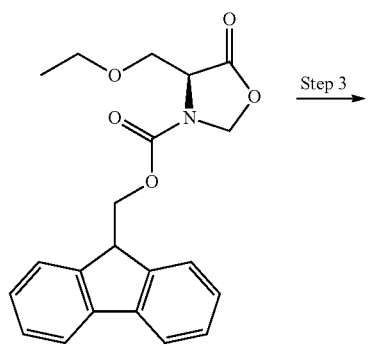

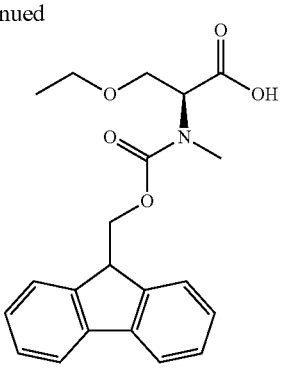

Step 1

To a solution of (S)-2-amino-3-ethoxypropanoic acid (1.5 g, 11.3 mmol) in THF (38 ml) and water (19 ml) was added sodium bicarbonate (2.37 g, 28.2 mmol) and Fmoc-OSu (3.80 g, 11.3 mmol). The resulting mixture was stirred for 16 h. After removal of THF, the residue was acidified with 1 N HCl, extracted with ethyl acetate, dried over $Na_2SO_4$, then concentrated to afford (S)-2-((((9H-fluoren-9-yl)methoxy) carbonyl)amino)-3-ethoxypropanoic acid as a white solid, 3.6 g (90%).

Step 2

A mixture containing paraformaldehyde (1.825 g, 60.8 mmol), (S)-2-((((9H-fluoren-9-yl)methoxy)carbonyl) amino)-3-ethoxypropanoic acid (3.6 g, 10.1 mmol), and p-toluenesulfonic acid (0.174 g, 1.01 mmol) in toluene (100 mL) was refluxed with Dean-Stark azeotropic removal of water for 2 h. The reaction was then cooled to RT, washed with aq. sat. sodium bicarbonate solution, followed by brine, dried over $MgSO_4$, then filtered and concentrated in vacuo to afford (S)-(9H-fluoren-9-yl)methyl 4-(ethoxymethyl)-5-oxooxazolidine-3-carboxylate as a yellow oil, 5.16 g.

Step 3

(S)-(9H-fluoren-9-yl)methyl 4-(2-methoxyethyl)-5-oxooxazolidine-3-carboxylate (0.4 g, 1.089 mmol) was dissolved in $CHCl_3$ (50 mL) and to the solution was added triethylsilane (0.869 mL, 5.44 mmol) followed by TFA (0.923 mL, 12.0 mmol). The solution was stirred at RT under positive pressure of $N_2$ for 18 h. The solution was then concentrated to afford an oil residue. The residue was dissolved in EtOAc and then extracted with aq. sat. sodium bicarbonate (2×100 mL). The aqueous phase and all solids suspended at the phase interface were collected. This mixture was acidified to pH 4-5 using aq. HCl, upon which a precipitate formed. The mixture was extracted with EtOAc (200 mL). The organic phase was washed with brine, dried over $MgSO_4$, filtered and concentrated in vacuo to afford (S)-2-((((9H-fluoren-9-yl)methoxy)carbonyl)(methyl) amino)-4-methoxybutanoic acid as a white solid, 0.35 g (87%) yield).

Preparation of Example 5001

Example 5001

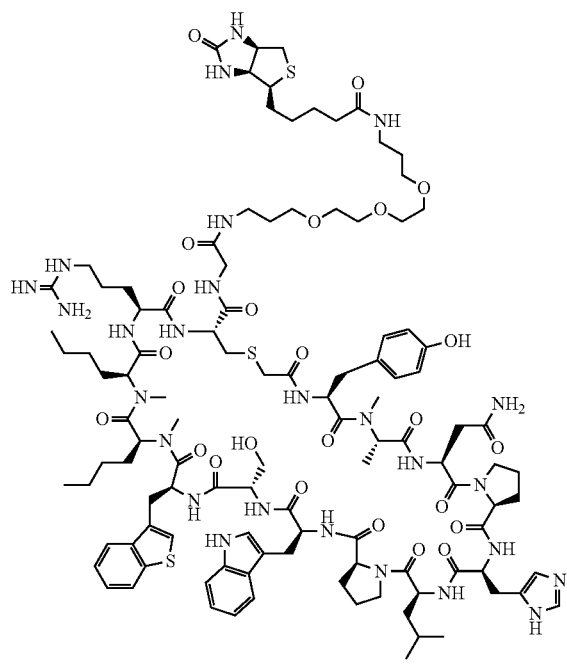

Example 5001 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 100%. Analysis condition A: Retention time=1.68 min; ESI-MS(+) m/z 1171.8 (M+2H); Analysis condition B: Retention time=2.83 min; ESI-MS(+) m/z 1171.7 (M+2H); ESI-HRMS(+) m/z: Calculated: 1170.5781. Found: 1170.5776.

Preparation of Example 5002

Example 5002

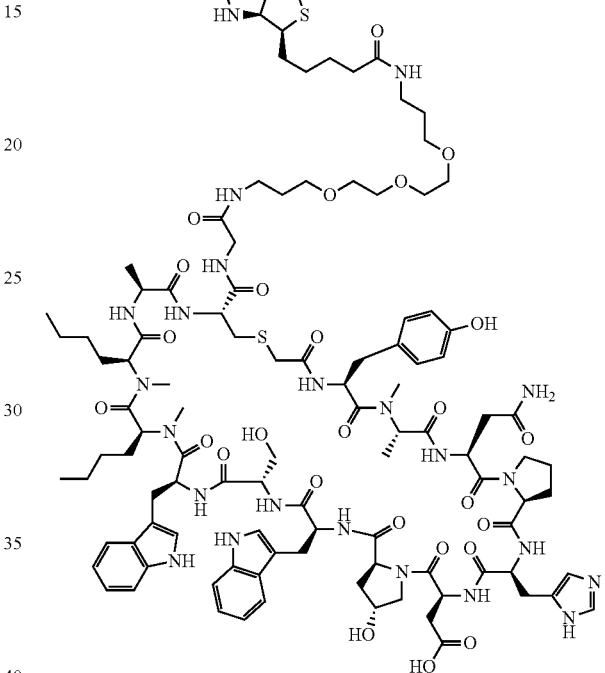

Example 5002 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 100%. Analysis condition A: Retention time=1.42 min; ESI-MS(+) m/z 1128.8 (M+2H); Analysis condition B: Retention time=2.57 min; ESI-MS(−) m/z 1126.8 (M−2H); ESI-HRMS(+) m/z: Calculated: 1128.5345 Found: 1128.5349.

Preparation of Example 5003

Preparation of Example 5004

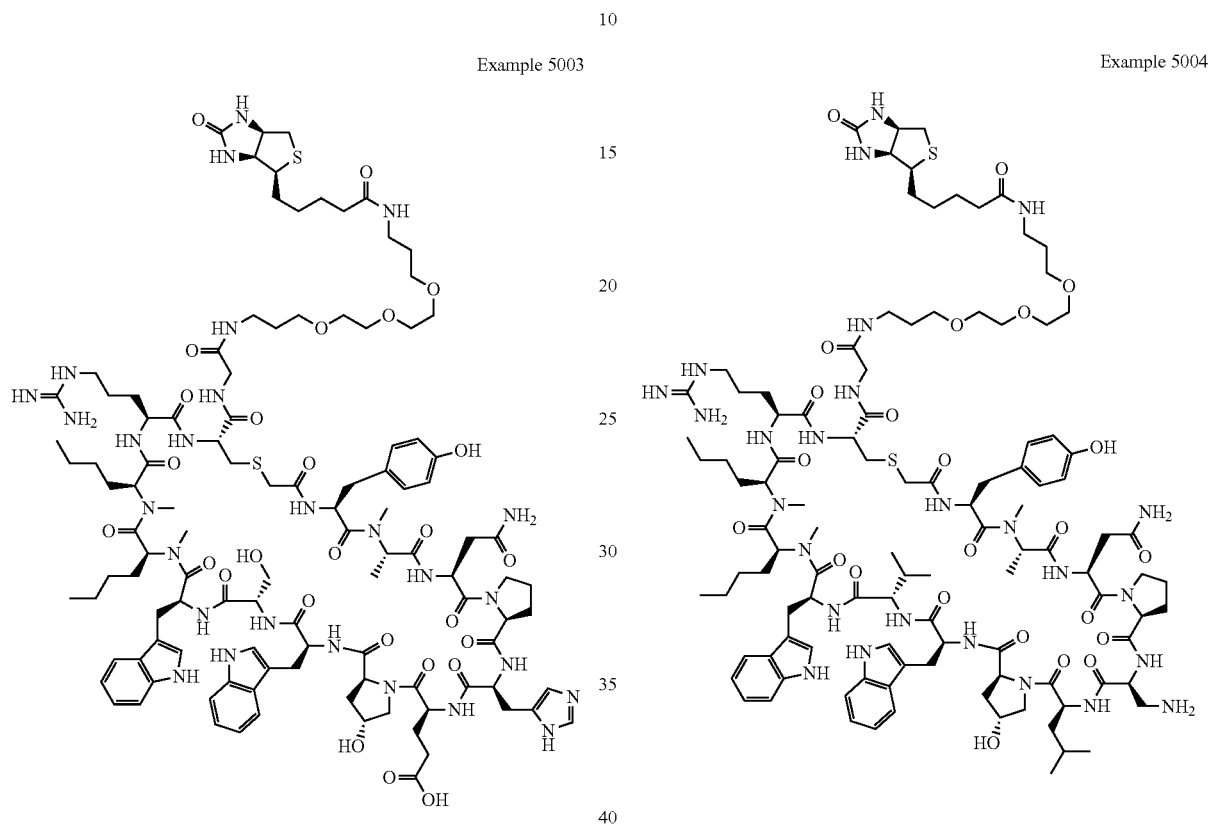

Example 5003

Example 5004

Example 5003 was prepared following "General Synthetic Sequence A". The crude material was purified via preparative LC/MS with the following conditions: Column: waters xbridge c-18, 19×200 mm, 5-µm particles; Mobile Phase A: 5:95 methanol: water with 0.1% trifluoroacetic acid; Mobile Phase B: 95:5 methanol: water with 0.1% trifluoroacetic acid; Gradient: 30-70% B over 30 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 99%. Analysis condition A: Retention time=1.44 min; ESI-MS(+) m/z 1172.4 (M+2H); Analysis condition B: Retention time=2.55 min; ESI-MS(+) m/z 1172.3 (M+2H); ESI-HRMS(+) m/z: Calculated: 1171.0847. Found: 1171.0862.

Example 5004 was prepared following "General Synthetic Sequence A". The crude material was purified via preparative LC/MS with the following conditions: Column: waters xbridge c-18, 19×200 mm, 5-µm particles; Mobile Phase A: 5:95 methanol: water with 0.1% trifluoroacetic acid; Mobile Phase B: 95:5 methanol: water with 0.1% trifluoroacetic acid; Gradient: 30-70% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 96%. Analysis condition A: Retention time=1.52 min; ESI-MS(+) m/z 1151.2 (M+2H); Analysis condition B: Retention time=2.61 min; ESI-MS(+) m/z 1151.3 (M+2H); ESI-HRMS(+) m/z: Calculated: 1150.6078. Found: 1150.6096.

Preparation of Example 5006

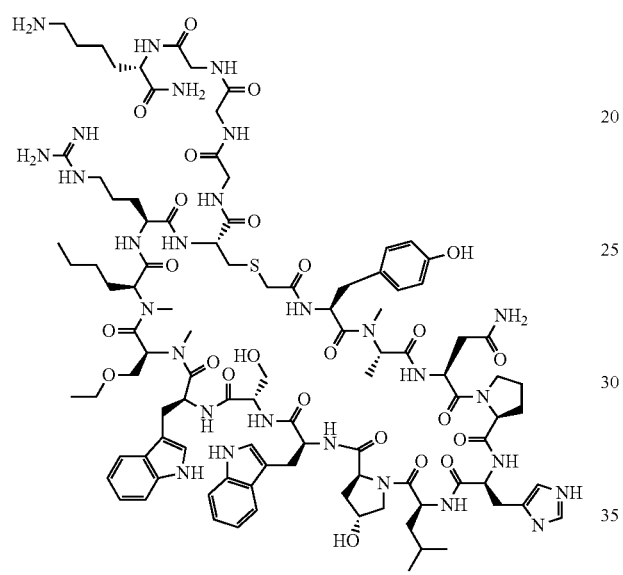

Example 5006

Preparation of Example 5007

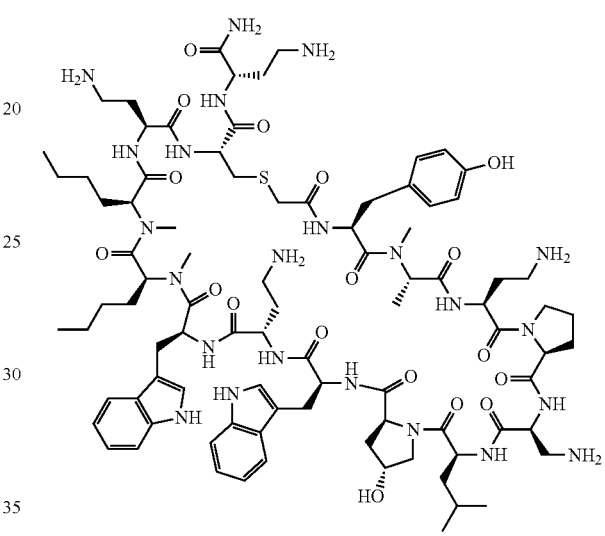

Example 5007

Example 5006 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 26.3 mg, and its estimated purity by LCMS analysis was 99%. Analysis condition A: Retention time=1.32 min; ESI-MS(+) m/z 1078.3 (M+2H); Analysis condition B: Retention time=2.42 min; ESI-MS(+) m/z 1078.2 (M+2H); ESI-HRMS(+) m/z: Calculated: 1077.5387 Found: 1077.5396.

Example 5007 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 36.9 mg, and its estimated purity by LCMS analysis was 100%; Analysis condition A: Retention time=1.10 min; ESI-MS(+) m/z 923.7 (M+2H); Analysis condition B: Retention time=2.29 min; ESI-MS(+) m/z 923.7 (M+2H).

Preparation of Example 5008

Example 5008

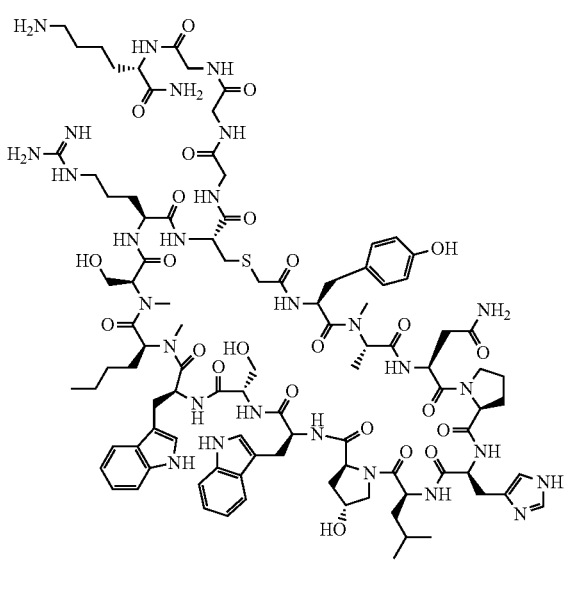

Example 5008 was prepared following "General Synthetic Sequence B" on a 0.600 mmol scale. The crude material was purified via preparative LC/MS with the following conditions: Column: waters xbridge c-18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol: water with 0.1% trifluoroacetic acid; Mobile Phase B: 95:5 methanol: water with 0.1% trifluoroacetic acid; Gradient: 25-70% B over 30 minutes, then a 5-minute hold at 100% B; Flow: 20 mL/min. Fractions containing the desired product were combined and dried via centrifugal evaporation. The yield of the product was 49.9 mg, and its estimated purity by LCMS analysis was 99%; Analysis condition A: Retention time=1.15 min; ESI-MS(+) m/z 1064.9 (M+2H); Analysis condition B: Retention time=2.19 min; ESI-MS(+) m/z 1064.2 (M+2H); ESI-HRMS(+) m/z: Calculated: 1063.5231. Found: 1063.5222.

Preparation of Example 5009

Example 5009

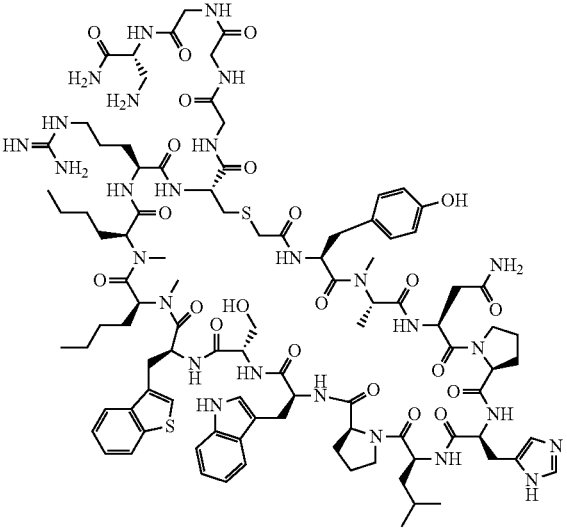

Example 5009 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 9.0 mg, and its estimated purity by LCMS analysis was 99%; Analysis condition A: Retention time=1.60 min; ESI-MS(+) m/z 1057.4 (M+2H); Analysis condition B: Retention time=2.81 min; ESI-MS(+) m/z 1056.6 (M+2H); ESI-HRMS(+) m/z: Calculated: 1056.0087. Found: 1056.0069.

Preparation of Example 5010

Example 5010

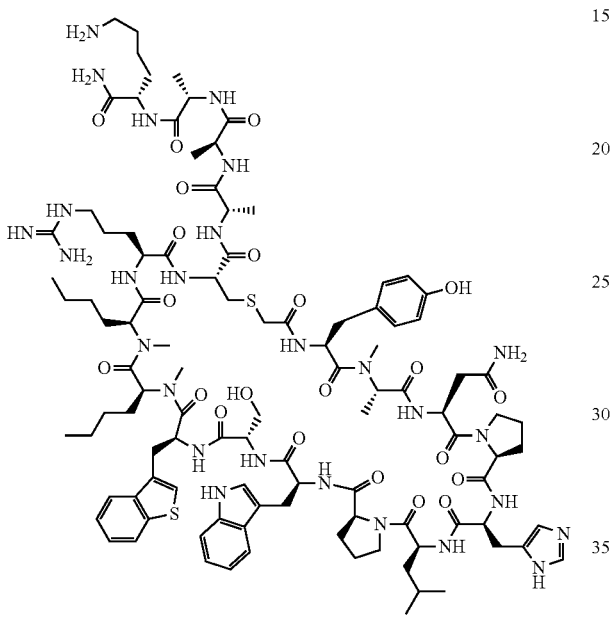

Example 5010 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 96%; Analysis condition A: Retention time=1.58 min; ESI-MS(+) m/z 1098.7 (M+2H); Analysis condition B: Retention time=2.76 min; ESI-MS(−) m/z 1096.6 (M−2H); ESI-HRMS(+) m/z: Calculated: 1098.0557. Found: 1098.0554.

Preparation of Example 5011

Example 5011

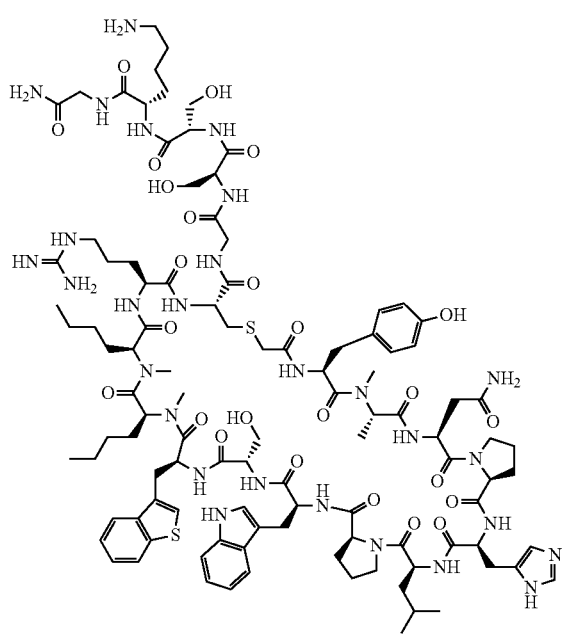

Example 5011 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 25.8 mg, and its estimated purity by LCMS analysis was 100%. Analysis condition A: Retention time=1.58 min; ESI-MS(+) m/z 1136.7 (M+2H); Analysis condition B: Retention time=2.75 min; ESI-MS(−) m/z 1134.3 (M−2H); ESI-HRMS(+) m/z: Calculated: 1135.5535. Found: 1135.5528.

Preparation of Example 5012

Example 5012

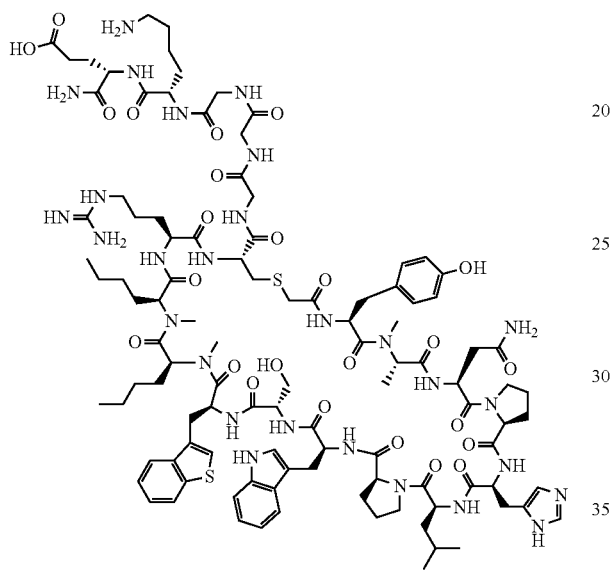

Example 5012 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-95% B over 30 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 100%; Analysis condition A: Retention time=1.59 min; ESI-MS(−) m/z 1140.3 (M−2H); Analysis condition B: Retention time=2.81 min; ESI-MS(+) m/z 1142.4 (M+2H; ESI-HRMS (+) m/z: Calculated: 1141.5535 Found: 1141.5539.

Preparation of Example 5013

Example 5013

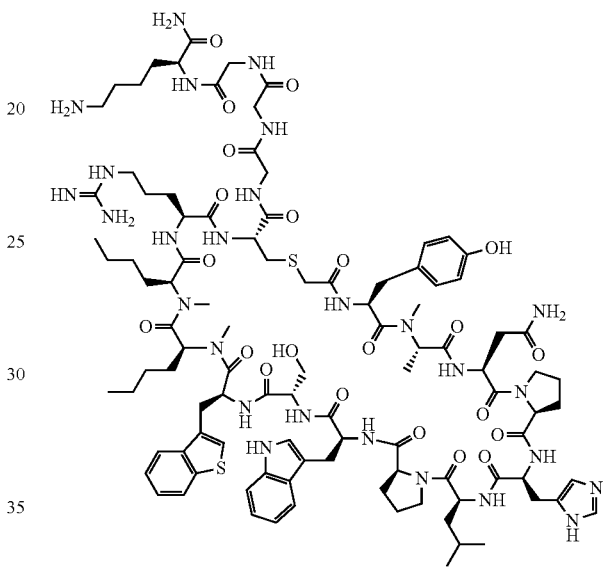

Example 5013 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 100%; Analysis condition A: Retention time=1.57 min; ESI-MS(−) m/z 1075.8 (M−2H; Analysis condition B: Retention time=2.75 min; ESI-MS(+) m/z 1077.8 (M+2H); ESI-HRMS(+) m/z: Calculated: 1077.0322 Found: 1077.0330.

Preparation of Example 5014

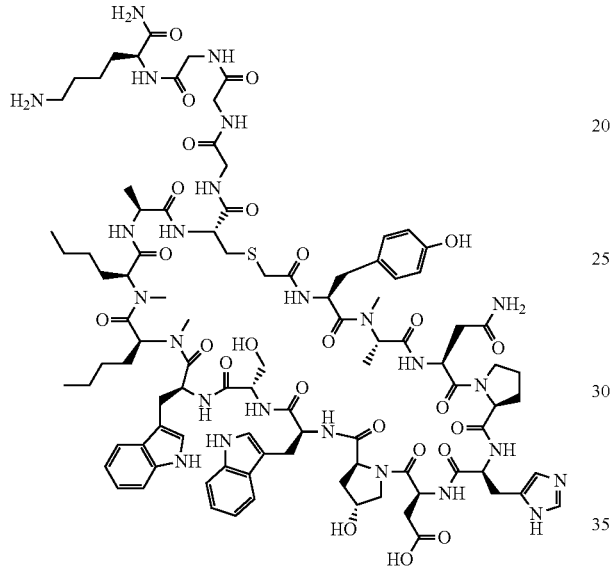

Example 5014

Example 5014 was prepared following "General Synthetic Sequence B". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 100%; Analysis condition A: Retention time=1.36 min; ESI-MS(+) m/z 1035.8 (M+2H); Analysis condition B: Retention time=2.52 min; ESI-MS(−) m/z 1033.7 (M−2H); ESI-HRMS(+) m/z: Calculated: 1034.9885. Found: 1034.9887.

Preparation of Example 5015

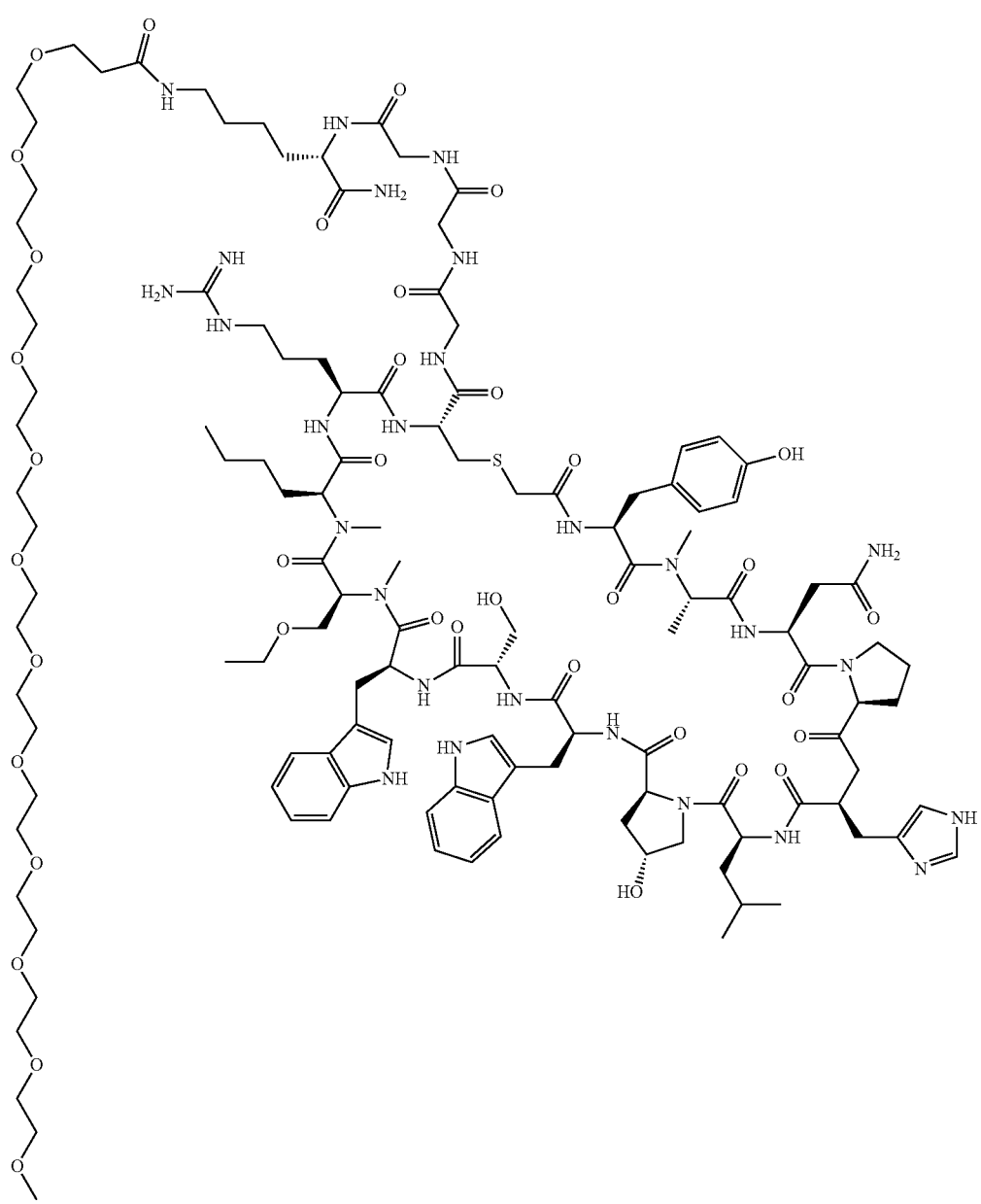

Example 5015

Example 5015 was prepared as follows: To a 1 dram vial charged with Example 5006 (5.8 mg, 2.7 μmol) was added dry NMP. The mixture was agitated until a homogeneous solution formed. To the solution was added DIPEA (0.025 mL, 0.143 mmol), then 2,5-dioxopyrrolidin-1-yl 2,5,8,11,14,17,20,23,26,29,32,35-dodecaoxaoctatriacontan-38-oate (3.5 mg, 5.1 μmol). The vial was placed on a shaker rotating at 500 rpm for 30 minutes. The reaction was quenced via the addition of ethanolamine (0.020 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 99%. Analysis condition A: Retention time=1.52 min; ESI-MS(−) m/z 1361.4 (M−2H); Analysis condition B: Retention time=2.61 min; ESI-MS(−) m/z 1361.7 (M−2H).

Preparation of Example 5016

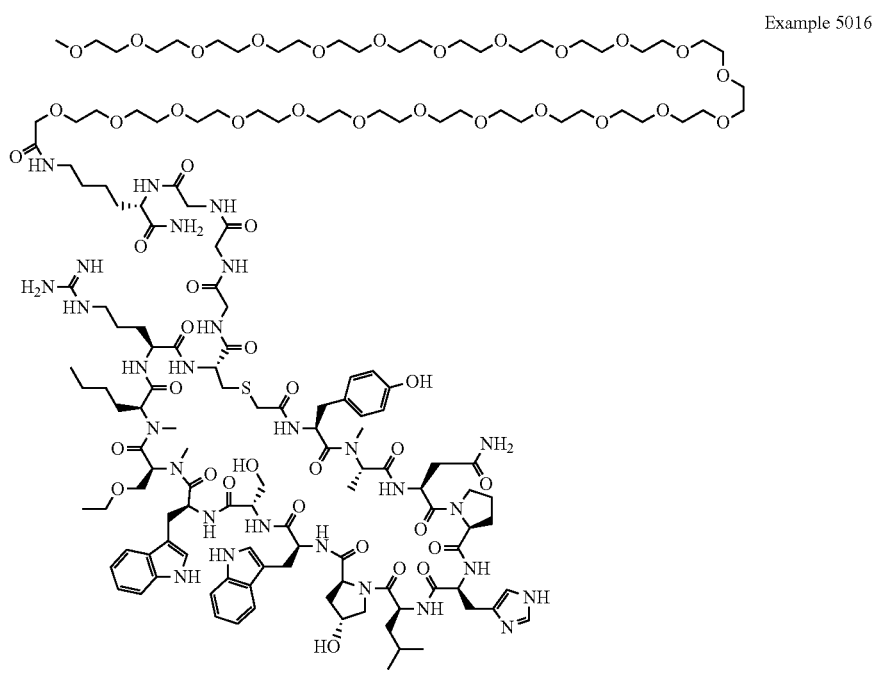 [SMILES: CCCC[C@H]1C(=O)N[C@@H](CCCNC(=N)N)C(=O)N[C@H](C(=O)NCC(=O)NCC(=O)NCC(=O)N[C@@H](CCCCNC(=O)COCCOCCOCCOCCOCCOCCOCCOCCOCCOCCOCCOCCOCCOCCOCCOCCOCCOCCOCCOCCOCCOCCOCCOC)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](COCC)C(=O)N1C]
Example 5016

Example 5016 was prepared as follows: To a 1 dram vial charged with Example 5006 (5.8 mg, 2.7 μmol) was added dry NMP. The mixture was agitated until a homogeneous solution formed. To the solution was added DIPEA (0.025 mL, 0.143 mmol), then 2,5-dioxopyrrolidin-1-yl 2,5,8,11,14,17,20,23,26,29,32,35,38,41,44,47,50,53,56,59,62,65,68,71-tetracosaoxatetraheptacontan-74-oate (3.27 mg, 2.69 μmol). The vial was placed on a shaker rotating at 500 rpm for 40 minutes. The reaction was quenced via the addition of ethanolamine (0.020 mL). The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 100%. Analysis condition A: Retention time=1.55 min; ESI-MS(−) m/z 1625.4 (M−2H); Analysis condition B: Retention time=2.67 min; ESI-MS(−) m/z 1625.7 (M−2H).

Preparation of Example 5017

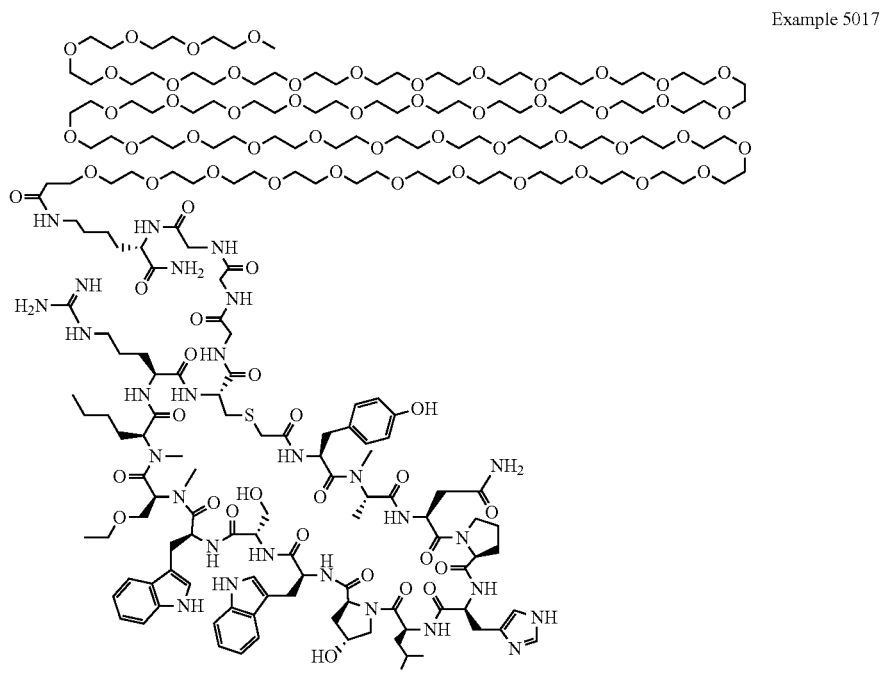

Example 5017

Example 5017 was prepared as follows: To a 1 dram vial charged with Example 5006 (5.8 mg, 2.7 µmol) was added dry NMP. The mixture was agitated until a homogeneous solution formed. To the solution was added DIPEA (0.025 mL, 0.143 mmol), then 2,5-dioxopyrrolidin-1-yl 2,5,8,11,14,17,20,23,26,29,32,35,38,41,44,47,50,53,56,59,62,65,68,71,74,77,80,83,86,89,92,95,98,101,104,107,110,113,116,119,122,125,128,131,134,137,140,143,146-nonatetracontaoxanonatetracontahectan-149-oate (6.2 mg, 2.7 µmol). The vial was placed a shaker rotating at 500 rpm for 30 minutes. The reaction was quenced via the addition of ethanolamine (0.020 mL). The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate;

Gradient: 50-90% B over 30 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 100%; Analysis condition A: Retention time=1.63 min; ESI-MS(+) m/z 882.5 (M+5H; Analysis condition B: Retention time=2.74 min; ESI-MS(+) m/z 882.6 (M+5H).

Preparation of Example 5018

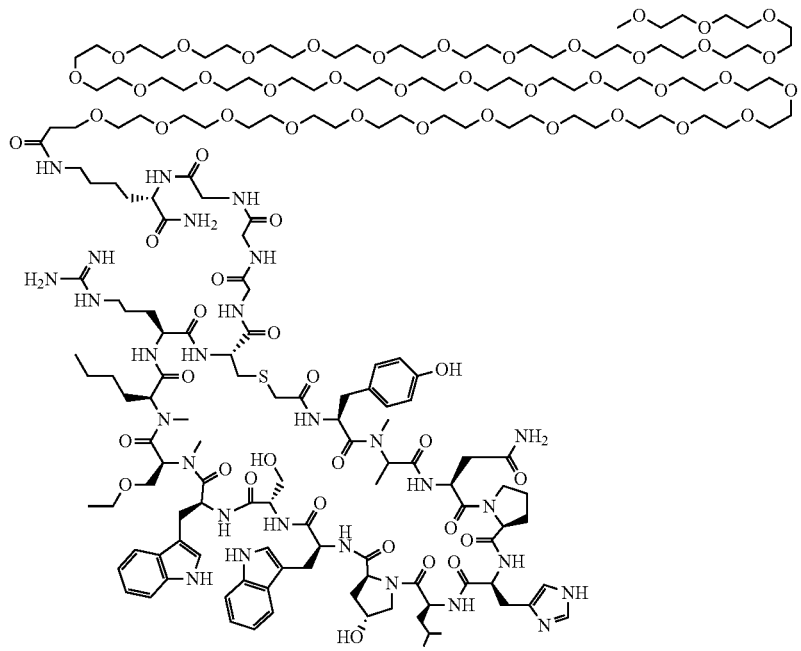

Example 5018

Example 5018 was prepared as follows: To a 1 dram vial charged with Example 5006 (5.8 mg, 2.7 μmol) was added dry NMP. The mixture was agitated until a homogeneous solution formed. To the solution was added DIPEA (0.025 mL, 0.143 mmol), then 2,5-dioxopyrrolidin-1-yl 2,5,8,11,14,17,20,23,26,29,32,35,38,41,44,47,50,53,56,59,62,65,68,71,74,77,80,83,86,89,92,95,98,101,104,107,110-heptatriacontaoxatridecahectan-113-oate (4.8 mg, 2.7 mol). The vial was placed a shaker rotating at 500 rpm for 40 minutes. The reaction was quenced via the addition of ethanolamine (0.020 mL). The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%; Analysis condition A: Retention time=1.63 min; ESI-MS(−) m/z 1914.0 (M−2H); Analysis condition B: Retention time=2.70 min; ESI-MS(−) m/z 1912.7 (M−2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

General Procedures.

Peptide Synthesis

The macrocyclic peptides of the present disclosure can be produced by methods known in the art, such as they can be synthesized chemically, recombinantly in a cell free system, recombinantly within a cell or can be isolated from a biological source. Chemical synthesis of a macrocyclic peptide of the present disclosure can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., Fmoc Solid Phase Synthesis, Oxford University Press, Oxford (2000); Barany, G. et al., The Peptides: Analysis, Synthesis, Biology, Vol. 2: "Special Methods in Peptide Synthesis, Part A", pp. 3-284, Gross, E. et al., eds., Academic Press, New York (1980); and in Stewart, J. M. et al., Solid-Phase Peptide Synthesis, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in The Peptides: Analysis, Synthesis, Biology, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

Useful Fmoc amino acids derivatives are shown below.

Examples of Orthogonally Protected Amino Acids used in Solid Phase Synthesis

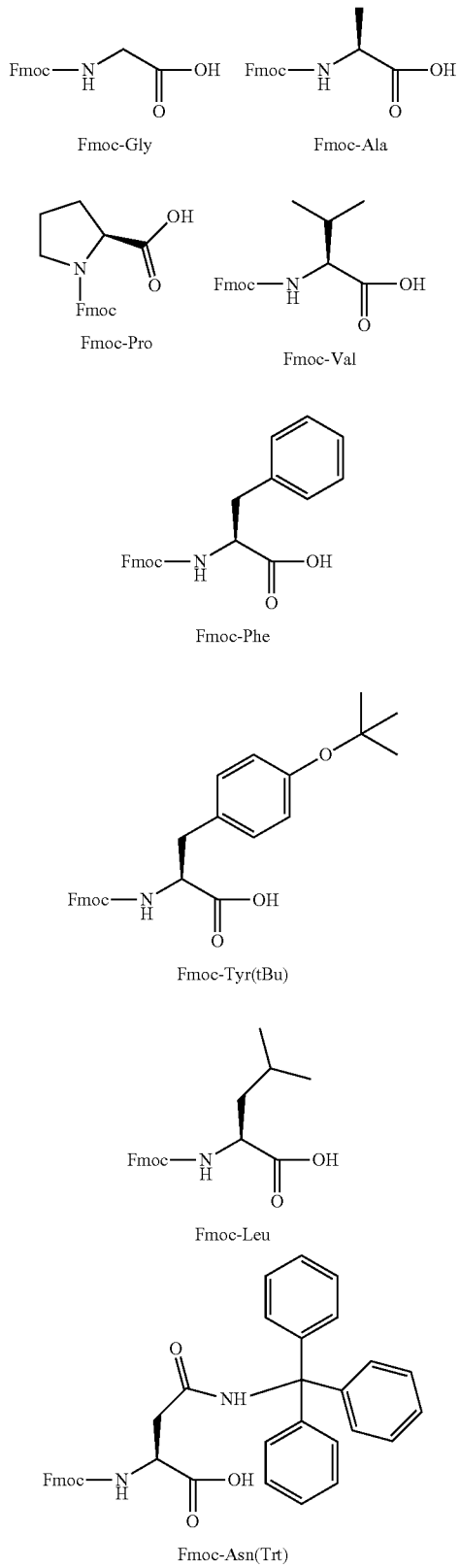

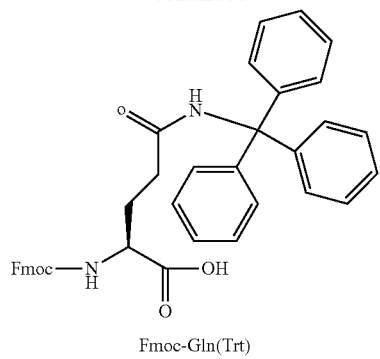
Fmoc-Gln(Trt)
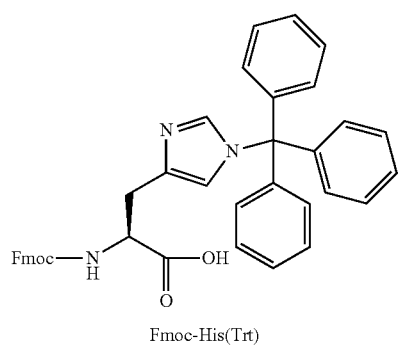
Fmoc-His(Trt)
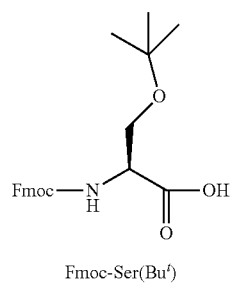
Fmoc-Ser(Bu$^t$)
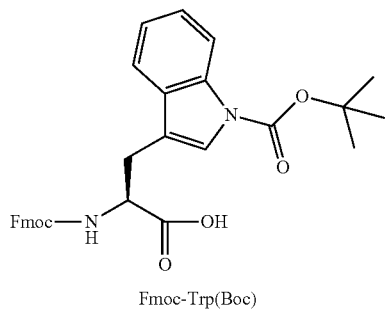
Fmoc-Trp(Boc)
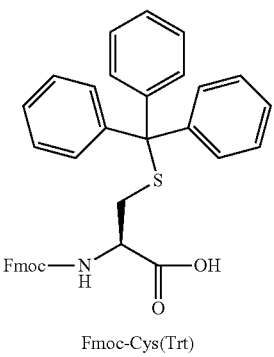
Fmoc-Cys(Trt)
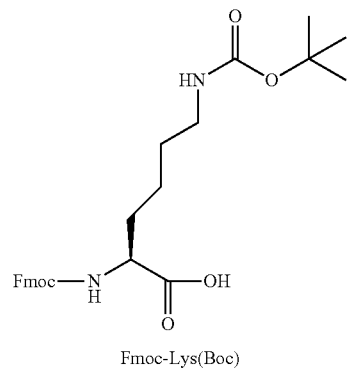
Fmoc-Lys(Boc)
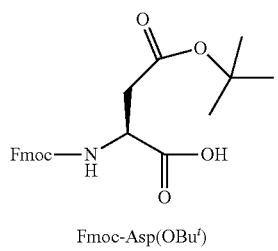
Fmoc-Asp(OBu$^t$)
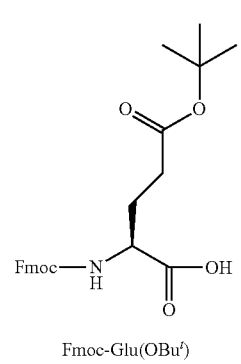
Fmoc-Glu(OBu$^t$)
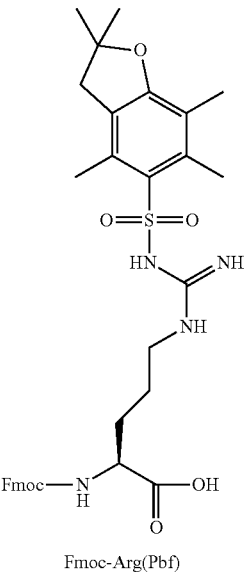
Fmoc-Arg(Pbf)

-continued

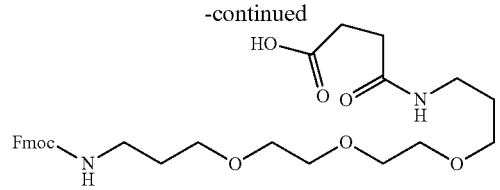
Fmoc-PEGsu

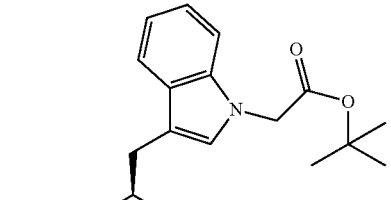
Fmoc-ATrp(Boc)

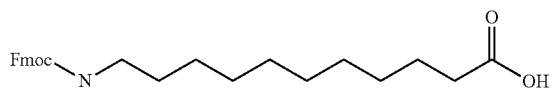
Fmoc-FAc11

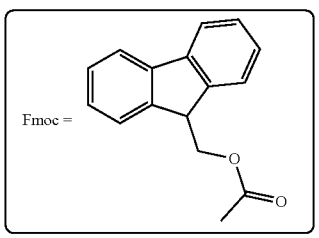
Fmoc =

The peptidyl-resin precursors for their respective peptides may be cleaved and deprotected using any standard procedure (see, for example, King, D. S. et al., Int. J. Peptide Protein Res., 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with Et$_2$O or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

List of non-naturally occurring amino acids referred to herein is provided below.

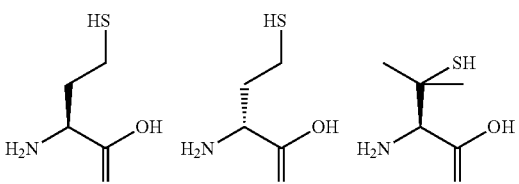
L-Homo-Cys    D-Homo-Cys    L-Pen

D-Pen    2-Nal

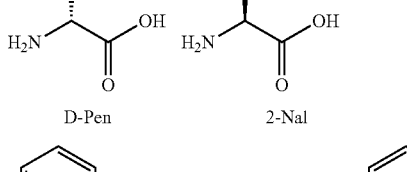
1-Nal    Bip

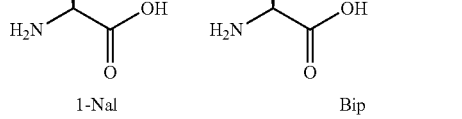
Tic    Phe(4-OMe)

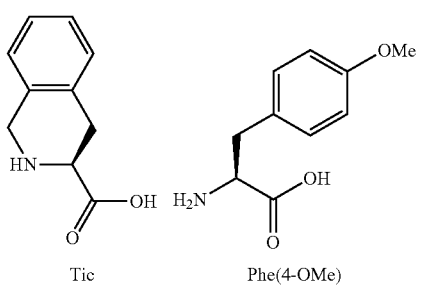
Phe(4-Me)    Azt

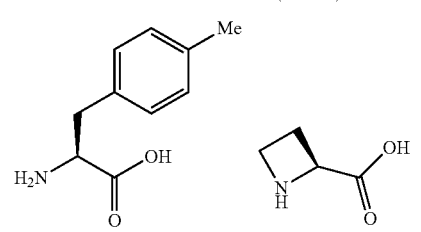
Pip    Phe(4-F)

113
-continued
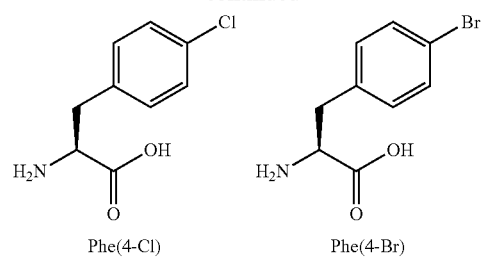
Phe(4-Cl)    Phe(4-Br)
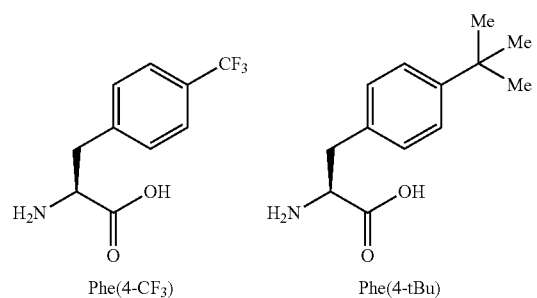
Phe(4-CF3)    Phe(4-tBu)
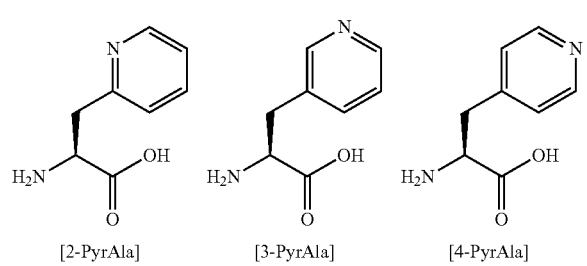
[2-PyrAla]    [3-PyrAla]    [4-PyrAla]
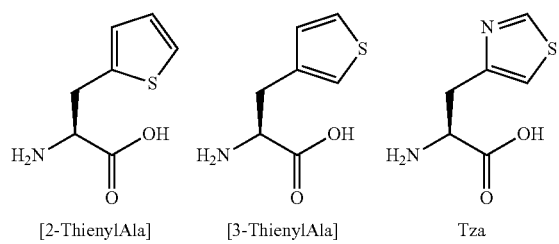
[2-ThienylAla]    [3-ThienylAla]    Tza
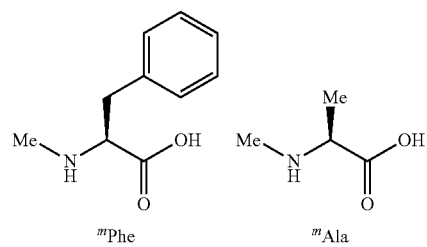
$^m$Phe    $^m$Ala
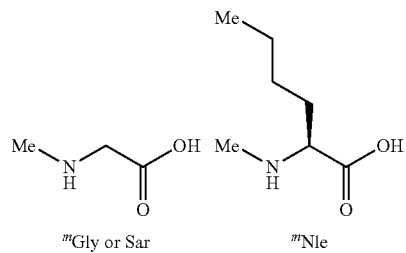
$^m$Gly or Sar    $^m$Nle
114
-continued
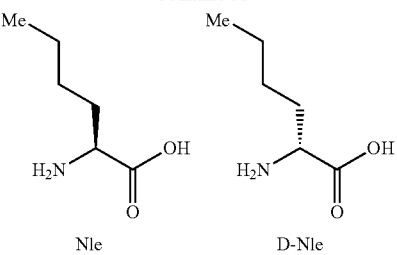
Nle    D-Nle
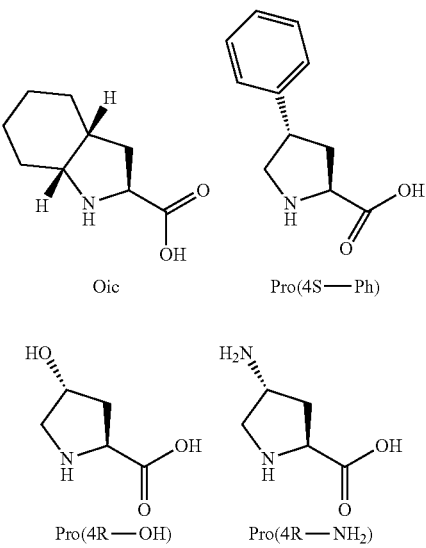
Oic    Pro(4S—Ph)
Pro(4R—OH)    Pro(4R—NH2)
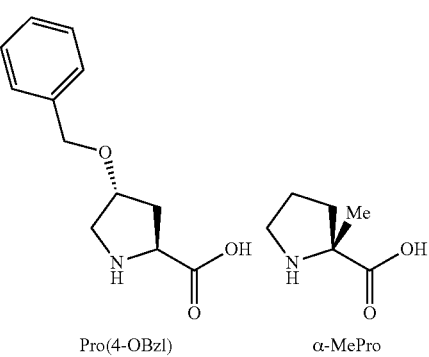
Pro(4-OBzl)    α-MePro
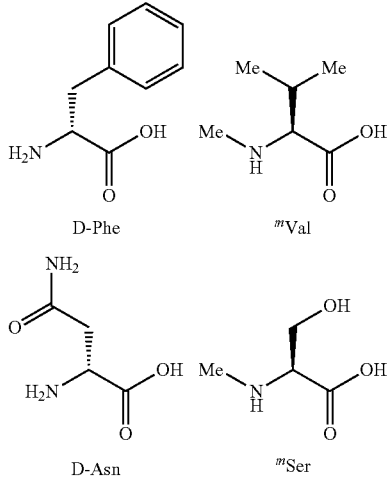
D-Phe    $^m$Val
D-Asn    $^m$Ser -continued

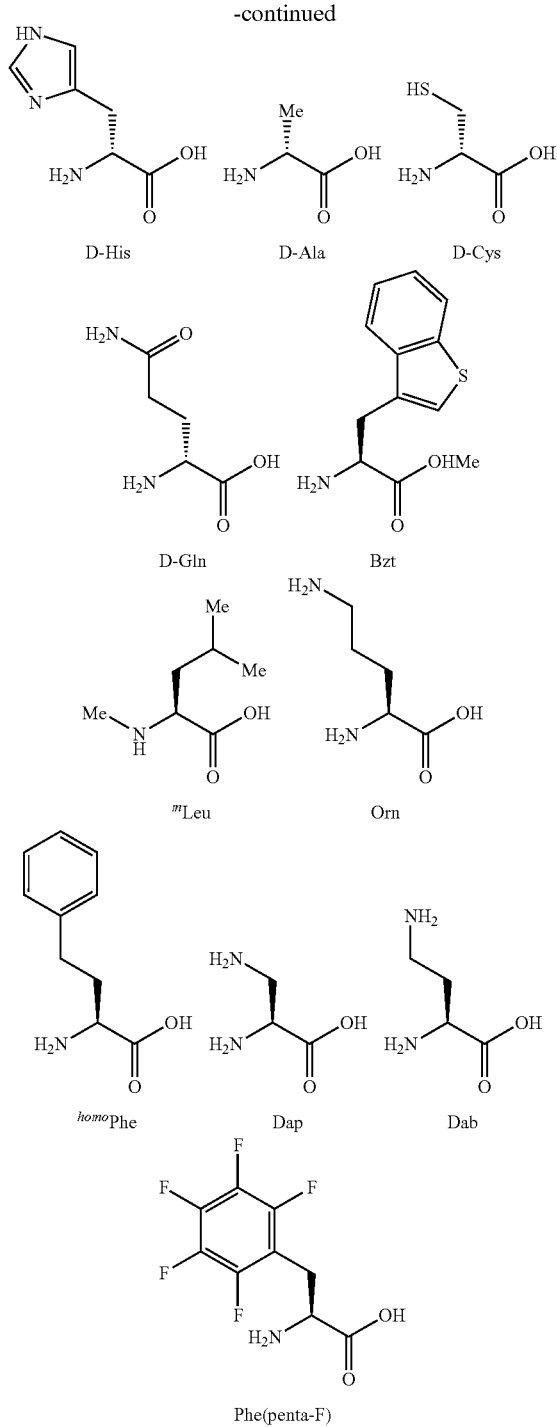

The following abbreviations are employed in the Examples and elsewhere herein:
Ph=phenyl
Bn=benzyl
i-Bu=iso-butyl
i-Pr=iso-propyl
Me=methyl
Et=ethyl
Pr=n-propyl
Bu=n-butyl
t-Bu=tert-butyl
Trt=trityl
TMS=trimethylsilyl
TIS=triisopropylsilane
Et$_2$O=diethyl ether
HOAc or AcOH=acetic acid
MeCN or AcCN=acetonitrile
DMF=N,N-dimethylformamide
EtOAc=ethyl acetate
THF=tetrahydrofuran
TFA=trifluoroacetic acid
TFE=α,α,α-trifluoroethanol
Et$_2$NH=diethylamine
NMM=N-methylmorpholine
NMP=N-methylpyrrolidone
DCM=dichloromethane
TEA=triethylamine
min.=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
BOP reagent=benzotriazol-1-yloxy-tris-dimethylamino-phosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyl-uronim hexafluorophosphate
HATU=O-(7-Azabenzotriazol-1-yl)-1,1,3,3-tetramethyl-uronim hexafluorophosphate
HCTU=2-(6-Chloro-1-H-benzotriazol-1-yl)-1,1,3,3-tetramethyluronium hexafluorophosphate
T3P=2,4,6-tripropyl-1,3,5,2,4,6-trioxatriphosphorinane-2,4,6-trioxide
DMAP=4-(dimethylamino)pyridine
DIEA=diisopropylethylamine
Fmoc or FMOC=fluorenylmethyloxycarbonyl
Boc or BOC=tert-butyloxycarbonyl
HOBT or HOBT.H$_2$O=1-hydroxybenzotriazole hydrate
Cl-HOBt=6-Chloro-benzotriazole
HOAT=1-hydroxy-7-azabenzotriazole
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal

EXAMPLES

Example 0001—Solid Phase Peptide Synthesis and Cyclization of Peptides

The procedures described in this example, either in whole or in part where noted, were used to synthesize the macrocyclic peptides shown in Tables 1, 2, 3, 4 and 5.

SCHEME 1 - COMMON SYNTHETIC METHOD USED FOR THIOETHER-CYCLIZED PEPTIDES
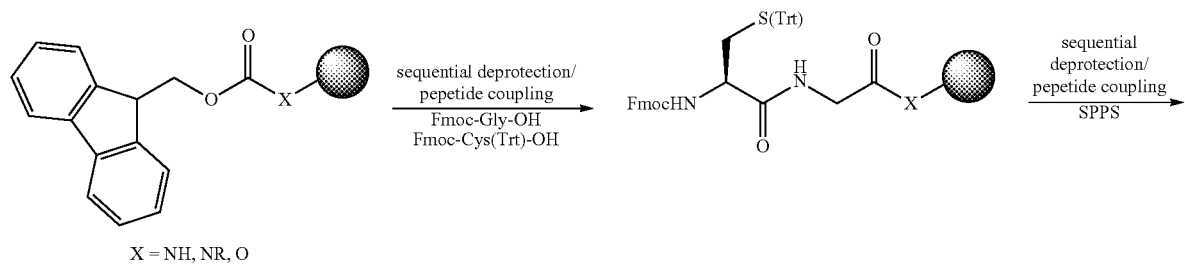
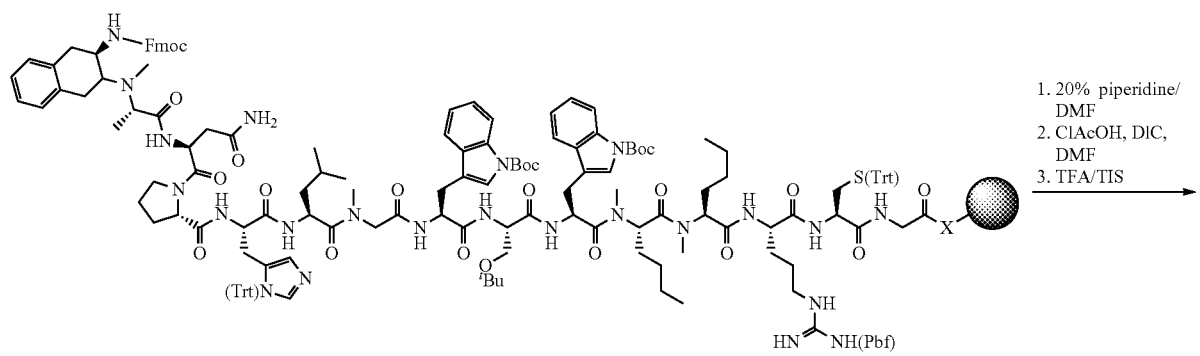
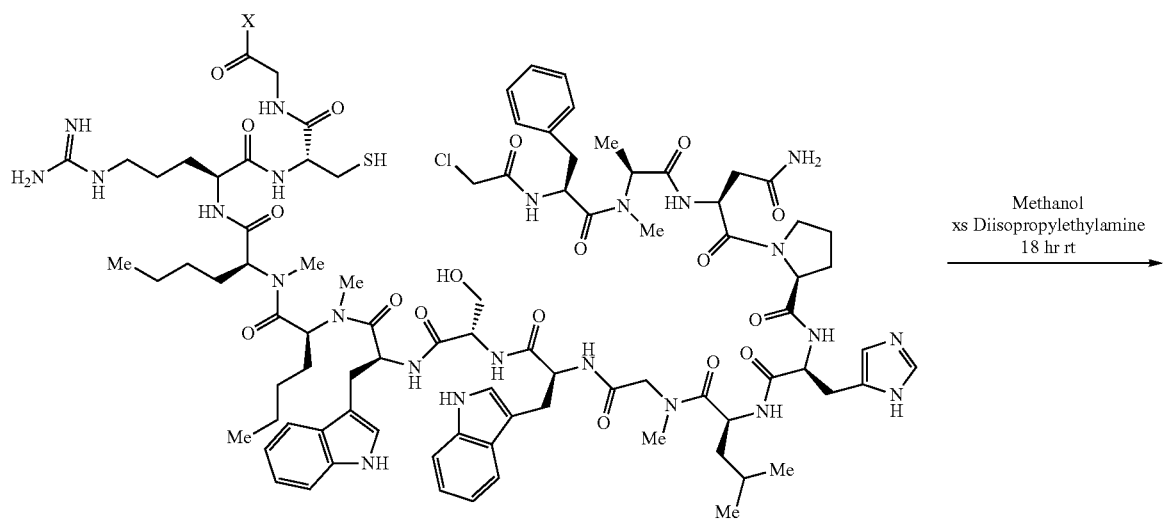

-continued

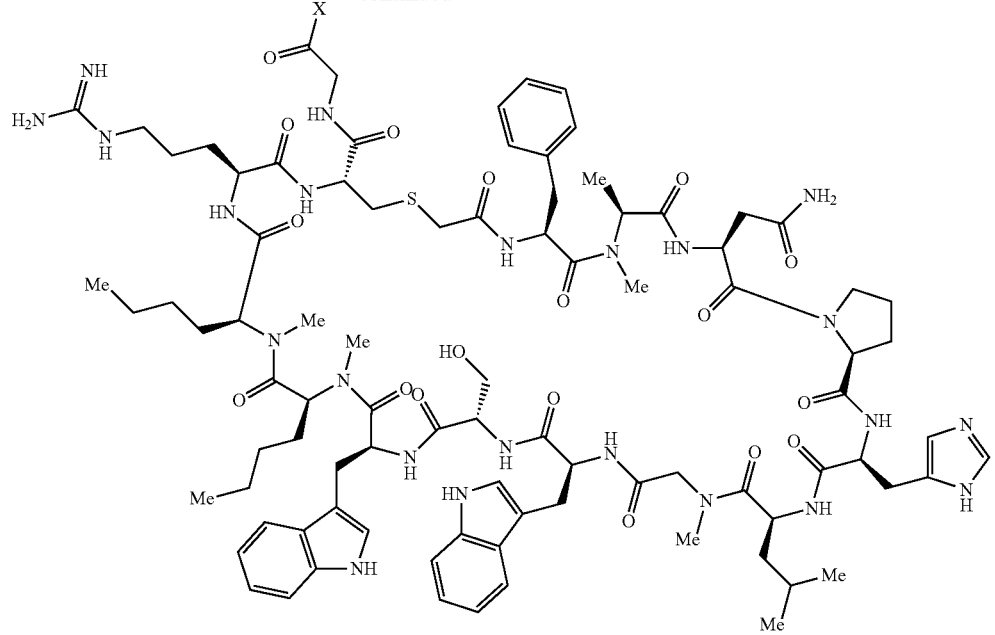

General protocol for solid-phase peptide synthesis and macrocyclization. On a Symphony Peptide Synthesizer (Protein Technology Inc. Tucson, Ariz.), Prelude Peptide Synthesizer (Protein Technology Inc. Tucson, Ariz.), or Liberty (CEM Matthews, N.C.), Sieber Amide resin (0.71 mmol/g, 0.100 mmol, 141 mg) was swelled with DMF (7 mL×4 min) and mixed with a gentle stream of $N_2$ every 30 seconds. The solvent was drained and the following method was used to couple the first amino acid: the Fmoc group was removed from the resin-supported building block by washing the resin twice with a solution of 20% piperidine in DMF (5 mL and 2.5 minutes per wash) and mixing with a gentle stream of $N_2$ every 30 seconds. The resin was washed three times with DMF (5-8 mL and 1.5 min per wash). 2-((((9H-Fluoren-9-yl)methoxy)carbonyl)amino)acetic acid (0.2 M solution in DMF, 0.5 mmol) was then added, followed by coupling activator (i.e., HATU (Chem-Impex Int'l, 0.4M solution in DMF, 1.25 mL, 0.5 mmol)) and base (i.e., N-methyl morpholine (Aldrich, 0.8 M in DMF, 1.25 mL, 1 mmol)). The reaction mixture was agitated by a gentle stream of nitrogen for 1 h. The reagents were drained from the reaction vessel, and the resin was washed three times with DMF (5 mL×1.5 min). It should be noted that the typical reagents for the Liberty CEM were the following: HCTU (0.45 M in DMF) as the coupling activator, DIEA (2M in NMP) as the base, and 5% piperazine in DMF with 0.1 M HOBt as the deprotect solution.

The resulting resin-supported Fmoc-protected dipeptide was then sequentially deprotected and coupled with third amino acid and so forth in an iterative fashion to give the desired resin-supported product.

LCMS analysis was performed on a peptide aliquot, which was cleaved from the resin (analytical amount was treated with a TFA/TIS (96:4) solution (0.2 mL) at room temperature. Following confirmation of the desired linear sequence, the Fmoc group was removed from the N-terminus upon washing the resin twice with a solution of 20% piperidine in DMF (5 mL and 2.5 minutes per wash) and vortexing the slurry. The resin was washed with DMF (2×5 mL). To the peptide-resin was added in succession 2-chloroacetic acid (0.6 mmol, 57 mg), DMF (5.26 mL), and DIC (0.6 mmol, 93 µL). The new slurry was vortexed for 1-2 days as which point the peptide-resin was washed with DMF (1×5 mL×1 min) and DCM (3×DCM×1 min).

The peptide was deprotected and cleaved from the resin upon treatment with a TFA/TIS (96:4) solution (10 mL) for 1 h. The resin was removed by filtration, washed with cleavage cocktail (2×1 mL), the combined filtrates were added to $Et_2O$ (10-15 mL) and the solution was chilled at 0° C. in order to effect the peptide to precipitate out of solution. The slurry is centrifuged to pellet the solids and the supernatant was decanted. Fresh $Et_2O$ (25 mL) was added and the process was repeated three times to wash the solids. To the wet solids was added a solution of 0.1 M $NH_4HCO_3$/Acetonitrile (from 1/1 to 3/1 (v/v), pH=8.6) or 6 M guanidine HCl in 100 mM $NaH_2PO_4$ (pH=8.4). The solution was stirred for 1-2 days and monitored by LCMS. The reaction solution was purified by preparative HPLC to obtain the desired product.

General Analytical Protocols and Synthesis Methods

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

General Procedures.
Symphony X Method A:

All manipulations were performed under automation on a Symphony X peptide synthesizer (Protein Technologies). All procedures were performed in a 10 mL polypropylene tube fitted with a bottom frit. The tube connects to the Symphony X peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; Rink=(2,4-dimethoxyphenyl)(4-alkoxyphenyl)methanamine, where "4-alkoxy" describes the position and type of connectivity to the polystyrene resin. The resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "Symphony X Method A" describe an experiment performed on a 0.100 mmol scale, where the scale is determined by the amount of Rink linker bound to the resin. This scale corresponds to approximately 178 mg of the Rink-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure A:

To a 10 mL polypropylene solid-phase reaction vessel was added Merrifield:Rink resin (178 mg, 0.100 mmol). The resin was washed (swelled) three times as follows: to the reaction vessel was added DMF (2.0 mL), upon which the mixture was periodically agitated for 10 minutes before the solvent was drained through the frit.

Single-Coupling Procedure A:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure A:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 90 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Symphony Amino Acid N-Terminal Stop Procedure.

To a 10 mL polypropylene solid-phase reaction vessel was added Merrifield:Rink resin (178 mg, 0.100 mmol). The resin was washed (swelled) three times as follows: to the reaction vessel was added DMF (2.0 mL), upon which the mixture was periodically agitated for 10 minutes before the solvent was drained through the frit.

To the reaction vessel containing Rink resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. To the reaction vessel was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively three times as follows: for each wash, DCM (2.0 mL) was added through the top of the vessel and the resulting mixture was periodically agitated for 90 seconds before the solution was drained through the frit. The resulting resin was placed under a stream on nitrogen for 15 minutes.

Chloroacetyl Chloride Coupling Procedure A:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added DIPEA (0.4M in DMF, 4.0 mL, 16 eq), then chloroacetyl chloride (0.8M in DMF, 1.50 mL). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit. The resulting resin was placed under a $N_2$ stream for 15 minutes.

Chloroacetic Acid Coupling Procedure A:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added the chloroacetic acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively three times as follows: for each wash, DMF (2.0 mL) was added through the top of the vessel and the resulting mixture was periodically agitated for 30 seconds before the solution was drained through the frit. The resin was washed successively four times as follows: for each wash, $CH_2Cl_2$ (2.0 mL) was added through the top of the vessel and the resulting mixture was periodically agitated for 90 seconds before the solution was drained through the frit. The resulting resin was dried for 5 minutes.

Global Deprotection Method A:

All manipulations were performed manually unless noted. The procedure of "Global Deprotection Method A" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 90 minutes). The mixture was filtered through 10 mL polypropylene tube fitted with a bottom frit allowing for dropwise addition to a 24 mL test tube containing 15 mL of diethyl ether resulting a white precipitate. The solids (resin) in the tube were extracted once with the "deprotection solution" (1.0 mL) allowing dropwise addition to the ether. The mixture was centrifuged for 7 minutes, then the solution was decanted away from the solids and discarded. The solids were suspended in $Et_2O$ (20 mL); then the mixture was centrifuged for 5 minutes; and the solution was decanted away from the solids and discarded. For a final time, the solids were suspended in $Et_2O$ (20 mL); the mixture was centrifuged for 5 minutes; and the solution was decanted away from the solids and discarded to afford the crude peptide as a white to off-white solid.

Cyclization Method A:

All manipulations were performed manually unless noted. The procedure of "Cyclization Method A" describes an experiment performed on a 0.100 mmol scale, where the scale is determined by the amount of Rink linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in Methanol (10 mL), and the solution was then carefully adjusted to pH=9.0-11 using N,N-Diisopropylamine. The solution was then allowed to stir for 18-24 h. The reaction solution was concentrated and the residue was then dissolved in MeOH. This solution was subjected to reverse-phase HPLC purification to afford the desired cyclic peptide.

Analysis Condition A:

Column: X-Bridge C18, 2.0×50 mm, 3.5-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 8 minutes, then a 1.0-minute hold at 100% B; Flow: 0.8 mL/min; Detection: UV at 220 nm.

Preparation of (S)-2-((((9H-fluoren-9-yl)methoxy) carbonyl)amino)-6-undecanamidohexanoic acid

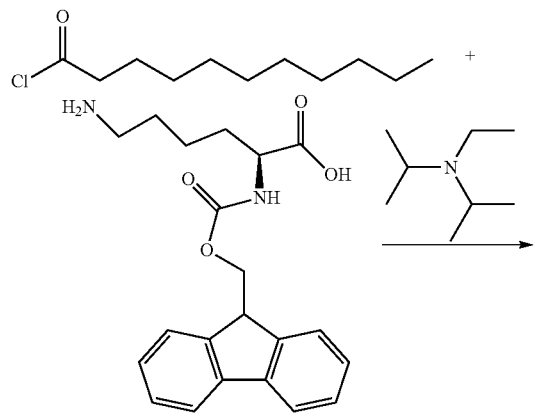

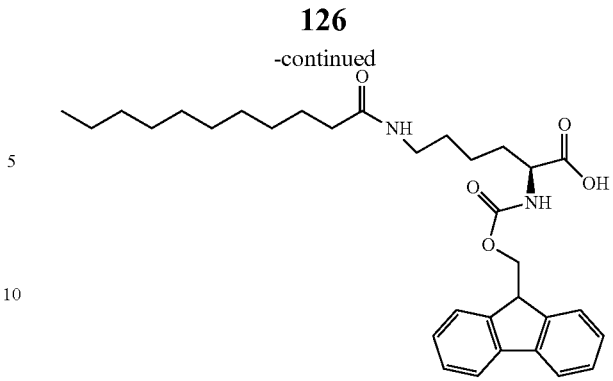

To a round-bottom flask charged with (S)-2-((((9H-fluoren-9-yl)methoxy)carbonyl)amino)-6-aminohexanoic acid (2.5 g, 6.79 mmol), undecanoyl chloride (1.647 ml, 7.46 mmol), and dichloromethane (27 ml) was added N-ethyl-N-isopropylpropan-2-amine (3.56 ml, 20.36 mmol). The initial suspension immediately turns yellow and then clear. After 10 minutes a solid begins to precipitate. The reaction was stirred for 20 hours at room temperature. The reaction mixture was diluted with 20 ml dichloromethane and poured into saturated ammonium chloride solution. The layers were separated and the aqueous was washed with a 20% methanol/chloroform solution. The combined organics were washed with brine, dried over magnesium sulfate, filtered, and concentrated to give a sticky yellow solid. The resulting residue was subjected to silica gel chromatography (0-5% methanol/dichloromethane gradient) to afford (S)-2-((((9H-fluoren-9-yl)methoxy)carbonyl)amino)-6-undecanamidohexanoic acid (2.81 g, 5.24 mmol, 77% yield) as a yellow foam. $^1$H NMR (400 MHz, CHLOROFORM-d) δ 7.80-7.71 (m, 2H), 7.63-7.52 (m, 2H), 7.39 (t, J=7.0 Hz, 2H), 7.34-7.27 (m, 2H), 4.49-4.29 (m, 2H), 4.27-4.14 (m, 1H), 3.24 (br. s., 1H), 2.35 (t, J=7.5 Hz, 1H), 2.29-2.06 (m, 2H), 1.89 (br. s., 1H), 1.86-1.72 (m, 1H), 1.72-1.63 (m, 1H), 1.62-1.46 (m, 4H), 1.39-1.14 (m, 18H), 0.92-0.86 (m, 3H).

(S)-2-((((9H-fluoren-9-yl)methoxy)carbonyl)amino)-6-tetradecanamidohexanoic acid

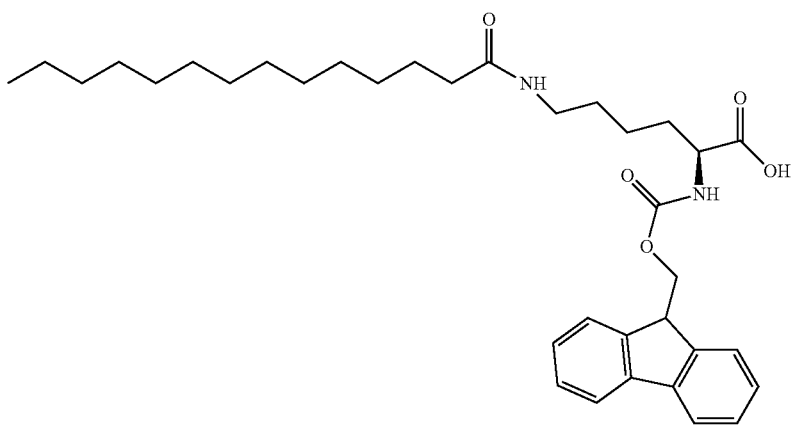 [SMILES: CCCCCCCCCCCCCC(=O)NCCCC[C@H](NC(=O)OCC1c2ccccc2-c2ccccc21)C(=O)O]

¹H NMR (400 MHz, DMSO-d₆) δ 7.88 (dd, J=7.2, 4.1 Hz, 2H), 7.77-7.69 (m, 2H), 7.44-7.37 (m, 2H), 7.35-7.28 (m, 2H), 4.29-4.17 (m, 2H), 3.95-3.84 (m, 1H), 3.63-3.52 (m, 1H), 3.10 (q, J=7.4 Hz, 1H), 3.05-2.94 (m, 2H), 2.01 (t, J=7.4 Hz, 2H), 1.46 (d, J=6.8 Hz, 3H), 1.34 (dd, J=13.1, 5.0 Hz, 3H), 1.24-1.20 (m, 22H), 0.86-0.82 (m, 3H)
(S)-2-((((9H-fluoren-9-yl)methoxy)carbonyl)amino)-6-stearamidohexanoic acid
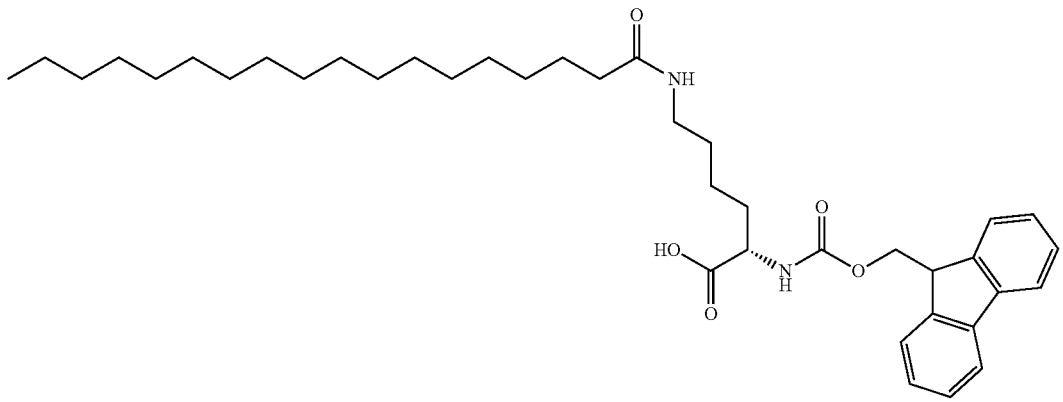 [SMILES: CCCCCCCCCCCCCCCCCC(=O)NCCCC[C@H](NC(=O)OCC1c2ccccc2-c2ccccc21)C(=O)O]
¹H NMR (400 MHz, DMSO-d₆) δ 7.92-7.84 (m, 2H), 7.72 (d, J=7.5 Hz, 2H), 7.44-7.36 (m, 2H), 7.36-7.26 (m, 2H), 4.35-4.22 (m, 2H), 4.20 (d, J=7.5 Hz, 1H), 3.94-3.85 (m, 1H), 3.00 (br. s., 2H), 2.17 (t, J=7.4 Hz, 1H), 2.09-1.91 (m, 1H), 1.69 (d, J=6.8 Hz, 1H), 1.65-1.51 (m, 1H), 1.46 (d, J=7.0 Hz, 2H), 1.34 (dd, J=13.1, 5.0 Hz, 2H), 1.24-1.19 (m, 30H), 0.87-0.82 (m, 3H).
Preparation of Modified Rink Resin A
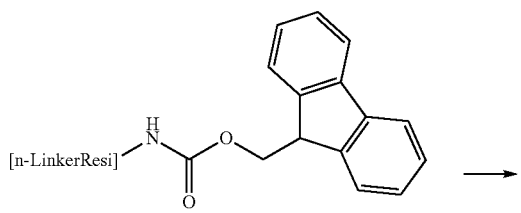
Resin = 0.56 mmol/g loading
1% DVB, 100-200 mesh
Linker = Rink
Cat# 12662 from Chem-Impex
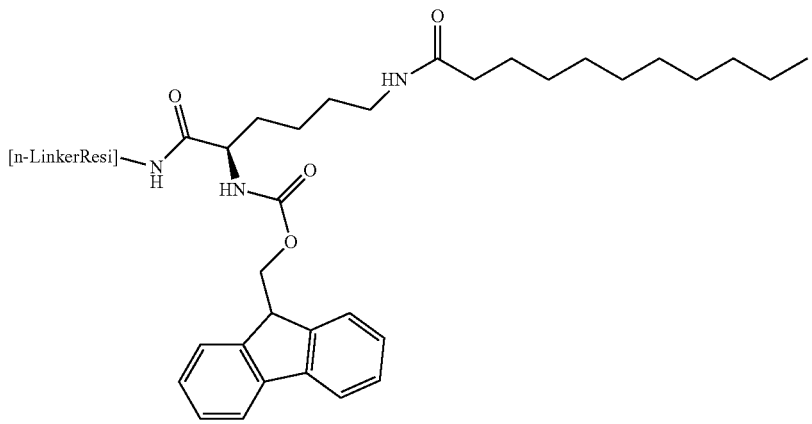

A 20 ml scintillation vial was charged with Merrifield Rink resin (0.56 mmol/g loading) (1.0 g, 0.560 mmol). The resin was swelled in 5 ml DMF for 10 minutes. A solution of 8 ml of a 20:80 piperidine:DMF solution was added and the resulting suspension was shaken on the mini-shaker for 2 hours. The resin was isolated by transferring the contents of the vial into 10 ml polypropylene reaction tube and filtering by vacuum filtration. The resin was washed with 30 ml DMF followed by 30 ml dichloromethane and lastly with 5 ml diethyl ether. The resin was transferred to 20 ml vial. To the vial containing the resin was added 5 ml DMF to swell the resin. After 10 minutes (S)-2-((((9H-fluoren-9-yl) methoxy)carbonyl)amino)-6-undecanamidohexanoic acid (0.601 g, 1.120 mmol), 0.2M 2-(3H-[1,2,3]triazolo[4,5-b]pyridin-3-yl)-1,1,3,3-tetramethylisouronium hexafluorophosphate(V) in DMF (5.60 ml, 1.120 mmol), and 0.4M N-ethyl-N-isopropylpropan-2-amine in DMF (5.60 ml, 2.240 mmol) were added. The vial was shaken overnight on the mini-shaker. The resin was isolated by transferring the contents of the vial into 10 ml polypropylene reaction tube and filtering by vacuum filtration. The resin was washed with 50 ml DMF, 50 ml dichloromethane, and 10 ml diethyl ether. The resulting resin was dried in vacuo and used as a 0.56 mmol/g loading.

Preparation of Modified Rink Resin B

Modified rink resin B was made following identical procedure to Modified Rink resin A.

Preparation of Modified Rink Resin C

Modified rink resin C was made following identical procedure to Modified Rink resin A with the only exception being the N-Fmoc-N Palmitoyl-L Lysine was purchased from Chem-Impex International.

Preparation of Modified Rink Resin D

Modified rink resin D was made following identical procedure to Modified Rink resin A.

Preparation of Modified 2-chlorotrityl chloride resin A

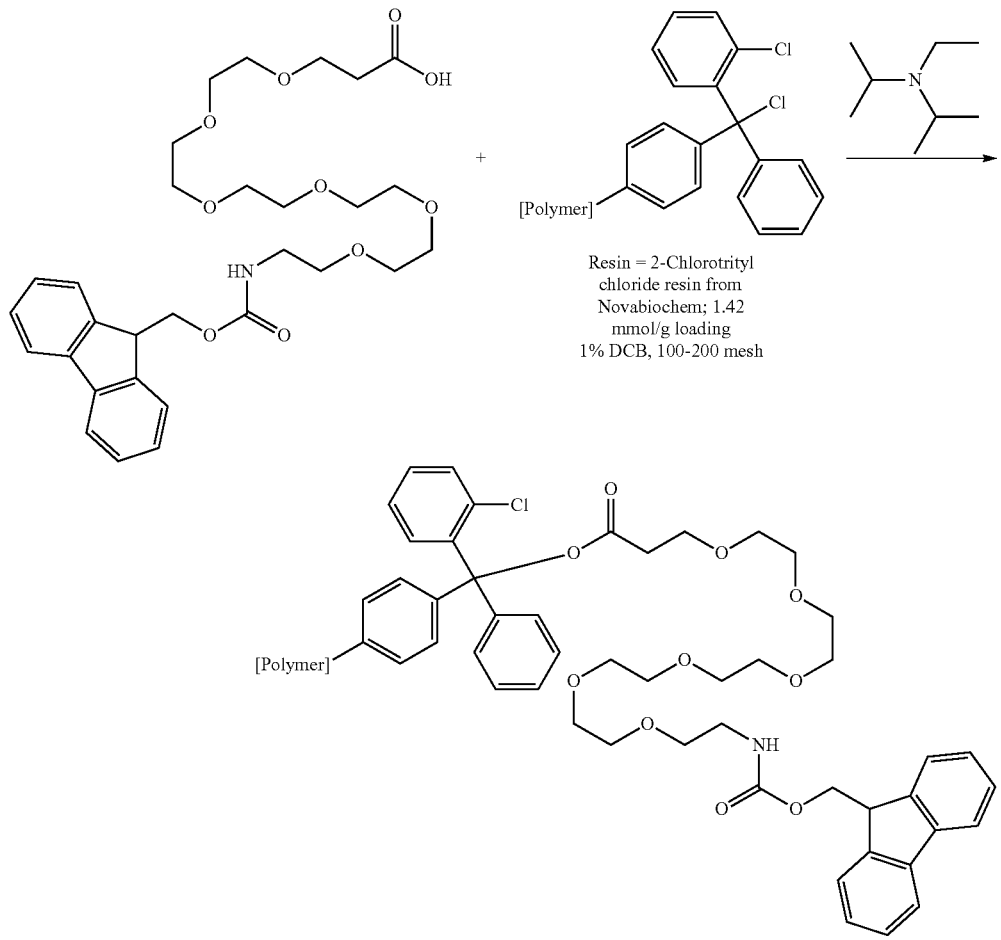

To a 40 mL vial was added 2-chlorotrityl chloride resin (1.42 mmol/g loading) (1.985 g, 2.78 mmol). The resin was swelled in 15 ml dichloromethane for 10 minutes. A solution of (0.5 g, 0.869 mmol), FMOC-21-amino-4,7,10,13,16,19-hexaoxaheneicosanoic acid in 2 ml dichloromethane followed by N-ethyl-N-isopropylpropan-2-amine (0.986 ml, 5.65 mmol) was added and the mixture was shaken overnight at rt on a mini shaker. After 20 h the mixture was diluted with 2 ml of methanol, and shaken for 2 hr to quench any unreacted chlorotrityl resin. The resin was vacuum filtered in a polypropylene reaction tube and washed with 100 ml DMF, 100 ml dichloromethane, and finally 10 ml diethyl ether. Resin was air dried and used as is assuming a 0.44 mmol/g loading.

Preparation of Modified 2-chlorotrityl chloride resin

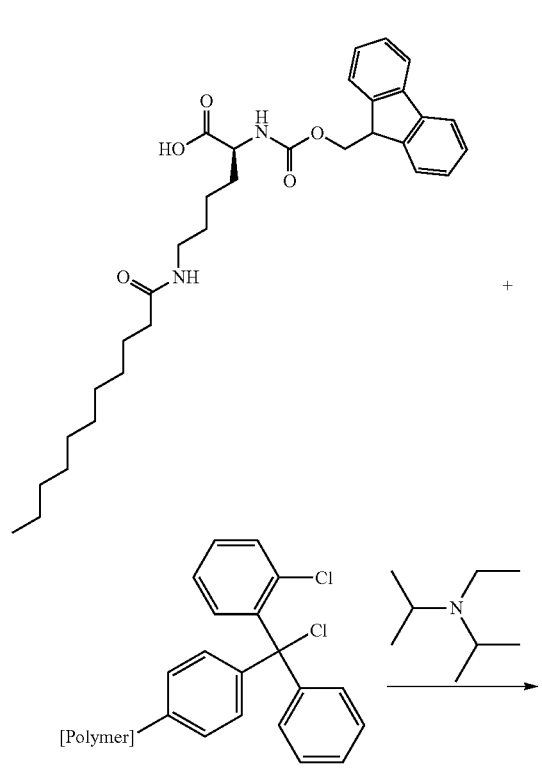

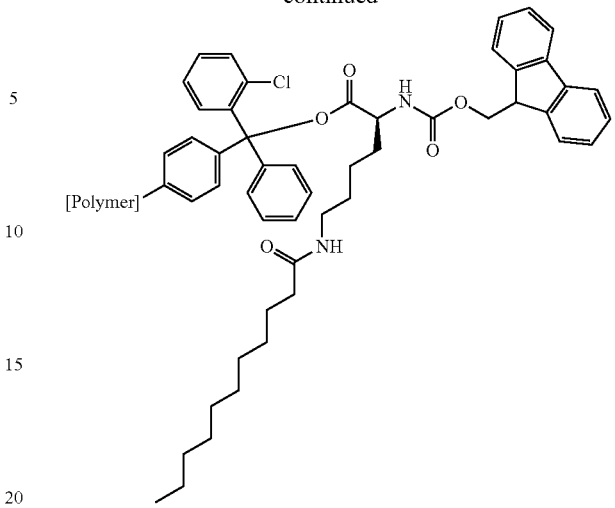

To a 40 mL vial was added 2-chlorotrityl chloride resin (1.42 mmol/g loading) (2.129 g, 2.98 mmol). The resin was swelled in 15 ml dichloromethane for 10 minutes. A solution of S)-2-(((((9H-fluoren-9-yl)methoxy)carbonyl)amino)-6-undecanamidohexanoic acid (0.5 g, 0.932 mmol), in 2 ml dichloromethane followed by N-ethyl-N-isopropylpropan-2-amine (1.06 ml, 6.06 mmol) was added and the mixture was shaken overnight at room temperature on a mini shaker. After 20 h the mixture was diluted with 2 ml of methanol, and shaken for 2 hr to quench any unreacted chlorotrityl resin. The resin was vacuum filtered in a polypropylene reaction tube and washed with 100 ml DMF, 100 ml dichloromethane, and finally 10 ml diethyl ether. Resin was air dried and used as is assuming a 0.44 mmol/g loading.

Preparation of Example 11001

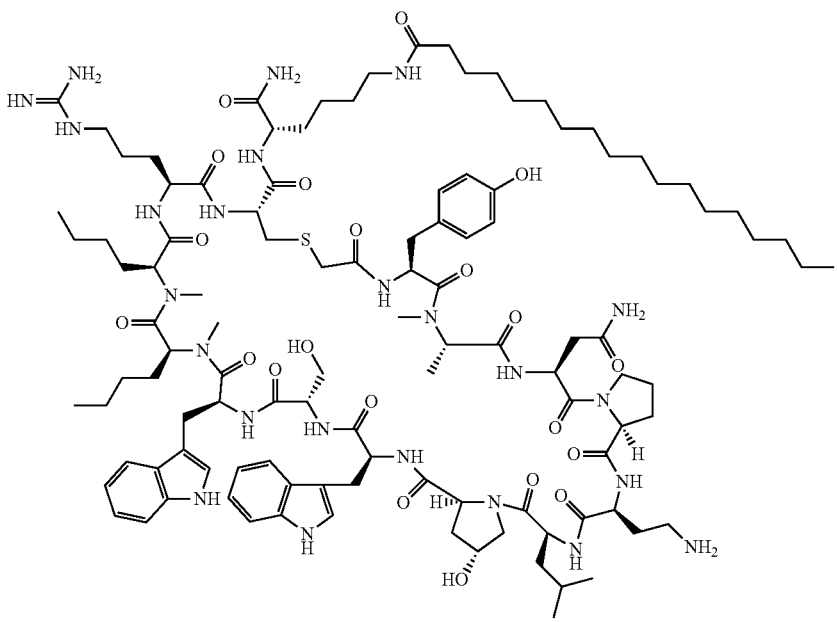 [SMILES: CCCCCCCCCCCCCCCCCC(=O)NCCCC[C@H](NC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11001 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetyl acid coupling procedure", "Global Deprotection Method A", and "Cyclization Method A". Modified Rink resin D was used in this synthesis.

The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 5.2 mg, and its estimated purity by LCMS analysis was 98%. Analysis LCMS Condition A: Retention time=7.34 min; ESI-MS(+) m/z 1105.4 (M+2H); ESI-HRMS(+) m/z: Calculated: 1105.6498 (M+2H). Found: 1105.6494 (M+2H).

Preparation of Example 11002

Example 11002 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin D was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 3.9 mg, and its estimated purity by LCMS analysis was 98%.

Analysis LCMS Condition A: Retention time=7.10 min; ESI-MS(+) m/z 1133.5 (M+2H); ESI-HRMS(+) m/z: Calculated: 1133.1543 (M+2H). Found: 1133.1496 (M+2H).

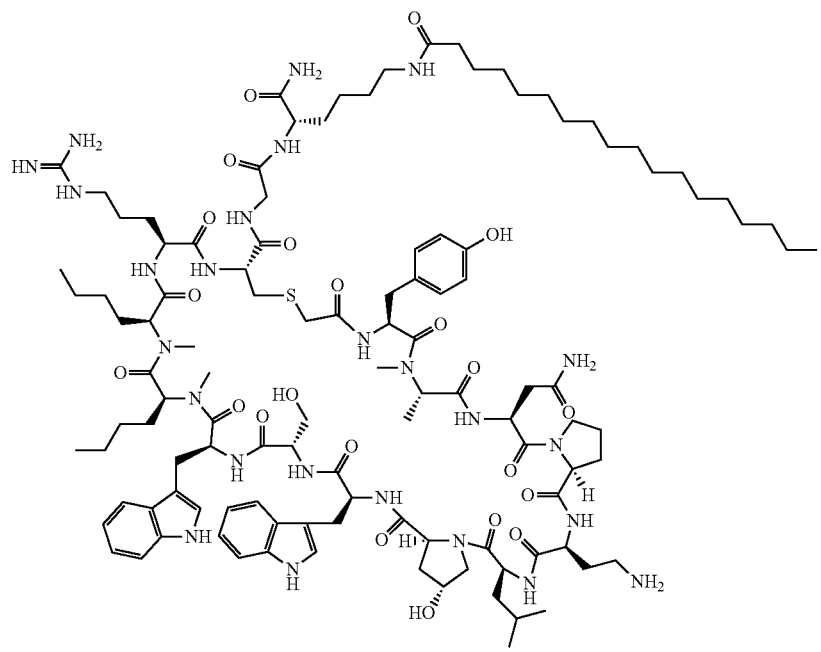 [SMILES: CCCCCCCCCCCCCCCCCC(=O)NCCCC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Preparation of Example 11003

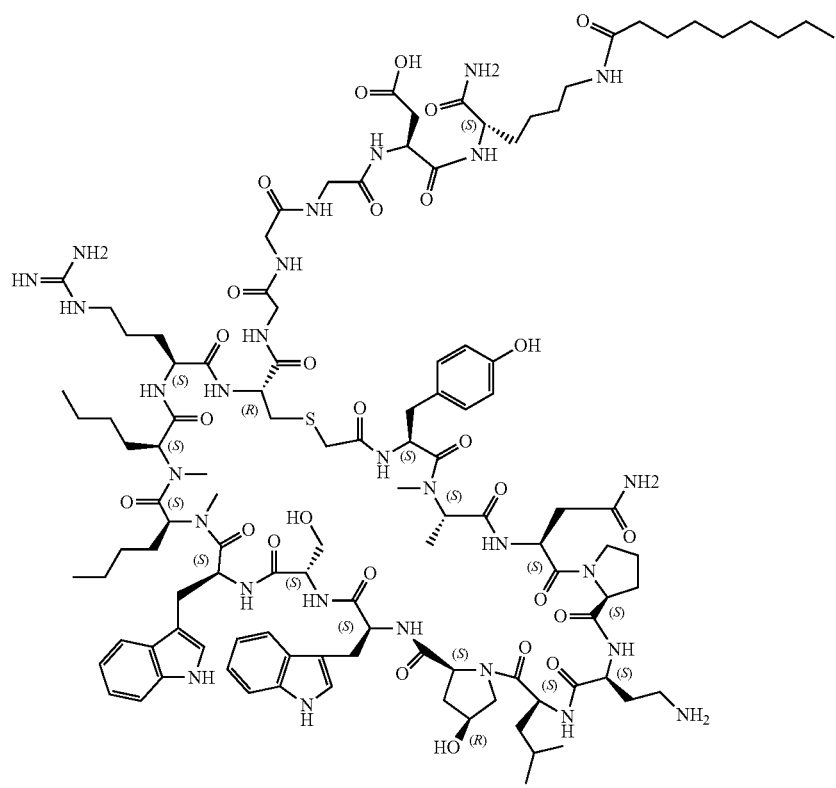

Example 11003 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 3.5 mg, and its estimated purity by LCMS analysis was 99%.

Analysis LCMS Condition A: Retention time=4.66 min; ESI-MS(+) m/z 1200.4 (M+2H).

Preparation of Example 11004

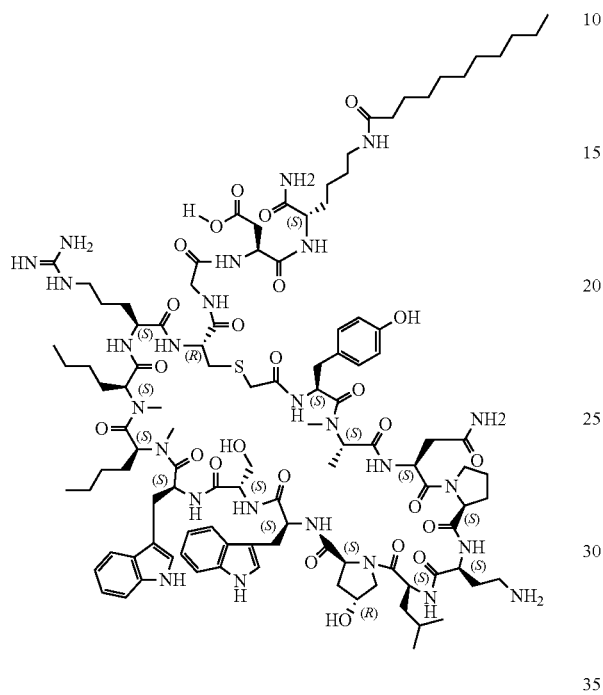

Example 11004 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 10.7 mg, and its estimated purity by LCMS analysis was 98%.

Analysis LCMS Condition A: Retention time=4.73 min; ESI-MS(+) m/z 1171.9 (M+2H); ESI-HRMS(+) m/z: Calculated: 1171.1299 (M+2H). Found: 1171.1302 (M+2H).

Preparation of Example 11005

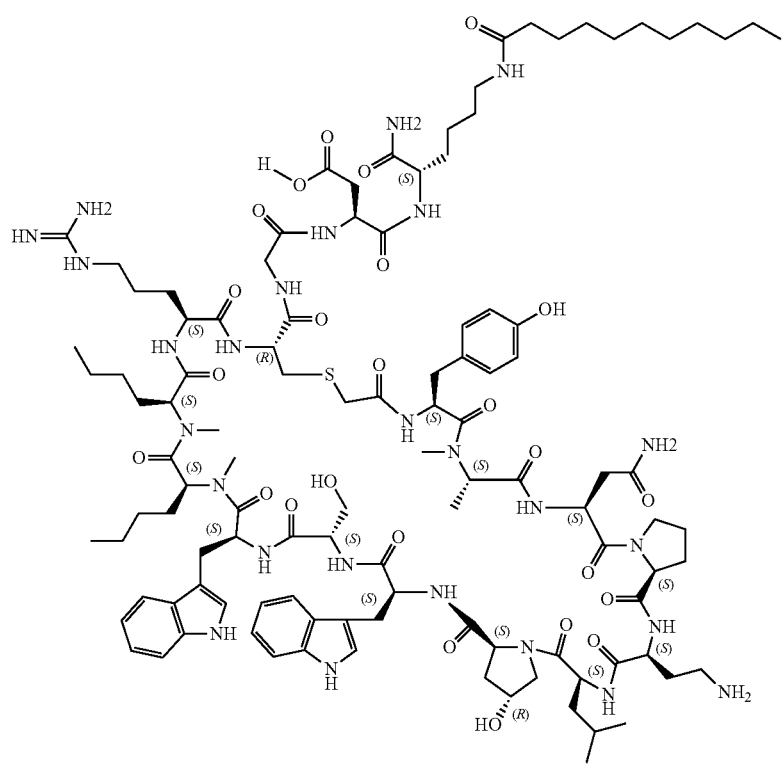

Example 11005 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 4.8 mg, and its estimated purity by LCMS analysis was 99%.

Analysis LCMS Condition A: Retention time=4.78 min; ESI-MS(+) m/z 1142.5 (M+2H); ESI-HRMS(+) m/z: Calculated: 1142.6192 (M+2H). Found: 1142.6193 (M+2H).

141
Preparation of Example 11006

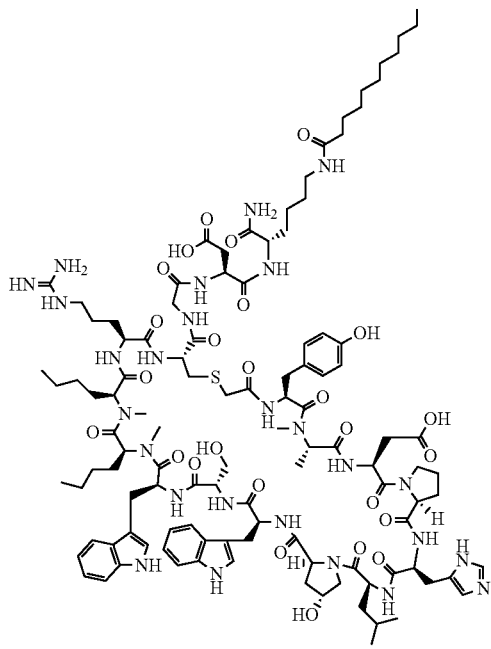 [SMILES: CCCCCCCCCCC(=O)NCCCC[C@H](NC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11006 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 9.2 mg, and its estimated purity by LCMS analysis was 98%.

Analysis LCMS Condition A: Retention time=4.66 min; ESI-MS(+) m/z 1161.7 (M+2H); ESI-HRMS(+) m/z: Calculated: 1161.6088 (M+2H). Found: 1161.6075 (M+2H).

142
Preparation of Example 11007

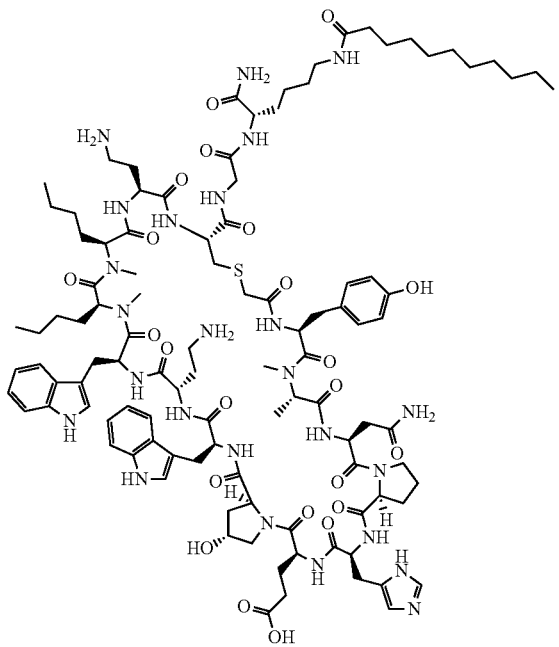 [SMILES: CCCCCCCCCCC(=O)NCCCC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N(C)[C@@H](CCCC)C(=O)N(C)[C@@H](CCCC)C(=O)N[C@@H](CCN)C(=O)N1)C(N)=O]

Example 11007 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 16.0 mg, and its estimated purity by LCMS analysis was 99%.

Analysis LCMS Condition A: Retention time=4.64 min; ESI-MS(+) m/z 1191.0 (M+2H); ESI-HRMS(+) m/z: Calculated: 1090.0797 (M+2H). Found: 1090.0779 (M+2H).

Preparation of Example 11008

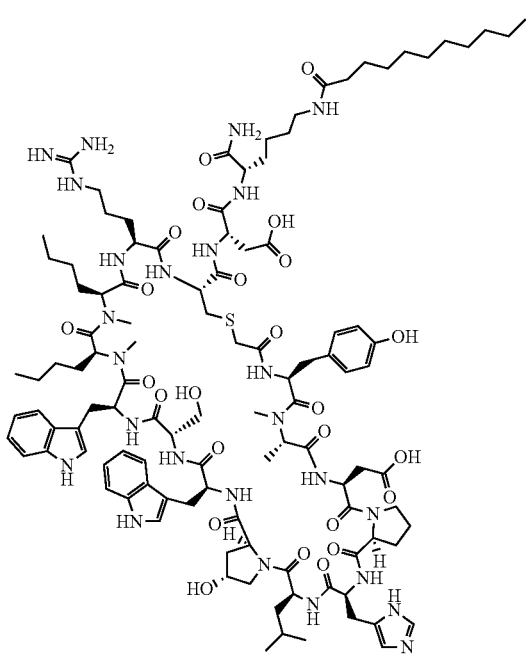 [SMILES: CCCCCCCCCCC(=O)NCCCC[C@H](NC(=O)[C@H](CC(=O)O)NC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Preparation of Example 11009

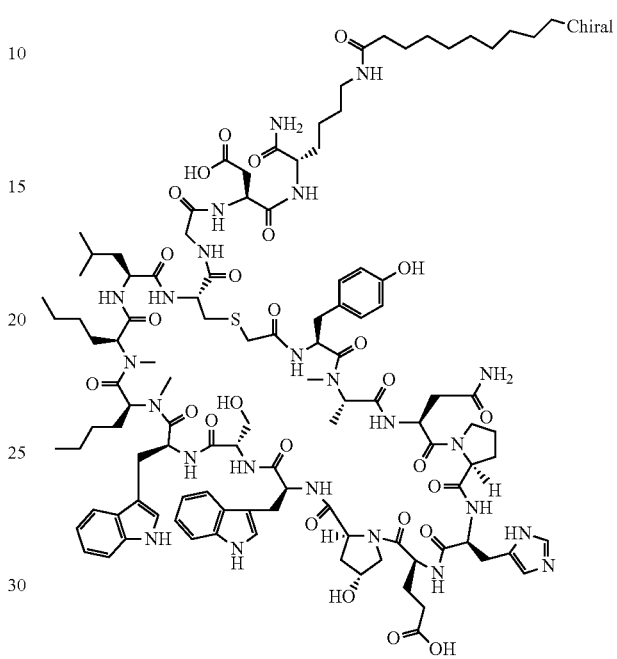

Example 11008 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 12.2 mg, and its estimated purity by LCMS analysis was 99%.

Analysis LCMS Condition A: Retention time=4.55 min; ESI-MS(+) m/z 1133.3 (M+2H); ESI-HRMS(+) m/z: Calculated: 1133.0981 (M+2H). Found: 1133.0950 (M+2H).

Example 11009 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 19.8 mg, and its estimated purity by LCMS analysis was 96%.

Analysis LCMS Condition A: Retention time=4.81 min; ESI-MS(+) m/z 1147.7 (M+2H); ESI-HRMS(+) m/z: Calculated: 1147.5875 (M+2H). Found: 1147.5867 (M+2H).

Preparation of Example 11010

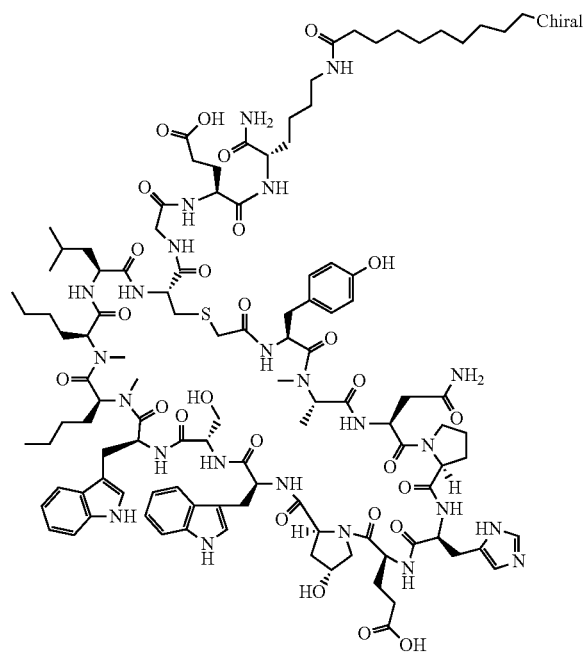

Example 11010 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 19.4 mg, and its estimated purity by LCMS analysis was 98%.

Analysis LCMS Condition A: Retention time=4.83 min; ESI-MS(+) m/z 1154.9 (M+2H); ESI-HRMS(+) m/z: Calculated: 1154.5954 (M+2H). Found: 1154.9533 (M+2H).

Preparation of Example 11011

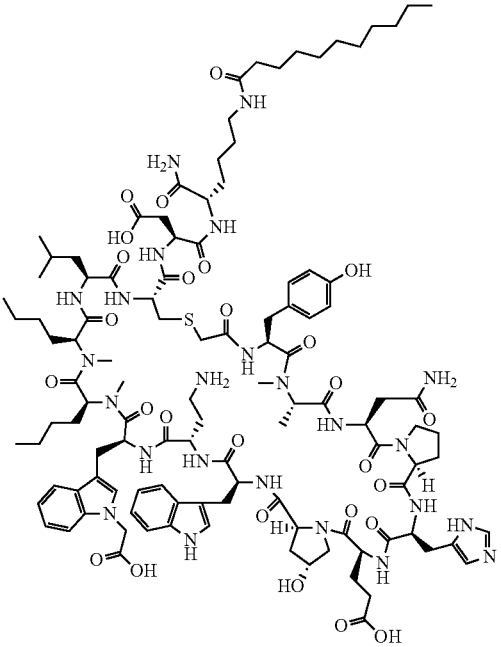 [SMILES: CCCCCCCCCCC(=O)NCCCC[C@H](NC(=O)[C@H](CC(=O)O)NC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(N)=O]

Example 11011 was prepared following the general synthetic sequence procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 8.7 mg, and its estimated purity by LCMS analysis was 96%.

Analysis LCMS Condition A: Retention time=4.37 min; ESI-MS(+) m/z 1154.8 (M+2H); ESI-HRMS(+) m/z: Calculated: 1154.5954 (M+2H). Found: 1154.5941 (M+2H).

Preparation of Example 11012

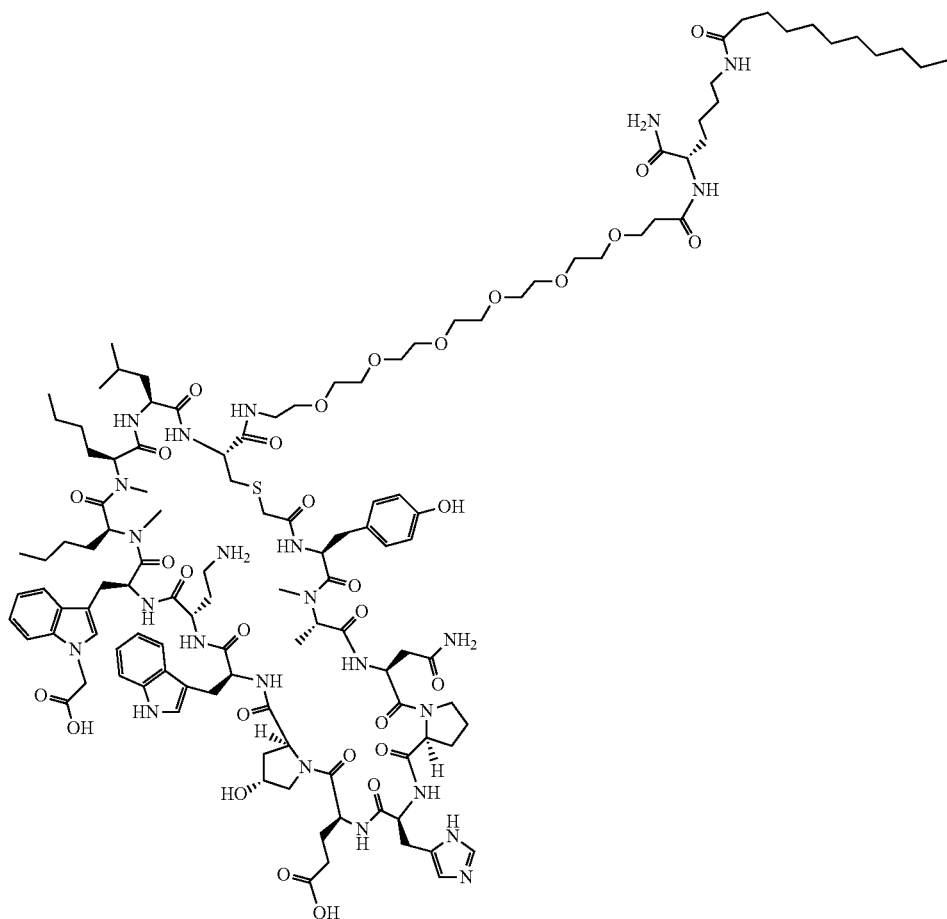 [SMILES: CCCCCCCCCCC(=O)NCCCC[C@H](NC(=O)CCOCCOCCOCCOCCOCCOCCNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(N)=O]

Example 11012 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 8.7 mg, and its estimated purity by LCMS analysis was 96%. Analysis LCMS Condition A: Retention time=4.68 min; ESI-MS(+) m/z 1265.3 (M+2H); ESI-HRMS(+) m/z: Calculated: 1264.6791 (M+2H).

Found: 1264.6764 (M+2H).

Preparation of Example 11013

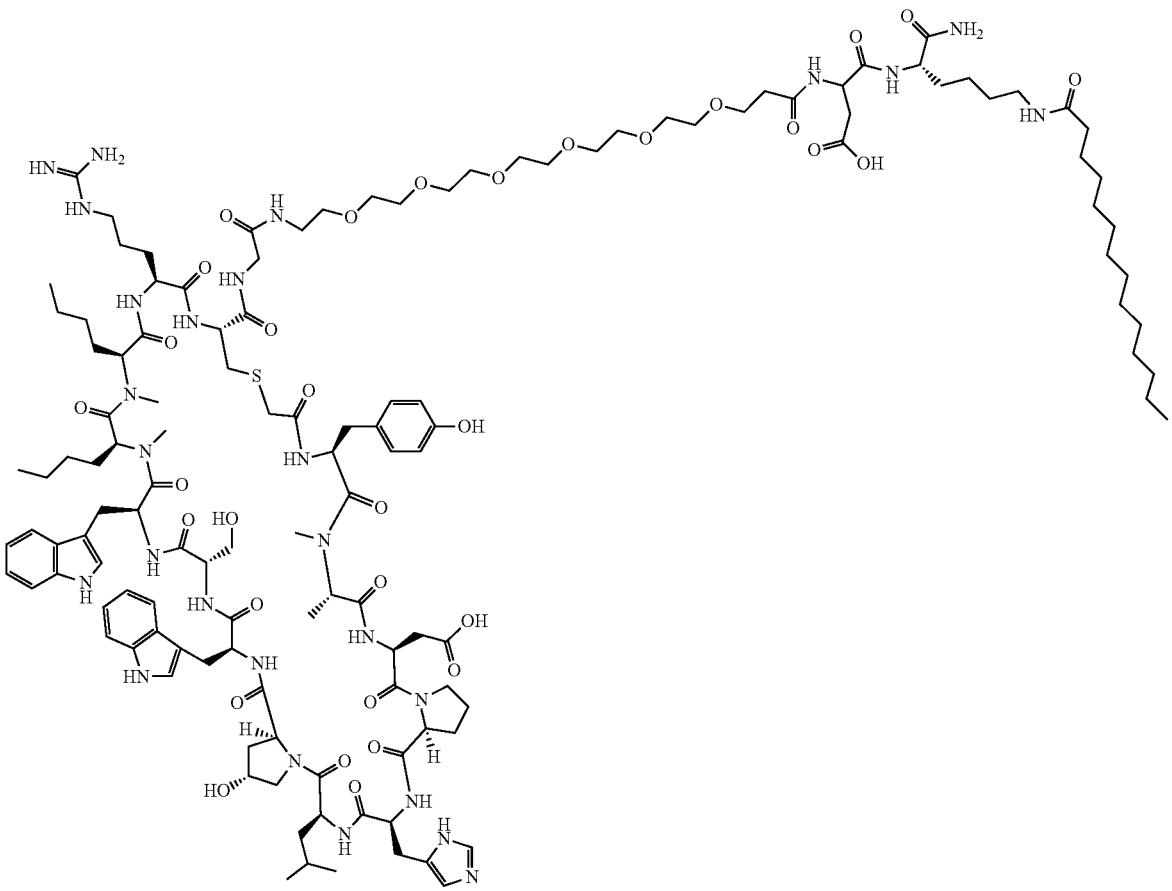 [SMILES: CCCCCCCCCCCCCC(=O)NCCCC[C@H](NC(=O)C(CC(=O)O)NC(=O)CCOCCOCCOCCOCCOCCOCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11013 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin B was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 12.7 mg, and its estimated purity by LCMS analysis was 98%. Analysis LCMS Condition A: Retention time=5.04 min; ESI-MS(+) m/z 1351.2 (M+2H).

Preparation of Example 11014

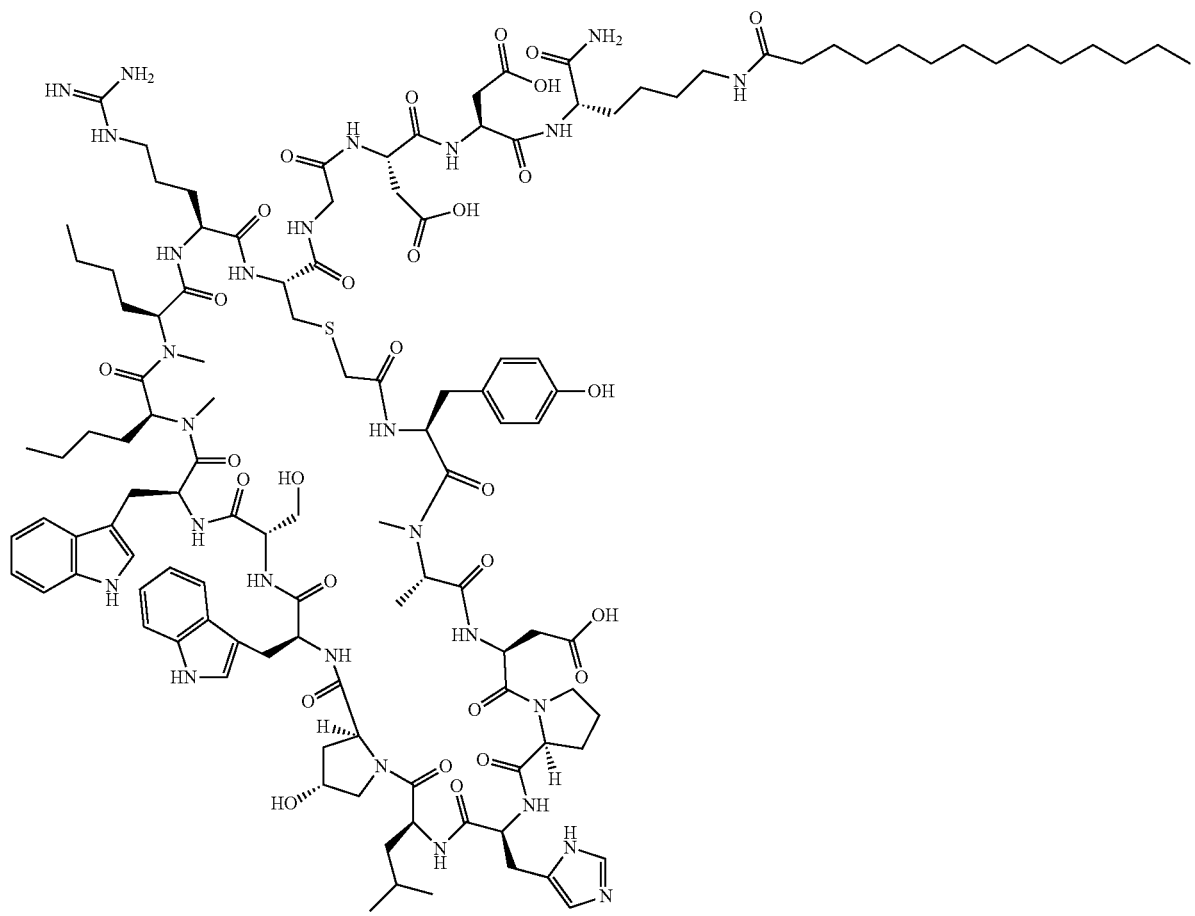 [SMILES: CCCCCCCCCCCCCC(=O)NCCCC[C@H](NC(=O)[C@H](CC(=O)O)NC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11014 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 7.7 mg, and its estimated purity by LCMS analysis was 98%. Analysis LCMS Condition A: Retention time=4.97 min; ESI-MS(+) m/z 1241.1 (M+2H).

Preparation of Example 11015

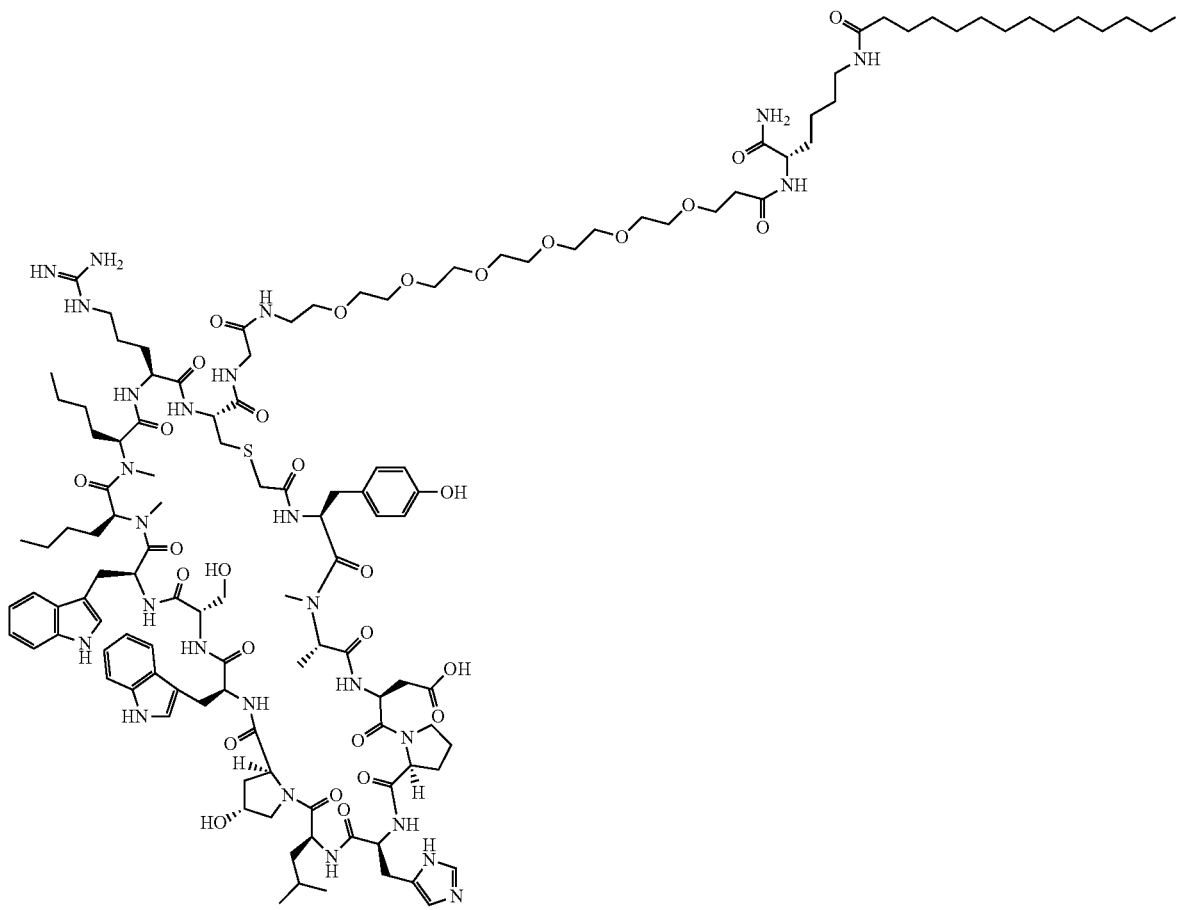 [SMILES: CCCCCCCCCCCCCC(=O)NCCCC[C@H](NC(=O)CCOCCOCCOCCOCCOCCOCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11015 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin B was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 7.1 mg, and its estimated purity by LCMS analysis was 99%. Analysis LCMS Condition A: Retention time=5.44 min; ESI-MS(+) m/z 1292.7 (M+2H); ESI-HRMS(+) m/z: Calculated: 1292.7160 (M+2H).

Found: 1292.7148 (M+2H).

Preparation of Example 11016

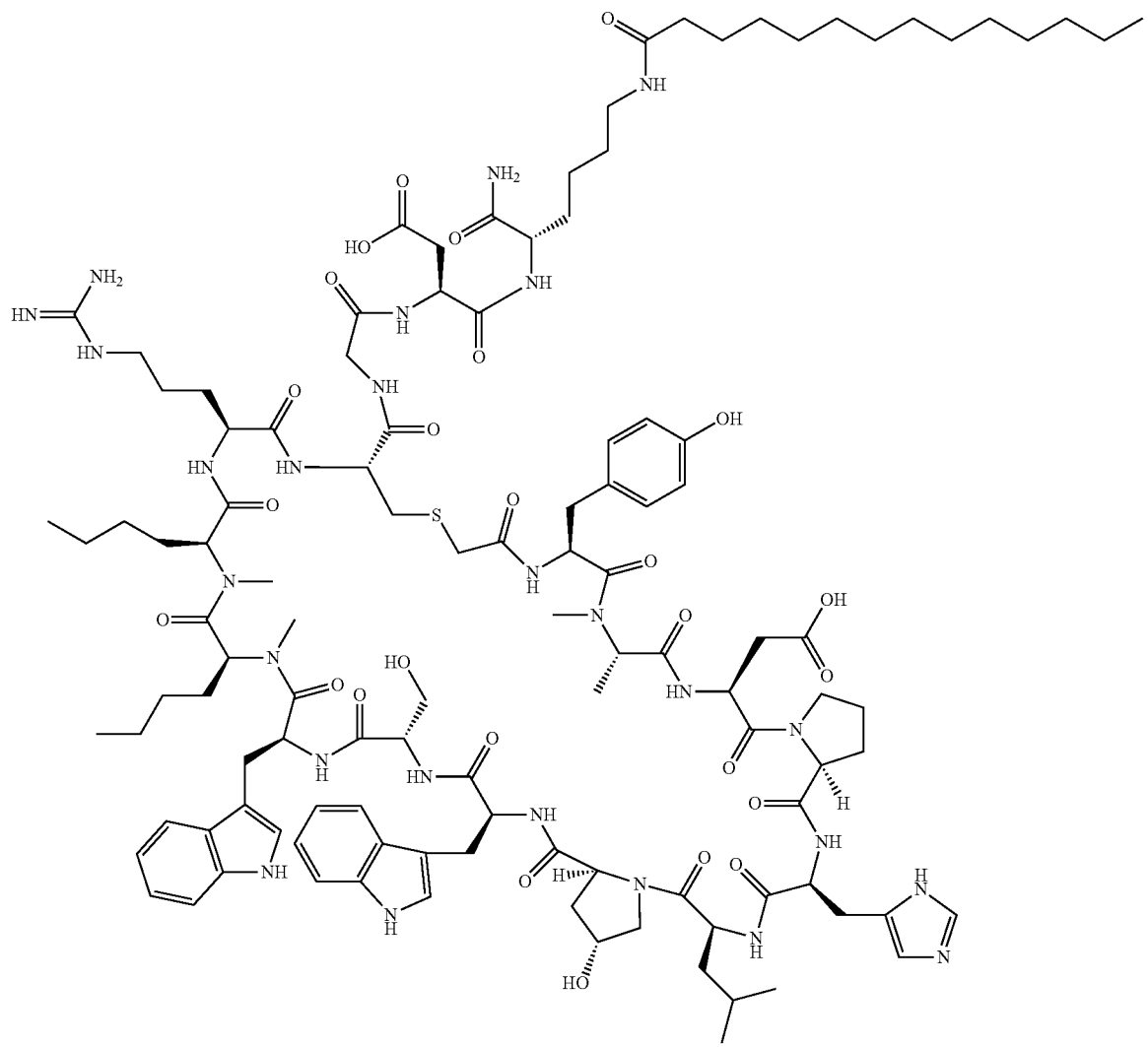 [SMILES: CCCCCCCCCCCCCC(=O)NCCCC[C@H](NC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11016 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 8.3 mg, and its estimated purity by LCMS analysis was 98%; Analysis LCMS Condition A: Retention time=5.27 min; ESI-MS(+) m/z 1182.7 (M+2H).

Preparation of Example 11017

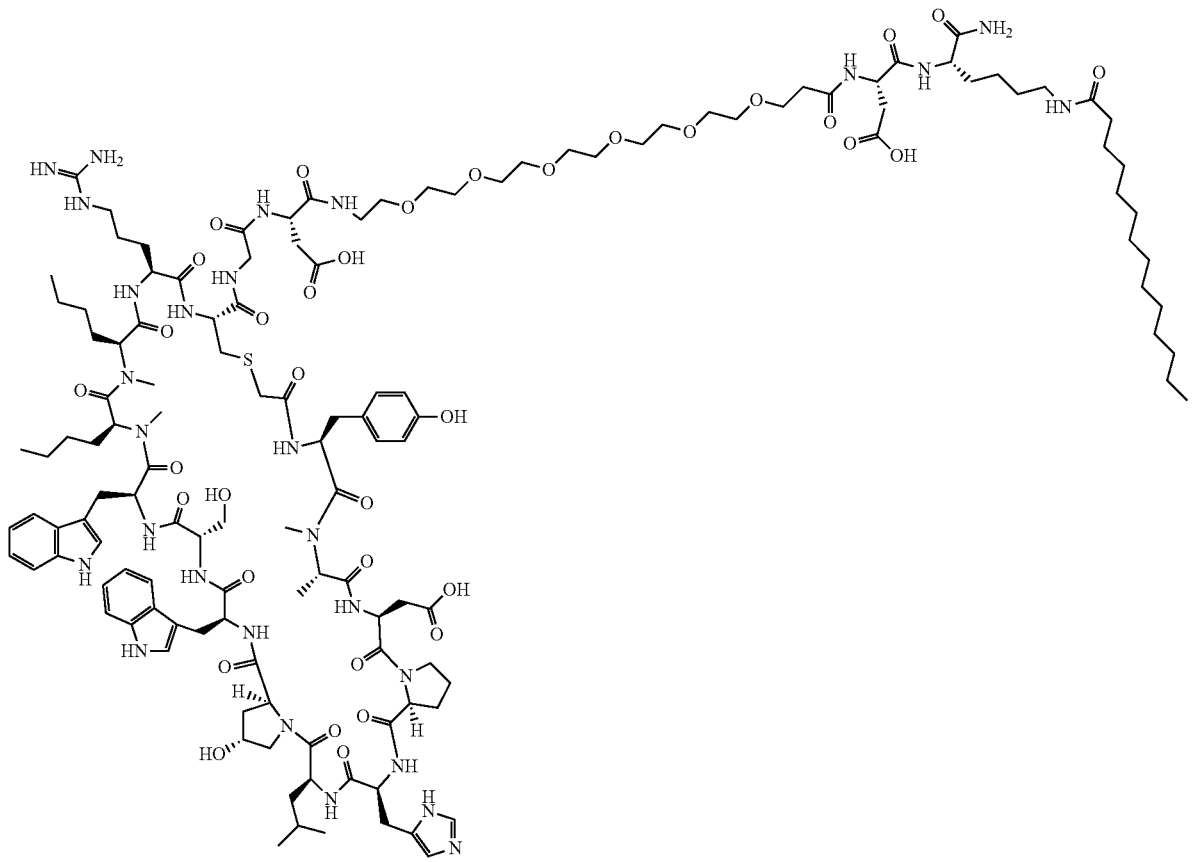 [SMILES: CCCCCCCCCCCCCC(=O)NCCCC[C@H](NC(=O)[C@H](CC(=O)O)NC(=O)CCOCCOCCOCCOCCOCCOCCNC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11017 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin B was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 5.2 mg, and its estimated purity by LCMS analysis was 95%. Analysis LCMS Condition A: Retention time=4.81 min; ESI-MS(+) m/z 1408.1 (M+2H); ESI-HRMS(+) m/z: Calculated: 1407.7431 (M+2H).

Found: 1407.7430 (M+2H).

Preparation of Example 11018

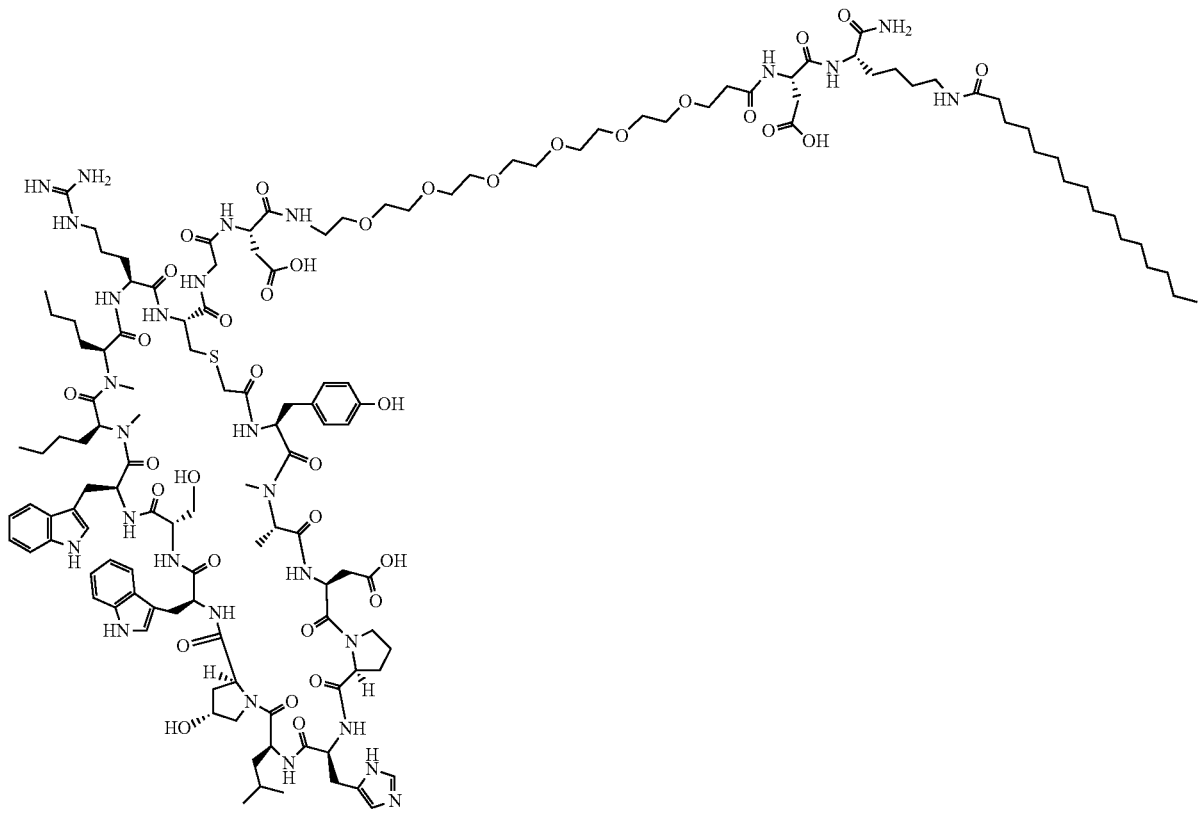 [SMILES: CCCCCCCCCCCCCCCC(=O)NCCCC[C@H](NC(=O)[C@H](CC(=O)O)NC(=O)CCOCCOCCOCCOCCOCCOCCNC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11018 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 11.2 mg, and its estimated purity by LCMS analysis was 96%. Analysis LCMS Condition A: Retention time=5.16 min; ESI-MS(+) m/z 1421.8 (M+2H).

Preparation of Example 11019

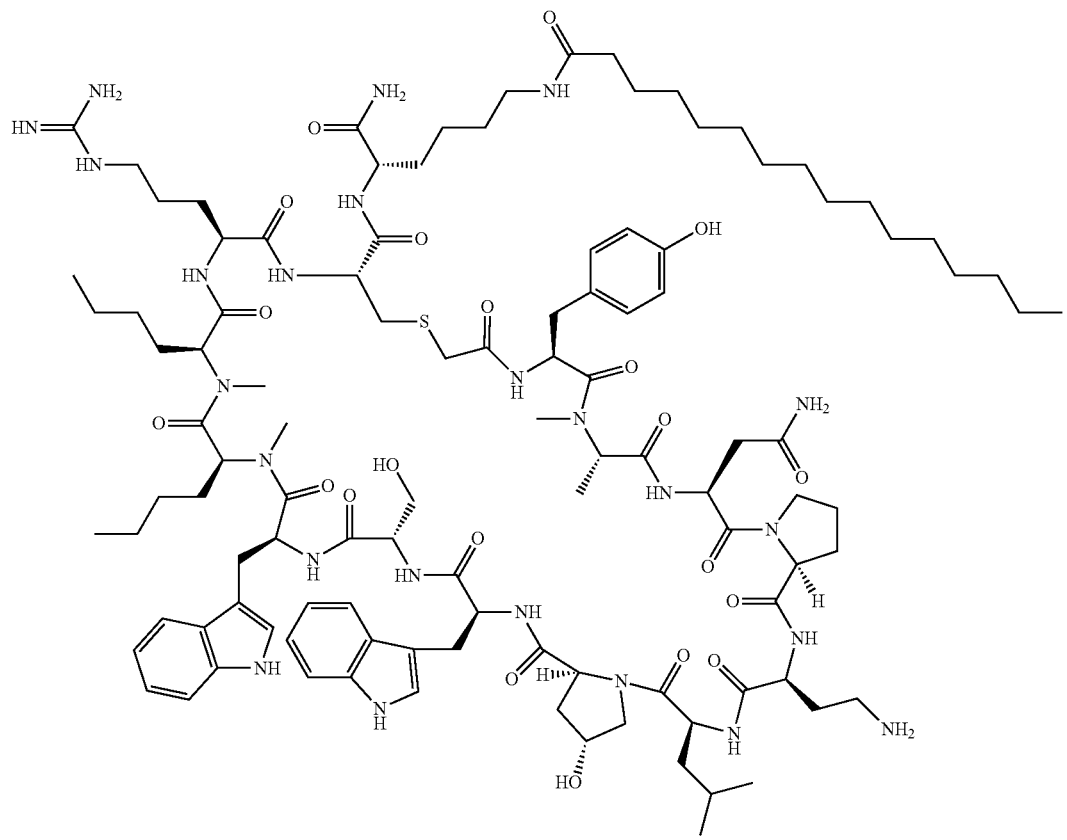 [SMILES: CCCCCCCCCCCCCCCC(=O)NCCCC[C@H](NC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11019 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 40.2 mg, and its estimated purity by LCMS analysis was 99%.

Analysis LCMS Condition A: Retention time=6.11 min; ESI-MS(+) m/z 1091.45 (M+2H).

Preparation of Example 11020

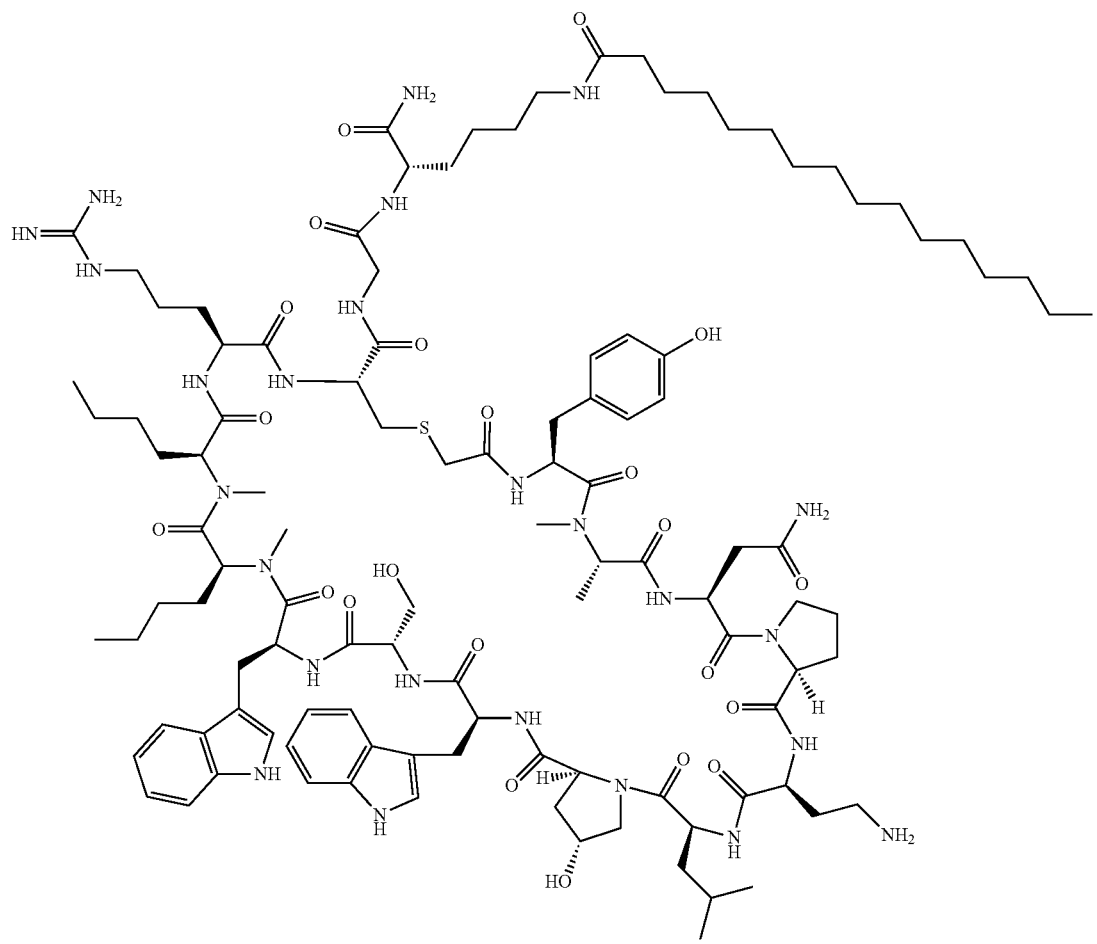 [SMILES: CCCCCCCCCCCCCCCC(=O)NCCCC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11020 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 41.0 mg, and its estimated purity by LCMS analysis was 97%.

Analysis LCMS Condition A: Retention time=5.93 min; ESI-MS(+) m/z 1119.83 (M+2H).

Preparation of Example 11021

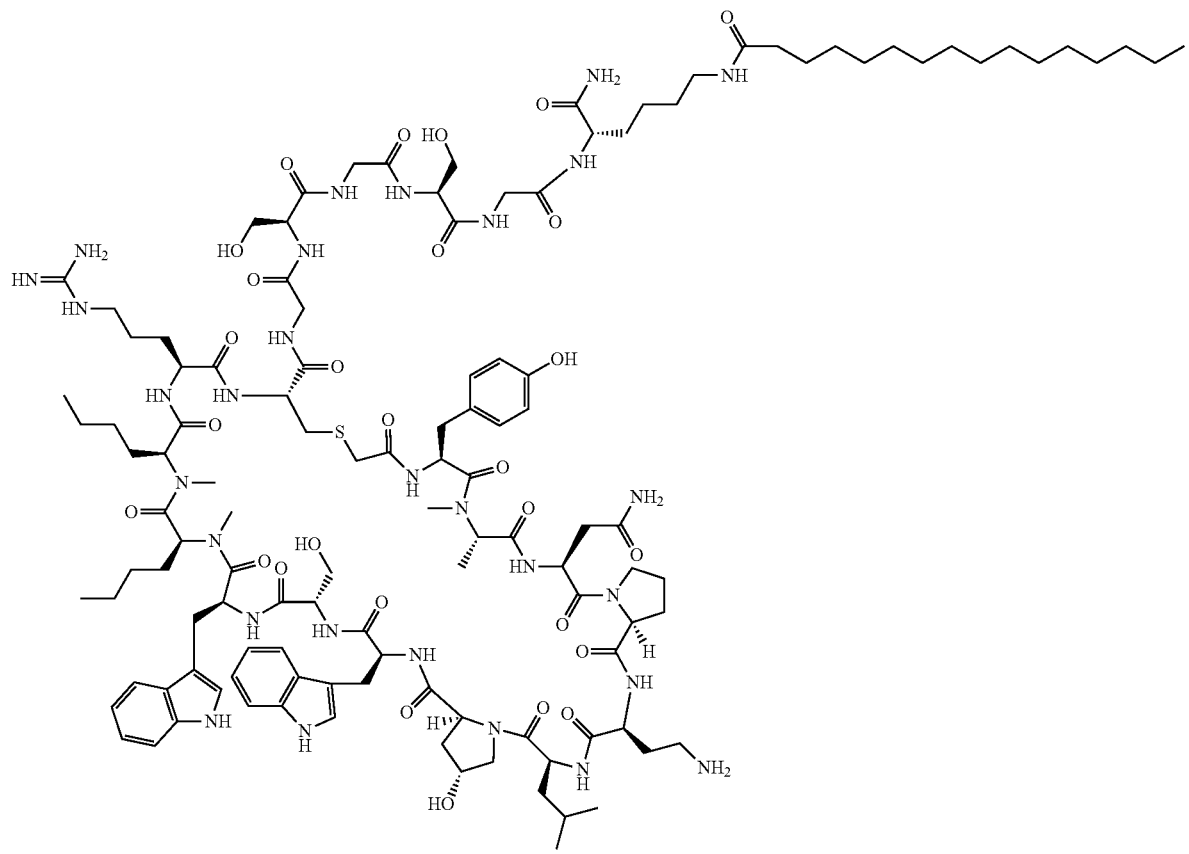 [SMILES: CCCCCCCCCCCCCCCC(=O)NCCCC[C@H](NC(=O)CNC(=O)[C@H](CO)NC(=O)CNC(=O)[C@H](CO)NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11021 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 14.4 mg, and its estimated purity by LCMS analysis was 98%.

Analysis LCMS Condition A: Retention time=6.36 min; ESI-MS(+) m/z 1265.9 (M+2H).

Preparation of Example 11022

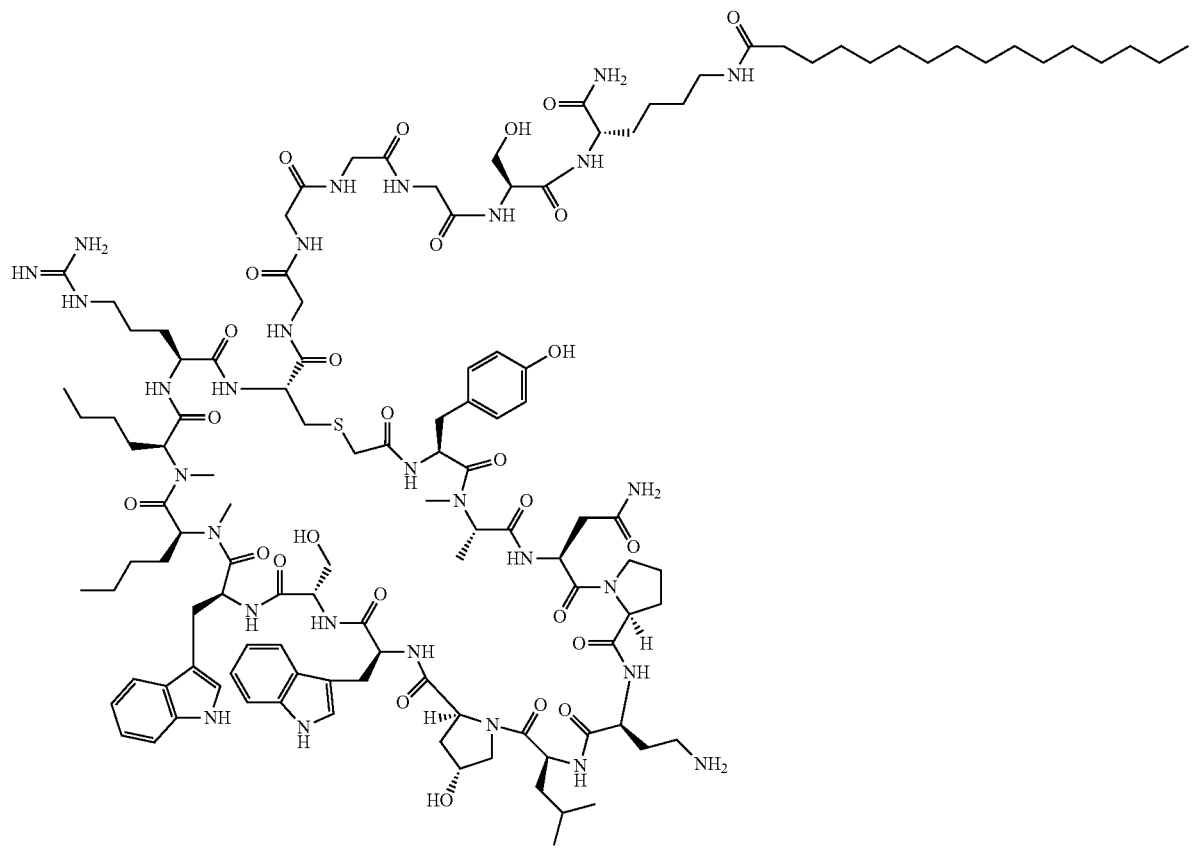 [SMILES: CCCCCCCCCCCCCCCC(=O)NCCCC[C@H](NC(=O)[C@H](CO)NC(=O)CNC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11022 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 5.7 mg, and its estimated purity by LCMS analysis was 97%.

Analysis LCMS Condition A: Retention time=6.13 min; ESI-MS(+) m/z 1250.51 (M+2H); ESI-HRMS(+) m/z: Calculated: 1249.1930 (M+2H). Found: 1249.1934 (M+2H).

Preparation of Example 11023

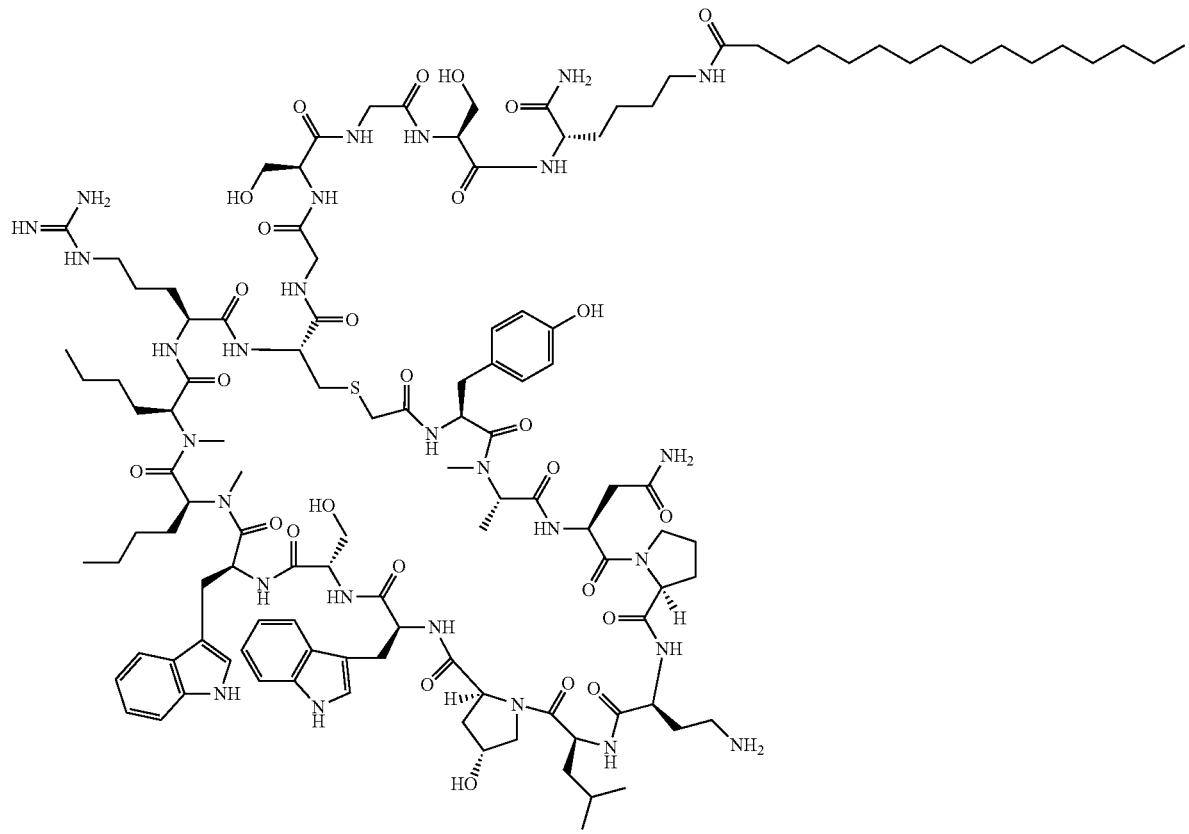 [SMILES: CCCCCCCCCCCCCCCC(=O)NCCCC[C@H](NC(=O)[C@H](CO)NC(=O)CNC(=O)[C@H](CO)NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11023 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 3.8 mg, and its estimated purity by LCMS analysis was 95%.

Analysis LCMS Condition A: Retention time=6.41 min; ESI-MS(+) m/z 1235.4 (M+2H); ESI-HRMS(+) m/z: Calculated: 1235.6878 (M+2H). Found: 1235.6832 (M+2H).

Preparation of Example 11024

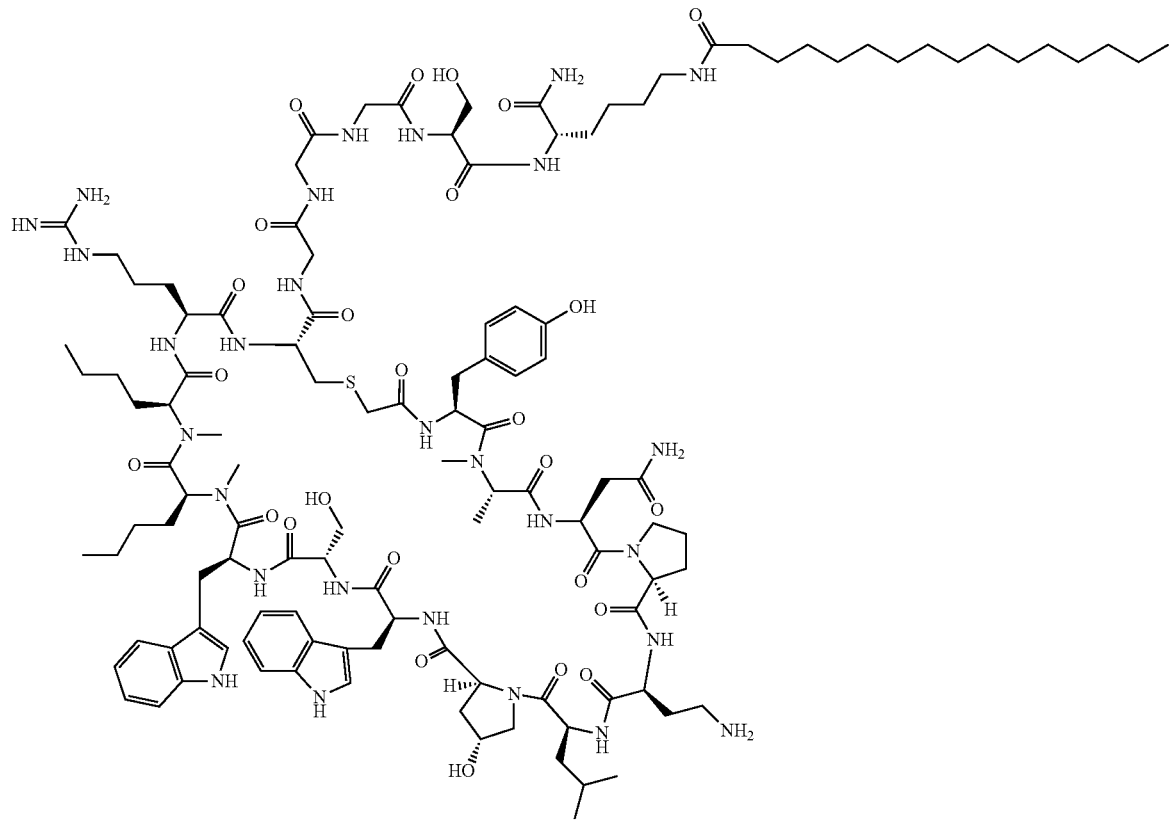 [SMILES: CCCCCCCCCCCCCCCC(=O)NCCCC[C@H](NC(=O)[C@H](CO)NC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11024 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 7.2 mg, and its estimated purity by LCMS analysis was 97%.

Analysis LCMS Condition A: Retention time=5.68 min; ESI-MS(+) m/z 1220.5 (M+2H); ESI-HRMS(+) m/z: Calculated: 1220.6823 (M+2H). Found: 1220.6810 (M+2H).

Preparation of Example 11025

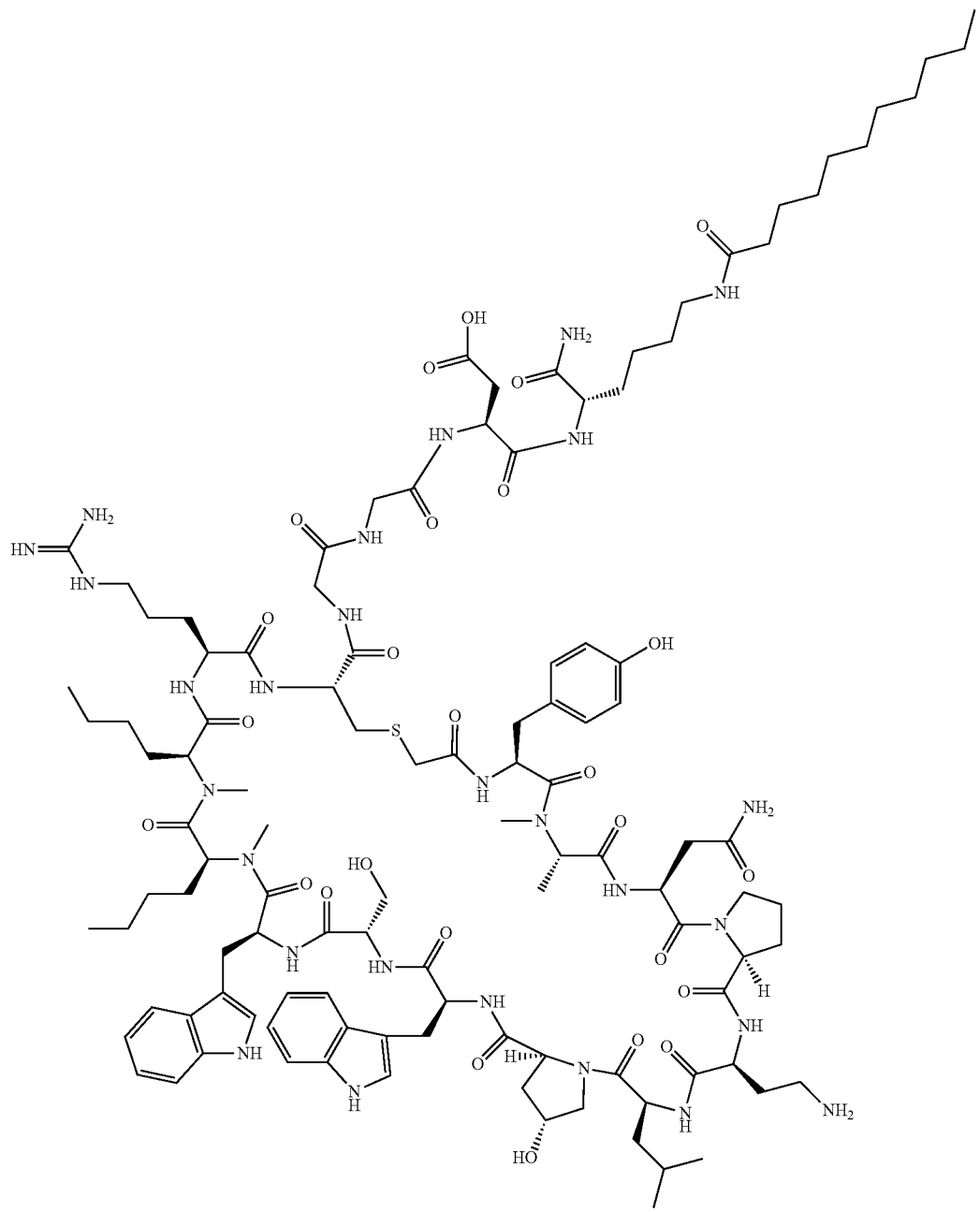 [SMILES: CCCCCCCCCCC(=O)NCCCC[C@H](NC(=O)[C@H](CC(=O)O)NC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11025 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 3.8 mg, and its estimated purity by LCMS analysis was 95%.

Analysis LCMS Condition A: Retention time=5.74 min; ESI-MS(+) m/z 1234.6 (M+2H); ESI-HRMS(+) m/z: Calculated: 1234.6798 (M+2H). Found: 1234.6796.

Preparation of Example 11026

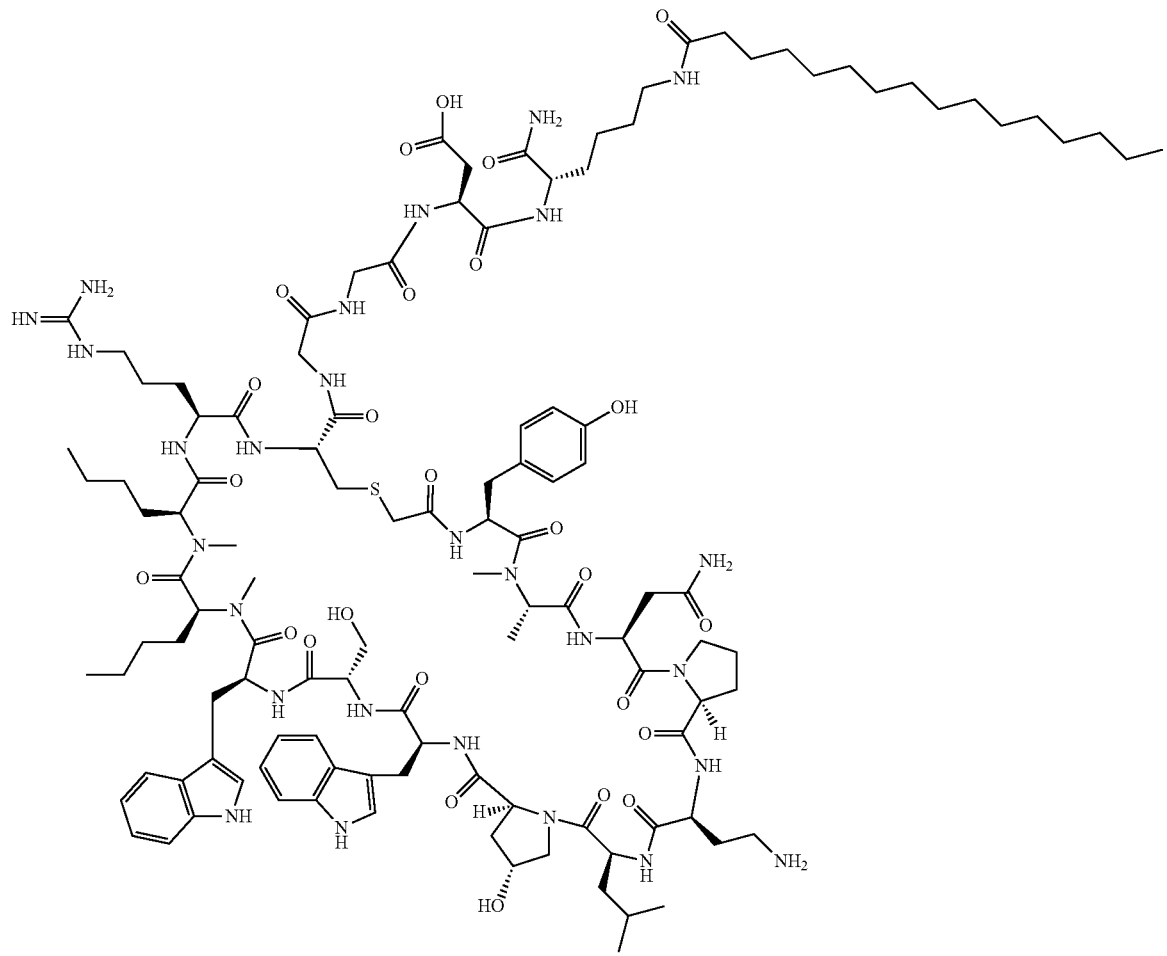 [SMILES: CCCCCCCCCCCCCCCC(=O)NCCCC[C@H](NC(=O)[C@H](CC(=O)O)NC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11026 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 11.7 mg, and its estimated purity by LCMS analysis was 99%.

Analysis LCMS Condition A: Retention time=5.81 min; ESI-MS(+) m/z 1206.0 (M+2H); ESI-HRMS(+) m/z: Calculated: 1206.1690 (M+2H). Found: 1206.1690 (M+2H).

Preparation of Example 11027

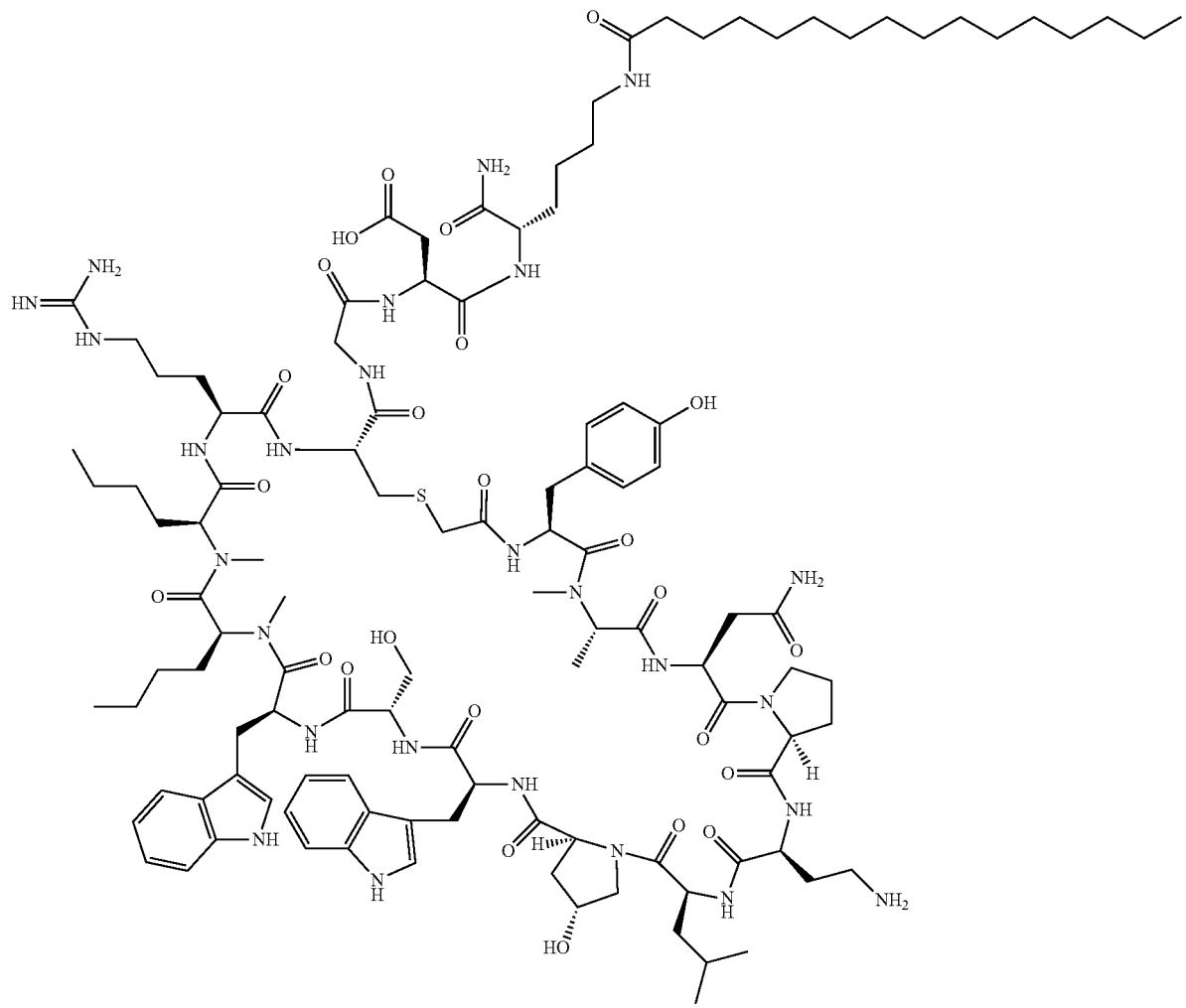 [SMILES: CCCCCCCCCCCCCCCC(=O)NCCCC[C@H](NC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11027 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 9.3 mg, and its estimated purity by LCMS analysis was 98%.

Analysis LCMS Condition A: Retention time=5.92 min; ESI-MS(+) m/z 1177.6 (M+2H); ESI-HRMS(+) m/z: Calculated: 1177.6583 (M+2H). Found: 1177.6585 (M+2H).

Preparation of Example 11028

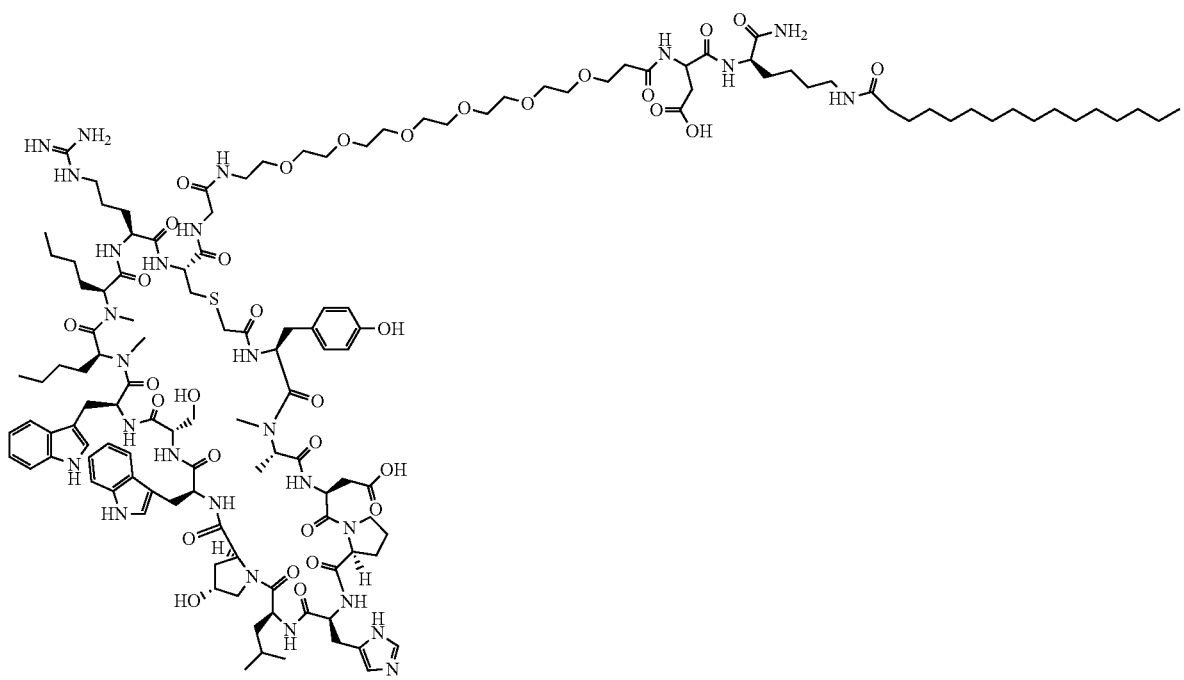 [SMILES: CCCCCCCCCCCCCCCC(=O)NCCCC[C@@H](NC(=O)C(CC(=O)O)NC(=O)CCOCCOCCOCCOCCOCCOCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11028 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 7.8 mg, and its estimated purity by LCMS analysis was 98%. Analysis LCMS Condition A: Retention time=5.57 min; ESI-MS(+) m/z 1363.2 (M+2H).

Preparation of Example 11029

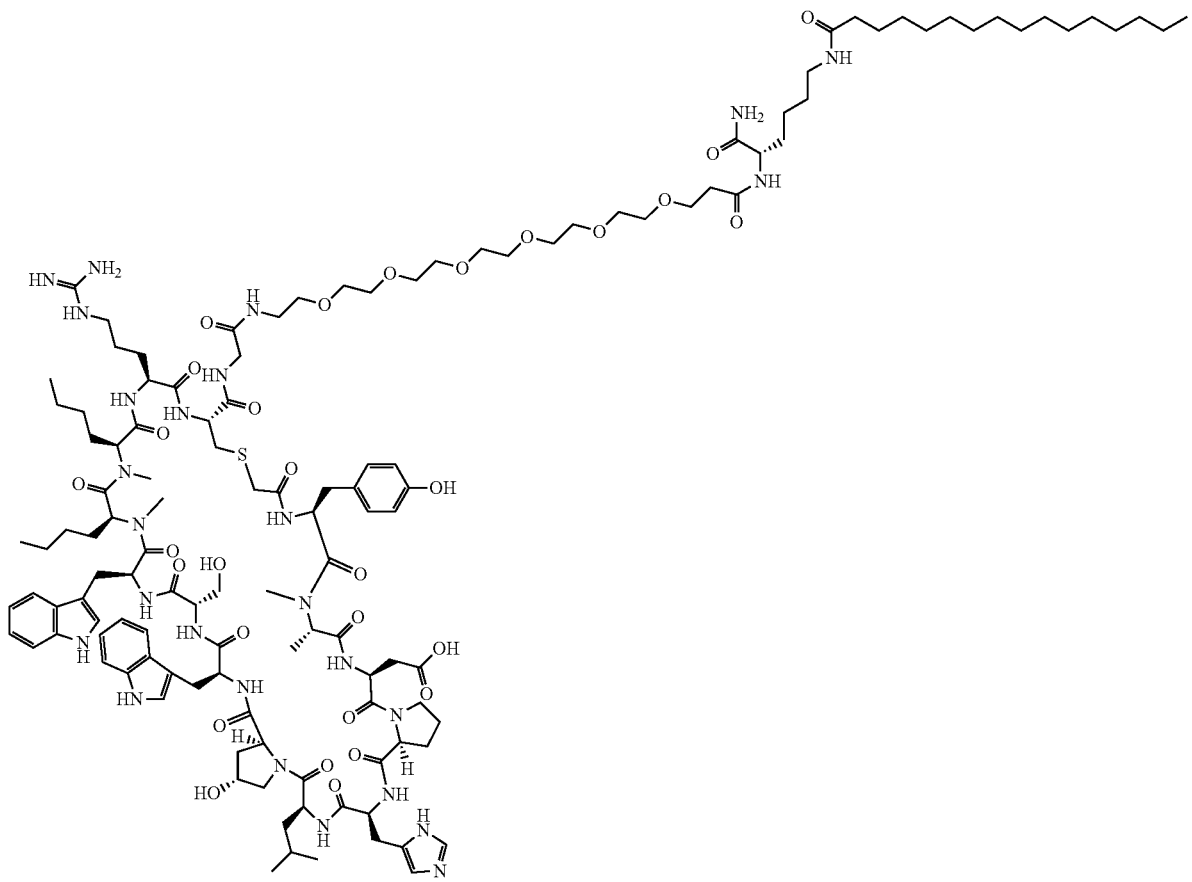 [SMILES: CCCCCCCCCCCCCCCC(=O)NCCCC[C@H](NC(=O)CCOCCOCCOCCOCCOCCOCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11029 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 16.7 mg, and its estimated purity by LCMS analysis was 99%. Analysis LCMS Condition A: Retention time=6.01 min; ESI-MS(+) m/z 1306.8 (M+2H).

Preparation of Example 11030

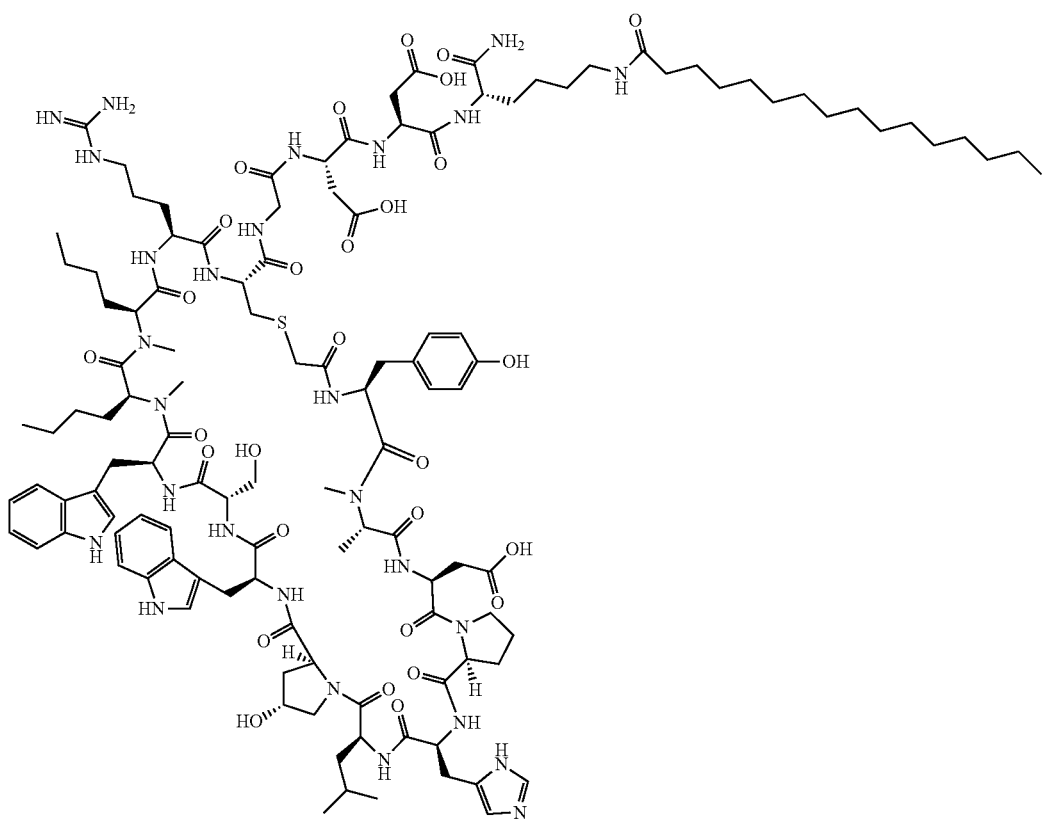 [SMILES: CCCCCCCCCCCCCCCC(=O)NCCCC[C@H](NC(=O)[C@H](CC(=O)O)NC(=O)[C@H](CC(=O)O)NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O]

Example 11030 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 7.2 mg, and its estimated purity by LCMS analysis was 95%. Analysis LCMS Condition A: Retention time=5.40 min; ESI-MS(+) m/z 1153.4 (M+2H).

Preparation of Example 11031

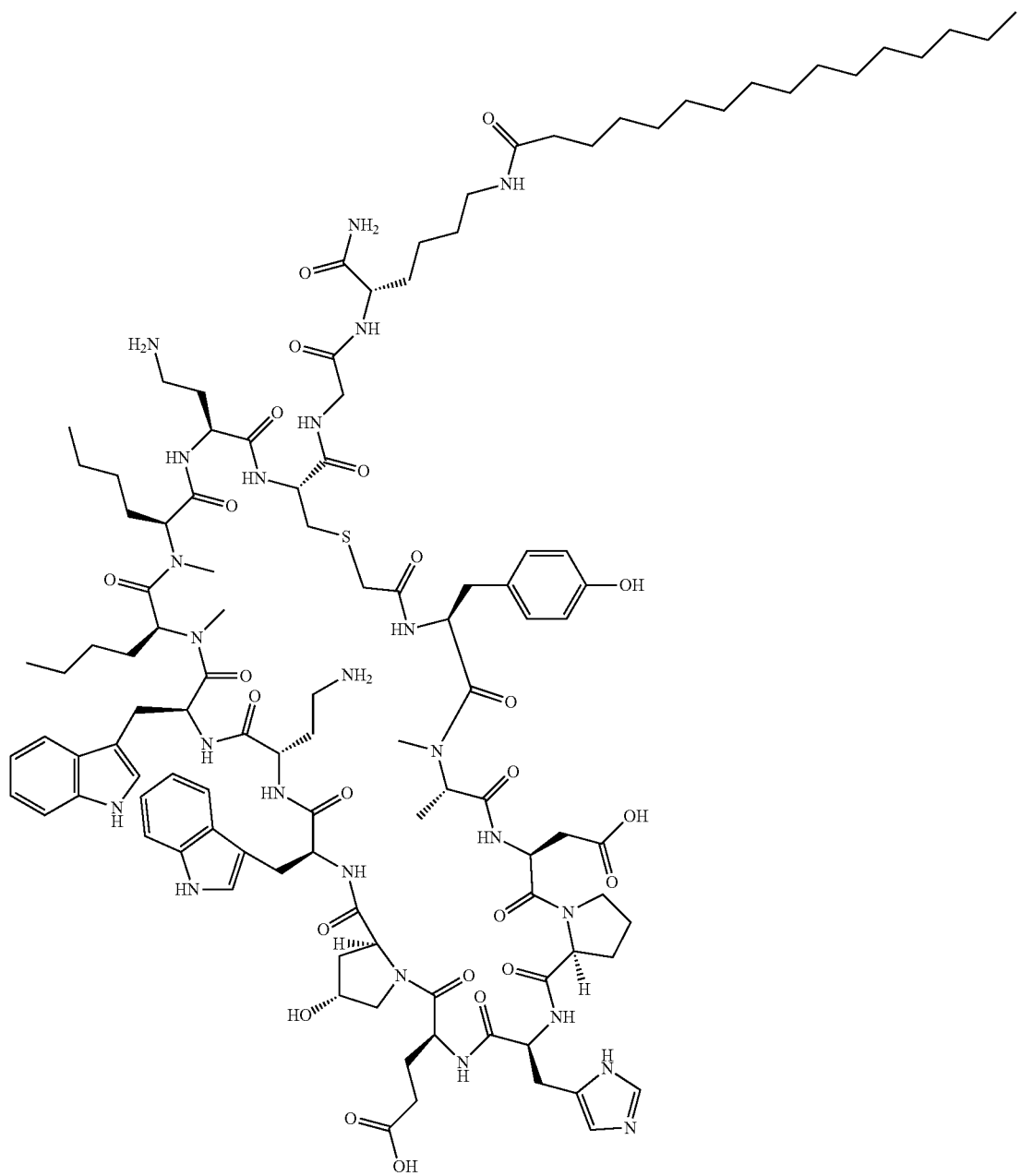 [SMILES: CCCCCCCCCCCCCCCC(=O)NCCCC[C@H](NC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N(C)[C@@H](CCCC)C(=O)N(C)[C@@H](CCCC)C(=O)N[C@@H](CCN)C(=O)N1)C(N)=O]

Example 11031 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 30 mL/min. Fractions containing the desired product were combined and dried via centrifugal evaporation. The yield of the product was 13.0 mg, and its estimated purity by LCMS analysis was 99%.

Analysis LCMS Condition A: Retention time=5.88 min; ESI-MS(+) m/z 1125.1 (M+2H).

Preparation of Example 11032

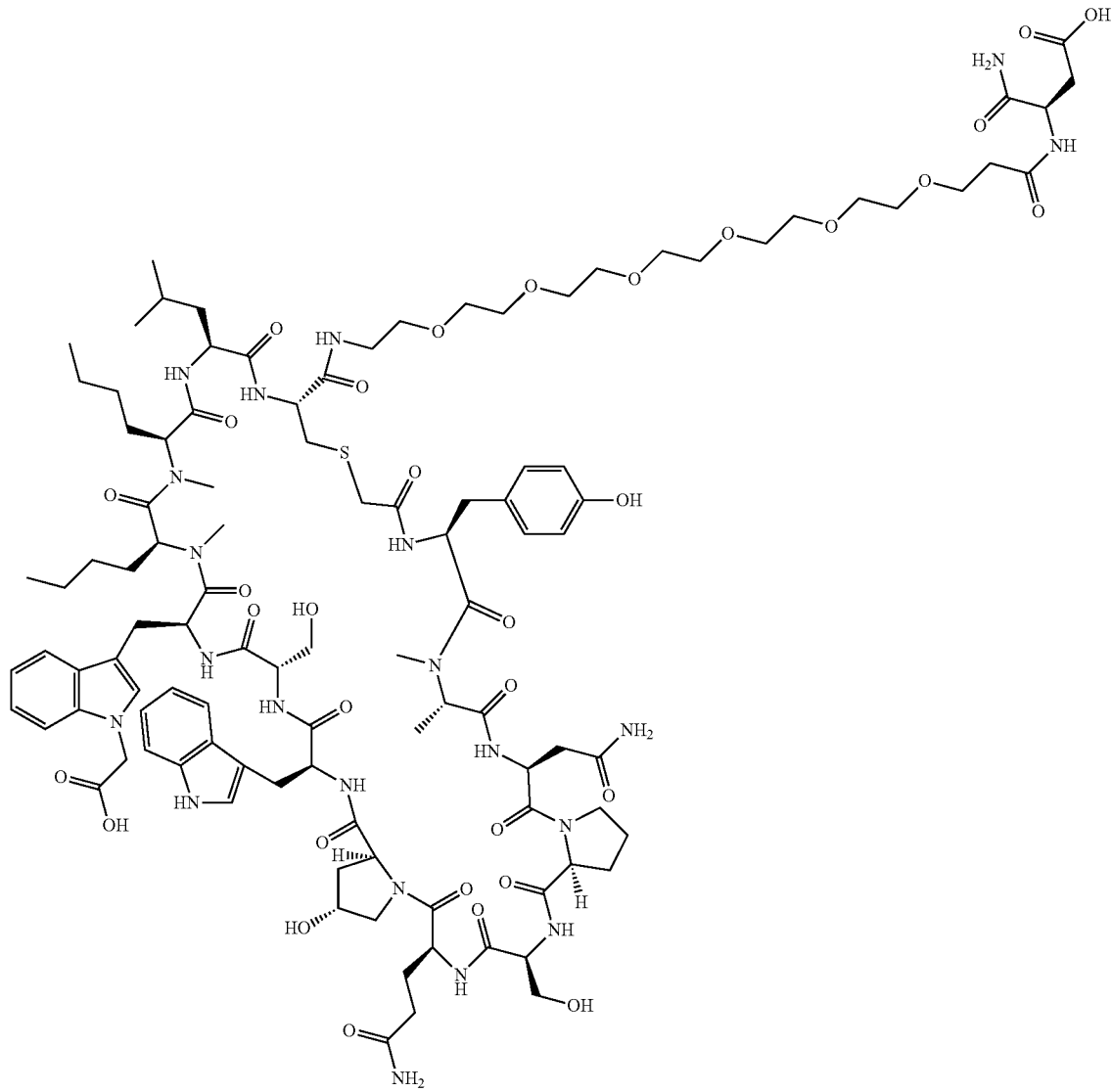 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)N[C@H](CC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11032 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 14.4 mg, and its estimated purity by LCMS analysis was 98%. Analysis LCMS Condition A: Retention time=2.99 min; ESI-MS(+) m/z 1442.3 (M+2H).

Preparation of Example 11033

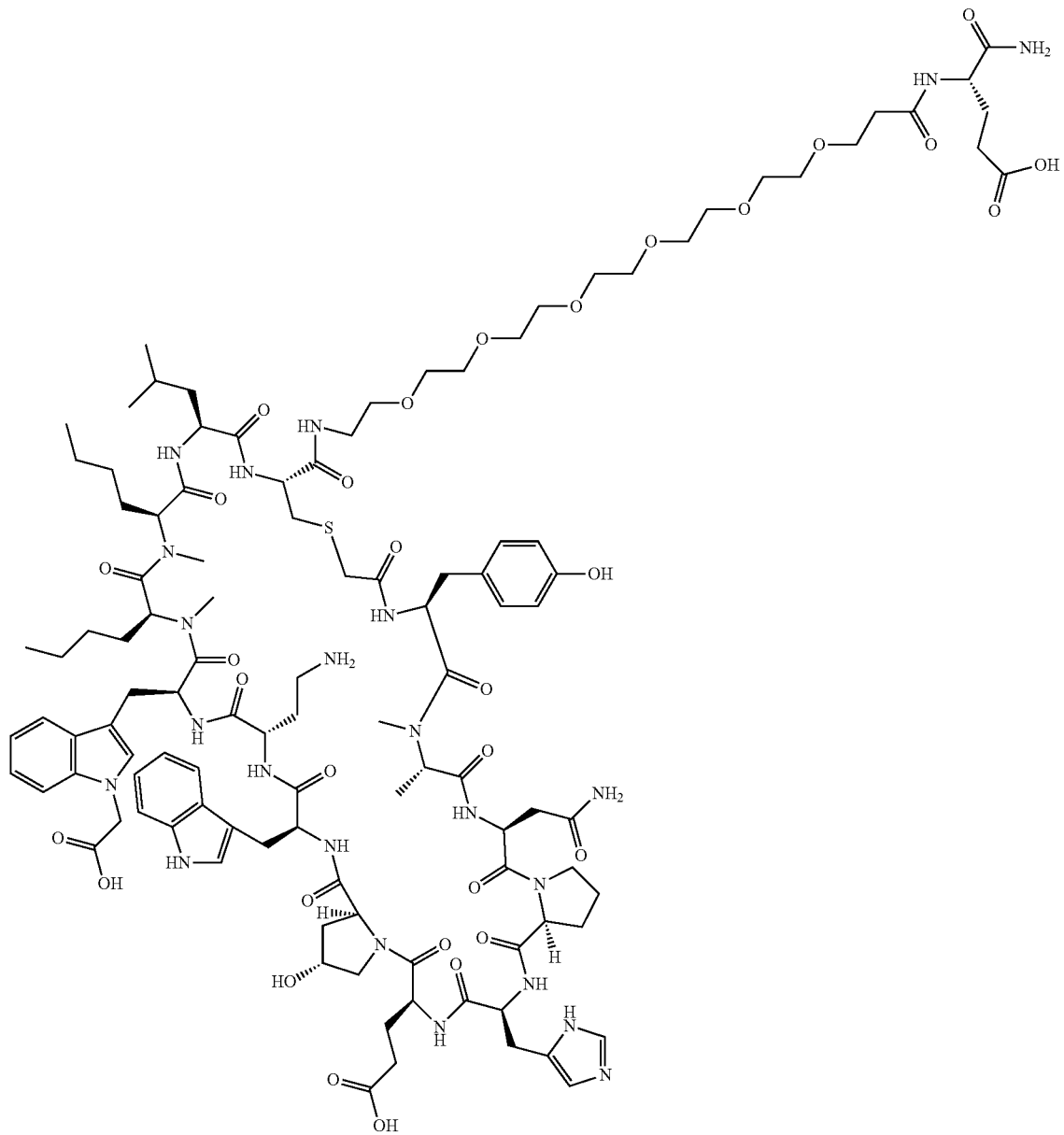 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)N[C@@H](CCC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11034 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method X". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 20.7 mg, and its estimated purity by LCMS analysis was 99%. Analysis LCMS Condition A: Retention time=3.26 min; ESI-MS(+) m/z 1181.4 (M+2H); ESI-HRMS(+) m/z: Calculated: 1181.0772 (M+2H).

Found: 1181.0757 (M+2H).

Preparation of Example 11034

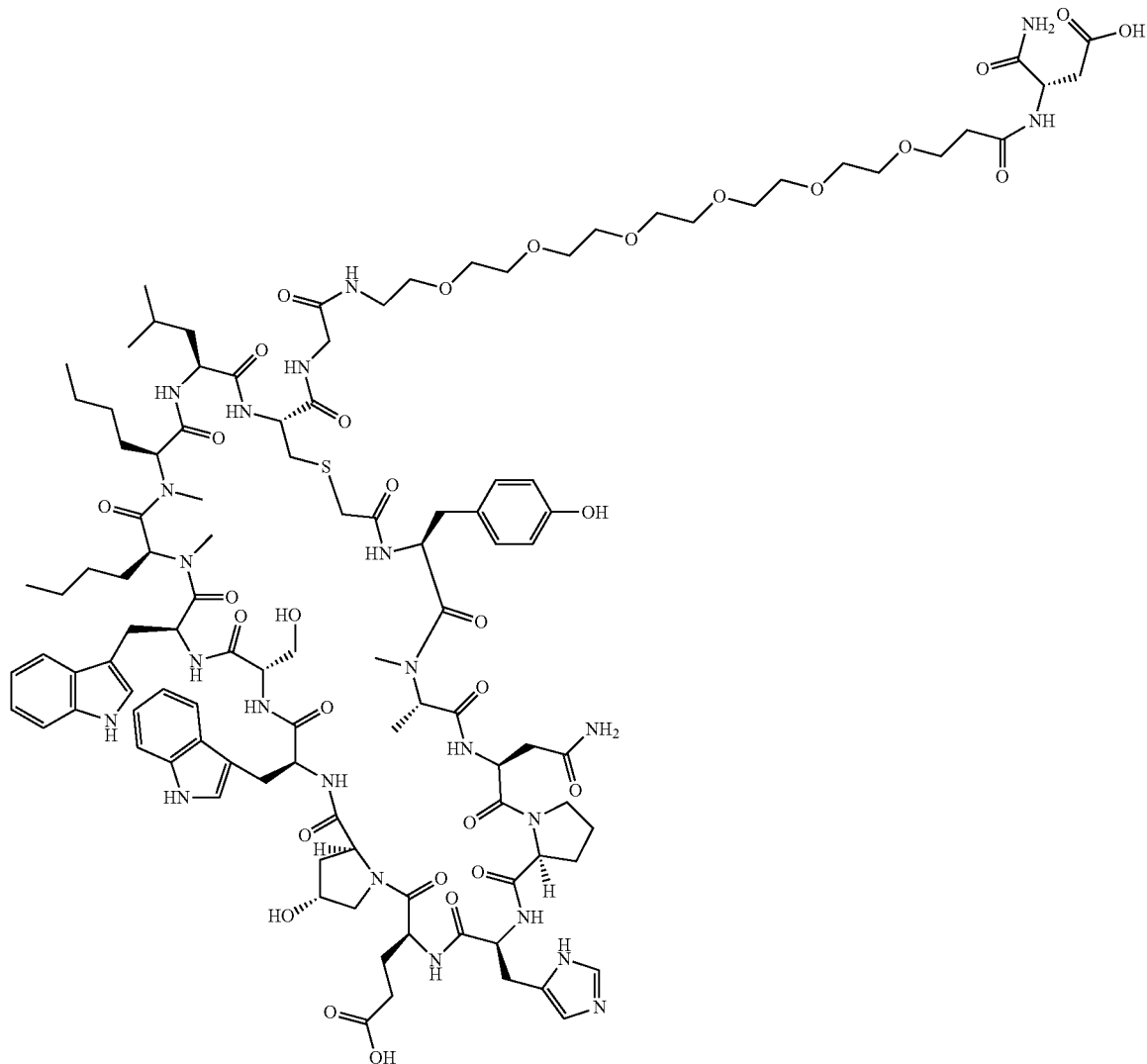 [SMILES: CCCC[C@H]1C(=O)N(C)[C@@H](CCCC)C(=O)N[C@@H](CC(C)C)C(=O)N[C@H](C(=O)NCC(=O)NCCOCCOCCOCCOCCOCCOCCC(=O)N[C@@H](CC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11034 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 20.8 mg, and its estimated purity by LCMS analysis was 98%. Analysis LCMS Condition A: Retention time=3.63 min; ESI-MS(+) m/z 1168.0 (M+2H); ESI-HRMS(+) m/z: Calculated: 1167.0616 (M+2H).

Found: 1167.0624 (M+2H).

Preparation of Example 11035

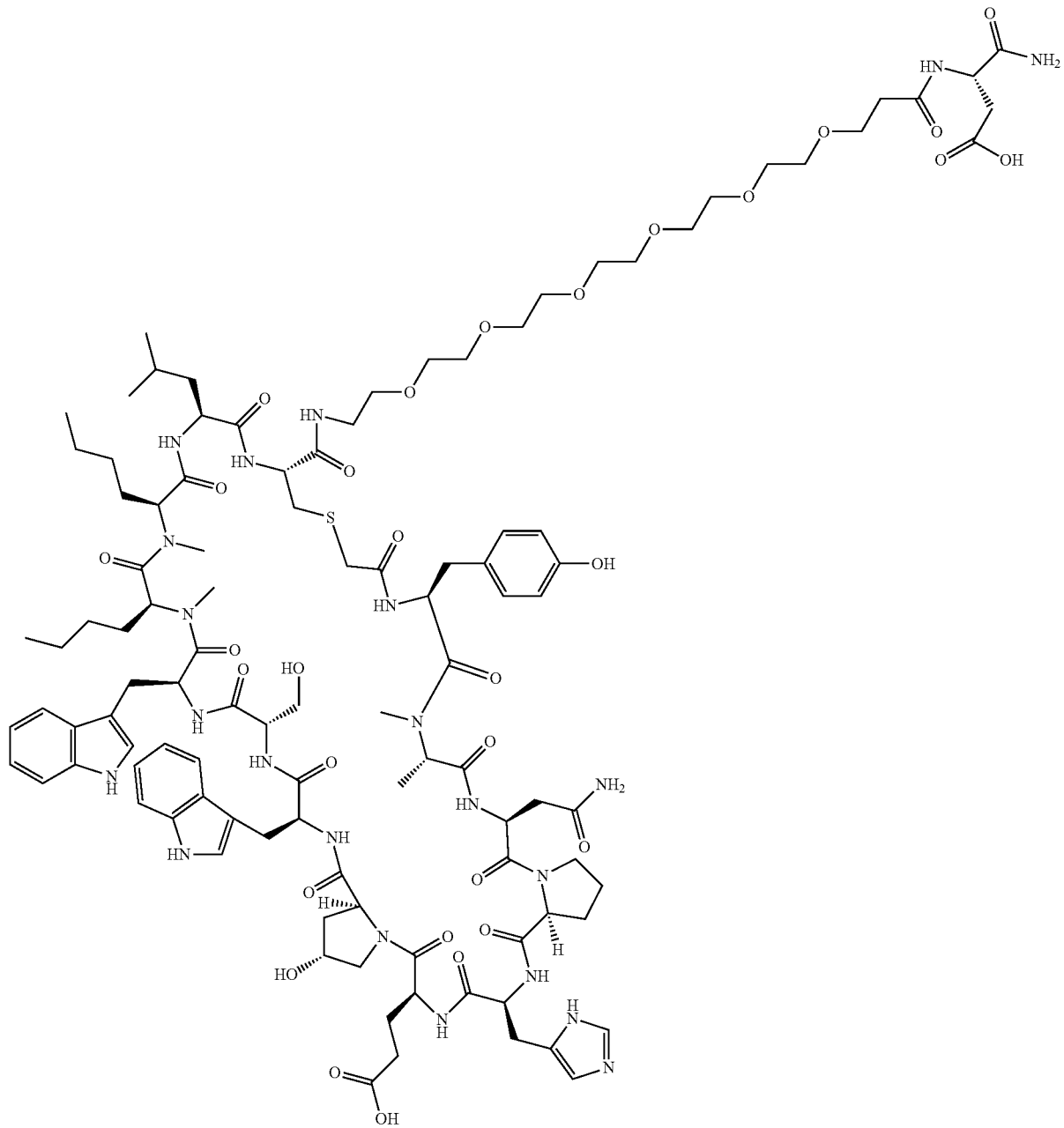 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)N[C@@H](CC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11035 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 33.2 mg, and its estimated purity by LCMS analysis was 98%. Analysis LCMS Condition A: Retention time=3.63 min; ESI-MS(+) m/z 1138.4 (M+2H); ESI-HRMS(+) m/z: Calculated: 1138.5517 (M+2H).

Found: 1138.5508 (M+2H).

Preparation of Example 11036

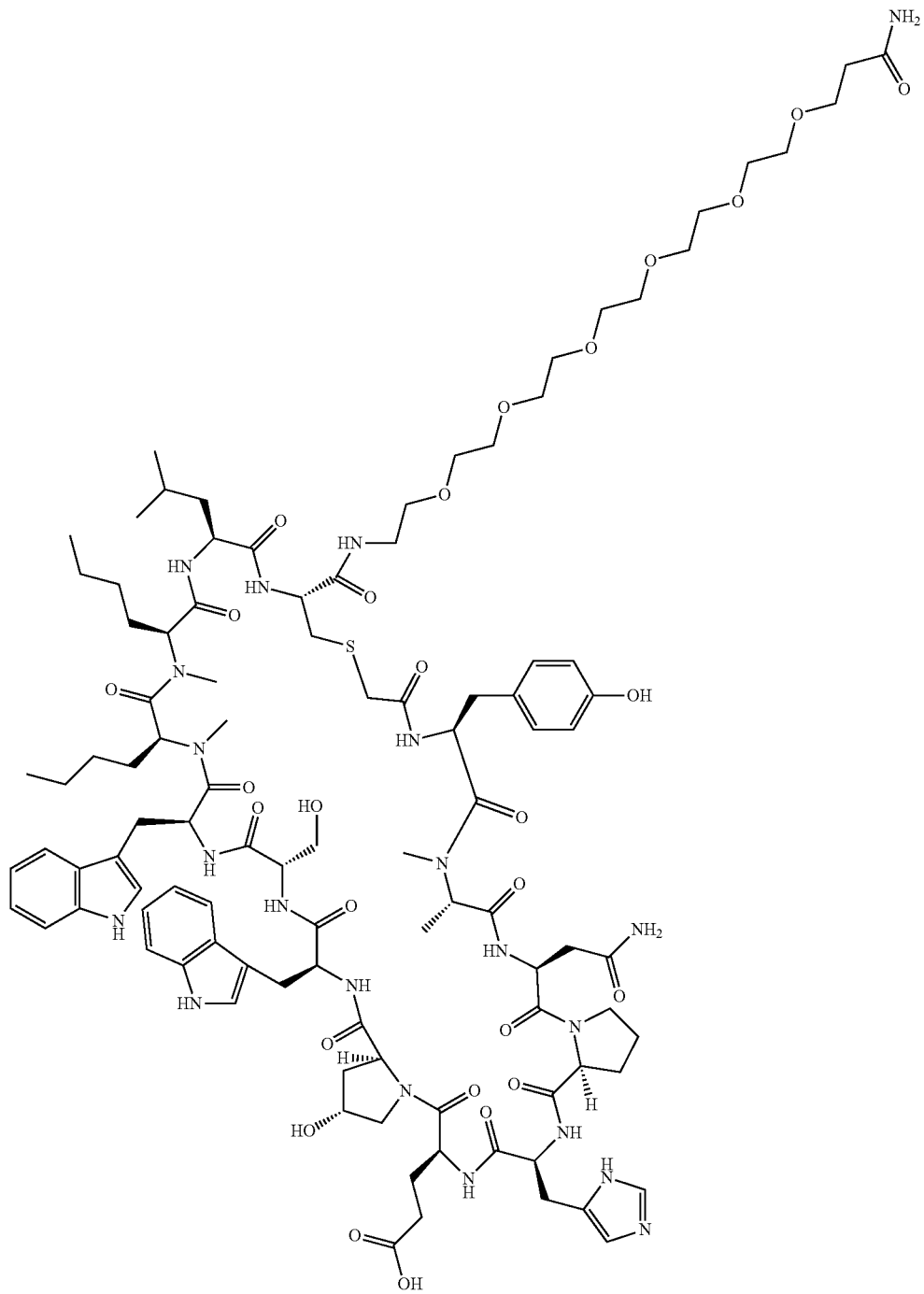 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11036 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 12.2 mg, and its estimated purity by LCMS analysis was 98%. Analysis LCMS Condition A: Retention time=3.88 min; ESI-MS(+) m/z 1081.9 (M+2H); ESI-HRMS(+) m/z: Calculated: 1081.0374 (M+2H). Found: 1081.0358 (M+2H).

Preparation of Example 11037

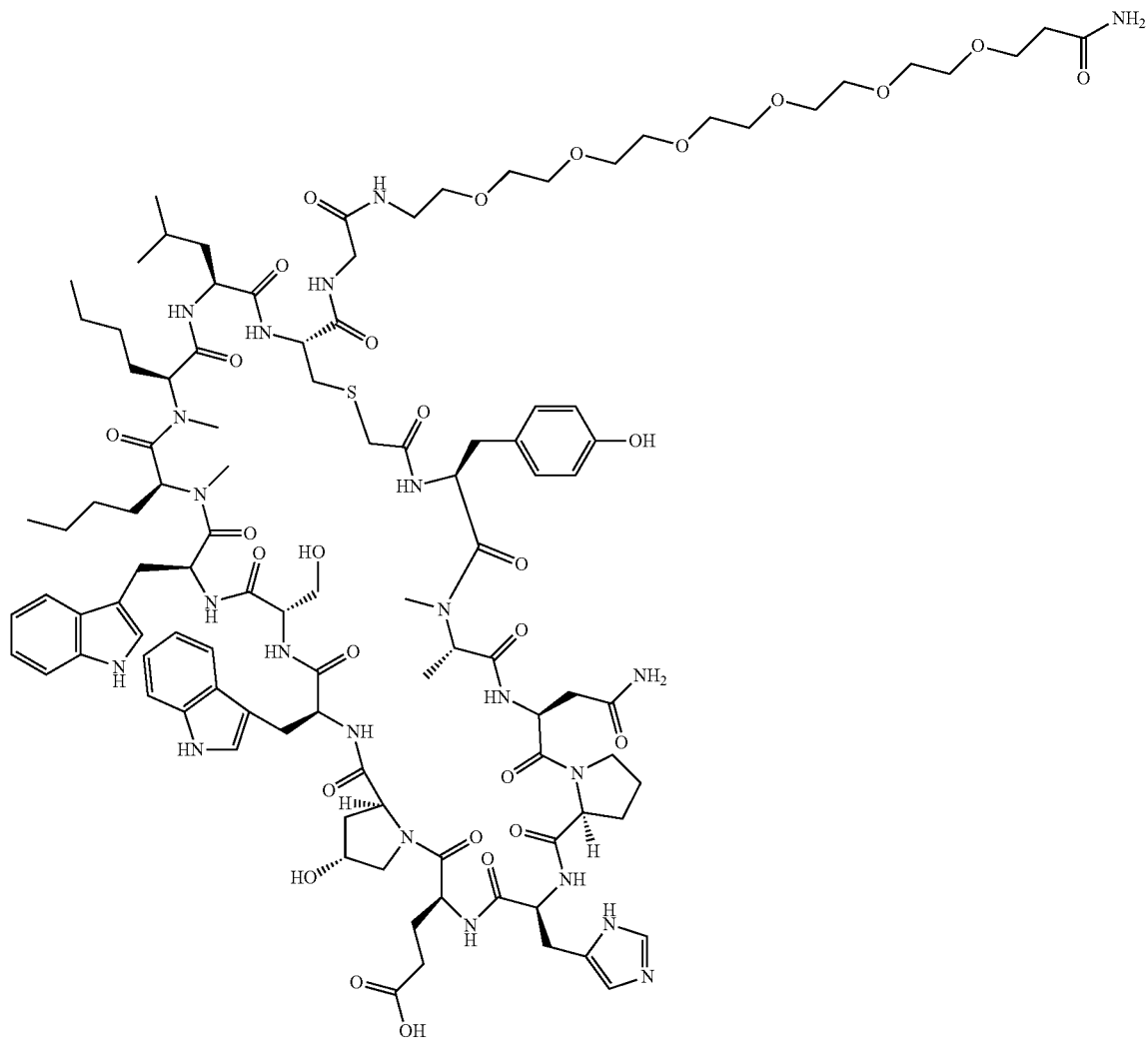 [SMILES: CCCC[C@H]1C(=O)N(C)[C@@H](CCCC)C(=O)N[C@@H](CC(C)C)C(=O)N[C@H](C(=O)NCC(=O)NCCOCCOCCOCCOCCOCCOCCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11037 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 11.4 mg, and its estimated purity by LCMS analysis was 98%. Analysis LCMS Condition A: Retention time=3.91 min; ESI-MS(+) m/z 1109.6 (M+2H); ESI-HRMS(+) m/z: Calculated: 1109.5481 (M+2H).

Found: 1109.5472 (M+2H).

Preparation of Example 11038

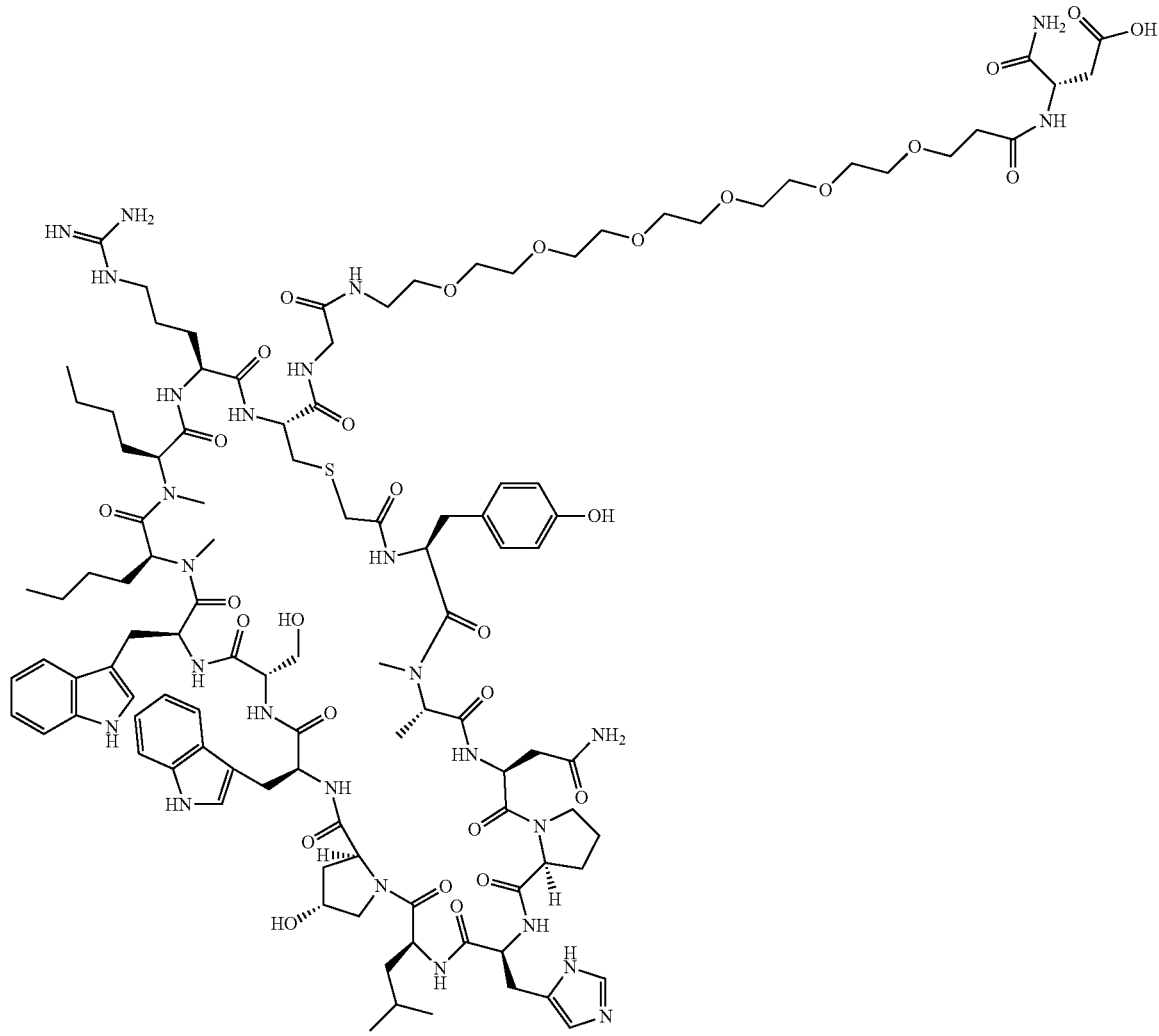 [SMILES: CCCC[C@H]1C(=O)N(C)[C@@H](CCCC)C(=O)N[C@@H](CCCNC(=N)N)C(=O)N[C@H](C(=O)NCC(=O)NCCOCCOCCOCCOCCOCCOCCC(=O)N[C@@H](CC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11038 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 18.7 mg, and its estimated purity by LCMS analysis was 98%. Analysis LCMS Condition A: Retention time=3.55 min; ESI-MS(+) m/z 1182.1 (M+2H); ESI-HRMS(+) m/z: Calculated: 1181.0828 (M+2H). Found: 1181.0816 (M+2H).

Preparation of Example 11039

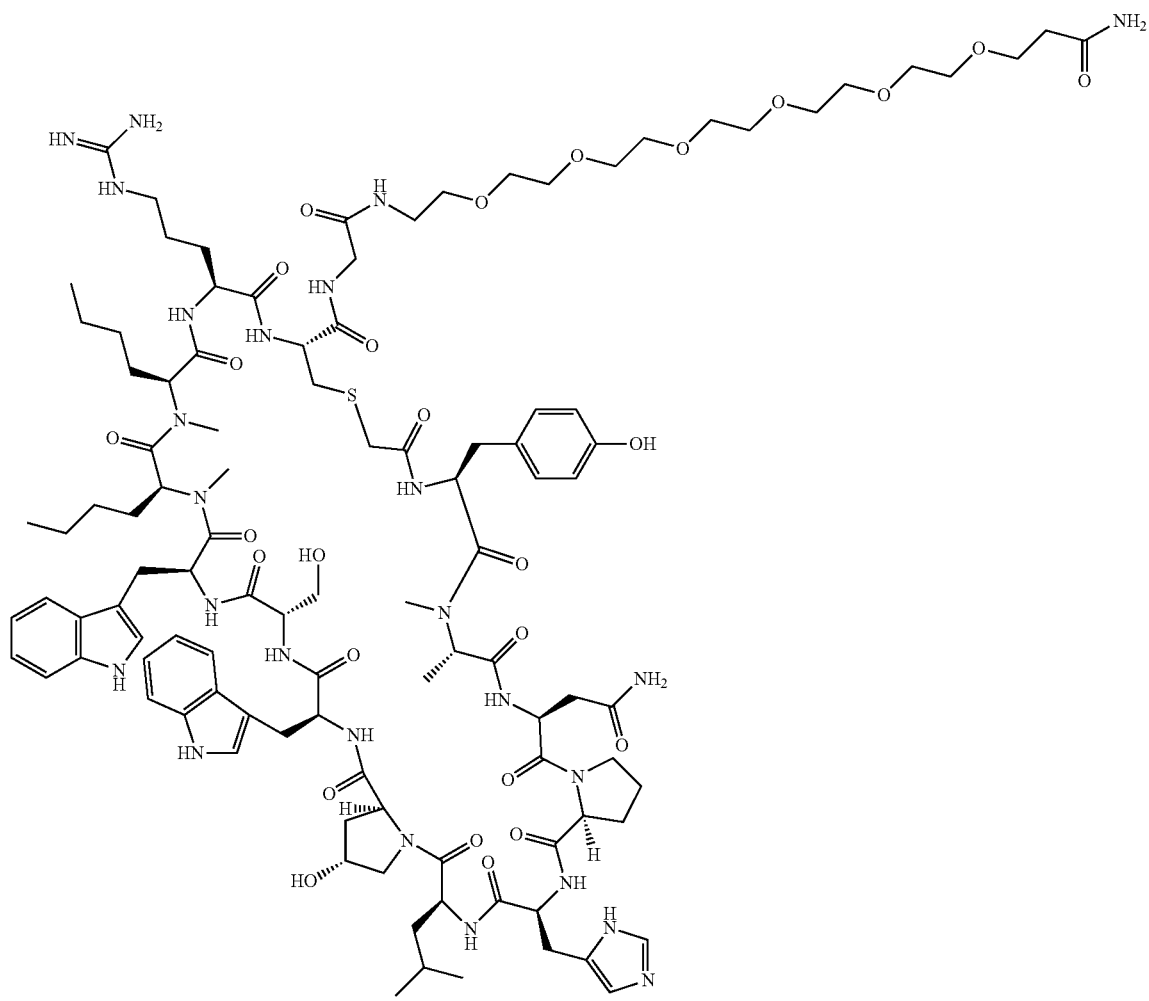 [SMILES: CCCC[C@H]1C(=O)N(C)[C@@H](CCCC)C(=O)N[C@@H](CCCNC(=N)N)C(=O)N[C@H](C(=O)NCC(=O)NCCOCCOCCOCCOCCOCCOCCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11039 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 13.7 mg, and its estimated purity by LCMS analysis was 98%. Analysis LCMS Condition A: Retention time=3.69 min; ESI-MS(+) m/z 1123.6 (M+2H); ESI-HRMS(+) m/z: Calculated: 1123.5677 (M+2H).

Found: 1123.5694 (M+2H).

Preparation of Example 11040

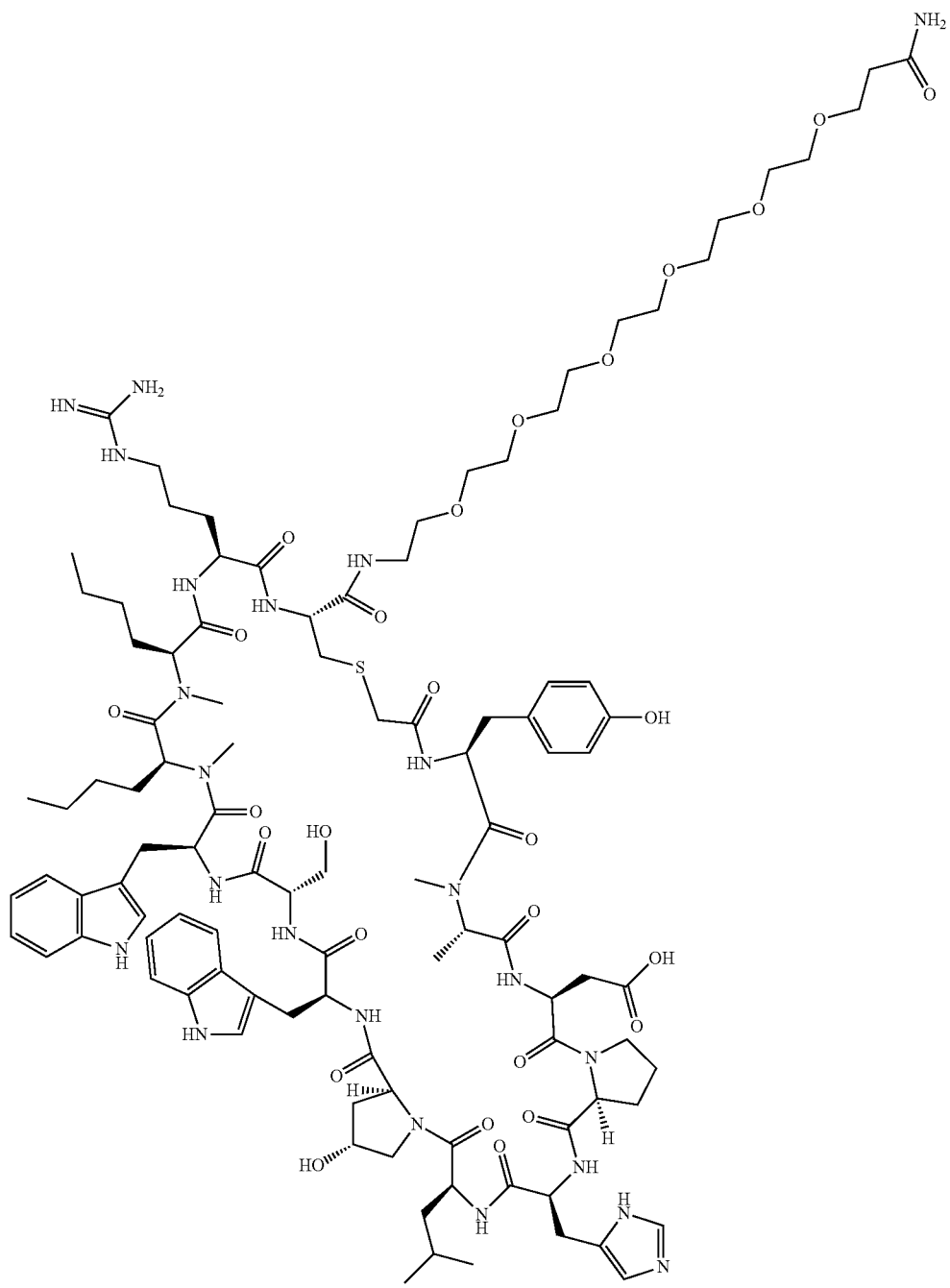 [SMILES: CCCC[C@H]1C(=O)N(C)[C@@H](CCCC)C(=O)N[C@@H](CCCNC(=N)N)C(=O)N[C@H](C(=O)NCCOCCOCCOCCOCCOCCOCCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11040 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 19.5 mg, and its estimated purity by LCMS analysis was 98%. Analysis LCMS Condition A: Retention time=3.69 min; ESI-MS(+) m/z 1096.0 (M+2H); ESI-HRMS(+) m/z: Calculated: 1095.0586 (M+2H).

Found: 1095.0567 (M+2H).

Preparation of Example 11041

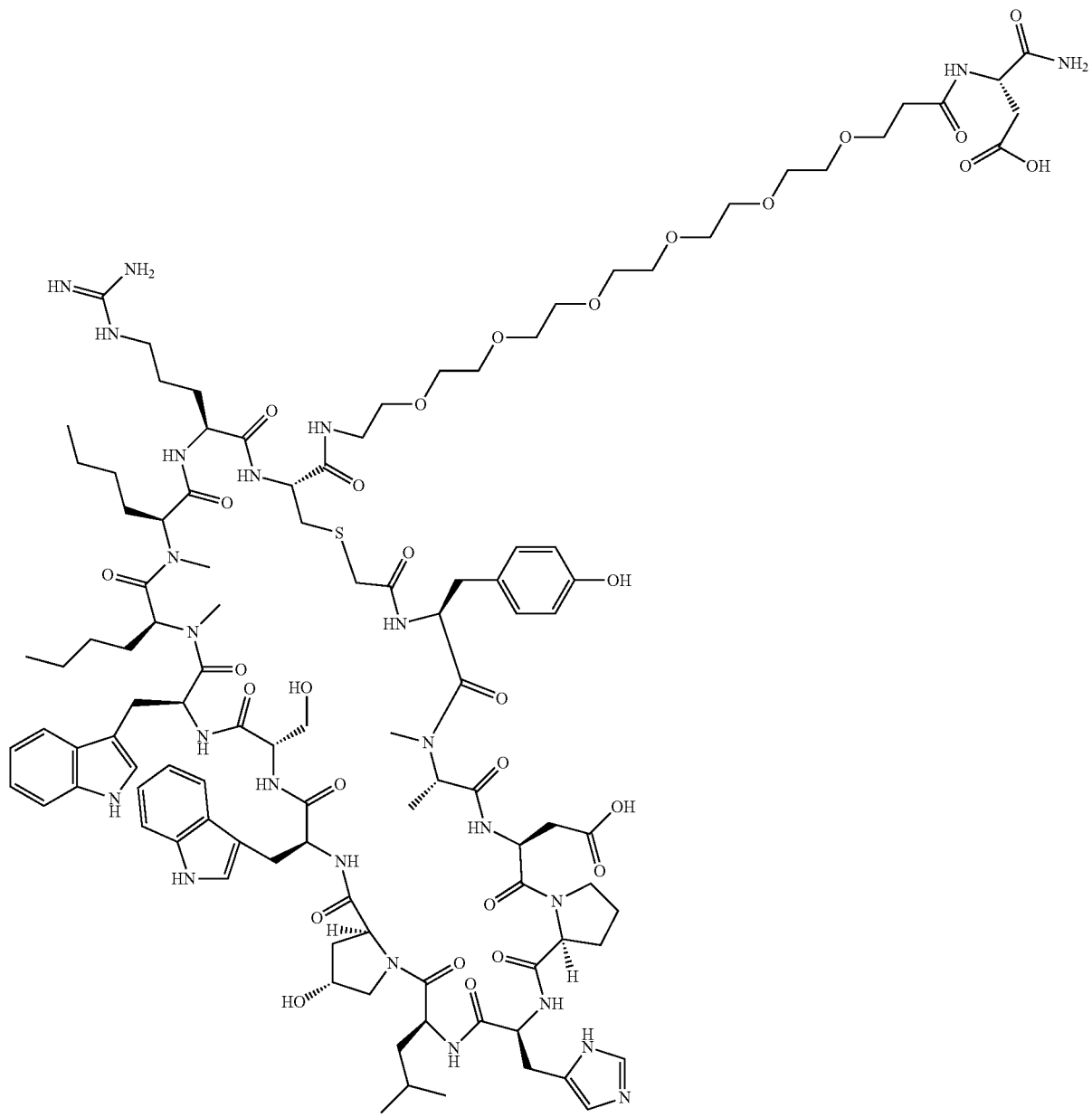 [SMILES: CCCC[C@H]1C(=O)N(C)[C@@H](CCCC)C(=O)N[C@@H](CCCNC(=N)N)C(=O)N[C@H](C(=O)NCCOCCOCCOCCOCCOCCOCCC(=O)N[C@@H](CC(=O)O)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11041 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 21.7 mg, and its estimated purity by LCMS analysis was 97%. Analysis LCMS Condition A: Retention time=3.50 min; ESI-MS(+) m/z 1153.7 (M+2H); ESI-HRMS(+) m/z: Calculated: 1152.5721 (M+2H).

Found: 1153.5719 (M+2H).

Preparation of Example 11042

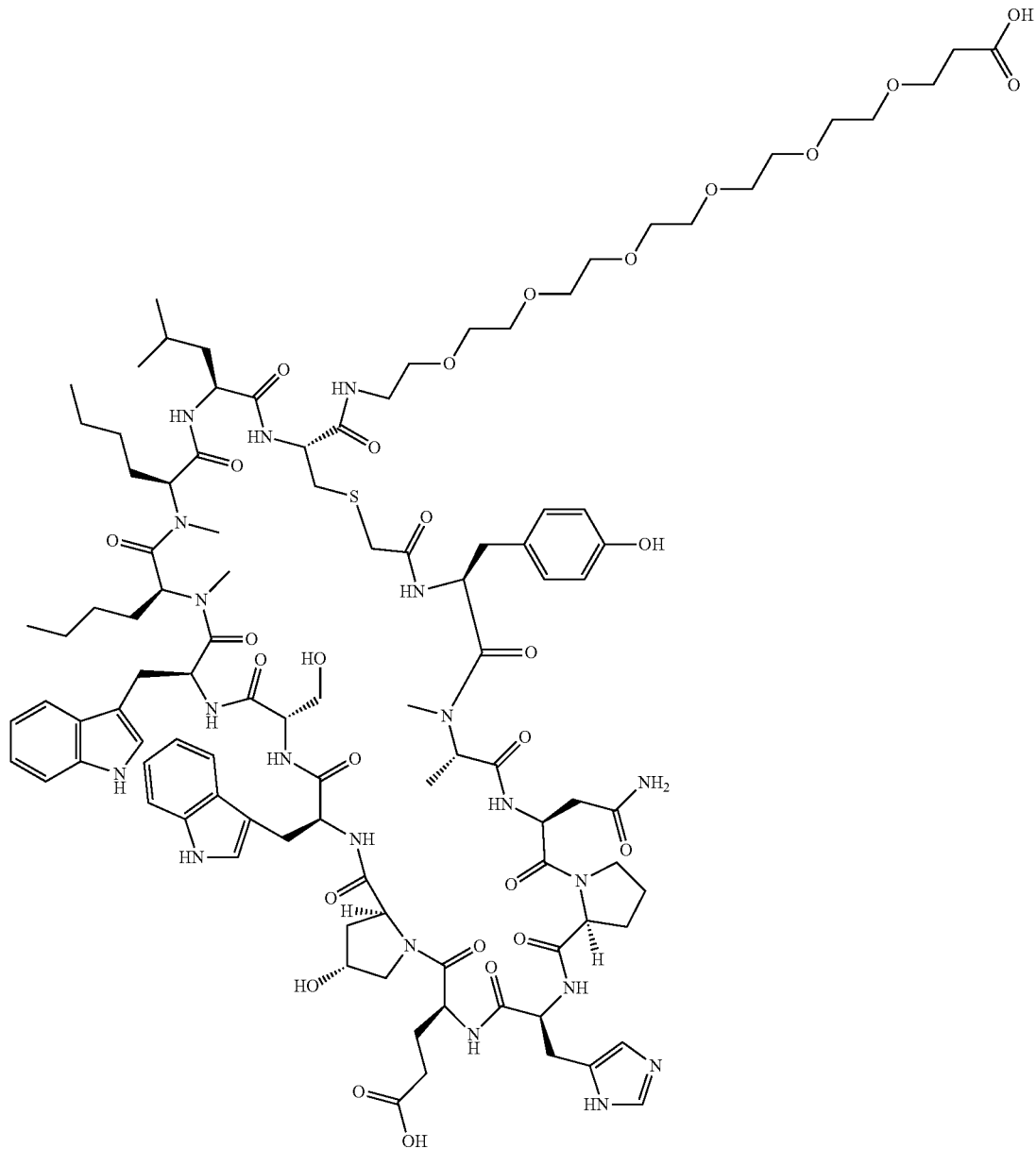 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11042 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 21.3 mg, and its estimated purity by LCMS analysis was 98%.

Analysis LCMS Condition A: Retention time=3.66 min; ESI-MS(+) m/z 1081.5 (M+2H); ESI-HRMS(+) m/z: Calculated: 1081.5294 (M+2H). Found: 1081.5288 (M+2H).

Preparation of Example 11043

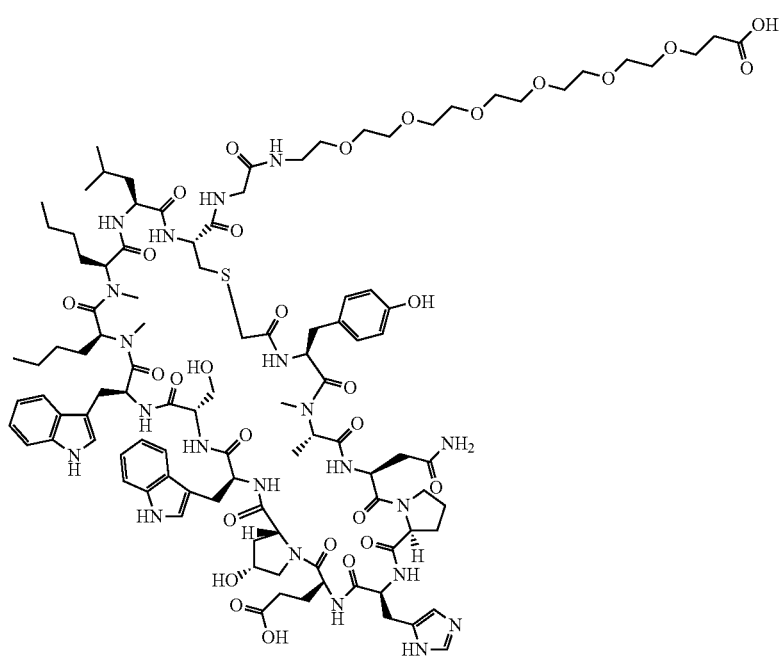 [SMILES: CCCC[C@H]1C(=O)N(C)[C@@H](CCCC)C(=O)N[C@@H](CC(C)C)C(=O)N[C@H](C(=O)NCC(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11043 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 20.7 mg, and its estimated purity by LCMS analysis was 97%.

Analysis LCMS Condition A: Retention time=3.66 min; ESI-MS(+) m/z 1110.8 (M+2H); ESI-HRMS(+) m/z: Calculated: 1110.0401 (M+2H). Found: 1110.0392 (M+2H).

Preparation of Example 11044

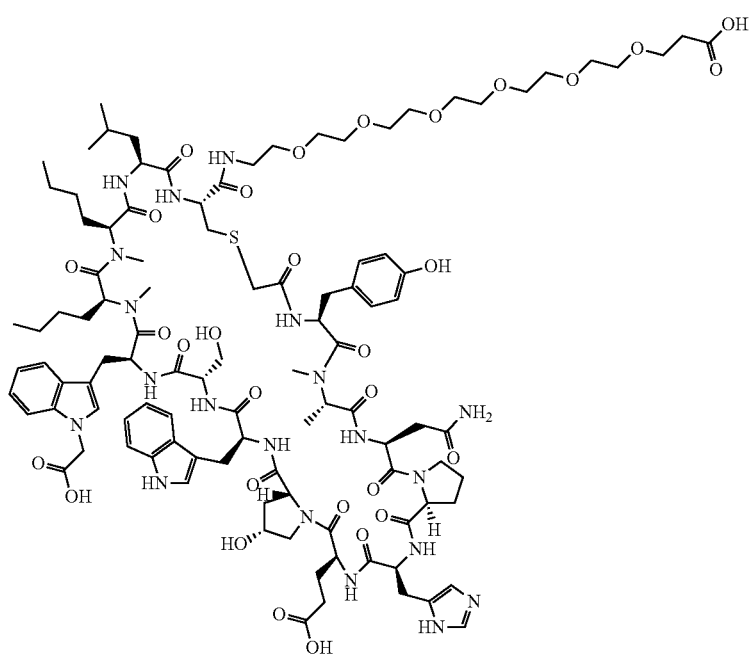 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11044 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 10.7 mg, and its estimated purity by LCMS analysis was 97%. Analysis LCMS Condition A: Retention time=3.66 min; ESI-MS(+) m/z 1117.1 (M+2H); ESI-HRMS(+) m/z: Calculated: 1117.0479 (M+2H). Found: 1117.0452 (M+2H).

Preparation of Example 11045

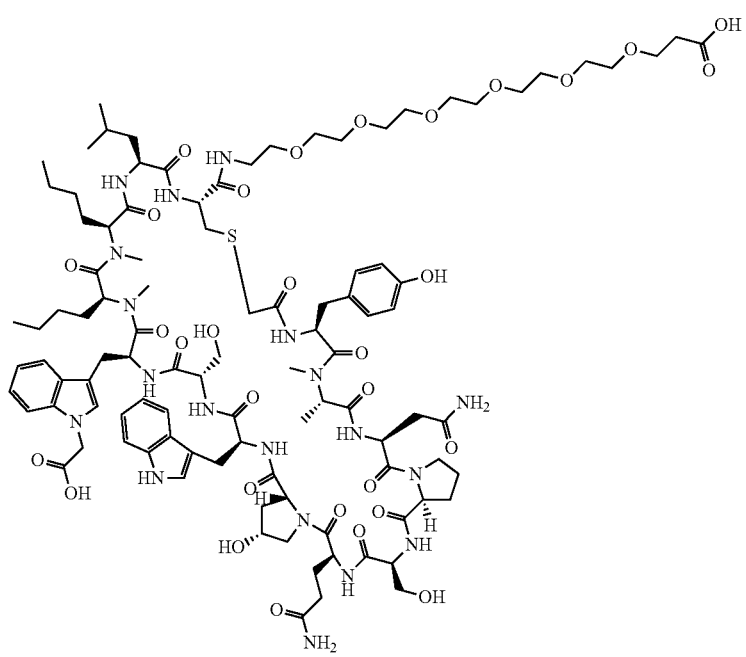 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11045 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 16.0 mg, and its estimated purity by LCMS analysis was 98%.

Analysis LCMS Condition A: Retention time=3.66 min; ESI-MS(+) m/z 1085.1 (M+2H).

Preparation of Example 11046

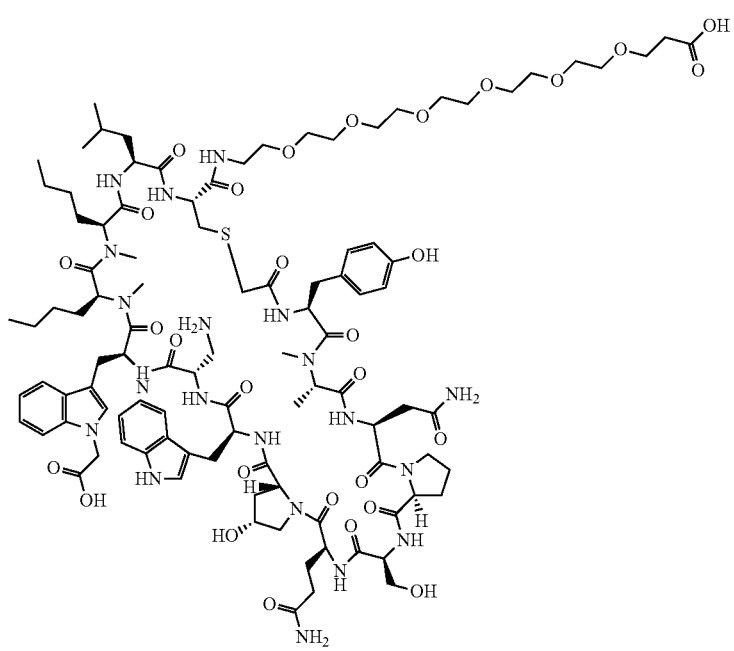 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@@H]2C(=O)N[C@@H](Cc2c[nH]c3ccccc23)C(=O)N[C@@H](CN)C(=O)N[C@@H](Cc2cn(CC(=O)O)c3ccccc23)C(=O)N1C]

Example 11046 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 21.4 mg, and its estimated purity by LCMS analysis was 98%.

Analysis LCMS Condition A: Retention time=3.48 min; ESI-MS(+) m/z 1084.5 (M+2H).

Preparation of Example 11047

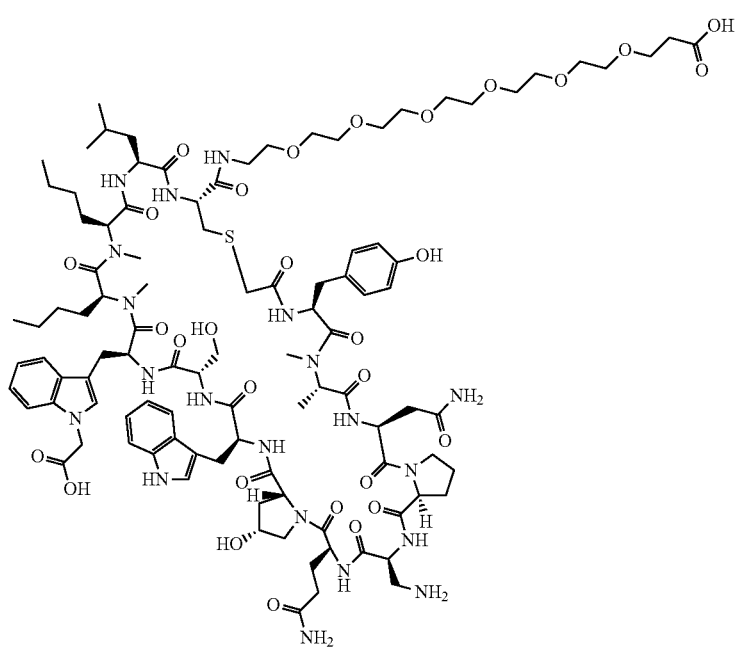 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11047 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 20.7 mg, and its estimated purity by LCMS analysis was 98%.

Analysis LCMS Condition A: Retention time=3.44 min; ESI-MS(+) m/z 1084.4 (M+2H); ESI-HRMS(+) m/z: Calculated: 1084.5346 (M+2H). Found: 1084.5362 (M+2H).

Preparation of Example 11060

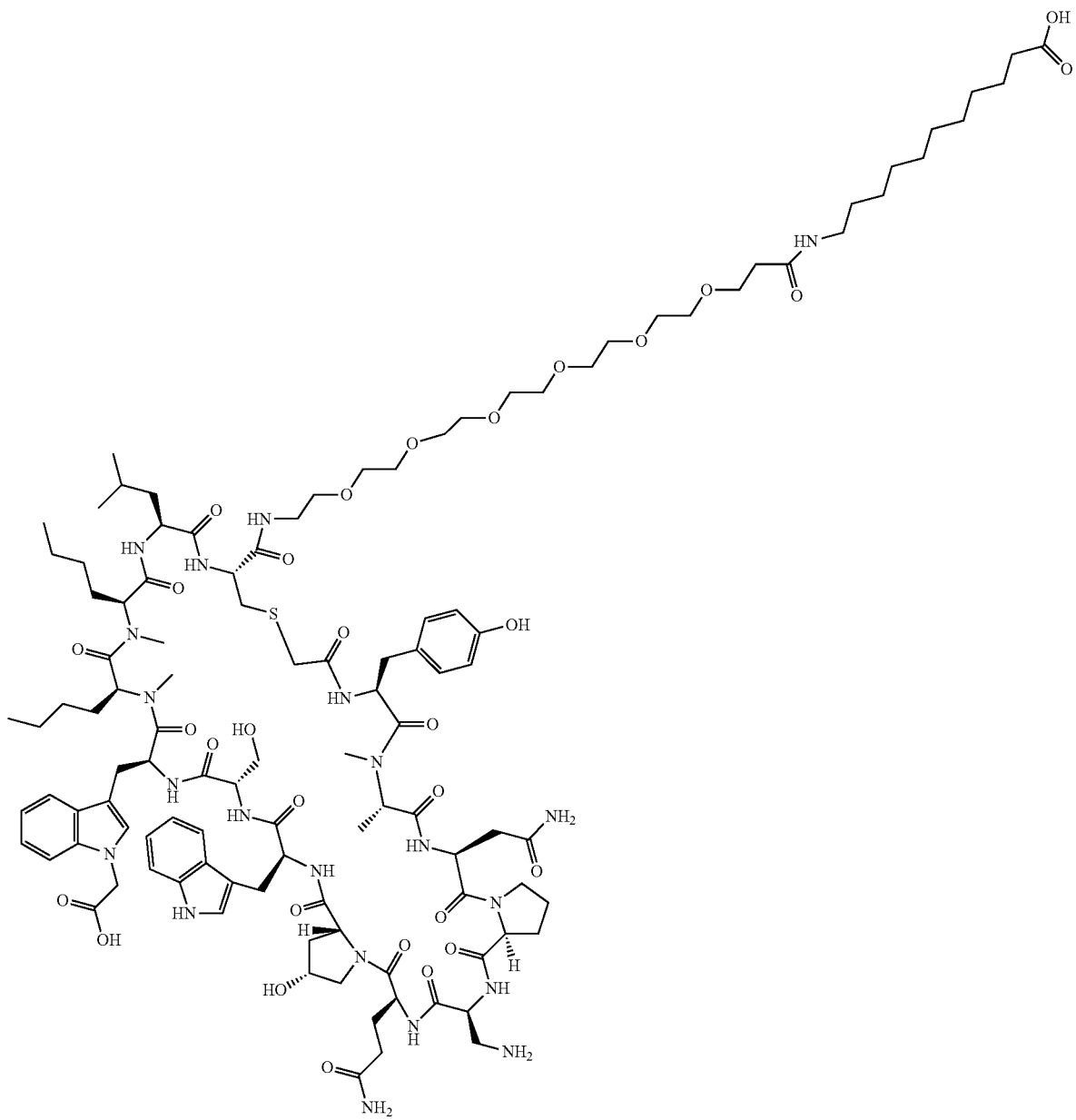 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11060 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 22.4 mg, and its estimated purity by LCMS analysis was 99%.

Analysis LCMS Condition A: Retention time=3.83 min; ESI-MS(+) m/z 1177.0 (M+2H).

Preparation of Example 11061

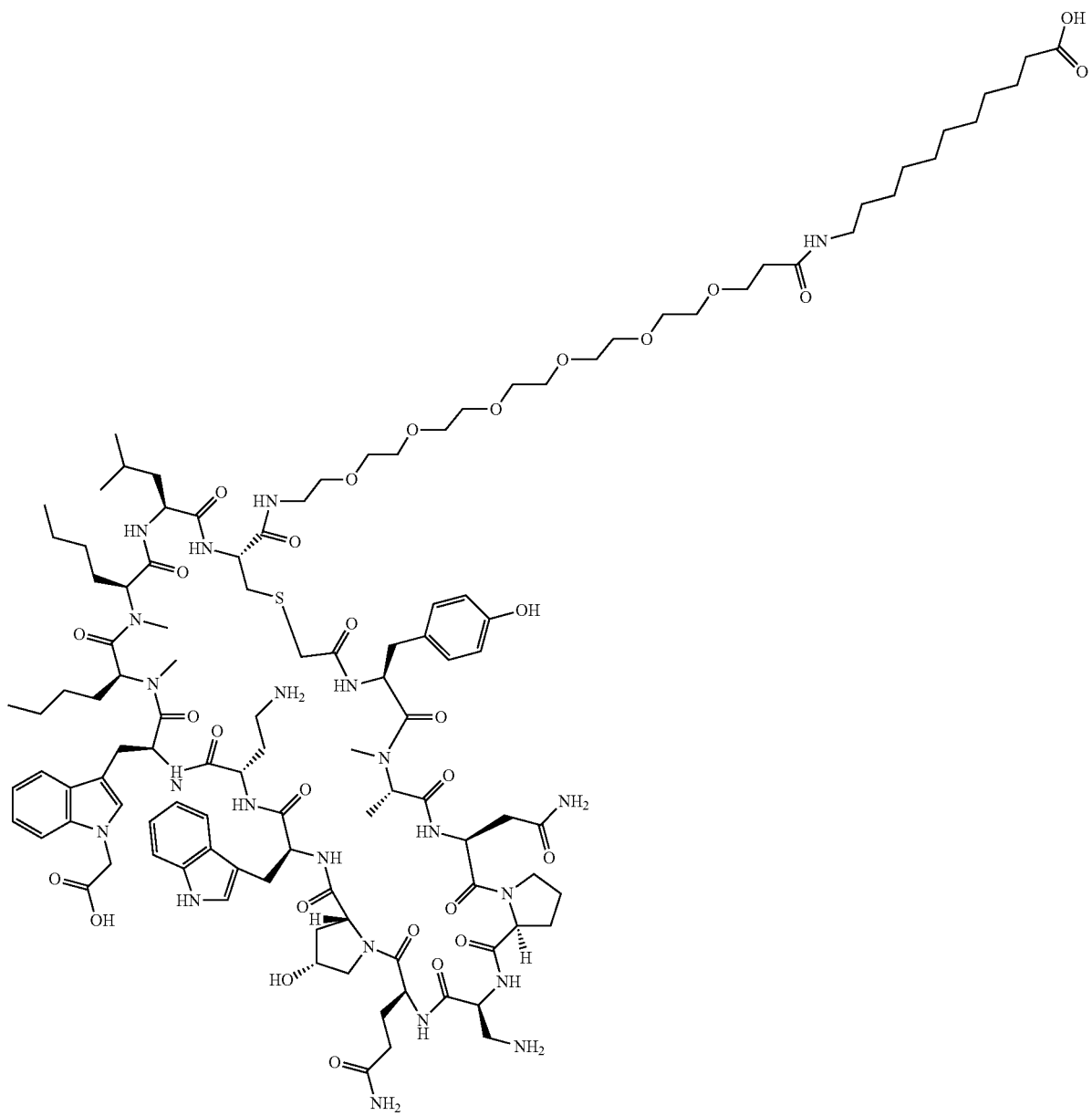 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11061 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 28.3 mg, and its estimated purity by LCMS analysis was 99%.

Analysis LCMS Condition A: Retention time=3.97 min; ESI-MS(+) m/z 1182.5 (M+2H); ESI-HRMS(+) m/z: Calculated: 1182.6316 (M+2H). Found: 1182.6275 (M+2H).

Preparation of Example 11062

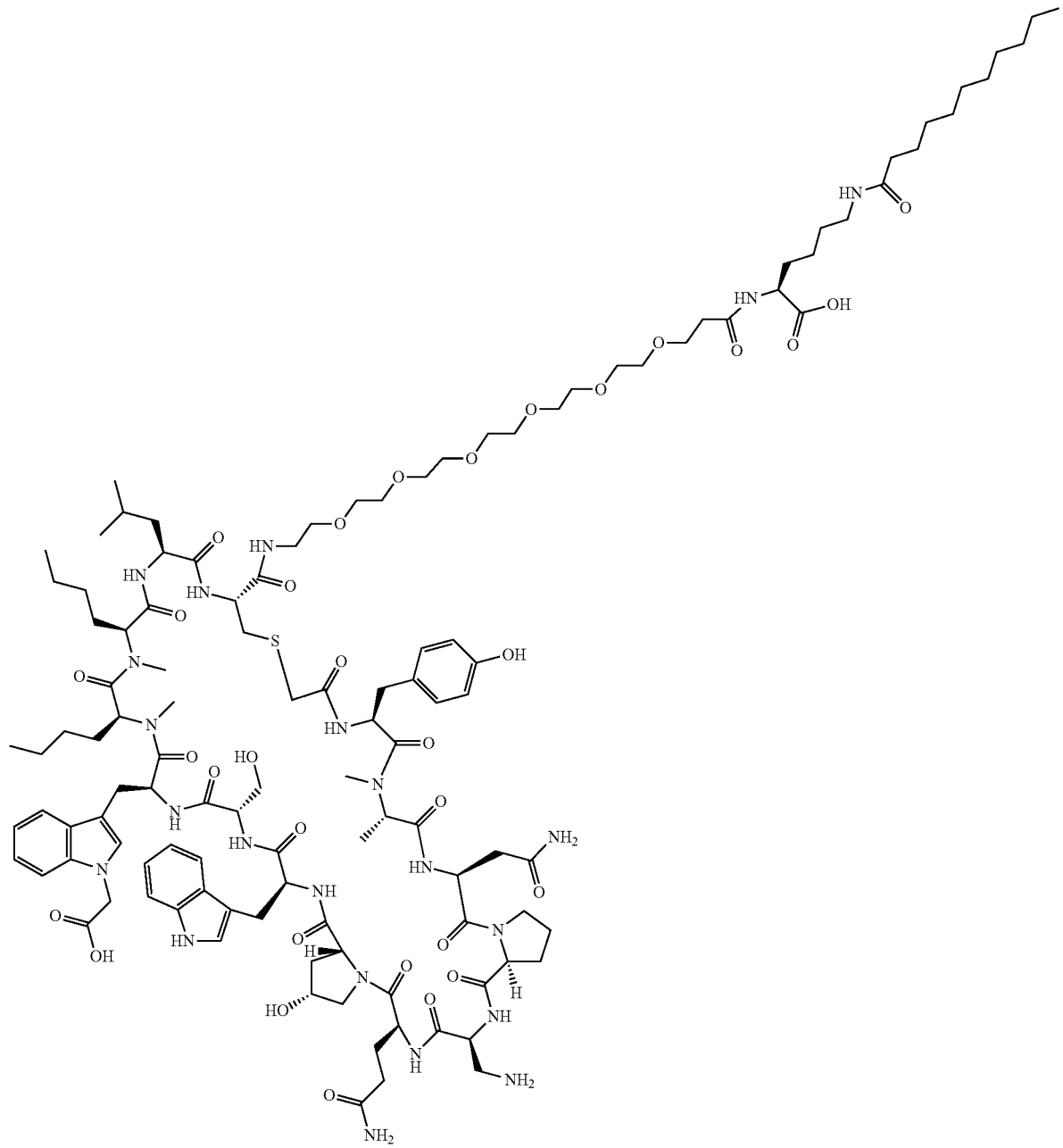 [SMILES: CCCCCCCCCCC(=O)NCCCC[C@H](NC(=O)CCOCCOCCOCCOCCOCCOCCNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@@H]2C(=O)N[C@@H](Cc2c[nH]c3ccccc23)C(=O)N[C@@H](CO)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)O]

Example 11062 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin B was used in this synthesis. FMOC-21-Amino-4,7,10,13,16,19-hexaoxaheneicosanoic acid was used with the "Custom amino acids-coupling procedure". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 30 mL/min. Fractions containing the desired product were combined and dried via centrifugal evaporation. The yield of the product was 2.8 mg, and its estimated purity by LCMS analysis was 98%. Analysis LCMS Condition A: Retention time=4.36 min; ESI-MS(+) m/z 1232.5 (M+2H).

Preparation of Example 11063

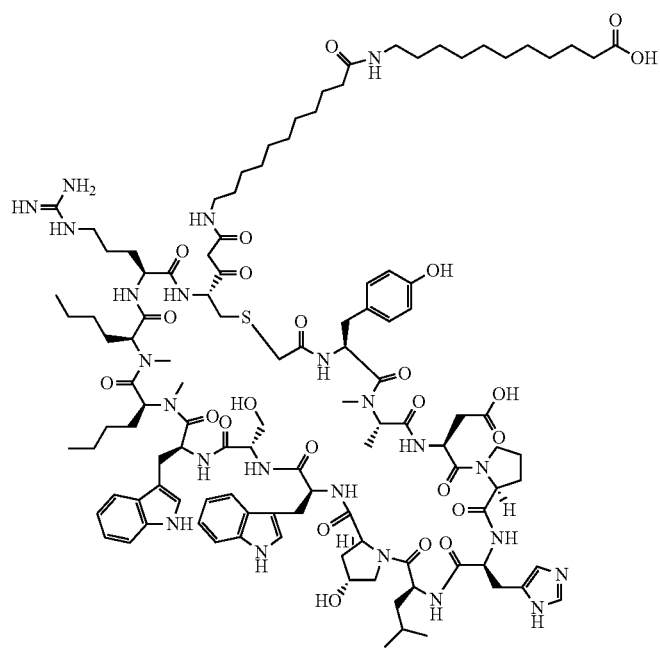

Example 11063 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 27.4 mg, and its estimated purity by LCMS analysis was 98%.

Analysis LCMS Condition A: Retention time=4.11 min; ESI-MS(+) m/z 1139.7 (M+2H); ESI-HRMS(+) m/z: Calculated: 1139.6265 (M+2H). Found: 1139.6252 (M+2H).

Preparation of Example 11064

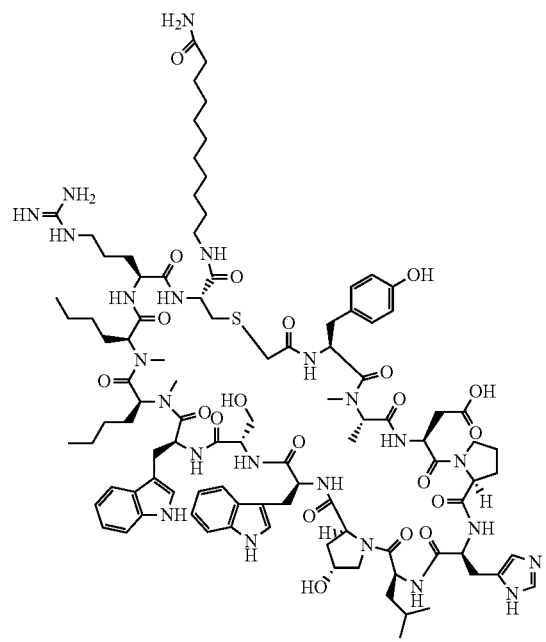 [SMILES: CCCC[C@H]1C(=O)N(C)[C@@H](CCCC)C(=O)N[C@@H](CCCNC(=N)N)C(=O)N[C@H](C(=O)NCCCCCCCCCCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11064 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure A", "Global Deprotection Method A", and "Cyclization Method A". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 26 mg, and its estimated purity by LCMS analysis was 98.7%;

Analysis LCMS Condition A: Retention time=3.90 min; ESI-MS(+) m/z 1019.9 (M+2H); ESI-HRMS(+) m/z: Calculated: 1019.0426 (M+2H). Found: 1019.0407 (M+2H).

Preparation of Example 11065

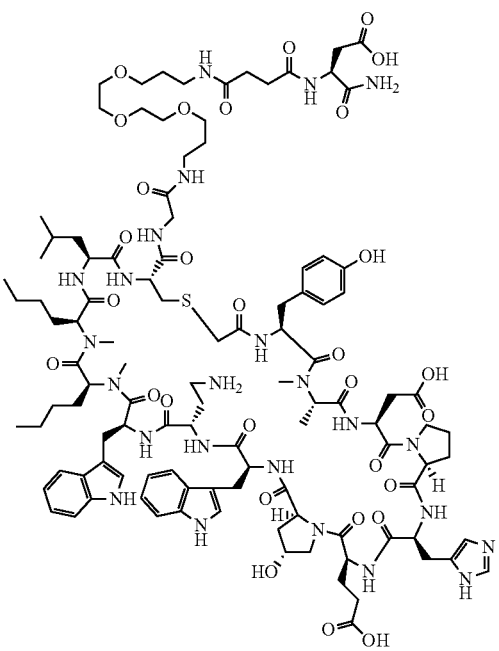 [SMILES: CCCC[C@H]1C(=O)N(C)[C@@H](CCCC)C(=O)N[C@@H](CC(C)C)C(=O)N[C@H](C(=O)NCC(=O)NCCCOCCOCCOCCCNC(=O)CCC(=O)N[C@@H](CC(=O)O)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Example 11065 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 37 mg, and its estimated purity by LCMS analysis was 97.3%.

Analysis LCMS Condition A: Retention time=3.706 min; ESI-MS(+) m/z 1158.0 (M+2H); ESI-HRMS(+) m/z: Calculated: 1157.0723 (M+2H). Found: 1157.0697 (M+2H).

Preparation of Example 11066

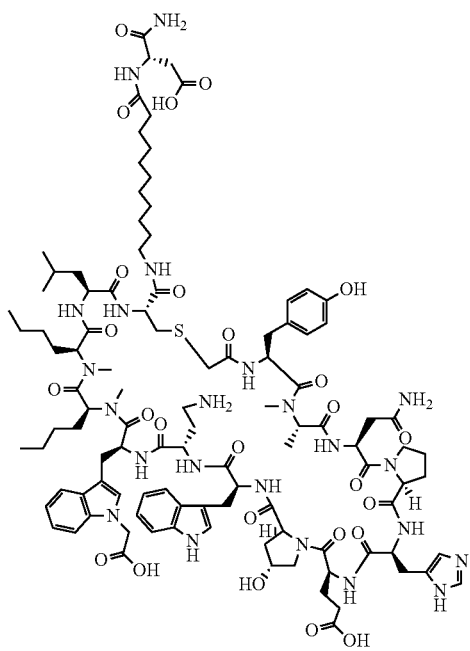 [SMILES: CCCC[C@H]1C(=O)N(C)[C@@H](CCCC)C(=O)N[C@@H](CC(C)C)C(=O)N[C@H](C(=O)NCCCCCCCCCCC(=O)N[C@@H](CC(=O)O)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11066 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 48 mg, and its estimated purity by LCMS analysis was 98.5%.

Analysis LCMS Condition A: Retention time=3.578 min; ESI-MS(+) m/z 1098.7 (M+2H); ESI-HRMS(+) m/z: Calculated: 1098.0533 (M+2H). Found: 1098.0513 (M+2H).

Preparation of Example 11067

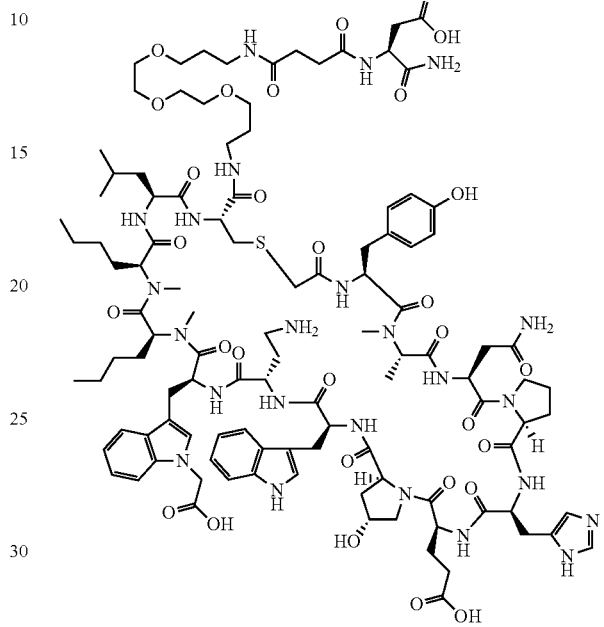

Example 11067 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 36.3 mg, and its estimated purity by LCMS analysis was 99%.

Analysis LCMS Condition A: Retention time=3.225 min; ESI-MS(+) m/z 1158.6 (M+2H); ESI-HRMS(+) m/z: Calculated: 1157.5643 (M+2H). Found: 1157.5622 (M+2H).

Preparation of Modified 2-chlorotrityl chloride resin C

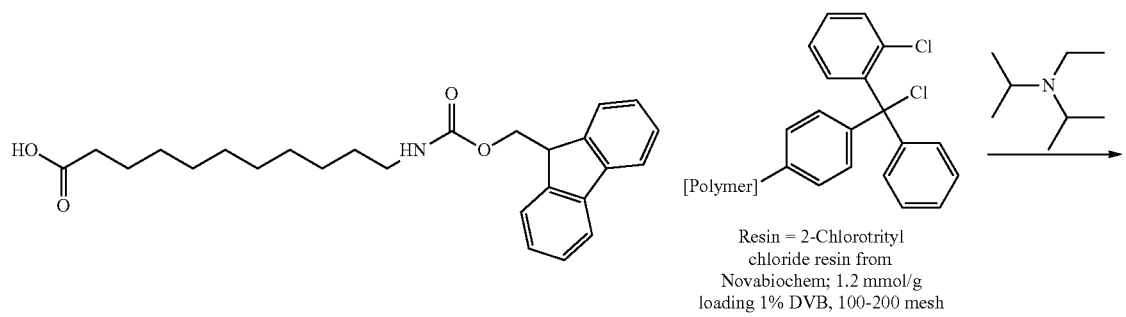

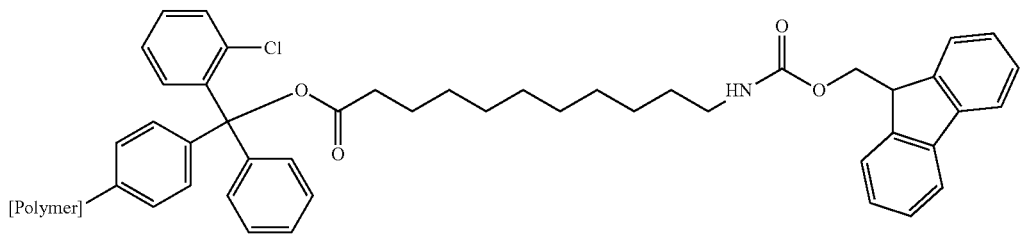

To a 40 mL vial was added 2-chlorotrityl chloride resin (1.2 mmol/g loading) (6.37 g, 7.65 mmol). The resin was swelled in 15 ml dichloromethane for 10 minutes. A solution of (1.2 g, 2.83 mmol), FMOC-added 11-((((9H-fluoren-9-yl)methoxy)carbonyl)amino)undecanoic acid in 5 ml dichloromethane followed by N-ethyl-N-isopropylpropan-2-amine (3.45 ml, 19.83 mmol) was added and the mixture was shaken overnight at rt on a mini shaker. After 20 h the mixture was diluted with 3 ml of methanol, and shaken for 2 hr to quench any unreacted chlorotrityl resin. The resin was vacuum filtered in a polypropylene reaction tube and washed with 100 ml DMF, 100 ml dichloromethane, and finally 10 ml diethyl ether. The resin was air dried and used as is assuming a 0.44 mmol/g loading.

Preparation of Example 11068

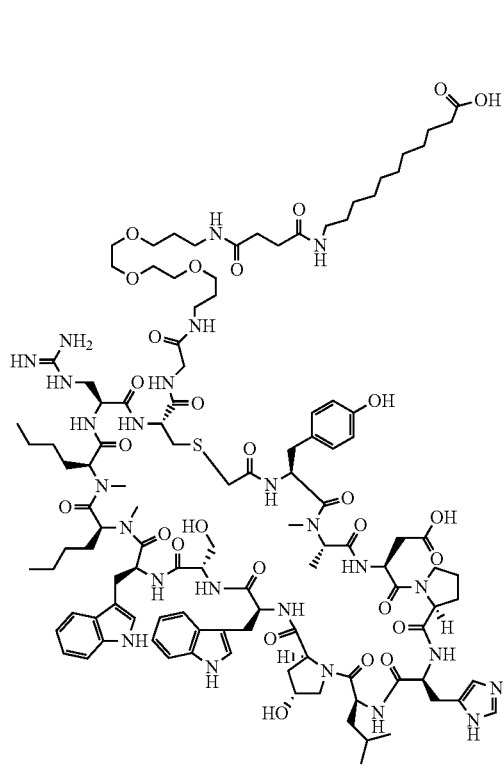 [SMILES: CCCC[C@H]1C(=O)N(C)[C@@H](CCCC)C(=O)N[C@@H](CNC(=N)N)C(=O)N[C@H](C(=O)NCC(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11068 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 32 mg, and its estimated purity by LCMS analysis was 99.2%. Analysis LCMS Condition A: Retention time=3.781 min; ESI-MS(+) m/z 1200.0 (M+2H); ESI-HRMS(+) m/z: Calculated: 1199.1374 (M+2H). Found: 1199.1379 (M+2H).

Preparation of Example 11069

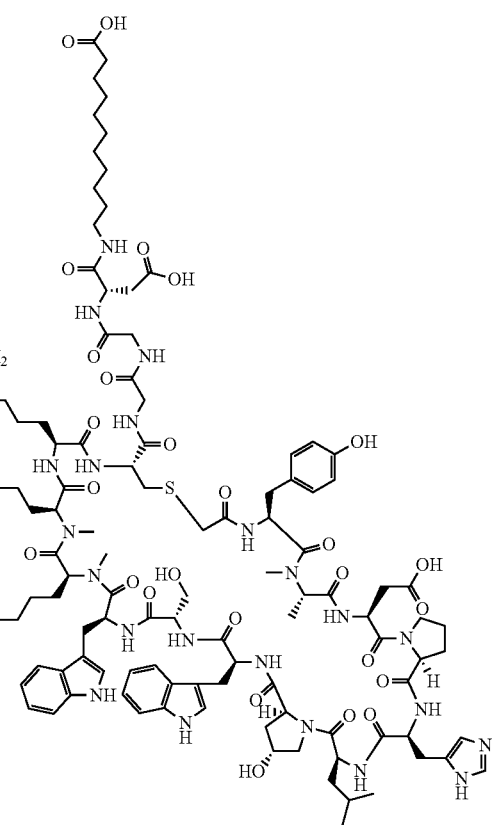

Example 11069 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 27 mg, and its estimated purity by LCMS analysis was 96.9%. Analysis LCMS Condition A: Retention time=3.598 min; ESI-MS(+) m/z 1135.2 (M+2H); ESI-HRMS(+) m/z: Calculated: 1134.0695 (M+2H). Found: 1134.0691 (M+2H).

Preparation of Example 11070

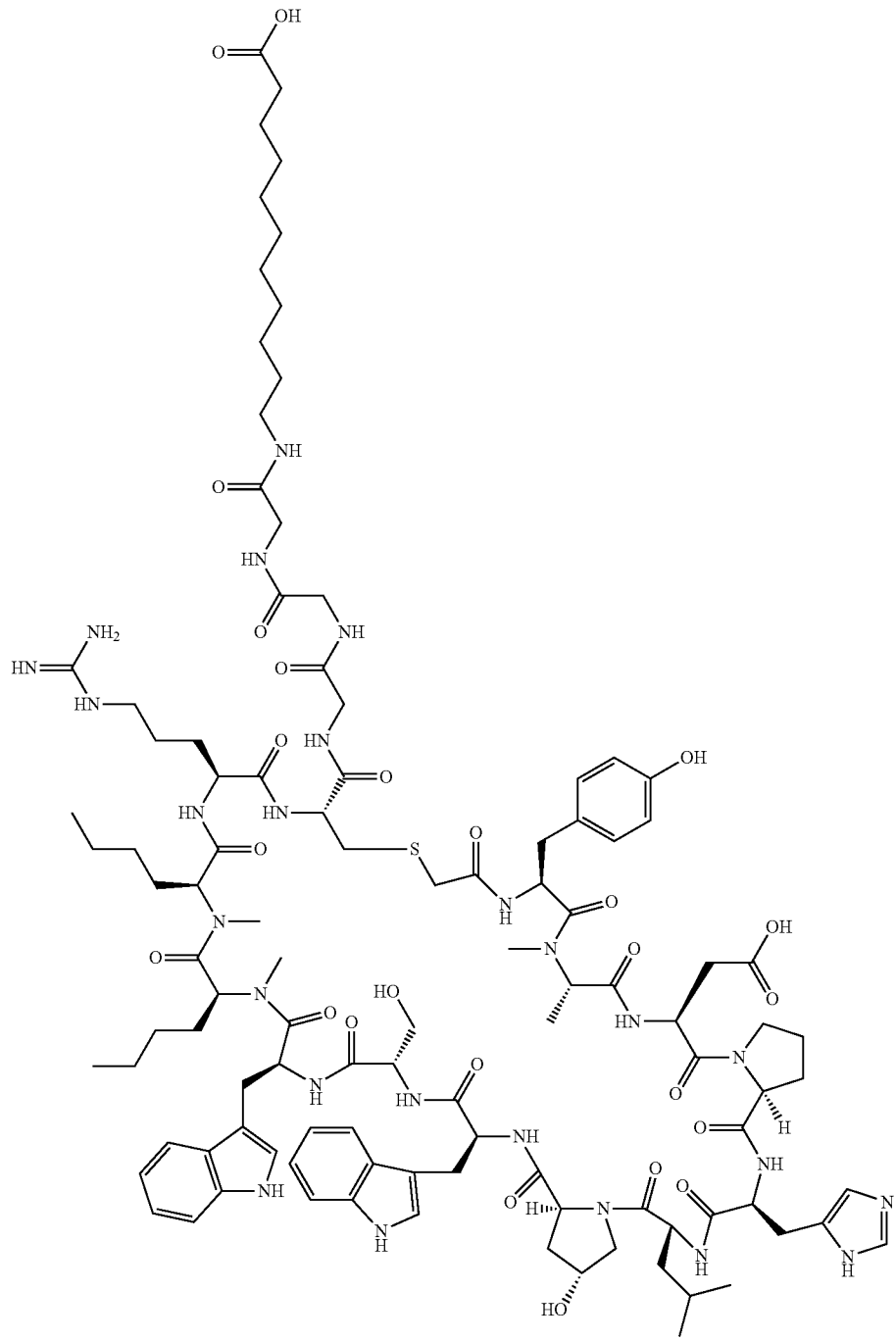 [SMILES: CCCC[C@H]1C(=O)N(C)[C@@H](CCCC)C(=O)N[C@@H](CCCNC(=N)N)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11070 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 31 mg, and its estimated purity by LCMS analysis was 98.4%. Analysis LCMS Condition A: Retention time=3.715 min; ESI-MS(+) m/z 1106.0 (M+2H); ESI-HRMS(+) m/z: Calculated: 1105.0668 (M+2H). Found: 1105.0663 (M+2H).

237
Preparation of Example 11071

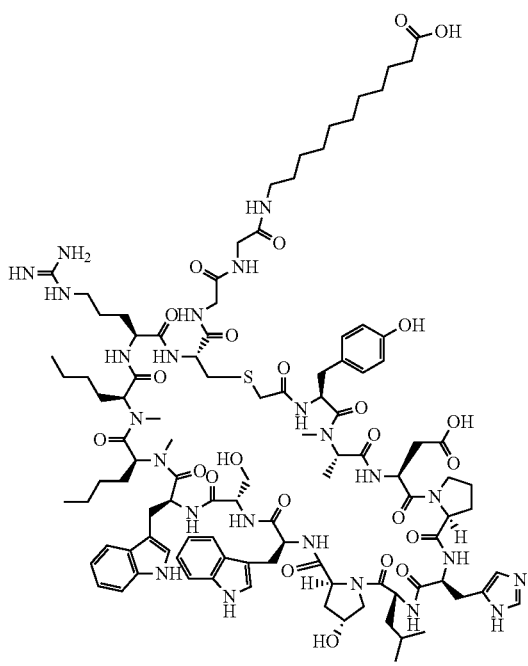 [SMILES: CCCC[C@H]1C(=O)N(C)[C@@H](CCCC)C(=O)N[C@@H](CCCNC(=N)N)C(=O)N[C@H](C(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11071 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 32 mg, and its estimated purity by LCMS analysis was 99.2%. Analysis LCMS Condition A: Retention time=3.733 min; ESI-MS(+) m/z 1077.3 (M+2H); ESI-HRMS(+) m/z: Calculated: 1076.5561 (M+2H). Found: 1076.5547 (M+2H).

238
Preparation of Example 11072

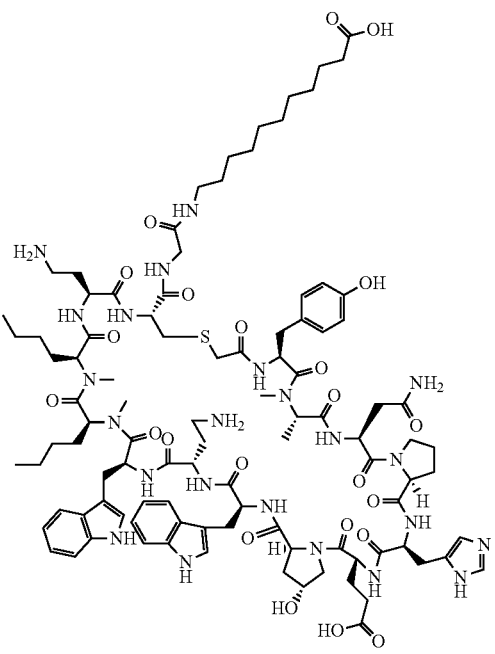 [SMILES: CCCC[C@H]1C(=O)N(C)[C@@H](CCCC)C(=O)N[C@@H](CCN)C(=O)N[C@H](C(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Example 11072 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 51 mg, and its estimated purity by LCMS analysis was 98.6%. Analysis LCMS Condition A: Retention time=3.655 min; ESI-MS(+) m/z 1035.0 (M+2H); ESI-HRMS(+) m/z: Calculated: 1034.0297 (M+2H). Found: 1034.0269 (M+2H).

Preparation of Example 11073

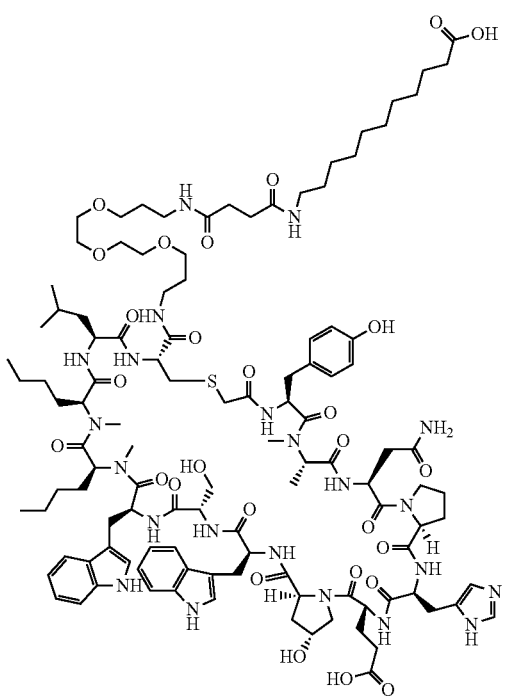 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11073 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 29 mg, and its estimated purity by LCMS analysis was 98.7%. Analysis LCMS Condition A: Retention time=4.038 min; ESI-MS(+) m/z 1157.6 (M+2H); ESI-HRMS(+) m/z: Calculated: 1156.6054 (M+2H). Found: 1156.6029 (M+2H).

Preparation of Example 11074

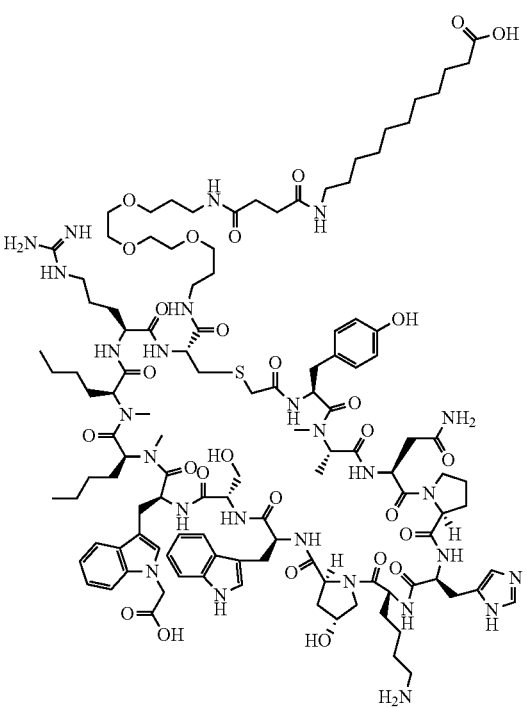 [SMILES: CCCC[C@H]1C(=O)N(C)[C@@H](CCCC)C(=O)N[C@@H](CCCNC(=N)N)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCCCN)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11074 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 29 mg, and its estimated purity by LCMS analysis was 98.7%. Analysis LCMS Condition A: Retention time=4.038 min; ESI-MS(+) m/z 1157.6 (M+2H); ESI-HRMS(+) m/z: Calculated: 1156.6054 (M+2H). Found: 1156.6029 (M+2H).

Preparation of Example 11075

Preparation of Example 11076

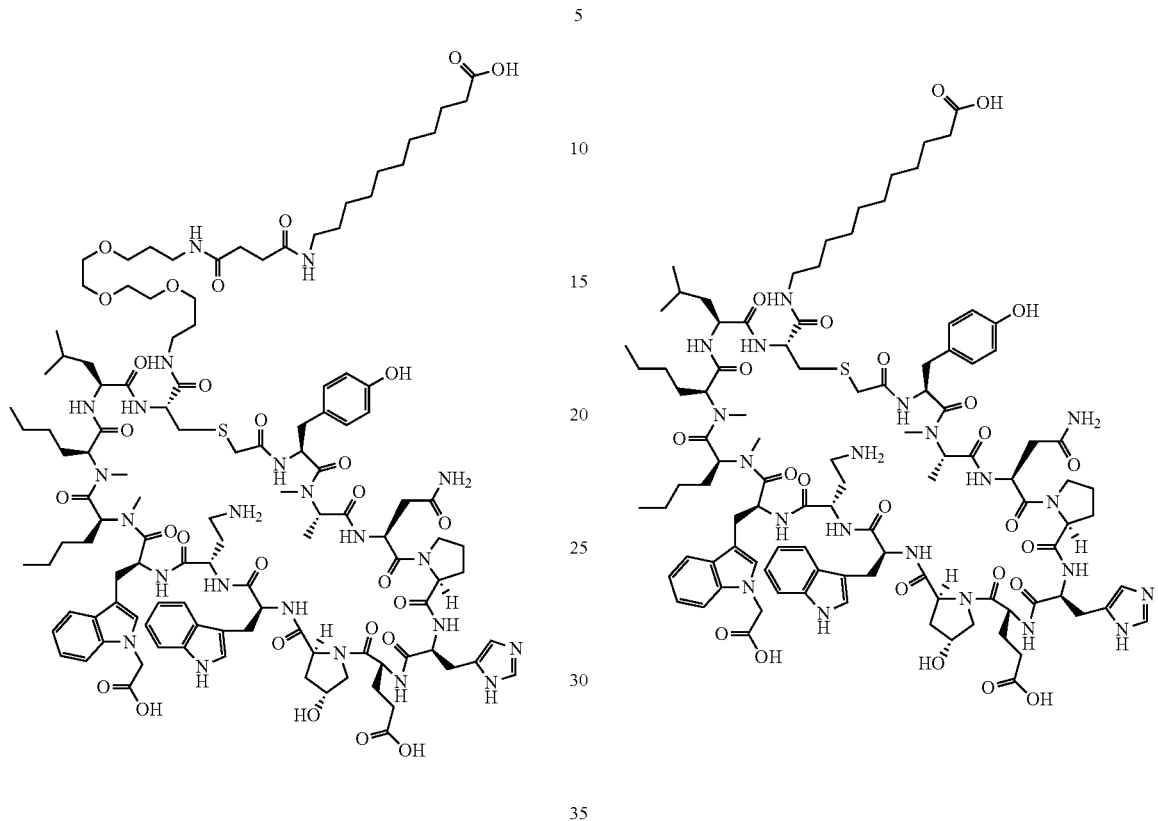

Example 11075 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 40 mg, and its estimated purity by LCMS analysis was 98.1%. Analysis LCMS Condition A: Retention time=3.878 min; ESI-MS(+) m/z 1193.2 (M+2H); ESI-HRMS(+) m/z: Calculated: 1192.1240 (M+2H). Found: 1192.1227 (M+2H).

Example 11076 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 42 mg, and its estimated purity by LCMS analysis was 100%. Analysis LCMS Condition A: Retention time=4.088 min; ESI-MS(+) m/z 1042.1 (M+2H); ESI-HRMS(+) m/z: Calculated: 1041.0319 (M+2H). Found: 1041.0309 (M+2H).

Preparation of Example 11077

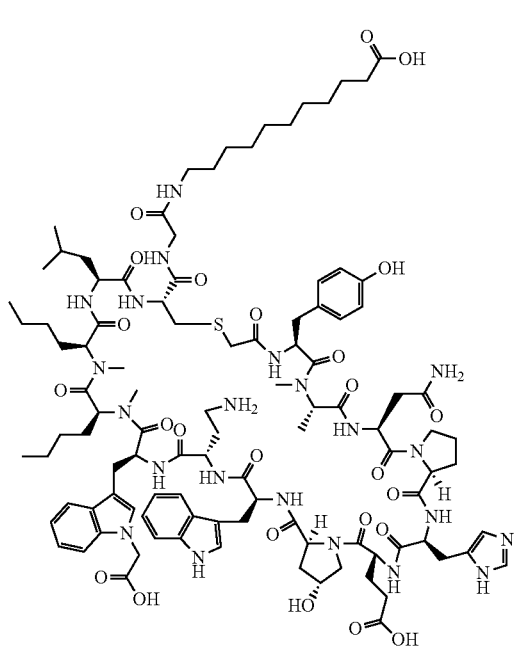 [SMILES: CCCC[C@H]1C(=O)N(C)[C@@H](CCCC)C(=O)N[C@@H](CC(C)C)C(=O)N[C@H](C(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11077 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 38 mg, and its estimated purity by LCMS analysis was 100%. Analysis LCMS Condition A: Retention time=4.050 min; ESI-MS(+) m/z 1070.4 (M+2H); ESI-HRMS(+) m/z: Calculated: 1069.5426 (M+2H). Found: 1069.5405 (M+2H).

Preparation of Example 11078

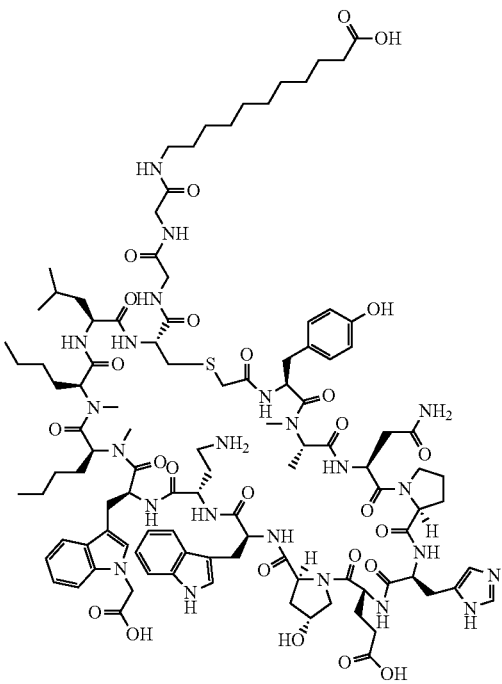 [SMILES: CCCC[C@H]1C(=O)N(C)[C@@H](CCCC)C(=O)N[C@@H](CC(C)C)C(=O)N[C@H](C(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11078 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 40 mg, and its estimated purity by LCMS analysis was 100%. Analysis LCMS Condition A: Retention time=3.903 min; ESI-MS(+) m/z 1098.7 (M+2H); ESI-HRMS(+) m/z: Calculated: 1098.0533 (M+2H). Found: 1098.0508 (M+2H).

245
Preparation of Example 11079

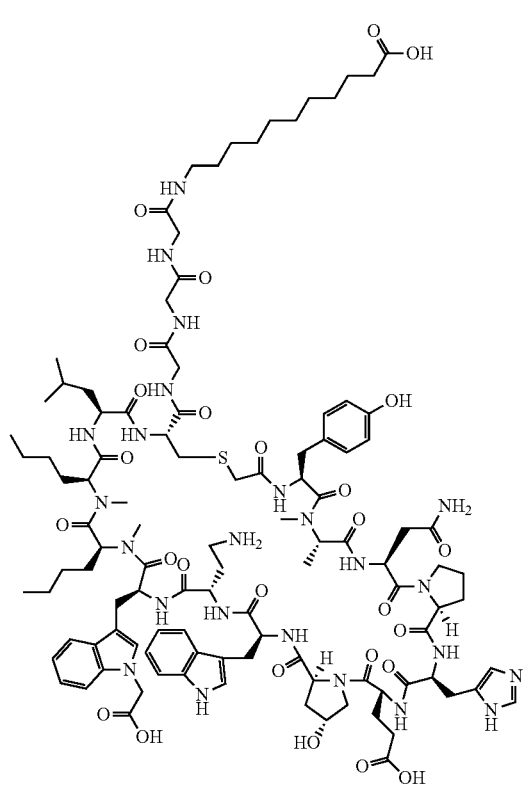 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11079 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 46 mg, and its estimated purity by LCMS analysis was 98.9%. Analysis LCMS Condition A: Retention time=3.533 min; ESI-MS(+) m/z 1127.7 (M+2H); ESI-HRMS(+) m/z:

Calculated: 1126.5641 (M+2H). Found: 1126.5608 (M+2H).

246
Preparation of Example 11080

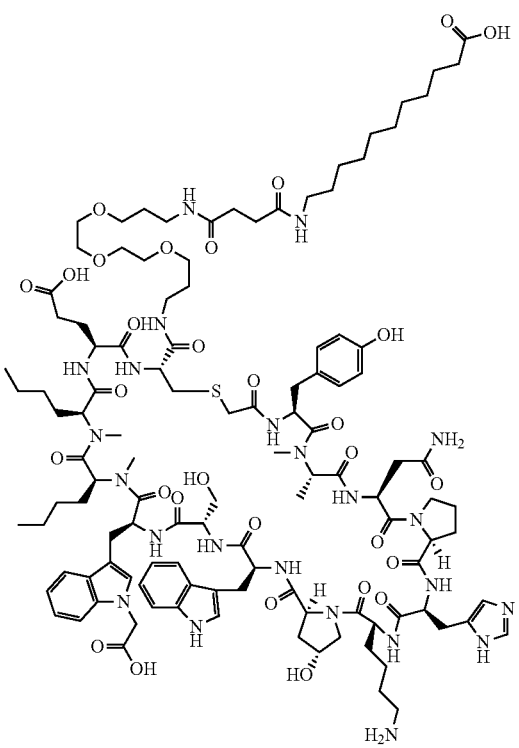 [SMILES: CCCC[C@H]1C(=O)N(C)[C@@H](CCCC)C(=O)N[C@@H](CCC(=O)O)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@H](CCCCN)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11080 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 27 mg, and its estimated purity by LCMS analysis was 99.0%. Analysis LCMS Condition A: Retention time=3.235 min; ESI-MS(+) m/z 1194.8 (M+2H); ESI-HRMS(+) m/z:

Calculated: 1193.1136 (M+2H). Found: 1193.1127 (M+2H).

Preparation of Example 11081

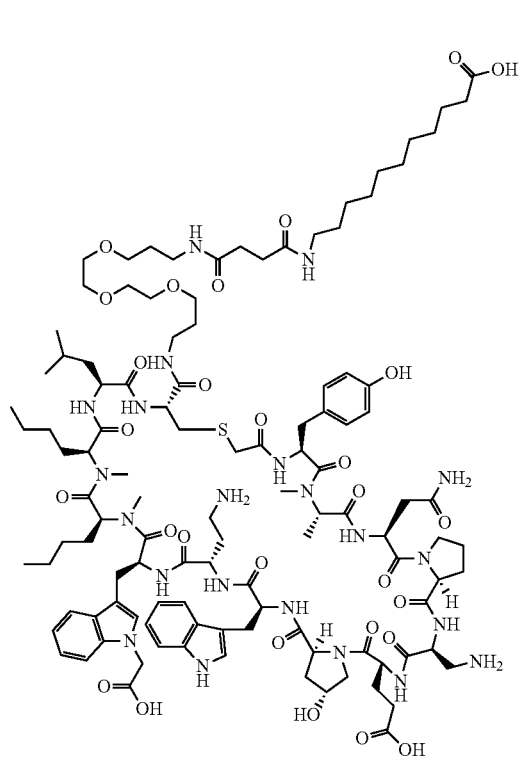 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11081 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 38 mg, and its estimated purity by LCMS analysis was 98.5%. Analysis LCMS Condition A: Retention time=3.743 min; ESI-MS(+) m/z 1167.8 (M+2H); ESI-HRMS(+) m/z: Calculated: 1166.6185 (M+2H). Found: 1166.6167 (M+2H).

Preparation of Example 11082

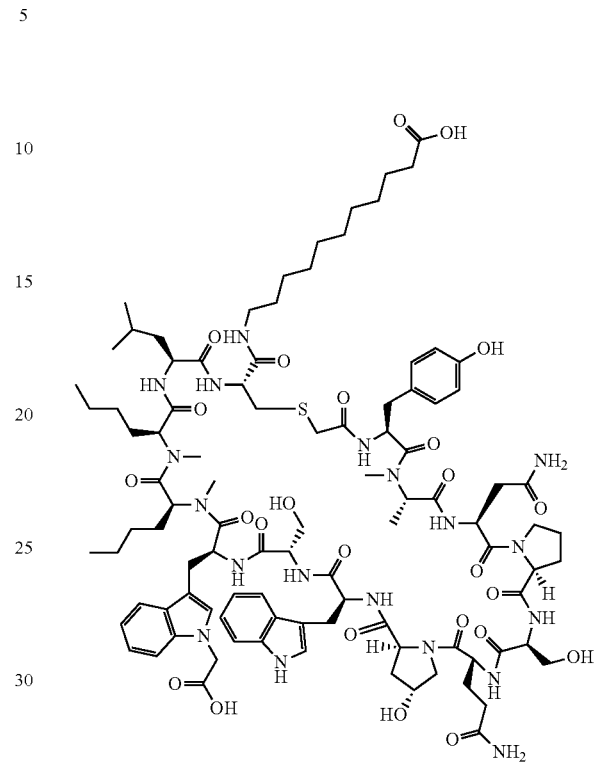

Example 11082 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 28 mg, and its estimated purity by LCMS analysis was 99.3%. Analysis LCMS Condition A: Retention time=3.688 min; ESI-MS(+) m/z 1010.1 (M+2H); ESI-HRMS(+) m/z: Calculated: 1009.0106 (M+2H). Found: 1009.0103 (M+2H).

Preparation of Example 11083

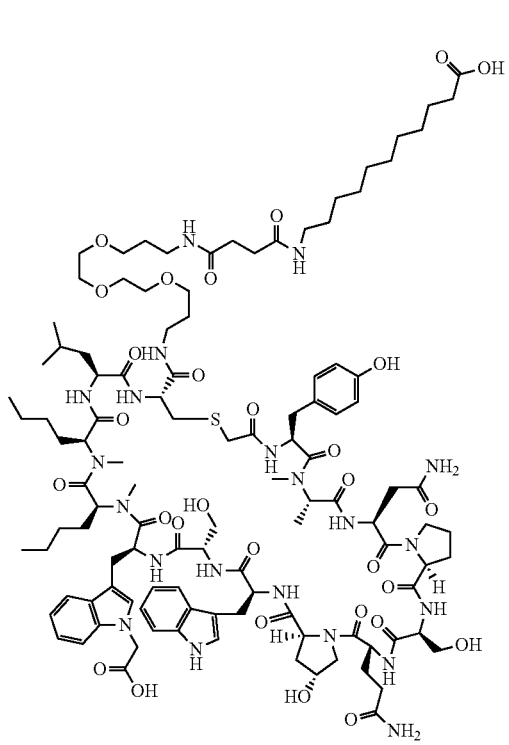 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CO)C(=O)N[C@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11083 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 31 mg, and its estimated purity by LCMS analysis was 98.8%. Analysis LCMS Condition A: Retention time=3.576 min; ESI-MS(+) m/z 1161.2 (M+2H); ESI-HRMS(+) m/z:

Calculated: 1160.1027 (M+2H). Found: 1160.1039 (M+2H).

Preparation of Example 11084

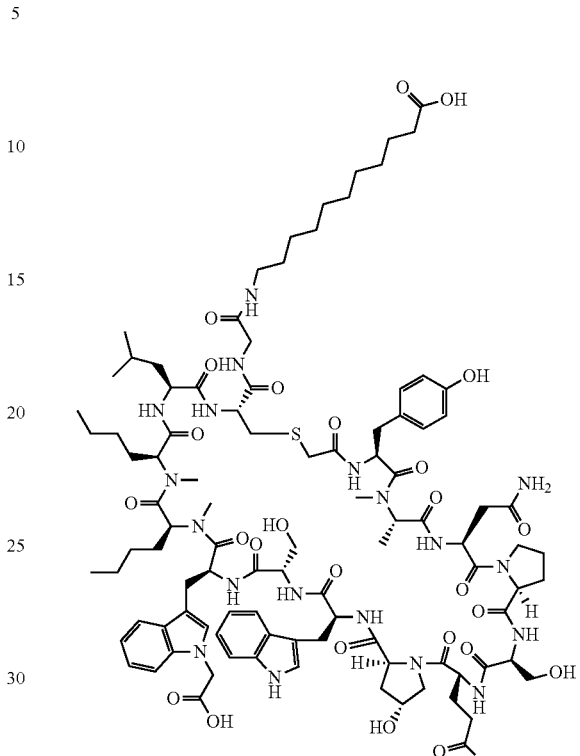

Example 11084 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 27 mg, and its estimated purity by LCMS analysis was 98.2%.

Analysis LCMS Condition A: Retention time=3.625 min; ESI-MS(+) m/z 1038.3 (M+2H); ESI-HRMS(+) m/z: Calculated: 1037.5213 (M+2H). Found: 1037.5221 (M+2H).

Preparation of Example 11085

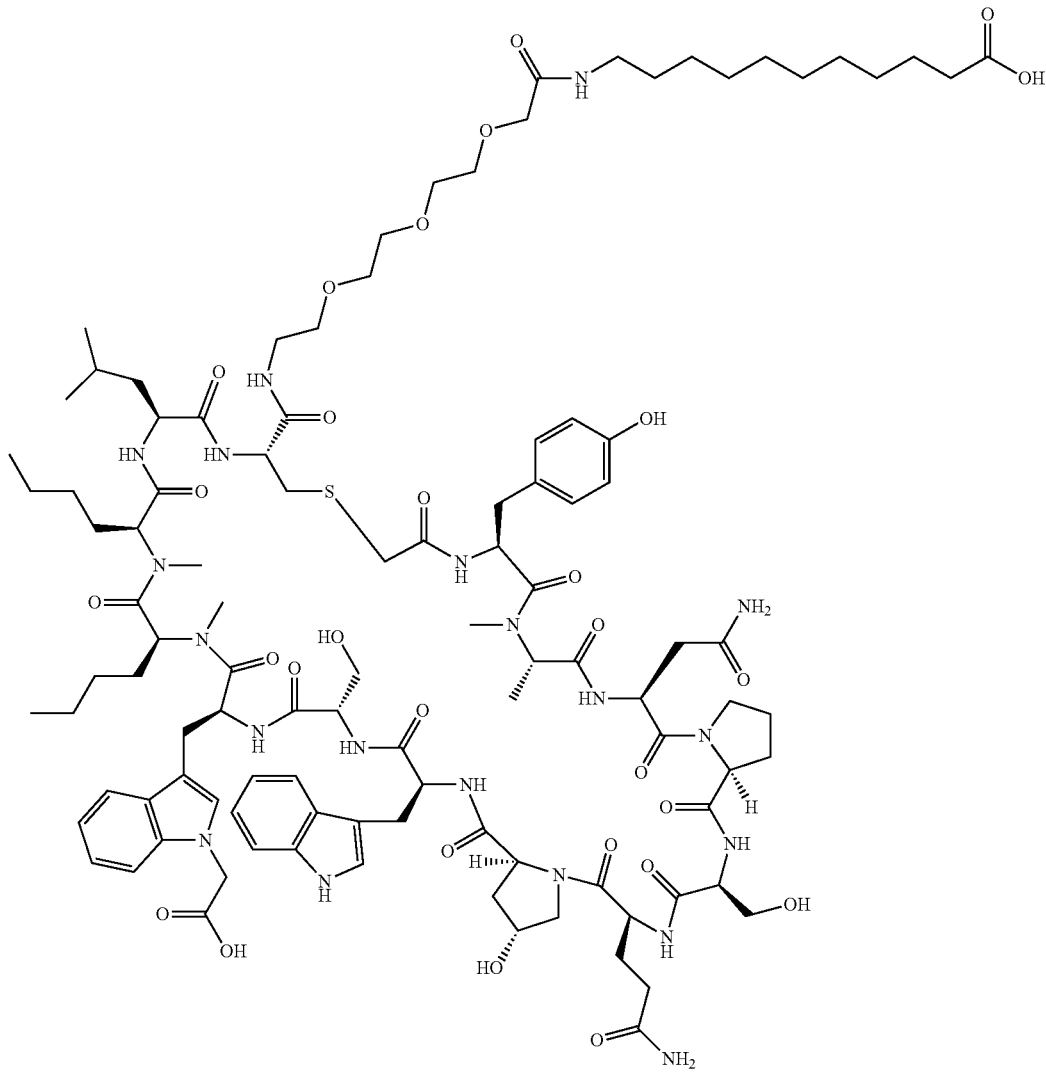 [SMILES: CCCC[C@H]1C(=O)N(C)[C@@H](CCCC)C(=O)N[C@@H](CC(C)C)C(=O)N[C@H](C(=O)NCCOCCOCCOCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11085 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 22 mg, and its estimated purity by LCMS analysis was 99.7%. Analysis LCMS Condition A: Retention time=3.951 min; ESI-MS(+) m/z 1104.7 (M+2H).

Preparation of Example 11086

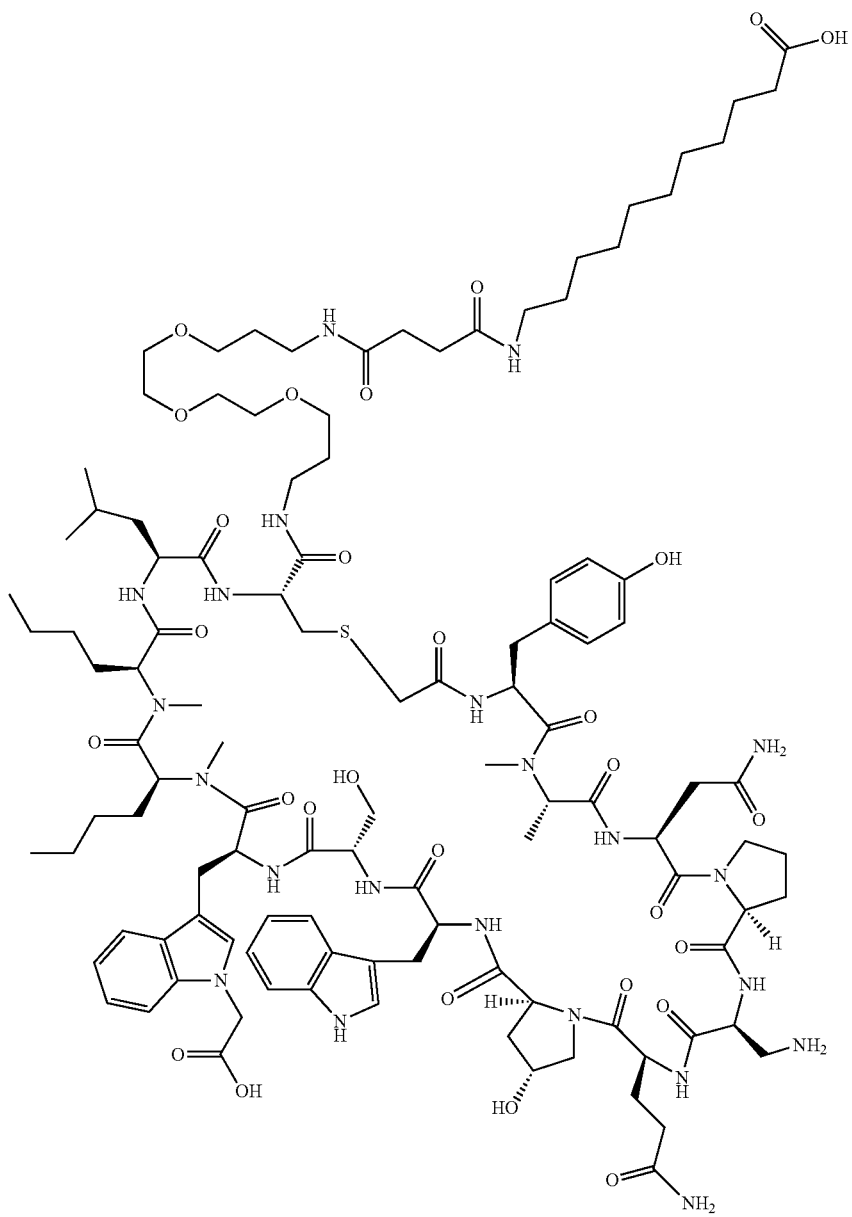 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11086 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 32 mg, and its estimated purity by LCMS analysis was 95.8%. Analysis LCMS Condition A: Retention time=4.088 min; ESI-MS(+) m/z 1160.8 (M+2H); ESI-HRMS(+) m/z: Calculated: 1159.6107 (M+2H). Found: 1159.6104 (M+2H).

Preparation of Example 11087

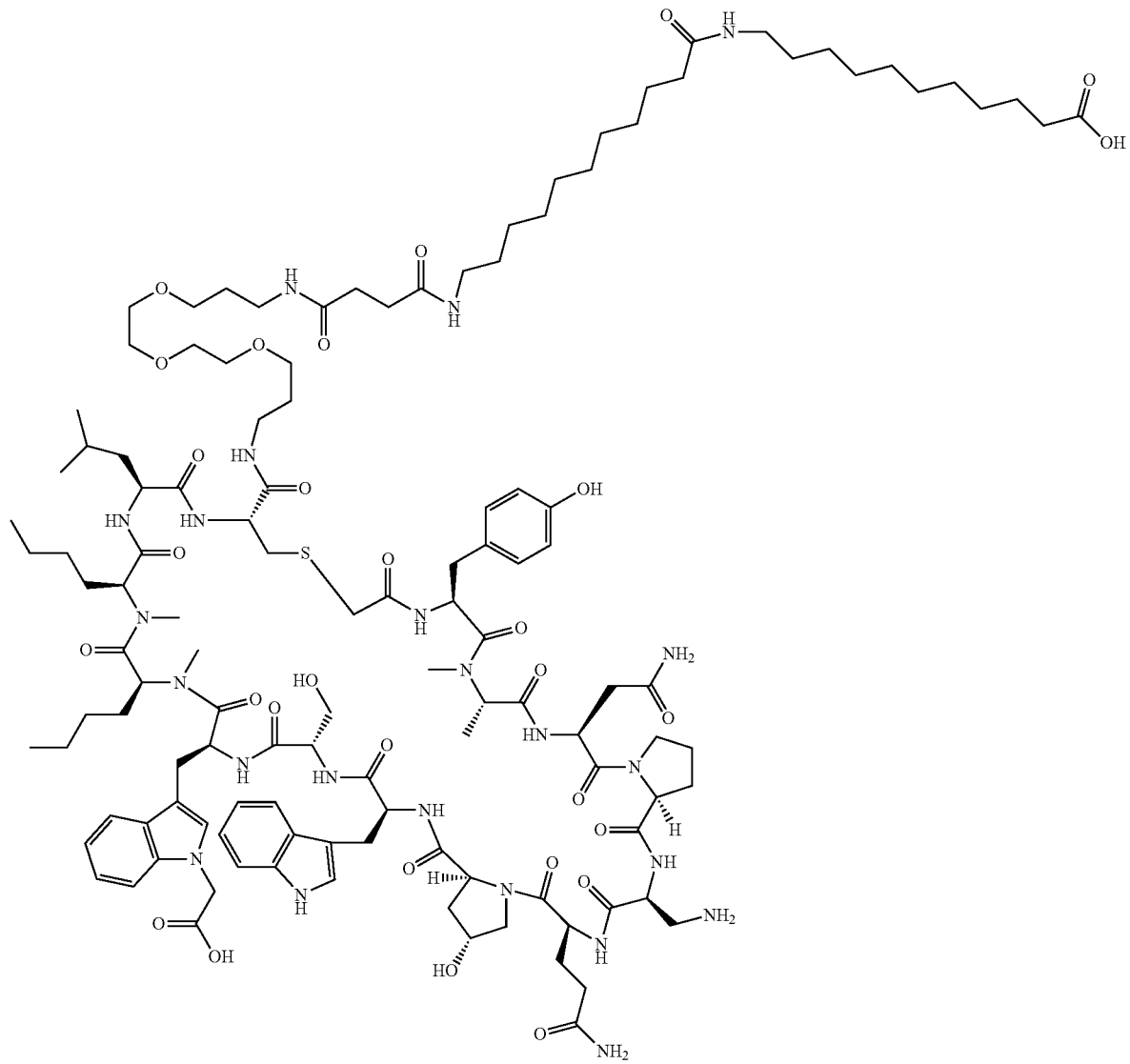 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11087 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 22 mg, and its estimated purity by LCMS analysis was 99.5%. Analysis LCMS Condition A: Retention time=4.595 min; ESI-MS(+) m/z 1252.0 (M+2H); ESI-HRMS(+) m/z: Calculated: 1251.1918 (M+2H). Found: 1251.1919 (M+2H).

Preparation of Example 11088

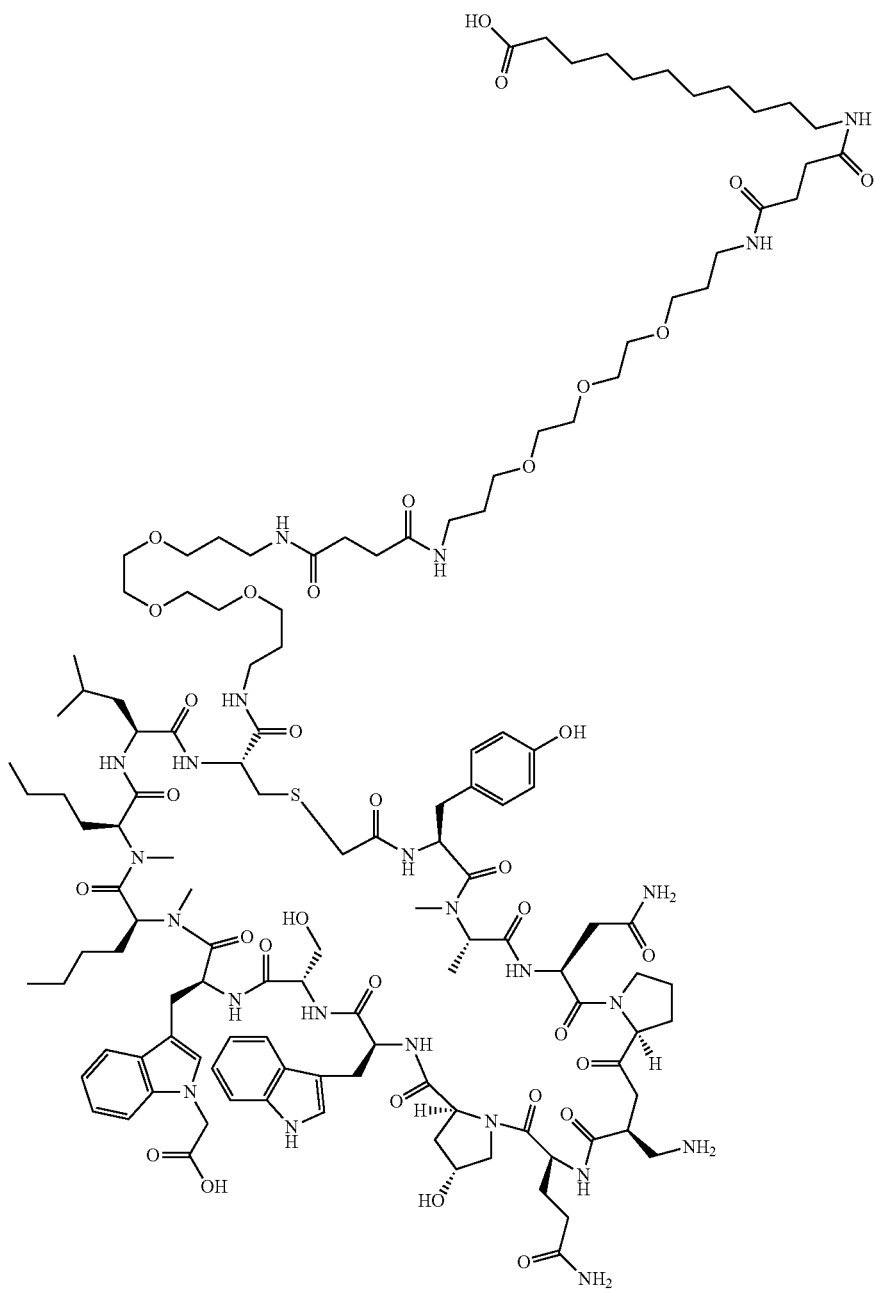 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)C[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11088 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 22 mg, and its estimated purity by LCMS analysis was 94.1%. Analysis LCMS Condition A: 4 min gradient 1 min hold: Retention time=2.300 min; ESI-MS(+) m/z 1311.5 (M+2H).

Preparation of Example 11089

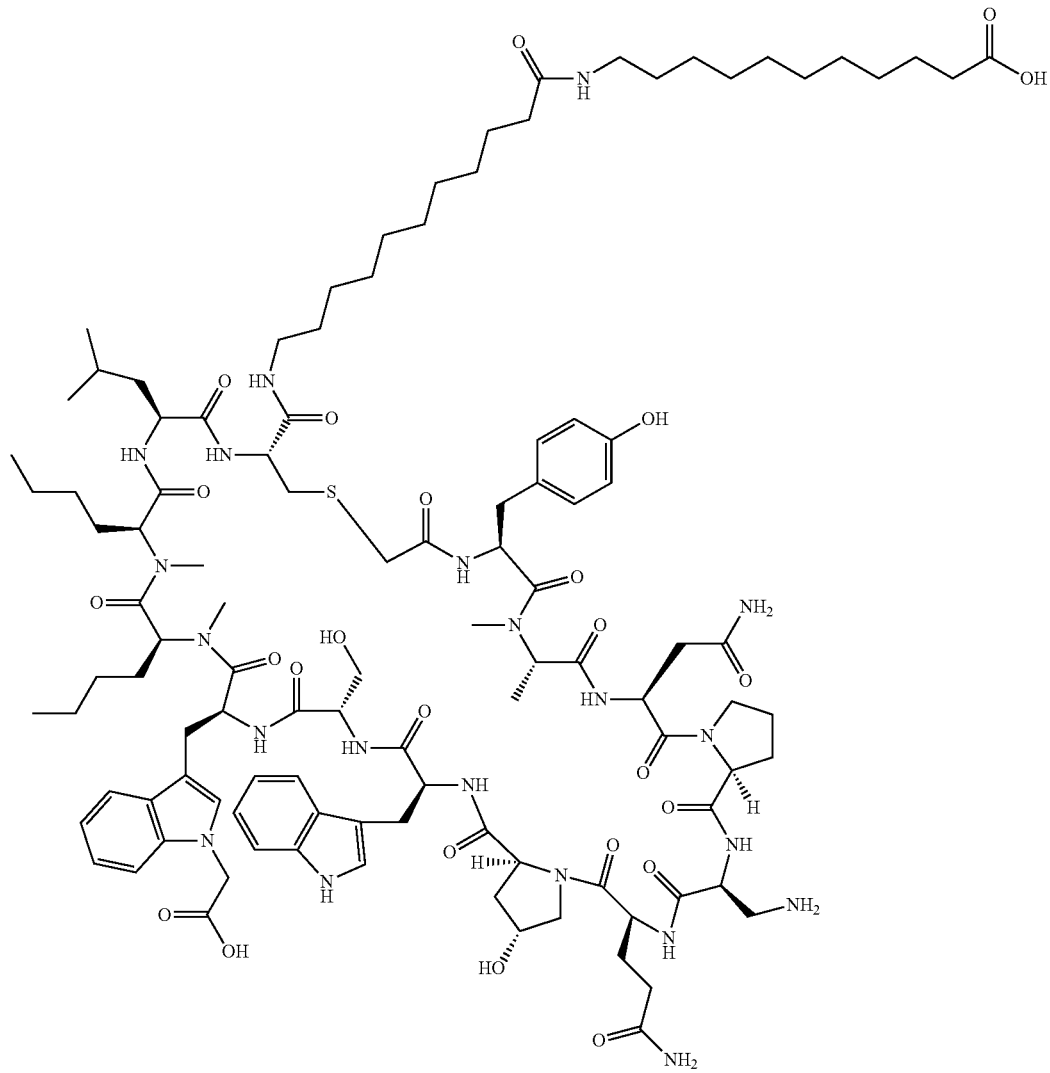 [SMILES: CCCC[C@H]1C(=O)N(C)[C@@H](CCCC)C(=O)N[C@@H](CC(C)C)C(=O)N[C@H](C(=O)NCCCCCCCCCCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11089 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 23 mg, and its estimated purity by LCMS analysis was 87.6%. Analysis LCMS Condition A: Retention time=4.923 min; ESI-MS(+) m/z 1100.9 (M+2H).

Preparation of Example 11090

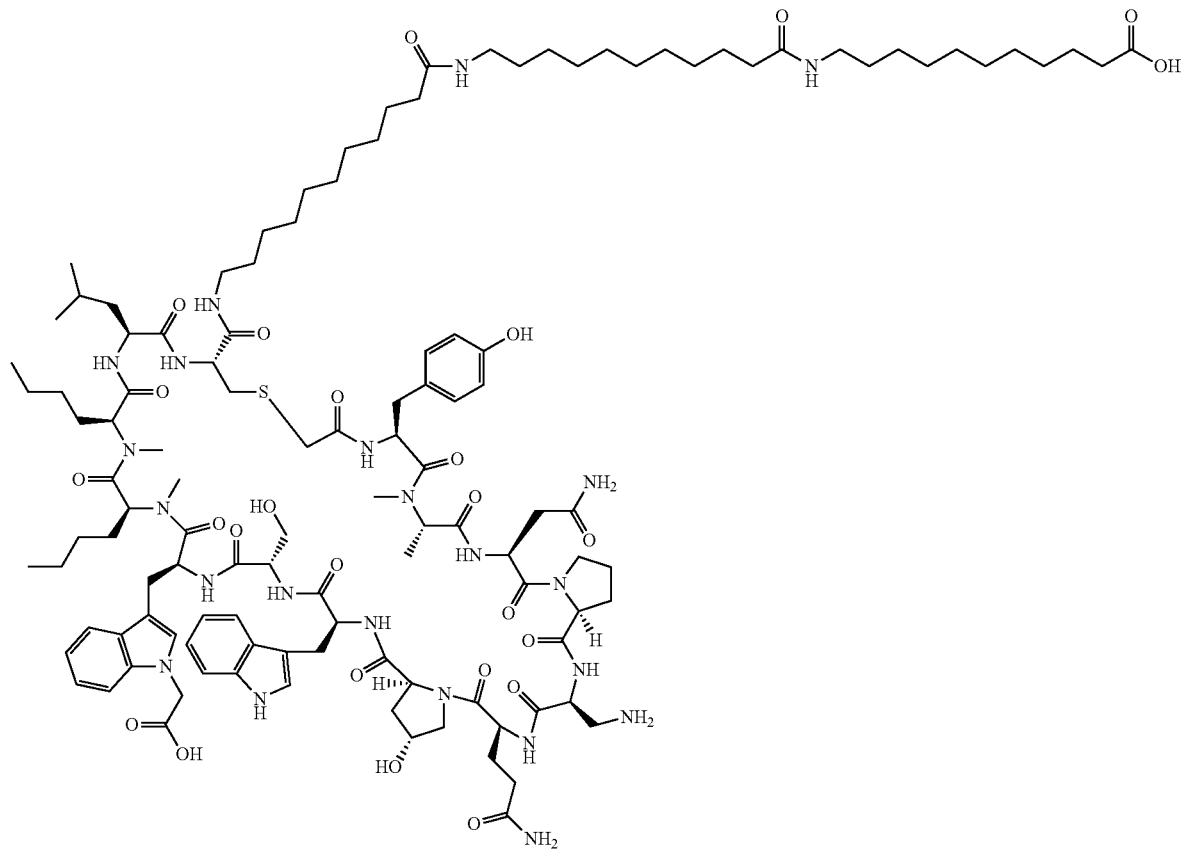 [SMILES: CCCC[C@H]1C(=O)N(C)[C@@H](CCCC)C(=O)N[C@@H](CC(C)C)C(=O)N[C@H](C(=O)NCCCCCCCCCCC(=O)NCCCCCCCCCCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11090 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 21 mg, and its estimated purity by LCMS analysis was 98.5%; Analysis LCMS Condition A: Retention time=5.395 min; ESI-MS(+) m/z 1192.7 (M+2H).

Preparation of Example 11091

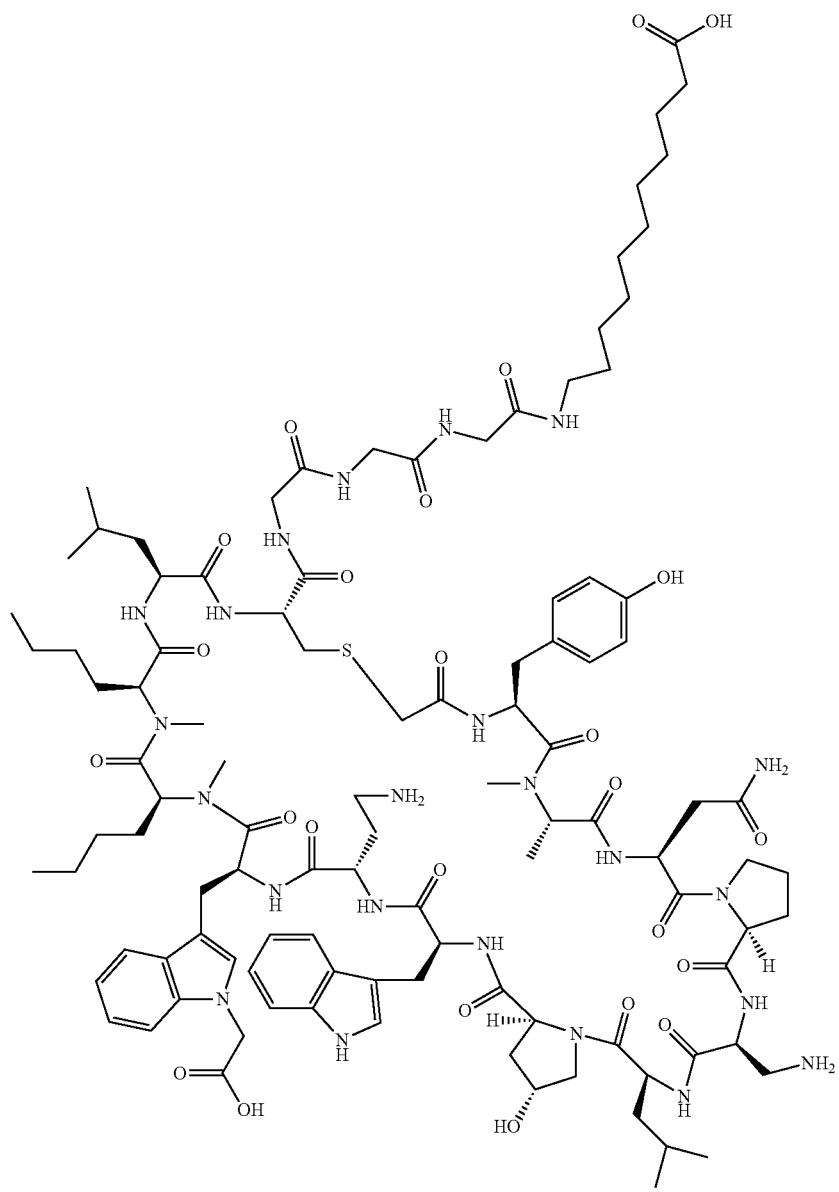 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11091 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 27 mg, and its estimated purity by LCMS analysis was 98.9%. Analysis LCMS Condition A: Retention time=4.256 min; ESI-MS(+) m/z 1093.9 (M+2H); ESI-HRMS(+) m/z: Calculated: 1093.0794 (M+2H). Found: 1093.0779 (M+2H).

Preparation of Example 11092

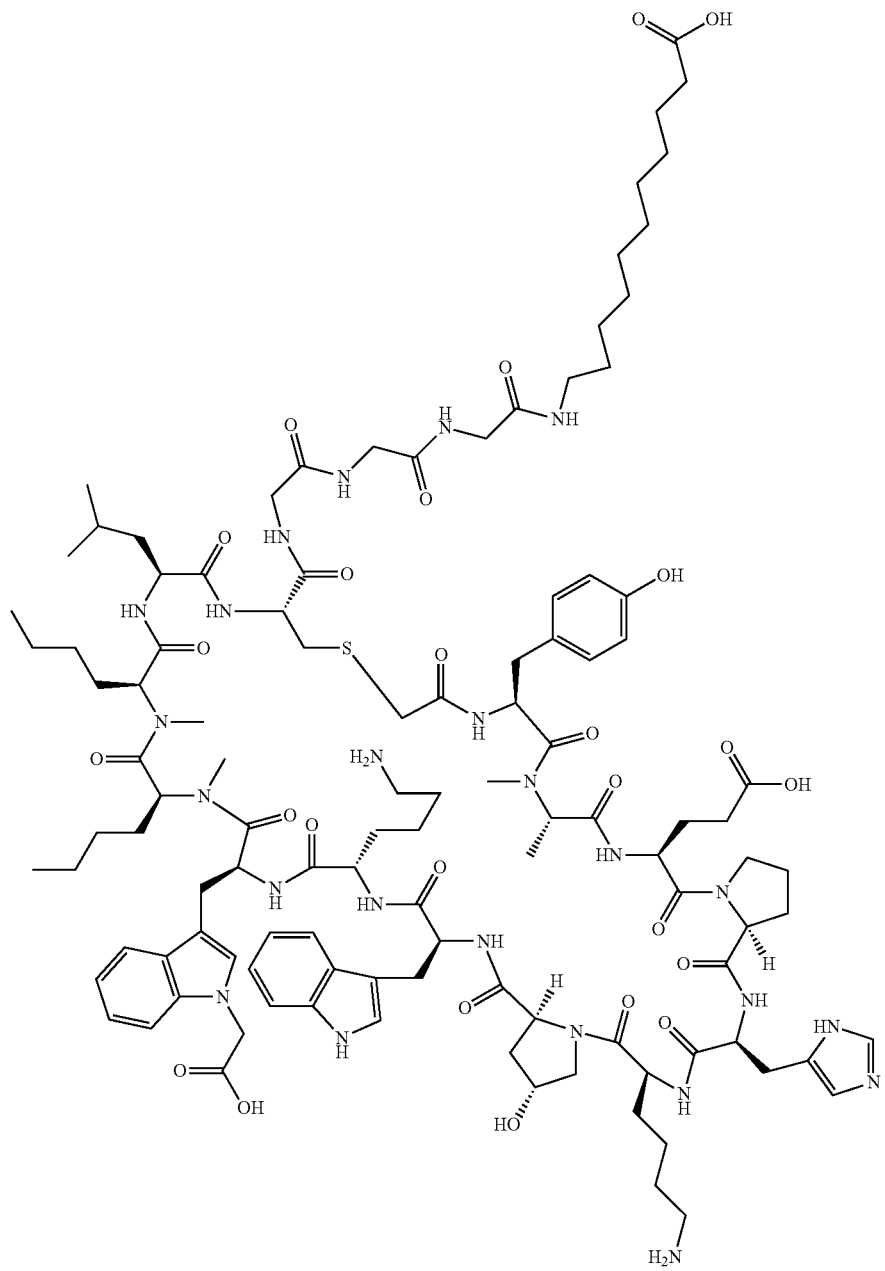 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CCC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11092 was prepared following the general synthetic sequence procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 31 mg, and its estimated purity by LCMS analysis was 95.9%. Analysis LCMS Condition A: Retention time=4.031 min; ESI-MS(+) m/z 1148.4 (M+2H); ESI-HRMS(+) m/z:

Calculated: 1159.6107 (M+2H). Found: 1159.6104 (M+2H).

Preparation of Example 11093

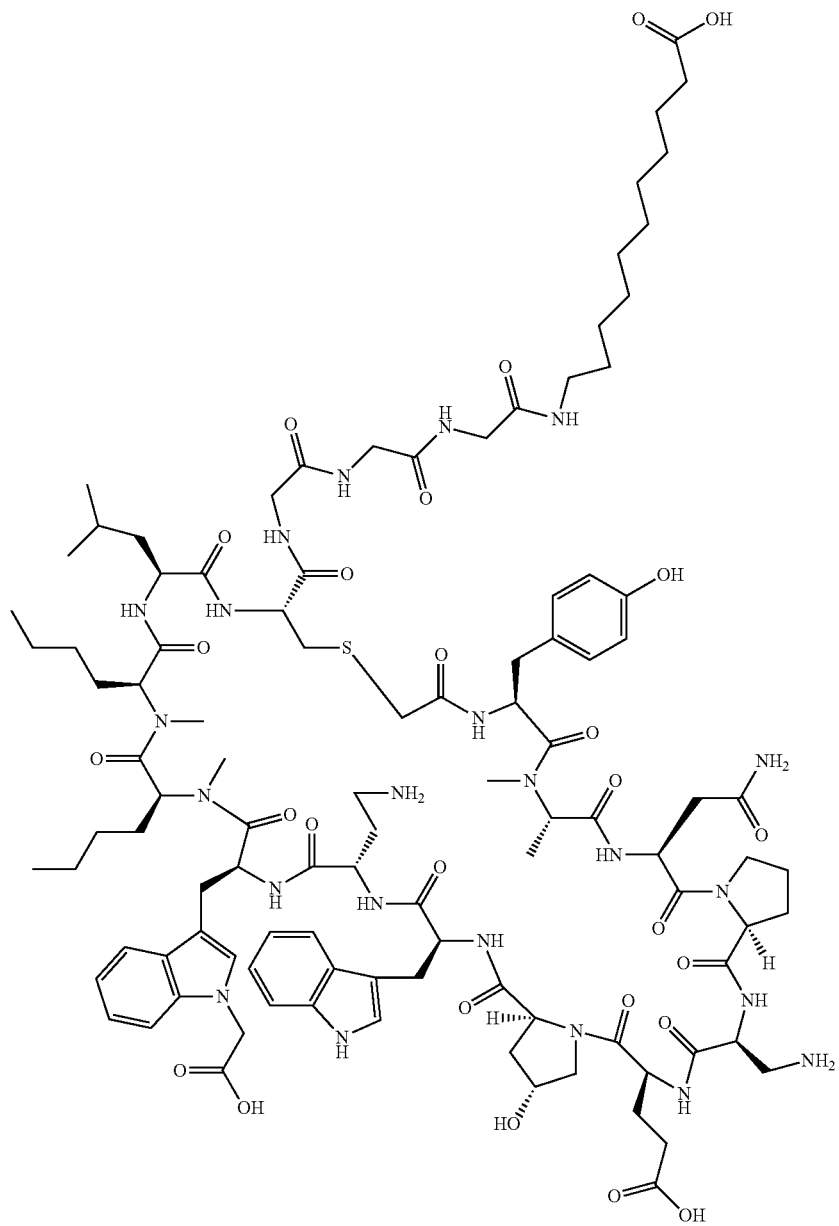 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11093 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 16 mg, and its estimated purity by LCMS analysis was 95.6%. Analysis LCMS Condition A: 9 min gradient 1 min hold: Retention time=3.920 min; ESI-MS(+) m/z 1101.9 (M+2H); ESI-HRMS(+) m/z: Calculated: 1101.0586 (M+2H). Found: 1101.0578 (M+2H).

Preparation of Example 11094

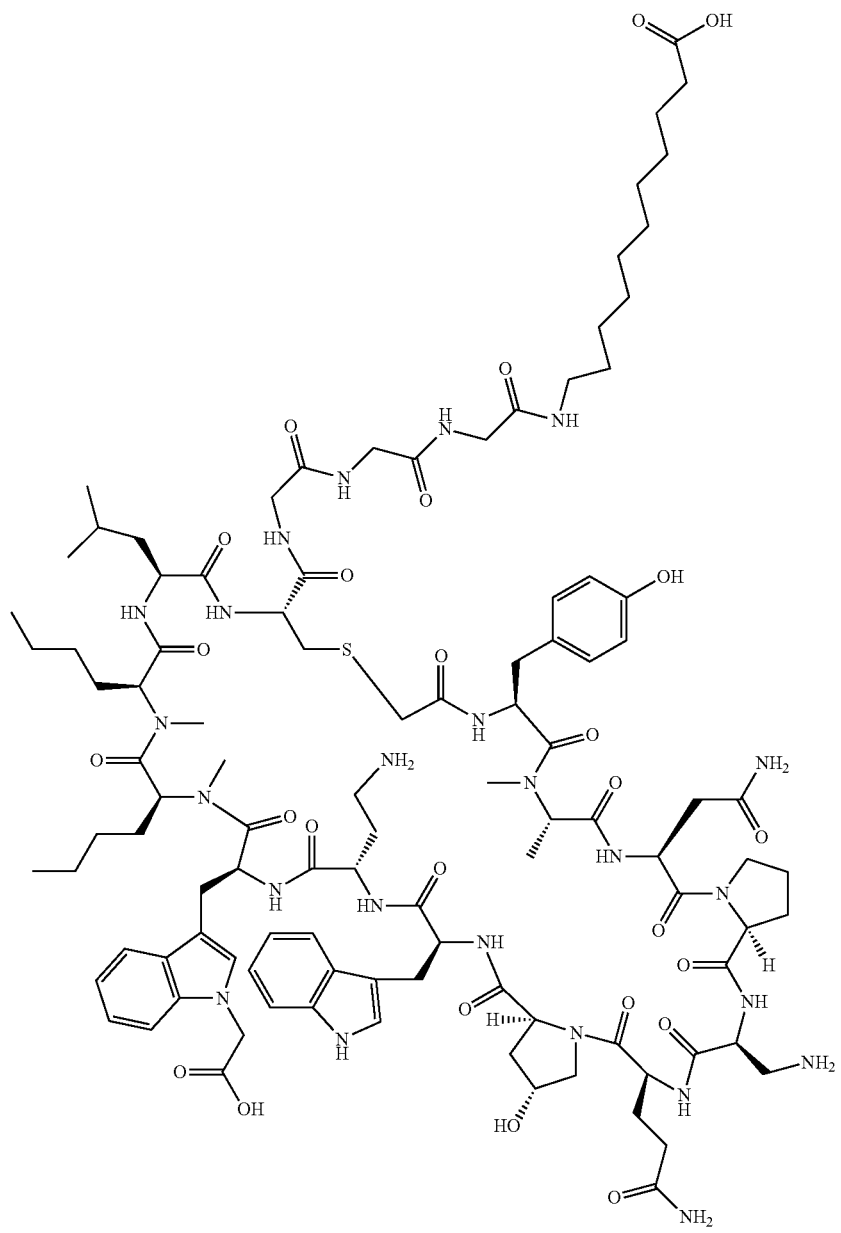 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11094 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 23 mg, and its estimated purity by LCMS analysis was 98.3%. Analysis LCMS Condition A: 9 min gradient 1 min hold: Retention time=4.023 min; ESI-MS(+) m/z 1101.5 (M+2H).

Preparation of Example 11095

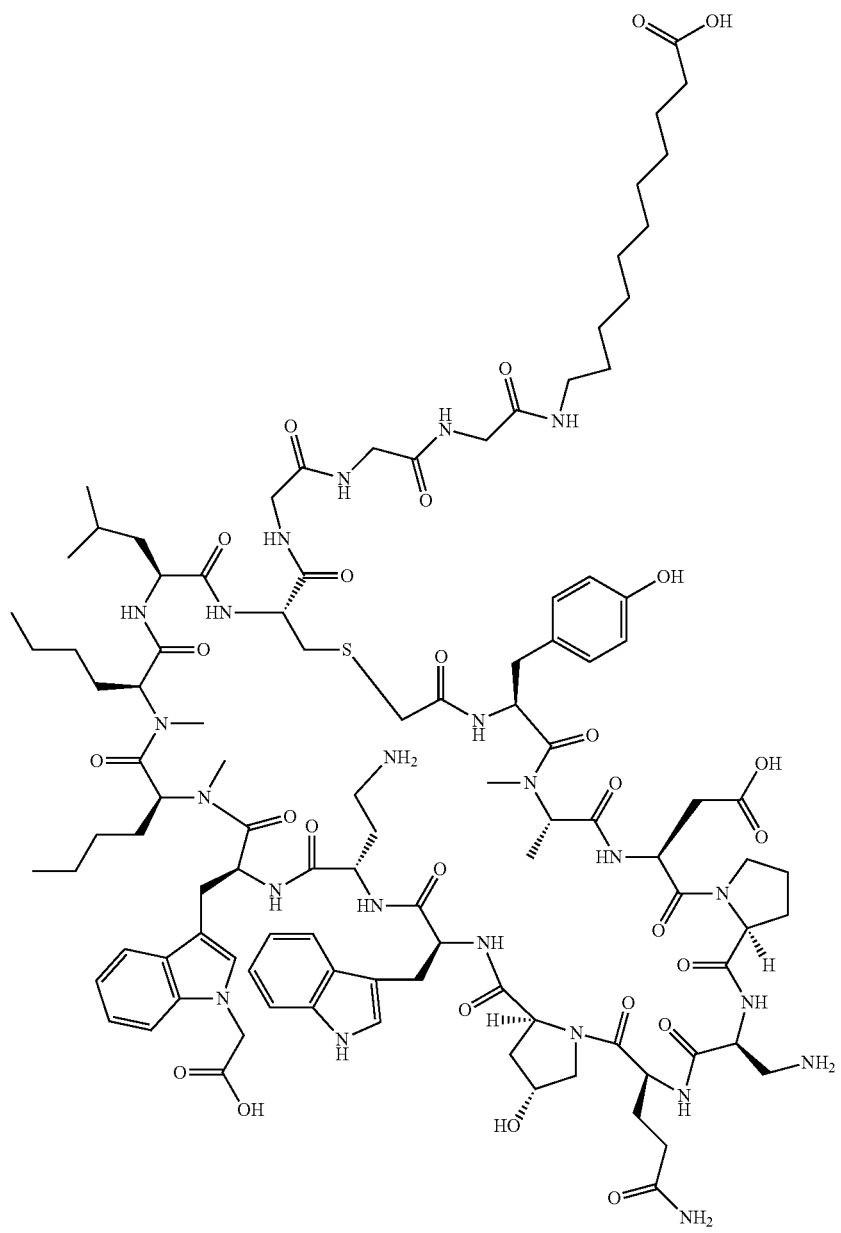

Example 11095 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 25 mg, and its estimated purity by LCMS analysis was 98.4%. Analysis LCMS Condition A: 4 min gradient 1 min hold: Retention time=2.288 min; ESI-MS(+) m/z 1101.9 (M+2H).

Preparation of Example 11096

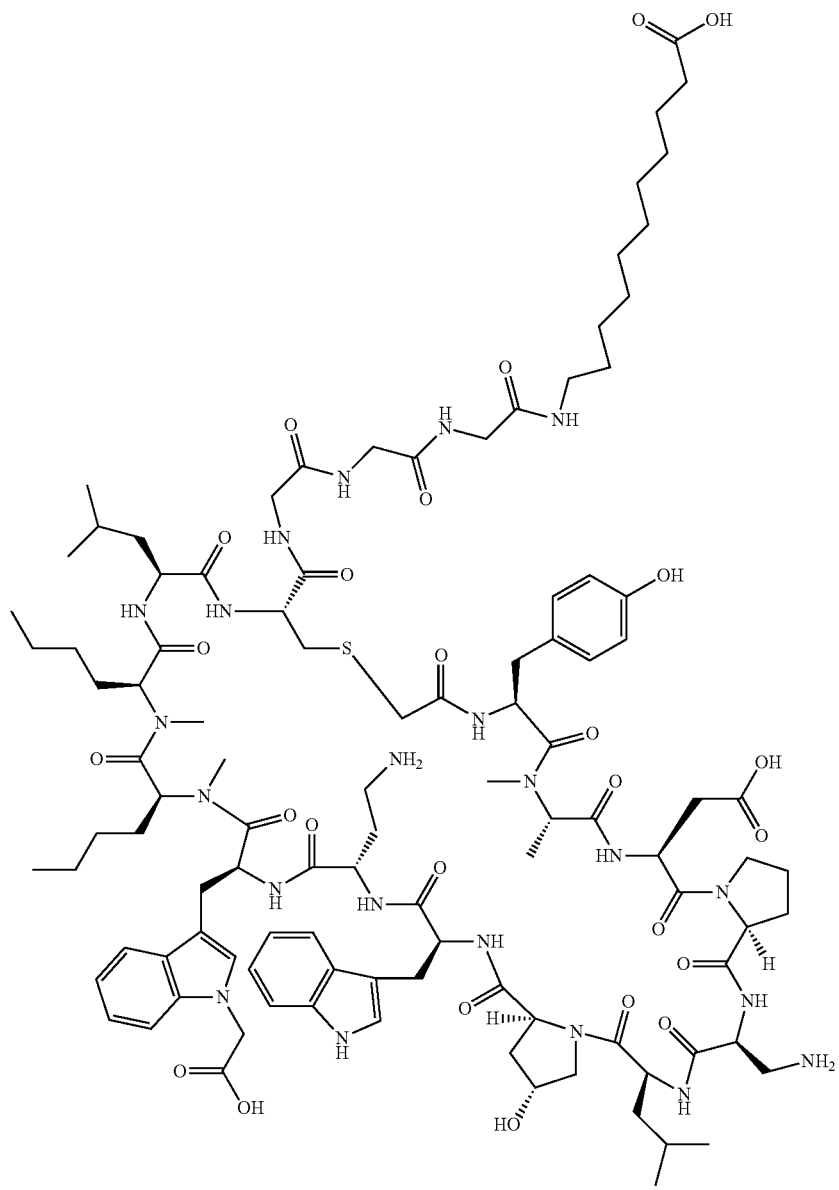 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11096 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 13 mg, and its estimated purity by LCMS analysis was 100%. Analysis LCMS Condition A: Retention time=4.056 min; ESI-MS(+) m/z 1094.4 (M+2H); ESI-HRMS(+) m/z: Calculated: 1093.5714 (M+2H). Found: 1093.5685 (M+2H).

Preparation of Example 11097

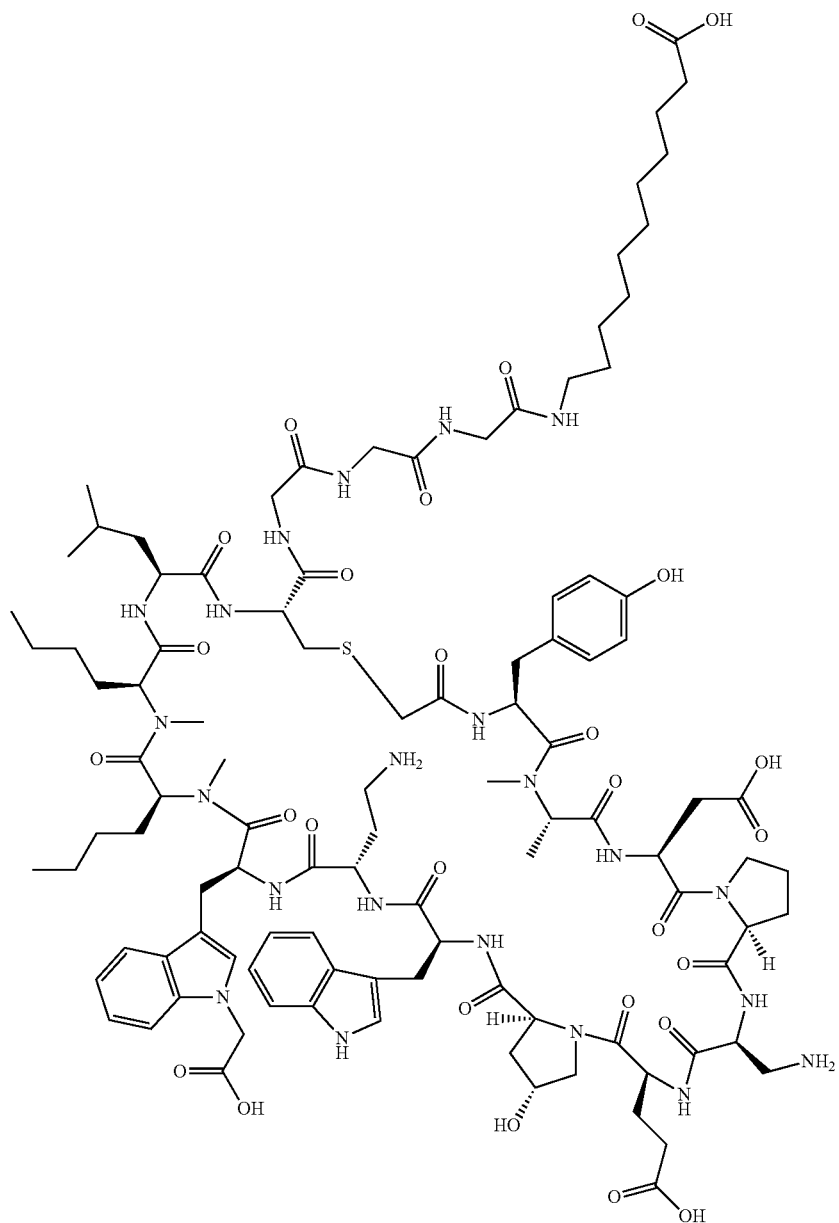 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11097 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 39 mg, and its estimated purity by LCMS analysis was 94.4%. Analysis LCMS Condition A: Retention time=3.953 min; ESI-MS(+) m/z 1102.3 (M+2H); ESI-HRMS(+) m/z: Calculated: 1101.5506 (M+2H). Found: 1101.5499 (M+2H).

Preparation of Example 11098

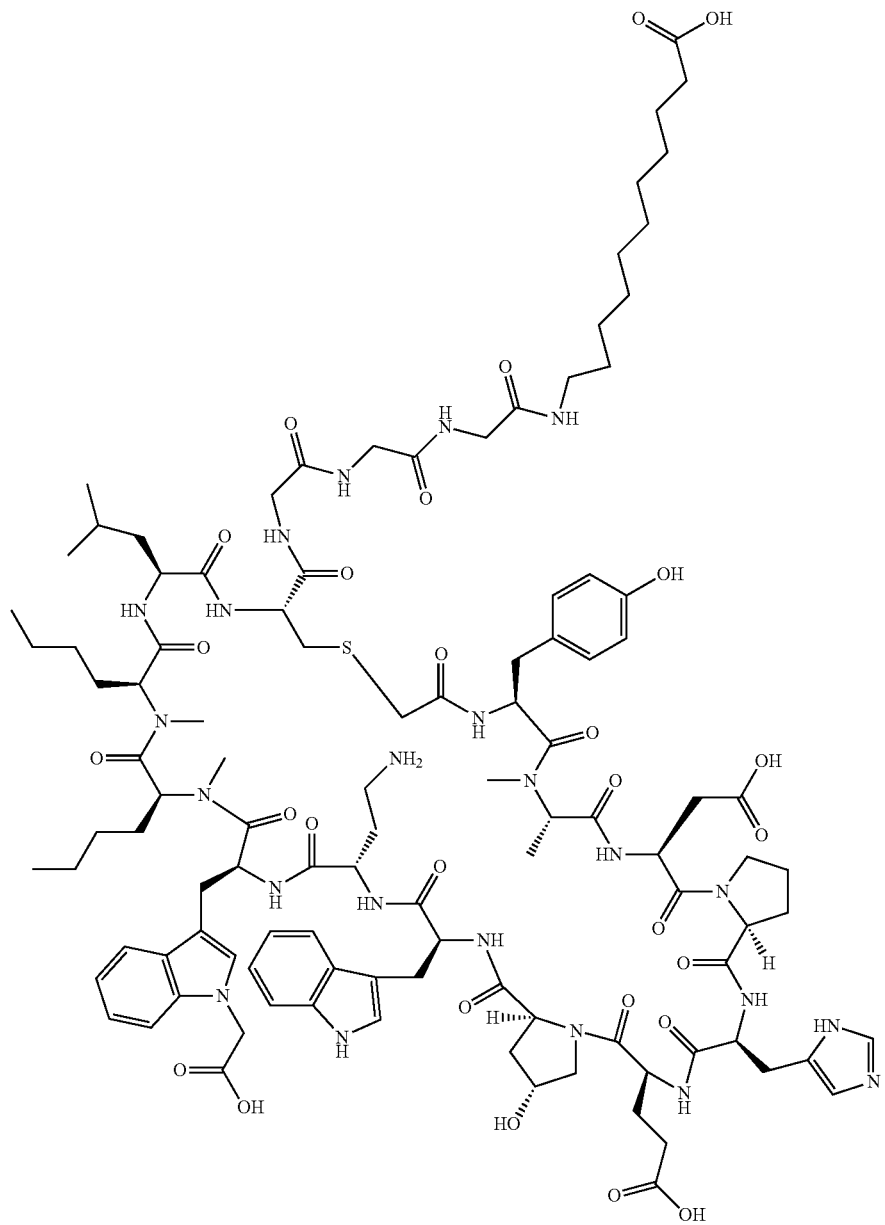 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11098 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 17 mg, and its estimated purity by LCMS analysis was 98.5%. Analysis LCMS Condition A: Retention time=3.878 min; ESI-MS(+) m/z 1127.9 (M+2H); ESI-HRMS(+) m/z: Calculated: 1127.0561 (M+2H). Found: 1127.0564 (M+2H).

Preparation of Example 11099

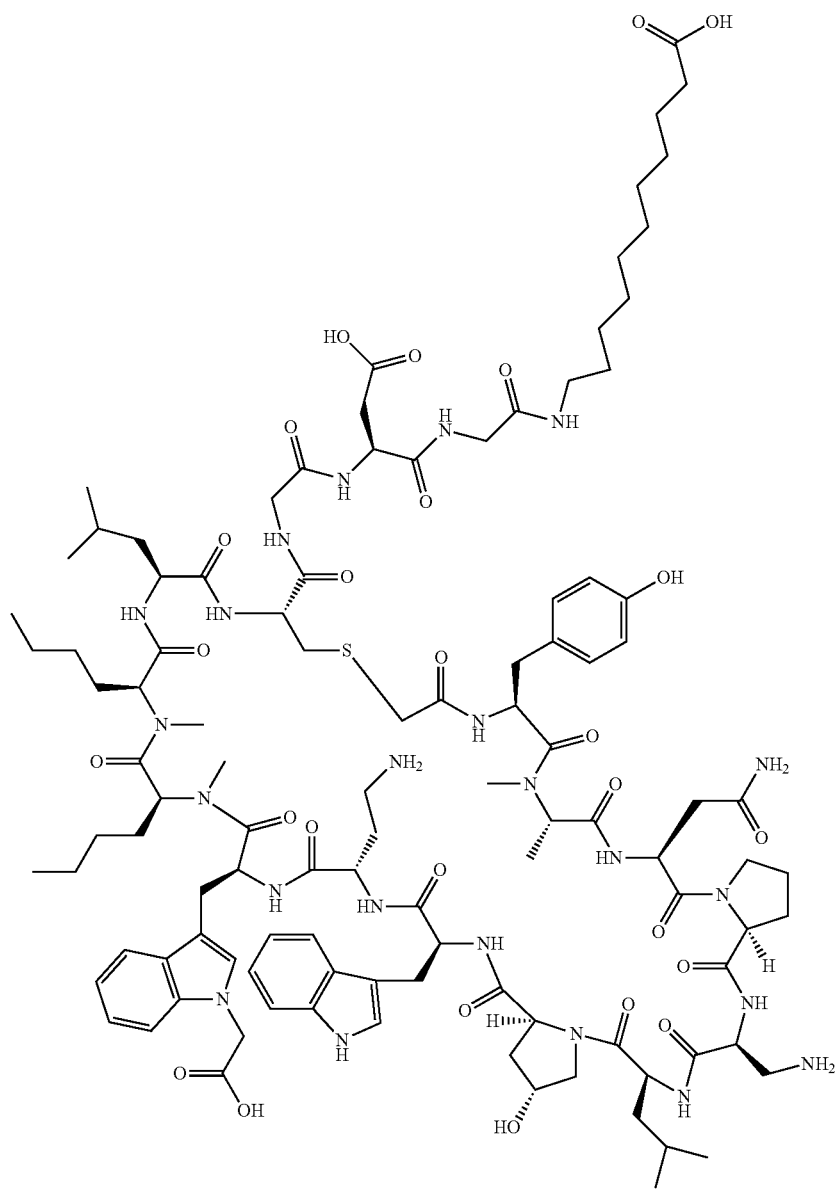 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11099 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 33 mg, and its estimated purity by LCMS analysis was 96.3%. Analysis LCMS Condition A: Retention time=4.035 min; ESI-MS(+) m/z 1122.8 (M+2H).

Preparation of Example 11100

Preparation of Example 11101

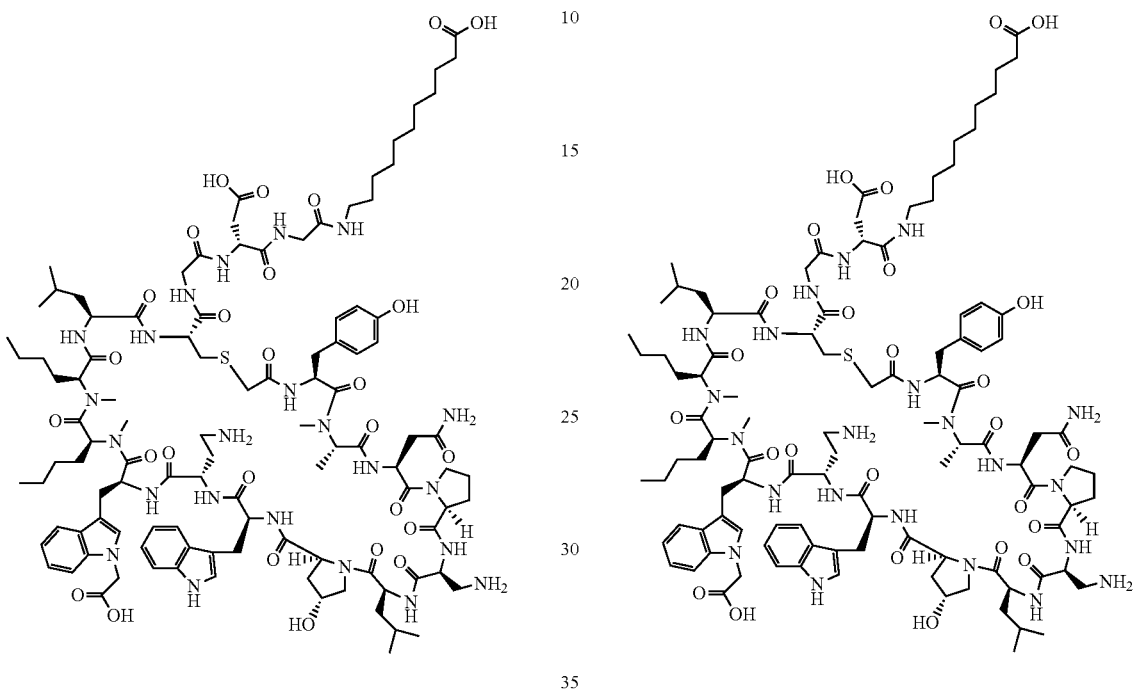

Example 11100 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 31 mg, and its estimated purity by LCMS analysis was 99%. Analysis LCMS Condition A: Retention time=4.08 min; ESI-MS(+) m/z 1122.8 (M+2H).

Example 11101 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 43 mg, and its estimated purity by LCMS analysis was 99%. Analysis LCMS Condition A: Retention time=4.16 min; ESI-MS(+) m/z 1094.3 (M+2H).

Preparation of Modified 2-chlorotrityl chloride resin D

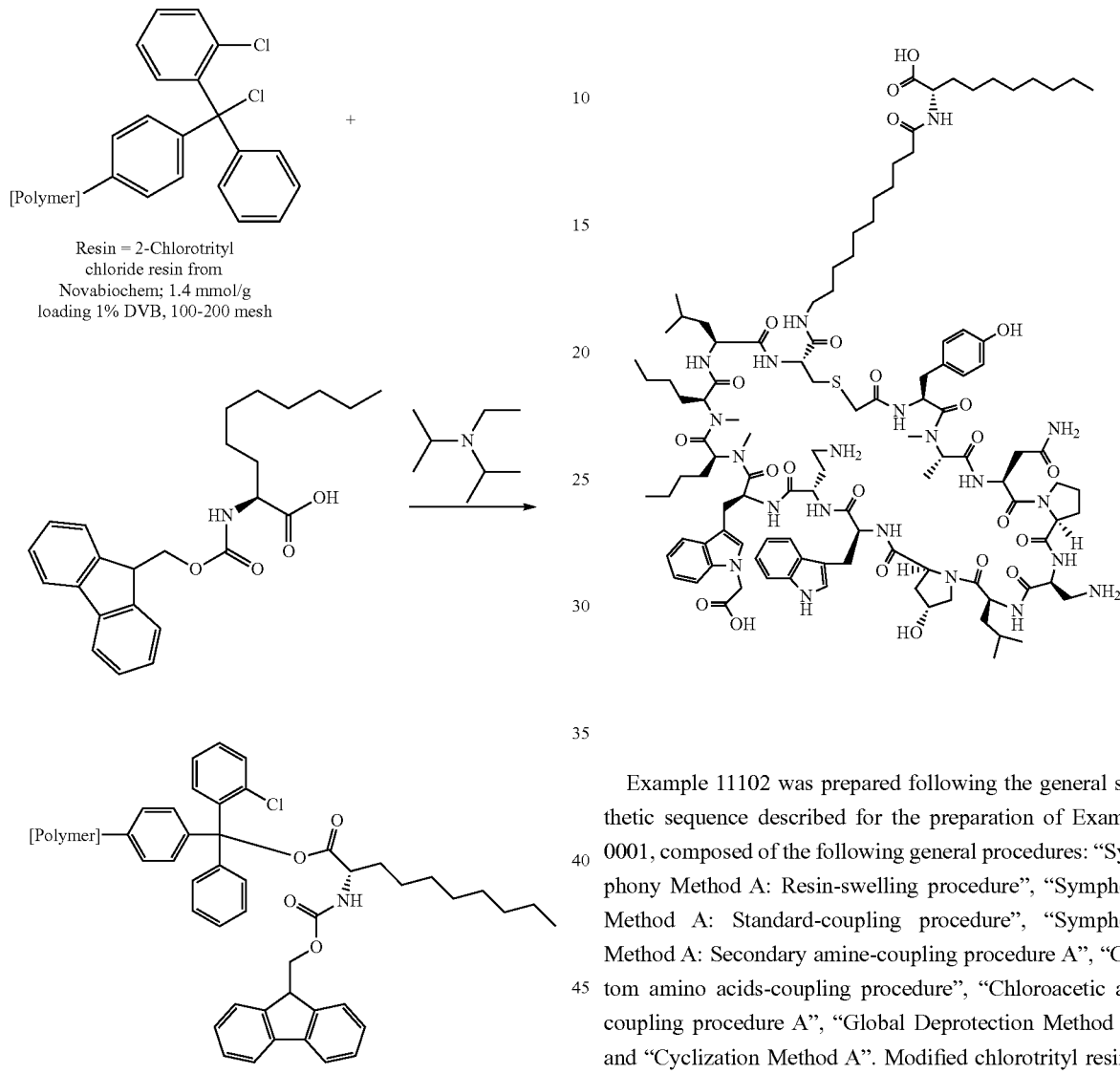

Preparation of Example 11102

To a 20 ml scintillation vial was added (S)—N-FMOC-OCTYLGLYCINE (180 mg, 0.440 mmol), 2-chlorotrityl chloride (1000 mg, 1.400 mmol), CH$_2$Cl$_2$ (10 mL), and N-ethyl-N-isopropylpropan-2-amine (398 mg, 3.08 mmol). The vial was sealed and shaken on a wrist action shaker overnight. The next day the reaction was terminated by adding 2 ml methanol and shaking the flask for an additional 2 hr. The resin was then filtered and washed with CH$_2$Cl$_2$, DMF 3×, CH$_2$Cl$_2$ 3×, and finally diethyl ether. The resin was dried in vacuo and used as is for peptide synthesis. The resin is used for peptide synthesis with an assumed loading of 0.44 meq/g.

Example 11102 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin D was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 30 mg, and its estimated purity by LCMS analysis was 98.4%. Analysis LCMS Condition A: Retention time=5.223 min; ESI-MS(+) m/z 1093.0 (M+2H); ESI-HRMS(+) m/z: Calculated: 1092.1205 (M+2H). Found: 1092.1202 (M+2H).

Preparation of Example 11103

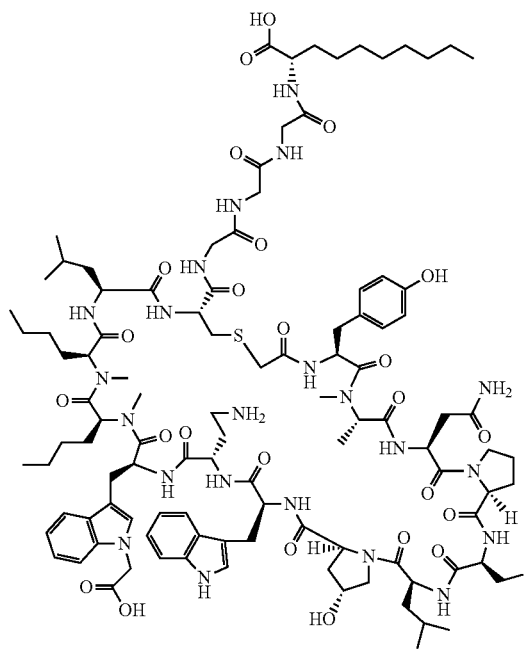

Example 11103 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin D was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 18 mg, and its estimated purity by LCMS analysis was 100%. Analysis LCMS Condition A: Retention time=4.445 min; ESI-MS(+) m/z 1086.9 (M+2H).

Preparation of $C_{16}$ amine modified 4-(4-Formyl-3-methoxy-phenoxy)butyryl AM resin A

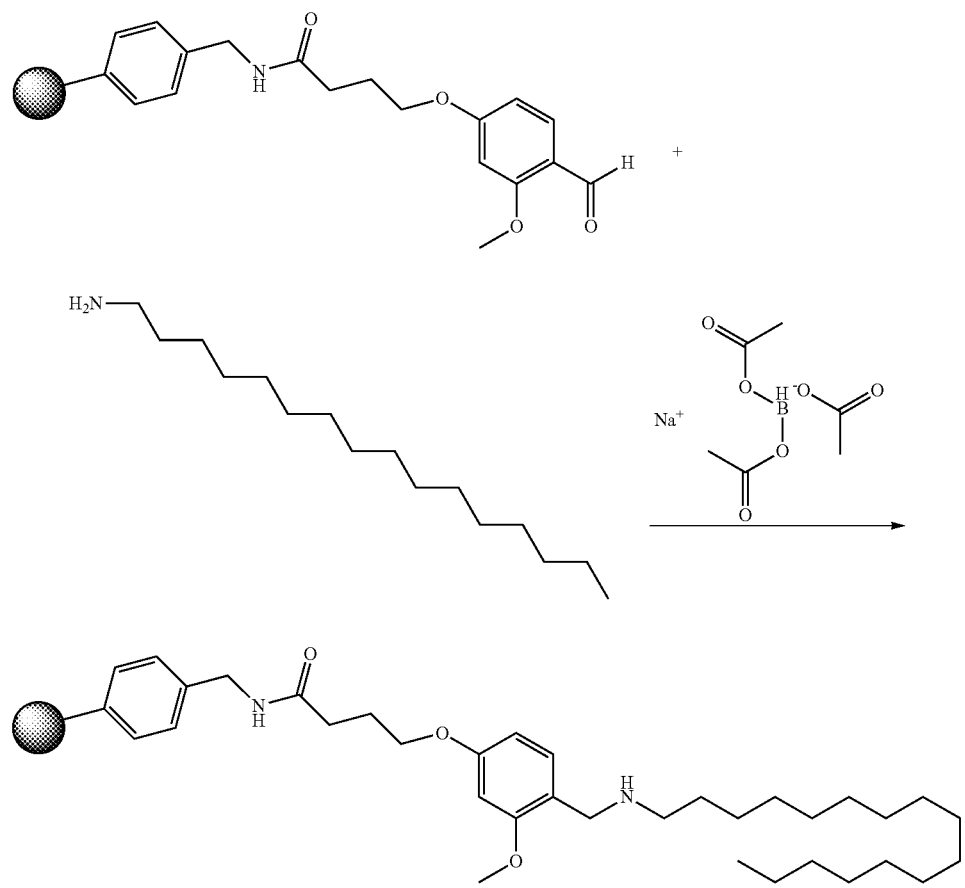

To a 20 ml vial was added 4-(4-formyl-3-methoxy-phenoxy)butyryl AM resin (0.94 mmol/g) (2 g, 1.880 mmol), hexadecan-1-amine (1.816 g, 7.52 mmol), Sodium Triacetoxyborohydride (1.594 g, 7.52 mmol), DMF (10 mL), and Acetic Acid (0.1 mL). The vial was sealed and shaken for 48 hr on an orbital shaker. After 48 hours the reaction mixture was filtered and the crude resin was washed 5× with DMF, 3× Methanol, 5×CH$_2$Cl$_2$, and finally with Diethyl ether. The resin was dried overnight under vacuum. The loading was assumed to be 0.94 mmol/g and used as is in subsequent steps.

Preparation of C$_{16}$ amine modified
4-(4-Formyl-3-methoxy-phenoxy)butyryl AM resin
B

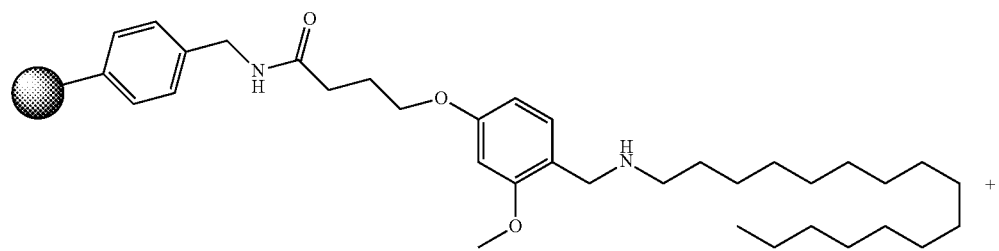

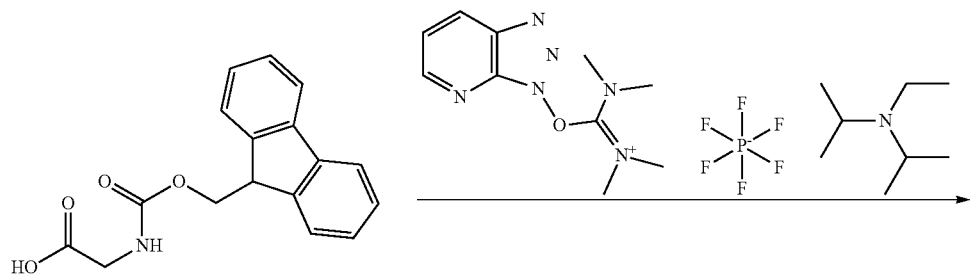

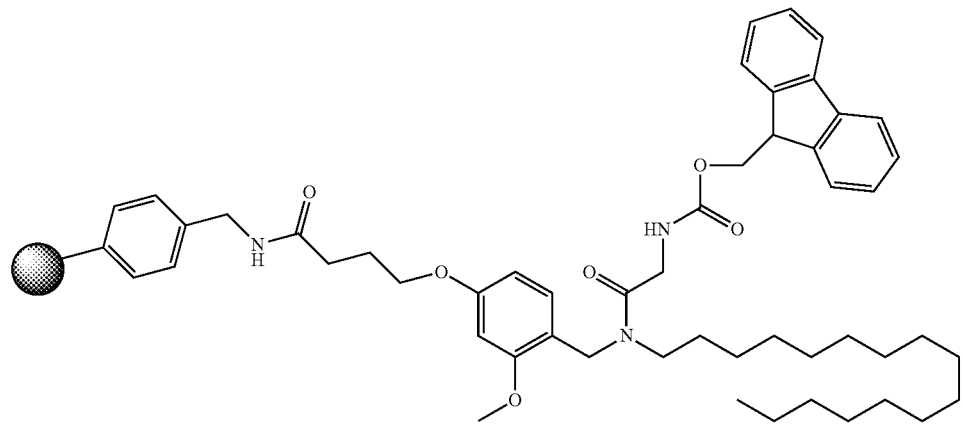

To a 40 ml vial was added $C_{16}$ amine modified 4-(4-Formyl-3-methoxy-phenoxy)butyryl AM resin A (1 g, 0.940 mmol), 0.2 M 2-((((9H-fluoren-9-yl)methoxy)carbonyl)amino)acetic acid in DMF (9.40 ml, 1.880 mmol), 0.2M HATU in DMF (9.40 ml, 1.880 mmol), and 0.2M Hunig's Base in DMF (9.40 ml, 3.76 mmol). The vial was sealed and agitated on an orbital shaker overnight. The next day the reaction mixture was filtered and the crude resin was washed 5× with DMF, 5×$CH_2Cl_2$, and finally with 2× Diethyl ether. The resin was dried overnight under vacuum. The loading was assumed to be 0.94 mmol/g and used as is in subsequent steps.

Preparation of Example 11104

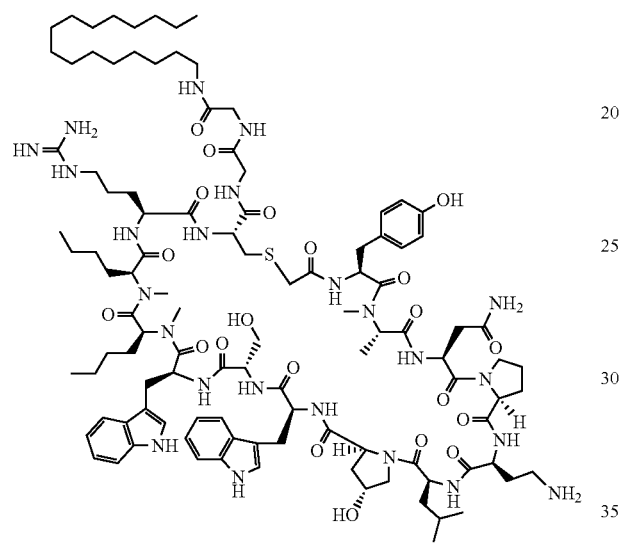

Example 11104 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 5 mg, and its estimated purity by LCMS analysis was 99.5%. Analysis LCMS Condition A: Retention time=6.025 min; ESI-MS(+) m/z 1078.25 (M+2H).

Preparation of $C_{18}$ amine modified 4-(4-Formyl-3-methoxy-phenoxy)butyryl AM resin A

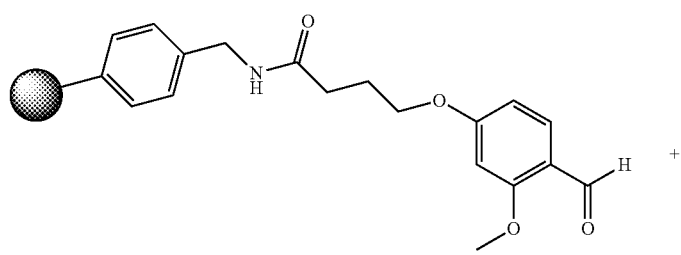

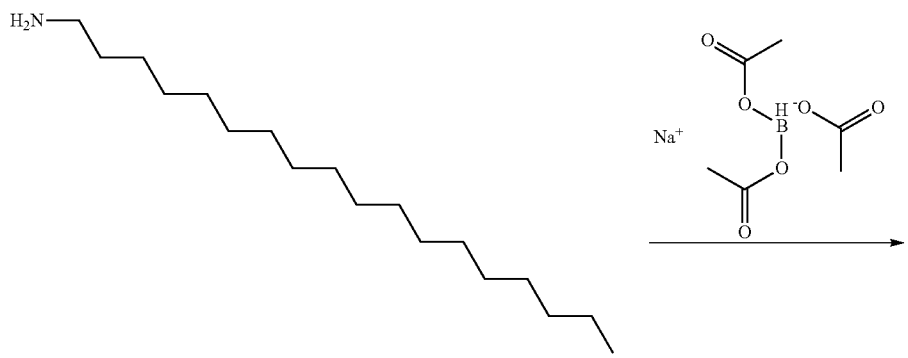

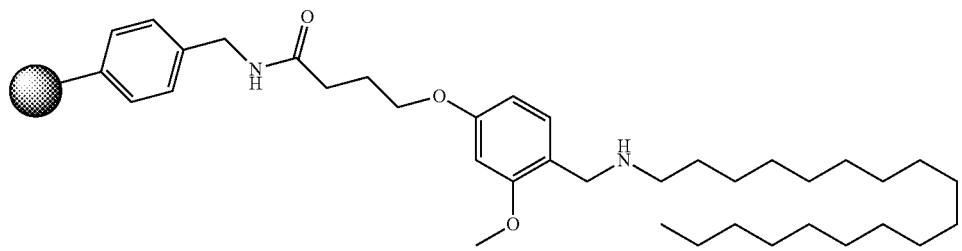

To a 20 ml vial was added 4-(4-Formyl-3-methoxyphenoxy)butyryl AM resin 0.94 mmol/g loading (2 g, 1.880 mmol), octadecan-1-amine (2.53 g, 9.40 mmol), DMF (10 mL), Acetic Acid (0.1 mL) and Sodium Triacetoxyborohydride (1.992 g, 9.40 mmol). The vial was sealed and shaken for 48 hr on an orbital shaker. After 48 hours the reaction mixture was filtered and the crude resin was washed 5× with DMF, 3× Methanol, 5×CH$_2$Cl$_2$, and finally with Diethyl ether. The resin was dried overnight under vacuum. The loading was assumed to be 0.94 mmol/g and used as is in subsequent steps.

Preparation of Example 11105

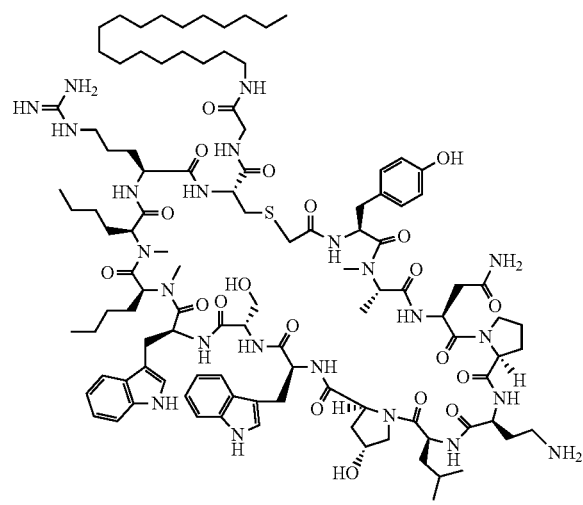 [SMILES: CCCCCCCCCCCCCCCCCCNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11105 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". C$_{18}$ amine modified 4-(4-Formyl-3-methoxy-phenoxy)butyryl AM resin A was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient 15-100% B over 25 minutes, then a 5-minute hold at 100% B; Flow: 30 mL/min. Fractions containing the desired product were combined and dried via centrifugal evaporation. The yield of the product was 5.8 mg, and its estimated purity by LCMS analysis was 99.5%. Analysis LCMS Condition A: Retention time=6.523 min; ESI-MS(+) m/z 1063.85 (M+2H).

Preparation of C$_{14}$ amine modified
4-(4-Formyl-3-methoxy-phenoxy)butyryl AM resin
A

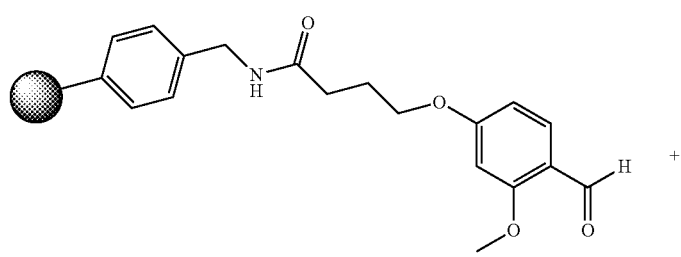

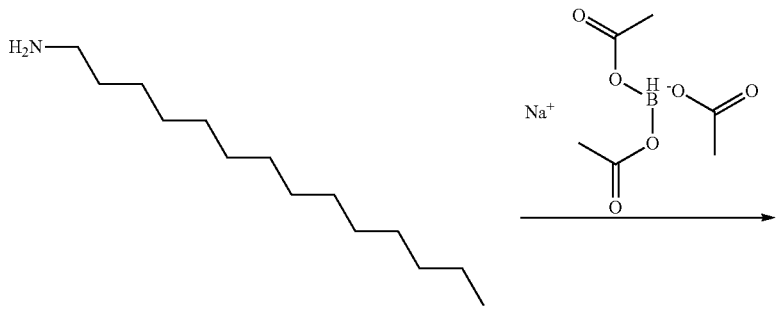

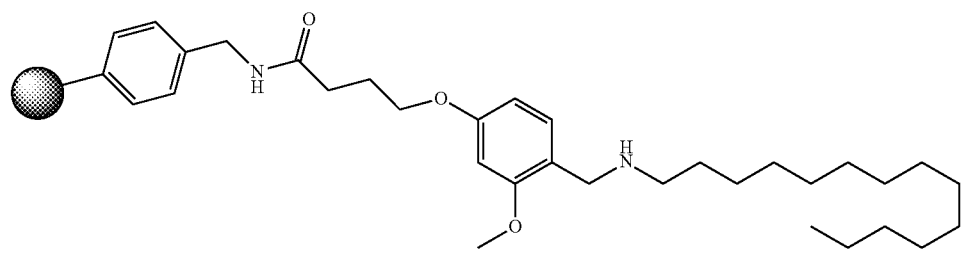

To a 20 ml vial was added 4-(4-Formyl-3-methoxyphenoxy)butyryl AM resin 0.94 mmol/g loading (2 g, 1.880 mmol), DMF (15 mL), tetradecan-1-amine (1.204 g, 5.64 mmol), Sodium triacetoxyborohydride (1.594 g, 7.52 mmol), and Acetic Acid (0.1 mL). The vial was sealed and shaken overnight on an orbital shaker. The next day the resin was filtered and washed 3× with methanol, 3× with DMF, 3× with $CH_2Cl_2$, and finally 1× with $Et_2O$. The resin was dried under vacuum and used as is in subsequent rxns. The loading was assumed to be 0.94 mmol/g and used as is in subsequent steps.

Preparation of $C_{14}$ amine modified
4-(4-Formyl-3-methoxy-phenoxy)butyryl AM resin

B

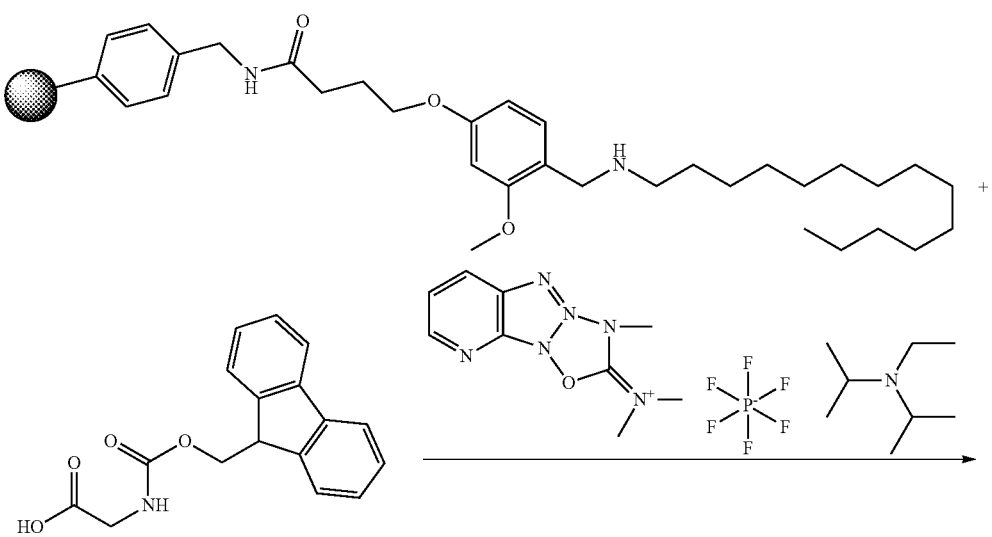

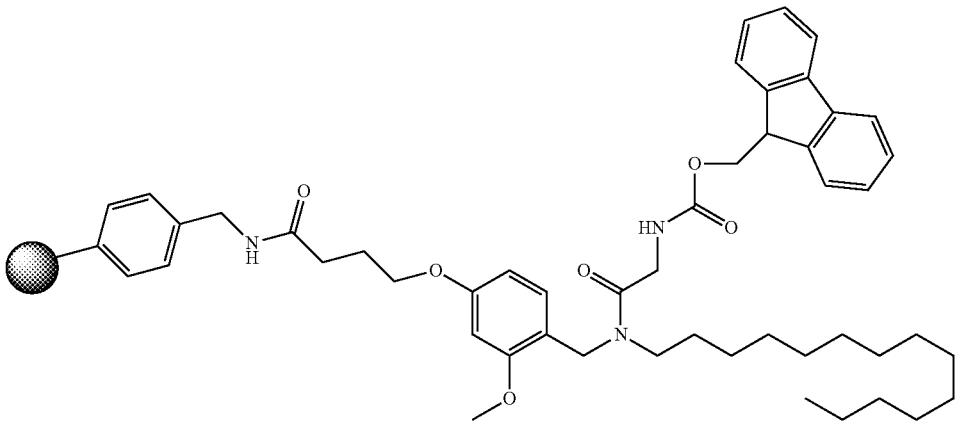

To a 40 ml vial was added $C_{14}$ amine modified 4-(4-Formyl-3-methoxy-phenoxy)butyryl AM resin A (1 g, 0.940 mmol), 0.2 M 2-((((9H-fluoren-9-yl)methoxy)carbonyl)amino)acetic acid in DMF (9.40 ml, 1.880 mmol) (99026-115), 0.2M HATU (9.40 ml, 1.880 mmol) in DMF, and 0.2 M Hunig's Base in DMF (9.40 ml, 3.76 mmol). The vial was sealed and shaken on an orbital shaker overnight. The next day the resin was filtered off and washed 3× with DMF, 3× with $CH_2Cl_2$, 3× with DMF, 1x with $CH_2Cl_2$, and finally 1× with $Et_2O$. The crude resin was dried under high vacuum. The loading was assumed to be 0.94 mmol/g and used as is in subsequent steps.

Preparation of Example 11106

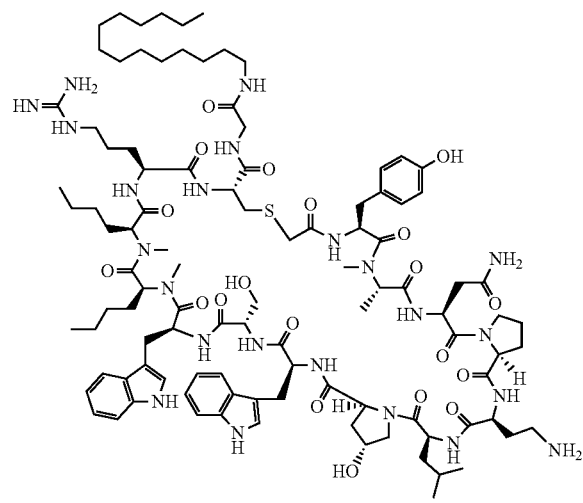 [SMILES: CCCCCCCCCCCCCCNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11106 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{14}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient 15-100% B over 25 minutes, then a 5-minute hold at 100% B; Flow: 30 mL/min. Fractions containing the desired product were combined and dried via centrifugal evaporation. The yield of the product was 13 mg, and its estimated purity by LCMS analysis was 98.9%. Analysis LCMS Condition A: Retention time=5.688 min; ESI-MS(+) m/z 1036.00 (M+2H); ESI-HRMS(+) m/z: Calculated: 1035.0921 (M+2H). Found: 1035.0925 (M+2H).

Preparation of Example 11107

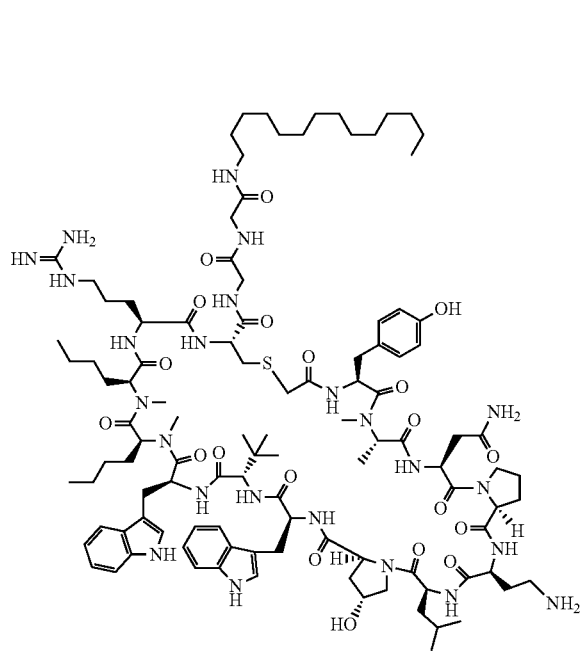 [SMILES: CCCCCCCCCCCCCCNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCN)C(=O)N[C@@H](CC(C)C)C(=O)N2C[C@H](O)C[C@H]2C(=O)N[C@@H](Cc2c[nH]c3ccccc23)C(=O)N[C@@H](C(C)(C)C)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11107 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{14}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 12 mg, and its estimated purity by LCMS analysis was 99.3%. Analysis LCMS Condition A: Retention time=5.883 min; ESI-MS(+) m/z 1077.47 (M+2H); ESI-HRMS(+) m/z: Calculated: 1076.6288 (M+2H). Found: 1076.6286 (M+2H), g.

Preparation of Example 11108

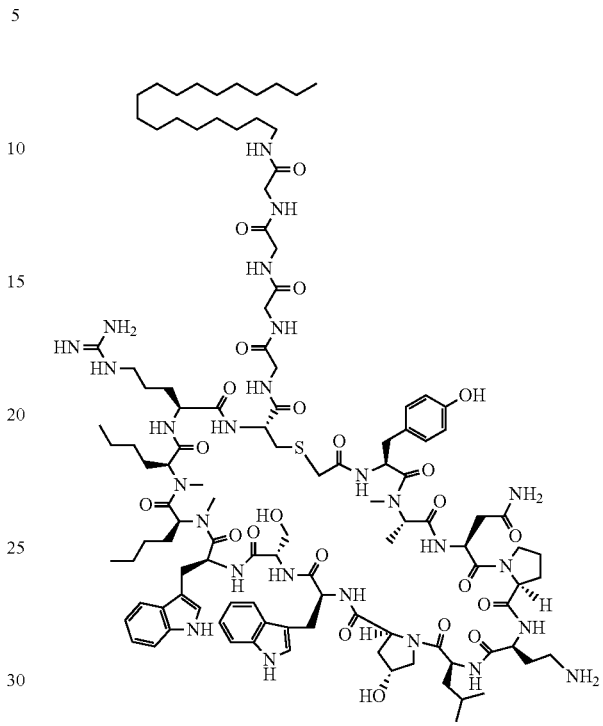

Example 11108 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 17 mg, and its estimated purity by LCMS analysis was 92%. Analysis LCMS Condition A: Retention time=6.185 min; ESI-MS(+) m/z 1127.9 (M+2H); ESI-HRMS(+) m/z: Calculated: 1127.6321 (M+2H).

Found: 1127.6329 (M+2H).

Preparation of Example 11109

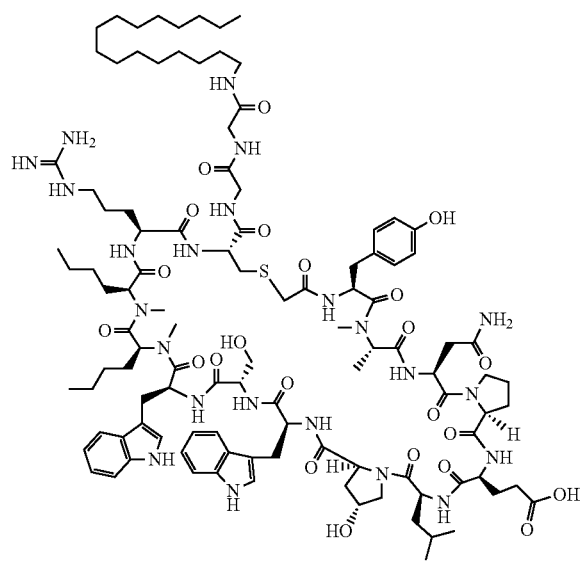 [SMILES: CCCCCCCCCCCCCCCCNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CCC(=O)O)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11109 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 23 mg, and its estimated purity by LCMS analysis was 91%. Analysis LCMS Condition A: Retention time=6.091 min; ESI-MS(+) m/z 1092.87 (M+2H); ESI-HRMS(+) m/z: Calculated: 1092.1079 (M+2H).

Found: 1092.1081 (M+2H).

Preparation of Example 11110

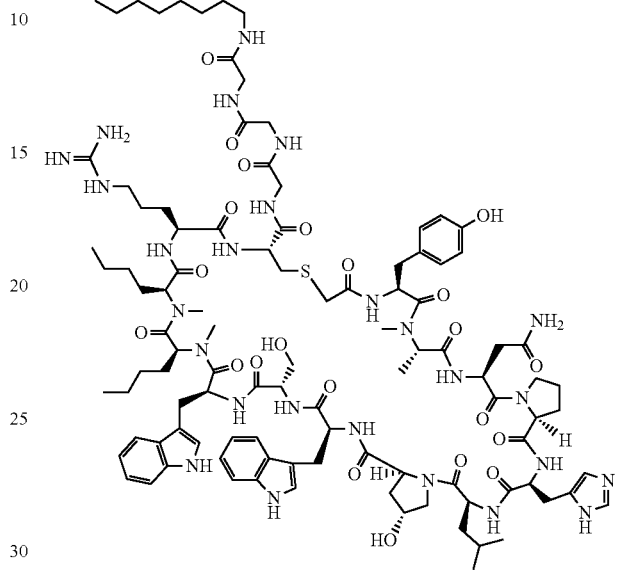

Example 11100 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 28 mg, and its estimated purity by LCMS analysis was 94%. Analysis LCMS Condition A: Retention time=6.488 min; ESI-MS(+) m/z 1125.34 (M+2H); ESI-HRMS(+) m/z: Calculated: 1124.6268 (M+2H).

Found: 1124.6228 (M+2H).

Preparation of Example 11111

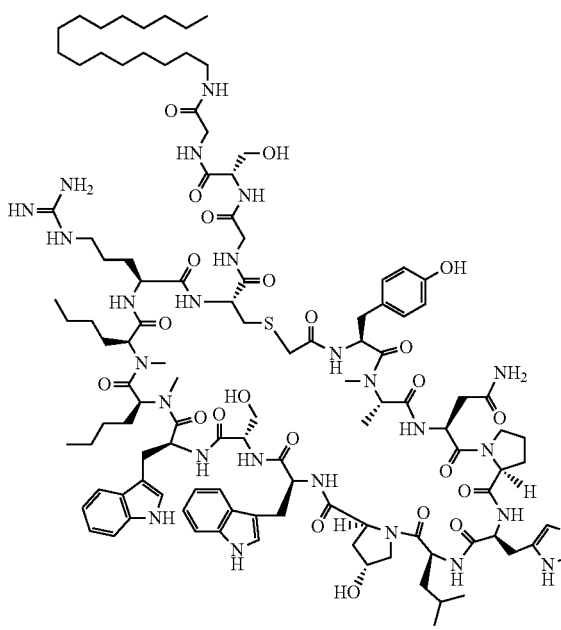

Example 11111 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin B was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 12.9 mg, and its estimated purity by LCMS analysis was 96%. Analysis LCMS Condition A: Retention time=6.473 min; ESI-MS(+) m/z 1140.55 (M+2H); ESI-HRMS(+) m/z: Calculated: 1139.6321 (M+2H).
Found: 1139.6274 (M+2H).

Preparation of $C_{16}$ amine modified
4-(4-Formyl-3-methoxy-phenoxy)butyryl AM resin
C

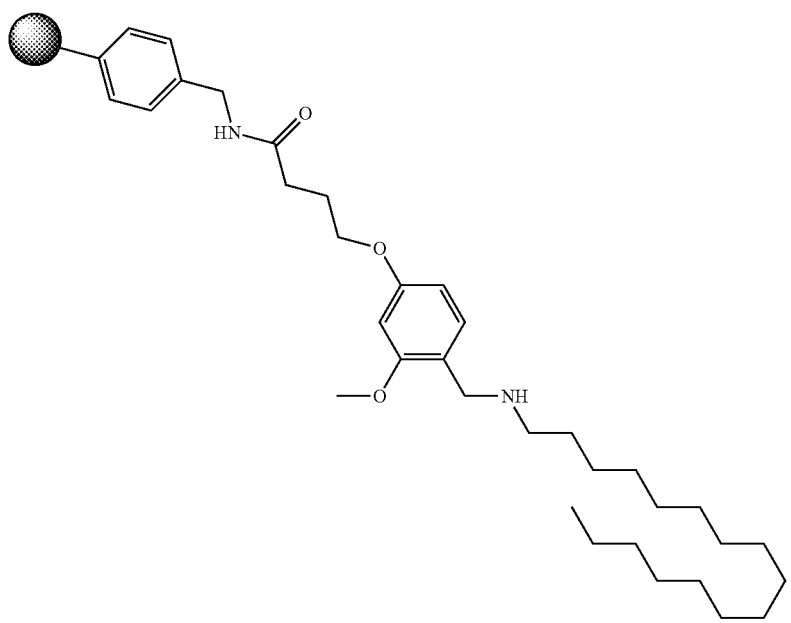

-continued

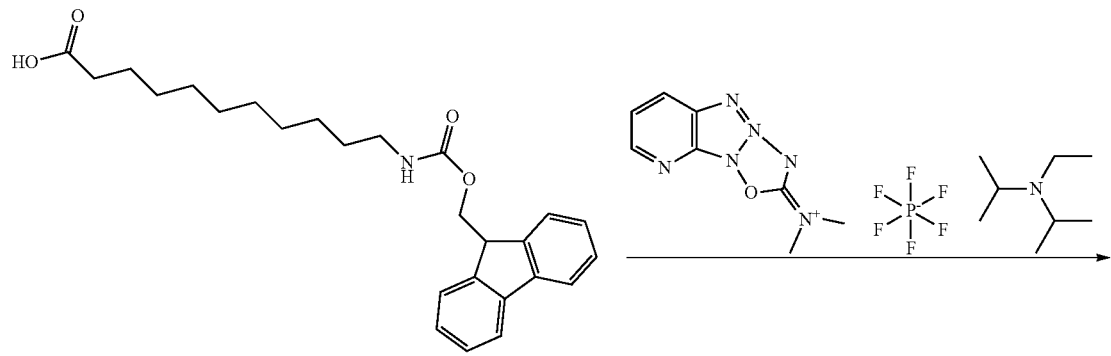

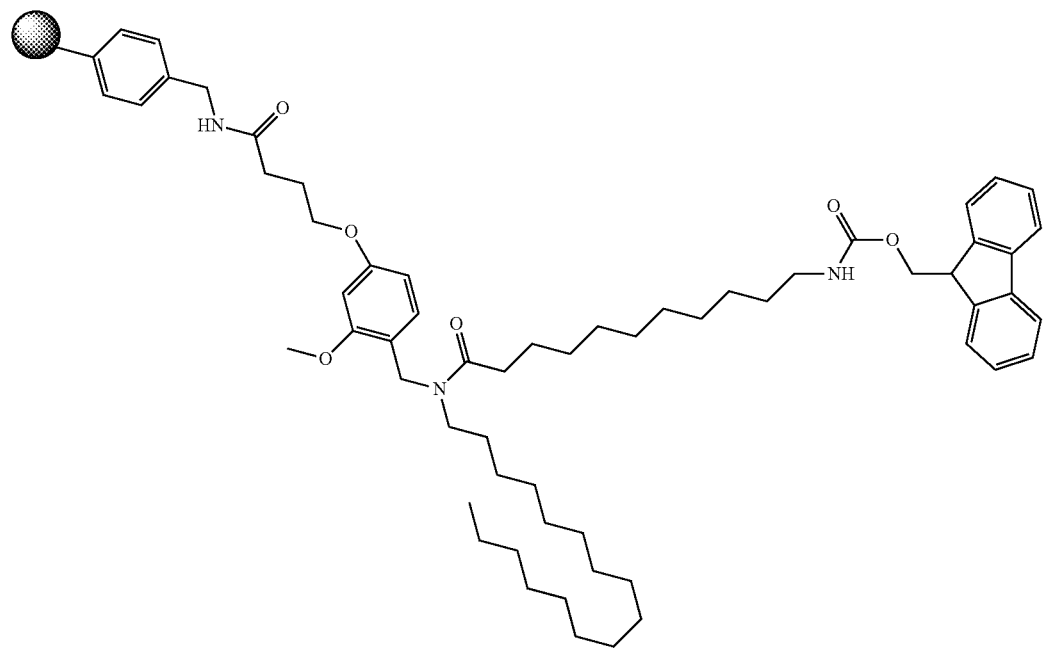

To a 20 ml vial was added C$_{16}$ amine modified 4-(4-Formyl-3-methoxy-phenoxy)butyryl AM resin A (600 mg, 0.540 mmol), 11-((((9H-fluoren-9-yl)methoxy)carbonyl)amino)undecanoic acid (457 mg, 1.080 mmol), DMF (5 mL), 0.2 M HATU in DMF (5.40 mL, 1.080 mmol), and 0.2M Hunig's Base in DMF (5.40 mL, 2.160 mmol). The vial was sealed and shaken for 24 hr on a orbital shaker. After 24 hours the reaction mixture was filtered and the crude resin was washed with methanol, 5× with DMF, 5×CH$_2$Cl$_2$, and finally with Diethyl ether. The resin was dried overnight under vacuum. The loading was assumed to be 0.94 mmol/g and used as is in subsequent steps.

Preparation of Example 11112

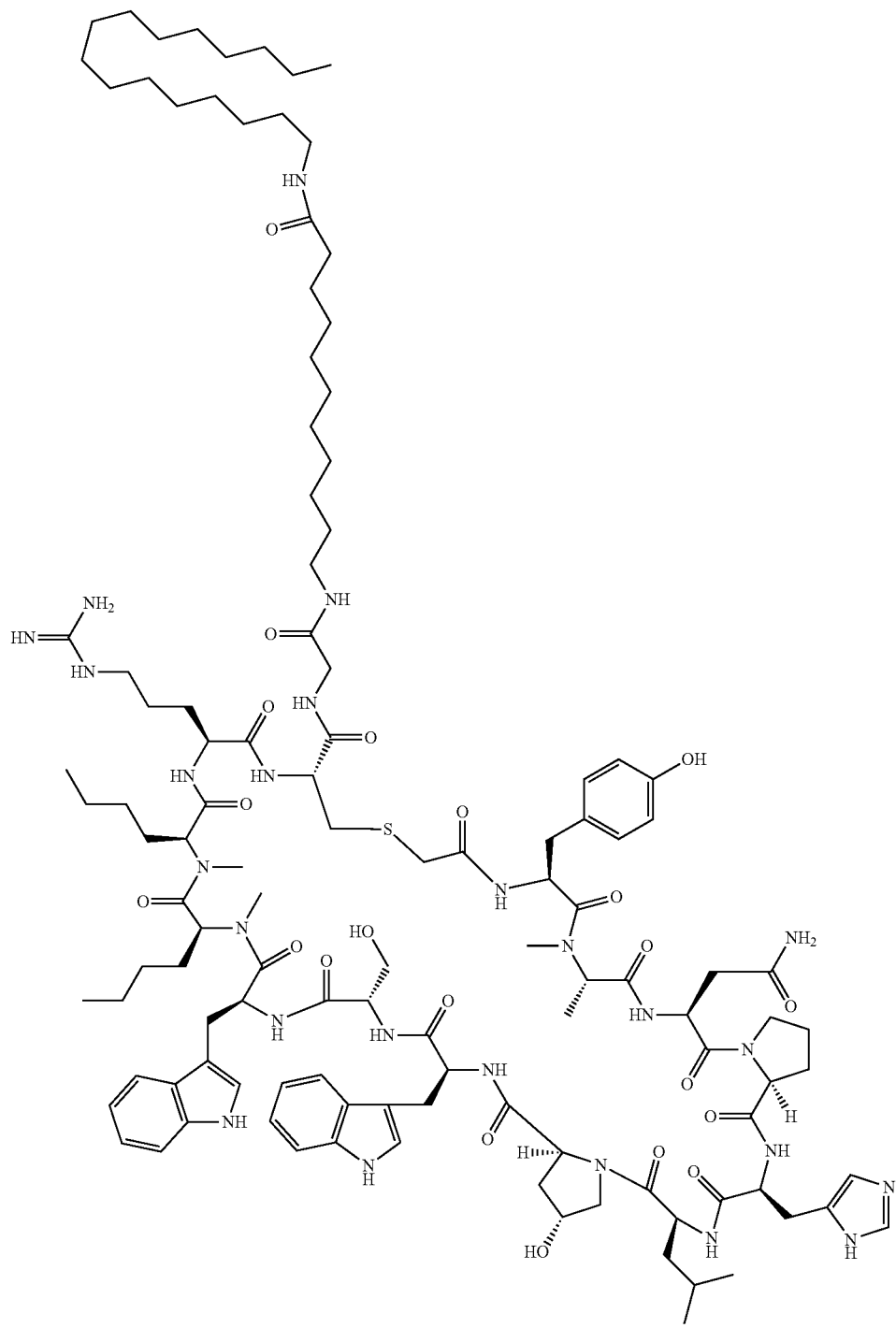 [SMILES: CCCCCCCCCCCCCCCCNC(=O)CCCCCCCCCCNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11112 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Global Deprotection Method A", and "Cyclization Method A". $C_{16}$ amine modified 4-(4-Formyl-3-methoxy-phenoxy) butyryl AM resin C was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 7 mg, and its estimated purity by LCMS analysis was 98%. Analysis LCMS Condition A: Retention time=6.958 min; ESI-MS(+) m/z 1160.02 (M+2H); ESI-HRMS(+) m/z: Calculated: 1159.1865 (M+2H).

Found: 1159.1849 (M+2H).

Preparation of (S)-2-((((9H-fluoren-9-yl)methoxy)carbonyl)amino)-6-((S)-5-(tert-butoxy)-5-oxo-4-tetradecanamidopentanamido)hexanoic acid at rt for 24 hr. After 24 hours the reaction mixture was purred into a separatory funnel and washed with sat ammonium chloride. The aqueous layer was extracted with a 10% methanol chloroform solution 3×. The organic fractions were combined and washed with brine. The organic layer was separated, dried over $Na_2SO_4$ and evaporated in vacuo affording (S)-5-(tert-butoxy)-5-oxo-4-tetradecanamidopentanoic acid (6.1 g, 14.75 mmol, 100% yield) as a thick oil. This material was used as is in the next step. $^1$H NMR (400 MHz, CHLOROFORM-d) δ 4.50-4.29 (m, 1H), 3.68 (quin, J=6.7 Hz, 1H), 3.09 (q, J=7.5 Hz, 1H), 2.43-2.27 (m, 2H), 2.27-2.06 (m, 2H), 1.73-1.55 (m, 2H), 1.47 (s, 9H), 1.39-1.17 (m, 20H), 1.00-0.80 (m, 3H).

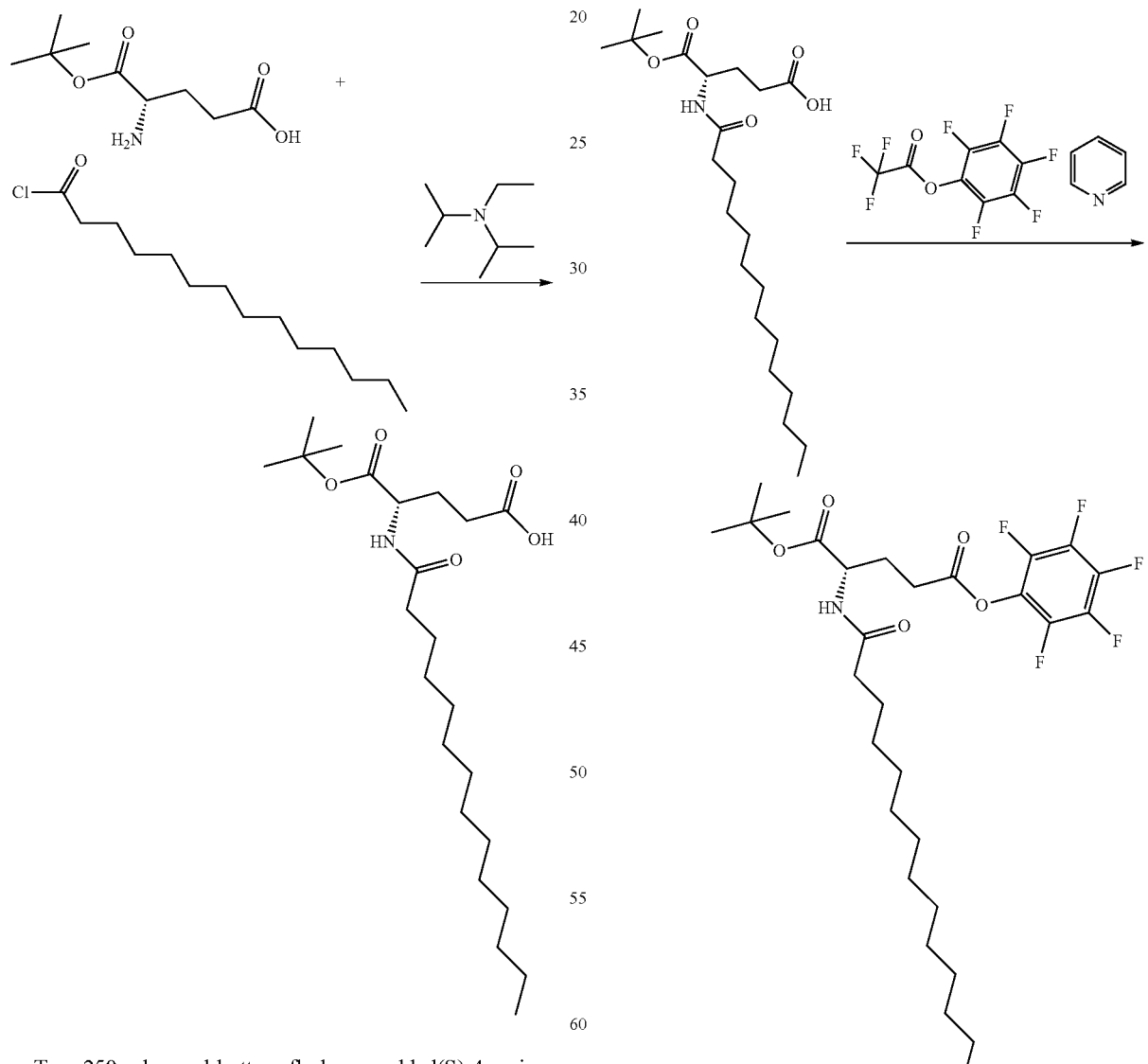

To a 250 ml round bottom flask was added (S)-4-amino-5-(tert-butoxy)-5-oxopentanoic acid (3 g, 14.76 mmol), $CH_2Cl_2$ (100 mL), tetradecanoyl chloride (4.01 g, 16.24 mmol), and Hunig's Base (5.67 mL, 32.5 mmol). The flask was kept under a blanket of nitrogen was sealed and stirred To a 50 ml round bottom flask was added (S)-5-(tert-butoxy)-5-oxo-4-tetradecanamidopentanoic acid (2 g, 4.84 mmol), DMF (10 mL), perfluorophenyl 2,2,2-trifluoroacetate (2.71 g, 9.67 mmol) and PYRIDINE (0.860 mL, 10.64 mmol). The flask was sealed with a septum and kept under a blanket of nitrogen and stirred overnight at rt. The next day the reaction was poured into a saturated citric acid solution and extracted with CH$_2$Cl$_2$ 3×. The organic layers were combined and washed with brine, dried over Na$_2$SO$_4$ and evaporated in vacuo. The crude product (S)-1-tert-butyl 5-(perfluorophenyl) 2-tetradecanamidopentanedioate (2.65 g, 4.57 mmol, 95% yield) was used as is without purification.

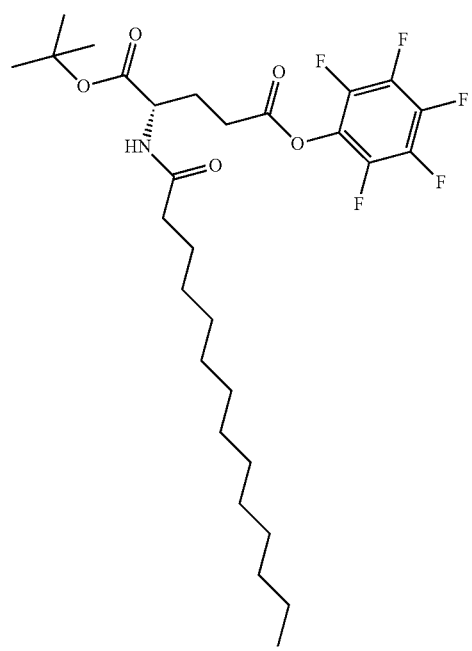

+

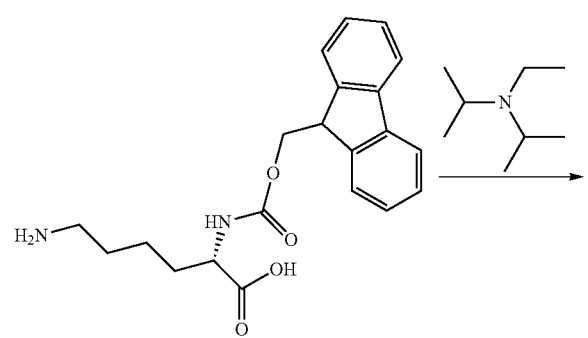

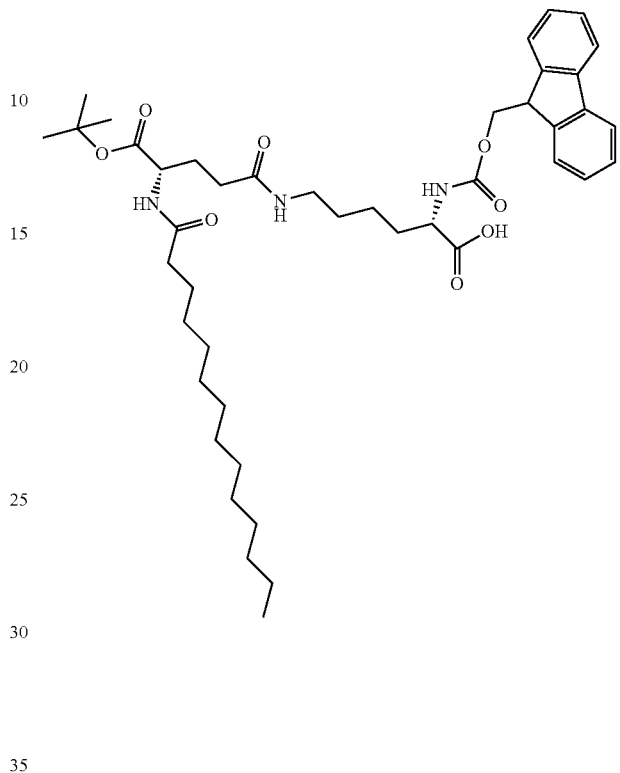

To a 50 ml round bottom flask was added (S)-2-((((9H-fluoren-9-yl)methoxy)carbonyl)amino)-6-aminohexanoic acid (1.653 g, 4.49 mmol), DMF (15 mL), (S)-1-tert-butyl 5-(perfluorophenyl) 2-tetradecanamidopentanedioate (2.6 g, 4.49 mmol), and Hunig's Base (0.940 mL, 5.38 mmol). The flask was sealed with a septum and kept under a blanket of nitrogen. The reaction was allowed to stir for 48 hr at rt. After 48 hr the reaction was homogeneous. The reaction mixture was poured into a saturated citric acid solution, and extracted with CH$_2$Cl$_2$ 3×. The organic fractions were combined, dried over Na2SO4 and evaporated in vacuo. The crude oil was purified by silica gel chromatography eluting with first 100% CH$_2$Cl$_2$, then 5% Methanol in 95% CH$_2$Cl$_2$. The pure fractions were combined and evaporated in vacuo affording (S)-2-((((9H-fluoren-9-yl)methoxy)carbonyl)amino)-6-((S)-5-(tert-butoxy)-5-oxo-4-tetradecanamidopentanamido)hexanoic acid (2.35 g, 2.92 mmol, 65.1% yield) as a viscous oil. $^1$H NMR (400 MHz, CHLOROFORM-d) δ 7.78 (d, J=7.5 Hz, 2H), 7.62 (br. s., 2H), 7.41 (t, J=7.4 Hz, 2H), 7.32 (t, J=7.4 Hz, 2H), 6.54 (br. s., 1H), 5.72 (m, 2H), 4.39 (m, 4H), 4.27-4.14 (m, 1H), 3.28 (m, 2H), 2.26 (m, 4H), 2.15 (m, 2H), 1.92 (m, 2H), 1.62 (m, 4H), 1.48 (s, 9H), 1.26 (br. s., 20H), 0.89 (t, J=6.8 Hz, 3H).

Preparation of Example 11114

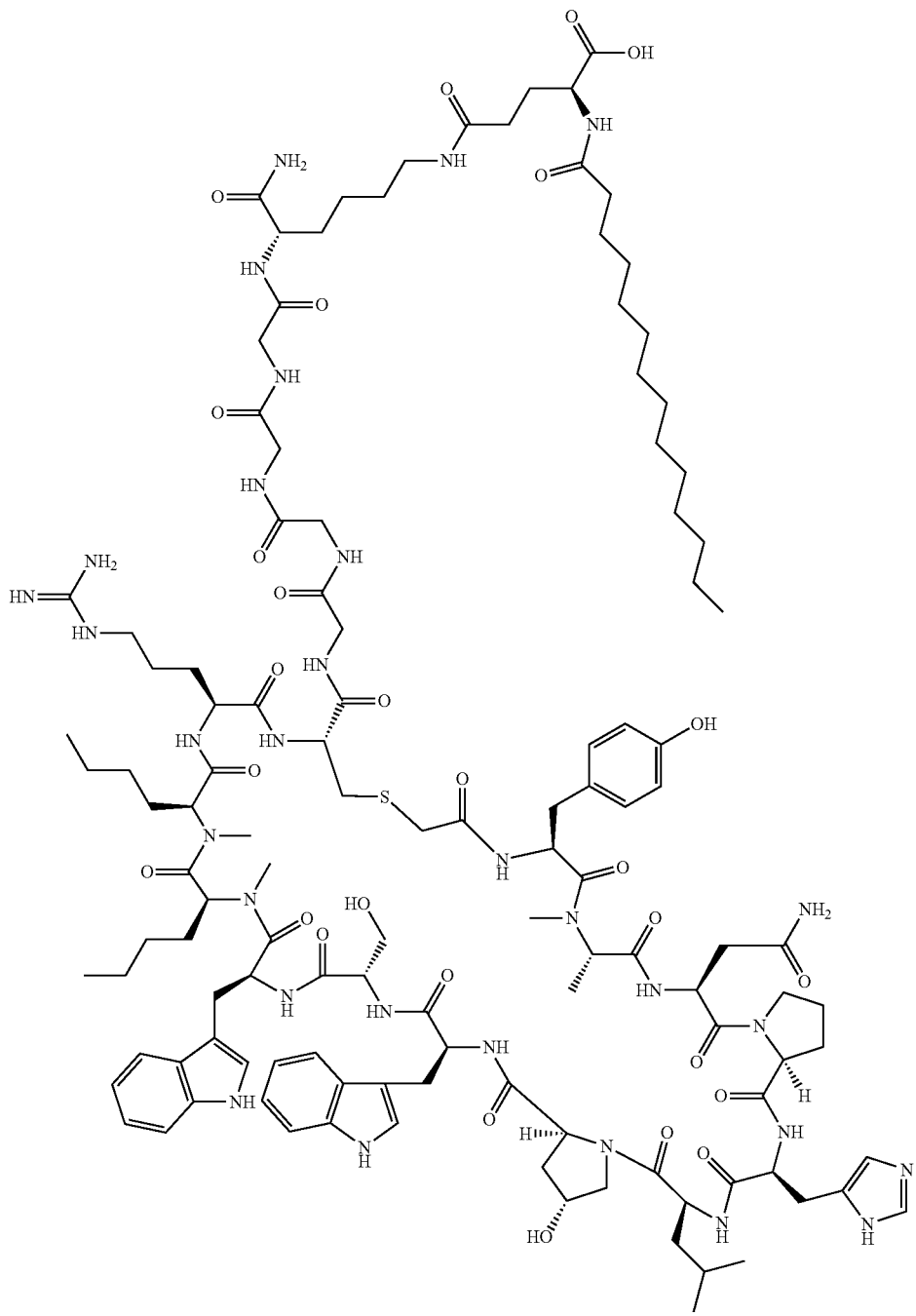 [SMILES: CCCCCCCCCCCCCC(=O)N[C@@H](CCC(=O)NCCCC[C@H](NC(=O)CNC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O)C(=O)O]

Example 11114 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified rink resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 15 mg, and its estimated purity by LCMS analysis was 99%. Analysis LCMS Condition A: Retention time=4.978 min; ESI-MS(+) m/z 1275.18 (M+2H); ESI-HRMS(+) m/z:

Calculated: 1274.6803 (M+2H). Found: 1274.6791 (M+2H).

Preparation of Example 11115

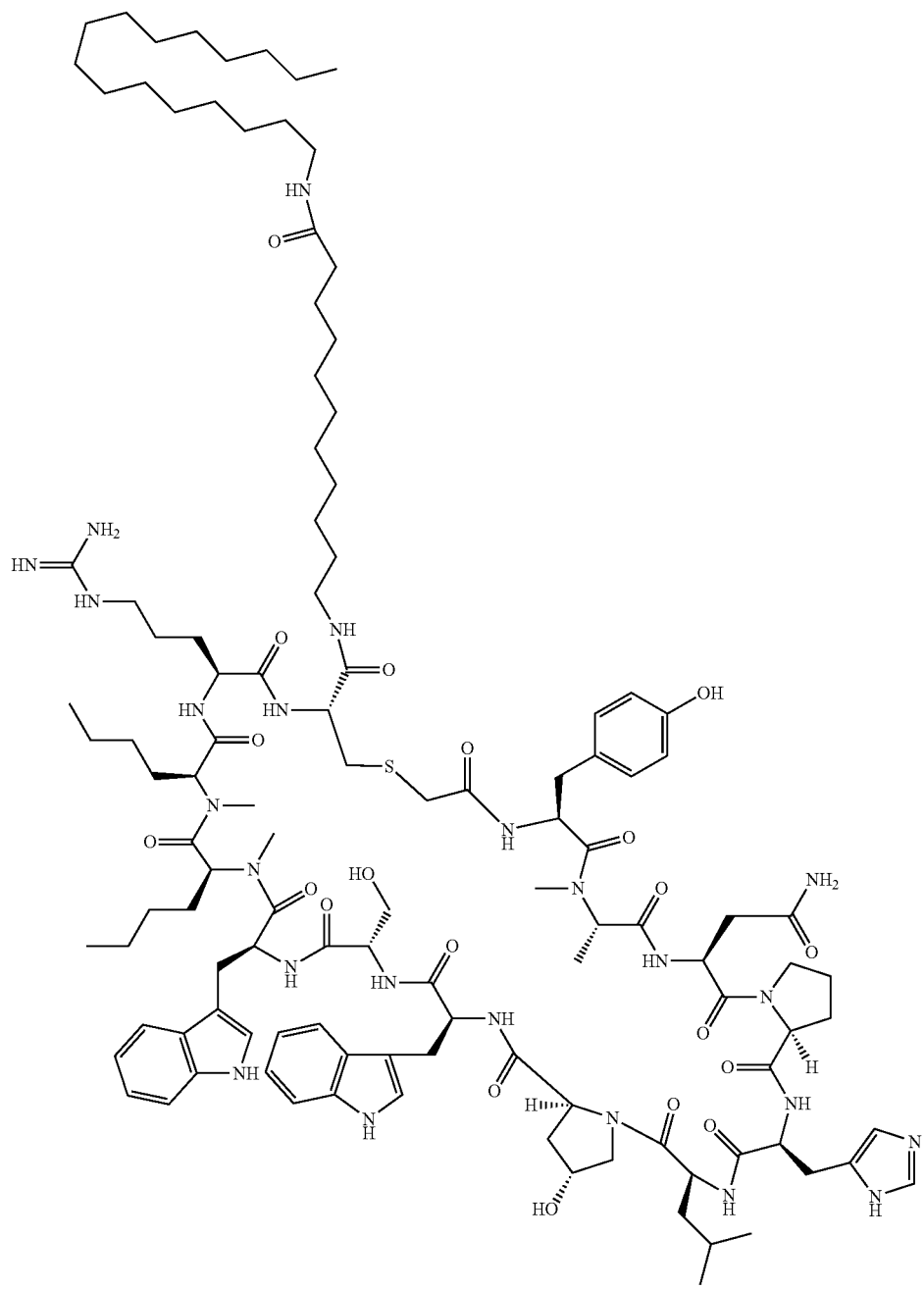 [SMILES: CCCCCCCCCCCCCCCCNC(=O)CCCCCCCCCCNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11115 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 4 mg, and its estimated purity by LCMS analysis was 95%. Analysis LCMS Condition A: Retention time=6.930 min; ESI-MS(+) m/z 1131.54 (M+2H); ESI-HRMS(+) m/z: Calculated: 1130.6758 (M+2H).

Found: 1130.6747 (M+2H).

Preparation of Example 11116

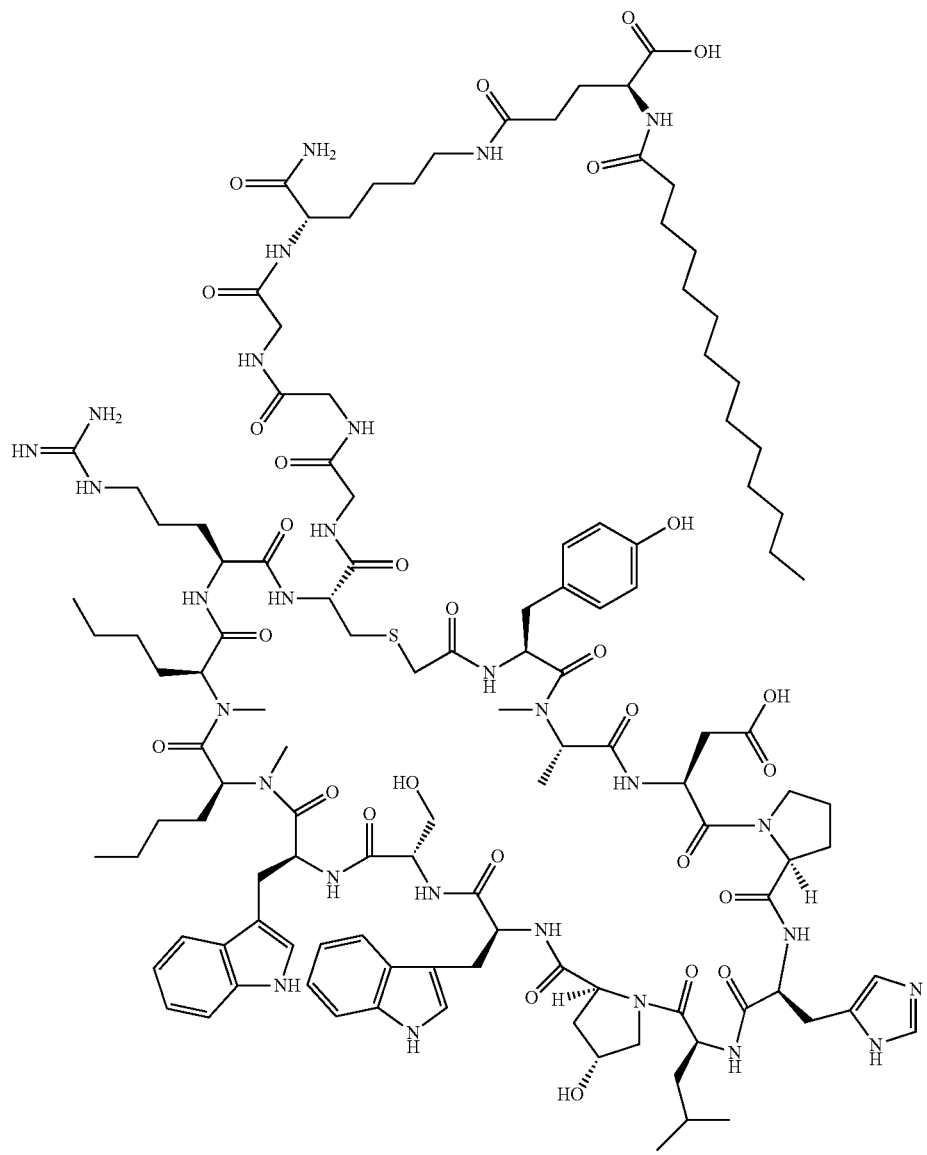 [SMILES: CCCCCCCCCCCCCC(=O)N[C@@H](CCC(=O)NCCCC[C@H](NC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O)C(=O)O]

Example 11116 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified rink resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 25 mg, and its estimated purity by LCMS analysis was 95.2%. Analysis LCMS Condition A: Retention time=5.106 min; ESI-MS(+) m/z 1247.0 (M+2H).

ESI-HRMS(+) m/z: Calculated: 1246.1696 (M+2H). Found: 1246.1684 (M+2H).

Preparation of Example 11119

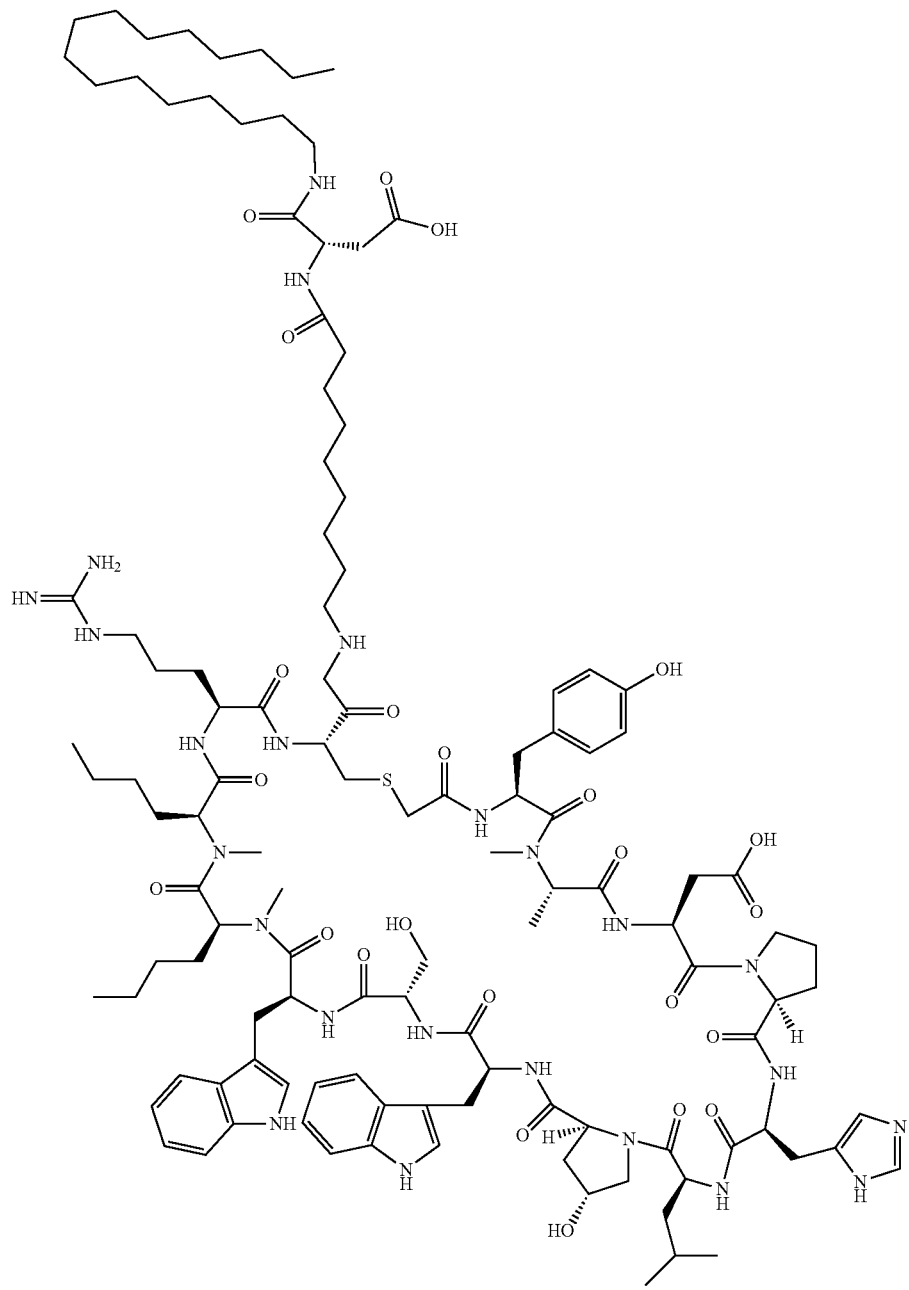 [SMILES: CCCCCCCCCCCCCCCCNC(=O)[C@H](CC(=O)O)NC(=O)CCCCCCCCNCC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11119 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 18 mg, and its estimated purity by LCMS analysis was 93%. Analysis LCMS Condition A: Retention time=5.968 min; ESI-MS(+) m/z 1189.5 (M+2H); ESI-HRMS(+) m/z: Calculated: 1188.6813 (M+2H).

Found: 1188.6821 (M+2H).

Preparation of Example 11120

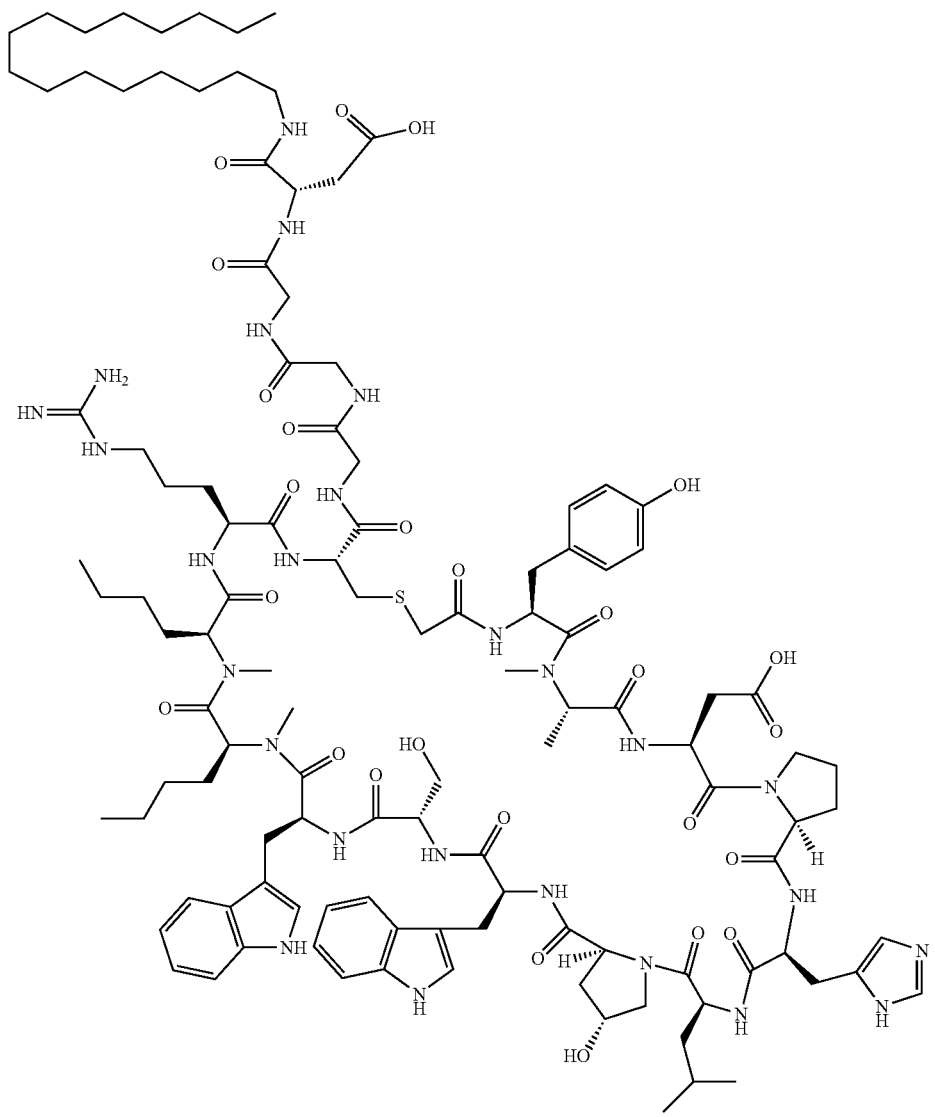 [SMILES: CCCCCCCCCCCCCCCCNC(=O)[C@H](CC(=O)O)NC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11120 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 12 mg, and its estimated purity by LCMS analysis was 99%. Analysis LCMS Condition A: Retention time=5.688 min; ESI-MS(+) m/z 1183.6 (M+2H); ESI-HRMS(+) m/z: Calculated: 1182.6323 (M+2H).

Found: 1182.6317 (M+2H).

Preparation of Example 11123

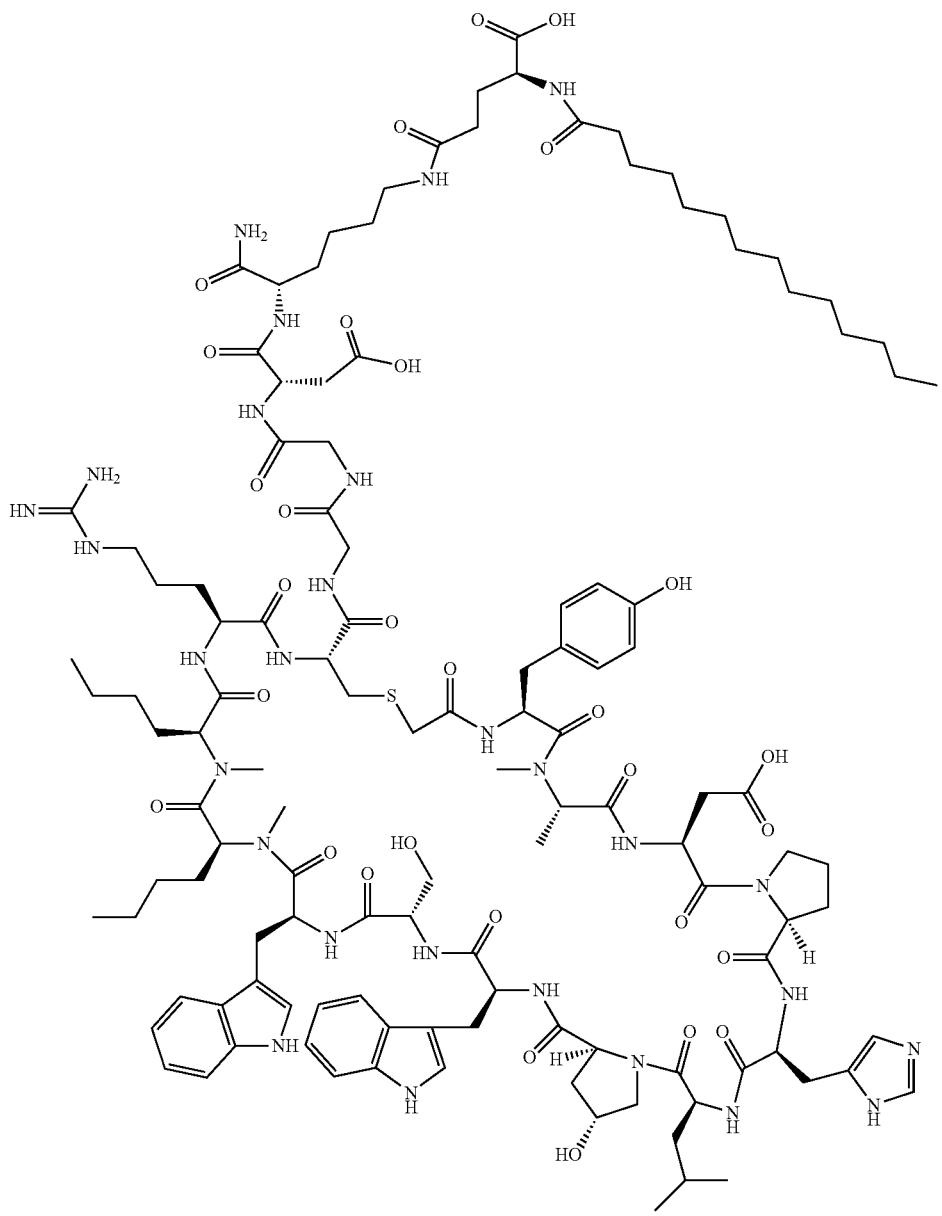 [SMILES: CCCCCCCCCCCCCC(=O)N[C@@H](CCC(=O)NCCCC[C@H](NC(=O)[C@H](CC(=O)O)NC(=O)CNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(N)=O)C(=O)O]

Example 11123 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 23 mg, and its estimated purity by LCMS analysis was 95.3%. Analysis LCMS Condition A: Retention time=4.773 min; ESI-MS(+) m/z 1276.7 (M+2H); ESI-HRMS(+) m/z: Calculated: 1275.6643 (M+2H). Found: 1275.6645 (M+2H).

Preparation of Example 11124

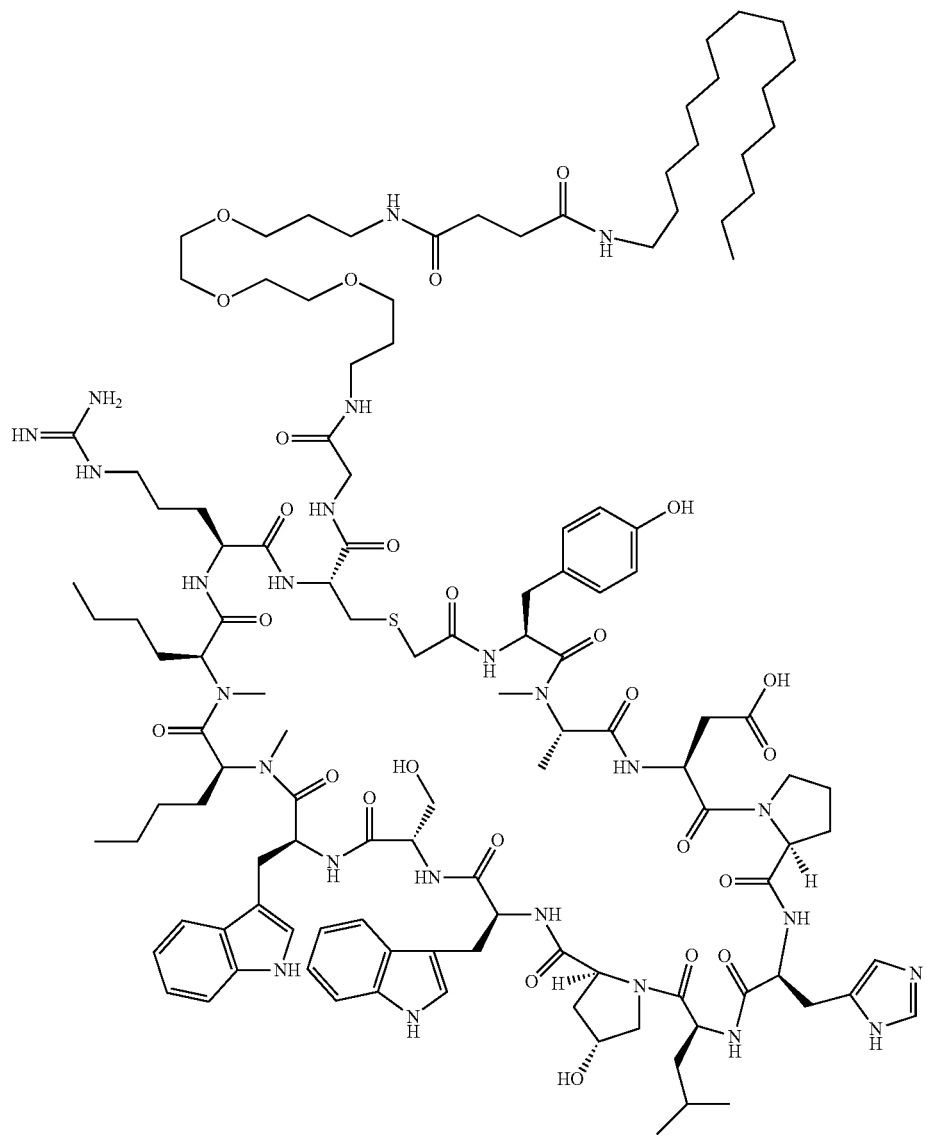 [SMILES: CCCCCCCCCCCCCCCCNC(=O)CCC(=O)NCCCOCCOCCOCCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1]

Example 11124 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 8 mg, and its estimated purity by LCMS analysis was 99%. Analysis LCMS Condition A: Retention time=6.405 min; ESI-MS(+) m/z 1220.3 (M+2H); ESI-HRMS(+) m/z: Calculated: 1219.1894 (M+2H).

Found: 1219.1888 (M+2H).

Preparation of Example 11125

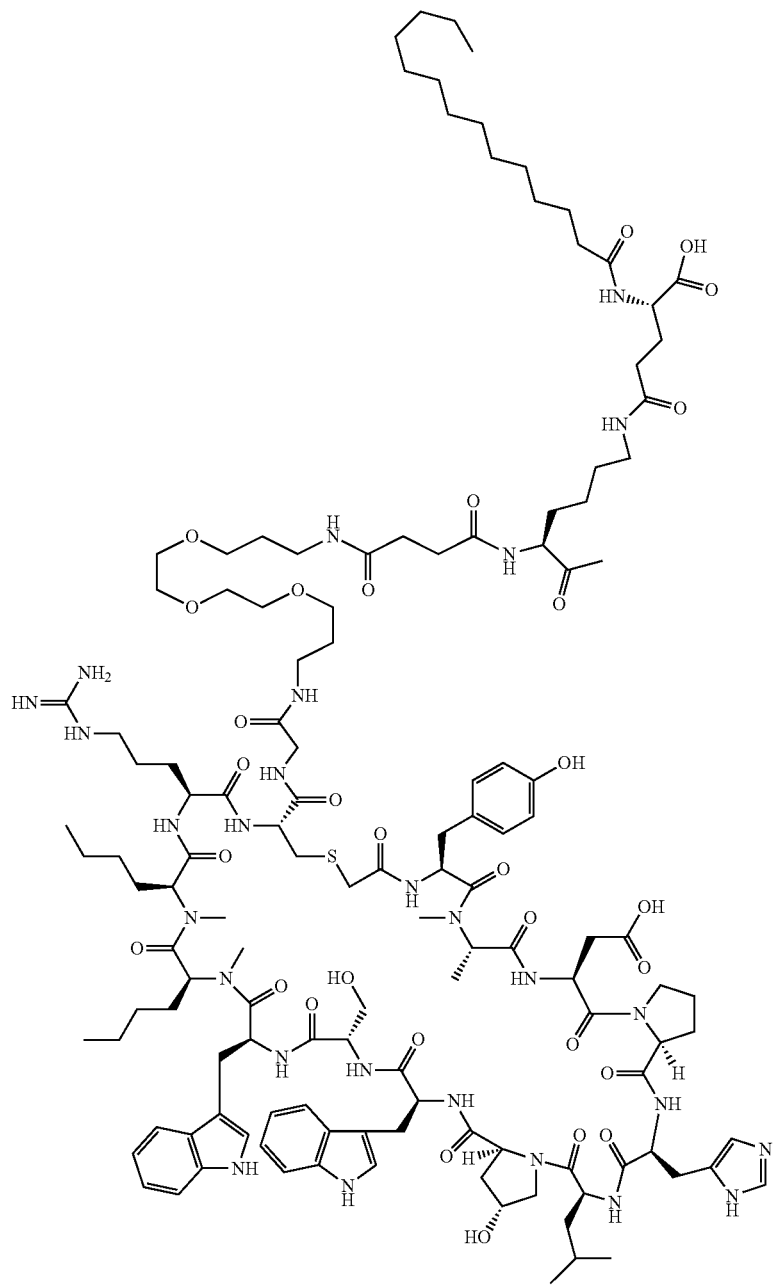 [SMILES: CCCCCCCCCCCCCC(=O)N[C@@H](CCC(=O)NCCCC[C@H](NC(=O)CCC(=O)NCCCOCCOCCOCCCNC(=O)CNC(=O)[C@@H]1CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N(C)[C@@H](CCCC)C(=O)N(C)[C@@H](CCCC)C(=O)N[C@@H](CCCNC(=N)N)C(=O)N1)C(C)=O)C(=O)O]

Example 11125 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified Rink resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 17 mg, and its estimated purity by LCMS analysis was 95%. Analysis LCMS Condition A: Retention time=4.780 min; ESI-MS(+) m/z 1341.8 (M+2H).

Preparation of Example 11126
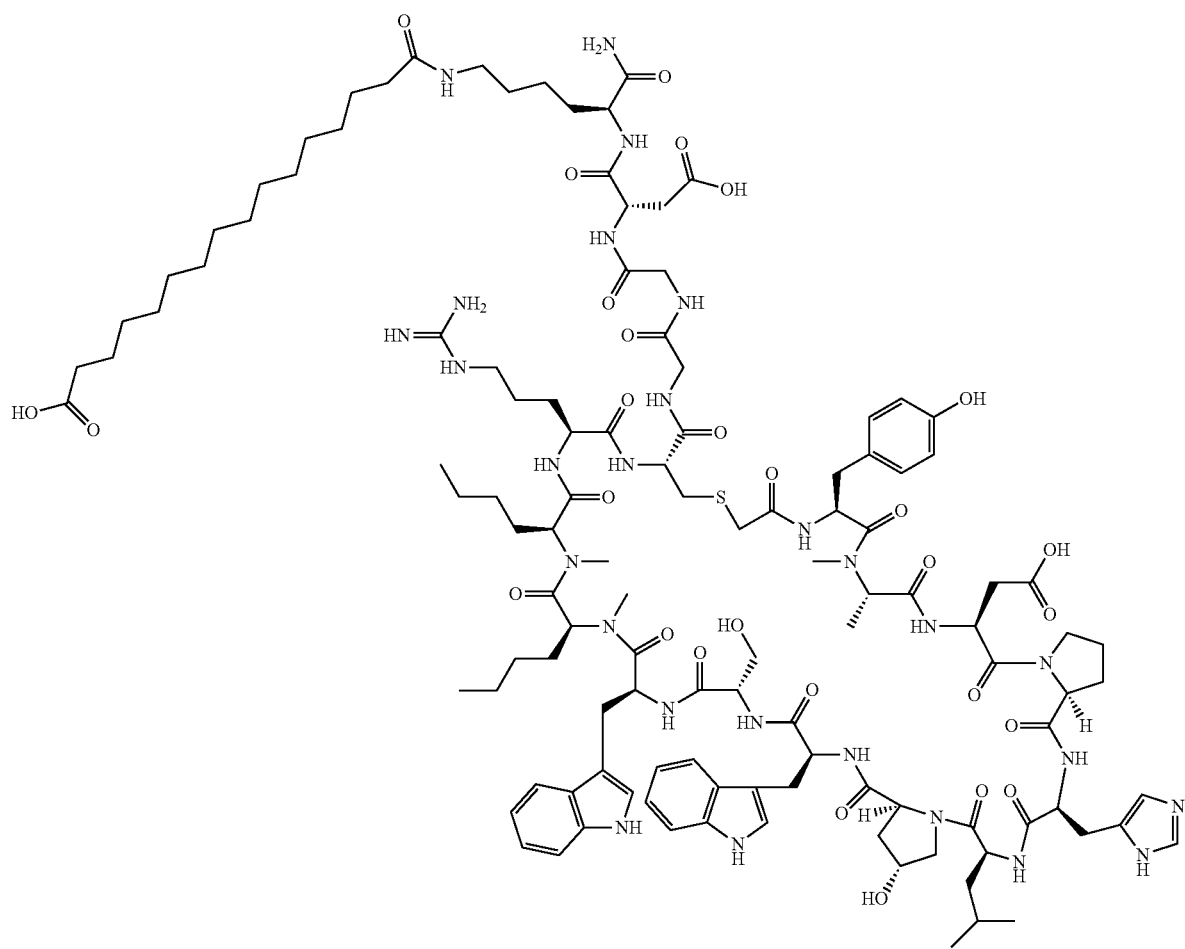 [SMILES: CCCC[C@H]1C(=O)N(C)[C@@H](CCCC)C(=O)N[C@@H](CCCNC(=N)N)C(=O)N[C@H](C(=O)NCC(=O)NCC(=O)N[C@@H](CC(=O)O)C(=O)N[C@@H](CCCCNC(=O)CCCCCCCCCCCCCCC(=O)O)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Preparation of Example 11126A

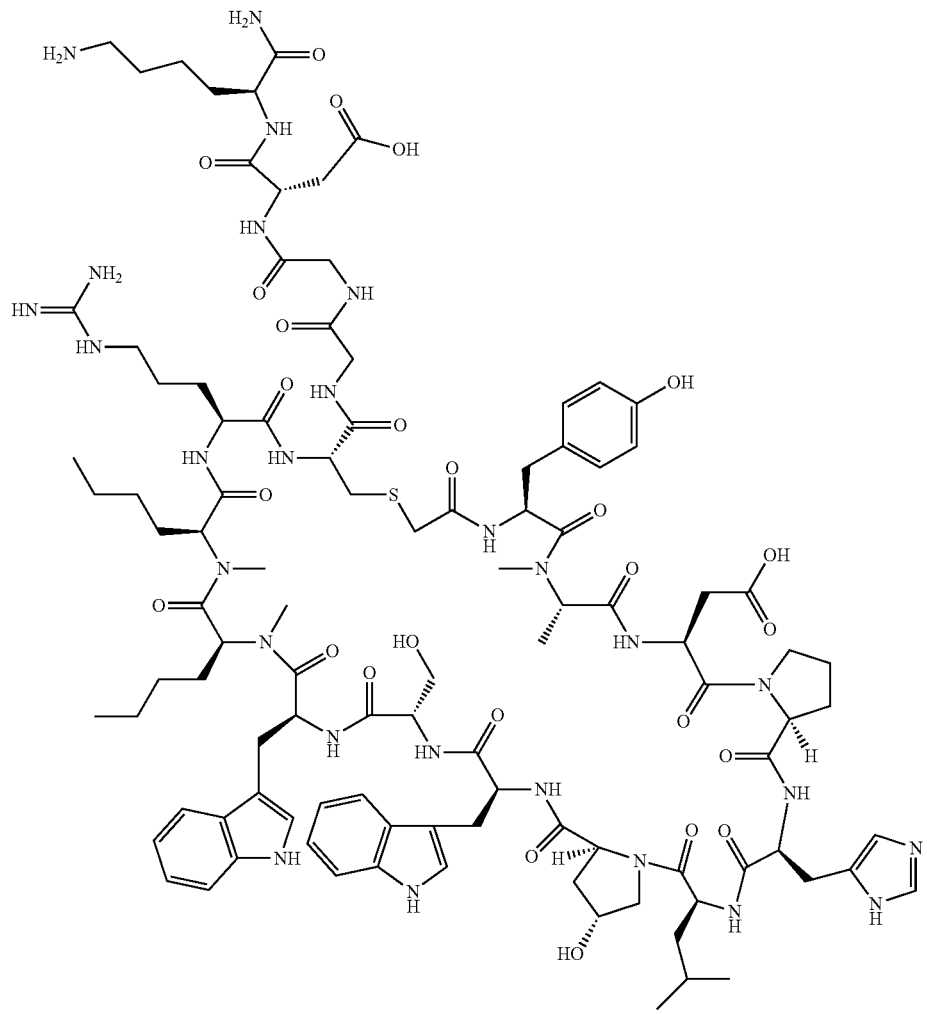 [SMILES: CCCC[C@H]1C(=O)N(C)[C@@H](CCCC)C(=O)N[C@@H](CCCNC(=N)N)C(=O)N[C@H](C(=O)NCC(=O)NCC(=O)N[C@@H](CC(=O)O)C(=O)N[C@@H](CCCCN)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11126A was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Rink resin was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 27 mg, and its estimated purity by LCMS analysis was 99%. Analysis LCMS Condition A: Retention time=3.625 min; ESI-MS (+) m/z 1107.0 (M+2H).

Preparation of 1-tert-butyl 16-(perfluorophenyl) hexadecanedioate

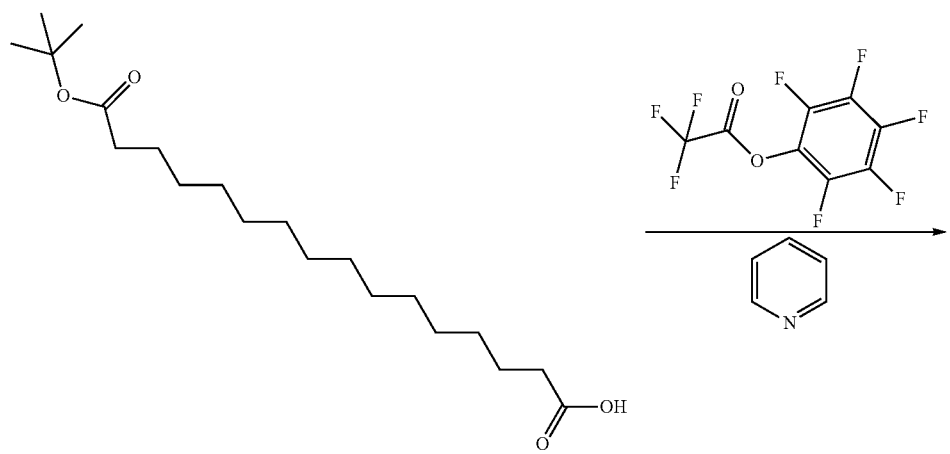

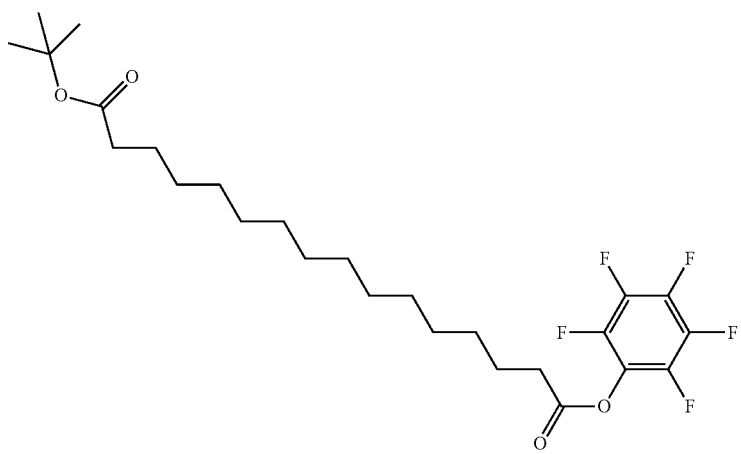

To a 1 dram vial was added 16-(tert-butoxy)-16-oxohexadecanoic acid (100 mg, 0.292 mmol), DMF (0.8 mL), perfluorophenyl 2,2,2-trifluoroacetate (164 mg, 0.584 mmol) and pyridine (0.052 mL, 0.642 mmol). The vial was sealed with a septum and stirred overnight at rt. The next day the crude reaction mixture was loaded onto a silica gel column and purified, eluting with a 5% EtOAc/95% Hexanes to 30% EtOAc/70% Hexanes. The desired product was the first eluting peak. very faint UV detection. The pure fractions were combined and evaporated in vacuo affording 1-tert-butyl 16-(perfluorophenyl) hexadecanedioate (132 mg, 0.260 mmol, 89% yield) as a white solid. $^1$H NMR (400 MHz, CHLOROFORM-d) δ 2.68 (s, 2H), 2.22 (s, 2H), 1.79 (s, 2H), 1.59 (s, 4H), 1.47 (s, 9H), 1.29 (br. s., 18H).

Preparation of 11126B

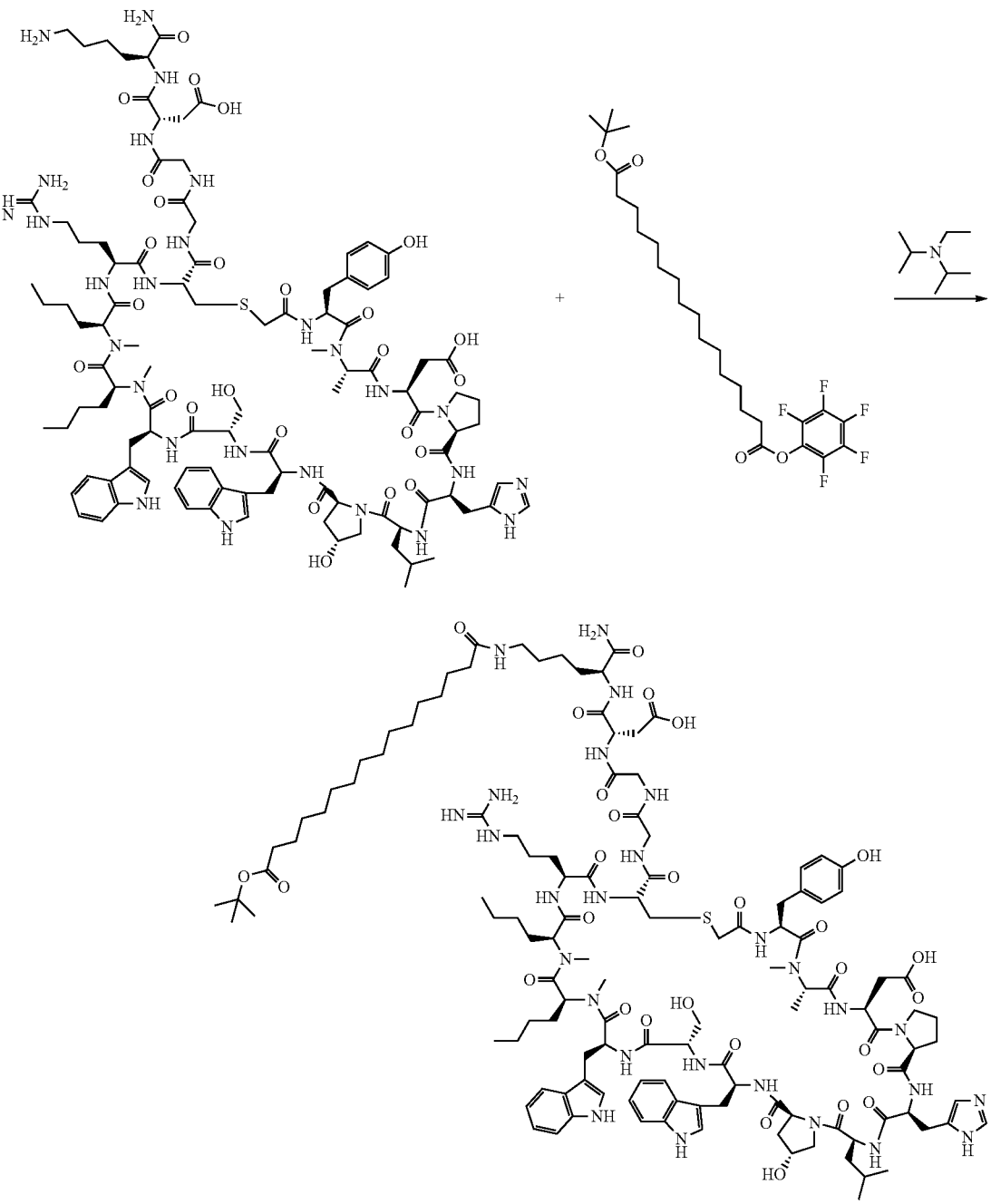

To a 1 dram vial was added Example 11126A (27 mg, 0.012 mmol), DMF (0.7 mL), N-ethyl-N-isopropylpropan-2-amine (9.47 mg, 0.073 mmol), and 1-tert-butyl 16-(perfluorophenyl) hexadecanedioate (11.18 mg, 0.022 mmol). The reaction was allowed to stir overnight at rt. The next day the reaction was complete by LC/MS. The crude reaction was poured into diethyl ether and a precipitate formed. This precipitate was collected by centrifugation and the diethyl ether was decanted off. The crude solid 14 mg was carried onto next step as is without purification. Analysis LCMS Condition A: Retention time=5.428 min; ESI-MS(+) m/z 1269.3 (M+2H).

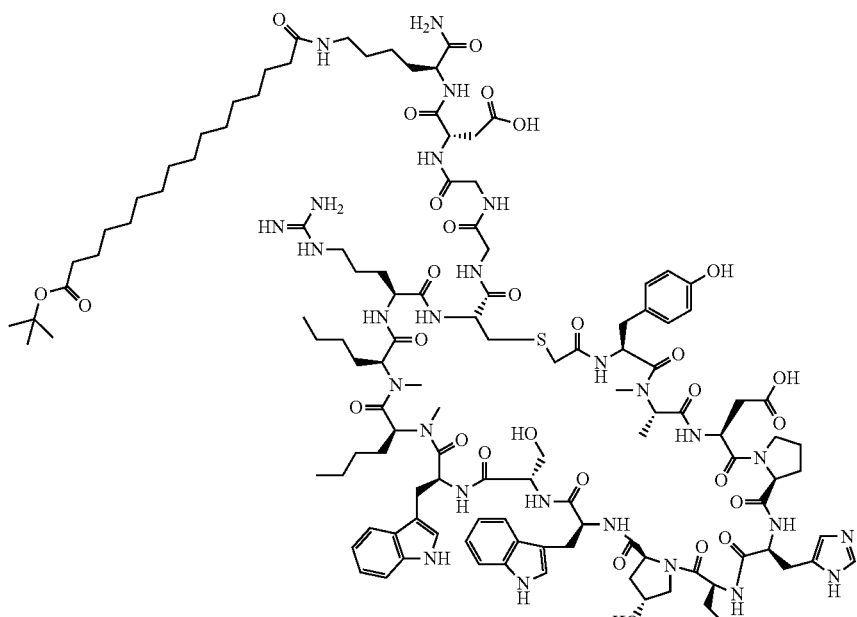
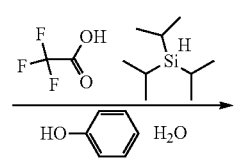
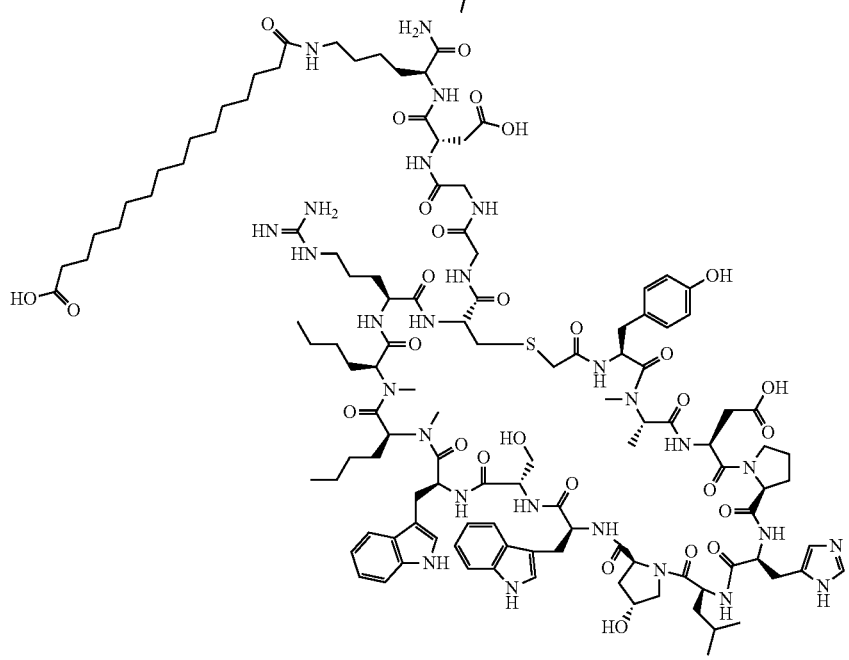

To a 1 dram vial was added Example 11126B (14 mg, 5.52 µmol), and 0.8 mL of Standard cleavage solution. The reaction was stirred at rt for 15 min and the reaction was checked by LC/MS. The reaction was complete and the crude reaction mixture was poured into 15 mL of diethyl ether. The resulting solid was collected after centrifugation. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 6 mg, and its estimated purity by LCMS analysis was 98.6%. Analysis LCMS Condition A: Retention time=4.040 min; ESI-MS(+) m/z 1241.1 (M+2H) ESI-HRMS(+) m/z: Calculated: 1240.1458 (M+2H).

Found: 1240.1445 (M+2H).

Preparation of Example 11128

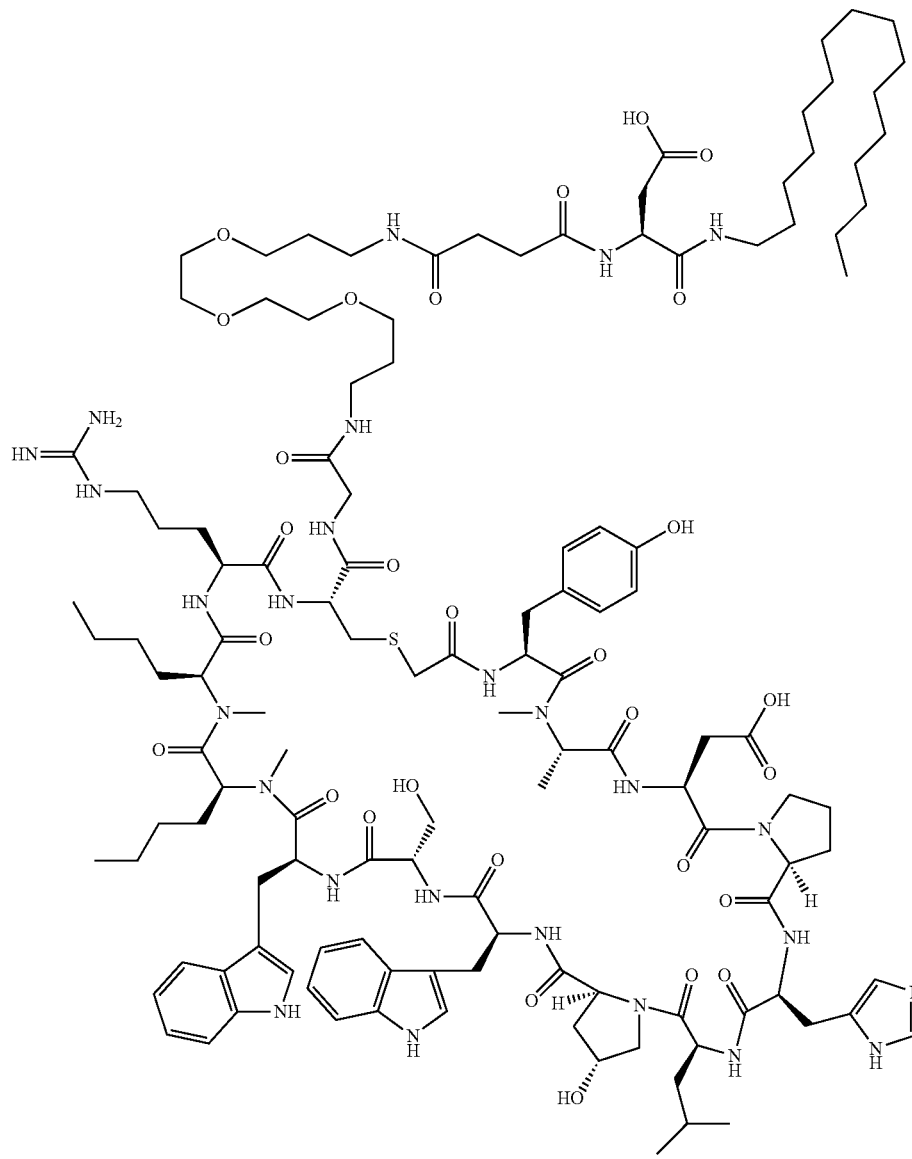

Example 11128 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". $C_{16}$ amine modified 4-(4-Formyl-3-methoxy-phenoxy)butyryl AM resin C was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 30 mL/min. Fractions containing the desired product were combined and dried via centrifugal evaporation. The yield of the product was 20 mg, and its estimated purity by LCMS analysis was 98.3%. Analysis LCMS Condition A: Retention time=5.568 min; ESI-MS(+) m/z 1277.8 (M+2H).

Preparation of Modified 2-chlorotrityl chloride resin E

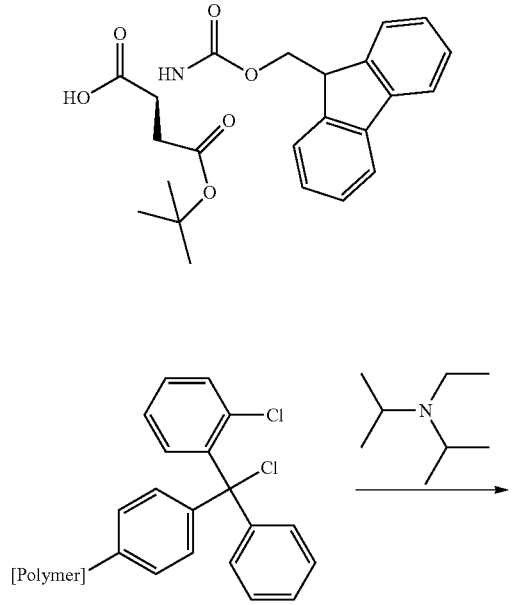

Resin = 2-Chlorotrityl chloride resin from Novabiochem; 1.42 mmol/g loading 1% DVB, 100-200 mesh

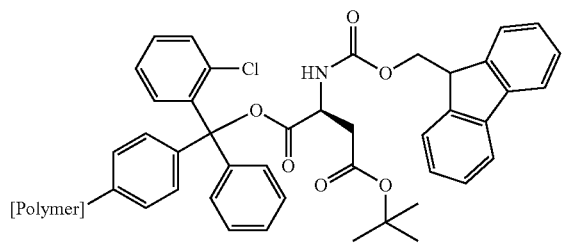

To a 20 ml scint vial was added (S)-2-((((9H-fluoren-9-yl)methoxy)carbonyl)amino)-4-(tert-butoxy)-4-oxobutanoic acid (0.370 g, 0.9 mmol), 2-chlorotrityl resin 1.42 mmol/g loading (2.057 g, 2.88 mmol), CH$_2$Cl$_2$ (15 mL), and Hunig's Base (1.022 mL, 5.85 mmol). The vial was sealed and shaken on an orbital shaker overnight at rt. The next day the reaction was diluted with 2 ml of methanol and shaken for an additional 2 hours. The resin was then filtered off, washed with DMF 3×, CH$_2$Cl$_2$ 4×, and finally Diethyl ether. The resin was dried in vacuo and used as is for peptide synthesis with an assumed loading of 0.44 meq/g.

Preparation of Example 11129

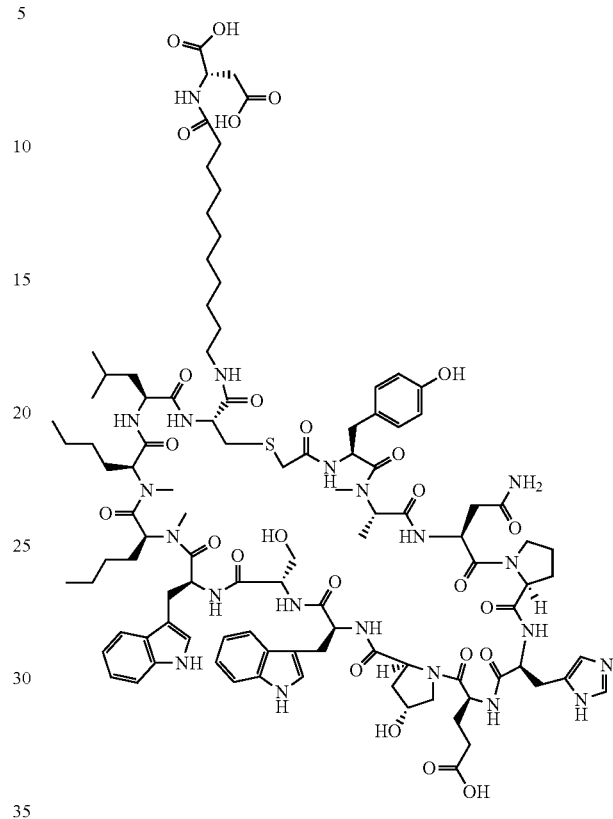

Example 11129 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 48 mg, and its estimated purity by LCMS analysis was 95.6%. Analysis LCMS Condition A: Retention time=3.828 min; ESI-MS(+) m/z 1070.4 (M+2H); ESI-HRMS(+) m/z: Calculated: 1069.5426 (M+2H). Found: 1069.5392 (M+2H).

341
Preparation of Modified 2-chlorotrityl chloride resin F

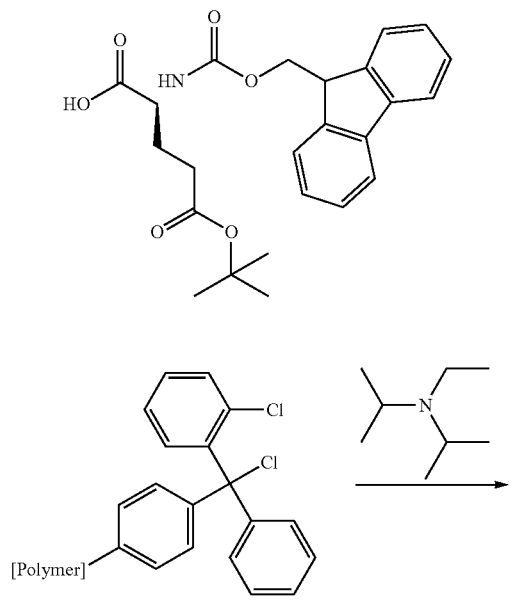

Resin = 2-Chlorotrityl chloride resin
from Novabiochem; 1.42 mmol/g loading
1% DVB, 100-200 mesh

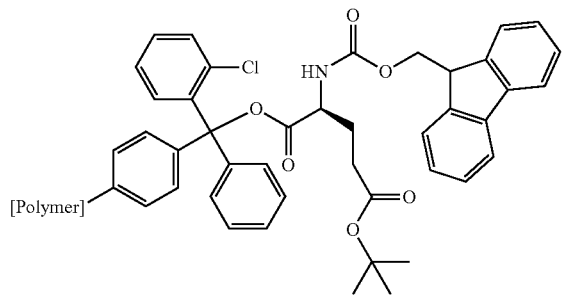

To a 20 ml scint vial was added (S)-2-(((((9H-fluoren-9-yl)methoxy)carbonyl)amino)-5-(tert-butoxy)-5-oxopentanoic acid (0.383 g, 0.9 mmol), 2-Chlorotrityl resin 1.42 mmol/g loading (2.057 g, 2.88 mmol), $CH_2Cl_2$ (15 mL), and Hunig's Base (1.022 mL, 5.85 mmol). The vial was sealed and shaken on an orbital shaker overnight at rt. The next day the reaction was diluted with 2 ml of methanol and shaken for an additional 2 hours. The resin was then filtered off, washed with DMF 3×, $CH_2Cl_2$ 4×, and finally Diethyl ether. The resin was dried in vacuo and used as is for peptide synthesis with an assumed loading of 0.44 meq/g.

342
Preparation of Example 11130

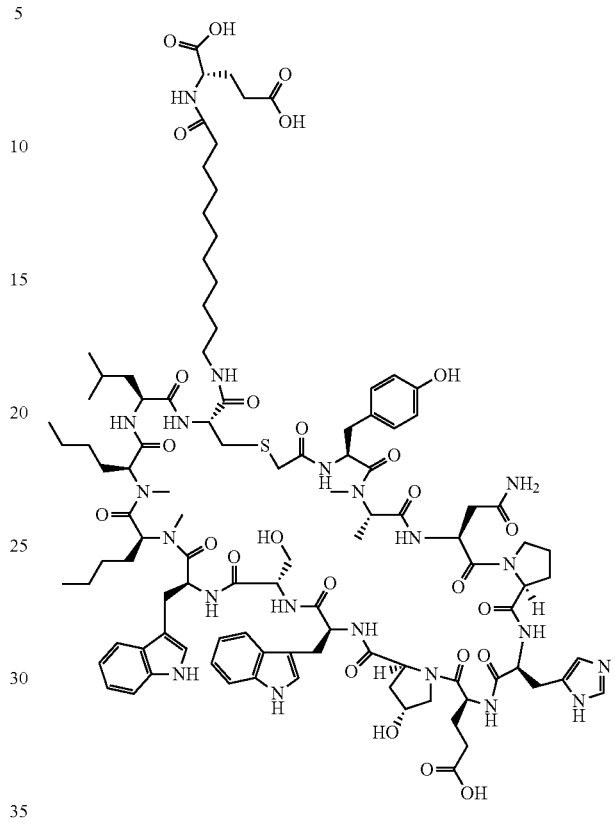

Example 11130 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin F was used in this synthesis. The crude material was purified via preparative LC/MS with the following conditions: Column: Waters XBridge C18, 30×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 32 mg, and its estimated purity by LCMS analysis was 100%. Analysis LCMS Condition A: Retention time=3.803 min; ESI-MS(+) m/z 1077.6 (M+2H); ESI-HRMS(+) m/z:

Calculated: 1076.5504 (M+2H). Found: 1076.5462 (M+2H).

Preparation of Example 11131

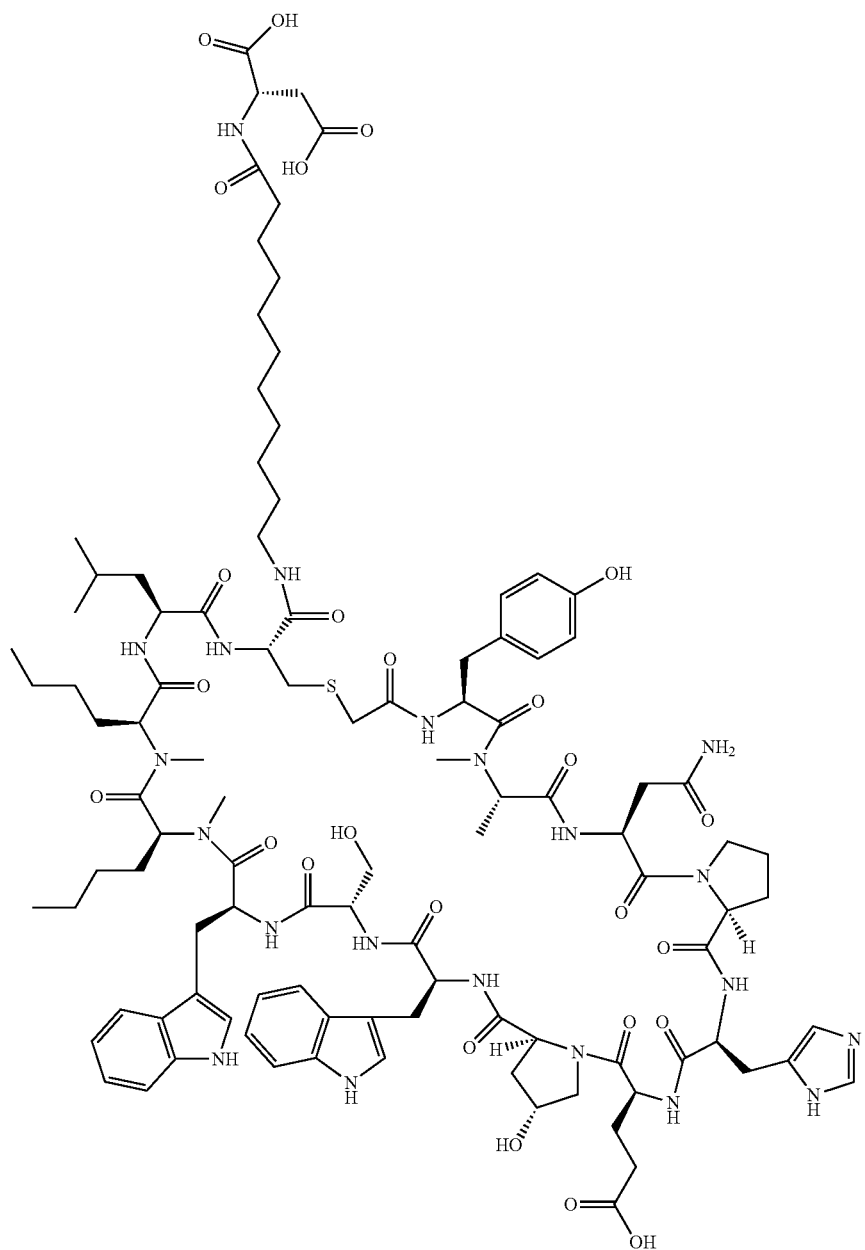 [SMILES: CCCC[C@H]1C(=O)N(C)[C@@H](CCCC)C(=O)N[C@@H](CC(C)C)C(=O)N[C@H](C(=O)NCCCCCCCCCCC(=O)N[C@@H](CC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 11131 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin E was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 40 mg, and its estimated purity by LCMS analysis was 98.8%. Analysis LCMS Condition A: Retention time=3.720 min; ESI-MS(+) m/z 1067.0 (M+2H); ESI-HRMS(+) m/z:

Calculated: 1066.0321 (M+2H). Found: 1066.0323 (M+2H).

Preparation of Example 11132

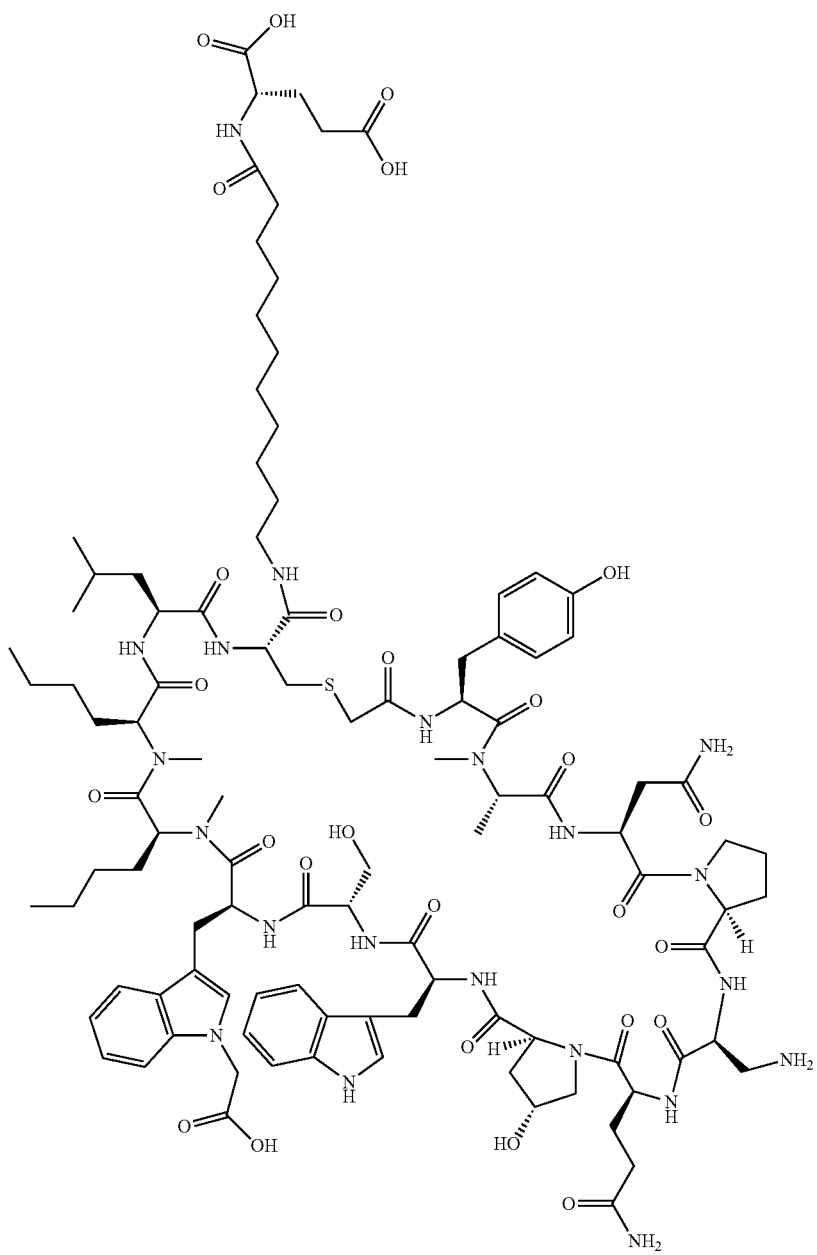 [SMILES: CCCC[C@H]1C(=O)N(C)[C@@H](CCCC)C(=O)N[C@@H](CC(C)C)C(=O)N[C@H](C(=O)NCCCCCCCCCCC(=O)N[C@@H](CCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11132 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin F was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 16 mg, and its estimated purity by LCMS analysis was 95.9%. Analysis LCMS Condition A: Retention time=3.725 min; ESI-MS(+) m/z 1074.0 (M+2H); ESI-HRMS(+) m/z: Calculated: 1073.0399 (M+2H). Found: 1073.0393 (M+2H).

Preparation of PEG amine modified 4-(4-Formyl-3-methoxy-phenoxy)butyryl AM resin

D

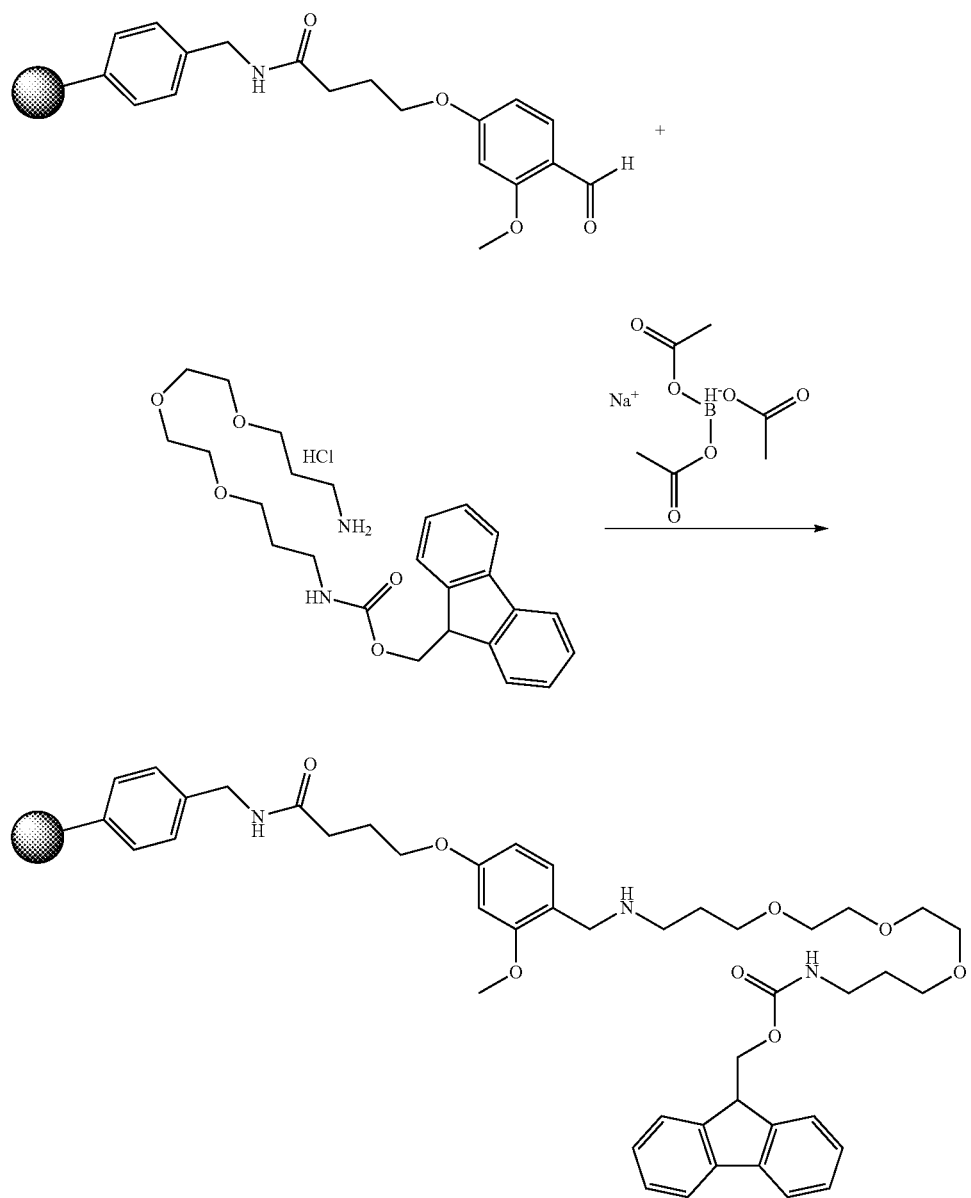

To a 50 ml pressure vessel was added 4-(4-formyl-3-methoxy-phenoxy)butyryl AM resin 0.94 mmol/g loading (1.5 g, 1.350 mmol), (9H-fluoren-9-yl)methyl(3-(2-(2-(3-aminopropoxy)ethoxy)ethoxy)propyl)carbamate hydrochloride (0.711 g, 1.485 mmol), sodium triacetoxyhydroborate (1.431 g, 6.75 mmol), DMF (20 mL), and Acetic Acid (0.2 mL). The flask was sealed and shaken overnight on a wrist action shaker. The next day the resin was filtered off and washed with Methanol 2×, DMF 3×, and $CH_2Cl_2$ 4×. The resin was dried overnight under vacuum. The loading was assumed to be 0.94 mmol/g and used as is in the subsequent step.

Preparation of PEG amine modified
4-(4-Formyl-3-methoxy-phenoxy)butyryl AM resin
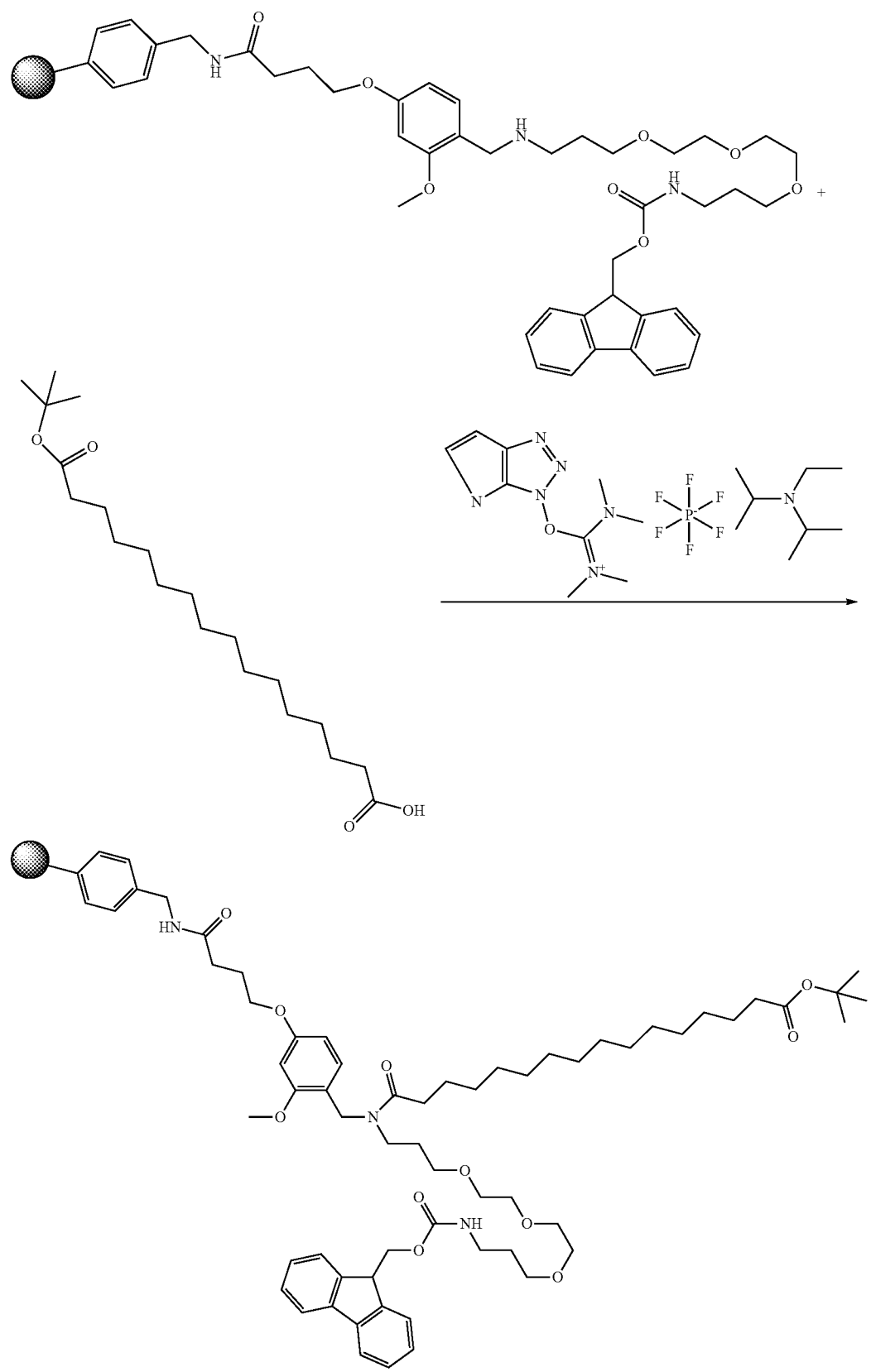

To a 7 ml vial was added PEG amine modified 4-(4-Formyl-3-methoxy-phenoxy)butyryl AM resin D (0.222 g, 0.2 mmol), 16-(tert-butoxy)-16-oxohexadecanoic acid (0.137 g, 0.400 mmol), HATU (2.000 mL, 0.400 mmol), N-ethyl-N-isopropylpropan-2-amine (2.000 mL, 0.800 mmol) and DMF (4 mL). The vial was shaken on a wrist action shaker overnight. The next day the resin was filtered and washed with DMF 3×, and CH$_2$Cl$_2$ 4×, then Et$_2$O. The resin was dried overnight under vacuum. The loading was assumed to be 0.94 mmol/g and used as is in subsequent steps.

Preparation of Example 11133

Example 11133 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". PEG amine modified 4-(4-Formyl-3-methoxy-phenoxy)butyryl AM resin E was used in this synthesis. The crude material was purified via preparative LC/MS with the following conditions: Column: Waters XBridge C18, 30×100 mm, 5-µm particles; Mobile

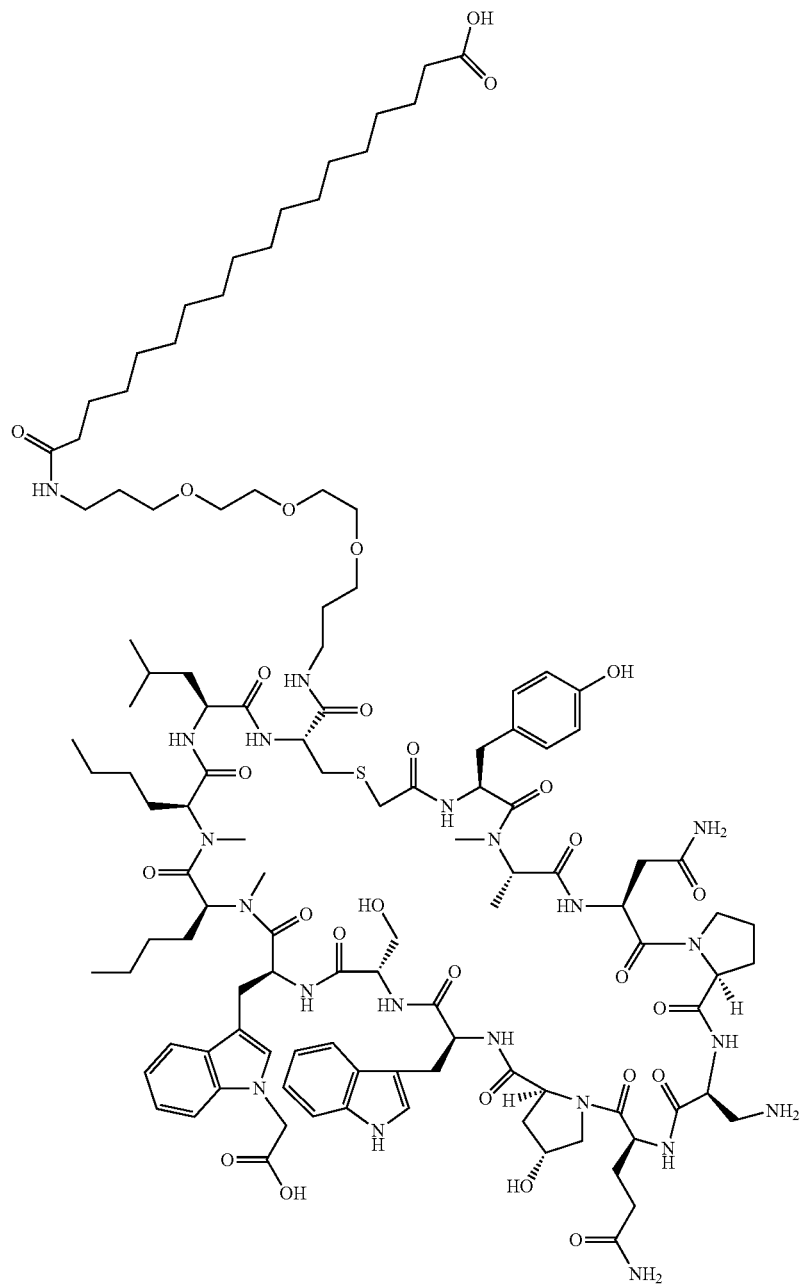 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Phase A: 5:95 acetonitrile:water with 10-mM ammonium acetate; Mobile Phase B: 95:5 acetonitrile:water with 10-mM ammonium acetate; Gradient 15-100% B over 25 minutes, then a 5-minute hold at 100% B; Flow: 30 mL/min. Fractions containing the desired product were combined and dried via centrifugal evaporation. The yield of the product was 3 mg, and its estimated purity by LCMS analysis was 99.6%. Analysis LCMS Condition A: Retention time=5.353 min; ESI-MS(+) m/z 1167.1 (M+2H); ESI-HRMS(+) m/z: Calculated: 1166.1391 (M+2H). Found: 1166.1370 (M+2H).

Preparation of 1-tert-butyl 16-(perfluorophenyl) hexadecanedioate

To a 50 ml round bottom flask was added 18-(tert-butoxy)-18-oxooctadecanoic acid (807 mg, 2.178 mmol), N,N-dimethylformamide (8 mL), pyridine (379 mg, 4.79 mmol), and perfluorophenyl 2,2,2-trifluoroacetate (1220 mg, 4.36 mmol). The flask was sealed with a septum and kept under a blanket of nitrogen and stirred overnight at rt. The next day the reaction was poured into a saturated citric acid solution and extracted with $CH_2Cl_2$ 3×. The organic layers were combined and washed with brine, dried over $Na_2SO_4$ and evaporated in vacuo. The crude product 1-tert-butyl 18-(perfluorophenyl)octadecanedioate (1.1 g, 2.050 mmol, 94% yield) was used as is without purification.

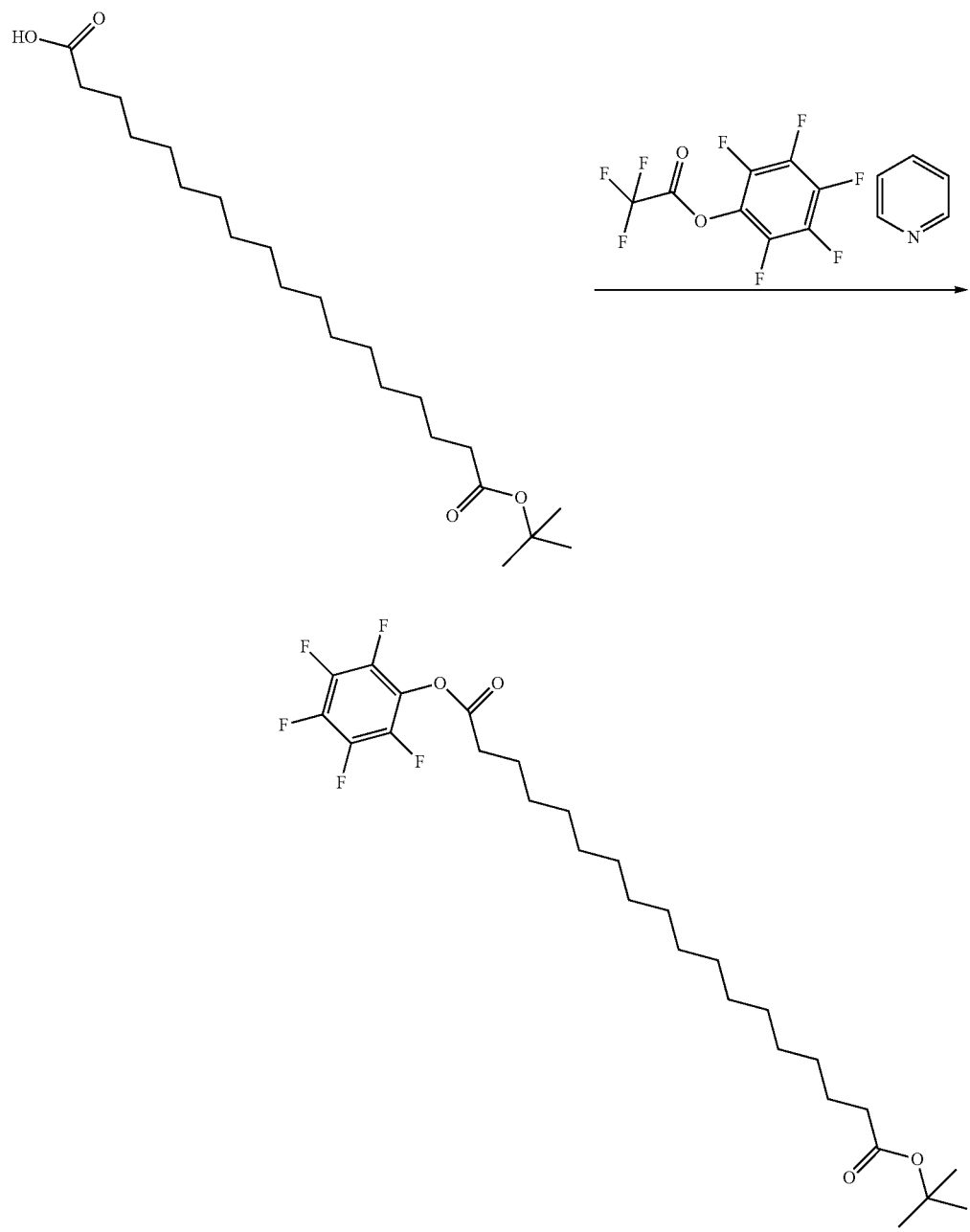

Preparation of (S)-5-(tert-butoxy)-4-(18-(tert-butoxy)-18-oxooctadecanamido)-5-oxopentanoic acid

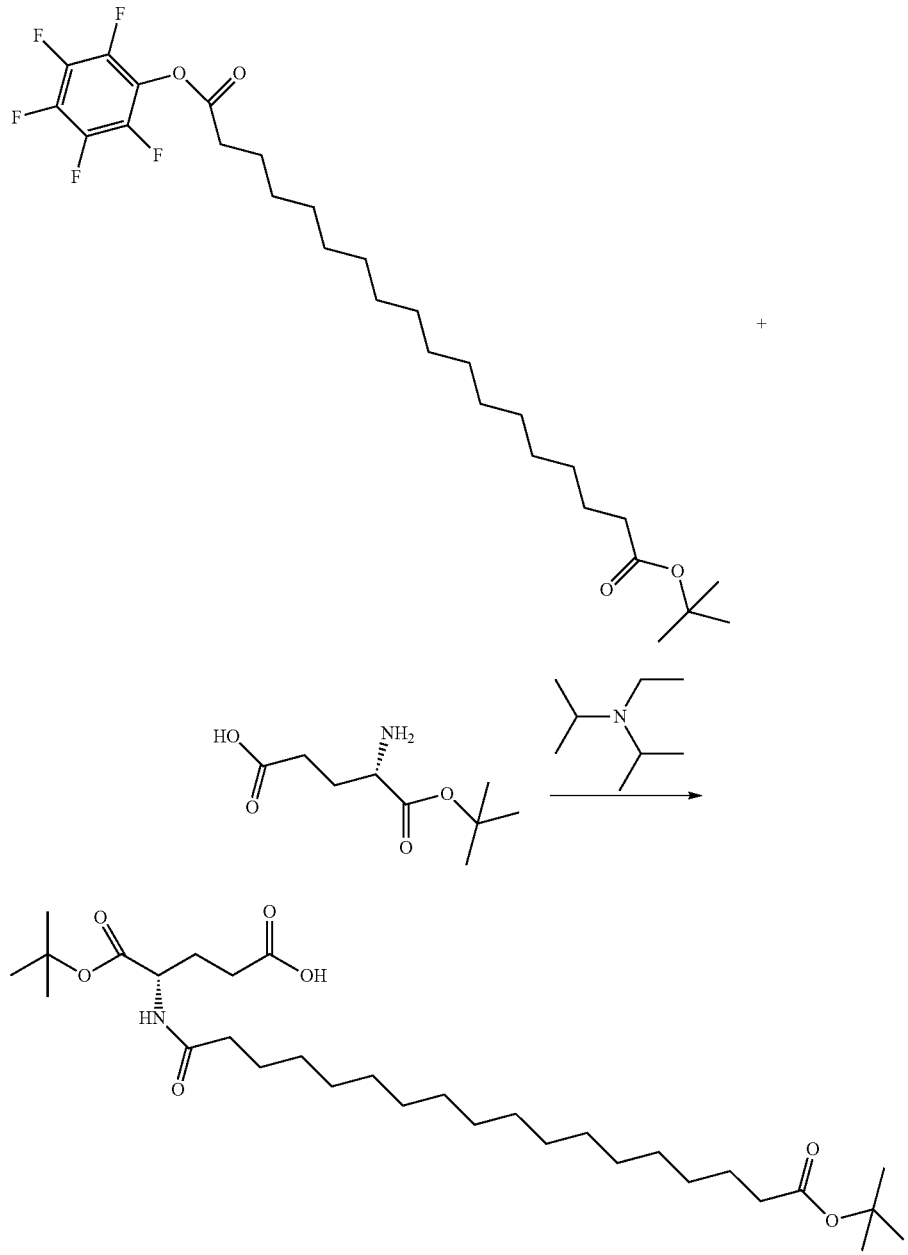

To a 20 ml scint vial was added 1-tert-butyl 18-(perfluorophenyl)octadecanedioate (500 mg, 0.932 mmol), (S)-4-amino-5-(tert-butoxy)-5-oxopentanoic acid (189 mg, 0.932 mmol), N,N-dimethylformamide (3 mL), and N-ethyl-N-isopropylpropan-2-amine (157 mg, 1.211 mmol). The reaction was allowed to stir for 24 hr at rt. After 24 hr the reaction was homogeneous. The reaction mixture was poured into a saturated citric acid solution, and extracted with $CH_2Cl_2$ 3x. The organic fractions were combined, washed with brine, dried over $Na_2SO_4$ and evaporated in vacuo. The crude oil (S)-5-(tert-butoxy)-4-(18-(tert-butoxy)-18-oxooctadecanamido)-5-oxopentanoic acid (518 mg, 0.932 mmol, 100% yield) was used as is without purification. $^1H$ NMR (400 MHz, CHLOROFORM-d) δ 6.33 (m., 1H), 4.56 (m, 1H), 2.45 (m, 2H), 2.24 (m, 5H), 1.95 (m, 1H), 1.61 (m., 5H), 1.49 (s, 9H), 1.46 (s, 9H), 1.26 (m, 23H) Preparation of (S)-1-tert-butyl 5-(perfluorophenyl) 2-(18-(tert-butoxy)-18-oxooctadecanamido)pentanedioate

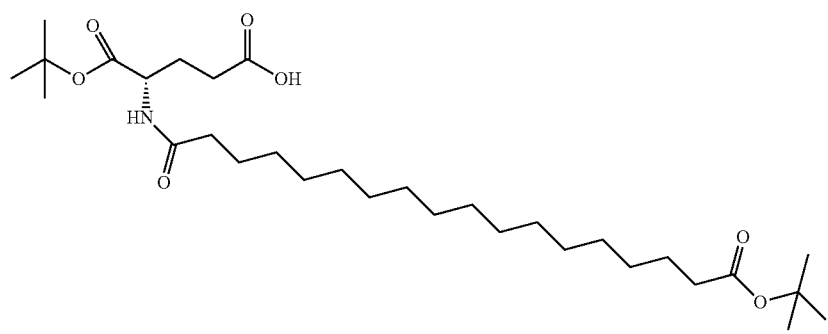
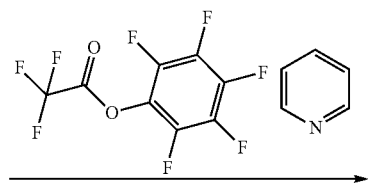

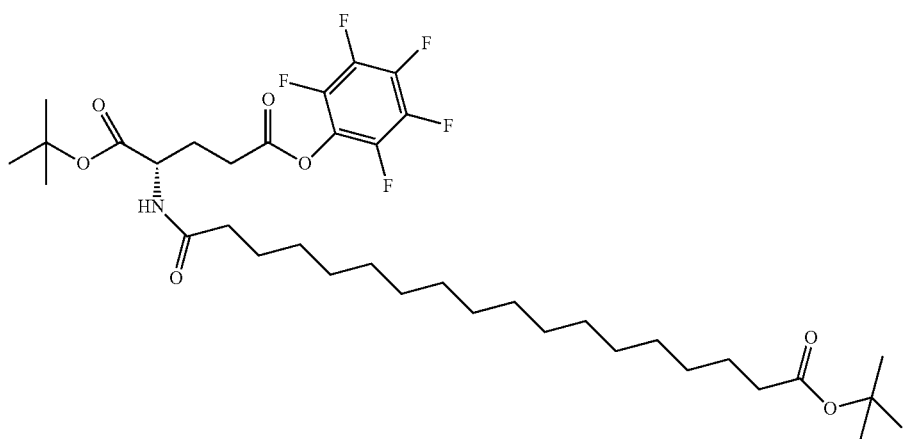

To a 20 ml scint vial was added (S)-5-(tert-butoxy)-4-(18-(tert-butoxy)-18-oxooctadecanamido)-5-oxopentanoic acid (518 mg, 0.932 mmol), N,N-dimethylformamide (3 mL), pyridine (162 mg, 2.050 mmol), and perfluorophenyl 2,2,2-trifluoroacetate (522 mg, 1.864 mmol). The reaction was allowed to stir for 24 hr at rt. After 24 hr the reaction mixture was poured into a saturated citric acid solution, and extracted with $CH_2Cl_2$ 3×. The organic fractions were combined, washed with brine, dried over $Na_2SO_4$ and evaporated in vacuo. The crude oil (S)-1-tert-butyl 5-(perfluorophenyl) 2-(18-(tert-butoxy)-18-oxooctadecanamido)pentanedioate (670 mg, 0.928 mmol, 100% yield) was used as is in the next step.

Preparation of (S)-2-(((((9H-fluoren-9-yl)methoxy)carbonyl)amino)-6-((S)-5-(tert-butoxy)-4-(18-(tert-butoxy)-18-oxooctadecanamido)-5-oxopentanamido)hexanoic acid

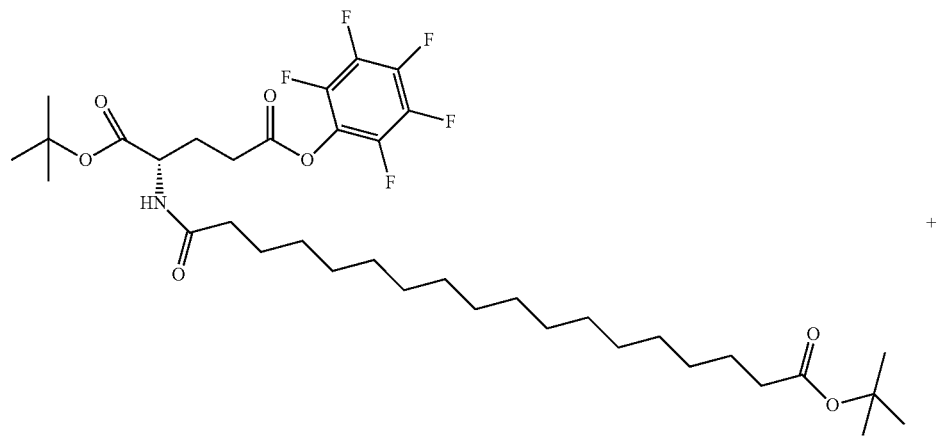

+

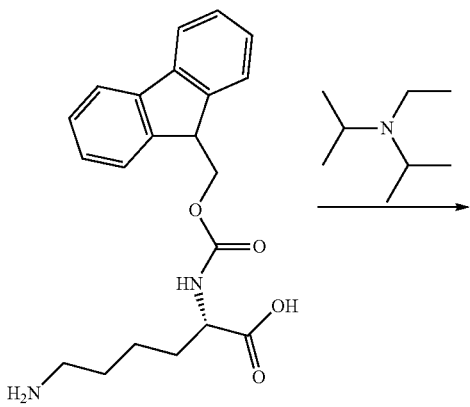

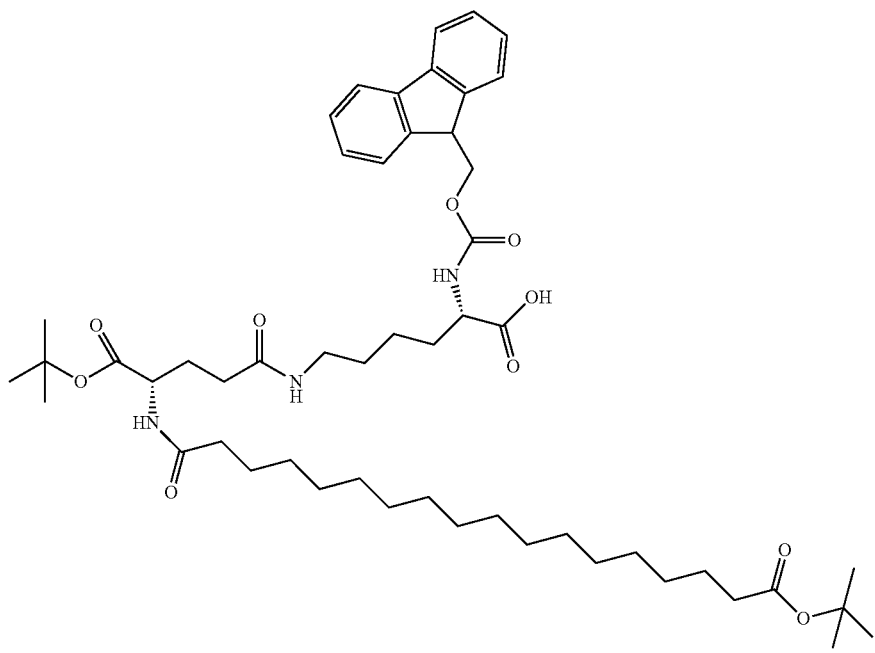

To a 1 dram vial was added (S)-1-tert-butyl 5-(perfluorophenyl) 2-(18-(tert-butoxy)-18-oxooctadecanamido)pentanedioate (330 mg, 0.457 mmol), N,N-Dimethylformamide (2 mL), N-ethyl-N-isopropylpropan-2-amine (177 mg, 1.372 mmol), and(S)-2-((((9H-fluoren-9-yl)methoxy)carbonyl)amino)-6-aminohexanoic acid (168 mg, 0.457 mmol). The reaction was allowed to stir for 24 hr at rt. After 24 hr the reaction was homogeneous. The reaction mixture was poured into a saturated citric acid solution, and extracted with $CH_2Cl_2$ 3×. The organic fractions were combined, dried over $Na2SO_4$ and evaporated in vacuo. The crude oil was purified by silica gel chromatography eluting with first 100% $CH_2Cl_2$, then 5% Methanol in 95% $CH_2Cl_2$. The pure fractions were combined and evaporated in vacuo affording (S)-2-((((9H-fluoren-9-yl)methoxy)carbonyl)amino)-6-((S)-5-(tert-butoxy)-4-(18-(tert-butoxy)-18-oxooctadecanamido)-5-oxopentanamido)hexanoic acid (106 mg, 0.117 mmol, 25.6% yield) as a viscous oil. Column PHENOMENEX-LUNA 2.0×30 mm 3 um particles; Mobile Phase A: 10:90 methanol:water with 10 mM trifluoroacetic acid; Mobile Phase B: 90:10 methanol:water with 10 mM trifluoroacetic acid; Temperature: 40° C.; Gradient: 0% B, 0-100% B over 5 minutes, then a 1.0-minute hold at 100% B; Flow: 0.8 mL/min; Detection: UV at 220 nm. Analysis LCMS: Retention time=5.740 min; ESI-MS(+) m/z 906.86 (M+H).

Preparation of Modified 2-chlorotrityl chloride resin
G
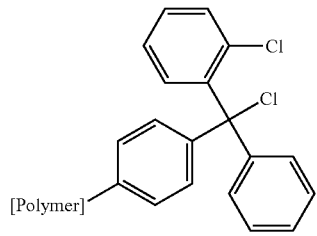
Resin = 2-Chlorotrityl chloride resin from Novabiochem; 1.42 mmol/g loading 1% DVB, 100-200 mesh
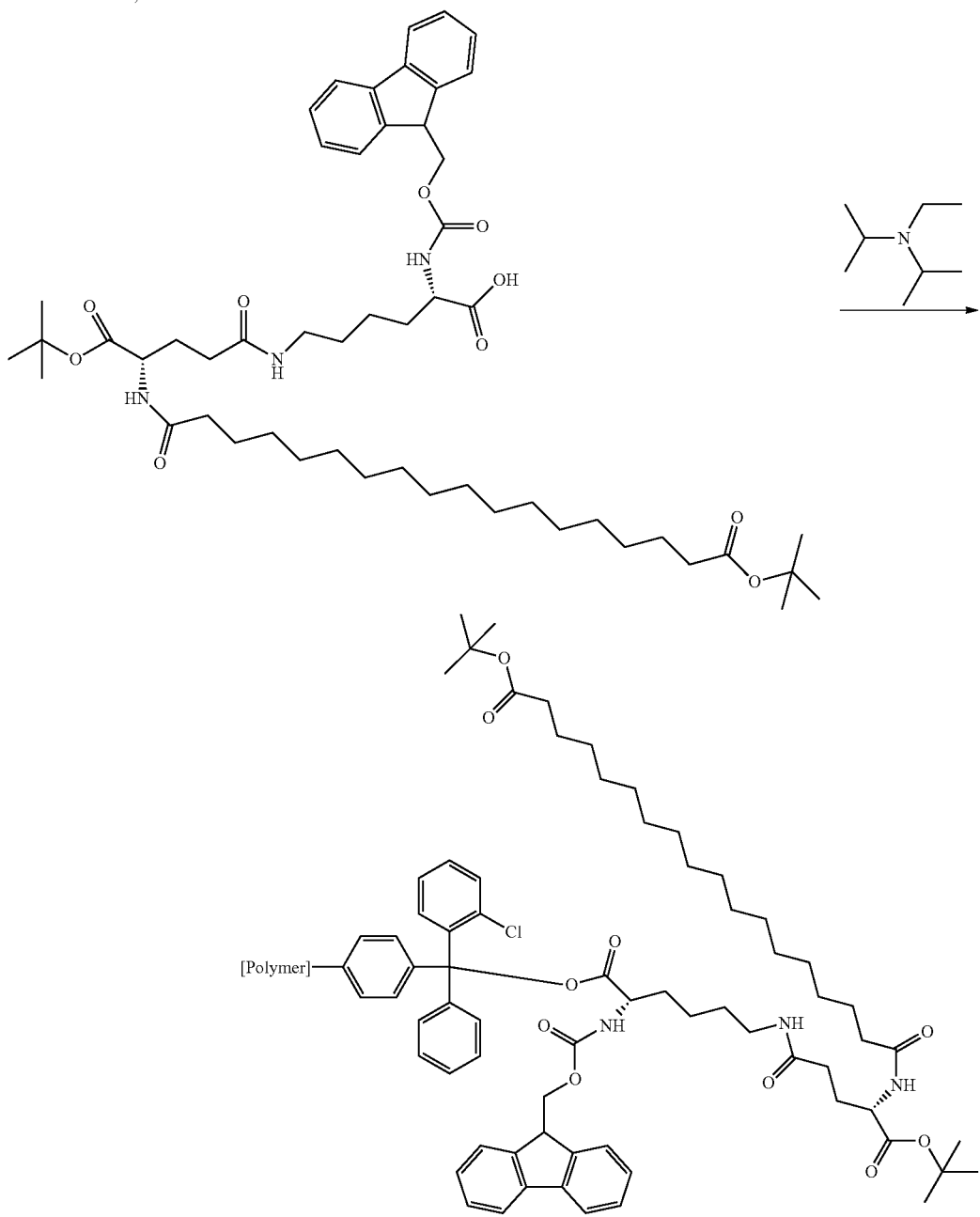

To a 20 ml scintillation vial was added 2-chlorotrityl resin 1.42 mmol/g loading (267 mg, 0.374 mmol), $CH_2Cl_2$ (4 mL), (S)-2-((((9H-fluoren-9-yl)methoxy)carbonyl)amino)-6-((S)-5-(tert-butoxy)-4-(18-(tert-butoxy)-18-oxooctadecanamido)-5-oxopentanamido)hexanoic acid (106 mg, 0.117 mmol), and N-ethyl-N-isopropylpropan-2-amine (106 mg, 0.819 mmol). The vial was sealed and shaken on a wrist action shaker overnight. The next day the reaction was terminated by adding 2 ml methanol and shaking the flask for an additional 2 hr. The resin was then filtered and washed with $CH_2Cl_2$, DMF 3×, $CH_2Cl_2$ 3× and finally diethyl ether. The resin was dried in vacuo and used as is for peptide synthesis with an assumed loading of 0.44 meq/g.

Preparation of Example 11134

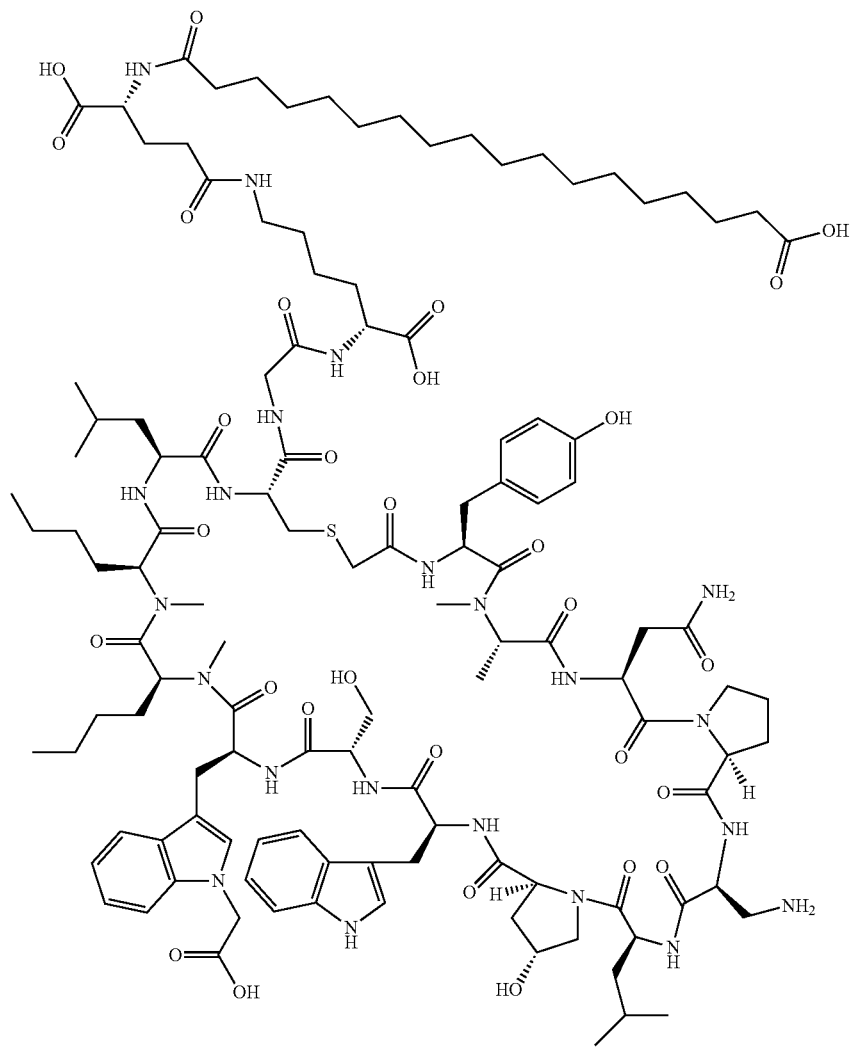 [SMILES: CCCC[C@H]1C(=O)N(C)[C@@H](CCCC)C(=O)N[C@@H](CC(C)C)C(=O)N[C@H](C(=O)NCC(=O)N[C@H](CCCCNC(=O)CC[C@@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 11134 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin G was used in this synthesis. The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 5-minute hold at 100% B; Flow: 30 mL/min. Fractions containing the desired product were combined and dried via centrifugal evaporation. The yield of the product was 26 mg, and its estimated purity by LCMS analysis was 100%. Analysis LCMS Condition A: Retention time=4.280 min; ESI-MS(+) m/z 1222.0 (M+2H).

Preparation of Example 11135

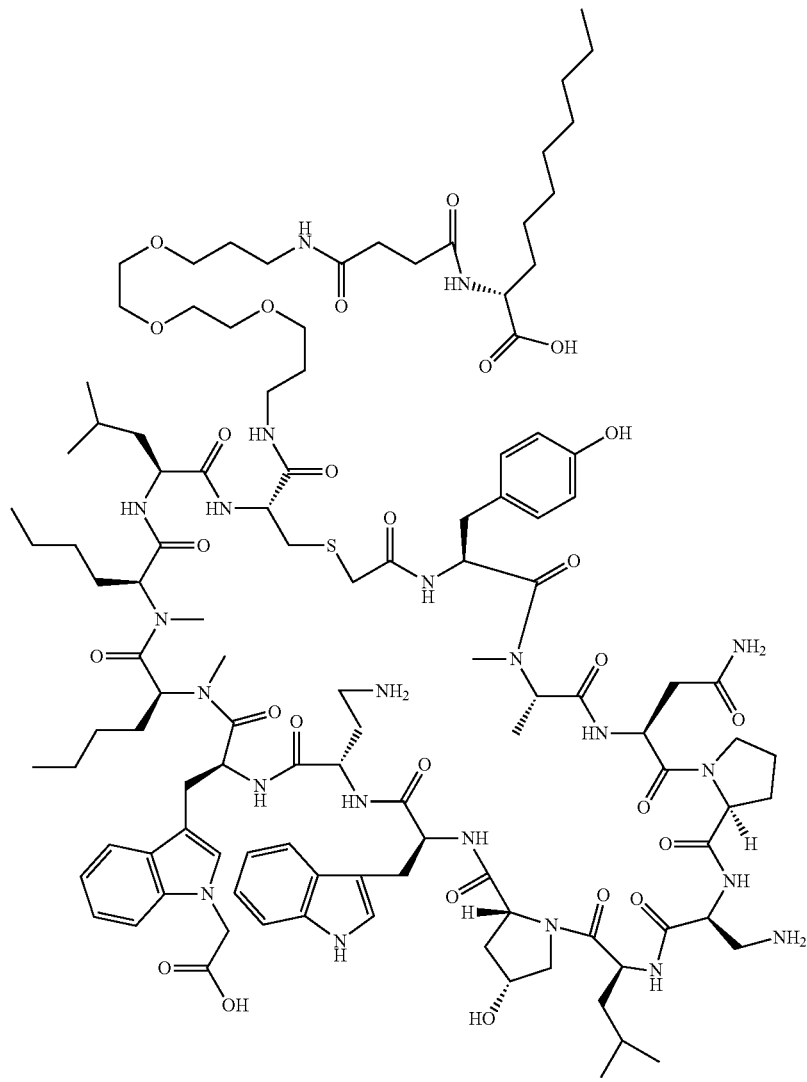 [SMILES: CCCCCCCC[C@@H](NC(=O)CCC(=O)NCCCOCCOCCOCCCNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)O]

Example 11135 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin D was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 24 mg, and its estimated purity by LCMS analysis was 98%. Analysis LCMS Condition A: Retention time=4.141 min.

Preparation of Example 11136

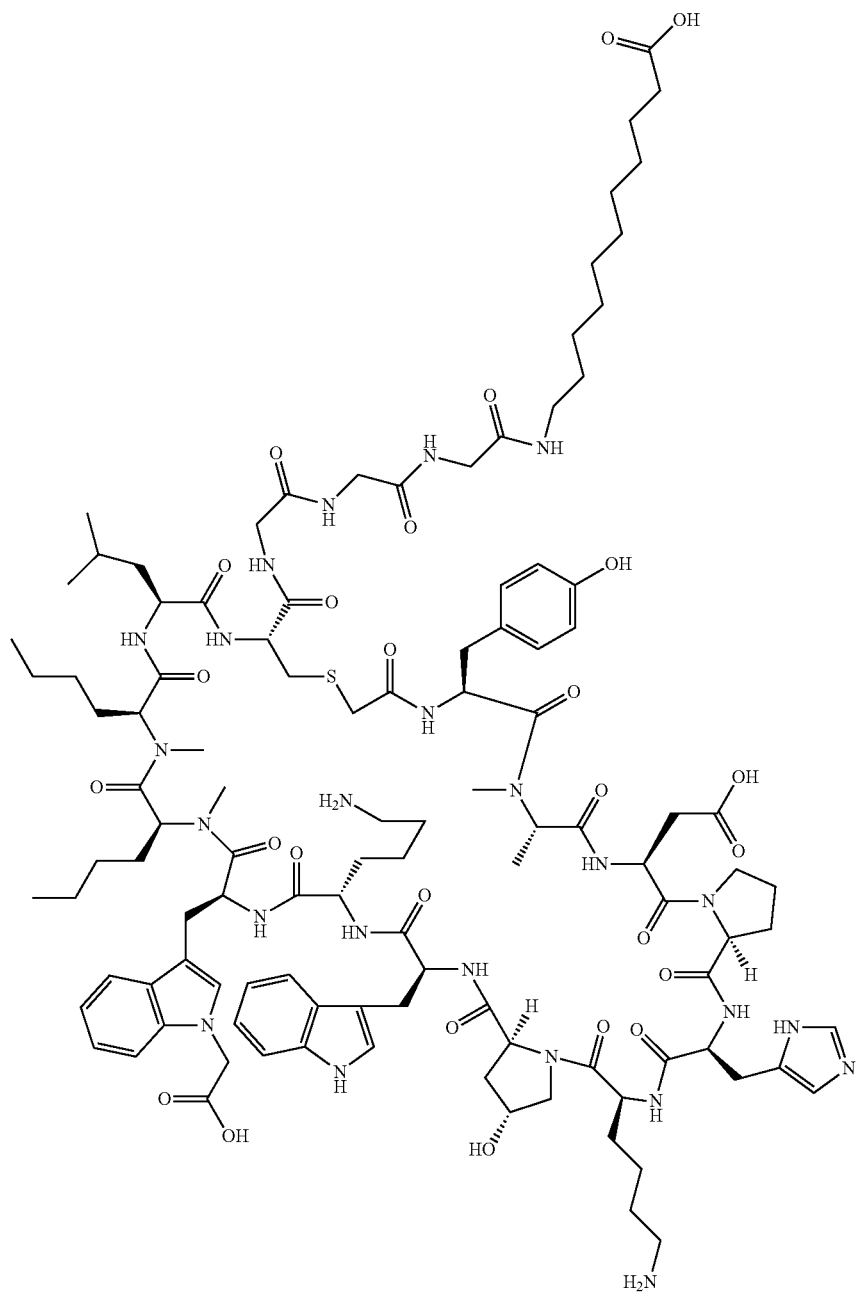 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11136 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 22 mg, and its estimated purity by LCMS analysis was 95.2%. Analysis LCMS Condition A: Retention time=3.930 min; ESI-MS(+) m/z 1141.0969 (M+2H).

Preparation of Modified 2-chlorotrityl chloride resin
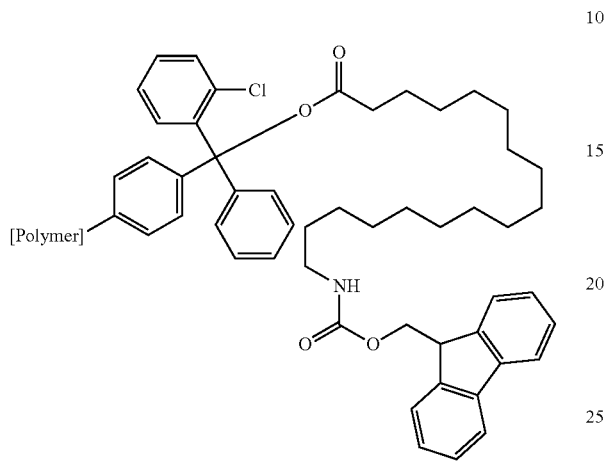
Step 1
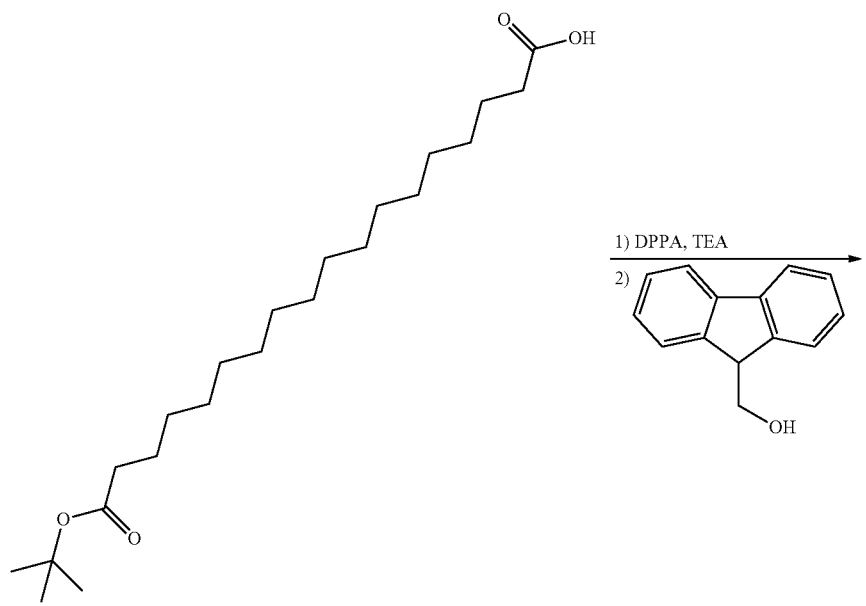

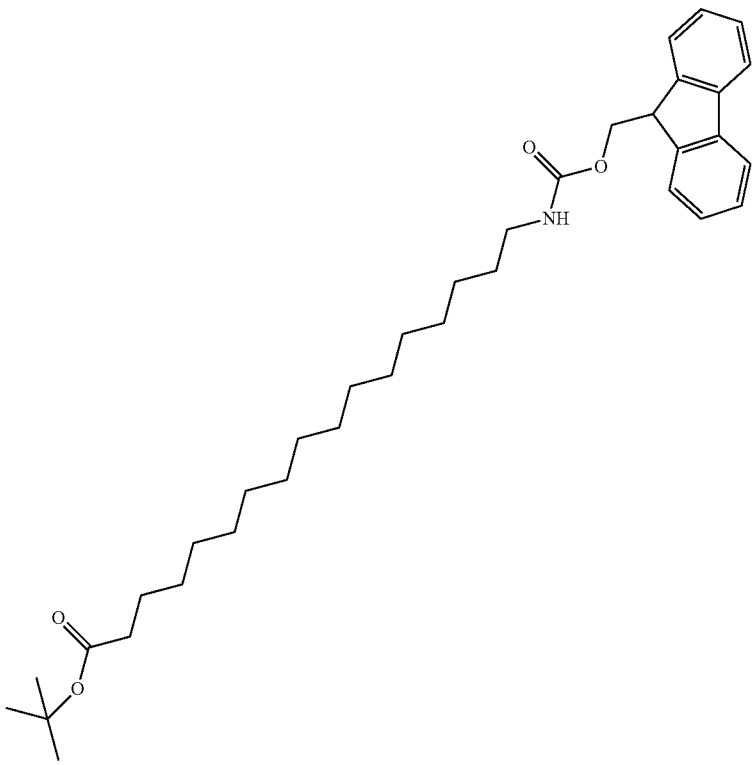

Diphenyl phosphorazidate (1.738 ml, 8.04 mmol) was added to a solution of 18-(tert-butoxy)-18-oxooctadecanoic acid (1.49 g, 4.02 mmol) and triethylamine (1.115 ml, 8.04 mmol) in Toluene (16.08 ml) at room temperature. The resulting mixture was heated under reflux overnight. The reaction mixture was cooled to room temperature and quenched with a 5% citric acid solution. The mixture was concentrated to half volume in vacuo and then extracted 3 times with dichloromethane. The combined organics were washed with brine, dried over MgSO$_4$, filtered, and concentrated to give crude product. The crude product was dissolved in dichloromethane and applied to a 40 g ISCO silica gel cartridge. The product was eluted by a 0-25% ethyl acetate/hexanes gradient. Like fractions were combined and concentrated to give tert-butyl 17-((((9H-fluoren-9-yl)methoxy)carbonyl)amino)heptadecanoate (0.384 g, 0.681 mmol, 16.94% yield) as a white solid. $^1$H NMR (400 MHz, CHLOROFORM-d) δ 7.78 (d, J=7.3 Hz, 2H), 7.61 (d, J=7.5 Hz, 2H), 7.41 (t, J=7.4 Hz, 2H), 7.33 (td, J=7.4, 1.0 Hz, 2H), 4.41 (d, J=7.0 Hz, 2H), 4.24 (d, J=6.8 Hz, 1H), 3.20 (q, J=6.8 Hz, 2H), 2.21 (t, J=7.5 Hz, 2H), 1.61-1.48 (m, 4H), 1.45 (s, 9H), 1.26 (s, 24H).

Step 2

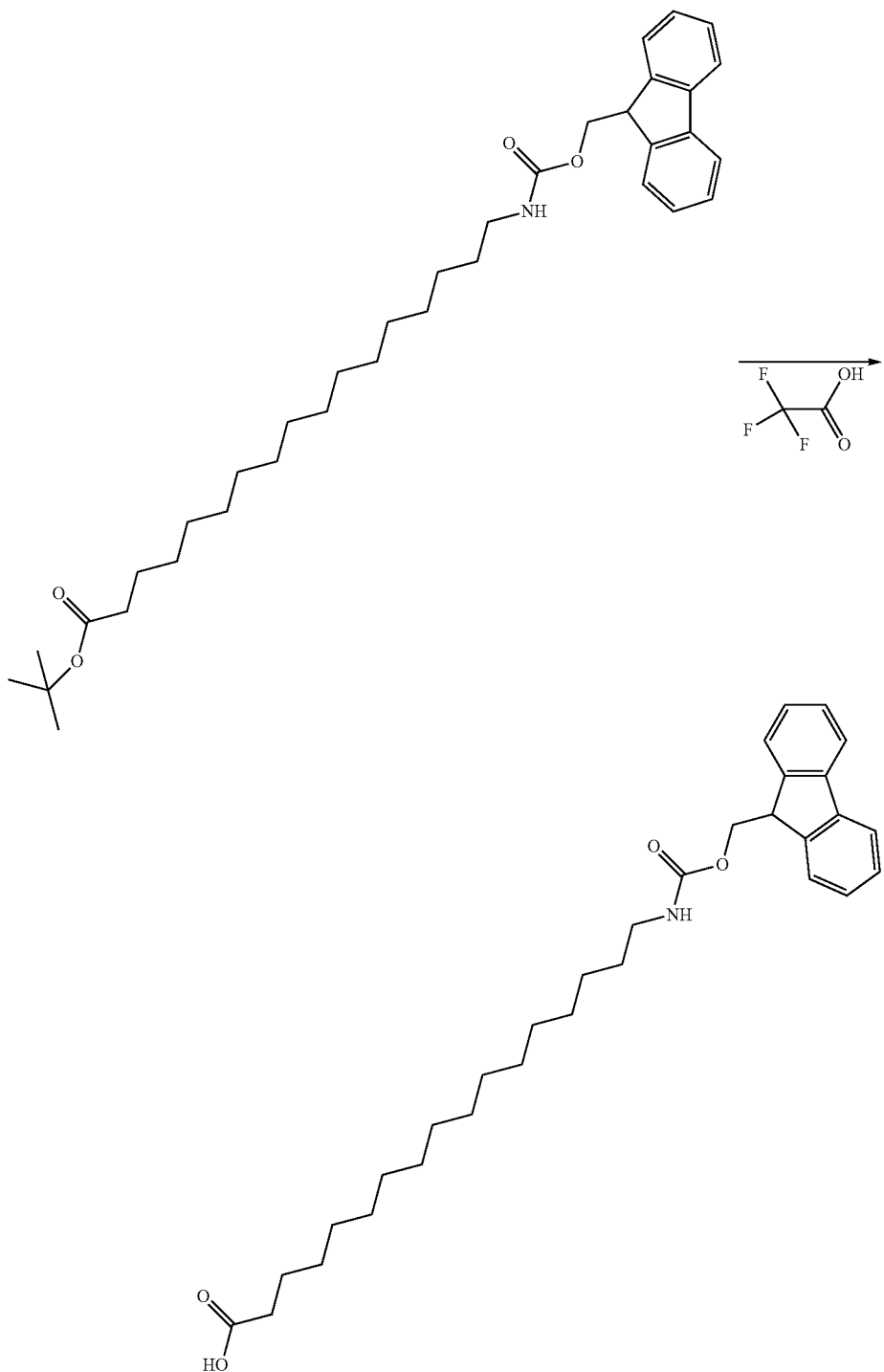

Trifluoroacetic acid (1.5 mL, 19.47 mmol) was added to a solution of tert-butyl 17-((((9H-fluoren-9-yl)methoxy)carbonyl)amino)heptadecanoate (0.375 g, 0.665 mmol) in Dichloromethane (5 mL). The reaction mixture turns dark from yellow after 2 minutes. The solution was stirred at room temperature for 3 hours. The reaction mixture was checked by $^1$HNMR and determined to be complete at this time. The reaction mixture was concentrated in vacuo. The resulting residue was taken up in 5 ml dichloromethane and concentrated again. This process was repeated 3 times and the resulting yellow solid was dried under vacuum overnight. 17-((((9H-fluoren-9-yl)methoxy)carbonyl)amino)heptadecanoic acid was isolated in quantitative yield as a yellow solid. $^1$H NMR (400 MHz, CHLOROFORM-d) δ 7.78 (d, J=7.5 Hz, 2H), 7.63-7.58 (m, 2H), 7.41 (t, J=7.4 Hz, 2H), 7.33 (td, J=7.5, 1.1 Hz, 2H), 4.41 (d, J=6.8 Hz, 2H), 4.27-4.19 (m, 1H), 3.25-3.09 (m, 2H), 2.36 (t, J=7.5 Hz, 2H), 1.70-1.59 (m, 2H), 1.55-1.40 (m, 2H), 1.27 (br. s., 24H).

Step 3

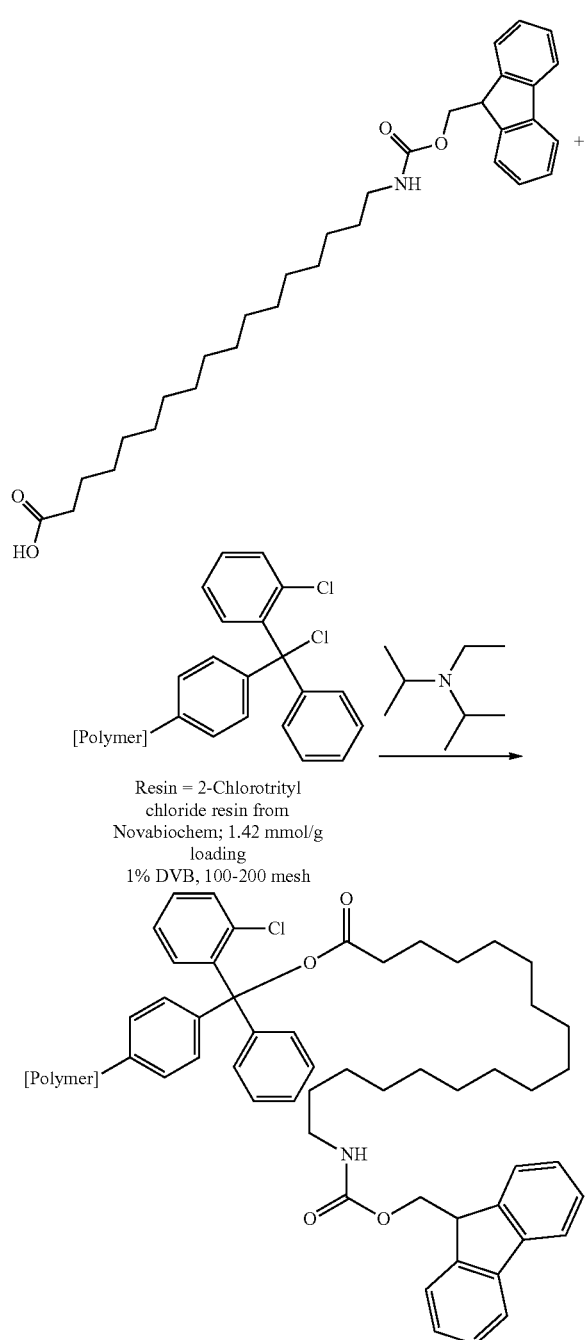

To a 20 mL vial was added 2-Chlorotrityl chloride resin (1.605 g, 1.926 mmol) and 7 ml dichloromethane to swell the resin. 9-((((16-carboxyhexadecyl)carbamoyl)oxy)methyl)-9H-fluoren-1-ylium (0.305 g, 0.602 mmol) in 5 ml dichloromethane and N-ethyl-N-isopropylpropan-2-amine (0.841 ml, 4.82 mmol) were added to the vial containing the resin. The vessel was sealed and shaken overnight at room temperature on a wrist action shaker. The next day the reaction was diluted with 5 ml of methanol, and the vessel was shaken for 2 hr to quench any unreacted chlorotrityl resin. The resin was filtered, and washed with DMF three times, CH$_2$Cl$_2$ 3 times, and finally Et$_2$O. The resulting resin was air dried and used as is assuming a 0.44 meq/g loading.

Preparation of Modified 2-chlorotrityl chloride resin I

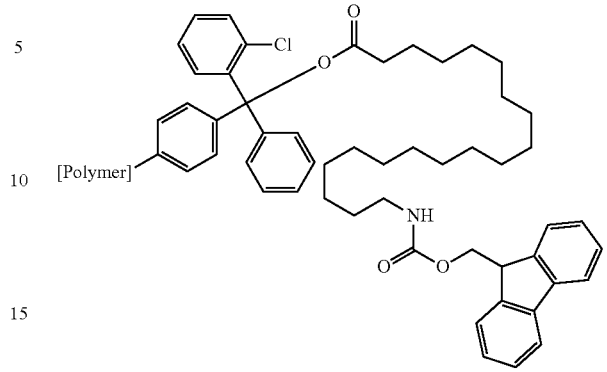

Modified 2-chlorotrityl chloride resin I was made following an identical procedure to Modified 2-chlorotrityl resin A.

Preparation of Modified 2-chlorotrityl chloride resin J

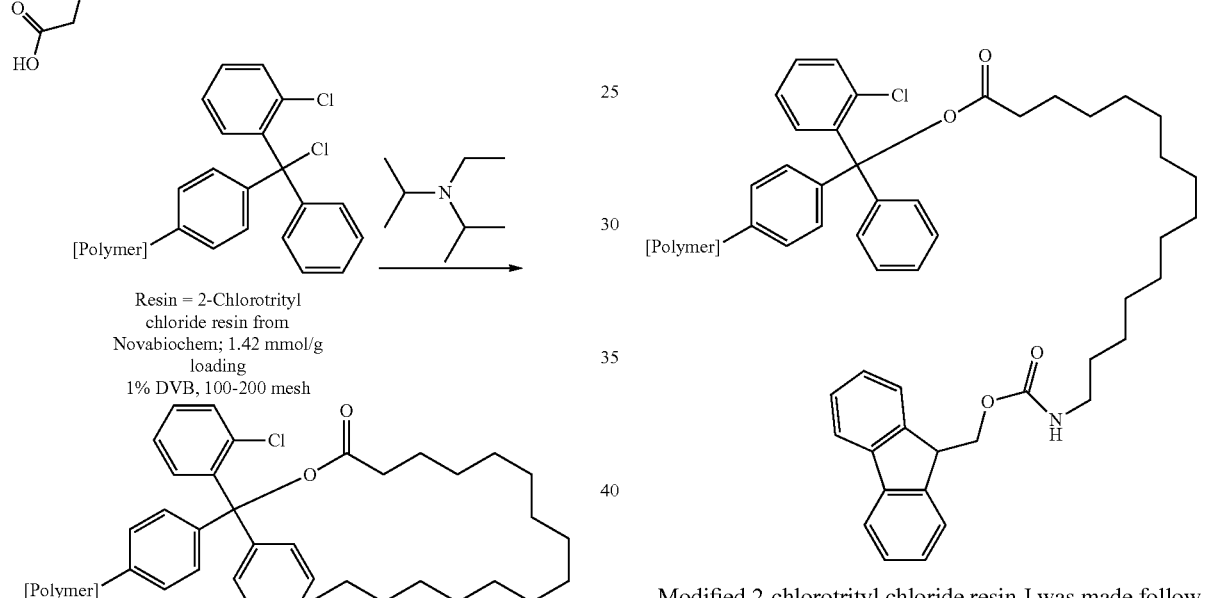

Modified 2-chlorotrityl chloride resin J was made following an identical procedure to Modified 2-chlorotrityl resin A.

Preparation of Modified 2-chlorotrityl chloride resin K

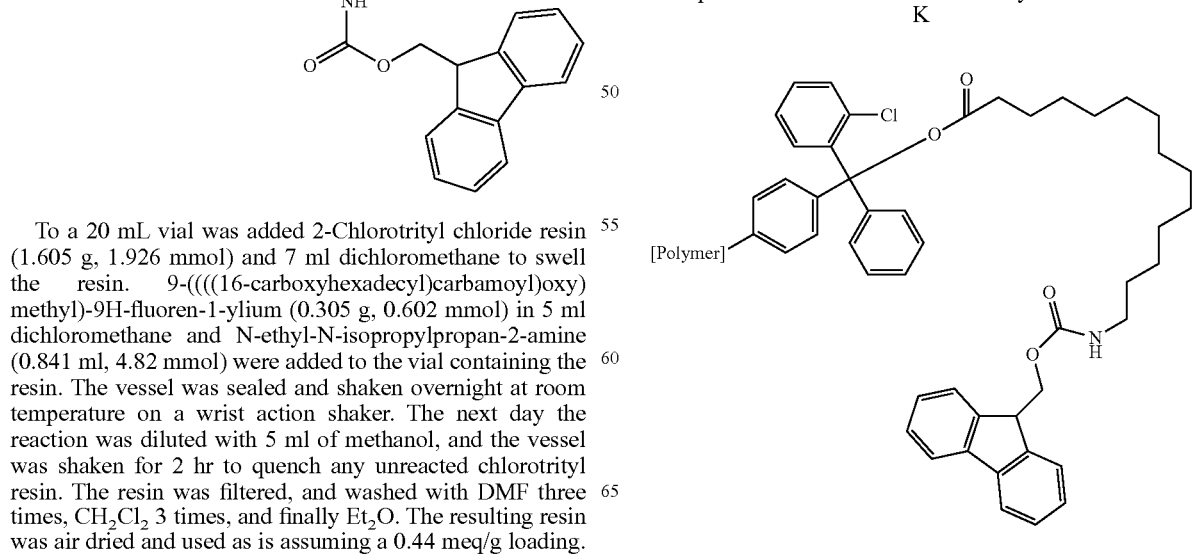

Modified 2-chlorotrityl chloride resin K was made following an identical procedure to Modified 2-chlorotrityl resin A.

Preparation of Modified 2-chlorotrityl chloride resin L

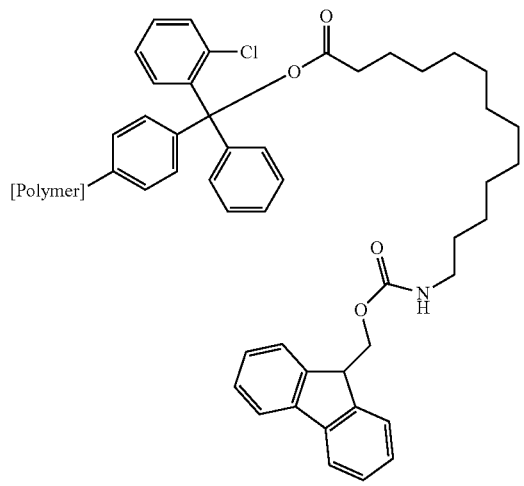

Modified 2-chlorotrityl chloride resin L was made following an identical procedure to Modified 2-chlorotrityl resin A.

Preparation of Modified 2-chlorotrityl chloride resin M

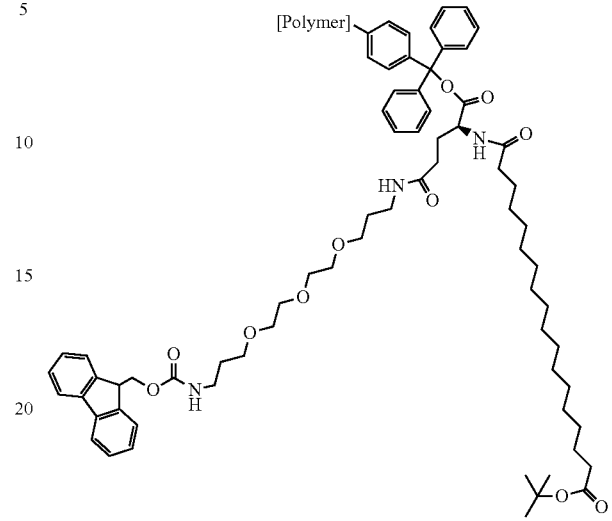

Step 1: Preparation of 18-(tert-butoxy)-18-oxooctadecanoic acid

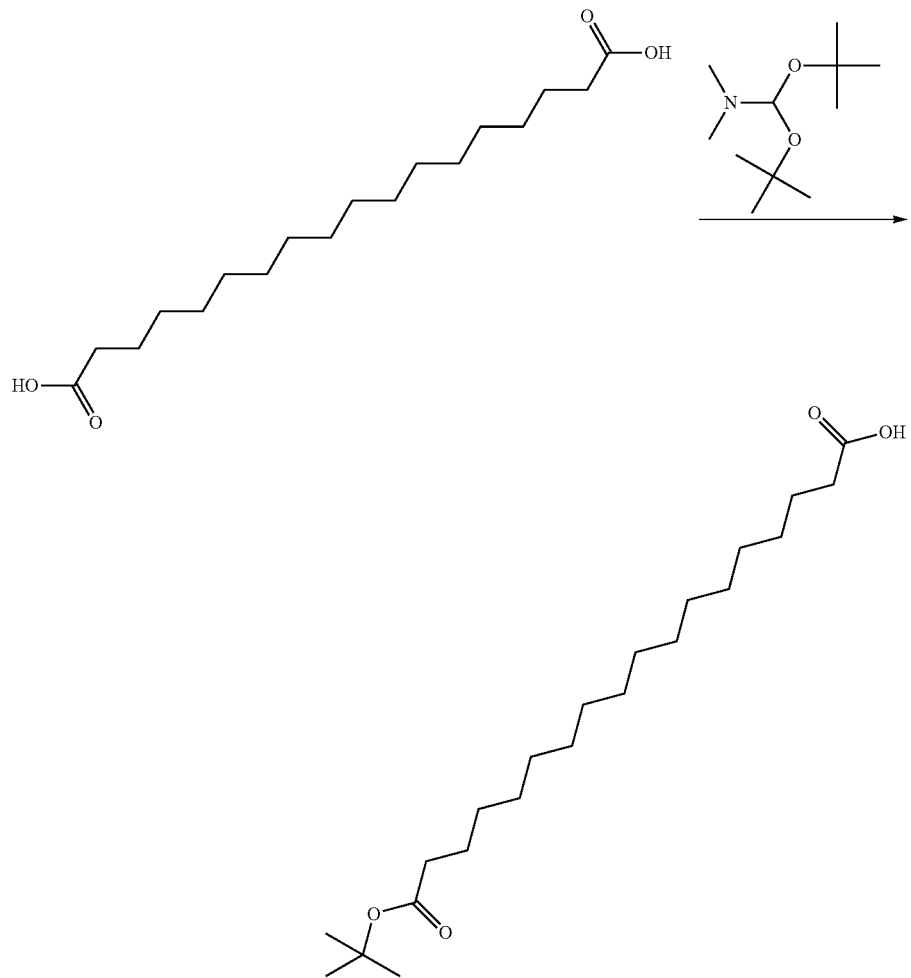

A suspension of octadecanedioic acid (15 g, 47.7 mmol) in Toluene (191 ml) was brought to reflux in 3 neck 1 L round bottom flask. When all of the acid was in solution, 1,1-di-tert-butoxy-N,N-dimethylmethanamine (22.87 ml, 95 mmol) was added dropwise over 30 minutes. The reaction mixture was heated under reflux overnight. The reaction was stopped after 20 total hours of heating. The reaction mixture was cooled to room temperature resulting in precipitation of solids. The mixture was filtered by vacuum filtration. The resulting white solid was suspended in 200 ml dichloromethane and stirred for 15 minutes. The remaining solids were removed via vacuum filtration. The collected solids were again suspended in dichloromethane and stirred for 15 minutes. After a second filtration the combined filtrates were concentrated in vacuo and the resulting white powder was dried under vacuum. 18-(tert-butoxy)-18-oxooctadecanoic acid (10.14 g, 27.4 mmol, 57.4% yield) was isolated as a white solid. $^1$H NMR (400 MHz, CHLOROFORM-d) δ 2.35 (t, J=7.5 Hz, 2H), 2.21 (t, J=7.5 Hz, 2H), 1.70-1.52 (m, 4H), 1.45 (s, 9H), 1.36-1.22 (m, 24H).

Step 2

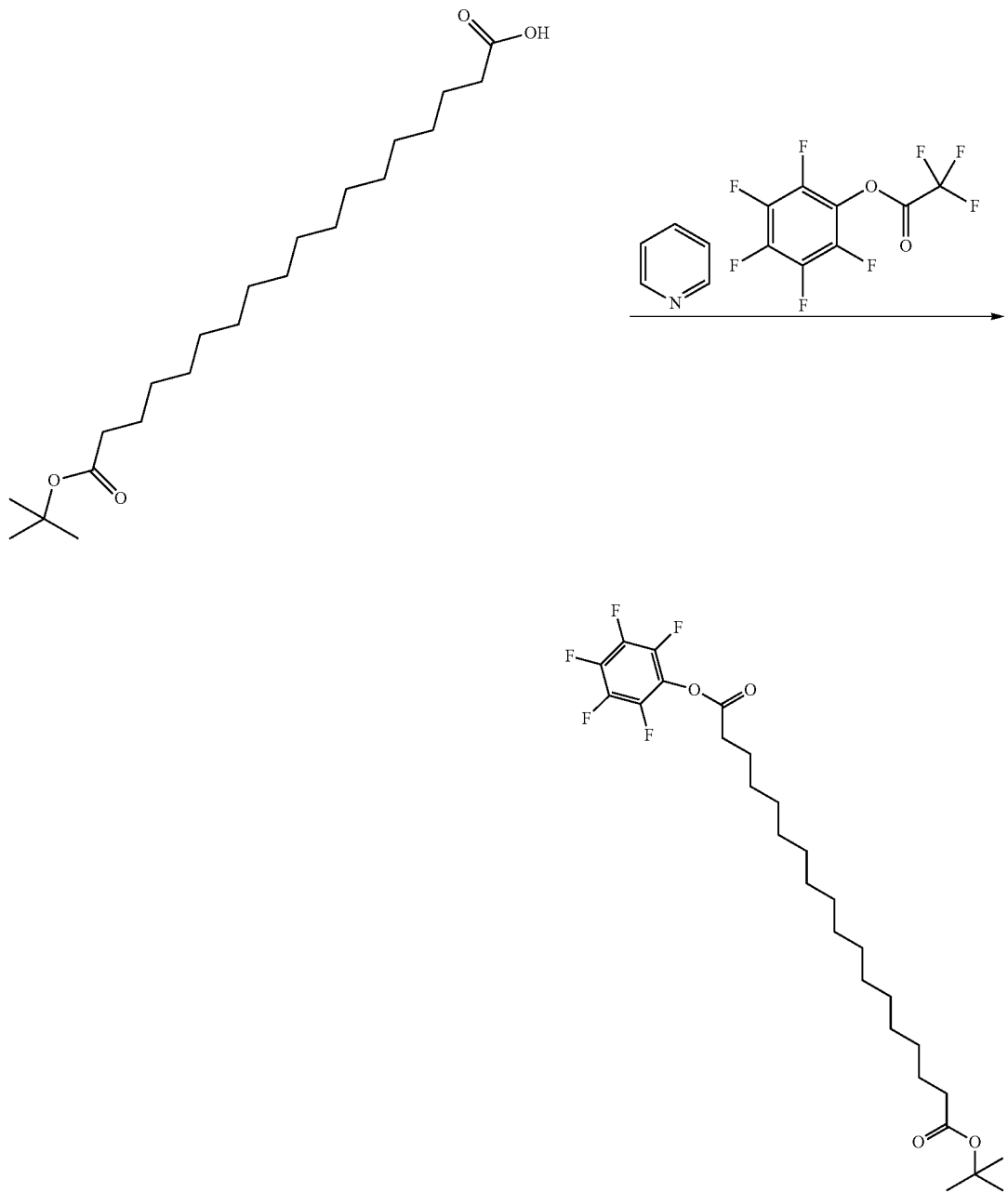

To a 250 ml round bottom flask was added 18-(tert-butoxy)-18-oxooctadecanoic acid (8.58 g, 23.15 mmol), pyridine (4.68 ml, 57.9 mmol), DMF (50 ml), and perfluorophenyl 2,2,2-trifluoroacetate (7.96 ml, 46.3 mmol). The flask was sealed with a septum and kept under a nitrogen atmosphere and stirred overnight at room temperature. The reaction mixture was poured into a saturated citric acid solution and extracted with $CH_2Cl_2$ three times. The organic layers were combined and washed with brine, dried over $MgSO_4$, and evaporated in vacuo. The crude product was purified on silica gel chromatography eluting with 0% ethyl acetate/100% hexanes to 55% ethyl acetate/45% hexanes. The pure fractions were combined and evaporated in vacuo affording 1-tert-butyl 18-(perfluorophenyl)octadecanedioate (8.37 g, 15.60 mmol, 67.4% yield) as a white solid. $^1$H NMR (400 MHz, CHLOROFORM-d) δ 2.66 (t, J=7.5 Hz, 2H), 2.23-2.19 (m, 2H), 1.84-1.73 (m, 2H), 1.59 (d, J=7.3 Hz, 2H), 1.45 (s, 9H), 1.44-1.38 (m, 2H), 1.33-1.25 (m, 24H).

Step 3

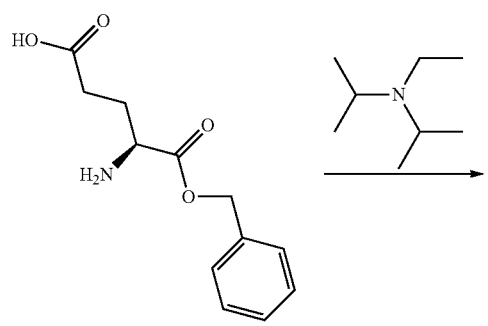

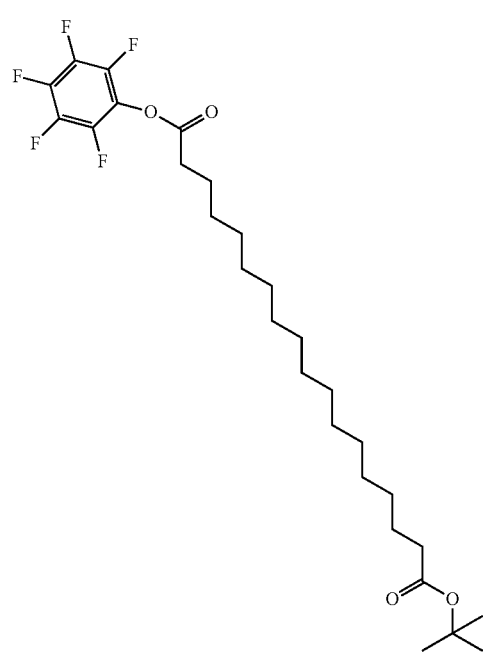

+

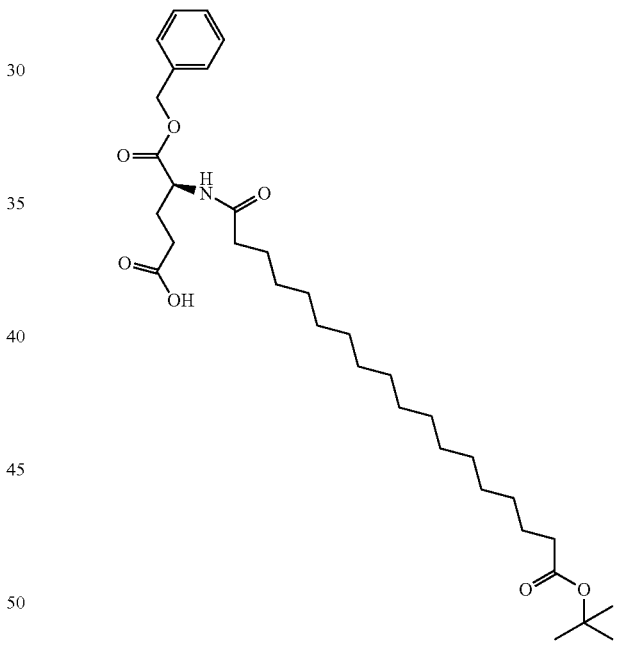

To a 500 ml round bottom flask was added 1-tert-butyl 18-(perfluorophenyl)octadecanedioate (14.2 g, 26.5 mmol), H-GLU-OBZL (5.71 g, 24.06 mmol), DMF (160 ml), and N-ethyl-N-isopropylpropan-2-amine (12.60 ml, 72.2 mmol). The flask was sealed with a septum and kept under a nitrogen atmosphere and stirred overnight at room temperature. The reaction mixture was heterogeneous. After 25 hours the reaction mixture was poured into a saturated citric acid solution and extracted with CH$_2$Cl$_2$ 3×. The organic layers were combined and washed with brine, dried over MgSO$_4$ and evaporated in vacuo. The crude product was purified on silica gel chromatography eluting with a 0-7% CH$_2$Cl$_2$/MeOH gradient. The pure fractions were combined and evaporated in vacuo affording (S)-5-(benzyloxy)-4-(18-(tert-butoxy)-18-oxooctadecanamido)-5-oxopentanoic acid (7.74 g, 13.12 mmol, 54.6% yield) as a white solid. $^1$H NMR (400 MHz, CHLOROFORM-d) δ 7.41-7.30 (m, 5H), 6.28 (d, J=7.8 Hz, 1H), 5.18 (s, 2H), 4.70 (td, J=8.0, 5.0 Hz, 1H), 2.46-2.32 (m, 2H), 2.22 (q, J=7.9 Hz, 5H), 2.05-1.91 (m, 1H), 1.60 (dt, J=15.3, 7.4 Hz, 4H), 1.45 (s, 9H), 1.30-1.25 (m, 24H).

Step 4

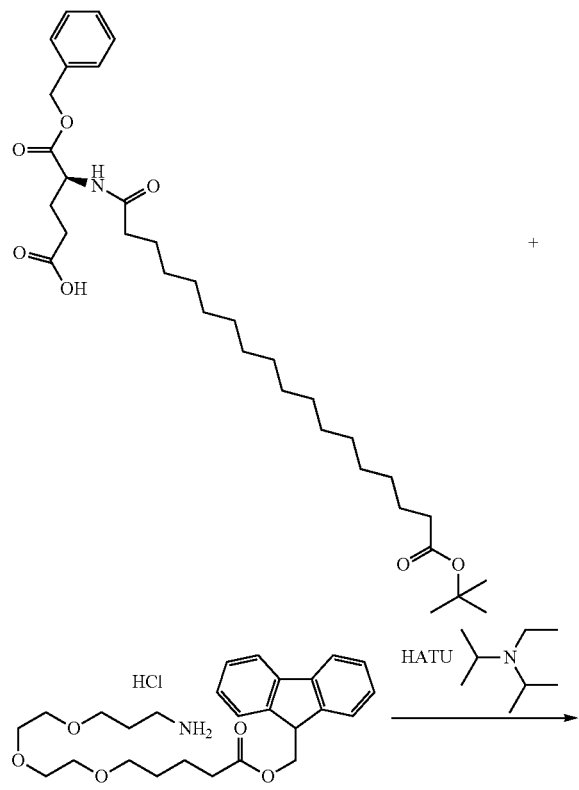

+

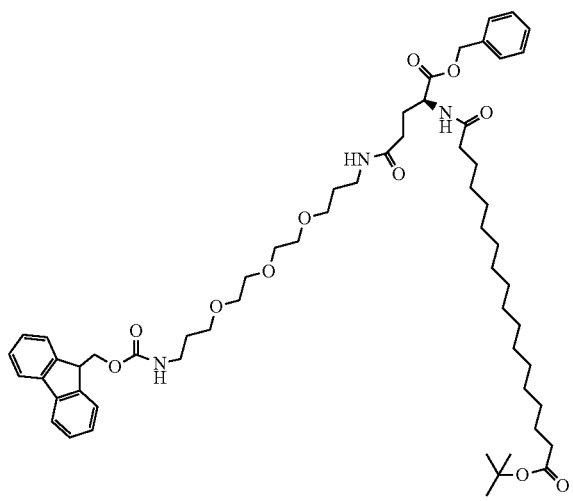

To a 100 ml round bottom flask was added (S)-5-(benzyloxy)-4-(18-(tert-butoxy)-18-oxooctadecanamido)-5-oxopentanoic acid (1.69 g, 2.87 mmol), Dichloromethane (14.33 ml), (9H-fluoren-9-yl)methyl(3-(2-(2-(3-aminopropoxy)ethoxy)ethoxy)propyl)carbamate hydrochloride (1.373 g, 2.87 mmol), 2-(3H-[1,2,3]triazolo[4,5-b]pyridin-3-yl)-1,1,3,3-tetramethylisouronium hexafluorophosphate(V) (1.416 g, 3.72 mmol), and N-ethyl-N-isopropylpropan-2-amine (1.497 ml, 8.60 mmol). The flask was sealed with a septum and kept under a blanket of nitrogen and stirred overnight at room temperature. The reaction was complete by LC/MS. The solvent was evaporated in vacuo. The crude product was purified on silica gel chromatography eluting with 20% acetone/hexanes to 60% acetone/40% hexanes. The pure fractions were combined and evaporated in vacuo affording (S)-tert-butyl 22-((benzyloxy)carbonyl)-1-(9H-fluoren-9-yl)-3,19,24-trioxo-2,8,11,14-tetraoxa-4,18,23-triazahentetracontan-41-oate (2.54 g, 2.504 mmol, 87% yield) as a yellow solid. $^1$H NMR (400 MHz, CHLOROFORM-d) δ 7.76 (d, J=7.5 Hz, 2H), 7.61 (d, J=7.5 Hz, 2H), 7.43-7.37 (m, 2H), 7.36-7.28 (m, 7H), 6.83 (d, J=7.3 Hz, 1H), 6.54 (br. s., 1H), 5.51-5.43 (m, 1H), 5.21-5.10 (m, 2H), 4.58-4.50 (m, 1H), 4.40 (d, J=7.0 Hz, 2H), 4.25-4.17 (m, 1H), 3.65-3.48 (m, 12H), 3.37-3.25 (m, 4H), 2.23-2.18 (m, 7H), 2.07-1.94 (m, 1H), 1.76-1.71 (m, 2H), 1.66-1.53 (m, 6H), 1.45 (s, 9H), 1.30-1.23 (m, 24H).

Step 5

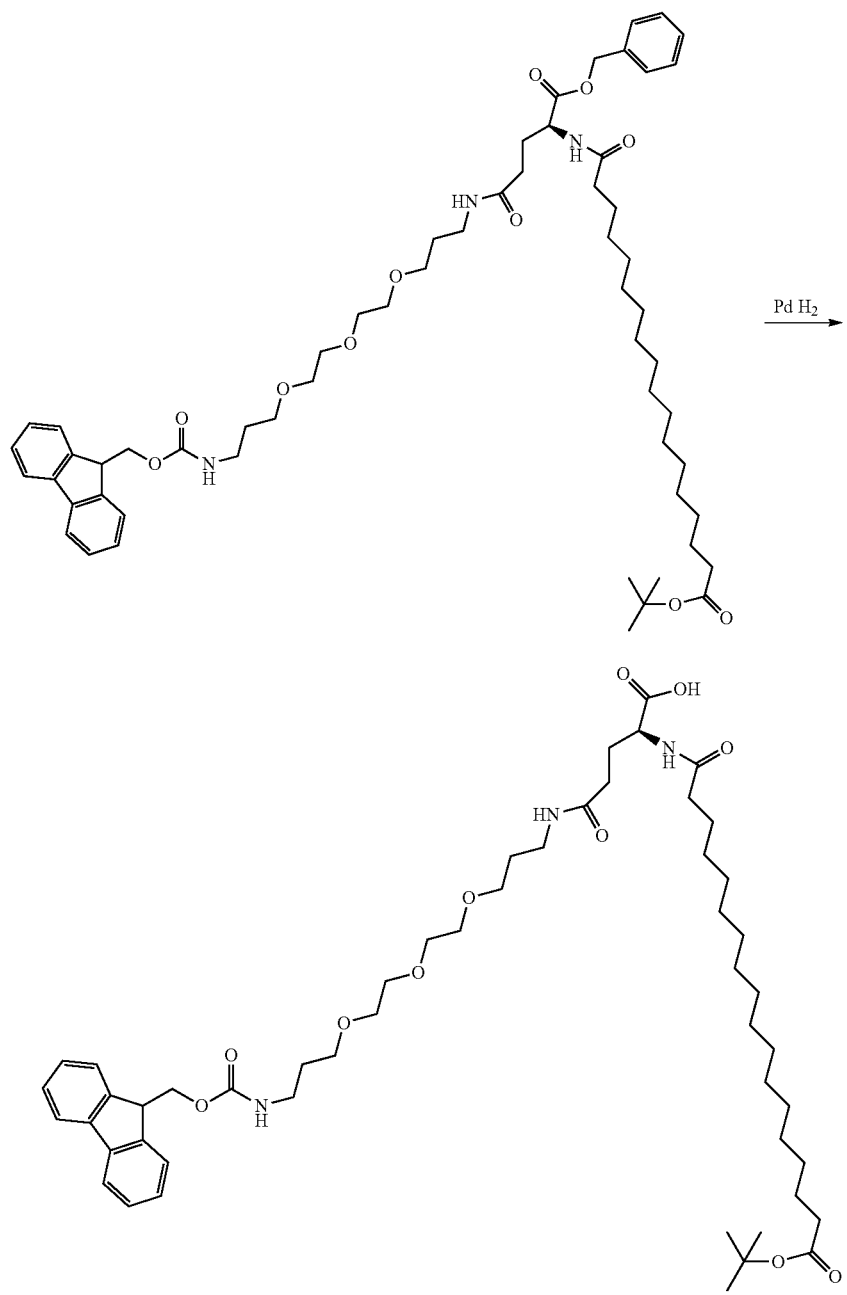

To a 100 ml round bottom flask was added (S)-tert-butyl 22-((benzyloxy)carbonyl)-1-(9H-fluoren-9-yl)-3,19,24-trioxo-2,8,11,14-tetraoxa-4,18,23-triazahentetracontan-41-oate (0.95 g, 0.937 mmol), Methanol (20 ml), and 10% palladium on carbon (0.100 g, 0.094 mmol). The flask was sealed with a septum and charged with hydrogen via a balloon. The mixture was allowed to stir overnight. The reaction was checked by LC/MS and was complete. The reaction was filtered through celite to remove the catalyst and the filtrate was evaporated in vacuo to give (S)-22-(18-(tert-butoxy)-18-oxooctadecanamido)-1-(9H-fluoren-9-yl)-3,19-dioxo-2,8,11,14-tetraoxa-4,18-diazatricosan-23-oic acid (0.76 g, 0.822 mmol, 88% yield). This material was used as is without purification. LC/MS: (M+H)$^+$=925.10.

Step 6: Modified 2-Chlorotrityl Resin M
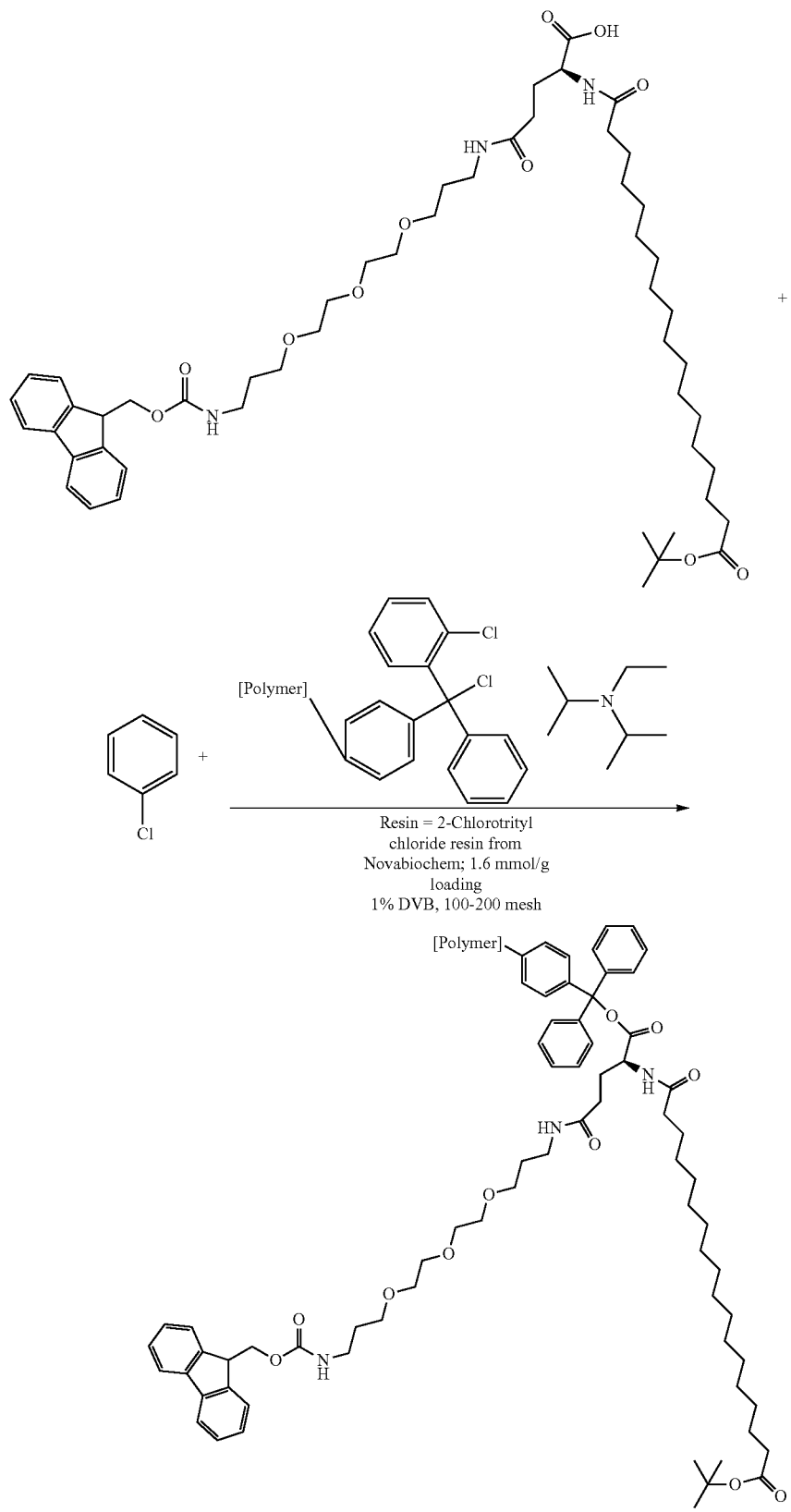

To a 75 ml peptide vessel was added 2-Chlorotrityl chloride resin (1.580 g, 2.53 mmol) and Dichloromethane (15.80 ml). After 10 minutes, (S)-22-(18-(tert-butoxy)-18-oxooctadecanamido)-1-(9H-fluoren-9-yl)-3,19-dioxo-2,8,11,14-tetraoxa-4,18-diazatricosan-23-oic acid (0.73 g, 0.790 mmol), 1-chloro-4-methylbenzene (0.093 ml, 0.790 mmol), and N-ethyl-N-isopropylpropan-2-amine (1.101 ml, 6.32 mmol) were added. The vessel was sealed and shaken on a wrist action shaker for 45 minutes. LC/MS analysis of the comparison of the ratio of the internal standard, 1-chloro-4-methylbenzene (68.1 mg, 0.538 mmol) vs starting acid indicates reaction completion or total consumption of the acid. The resin was then diluted with 20 ml of a 9:1 Methanol/Hunigs base solution and quickly filtered and washed with DMF three times, $CH_2Cl_2$ 3 times, and finally diethyl ether. The resin was dried in vacuo and used as is for peptide synthesis with an assumed loading of 0.5 meq/g.

Preparation of Modified 2-chlorotrityl chloride resin N

Preparation of Modified 2-chlorotrityl chloride resin O

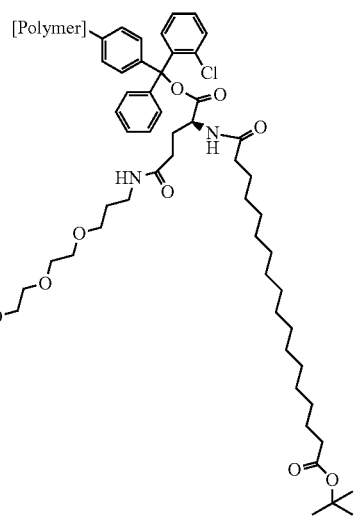

Modified 2-chlorotrityl chloride resin O was made following an identical procedure to Modified 2-chlorotrityl resin M.

Preparation of Modified 2-chlorotrityl chloride resin P

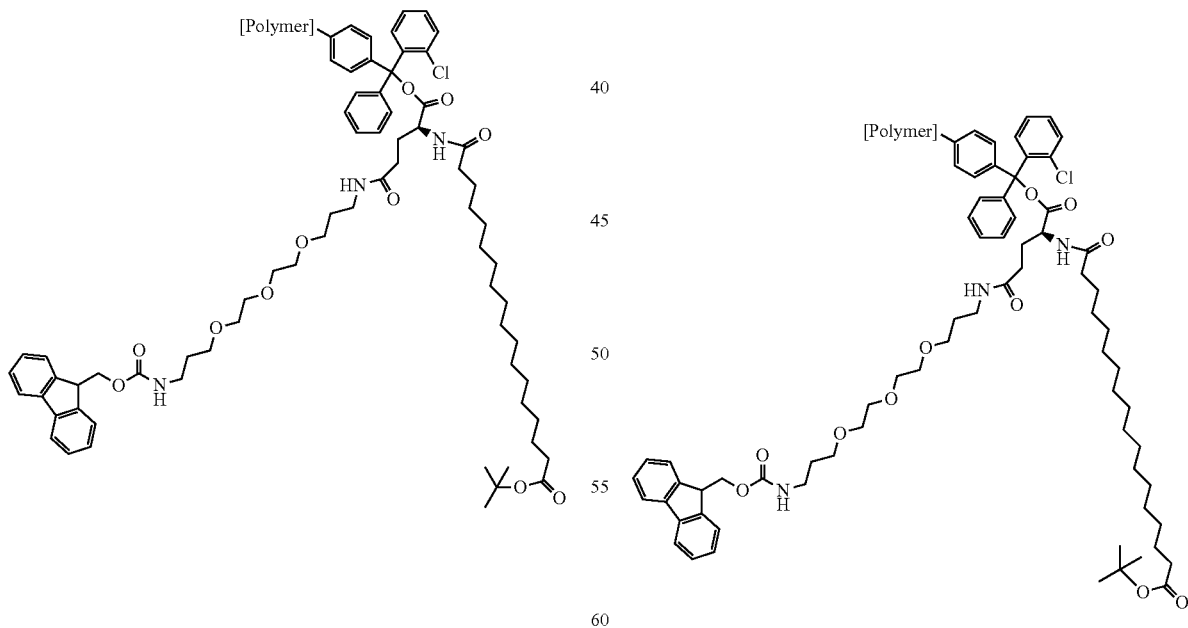

Modified 2-chlorotrityl chloride resin N was made following an identical procedure to Modified 2-chlorotrityl resin M.

Modified 2-chlorotrityl chloride resin P was made following an identical procedure to Modified 2-chlorotrityl resin M.

Preparation of Modified 2-chlorotrityl chloride resin Q

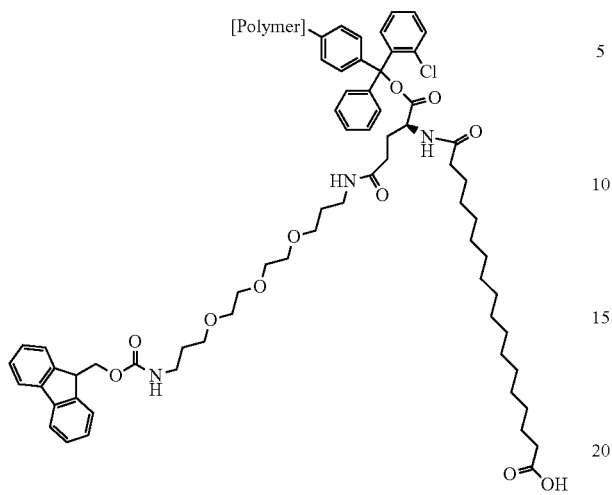

Modified 2-chlorotrityl chloride resin Q was made following an identical procedure to Modified 2-chlorotrityl resin M.

Preparation of Modified 2-chlorotrityl chloride resin R

To a peptide vessel was added 5-((((9H-fluoren-9-yl)methoxy)carbonyl)amino)pentanoic acid (0.118 g, 0.348 mmol), Chlorotrityl resin (0.795 g, 1.113 mmol), N-ethyl-N-isopropylpropan-2-amine (0.424 mL, 2.434 mmol), and $CH_2Cl_2$ (6 mL). The vessel was sealed and shaken on a wrist action shaker overnight. The next day the reaction was terminated by adding 3 ml methanol and shaking the flask for an additional 2 hr. The resin was then filtered and washed with $CH_2Cl_2$, DMF 3×, $CH_2Cl_2$ 3× and finally diethyl ether. The resin was dried in vacuo and used as is, the assumed loading of 0.44 meq/g was used for preparation of the desired peptides.

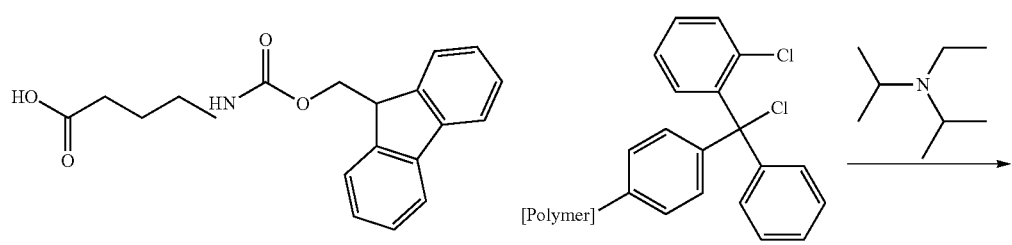

Resin = 2-Chlorotrityl chloride resin from Novabiochem; 1.42 mmol/g loading
1% DVB, 100-200 mesh

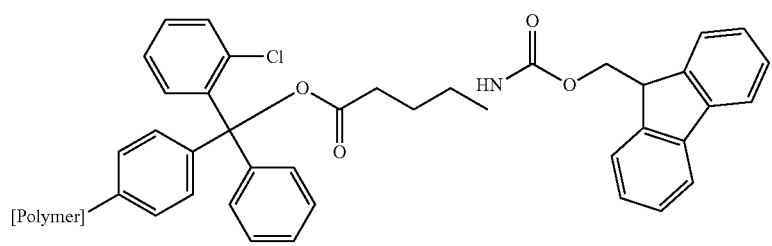

393
Preparation of Example 11137

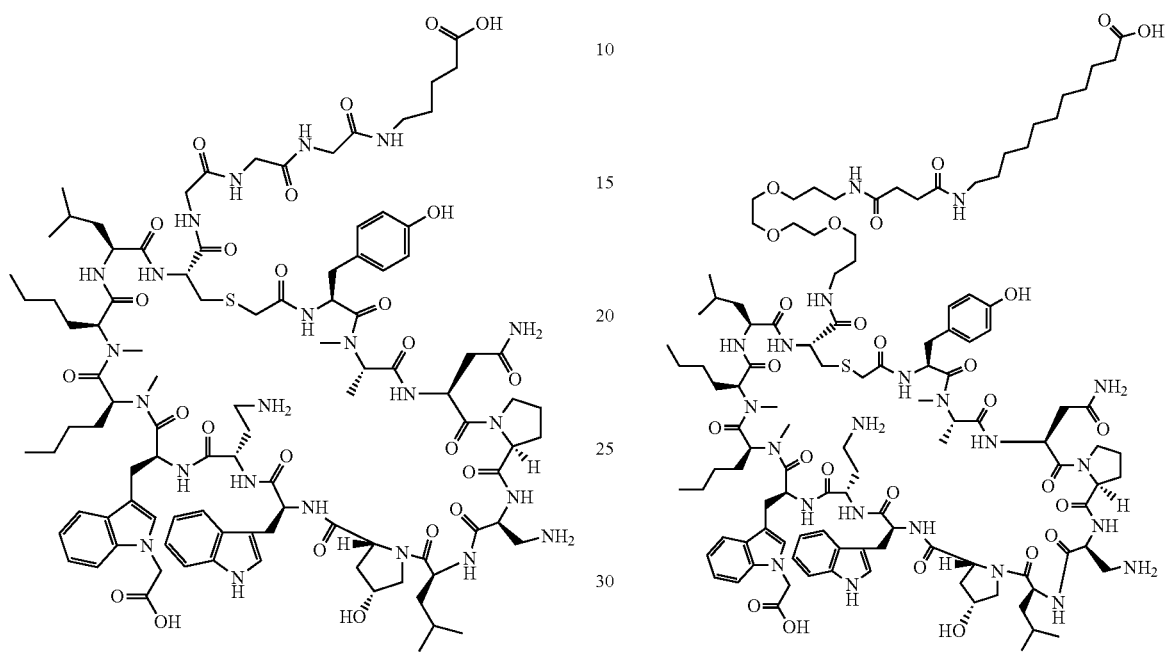

Example 11137 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin R was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 16 mg, and its estimated purity by LCMS analysis was 92.2%. Analysis LCMS Condition A: Retention time=4.120 min.

394
Preparation of Example 11138

Example 11138 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 7 mg, and its estimated purity by LCMS analysis was 95.1%. Analysis LCMS Condition A: Retention time=4.641 min; ESI-MS(+) m/z 1159.1391 (M+2H).

Preparation of Example 11139

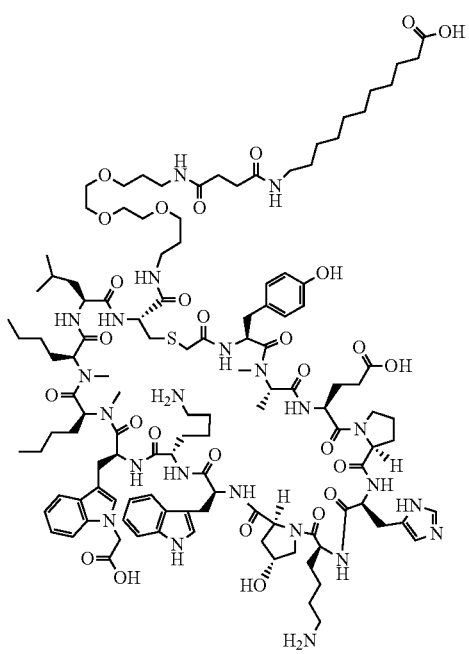 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCC(=O)O)CSCC(=O)N[C@@H](Cc2ccc(O)cc2)C(=O)N(C)[C@@H](C)C(=O)N[C@@H](CCC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11139 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 100%. Analysis LCMS Condition A: Retention time=4.286 min; ESI-MS(+) m/z 1213.6656 (M+2H).

Preparation of Example 11140

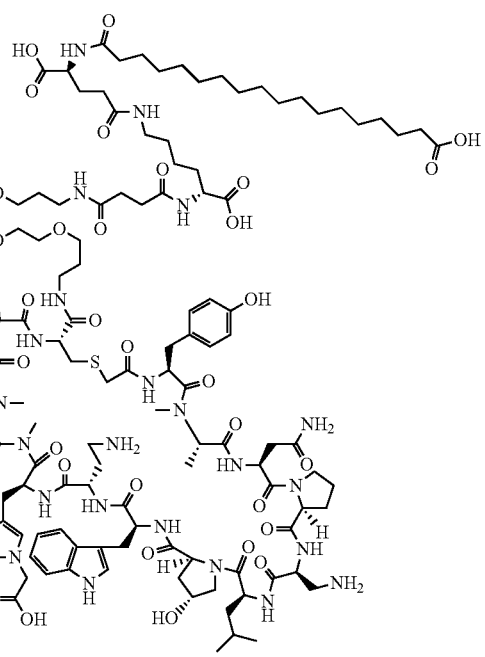

Example 11140 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin G was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 97.3%. Analysis LCMS Condition A: Retention time=4.435 min.

Preparation of Modified 2-chlorotrityl chloride resin
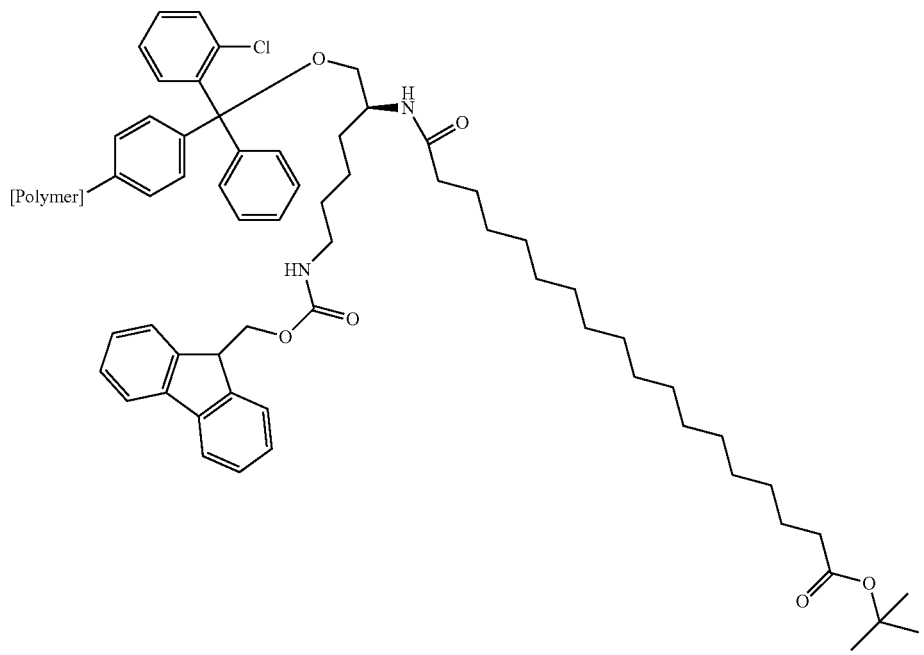
Step 1
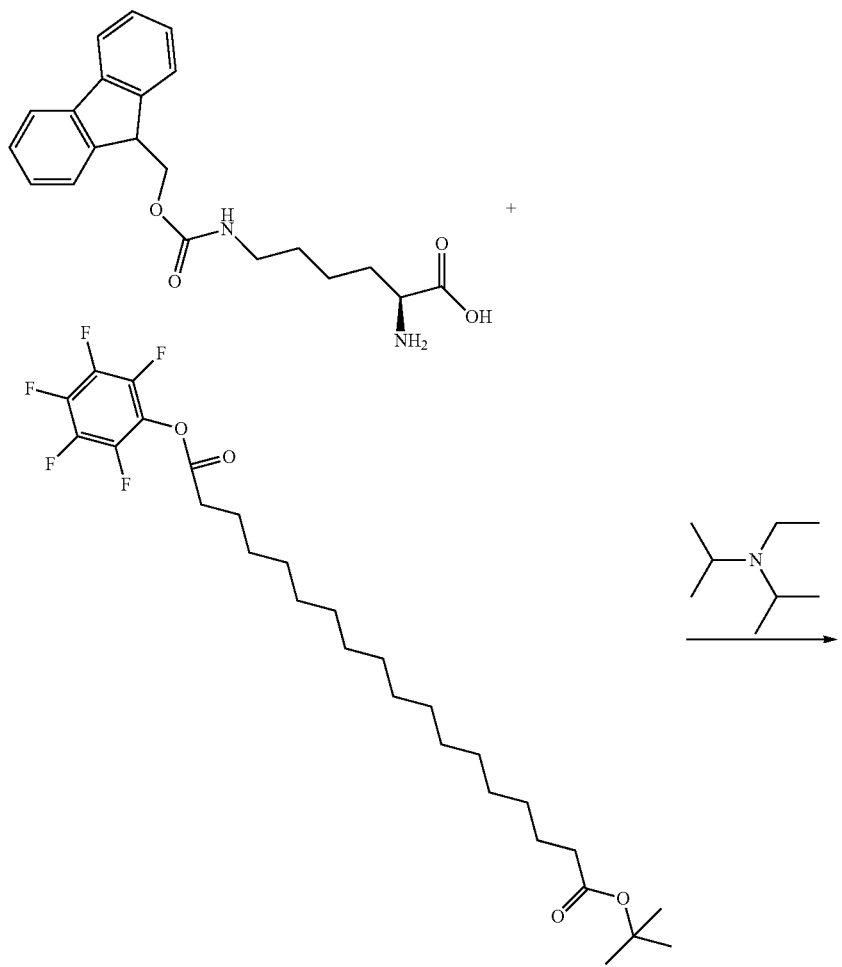

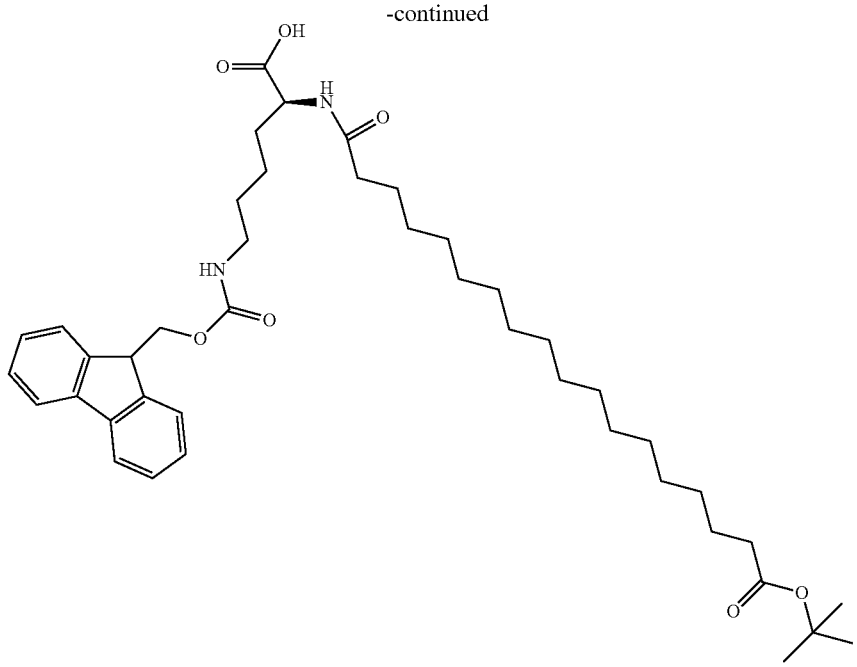

To a 50 ml round bottom flask was added H-LYS (FMOC)-OH (367 mg, 0.996 mmol), N,N-Dimethylformamide (8 mL), 1-tert-butyl 18-(perfluorophenyl)octadecanedioate (641 mg, 1.195 mmol), and Hunig's Base (0.522 mL, 2.99 mmol). The flask was sealed with a septum and kept under a blanket of nitrogen and stirred overnight at rt. The next day the reaction was poured into a saturated citric acid solution and extracted with $CH_2Cl_2$ 3×. The organic layers were combined and washed with brine, dried over Na2SO4 and evaporated in vacuo. The crude product was purified on silica gel chromatography eluting with 100% $CH_2Cl_2$ then 5% MeOH in 95% $CH_2Cl_2$. The pure fractions were combined and evaporated in vacuo affording (S)-6-((((9H-fluoren-9-yl)methoxy)carbonyl)amino)-2-(18-(tert-butoxy)-18-oxooctadecanamido)hexanoic acid (332 mg, 0.460 mmol, 46.2% yield). $^1H$ NMR (400 MHz, CHLOROFORM-d) δ 7.79 (d, J=7.5 Hz, 2H), 7.60 (d, J=7.3 Hz, 2H), 7.47-7.38 (m, 2H), 7.37-7.30 (m, 2H), 6.44 (m, 1H), 5.00 (t, J=6.3 Hz, 1H), 4.60-4.50 (m, 1H), 4.50-4.33 (m, 2H), 4.30-4.14 (m, 1H), 3.22 (m, 2H), 2.42-2.33 (m, 1H), 2.22 (t, J=7.5 Hz, 4H), 1.94 (br. s., 1H), 1.80 (m, 1H), 1.71-1.51 (m, 6H), 1.48-1.45 (m, 9H), 1.38-1.12 (m, 24H).

Step 2

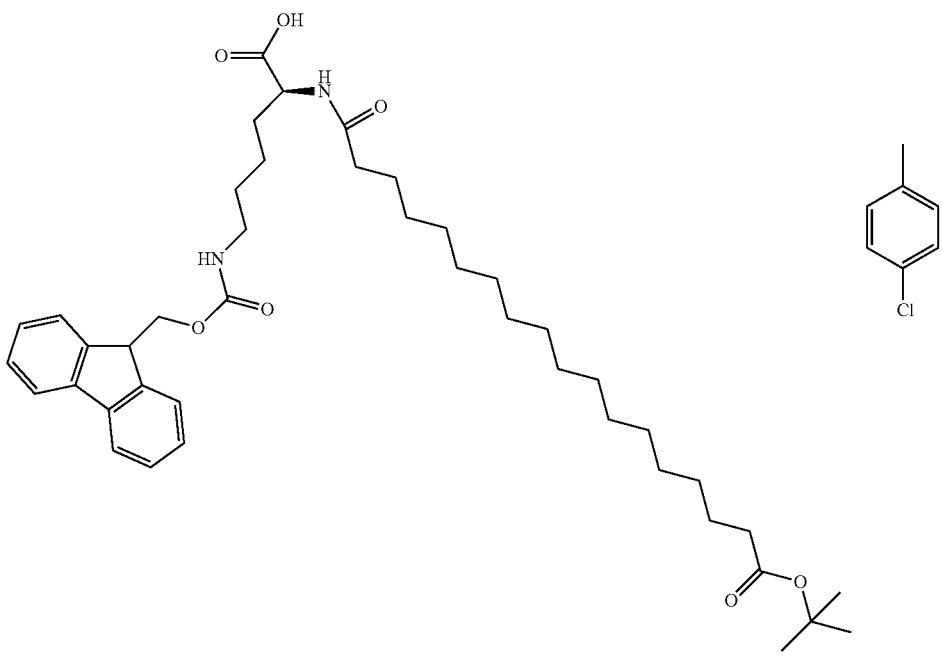

-continued

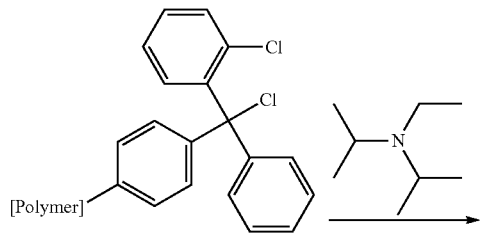

Resin = 2-Chlorotrityl
chloride resin from
Navabiochem; 1.6
mmol/g loading
1% DVB, 100-200 mesh

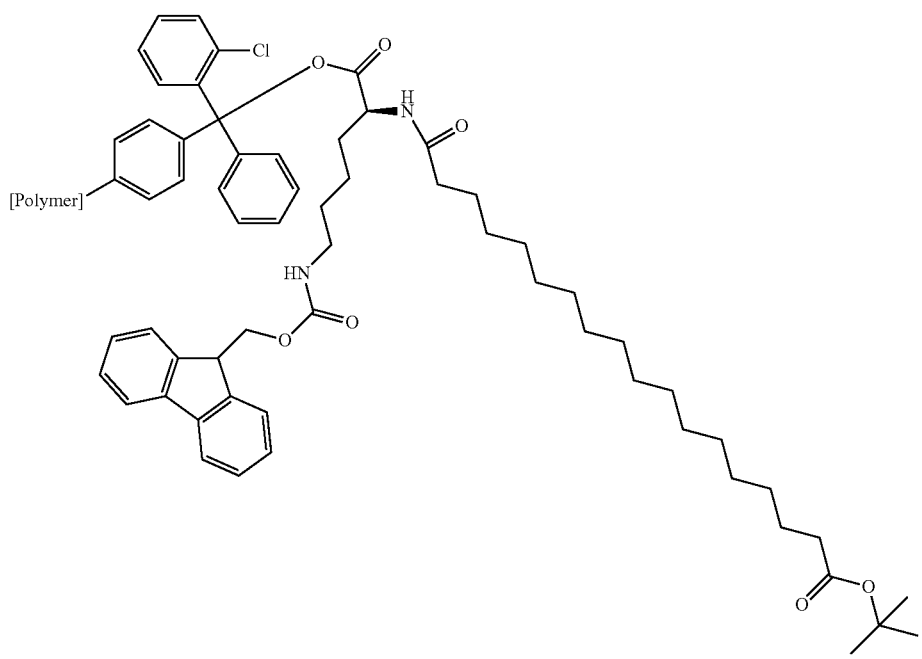

To a peptide vessel was added Chlorotrityl resin (921 mg, 1.474 mmol), (S)-6-((((9H-fluoren-9-yl)methoxy)carbonyl) amino)-2-(18-(tert-butoxy)-18-oxooctadecanamido) hexanoic acid (332 mg, 0.460 mmol), CH$_2$Cl$_2$ (10 mL), 1-chloro-4-methylbenzene (17.49 mg, 0.138 mmol), and N-ethyl-N-isopropylpropan-2-amine (0.561 mL, 3.22 mmol). The vessel was sealed and shaken on a wrist action shaker for 30 min. The reaction was complete by analyzing the LC/MS and comparing the ratio of the internal standard 1-chloro-4-methylbenzene (17.49 mg, 0.138 mmol) vs. starting acid. The resin was then diluted with 20 ml of a 9:1 Methanol/Hunigs base solution and quickly filtered and washed with DMF 3×, CH$_2$Cl$_2$ 2× and finally diethyl ether. The resin was dried in vacuo and was used as is with an assumed loading of 0.5 meq/g for the synthesis of the desired proteins.

Preparation of Example 11141

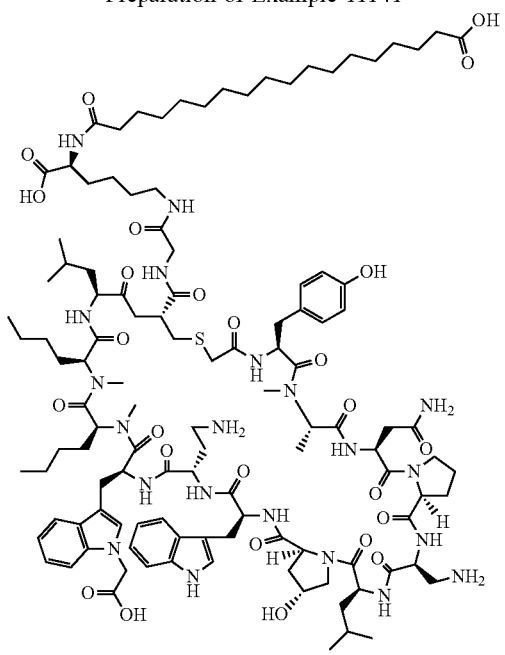

Example 11141 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 12 mg, and its estimated purity by LCMS analysis was 95.9%. Analysis LCMS Condition A: Retention time=5.230 min; ESI-MS(+) m/z 1157.1375 (M+2H).

Preparation of Example 11142

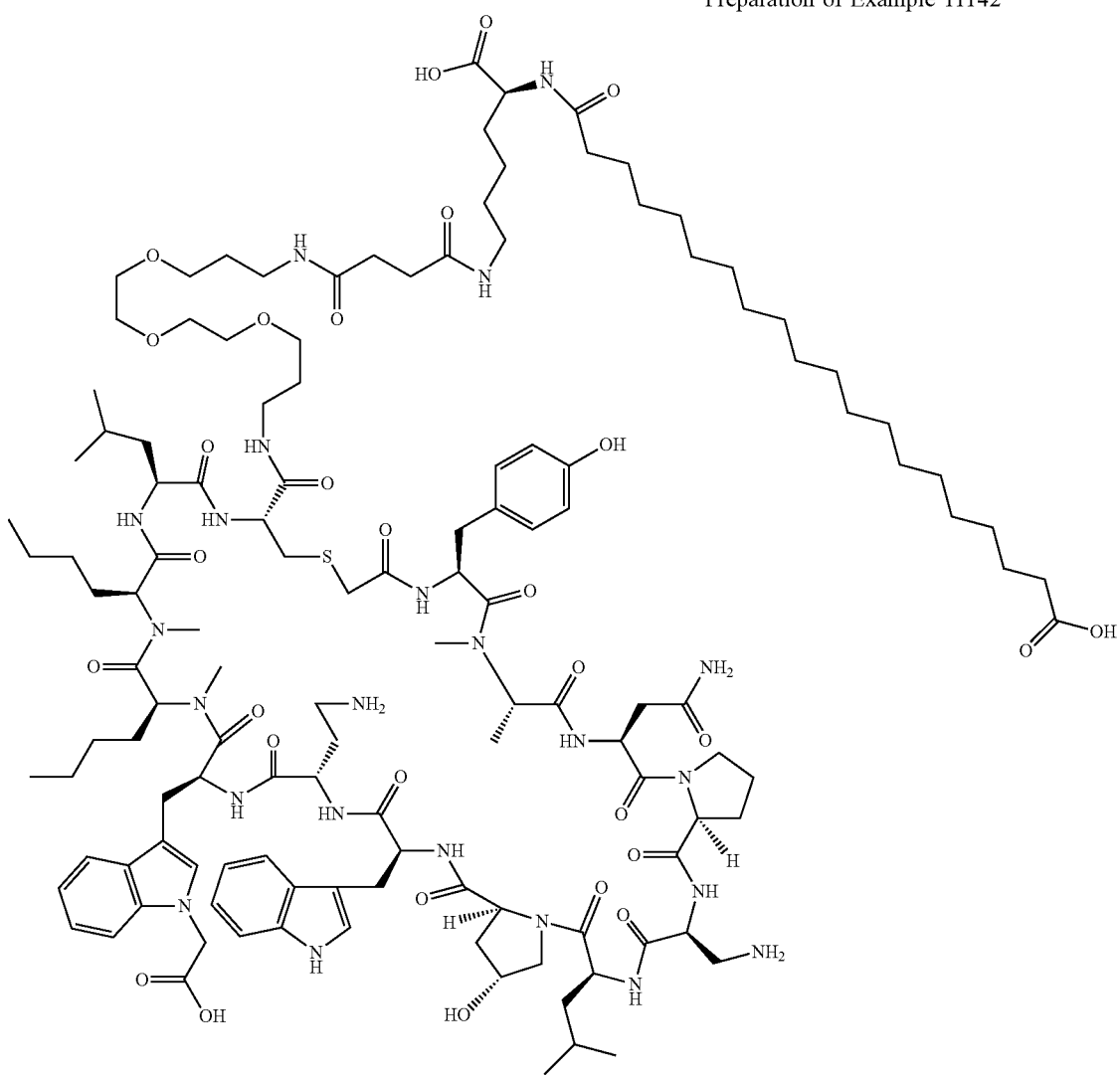

Example 11142 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 9 mg, and its estimated purity by LCMS analysis was 97.6%. Analysis LCMS Condition A: Retention time=4.743 min; ESI-MS(+) m/z 1279.7212 (M+2H).

Preparation of Example 11143

Example 11143 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 3 mg, and its estimated purity by LCMS analysis was 100%. Analysis LCMS Condition A: Retention time=4.895 min; ESI-MS(+) m/z 1128.6300 (M+2H).

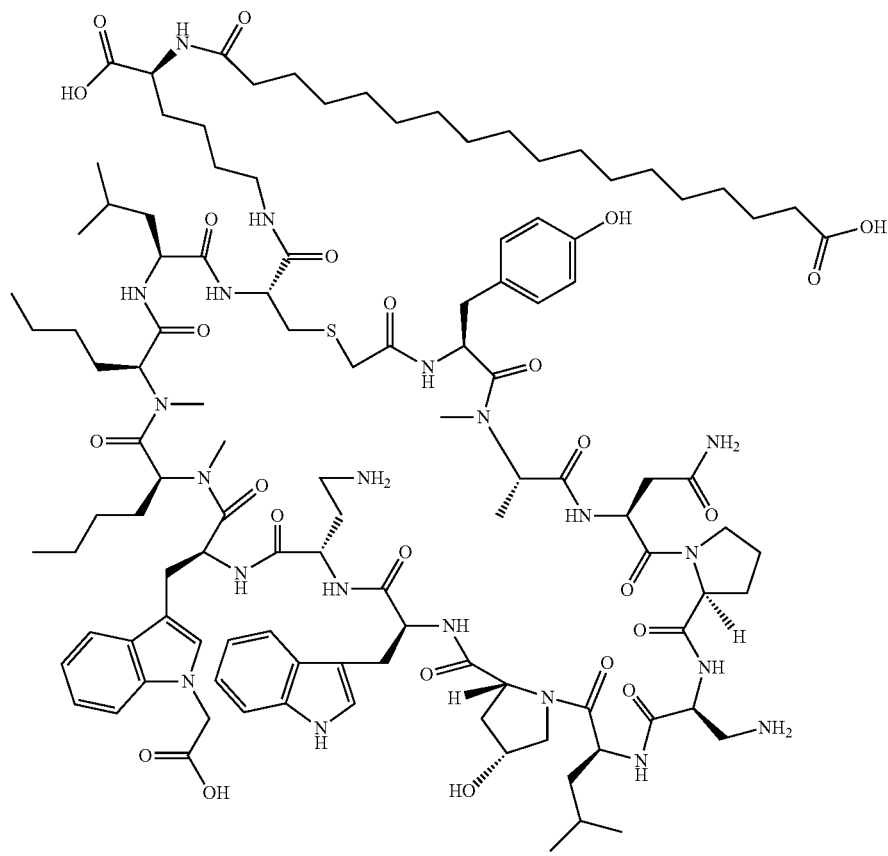 [SMILES: CCCC[C@H]1C(=O)N(C)[C@@H](CCCC)C(=O)N[C@@H](CC(C)C)C(=O)N[C@H](C(=O)NCCCC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

407
Preparation of Example 11144

408
Preparation of Example 11145

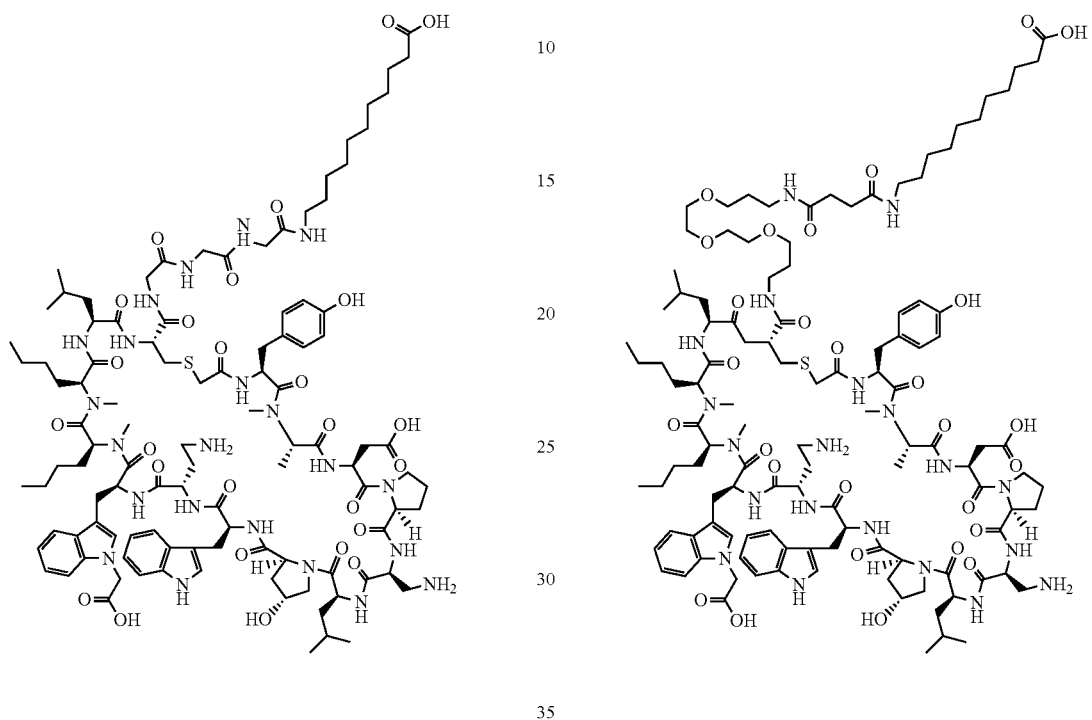

Example 11139 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 100%. Analysis LCMS Condition A: Retention time=4.286 min; ESI-MS(+) m/z 1213.6656 (M+2H).

Example 11145 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 13 mg, and its estimated purity by LCMS analysis was 100%. Analysis LCMS Condition A: Retention time=3.505 min; ESI-MS(+) m/z 1167.6096 (M+2H).

Preparation of Example 11146

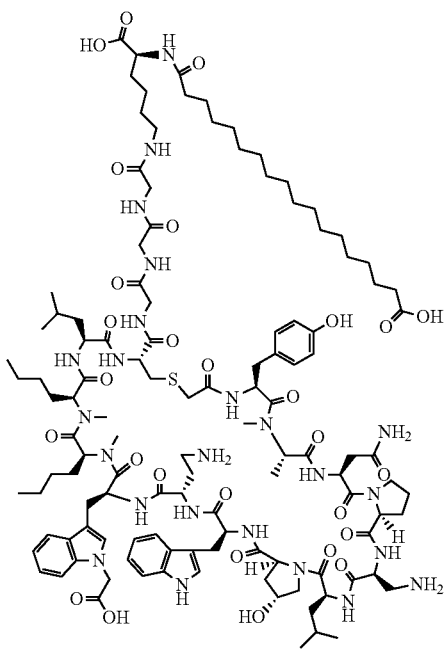 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11146 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 100%. Analysis LCMS Condition A: Retention time=4.691 min; ESI-MS(+) m/z 1214.1614 (M+2H).

Preparation of Example 11147

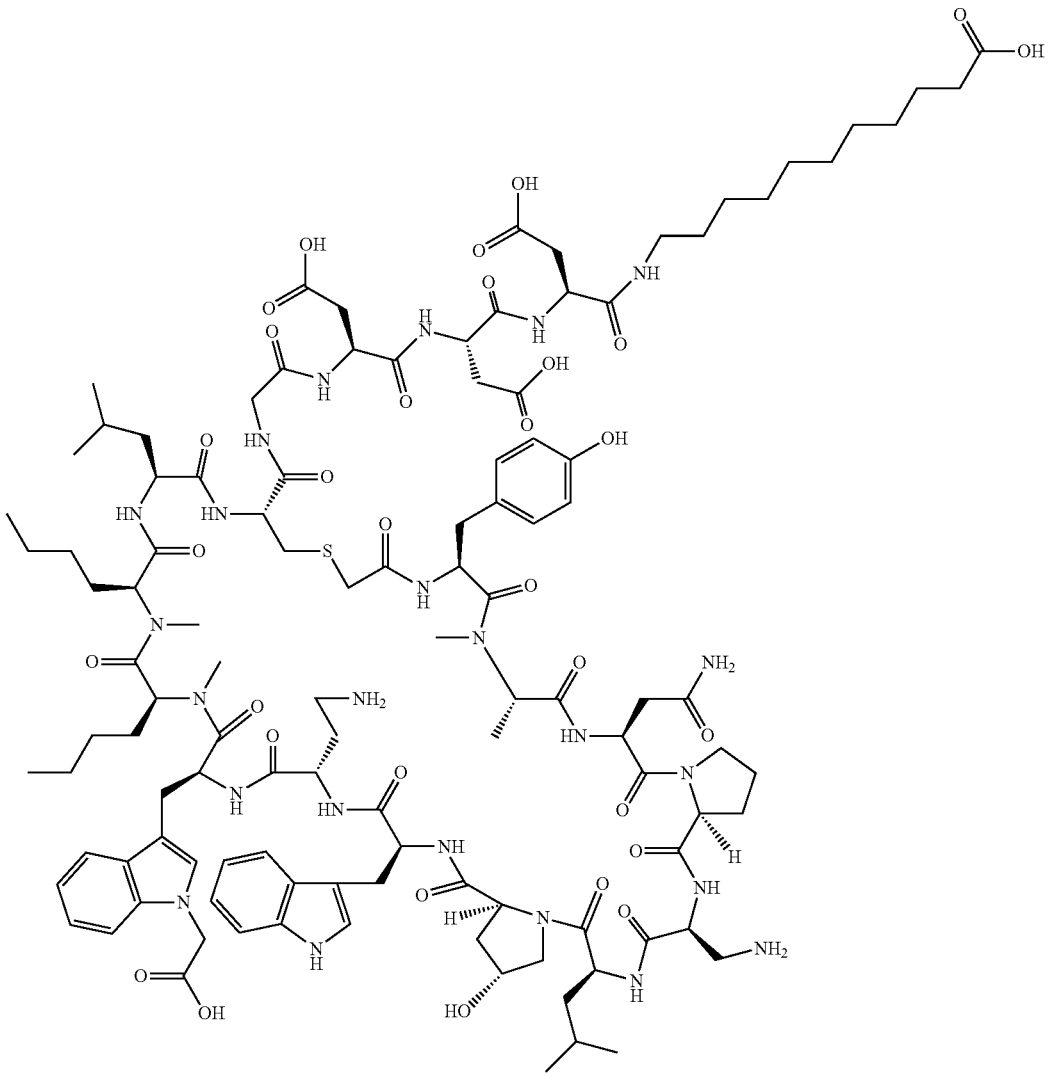 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)O)C(=O)N[C@@H](CC(=O)O)C(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11147 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 24 mg, and its estimated purity by LCMS analysis was 89.3%. Analysis LCMS Condition A: Retention time=3.501 min; ESI-MS(+) m/z 1209.0971 (M+2H).

Preparation of Example 11148

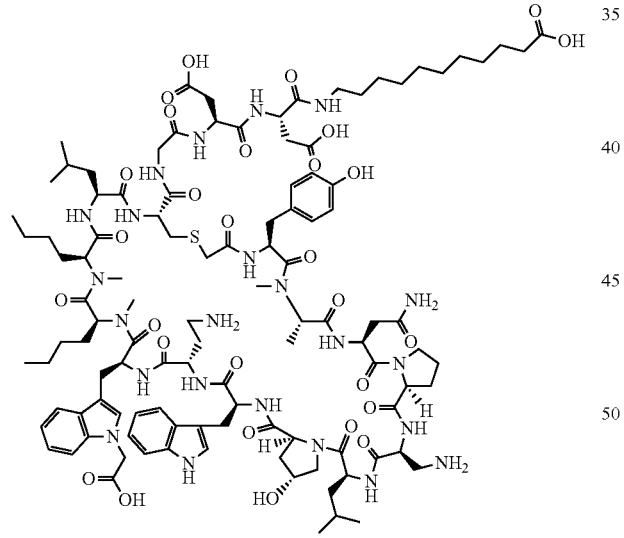

Example 11148 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 14 mg, and its estimated purity by LCMS analysis was 100%. Analysis LCMS Condition A: Retention time=3.696 min; ESI-MS(+) m/z 1151.5832 (M+2H).

Preparation of Example 11149

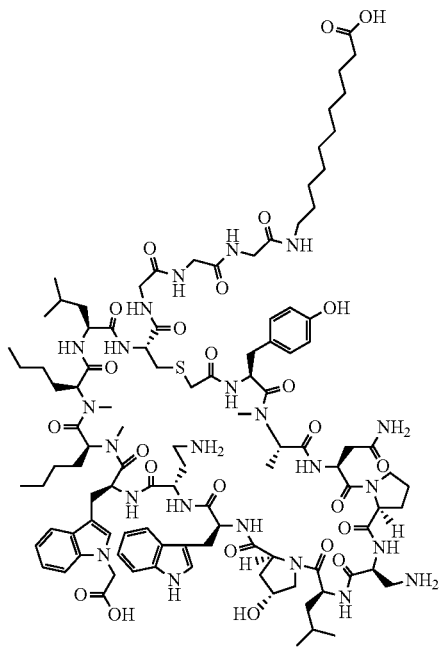 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11149 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 18 mg, and its estimated purity by LCMS analysis was 92.1%. Analysis LCMS Condition A: Retention time=3.865 min; ESI-MS(+) m/z 1051.5311 (M+2H).

Preparation of Example 11150

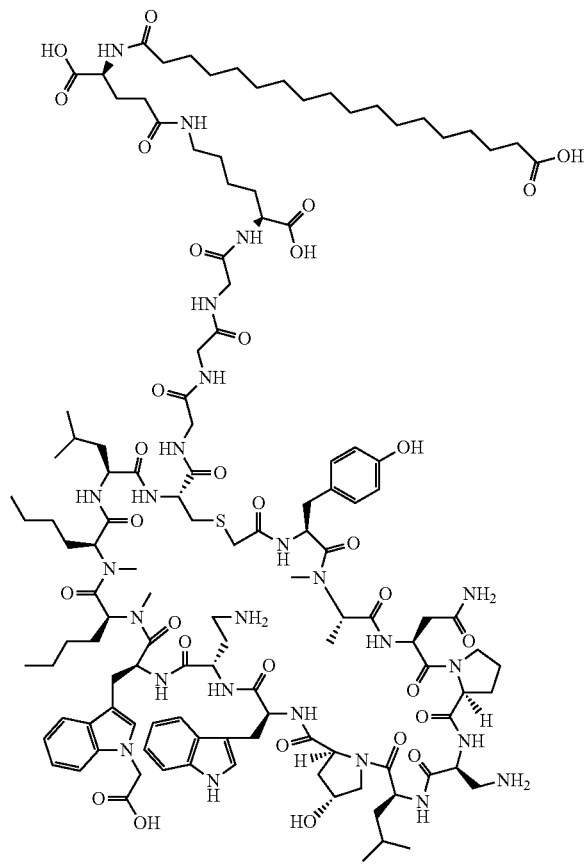 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)N[C@@H](CCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11150 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin G was used in this synthesis. The crude material was purified via preparative LC/MS with the following conditions: The crude material was purified via preparative LC with the following conditions: Column: XSelect CSH Prep C18, 5-µm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 100%. Analysis LCMS Condition A: Retention time=4.425 min; ESI-MS(+) m/z 1278.6850 (M+2H).

Preparation of Example 11151

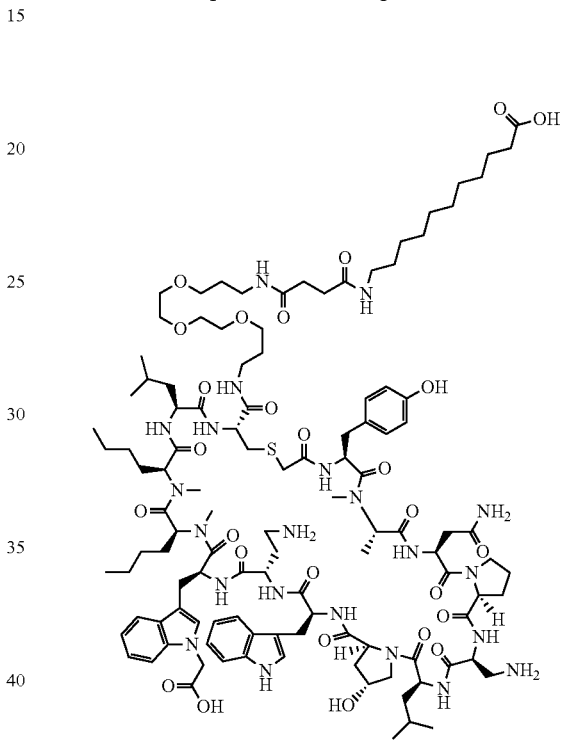

Example 11151 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-µm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 11 mg, and its estimated purity by LCMS analysis was 98.8%. Analysis LCMS Condition A: Retention time=4.235 min; ESI-MS(+) m/z 1167.1178 (M+2H).

Preparation of Example 11152

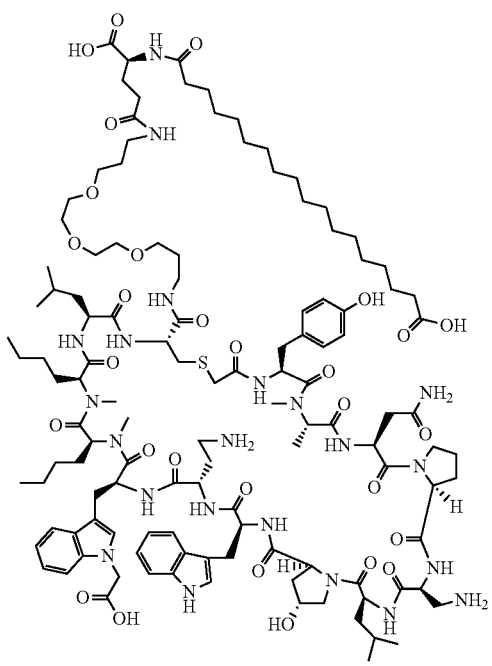 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11152 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 7 mg, and its estimated purity by LCMS analysis was 96.9%. Analysis LCMS Condition A: Retention time=4.945 min; ESI-MS(+) m/z 1230.1853 (M+2H).

Preparation of Modified 2-chlorotrityl chloride resin T

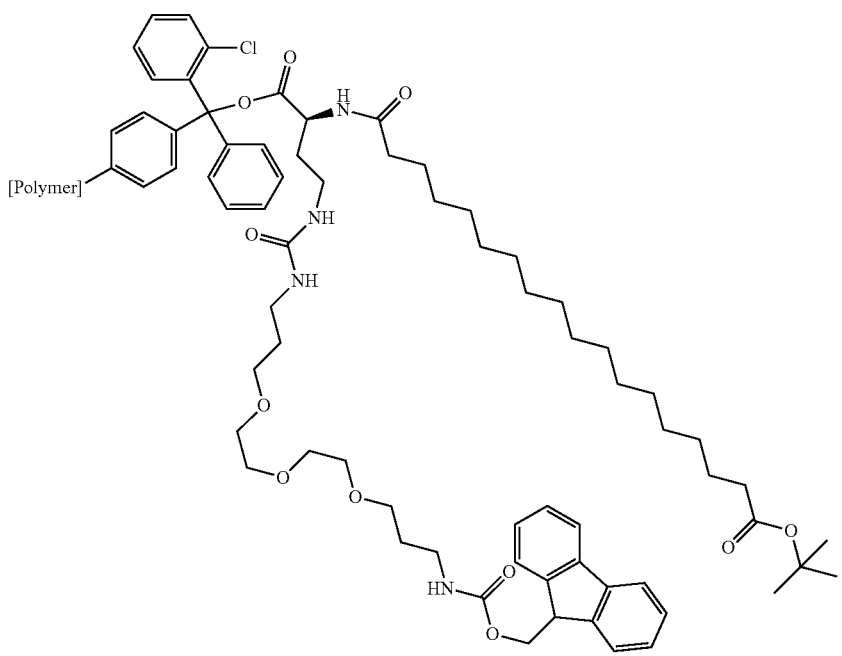

Step 1

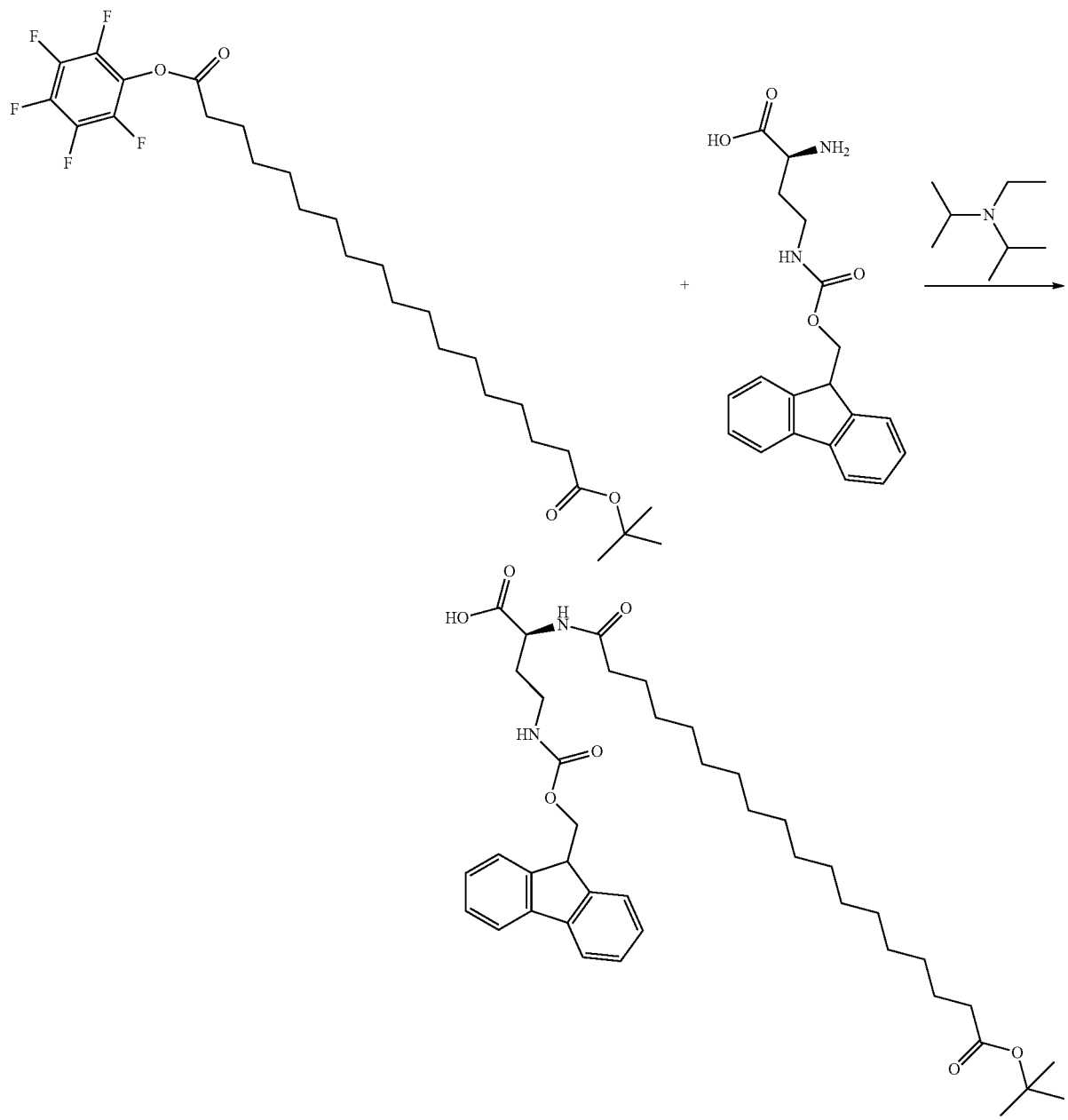

To a 50 ml round bottom flask was added (S)-4-((((9H-fluoren-9-yl)methoxy)carbonyl)amino)-2-aminobutanoic acid (200 mg, 0.588 mmol), N,N-dimethylformamide (5 mL), 1-tert-butyl 18-(perfluorophenyl)octadecanedioate (347 mg, 0.646 mmol), and Hunig's Base (0.308 mL, 1.763 mmol). The flask was sealed with a septum and kept under a blanket of nitrogen and stirred overnight at rt. The next day the reaction was poured into a saturated citric acid solution and extracted with $CH_2Cl_2$ 3×. The organic layers were combined and washed with brine, dried over Na2SO4 and evaporated in vacuo. The crude product was purified on silica gel chromatography eluting with 100% $CH_2Cl_2$ then 5% MeOH in 95% $CH_2Cl_2$. The pure fractions were combined and evaporated in vacuo affording (S)-4-((((9H-fluoren-9-yl)methoxy)carbonyl)amino)-2-(18-(tert-butoxy)-18-oxooctadecanamido)butanoic acid (67 mg, 0.097 mmol, 16.46% yield). Column: X-Bridge C18, 2.0×50 mm, 3.5-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 5 minutes, then a 1.0-minute hold at 100% B; Flow: 0.8 mL/min; Detection: UV at 220 nm. Retention time=3.866 min; ESI-MS(−) m/z 691.6 (M−H).

Step 2

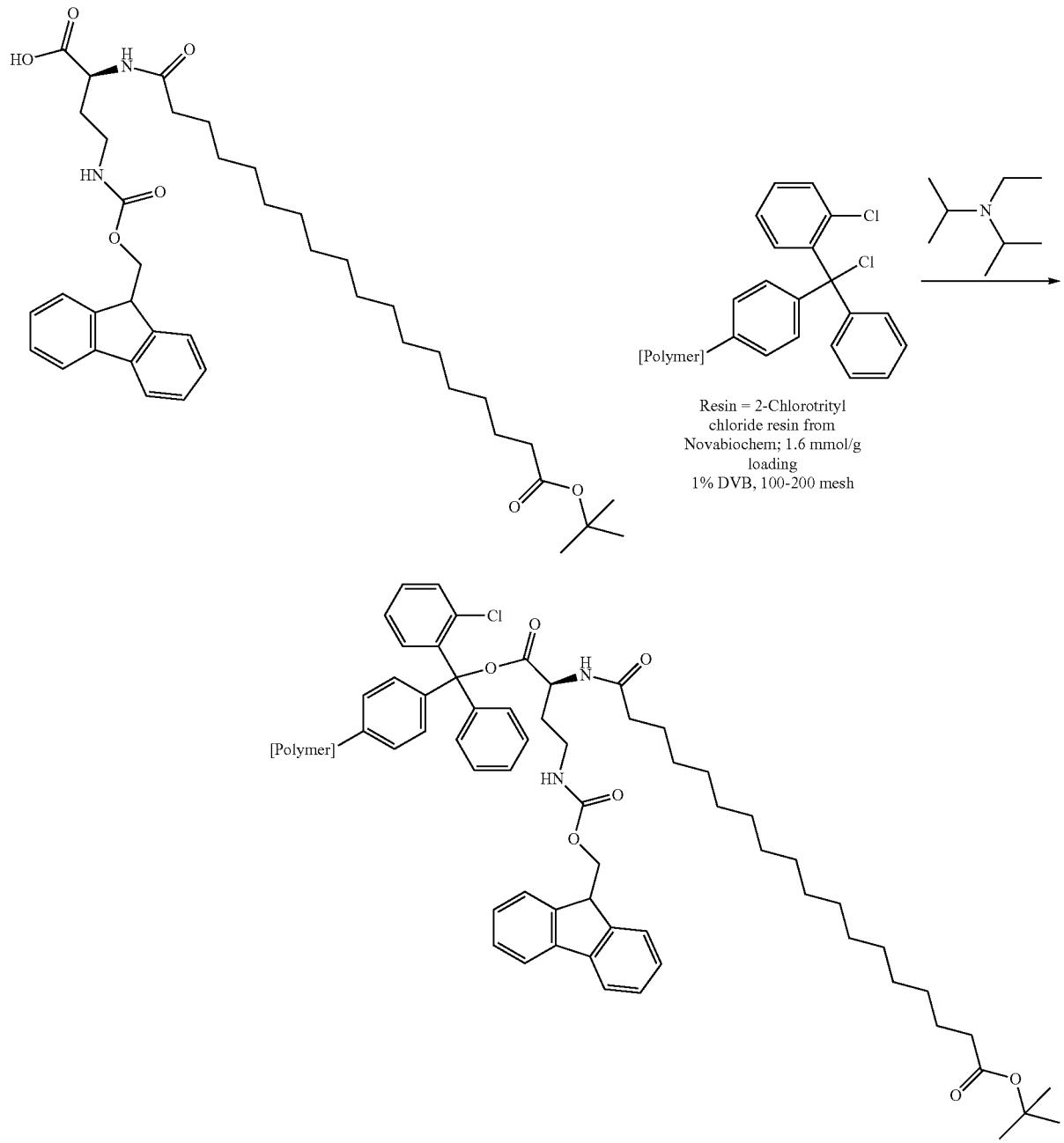

To a 20 ml scintillation vial was added (S)-4-((((9H-fluoren-9-yl)methoxy)carbonyl)amino)-2-(18-(tert-butoxy)-18-oxooctadecanamido)butanoic acid (64 mg, 0.092 mmol), Chlorotrityl resin (196 mg, 0.314 mmol), CH$_2$Cl$_2$ (4 mL), and N-ethyl-N-isopropylpropan-2-amine (0.113 mL, 0.647 mmol). The vial was sealed and shaken on a wrist action shaker overnight. The next day the reaction was terminated by adding 3 ml methanol and shaking the flask for an additional 1 hr. The resin was then filtered and washed with CH$_2$Cl$_2$, DMF 3×, CH$_2$Cl$_2$ 3× and finally diethyl ether. The resin was used as is with an assumed loading of 0.5 meq/g for the subsequent synthetic steps.

Step 3

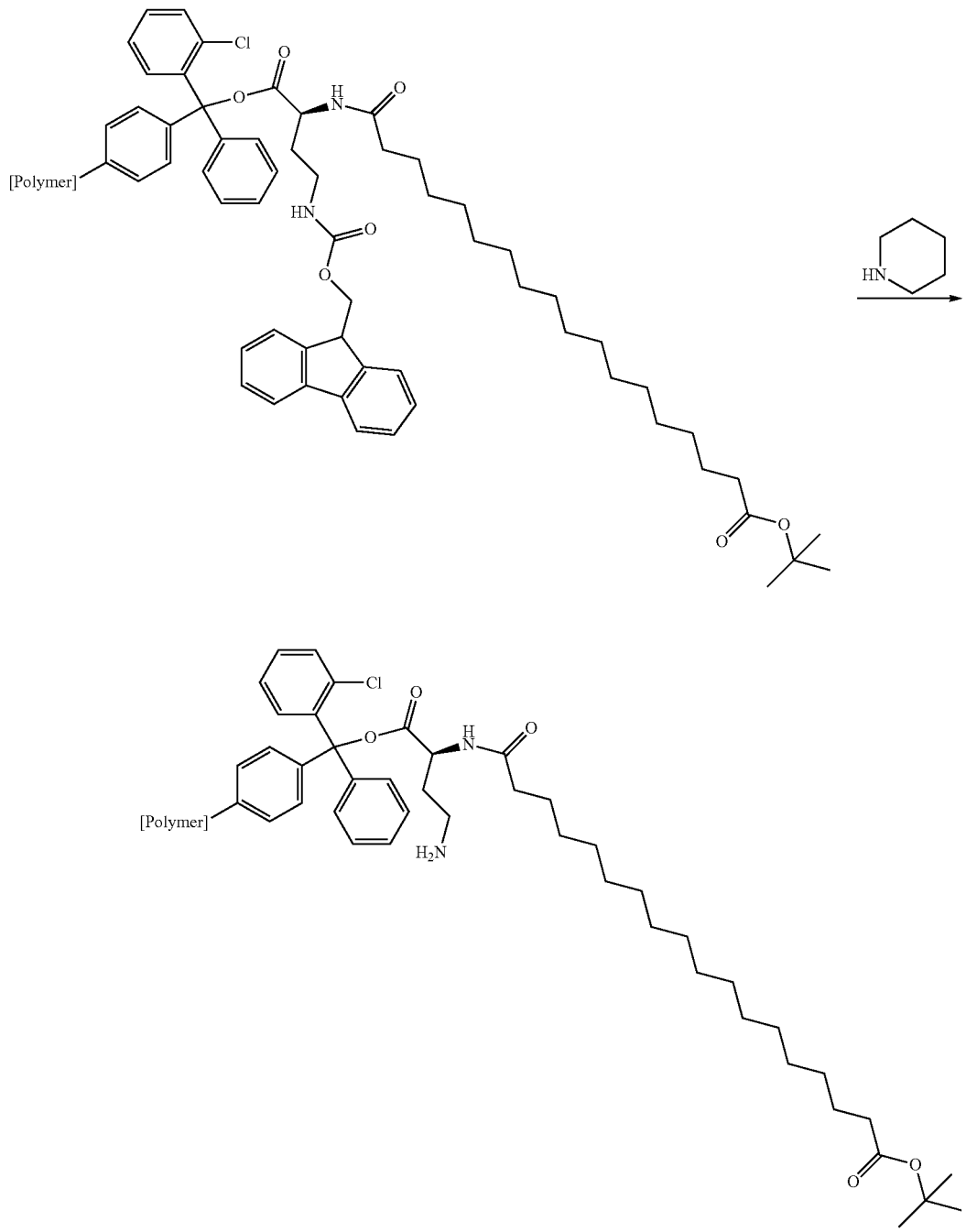

To a peptide vessel was added the indicated resin (0.209 g, 0.092 mmol), DMF (3 mL), PIPERIDINE (0.182 mL, 1.840 mmol) and the vessel was sealed and shaken on a wrist action shaker for 1 h. After 1 hour, the resin was then filtered and washed with $CH_2Cl_2$, DMF 3×, $CH_2Cl_2$ 3× and finally diethyl ether. The resin was dried in vacuo and used as is in the next step. The resin was used as is with an assumed loading of 0.5 meq/g for the subsequent synthetic steps.

Step 4

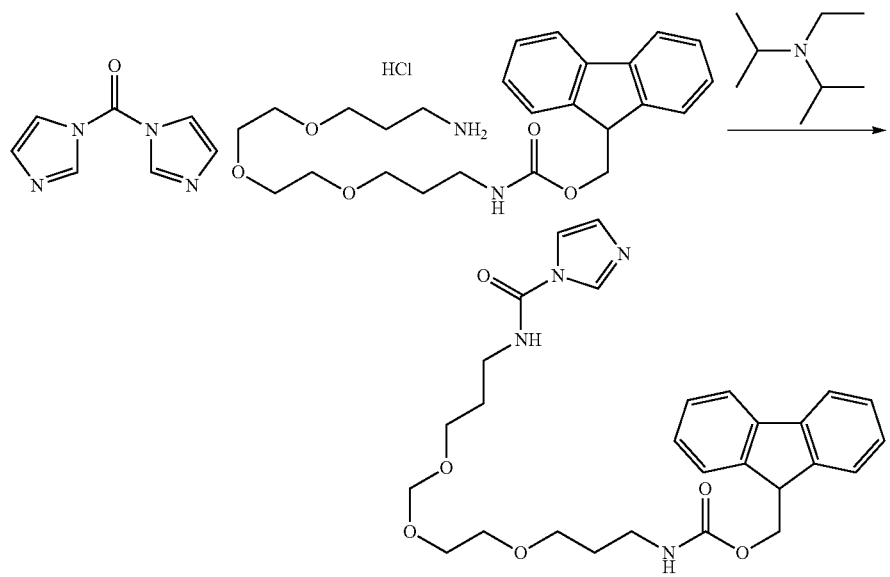

To a 50 ml round bottom flask was added 1-(9-FLUO-RENYLMETHYLOXYCARBONYL-AMINO)-4,7,10-TRIOXA-13-TRIDECANAMINE HYDROCHLORIDE (lg, 2.088 mmol), THF (15 mL), Hunig's Base (0.474 mL, 2.71 mmol), and 1,1'-CARBONYLDIIMIDAZOLE (0.372 g, 2.296 mmol). The solution was stirred under a blanket of nitrogen overnight. The next day the reaction was checked by LC/MS and the reaction was complete. The reaction solvent was evaporated in vacuo and the crude oil was purified by silica gel chromatography eluting with 3%/97% meoH/CH2CL2. The pure fractions were combined and evaporated in vacuo affording (9H-fluoren-9-yl)methyl(1-(1H-imidazol-1-yl)-1-oxo-6,9,12-trioxa-2-azapentadecan-15-yl)carbamate (1.022 g, 1.905 mmol, 91% yield). $^1$H NMR (400 MHz, CHLOROFORM-d) δ 8.18 (s, 1H), 7.78 (d, J=7.5 Hz, 2H), 7.61 (d, J=7.5 Hz, 2H), 7.47 (s, 1H), 7.41 (t, J=7.4 Hz, 2H), 7.32 (td, J=7.5, 0.9 Hz, 2H), 7.21 (br. s., 1H), 7.05 (dd, J=1.5, 0.8 Hz, 1H), 5.57 (br. s., 1H), 4.43 (d, J=7.5 Hz, 2H), 4.30-4.16 (m, 1H), 3.72-3.60 (m, 8H), 3.60-3.53 (m, 4H), 3.49 (t, J=5.3 Hz, 2H), 3.30 (q, J=5.9 Hz, 2H), 1.96-1.85 (m, 2H), 1.80-1.69 (m, 2H). Column: X-Bridge C18, 2.0×50 mm, 3.5-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 4 minutes, then a 1.0-minute hold at 100% B; Flow: 0.8 mL/min; Detection: UV at 220 nm. Retention time=2.538 min; ESI-MS(+) m/z 537.3 (M+H).

Step 5

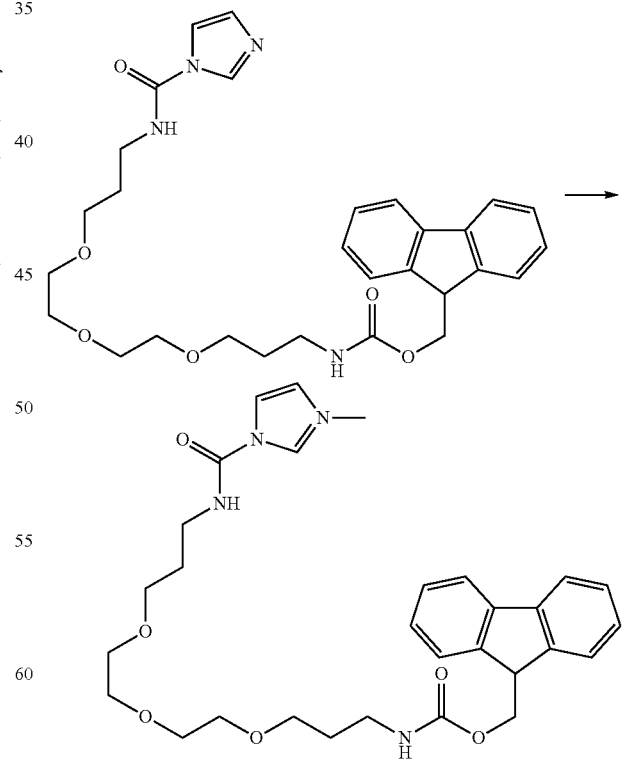

To a 25 ml round bottom flask was added (9H-fluoren-9-yl)methyl(1-(1H-imidazol-1-yl)-1-oxo-6,9,12-trioxa-2- azapentadecan-15-yl)carbamate (400 mg, 0.745 mmol), Acetonitrile (3 mL) and IODOMETHANE (0.093 mL, 1.491 mmol). The reaction was stirred under a blanket of nitrogen overnight. The next day the reaction was checked by LC/MS and was complete. The reaction solvent was evaporated in vacuo and the crude solid was used as is without purification. Column: X-Bridge C18, 2.0×50 mm, 3.5-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 4 minutes, then a 1.0-minute hold at 100% B; Flow: 0.8 mL/min; Detection: UV at 220 nm. Retention time=3.256 min.

Step 6

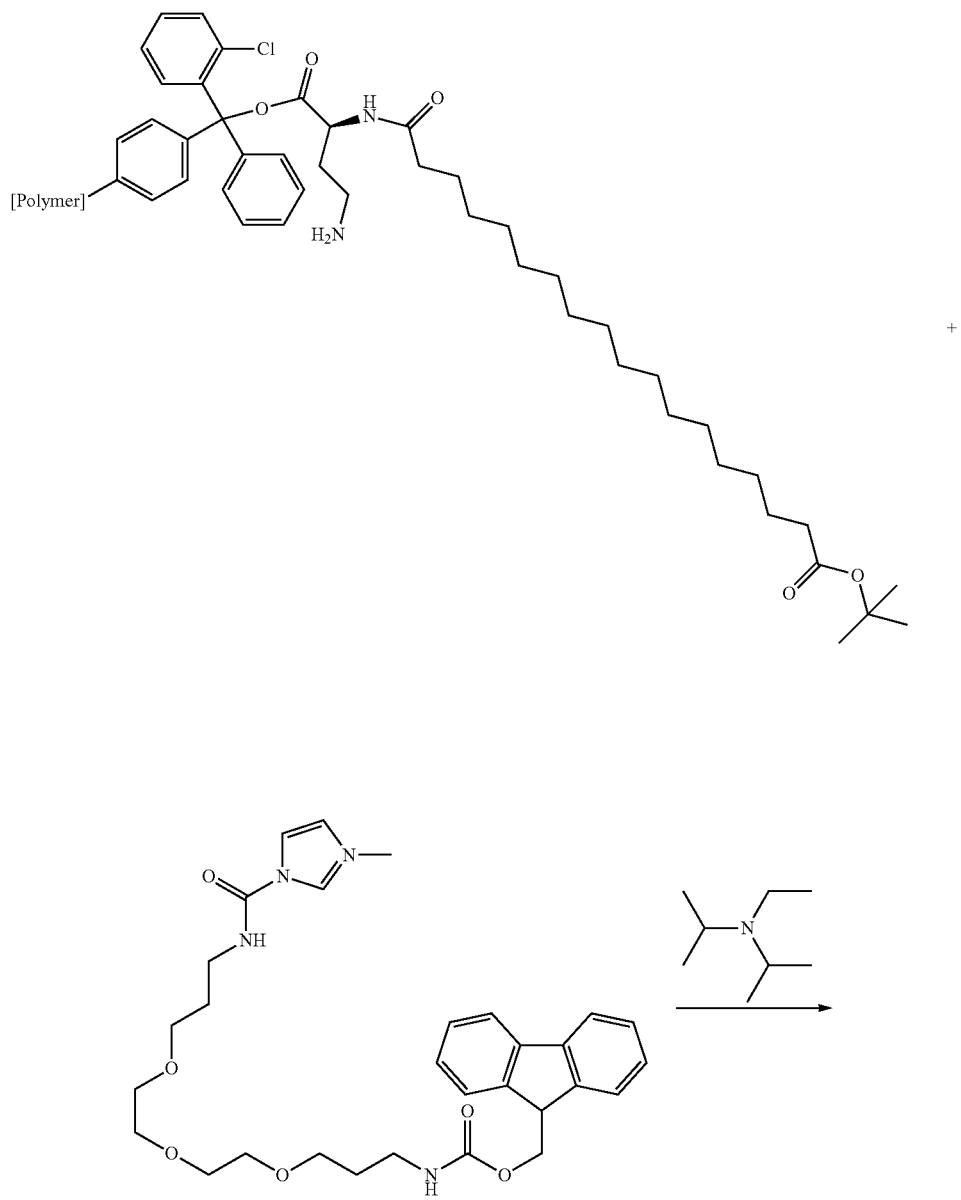

-continued

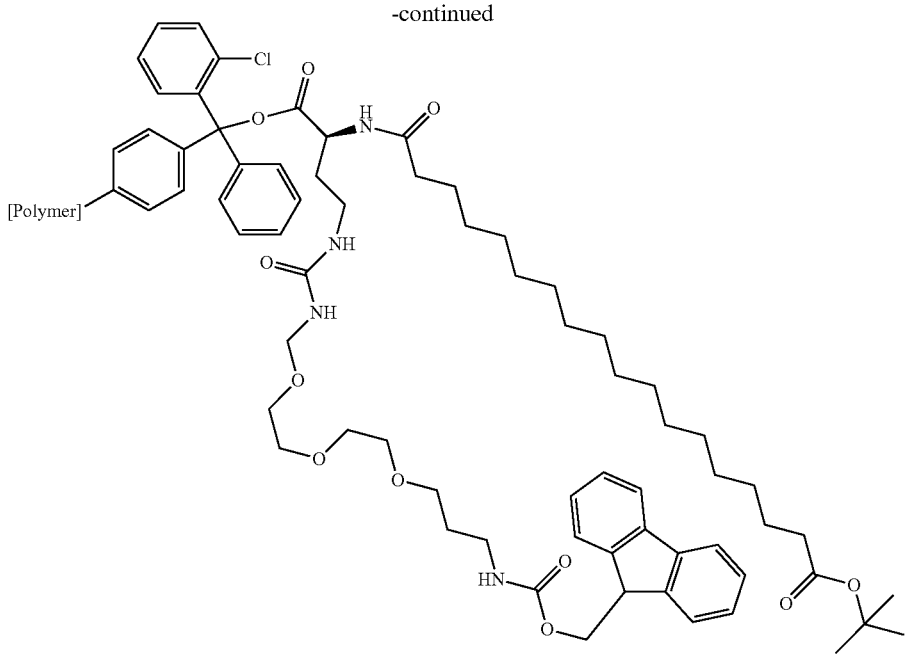

To a peptide vessel was added the above modified chlorotrityl resin (0.069 g, 0.092 mmol), $CH_2Cl_2$ (2 mL), Hunig's Base (0.064 mL, 0.368 mmol) and the Iodomethylimidazolium reagent (0.076 g, 0.138 mmol). The vessel was sealed and shaken on a wrist action shaker overnight. The next day the resin was filtered and washed with $CH_2Cl_2$, DMF 3×, $CH_2Cl_2$ 3× and finally diethyl ether. The resin was dried in vacuo and used as is for peptide synthesis. Assumed loading of 0.44 meq/g.

Preparation of Example 11153

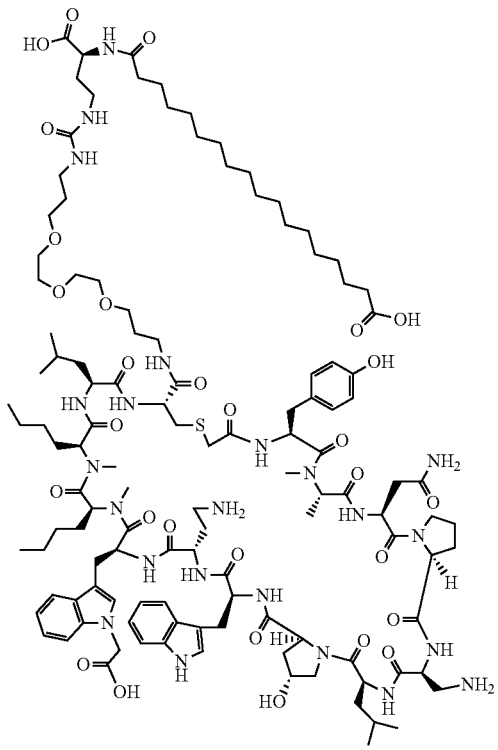 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)NCC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11153 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin T was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 3.6 mg, and its estimated purity by LCMS analysis was 97%. Analysis LCMS Condition A: Retention time=4.848 min; ESI-MS(+) m/z 1237.6914 (M+2H).

Preparation of Example 11154

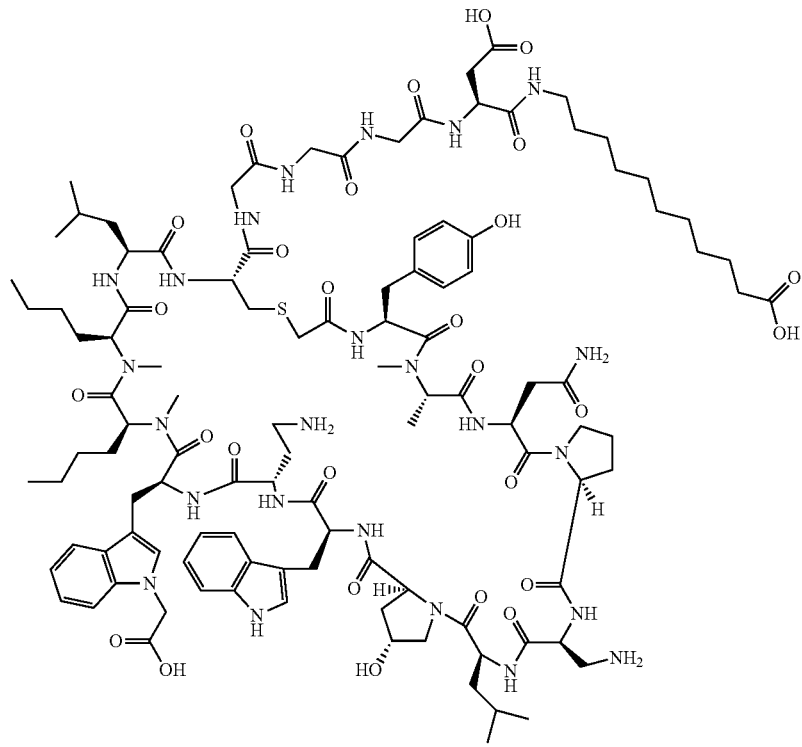 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)N[C@@H](CC(=O)O)C(=O)NCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11154 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin C was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 15 mg, and its estimated purity by LCMS analysis was 97.7%. Analysis LCMS Condition A: Retention time=3.581 min.

431
Preparation of Example 11155

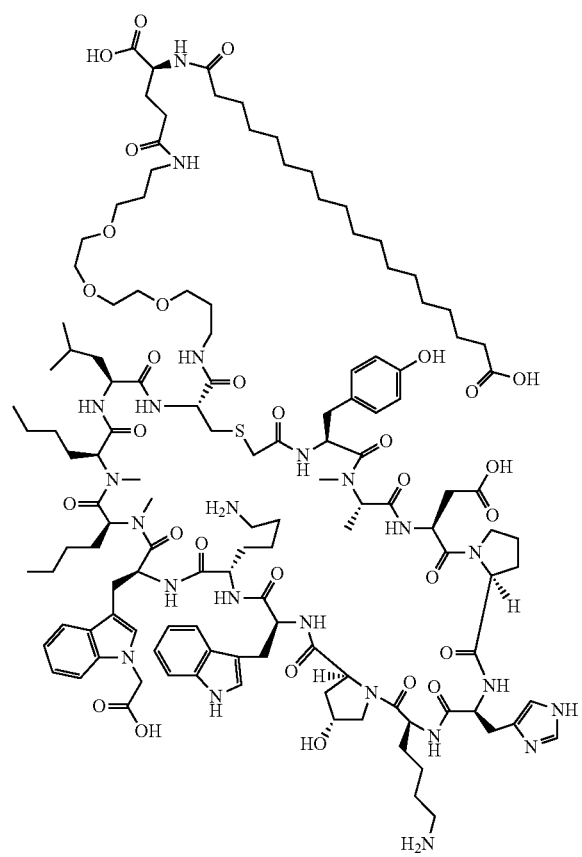 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11155 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 3 mg, and its estimated purity by LCMS analysis was 97.3%. Analysis LCMS Condition A: Retention time=4.100 min; ESI-MS(+) m/z 1277.7061 (M+2H).

432
Preparation of Example 11156

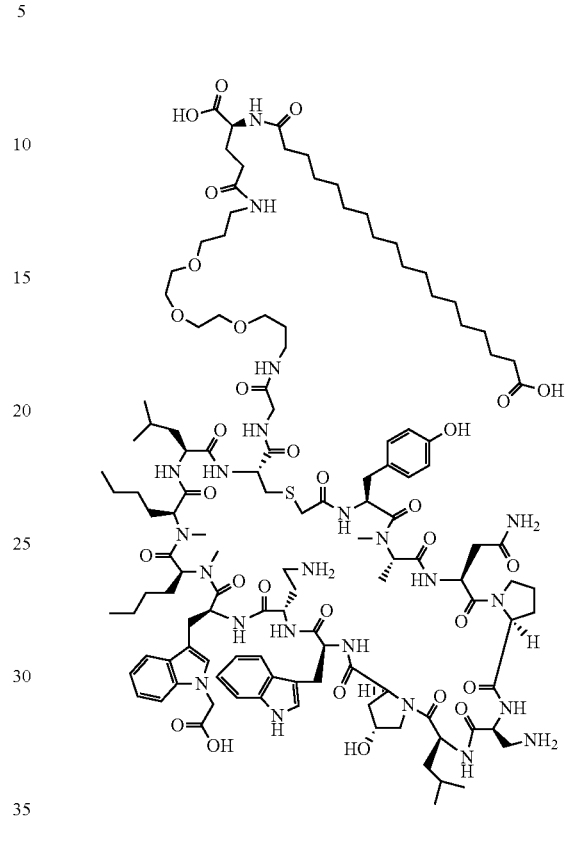

Example 11156 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 16 mg, and its estimated purity by LCMS analysis was 100%. Analysis LCMS Condition A: Retention time=4.335 min; ESI-MS(+) m/z 1258.6989 (M+2H).

Preparation of Modified 2-chlorotrityl chloride resin
U
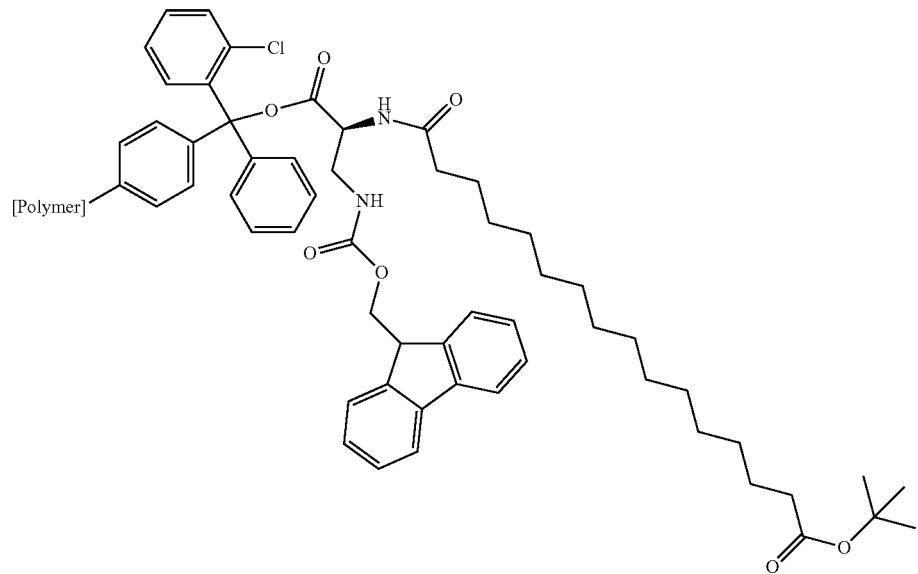
Step 1
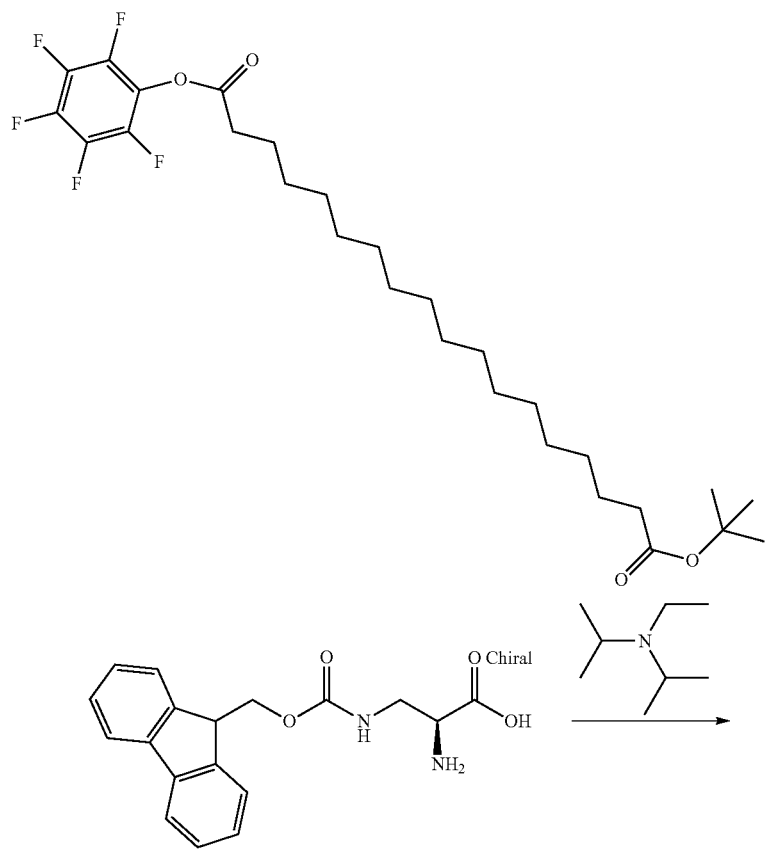

-continued

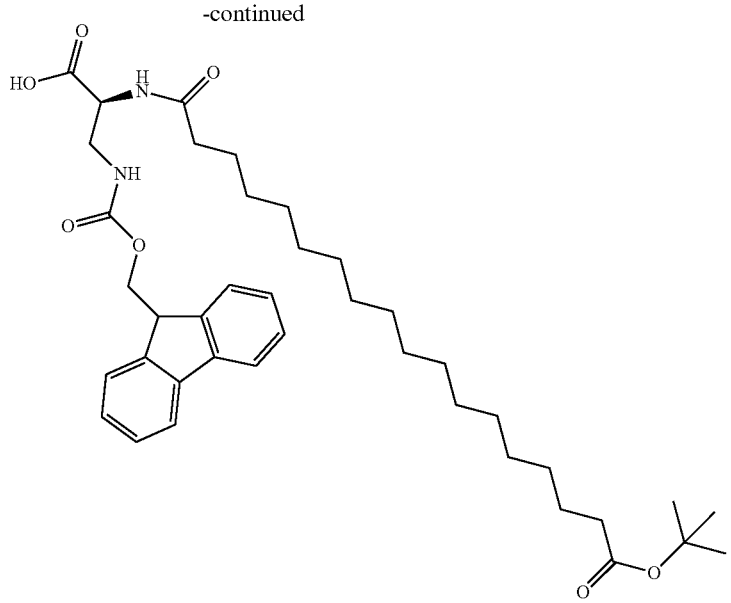

To a 50 ml round bottom flask was added (S)-3-((((9H-fluoren-9-yl)methoxy)carbonyl)amino)-2-aminopropanoic acid, HCl (218 mg, 0.6 mmol), N,N-dimethylformamide (6 mL), 1-tert-butyl 16-(perfluorophenyl) hexadecanedioate (397 mg, 0.780 mmol), and Hunig's Base (0.314 mL, 1.800 mmol). The flask was sealed with a septum and kept under a blanket of nitrogen and stirred overnight at rt. The next day the reaction was poured into a saturated citric acid solution and extracted with $CH_2Cl_2$ 3×. The organic layers were combined and washed with brine, dried over $Na2SO_4$ and evaporated in vacuo. The crude product was purified on silica gel chromatography eluting with 100% $CH_2Cl_2$ then 5% MeOH in 95% $CH_2Cl_2$. The pure fractions were combined and evaporated in vacuo affording (S)-3-((((9H-fluoren-9-yl)methoxy)carbonyl)amino)-2-(16-(tert-butoxy)-16-oxohexadecanamido)propanoic acid (386 mg, 0.593 mmol, 99% yield). Column: X-Bridge C18, 2.0×50 mm, 3.5-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0% B, 0-100% B over 6 minutes, then a 1.0-minute hold at 100% B; Flow: 0.8 mL/min; Detection: UV at 220 nm. Retention time=4.570 min; ESI-MS(−) m/z 649.7 (M−H).

Step 2

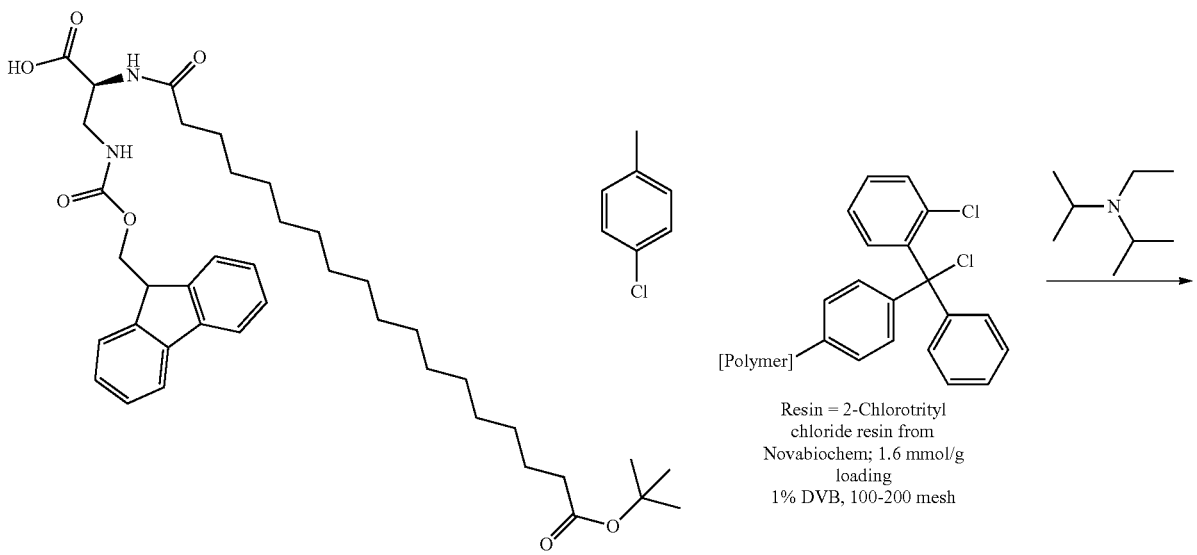

Resin = 2-Chlorotrityl chloride resin from Novabiochem; 1.6 mmol/g loading
1% DVB, 100-200 mesh

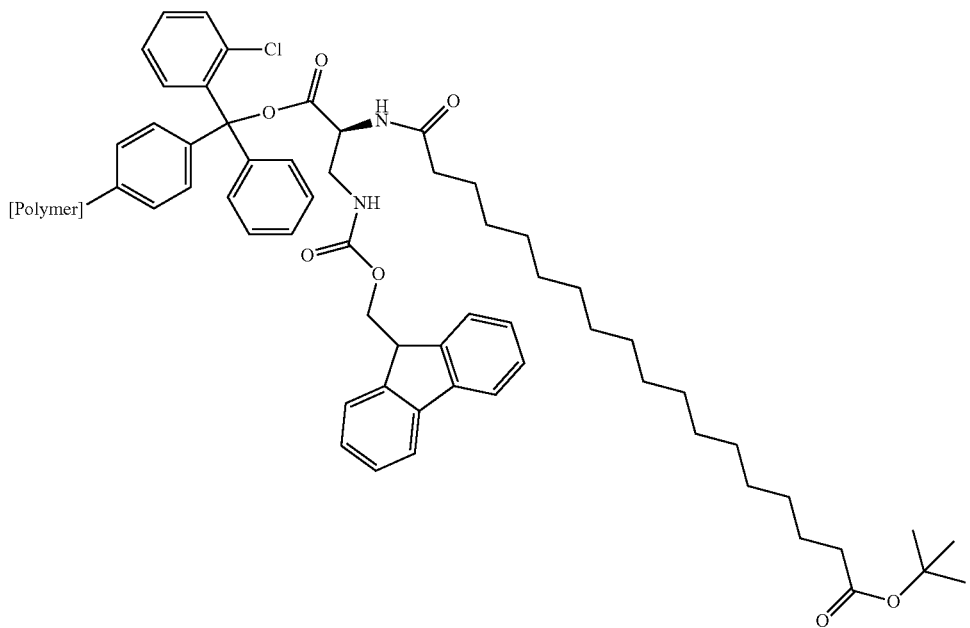

To a peptide vessel was added Chlorotrityl resin (1076 mg, 1.721 mmol), (S)-3-((((9H-fluoren-9-yl)methoxy)carbonyl)amino)-2-(16-(tert-butoxy)-16-oxohexadecanamido)propanoic acid (350 mg, 0.538 mmol), CH$_2$Cl$_2$ (8 mL), 1-chloro-4-methylbenzene (68.1 mg, 0.538 mmol), and N-ethyl-N-isopropylpropan-2-amine (0.656 mL, 3.76 mmol). The vessel was sealed and shaken on a wrist action shaker for 20 min. The reaction was complete by analyzing the LC/MS and comparing the ratio of the internal standard 1-chloro-4-methylbenzene (68.1 mg, 0.538 mmol) vs. starting acid. The resin was then diluted with 20 ml of a 9:1 Methanol/Hunigs base solution and quickly filtered and washed with DMF 3×, CH$_2$Cl$_2$ 2× and finally diethyl ether. The resin was dried in vacuo and used as is with an assumed loading of 0.5 meq/g.

Preparation of Example 11157

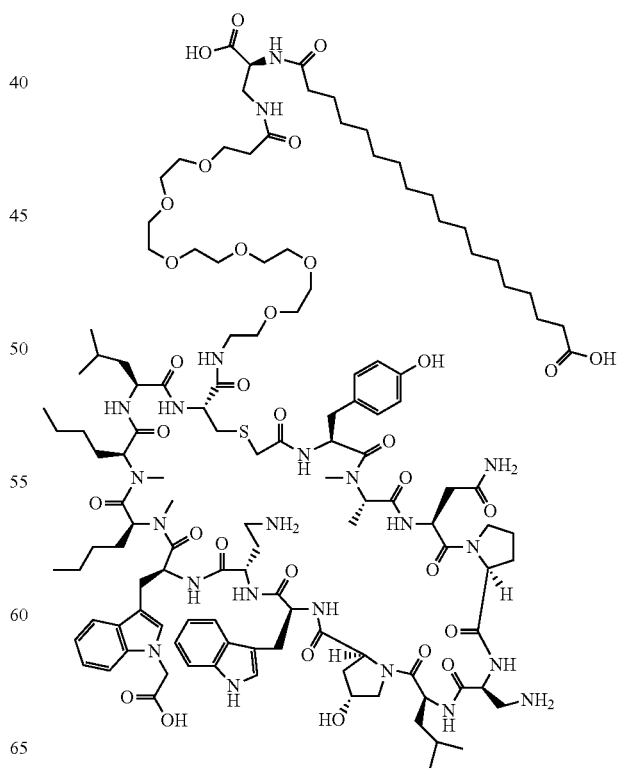

Example 11157 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin U was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 22 mg, and its estimated purity by LCMS analysis was 99%. Analysis LCMS Condition A: Retention time=4.103 min; ESI-MS(+) m/z 1261.1862 (M+2H).

Preparation of Modified 2-chlorotrityl chloride resin V

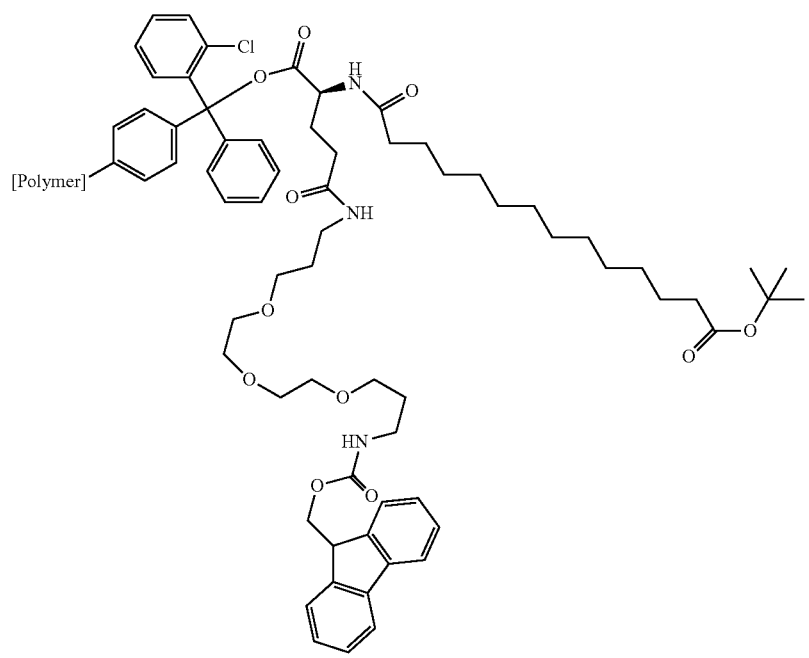

Step 1

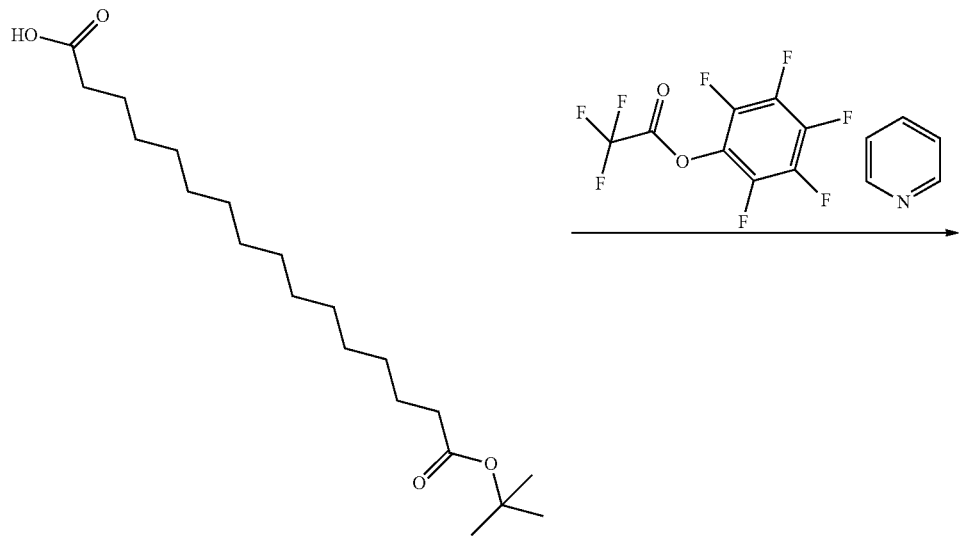

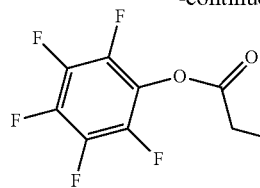

To a 100 ml round bottom flask was added 16-(tert-butoxy)-16-oxohexadecanoic acid (5900 mg, 17.23 mmol), N,N-dimethylformamide (30 mL), pyridine (3.48 mL, 43.1 mmol), and perfluorophenyl 2,2,2-trifluoroacetate (9649 mg, 34.5 mmol). The flask was sealed with a septum and kept under a blanket of nitrogen and stirred overnight at rt. The next day the reaction was poured into a saturated citric acid solution and extracted with CH$_2$Cl$_2$ 3×. The organic layers were combined and washed with brine, dried over Na2SO$_4$ and evaporated in vacuo. The crude product 1-tert-butyl 16-(perfluorophenyl) hexadecanedioate (8.7 g, 17.11 mmol, 99% yield) was used as is without purification. $^1$H NMR (400 MHz, CHLOROFORM-d) δ 2.68 (t, J=7.4 Hz, 2H), 2.23 (t, J=7.5 Hz, 2H), 1.89-1.71 (m, 2H), 1.65-1.54 (m, 2H), 1.47 (s, 9H), 1.28 (m, 20H).

Step 2

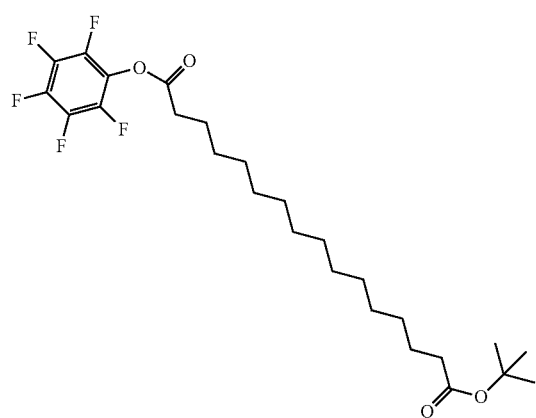

+

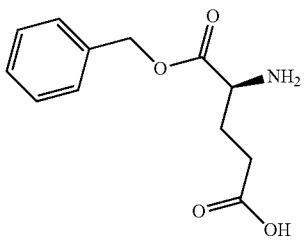

To a 50 ml round bottom flask was added (S)-4-amino-5-(benzyloxy)-5-oxopentanoic acid (800 mg, 3.37 mmol), N,N-Dimethylformamide (8 mL), 1-tert-butyl 16-(perfluorophenyl) hexadecanedioate (2229 mg, 4.38 mmol), and Hunig's Base (1.767 mL, 10.12 mmol). The flask was sealed with a septum and kept under a blanket of nitrogen and stirred overnight at rt. The next day the reaction was poured into a saturated citric acid solution and extracted with CH$_2$Cl$_2$ 3×. The organic layers were combined and washed with brine, dried over Na2SO4 and evaporated in vacuo. The crude product was purified on silica gel chromatography eluting with 100% CH$_2$Cl$_2$ then 5% MeOH in 95% CH$_2$Cl$_2$. The pure fractions were combined and evaporated in vacuo affording (S)-5-(benzyloxy)-4-(16-(tert-butoxy)-16-oxo-hexadecanamido)-5-oxopentanoic acid (0.836 g, 1.488 mmol, 44.1% yield). Analysis LCMS Condition A: Retention time=4.641 min; ESI-MS(−) m/z 560.6 (M−H); $^1$H NMR (400 MHz, CHLOROFORM-d) δ 7.36 (m, 5H), 6.37 (m, 1H), 5.18 (s, 2H), 4.67 (m, 1H), 2.40 (m, 1H), 2.21 (m, 6H), 2.02 (m, 1H), 1.61 (m, 6H), 1.45 (s, 9H), 1.40-1.16 (m, 18H).

Step 3

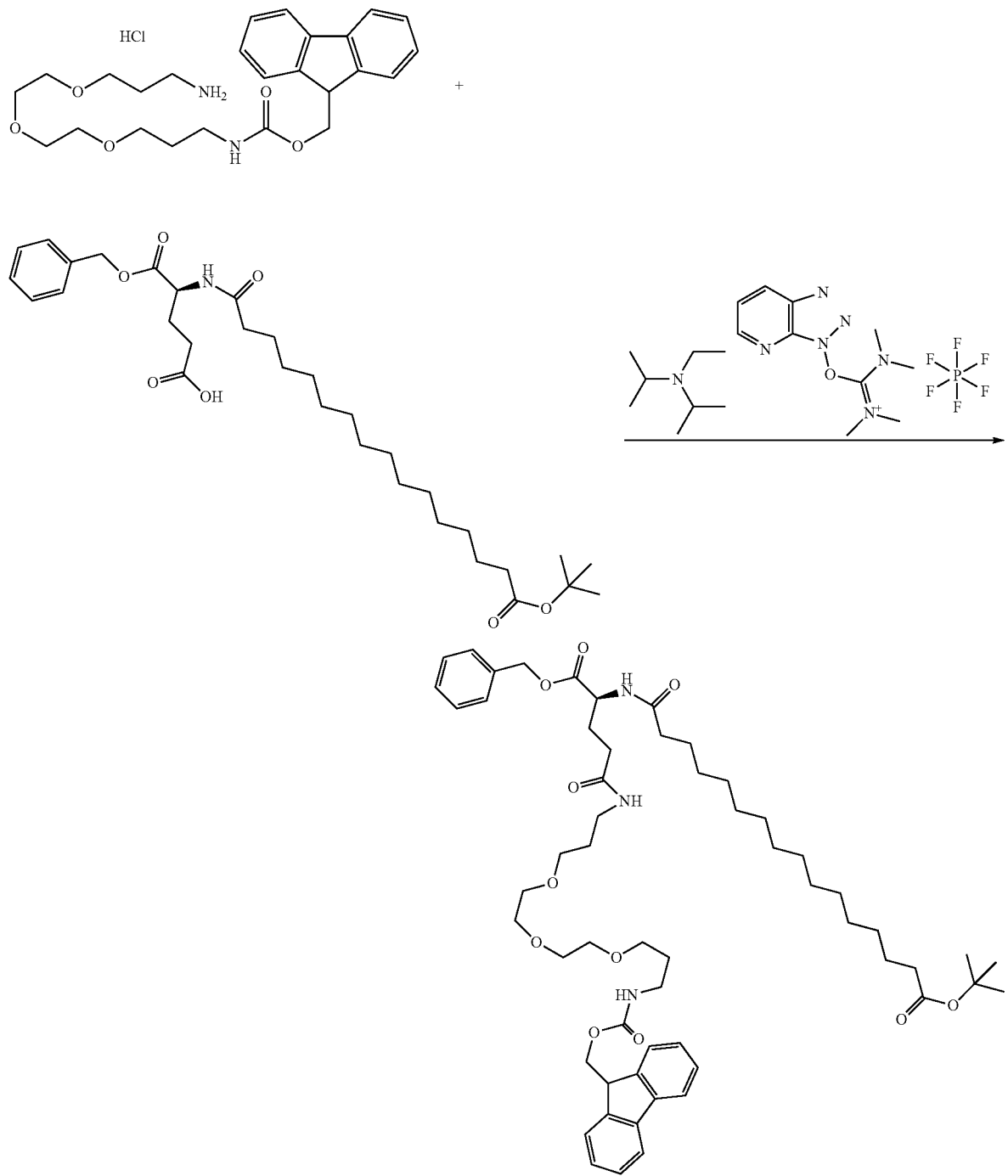

To a 50 ml round bottom flask was added (S)-5-(benzyloxy)-4-(16-(tert-butoxy)-16-oxohexadecanamido)-5-oxopentanoic acid (836 mg, 1.488 mmol), CH₂Cl₂ (8 mL), 1-(9-Fluorenylmethyloxycarbonyl-amino)-4,7,10-trioxa-13-tridecanamine hydrochloride (713 mg, 1.488 mmol), Hunig's Base (0.780 mL, 4.46 mmol) and HATU (736 mg, 1.935 mmol). The flask was sealed with a septum and kept under a blanket of nitrogen and stirred overnight at rt. The next day the reaction solvent was evaporated in vacuo. The crude product was purified on silica gel chromatography eluting with 20% Acetone/80% Hexanes to 60% Acetone/40% hexanes. The pure fractions were combined and evaporated in vacuo affording (S)-tert-butyl 22-((benzyloxy)carbonyl)-1-(9H-fluoren-9-yl)-3,19,24-trioxo-2,8,11,14-tetraoxa-4,18,23-triazanonatriacontan-39-oate (520 mg, 0.527 mmol, 35.4% yield). Analysis LCMS Condition A: Retention time=6.096 min; ESI-MS(+) m/z 987.0 (M+H); $^1$H NMR (400 MHz, CHLOROFORM-d) δ 7.79 (d, J=8.0 Hz, 2H), 7.63 (d, J=8.0 Hz, 2H), 7.42 (t, J=8.0 Hz, 2H), 7.38-7.30 (m, 7H), 6.83 (m, 1H), 6.53 (m, 1H), 5.49 (m, 1H), 5.18 (m, 2H), 4.58 (m, 1H), 4.42 (d, J=4.0 Hz, 2H), 4.23 (m, 1H), 3.63 (m, 6H), 3.55 (m, 6H), 3.33 (m, 4H), 2.22 (m, 7H), 2.02 (m, 1H), 1.77 (m, 4H), 1.63 (m, 4H), 1.47 (s, 9H), 1.37-1.20 (m, 20H).

Step 4

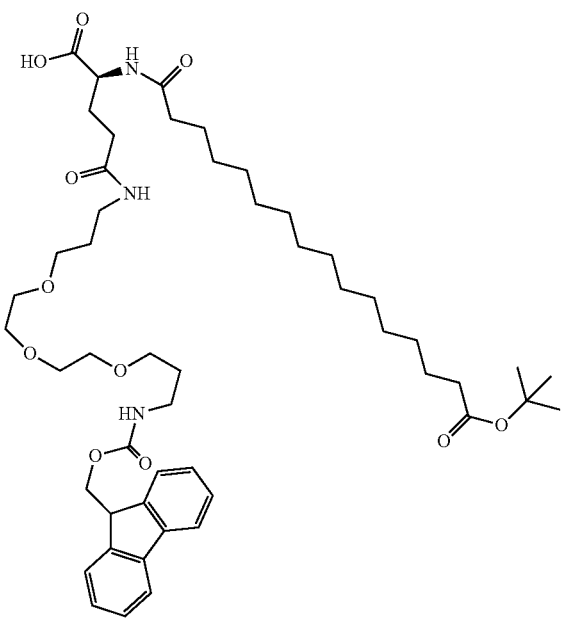

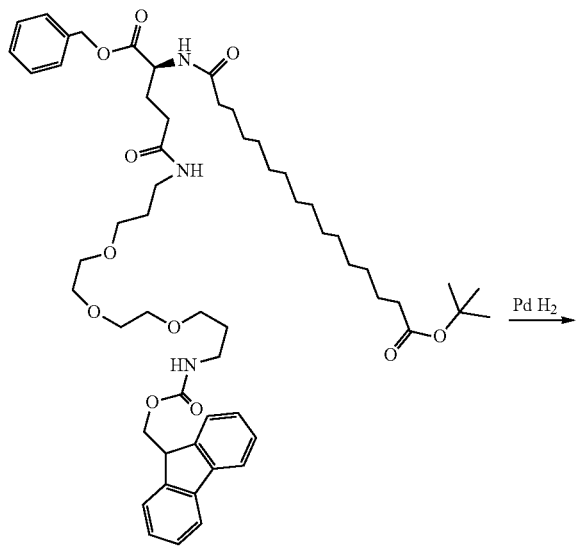

To a 25 ml round bottom flask was added(S)-tert-butyl 22-((benzyloxy)carbonyl)-1-(9H-fluoren-9-yl)-3,19,24-trioxo-2,8,11,14-tetraoxa-4,18,23-triazanonatriacontan-39-oate (520 mg, 0.527 mmol), Methanol (10 mL), and PALLADIUM ON CARBON (56.1 mg, 0.053 mmol). The flask was sealed with a septum and charged with HYDROGEN (1.063 mg, 0.527 mmol) via a balloon. The next day the reaction was checked by LC/MS and was complete. The reaction was filtered through celite to remove the catalyst and the filtrate was evaporated in vacuo affording (S)-22-(16-(tert-butoxy)-16-oxohexadecanamido)-1-(9H-fluoren-9-yl)-3,19-dioxo-2,8,11,14-tetraoxa-4,18-diazatricosan-23-oic acid (415 mg, 0.463 mmol, 88% yield). This material was used as is without purification. Analysis LCMS Condition A: Retention time=4.535 min; ESI-MS(−) m/z 895.0 (M−H).

Step 5: Modified Chlorotrityl Resin V

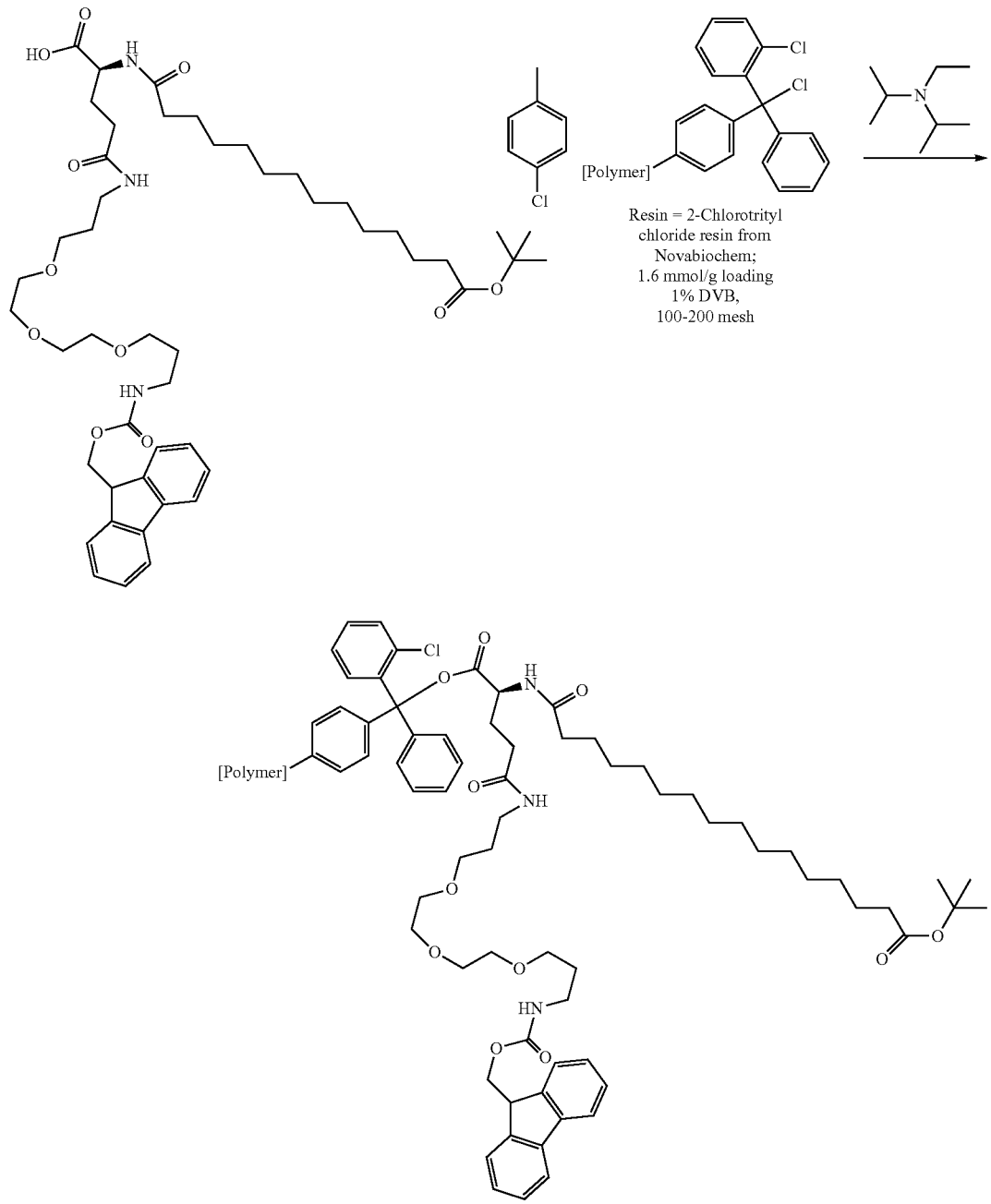

To a peptide vessel was added 2-chlorotrityl resin (926 mg, 1.482 mmol), (S)-22-(16-(tert-butoxy)-16-oxohexadecanamido)-1-(9H-fluoren-9-yl)-3,19-dioxo-2,8,11,14-tetraoxa-4,18-diazatricosan-23-oic acid (415 mg, 0.463 mmol), CH$_2$Cl$_2$ (8 mL), 1-chloro-4-methylbenzene (58.6 mg, 0.463 mmol), and N-ethyl-N-isopropylpropan-2-amine (0.565 mL, 3.24 mmol). The vessel was sealed and shaken on a wrist action shaker for 30 min. The reaction was complete by analyzing the LC/MS and comparing the ratio of the internal standard 1-chloro-4-methylbenzene (58.6 mg, 0.463 mmol) vs. starting acid. The resin was then diluted with 20 ml of a 9:1 Methanol/Hunigs base solution and quickly filtered and washed with DMF 3×, CH$_2$Cl$_2$ 3× and finally diethyl ether. The resin was dried in vacuo and used as is for peptide synthesis with an assumed loading of 0.5 meq/g.

449
Preparation of Example 11158

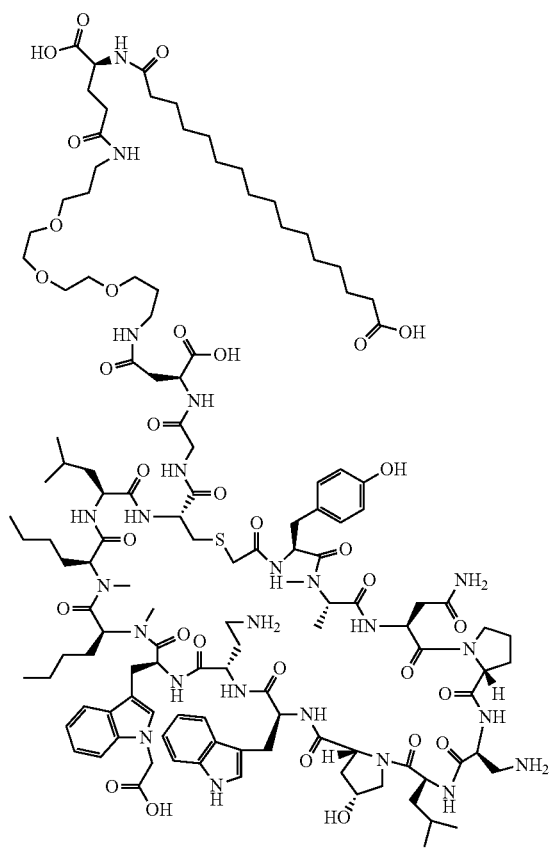 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11158 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 42 mg, and its estimated purity by LCMS analysis was 99%. Analysis LCMS Condition A: Retention time=3.710 min; ESI-MS(+) m/z 1302.1958 (M+2H).

450
Preparation of Example 11159

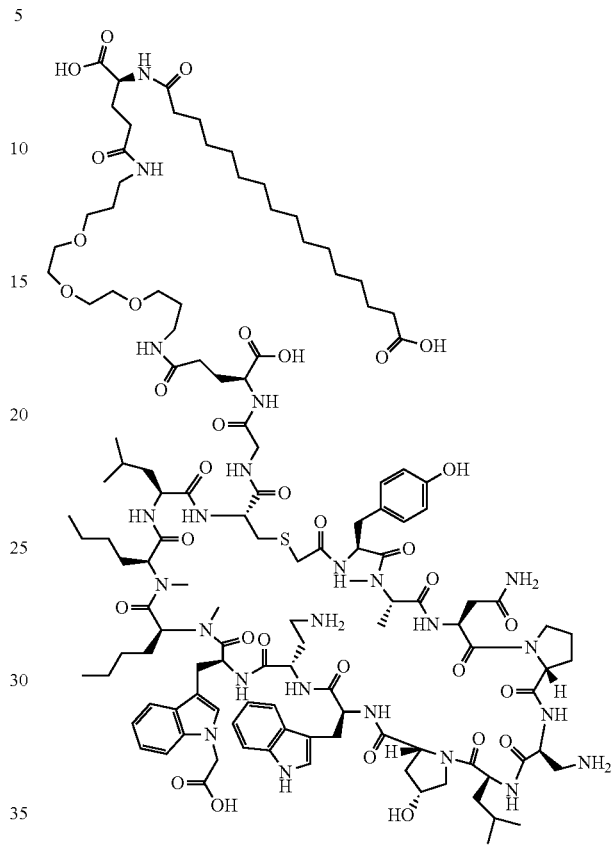

Example 11159 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 30 mg, and its estimated purity by LCMS analysis was 97.9%. Analysis LCMS Condition A: Retention time=3.701 min; ESI-MS(+) m/z 1309.2045 (M+2H).

Preparation of Example 11160

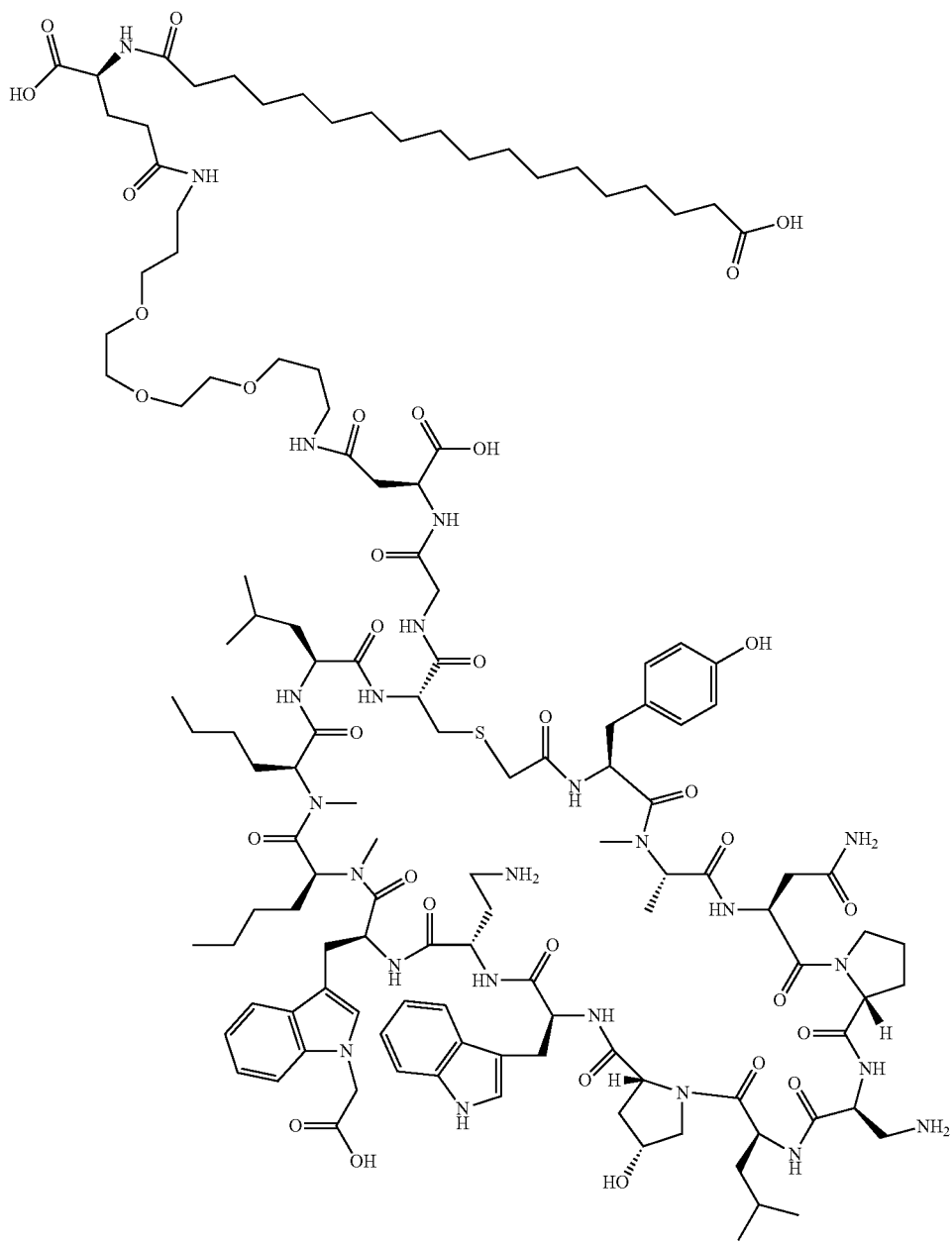 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11160 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-µm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 23 mg, and its estimated purity by LCMS analysis was 97.1%. Analysis LCMS Condition A: Retention time=4.636 min; ESI-MS(+) m/z 1316.2122 (M+2H).

453
Preparation of Example 11161

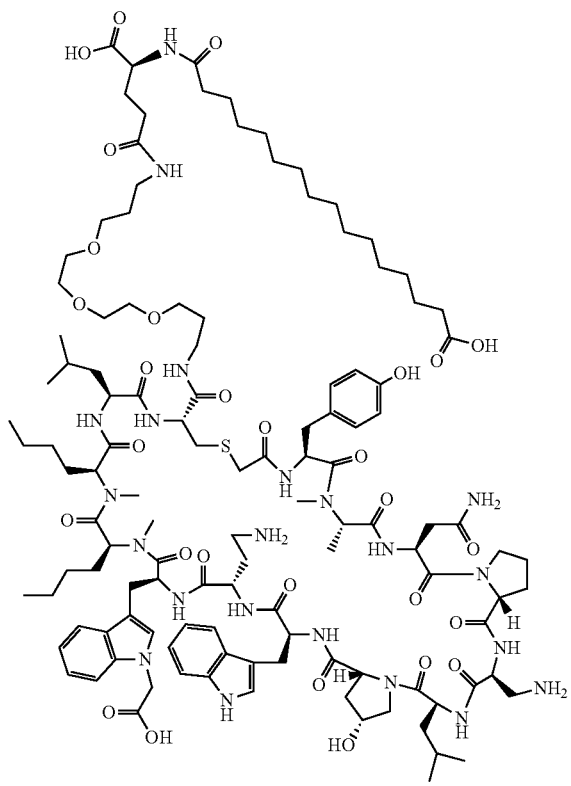 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CC[C@H](NC(=O)CCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11161 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 40 mg, and its estimated purity by LCMS analysis was 97.9%. Analysis LCMS Condition A: Retention time=4.161 min; ESI-MS(+) m/z 1216.1731 (M+2H).

454
Preparation of Example 11162

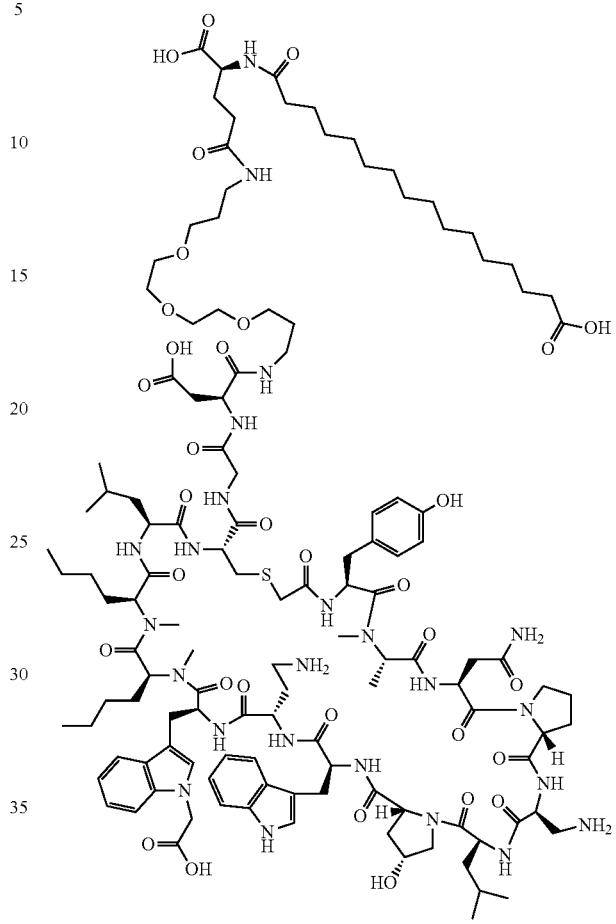

Example 11162 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 22 mg, and its estimated purity by LCMS analysis was 96.3%. Analysis LCMS Condition A: Retention time=3.825 min.

Preparation of Example 11163

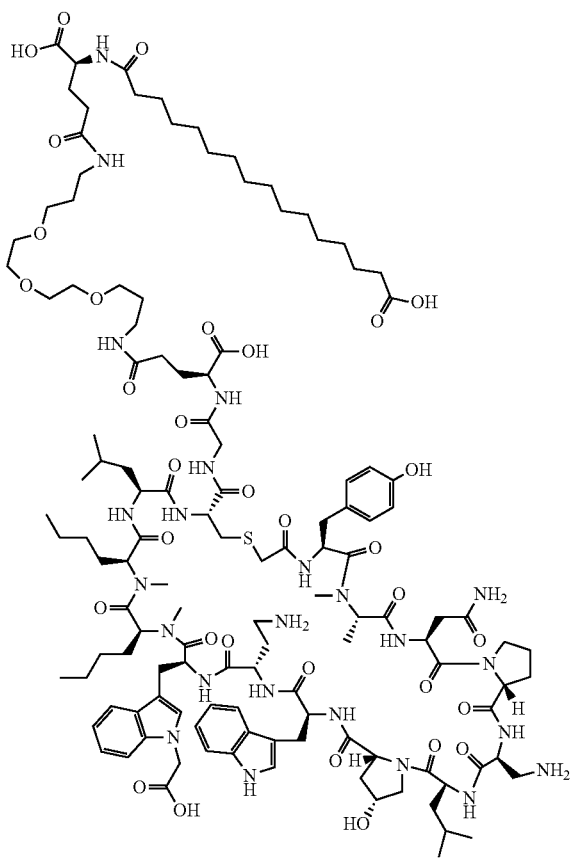 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCCOCCOCCOCCCNC(=O)CC[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11163 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 11 mg, and its estimated purity by LCMS analysis was 100%. Analysis LCMS Condition A: Retention time=4.066 min; ESI-MS(+) m/z 1323.2176 (M+2H).

Preparation of Example 11164

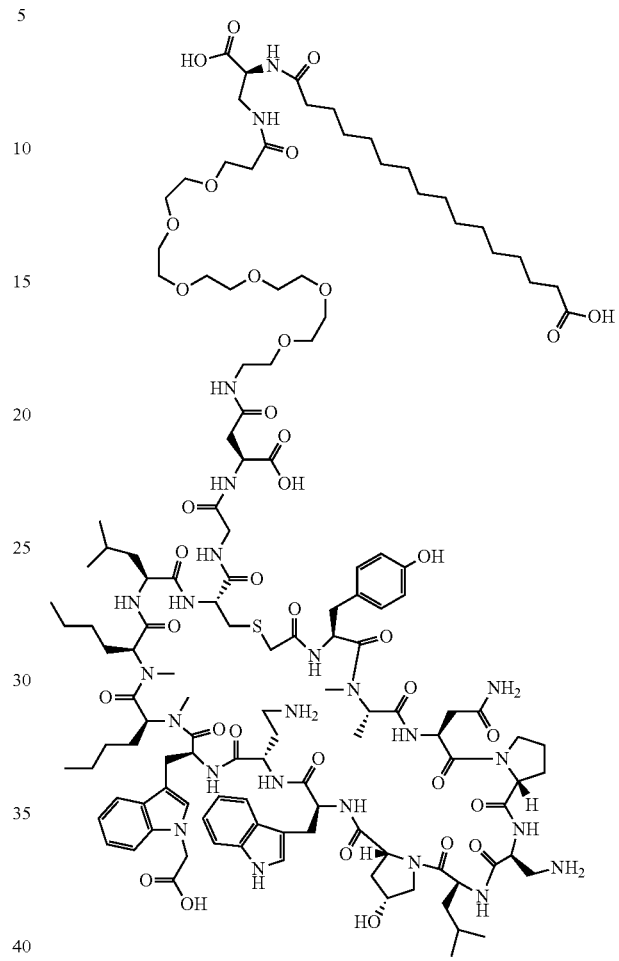

Example 11164 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin U was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 7 mg, and its estimated purity by LCMS analysis was 98%. Analysis LCMS Condition A: Retention time=3.668 min; ESI-MS(+) m/z 1347.2103 (M+2H).

Preparation of Example 11165

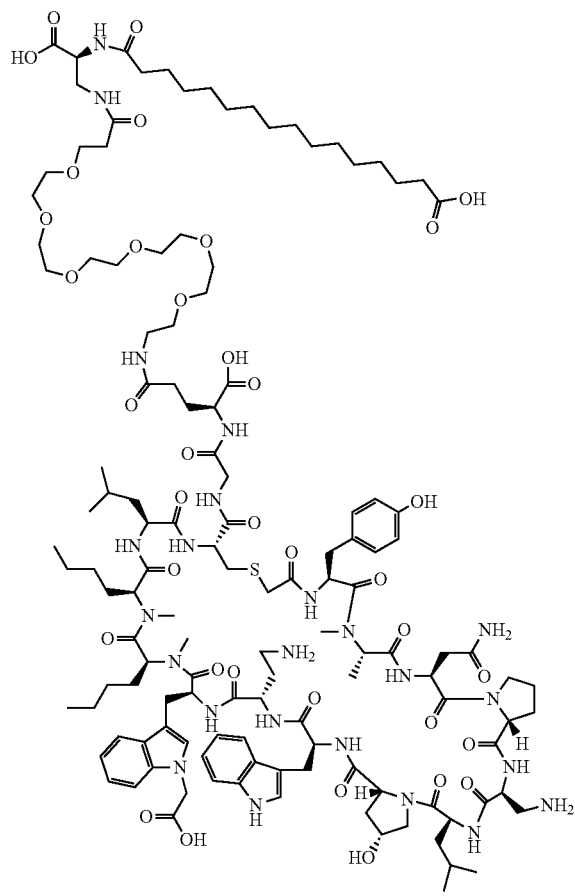 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCOCCOCCOCCOCCOCCOCCC(=O)NC[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11165 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin U was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 28 mg, and its estimated purity by LCMS analysis was 94.8%. Analysis LCMS Condition A: Retention time=3.653 min; ESI-MS(+) m/z 1354.2194 (M+2H).

Preparation of Example 11166

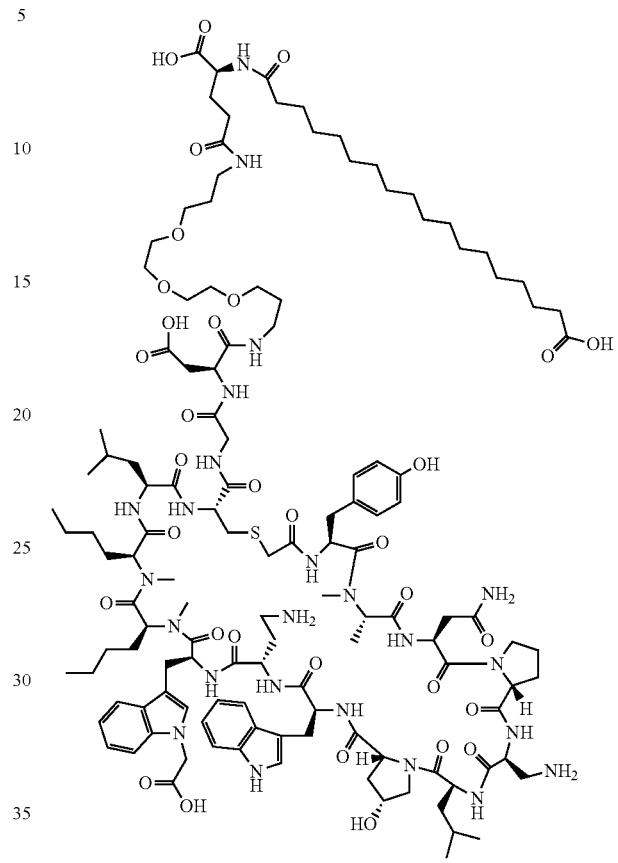

Example 11166 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 12 mg, and its estimated purity by LCMS analysis was 93.1%. Analysis LCMS Condition A: Retention time=3.690 min; ESI-MS(+) m/z 1316.2126 (M+2H).

Preparation of Example 11167

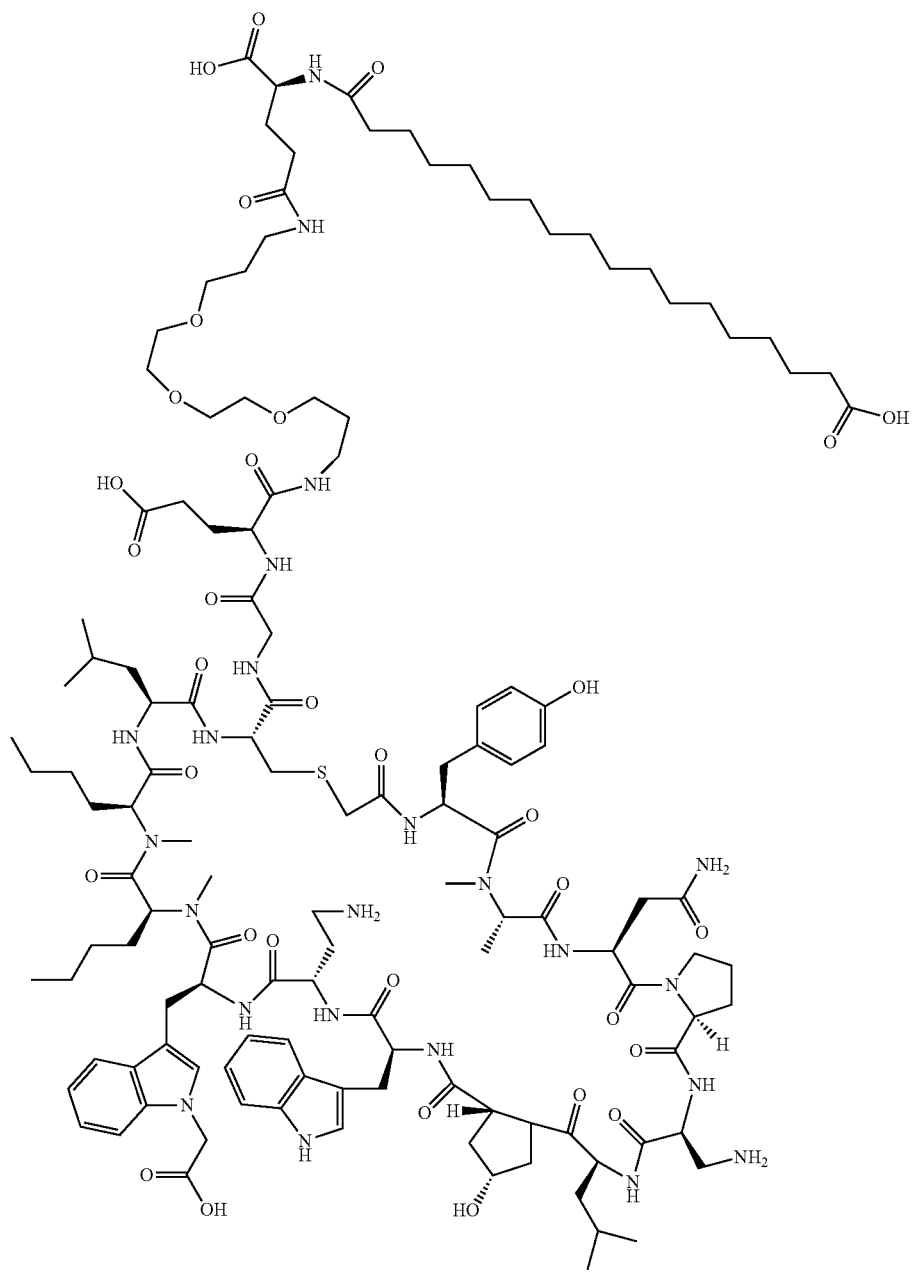 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)C2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11167 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 24 mg, and its estimated purity by LCMS analysis was 100%. Analysis LCMS Condition A: Retention time=3.811 min; ESI-MS(+) m/z 1323.2204 (M+2H).

Preparation of Example 11168

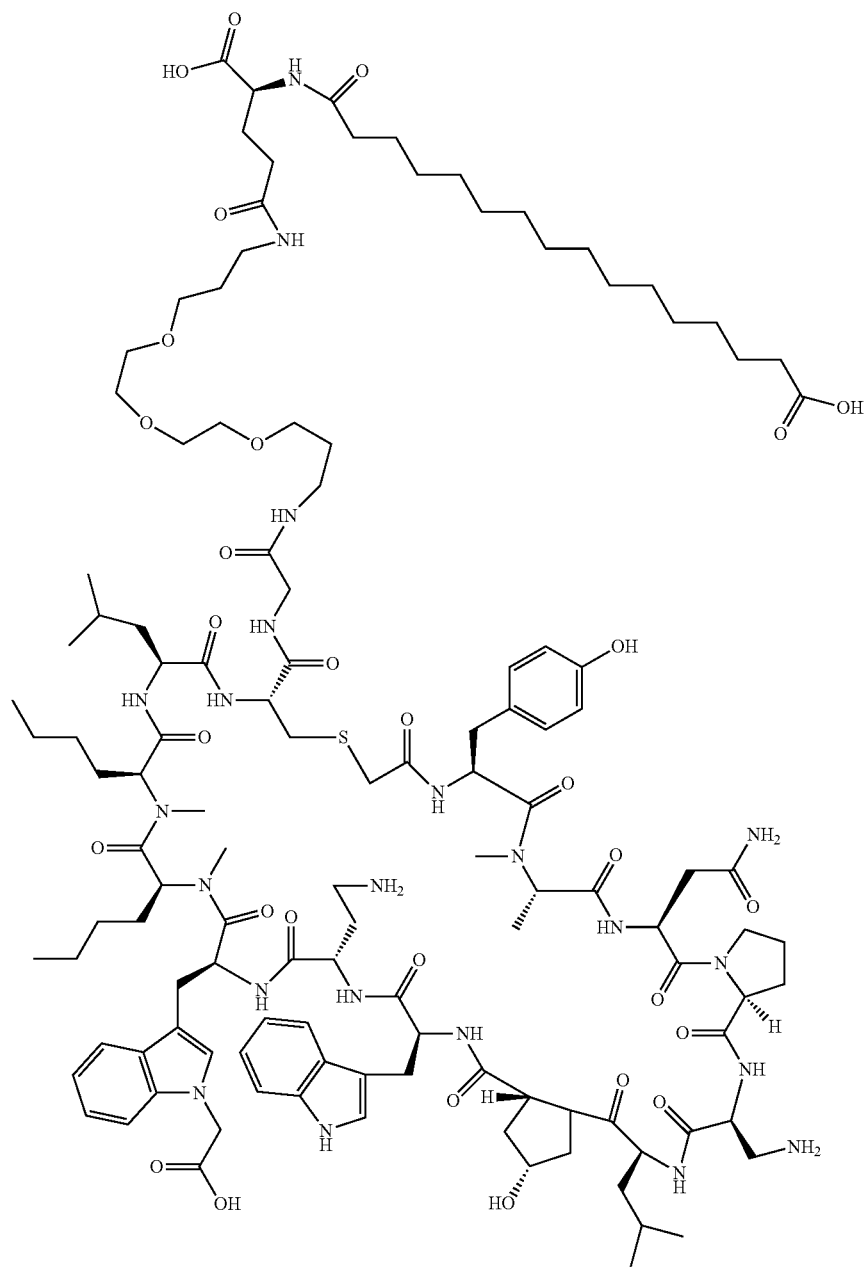 [SMILES: CCCC[C@H]1C(=O)N(C)[C@@H](CCCC)C(=O)N[C@@H](CC(C)C)C(=O)N[C@H](C(=O)NCC(=O)NCCCOCCOCCOCCCNC(=O)CC[C@H](NC(=O)CCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)C2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11168 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 34 mg, and its estimated purity by LCMS analysis was 100%. Analysis LCMS Condition A: Retention time=3.798 min; ESI-MS(+) m/z 1244.6830 (M+2H).

Preparation of Example 11169

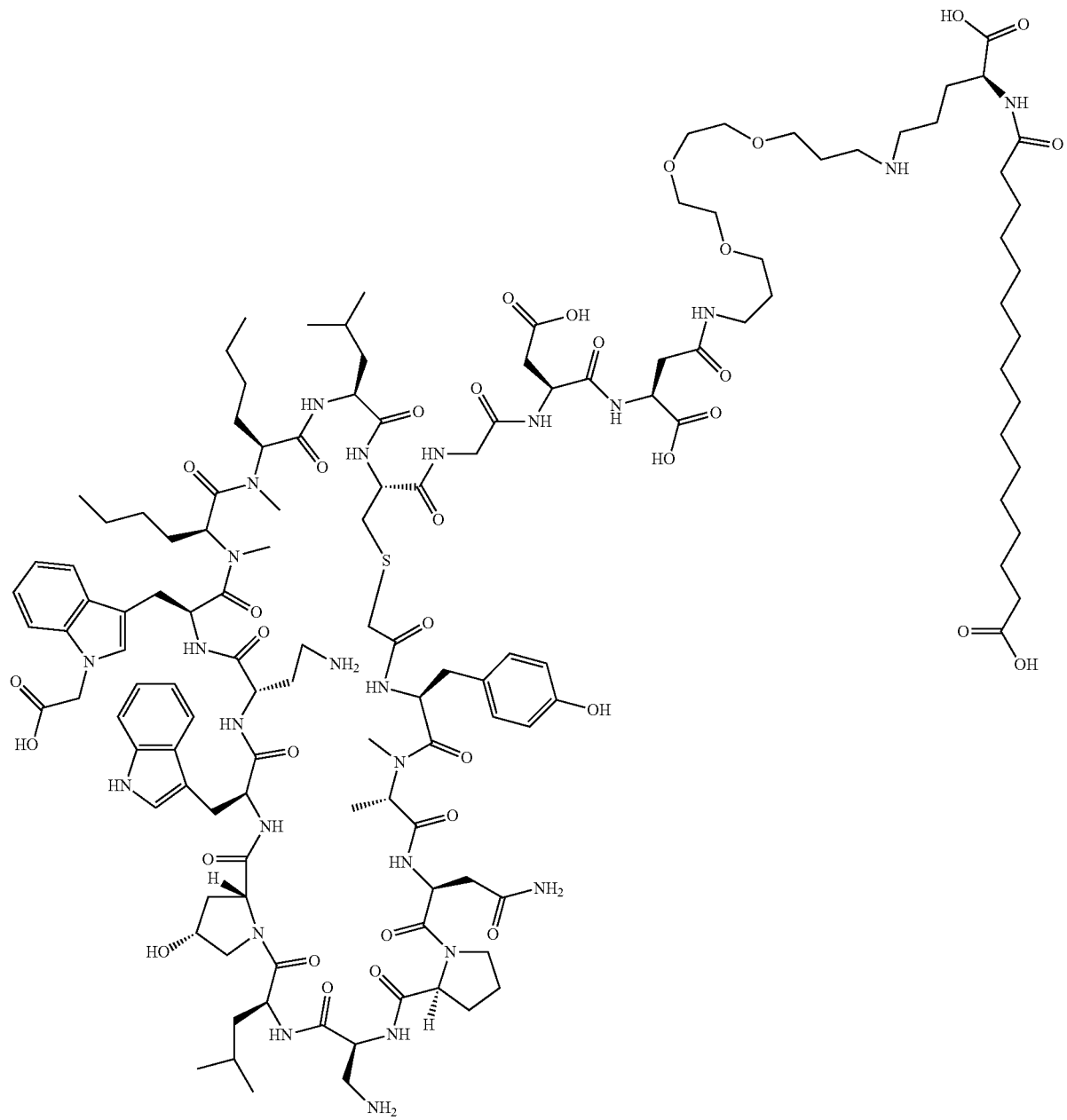 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)NCCCOCCOCCOCCCNCCC[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11169 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 29 mg, and its estimated purity by LCMS analysis was 96%. Analysis LCMS Condition A: Retention time=3.423 min; ESI-MS(+) m/z 1359.7108 (M+2H).

Preparation of Example 11170

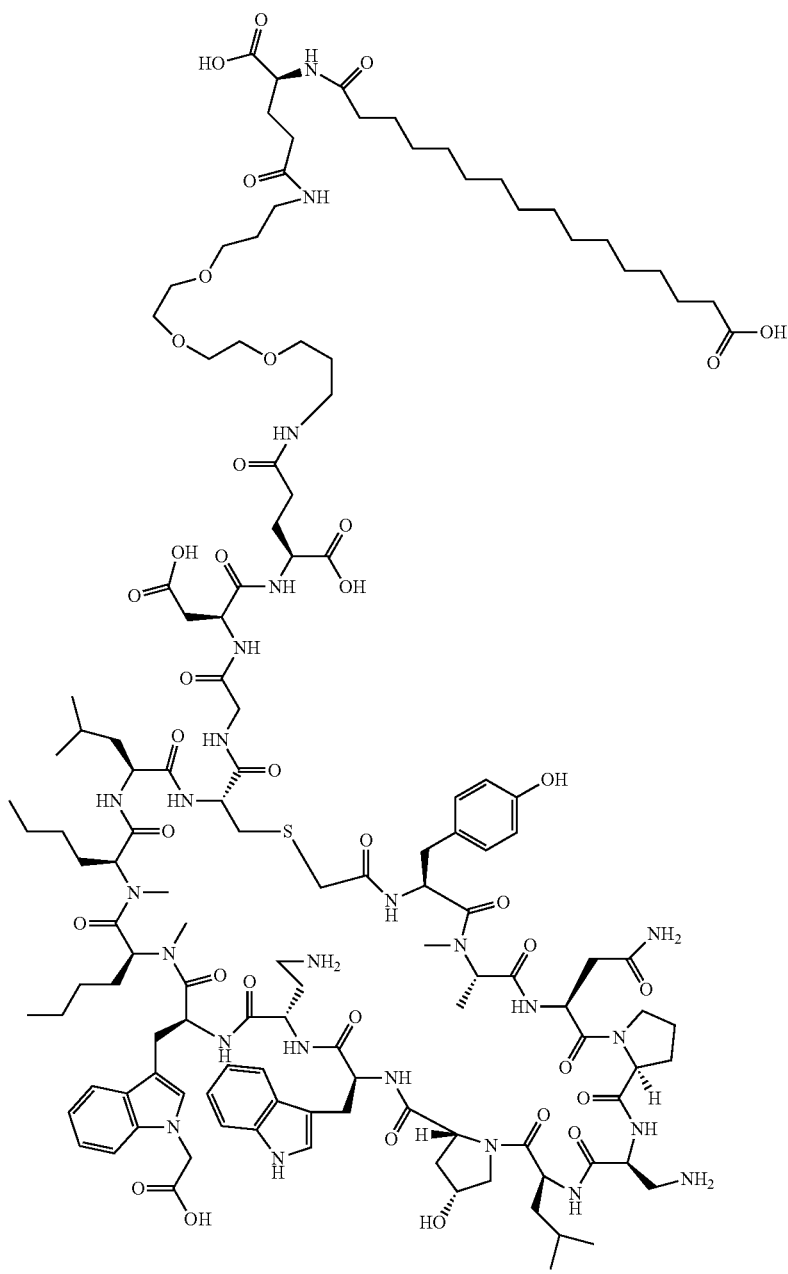 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CCC(=O)NCCCOCCOCCOCCCNC(=O)CC[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11170 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 32 mg, and its estimated purity by LCMS analysis was 96.3%. Analysis LCMS Condition A: Retention time=3.426 min; ESI-MS(+) m/z 1366.7180 (M+2H).

Preparation of Example 11171

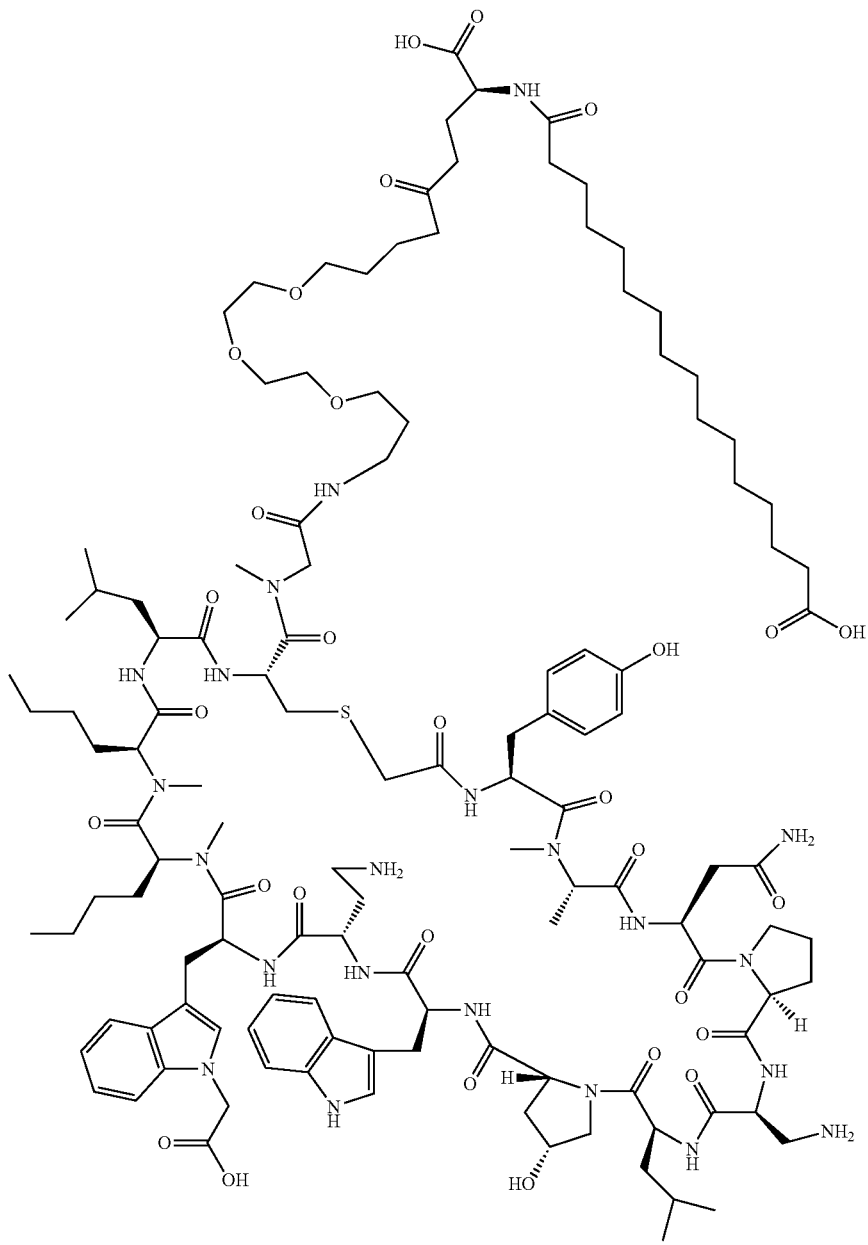 [SMILES: CCCC[C@H]1C(=O)N(C)[C@@H](CCCC)C(=O)N[C@@H](CC(C)C)C(=O)N[C@H](C(=O)N(C)CC(=O)NCCCOCCOCCOCCCCC(=O)CC[C@H](NC(=O)CCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11171 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 35 mg, and its estimated purity by LCMS analysis was 100%. Analysis LCMS Condition A: Retention time=4.001 min; ESI-MS(+) m/z 1251.6929 (M+2H).

Preparation of Modified Chlorotrityl Chloride Resin
W
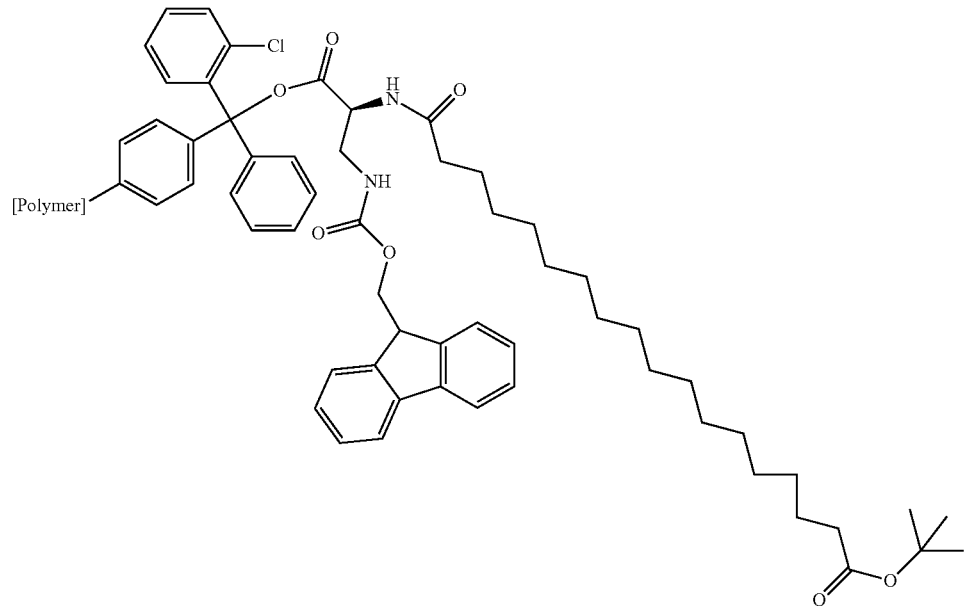
Step 1
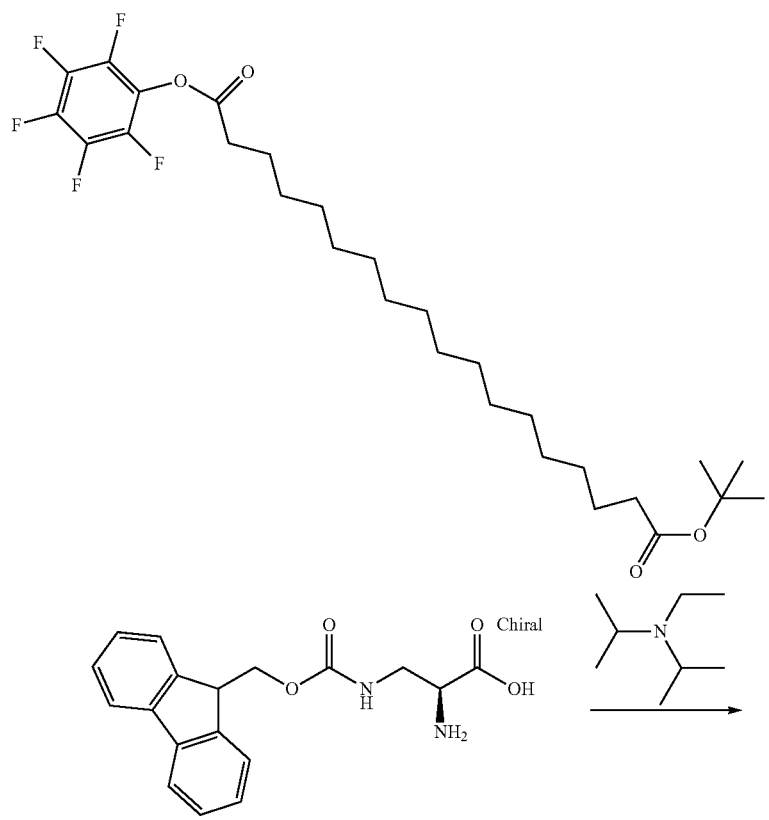

-continued

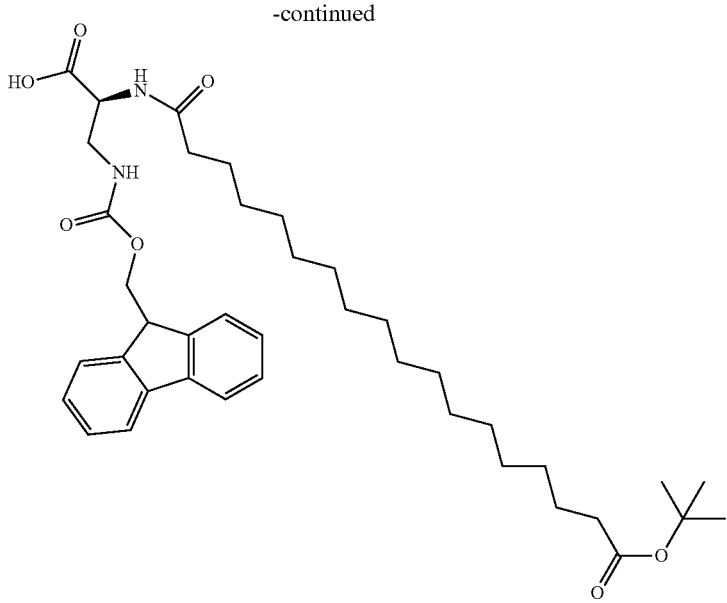

To a 50 ml round bottom flask was added (S)-3-((((9H-fluoren-9-yl)methoxy)carbonyl)amino)-2-aminopropanoic acid, HCl (500 mg, 1.378 mmol), N,N-Dimethylformamide (12 mL), 1-tert-butyl 18-(perfluorophenyl)octadecanedioate (1109 mg, 2.067 mmol), and Hunig's Base (0.963 mL, 5.51 mmol). The flask was sealed with a septum and kept under a blanket of nitrogen and stirred overnight at rt. The next day the reaction was poured into a saturated citric acid solution and extracted with $CH_2Cl_2$ 3×. The organic layers were combined and washed with brine, dried over Na2SO4 and evaporated in vacuo. The crude product was purified on silica gel chromatography eluting with 100% $CH_2Cl_2$ then 5% MeOH in 95% $CH_2Cl_2$. The pure fractions were combined and evaporated in vacuo affording (S)-3-((((9H-fluoren-9-yl)methoxy)carbonyl)amino)-2-(18-(tert-butoxy)-18-oxooctadecanamido)propanoic acid (774 mg, 1.140 mmol, 83% yield). Analysis LCMS Condition A: Retention time=3.698 min; ESI-MS(-) m/z 677.7 (M-H); $^1$H NMR (400 MHz, CHLOROFORM-d) δ 7.78 (d, J=7.5 Hz, 2H), 7.59 (d, J=7.5 Hz, 2H), 7.42 (t, J=7.4 Hz, 2H), 7.33 (t, J=7.2 Hz, 2H), 7.26 (d, J=5.0 Hz, 1H), 5.67 (s, 1H), 4.59-4.49 (m, 1H), 4.41 (d, J=7.0 Hz, 2H), 4.23 (t, J=7.2 Hz, 1H), 3.83-3.69 (m, 1H), 3.67-3.55 (m, 1H), 2.32-2.16 (m, 4H), 1.70-1.53 (m, 4H), 1.46 (s, 9H), 1.36-1.17 (m, 24H).

Step 2

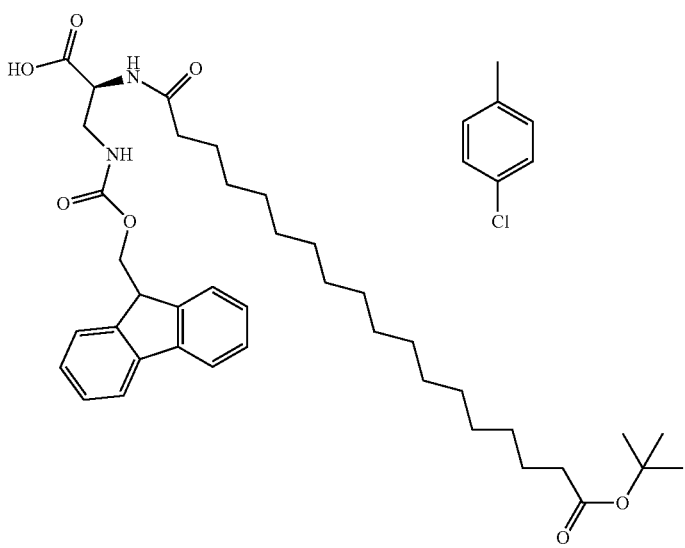 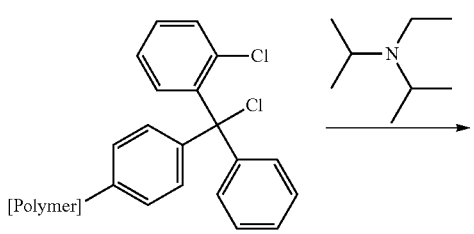

Resin = 2-Chlorotrityl chloride resin from Novabiochem; 1.6 mmol/g loading 1% DVB, 100-200 mesh

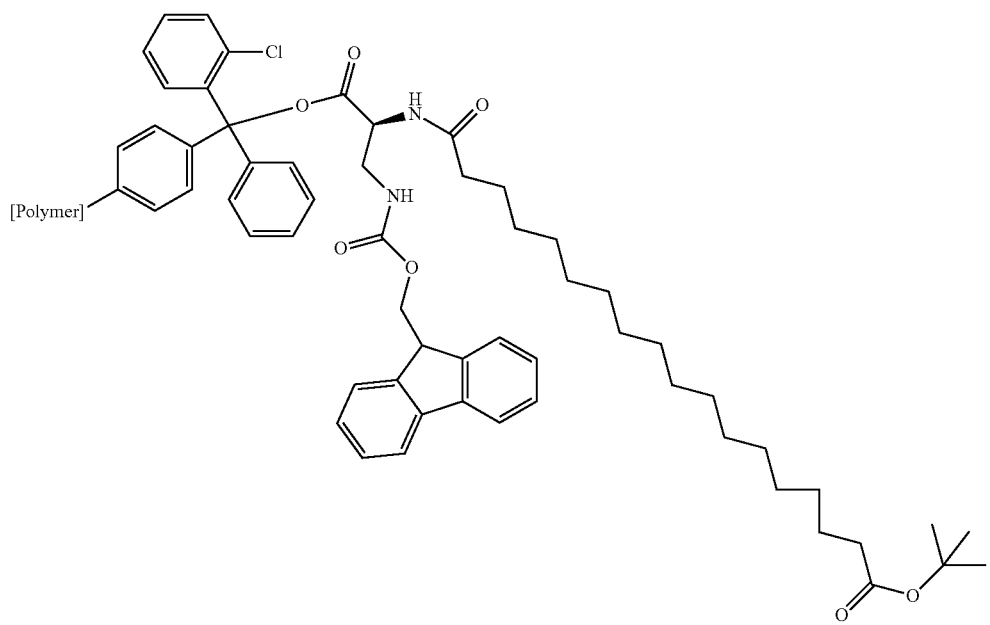

To a peptide vessel was added 2-Chlorotrityl resin (2280 mg, 3.65 mmol), (S)-3-((((9H-fluoren-9-yl)methoxy)carbonyl)amino)-2-(18-(tert-butoxy)-18-oxooctadecanamido) propanoic acid (774 mg, 1.140 mmol), CH$_2$Cl$_2$ (16 mL), 1-chloro-4-methylbenzene (43.3 mg, 0.342 mmol), and N-ethyl-N-isopropylpropan-2-amine (1.390 mL, 7.98 mmol). The vessel was sealed and shaken on a wrist action shaker for 30 min. The reaction was complete by analyzing the LC/MS and comparing the ratio of the internal standard 1-chloro-4-methylbenzene (43.3 mg, 0.342 mmol) vs. starting acid. The resin was then diluted with 20 ml of a 9:1 Methanol/Hunigs base solution and quickly filtered and washed with DMF 3×, CH$_2$Cl$_2$ 3× and finally diethyl ether. The resin was dried in vacuo and was used as is with an assumed loading of 0.5 meq/g for the synthesis of the desired proteins.

Preparation of Example 11172

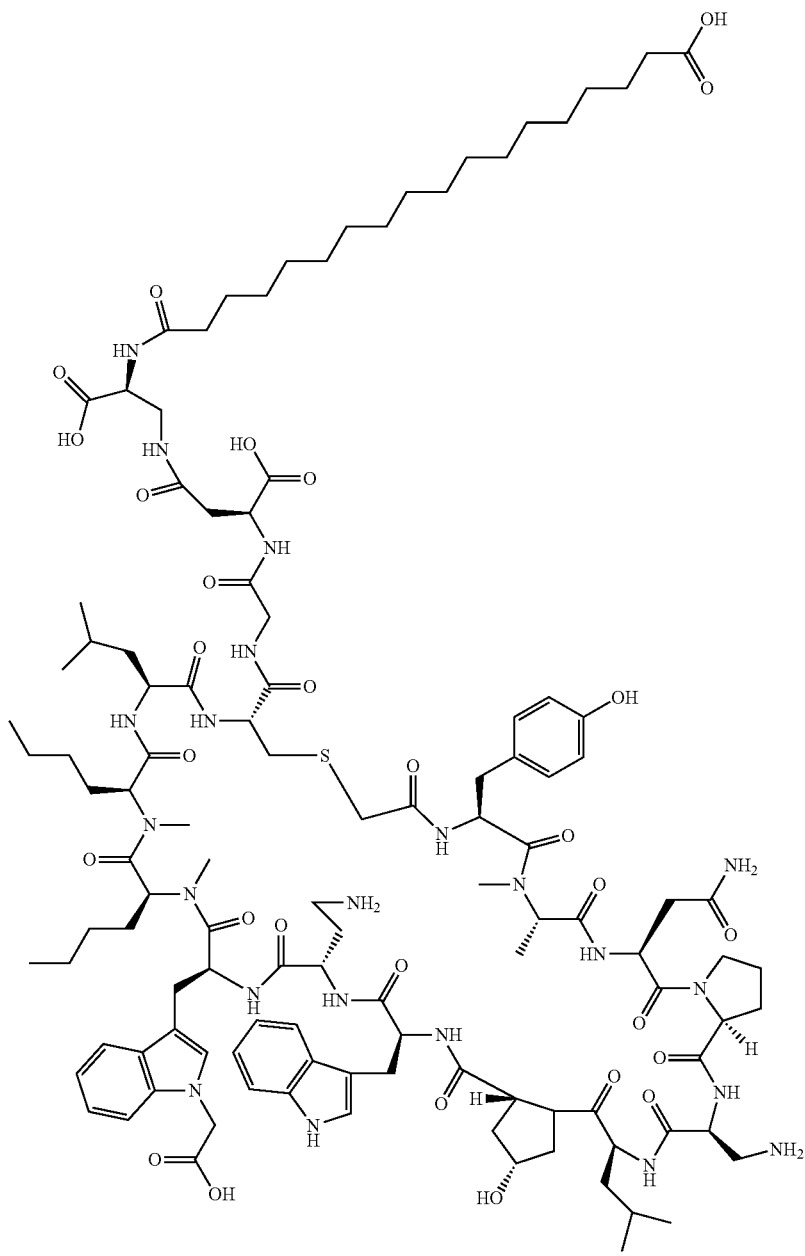 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)C2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11172 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 27 mg, and its estimated purity by LCMS analysis was 93.5%. Analysis LCMS Condition A: Retention time=4.218 min; ESI-MS(+) m/z 1193.6278 (M+2H).

Preparation of Example 11173

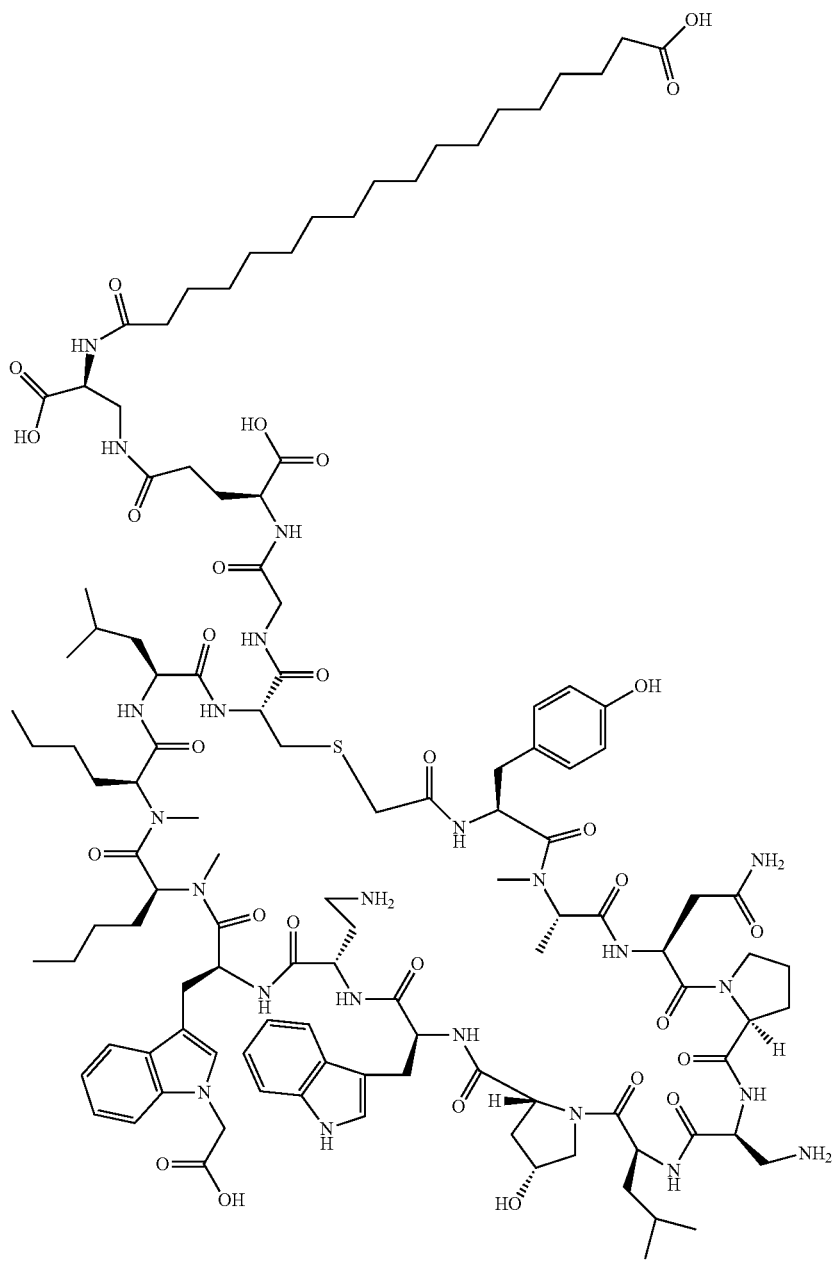 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11173 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 35 mg, and its estimated purity by LCMS analysis was 95.9%. Analysis LCMS Condition A: Retention time=4.218 min; ESI-MS(+) m/z 1200.6358 (M+2H).

Preparation of Example 11174

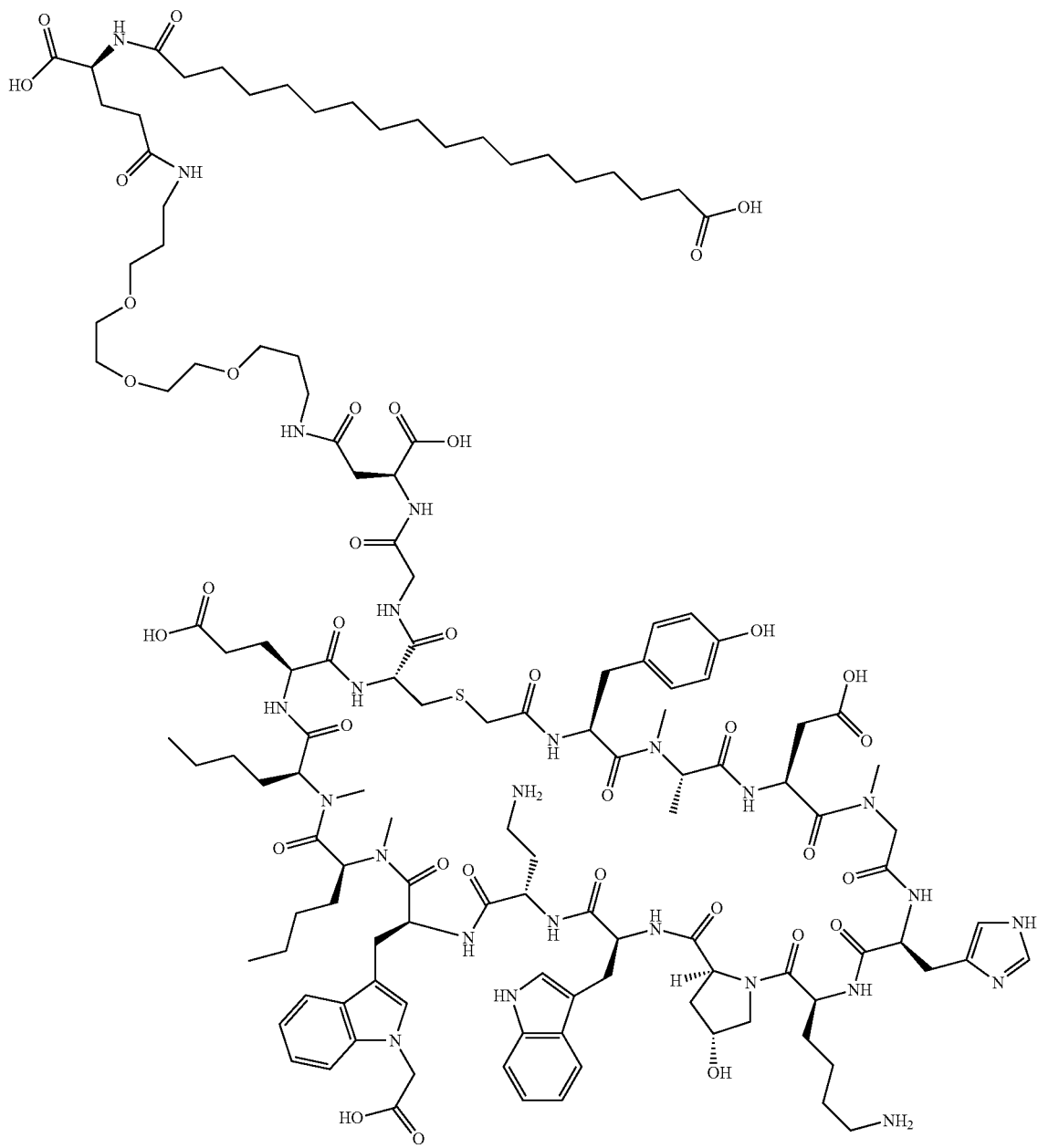 [SMILES: CCCC[C@H]1C(=O)N(C)[C@@H](CCCC)C(=O)N[C@@H](CCC(=O)O)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(=O)O)C(=O)N(C)CC(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11174 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 29 mg, and its estimated purity by LCMS analysis was 95.3%. Analysis LCMS Condition A: Retention time=3.303 min; ESI-MS(+) m/z 1344.6838 (M+2H).

Preparation of Example 11175

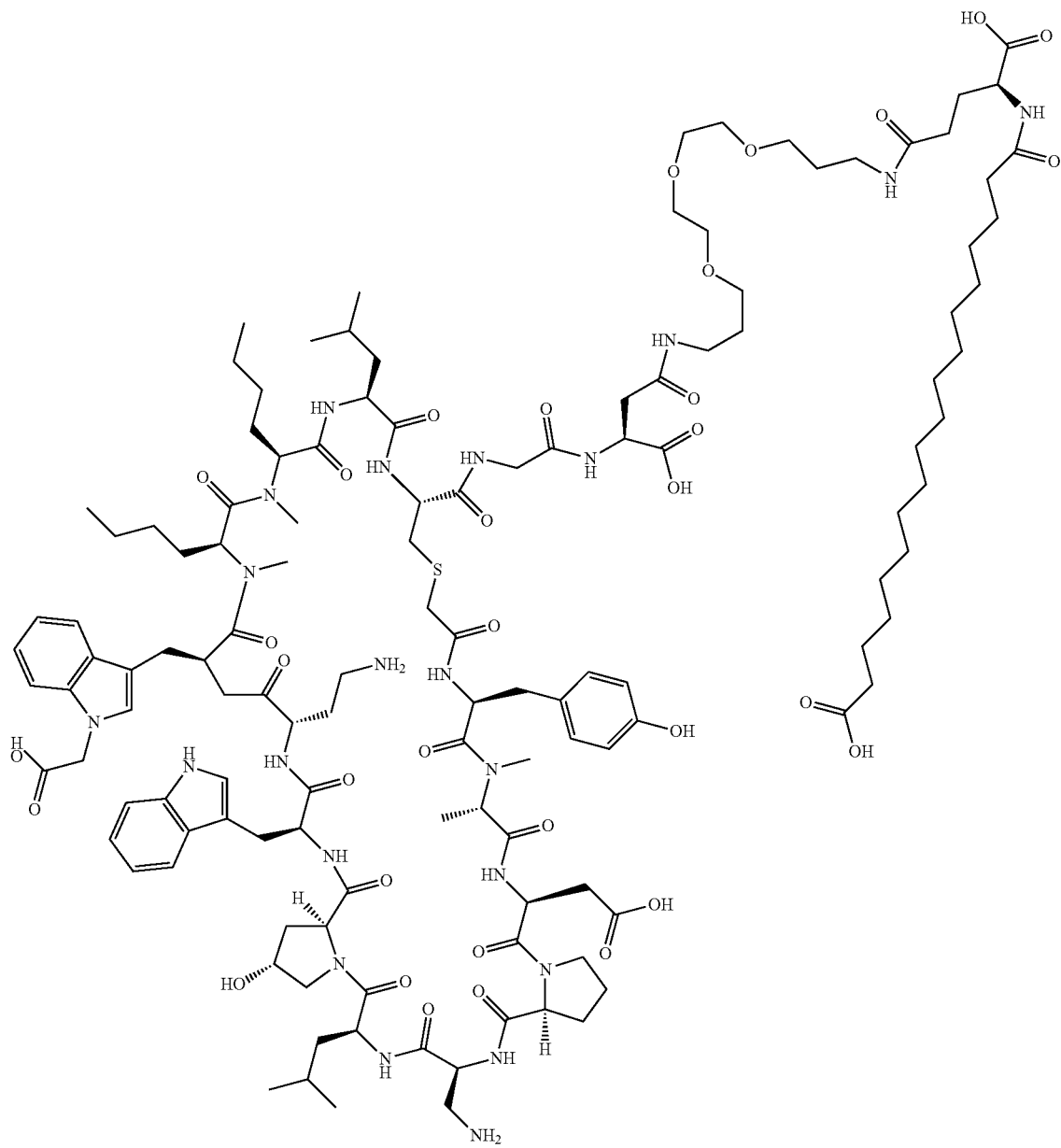 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)C[C@@H](Cc2cn(CC(=O)O)c3ccccc23)C(=O)N1C]

Example 11175 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 19 mg, and its estimated purity by LCMS analysis was 97.8%. Analysis LCMS Condition A: Retention time=3.71 min; ESI-MS(+) m/z 1316.7013 (M+2H).

Preparation of Example 11176

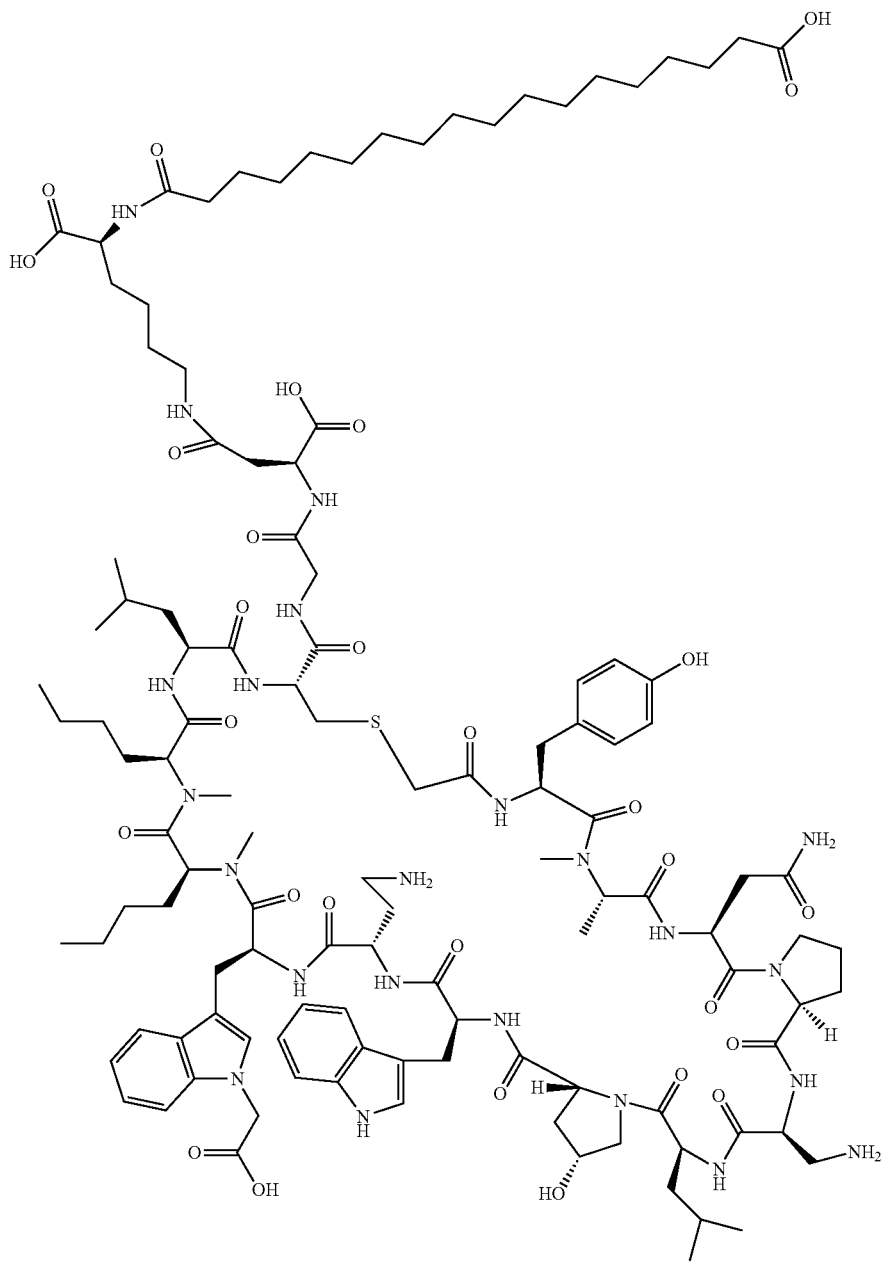 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11176 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 25 mg, and its estimated purity by LCMS analysis was 97.5%. Analysis LCMS Condition A: Retention time=4.005 min; ESI-MS(+) m/z 1214.6502 (M+2H).

Preparation of Example 11177

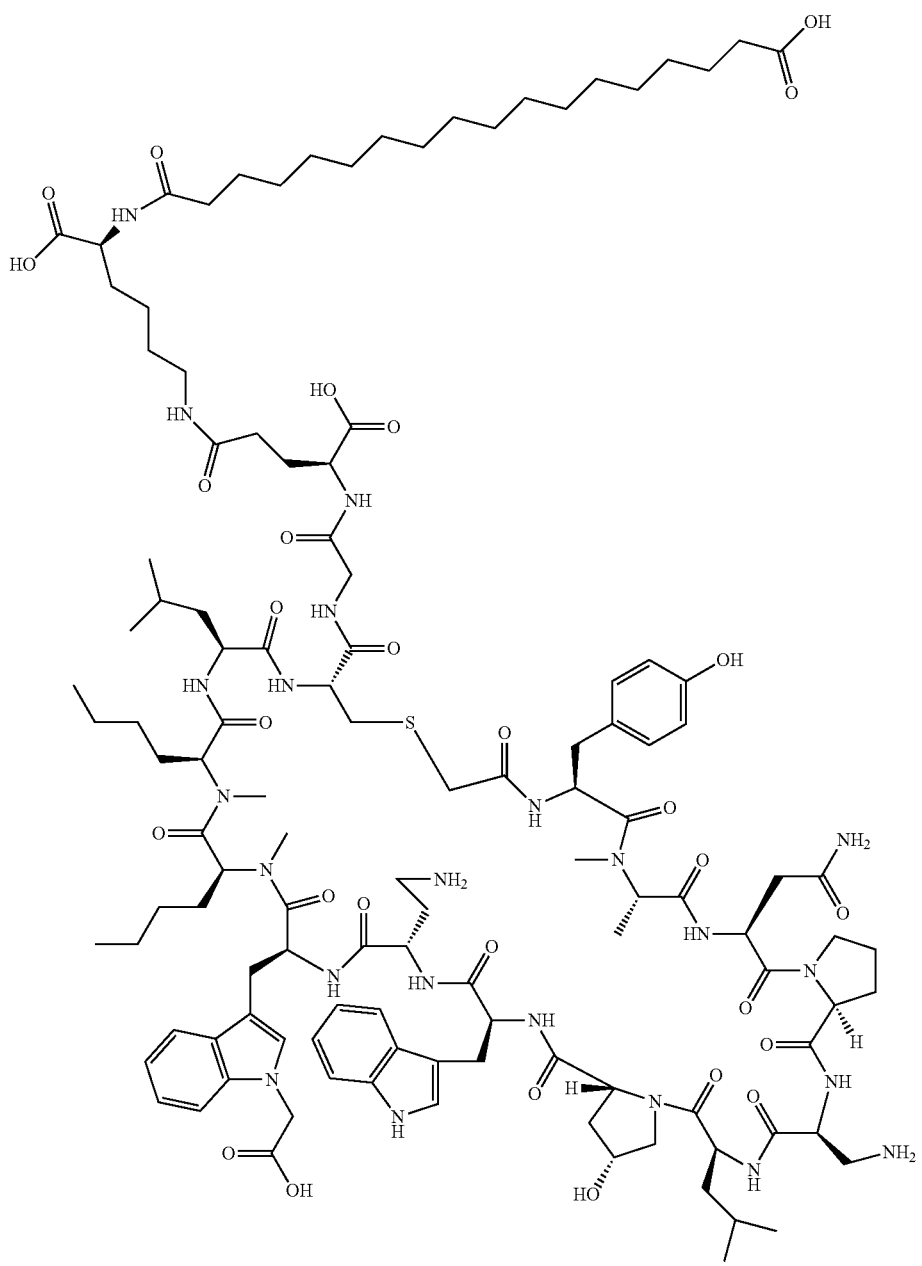 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCCC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11177 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 27 mg, and its estimated purity by LCMS analysis was 98.6%. Analysis LCMS Condition A: Retention time=4.010 min; ESI-MS(+) m/z 1221.6584 (M+2H).

Preparation of Example 11178

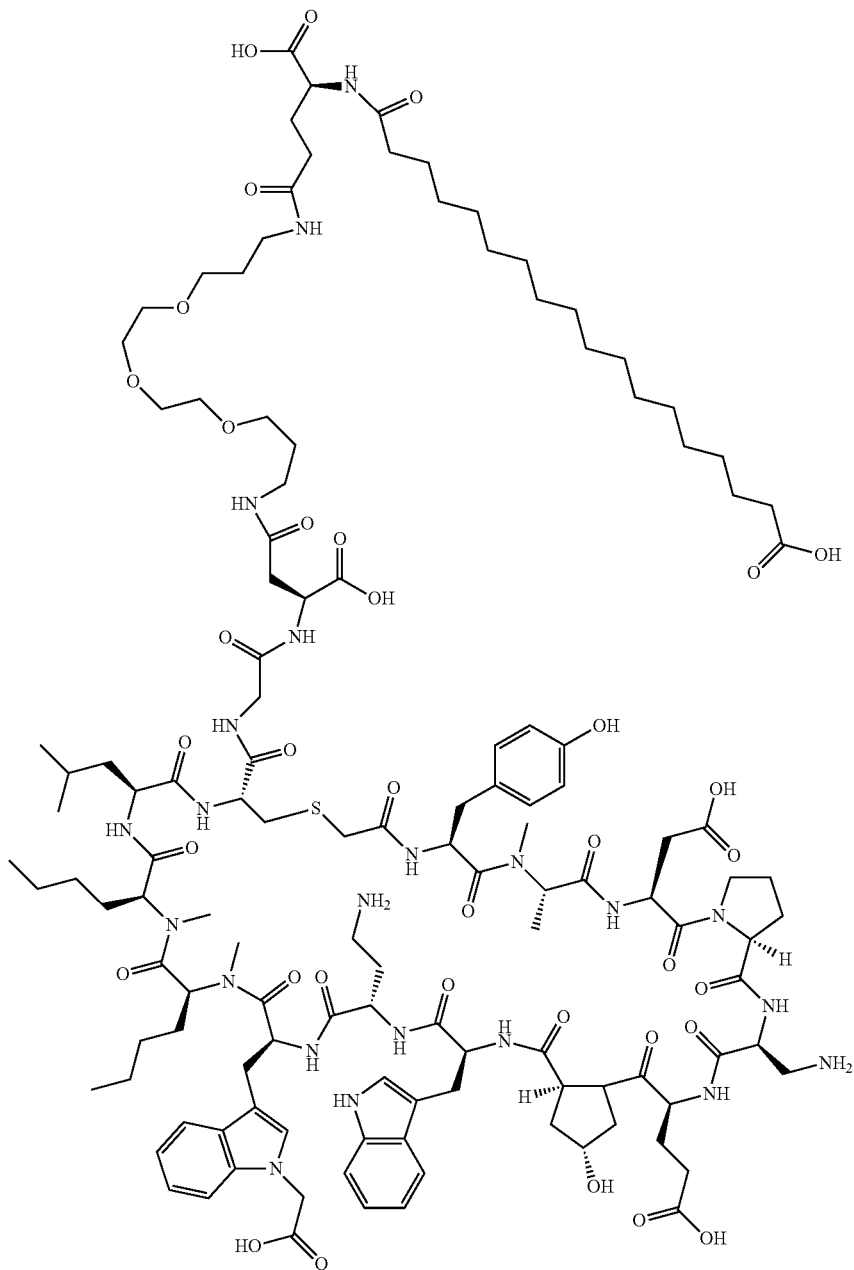 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CN)C(=O)N[C@@H](CCC(=O)O)C(=O)C2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11178 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 25 mg, and its estimated purity by LCMS analysis was 96.7%. Analysis LCMS Condition A: Retention time=3.985 min; ESI-MS(+) m/z 1324.6806 (M+2H).

Preparation of Example 11179

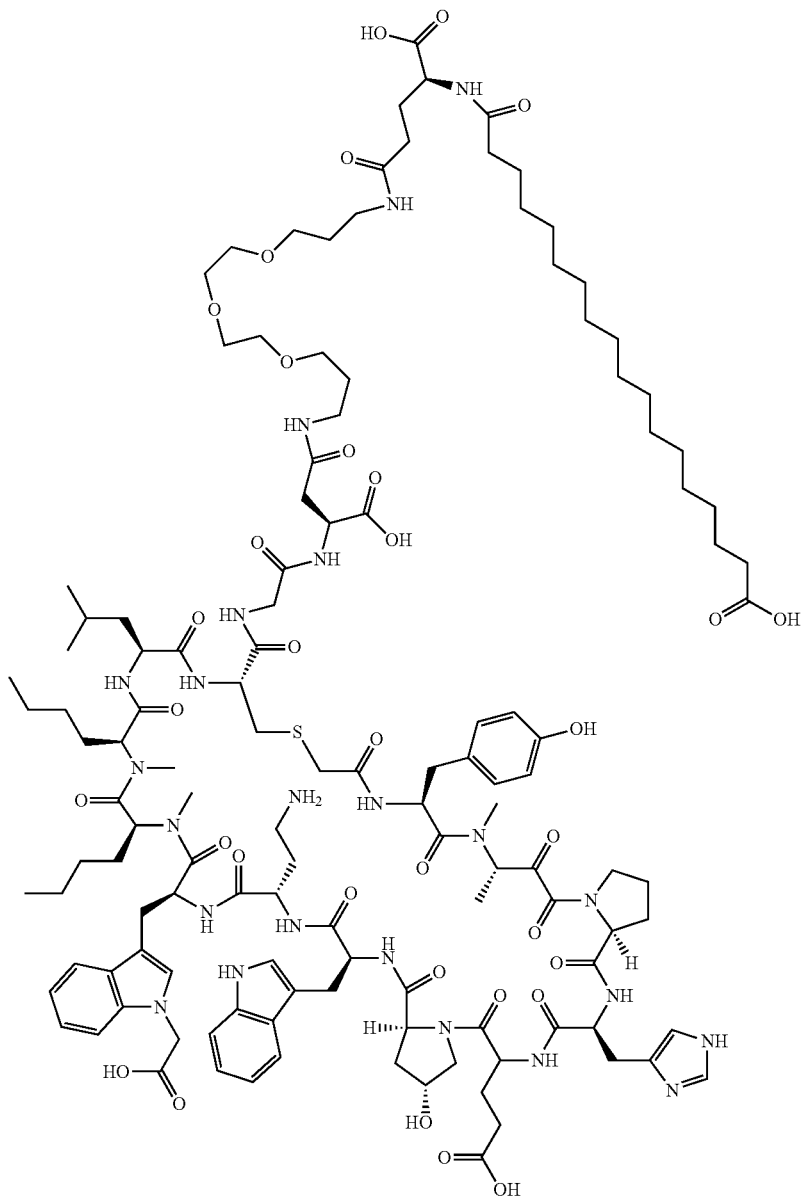 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)C(=O)N2CCC[C@H]2C(=O)N[C@@H](Cc2c[nH]cn2)C(=O)NC(CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11179 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin M was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 30 mg, and its estimated purity by LCMS analysis was 95.5%. Analysis LCMS Condition A: Retention time=3.928 min; ESI-MS(+) m/z 1350.1861 (M+2H).

491
Preparation of Example 11180

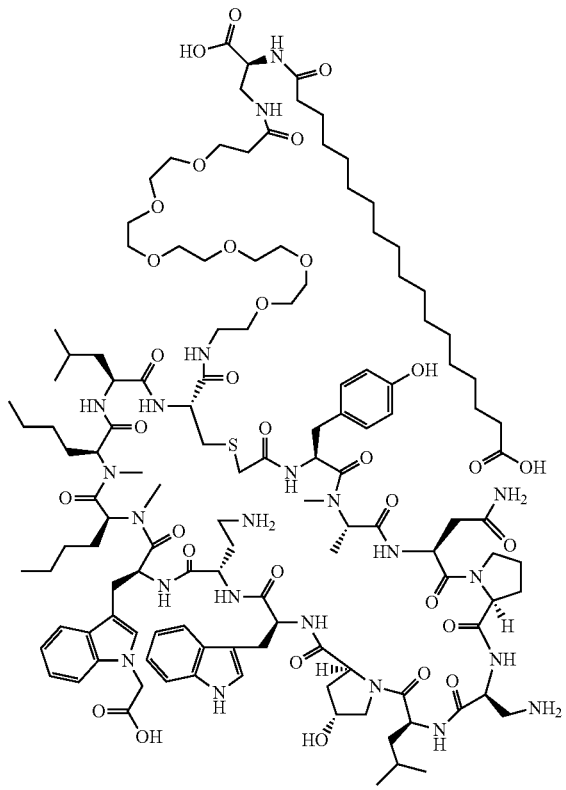 [SMILES: CCCC[C@H]1C(=O)N(C)[C@@H](CCCC)C(=O)N[C@@H](CC(C)C)C(=O)N[C@H](C(=O)NCCOCCOCCOCCOCCOCCOCCC(=O)NC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11180 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 40 mg, and its estimated purity by LCMS analysis was 97.7%. Analysis LCMS Condition A: Retention time=4.750 min; ESI-MS(+) m/z 1275.2005 (M+2H).

492
Preparation of Example 11181

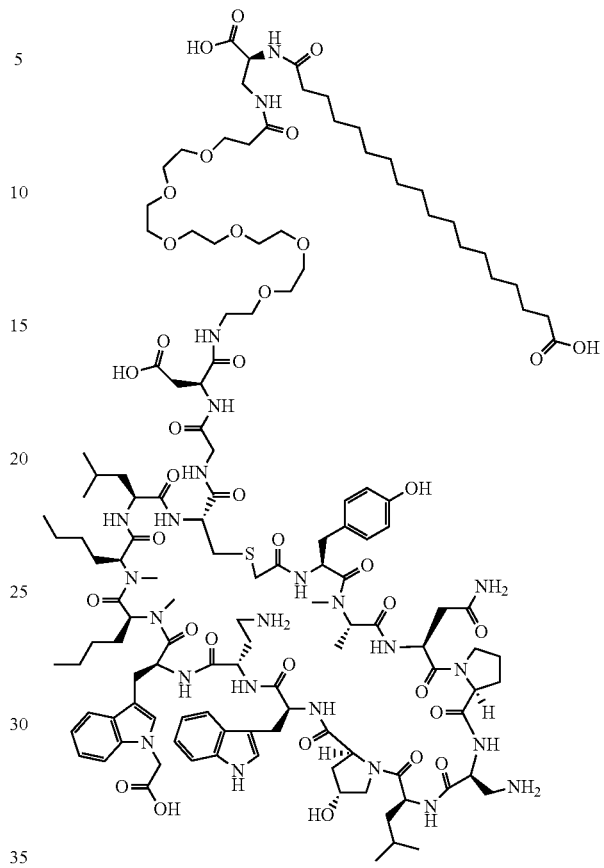

Example 11181 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-N-m OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 25 mg, and its estimated purity by LCMS analysis was 97.8%. Analysis LCMS Condition A: Retention time=4.383 min; ESI-MS(+) m/z 1361.2253 (M+2H).

Preparation of Example 11182

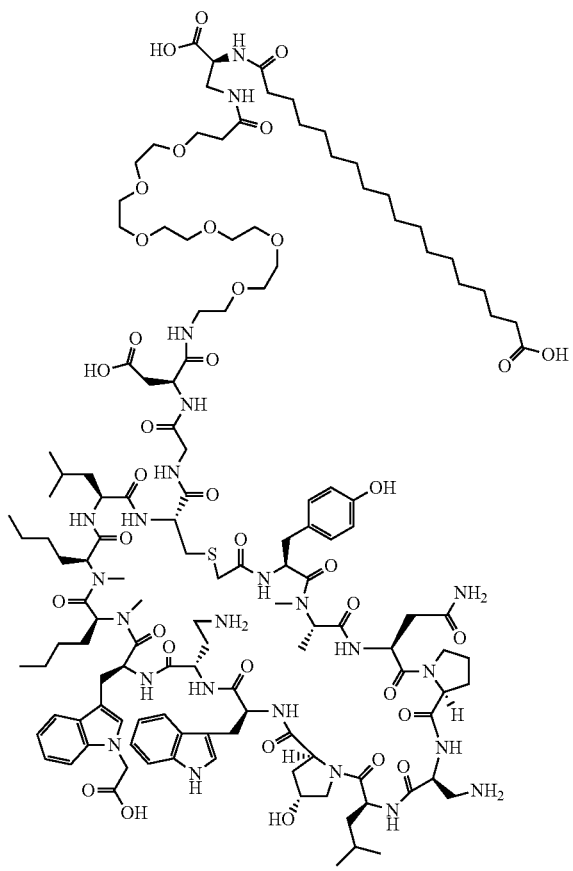 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCOCCOCCOCCOCCOCCOCCC(=O)NC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11182 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 94.9%. Analysis LCMS Condition A: Retention time=4.000 min.

Preparation of Example 11183

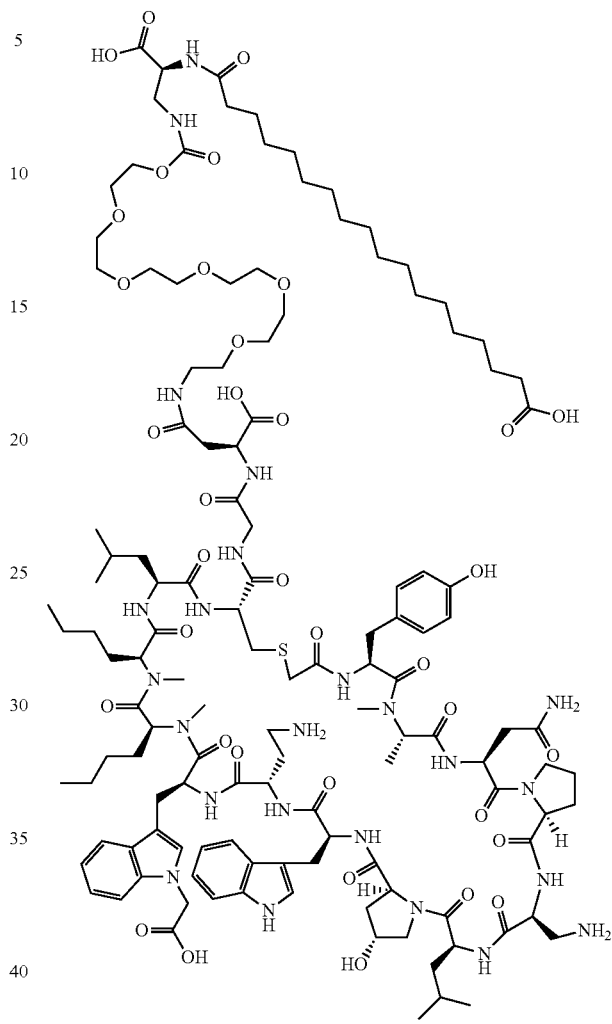

Example 11183 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 27 mg, and its estimated purity by LCMS analysis was 97.0%. Analysis LCMS Condition A: Retention time=3.933 min.

Preparation of Example 11184

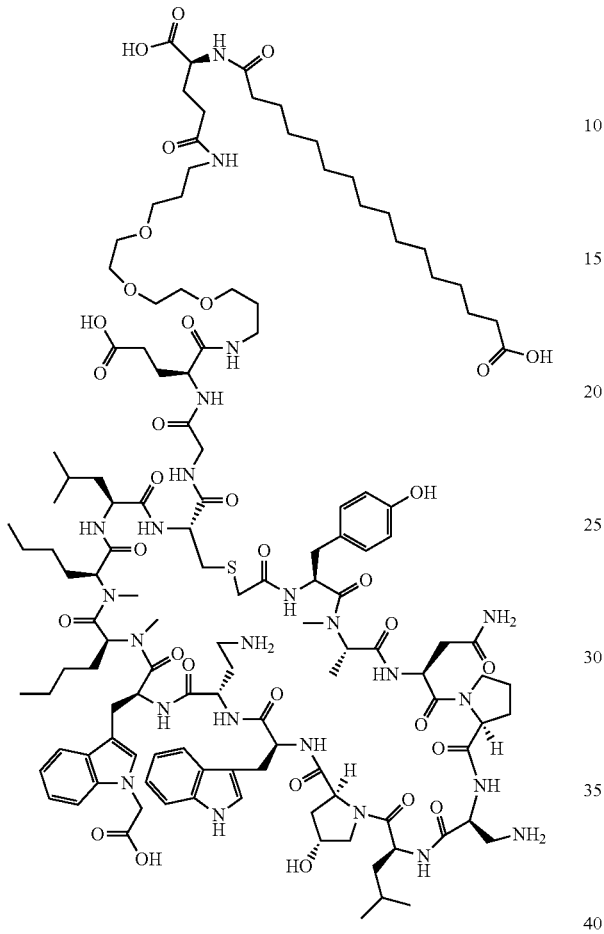

Example 11184 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin V was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 96.0%. Analysis LCMS Condition A: Retention time=3.803 min.

Preparation of Example 11185

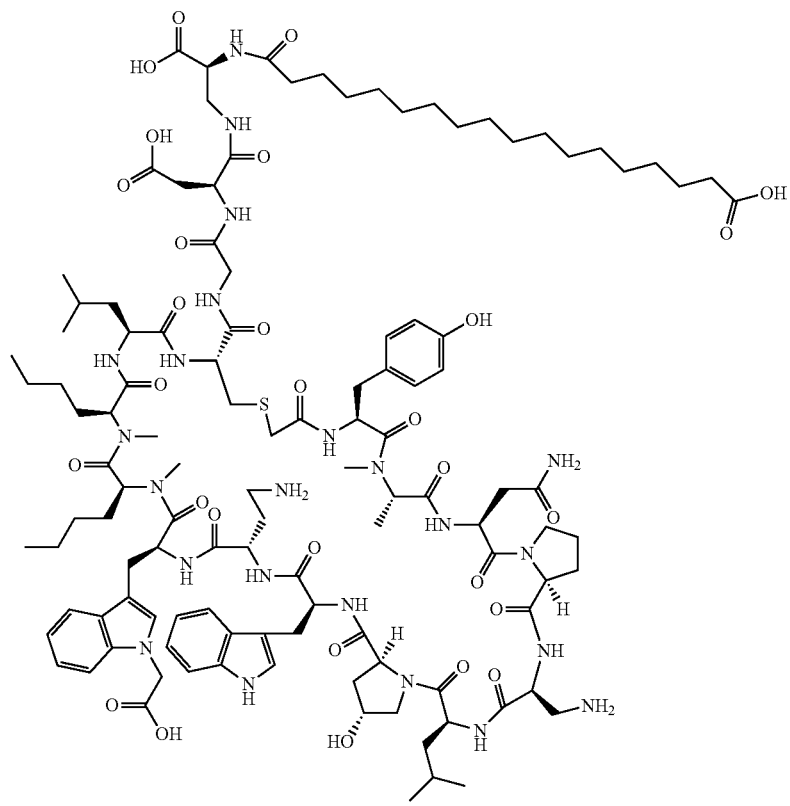 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11185 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 25 mg, and its estimated purity by LCMS analysis was 94.5%. Analysis LCMS Condition A: Retention time=4.056 min.

499
Preparation of Example 11186

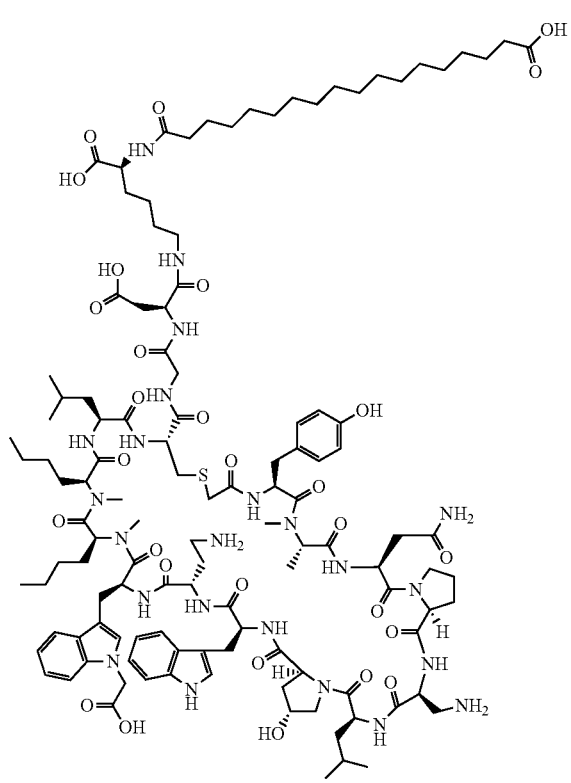 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11186 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin S was used in this synthesis. The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile: water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 30 mg, and its estimated purity by LCMS analysis was 95%. Analysis LCMS Condition A: Retention time=4.163 min.

500
Preparation of Example 11187

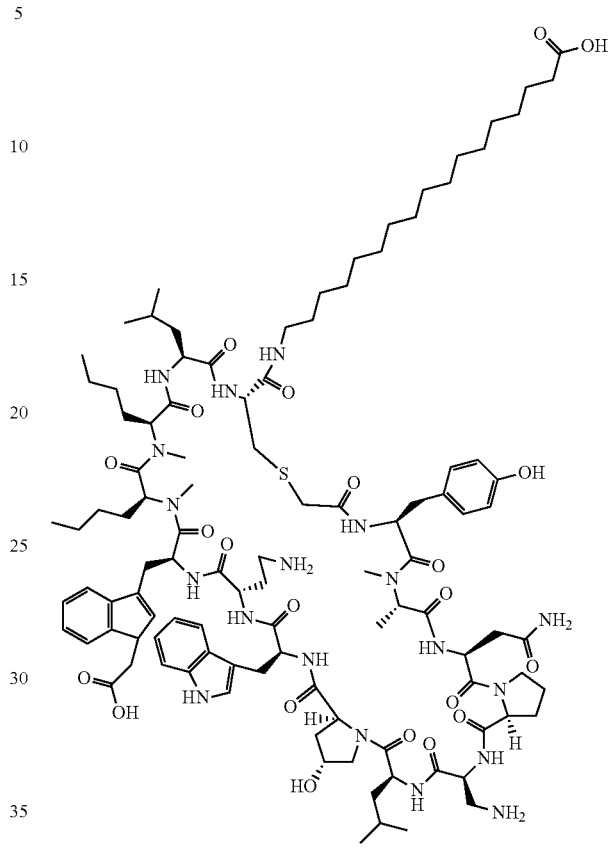

Example 11187 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin A was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 98%. Analysis LCMS Condition C: Retention time=2.01 min; ESI-MS(+) m/z 1050.2 (M+2H); ESI-HRMS(+) m/z: 1050.0926 (M+2H).

Preparation of Example 11188

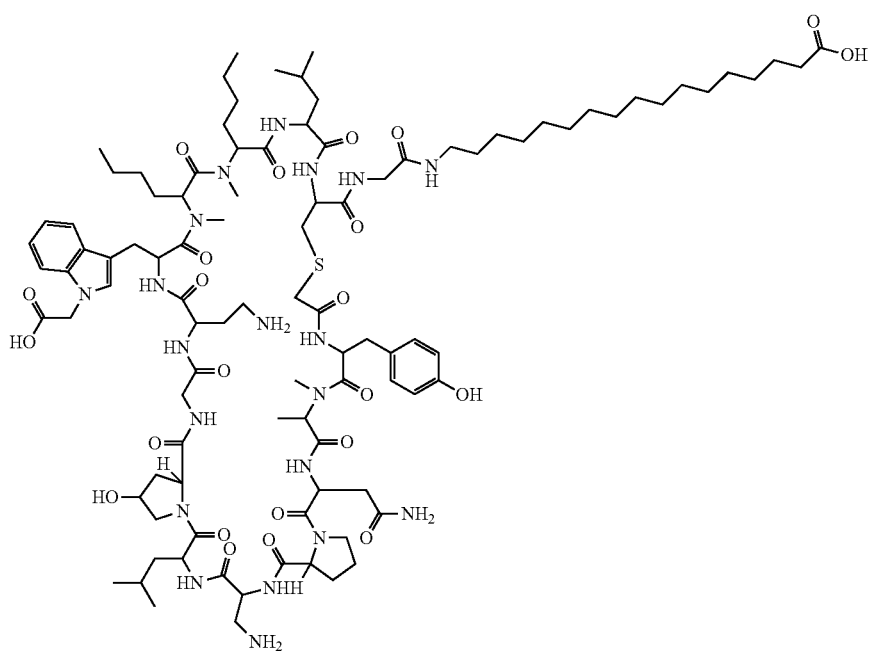 [SMILES: CCCCC1C(=O)N(C)C(CCCC)C(=O)NC(CC(C)C)C(=O)NC(C(=O)NCC(=O)NCCCCCCCCCCCCCCCCC(=O)O)CSCC(=O)NC(Cc2ccc(O)cc2)C(=O)N(C)C(C)C(=O)NC(CC(N)=O)C(=O)N2CCCC2C(=O)NC(CN)C(=O)NC(CC(C)C)C(=O)N2CC(O)CC2C(=O)NCC(=O)NC(CCN)C(=O)NC(Cc2cn(CC(=O)O)c3ccccc23)C(=O)N1C]

Example 11188 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin A was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 98%. Analysis LCMS Condition A: Retention time=5.12 min; ESI-MS(+) m/z 1078.9 (M+2H); ESI-HRMS(+) m/z: 1078.6024 (M+2H).

Preparation of Example 11189

Preparation of Example 11190

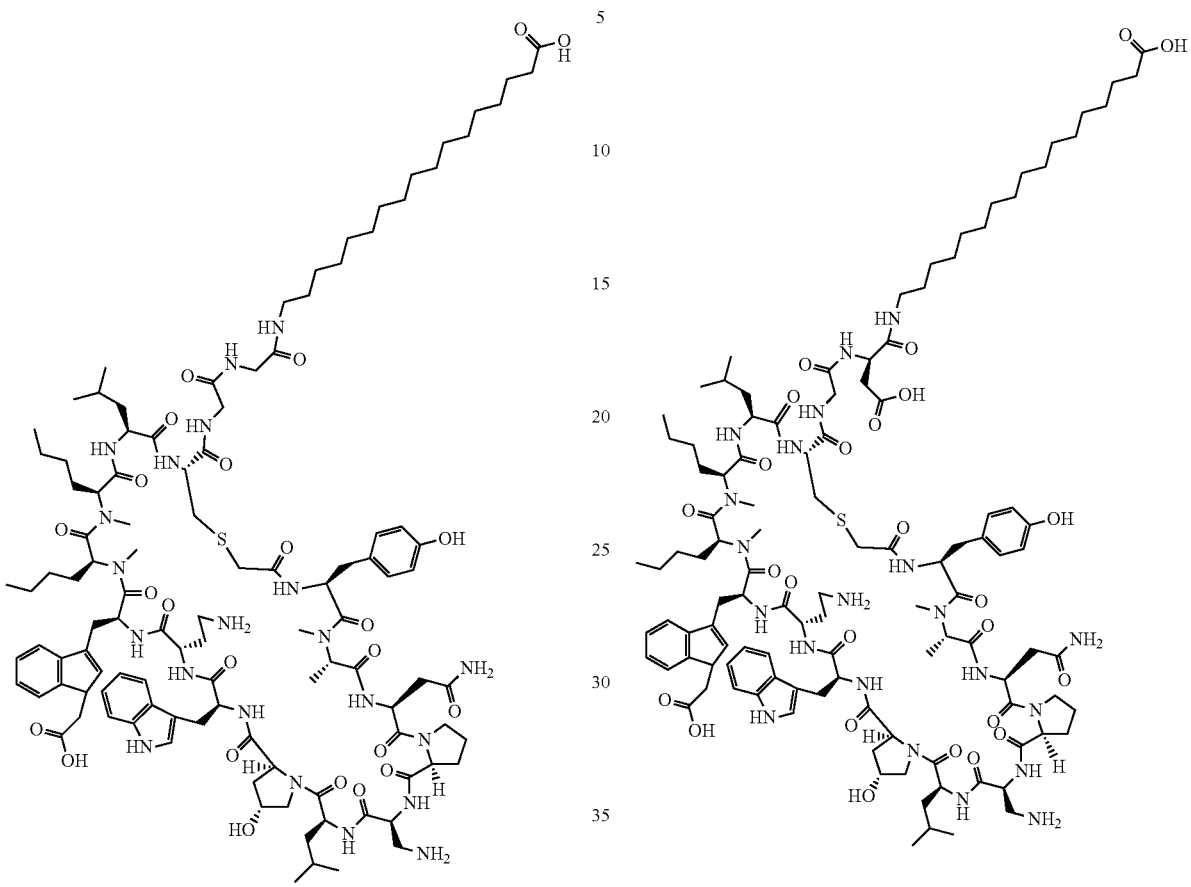

Example 11189 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin A was used in this synthesis. The crude material was purified via preparative LC/MS with the following conditions: Column: waters CSH C-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired product were combined and dried via centrifugal evaporation. The yield of the product was 17 mg, and its estimated purity by LCMS analysis was 100%. Analysis LCMS Condition C: Retention time=2.06 min; ESI-MS(+) m/z 1107.3 (M+2H); ESI-HRMS(+) m/z: 1107.1154 (M+2H).

Example 11190 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin A was used in this synthesis. The crude material was purified via preparative LC/MS with the following conditions Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%. Analysis LCMS Condition C: Retention time=4.46 min; ESI-MS(+) m/z 1136.5 (M+2H); ESI-HRMS(+) m/z: 1136.1179 (M+2H).

Preparation of Example 11191

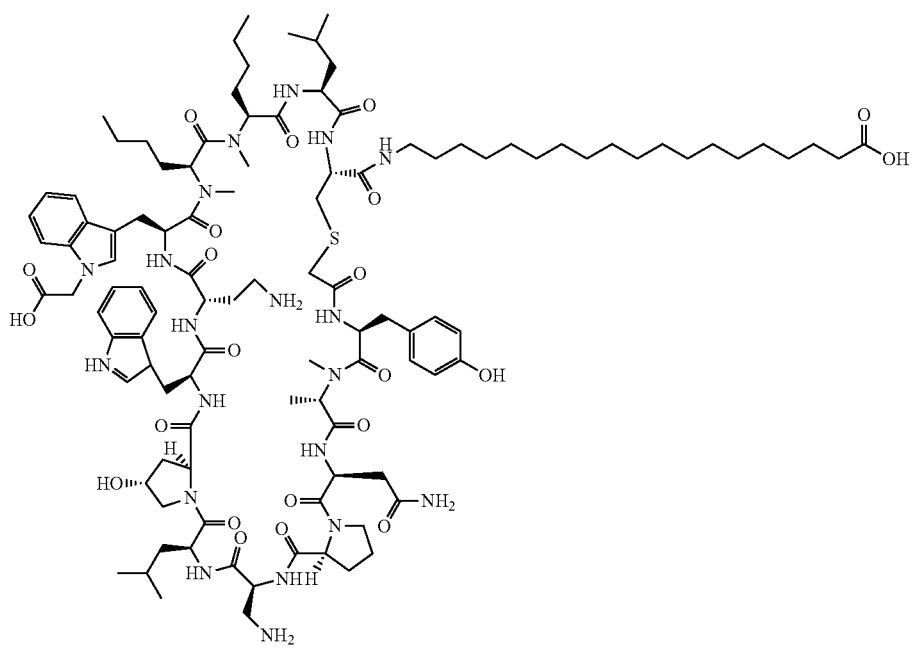 [SMILES: CCCC[C@H]1C(=O)N(C)[C@@H](CCCC)C(=O)N[C@@H](CC(C)C)C(=O)N[C@H](C(=O)NCCCCCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](CC2C=Nc3ccccc32)C(=O)N[C@@H](CCN)C(=O)N[C@@H](Cc2cn(CC(=O)O)c3ccccc23)C(=O)N1C]

Example 11191 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin B was used in this synthesis. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 96%. Analysis LCMS Condition D: Retention time=2.54 min; ESI-MS(+) m/z 1064.0 (M+2H); ESI-HRMS(+) m/z: 1064.1084 (M+2H).

Preparation of Example 11192

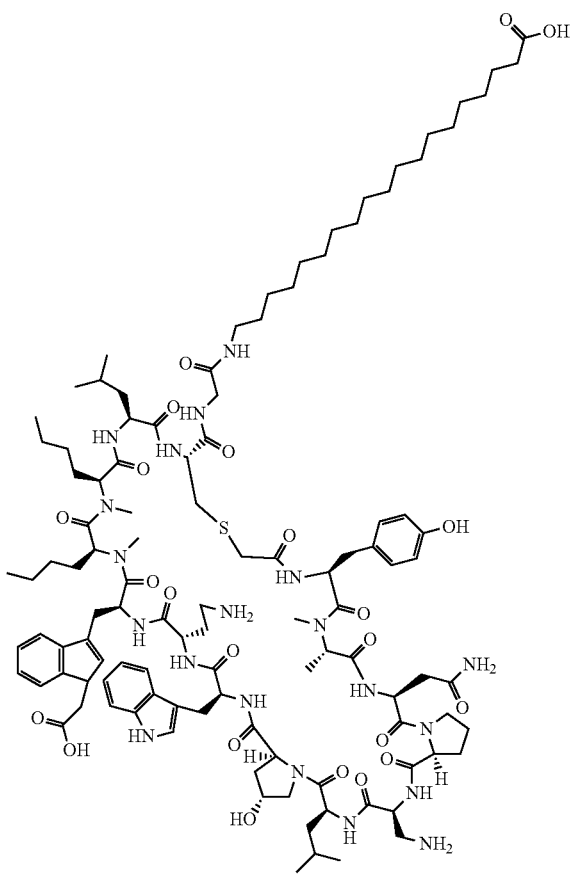 [SMILES: CCCC[C@H]1C(=O)N(C)[C@@H](CCCC)C(=O)N[C@@H](CC(C)C)C(=O)N[C@H](C(=O)NCC(=O)NCCCCCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](CC2=CC(CC(=O)O)c3ccccc32)C(=O)N1C]

Example 11192 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin B was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-85% B over 30 minutes, then a 5-minute hold at 100% B; Flow: 20 mL/min. Fractions containing the desired product were combined and dried via centrifugal evaporation. The yield of the product was 7.1 mg, and its estimated purity by LCMS analysis was 100%. Analysis LCMS Condition C: Retention time=2.08 min; ESI-MS(+) m/z 1092.5 (M+2H); ESI-HRMS(+) m/z: 1092.6200 (M+2H).

Preparation of Example 11193

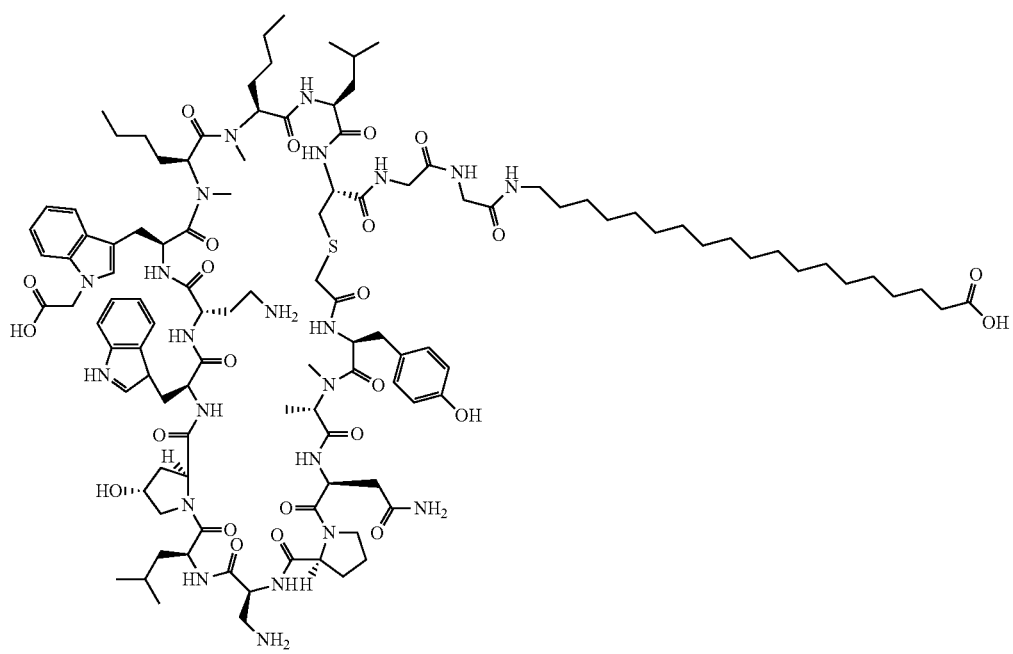 [SMILES: CCCC[C@H]1C(=O)N(C)[C@@H](CCCC)C(=O)N[C@@H](CC(C)C)C(=O)N[C@H](C(=O)NCC(=O)NCC(=O)NCCCCCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](CC2C=Nc3ccccc32)C(=O)N[C@@H](CCN)C(=O)N[C@@H](Cc2cn(CC(=O)O)c3ccccc23)C(=O)N1C]

Example 11205 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin B was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 98%. Analysis LCMS Condition A: Retention time=5.14 min; ESI-MS(+) m/z 1121.4 (M+2H); ESI-HRMS(+) m/z: 1121.1305 (M+2H).

Preparation of Example 11194

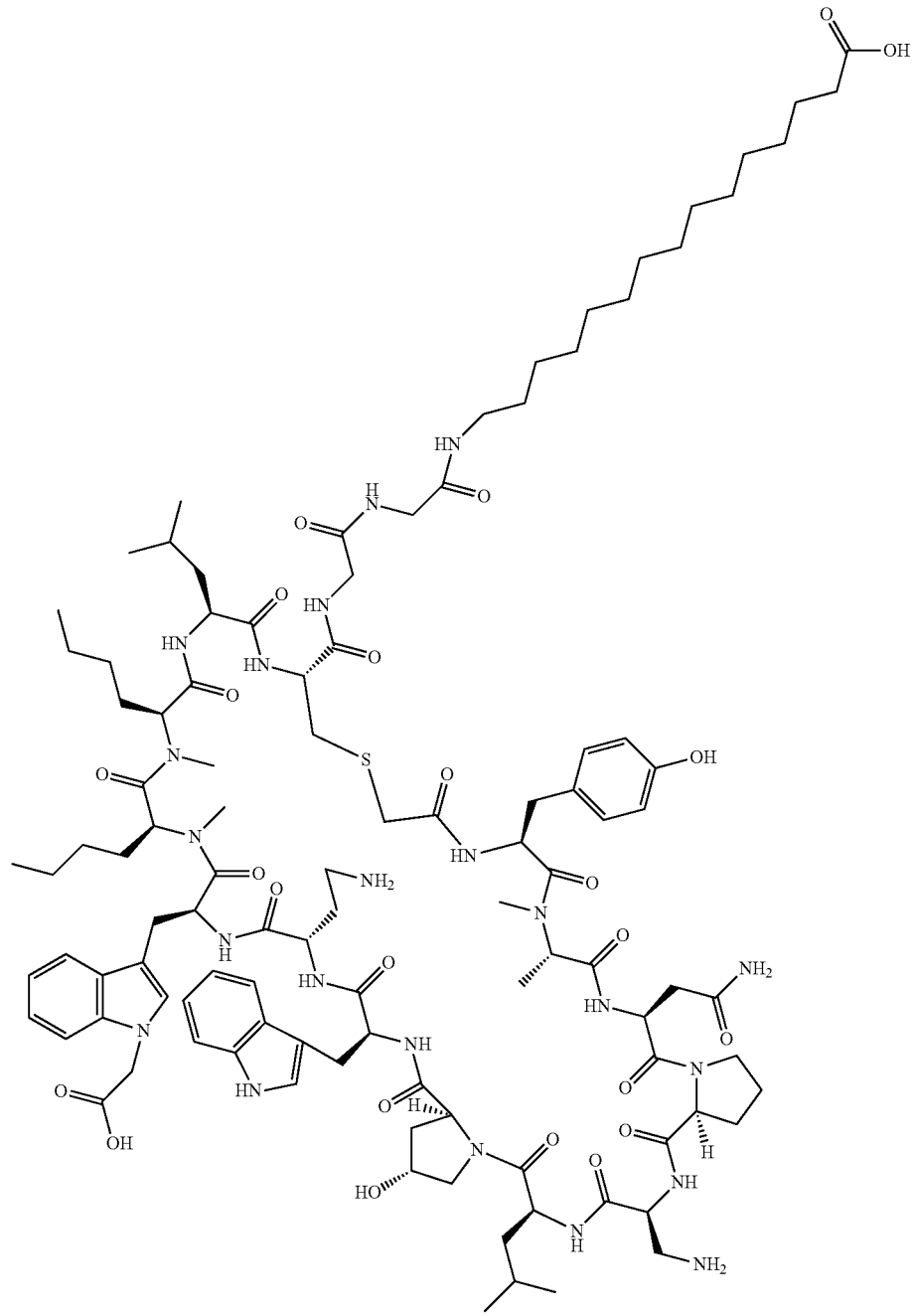 [SMILES: CCCC[C@H]1C(=O)N(C)[C@@H](CCCC)C(=O)N[C@@H](CC(C)C)C(=O)N[C@H](C(=O)NCC(=O)NCC(=O)NCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11194 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin C was used in this synthesis. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 9.2 mg, and its estimated purity by LCMS analysis was 100%. Analysis LCMS Condition C: Retention time=1.80 min; ESI-MS(+) m/z 1093.3 (M+2H); ESI-HRMS(+) m/z: 1093.0963 (M+2H).

Preparation of Example 11195

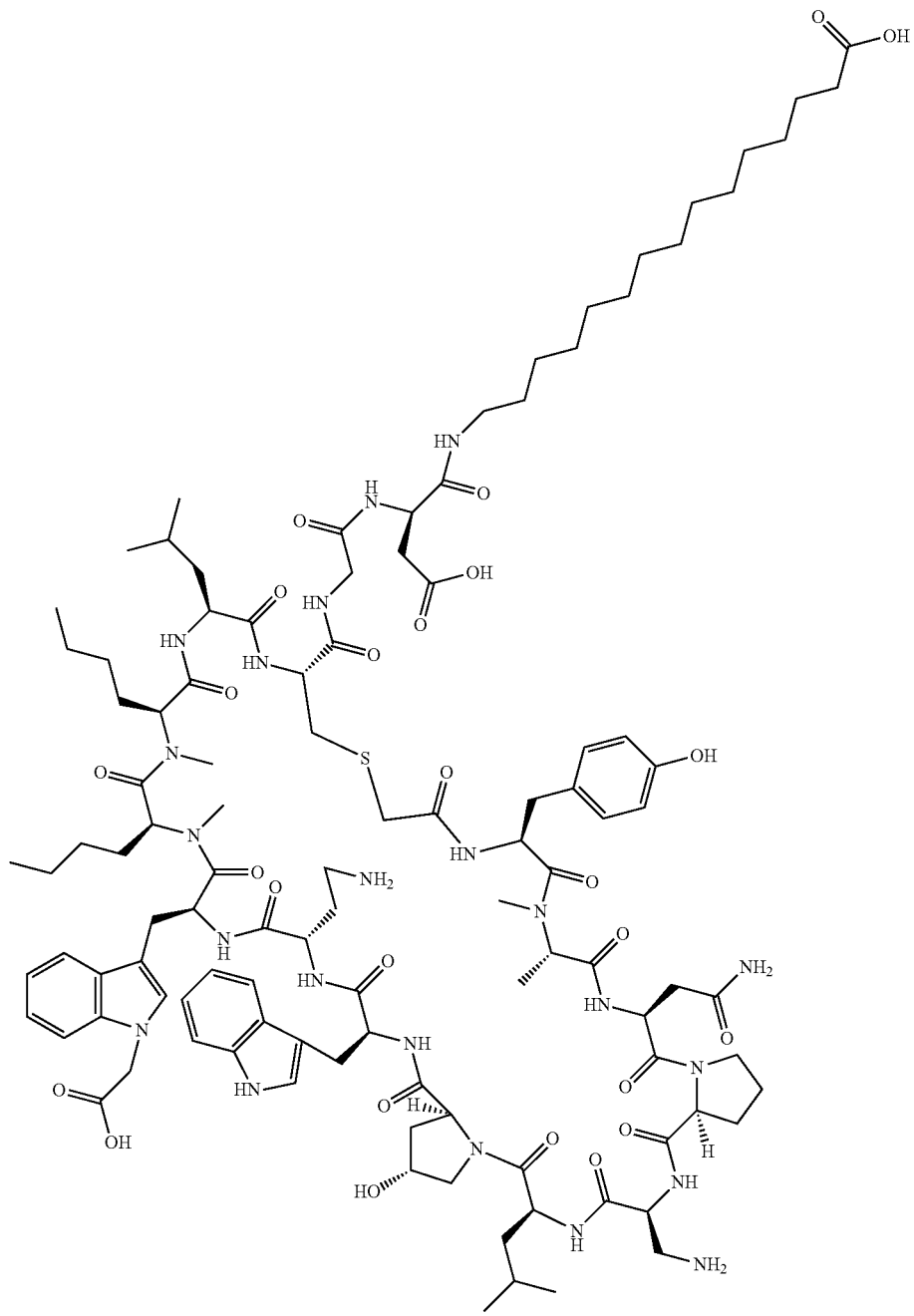 [SMILES: CCCC[C@H]1C(=O)N(C)[C@@H](CCCC)C(=O)N[C@@H](CC(C)C)C(=O)N[C@H](C(=O)NCC(=O)N[C@H](CC(=O)O)C(=O)NCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11195 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin C was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 97%. Analysis LCMS Condition D: Retention time=1.82 min; ESI-MS(+) m/z 1122.4 (M+2H); ESI-HRMS(+) m/z: 1122.0992 (M+2H).

Preparation of Example 11196

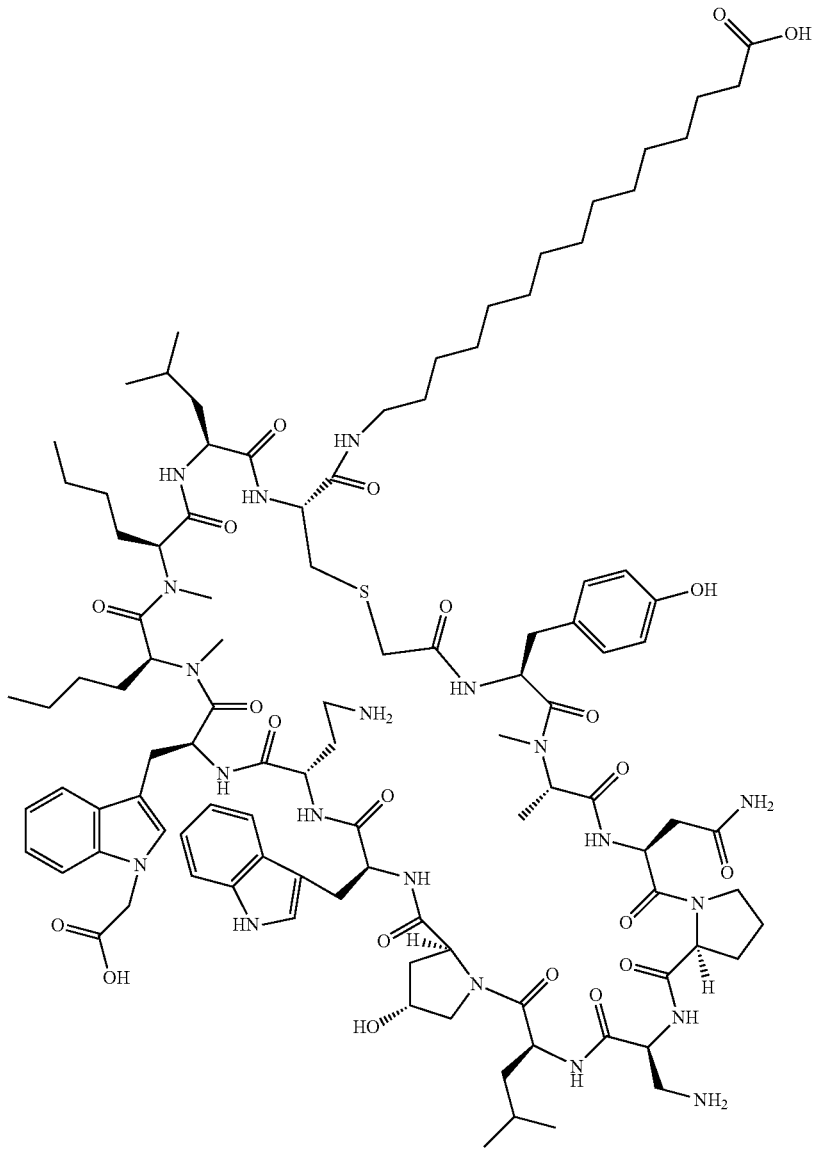 [SMILES: CCCC[C@H]1C(=O)N(C)[C@@H](CCCC)C(=O)N[C@@H](CC(C)C)C(=O)N[C@H](C(=O)NCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11196 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin C was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 97%.

Analysis LCMS Condition A: Retention time=4.84 min; ESI-MS(+) m/z 1036.3 (M+2H); ESI-HRMS(+) m/z: 1036.0766 (M+2H).

Preparation of Example 11197

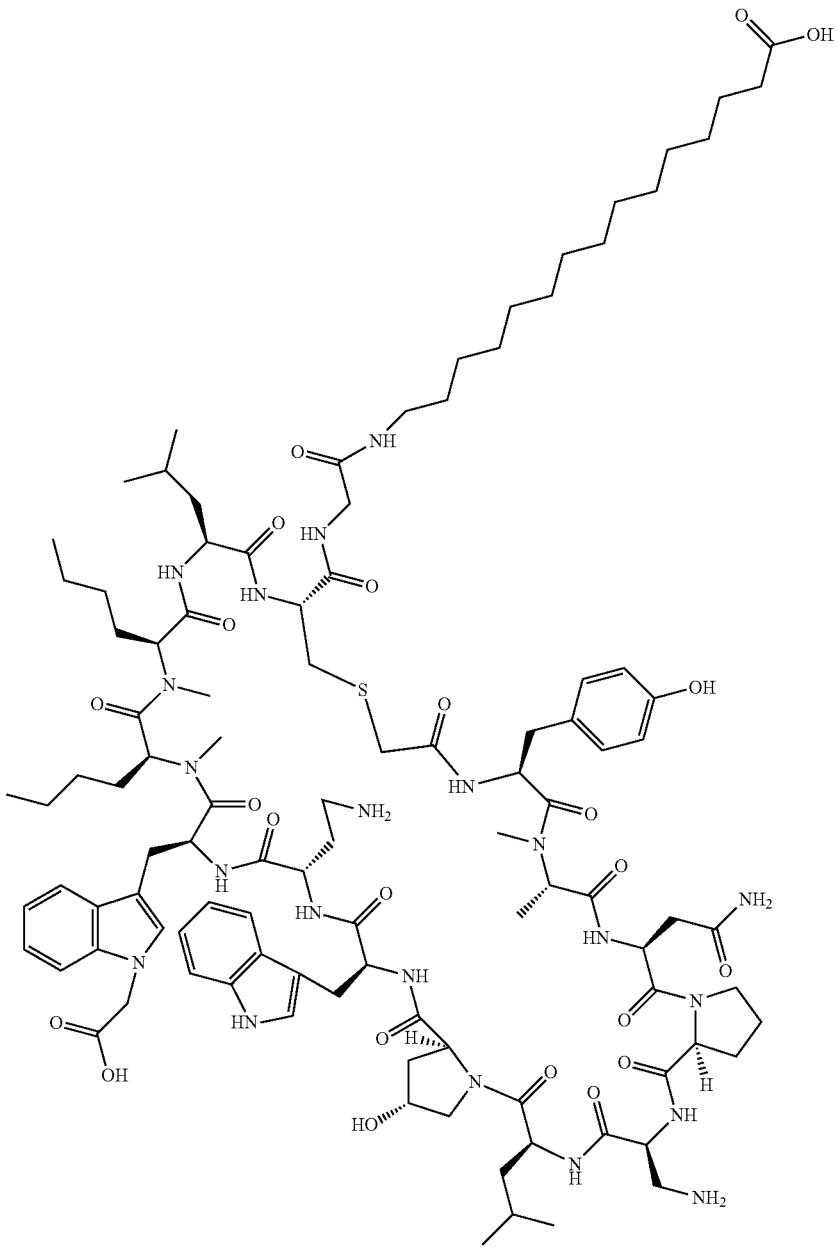 [SMILES: CCCC[C@H]1C(=O)N(C)[C@@H](CCCC)C(=O)N[C@@H](CC(C)C)C(=O)N[C@H](C(=O)NCC(=O)NCCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11197 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin C was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 98%.

Analysis LCMS Condition A: Retention time=4.73 min; ESI-MS(+) m/z 1064.7 (M+2H); ESI-HRMS(+) m/z: 1064.5886 (M+2H).

Preparation of Example 11198

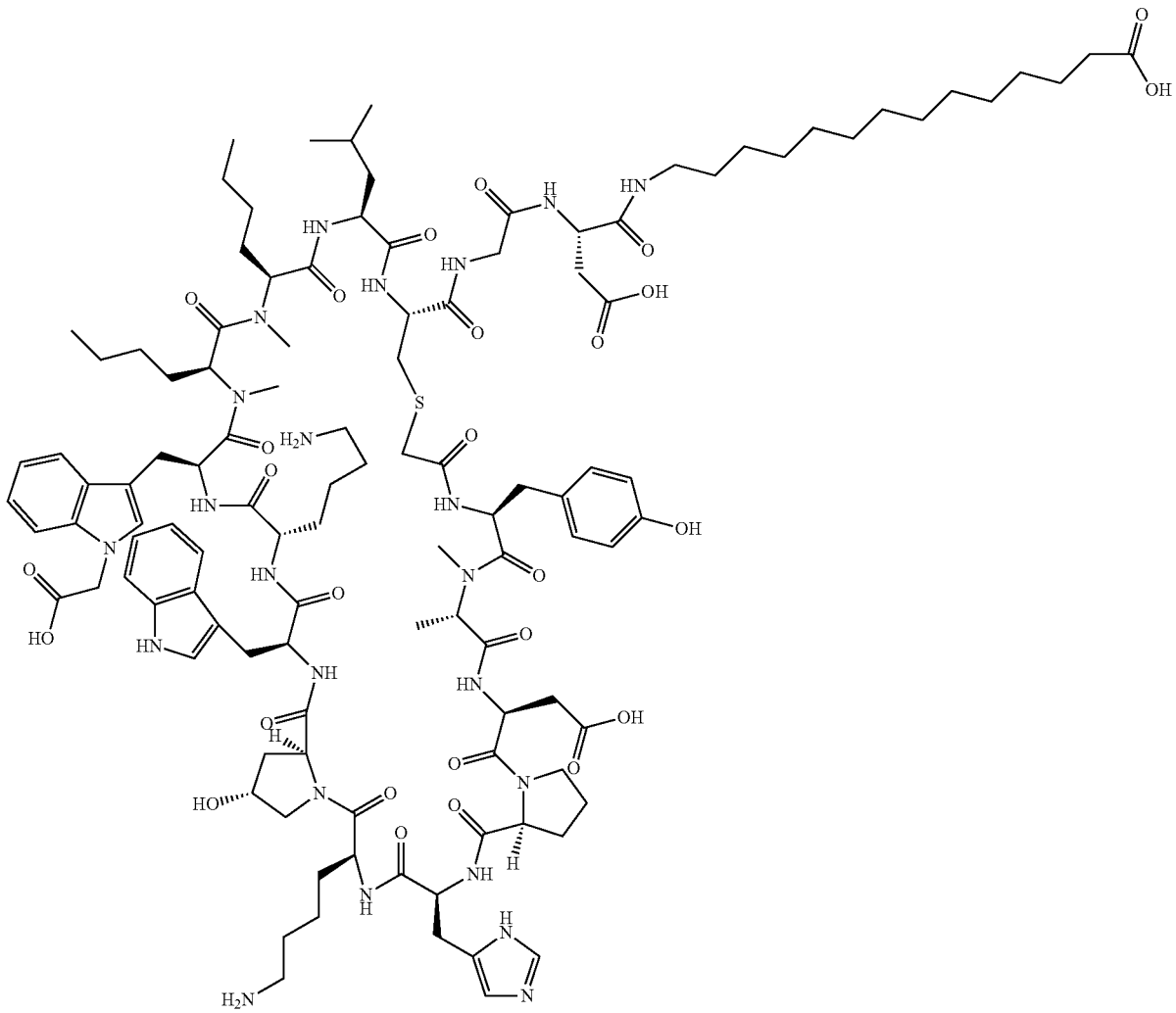 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11198 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 17.1 mg, and its estimated purity by LCMS analysis was 98%. Analysis LCMS Condition B: Retention time=2.25 min; ESI-MS(+) m/z 1162.7 (M+2H); ESI-HRMS(+) m/z: 1162.6110 (M+2H).

Preparation of Example 11199

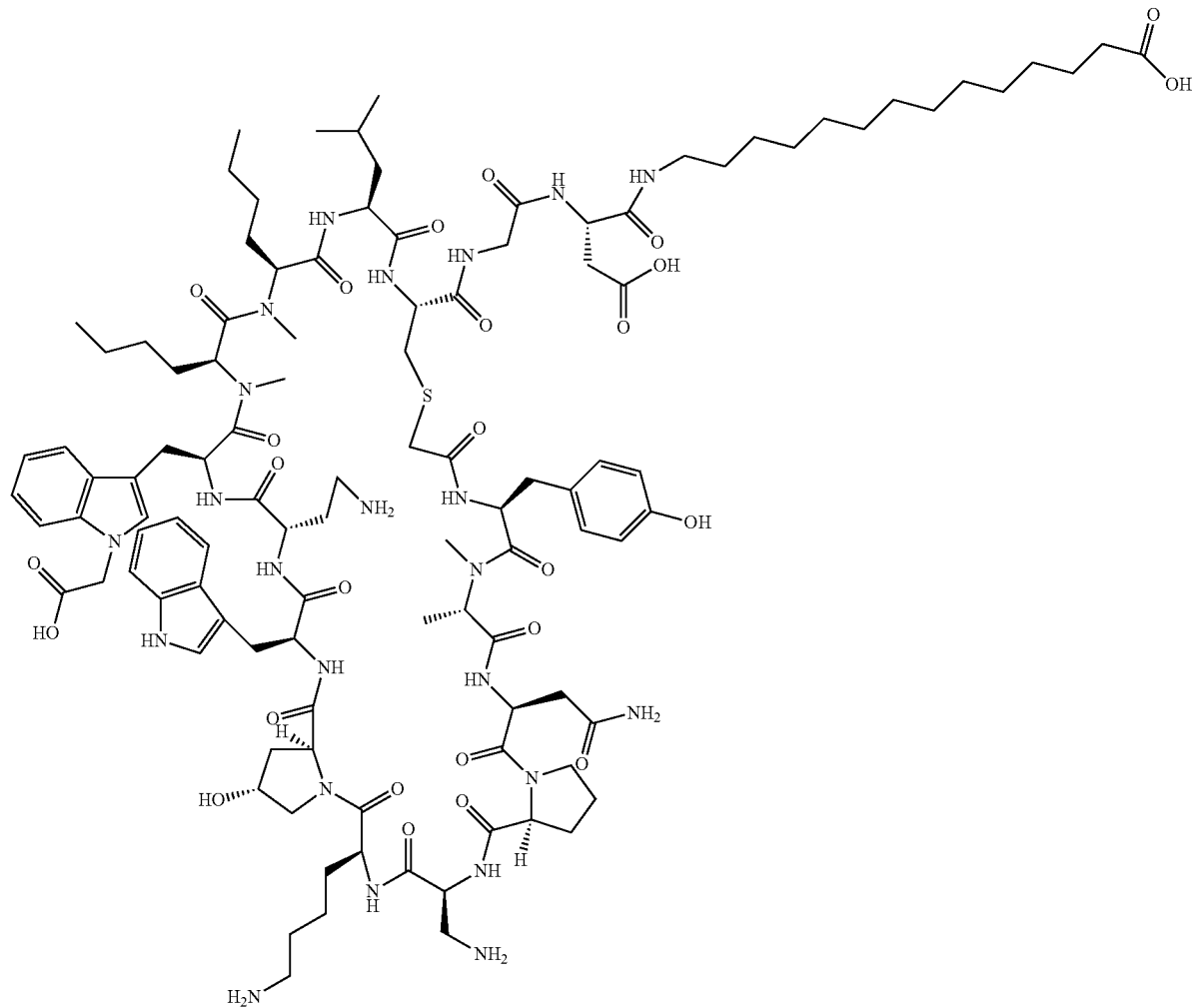 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11199 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 99%.

Analysis LCMS Condition B: Retention time=3.38 min; ESI-MS(+) m/z 1115.4 (M+2H).

Preparation of Example 11200

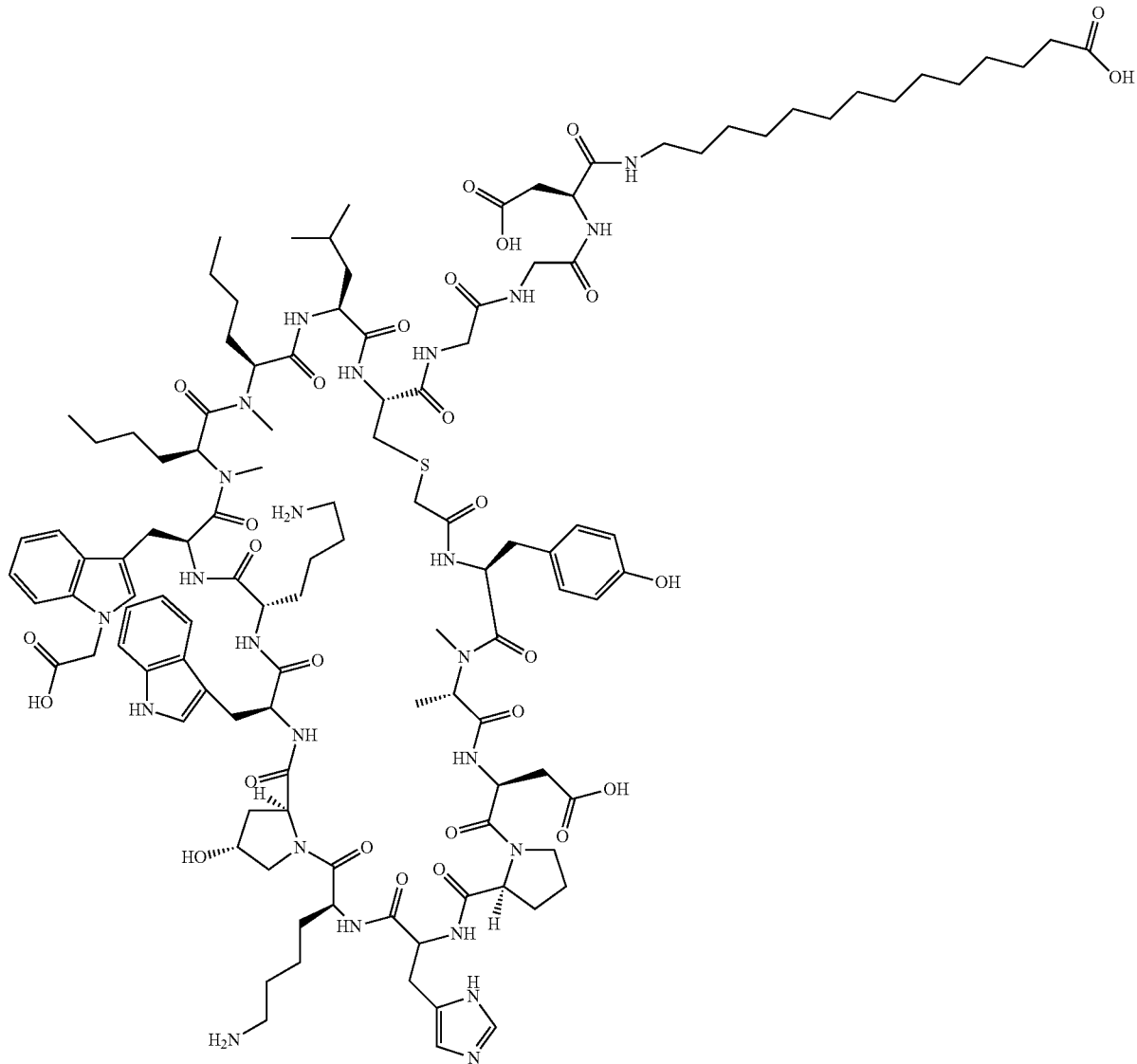 [SMILES: CCCC[C@H]1C(=O)N(C)[C@@H](CCCC)C(=O)N[C@@H](CC(C)C)C(=O)N[C@H](C(=O)NCC(=O)NCC(=O)N[C@@H](CC(=O)O)C(=O)NCCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)NC(Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11200 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-85% B over 25 minutes, then a 5-minute hold at 100% B; Flow: 20 mL/min. Fractions containing the desired product were combined and dried via centrifugal evaporation. The yield of the product was 20.5 mg, and its estimated purity by LCMS analysis was 99%.

Analysis LCMS Condition B: Retention time=2.22 min; ESI-MS(+) m/z 1191.4 (M+2H); ESI-HRMS(+) m/z: 1191.1218 (M+2H).

Preparation of Example 11201

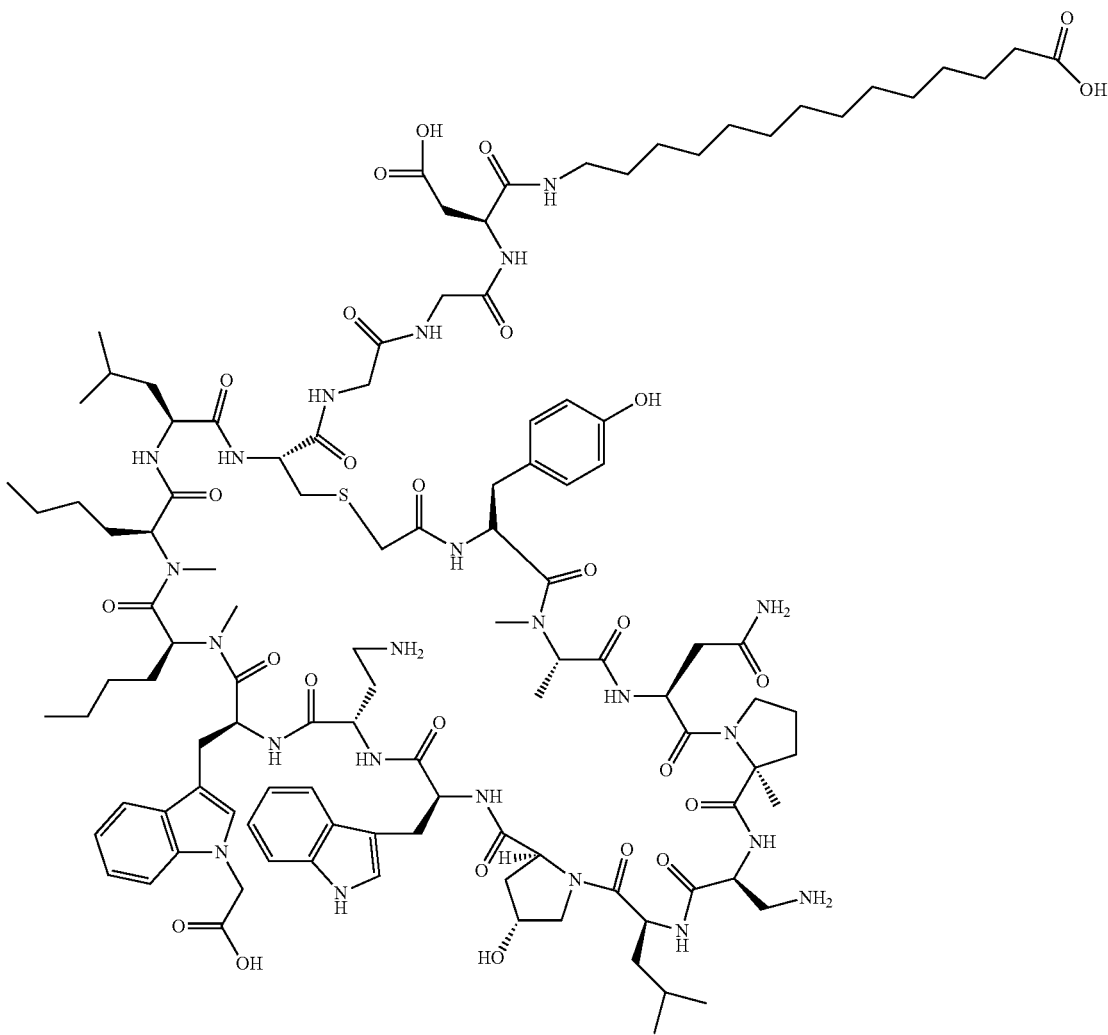

Example 11201 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile: water with 0.1% TFA; Mobile Phase B: 90:10 acetonitrile: water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 98%.

Analysis LCMS Condition B: Retention time=2.40 min; ESI-MS(+) m/z 1143.7 (M+2H); ESI-HRMS(+) m/z: 1143.6036 (M+2H).

Preparation of Example 11202

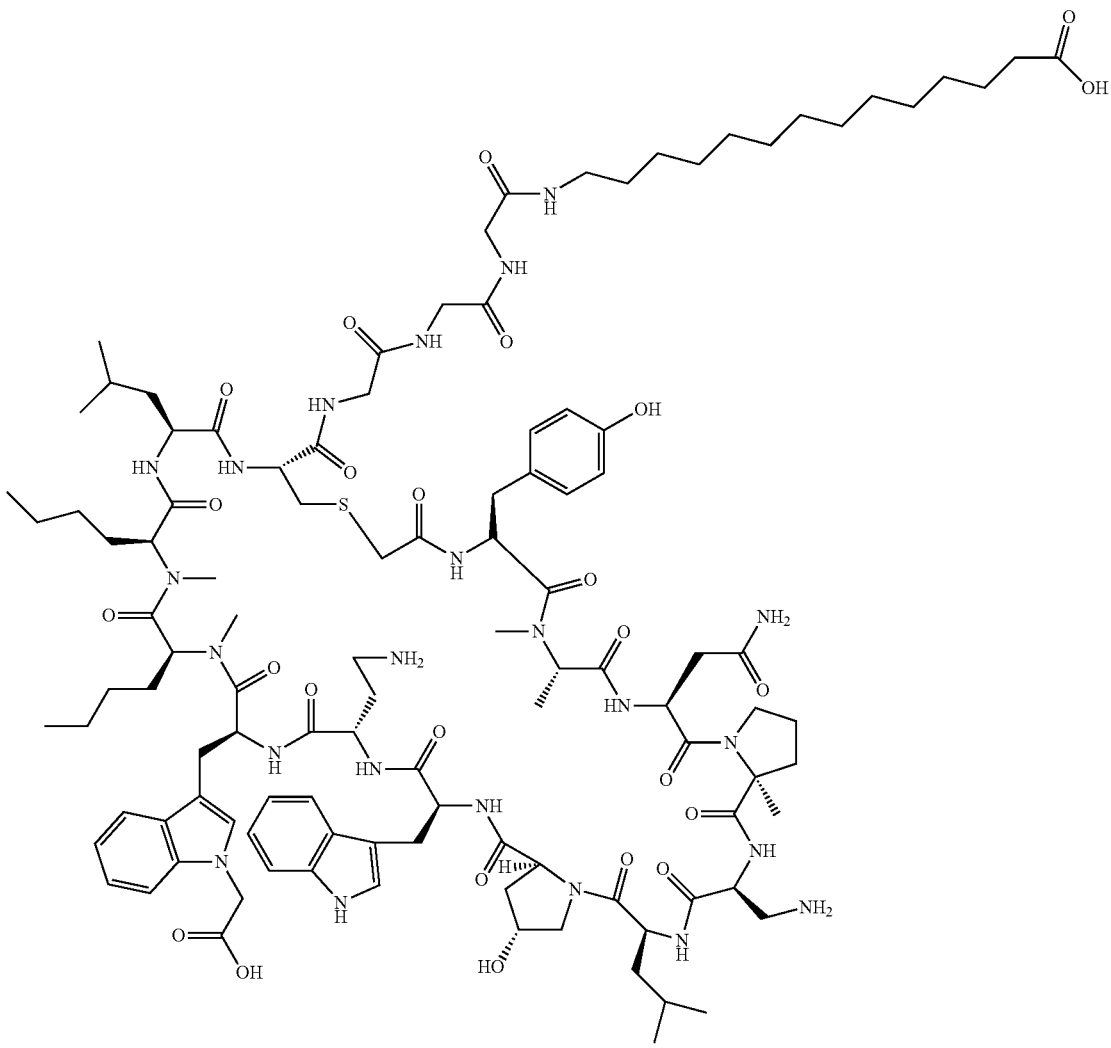

Example 11202 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min.

Fractions containing the desired product were combined and dried via centrifugal evaporation. The yield of the product was 14 mg, and its estimated purity by LCMS analysis was 98%. Analysis LCMS Condition B: Retention time=2.57 min; ESI-MS(+) m/z 1114.8 (M+2H); ESI-HRMS(+) m/z: 1114.6003 (M+2H).

Preparation of Example 11203

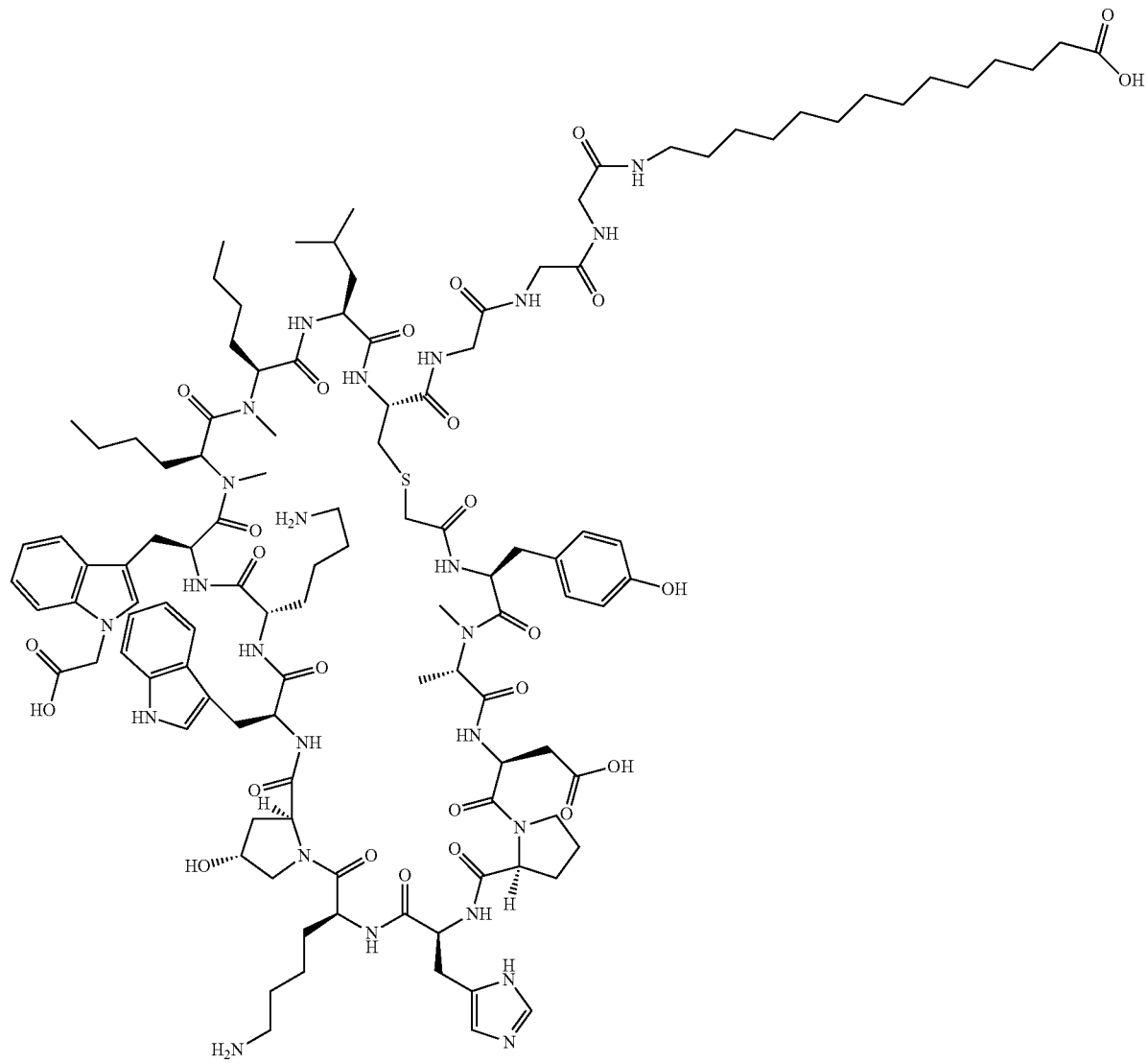 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11203 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin D was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-85% B over 25 minutes, then a 5-minute hold at 100% B; Flow: 20 mL/min. Fractions containing the desired product were combined and dried via centrifugal evaporation. The yield of the product was 19 mg, and its estimated purity by LCMS analysis was 99%. Analysis LCMS Condition B: Retention time=2.44 min; ESI-MS(+) m/z 1162.4 (M+2H); ESI-HRMS(+) m/z: 1162.1192 (M+2H).

Preparation of Example 11204

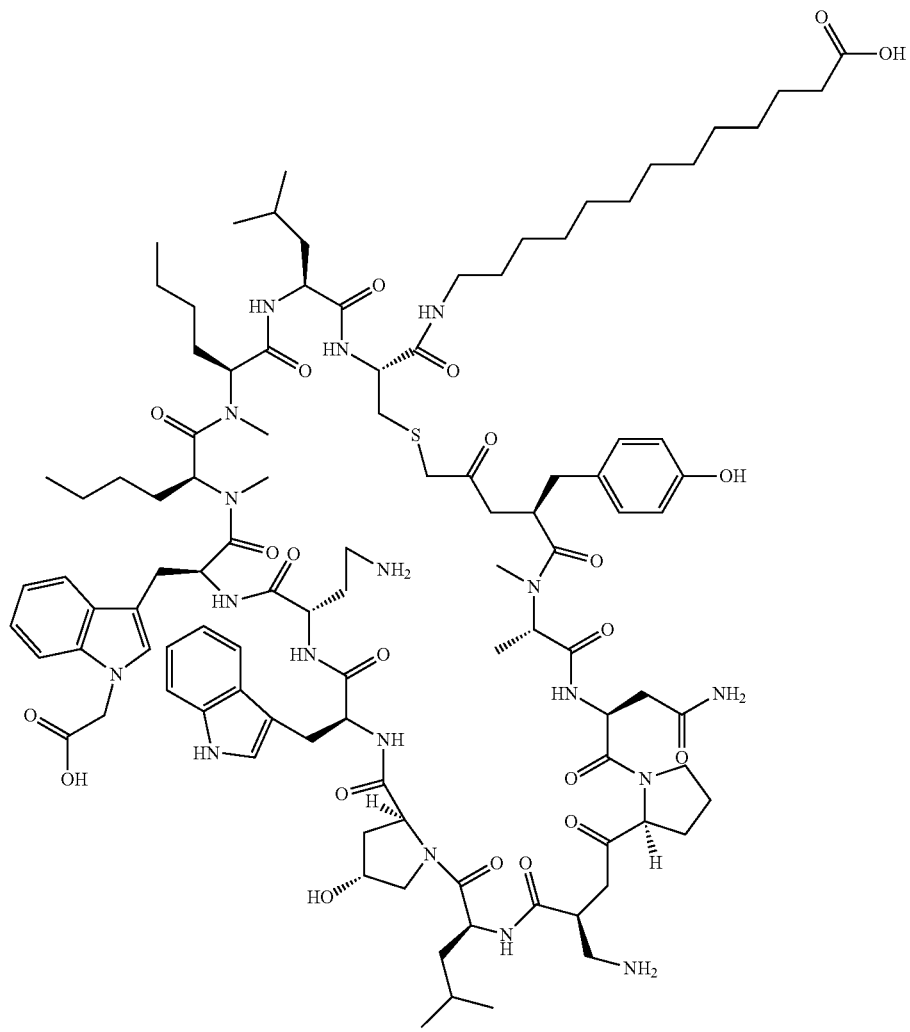

Example 11204 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 16.7 mg, and its estimated purity by LCMS analysis was 97%. Analysis LCMS Condition D: Retention time=1.94 min; ESI-MS(+) m/z 1022.4 (M+2H); ESI-HRMS(+) m/z: 1022.0615 (M+2H).

Preparation of Example 11205

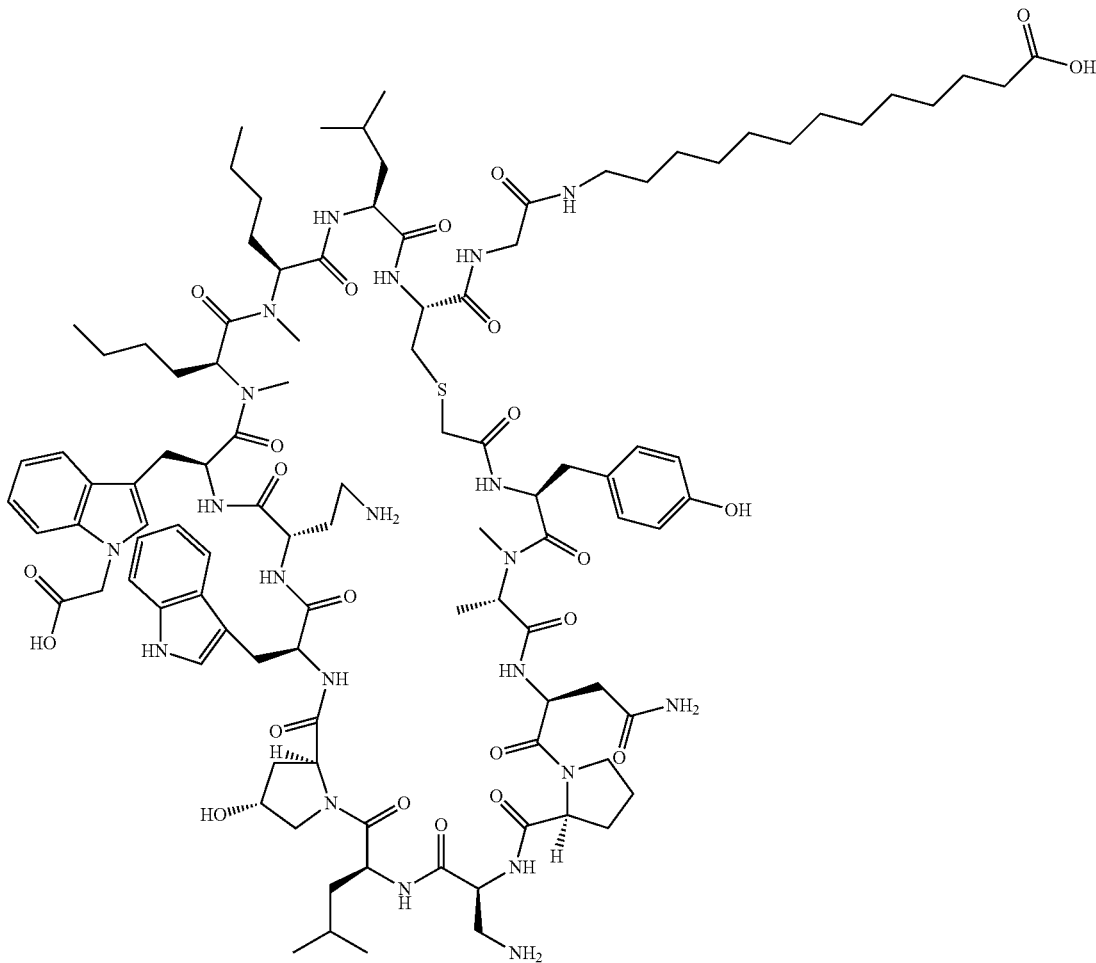 [SMILES: CCCC[C@H]1C(=O)N(C)[C@@H](CCCC)C(=O)N[C@@H](CC(C)C)C(=O)N[C@H](C(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11205 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 95%. Analysis LCMS Condition D: Retention time=1.87 min; ESI-MS(+) m/z 1050.3 (M+2H); ESI-HRMS(+) m/z: 1050.5731 (M+2H).

Preparation of Example 11206

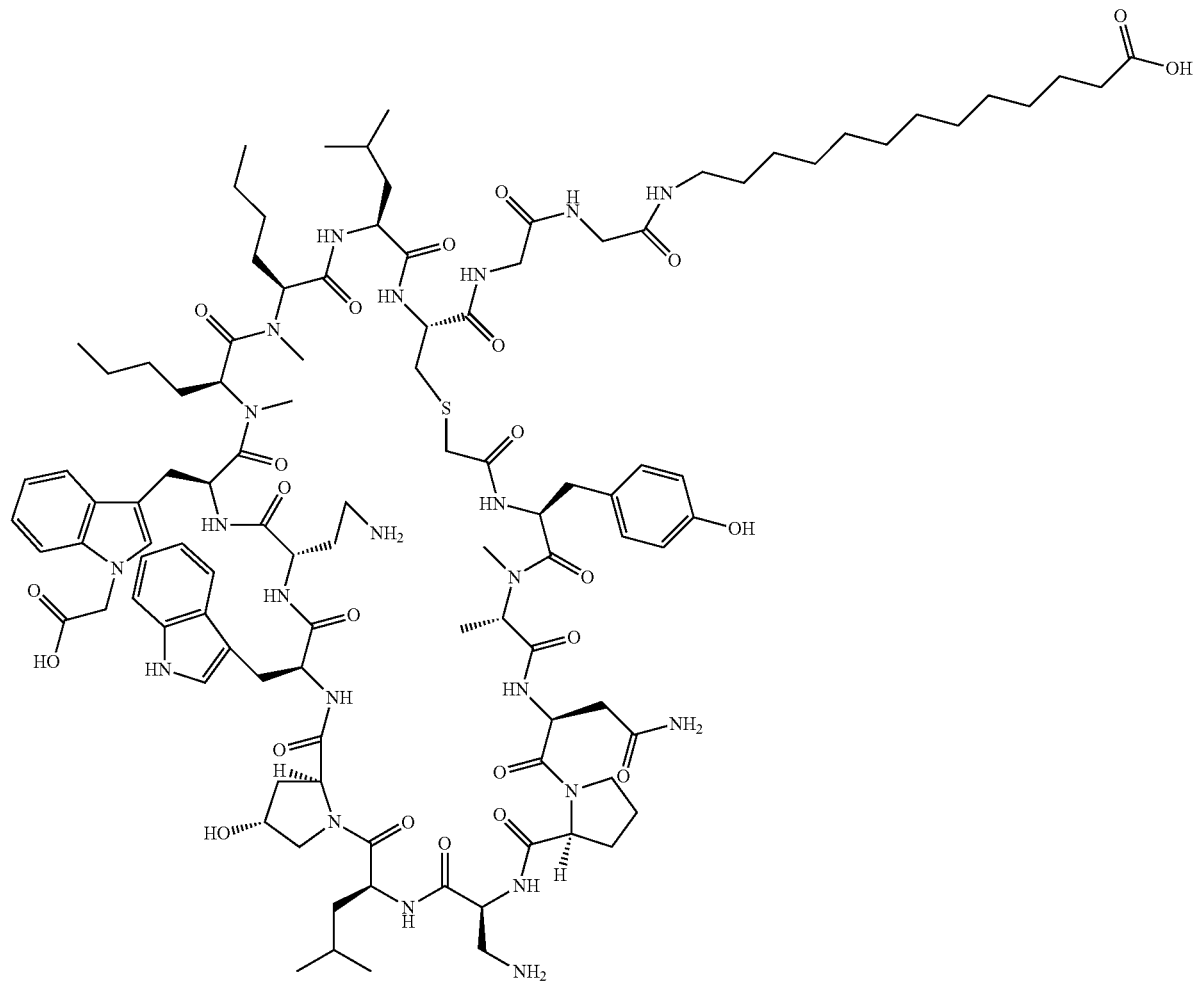 [SMILES: CCCC[C@H]1C(=O)N(C)[C@@H](CCCC)C(=O)N[C@@H](CC(C)C)C(=O)N[C@H](C(=O)NCC(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11206 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 95%. Analysis LCMS Condition D: Retention time=1.84 min; ESI-MS(+) m/z 1079.1 (M+2H); ESI-HRMS(+) m/z: 1079.0823 (M+2H).

Preparation of Example 11207

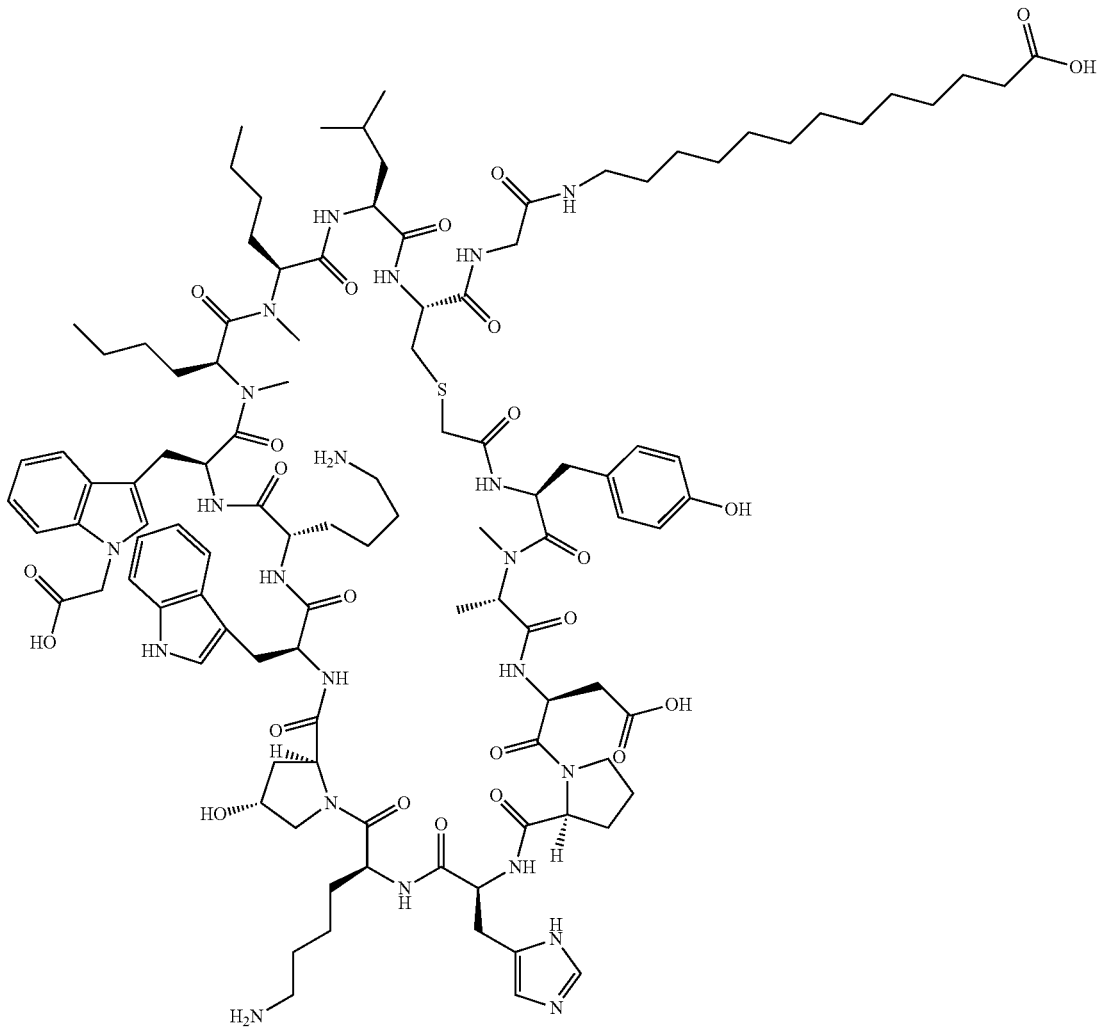 [SMILES: CCCC[C@H]1C(=O)N(C)[C@@H](CCCC)C(=O)N[C@@H](CC(C)C)C(=O)N[C@H](C(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11207 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 98%. Analysis LCMS Condition A: Retention time=4.14 min; ESI-MS(+) m/z 1098.2 (M+2H); ESI-HRMS(+) m/z: 1098.0917 (M+2H).

Preparation of Example 11208

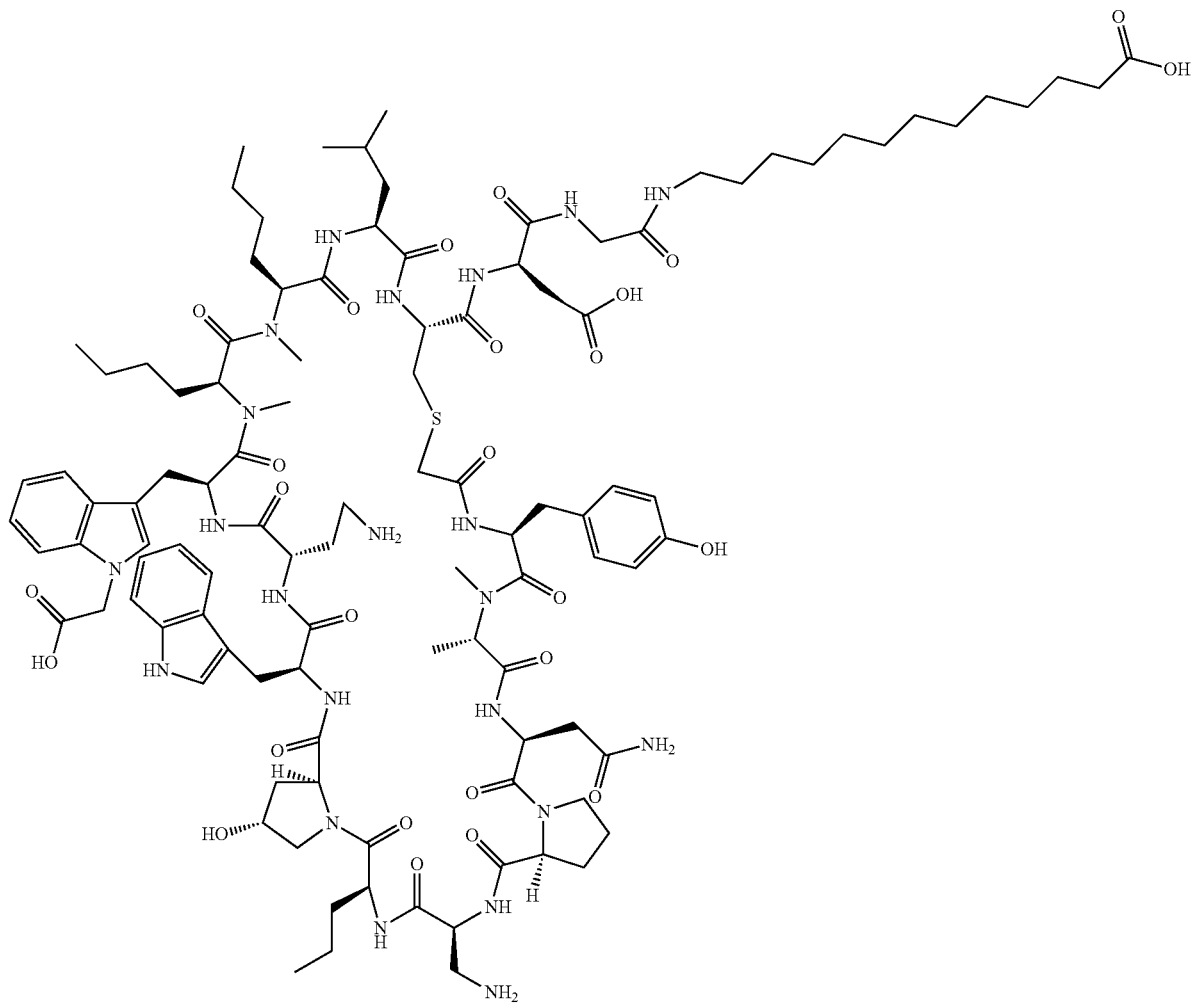 [SMILES: CCCC[C@H]1C(=O)N(C)[C@@H](CCCC)C(=O)N[C@@H](CC(C)C)C(=O)N[C@H](C(=O)N[C@H](CC(=O)O)C(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CCC)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11208 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6 mg, and its estimated purity by LCMS analysis was 100%. Analysis LCMS Condition B: Retention time=2.41 min; ESI-MS(+) m/z 1108.5 (M+2H); ESI-HRMS(+) m/z: 1108.0856 (M+2H).

Preparation of Example 11209

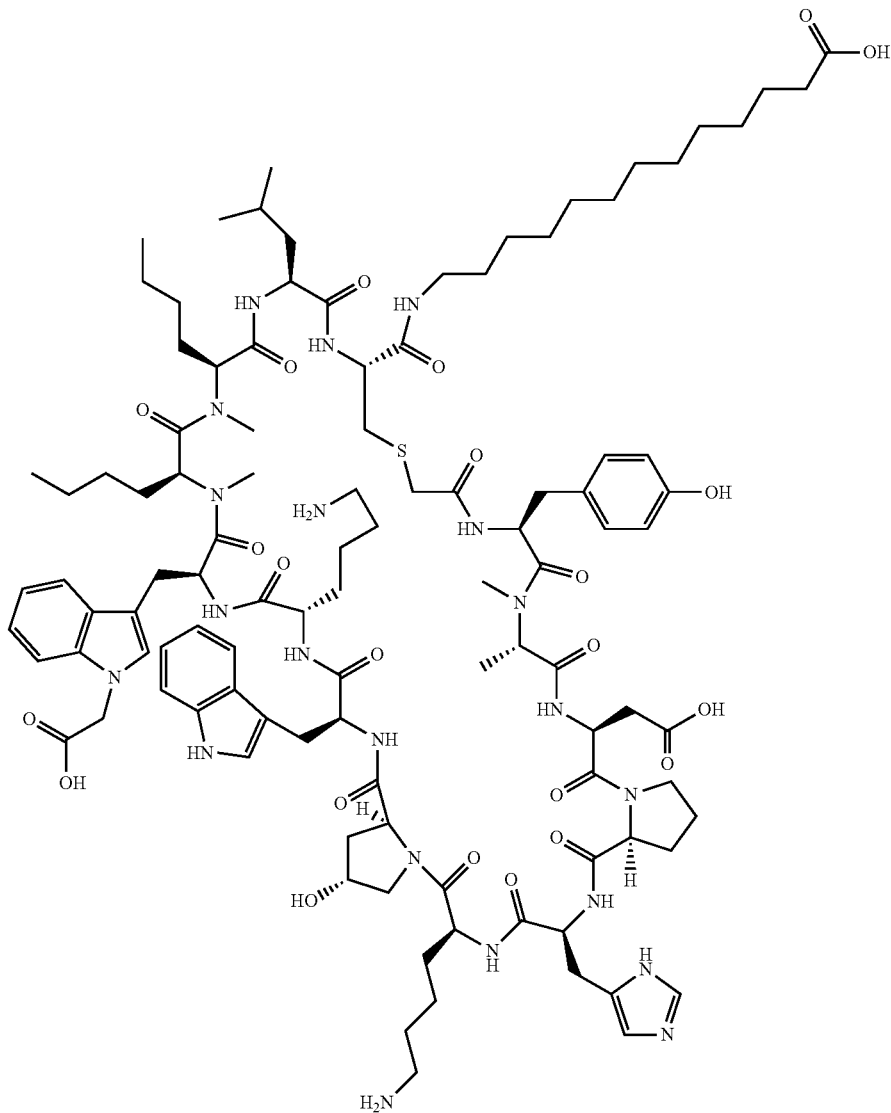 [SMILES: CCCC[C@H]1C(=O)N(C)[C@@H](CCCC)C(=O)N[C@@H](CC(C)C)C(=O)N[C@H](C(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11209 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 100%. Analysis LCMS Condition D: Retention time=1.83 min; ESI-MS(+) m/z 1070.0 (M+2H); ESI-HRMS(+) m/z: 1069.5802 (M+2H).

Preparation of Example 11210

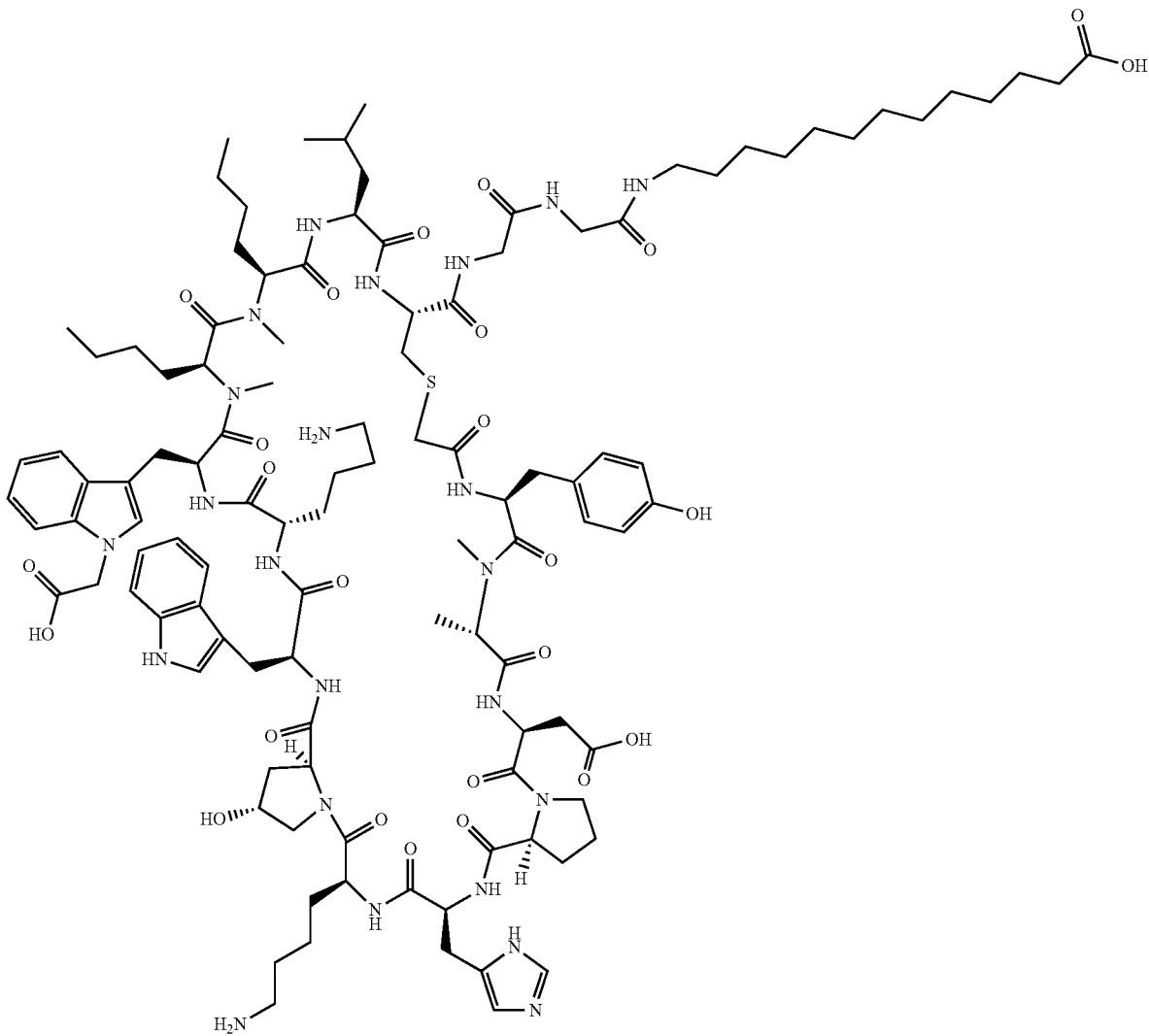 [SMILES: CCCC[C@H]1C(=O)N(C)[C@@H](CCCC)C(=O)N[C@@H](CC(C)C)C(=O)N[C@H](C(=O)NCC(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11210 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 100%. Analysis LCMS Condition A: Retention time=3.96 min; ESI-MS(+) m/z 1126.8 (M+2H); ESI-HRMS(+) m/z: 1126.6015 (M+2H).

Preparation of Example 11211

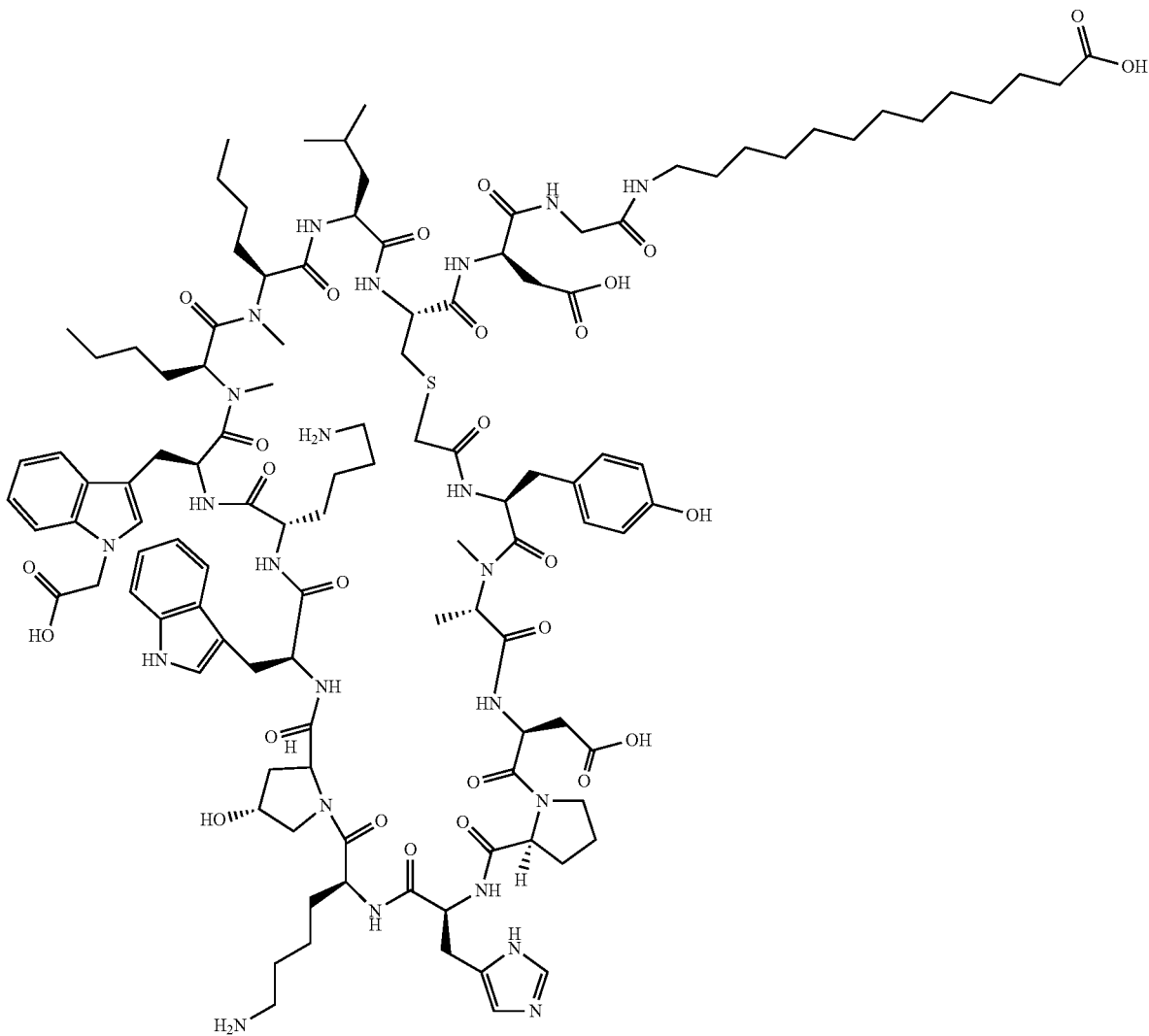

Example 11211 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 7.6 mg, and its estimated purity by LCMS analysis was 96%. Analysis LCMS Condition C: Retention time=1.46 min; ESI-MS(+) m/z 1155.2 (M+2H); ESI-HRMS(+) m/z: 1155.6043 (M+2H).

Preparation of Example 11212

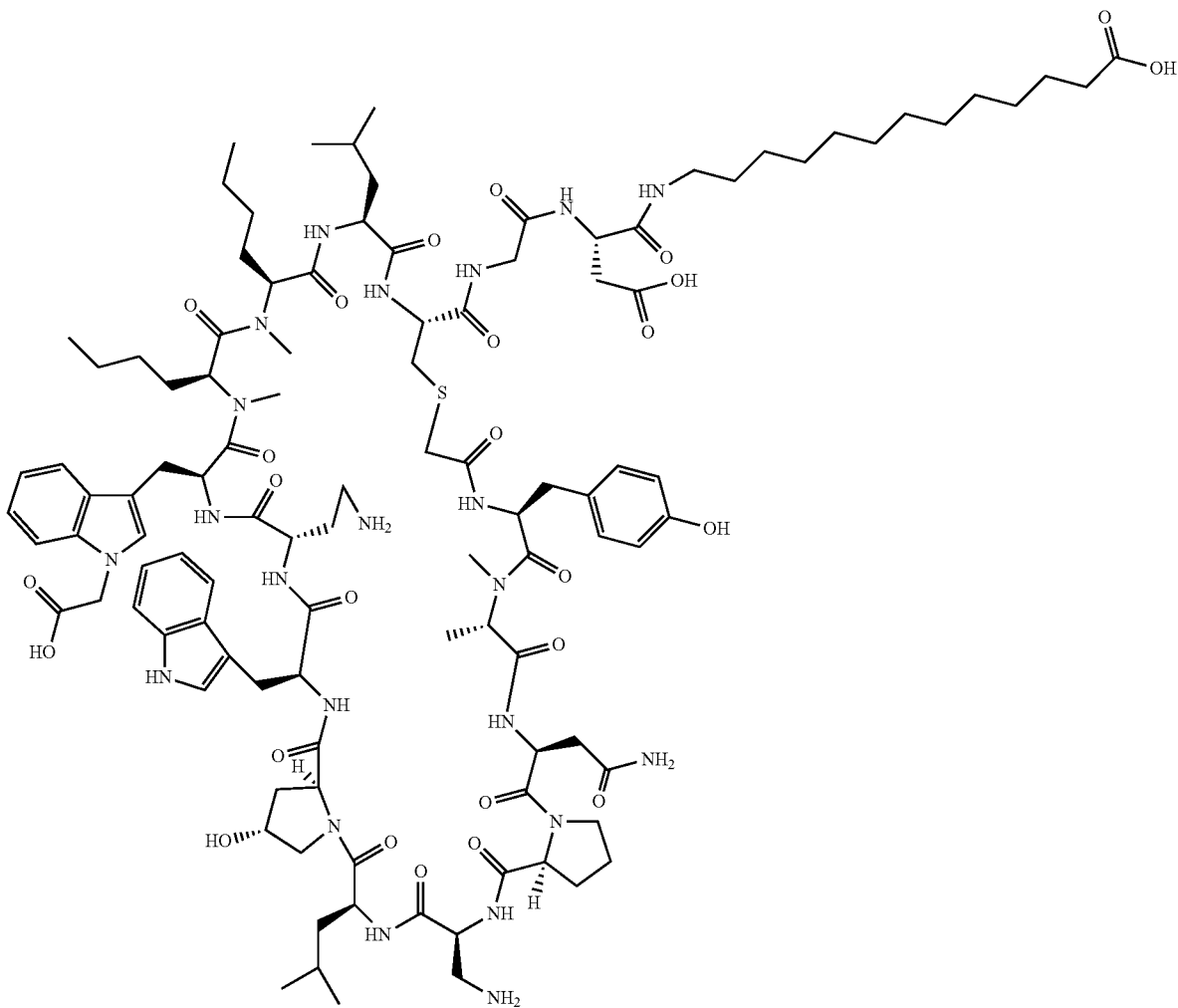 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11212 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 18 mg, and its estimated purity by LCMS analysis was 97%. Analysis LCMS Condition A: Retention time=3.97 min; ESI-MS(+) m/z 1108.2 (M+2H); ESI-HRMS(+) m/z: 1108.0828 (M+2H).

Preparation of Example 11213

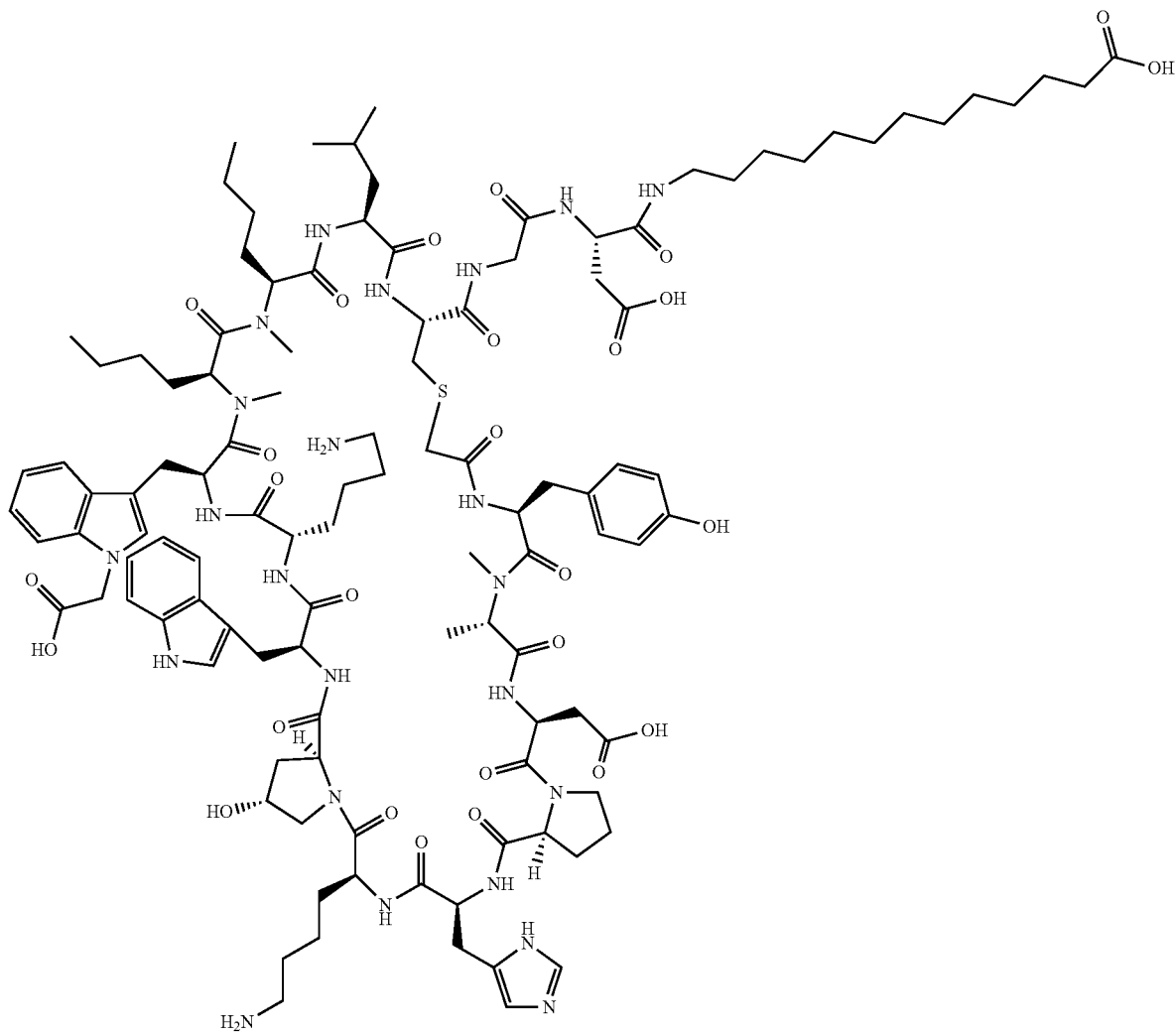 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11213 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 98%. Analysis LCMS Condition A: Retention time=3.58 min; ESI-MS(+) m/z 1155.9 (M+2H); ESI-HRMS(+) m/z: 1155.6020 (M+2H).

Preparation of Example 11214

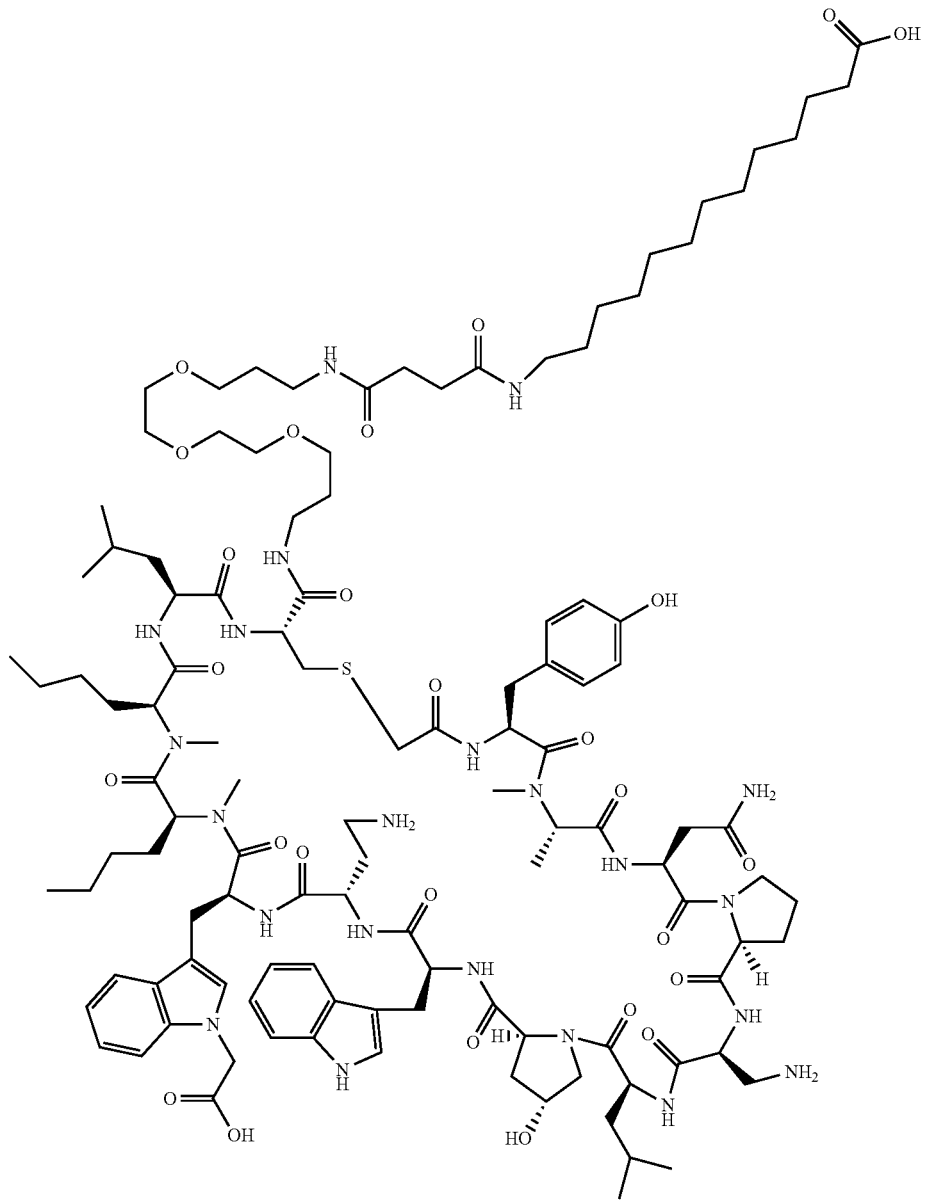 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11214 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 99%. Analysis LCMS Condition A: Retention time=4.34 min; ESI-MS(+) m/z 1173.3 (M+2H); ESI-HRMS(+) m/z: 1173.1503 (M+2H).

Preparation of Example 11215

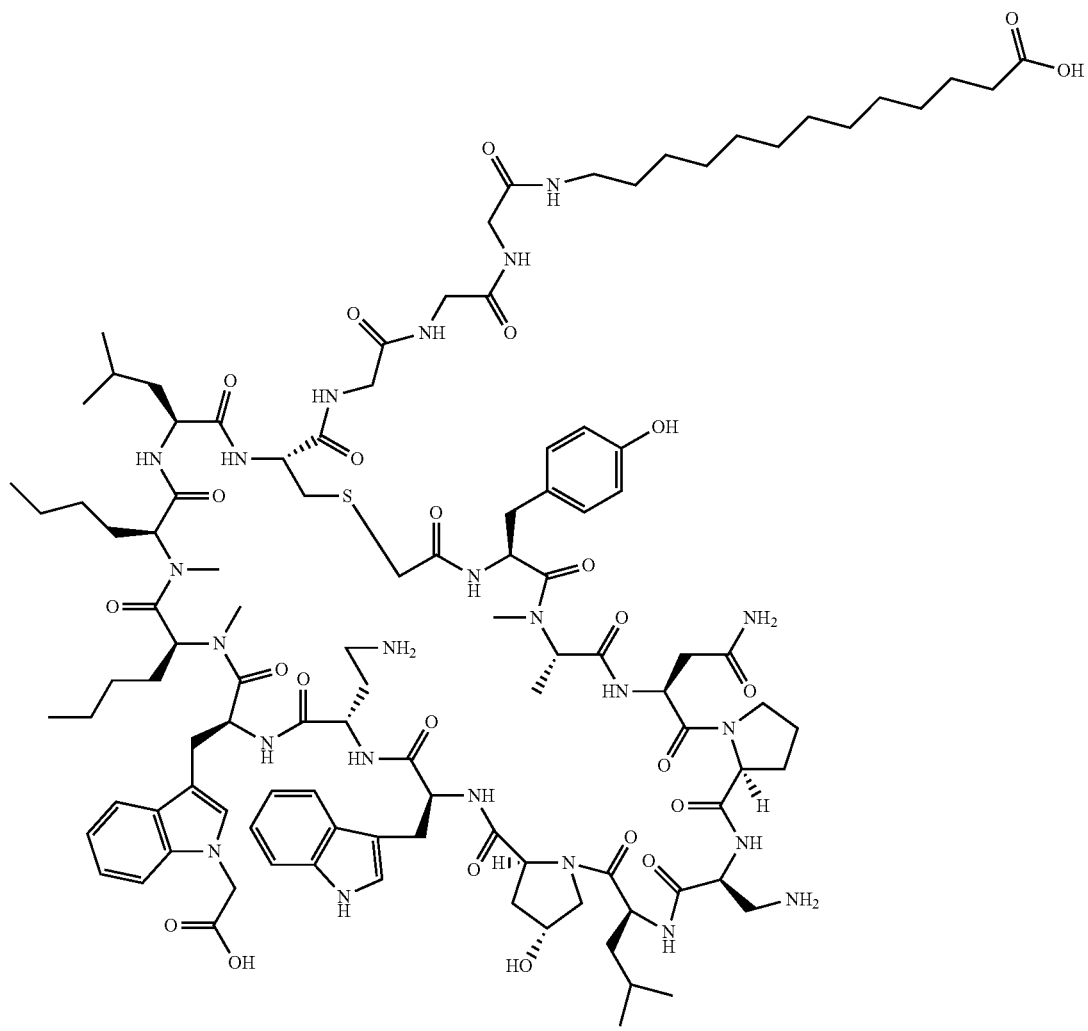 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11215 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 13 mg, and its estimated purity by LCMS analysis was 99%. Analysis LCMS Condition A: Retention time=4.02 min; ESI-MS(+) m/z 1108.3 (M+2H); ESI-HRMS(+) m/z: 1107.5930 (M+2H).

Preparation of Example 11216

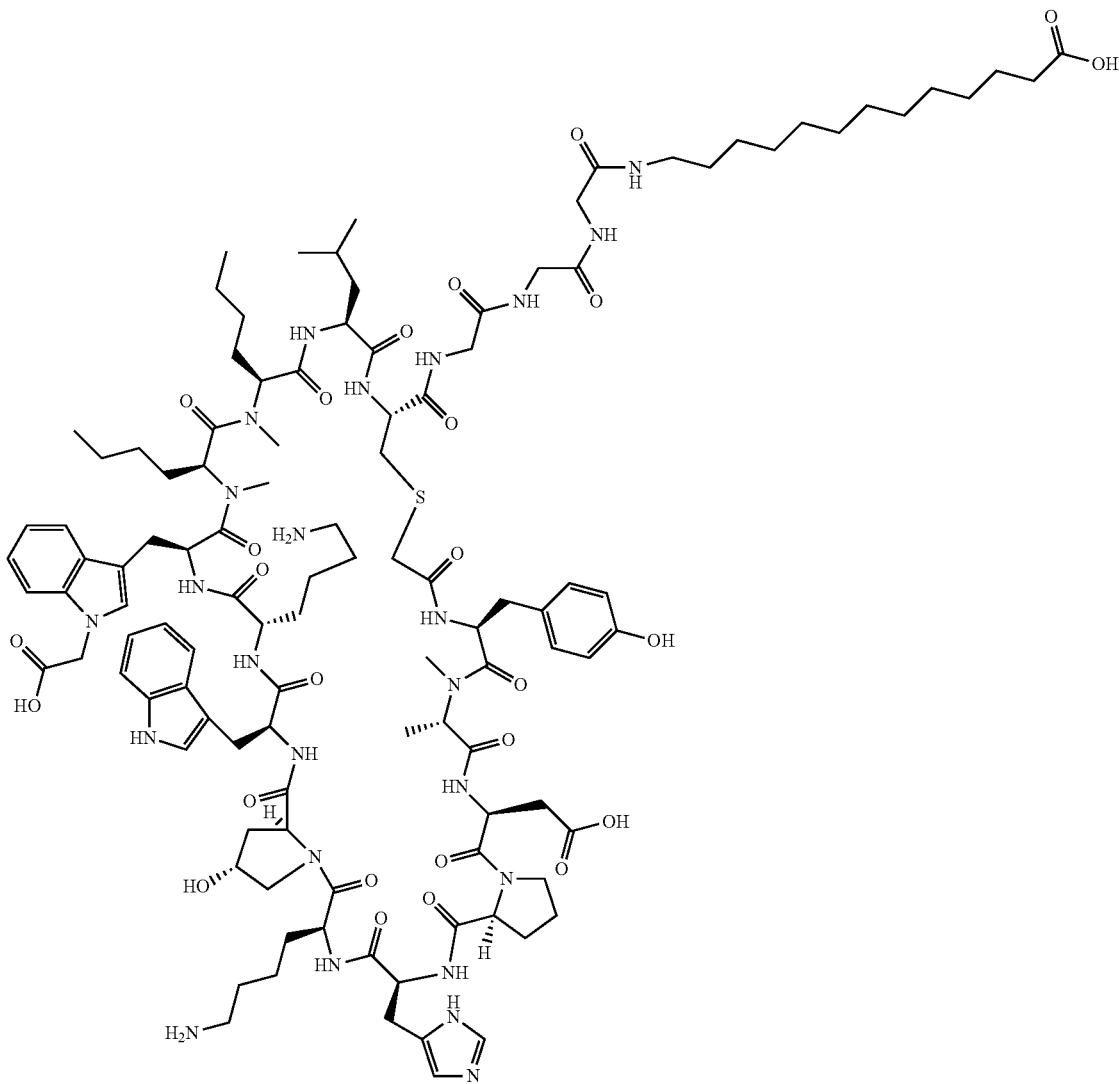 [SMILES: CCCC[C@H]1C(=O)N(C)[C@@H](CCCC)C(=O)N[C@@H](CC(C)C)C(=O)N[C@H](C(=O)NCC(=O)NCC(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11216 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile: water with 0.1% TFA; Mobile Phase B: 90:10 acetonitrile: water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 98%.

Analysis LCMS Condition A: Retention time=3.72 min; ESI-MS(+) m/z 1155.3 (M+2H); ESI-HRMS(+) m/z: 1155.1126 (M+2H).

Preparation of Example 11217

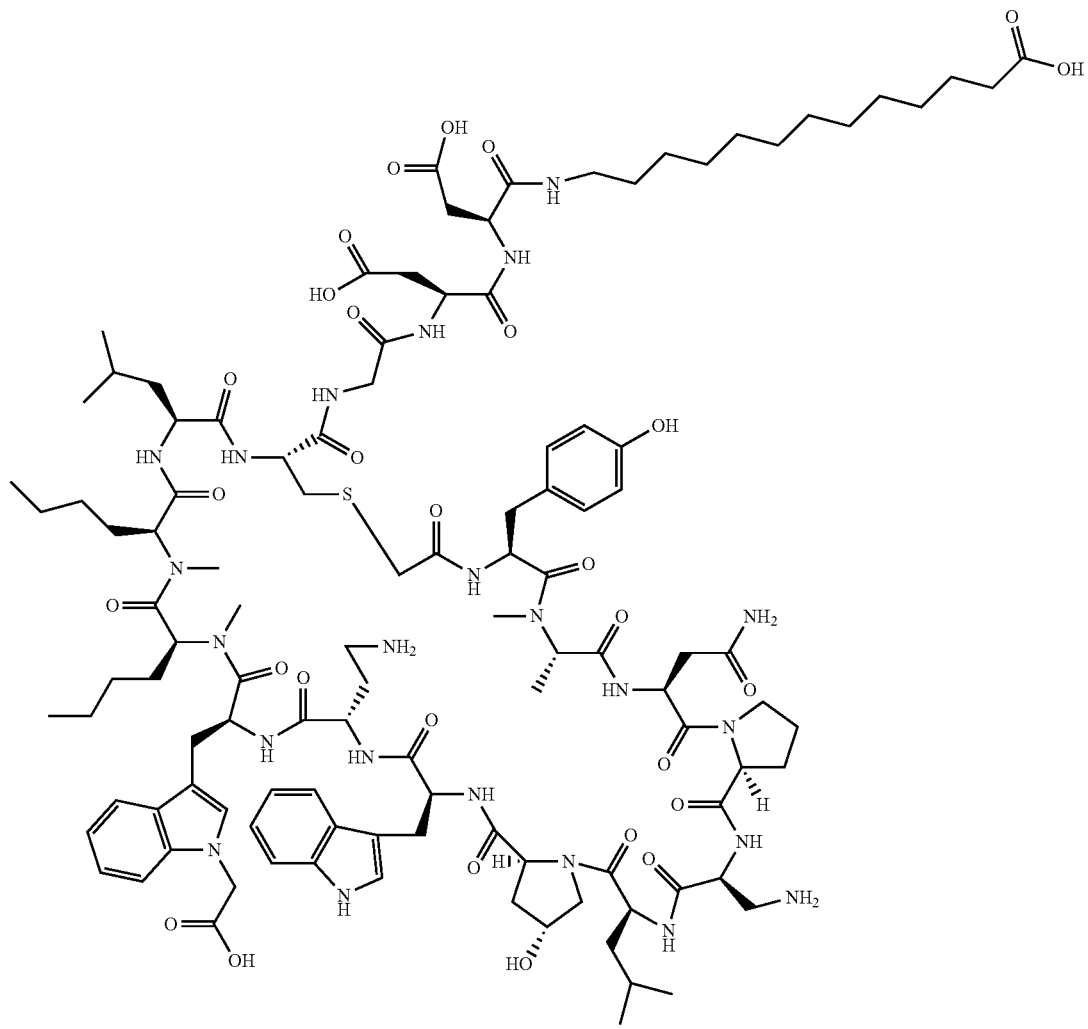 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11217 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 17.9 mg, and its estimated purity by LCMS analysis was 98%. Analysis LCMS Condition A: Retention time=3.55 min; ESI-MS(+) m/z 1165.6 (M+2H); ESI-HRMS(+) m/z: 1165.5995 (M+2H).

Preparation of Example 11218

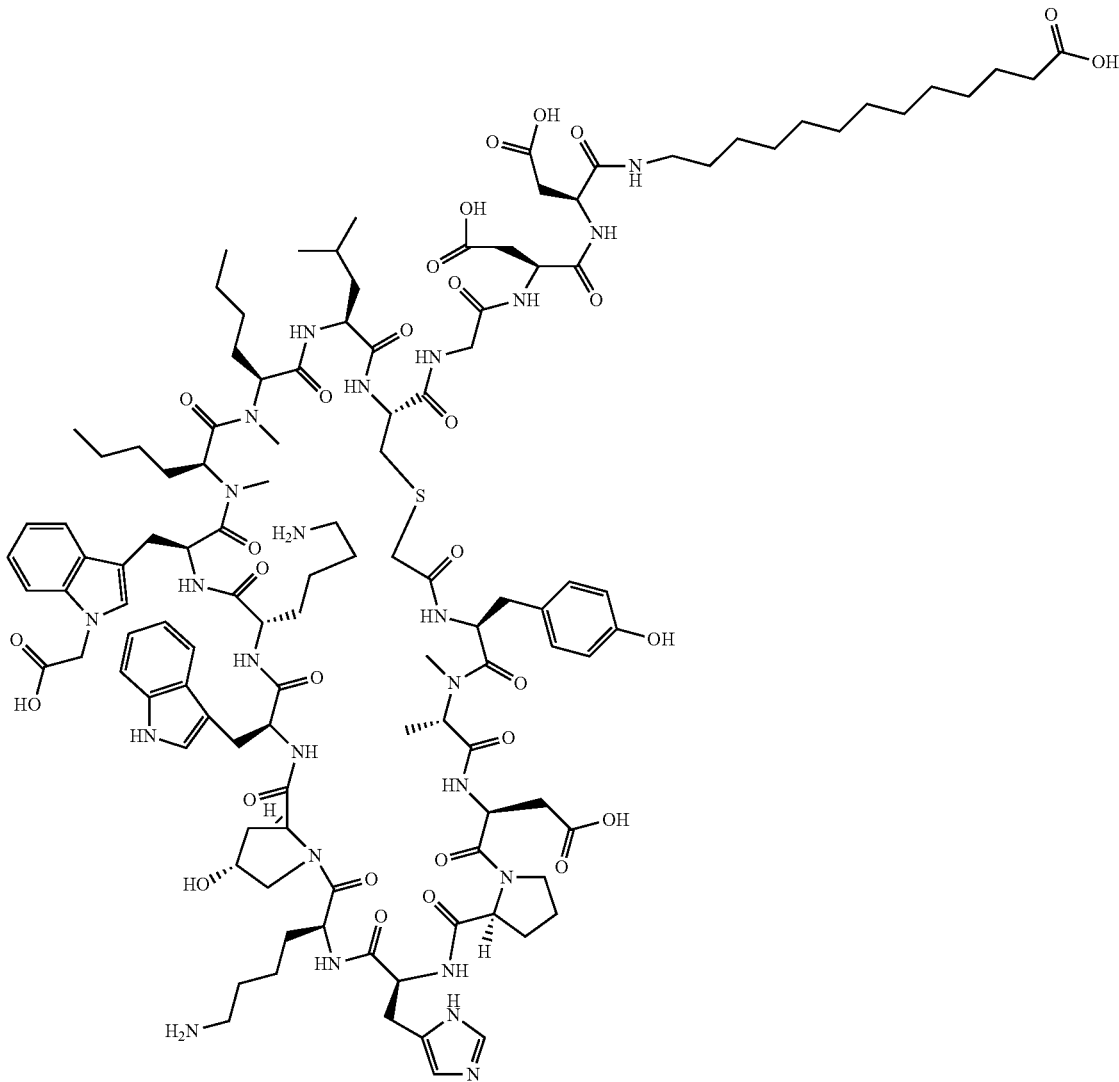 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11218 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 98%. Analysis LCMS Condition A: Retention time=3.17 min; ESI-MS(+) m/z 1213.1 (M+2H); ESI-HRMS(+) m/z: 1213.1169 (M+2H).

Preparation of Example 11219

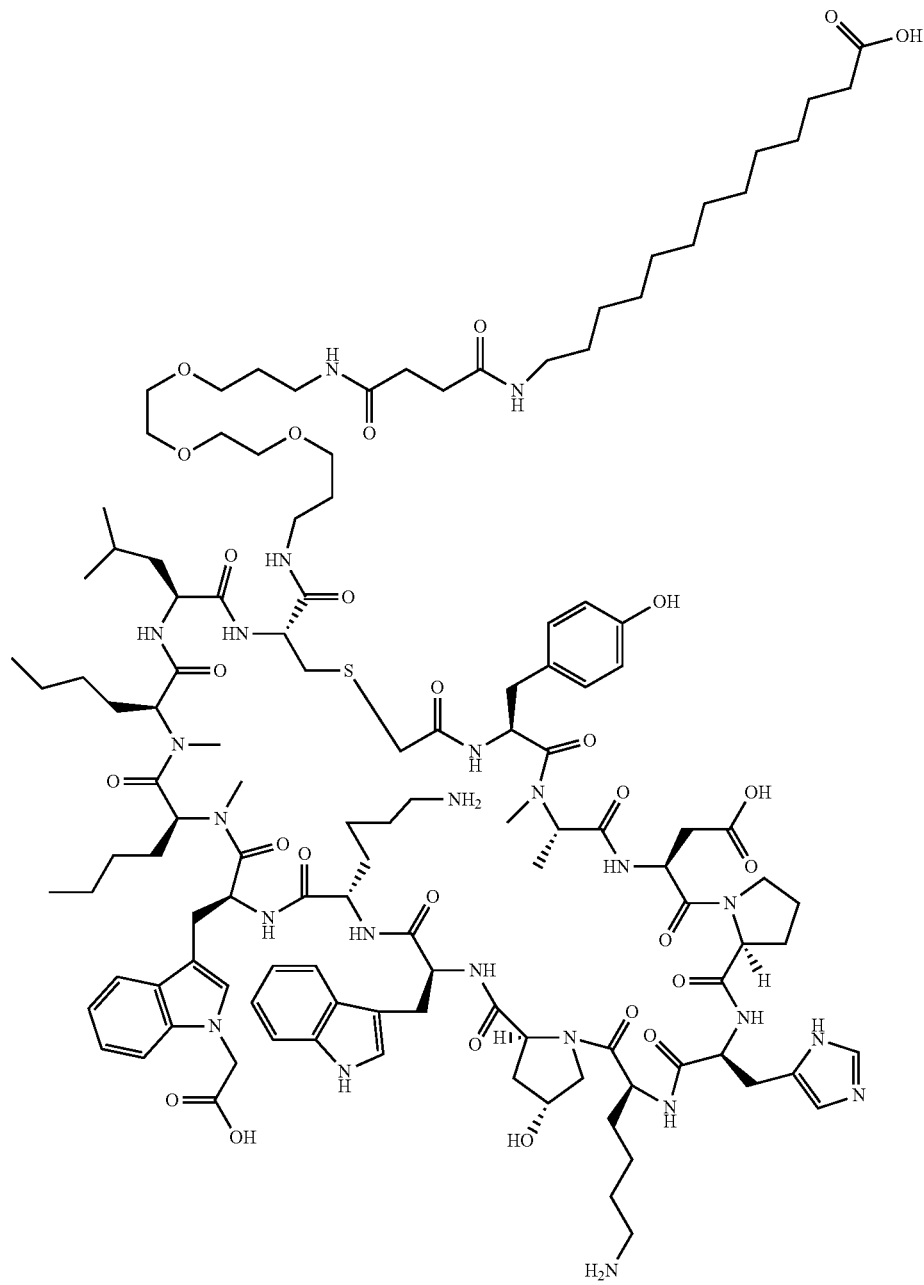 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CCC(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11219 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 21.7 mg, and its estimated purity by LCMS analysis was 96%. Analysis LCMS Condition A: Retention time=3.83 min; ESI-MS(+) m/z 1220.8 (M+2H); ESI-HRMS(+) m/z: 1220.6713 (M+2H).

Preparation of Example 11220

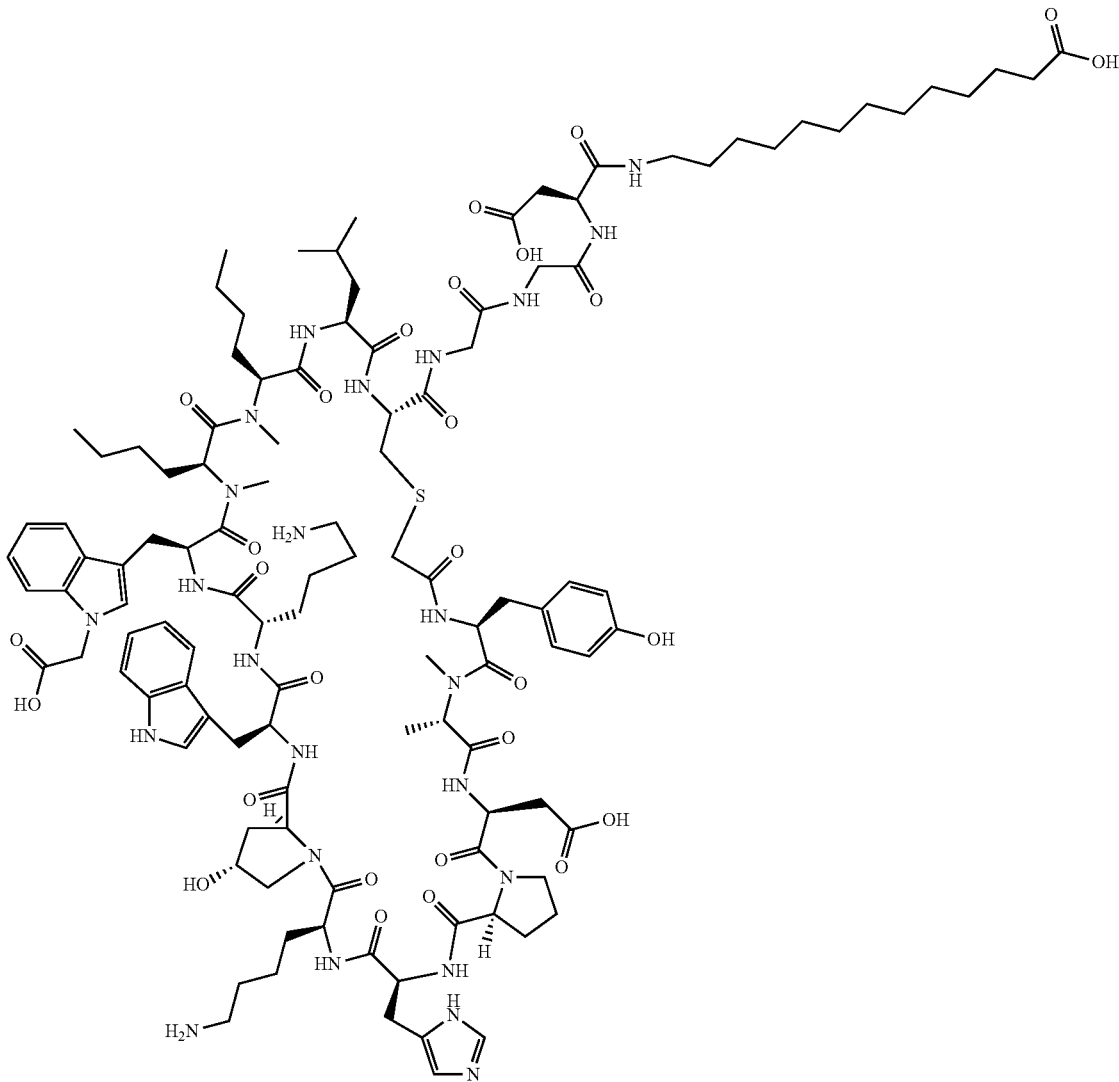 [SMILES: CCCC[C@H]1C(=O)N(C)[C@@H](CCCC)C(=O)N[C@@H](CC(C)C)C(=O)N[C@H](C(=O)NCC(=O)NCC(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11220 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 17.3 mg, and its estimated purity by LCMS analysis was 99%. Analysis LCMS Condition A: Retention time=3.49 min; ESI-MS(+) m/z 1184.2 (M+2H); ESI-HRMS(+) m/z: 1184.1140 (M+2H).

Preparation of Example 11221

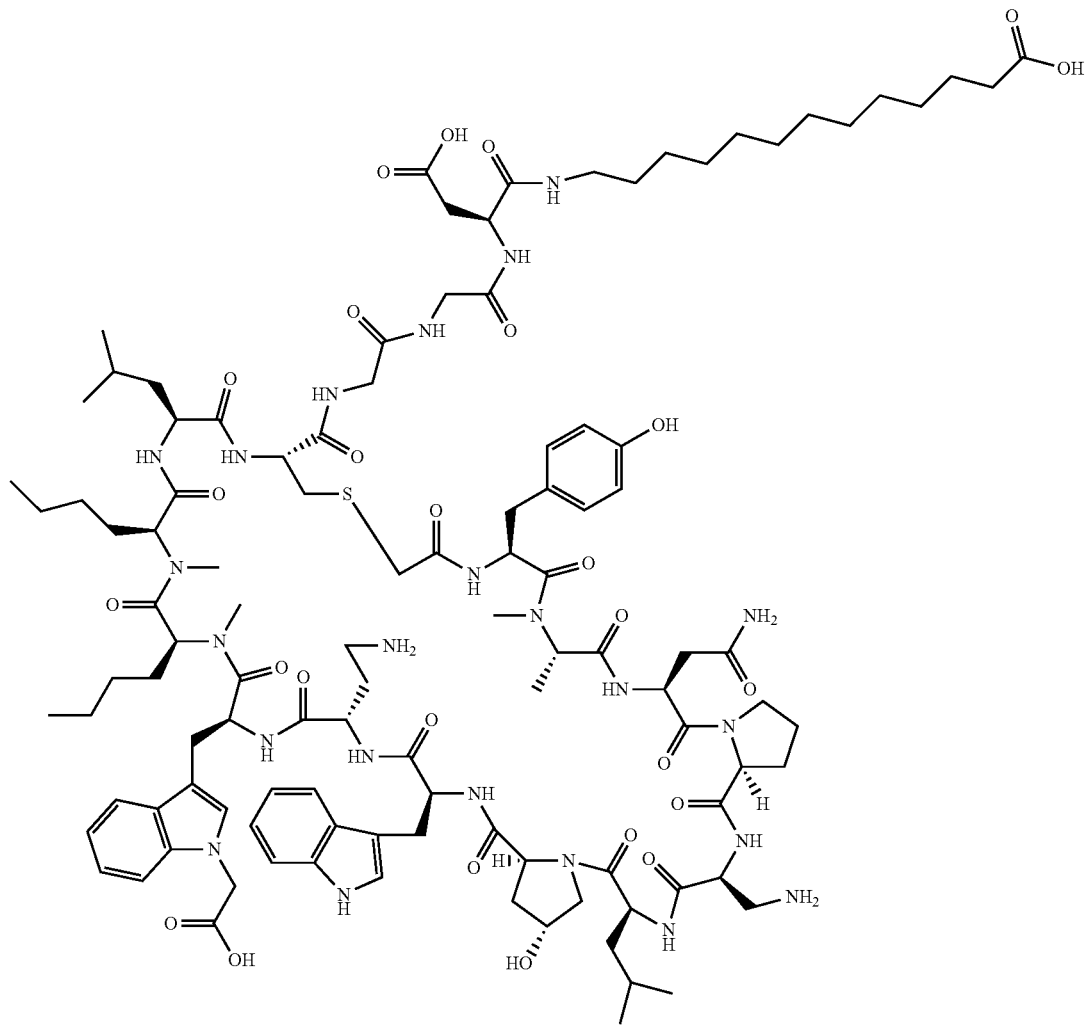 [SMILES: CCCC[C@H]1C(=O)N(C)[C@@H](CCCC)C(=O)N[C@@H](CC(C)C)C(=O)N[C@H](C(=O)NCC(=O)NCC(=O)N[C@@H](CC(=O)O)C(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11221 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 99%. Analysis LCMS Condition A: Retention time=3.79 min; ESI-MS(+) m/z 1136.6 (M+2H); ESI-HRMS(+) m/z: 1136.5948 (M+2H).

Preparation of Example 11222

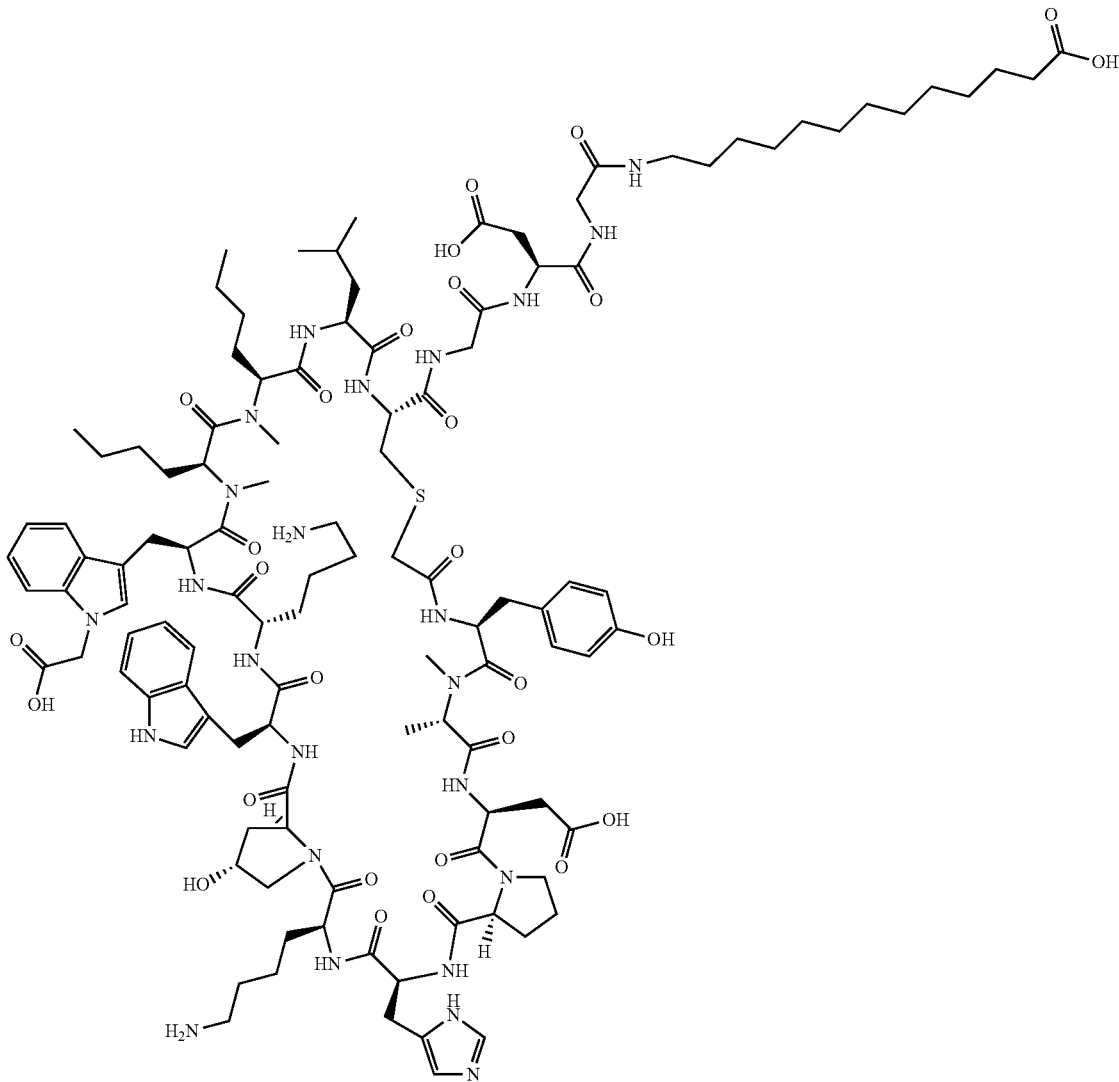 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 11222 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 23.7 mg, and its estimated purity by LCMS analysis was 97%.

Analysis LCMS Condition A: Retention time=3.47 min; ESI-MS(+) m/z 1184.3 (M+2H); ESI-HRMS(+) m/z: 1184.1132 (M+2H).

Preparation of Example 11223

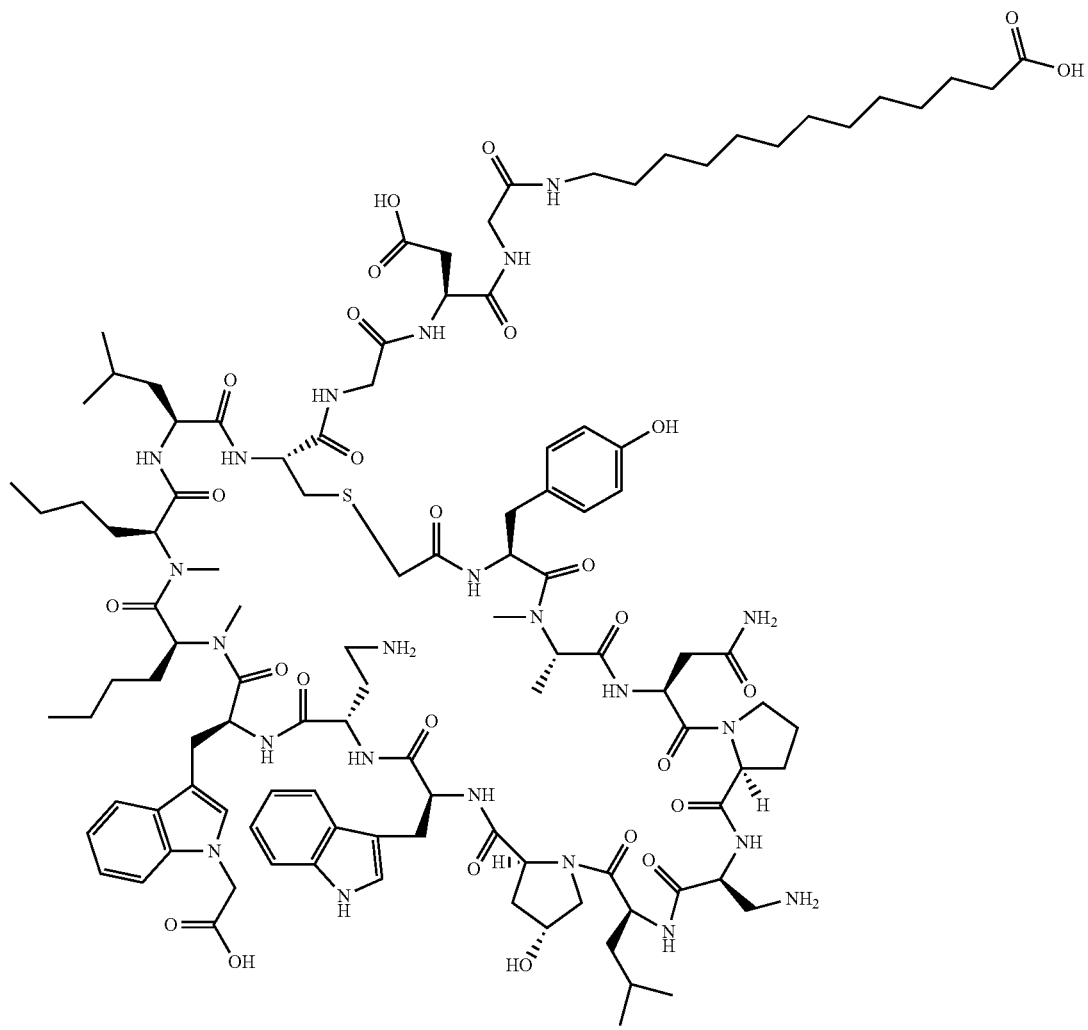 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCC(=O)NCCCCCCCCCCCCC(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11223 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetyl chloride coupling procedure A", "Global Deprotection Method A", and "Cyclization Method A". Modified 2-chlorotrityl chloride resin E was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-80% B over 25 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 98%. Analysis LCMS Condition A: Retention time=3.79 min; ESI-MS(+) m/z 1136.8 (M+2H); ESI-HRMS(+) m/z: 1136.5948 (M+2H).

Preparation of Example 11224

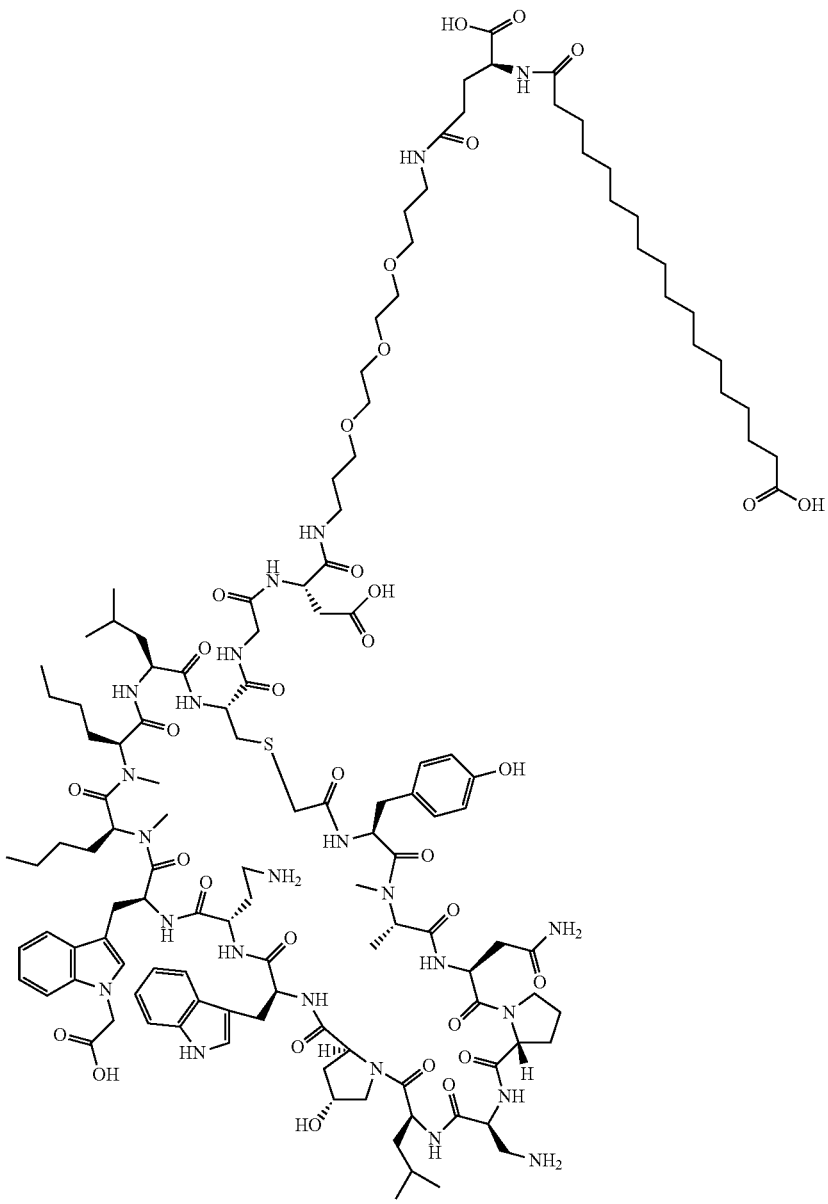 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11224 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 14 mg, and its estimated purity by LCMS analysis was 99%. Analysis LCMS Condition B: Retention time=2.13 min; ESI-MS (+) m/z 1317.0 (M+2H); ESI-HRMS(+) m/z: 1316.2122 (M+2H).

Preparation of Example 11225

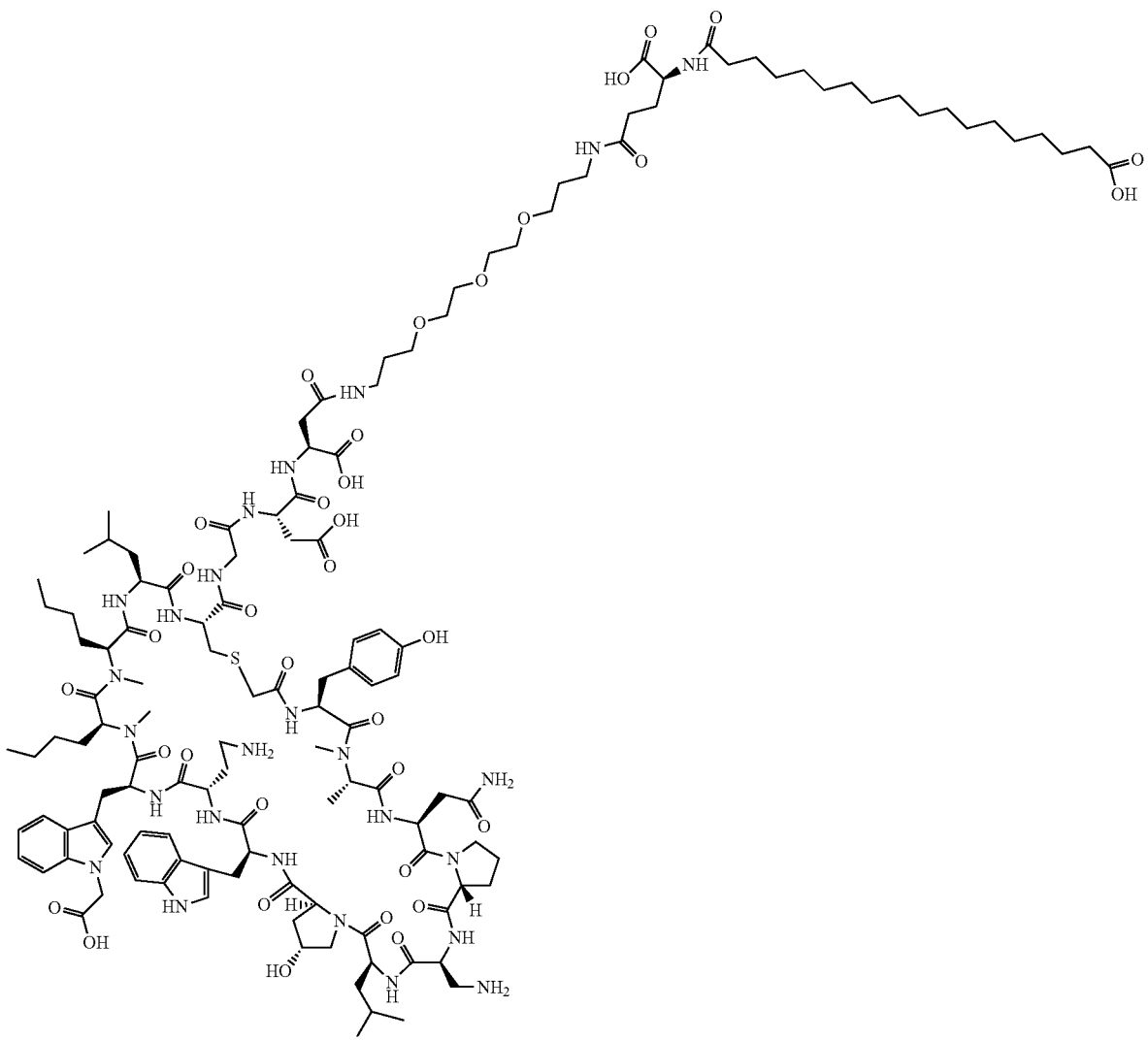 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11225 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 35.3 mg, and its estimated purity by LCMS analysis was 98%. Analysis LCMS Condition B: Retention time=2.27 min; ESI-MS(+) m/z 1374.2 (M+2H); ESI-HRMS(+) m/z: 1373.7259 (M+2H).

Preparation of Example 11226

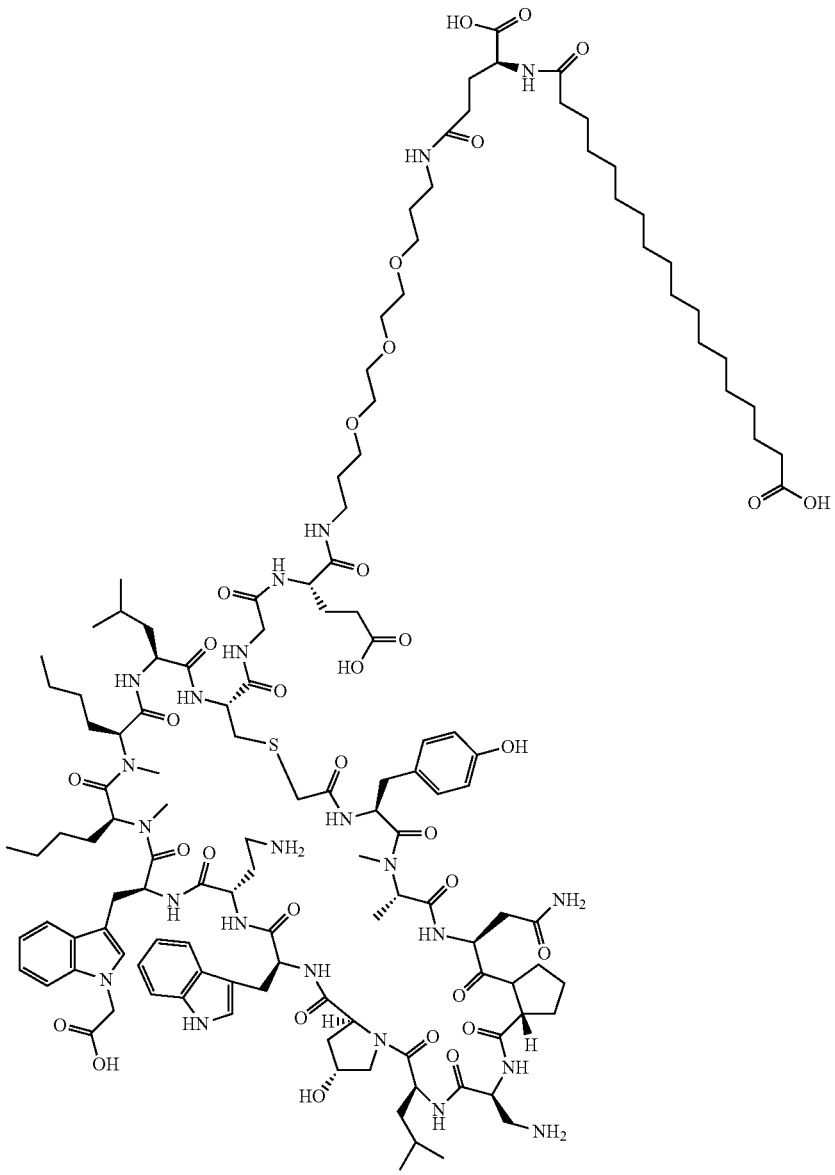 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)C2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11226 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 18.7 mg, and its estimated purity by LCMS analysis was 100%. Analysis LCMS Condition B: Retention time=2.54 min; ESI-MS(+) m/z 1337.5 (M+2H); ESI-HRMS(+) m/z: 1337.2332 (M+2H).

Preparation of Example 11227

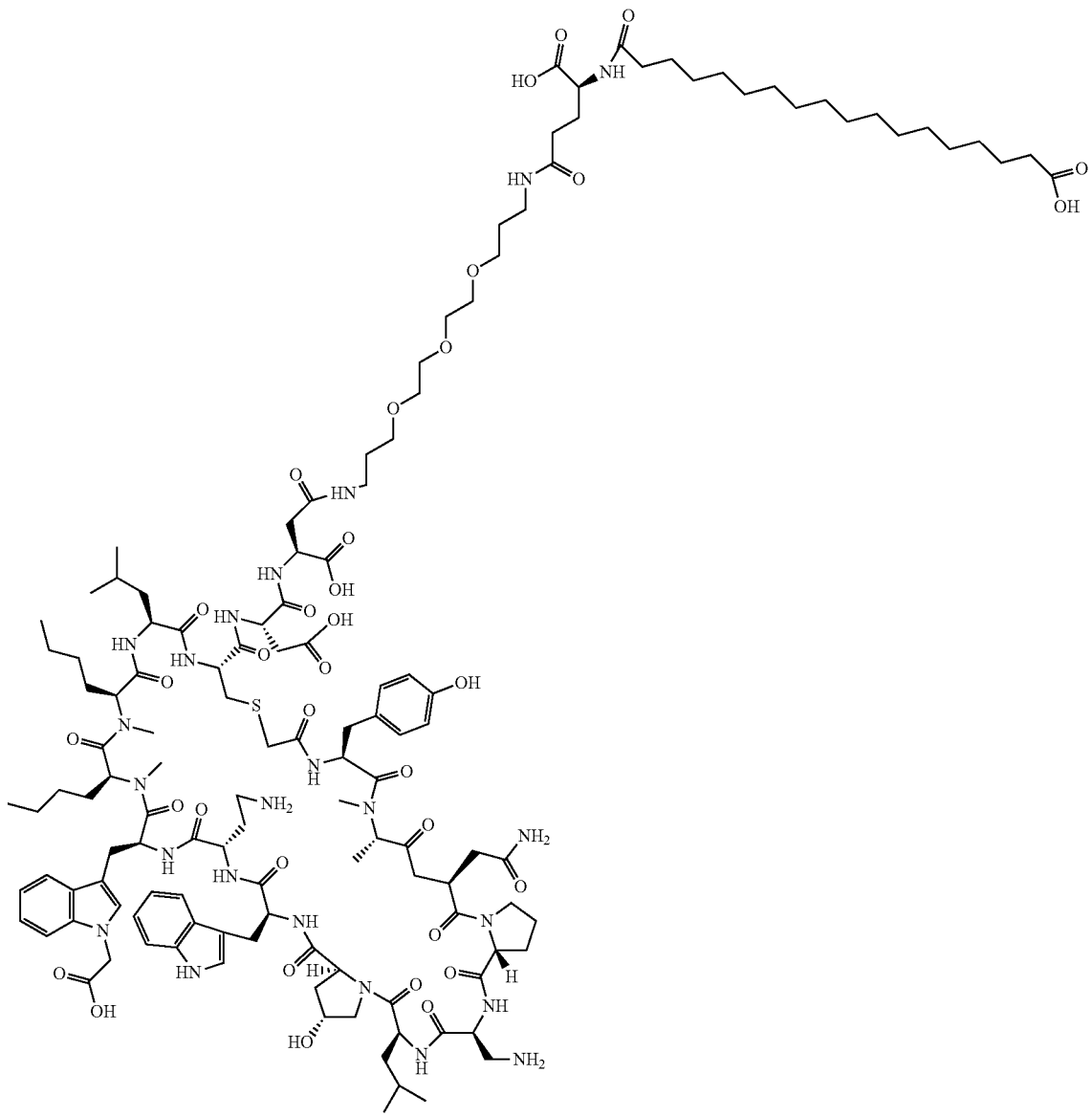 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)C[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11227 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 99%.

Analysis LCMS Condition B: Retention time=2.32 min; ESI-MS(+) m/z 1345.5 (M+2H); ESI-HRMS(+) m/z: 1345.2147 (M+2H).

Preparation of Example 11228

Example 11228 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 100%.

Analysis LCMS Condition B: Retention time=2.28 min; ESI-MS(+) m/z 1352.7 (M+2H); ESI-HRMS(+) m/z: 1352.2227 (M+2H).

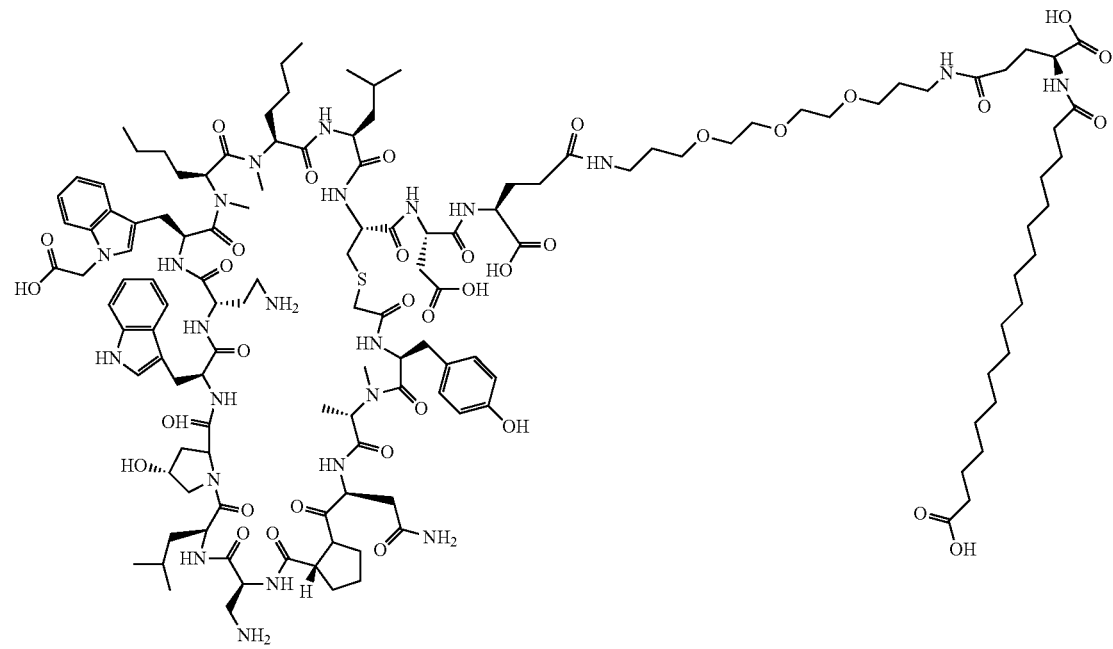 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CCC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)C2CCC[C@@H]2C(=O)N[C@@H](CN)C(=O)N[C@@H](CC(C)C)C(=O)N2C[C@H](O)CC2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Preparation of Example 11229

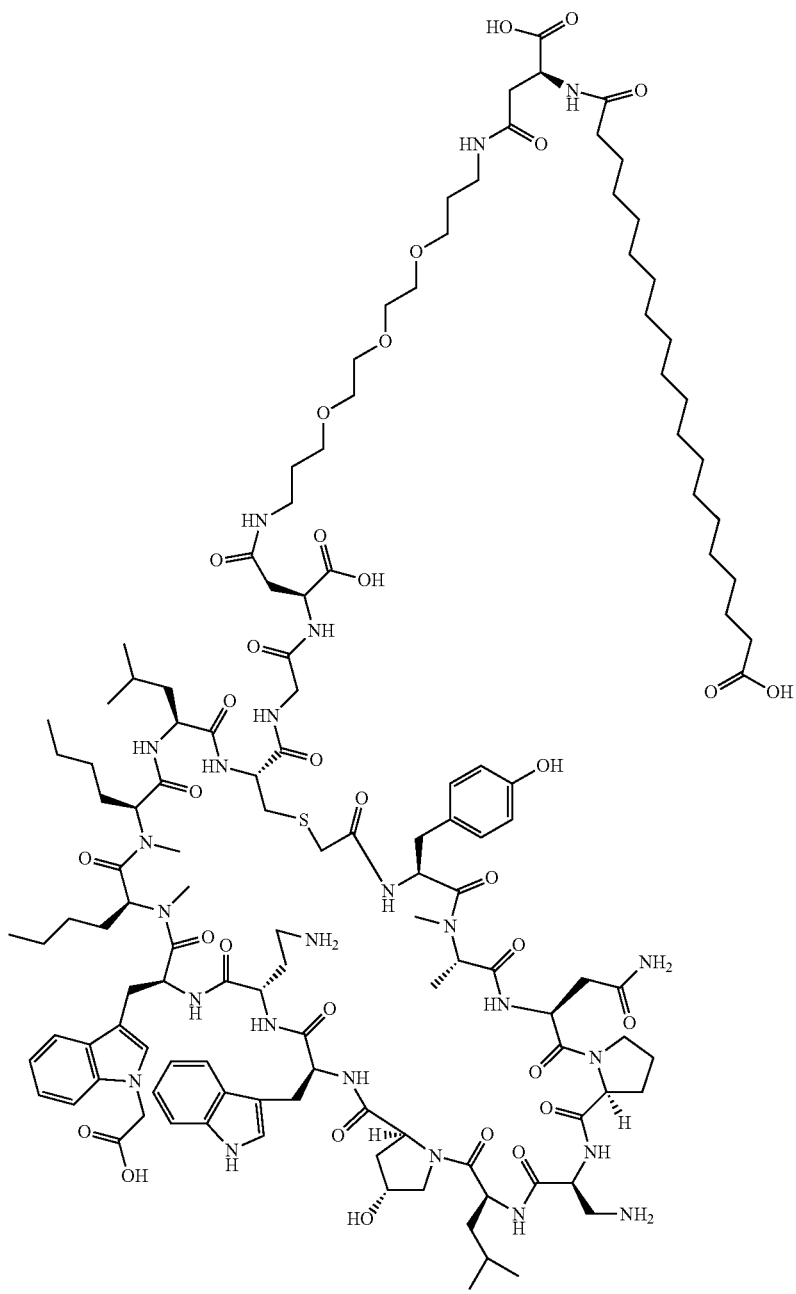 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)C[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11229 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 98%.

Analysis LCMS Condition B: Retention time=2.35 min; ESI-MS(+) m/z 1309.8 (M+2H); ESI-HRMS(+) m/z: 1309.2043 (M+2H).

Preparation of Example 11230

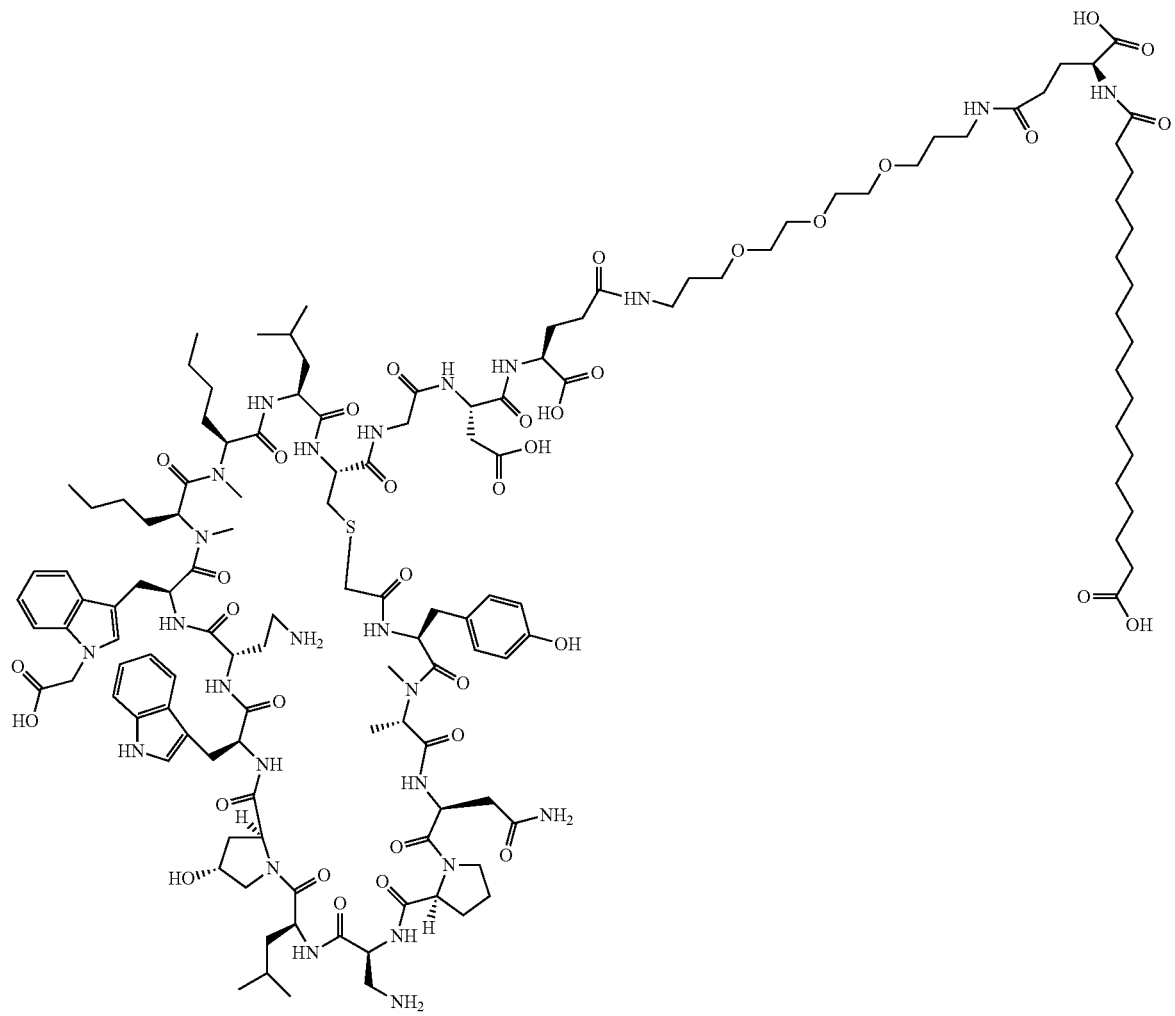 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CCC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11230 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 98%.

Analysis LCMS Condition B: Retention time=2.68 min; ESI-MS(+) m/z 1380.5 (M+2H); ESI-HRMS(+) m/z: 1380.7350 (M+2H).

Preparation of Example 11231

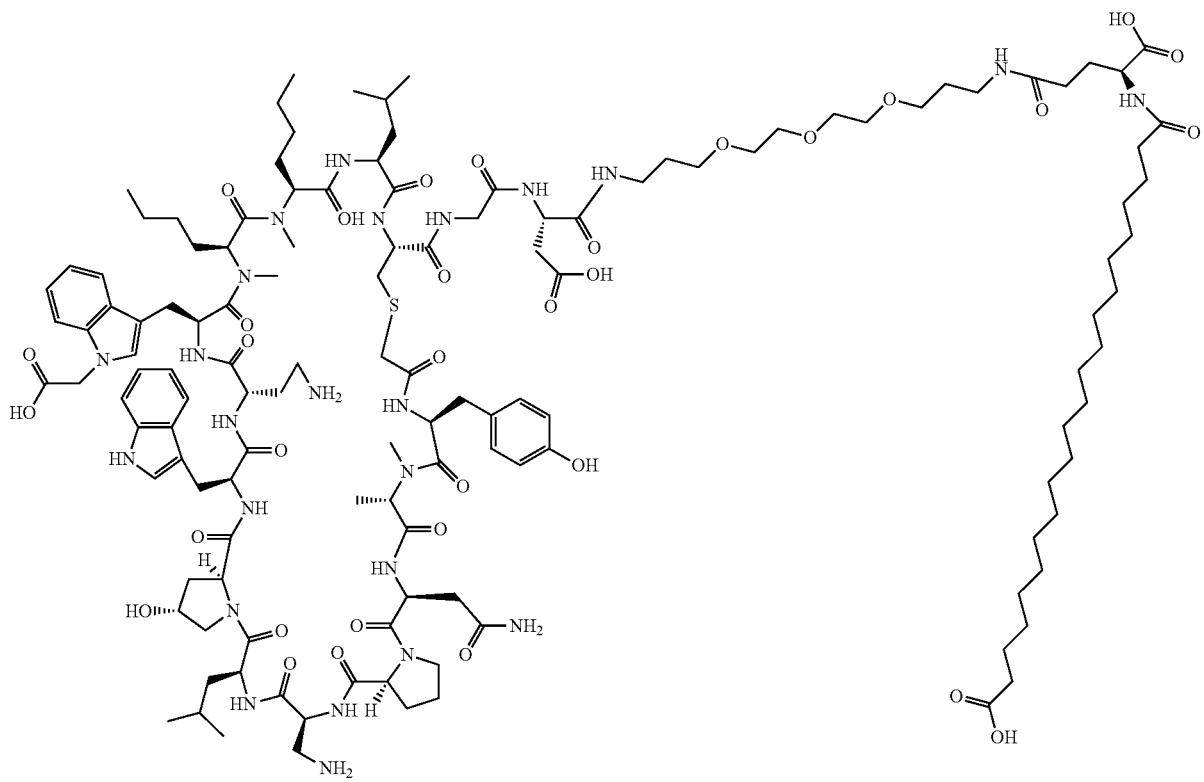 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)CC[C@H](NC(=O)CCCCCCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11231 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin F was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 19 mg, and its estimated purity by LCMS analysis was 98%. Analysis LCMS Condition B: Retention time=2.54 min; ESI-MS (+) m/z 1330.5 (M+2H); ESI-HRMS(+) m/z: 1330.2260 (M+2H).

Preparation of Example 11232

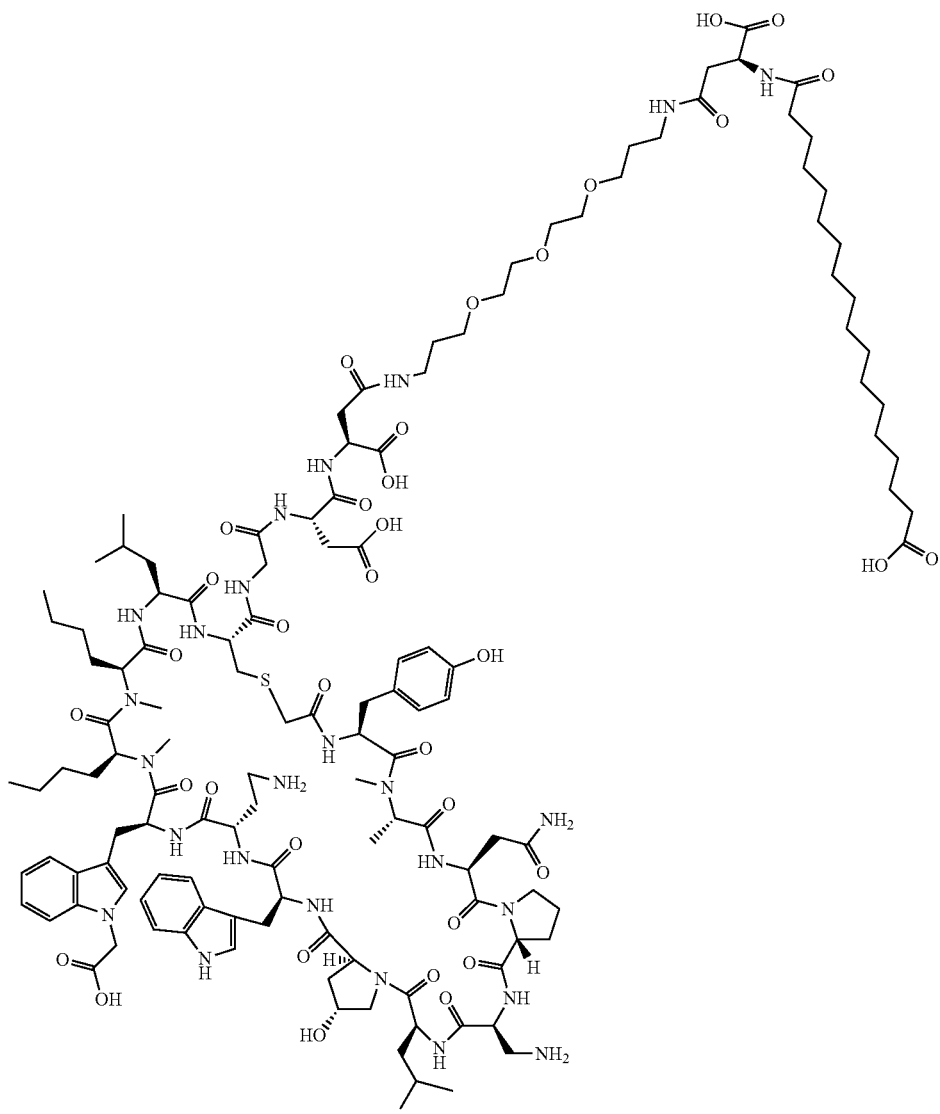 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)NCCCOCCOCCOCCCNC(=O)C[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11232 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 98%. Analysis LCMS Condition B: Retention time=2.28 min; ESI-MS(+) m/z 1367.1 (M+2H); ESI-HRMS(+) m/z: 1366.7180 (M+2H).

Preparation of Example 11233

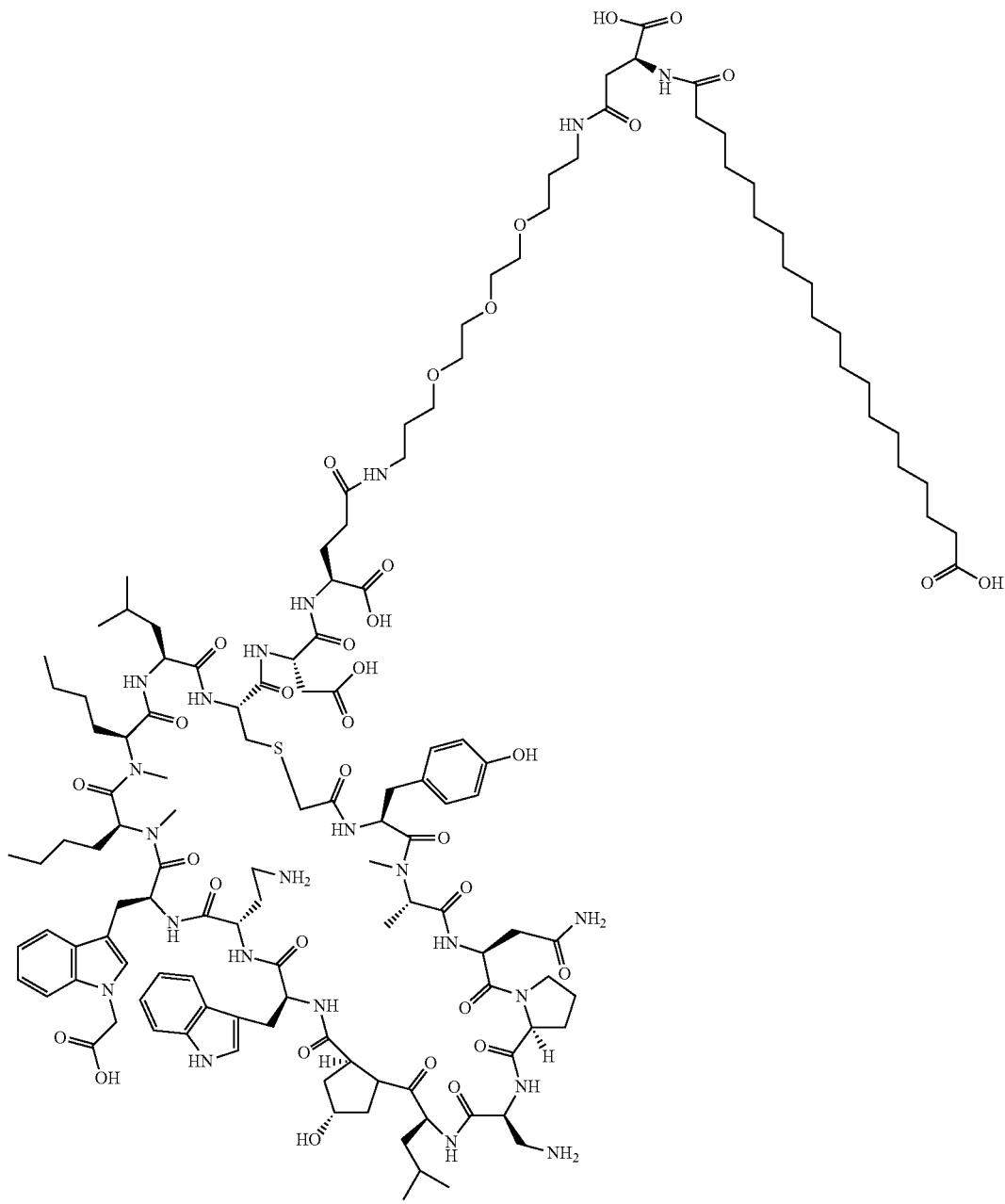 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CCC(=O)NCCCOCCOCCOCCCNC(=O)C[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)C2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11233 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 29.4 mg, and its estimated purity by LCMS analysis was 98%. Analysis LCMS Condition B: Retention time=2.18 min; ESI-MS(+) m/z 1345.3 (M+2H); ESI-HRMS(+) m/z: 1345.2151 (M+2H).

Preparation of Example 11234

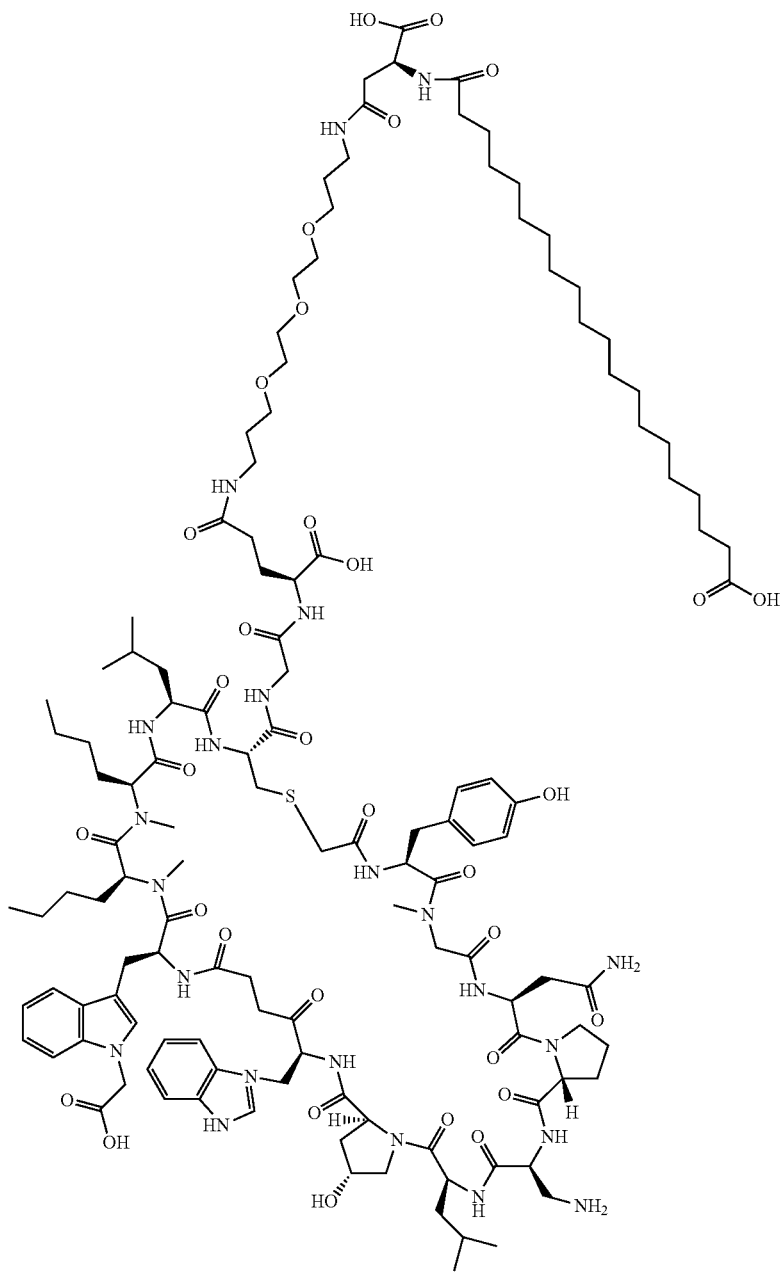

Example 11234 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 98%.

Analysis LCMS Condition B: Retention time=2.35 min; ESI-MS(+) m/z 1317.1 (M+2H); ESI-HRMS(+) m/z: 1316.2133 (M+2H).

Preparation of Example 11235

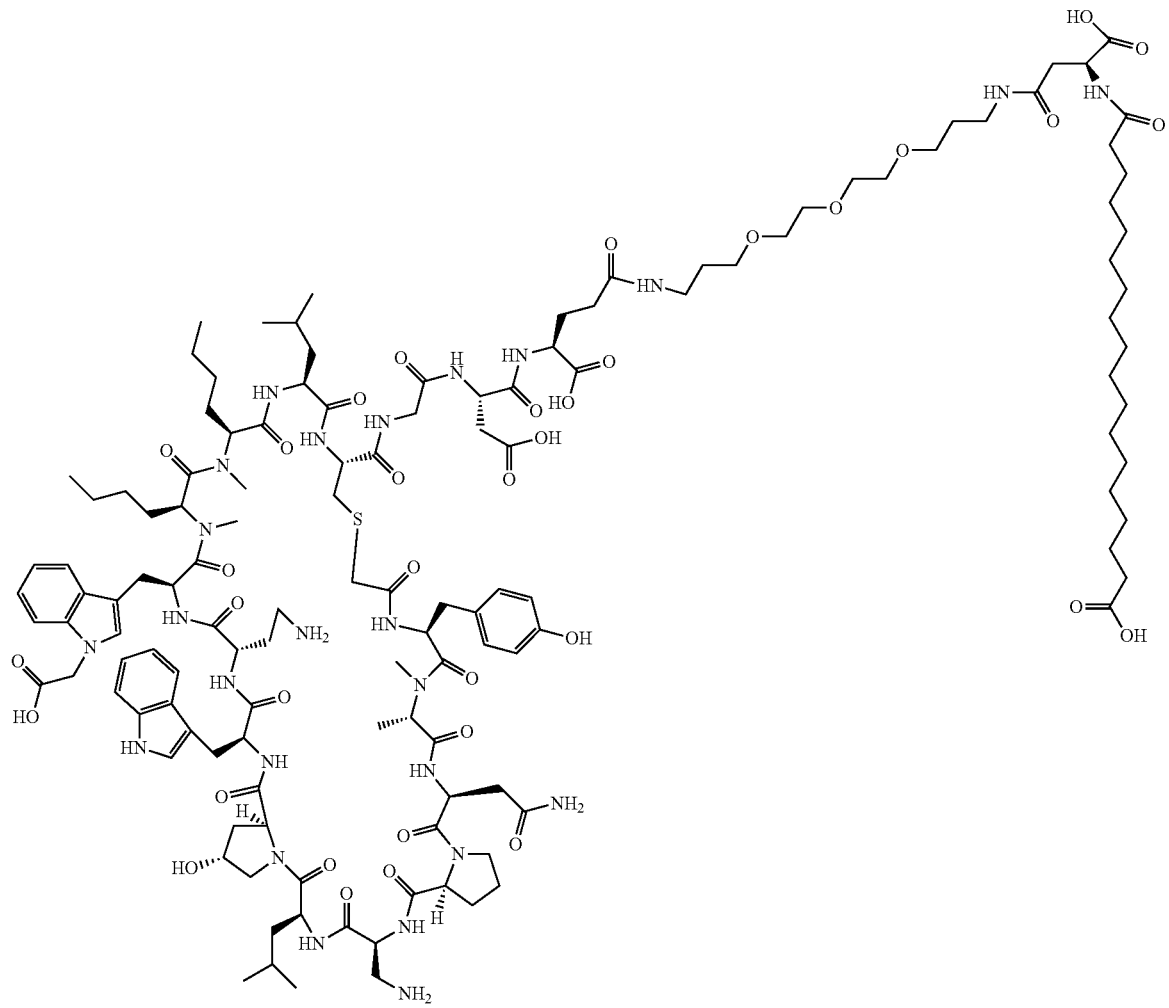 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CCC(=O)NCCCOCCOCCOCCCNC(=O)C[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11235 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 18.4 mg, and its estimated purity by LCMS analysis was 99%. Analysis LCMS Condition B: Retention time=2.26 min; ESI-MS(+) m/z 1374.1 (M+2H); ESI-HRMS(+) m/z: 1373.7263 (M+2H).

Preparation of Example 11236

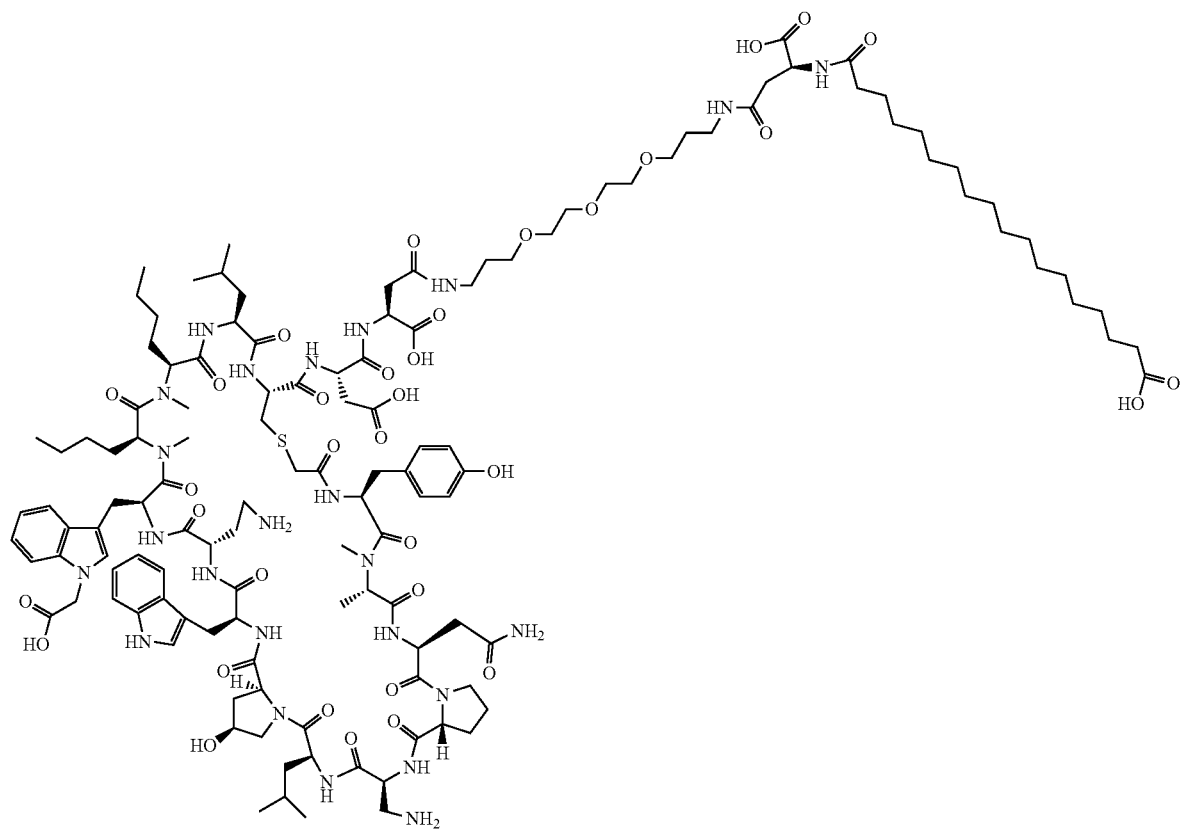 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CC(=O)NCCCOCCOCCOCCCNC(=O)C[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11236 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 97%.

Analysis LCMS Condition B: Retention time=2.31 min; ESI-MS(+) m/z 1338.1 (M+2H); ESI-HRMS(+) m/z: 1338.2058 (M+2H).

Preparation of Example 11237

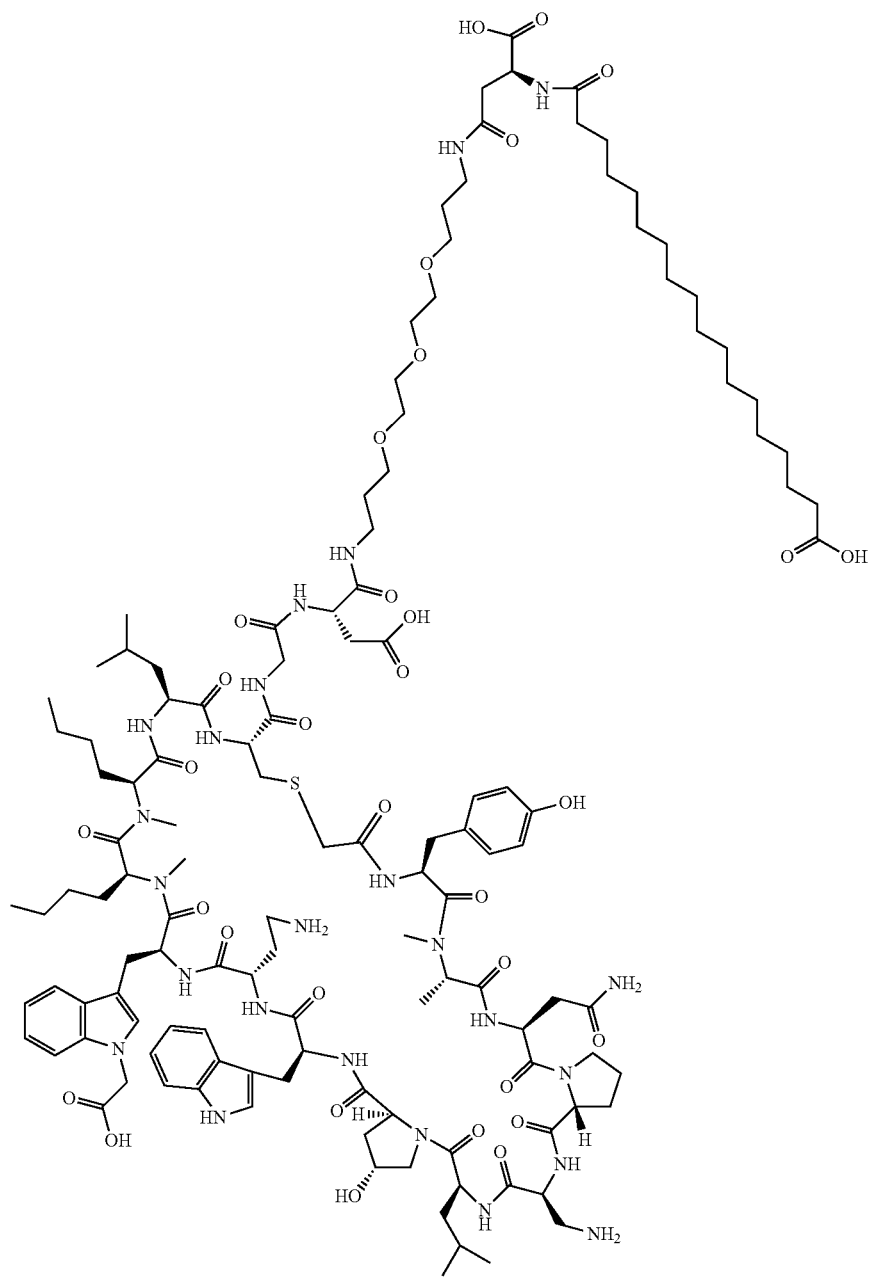 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)C[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11237 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin G was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 97%.

Analysis LCMS Condition B: Retention time=2.45 min; ESI-MS(+) m/z 1309.3 (M+2H); ESI-HRMS(+) m/z: 1309.2068 (M+2H).

Preparation of Example 11238

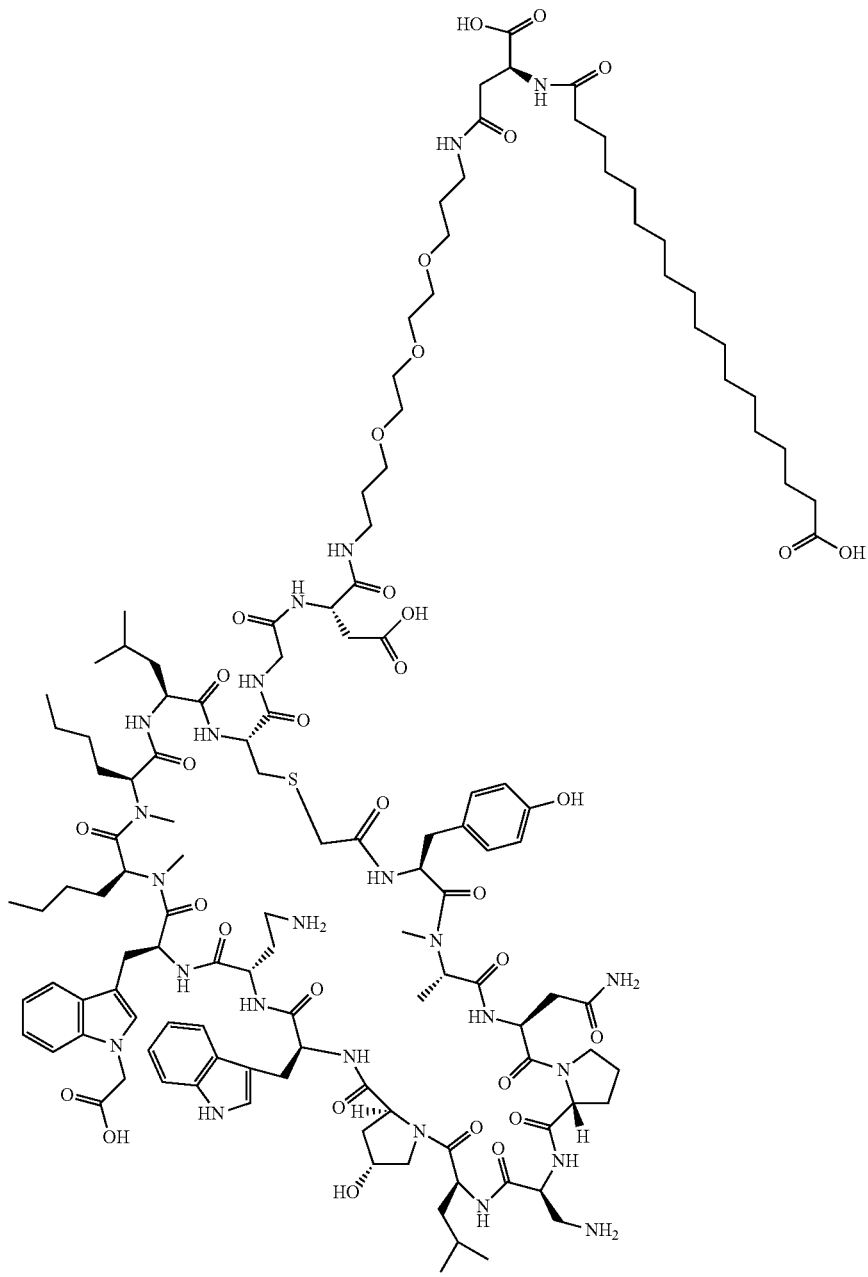 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)C[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11238 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-80% B over 25 minutes, then a 5-minute hold at 100% B; Flow: 20 mL/min. Fractions containing the desired product were combined and dried via centrifugal evaporation. The yield of the product was 27.7 mg, and its estimated purity by LCMS analysis was 99%.

Analysis LCMS Condition B: Retention time=2.37 min; ESI-MS(+) m/z 1295.5 (M+2H); ESI-HRMS(+) m/z: 1295.1866 (M+2H).

Preparation of Example 11239

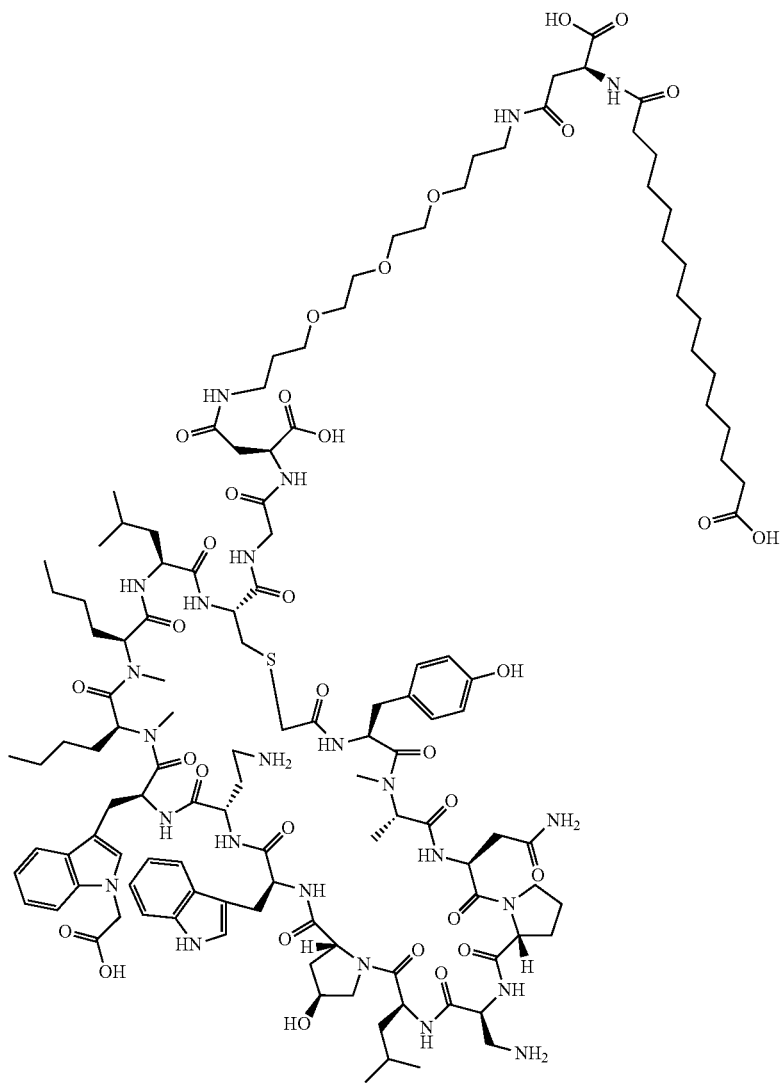 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11239 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 15-80% B over 25 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 99%.

Analysis LCMS Condition B: Retention time=2.42 min; ESI-MS(+) m/z 1295.6 (M+2H); ESI-HRMS(+) m/z: 1295.1864 (M+2H).

Preparation of Example 11240

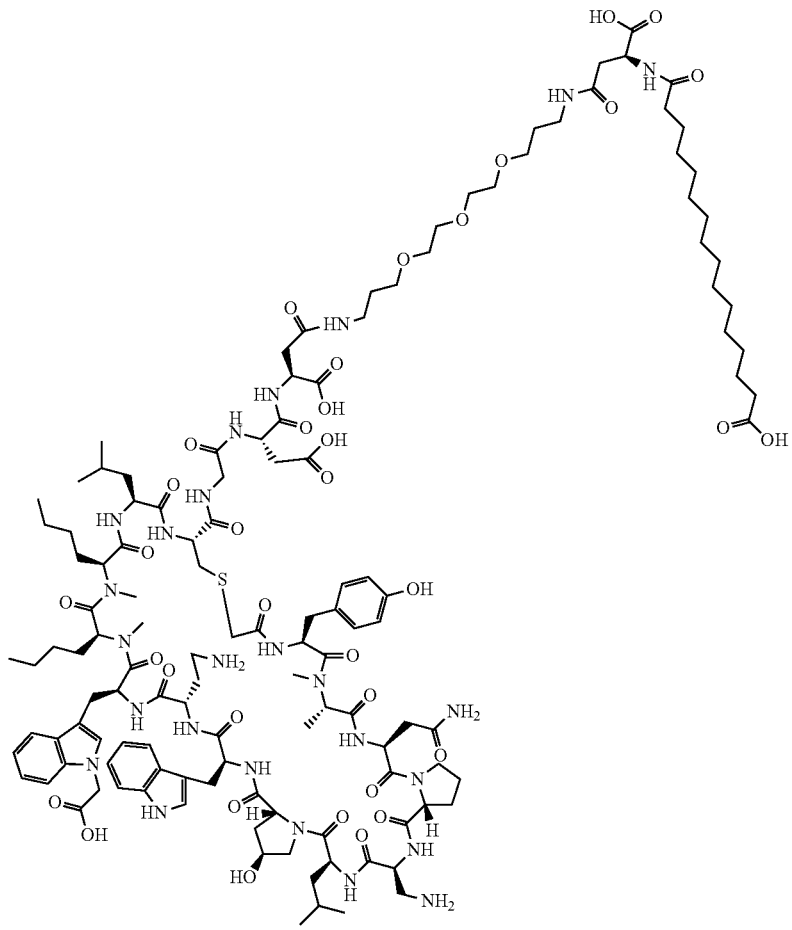 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11240 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 25.7 mg, and its estimated purity by LCMS analysis was 99%.

Analysis LCMS Condition B: Retention time=2.35 min; ESI-MS(+) m/z 1353.1 (M+2H); ESI-HRMS(+) m/z: 1352.7005 (M+2H).

Preparation of Example 11241

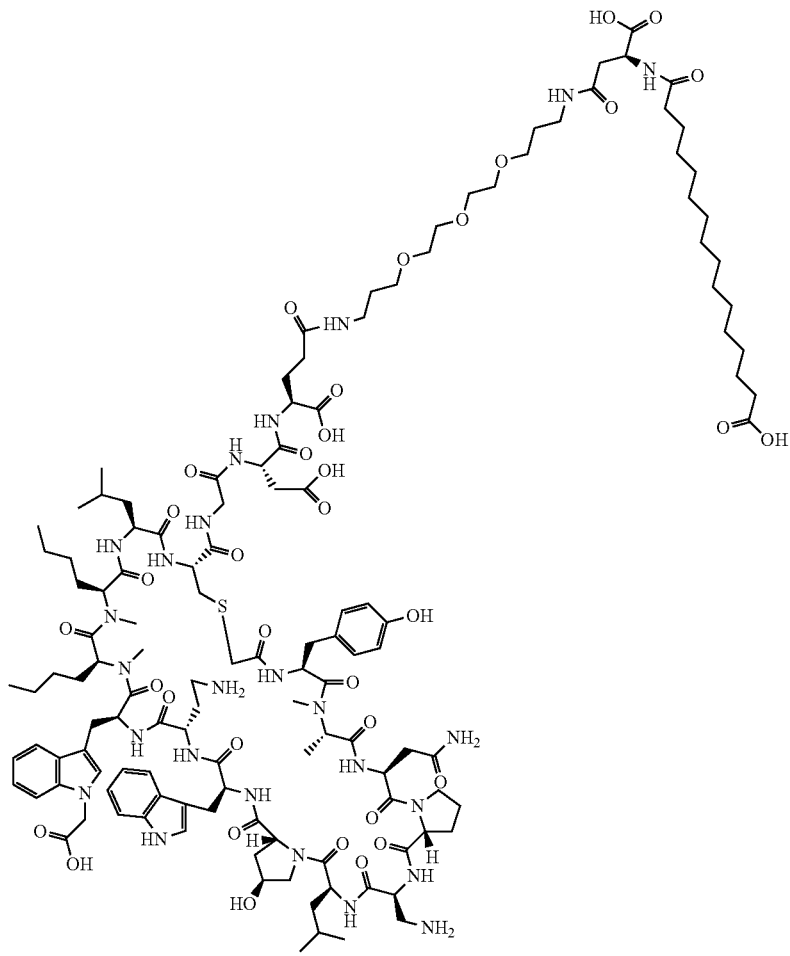 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CCC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11241 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 18.4 mg, and its estimated purity by LCMS analysis was 99%.

Analysis LCMS Condition B: Retention time=2.31 min; ESI-MS(+) m/z 1360.0 (M+2H); ESI-HRMS(+) m/z: 1359.7091 (M+2H).

Preparation of Example 11242

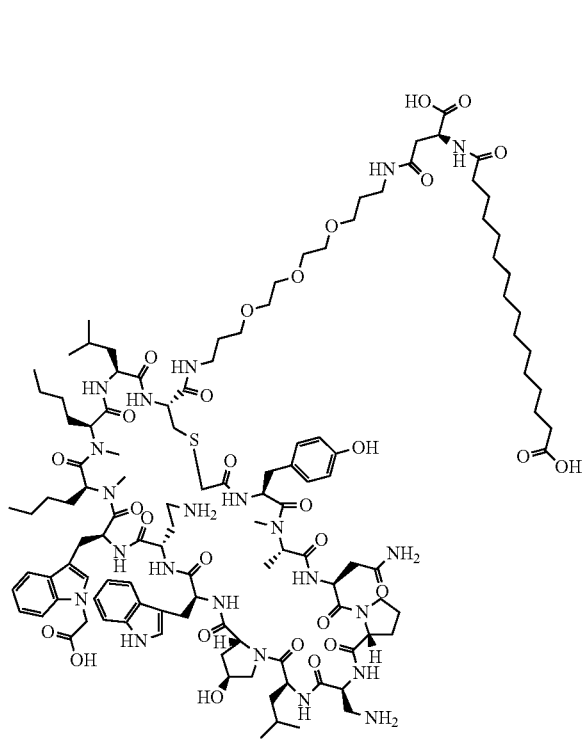 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)C[C@H](NC(=O)CCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11242 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-80% B over 25 minutes, then a 5-minute hold at 100% B; Flow: 20 mL/min. Fractions containing the desired product were combined and dried via centrifugal evaporation. The yield of the product was 27.4 mg, and its estimated purity by LCMS analysis was 98%.

Analysis LCMS Condition B: Retention time=2.54 min; ESI-MS(+) m/z 1209.3 (M+2H); ESI-HRMS(+) m/z: 1209.1651 (M+2H).

Preparation of Example 11243

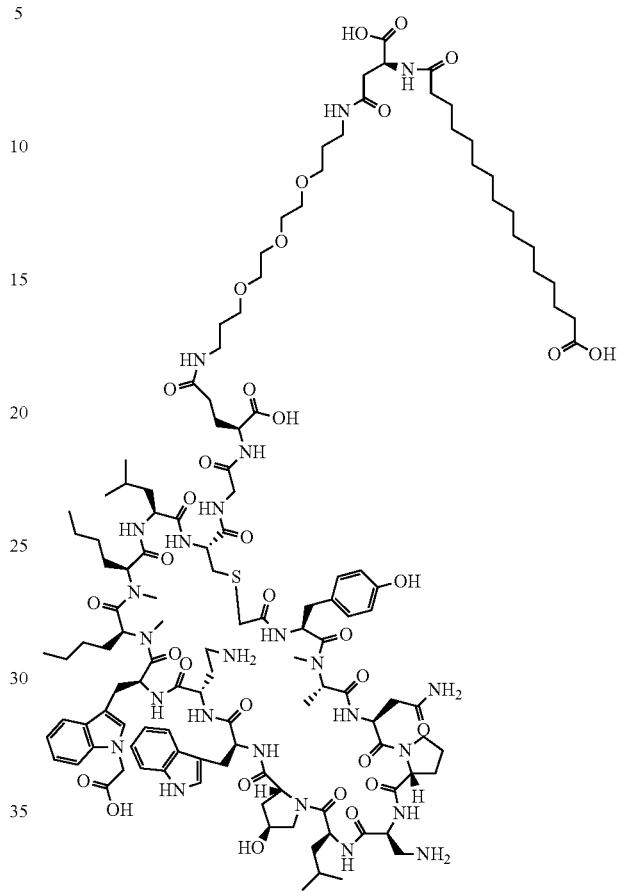

Example 11243 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-75% B over 25 minutes, then a 5-minute hold at 100% B; Flow: 20 mL/min. Fractions containing the desired product were combined and dried via centrifugal evaporation. The yield of the product was 21.7 mg, and its estimated purity by LCMS analysis was 99%.

Analysis LCMS Condition B: Retention time=2.34 min; ESI-MS(+) m/z 1302.5 (M+2H); ESI-HRMS(+) m/z: 1302.1978 (M+2H).

Preparation of Example 11244

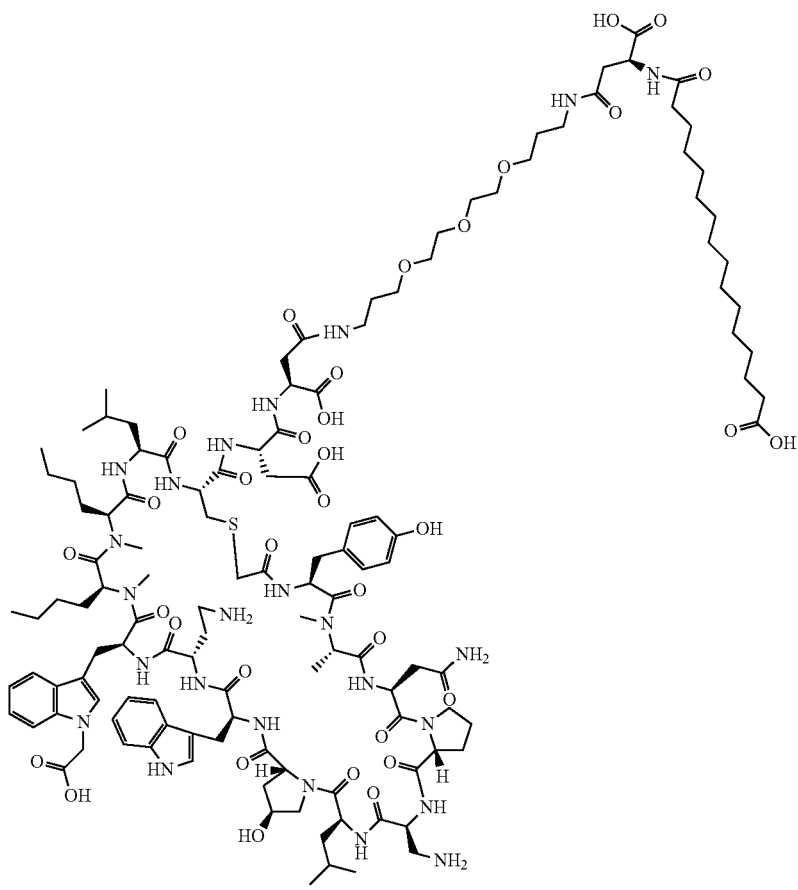 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11244 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 33.7 mg, and its estimated purity by LCMS analysis was 96%. Analysis LCMS Condition B: Retention time=2.14 min; ESI-MS(+) m/z 1324.3 (M+2H); ESI-HRMS(+) m/z: 1324.1926 (M+2H).

Preparation of Example 11245

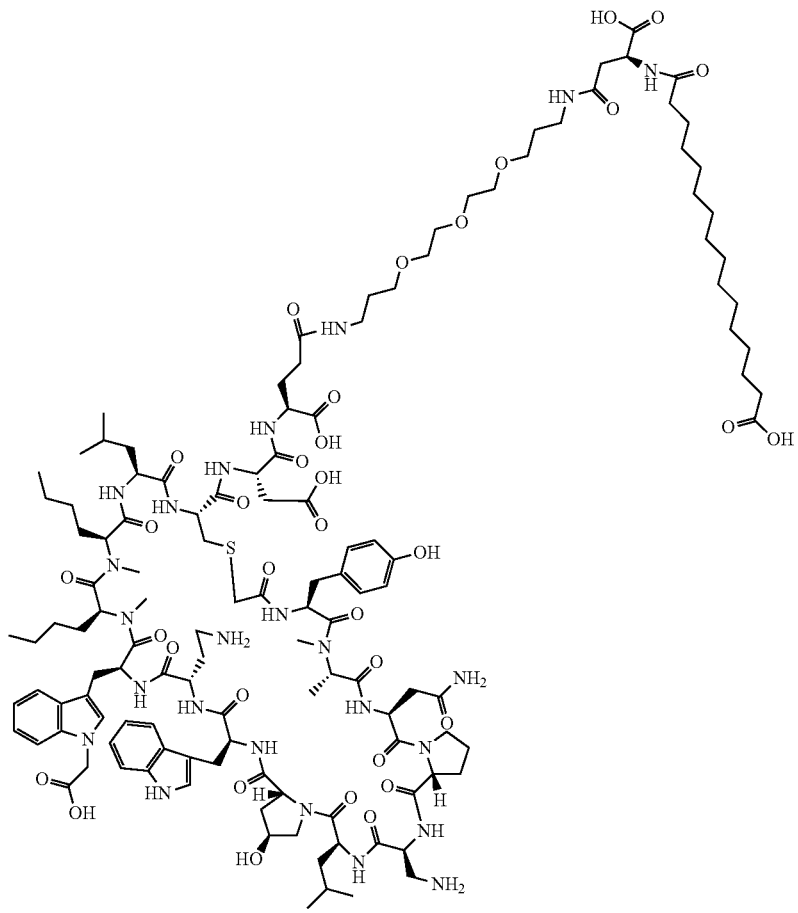 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CCC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11245 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin H was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 26.3 mg, and its estimated purity by LCMS analysis was 99%. Analysis LCMS Condition B: Retention time=2.15 min; ESI-MS(+) m/z 1331.5 (M+2H); ESI-HRMS(+) m/z: 1331.2001 (M+2H).

Preparation of Example 11246

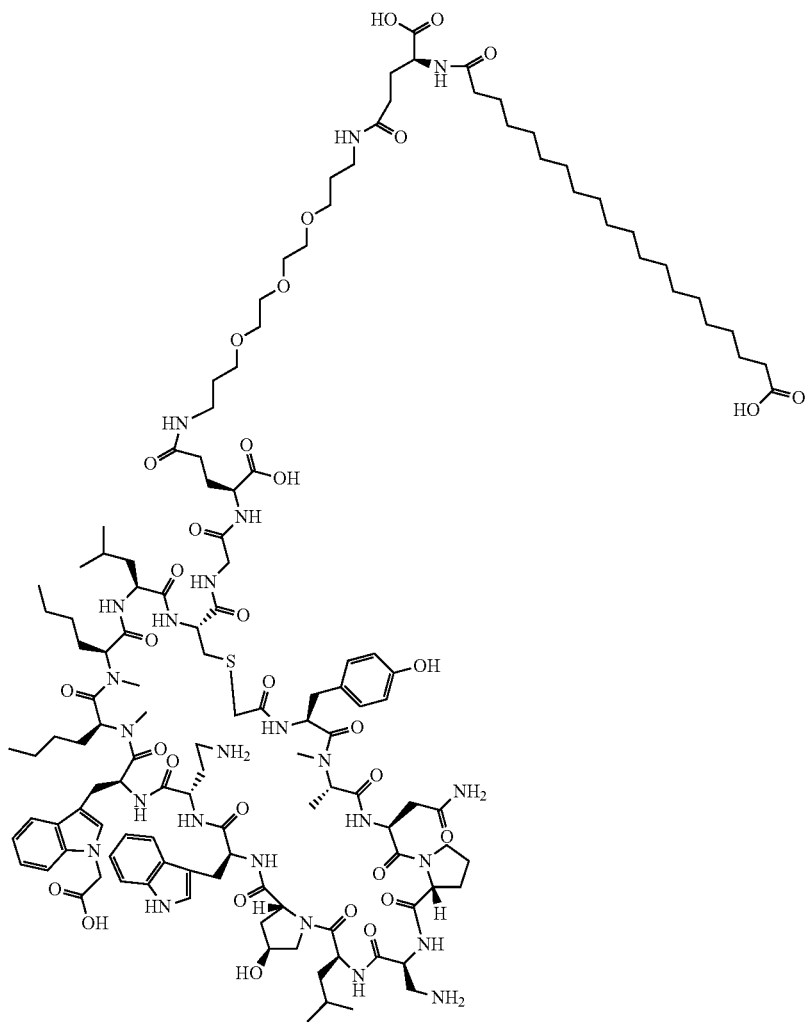 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCCOCCOCCOCCCNC(=O)CC[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11246 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 99%.

Analysis LCMS Condition B: Retention time=2.59 min; ESI-MS(+) m/z 1337.4 (M+2H); ESI-HRMS(+) m/z: 1337.2369 (M+2H).

Preparation of Example 11247

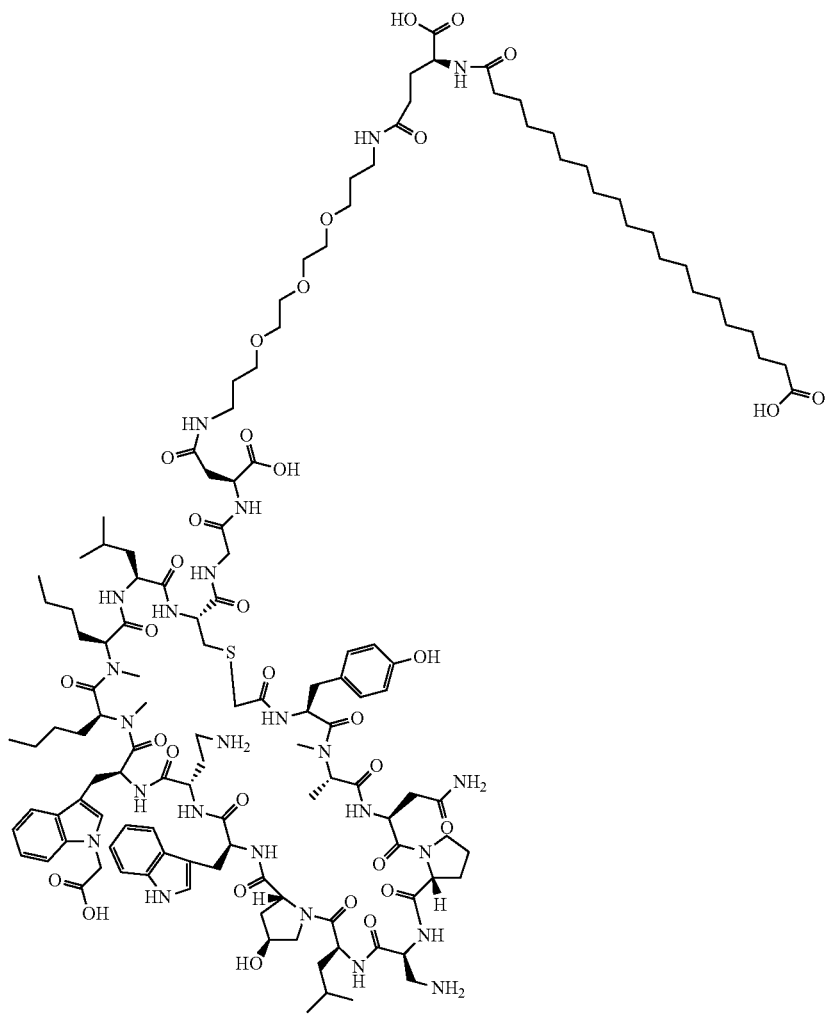 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11247 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 98%. Analysis LCMS Condition B: Retention time=2.61 min; ESI-MS(+) m/z 1330.4 (M+2H); ESI-HRMS(+) m/z: 1330.2305 (M+2H).

Preparation of Example 11248

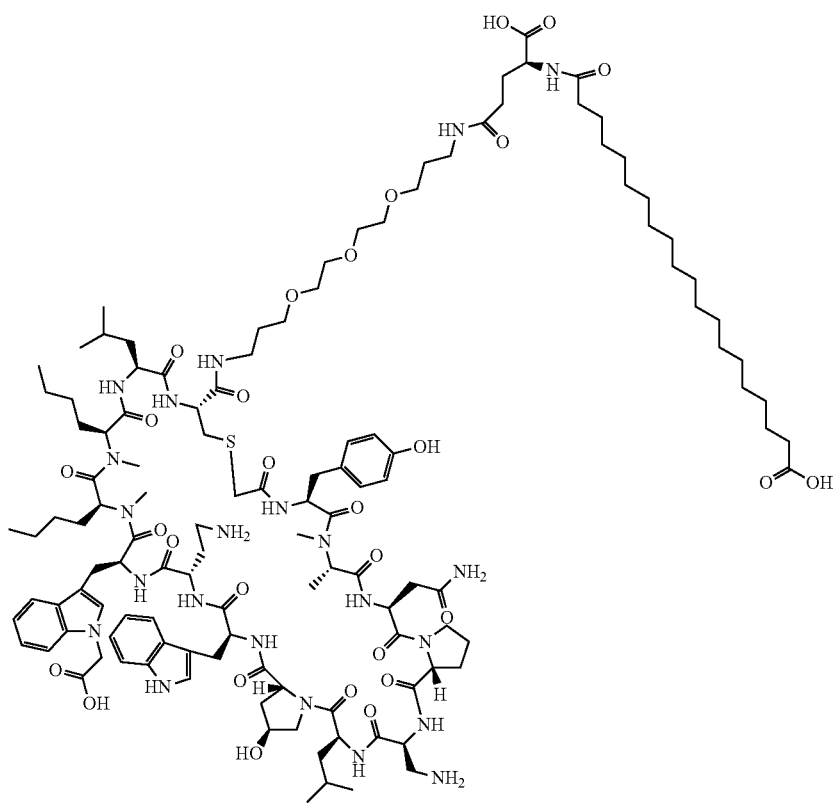 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)CC[C@H](NC(=O)CCCCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11248 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-µm OBD, 19 mm×250 mm; Mobile Phase A: 10:90 acetonitrile:water with 0.1% TFA; Mobile Phase B: 90:10 acetonitrile:water with 0.1% TFA; Gradient: 15-70% B over 25 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 98%. Analysis LCMS Condition B: Retention time=2.79 min; ESI-MS(+) m/z 1244.5 (M+2H); ESI-HRMS(+) m/z: 1244.2027 (M+2H).

Preparation of Example 11249

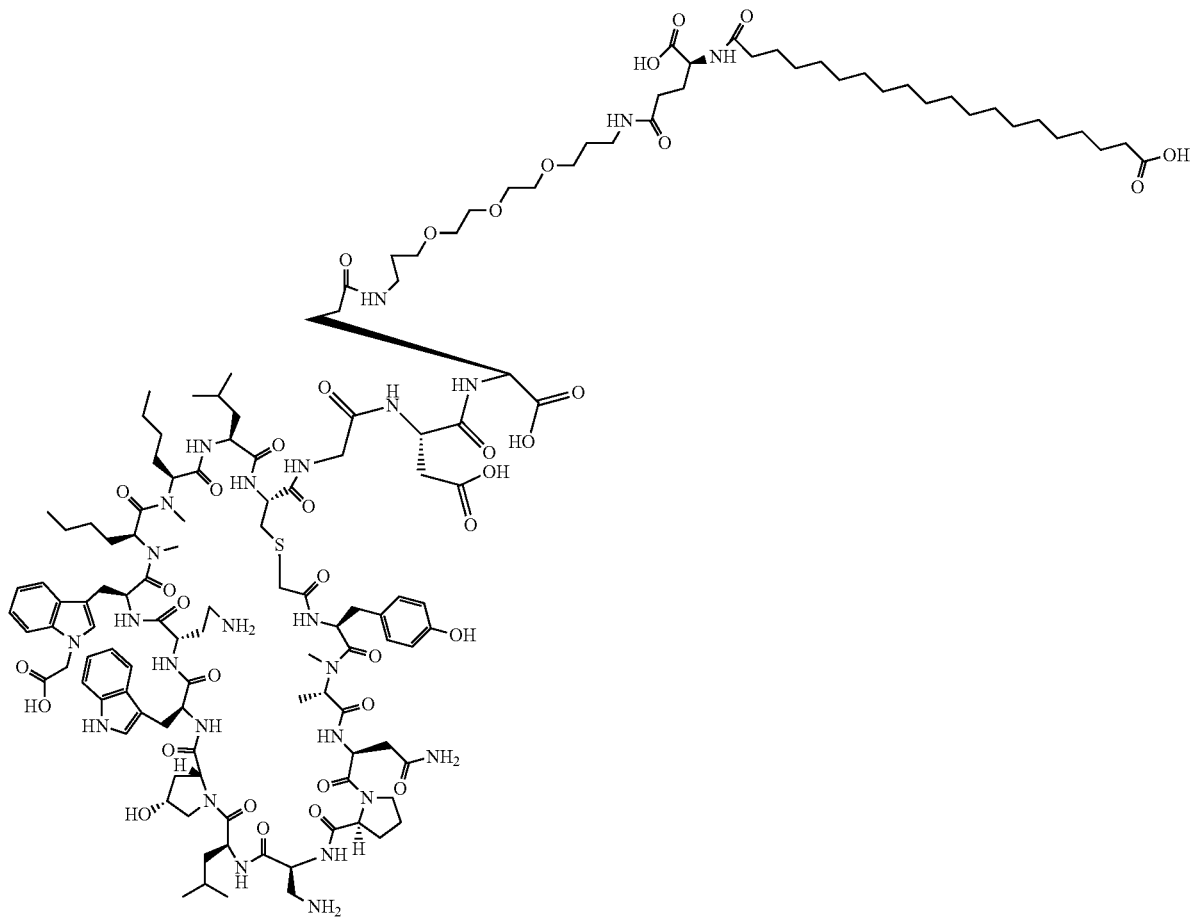 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CCC(=O)NCCCOCCOCCOCCCNC(=O)CC[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11249 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 97%. Analysis LCMS Condition B: Retention time=2.49 min; ESI-MS(+) m/z 1395.2.

Preparation of Example 11250

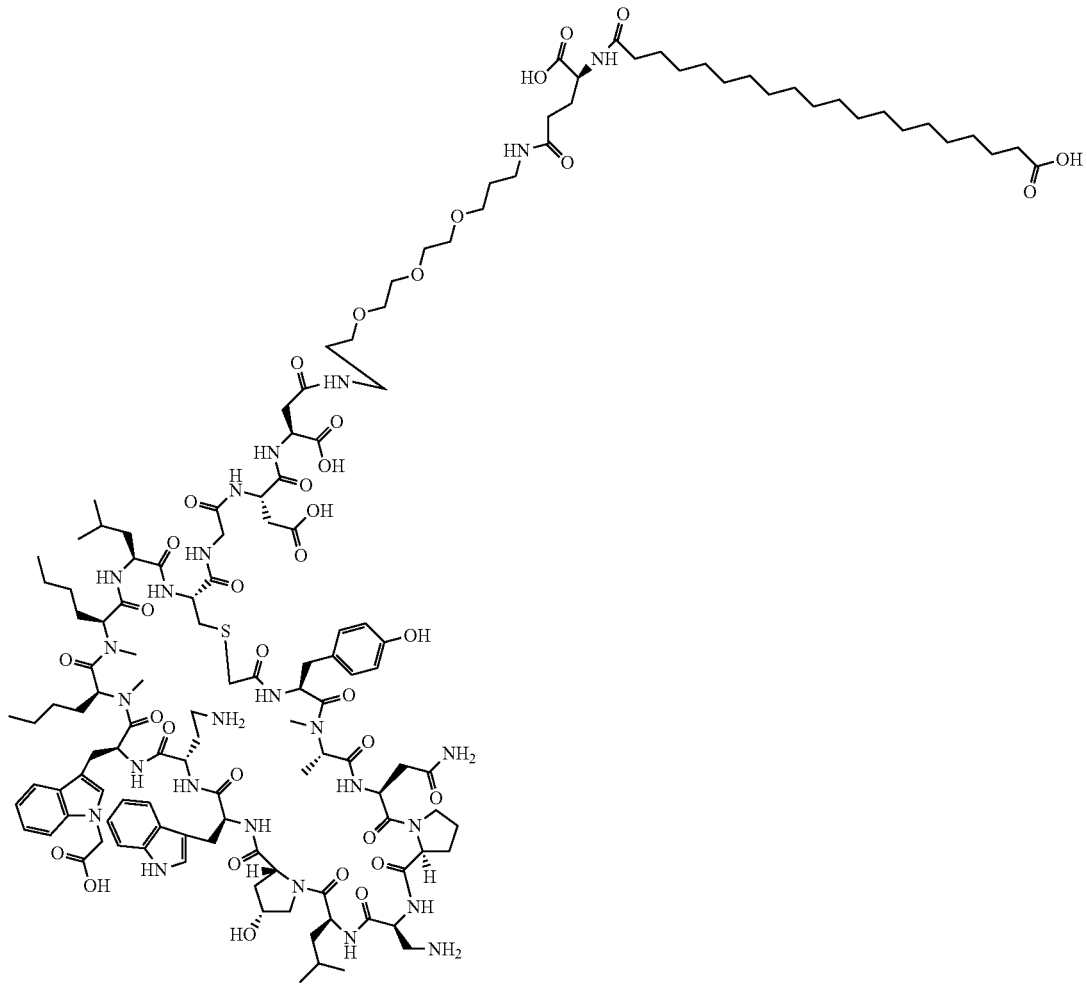 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)N[C@@H](CC(=O)NCCCOCCOCCOCCCNC(=O)CC[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11250 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 12.4 mg, and its estimated purity by LCMS analysis was 98%. Analysis LCMS Condition B: Retention time=2.49 min; ESI-MS(+) m/z 1388.2.

Preparation of Example 11251

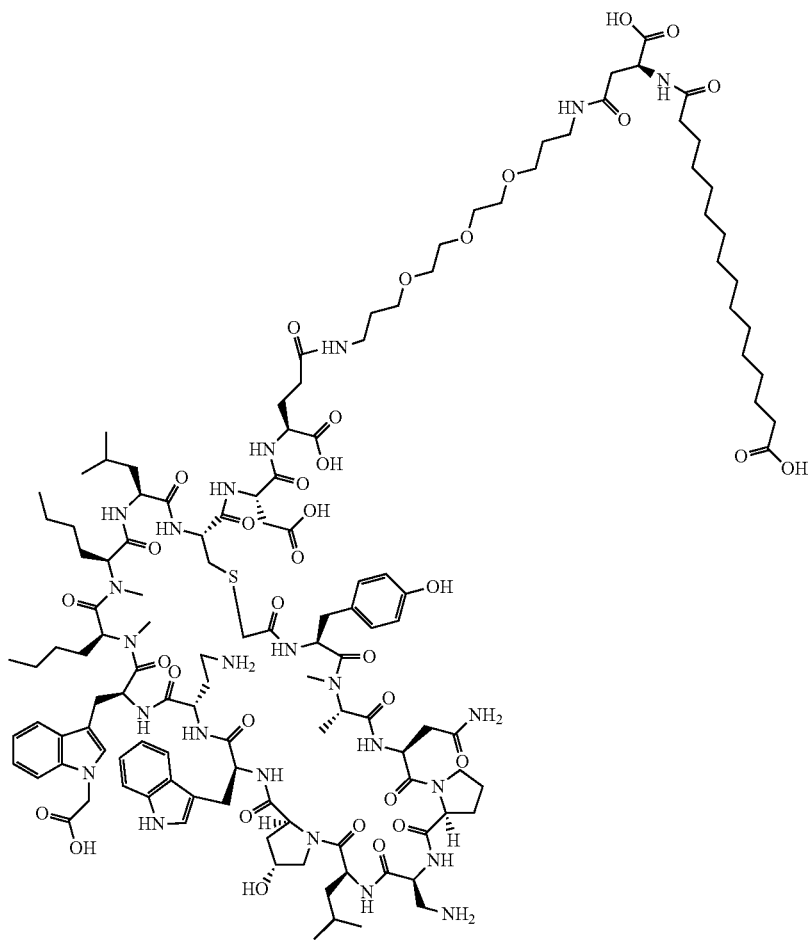 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CCC(=O)NCCCOCCOCCOCCCNC(=O)C[C@H](NC(=O)CCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11251 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-µm OBD, 30 mm×250 mm; Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 17 mg, and its estimated purity by LCMS analysis was 98%.

Analysis LCMS Condition B: Retention time=2.47 min; ESI-MS(+) m/z 1366.7.

Preparation of Example 11252

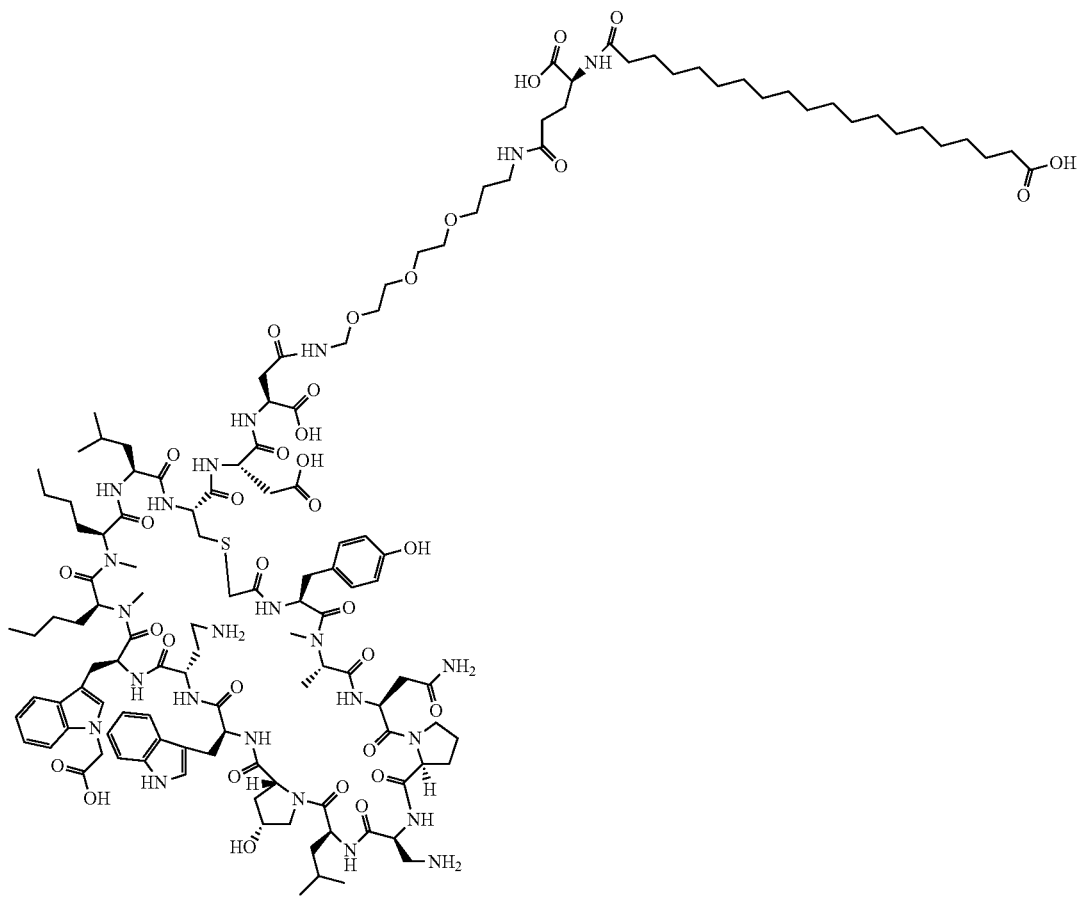 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CC(=O)NCOCCOCCOCCCNC(=O)CC[C@H](NC(=O)CCCCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11252 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin I was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 20-60% B over 25 minutes, then a 5-minute hold at 100% B; Flow: 20 mL/min. Fractions containing the desired product were combined and dried via centrifugal evaporation. The yield of the product was 18 mg, and its estimated purity by LCMS analysis was 97%.

Analysis LCMS Condition B: Retention time=2.47 min; ESI-MS(+) m/z 1359.7.

Preparation of Example 11253

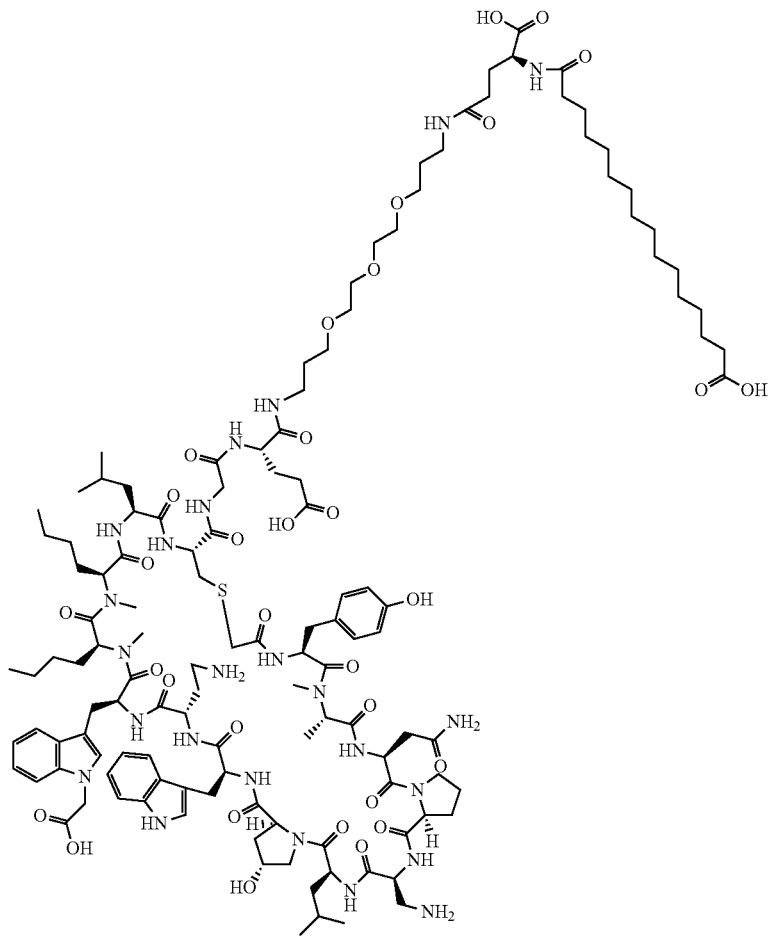 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)CC[C@H](NC(=O)CCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11253 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin J was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-65% B over 25 minutes, then a 5-minute hold at 100% B; Flow: 20 mL/min. Fractions containing the desired product were combined and dried via centrifugal evaporation. The yield of the product was 18.5 mg, and its estimated purity by LCMS analysis was 95%. Analysis LCMS Condition B: Retention time=2.23 min; ESI-MS(+) m/z 1295.4.

Preparation of Example 11254

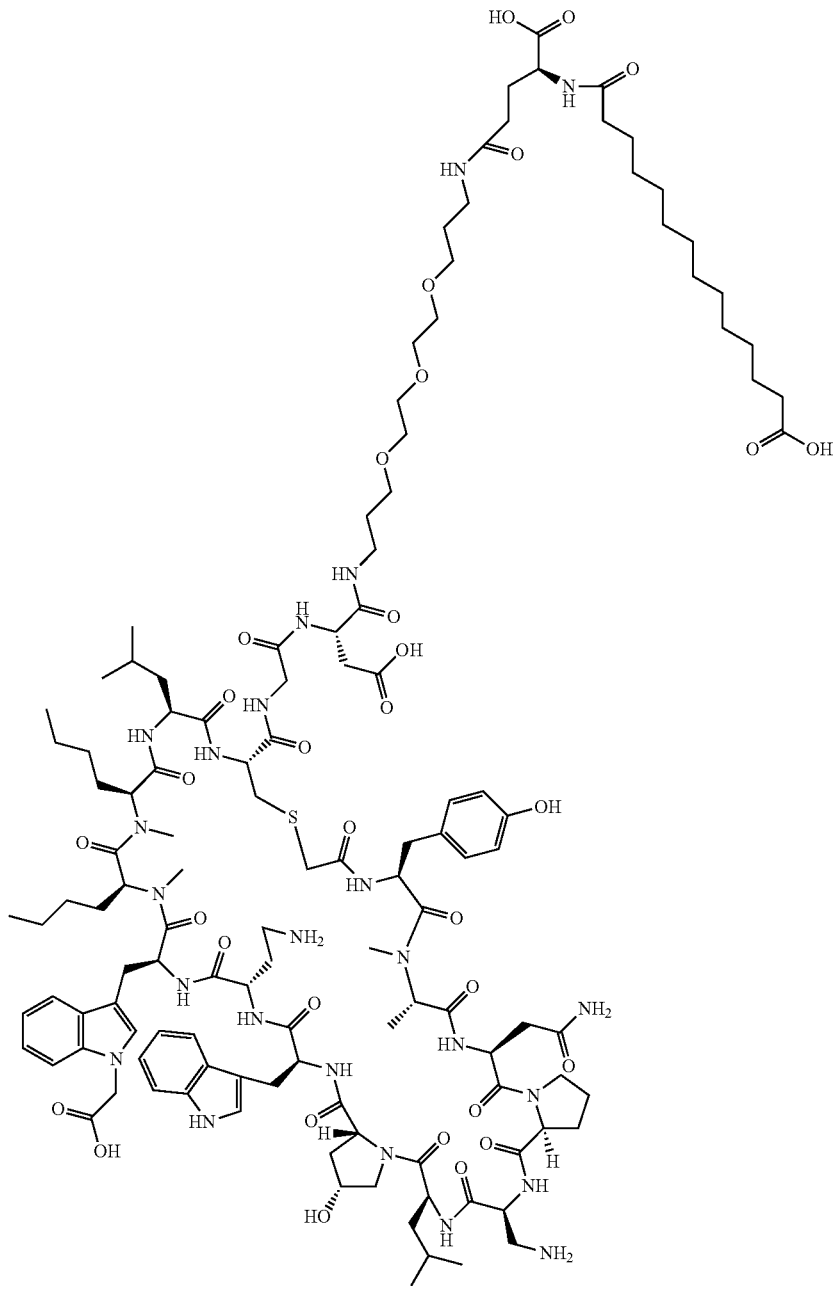 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)CC[C@H](NC(=O)CCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11254 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin J was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-70% B over 25 minutes, then a 5-minute hold at 100% B; Flow: 20 mL/min. Fractions containing the desired product were combined and dried via centrifugal evaporation. The yield of the product was 30.6 mg, and its estimated purity by LCMS analysis was 98%. Analysis LCMS Condition B: Retention time=2.21 min; ESI-MS(+) m/z 1288.5.

Preparation of Example 11255

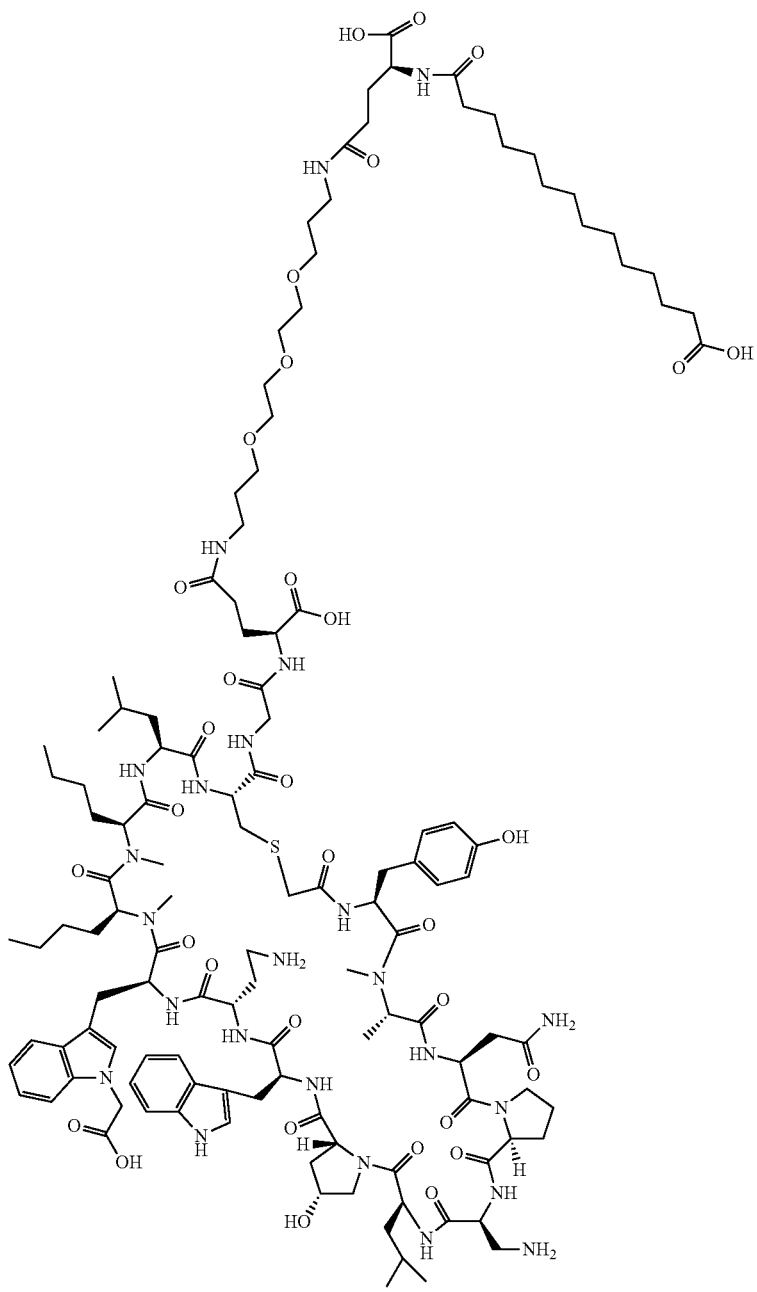 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCCOCCOCCOCCCNC(=O)CC[C@H](NC(=O)CCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11255 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin J was used in this synthesis. The crude material was purified via preparative LC/MS with the following conditions: Column: XSelect CSH Prep C18, 5-µm OBD, 30 mm×250 mm; Mobile Phase A: 10:90 acetonitrile:water with 0.1% TFA; Mobile Phase B: 90:10 acetonitrile:water with 0.1% TFA; Gradient: 25-70% B over 25 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 96%. Analysis LCMS Condition B: Retention time=2.20 min; ESI-MS(+) m/z 1295.4.

Preparation of Example 11256

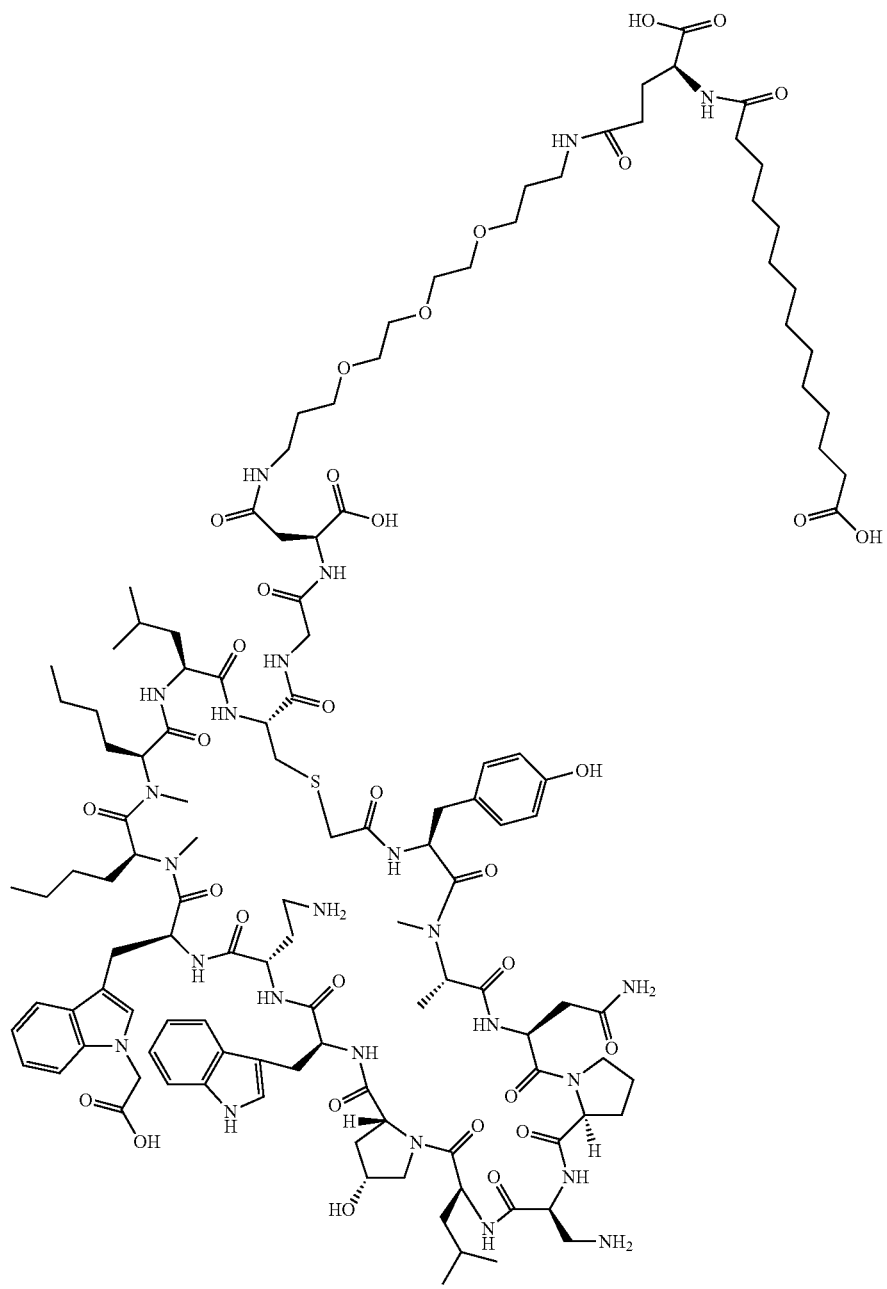 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11256 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin J was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-70% B over 25 minutes, then a 5-minute hold at 100% B; Flow: 20 mL/min. Fractions containing the desired product were combined and dried via centrifugal evaporation. The yield of the product was 21.5 mg, and its estimated purity by LCMS analysis was 97%. Analysis LCMS Condition B: Retention time=2.20 min; ESI-MS(+) m/z 1288.5.

Preparation of Example 11257

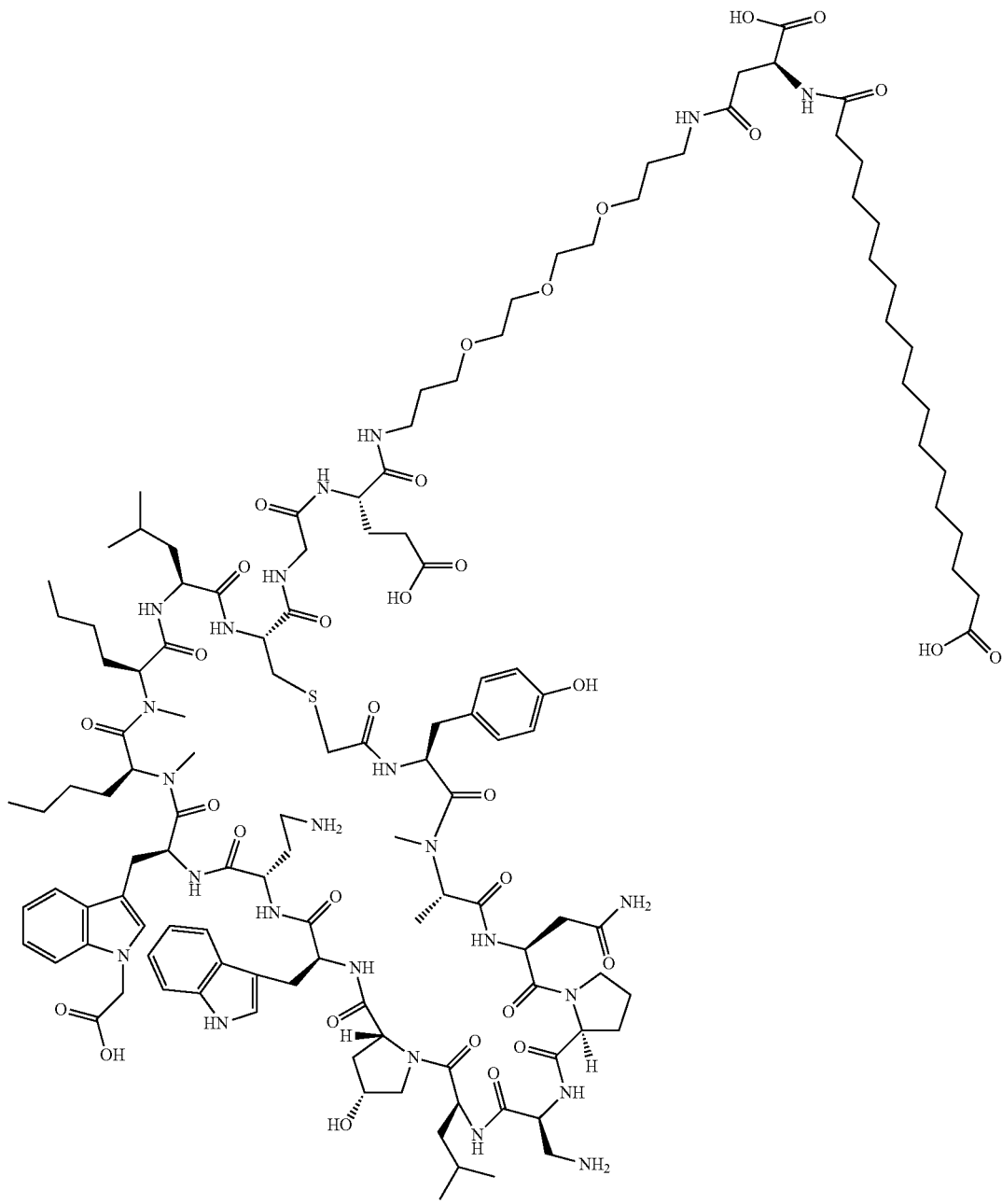 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)C[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11257 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin N was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 22.1 mg, and its estimated purity by LCMS analysis was 97%.

Analysis LCMS Condition B: Retention time=2.38 min; ESI-MS(+) m/z 1316.7 (M+2H); ESI-HRMS(+) m/z: 1316.2101 (M+2H).

Preparation of Example 11258

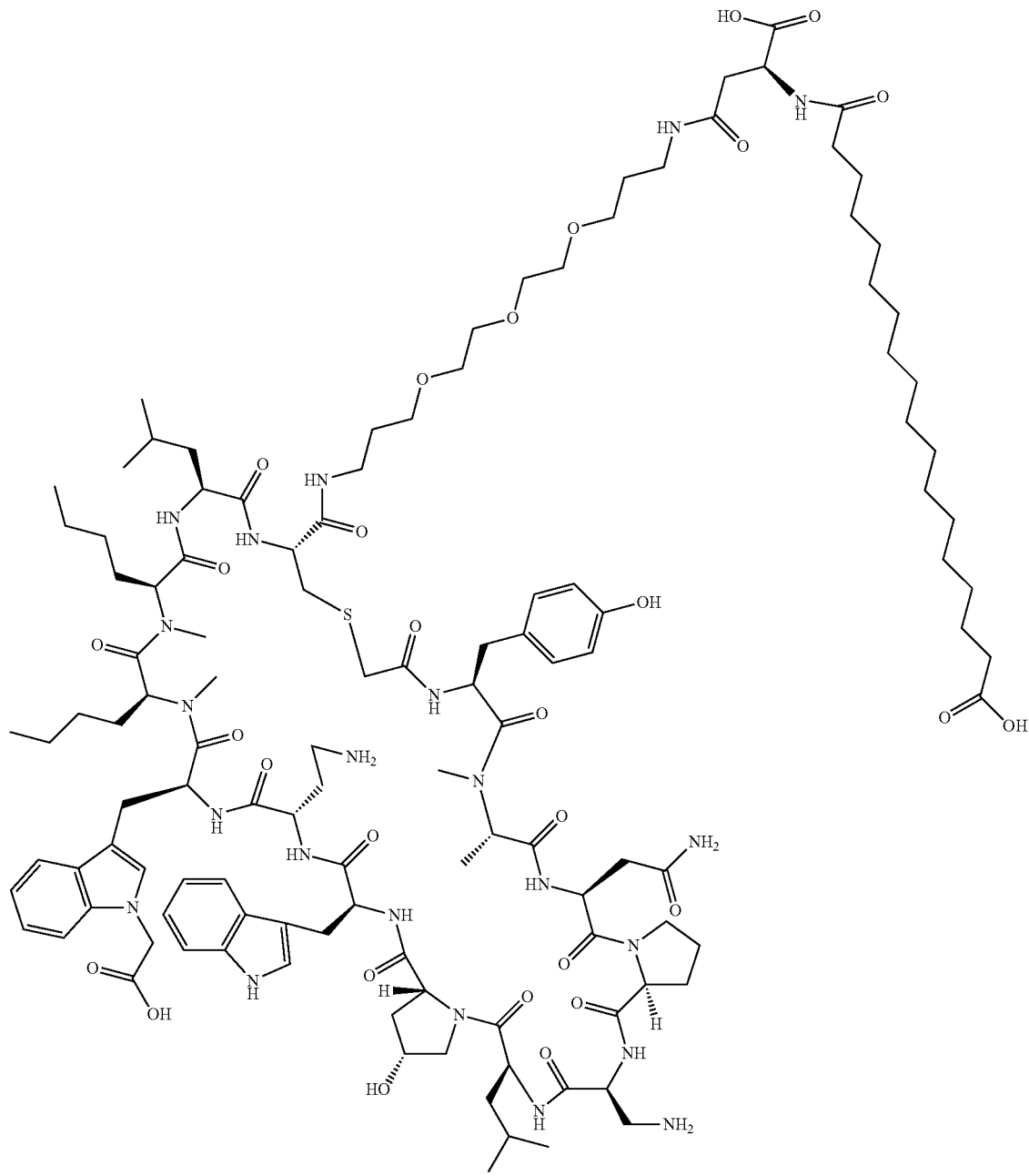 [SMILES: CCCC[C@H]1C(=O)N(C)[C@@H](CCCC)C(=O)N[C@@H](CC(C)C)C(=O)N[C@H](C(=O)NCCCOCCOCCOCCCNC(=O)C[C@H](NC(=O)CCCCCCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11258 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin N was used in this synthesis. The crude material was purified via preparative LC/MS with the following conditions: Column: XSelect CSH Prep C18, 5-μm OBD, 19 mm×250 mm; Mobile Phase A: 10:90 acetonitrile:water with 0.1% TFA; Mobile Phase B: 90:10 acetonitrile:water with 0.1% TFA; Gradient: 10-75% B over 25 minutes, then a 5-minute hold at 100% B; Flow: 20 mL/min. Fractions containing the desired product were combined and dried via centrifugal evaporation. The yield of the product was 23.1 mg, and its estimated purity by LCMS analysis was 98%.

Analysis LCMS Condition B: Retention time=2.66 min; ESI-MS(+) m/z 1223.4 (M+2H); ESI-HRMS(+) m/z: 1223.1770 (M+2H).

Preparation of Example 11259

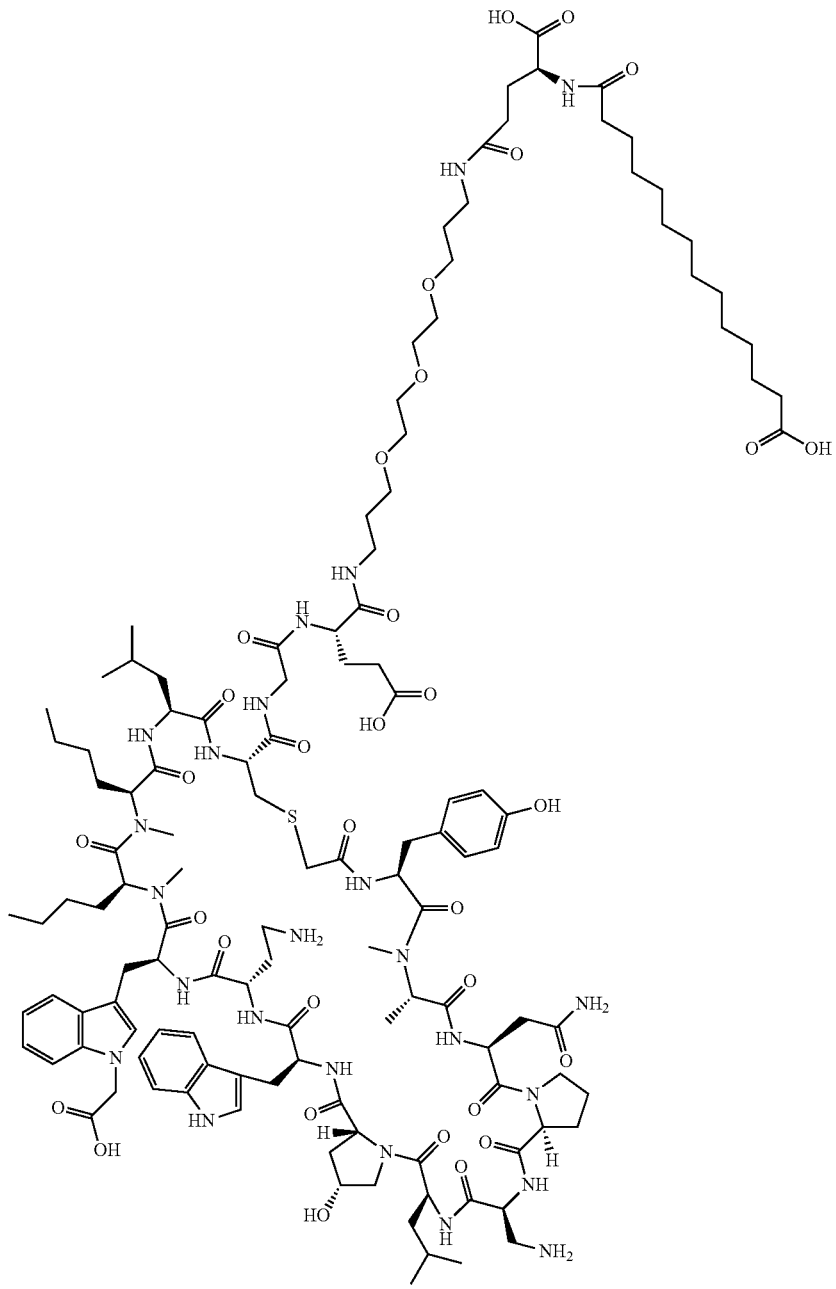 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)CC[C@H](NC(=O)CCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11259 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin Q was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-65% B over 25 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 98%.

Analysis LCMS Condition B: Retention time=2.40 min; ESI-MS(+) m/z 1202.5.

Preparation of Example 11260

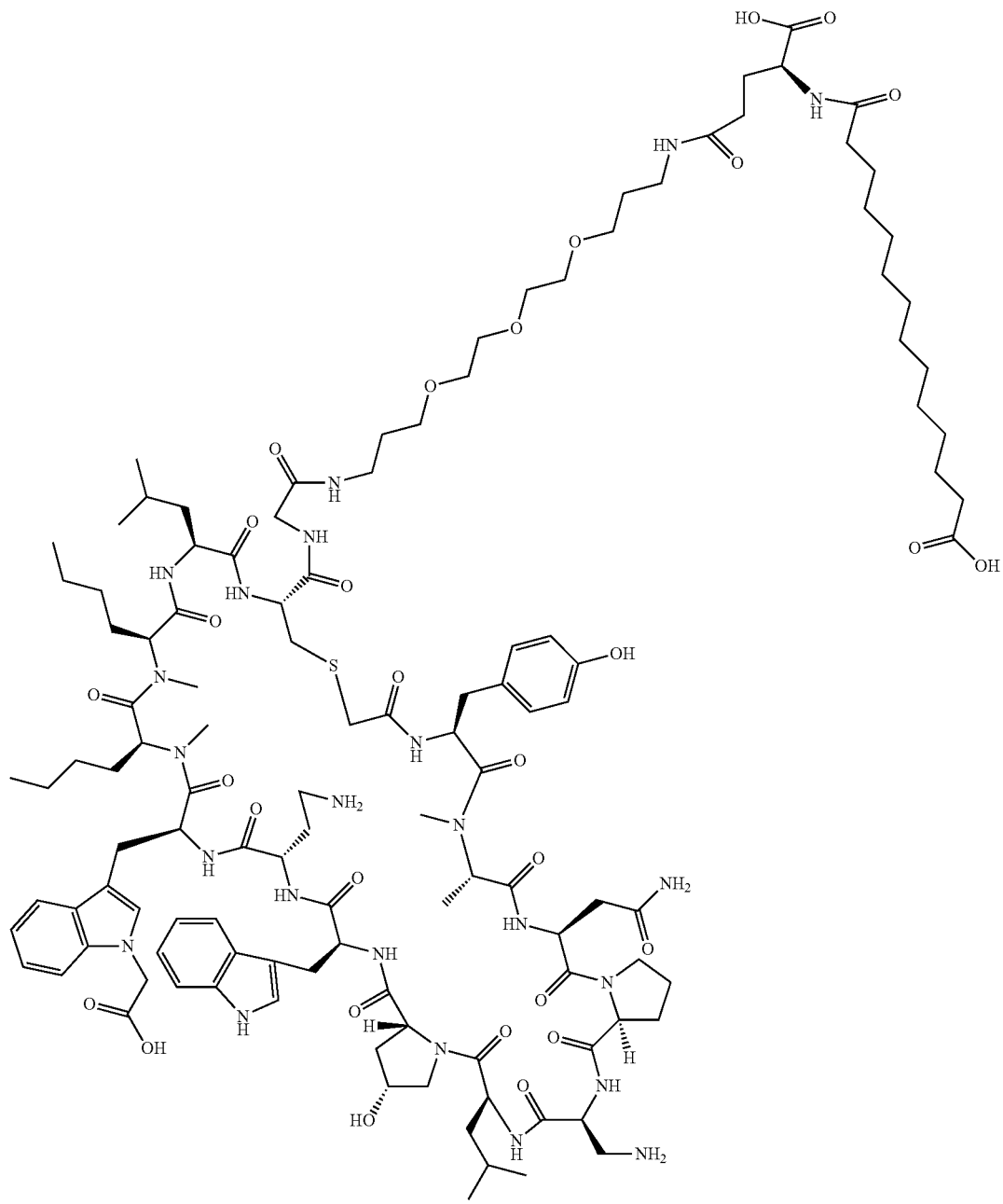 [SMILES: CCCC[C@H]1C(=O)N(C)[C@@H](CCCC)C(=O)N[C@@H](CC(C)C)C(=O)N[C@H](C(=O)NCC(=O)NCCCOCCOCCOCCCNC(=O)CC[C@H](NC(=O)CCCCCCCCCCCCC(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11260 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin Q was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-65% B over 25 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 99%.

Analysis LCMS Condition B: Retention time=2.34 min; ESI-MS(+) m/z 1231.1

Preparation of Example 11261

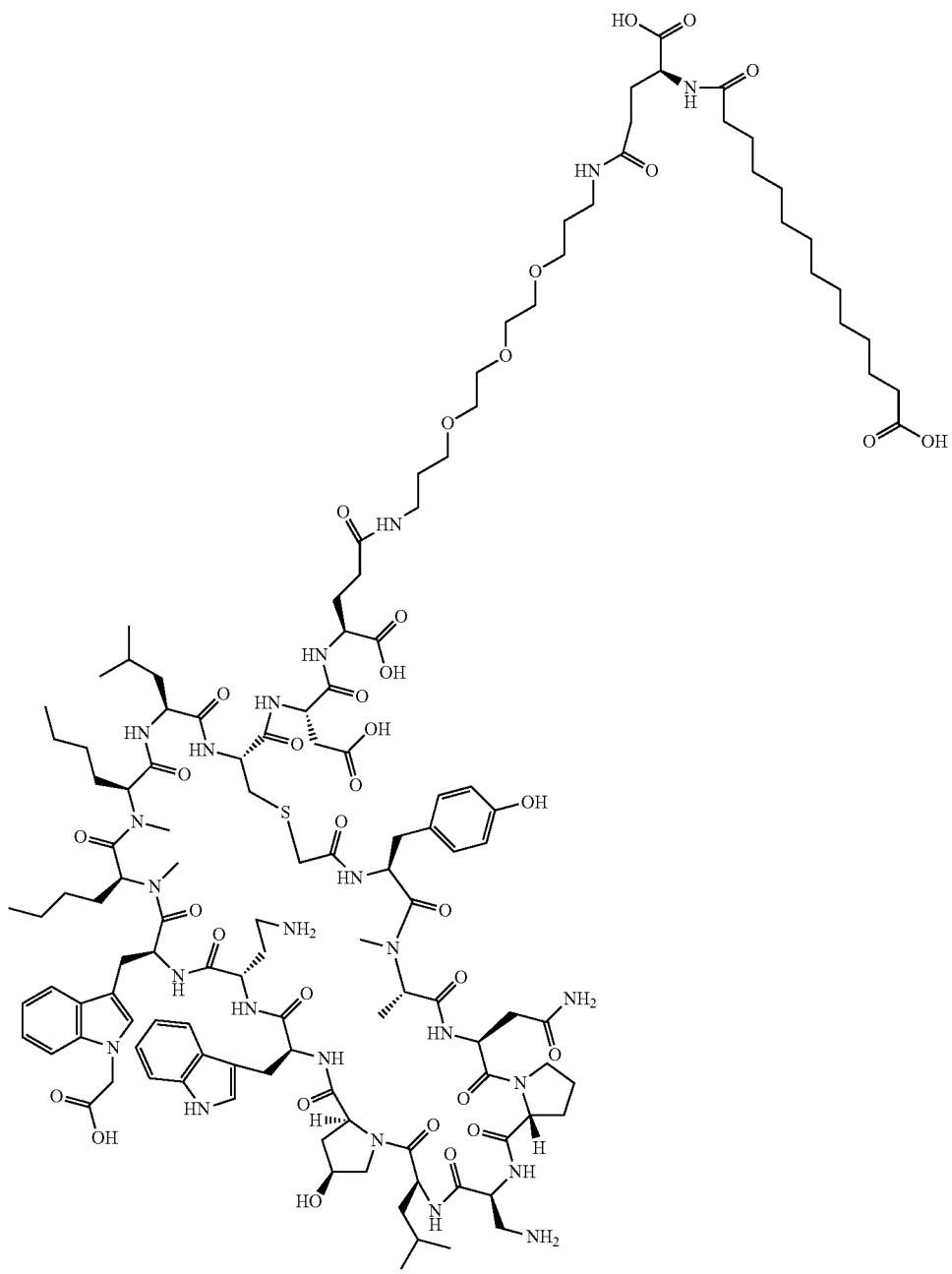 [SMILES: CCCC[C@H]1C(=O)N(C)[C@@H](CCCC)C(=O)N[C@@H](CC(C)C)C(=O)N[C@H](C(=O)N[C@@H](CC(=O)O)C(=O)N[C@@H](CCC(=O)NCCCOCCOCCOCCCNC(=O)CC[C@H](NC(=O)CCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@@H]2C(=O)N[C@@H](CN)C(=O)N[C@@H](CC(C)C)C(=O)N2C[C@@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11261 was prepared following the general synthetic sequence described for the preparation of Example 0001, composed of the following general procedures: "Symphony Method A: Resin-swelling procedure", "Symphony Method A: Standard-coupling procedure B", "Symphony Method A: Secondary amine-coupling procedure B", "Custom amino acids-coupling procedure", "Chloroacetic acid coupling procedure A", "Global Deprotection Method A", and "Cyclization Method A". Modified 2-chlorotrityl chloride resin Q was used in this synthesis. The crude material was purified via preparative LC/MS with the following conditions: Column: XSelect CSH Prep C18, 5-μm OBD, 30 mm×250 mm; Mobile Phase A: 10:90 acetonitrile:water with 0.1% TFA; Mobile Phase B: 90:10 acetonitrile:water with 0.1% TFA; Gradient: 25-65% B over 25 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 97%.

Analysis LCMS Condition B: Retention time=2.11 min; ESI-MS(+) m/z 1324.7

Preparation of Example 11262

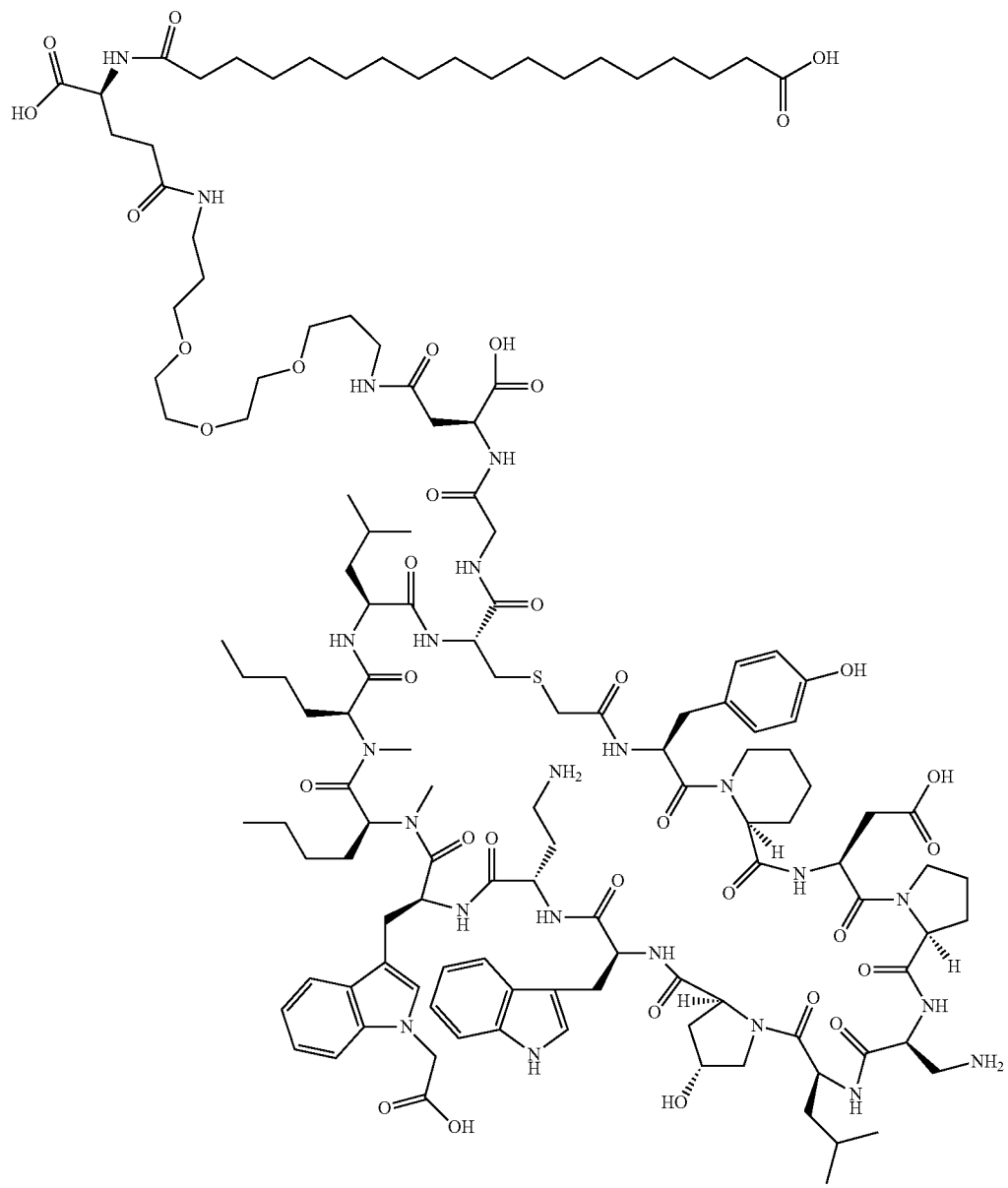 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11262 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 90.9%.

Analysis LCMS Condition A:

Retention time=3.83 min; ESI-HRMS(+) m/z: 1329.7089 (M+2H).

Preparation of Example 11263

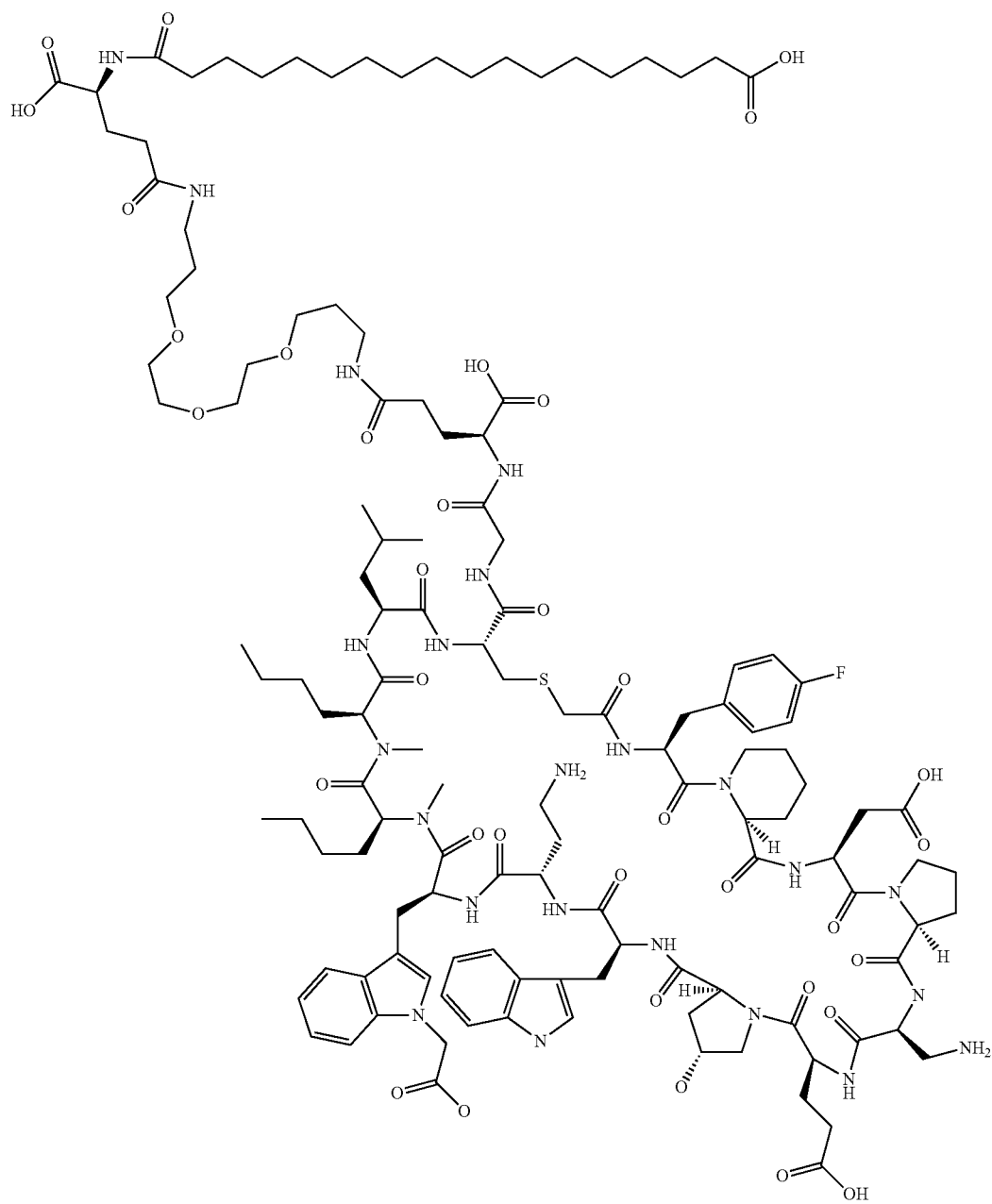 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11263 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 19 mg, and its estimated purity by LCMS analysis was 95.7%.

Analysis LCMS Condition A: Retention time=4.17 min; ESI-HRMS(+) m/z: 1345.6943 (M+2H).

Preparation of Example 11264

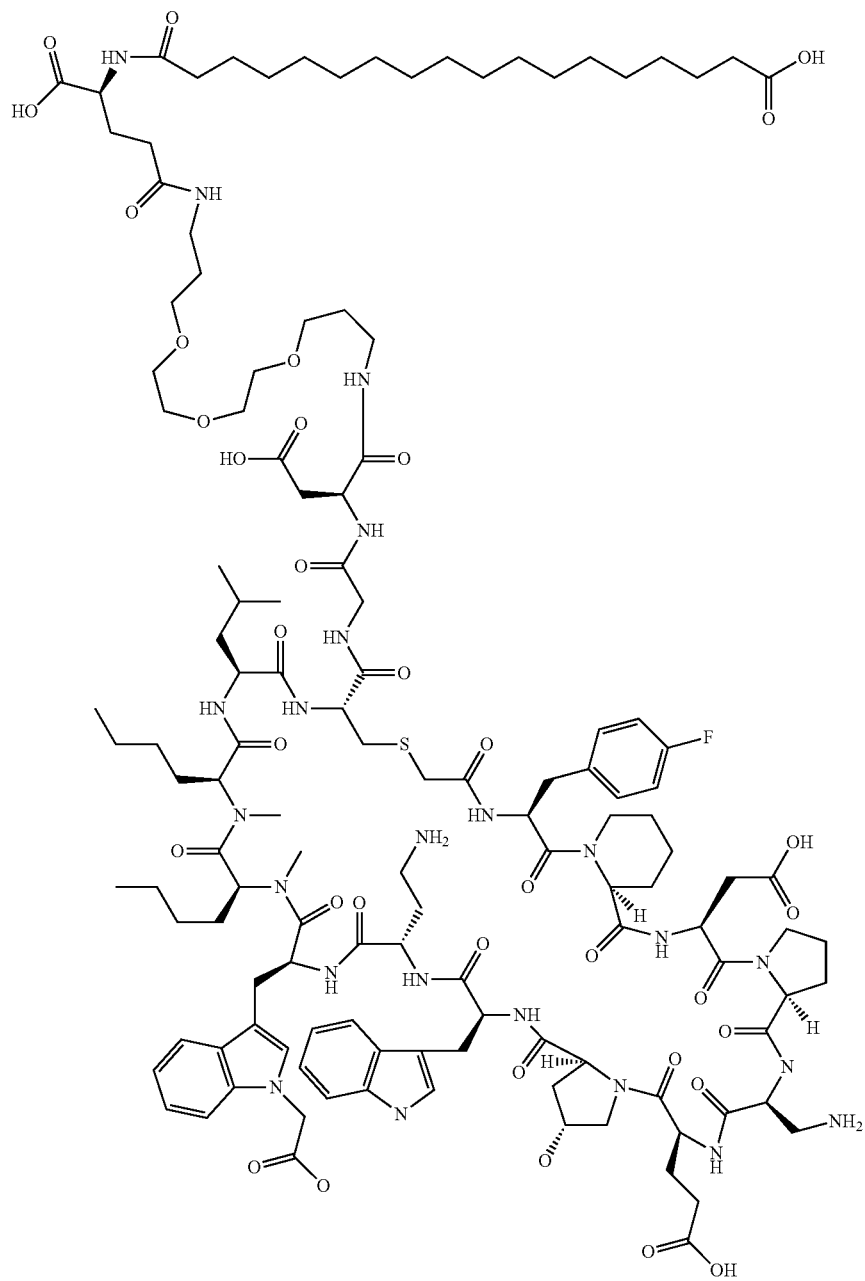 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)O)C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11264 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 97.3%.

Analysis LCMS Condition A: Retention time=4.23 min; ESI-HRMS(+) m/z: 1338.6835 (M+2H).

Preparation of Example 11265

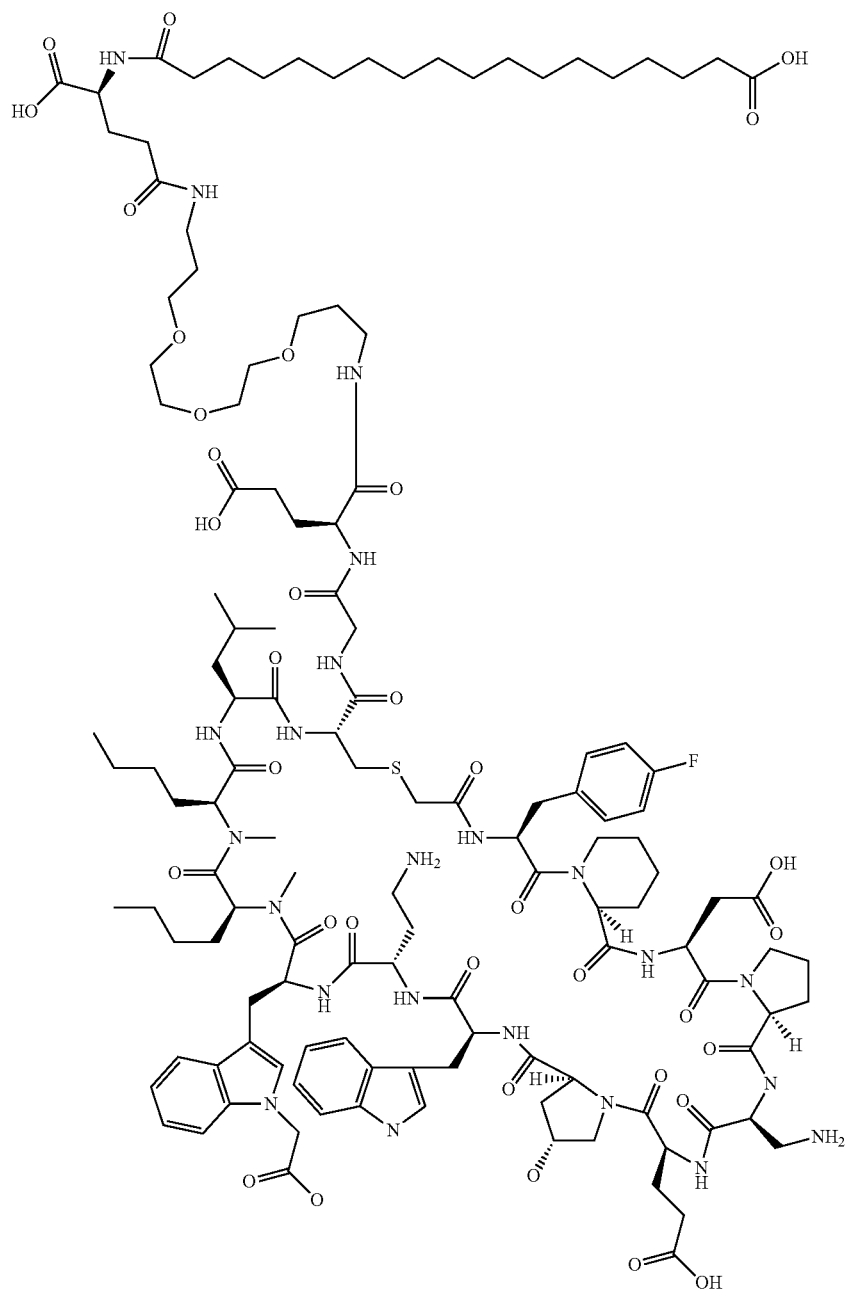 [SMILES: CCCC[C@H]1C(=O)N(C)[C@@H](CCCC)C(=O)N[C@@H](CC(C)C)C(=O)N[C@H](C(=O)NCC(=O)N[C@@H](CCC(=O)O)C(=O)NCCCOCCOCCOCCCNC(=O)CC[C@H](NC(=O)CCCCCCCCCCCCCCCCC(=O)O)C(=O)O)CSCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11265 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 23 mg, and its estimated purity by LCMS analysis was 98.4%.

Analysis LCMS Condition A: Retention time=4.23 min; ESI-HRMS(+) m/z: 1345.6946 (M+2H).

Preparation of Example 11266

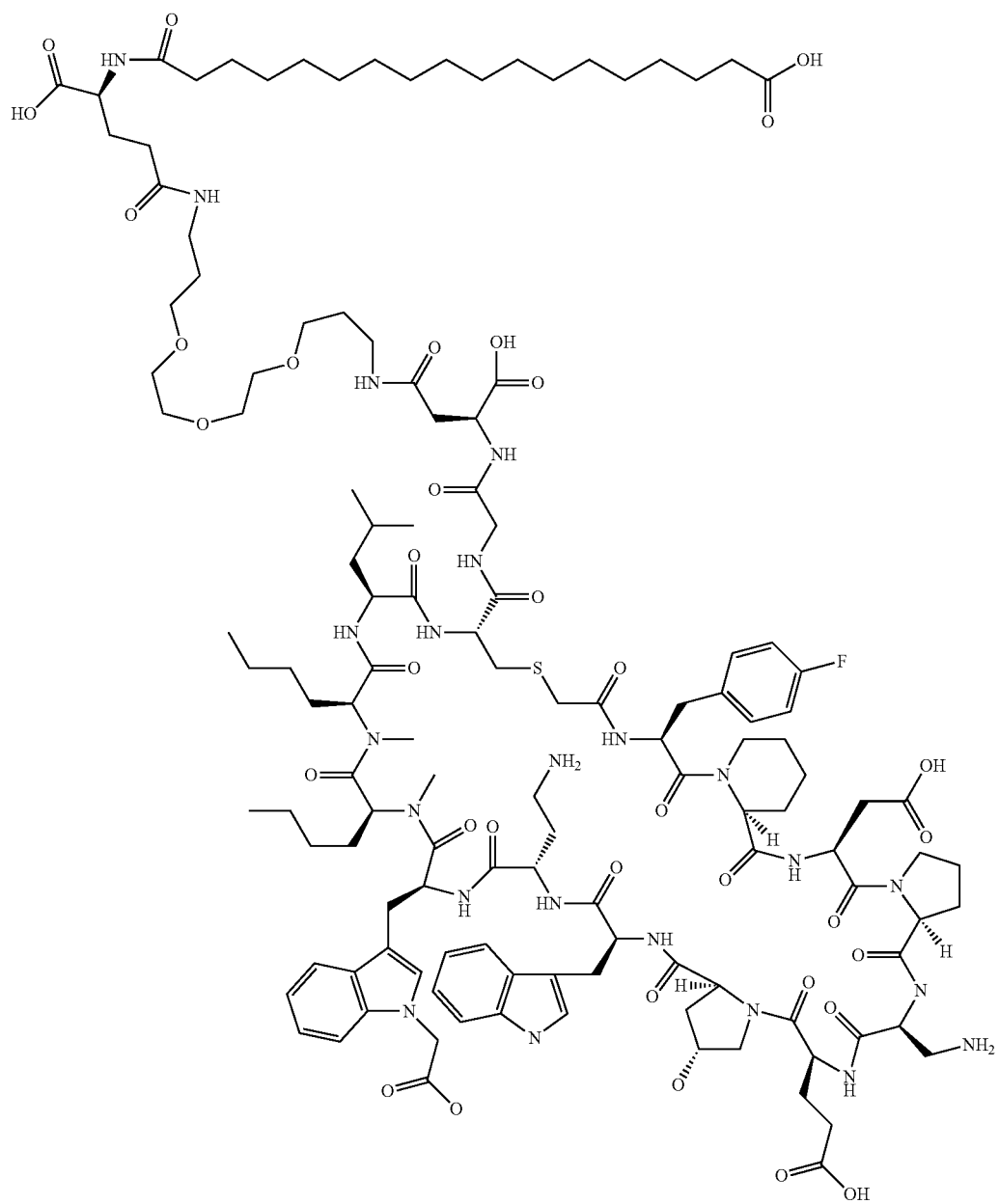 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11266 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 24 mg, and its estimated purity by LCMS analysis was 98.0%.

Analysis LCMS Condition A: Retention time=4.19 min.

Preparation of Example 11267

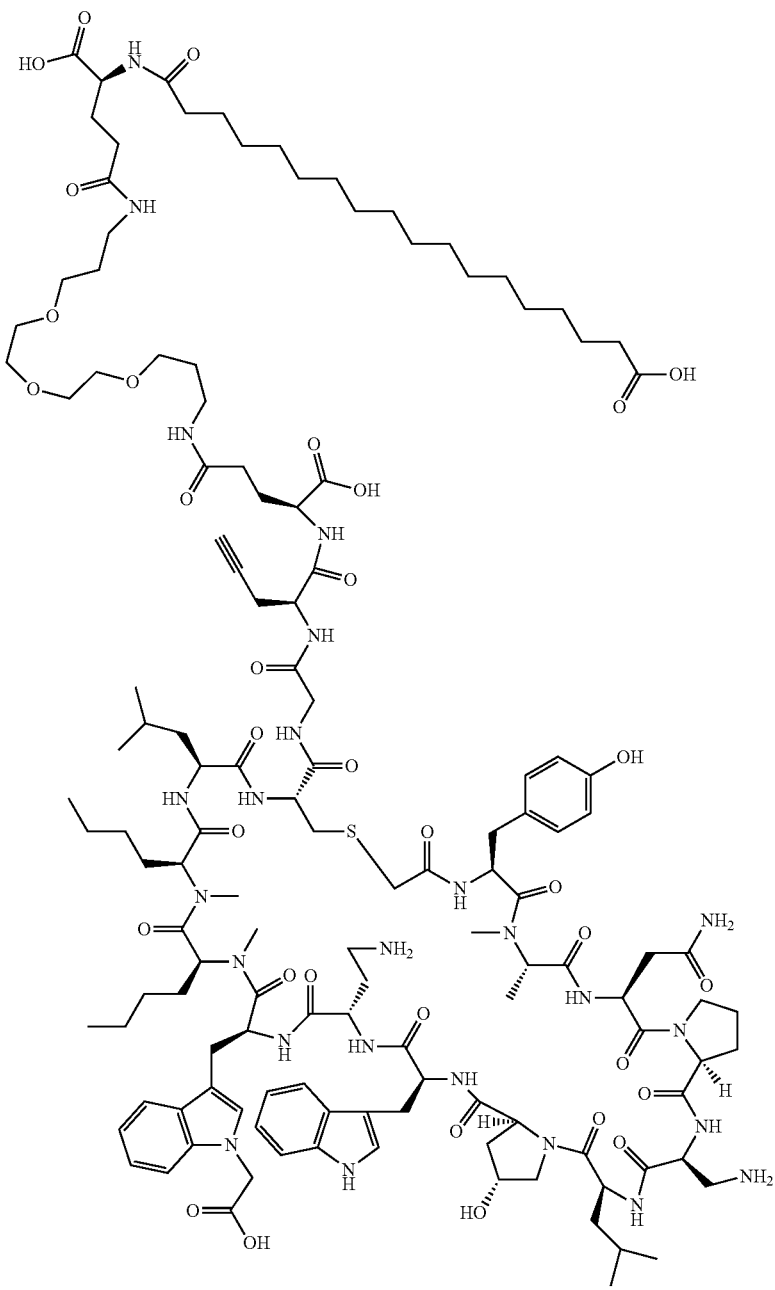 [SMILES: C#CC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)N[C@@H](CCC(=O)NCCCOCCOCCOCCCNC(=O)CC[C@H](NC(=O)CCCCCCCCCCCCCCCCC(=O)O)C(=O)O)C(=O)O]

Example 11267 was prepared following the general synthetic sequence described for the preparation of Example 0001 except that the reaction was run on 0.6 mmol scale, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 280 mg, and its estimated purity by LCMS analysis was 95.6%.

Analysis LCMS Condition A: Retention time=3.98 min; ESI-HRMS(+) m/z: 1370.7382 (M+2H).

Preparation of Example 11268
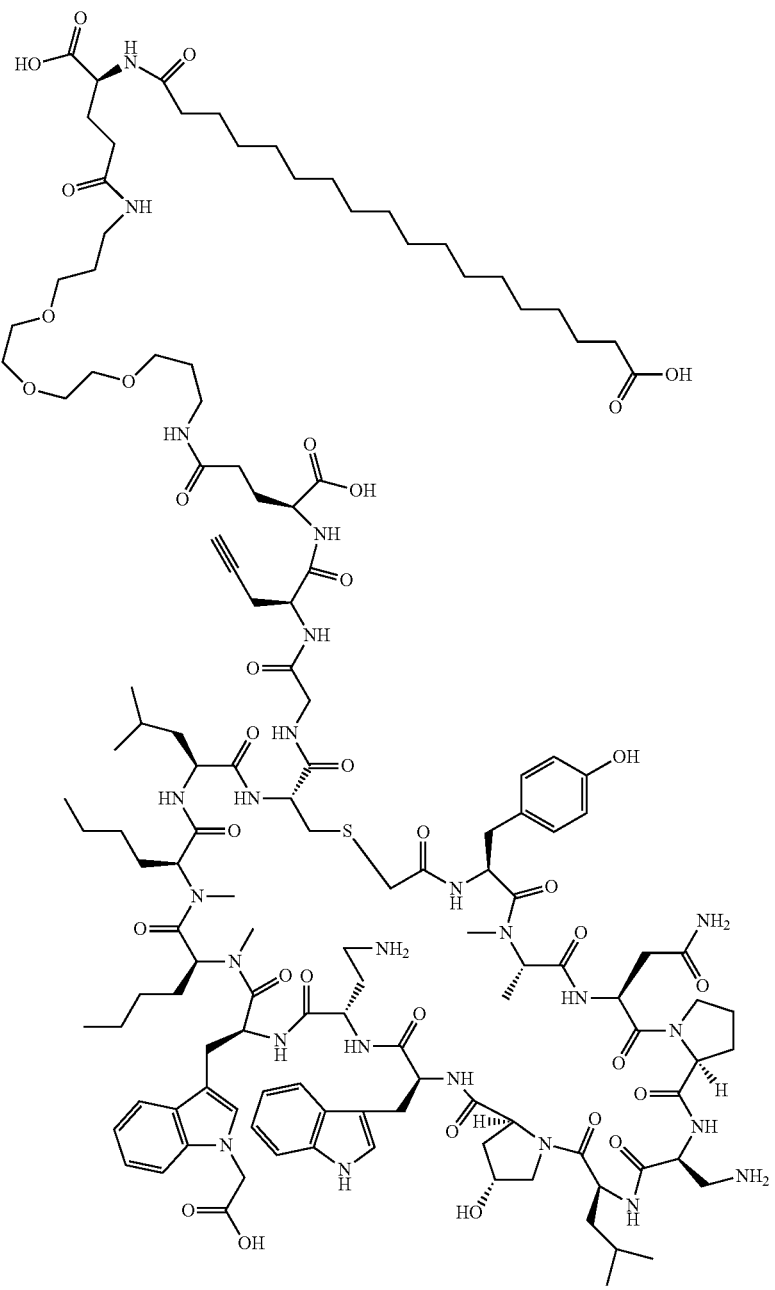 [SMILES: C#CC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)N[C@@H](CCC(=O)NCCCOCCOCCOCCCNC(=O)CC[C@H](NC(=O)CCCCCCCCCCCCCCCCC(=O)O)C(=O)O)C(=O)O]

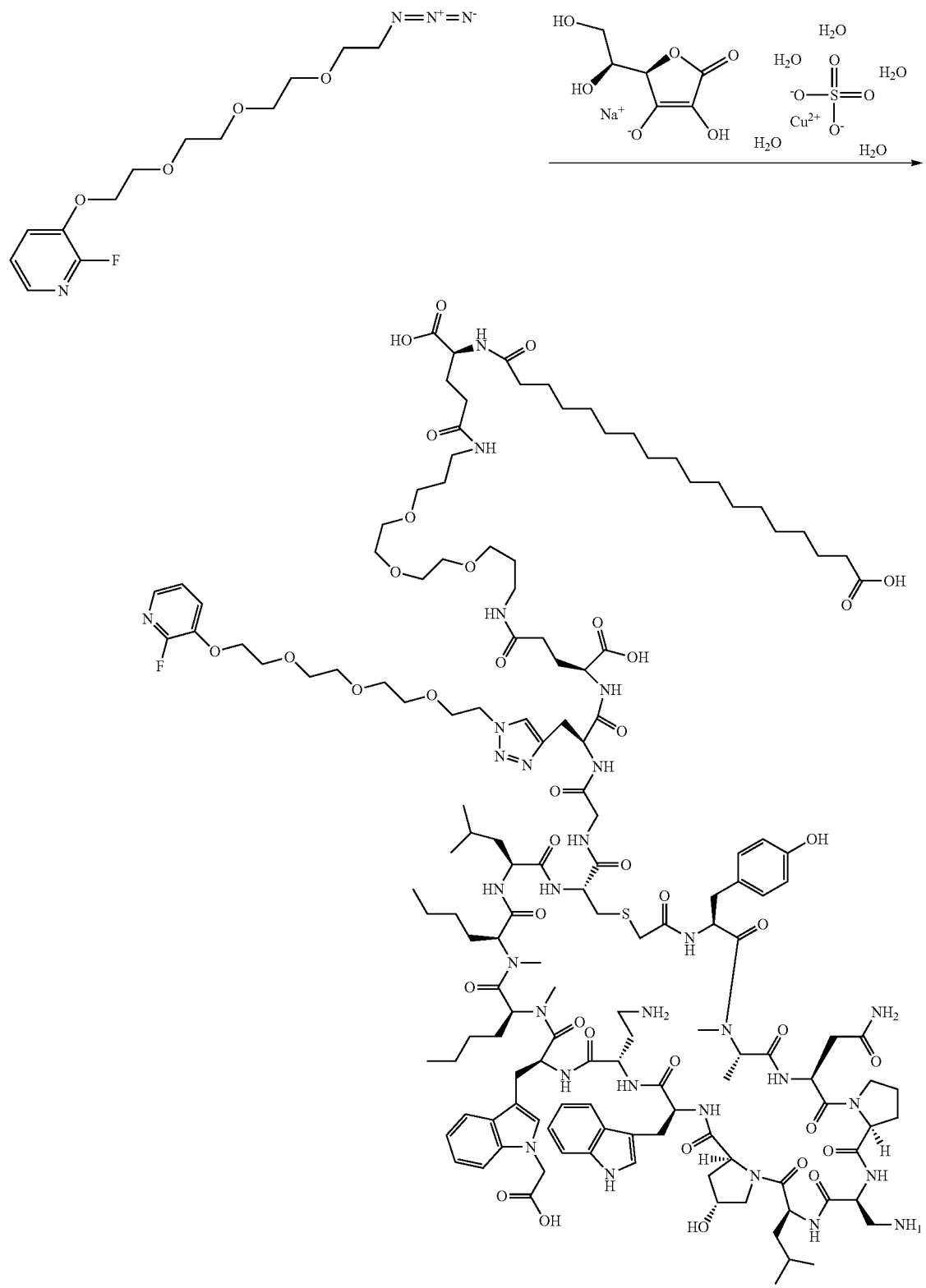
Example 11268 was prepared as follows. To a 1 dram vial was added Example 11267 (30 mg, 10.11 μmol) in Water (0.5 mL). To this was added t-BuOH (0.5 mL) and 3-(2-(2-(2-(2-azidoethoxy)ethoxy)ethoxy)ethoxy)-2-fluoropyridine (6.35 mg, 0.020 mmol). The solution was stirred and then SODIUM ASCORBATE (2.60 mg, 0.013 mmol) and a solution of copper(II) sulfate pentahydrate (0.015 mL, 3.03 μmol) was added. The reaction was allowed to stir at rt for 2 hr. The reaction was checked by LC/MS and was complete. The crude reaction mixture was injected directly onto a reverse phase chromatography column.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 16.3 mg, and its estimated purity by LCMS analysis was 98.7%.

Analysis LCMS Condition A: Retention time=4.01 min; ESI-HRMS(+) m/z: 1528.6 (M+2H).

Preparation of Example 11269

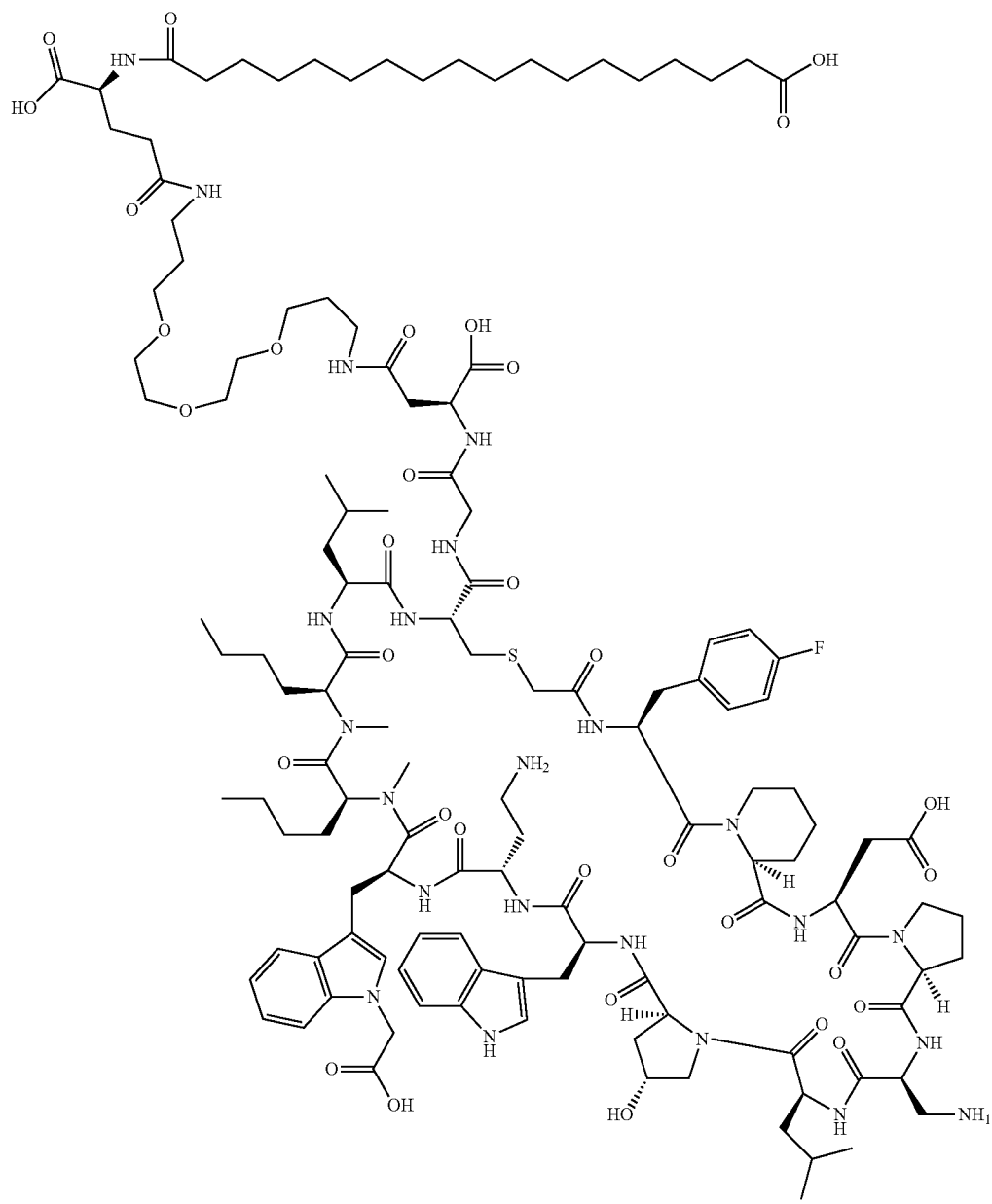 [SMILES: CCCC[C@H]1C(=O)N(C)[C@@H](CCCC)C(=O)N[C@@H](CC(C)C)C(=O)N[C@H](C(=O)NCC(=O)N[C@@H](CC(=O)NCCCOCCOCCOCCCNC(=O)CC[C@H](NC(=O)CCCCCCCCCCCCCCCCC(=O)O)C(=O)O)C(=O)O)CSCC(=O)N[C@@H](Cc2ccc(F)cc2)C(=O)N2CCCC[C@H]2C(=O)N[C@@H](CC(=O)O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 11269 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 21 mg, and its estimated purity by LCMS analysis was 90.6%.

Analysis LCMS Condition A: Retention time=4.25 min; ESI-HRMS(+) m/z: 1330.7059 (M+2H).

Preparation of Example 11270

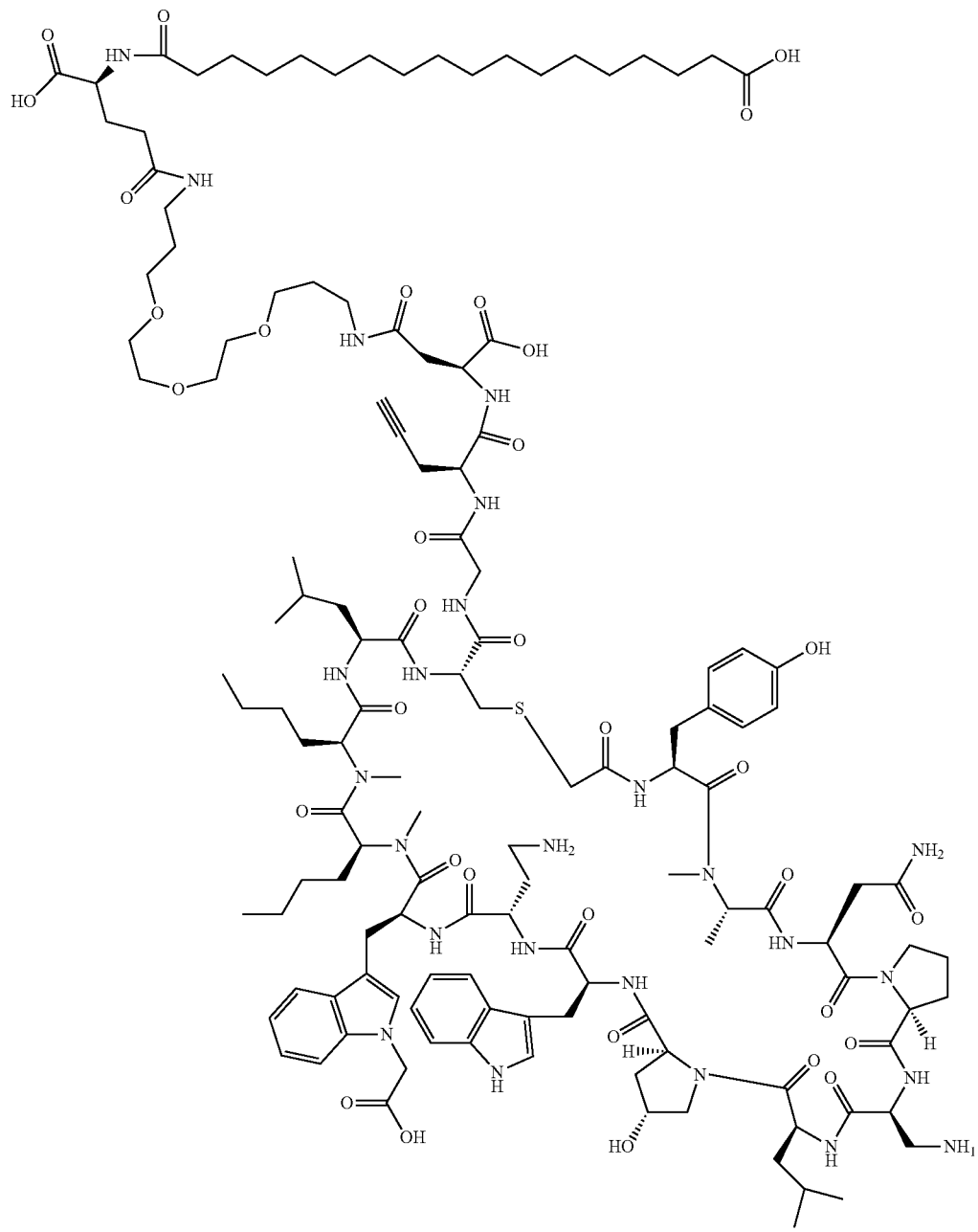 [SMILES: C#CC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)N[C@@H](CC(=O)NCCCOCCOCCOCCCNC(=O)CC[C@H](NC(=O)CCCCCCCCCCCCCCCCC(=O)O)C(=O)O)C(=O)O]

Example 11270 was prepared following the general synthetic sequence described for the preparation of Example 0001 except that it was run on 0.8 mmol scale and composed of the following general procedures: "Symphony Method A: Resin-swelling procedure", "Symphony Method A: Standard-coupling procedure", "Symphony Method A: Secondary amine-coupling procedure A", "Custom amino acids-coupling procedure", "Chloroacetic acid coupling procedure A", "Global Deprotection Method A", and "Cyclization Method A". Modified chlorotrityl resin W was used in this synthesis.

The crude material was purified via preparative LC/MS with the following conditions: The crude material was purified via preparative LC with the following conditions: Column: XSelect CSH Prep C18, 5-μm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 140 mg, and its estimated purity by LCMS analysis was 97.4%.

Analysis LCMS Condition A: Retention time=4.07 min; ESI-HRMS(+) m/z: 1363.7277 (M+2H).

Preparation of Example 11271

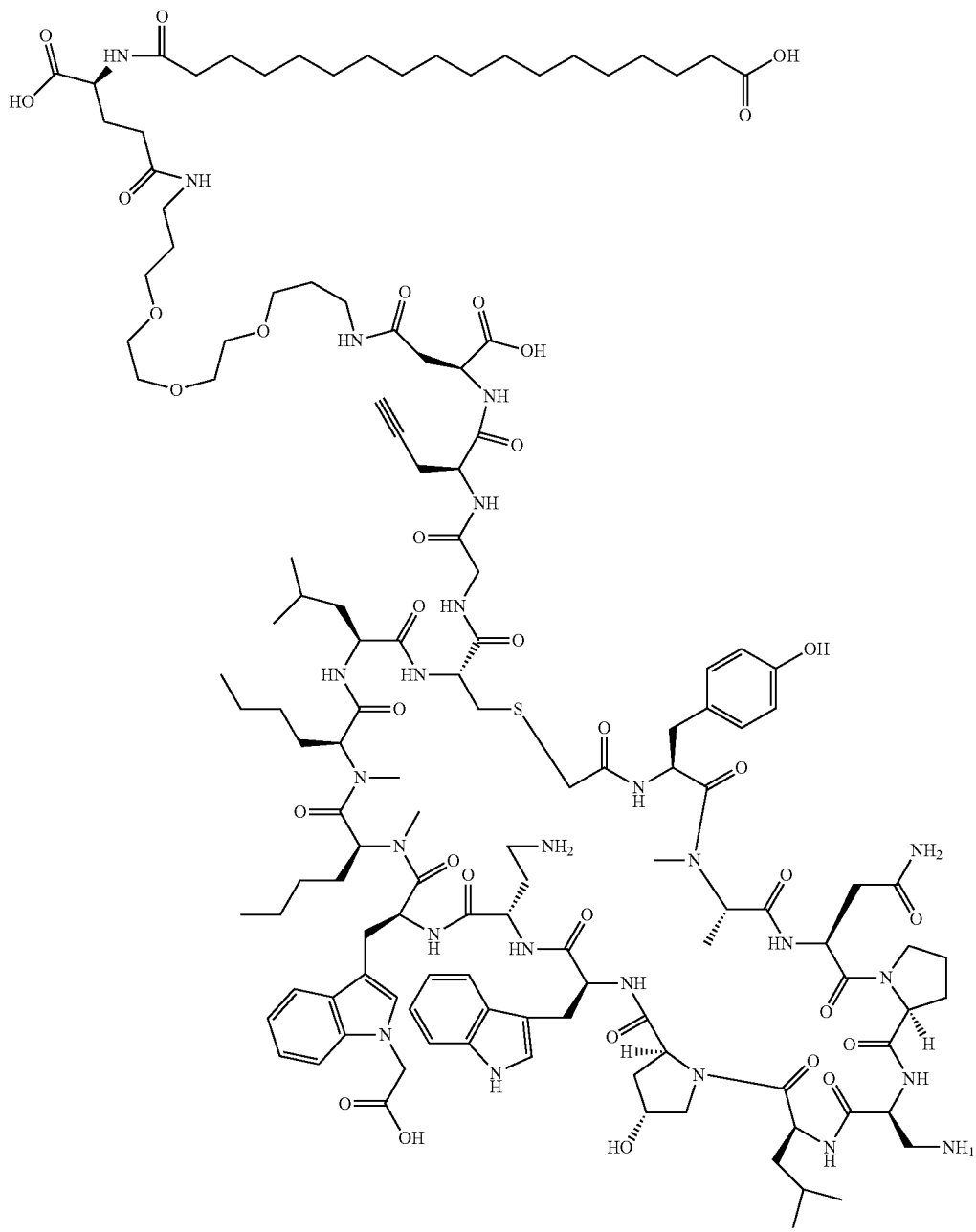 [SMILES: C#CC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)N[C@@H](CC(=O)NCCCOCCOCCOCCCNC(=O)CC[C@H](NC(=O)CCCCCCCCCCCCCCCCC(=O)O)C(=O)O)C(=O)O]

665 666
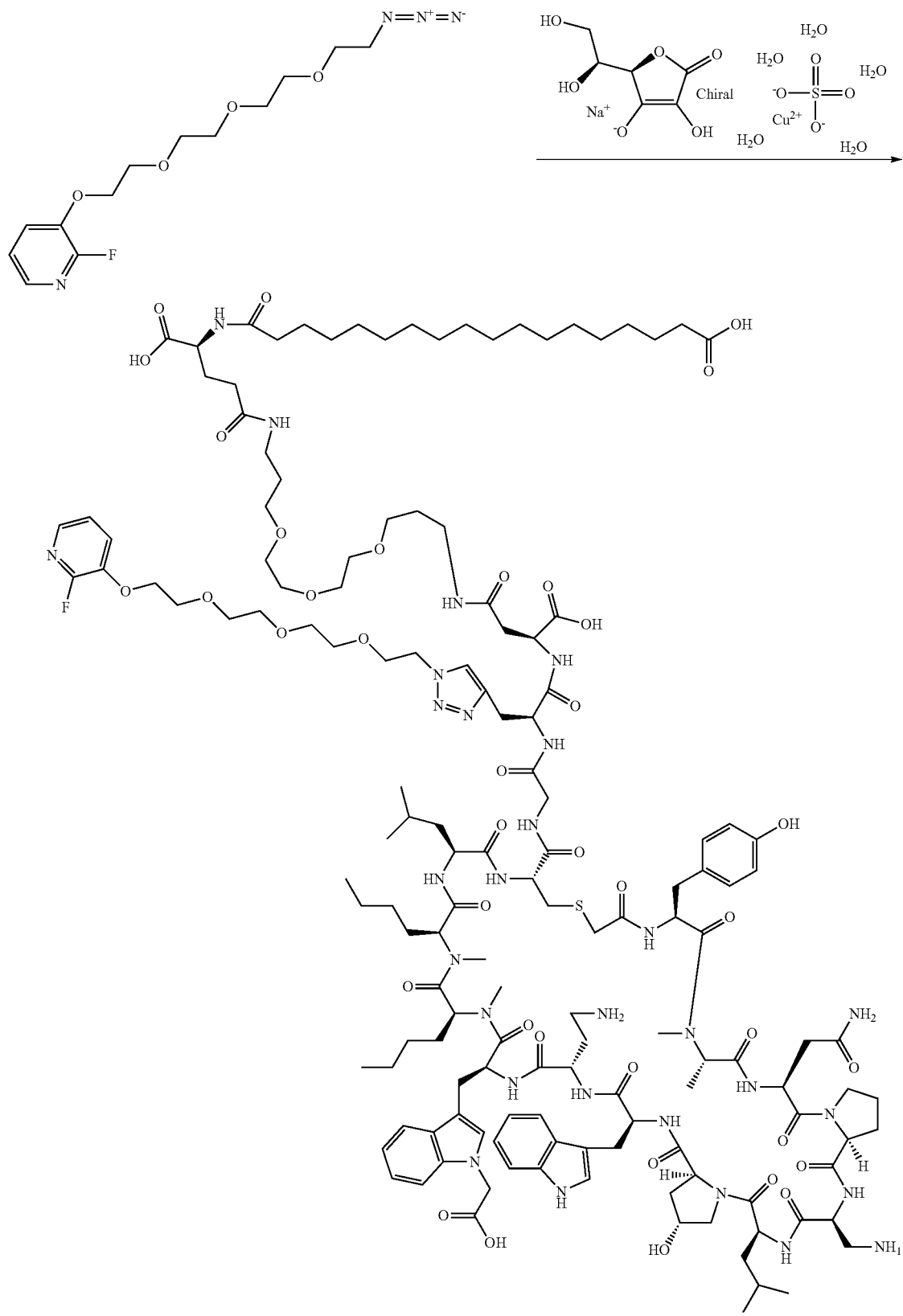
Example 11271 was prepared as follows. To a 1 dram vial was added Example 11270 (40 mg, 0.015 mmol) in Water (0.5 mL). To this was added t-BuOH (0.5 mL) and 3-(2-(2-(2-(2-azidoethoxy)ethoxy)ethoxy)ethoxy)-2-fluoropyridine (9.22 mg, 0.029 mmol). The solution was stirred and then SODIUM ASCORBATE (3.78 mg, 0.019 mmol) and a solution of copper(II) sulfate pentahydrate (0.022 mL, 4.40 µmol) was added. The reaction was allowed to stir at rt for 2 hr. The reaction was checked by LC/MS and was complete. The crude reaction mixture was injected directly onto a reverse phase chromatography column.

The crude material was purified via preparative LC/MS with the following conditions: The crude material was purified via preparative LC with the following conditions: Column: XSelect CSH Prep C18, 5-µm OBD, 19 mm×250 mm. Mobile Phase A: 10:90 acetonitrile:water with 0.1% TFA; Mobile Phase B: 90:10 acetonitrile:water with 0.1% TFA; Gradient: 20-65% B over 25 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 93.0%.

Analysis LCMS Condition A: Retention time=4.24 min; ESI-HRMS(+) m/z: 1520.7970 (M+2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:

Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:

Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis Condition C:

Column: Waters Aquity UPLC BEH C18, 2.1×50 mm, 1.7-µm particles; Mobile Phase A: 100% Water: 0.05% TFA; Mobile Phase B: 100% Acetonitrile: 0.05% TFA; Temperature: 40° C.; Gradient: 2-98% B over 1.5 minutes, then a 0.5-minute hold at 100% B; Flow: 0.8 mL/min; Detection: UV at 220 nm.

Analysis Condition D:

Column: PHENOMENEX-LUNA 2.0×30 mm 3 um; Mobile Phase A: 90% Water-10% Methanol-0.1% TFA; Mobile Phase B: 10% Water-90% Methanol-0.1% TFA; Gradient: 0-100% B over 2 minutes, then a 1 to 4 minute hold at 100% B; Flow: 1 mL/min; Detection: UV at 220 nm.

Analysis Condition E:

Column: Xbridge Phenyl, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 5-100% B over 15 minutes; Flow: 0.5 mL/min; Detection: UV at 220 nm.

Analysis Condition F:

Column: XBridge C18, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 10-100% B over 30 minutes; Flow: 0.5 mL/min; Detection: UV at 220 nm.

Analysis Condition G:

Column: Waters CSH C18, 2.0×50 mm, 1.7-µm particles; Mobile Phase A: 5:95 acetonitrile:water with 0.1% TFA; Mobile Phase B: 95:5 acetonitrile:water with 0.1% TFA; Temperature: 50° C.; Gradient: 0% B, 0-100% B over 3 minutes, then a 0.5-minute hold at 100% B; Flow: 1 mL/min; Detection: UV at 220 nm.

Analysis Condition H:

Column: Xbridge C18, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 10-100% B over 18 minutes; Flow: 0.5 mL/min; Detection: UV at 220 nm.

Analysis Condition I:

Column: XSelectCSH C18, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 1.0 mL/min; Detection: UV at 220 nm.

Analysis Condition J:

Column: Zorbax Bonus RP, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 1.0 mL/min; Detection: UV at 220 nm.

Analysis Condition K:

Column: Waters Aquity UPLC BEH C18, 2.1×50 mm, 1.7-µm particles; Mobile Phase A: 100% Water: 0.05% TFA; Mobile Phase B: 100% Acetonitrile: 0.05% TFA; Temperature: 50° C.; Gradient: 2-98% B over 3.0 minutes, then a 0.5-minute hold at 100% B; Flow: 0.8 mL/min; Detection: UV at 220 nm.

General Procedures for Examples Intermediates 1300A-1400L

All manipulations were performed under automation on a Symphony-X peptide synthesizer (Protein Technologies). All procedures unless noted were performed in a 10 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solution was used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; Rink=(2,4-dimethoxyphenyl)(4-alkoxyphenyl)methanamine, where "4-alkoxy" describes the position and type of connectivity to the polystyrene resin. The resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pra-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

For carboxamide products: the procedures describe an experiment performed on a 0.100 mmol scale, where the scale is determined by the amount of Rink linker bound to the resin. This scale corresponds to approximately 178 mg of the Rink-Merrifield resin described above. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

To a 10 mL polypropylene solid-phase reaction vessel was added Merrifield:Rink resin (178 mg, 0.100 mmol). The resin was washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added to top of the vessel (not through the bottom frit) and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Single-coupling for —(S)-2-amino-3-(1-(carboxymethyl)-1H-indol-3-yl)propanoic acid The coupling was performed as above, only a 30 min agitation time was used.

Double-Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Chloroacetyl Chloride Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added DIPEA (0.4M in DMF, 3.0 mL, 24 eq), then chloroacetyl chloride (0.8M in DMF, 1.5 mL, 13.2 eq). The mixture was periodically agitated for 30 minutes, then the solution was drained through the frit. The resin was washed successively three times as follows: for each wash, DMF (2.0 mL) was added to top of the vessel (not through the bottom frit) and the resulting mixture was periodically agitated for 90 seconds before the solution was drained through the frit. The resin was washed successively four times as follows: for each wash, $CH_2Cl_2$ (2.0 mL) was added to top of the vessel (not through the bottom frit) and the resulting mixture was periodically agitated for 90 seconds before the solution was drained through the frit. The resulting resin was placed under a $N_2$ stream for 15 minutes upon which the resin became rigid and easily handled.

For Carboxylic Acid C-Terminal Products:

The procedures describe an experiment performed on a 0.100 mmol scale, where the scale is determined by the amount of 2-chlorotrityl linker bound to the resin. Commercial Fmoc-Gly-2-chlorotrityl resin was used, usually as a 0.92 meq/g loading. This scale corresponds to approximately 109 mg of the Fmoc-Gly-2-chlorotrityl resin described above. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

To a 10 mL polypropylene solid-phase reaction vessel was added Merrifield:Rink resin (178 mg, 0.100 mmol). The resin was washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added to top of the vessel (not through the bottom frit) and the resulting mixture was periodically agitated for 30 seconds before the solution was drained through the frit. To the reaction vessel was added DIPEA (0.4M in DMF, 1.0 mL, 4 eq), then acetic anhydride (2.0 mL). The mixture was periodically agitated for 10 minutes, then the solution was drained through the frit. The resin was washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Single-coupling for —(S)-2-amino-3-(1-(carboxymethyl)-1H-indol-3-yl)propanoic acid The coupling was performed as above, only a 30 min agitation time was used.

Double-Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added DIPEA (0.4M in DMF, 1.0 mL, 4 eq), then acetic anhydride (2.0 mL). The mixture was periodically agitated for 10 minutes, then the solution was drained through the frit. The resin was washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Chloroacetyl Chloride Coupling Procedure:

To the reaction vessel containing resin from the previous step was added piperdine:DMF (20:80 v/v, 2.0 mL). The mixture was periodically agitated for 3 minutes and then the solution was drained through the frit. To the reaction vessel was added piperdine:DMF (20:80 v/v, 2.0 mL). The mixture was periodically agitated for 3 minutes and then the solution was drained through the frit. The resin was washed successively six times as follows: for each wash, DMF (2.0 mL) was added to top of the vessel (not through the bottom frit) and the resulting mixture was periodically agitated for 30 seconds before the solution was drained through the frit. To the reaction vessel was added DIPEA (0.4M in DMF, 3.0 mL, 24 eq), then chloroacetyl chloride (0.8M in DMF, 1.5 mL, 13.2 eq). The mixture was periodically agitated for 30 minutes, then the solution was drained through the frit. The resin was washed successively three times as follows: for each wash, DMF (2.0 mL) was added to top of the vessel (not through the bottom frit) and the resulting mixture was periodically agitated for 90 seconds before the solution was drained through the frit. The resin was washed successively four times as follows: for each wash, $CH_2Cl_2$ (2.0 mL) was added to top of the vessel (not through the bottom frit) and the resulting mixture was periodically agitated for 90 seconds before the solution was drained through the frit. The resulting resin was placed under a $N_2$ stream for 15 minutes upon which the resin became rigid and easily handled.

Global Deprotection Procedure:

A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 1.5 h). The mixture was filtered through a 0.2 micron syringe filter into a 18×150 mm test tube, and the solids were extracted with a second portion of the "deprotection solution" (1.0 mL). The combined filtrates, in the 18×150 mm test tube, were diluted with $Et_2O$ (15 mL) upon which a significant amount of a white solid precipitated. The mixture was centrifuged for 2 minutes, then the solution was decanted. The solids were suspended in $Et_2O$ (20 mL); the mixture was centrifuged for 5 minutes; and the solution was decanted. For a final time, the solids were suspended in Et$_2$O (20 mL); the mixture was centrifuged for 5 minutes; and the solution was decanted.

Cyclization Procedure:

The solids were dissolved in 20 mL MeCN:aq. 0.1M NH$_4$OAc (1:1), and the solution was carefully adjusted to pH=8.5-9.0 using aq NaOH (1.0M). The solution was then allowed to stand (stirring not necessary) overnight (app. 18 h). 1 mL DMSO was added, and the reaction solution was concentrated in a SpeedVac centrifuge evaporator overnight with mild heating. Approximately 1 mL of MeOH was added to the residue, and the resulting solution was purified by the method described in the individual examples. As an alternate cyclization procedure, the material obtained from a 0.1 mmol scale reaction was taken up in ~20 mL MeOH containing ~5 drops of Hunig's base (pH ~10). This was left to stand at rt without stirring overnight. Solvents were removed in vacuo and the residue purified as described in the individual examples.

General Triazole Formation Procedure for Examples 13051-13077, 13120-13128, 13141-13164, and 14121-14126

To a solution (or in some cases a suspension) of the alkyne and azide components in 1:1 water:tBuOH (~0.016 M) was added 1.3 eq. (vs. peptide) of sodium (R)-2-((S)-1,2-dihydroxyethyl)-4-hydroxy-5-oxo-2,5-dihydrofuran-3-olate. Then 0.2 eq (vs. peptide) of CuSO$_4$ (as a 0.05 mg/µL aqueous solution) was added, and the resulting solution was stirred at rt for ~18 h. The mixture was injected directly on a preparatory HPLC, as described in the specific examples.

General Triazole Formation Procedure for Examples 14051-14102

The mixture of INT-1400J (48 mg, 0.023 mmol), (R)-2,5,7,8-tetramethyl-2-((4R,8R)-4,8,12-trimethyltridecyl)chroman-6-yl 4-((5-azidopentyl)amino)-4-oxobutanoate (17.64 mg, 0.028 mmol), sodium (R)-2-((S)-1,2-dihydroxyethyl)-4-hydroxy-5-oxo-2,5-dihydrofuran-3-olate (6.39 mg, 0.032 mmol) and Copper(II) sulfate pentahydrate (2.290 mg, 9.17 µmol) in t-BuOH (459 µl)/Water (459 µl) was stirred at rt overnight.

Preparation of Fmoc-(S)-propargylglycine-2-chlorotrityl resin

To a solution of 2-((((9H-fluoren-9-yl)methoxy)carbonyl)amino)pent-4-ynoic acid (0.671 g, 2.000 mmol) in 3 mL DMF and 20 mL DCM was added DIPEA (1.397 ml, 8.00 mmol). The resulting solution was added to 2.0 g chlorotrityl chloride resin (1.2 meq/g), and the resulting mixture was shaken for 2 h at rt. The solvents were filtered off, and the resin was capped with 17:2:1 DCM/MeOH/DIPEA (shaken with 10 mL of the solution for 15 min then filtered). This was repeated twice more. The resin was washed twice with DCM, 4 times with DMF, and 6 times with DCM. (each cycle was ~10 min, followed by filtration (Buchner funnel). The resin was dried under N$_2$, yielding 2.2 g of resin, estimated loading of 0.9 mmol/g.

Preparation of 2-(2-(2-methoxyethoxy)ethoxy)-N-(prop-2-yn-1-yl)acetamide

Scheme:

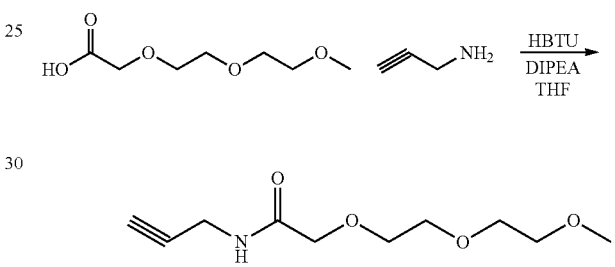

To a solution of 2-(2-(2-methoxyethoxy)ethoxy)acetic acid (1.53 g, 8.59 mmol) in THF (28.6 ml) was added prop-2-yn-1-amine (0.660 ml, 10.30 mmol) and DIPEA (3.00 ml, 17.17 mmol). HBTU (3.91 g, 10.30 mmol) was then added, and the mixture stirred at rt. After ~1.5 h, LC/MS indicated that the reaction had advanced to near-completion. The solvent was decanted from the white precipitate, and was concentrated in vacuo. The residue was taken up in EtOAc, then extracted with NaHCO$_3$ to remove any unreacted acid. The organic layer was then extracted twice with 0.1 M HCl to remove excess base. The organic extracts were then dried over MgSO$_4$, filtered, and concentrated in vacuo. The residue was applied to silica gel (40 g) and eluted with CH$_2$Cl$_2$ (60 mL), then a gradient to 25% acetone/CH$_2$Cl$_2$ over 600 mL, and finally a hold at 25% acetone/CH$_2$Cl$_2$ for 300 mL. The appropriate fractions were combined to obtain 2-(2-(2-methoxyethoxy)ethoxy)-N-(prop-2-yn-1-yl)acetamide (102.2 mg, 0.475 mmol, 5.53% yield). $^1$H NMR (500 MHz, CHLOROFORM-d) δ 7.41 (br. s., 1H), 4.11 (dd, J=5.6, 2.6 Hz, 2H), 4.05 (s, 2H), 3.74-3.67 (m, 6H), 3.63-3.60 (m, 2H), 3.43 (s, 3H), 2.23 (t, J=2.5 Hz, 1H).

Preparation of N-(prop-2-yn-1-yl)stearamide

Scheme:

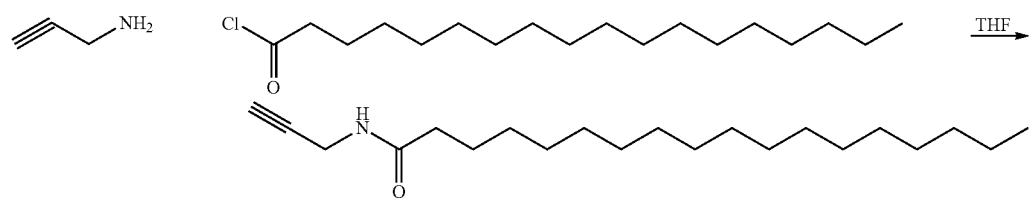

To a solution of tetradecanoyl chloride (200 mg, 0.810 mmol) in Tetrahydrofuran (2026 μl) was added prop-2-yn-1-amine (208 μl, 3.24 mmol). After the weekend, the desired product was found by LC/MS. Excess solvent was removed in vacuo, and water was added. The pH was adjusted to ~10 with 1M NaOH, and the mixture extracted 3 times into $CH_2Cl_2$. The combined organic extracts were dried over MgSO4, filtered, and concentrated in vacuo. Chromatography with a EtOAc/Hexane gradient yielded the desired material. $^1$H NMR (500 MHz, CHLOROFORM-d) δ 5.57 (br. s., 1H), 4.08 (dd, J=5.3, 2.5 Hz, 2H), 2.25 (t, J=2.6 Hz, 1H), 2.23-2.19 (m, 2H), 1.65 (m, 6H), 1.31 (m, 24H), 0.92-0.87 (m, 3H).

Preparation of N-(5-azidopentyl)-2-(2-(2-methoxyethoxy)ethoxy)acetamide

Scheme:

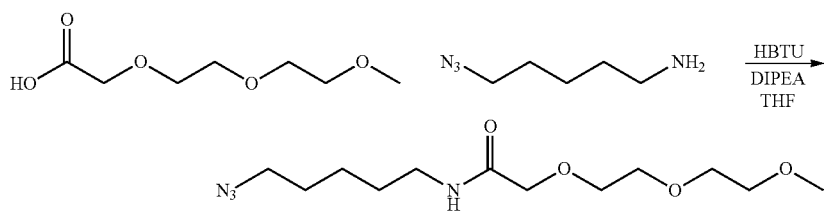

To a solution of 2-(2-(2-methoxyethoxy)ethoxy)acetic acid (400 mg, 2.245 mmol) in THF (7483 μl) was added 5-azidopentan-1-amine (317 mg, 2.469 mmol) and DIPEA (784 μl, 4.49 mmol). HBTU (936 mg, 2.469 mmol) was then added, and the mixture stirred at rt. After ~1.5 h, LC/MS indicated that the reaction had advanced to near-completion. The solvent was decanted from the white precipitate, and was concentrated in vacuo. The residue was taken up in EtOAc, then extracted with NaHCO$_3$ to remove any unreacted acid. The organic layer was then extracted twice with 0.1 M HCl to remove excess base. The organic extracts were then dried over MgSO4, filtered, and concentrated in vacuo. The material was used as-is for further chemistry. LC/MS: (M+H)$^+$=289.15.

(R)-2,5,7,8-tetramethyl-2-((4R,8R)-4,8,12-trimethyltridecyl)chroman-6-yl 4-((5-azidopentyl)amino)-4-oxobutanoate

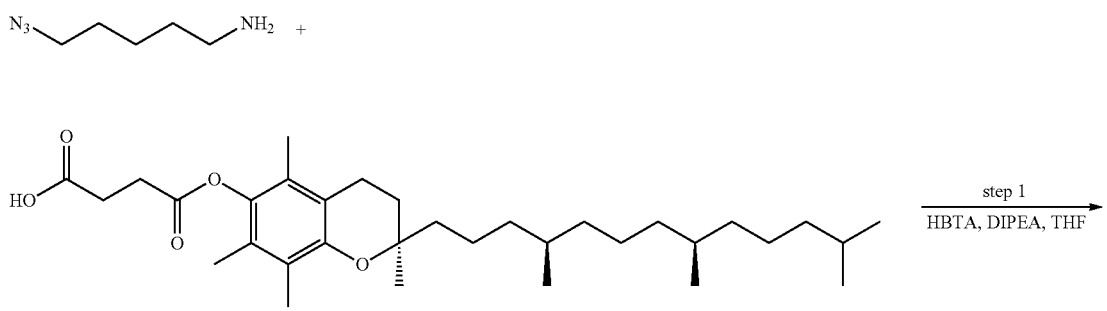

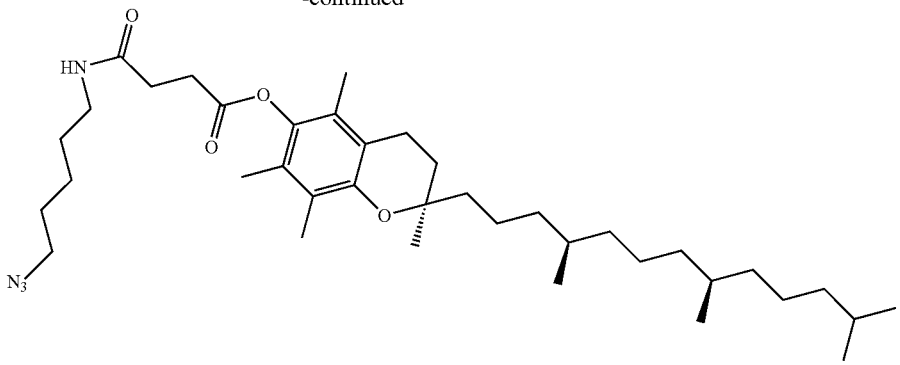

Step 1: Preparation of (R)-2,5, 7,8-tetramethyl-2-((4R,8R)-4,8,12-trimethyltridecyl)chroman-6-yl 4-((5-azidopentyl)amino)-4-oxobutanoate The mixture of 5-azidopentan-1-amine (0.320 g, 2.419 mmol), Vitamin E succinate (1.07 g, 2.016 mmol), DIPEA (0.704 ml, 4.03 mmol) and HBTU (0.765 g, 2.016 mmol) in THF (6.72 ml) was stirred at rt overnight. The resulting crude product was purified by Biotage (silic gel, 300 g, 0 to 20% acetone/$CH_2Cl_2$) to get (R)-2,5,7,8-tetramethyl-2-((4R, 8R)-4,8,12-trimethyltridecyl)chroman-6-yl 4-((5-azidopentyl)amino)-4-oxobutanoate (1.29 g, 2.013 mmol, 100% yield). Analysis condition D: Retention time=4.87 min; ESI-MS(+) m/z 641.4 (M+H)$^+$; $^1$H NMR (500 MHz, METHANOL-$d_4$) δ 3.26-3.15 (m, 4H), 2.95 (t, J=6.7 Hz, 2H), 2.62 (dt, J=12.8, 6.6 Hz, 4H), 2.13-2.06 (m, 3H), 1.99-1.96 (m, 3H), 1.84-1.81 (m, 3H), 1.90-1.76 (m, 2H), 1.69-1.02 (m, 30H), 0.98-0.79 (m, 12H)

2-(2-(2-(2-azidoethoxy)ethoxy)ethoxy)ethyl((R)-2,5,7,8-tetramethyl-2-((4R,8R)-4,8,12-trimethyltridecyl)chroman-6-yl) succinate

Step 1: Preparation of 2-(2-(2-(2-azidoethoxy)ethoxy)ethoxy)ethyl((R)-2,5,7,8-tetramethyl-2-((4R, 8R)-4,8,12-trimethyltridecyl)chroman-6-yl) succinate The mixture of 2-(2-(2-(2-azidoethoxy)ethoxy)ethoxy)ethanol in t-butylmethyl ether (3.77 ml, 1.884 mmol), Vitamin E succinate (1.0 g, 1.884 mmol), DMAP (0.092 g, 0.754 mmol) and EDCI (1.138 g, 5.93 mmol) in $CH_2Cl_2$ (11.35 ml) was stirred at rt overnight. The resulting crude product was purified by Biotage (silic gel, 300 g, 0 to 20% acetone/$CH_2Cl_2$) to get 2-(2-(2-(2-azidoethoxy)ethoxy)ethoxy)ethyl ((R)-2,5,7,8-tetramethyl-2-((4R,8R)-4,8,12-trimethyltridecyl)chroman-6-yl) succinate (1.37 g, 1.872 mmol, 99% yield). Analysis condition D: Retention time=5.18 min; ESI-MS(+) m/z 732.5 (M+H)$^+$ $^1$H NMR (500 MHz, METHANOL-$d_4$) δ 4.31-4.21 (m, 2H), 3.74-3.60 (m, 12H), 3.38-3.34 (m, 2H), 2.95 (dd, J=7.5, 5.3 Hz, 2H), 2.78 (dd, J=7.4, 5.4 Hz, 2H), 2.64 (t, J=6.8 Hz, 2H), 2.12-2.07 (m, 3H), 2.01 (s, 3H), 1.99-1.94 (m, 3H), 1.90-1.75 (m, 2H), 1.66-1.03 (m, 24H), 0.94-0.83 (m, 12H)

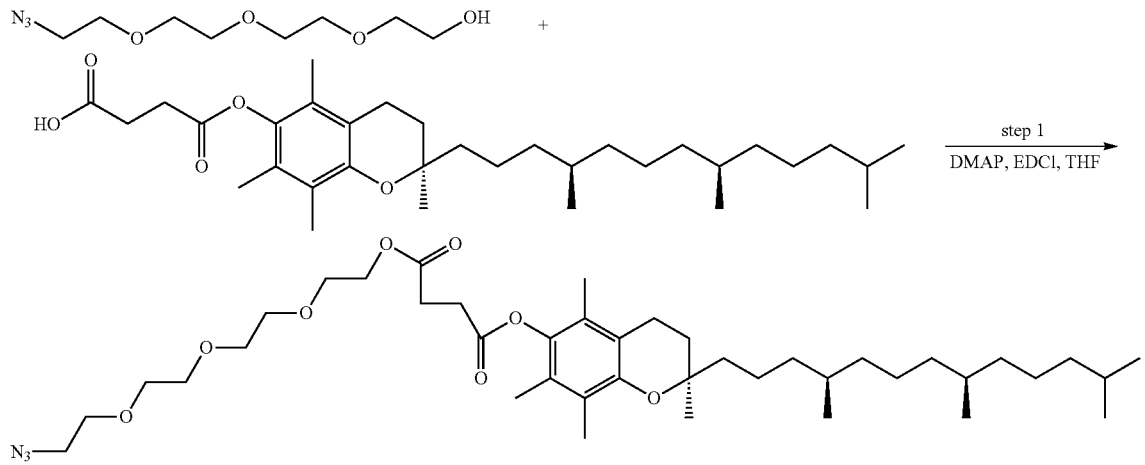

17-azido-3,6,9,12,15-pentaoxaheptadecyl ((R)-2,5,7,8-tetramethyl-2-((4R,8R)-4,8,12-trimethyltridecyl)chroman-6-yl) succinate

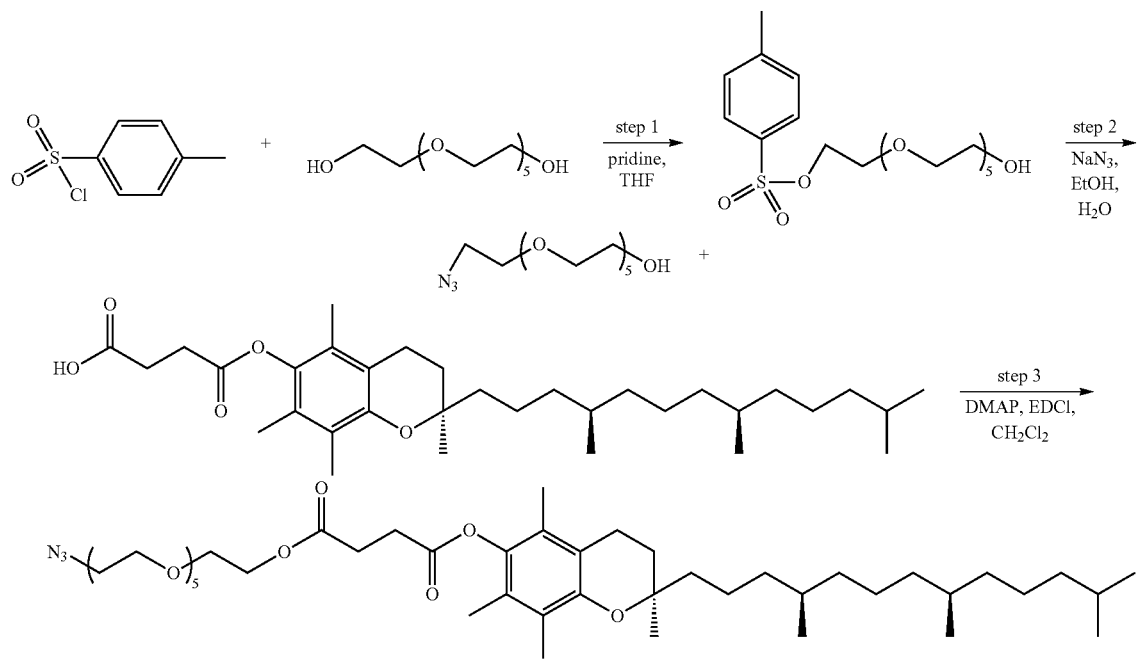

Step 1: Preparation of 17-hydroxy-3,6,9,12,15-pentaoxaheptadecyl 4-methylbenzenesulfonate 3,6,9,12,15-Pentaoxaheptadecane-1,17-diol (8 g, 28.3 mmol) was dissolved in THF (30 mL). pyridine (7.13 mL, 88 mmol) was added to the mixture followed by 4-methylbenzene-1-sulfonyl chloride (5.41 g, 28.4 mmol). Mixture was stirred at room temperature for 3 hours. Mixture was concentrated by roto-vap. The resulting residue was dissolved in dichloromethane, washed twice with saturated aqueous sodium bicarbonate. The combined aqueous layers were back-extracted with dichloromethane. The combined organics were washed twice with 1N hydrochloric acid and once with brine. Organics were dried over MgSO₄, filtered, concentrated to dryness to get 17-hydroxy-3,6,9,12,15-pentaoxaheptadecyl 4-methylbenzenesulfonate (5.10 g, 11.68 mmol, 41.2% yield) which was used as is in the next step. Analysis condition D: Retention time=1.37 min; ESI-MS(+) m/z 437.3 (M+H)⁺

Step 2: Preparation of 17-azido-3,6,9,12,15-pentaoxaheptadecan-1-ol

17-Hydroxy-3,6,9,12,15-pentaoxaheptadecyl 4-methylbenzenesulfonate (5.10 g, 11.68 mmol) was dissolved in EtOH (37.4 ml). Sodium azide (2.97 g, 45.7 mmol) was added to the mixture followed by water (1.498 ml). Mixture was warmed to reflux and held with stirring for 15 hours. The cloudy reaction mixture was concentrated by roto-vap. The residue was treated with water. The mixture was extracted twice with dichloromethane. The combined organics were washed twice with aqueous sodium bicarbonate. Organics were dried over MgSO₄, filtered and then concentrated to dryness. The residue was purified via Biotage (Silica; 300 g; 0 to 9% D MeOH/Dichloromethane over 2400 mL). All effluent was collected in 16×150 culture tubes. Major peak fractions, as determined by TLC (silica; 5% MeOH—CH₂Cl₂; iodine chamber) was isolated and concentrated to dryness. 17-azido-3,6,9,12,15-pentaoxaheptadecan-1-ol (3.08 g, 10.02 mmol, 86% yield) was obtained as clear colorless oil. Analysis condition D: Retention time=1.19 min; ESI-MS(+) m/z 330.2 (M+Na); $^1$H NMR (500 MHz, METHANOL-d₄) δ 3.73-3.61 (m, 20H), 3.60-3.55 (m, 2H), 3.39 (t, J=4.9 Hz, 2H).

Step 3: Preparation of 17-azido-3,6,9,12,15-pentaoxaheptadecan-1-ol

The mixture of 17-azido-3,6,9,12,15-pentaoxaheptadecan-1-ol (0.579 g, 1.884 mmol), Vitamin E succinate (1.0 g, 1.884 mmol), DMAP (0.092 g, 0.754 mmol) and EDCI (1.138 g, 5.93 mmol) in CH₂Cl₂ (11.35 ml) was stirred at rt overnight. The resulting crude product was purified by Biotage (SG, 300 g, 0 to 40% acetone/CH₂Cl₂) to get 17-azido-3,6,9,12,15-pentaoxaheptadecyl ((R)-2,5,7,8-tetramethyl-2-((4R,8R)-4,8,12-trimethyltridecyl)chroman-6-yl) succinate (1.20 g, 1.463 mmol, 78% yield). Analysis condition D: Retention time=5.50 min; ESI-MS(+) m/z 842.6 (M+Na).

$^1$H NMR (500 MHz, METHANOL-d$_4$) δ 4.31-4.23 (m, 2H), 3.73-3.70 (m, 2H), 3.69-3.59 (m, 18H), 3.40-3.30 (m, 2H), 2.98-2.91 (m, 2H), 2.80-2.75 (m, 2H), 2.64 (t, J=6.8 Hz, 2H), 2.09 (s, 3H), 2.01 (s, 3H), 1.98 (s, 3H), 1.89-1.76 (m, 2H), 1.61-1.50 (m, 4H), 1.48-1.01 (m, 20H), 0.94-0.83 (m, 12H).

23-azido-3,6,9,12,15,18,21-heptaoxatricosyl((R)-2,5,7,8-tetramethyl-2-((4R,8R)-4,8,12-trimethyltridecyl)chroman-6-yl) succinate ics were washed twice with 1N hydrochloric acid and once with brine. The organics were dried MgSO$_4$, filtered, concentrated to dryness to get 23-hydroxy-3,6,9,12,15,18,21-heptaoxatricosyl 4-methylbenzenesulfonate (2.58 g, 4.92 mmol, 33.1% yield) which is used as is in the next step. Analysis condition D: Retention time=1.41 min; ESI-MS(+) m/z 525.3 (M+H)$^+$ Step 2: Preparation of 23-azido-3,6,9,12,15,18,21-heptaoxatricosan-1-ol 23-Hydroxy-3,6,9,12,15,18,21-heptaoxatricosyl 4-methylbenzenesulfonate (2.58 g, 4.92 mmol) was dissolved in EtOH (15.76 ml). Sodium azide (1.250 g, 19.23 mmol) was

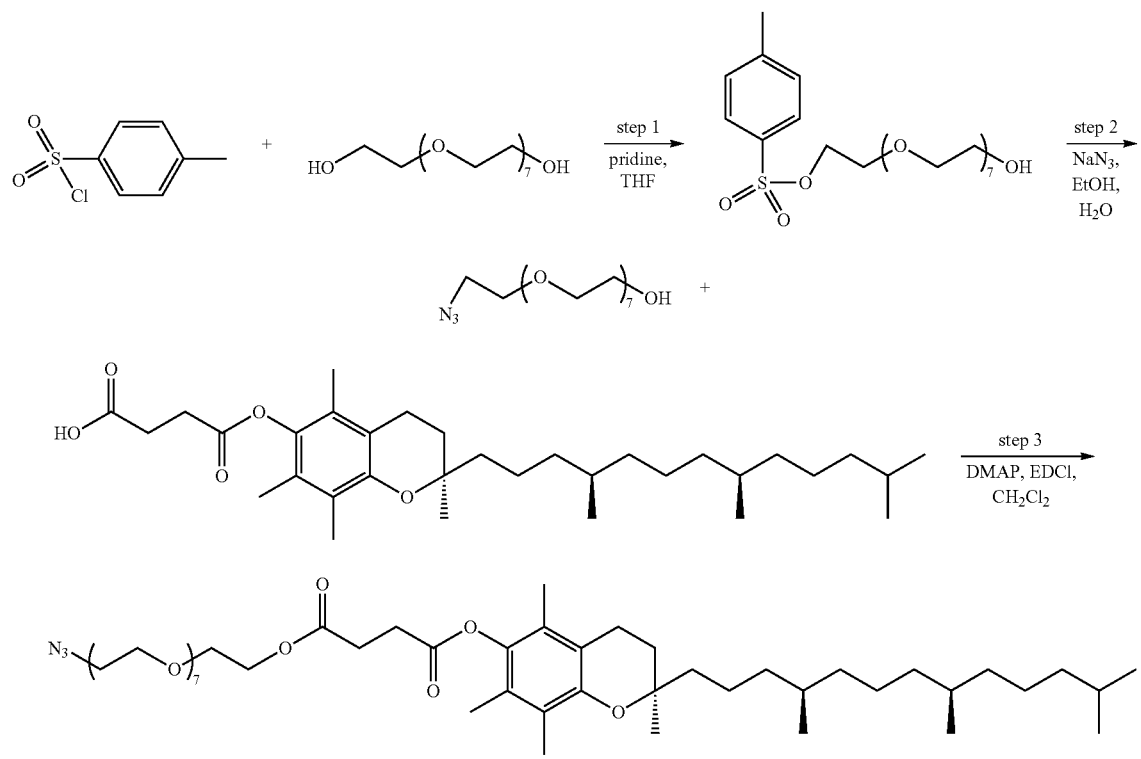

Step 1: Preparation of 23-hydroxy-3,6,9,12,15,18,21-heptaoxatricosyl 4-methylbenzenesulfonate 3,6,9,12,15,18,21-Heptaoxatricosane-1,23-diol (5.5 g, 14.85 mmol) was dissolved in THF (30 mL). pyridine (3.73 mL, 46.2 mmol) was added to the mixture followed by 4-methylbenzene-1-sulfonyl chloride (2.84 g, 14.88 mmol). The mixture stirred at room temperature overnight. Mixture was concentrated by roto-vap. Residue was dissolved in dichloromethane, washed twice with saturated aqueous sodium bicarbonate. The combined aqueous layers were back-extracted with dichloromethane. The combined organadded to the mixture followed by water (0.630 ml). Mixture was warmed to reflux and held with stirring for 15 hours. The cloudy reaction mixture was concentrated by roto-vap. Residue was treated with water. Material was extracted twice with dichloromethane. Combined organics were washed twice with aqueous sodium bicarbonate. Organics were dried MgSO$_4$, filtered and then concentrated to dryness. The residue was purified via Biotage (Silica; 300 g; 0 to 10% MeOH/Dichloromethane over 2400 mL). All effluent was collected in 16×150 culture tubes. Major peak fractions, as determined by TLC (silica; 5% MeOH—CH$_2$Cl$_2$; iodine chamber) was isolated and concentrated to dryness. 23-azido-3,6,9,12,15,18,21-heptaoxatricosan-1-ol (1.55 g, 3.92 mmol, 80% yield) was obtained as clear colorless oil. Analysis condition D: Retention time=1.18 min; ESI-MS(+) m/z 396.3 (M+H)+; 1H NMR (500 MHz, METHANOL-d4) δ 3.75-3.60 (m, 28H), 3.60-3.54 (m, 2H), 3.43-3.37 (m, 2H).

Step 3: Preparation of 17-azido-3,6,9,12,15-pentaoxaheptadecan-1-ol

The mixture of 23-azido-3,6,9,12,15,18,21-heptaoxatricosan-1-ol (0.745 g, 1.884 mmol), Vitamin E succinate (1.0 g, 1.884 mmol), DMAP (0.092 g, 0.754 mmol) and EDCI (1.138 g, 5.93 mmol) in CH2Cl2 (11.35 ml) was stirred at rt overnight. The resulting crude product was purified by Biotage (SG, 300 g, 0 to 50% acetone/CH2Cl2) to get 23-azido-3,6,9,12,15,18,21-heptaoxatricosyl((R)-2,5,7,8-tetramethyl-2-((4R,8R)-4,8,12-trimethyltridecyl)chroman-6-yl) succinate (0.77 g, 0.848 mmol, 45.0% yield).

Analysis condition D: Retention time=5.04 min; ESI-MS (+) m/z 908.9 (M+H)+ 1H NMR (500 MHz, METHANOL-d4) δ 4.30-4.23 (m, 2H), 3.77-3.56 (m, 28H), 3.42-3.35 (m, 2H), 2.96 (dd, J=7.5, 5.3 Hz, 2H), 2.84-2.73 (m, 2H), 2.64 (t, J=6.8 Hz, 2H), 2.09 (s, 3H), 2.00 (d, J=17.1 Hz, 6H), 1.83 (dq, J=18.4, 6.7 Hz, 2H), 1.64-1.04 (m, 24H), 0.97-0.79 (m, 12H).

23-azido-3,6,9,12,15,18,21-heptaoxatricosyl((R)-2,5,7,8-tetramethyl-2-((4R,8R)-4,8,12-trimethyltridecyl)chroman-6-yl) succinate

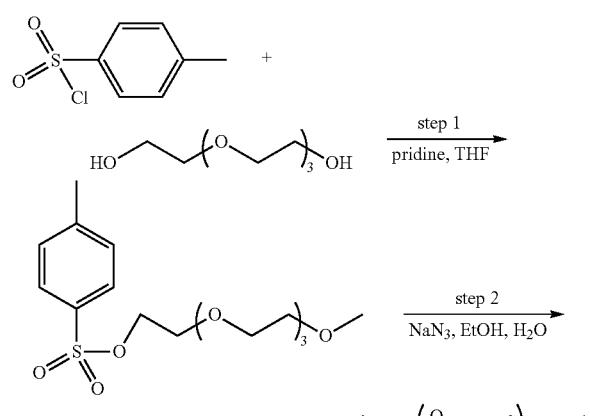

Step 1: Preparation of 2,5,8,11-tetraoxatridecan-13-yl 4-methylbenzenesulfonate 2,5,8,11-Tetraoxatridecan-13-ol (5.0 g, 24.01 mmol) was dissolved in THF (20.01 ml). pyridine (5.83 ml, 72.0 mmol) was added to the mixture followed by 4-methylbenzene-1-sulfonyl chloride (5.49 g, 28.8 mmol). The mixture stirred at room temperature overnight. Mixture was concentrated by roto-vap. Residue was dissolved in dichloromethane. Material was washed twice with saturated aqueous sodium bicarbonate. Combined aqueous layers were back-extracted with dichloromethane. Combined organics were washed twice with 1N hydrochloric acid and once with brine. Organics were dried MgSO4, filtered and then concentrated to dryness to get 2,5,8,11-tetraoxatridecan-13-yl 4-methylbenzenesulfonate (4.12 g, 11.37 mmol, 47.3% yield) which was used as is in the next step.

Step 2: Preparation of 13-azido-2,5,8,11-tetraoxatridecane 2,5,8,11-Tetraoxatridecan-13-yl 4-methylbenzenesulfonate (4.12 g, 11.37 mmol) was dissolved in EtOH (18.22 ml). Sodium azide (1.478 g, 22.73 mmol) was added to the mixture followed by water (0.729 ml). The mixture was warmed to reflux and held with stirring for 15 hours. The cloudy reaction mixture was concentrated by roto-vap. Residue was treated with water. Material was extracted twice with dichloromethane. Combined organics were washed twice with aqueous sodium bicarbonate. Organics were dried MgSO4, filtered and then concentrated to dryness. The residue was purified via Biotage (Silica; 300 g; 0 to 9% D MeOH/Dichloromethane over 2400 mL). All effluent was collected in 16×150 culture tubes. Major peak fractions, as determined by TLC (silica; 5% MeOH—CH2Cl2; iodine chamber) was isolated and concentrated to dryness. 13-azido-2,5,8,11-tetraoxatridecane (1.17 g, 5.02 mmol, 44.1% yield) was obtained as clear colorless oil. [M+H]+ at m/z 234, and sodium adduct [M+Na]+ at m/z 256; 1H NMR (400 MHz, METHANOL-d4) δ 3.74-3.60 (m, 12H), 3.58-3.53 (m, 2H), 3.43-3.35 (m, 5H).

(S)-16-((3-azido-1-carboxypropyl)amino)-16-oxohexadecanoic acid

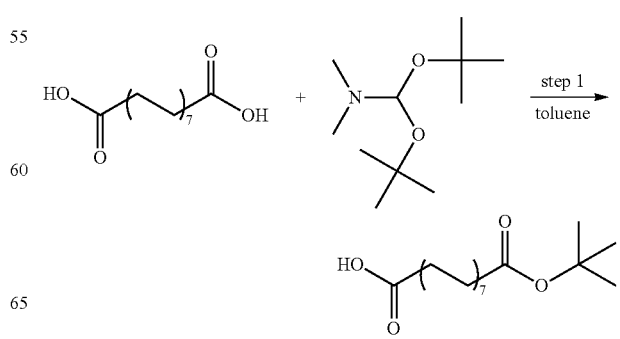

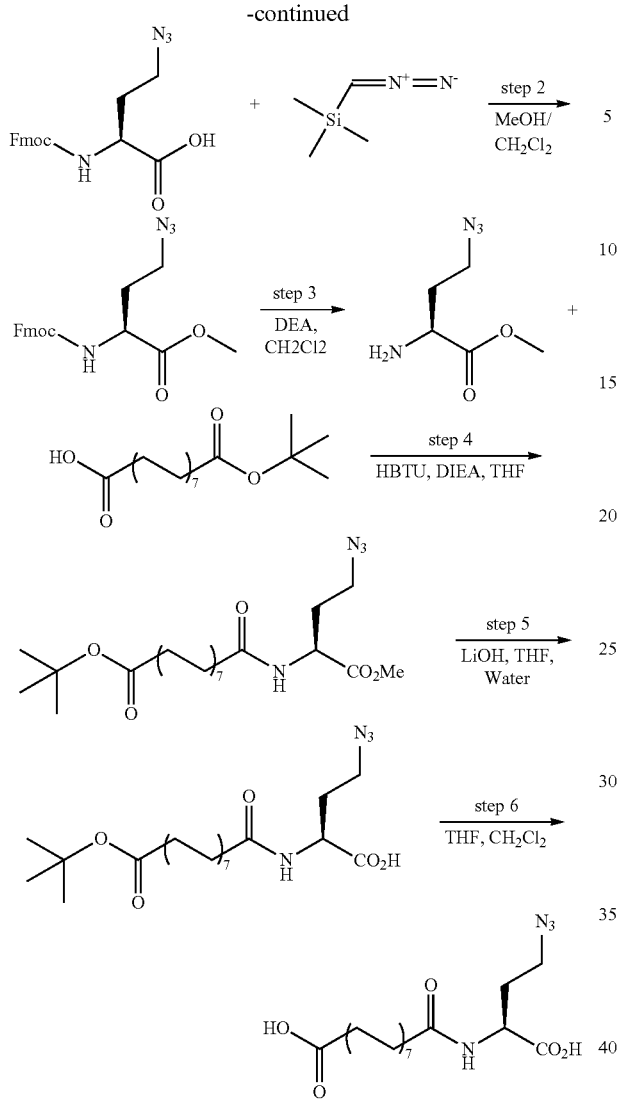

Step 1: Preparation of 16-(tert-butoxy)-16-oxohexadecanoic acid

Hexadecanedioic acid (4.5 g, 15.71 mmol) was suspended in Toluene (28.1 ml) and the mixture was heated to reflux. 1,1-di-tert-butoxy-N,N-dimethylmethanamine (10.10 ml, 42.1 mmol) was added drop-wise over 30 min. The mixture was reflux overnight. The solvent was removed in vacuo at 50° C. and the crude material was suspended in $CH_2Cl_2$/ EtOAc (75 mL. 1:1) and stirred for 15 min. The solids were removed by filtration and washed with $CH_2Cl_2$ (25 mL). The filtration was evaporated in vacuo. The resulting material was suspended in $CH_2Cl_2$ (6 mL), cooled with ice for 10 mins, and filtered. The solvent was removed in vacuo to leave crude product which was purified by flash chromatography (silic gel, EtOAc/Hexane) to get 16-(tert-butoxy)-16-oxohexadecanoic acid (2.56 g, 7.47 mmol, 47.6% yield). Analysis condition D: Retention time=5.04 min; ESI-MS(+) m/z 269.3 [M–OC(CH$_3$)$_3$]; $^1$H NMR (500 MHz, METHANOL-d$_4$) δ 2.33-2.18 (m, 4H), 1.66-1.54 (m, 4H), 1.50-1.43 (m, 9H), 1.40-1.25 (m, 20H).

Step 2: Preparation of (S)-methyl 2-((((9H-fluoren-9-yl)methoxy)carbonyl)amino)-4-azidobutanoate To a mixture of (2S)—N-FMOC-4-AZIDO-BUTANOIC ACID (1.0 g, 2.73 mmol) in MeOH (4.21 ml)/$CH_2Cl_2$ (12.64 ml) was added (TRIMETHYLSILYL)DIAZOMETHANE in diethyl ether (2.047 ml, 4.09 mmol). The resulting mixture was stirred at rt for 2 h. The mixture was concentrated to get (S)-methyl 2-((((9H-fluoren-9-yl)methoxy)carbonyl)amino)-4-azidobutanoate, which was used as is in the next step. $^1$H NMR (500 MHz, METHANOL-d$_4$) δ 7.81 (d, J=7.6 Hz, 2H), 7.73-7.63 (m, 2H), 7.47-7.22 (m, 4H), 4.41 (d, J=6.7 Hz, 2H), 4.35-4.17 (m, 2H), 3.82-3.70 (m, 3H), 3.49-3.34 (m, 2H), 2.21-2.04 (m, 1H), 1.97-1.80 (m, 1H).

Step 3: Preparation of (S)-methyl 4-azido-2-((tert-butoxycarbonyl)amino)butanoate The mixture of (S)-methyl 2-((((9H-fluoren-9-yl)methoxy)carbonyl)amino)-4-azidobutanoate (1.038 g, 2.73 mmol) and diethylamine (4.0 mL, 38.3 mmol) in $CH_2Cl_2$ (4 mL) was stirred at rt for 2 h. LCMS showed disappearance of S.M. and product formation along with FMOC related peaks. Concentrated and the resulting product was used as is in the next step. $^1$H NMR (500 MHz, METHANOL-d$_4$) 63.85-3.69 (m, 3H), 3.63-3.52 (m, 1H), 3.51-3.40 (m, 2H), 2.05-1.91 (m, 1H), 1.88-1.76 (m, 1H).

Step 4: Preparation of (S)-tert-butyl 16-((4-azido-1-methoxy-1-oxobutan-2-yl)amino)-16-oxohexadecanoate The mixture of (S)-methyl 2-amino-4-azidobutanoate (0.432 g, 2.73 mmol), 16-(tert-butoxy)-16-oxohexadecanoic acid (0.935 g, 2.73 mmol), DIPEA (1.907 ml, 10.92 mmol) and HBTU (1.035 g, 2.73 mmol) in THF (27.3 ml) was stirred at rt overnight. The resulting crude product was purified by Biotage (SG, 300 g, 0 to 10% acetone/$CH_2Cl_2$) to get (S)-tert-butyl 16-((4-azido-1-methoxy-1-oxobutan-2-yl)amino)-16-oxohexadecanoate (1.3 g, 2.69 mmol, 99% yield). Analysis condition D: Retention time=2.62 min; ESI-MS(+) m/z 483.3 (M+H)$^+$

Step 5: Preparation of (S)-4-azido-2-(16-(tert-butoxy)-16-oxohexadecanamido)butanoic acid (S)-tert-Butyl 16-((4-azido-1-methoxy-1-oxobutan-2-yl)amino)-16-oxohexadecanoate (1.3 g, 2.69 mmol), was dissolved in THF (13.47 ml) followed by the addition of LiOH (0.323 g, 13.47 mmol) and Water (13.47 ml). The reaction was stirred at rt for 3 h. Concentrated the reaction mixture to dryness. The resulting (S)-4-azido-2-(16-(tert-butoxy)-16-oxohexadecanamido)butanoic acid was used as is in the next step.

Analysis condition D: Retention time=2.56 min; ESI-MS (+) m/z 469.4 (M+H)+

Step 6: Preparation of (S)-16-((3-azido-1-carboxypropyl)amino)-16-oxohexadecanoic acid The mixture of (S)-4-azido-2-(16-(tert-butoxy)-16-oxohexadecanamido)butanoic acid (1261 mg, 2.69 mmol) and TFA (3 mL, 38.9 mmol) in DCM (20 mL) was stirred at rt for 2 h. The resulting crude product was purified by Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 50-100% B, 10 min and stop at 12 min) to obtain (S)-16-((3-azido-1-carboxypropyl)amino)-16-oxohexadecanoic acid (326 mg, 0.790 mmol, 29.4% yield). Analysis condition D: Retention time=2.30 min; ESI-MS(+) m/z 413.3 (M+H)+; $^1$H NMR (500 MHz, METHANOL-d$_4$) δ 4.52 (dd, J=9.3, 4.7 Hz, 1H), 3.53-3.35 (m, 2H), 2.34-2.21 (m, 4H), 2.19-2.07 (m, 1H), 1.99-1.84 (m, 1H), 1.63 (dquin, J=14.1, 7.1 Hz, 4H), 1.48-1.17 (m, 20H).

(S)-methyl 4-azido-2-palmitamidobutanoate

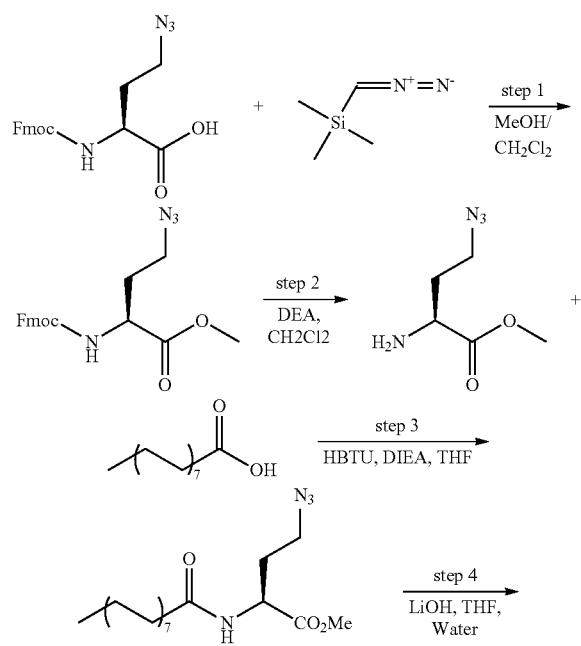

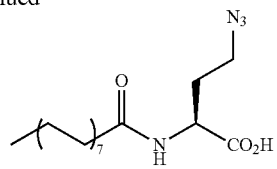

Step 1: Preparation of (S)-methyl 2-((((9H-fluoren-9-yl)methoxy)carbonyl)amino)-4-azidobutanoate To a mixture of (2S)—N-FMOC-4-AZIDO-BUTANOIC ACID (1.0 g, 2.73 mmol) in MeOH (4.21 ml)/CH$_2$Cl$_2$ (12.64 ml) was added (TRIMETHYLSILYL)DIAZOMETHANE in diethyl ether (2.047 ml, 4.09 mmol). The resulting mixture was stirred at rt for 2 h. The mixture was concentrated to get (S)-methyl 2-((((9H-fluoren-9-yl)methoxy)carbonyl)amino)-4-azidobutanoate, which was used as is in the next step. $^1$H NMR (500 MHz, METHANOL-d$_4$) δ 7.81 (d, J=7.6 Hz, 2H), 7.73-7.63 (m, 2H), 7.47-7.22 (m, 4H), 4.41 (d, J=6.7 Hz, 2H), 4.35-4.17 (m, 2H), 3.82-3.70 (m, 3H), 3.49-3.34 (m, 2H), 2.21-2.04 (m, 1H), 1.97-1.80 (m, 1H).

Step 2: Preparation of (S)-methyl 4-azido-2-((tert-butoxycarbonyl)amino)butanoate The mixture of (S)-methyl 2-((((9H-fluoren-9-yl)methoxy)carbonyl)amino)-4-azidobutanoate (1.038 g, 2.73 mmol) and diethylamine (4.0 mL, 38.3 mmol) in CH$_2$Cl$_2$ (4 mL) was stirred at rt for 2 h. LCMS showed disappearance of S.M. and product formation along with FMOC related peaks. Concentrated and the resulting product was used as is in the next step. $^1$H NMR (500 MHz, METHANOL-d$_4$) δ 3.85-3.69 (m, 3H), 3.63-3.52 (m, 1H), 3.51-3.40 (m, 2H), 2.05-1.91 (m, 1H), 1.88-1.76 (m, 1H).

Step 3: Preparation of (S)-methyl 4-azido-2-palmitamidobutanoate

The mixture of (S)-methyl 2-amino-4-azidobutanoate, TFA (544 mg, 2.00 mmol), palmitic acid (513 mg, 2.000 mmol), DIPEA (1397 μl, 8.00 mmol) and HBTU (758 mg, 2.000 mmol) in THF (6667 μl) was stirred at rt overnight. The resulting crude product was purified by Biotage (SG, 300 g, 0 to 85% EtOAc/Hexane) to get (S)-methyl 4-azido-2-palmitamidobutanoate (477 mg, 1.203 mmol, 60.1% yield). Analysis condition D: Retention time=2.75 min; ESI-MS(+) m/z 397.3 (M+H)+; $^1$H NMR (500 MHz, METHANOL-d$_4$) δ 4.53 (dd, J=9.2, 5.0 Hz, 1H), 3.74 (s, 3H), 3.51-3.35 (m, 2H), 2.31-2.22 (m, 2H), 2.15-2.06 (m, 1H), 1.97-1.86 (m, 1H), 1.70-1.57 (m, 2H), 1.41-1.28 (m, 24H), 0.94-0.84 (m, 3H).

Step 4: Preparation of (S)-methyl 4-azido-2-palmitamidobutanoate (S)-Methyl 4-azido-2-palmitamidobutanoate (477 mg, 1.203 mmol), was dissolved in THF (6014 μl) followed by the addition of LiOH (144 mg, 6.01 mmol) and water (6014 μl). The reaction was stirred at rt for 3 h. Concentrated the reaction mixture to dryness. Diluted the residue with water and added 1 N HCl to acidified. Extracted with $CH_2Cl_2$ (×3). The organic layer was collected, dried over MgSO4, filtered and concentrated to get (S)-4-azido-2-palmitamidobutanoic acid (440 mg, 1.150 mmol, 96% yield). Analysis condition D: Retention time=2.71 min; ESI-MS(+) m/z 383.3 $(M+H)^+$ $^1$H NMR (500 MHz, METHANOL-$d_4$) δ 4.56-4.47 (m, 1H), 3.52-3.34 (m, 2H), 2.32-2.22 (m, 2H), 2.14 (dddd, J=14.3, 7.8, 6.9, 4.9 Hz, 1H), 2.01-1.86 (m, 1H), 1.72-1.56 (m, 2H), 1.49-1.12 (m, 24H), 1.01-0.80 (m, 3H).

(S)-1-azido-40-carboxy-37,42-dioxo-3,6,9,12,15,18, 21,24,27,30,33-undecaoxa-36,41-diazanonanenta- contan-59-oic acid

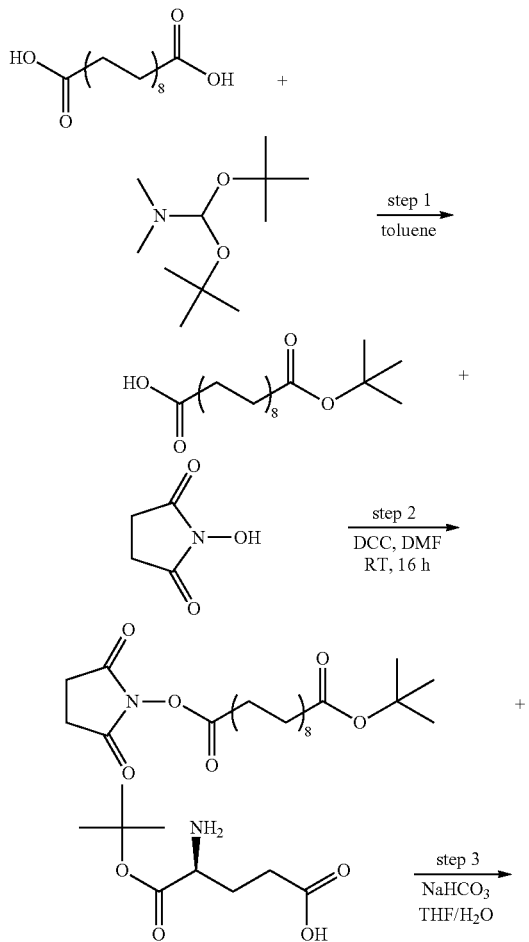

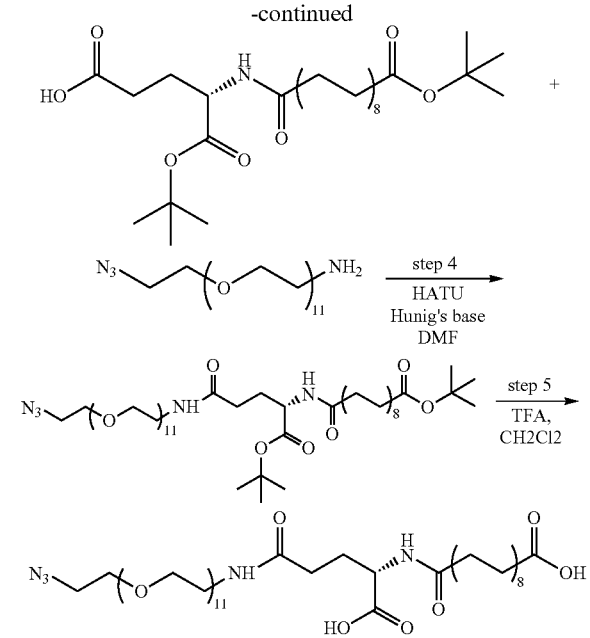

Step 1: Preparation of 18-(tert-butoxy)-18-oxooctadecanoic acid

Octadecanoic acid (7.5 g, 23.85 mmol) was suspended in toluene (42.6 ml) and the mixture was heated to reflux. 1,1-di-tert-butoxy-N,N-dimethylmethanamine (15.33 ml, 63.9 mmol) was added drop-wise over 30 min. The mixture was reflux overnight. The solvent was removed in vacuo at 50° C. and the crude material was suspended in $CH_2Cl_2$/ EtOAc (110 mL. 1:1) and stirred for 15 min. The solids were removed by filtration and washed with $CH_2Cl_2$ (40 mL). The filtration was evaporated in vacuo. The crude product was purified by flash chromatography (SG, 0 to 25% Aceton/ $CH_2Cl_2$) to get 18-(tert-butoxy)-18-oxooctadecanoic acid (3.95 g, 10.66 mmol, 44.7% yield).

Analysis condition D: Retention time=5.04 min; ESI-MS (+) m/z 297.3 $[M-OC(CH_3)_3]$ $^1$H NMR (500 MHz, METHANOL-$d_4$) δ 2.29 (t, J=7.5 Hz, 2H), 2.22 (t, J=7.4 Hz, 2H), 1.67-1.53 (m, 4H), 1.50- 1.42 (m, 9H), 1.40-1.25 (m, 24H).

Step 2: Preparation of 1-tert-butyl 18-(2,5-dioxopyrrolidin-1-yl)octadecanedioate DCC (5.11 ml, 5.11 mmol) was added to a solution of 18-(tert-butoxy)-18-oxooctadecanoic acid (1.72 g, 4.64 mmol) and 1-hydroxypyrrolidine-2,5-dione (0.588 g, 5.11 mmol) in DMF (48 mL). The mixture was stirred at rt overnight. The mixture was filtered and concentrated to get 1-tert-butyl 18-(2,5-dioxopyrrolidin-1-yl)octadecanedioate which was used as is in the next step.

Step 3: Preparation of (S)-5-(tert-butoxy)-4-(18-(tert-butoxy)-18-oxooctadecanamido)-5-oxopentanoic acid Water (5.80 ml) was added to a mixture of (S)-4-amino-5-(tert-butoxy)-5-oxopentanoic acid (1.038 g, 5.11 mmol), 1-tert-butyl 18-(2,5-dioxopyrrolidin-1-yl)octadecanedioate (2.171 g, 4.64 mmol), SODIUM BICARBONATE (0.468 g, 5.57 mmol) in THF (17.41 ml). The resulting clear solution was stirred at rt for 4 h. All THF was removed, HCl (6.04 ml, 6.04 mmol) was added and the pH was adjusted to 2-3 at 0° C. The resulting suspension was extracted with $CH_2Cl_2$ (×3), The organic layer was concentrated. The resulting crude product was purified by flash chromatography (aceton/$CH_2Cl_2$ 0 to 25%) to afford (S)-5-(tert-butoxy)-4-(18-(tert-butoxy)-18-oxooctadecanamido)-5-oxopentanoic acid (2.29 g, 4.12 mmol, 89% yield) as a white solid. Analysis condition D: Retention time=2.74 min; ESI-MS(+) m/z 555.6 $(M+H)^+$ $^1$H NMR (500 MHz, METHANOL-$d_4$) δ 4.32 (dd, J=9.0, 5.3 Hz, 1H), 2.45-2.33 (m, 2H), 2.30-2.06 (m, 5H), 1.99-1.82 (m, 3H), 1.78-1.53 (m, 2H), 1.53-1.44 (m, 18H), 1.44-1.26 (m, 24H).

Step 4: Preparation of (S)-tert-butyl 1-azido-40-(tert-butoxycarbonyl)-37,42-dioxo-3,6,9,12,15,18,21,24,27,30,33-undecaoxa-36,41-diazanonapentacontan-59-oate To a solution of (S)-5-(tert-butoxy)-4-(18-(tert-butoxy)-18-oxooctadecanamido)-5-oxopentanoic acid (438 mg, 0.789 mmol) in DMF (1593 μl) was added Hunig's Base (275 μl, 1.577 mmol) and HATU (400 mg, 1.051 mmol). 35-azido-3,6,9,12,15,18,21,24,27,30,33-undecaoxapentatriacontan-1-amine (300 mg, 0.526 mmol) was then added, and the solution stirred at rt. The mixture was stirred overnight.

The mixture was poured into water and extracted 3 times into $CH_2Cl_2$. The combined organic extracts were dried over MgSO4, filtered, and concentrated in vacuo to get (S)-tert-butyl 1-azido-40-(tert-butoxycarbonyl)-37,42-dioxo-3,6,9,12,15,18,21,24,27,30,33-undecaoxa-36,41-diazanonapentacontan-59-oate which is used as is in the next step. Analysis condition D: Retention time=2.84 min; ESI-MS(+) m/z 1109.1 $(M+H)^+$

Step 5: Preparation of (S)-1-azido-40-carboxy-37,42-dioxo-3,6,9,12,15,18,21,24,27,30,33-undecaoxa-36,41-diazanonapentacontan-59-oic acid The mixture of (S)-tert-butyl 1-azido-40-(tert-butoxycarbonyl)-37,42-dioxo-3,6,9,12,15,18,21,24,27,30,33-undecaoxa-36,41-diazanonapentacontan-59-oate (280 mg, 0.253 mmol) and TFA (3 mL, 38.9 mmol) in DCM (3.0 mL) was stirred at rt for 2 h. The resulting crude product was purified by Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 50-100% B, 10 min and stop at 12 min) to obtain (S)-1-azido-40-carboxy-37,42-dioxo-3,6,9,12,15,18,21,24,27,30,33-undecaoxa-36,41-diazanonapentacontan-59-oic acid (124 mg, 0.124 mmol, 49.3% yield). Analysis condition D: Retention time=2.43 min; ESI-MS(+) m/z 996.9 $(M+H)^+$; $^1$H NMR (500 MHz, METHANOL-$d_4$) δ 4.44-4.35 (m, 1H), 3.84-3.27 (m, 48H), 2.39-2.11 (m, 7H), 2.04-1.87 (m, 1H), 1.71-1.55 (m, 4H), 1.44-1.18 (m, 24H).

(S)-1-azido-16-carboxy-13,18-dioxo-3,6,9-trioxa-12,17-diazapentatriacontan-35-oic acid

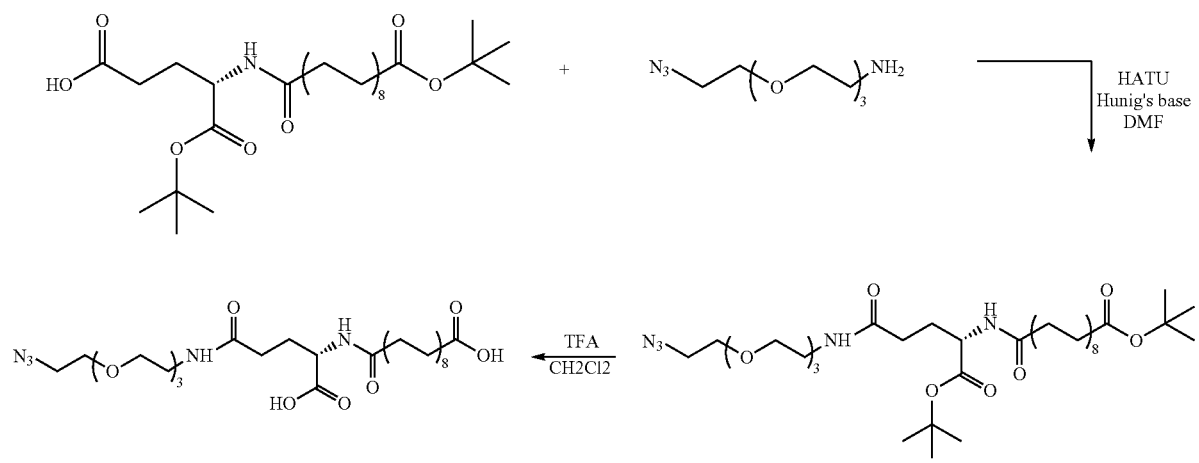

Step 1

To a solution of 2-(2-(2-(2-azidoethoxy)ethoxy)ethoxy)ethanamine (113 mg, 0.517 mmol) in DMF (4498 µl) was added Hunig's Base (314 µl, 1.799 mmol), then (S)-5-(tert-butoxy)-4-(18-(tert-butoxy)-18-oxooctadecanamido)-5-oxopentanoic acid (250 mg, 0.450 mmol). HATU (342 mg, 0.900 mmol) was then added, and the resulting solution was stirred at rt. LC/MS showed conversion to the desired m/z. Removed DMF on high vacuum, then the residue was applied to silica gel (40 g) and eluted with DCM (100 mL), then a gradient to 75% DCM/acetone over 540 mL and finally a hold at 75% DCM/acetone for 150 mL. The desired fractions were combined. The material was taken into the next step as is.

Step 2

To a solution of (S)-tert-butyl 1-azido-16-(tert-butoxycarbonyl)-13,18-dioxo-3,6,9-trioxa-12,17-diazapentatriacontan-35-oate (414.0 mg, 0.548 mmol) in DCM (5476 µl) was added TFA (1266 µl, 16.43 mmol). LC/MS indicated a slow reaction, so another 14 eq TFA was added and the mixture stirred further. After another ~6 h, LC/MS indicated a nearly complete reaction. Solvents were removed in vacuo. The mixture was taken up in Hunig's base/MeOH (~1%). The reaction mixture was purified by PREP HPLC in 5 injections: (30×100 mm HPLC Luna Axia C18 50 to 100% A:B over 10 min, 5 min at 100% B (A is 90:10:0.1 water:MeOH:TFA; B is 90:10:0.1 MeOH:water:TFA)). The desired fractions were combined and concentrated to afford (S)-1-azido-16-carboxy-13,18-dioxo-3,6,9-trioxa-12,17-diazapentatriacontan-35-oic acid (112.4 mg, 0.124 mmol, 22.64% yield). LC/MS: (M+H)$^+$=644.45.

(S)-1-azido-22-carboxy-19,24-dioxo-3,6,9,12,15-pentaoxa-18,23-diazahentetracontan-41-oic acid

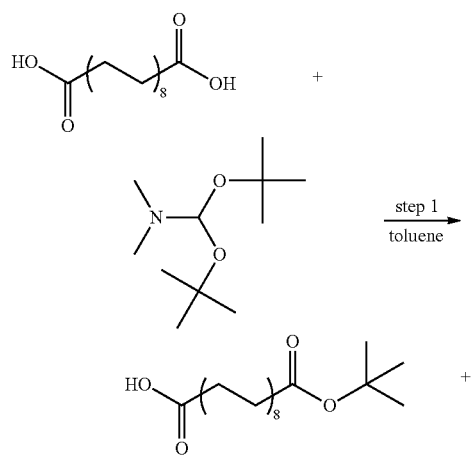

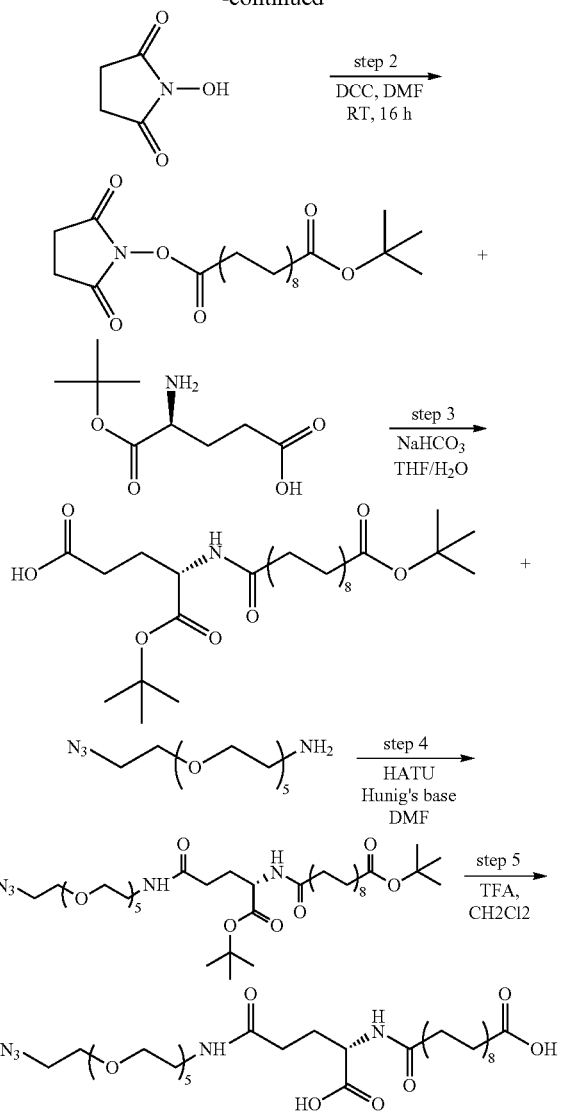

Step 1: Preparation of 18-(tert-butoxy)-18-oxooctadecanoic acid

OCTADECANEDIOIC ACID (7.5 g, 23.85 mmol) was suspended in toluene (42.6 ml) and the mixture was heated to reflux. 1,1-di-tert-butoxy-N,N-dimethylmethanamine (15.33 ml, 63.9 mmol) was added dropwise over 30-2,5-din. The mixture was reflux overnight. The solvent was removed in vacuo at 50° C. and the crude material was suspended in CH$_2$Cl$_2$/EtOAc (110 mL. 1:1) and stirred for 15 min. The solids were removed by filtration and washed with CH$_2$Cl$_2$ (40 mL). The filtration was evaporated in vacuo. The crude product was purified by flash chromatography (SG, 0 to 25% acetone/CH$_2$Cl$_2$) to get 18-(tert-butoxy)-18-oxooctadecanoic acid (3.95 g, 10.66 mmol, 44.7% yield). Analysis condition D: Retention time=5.04 min; ESI-MS(+) m/z 297.3 [M–OC(CH$_3$)$_3$]; $^1$H NMR (500 MHz, METHANOL-d₄) δ 2.29 (t, J=7.5 Hz, 2H), 2.22 (t, J=7.4 Hz, 2H), 1.67-1.53 (m, 4H), 1.50-1.42 (m, 9H), 1.40-1.25 (m, 24H).

Step 2: Preparation of 1-tert-butyl 18-(2,5-dioxopyrrolidin-1-yl)octadecanedioate DCC (5.11 ml, 5.11 mmol) was added to a solution of 18-(tert-butoxy)-18-oxooctadecanoic acid (1.72 g, 4.64 mmol) and 1-hydroxypyrrolidine-2,5-dione (0.588 g, 5.11 mmol) in DMF (48 mL). The mixture was stirred at rt overnight. The mixture was filtered and concentrated to get 1-tert-butyl 18-(2,5-dioxopyrrolidin-1-yl)octadecanedioate which was used as is in the next step.

Step 3: Preparation of (S)-5-(tert-butoxy)-4-(18-(tert-butoxy)-18-oxooctadecanamido)-5-oxopentanoic acid Water (5.80 ml) was added to a mixture of (S)-4-amino-5-(tert-butoxy)-5-oxopentanoic acid (1.038 g, 5.11 mmol), 1-tert-butyl 18-(2,5-dioxopyrrolidin-1-yl)octadecanedioate (2.171 g, 4.64 mmol), SODIUM BICARBONATE (0.468 g, 5.57 mmol) in THF (17.41 ml). The resulting clear solution was stirred at rt for 4 h. All THF was removed, HCl (6.04 ml, 6.04 mmol) was added and the pH was adjusted to 2-3 at 0° C. The resulting suspension was extracted with $CH_2Cl_2$ (×3). The organic layer was concentrated. The resulting crude product was purified by flash chromatography (aceton/$CH_2Cl_2$ 0 to 25%) to afford (S)-5-(tert-butoxy)-4-(18-(tert-butoxy)-18-oxooctadecanamido)-5-oxopentanoic acid (2.29 g, 4.12 mmol, 89% yield) as a white solid. Analysis condition D: Retention time=2.74 min; ESI-MS(+) m/z 555.6 (M+H)⁺ ¹H NMR (500 MHz, METHANOL-d₄) δ 4.32 (dd, J=9.0, 5.3 Hz, 1H), 2.45-2.33 (m, 2H), 2.30-2.06 (m, 5H), 1.99-1.82 (m, 3H), 1.78-1.53 (m, 2H), 1.53-1.44 (m, 18H), 1.44-1.26 (m, 24H).

Step 4: Preparation of (S)-tert-butyl 1-azido-22-(tert-butoxycarbonyl)-19,24-dioxo-3,6,9,12,15-pentaoxa-18,23-diazahentetracontan-41-oate To a solution of (S)-5-(tert-butoxy)-4-(18-(tert-butoxy)-18-oxooctadecanamido)-5-oxopentanoic acid (225 mg, 0.405 mmol) in DMF (4048 μl) was added Hunig's Base (212 μl, 1.214 mmol) and HATU (308 mg, 0.810 mmol). 17-azido-3,6,9,12,15-pentaoxaheptadecan-1-amine, HCl (139 mg, 0.405 mmol) was then added, and the solution stirred at rt. The crude product was purified by flash chromatography (220 g, silic gel, 10 to 60% Aceton/$CH_2Cl_2$) to get (S)-tert-butyl 1-azido-22-(tert-butoxycarbonyl)-19,24-dioxo-3,6,9,12,15-pentaoxa-18,23-diazahentetracontan-41-oate (330 mg, 0.391 mmol, 97% yield). Analysis condition D: Retention time=2.88 min; ESI-MS(+) m/z 844.7 (M+H)⁺; ¹H NMR (500 MHz, METHANOL-d₄) δ 4.30-4.23 (m, 1H), 3.74-3.60 (m, 18H), 3.60-3.52 (m, 2H), 3.43-3.35 (m, 4H), 2.34-2.28 (m, 2H), 2.28-2.19 (m, 4H), 2.15-2.08 (m, 1H), 1.98-1.87 (m, 1H), 1.69-1.53 (m, 4H), 1.52-1.44 (m, 18H), 1.41-1.27 (m, 24H).

Step 5: Preparation (S)-1-azido-22-carboxy-19,24-dioxo-3,6,9,12,15-pentaoxa-18,23-diazahentetracontan-41-oic acid The mixture of (S)-tert-butyl 1-azido-22-(tert-butoxycarbonyl)-19,24-dioxo-3,6,9,12,15-pentaoxa-18,23-diazahentetracontan-41-oate (330 mg, 0.391 mmol) and TFA (0.422 mL, 5.47 mmol) in DCM (3.0 mL) was stirred at rt for 2 h. The resulting crude product was purified by Prep-HPLC (Solvent A=10% MeOH-90% H2O-0.1% TFA, Solvent B=90% MeOH-10% H₂O-0.1% TFA. Column: PHENOMENEX LUNA 30×150 mm, S10, Flow rate: 40 ml/min, 50-100% B, 10 min and stop at 13 min) to obtain (S)-1-azido-22-carboxy-19,24-dioxo-3,6,9,12,15-pentaoxa-18,23-diazahentetracontan-41-oic acid (101 mg, 0.138 mmol, 35.3% yield). Analysis condition D: Retention time=2.42 min; ESI-MS(+) m/z 732.5 (M+H)⁺

(S)-1-azido-28-carboxy-25,30-dioxo-3,6,9,12,15,18, 21-heptaoxa-24,29-diazaheptatetracontan-47-oic acid

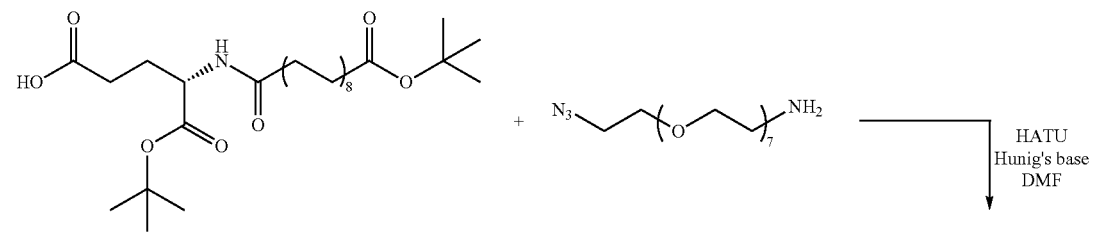

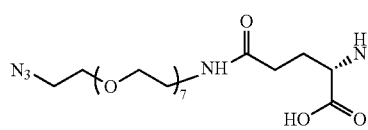 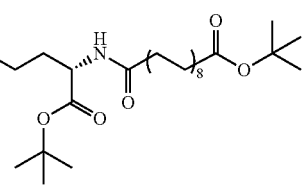

Step 1

To a solution of 23-azido-3,6,9,12,15,18,21-heptaoxatricosan-1-amine (204 mg, 0.517 mmol) in DMF (4498 μl) was added Hunig's Base (314 μl, 1.799 mmol), then (S)-5-(tert-butoxy)-4-(18-(tert-butoxy)-18-oxooctadecanamido)-5-oxopentanoic acid (250 mg, 0.450 mmol). HATU (342 mg, 0.900 mmol) was then added, and the resulting solution was stirred at rt. LC/MS showed conversion to the desired m/z. Removed DMF on high vacuum, then the residue was applied to silica gel (40 g) and eluted with DCM (90 mL), then a gradient to 75% DCM/acetone over 540 mL and finally a hold at 75% DCM/acetone for 150 mL. The desired fractions were combined to obtain (S)-tert-butyl 1-azido-28-(tert-butoxycarbonyl)-25,30-dioxo-3,6,9,12,15,18,21-heptaoxa-24,29-diazaheptatetracontan-47-oate (394.2 mg, 0.423 mmol, 94% yield).

Step 2

To a solution of (S)-tert-butyl 1-azido-28-(tert-butoxycarbonyl)-25,30-dioxo-3,6,9,12,15,18,21-heptaoxa-24,29-diazaheptatetracontan-47-oate (394.2 mg, 0.423 mmol) in DCM (4229 μl) was added TFA (456 μl, 5.92 mmol). LC/MS indicated a slow reaction, so another 14 eq TFA was added and the mixture stirred further. After another ~6 h, LC/MS indicated a nearly complete reaction. Solvents were removed in vacuo. The mixture was taken up in MeOH. The reaction mixture was purified by PREP HPLC in 7 injections: (30×100 mm HPLC Luna Axia C18 50 to 100% A:B over 10 min, 5 min at 100% B (A is 90:10:0.1 water:MeOH:TFA; B is 90:10:0.1 MeOH:water:TFA)). Speedvac'd appropriate fractions. Isolated (S)-1-azido-28-carboxy-25,30-dioxo-3,6,9,12,15,18,21-heptaoxa-24,29-diazaheptatetracontan-47-oic acid (121.0 mg, 0.148 mmol, 34.9% yield). LC/MS: (M+H)$^+$=820.60. $^1$H NMR (500 MHz, CHLOROFORM-d) δ 7.30 (d, J=6.4 Hz, 1H), 7.04 (t, J=5.2 Hz, 1H), 4.51 (q, J=6.2 Hz, 1H), 3.72-3.64 (m, 27H), 3.63-3.59 (m, 2H), 3.56-3.49 (m, 1H), 3.47-3.39 (m, 3H), 2.62-2.54 (m, 1H), 2.48-2.40 (m, 1H), 2.36 (t, J=7.4 Hz, 2H), 2.26 (t, J=7.6 Hz, 2H), 2.19-2.08 (m, 2H), 1.65 (quin, J=7.4 Hz, 4H), 1.39-1.24 (m, 25H).

(S)-18-((3-azido-1-carboxypropyl)amino)-18-oxooctadecanoic acid

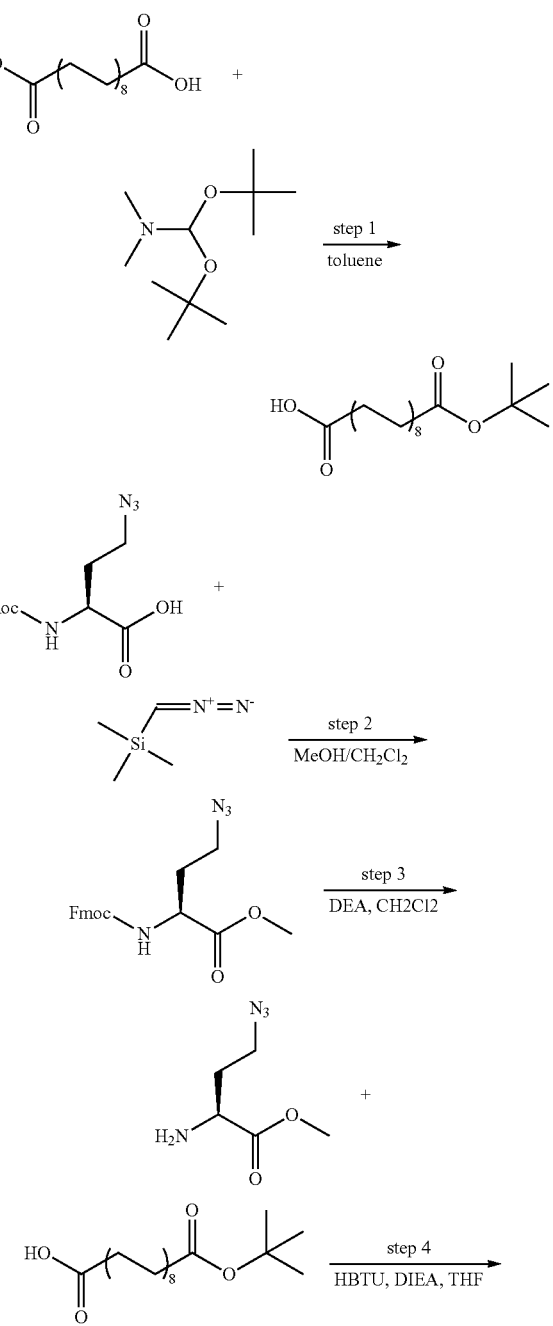

-continued

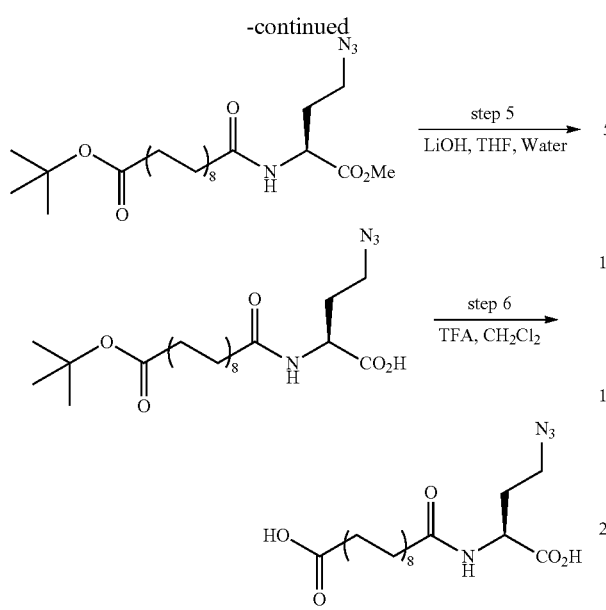

Step 1: Preparation of 18-(tert-butoxy)-18-oxooctadecanoic acid

OCTADECANEDIOIC ACID (7.5 g, 23.85 mmol) was suspended in Toluene (42.6 ml) and the mixture was heated to reflux. 1,1-di-tert-butoxy-N,N-dimethylmethanamine (15.33 ml, 63.9 mmol) was added dropwise over 30 min. The mixture was reflux overnight. The solvent was removed in vacuo at 50° C. and the crude material was suspended in $CH_2Cl_2$/EtOAc (110 mL, 1:1) and stirred for 15 min. The solids were removed by filtration and washed with $CH_2Cl_2$ (40 mL). The filtration was evaporated in vacuo. The crude product was purified by flash chromatography (300 g, SG, 100% CH2Cl2 1000 mL first and then 0 to 25% acetone/ $CH_2Cl_2$, 2000 mL) to get 18-(tert-butoxy)-18-oxooctadecanoic acid (3.82 g, 10.31 mmol, 43.2% yield).

Analysis condition D: Retention time=2.85 min; ESI-MS (+) m/z 297.3 [M–OC(CH$_3$)$_3$]; $^1$H NMR (500 MHz, METHANOL-d$_4$) δ 2.29 (t, J=7.5 Hz, 2H), 2.22 (t, J=7.3 Hz, 2H), 1.67-1.53 (m, 4H), 1.46 (s, 9H), 1.31 (m, 24H).

Step 2: Preparation of (S)-methyl 2-((((9H-fluoren-9-yl)methoxy)carbonyl)amino)-4-azidobutanoate To a mixture of (2S)—N-FMOC-4-AZIDO-BUTANOIC ACID (1.0 g, 2.73 mmol) in MeOH (4.21 ml)/$CH_2Cl_2$ (12.64 ml) was added (TRIMETHYLSILYL)DIAZOMETHANE in diethyl ether (2.047 ml, 4.09 mmol). The resulting mixture was stirred at rt for 2 h. The mixture was concentrated to get (S)-methyl 2-((((9H-fluoren-9-yl)methoxy)carbonyl)amino)-4-azidobutanoate, which was used as is in the next step. $^1$H NMR (500 MHz, METHANOL-d$_4$) δ 7.81 (d, J=7.6 Hz, 2H), 7.73-7.63 (m, 2H), 7.47-7.22 (m, 4H), 4.41 (d, J=6.7 Hz, 2H), 4.35-4.17 (m, 2H), 3.82-3.70 (m, 3H), 3.49-3.34 (m, 2H), 2.21-2.04 (m, 1H), 1.97-1.80 (m, 1H).

Step 3: Preparation of (S)-methyl 4-azido-2-((tert-butoxycarbonyl)amino)butanoate The mixture of (S)-methyl 2-((((9H-fluoren-9-yl)methoxy)carbonyl)amino)-4-azidobutanoate (1.038 g, 2.73 mmol) and diethylamine (4.0 mL, 38.3 mmol) in $CH_2Cl_2$ (4 mL) was stirred at rt for 2 h. LCMS showed disappearance of S.M. and product formation along with FMOC related peaks. Concentrated and the resulting product was used as is in the next step. $^1$H NMR (500 MHz, METHANOL-d$_4$) δ 3.85-3.69 (m, 3H), 3.63-3.52 (m, 1H), 3.51-3.40 (m, 2H), 2.05-1.91 (m, 1H), 1.88-1.76 (m, 1H).

Step 4: Preparation of (S)-tert-butyl 18-((4-azido-1-methoxy-1-oxobutan-2-yl)amino)-18-oxooctadecanoate The mixture of (S)-methyl 2-amino-4-azidobutanoate (0.432 g, 2.73 mmol), 18-(tert-butoxy)-18-oxooctadecanoic acid (1.012 g, 2.73 mmol), DIPEA (1.907 ml, 10.92 mmol) and HBTU (1.035 g, 2.73 mmol) in THF (27.3 ml) was stirred at rt overnight. The resulting crude product was purified by Biotage (silic gel, 300 g, 0 to 10% acetone/ $CH_2Cl_2$) to get (S)-tert-butyl 18-((4-azido-1-methoxy-1-oxobutan-2-yl)amino)-18-oxooctadecanoate (1.37 g, 2.68 mmol, 98% yield). Analysis condition D: Retention time=2.87 min; ESI-MS(+) m/z 533.3 (M+Na)+; $^1$H NMR (500 MHz, METHANOL-d$_4$) δ 4.54 (dd, J=9.2, 5.0 Hz, 1H), 3.78-3.70 (m, 3H), 3.49-3.37 (m, 2H), 2.30-2.19 (m, 2H), 2.15-2.04 (m, 1H), 1.97-1.91 (m, 1H), 1.91-1.83 (m, 2H), 1.68-1.53 (m, 4H), 1.46 (s, 9H), 1.31 (br. s., 24H).

Step 5: Preparation of (S)-4-azido-2-(18-(tert-butoxy)-18-oxooctadecanamido)butanoic acid (S)-tert-Butyl 18-((4-azido-1-methoxy-1-oxobutan-2-yl)amino)-18-oxooctadecanoate (1.37 g, 2.68 mmol), was dissolved in THF (13.41 ml) followed by the addition of lithium hydroxide (0.321 g, 13.41 mmol) and water (13.41 ml). The reaction was stirred at rt overnight. Concentrated the reaction mixture to dryness. The resulting (S)-4-azido-2-(18-(tert-butoxy)-18-oxooctadecanamido)butanoic acid was used as is in the next step. Analysis condition D: Retention time=2.62 min; ESI-MS(+) m/z 497.4 (M+H)$^+$.

Step 6: Preparation of (S)-18-((3-azido-1-carboxypropyl)amino)-18-oxooctadecanoic acid The mixture of (S)-4-azido-2-(18-(tert-butoxy)-18-oxooctadecanamido)butanoic acid (1.332 g, 2.68 mmol) and TFA (2.89 ml, 37.5 mmol) in DCM (20 ml) was stirred at rt for 2 h. The resulting crude product was purified by Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 50-100% B, 10 min and stop at 12 min) to obtain (S)-18-((3-azido-1-carboxypropyl)amino)-18-oxooctadecanoic acid (451 mg, 1.024 mmol, 38.2% yield). Analysis condition D: Retention time=2.42 min; ESI-MS(+) m/z 441.2 (M+H)$^+$; $^1$H NMR (500 MHz, METHANOL-$d_4$) δ 4.51 (dd, J=9.4, 4.8 Hz, 1H), 3.51-3.36 (m, 3H), 2.37-2.22 (m, 4H), 2.19-2.08 (m, 1H), 1.99-1.88 (m, 1H), 1.68-1.54 (m, 4H), 1.40-1.22 (m, 24H).

(S)-1-azido-39-carboxy-37,41-dioxo-3,6,9,12,15,18,21,24,27,30,33-undecaoxa-36,40-diazaoctapentaconacontan-58-oic acid Step 1: Preparation of 18-(tert-butoxy)-18-oxooctadecanoic acid OCTADECANEDIOIC ACID (7.5 g, 23.85 mmol) was suspended in Toluene (42.6 ml) and the mixture was heated to reflux. 1,1-di-tert-butoxy-N,N-dimethylmethanamine (15.33 ml, 63.9 mmol) was added drop-wise over 30 min. The mixture was reflux overnight. The solvent was removed in vacuo at 50° C. and the crude material was suspended in $CH_2Cl_2$/EtOAc (110 mL. 1:1) and stirred for 15 min. The solids were removed by filtration and washed with $CH_2Cl_2$ (40 mL). The filtration was evaporated in vacuo. The crude product was purified by flash chromatography (SG, 0 to 25% acetone/$CH_2Cl_2$) to get 18-(tert-butoxy)-18-oxooctadecanoic acid (3.95 g, 10.66 mmol, 44.7% yield). Analysis condition D: Retention time=5.04 min; ESI-MS(+) m/z 297.3 [M-OC(CH$_3$)$_3$]; $^1$H NMR (500 MHz, METHANOL-

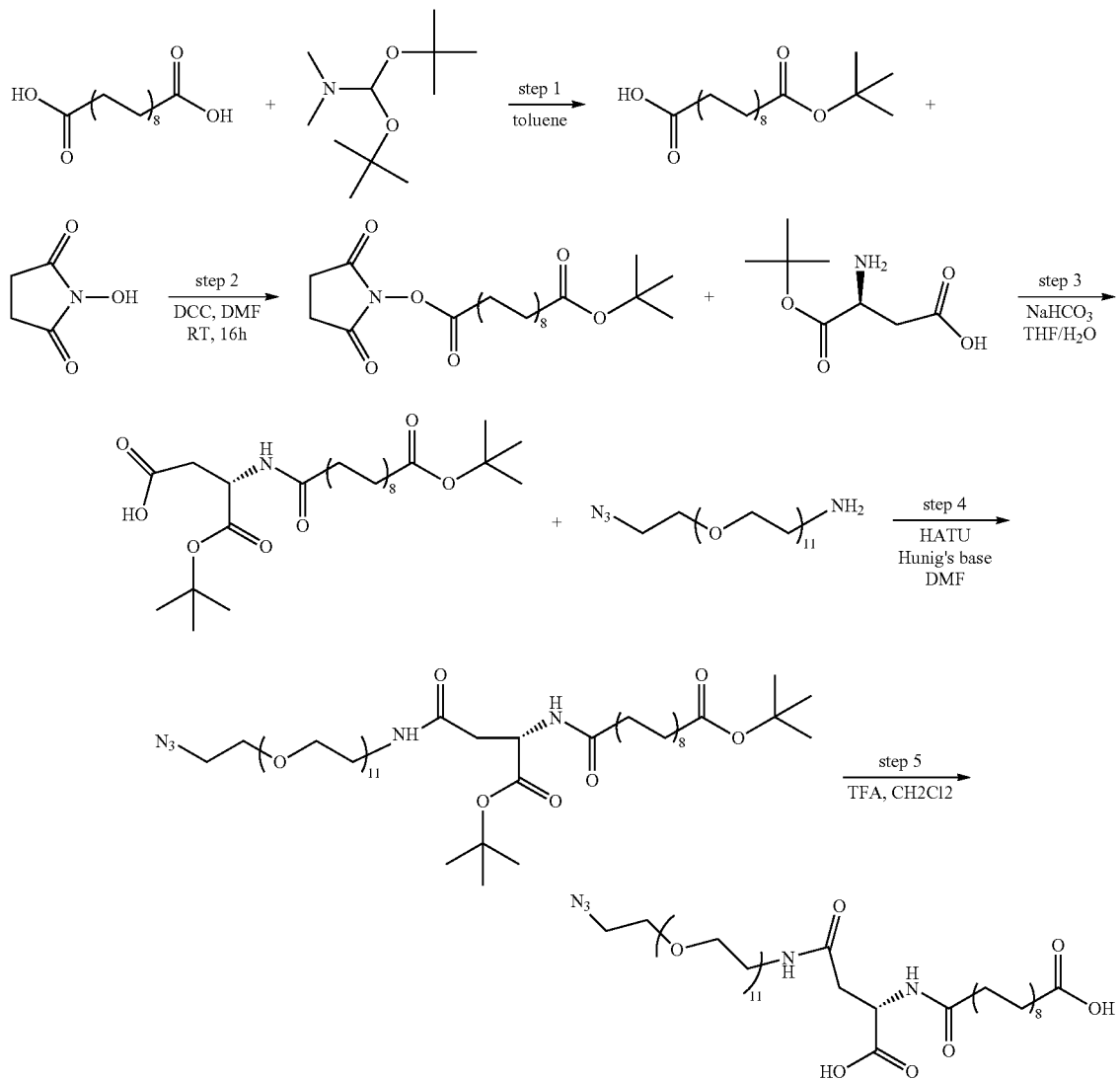

d$_4$) δ 2.29 (t, J=7.5 Hz, 2H), 2.22 (t, J=7.4 Hz, 2H), 1.67-1.53 (m, 4H), 1.50-1.42 (m, 9H), 1.40-1.25 (m, 24H).

Step 2: Preparation of 1-tert-butyl 18-(2,5-dioxopyrrolidin-1-yl)octadecanedioate DCC (5.11 ml, 5.11 mmol) was added to a solution of 18-(tert-butoxy)-18-oxooctadecanoic acid (1.72 g, 4.64 mmol) and 1-hydroxypyrrolidine-2,5-dione (0.588 g, 5.11 mmol) in DMF (48 mL). The mixture was stirred at rt overnight. The mixture was filtered and concentrated to get 1-tert-butyl 18-(2,5-dioxopyrrolidin-1-yl)octadecanedioate which was used as is in the next step.

Step 3: Preparation of (S)-4-(tert-butoxy)-3-(18-(tert-butoxy)-18-oxooctadecanamido)-4-oxobutanoic acid Water (6.74 ml) was added to a mixture of (S)-3-amino-4-(tert-butoxy)-4-oxobutanoic acid (1.122 g, 5.93 mmol), 1-tert-butyl 18-(2,5-dioxopyrrolidin-1-yl)octadecanedioate (2.52 g, 5.39 mmol), SODIUM BICARBONATE (0.543 g, 6.47 mmol) in THF (20.21 ml). The resulting clear solution was stirred at rt for 4 h. All THF was removed, HCl (7.01 ml, 7.01 mmol) was added and the pH was adjusted to 2-3 at 0° C. The resulting suspension was extracted with CH$_2$Cl$_2$ (×3), The organic layer was concentrated. The resulting product was used as is. Analysis condition D: Retention time=2.83 min; ESI-MS(+) m/z 542.3 (M+H)$^+$; $^1$H NMR (500 MHz, METHANOL-d$_4$) δ 4.64 (t, J=6.1 Hz, 1H), 2.83-2.67 (m, 2H), 2.29-2.18 (m, 2H), 1.91-1.81 (m, 1H), 1.78-1.67 (m, 1H), 1.67-1.53 (m, 4H), 1.53-1.39 (m, 18H), 1.39-1.26 (m, 24H).

Step 4: Preparation of (S)-tert-butyl 1-azido-39-(tert-butoxycarbonyl)-37,41-dioxo-3,6,9,12,15,18, 21,24,27,30,33-undecaoxa-36,40-diazaoctapentacontan-58-oate To a solution of (S)-4-(tert-butoxy)-3-(18-(tert-butoxy)-18-oxooctadecanamido)-4-oxobutanoic acid (200 mg, 0.369 mmol) in DMF (3692 µl) was added Hunig's Base (193 µl, 1.108 mmol) and HATU (281 mg, 0.738 mmol). 35-azido-3,6,9,12,15,18,21,24,27,30,33-undecaoxapentatriacontan-1-amine (211 mg, 0.369 mmol) was then added, and the solution stirred at rt for 3 h. The resulting product was used as is. Analysis condition D: Retention time=2.79 min; ESI-MS(+) m/z 1194.7 (M+H)$^+$.

Step 5: Preparation of (S)-1-azido-39-carboxy-37, 41-dioxo-3,6,9,12,15,18,21,24,27,30,33-undecaoxa-36,40-diazaoctapentaconacontan-58-oic acid The mixture of (S)-tert-butyl 1-azido-39-(tert-butoxycarbonyl)-37,41-dioxo-3,6,9,12,15,18,21,24,27,30,33-undecaoxa-36,40-diazaoctapentacontan-58-oate (404 mg, 0.369 mmol) and TFA (2 mL, 26.0 mmol) in DCM (5 mL) was stirred at rt for 2 h. The resulting crude product was purified by Prep-HPLC (Solvent A=10% MeOH-90% H$_2$O-0.1% TFA, Solvent B=90% MeOH-10% H$_2$O-0.1% TFA. Column: PHENOMENEX LUNA 30×150 mm, S10, Flow rate: 40 ml/min, 50-100% B, 12 min and stop at 13 min) to obtain (S)-1-azido-39-carboxy-37,41-dioxo-3,6,9,12,15,18,21,24,27,30,33-undecaoxa-36,40-diazaoctapentacontan-58-oic acid (128 mg, 0.130 mmol, 35.3% yield) (4 steps yield). Analysis condition D: Retention time=2.44 min; ESI-MS(+) m/z 982.5 (M+H)$^+$.

(S)-1-azido-15-carboxy-13,17-dioxo-3,6,9-trioxa-12, 16-diazatetratriacontan-34-oic acid

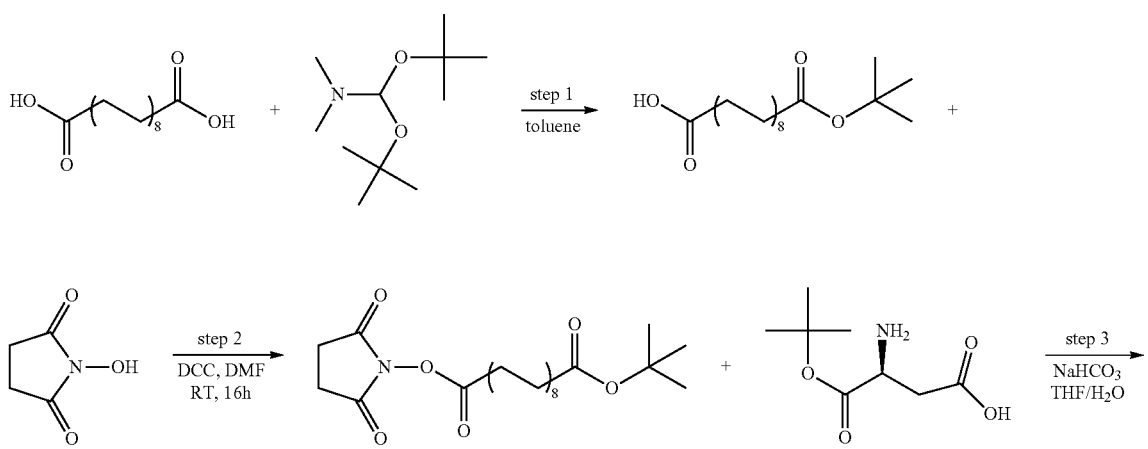

-continued

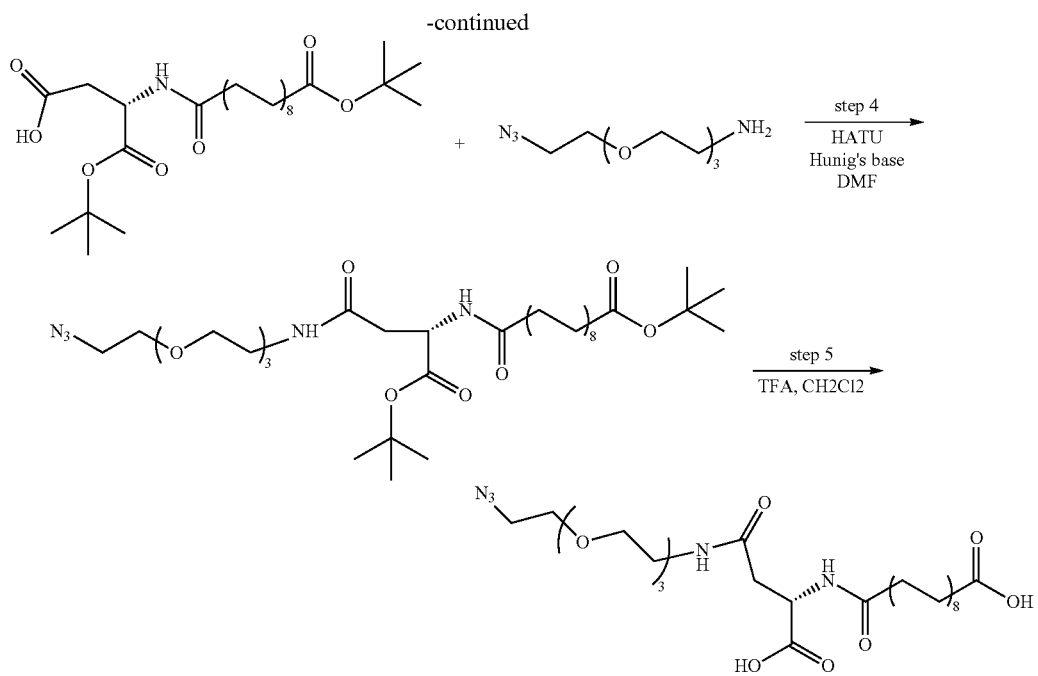

Step 1: Preparation of 18-(tert-butoxy)-18-oxooctadecanoic acid

OCTADECANEDIOIC ACID (7.5 g, 23.85 mmol) was suspended in toluene (42.6 ml) and the mixture was heated to reflux. 1,1-di-tert-butoxy-N,N-dimethylmethanamine (15.33 ml, 63.9 mmol) was added drop-wise over 30 min. The mixture was reflux overnight. The solvent was removed in vacuo at 50° C. and the crude material was suspended in $CH_2Cl_2$/EtOAc (110 mL. 1:1) and stirred for 15 min. The solids were removed by filtration and washed with $CH_2Cl_2$ (40 mL). The filtration was evaporated in vacuo. The crude product was purified by flash chromatography (SG, 0 to 25% Aceton/$CH_2Cl_2$) to get 18-(tert-butoxy)-18-oxooctadecanoic acid (3.95 g, 10.66 mmol, 44.7% yield). Analysis condition D: Retention time=5.04 min; ESI-MS(+) m/z 297.3 [M−OC($CH_3$)$_3$]; $^1$H NMR (500 MHz, METHANOL-$d_4$) δ 2.29 (t, J=7.5 Hz, 2H), 2.22 (t, J=7.4 Hz, 2H), 1.67-1.53 (m, 4H), 1.50-1.42 (m, 9H), 1.40-1.25 (m, 24H).

Step 2: Preparation of 1-tert-butyl 18-(2,5-dioxopyrrolidin-1-yl)octadecanedioate DCC (5.11 ml, 5.11 mmol) was added to a solution of 18-(tert-butoxy)-18-oxooctadecanoic acid (1.72 g, 4.64 mmol) and 1-hydroxypyrrolidine-2,5-dione (0.588 g, 5.11 mmol) in DMF (48 mL). The mixture was stirred at rt overnight. The mixture was filtered and concentrated to get 1-tert-butyl 18-(2,5-dioxopyrrolidin-1-yl)octadecanedioate which was used as is in the next step.

Step 3: Preparation of (S)-4-(tert-butoxy)-3-(18-(tert-butoxy)-18-oxooctadecanamido)-4-oxobutanoic acid Water (6.74 ml) was added to a mixture of (S)-3-amino-4-(tert-butoxy)-4-oxobutanoic acid (1.122 g, 5.93 mmol), 1-tert-butyl 18-(2,5-dioxopyrrolidin-1-yl)octadecanedioate (2.52 g, 5.39 mmol), SODIUM BICARBONATE (0.543 g, 6.47 mmol) in THF (20.21 ml). The resulting clear solution was stirred at rt for 4 h. All THF was removed, HCl (7.01 ml, 7.01 mmol) was added and the pH was adjusted to 2-3 at 0° C. The resulting suspension was extracted with $CH_2Cl_2$ (×3), The organic layer was concentrated. The resulting product was used as is. Analysis condition D: Retention time=2.83 min; ESI-MS(+) m/z 542.3 (M+H)$^+$; $^1$H NMR (500 MHz, METHANOL-$d_4$) δ 4.64 (t, J=6.1 Hz, 1H), 2.83-2.67 (m, 2H), 2.29-2.18 (m, 2H), 1.91-1.81 (m, 1H), 1.78-1.67 (m, 1H), 1.67-1.53 (m, 4H), 1.53-1.39 (m, 18H), 1.39-1.26 (m, 24H).

Step 4: Preparation of (S)-tert-butyl 1-azido-15-(tert-butoxycarbonyl)-13,17-dioxo-3,6,9-trioxa-12,16-diazatetratriacontan-34-oate To a solution of (S)-4-(tert-butoxy)-3-(18-(tert-butoxy)-18-oxooctadecanamido)-4-oxobutanoic acid (350 mg, 0.646 mmol) in DMF (6460 μl) was added Hunig's Base (338 μl, 1.938 mmol) and HATU (491 mg, 1.292 mmol). 2-(2-(2-(2-azidoethoxy)ethoxy)ethoxy)ethanamine (141 mg, 0.646 mmol) was then added, and the solution stirred at rt for 3 h.

The resulting product was used as is. Analysis condition D: Retention time=2.90 min; ESI-MS(+) m/z 742.5 (M+H)+

Step 5: Preparation of (S)-1-azido-15-carboxy-13,17-dioxo-3,6,9-trioxa-12,16-diazatetratriacontan-34-oic acid The mixture of (S)-tert-butyl 1-azido-15-(tert-butoxycarbonyl)-13,17-dioxo-3,6,9-trioxa-12,16-diazatetratriacontan-34-oate (479 mg, 0.646 mmol) and TFA (2 mL, 26.0 mmol) in DCM (10 mL) was stirred at rt for 2 h. The resulting crude product was purified by Prep-HPLC (Solvent A=10% MeOH-90% H$_2$O-0.1% TFA, Solvent B=90% MeOH-10% H$_2$O-0.1% TFA. Column: PHENOMENEX LUNA 30×150 mm, S10, Flow rate: 40 ml/min, 50-100% B, 10 min and stop at 12 min) to obtain (S)-1-azido-15-carboxy-13,17-dioxo-3,6,9-trioxa-12,16-diazatetratriacontan-34-oic acid (119 mg, 0.189 mmol, 29.2% yield) (4 steps yield); Analysis condition D: Retention time=2.44 min; ESI-MS(+) m/z 630.2 (M+H)+.

Preparation of INT-1300A

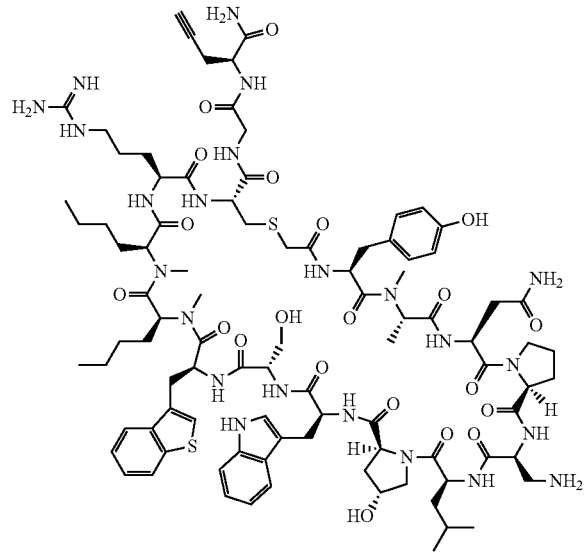

INTERMEDIATE 1300A

The following peptide was synthesized on a 0.2 mmol scale according to the procedures above. The underlined steps employed the double-coupling procedure. ClAc-Tyr-[N-Me]Ala-Asn-Pro-Dap-Leu-Hyp-Trp-Ser-Bzt-[N-Me]Nle-[N-Me]Nle-Arg-Cys-Gly-[(S)-propargylglycine]. After deprotection and cyclization according to the procedures above, the compound was purified as follows: The crude material was purified via preparative LC/MS with the following conditions: Column: waters xbridge c-18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.8 mg, and its estimated purity by LCMS analysis was 100%. Analysis condition A: Retention time=1.56 min; ESI-MS(+) m/z 986.7 (M+2H), most abundant ion; Analysis condition B: Retention time=2.86 min; ESI-MS(+) m/z 986.7 (M+2H), most abundant ion.

Preparation of INT-1300B

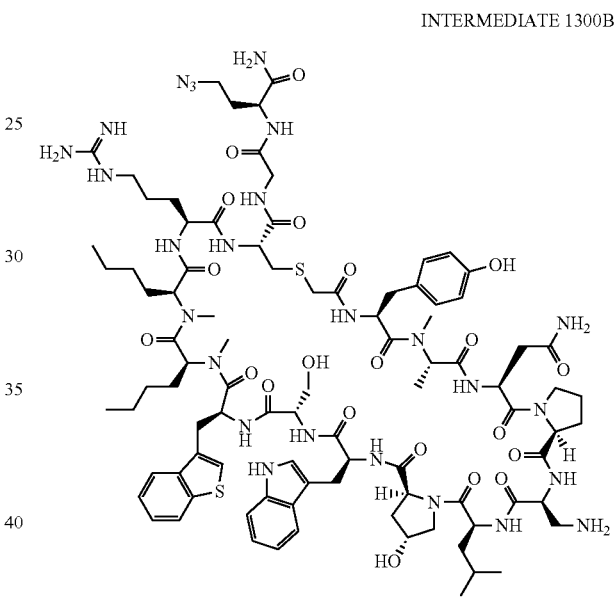

INTERMEDIATE 1300B

The following peptide was synthesized on a 0.2 mmol scale according to the procedures above. The underlined steps employed the double-coupling procedure. ClAc-Tyr-[N-Me]Ala-Asn-Pro-Dap-Leu-Hyp-Trp-Ser-Bzt-[N-Me]Nle-[N-Me]Nle-Arg-Cys-Gly-[(S)-azido-Dab]. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 50.4 mg, and its estimated purity by LCMS analysis was 100%. Analysis condition A: Retention time=1.61 min; ESI-MS(+) m/z 1002.2 (M+2H), most abundant ion; Analysis condition B: Retention time=2.82 min; ESI-MS(+) m/z 1002.2 (M+2H), most abundant ion.

Preparation of INT-1300C

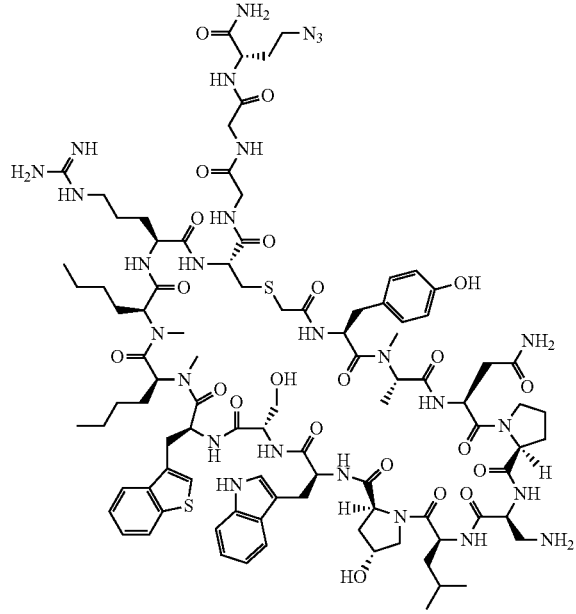

INTERMEDIATE 1300C

The following peptide was synthesized on a 0.1 mmol scale according to the procedures above. The underlined steps employed the double-coupling procedure. ClAc-Tyr-[N-Me]Ala-<u>Asn</u>-Pro-Dap-<u>Leu</u>-Hyp-Trp-Ser-<u>Bzt</u>-[N-Me]Nle-[N-Me]Nle-Arg-Cys-Gly-Gly-[(S)-azido-Dab]; After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.3 mg, and its estimated purity by LCMS analysis was 100%. Analysis condition A: Retention time=5=1.60 min; ESI-MS(+) m/z 1030.7 (M+2H), most abundant ion; Analysis condition B: Retention time=2.83 min; ESI-MS(+) m/z 1030.6 (M+2H), most abundant ion; ESI-HRMS(+) m/z: Calculated: 1029.9931 (M+2H). Found: 1029.9898 (M+2H).

Preparation of INT-1300V

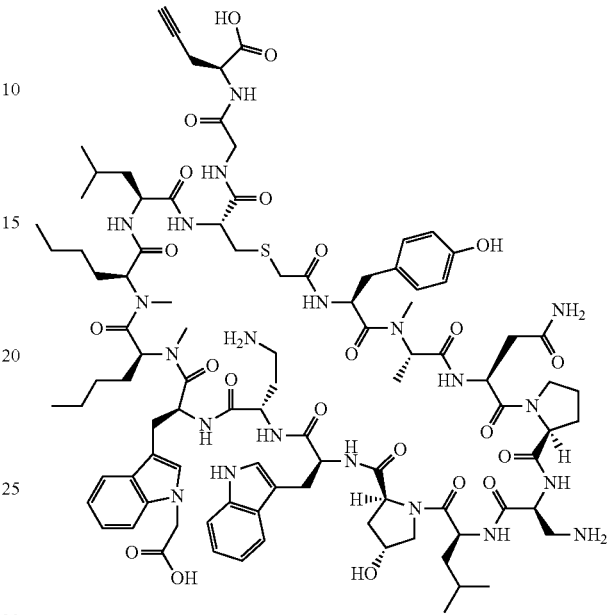

INTERMEDIATE 1300V

The following peptide was synthesized on a 0.1 mmol scale according to the procedures above. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[(S)-propargylglycine]; where the (S) propargylglycine was incorporated onto 2-chlorotrityl resin. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.4 mg, and its estimated purity by LCMS analysis was 96%. Analysis condition A: Retention time=1.49 min; ESI-MS(+) m/z 992.3 (M+2H), most abundant ion. Analysis condition B: Retention time=3.02 min; ESI-MS(+) m/z 992.3 (M+2H), most abundant ion; ESI-HRMS(+) m/z: Calculated: 991.9953 (M+2H). Found: 991.9926 (M+2H).

Preparation of INT-1300W

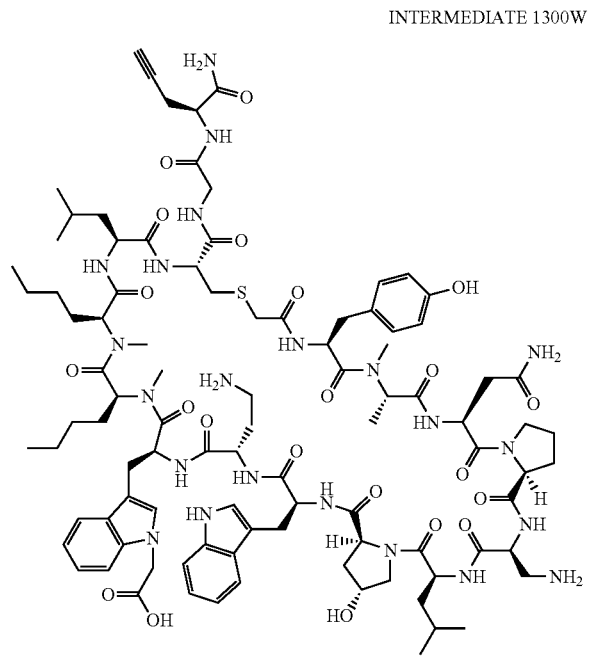 [SMILES: C#CC[C@H](NC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(N)=O]

INTERMEDIATE 1300W

The following peptide was synthesized on a 0.2 mmol scale according to the procedures above. The underlined steps employed the double-coupling procedure, and italicized residues were coupled with a 30 min single coupling. ClAc-<u>Tyr</u>-[N-Me]Ala-<u>Asn</u>-Pro-Dap-<u>Leu</u>-Hyp-Trp-Dab-[(S)-2-amino-3-(1-(carboxymethyl)-1H-indol-3-yl)propanoic acid]-<u>[N-Me]Nle</u>-[N-Me]Nle-Leu-Cys-Gly-[(S)-propargylglycine]. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 58.8 mg, and its estimated purity by LCMS analysis was 97%. Analysis condition A: Retention time=1.55 min; ESI-MS(+) m/z 991.9 (M+2H), most abundant ion; Analysis condition B: Retention time=3.11 min; ESI-MS(+) m/z 991.8 (M+2H), most abundant ion.

Preparation of INT-1300X

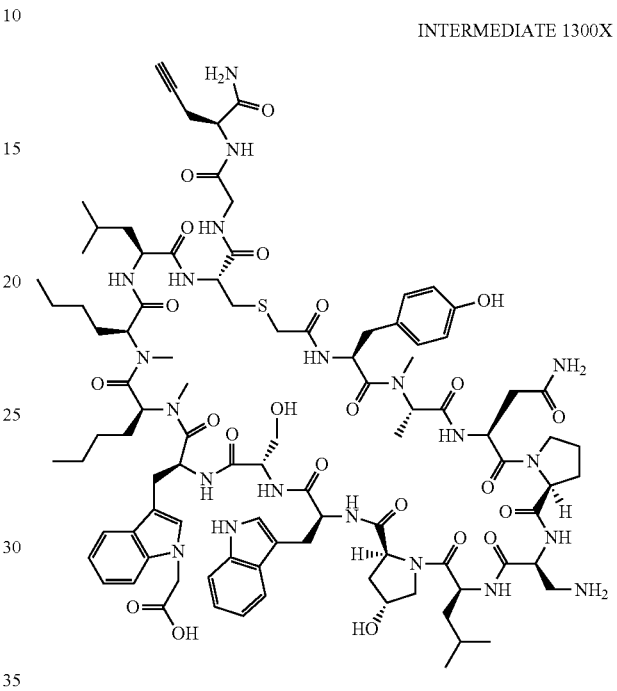

INTERMEDIATE 1300X

The following peptide was synthesized on a 0.2 mmol scale according to the procedures above. The underlined steps employed the double-coupling procedure, and italicized residues were coupled with a 30 min single coupling. ClAc-<u>Tyr</u>-[N-Me]Ala-<u>Asn</u>-Pro-Dap-<u>Leu</u>-Hyp-Trp-Ser-[(S)-2-amino-3-(1-(carboxymethyl)-1H-indol-3-yl)propanoic acid]-<u>[N-Me]Nle</u>-[N-Me]Nle-Leu-Cys-Gly-[(S)-propargylglycine]; After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 39.9 mg, and its estimated purity by LCMS analysis was 99%. Analysis condition A: Retention time=1.51 min; ESI-MS(+) m/z 985.2 (M+2H), most abundant ion.

Analysis condition B: Retention time=2.62 min; ESI-MS(+) m/z 985.4 (M+2H), most abundant ion ESI-HRMS(+) m/z: Calculated: 984.9875 (M+2H).

Found: 984.9877 (M+2H).

715
Preparation of INT-1300Y

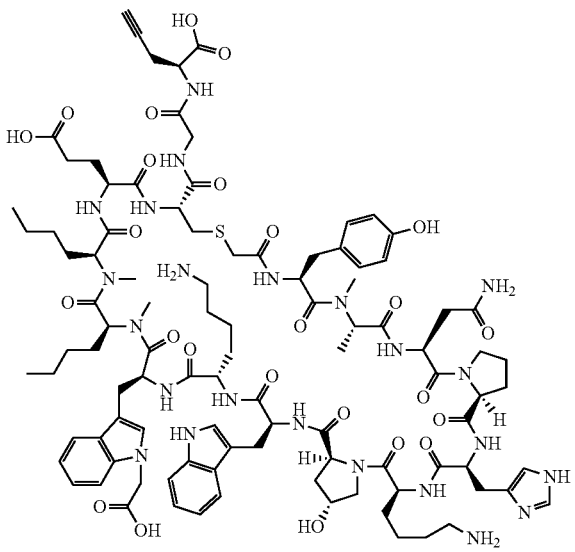

INTERMEDIATE 1300Y

The following peptide was synthesized on a 0.4 mmol scale according to the procedures above. The underlined steps employed the double-coupling procedure, and italicized residues were coupled with a 30 min single coupling. ClAc-Tyr-[N-Me]Ala-Asp-Pro-His-Lys-Hyp-Trp-Lys-[(S)-2-amino-3-(1-(carboxymethyl)-1H-indol-3-yl)propanoic acid]-[N-Me]Nle-[N-Me]Nle-Glu-Cys-Gly-[(S)-propargylglycine]; where the (S) propargylglycine was incorporated onto 2-chlorotrityl resin. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 56.8 mg, and its estimated purity by LCMS analysis was 100%. Analysis condition A: Retention time=1.06 min; ESI-MS(+) m/z 1047.8 (M+2H), most abundant ion; Analy-

716 sis condition B: Retention time=2.19 min; ESI-MS(+) m/z 1048.0 (M+2H), most abundant ion; ESI-HRMS(+) m/z:

Calculated: 1047.4931 (M+2H). Found: 1047.4899 (M+2H).

Preparation of INT-130AA

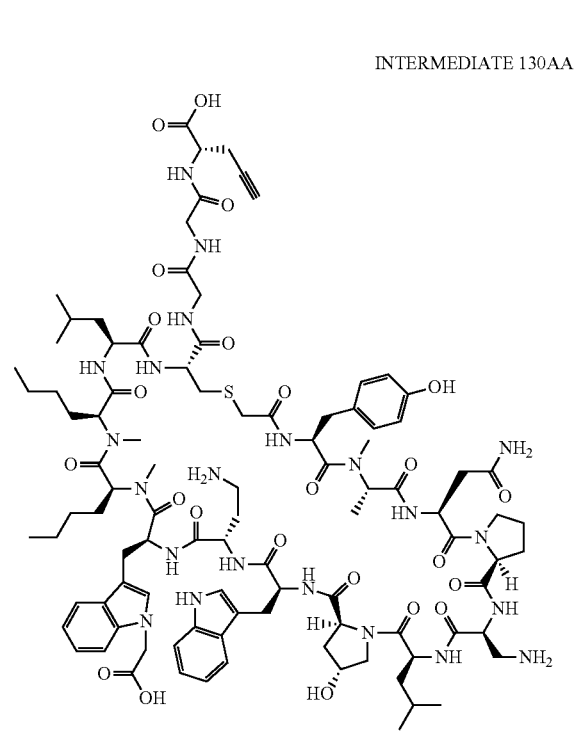 [SMILES: C#CC[C@H](NC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)O]

INTERMEDIATE 130AA

The following peptide was synthesized on a 0.8 mmol scale according to the procedures above. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Gly-[(S)-propargylglycine]; where the (S) propargylglycine was incorporated onto 2-chlorotrityl resin. After deprotection and cyclization according to the procedures above, the compound was purified as follows: The crude material was purified via preparative LC/MS with the following conditions: Column: CSH C18, 30×150 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 7-minute hold at 100% B; Flow: 50 mL/min. The sample was divided into 6 injections at a concentration of 130 umol per injection. Fractions containing the desired product were combined and dried via centrifugal evaporation. The yield of the product was 102.7 mg, and its estimated purity by LCMS analysis was 99%. Analysis condition A: Retention time=1.69 min; ESI-MS(+) m/z 1021.1 (M+2H), most abundant ion; Analysis condition G: Retention time=1.56 min; ESI-MS(+) m/z 1021.3 (M+2H), most abundant ion; ESI-HRMS(+) m/z: Calculated: 1020.5060 (M+2H). Found: 1020.5045 (M+2H).

Preparation of INT-130AB

INTERMEDIATE 130AB

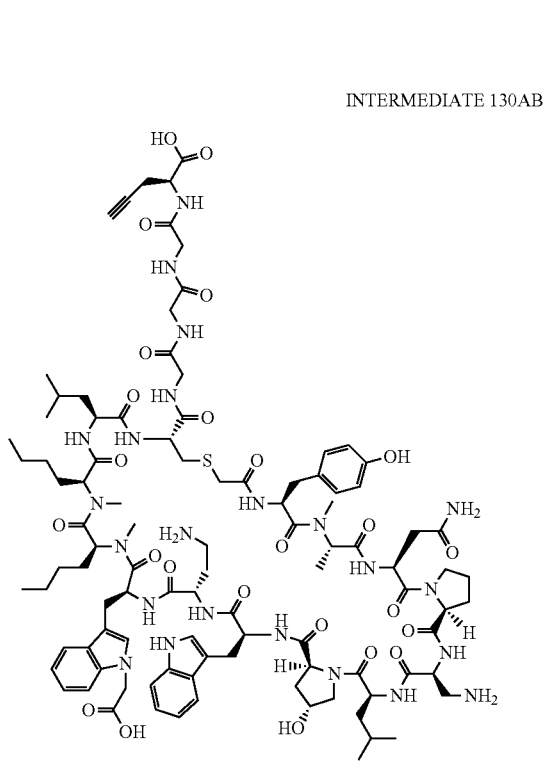 [SMILES: C#CC[C@H](NC(=O)CNC(=O)CNC(=O)CNC(=O)[C@@H]1CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N(C)[C@@H](CCCC)C(=O)N(C)[C@@H](CCCC)C(=O)N[C@@H](CC(C)C)C(=O)N1)C(=O)O]

The following peptide was synthesized on a 0.8 mmol scale according to the procedures above. The underlined steps employed the double-coupling procedure, and italicized residues were coupled with a 30 min single coupling. ClAc-Tyr-[N-Me]Ala-Asn-Pro-Dap-Leu-Hyp-Trp-Dab-(S)-2-amino-3-(1-(carboxymethyl)-1H-indol-3-yl)propanoic acid-[N-Me]Nle-[N-Me]Nle-Leu-Cys-Gly-Gly-Gly-[(S)-propargylglycine]; where the (S) propargylglycine was incorporated onto 2-chlorotrityl resin. After deprotection and cyclization according to the procedures above, the compound was purified as follows: The crude material was purified via preparative LC/MS with the following conditions: Column: Waters CSH C18, 30×150 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The yield of the product was 132.1 mg, and its estimated purity by LCMS analysis was 98%. Analysis condition A: Retention time=1.47 min; Analysis condition B: Retention time=1.51 min; ESI-MS(+) m/z 1050.3 (M+2H), most abundant ion; ESI-HRMS(+) m/z: Calculated: 1049.0168 (M+2H). Found: 1049.0156 (M+2H).

Preparation of INT-130AD

INTERMEDIATE 130AD

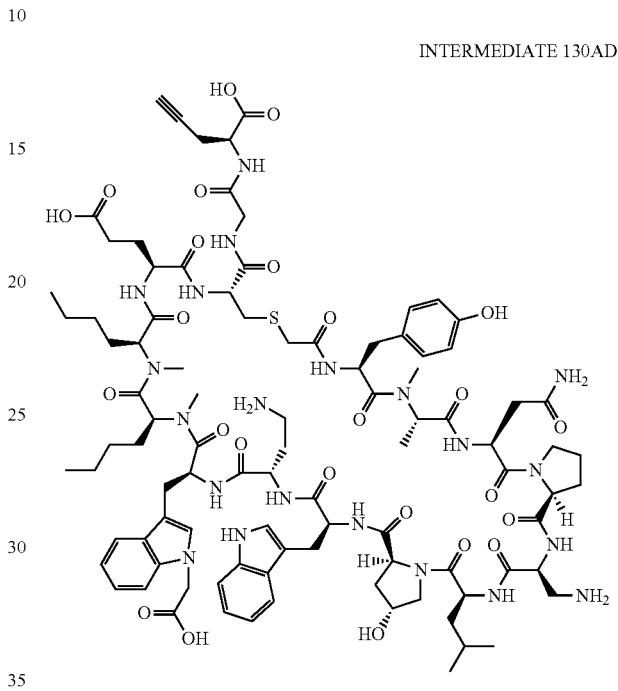

The following peptide was synthesized on a 0.4 mmol scale according to the procedures above. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Glu-Cys-Gly-[Pra]; where the propargylglycine was incorporated onto 2-chlorotrityl resin. After deprotection and cyclization according to the procedures above, the compound was purified as follows: The crude material was purified via preparative LC/MS with the following conditions: Column: Waters CSH C18, 30×150 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 50 mL/min. Fractions containing the desired product were combined and dried via centrifugal evaporation. The yield of the product was 46.7 mg, and its estimated purity by LCMS analysis was 97%. Analysis condition A: Retention time=1.31 min; ESI-MS(+) m/z 1001.3 (M+2H), most abundant ion; Analysis condition G: Retention time=2.19 min; ESI-MS(+) m/z 1000.2 (M+2H); ESI-HRMS(+) m/z: Calculated: 999.9746 (M+2H).

Found: 999.9723 (M+2H).

Preparation of INT-130AE

Preparation of INT-130AF

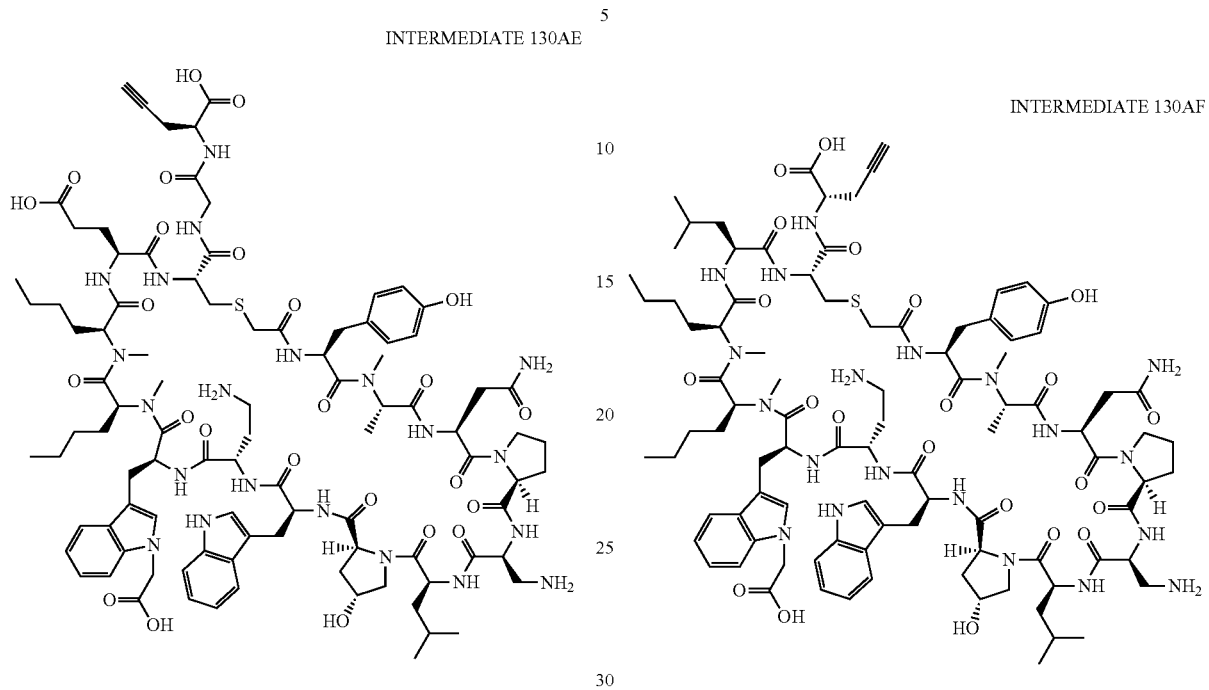

INTERMEDIATE 130AE

INTERMEDIATE 130AF

The following peptide was synthesized on a 0.4 mmol scale according to the procedures above. The underlined steps employed the double-coupling procedure, and italicized residues were coupled with a 30 min single coupling. ClAc-Tyr-[N-Me]Ala-Asp-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Glu-Cys-Gly-[Pra]; where the propargylglycine was incorporated onto 2-chlorotrityl resin. After deprotection and cyclization according to the procedures above, the compound was purified as follows: The crude material was purified via preparative LC/MS with the following conditions: Column: Waters CSH C18, 30×150 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 50 mL/min. Fractions containing the desired product were combined and dried via centrifugal evaporation. The yield of the product was 51.0 mg, and its estimated purity by LCMS analysis was 96%. Analysis condition A: Retention time=1.23 min; ESI-MS(+) m/z 1001.2 (M+2H), most abundant ion. Analysis condition G: Retention time=1.27 min; ESI-MS(+) m/z 1000.9 (M+2H); ESI-HRMS(+) m/z: Calculated: 1000.4666 (M+2H).

Found: 1000.4646 (M+2H).

The following peptide was synthesized on a 0.8 mmol scale according to the procedures above. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-[Pra]; where the propargylglycine was incorporated onto 2-chlorotrityl resin. After deprotection and cyclization according to the procedures above, the compound was purified as follows: The crude material was purified via preparative HPLC with the following conditions: Column: Phenomenex Gemini NX-C18, 50×250 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: 10-50% B over 30 minutes, then a 5-minute hold at 100% B; Flow: 125 mL/min. Fractions containing the desired product were combined and dried via centrifugal evaporation. The yield of the product was 152.1 mg, and its estimated purity by LCMS analysis was 100%. Analysis condition A: Retention time=1.56 min; ESI-MS(+) m/z 964.1 (M+2H); Analysis condition G: Retention time=1.39 min; ESI-MS(+) m/z 965.2 (M+2H), most abundant ion; ESI-HRMS(+) m/z: Calculated: 963.4846 (M+2H).

Found: 963.4825 (M+2H).

721
Preparation of INT-130AG

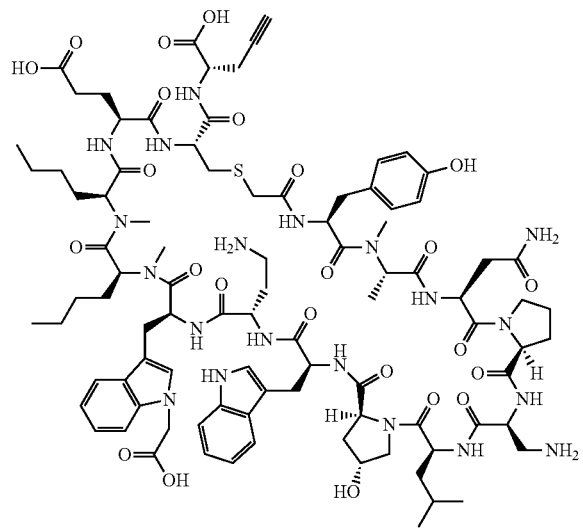

INTERMEDIATE 130AG

The following peptide was synthesized on a 0.8 mmol scale according to the procedures above. The underlined steps employed the double-coupling procedure, and italicized residues were coupled with a 30 min single coupling. ClAc-<u>Tyr</u>-[N-Me]Ala-<u>Asn</u>-Pro-Dap-<u>Leu</u>-Hyp-Trp-Dab-[(S)-2-amino-3-(1-(carboxymethyl)-1H-indol-3-yl)propanoic acid]-<u>[N-Me]Nle</u>-[N-Me]Nle-Glu-Cys-[Pra]; where the propargylglycine was incorporated onto 2-chlorotrityl resin. After deprotection and cyclization according to the procedures above, the compound was purified as follows: The crude material was purified via preparative LC/MS with the following conditions: Column: Phenomenex Gemini NX-C18, 50×250 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: 5-45% B over 30 minutes, then a 5-minute hold at 100% B; Flow: 125 mL/min. Fractions containing the desired product were combined and dried via centrifugal evaporation. The yield of the product was 154.1 mg, and its estimated purity by LCMS analysis was 100%. Analysis condition A: Retention time=1.28 min Analysis condition G: Retention time=1.25 min; ESI-HRMS(+) m/z:

Calculated: 971.4638 (M+2H). Found: 971.4620 (M+2H).

722
Preparation of INT-130AH

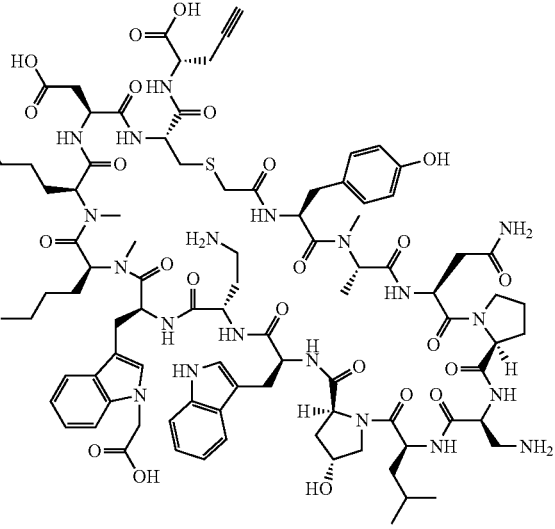

INTERMEDIATE 130AH

The following peptide was synthesized on a 0.8 mmol scale according to the procedures above. The underlined steps employed the double-coupling procedure, and italicized residues were coupled with a 30 min single coupling. ClAc-<u>Tyr</u>-[N-Me]Ala-<u>Asn</u>-Pro-Dap-<u>Leu</u>-Hyp-Trp-Dab-[(S)-2-amino-3-(1-(carboxymethyl)-1H-indol-3-yl)propanoic acid]-<u>[N-Me]Nle</u>-[N-Me]Nle-Asp-Cys-[Pra]; where the propargylglycine was incorporated onto 2-chlorotrityl resin. After deprotection and cyclization according to the procedures above, the compound was purified as follows: The crude material was purified via preparative HPLC with the following conditions: Column: Phenomenex Gemini NX-C18, 50×250 mm, 5-μm particles; Mobile Phase A: 5:95 acetonitrile:water with 0.05 trifluoroacetic acid; Mobile Phase B: 95:5 acetonitrile:water with 0.05% trifluoroacetic acid; Gradient: 5-45% B over 30 minutes, then a 5-minute hold at 100% B; Flow: 125 mL/min. Fractions containing the desired product were combined and dried via centrifugal evaporation. The yield of the product was 147.7 mg, and its estimated purity by LCMS analysis was 100%. Analysis condition A: Retention time=1.29 min; ESI-MS(+) m/z 965.3 (M+2H); Analysis condition G: Retention time=1.24 min; ESI-MS(+) m/z 964.9 (M+2H); ESI-HRMS(+) m/z: Calculated: 964.4560 (M+2H). Found: 964.4535 (M+2H).

Preparation of INT-130AI

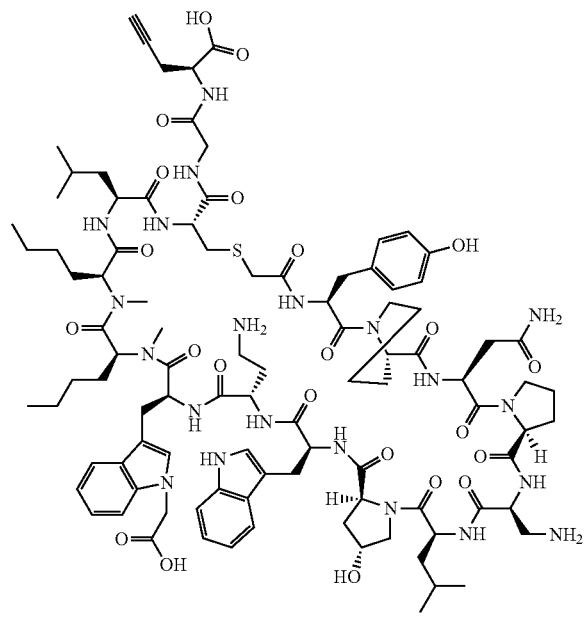

Intermediate 130AI

The following peptide was synthesized on a 0.1 mmol scale according to the procedures above. The underlined steps employed the double-coupling procedure, whereas the italicized coupling was a single, 30 min coupling. ClAc-Tyr-hPro-Asn-Pro-Dap-Leu-Hyp-Trp-Dab-[(S)-2-amino-3-(1-(carboxymethyl)-1H-indol-3-yl)propanoic acid]-mNle-mNle-Leu-Cys-Gly-[(S)-propargylglycine]. After deprotection and cyclization according to the procedures above, the compound was purified as follows: The crude material was purified via preparative LC/MS with the following conditions: Column: Phenomenex Gemini NX-C18, 50×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 100 mL/min. Fractions containing the desired product were combined and dried via centrifugal evaporation. The yield of the product was 158.7 mg, and its estimated purity by LCMS analysis was 98%. Analysis condition A: Retention time=1.556 min; ESI-MS(+) m/z 1005.1 (M+2H), most abundant ion; Analysis condition G: Retention time=1.382 min; ESI-MS(+) m/z 1005.3 (M+2H), most abundant ion; ESI-HRMS(+) m/z: Calculated: 1005.0031 (M+2H). Found: 1005.0015 (M+2H).

Preparation of INT-130AJ

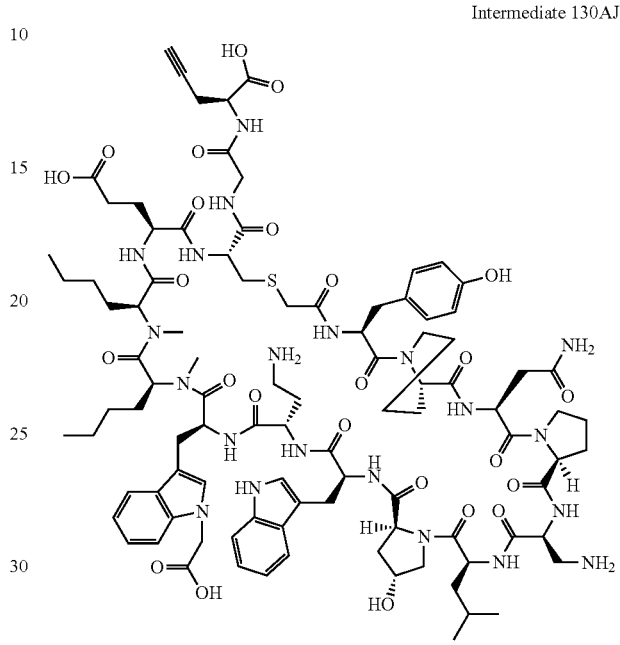

Intermediate 130AJ

The following peptide was synthesized on a 0.1 mmol scale according to the procedures above. The underlined steps employed the double-coupling procedure. ClAc-Tyr-hPro-Asn-Pro-Dap-Leu-Hyp-Trp-Dab-[(S)-2-amino-3-(1-(carboxymethyl)-1H-indol-3-yl)propanoic acid]-mNle-mNle-Glu-Cys-Gly-[(S)-propargyl glycine]. After deprotection and cyclization according to the procedures above, the compound was purified as follows: The crude material was purified via preparative LC/MS with the following conditions: Column: Phenomenex Gemini NX-C18, 50×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 100 mL/min. Fractions containing the desired product were combined and dried via centrifugal evaporation. The yield of the product was 107.7 mg, and its estimated purity by LCMS analysis was 100%. Analysis condition A: Retention time=1.281 min; ESI-MS(+) m/z 1013.1 (M+2H), most abundant ion; Analysis condition G: Retention time=1.282 min; ESI-MS(+) m/z 1013.2 (M+2H), most abundant ion; ESI-HRMS(+) m/z: Calculated: 1012.9824 (M+2H). Found: 1012.9797 (M+2H).

725
Preparation of INT-130AK

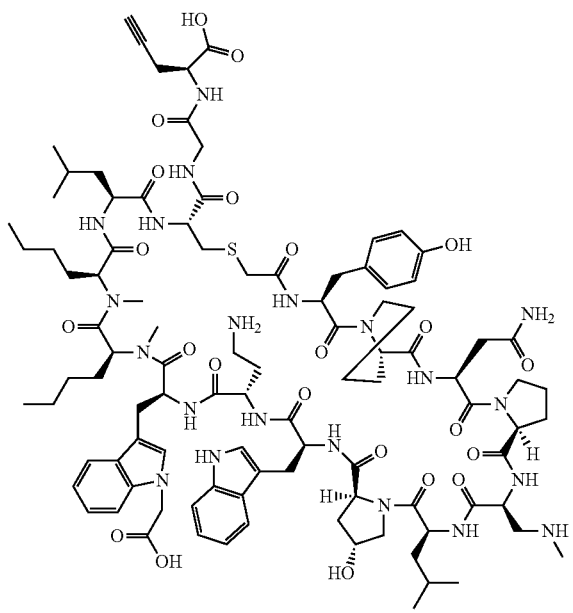

Intermediate 130AK

726
Preparation of INT-130AL

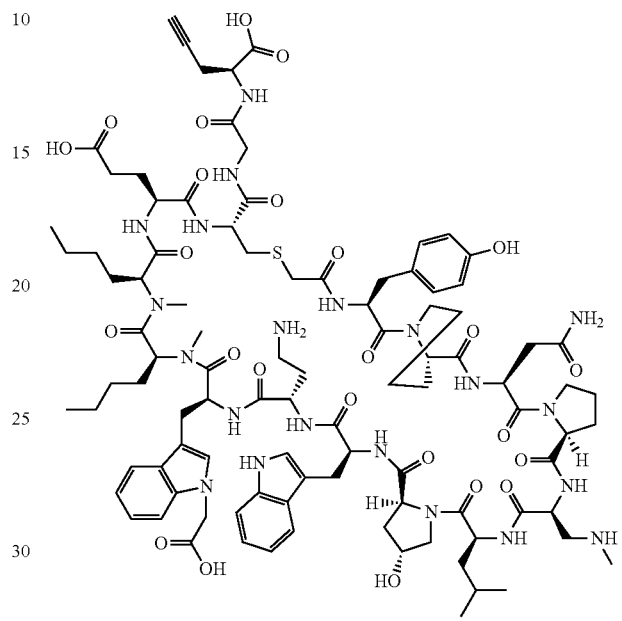

Intermediate 130AL

The following peptide was synthesized on a 0.1 mmol scale according to the procedures above. The underlined steps employed the double-coupling procedure. ClAc-Try-hPro-Asn-Pro-DapMe-Leu-Hyp-Trp-Dab-[(S)-2-amino-3-(1-(carboxymethyl)-1H-indol-3-yl)propanoic acid]-mNle-mNle-Leu-Cys-Gly-[(S)-propargylglycine]. After deprotection and cyclization according to the procedures above, the compound was purified as follows: The crude material was purified via preparative Prep HPLC with the following conditions: Column: Phenomenex Gemini NX-C18, 50×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 125 mL/min. Fractions containing the desired product were combined and dried via centrifugal evaporation. The yield of the product was 241.9 mg, and its estimated purity by LCMS analysis was 98%. Analysis condition A: Retention time=1.555 min; ESI-MS(+) m/z 1012.1 (M+2H), most abundant ion; Analysis condition G: Retention time=1.396 min; ESI-MS(+) m/z 1012.2 (M+2H), most abundant ion; ESI-HRMS(+) m/z: Calculated: 1012.0109 (M+2H). Found: 1012.0089 (M+2H).

The following peptide was synthesized on a 0.1 mmol scale according to the procedures above. The underlined steps employed the double-coupling procedure. ClAc-Tyr-hPro-Asn-Pro-DapMe-Leu-Hyp-Trp-Dab-[(S)-2-amino-3-(1-(carboxymethyl)-1H-indol-3-yl)propanoic acid]-mNle-mNle-Glu-Cys-Gly-[(S)-propargylglycine]. After deprotection and cyclization according to the procedures above, the compound was purified as follows: The crude material was purified via preparative LC/MS with the following conditions: Column: Phenomenex Gemini NX-C18, 50×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 7-minute hold at 100% B; Flow: 100 mL/min. Fractions containing the desired product were combined and dried via centrifugal evaporation. The yield of the product was 218.0 mg, and its estimated purity by LCMS analysis was 100%. Analysis condition A: Retention time=1.316 min; ESI-MS(+) m/z 1020.2 (M+2H), most abundant ion; Analysis condition G: Retention time=1.294 min; ESI-MS(+) m/z 1020.2 (M+2H), most abundant ion; ESI-HRMS(+) m/z: Calculated: 1019.9902 (M+2H). Found: 1019.9881 (M+2H).

Preparation of Example 13051

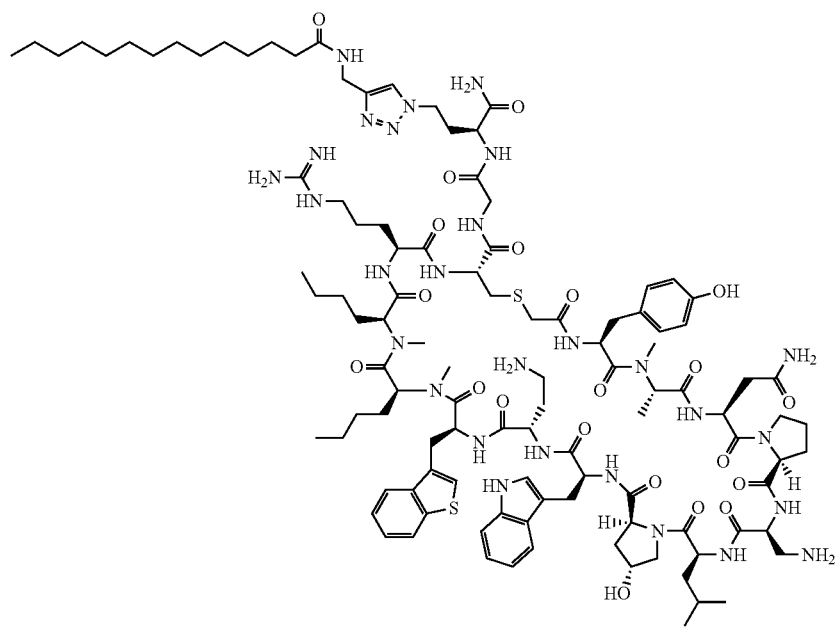

Example 13051

Intermediate 1300B (10 mg, 4.99 □mol) and N-(prop-2-yn-1-yl)tetradecanamide (3.98 mg, 0.015 mmol) were reacted as in the general triazole formation procedure to afford crude product. The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-µm particles; Mobile Phase A: 5:95 methanol: water with 10-mM ammonium acetate; Mobile Phase B: 95:5 methanol: water with 10-mM ammonium acetate; Gradient: 60-100% B over 20 minutes, then a 10-minute hold at 100% B; Flow: 20 mL/min. Fractions containing the desired product were combined and dried via centrifugal evaporation. The yield of the product was 2.5 mg, and its estimated purity by LCMS analysis was 100%. Analysis condition A: Retention time=2.32 min; ESI-MS(+) m/z 1134.9 (M+2H); Analysis condition B: Retention time=3.35 min; ESI-MS(+) m/z 1135.1 (M+2H), most abundant ion; ESI-HRMS(+) m/z: Calculated: 1134.1026 (M+2H).

Found: 1134.1028 (M+2H).

Preparation of Example 13052

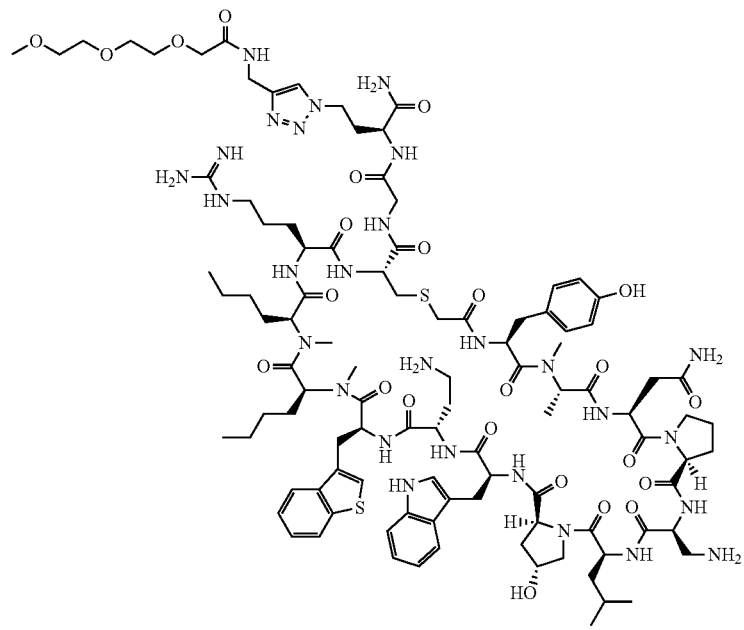

Example 13052

Intermediate 1300B (8.5 mg, 4.25 μmol) and 2-(2-(2-methoxyethoxy)ethoxy)-N-(prop-2-yn-1-yl)acetamide (2.74 mg, 0.013 mmol) were reacted as in the general triazole formation procedure to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 100%. Analysis condition A: Retention time=1.56 min; ESI-MS(+) m/z 1109.9 (M+2H); Analysis condition B: Retention time=2.81 min; ESI-MS(+) m/z 1109.8 (M+2H), most abundant ion.

Preparation of Example 13121

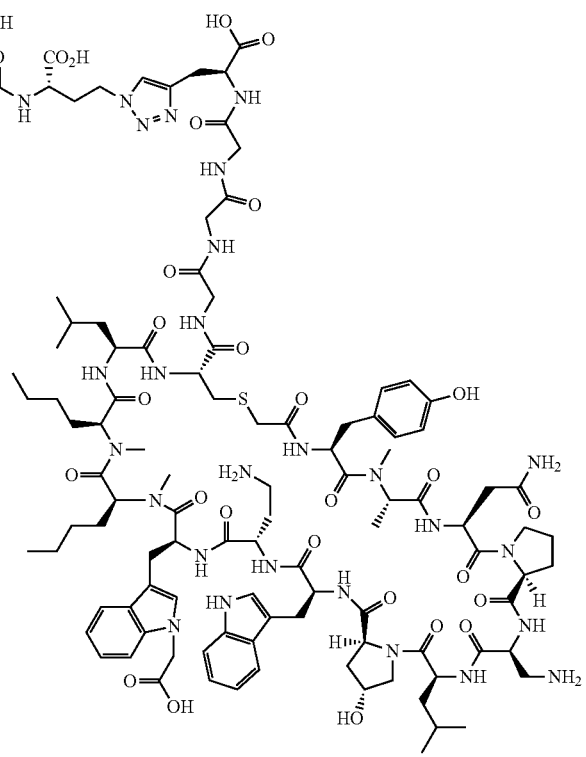

Example 13121

Intermediate 130AB (26.1 mg, 12 μmol) and (S)-4-azido-2-palmitamidobutanoic acid (13.7 mg, 0.031 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:CH₃CN w/0.1% TFA; B is 10:90 water:CH₃CN w/0.1% TFA)). The yield of the product was 11.7 mg, and its estimated purity by LCMS analysis was 99%. Analysis condition H: Retention time=10.92 min Analysis condition I: Retention time=9.94 min; ESI-HRMS(+) m/z:

Calculated: 1269.1667 (M+2H). Found: 1269.1648 (M+2H).

Preparation of Example 13122

Example 13122

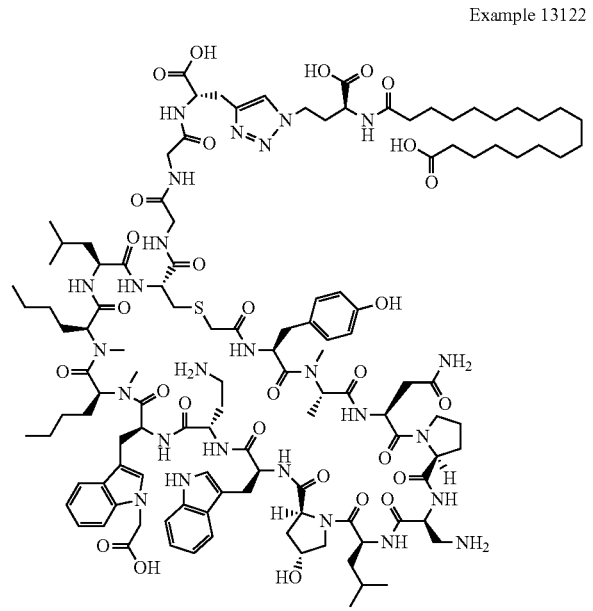 [SMILES: CCCC[C@H]1C(=O)N(C)[C@@H](CCCC)C(=O)N[C@@H](CC(C)C)C(=O)N[C@H](C(=O)NCC(=O)NCC(=O)N[C@@H](Cc2cn(CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Intermediate 130AA (25.5 mg, 13 μmol) and (S)-4-azido-2-palmitamidobutanoic acid (13.8 mg, 0.031 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:CH₃CN w/0.1% TFA; B is 10:90 water:CH₃CN w/0.1% TFA)). The yield of the product was 8.1 mg, and its estimated purity by LCMS analysis was 94%. Analysis condition I: Retention time=10.06 min Analysis condition J: Retention time=8.63 min; ESI-HRMS(+) m/z:

Calculated: 1240.6560 (M+2H). Found: 1240.6546 (M+2H).

Preparation of Example 13123

Example 13123

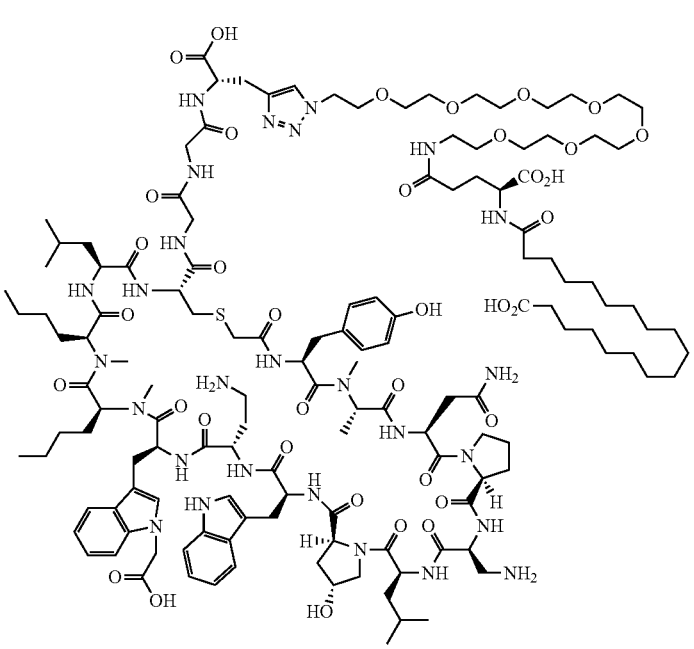

Intermediate 130AA (41.3 mg, 20 μmol) and (S)-1-azido-28-carboxy-25,30-dioxo-3,6,9,12,15,18,21-heptaoxa-24,29-diazaheptatetracontan-47-oic acid (24.9 mg, 0.030 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:CH$_3$CN w/0.1% TFA; B is 10:90 water:CH$_3$CN w/0.1% TFA)). The yield of the product was 26.2 mg, and its estimated purity by LCMS analysis was 94%. Analysis condition I: Retention time=9.54 min Analysis condition J: Retention time=8.13 min; ESI-HRMS(+) m/z:

Calculated: 1430.2663 (M+2H). Found: 1430.2656 (M+2H).

Preparation of Example 13124

Intermediate 130AB (40.7 mg, 19 μmol) and (S)-1-azido-28-carboxy-25,30-dioxo-3,6,9,12,15,18,21-heptaoxa-24,29-diazaheptatetracontan-47-oic acid (23.9 mg, 0.029 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:CH$_3$CN w/0.1% TFA; B is 10:90 water:CH$_3$CN w/0.1% TFA)). The yield of the product was 24.3 mg, and its estimated purity by LCMS analysis was 95%. Analysis condition I: Retention time=9.49 min; Analysis condition J: Retention time=8.08 min; ESI-HRMS(+) m/z:

Calculated: 1458.7770 (M+2H). Found: 1458.7743 (M+2H).

Example 13124

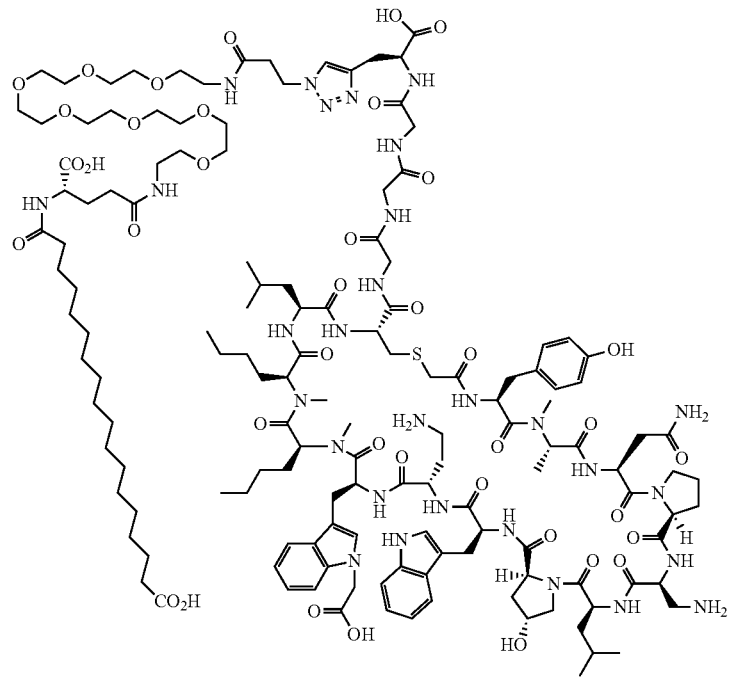

Preparation of Example 13125

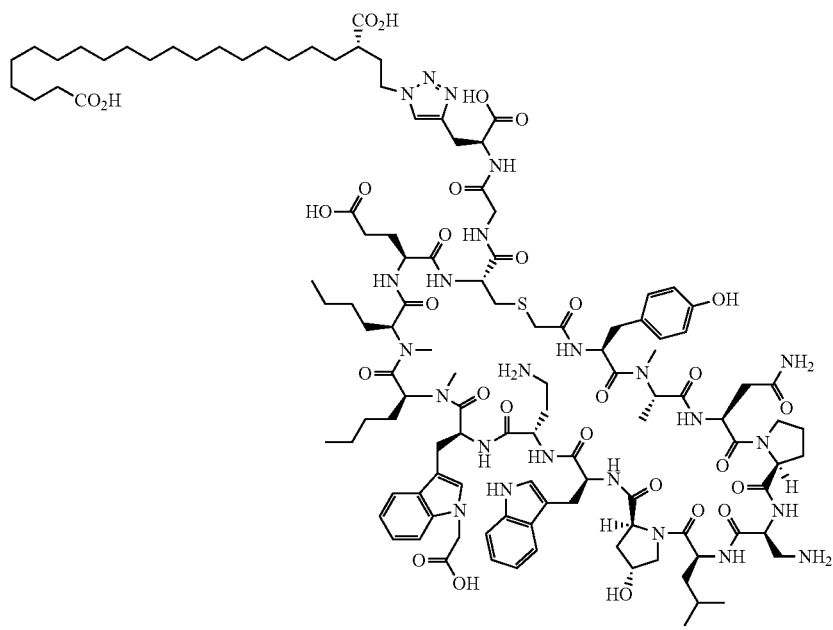

Example 13125

Intermediate 130AD (22.1 mg, 11 μmol) and (S)-4-azido-2-palmitamidobutanoic acid (6.1 mg, 0.014 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:$CH_3CN$ w/0.1% TFA; B is 10:90 water:$CH_3CN$ w/0.1% TFA)). The yield of the product was 9.5 mg, and its estimated purity by LCMS analysis was 90%. Analysis condition I: Retention time=9.24 min; Analysis condition J: Retention time=8.00 min; ESI-HRMS(+) m/z: Calculated: 1220.1245 (M+2H). Found: 1220.1208 (M+2H).

Preparation of Example 13126

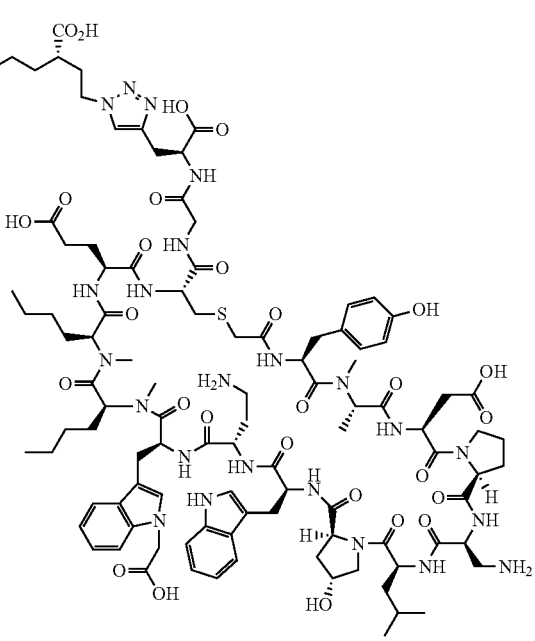

Example 13126

Intermediate 130AE (24.5 mg, 12 μmol) and (S)-4-azido-2-palmitamidobutanoic acid (6.8 mg, 0.015 mmol) were reacted as in the general triazole formation procedure to afford crude product. The reaction solution was diluted slightly in MeOH and purified by prep HPLC (2 injections): 30×100 mm HPLC Phenomenex Luna 5 μm 10 to 100% A:B over 15 min, 3 min at 100% B (A is 90:10 water:CH$_3$CN w/0.1% TFA; B is 10:90 water:CH$_3$CN w/0.1% TFA)). The yield of the product was 10.3 mg, and its estimated purity by LCMS analysis was 95%. Analysis condition I: Retention time=9.36 min Analysis condition J: Retention time=8.15 min; ESI-HRMS(+) m/z:

Calculated: 1220.6165 (M+2H). Found: 1220.6133 (M+2H).

Preparation of Example 13129

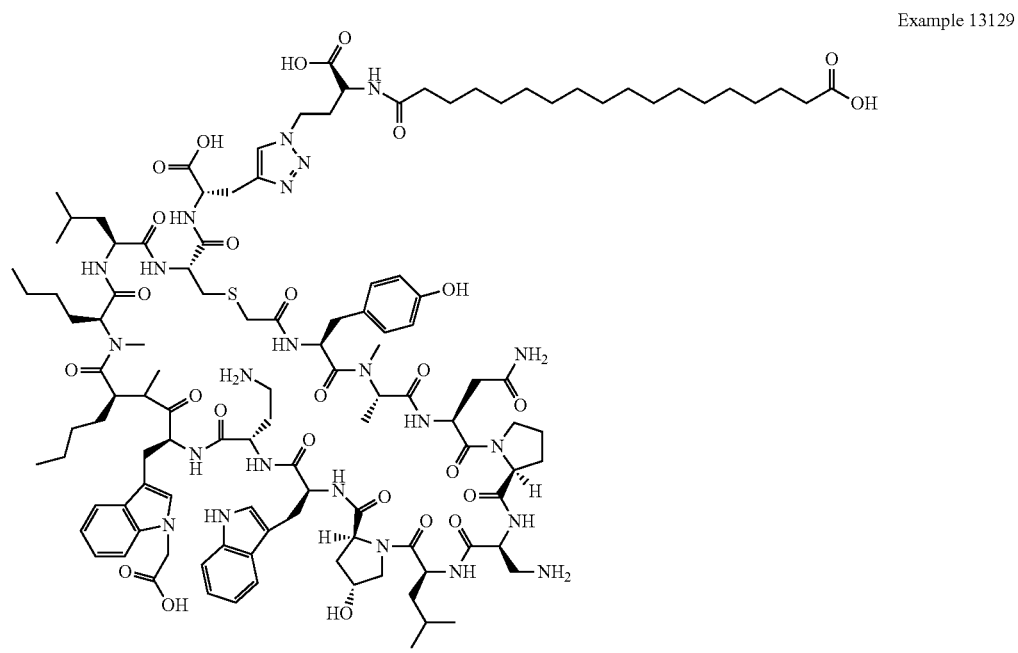

Example 13129

Intermediate 130AF (35 mg, 18.0 μmol) and (S)-18-((3-azido-1-carboxypropyl)amino)-18-oxooctadecanoic acid (10.01 mg, 0.023 mmol), were reacted as in the general triazole formation procedure above to afford crude product. The crude product was purified by Prep-HPLC (Column: Phenomenex Luna C18 30×100 mm 5 um, Solvent A=90:10 H$_2$O:ACN 0.1% TFA, Solvent B=10:90 H$_2$O:CAN 0.1% TFA. Flow rate: 40 ml/min, 10-100% B. Fractions containing the desired product were combined and dried via centrifugal evaporation. The yield of the product was 11.7 mg, and its estimated purity by LCMS analysis was 96%. Analysis condition C: Retention time=1.162 min; ESI-MS(+) m/z 1185.50 (M+2H), most abundant ion.

Preparation of Example 13130

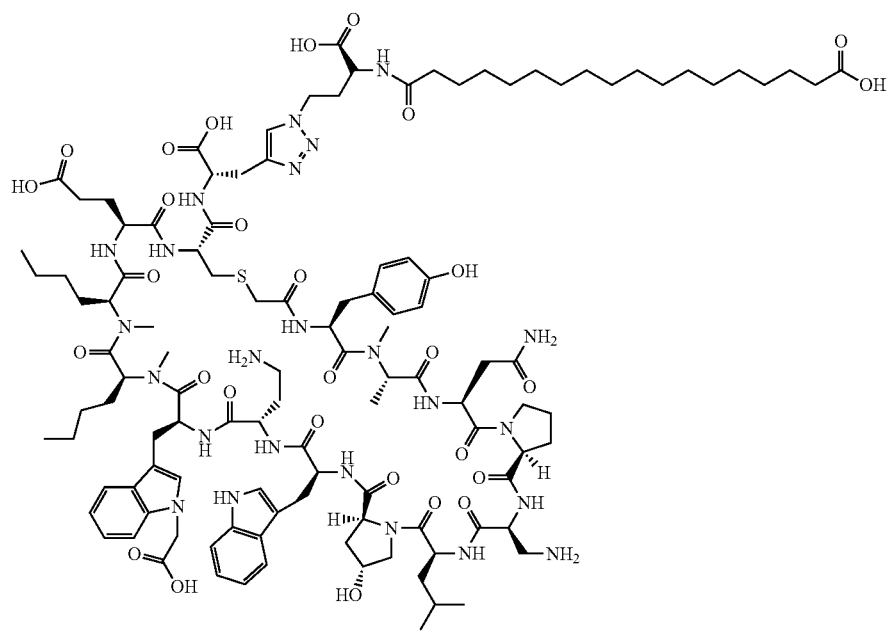

Example 13130

Intermediate 130AG (40.65 mg, 21.0 μmol) and (S)-18-((3-azido-1-carboxypropyl)amino)-18-oxooctadecanoic acid (11.53 mg, 0.026 mmol), were reacted as in the general triazole formation procedure above to afford crude product. The crude material was purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 93%. Analysis condition A: Retention time=1.541 min; ESI-MS(+) m/z 1191.5 (M+2H), most abundant ion; Analysis condition G: Retention time=1.682 min; ESI-MS(+) m/z 1192.2 (M+2H), most abundant ion; ESI-HRMS(+) m/z: Calculated: 1191.6138 (M+2H). Found: 1191.6106 (M+2H).

Preparation of Example 13131

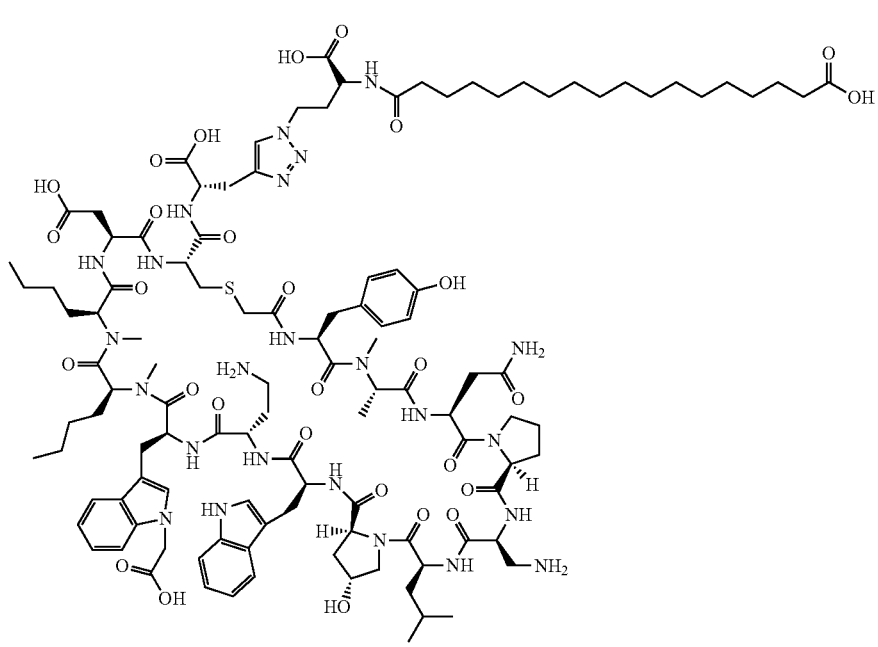

Example 13131

Intermediate 130AH (40.37 mg, 21.0 μmol) and (S)-18-((3-azido-1-carboxypropyl)amino)-18-oxooctadecanoic acid (11.53 mg, 0.026 mmol), were reacted as in the general triazole formation procedure above to afford crude product. The crude material was purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 95%. Analysis condition A: Retention time=1.815 min; Analysis condition K: Retention time=1.684 min; ESI-MS(+) m/z 1185.2 (M+2H), most abundant ion; ESI-HRMS(+) m/z:

Calculated: 1184.6059 (M+2H). Found: 1184.6031 (M+2H).

Intermediate 130AI (46.4 mg, 23.0 μmol) and (S)-18-((3-azido-1-carboxypropyl)amino)-18-oxooctadecanoic acid (11.19 mg, 0.025 mmol), were reacted as in the general triazole formation procedure above to afford crude product. The crude material was purified via preparative LC/MS with the following conditions: Column: Waters CSH C18, 19×mm, 5-μm particles; Mobile Phase A: 5:95 acetonitrile: water with 0.1% trifluoroacetic acid; Mobile Phase B: 95:5 acetonitrile:water with 0.1% trifluoroacetic acid; Gradient: 30-70% B over 30 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 100%. Analysis condition G: Retention time=1.888 min; ESI-MS(+) m z 817.9 (M+3H), most abundant ion; ESI-HRMS(+) m z: Calculated: 1225.1531 (M+2H).

Found: 1225.1521 (M+2H).

Preparation of Example 13132

Example 13132

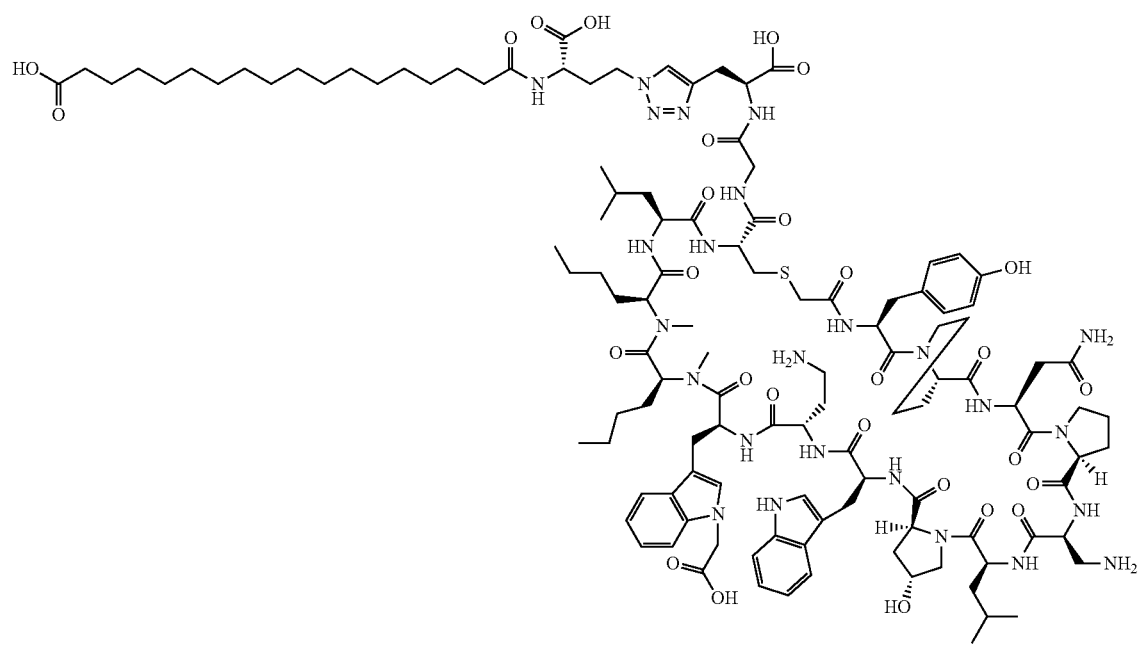

Preparation of Example 13133

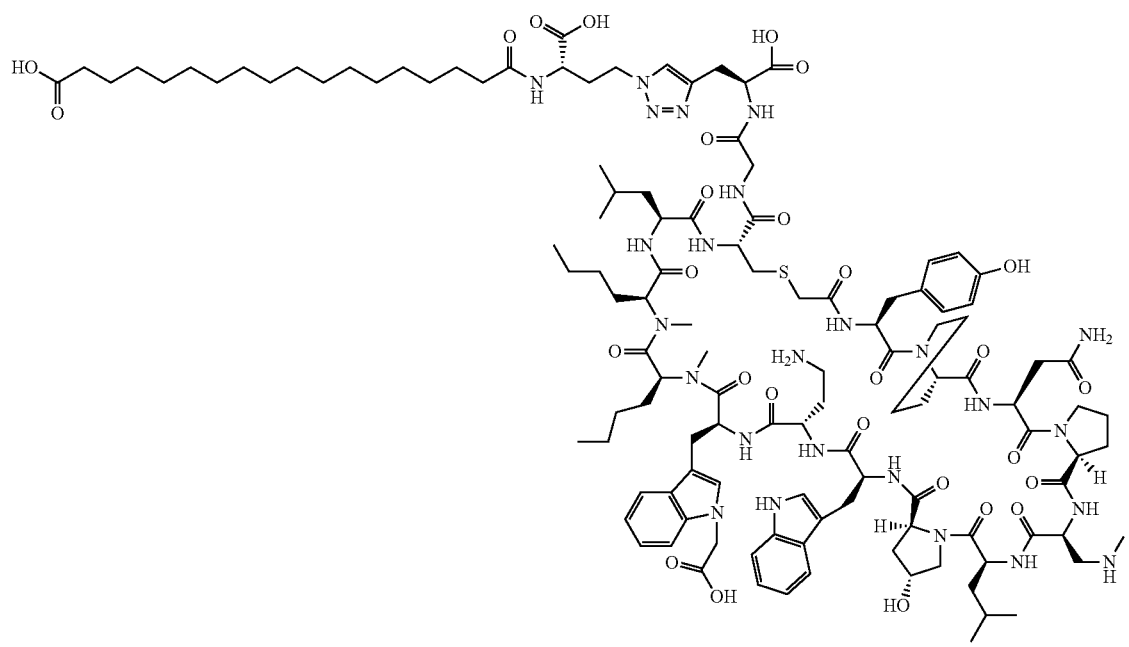

Example 13133

Intermediate 130AK (56.5 mg, 28.0 µmol) and (S)-18-((3-azido-1-carboxypropyl)amino)-18-oxooctadecanoic acid (13.53 mg, 0.031 mmol), were reacted as in the general triazole formation procedure above to afford crude product. The crude material was purified via preparative LC/MS with the following conditions: Column: Waters CSH C18, 19×mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 30 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 99%. Analysis condition A: Retention time=1.788 min; ESI-MS(+) m/z 1232.2 (M+2H), most abundant ion; Analysis condition G: Retention time=1.843 min; ESI-MS(+) m/z 1233.1 (M+2H), most abundant ion; ESI-HRMS(+) m/z: Calculated: 1232.1609 (M+2H). Found: 1232.1579 (M+2H).

Cyclization Method B:

All manipulations were performed manually unless noted. The procedure of "Cyclization Method B" describes an experiment performed on a 0.100 mmol scale, where the scale is determined by the amount resin used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in Methanol (~24 mL) containing ~3 drops of N,N-Diisopropylethylamine. The basic (pH>9) solution was then allowed to stand for 18-24 h. To the resulting solution, 1 mL DMSO was added, and the methanol portion evaporated under reduced pressure to afford a concentrated DMSO solution of the crude, cyclized product. This solution was subjected to reverse-phase HPLC purification to afford the desired cyclic peptide.

Analysis Condition 13A:

Column: X-Select CSH C18, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 0.5 mL/min; Detection: UV at 220 nm.

Analysis Condition 13B:

Column: Zorbax Bonus-RP C18, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 0.5 mL/min; Detection: UV at 220 nm.

Preparation of 1-tert-butyl 18-(perfluorophenyl)octadecanedioate

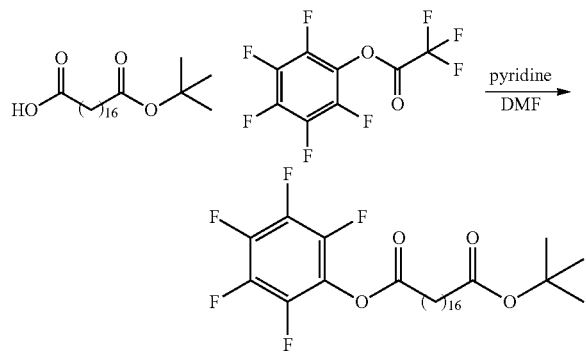

To a solution of 18-(tert-butoxy)-18-oxooctadecanoic acid (5.00 g, 13.49 mmol) in DMF (54.0 ml) was added pyridine (3.82 ml, 47.2 mmol), followed by pentafluorophenyl trifluoroacetate (5.81 ml, 33.7 mmol). A gel formed, and an additional stir bar was added to the reaction mixture. The mixture was stirred vigorously overnight. The reaction mixture was filtered (Buchner funnel/paper) to afford a white solid, which was washed with a small amount of DMF. A nitrogen-rich atmosphere was sucked through the filter cake for a few hours to provide 1-tert-butyl 18-(perfluorophenyl) octadecanedioate (6.24 g, 11.63 mmol, 86% yield).

Preparation of (S)-1-tert-butyl 5-(perfluorophenyl) 2-(18-(tert-butoxy)-18-oxooctadecanamido)pentanedioate

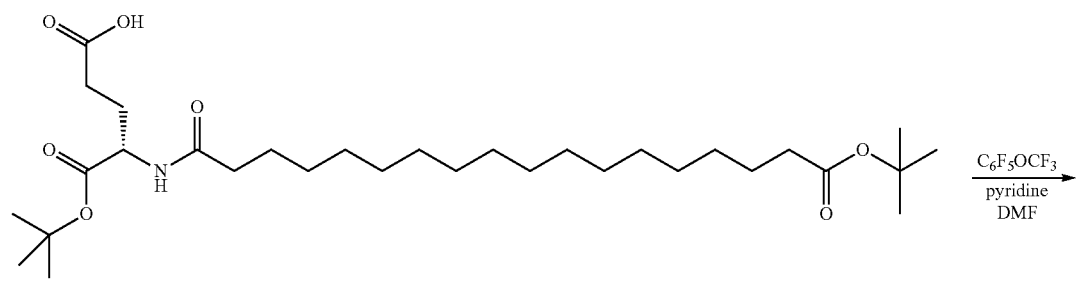

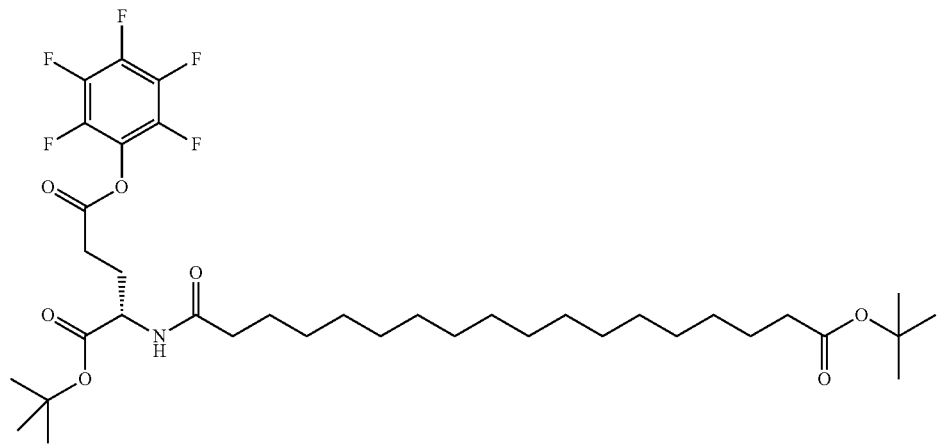

To a solution of (S)-5-(tert-butoxy)-4-(18-(tert-butoxy)-18-oxooctadecanamido)-5-oxopentanoic acid (350 mg, 0.630 mmol) in DMF (2519 μl) was added pyridine (178 μl, 2.204 mmol), followed by pentafluorophenyl trifluoroacetate (271 μl, 1.574 mmol). The vial containing the resulting solution was flushed with nitrogen, and capped overnight. The observed product was observed by LC/MS. The mixture was diluted with water and citric acid, and extracted 3 times with EtOAc. The combined organic extracts were dried over MgSO₄, filtered, and concentrated in vacuo. The residue was used as-is for further chemistry.

Preparation of (S)-5-((((9H-fluoren-9-yl)methoxy)carbonyl)amino)-2-(18-(tert-butoxy)-18-oxooctadecanamido)pentanoic acid extracted 3 times into CH₂Cl₂. The combined organic extracts were dried over MgSO₄, filtered, and concentrated in vacuo.

The bulk material was purified by PREP HPLC: (50×250 mm HPLC Sunfire C18 10 μm 0 to 100% A:B over 40 min, 10 min at 100% B (A is 90:10:0.1 water:MeOH:TFA; B is 90:10:0.1 MeOH:water:TFA)). Subsequent runs were purified at 100% B (isocratic) for 15 min. Fractions were pooled, adjusted to neutral pH with Hunig's base, and concentrated in the rotovap. The residual aqueous layer was extracted 3 times with EtOAc, filtered, and concentrated in vacuo to afford (S)-5-((((9H-fluoren-9-yl)methoxy)carbonyl)amino)-

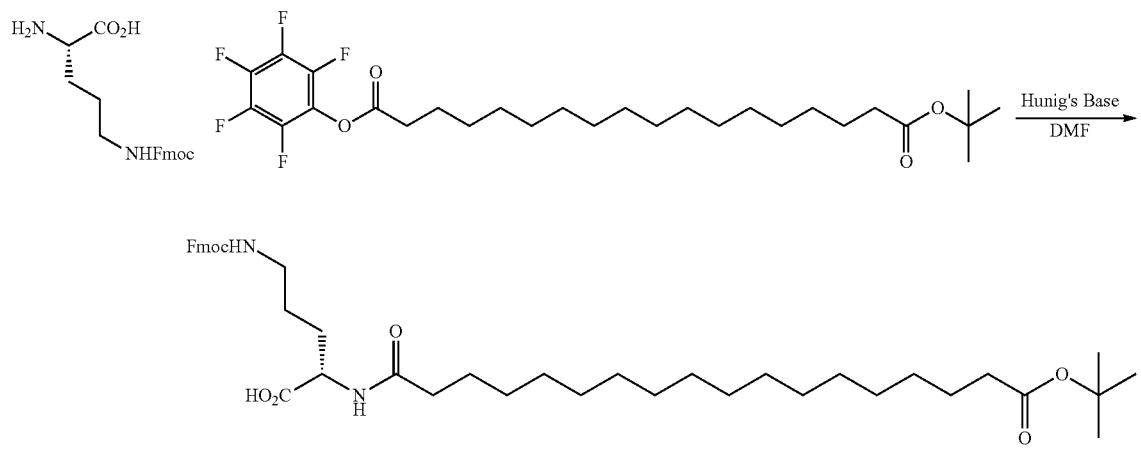

To a solution of 1-tert-butyl 18-(perfluorophenyl)octadecanedioate (1.666 g, 3.10 mmol) in DMF (21.71 ml) was added (S)-5-((((9H-fluoren-9-yl)methoxy)carbonyl)amino)-2-aminopentanoic acid (1.0 g, 2.82 mmol) and Hunig's Base (1.478 ml, 8.47 mmol). The mixture was stirred at rt. LC/MS showed the formation of the desired product. The mixture was diluted with an aqueous citric acid solution, and was 2-(18-(tert-butoxy)-18-oxooctadecanamido)pentanoic acid (1.33 g, 1.881 mmol, 66.7% yield).

Preparation of (S)-4-((((9H-fluoren-9-yl)methoxy)carbonyl)amino)-2-(18-(tert-butoxy)-18-oxooctadecanamido)butanoic acid

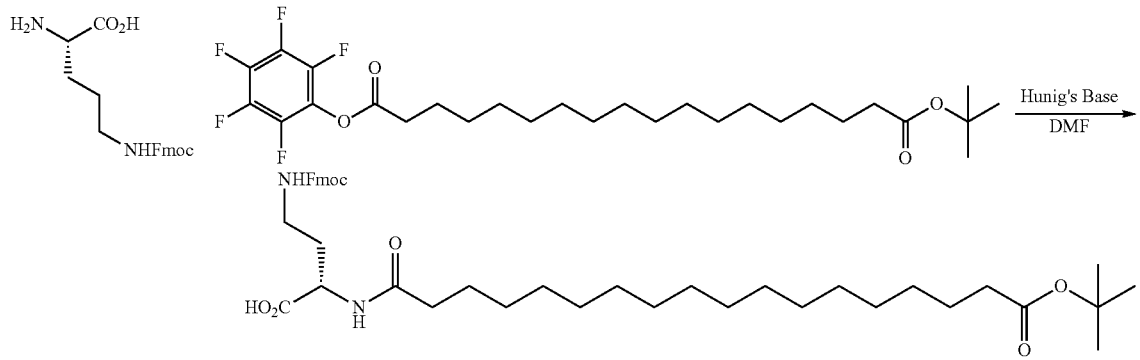

To a suspension of 1-tert-butyl 18-(perfluorophenyl)octadecanedioate (1.155 g, 2.152 mmol) in DMF (1.66E+04 µl) was added (S)-4-((((9H-fluoren-9-yl)methoxy)carbonyl)amino)-2-aminobutanoic acid (827 mg, 2.430 mmol) and Hunig's Base (1128 µl, 6.46 mmol). The mixture was stirred vigourously over the weekend. The LC/MS showed the desired product. The mixture was diluted with aqueous citric acid, and extracted 3 times into $CH_2Cl_2$. The combined organic extracts were dried over $MgSO_4$, filtered, and concentrated in vacuo. The material was taken up in a cloudy solution in MeOH. Filtration through a 0.45 um fritt was slow (several filters were used) to give a clear solution. Purified by PREP HPLC: (50×250 mm HPLC Sunfire C18 10 µm 100% B over 14 min, (A is 90:10:0.1 water:MeOH:TFA; B is 90:10:0.1 MeOH:water:TFA)). Fractions were pooled, adjusted to neutral with Hunig's base, and concentrated in the rotovap. Isolated (S)-4-((((9H-fluoren-9-yl)methoxy)carbonyl)amino)-2-(18-(tert-butoxy)-18-oxooctadecanamido)butanoic acid (778.42 mg, 1.123 mmol, 52.2% yield).

Preparation of (S)-2-(((((9H-fluoren-9-yl)methoxy)carbonyl)amino)-4-((S)-5-(tert-butoxy)-4-(18-(tert-butoxy)-18-oxooctadecanamido)-5-oxopentanamido)butanoic acid To a solution of crude(S)-1-tert-butyl 5-(perfluorophenyl) 2-(18-(tert-butoxy)-18-oxooctadecanamido)pentanedioate (455 mg, 0.63 mmol) in DMF (6300 µl) was added Hunig's Base (440 µl, 2.52 mmol), then (S)-2-((((9H-fluoren-9-yl)methoxy)carbonyl)amino)-4-aminobutanoic acid (214 mg, 0.630 mmol). The mixture was stirred at rt overnight. The mixture was diluted with citric acid and extracted 3 times into EtOAc. The combined organic extracts were washed with brine, dried over $MgSO_4$, filtered, and concentrated in vacuo. The residue was purified by PREP HPLC: (50×250 mm HPLC Sunfire C18 10 µm 10 to 100% A:B over 30 min, 5 min at 100% B (A is 90:10:0.1 water:MeOH:TFA; B is 90:10:0.1 MeOH:water:TFA)). The material eluted during the 100% B isocratic section, so the gradient was not necessary. Fractions were neutralized with Hunig's base and concentrated on the speedvac. The residue was taken up in EtOAc and washed twice with water and once with brine. The organic layer was dried over MgSO4, filtered, and concentrated in vacuo to afford (S)-2-((((9H-fluoren-9-yl)methoxy)carbonyl)amino)-4-((S)-5-(tert-butoxy)-4-(18-(tert-butoxy)-18-oxooctadecanamido)-5-oxopentanamido)butanoic acid (288 mg, 0.328 mmol, 52.1% yield).

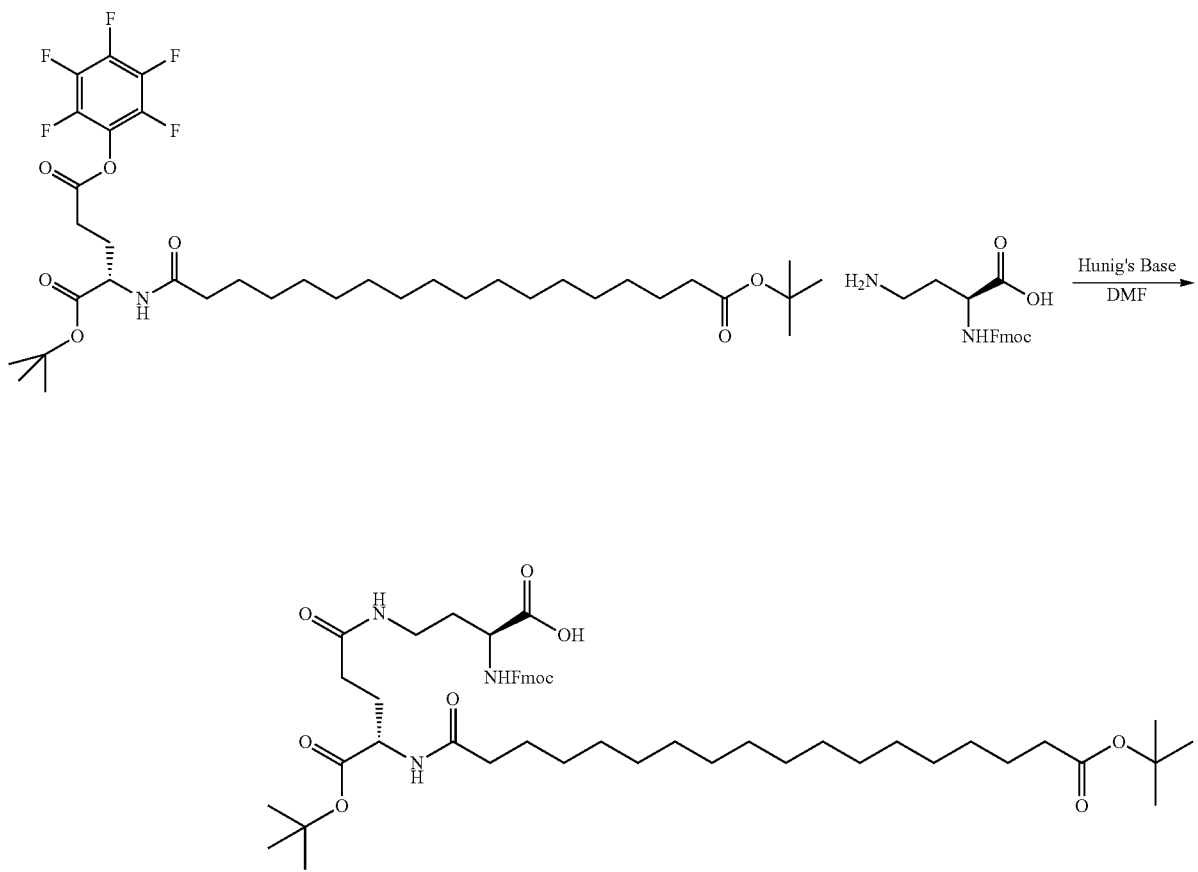

Preparation of (S)-2-((((9H-fluoren-9-yl)methoxy) carbonyl)amino)-3-((S)-5-(tert-butoxy)-4-(18-(tert-butoxy)-18-oxooctadecanamido)-5-oxopentanamido) propanoic acid trated on the rotovap to afford (S)-2-((((9H-fluoren-9-yl)methoxy)carbonyl)amino)-3-((S)-5-(tert-butoxy)-4-(18-(tert-butoxy)-18-oxooctadecanamido)-5-oxopentanamido) propanoic acid (940 mg, 1.088 mmol, 67.5% yield).

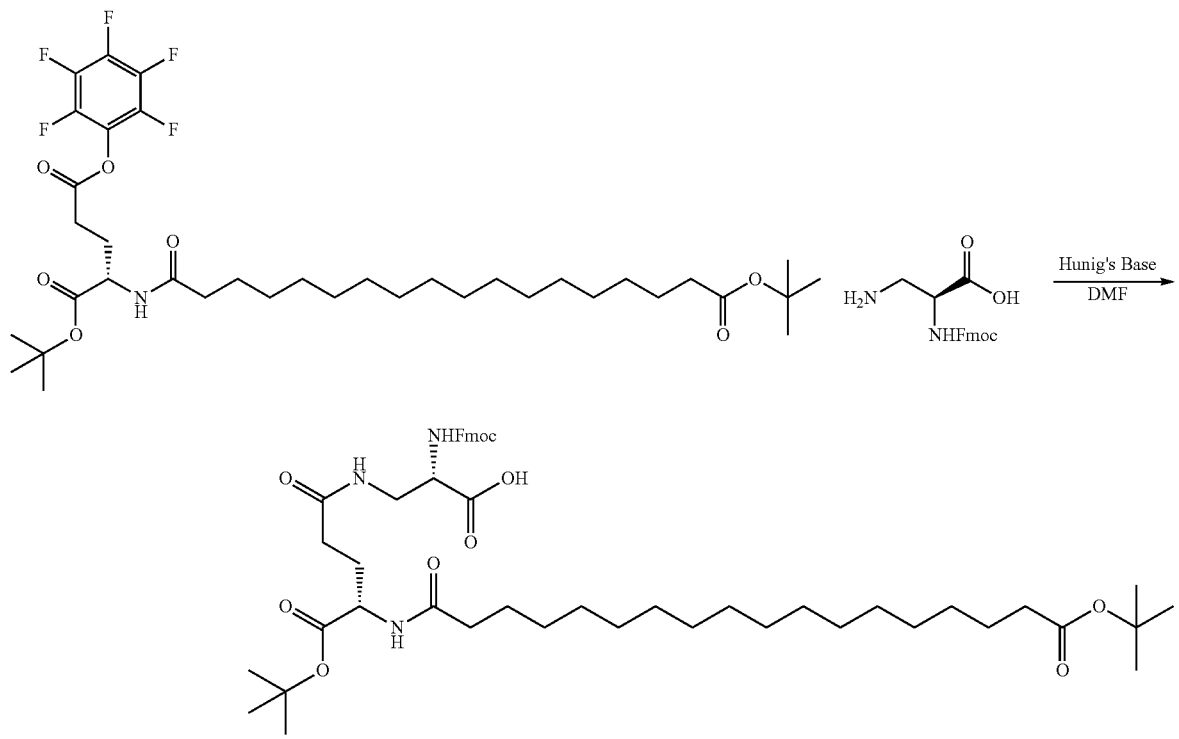

To a solution of crude(S)-1-tert-butyl 5-(perfluorophenyl) 2-(18-(tert-butoxy)-18-oxooctadecanamido)pentanedioate (1163 mg, 1.611 mmol) in DMF (1.61E+04 µl) was added Hunig's Base (1125 µl, 6.44 mmol), then (S)-2-((((9H-fluoren-9-yl)methoxy)carbonyl)amino)-3-aminopropanoic acid (578 mg, 1.772 mmol). The mixture was left to stir at rt overnight. LC/MS showed the formation of product. The mixture was diluted with water. Citric acid was added, resulting in a white precipitate. The mixture was extracted with EtOAc, and after vigorous shaking the solid dissolved. An emulsion formed, and DCM and salt water were added to aid in the layer separation. The combined layers were passed through a pad of celite to aid in emulsion separation, leaving a gooey residue on the celite. The layers were separated, and the aqueous phase was washed with DCM. The combined organic extracts were washed with brine, dried over MgSO4, filtered, and concentrated in vacuo. The residue was purified by PREP HPLC: (50×250 mm HPLC Sunfire C18 10 µm 100% B for 14 min (A is 90:10:0.1 water:MeOH:TFA; B is 90:10:0.1 MeOH:water:TFA)). Fractions were neutralized with Hunig's base and concen- Preparation of Modified Chlorotrityl Resin 13A 2-Chlorotrityl resin (713 mg, 1.141 mmol) was swelled with $CH_2Cl_2$ (7 mL). A solution of (S)-5-((((9H-fluoren-9-yl)methoxy)carbonyl)amino)-2-(18-(tert-butoxy)-18-oxooctadecanamido)pentanoic acid (252 mg, 0.356 mmol), Hunig's Base (0.405 mL, 2.317 mmol), and 1-chloro-4-methylbenzene (0.021 mL, 0.178 mmol) in $CH_2Cl_2$ (3.5 mL) was prepared, analyzed by LC/MS, and added to the swelled resin. The mixture was shaken at rt, monitoring for disappearance of SM. After ~45 min, the material was almost completely attached to the resin. 13 mL of 9:1 MeOH/Hunig's base was added, and the mixture filtered within 1 minute. The resin was rinsed 3 times with DCM (stirring for ~20 s in between washes). The resin was then shaken with ~20 mL DMF for 5 min, then filtered. This was repeated 2 more times with DMF, then 3 times with DCM. The resin was dried on the fritted funnel with N2 being passed through the resin.

Total weight of resin is 0.76 g. 60.06 mg of resin was taken and was shaken for 1 min with 1 mL of 20% hexafluoroisopropanol in DCM. Filtered and rinsed with more cleavage solution, then DCM. Concentration of the combined filtrates yielded 11.94 mg (0.01689 mmol) cleaved material. Thus the measured loading was 0.281 meq/g, and the incorporated yield was 60%.

Preparation of Modified Chlorotrityl Resin 13B

2-Chlorotrityl resin (1622 mg, 2.60 mmol) was swelled with $CH_2Cl_2$ (1.59E+04 µl). A solution of (S)-4-((((9H-fluoren-9-yl)methoxy)carbonyl)amino)-2-(18-(tert-butoxy)-18-oxooctadecanamido)butanoic acid (561.95 mg, 0.811 mmol), Hunig's Base (921 µl, 5.27 mmol), and 1-chloro-4-methylbenzene (48.0 µl, 0.405 mmol) in $CH_2Cl_2$ (7951 µl) was prepared, analyzed by LC/MS, and added to the swelled resin. The mixture was shaken at rt, monitoring for disappearance of SM. After ~45 min, the material was almost completely attached to the resin. 30 mL of 9:1 MeOH/Hunig's base was added, and the mixture filtered within 1 minute. The resin was rinsed 3 times with DCM (stirring for ~20 s in between washes). The resin was then shaken with ~20 mL DMF for 5 min, then filtered. This was repeated 2 more times with DMF, then 3 times with DCM. The resin was dried on the fritted funnel with $N_2$ being passed through the resin. The total weight of resin was 1.93 g. 76.45 mg of resin and was shaken for 1 min with 1 mL of 20% hexafluoroisopropanol in DCM. Filtered and rinsed with more cleavage solution, then DCM. Concentration of the combined filtrates yielded 20.67 mg (0.02983 mmol) cleaved material. Thus, the measured loading was 0.39 meq/g, and the incorporated yield is 93%.

Preparation of Modified Chlorotrityl Resin 13C

2-Chlorotrityl resin (656 mg, 1.049 mmol) was swelled with $CH_2Cl_2$ (6431 µl). After 10 min, 186 uL of Hunig's base was added, and the resulting white smoke was flushed out of the flask with nitrogen. A solution of (S)-2-((((9H-fluoren-9-yl)methoxy)carbonyl)amino)-4-((S)-5-(tert-butoxy)-4-(18-(tert-butoxy)-18-oxooctadecanamido)-5-oxopentanamido)butanoic acid (288 mg, 0.328 mmol), Hunig's Base (372 µl, 2.132 mmol), and 1-chloro-4-methylbenzene (19.42 µl, 0.164 mmol) in $CH_2Cl_2$ (3215 µl) was prepared, analyzed by LC/MS, and added to the swelled resin. NOTE: a 0.5 mL portion of DMF was added to aid in the dissolution of the starting material. The mixture was shaken at rt, monitoring for disappearance of SM. The reaction appeared to stall, so another 186 uL of Hunig's base was added. After an additional 30 min no meaningful progress was seen. 131 mg of chlorotrityl resin was added, and again the mixture was shaken at rt overnight. LC/MS still showed SM, but the reaction was terminated anyway. 30 mL of 9:1 MeOH/Hunig's base was added, and the mixture filtered within a minute. The resin was rinsed 3 times with DCM (stirring for ~20 s in between washes). The resin was then shaken with ~20 mL DMF for 5 min, then filtered. This was repeated 2 more times with DMF, then 3 times with DCM. The resin was dried on the fritted funnel with N2 being passed through the resin.

The total weight of resin was 954 mg. 49.96 mg of resin was shaken for 1 min with 2 mL of 20% hexafluoroisopropanol in DCM. Filtered and rinsed with more cleavage solution, then DCM. Concentration of the combined filtrates yielded 10.16 mg (0.01157 mmol) cleaved material. Thus, the measured loading was 0.23 meq/g, and the incorporated yield was 67%.

Preparation of Modified Chlorotrityl Resin 13D

2-Chlorotrityl resin (2176 mg, 3.48 mmol) was swelled with $CH_2Cl_2$ (2.13E+04 µl). After 10 min, 186 uL of Hunig's base was added, and the resulting white smoke was flushed out of the flask with nitrogen. A solution of (S)-2-((((9H-fluoren-9-yl)methoxy)carbonyl)amino)-3-((S)-5-(tert-butoxy)-4-(18-(tert-butoxy)-18-oxooctadecanamido)-5-oxopentanamido)propanoic acid (940 mg, 1.088 mmol), Hunig's Base (1235 µl, 7.07 mmol), and 1-chloro-4-methylbenzene (64.4 µl, 0.544 mmol) in $CH_2Cl_2$ (1.07E+04 µl) was prepared, analyzed by LC/MS, and added to the swelled resin. The mixture was shaken at rt, monitoring for disappearance of SM. The reaction was ~97% complete at ~1 h. 100 mL of 9:1 MeOH/Hunig's base was added, and the mixture filtered within 1 minute. The resin was rinsed 3 times with DCM (stirring for ~20 s in between washes). The resin was then shaken with ~60 mL DMF for 5 min, then filtered. This was repeated 2 more times with DMF, then 3 times with DCM. The resin was dried on the fritted funnel with $N_2$ being passed through the resin. The total weight of resin was 2.57 g. 85.11 mg of resin was shaken for 1 min with 2 mL of 20% hexafluoroisopropanol in DCM. Filtered and rinsed with more cleavage solution, then DCM. Concentration of the combined filtrates yielded 17.51 mg (0.02026 mmol) cleaved material. Thus, the measured loading was 0.238 meq/g, and the incorporated yield was 56%.

Preparation of Example 13141

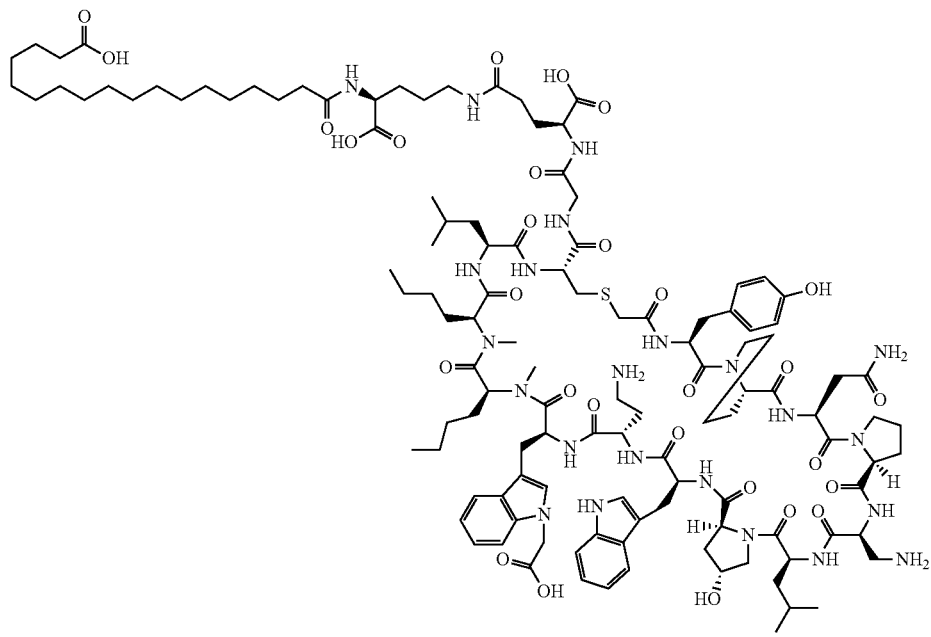

Example 13141 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Asp(OtBu)-[Modified resin 13A]. After deprotection following Global Deprotection procedure B and cyclization according to Cyclization method B, the compound was purified as follows: The residue was split and multiple injections were made to a 19×250 XSelect CSH Prep C18 5 um OBD column, 20 mL/min, 20 to 65% B over 25 min, 5 min at 100% B, 5 min at 20% B (A is 90% water/10% ACN/0.1% TFA; B is 90% ACN/10% water/0.1% TFA). Conc ammonia was used to adjust the fractions to pH 7, and the fractions concentrated on the speedvac. Analytical data supported the submission of (6S,13S)-1-((7S,13R,16S,19S,22S,25S,28S,31S,33aS, 35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m:1',2'-v][1,4,7,10,13,16,19,22,25,28,31,34,37,40,43]thiatetradecaazacyclopentatetracontin-13-yl)-1,4,8,15-tetraoxo-2,5,9,14-tetraazahentriacontane-6,13,31-tricarboxylic acid (6.01 mg, 2.242 µmol, 2.242% yield). Analysis condition 13A: rt 9.96 min. Analysis condition 13B: rt 8.61 min.; ESI-HRMS(+) m/z: Calculated: 1220.1553 (M+2H). Found: 1220.1573 (M+2H).

Preparation of Example 13142

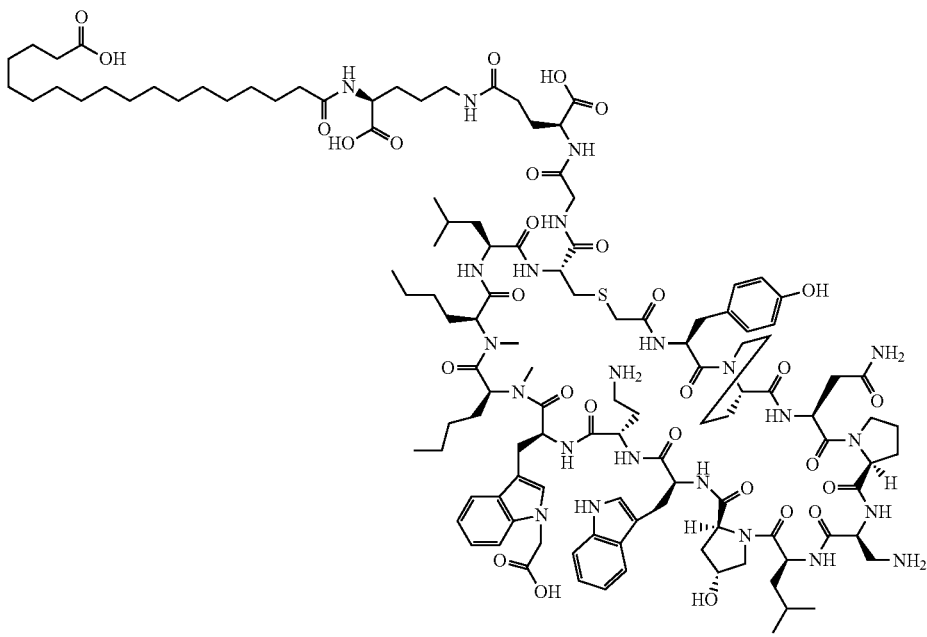

Example 13142 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Glu(OtBu)-[Modified resin 13A]. After deprotection following Global Deprotection procedure B and cyclization according to Cyclization method B, the compound was purified as follows: The residue was split and multiple injections were made to a 19×250 XSelect CSH Prep C18 5 um OBD column, 20 mL/min, 20 to 65% B over 25 min, 5 min at 100% B, 5 min at 20% B (A is 90% water/10% ACN/0.1% TFA; B is 90% ACN/10% water/0.1% TFA). Conc. ammonia was used to adjust the fractions to pH 7, and the fractions concentrated on the speedvac. The residual solid contained a large amount of ammonium trifluoroacetate, which was removed by multiple lyophilization cycles to afford (6S,14S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m:1',2'-v][1,4,7,10,13,16,19,22,25,28,31,34,37,40,43]thiatetradecaazacyclopentatetracontin-13-yl)-1,4,9,16-tetraoxo-2,5,10,15-tetraazadotriacontane-6,14,32-tricarboxylic acid, 2 TFA (3.66 mg, 1.296 μmol, 1.296% yield). Analysis condition 13A: rt 10.00 min. Analysis condition 13B: rt 8.64 min.; ESI-HRMS(+) m/z: Calculated: 1227.1631 (M+2H). Found: 1227.1669 (M+2H).

Preparation of Example 13143

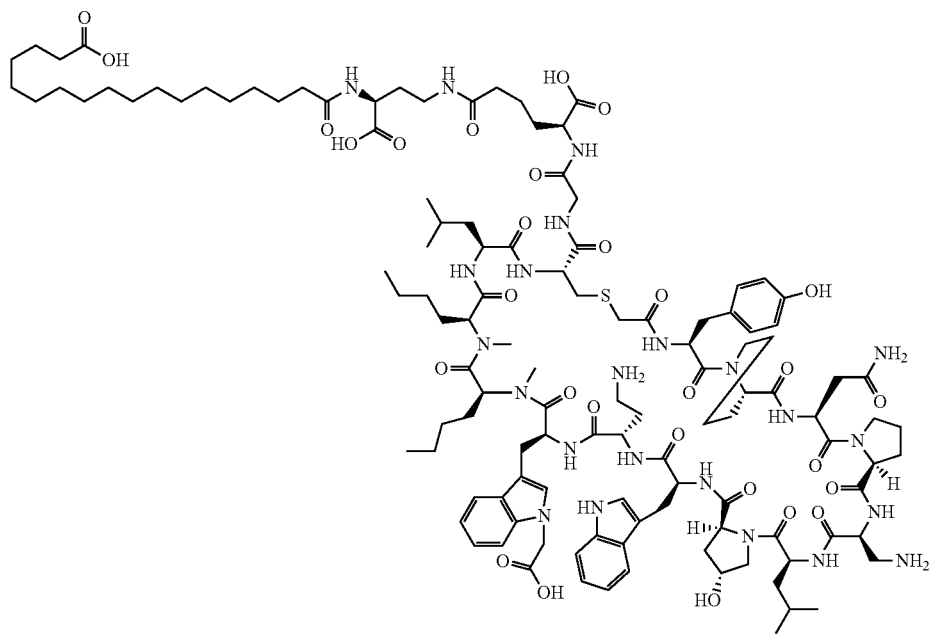

Example 13143 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Glu(OtBu)-[Modified resin 13B]. After deprotection following Global Deprotection procedure B and cyclization according to Cyclization method B, the compound was purified as follows: The residue was split and multiple injections were made to a 19×250 XSelect CSH Prep C18 5 um OBD column, 20 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m:1',2'-v][1,4,7,10,13,16,19,22,25,28,31,34,37,40,43]thiatetradecaazacyclopentatetracontin-13-yl)-1,4,9,15-tetraoxo-2,5,10,14-tetraazahentriacontane-6,13,31-tricarboxylic acid (5.93 mg, 2.406 μmol, 2.406% yield). Analysis condition 13A: rt 9.97 min. Analysis condition 13B: rt 8.61 min.; ESI-HRMS(+) m/z: Calculated: 1220.1553 (M+2H).

Found: 1220.1601 (M+2H).

Preparation of Example 13144

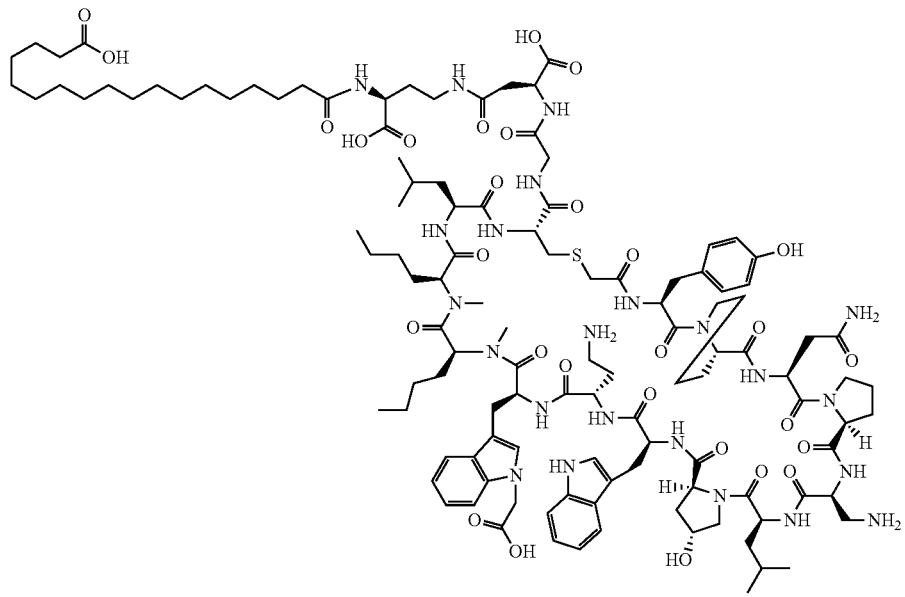

Example 13144 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontin-13-yl)-1,4,8,14-tetraoxo-2,5,9,13-tetraazatriacontane-6,12,30-tricarboxylic acid, 2 TFA (9.57 mg, 3.43 μmol, 3.43% yield). Analysis condition 13A: rt 9.98 min. Analysis condition 13B: rt 8.66 min.; ESI-HRMS(+) m/z: Calculated: 1213.1474 (M+2H). Found: 1213.1513 (M+2H).

Preparation of Example 13145

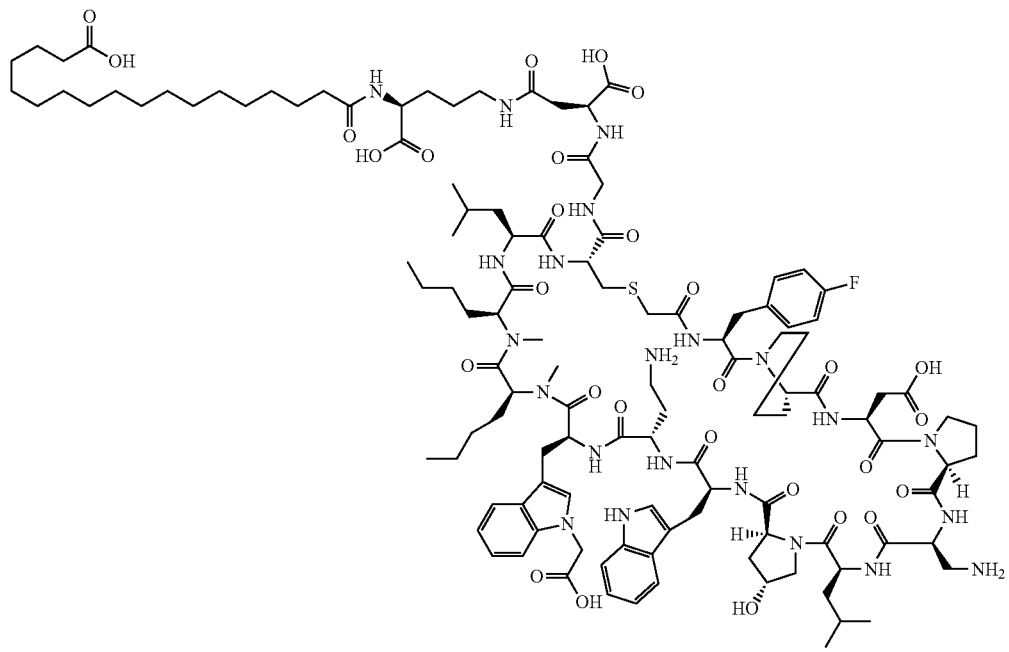

Example 13145 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Fluorophenylalanine]-Pip-Asp-Pro-Dap-Leu-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-Asp(OtBu)-[Modified resin 13A]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25S,28S,31S,33aS,35R, 39S,42S,44aS,50S,52aR)-31-((1H-indol-3-yl)methyl)-28-(2-aminoethyl)-42-(aminomethyl)-19,22-dibutyl-50-(carboxymethyl)-25-((1-(carboxymethyl)-1H-indol-3-yl) methyl)-7-(4-fluorobenzyl)-35-hydroxy-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43] thiatetradecaazacyclopentatetracontin-13-yl)-1,4,8,15-tetraoxo-2,5,9,14-tetraazahentriacontane-6,13,31-tricarboxylic acid, 2 TFA (10.57 mg, 3.88 µmol). Analysis condition 13A: rt 11.43 min. Analysis condition 13B: rt 9.57 min.; ESI-HRMS(+) m/z: Calculated: 814.7658 (M+3H).

Found: 814.7697 (M+3H).

Preparation of Example 13146

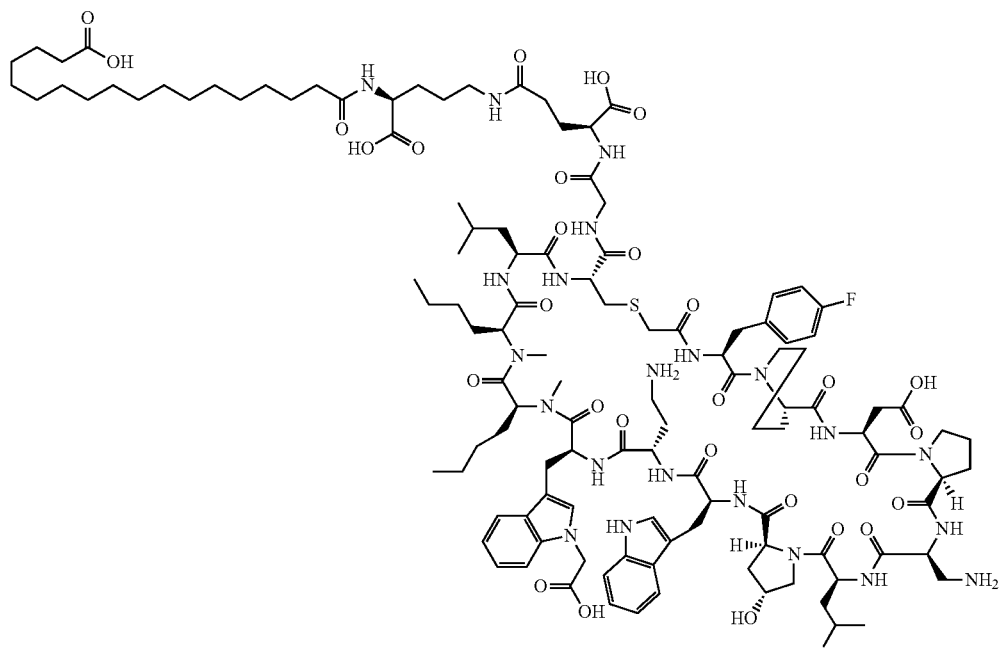

Example 13146 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Fluorophenylalanine]-Pip-Asp-Pro-Dap-Leu-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-Glu (OtBu)-[Modified resin 13A]. After deprotection following Global Deprotection procedure B and cyclization according to Cyclization method B, the compound was purified as follows: The residue was split and two injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,14S)-1-((7S,13R,16S,19S,22S,25S,28S,31S,33aS,35R, 39S,42S,44aS,50S,52aR)-31-((1H-indol-3-yl)methyl)-28-(2-aminoethyl)-42-(aminomethyl)-19,22-dibutyl-50-(carboxymethyl)-25-((1-(carboxymethyl)-1H-indol-3-yl) methyl)-7-(4-fluorobenzyl)-35-hydroxy-16,39-diisobutyl-20,23-dimethyl-6,9,15,18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,9,16-tetraoxo-2,5,10,15-tetraazadotriacontane-6,14,32-tricarboxylic acid, 2 TFA (4.03 mg, 1.441 μmol). Analysis condition 13A: rt 11.50 min. Analysis condition 13B: rt 9.55 min.; ESI-HRMS(+) m/z: Calculated: 1228.6529 (M+2H). Found: 1228.6581 (M+2H).

Preparation of Example 13147

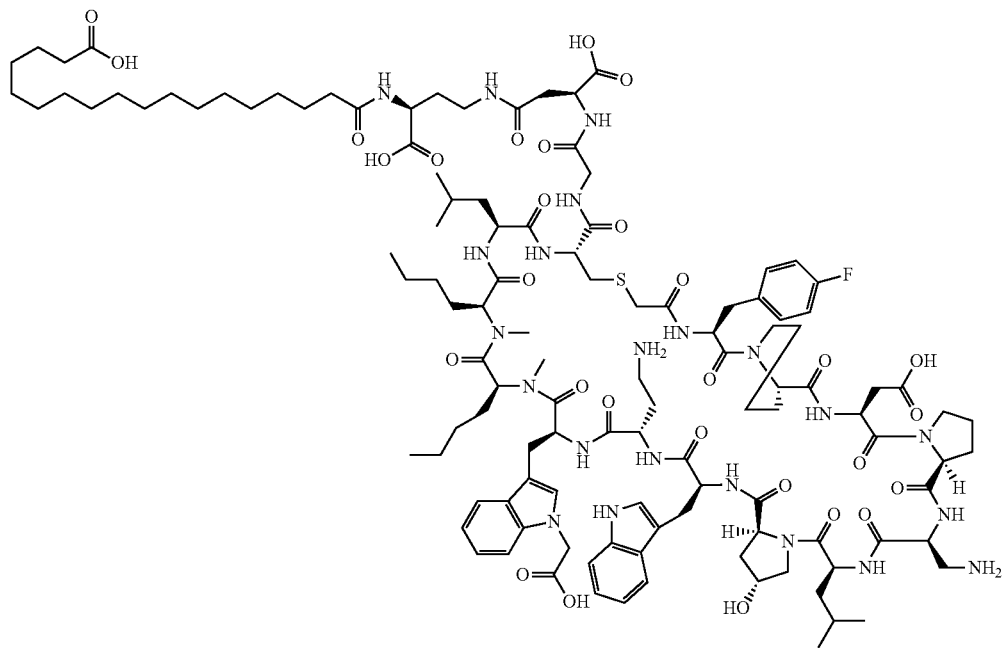

Example 13147 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Fluorophenylalanine]-Pip-Asp-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-Asp(OtBu)-[Modified resin 13B]. After deprotection following Global Deprotection procedure B and cyclization according to Cyclization method B, the compound was purified as follows: The residue was split and two injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25S,28S,31S,33aS,35R,39S,42S,44aS,50,52aR)-31-((1H-indol-3-yl)methyl)-28-(2-aminoethyl)-42-(aminomethyl)-19,22-dibutyl-50-(carboxymethyl)-25-((1-(carboxymethyl)-1H-indol-3-yl)methyl)-7-(4-fluorobenzyl)-35-hydroxy-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontin-13-yl)-1,4,8,14-tetraoxo-2,5,9,13-tetraazatriacontane-6,12,30-tricarboxylic acid, 2 TFA (17.72 mg, 6.60 μmol). Analysis condition 13A: rt 11.38 min. Analysis condition 13B: rt 9.47 min.; ESI-HRMS(+) m/z: Calculated: 1214.6355 (M+2H).

Found: 1214.6373 (M+2H).

Preparation of Example 13148

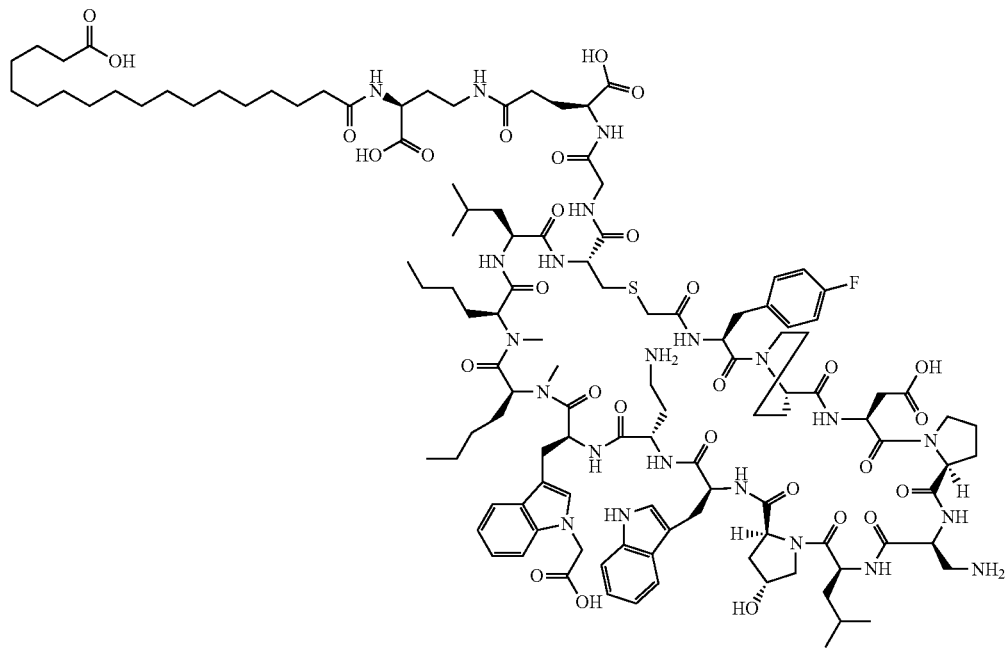

Example 13148 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Fluorophenylalanine]-Pip-Asp-Pro-Dap-Leu-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-Glu (OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25S,28S,31S, 33aS,35R,39S,42S,44aS,50S,52aR)-31-((1H-indol-3-yl) methyl)-28-(2-aminoethyl)-42-(aminomethyl)-19,22-dibutyl-50-(carboxymethyl)-25-((1-(carboxymethyl)-1H-indol-3-yl)methyl)-7-(4-fluorobenzyl)-35-hydroxy-16,39-diisobutyl-20,23-dimethyl-6,9,15,18,21,24,27,30,33,38,41, 44,49,52-tetradecaoxopentacontahydro-1H-pyrido[1,2-g] dipyrrolo[1,2-m: 1',2'-v][1,4,7,10,13,16,19,22,25,28,31,34, 37,40,43]thiatetradecaazacyclopentatetracontin-13-yl)-1,4, 9,15-tetraoxo-2,5,10,14-tetraazahentriacontane-6,13,31-tricarboxylic acid, 2 TFA (13.42 mg, 4.77 μmol). Analysis condition 13A: rt 12.60 min. Analysis condition 13B: rt 10.67 min.; ESI-HRMS(+) m/z: Calculated: 1221.6451 (M+2H). Found: 1221.6421 (M+2H).

Preparation of Example 13149

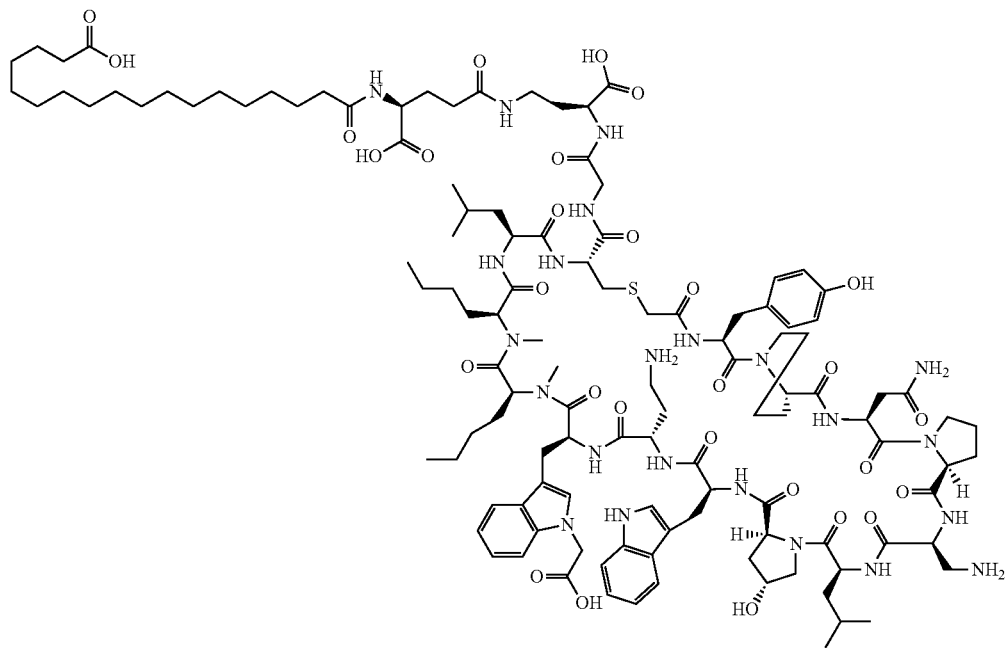

Example 13149 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[Modified resin 13C]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25S,28S,31S,33aS,35R, 39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g] dipyrrolo[1,2-m: 1',2'-v][1,4,7,10,13,16,19,22,25,28,31,34,37,40,43]thiatetradecaazacyclopentatetracontin-13-yl)-1,4,10,15-tetraoxo-2,5,9,14-tetraazahentriacontane-6,13,31-tricarboxylic acid, 2 TFA (22.17 mg, 7.64 μmol). Analysis condition 13A: rt 11.04 min. Analysis condition 13B: rt 9.76 min.; ESI-HRMS(+) m/z: Calculated: 1220.1553 (M+2H). Found: 1220.1526 (M+2H).

Preparation of Example 13150

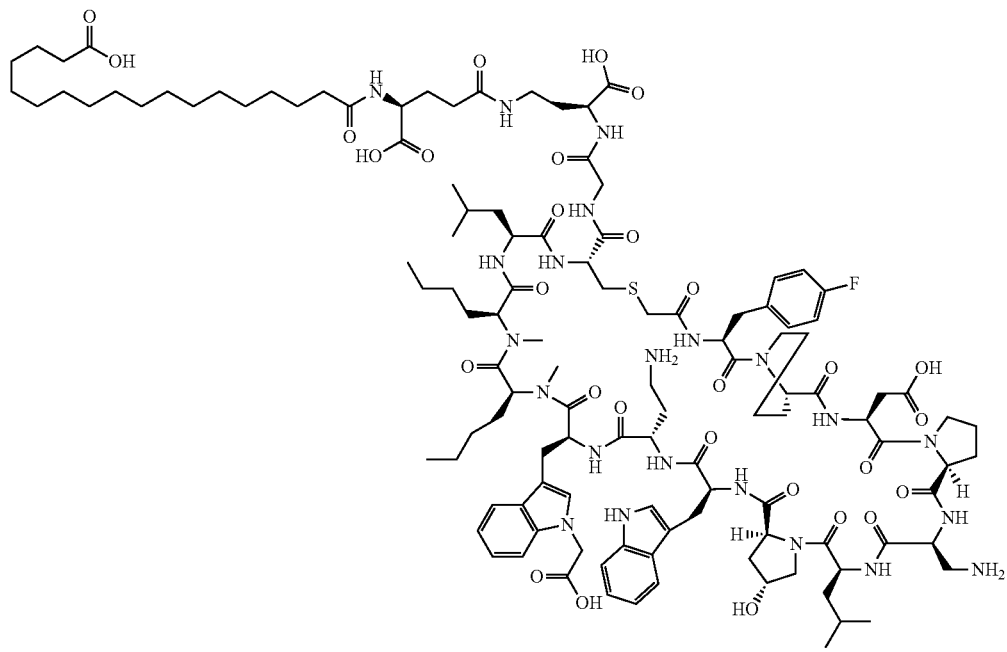

Example 13150 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Fluorophenylalanine]-Pip-Asp-Pro-Dap-Leu-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-[Modified resin 13C]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25S,28S,31S, 33aS,35R,39S,42S,44aS,50S,52aR)-31-((1H-indol-3-yl) methyl)-28-(2-aminoethyl)-42-(aminomethyl)-19,22-dibutyl-50-(carboxymethyl)-25-((1-(carboxymethyl)-1H-indol-3-yl)methyl)-7-(4-fluorobenzyl)-35-hydroxy-16,39-diisobutyl-20,23-dimethyl-6,9,15,18,21,24,27,30,33,38,41, 44,49,52-tetradecaoxopentacontahydro-1H-pyrido[1,2-g] dipyrrolo[1,2-m: 1',2'-v][1,4,7,10,13,16,19,22,25,28,31,34, 37,40,43]thiatetradecaazacyclopentatetracontin-13-yl)-1,4, 10,15-tetraoxo-2,5,9,14-tetraazahentriacontane-6,13,31-tricarboxylic acid, 2 TFA (12.96 mg, 4.37 µmol). Analysis condition 13A: rt 12.52 min. Analysis condition 13B: rt 10.61 min.; ESI-HRMS(+) m/z: Calculated: 1221.6451 (M+2H).

Found: 1221.6429 (M+2H).

Preparation of Example 13151

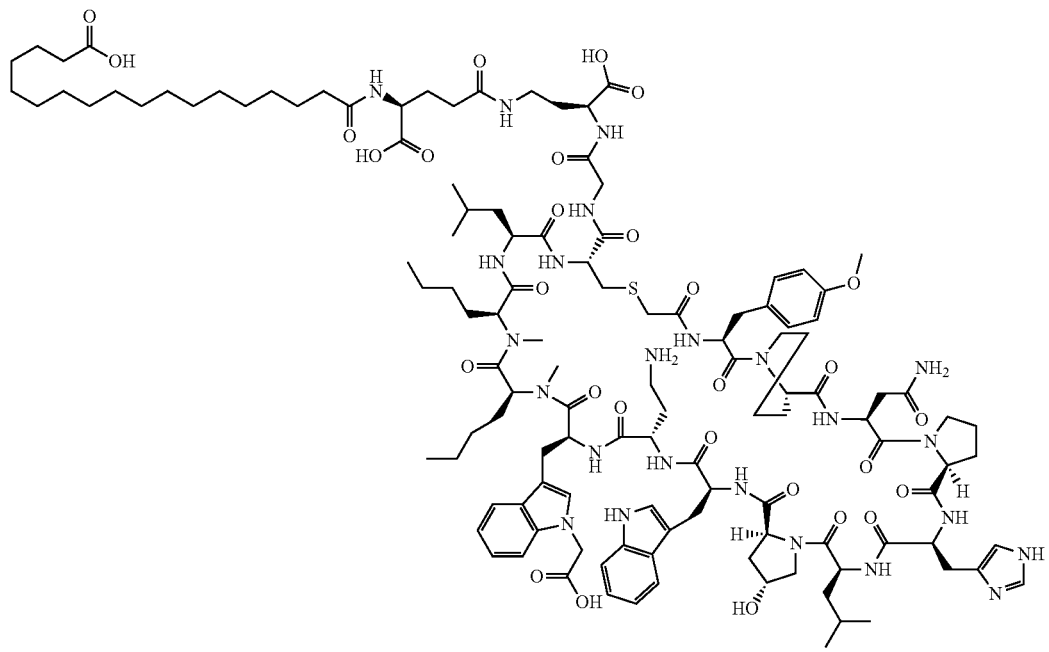

Example 13151 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Methoxyphenylalanine]-Pip-Asn-Pro-His-Leu-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-[Modified resin 13C]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,13S)-1-((7S,13R,16S,19S,22S,25 S,28S,31S, 33aS,35R,39S,42S,44aS,50S,52aR)-42-((1H-imidazol-4-yl) methyl)-31-((1H-indol-3-yl)methyl)-50-(2-amino-2-oxoethyl)-28-(2-aminoethyl)-19,22-dibutyl-25-((1-(carboxymethyl)-1H-indol-3-yl)methyl)-35-hydroxy-16,39-diisobutyl-7-(4-methoxybenzyl)-20,23-dimethyl-6,9,15,18, 21,24,27,30,33,38,41,44,49,52-tetradecaoxopentacontahydro-1H-pyrido[1,2-g]dipyrrolo[1, 2-m:1',2'-v][1,4,7,10,13,16,19,22,25,28,31,34,37,40,43] thiatetradecaazacyclopentatetracontin-13-yl)-1,4,10,15-tetraoxo-2,5,9,14-tetraazahentriacontane-6,13,31-tricarboxylic acid, 2 TFA (18.49 mg, 6.63 µmol). Analysis condition 13A: rt 11.80 min. Analysis condition 13B: rt 10.12 min.; ESI-HRMS(+) m/z: Calculated: 1252.6685 (M+2H).

Found: 1252.6670 (M+2H).

Preparation of Example 13152

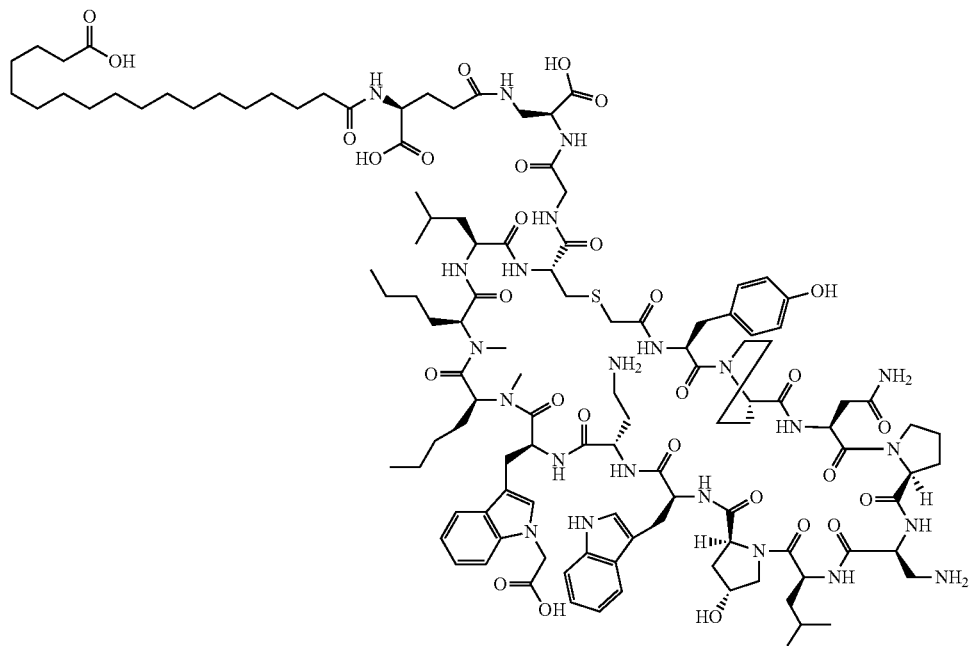

Example 13152 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[Modified resin 13D]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/ 0.1% TFA). ACN was removed from the fractions on the rotovap, and the aqueous portion was lyophilized. Analytical data confirms (6S,12S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m:1',2'-v][1,4,7,10,13,16,19,22,25,28,31,34,37,40,43]thiatetradecaazacyclopentatetracontin-13-yl)-1,4,9,14-tetraoxo-2,5,8,13-tetraazatriacontane-6,12,30-tricarboxylic acid, 2 TFA (20.36 mg, 6.90 µmol, 6.90% yield). Analysis condition 13A: rt 10.51 min. Analysis condition 13B: rt 9.22 min.; ESI-HRMS(+) m/z: Calculated: 1213.1474 (M+2H). Found: 1213.1440 (M+2H).

Preparation of Example 13153

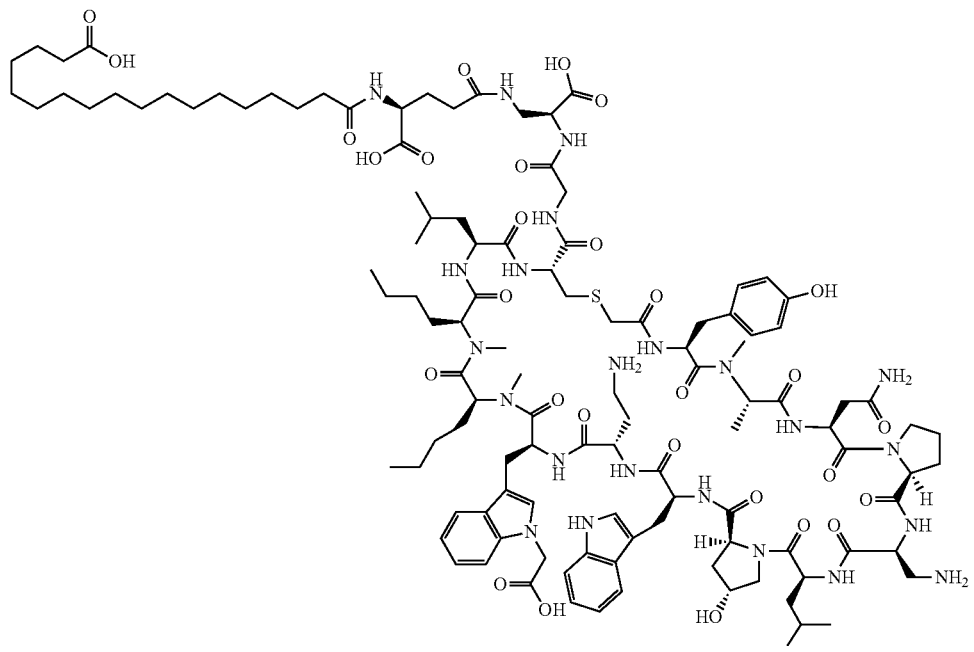 [SMILES: CCCC[C@H]1C(=O)N(C)[C@@H](CCCC)C(=O)N[C@@H](CC(C)C)C(=O)N[C@H](C(=O)NCC(=O)N[C@@H](CNC(=O)CC[C@H](NC(=O)CCCCCCCCCCCCCCCCC(=O)O)C(=O)O)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 13153 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-[N-Me]Ala-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[Modified resin 13D]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((6S,9S,12S,18R,21 S,24S,27S,30S,33 S,36S, 38aS,40R,44S,47S,49aS)-36-((1H-indol-3-yl)methyl)-6-(2-amino-2-oxoethyl)-33-(2-aminoethyl)-47-(aminomethyl)-24,27-dibutyl-30-((1-(carboxymethyl)-1H-indol-3-yl)methyl)-40-hydroxy-12-(4-hydroxybenzyl)-21,44-diisobutyl-9,10,25,28-tetramethyl-5,8,11,14,20,23,26,29,32,35,38,43,46,49-tetradecaoxooctatetracontahydrodipyrrolo[2,1-g$_1$:2',1'-x][1,4,7,10,13,16,19,22,25,28,31,34,37,40,43]thiatetradecaazacyclopentatetracontin-18-yl)-1,4,9,14-tetraoxo-2,5,8,13-tetraazatriacontane-6,12,30-tricarboxylic acid, 2 TFA (21.88 mg, 7.91 μmol, 7.91% yield). Analysis condition 13A: rt 10.37 min. Analysis condition 13B: rt 9.04 min.; ESI-HRMS(+) m/z: Calculated: 1200.1396 (M+2H). Found: 1200.1373 (M+2H).

Preparation of Example 13154

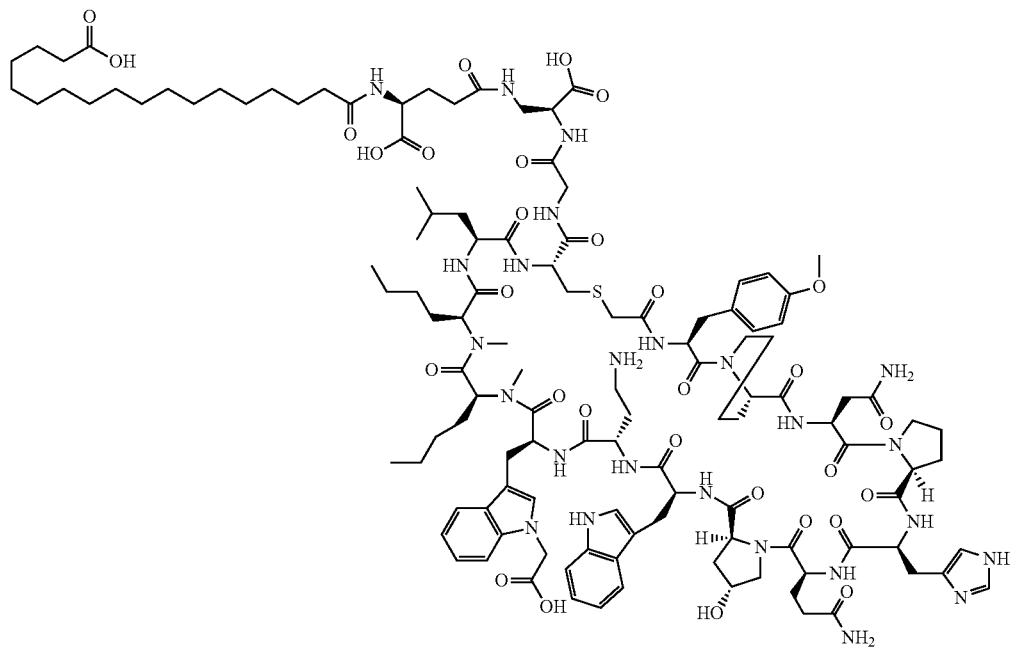

Example 13154 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Methoxyphenylalanine]-Pip-Asn-Pro-His-Gln-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-[Modified resin 13D]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25S,28S,31S, 33aS,35R,39S,42S,44aS,50S,52aR)-42-((1H-imidazol-4-yl) methyl)-31-((1H-indol-3-yl)methyl)-50-(2-amino-2-oxoethyl)-39-(3-amino-3-oxopropyl)-28-(2-aminoethyl)-19,22-dibutyl-25-((1-(carboxymethyl)-1H-indol-3-yl) methyl)-35-hydroxy-16-isobutyl-7-(4-methoxybenzyl)-20, 23-dimethyl-6,9,15,18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,9,14-tetraoxo-2,5,8,13-tetraazatriacontane-6,12,30-tricarboxylic acid, 2 TFA (6.71 mg, 2.209 μmol, 2.209% yield). Analysis condition 13A: rt 11.04 min. Analysis condition 13B: rt 9.34 min.; ESI-HRMS(+) m/z: Calculated: 1253.1480 (M+2H). Found: 1253.1443 (M+2H).

Preparation of Example 13155

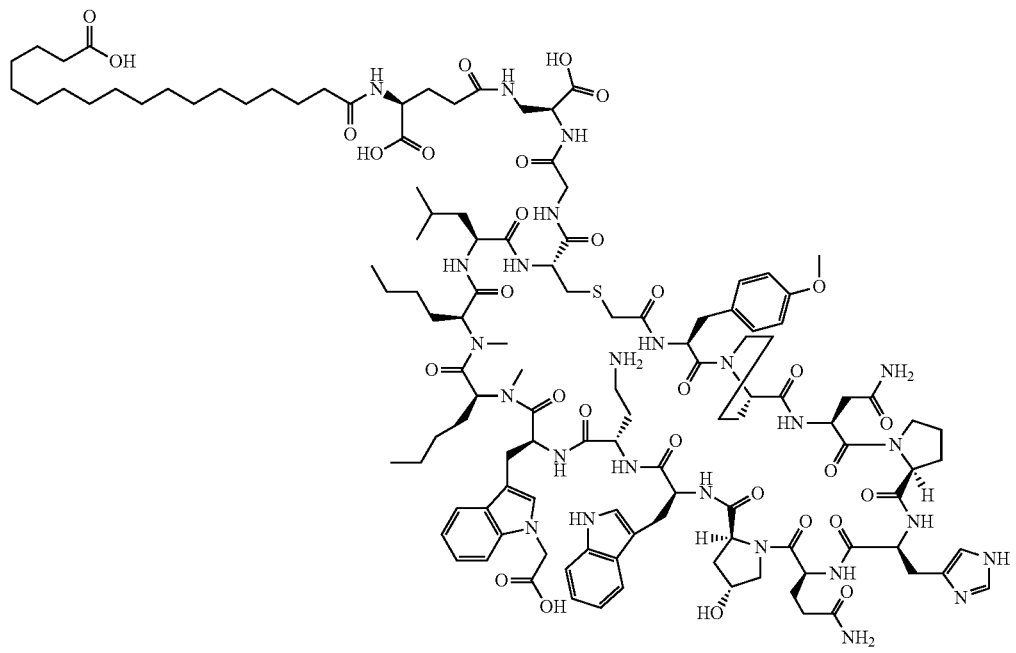

Example 13155 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Methoxyphenylalanine]-Pip-Asn-Pro-His-Gln-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-[Modified resin 13D]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25S,28S,31S, 33aS,35R,39S,42S,44aS,50S,52aR)-42-((1H-imidazol-4-yl) methyl)-31-((1H-indol-3-yl)methyl)-39-(3-amino-3-oxopropyl)-28-(2-aminoethyl)-19,22-dibutyl-50-(carboxymethyl)-25-((1-(carboxymethyl)-1H-indol-3-yl) methyl)-35-hydroxy-16-isobutyl-7-(4-methoxybenzyl)-20, 23-dimethyl-6,9,15,18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,9,14-tetraoxo-2,5,8,13-tetraazatriacontane-6,12,30-tricarboxylic acid, 2 TFA (10.61 mg, 3.49 µmol, 3.49% yield). Analysis condition 13A: rt 11.19 min. Analysis condition 13B: rt 9.48 min.; ESI-HRMS(+) m/z: Calculated: 1253.6400 (M+2H). Found: 1253.6372 (M+2H).

Preparation of Example 13156

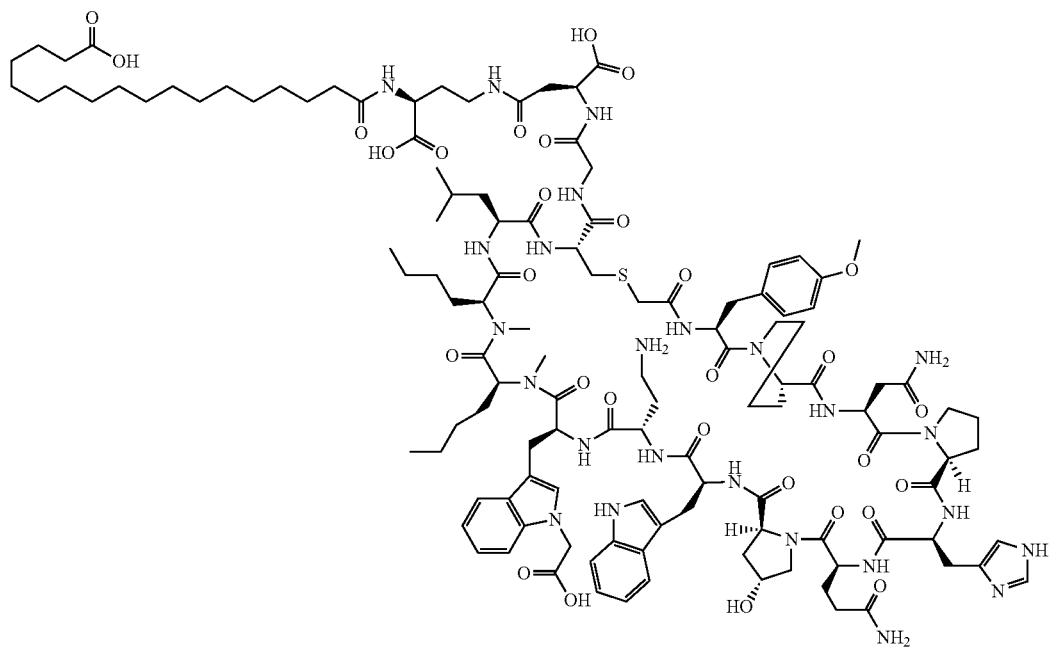

Example 13156 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Methoxyphenylalanine]-Pip-Asn-Pro-His-Gln-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-Asp (OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25 S,28S,31S, 33aS,35R,39S,42S,44aS,50S,52aR)-42-((1H-imidazol-4-yl) methyl)-31-((1H-indol-3-yl)methyl)-50-(2-amino-2-oxoethyl)-39-(3-amino-3-oxopropyl)-28-(2-aminoethyl)-19,22-dibutyl-25-((1-(carboxymethyl)-1H-indol-3-yl) methyl)-35-hydroxy-16-isobutyl-7-(4-methoxybenzyl)-20, 23-dimethyl-6,9,15,18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,8,14-tetraoxo-2,5,9,13-tetraazatriacontane-6,12,30-tricarboxylic acid, 2 TFA (10.73 mg, 3.53 μmol, 3.53% yield). Analysis condition 13A: rt 10.92 min. Analysis condition 13B: rt 9.27 min.; ESI-HRMS(+) m/z: Calculated: 1253.1480 (M+2H). Found: 1253.1448 (M+2H).

Preparation of Example 13157

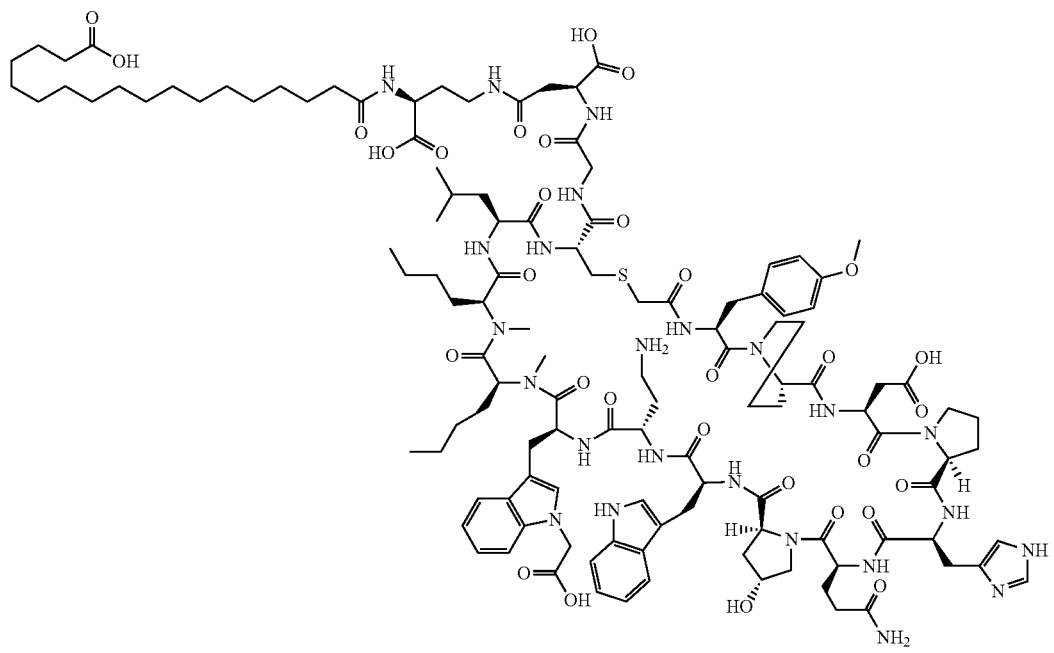

Example 13157 was synthesized on a 0.1 mmol scale according to the general procedures above, including chloroacetic acid coupling procedure A. The underlined steps employed the double-coupling procedure, and italicized residues were coupled with a 30 min single coupling. ClAc-[p-Methoxyphenylalanine]-Pip-Asp-Pro-His-Gln-Hyp-Trp-Dab-[(S)-2-amino-3-(1-(carboxymethyl)-1H-indol-3-yl) propanoic acid]-[N-Me]Nle-[N-Me]Nle-Leu-Cys-Gly-Asp (OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,12S)-1-((7S,13R,16S,19S,22S,25 S,28S,31S, 33aS,35R,39S,42S,44aS,50S,52aR)-42-((1H-imidazol-4-yl) methyl)-31-((1H-indol-3-yl)methyl)-39-(3-amino-3-oxopropyl)-28-(2-aminoethyl)-19,22-dibutyl-50-(carboxymethyl)-25-((1-(carboxymethyl)-1H-indol-3-yl) methyl)-35-hydroxy-16-isobutyl-7-(4-methoxybenzyl)-20, 23-dimethyl-6,9,15,18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,8,14-tetraoxo-2,5,9,13-tetraazatriacontane-6,12,30-tricarboxylic acid, 2 TFA (12.14 mg, 4.22 μmol, 4.22% yield). Analysis condition 13A: rt 11.09 min. Analysis condition 13B: rt 9.42 min.; ESI-HRMS(+) m/z: Calculated: 1253.6400 (M+2H). Found: 1253.6367 (M+2H).

Preparation of Example 13158

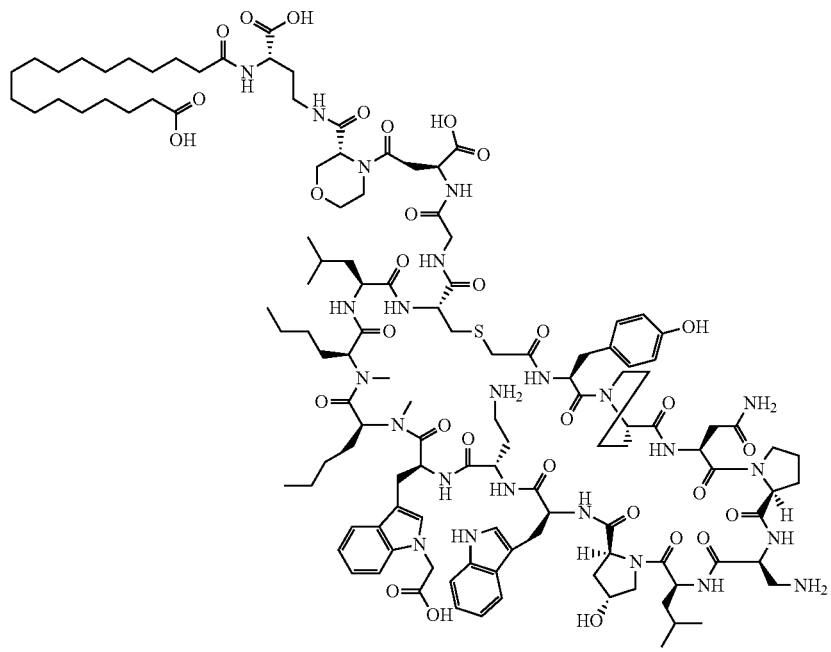

Example 13158 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[morpholine-3R-carboxylic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of 18-(((S)-3-((R)-4-((S)-3-(2-((7S,13R,16S,19S,22S,25S,28S,31S,33aS,35R,39S,42S,44aS,50,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontine-13-carboxamido)acetamido)-3-carboxypropanoyl)morpholine-3-carboxamido)-1-carboxypropyl)amino)-18-oxooctadecanoic acid, 2 TFA (22.68 mg, 7.38 µmol, 7.38% yield). Analysis condition 13A: rt 10.15 min. Analysis condition 13B: rt 8.82 min.; ESI-HRMS(+) m/z: Calculated: 1269.6713 (M+2H). Found: 1269.6671 (M+2H).

Preparation of Example 13159

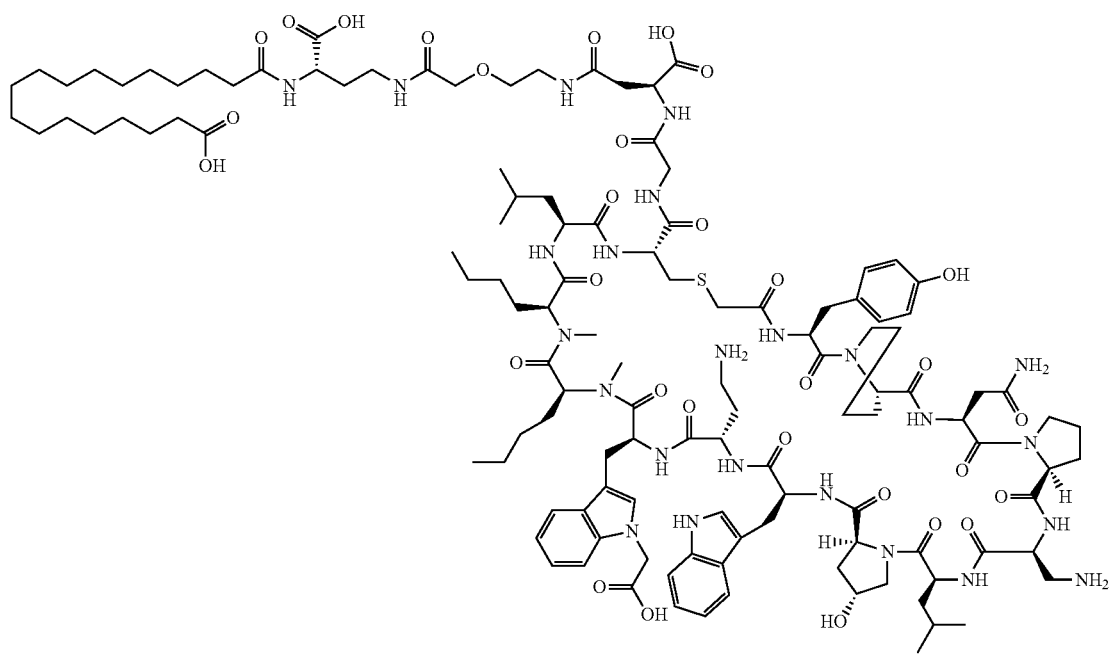

Example 13159 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[2-(2-aminoethoxy) acetic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/ 0.1% TFA). ACN was removed from the fractions on the rotovap, and the aqueous portion was lyophilized. Analytical data supported the submission of (6S,18S)-1-((7S,13R,16S, 19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15, 18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,8,14,20-pentaoxo-12-oxa-2,5,9,15,19-pentaazahexatriacontane-6, 18,36-tricarboxylic acid, 2 TFA (12.14 mg, 3.97 µmol, 3.97% yield). Analysis condition 13A: rt 10.01 min. Analysis condition 13B: rt 8.70 min.; ESI-HRMS(+) m/z: Calculated: 1263.6713 (M+2H). Found: 1263.6668 (M+2H).

Preparation of Example 13160

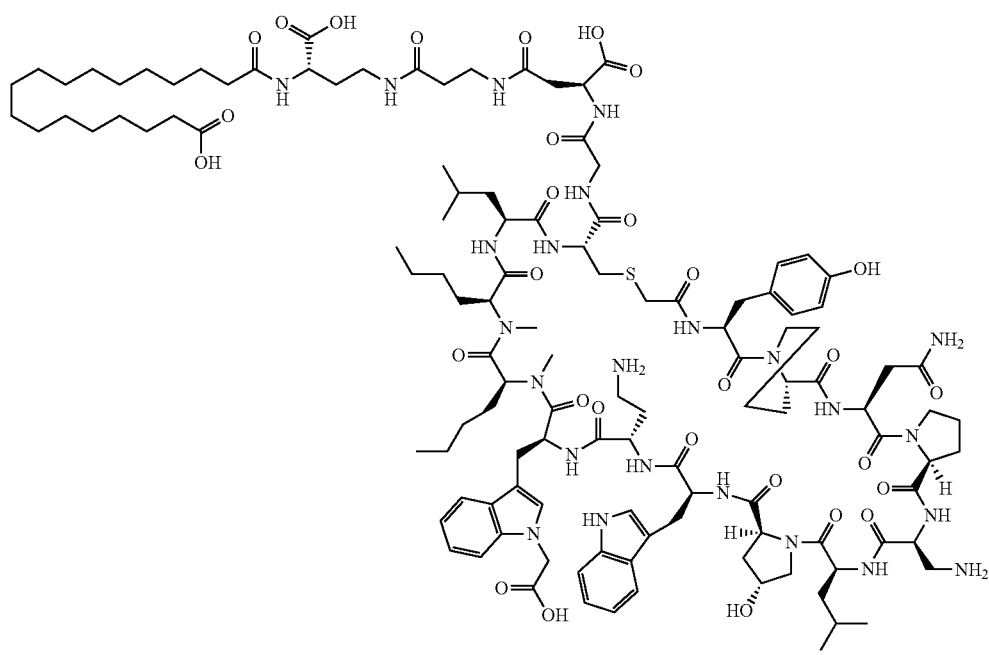

Example 13160 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[3-aminopropanoic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA).

ACN was removed from the fractions on the rotovap, and the aqueous portion was lyophilized. Analytical data supported the submission of (6S,16S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontin-13-yl)-1,4,8,12,18-pentaoxo-2,5,9,13,17-pentaazatetratriacontane-6,16,34-tricarboxylic acid, 2 TFA (11.56 mg, 4.03 μmol). Analysis condition 13A: rt 10.00 min. Analysis condition 13B: rt 8.69 min.; ESI-HRMS(+) m/z: Calculated: 1248.6660 (M+2H). Found: 1248.6622 (M+2H).

Preparation of Example 13161

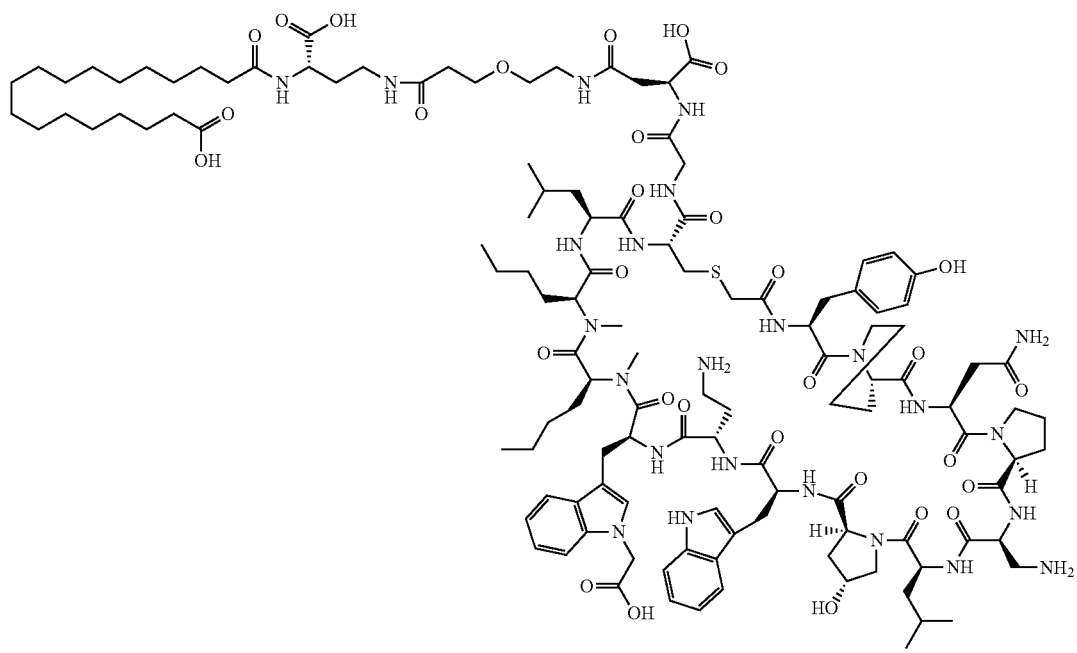

Example 13161 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[3-(2-aminoethoxy)propanoic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,19S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m:1',2'-v][1,4,7,10,13,16,19,22,25,28,31,34,37,40,43]thiatetradecaazacyclopentatetracontin-13-yl)-1,4,8,15,21-pentaoxo-12-oxa-2,5,9,16,20-pentaazaheptatriacontane-6,19,37-tricarboxylic acid, 2 TFA (22.02 mg, 7.55 μmol, 7.55% yield). Analysis condition 13A: rt 10.01 min. Analysis condition 13B: rt 8.69 min.; ESI-HRMS(+) m/z: Calculated: 1270.6791 (M+2H). Found: 1270.6751 (M+2H).

Preparation of Example 13162

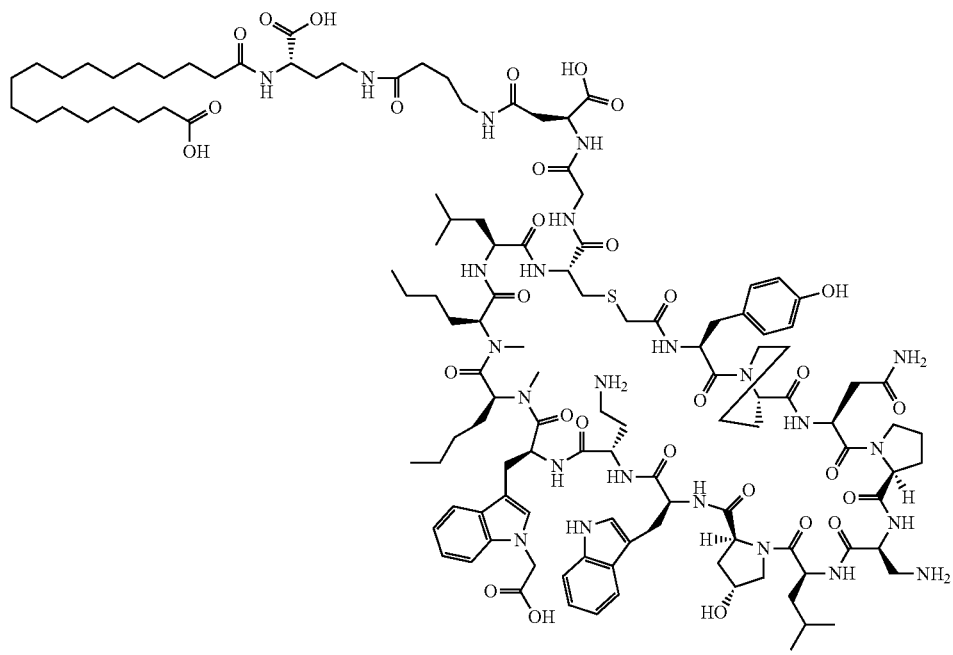

Example 13162 was synthesized on a 0.1 mmol scale according to the general procedures above, including chloroacetic acid coupling procedure A. The underlined steps employed the double-coupling procedure, and italicized residues were coupled with a 30 min single coupling. ClAc-T v-Pip-<u>Asn</u>-Pro-Dap-<u>Leu</u>-Hyp-Trp-Dab-[(S)-2-amino-3-(1-(carboxymethyl)-1H-indol-3-yl)propanoic acid]-[<u>N-Me</u>]<u>Nle</u>-[N-Me]Nle-Leu-Cys-Gly-[4-aminobutanoic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/ 0.1% TFA). ACN was removed from the fractions on the rotovap, and the aqueous portion was lyophilized. Analytical data supported the submission of (6S,17S)-1-((7S,13R,16S, 19S,22S,25S,28S,31S,33aS,35R,39S,42S,44aS,50,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15, 18,21,24,27,30,33,38,41,44,49,52-tetradecaoxopentacontahydro-1H-pyrido[1,2-g]dipyrrolo[1, 2-m: 1',2'-v][1,4,7,10,13,16,19,22,25,28,31,34,37,40,43] thiatetradecaazacyclopentatetracontin-13-yl)-1,4,8,13,19-pentaoxo-2,5,9,14,18-pentaazapentatriacontane-6,17,35-tricarboxylic acid, 2 TFA (17.91 mg, 6.08 μmol, 6.08% yield). Analysis condition 13A: rt 10.07 min. Analysis condition 13B: rt 8.73 min.; ESI-HRMS(+) m/z: Calculated: 1255.6738 (M+2H). Found: 1255.6692 (M+2H).

Preparation of Example 13163

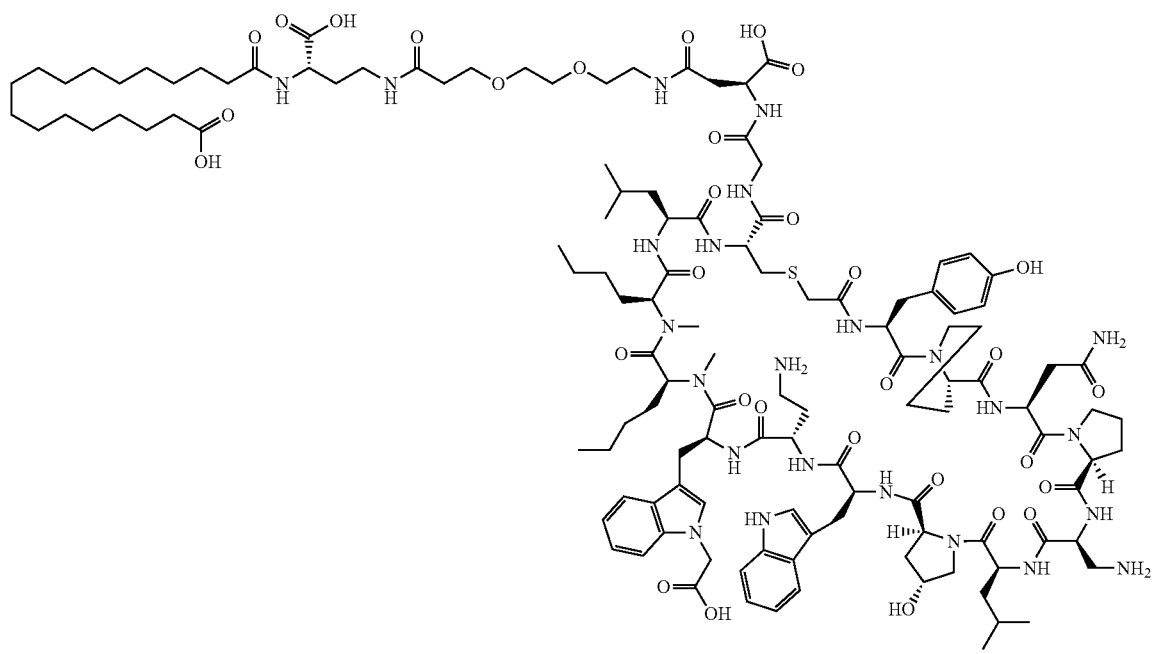

Example 13163 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[3-(2-(2-aminoethoxy)ethoxy)propanoic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,22S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontin-13-yl)-1,4,8,18,24-pentaoxo-12,15-dioxa-2,5,9,19,23-pentaazatetracontane-6,22,40-tricarboxylic acid, 2 TFA (18.29 mg, 5.85 μmol, 5.85% yield). Analysis condition 13A: rt 10.00 min. Analysis condition 13B: rt 8.68 min.; ESI-HRMS(+) m/z: Calculated: 1292.6713 (M+2H). Found: 1292.6887 (M+2H).

Preparation of Example 13164

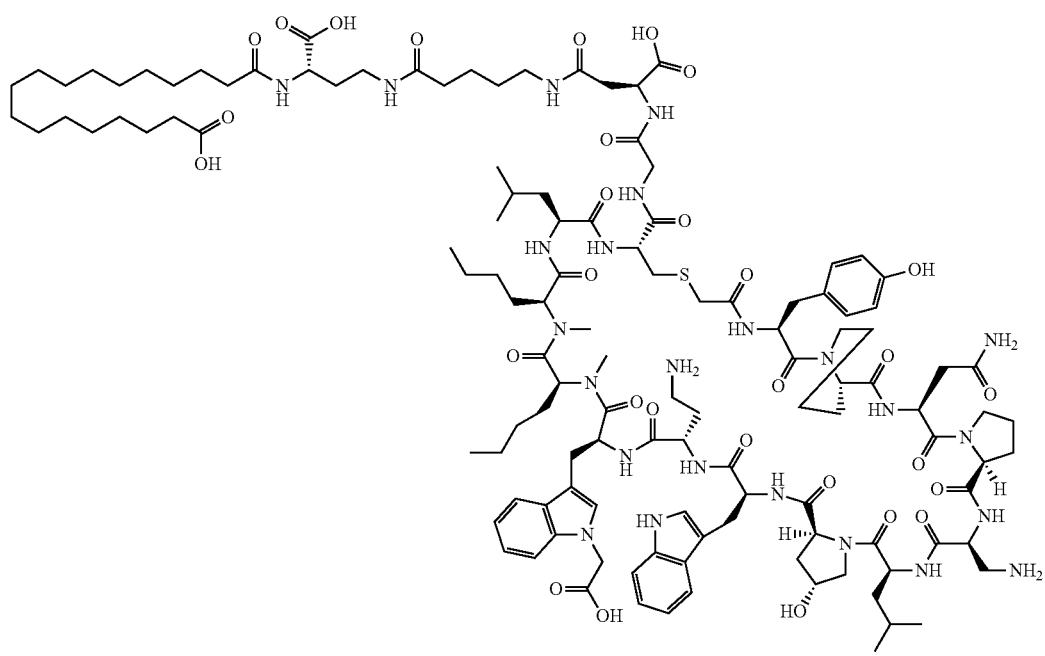

Example 13164 was synthesized on a 0.1 mmol scale according to the general procedures above, including chloroacetic acid coupling procedure A. The underlined steps employed the double-coupling procedure, and italicized residues were coupled with a 30 min single coupling. ClAc-Tyr-Pip-Asn-Pro-Dap-Leu-Hyp-Trp-Dab-[(S)-2-amino-3-(1-(carboxymethyl)-1H-indol-3-yl)propanoic acid]-[N-Me]Nle-[N-Me]Nle-Leu-Cys-Gly-[5-aminopentanoic acid]-Asp(OtBu)-[Modified resin 13B]. After deprotection following Global Deprotection procedure B and cyclization according to Cyclization method B, the compound was purified as follows: The residue was split and multiple injections were made to a 30×150 XSelect CSH Prep C18 5 um OBD column, 40 mL/min, 20 to 65% B over 25 min, 5 min at 100% B, 5 min at 20% B (A is 90% water/10% ACN/0.1% TFA; B is 90% ACN/10% water/0.1% TFA). ACN was removed from the fractions on the rotovap, and the aqueous portion was lyophilized. Analytical data supported the submission of (6S,18S)-1-((7S,13R,16S,19S,22S,25S,28S,31S,33aS,35R,39S,42S,44aS,50S,52aR)-31-((1H-indol-3-yl)methyl)-50-(2-amino-2-oxoethyl)-28-(2-aminoethyl)-42-(aminomethyl)-19,22-dibutyl-25-((1-(carboxymethyl)-1H-indol-3-yl)methyl)-35-hydroxy-7-(4-hydroxybenzyl)-16,39-diisobutyl-20,23-dimethyl-6,9,15,18,21,24,27,30,33,38,41,44,49,52-tetradecaoxopentacontahydro-1H-pyrido[1,2-g]dipyrrolo[1,2-m: 1',2'-v][1,4,7,10,13,16,19,22,25,28,31,34,37,40,43]thiatetradecaazacyclopentatetracontin-13-yl)-1,4,8,14,20-pentaoxo-2,5,9,15,19-pentaazahexatriacontane-6,18,36-tricarboxylic acid, 2 TFA (10.63 mg, 3.48 μmol, 3.48% yield). Analysis condition 13A: rt 10.06 min. Analysis condition 13B: rt 8.73 min.; ESI-HRMS(+) m/z: Calculated: 1262.6816 (M+2H). Found: 1262.6773 (M+2H).

803
Preparation of INT-1400A

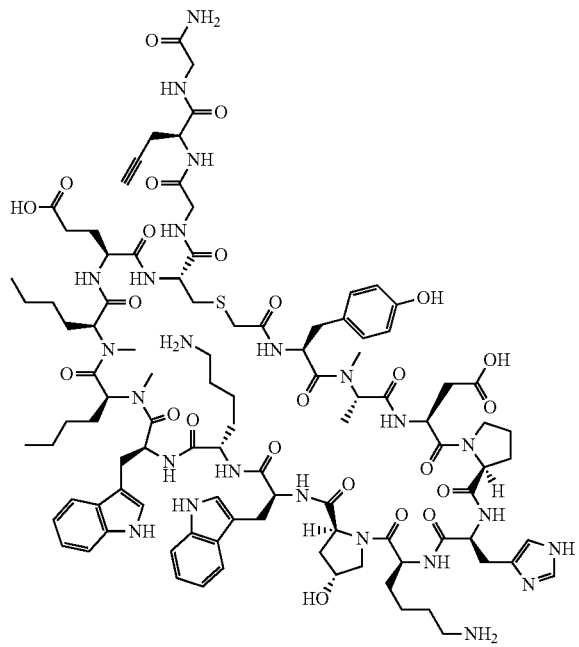

INTERMEDIATE 1400A

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-Trp-mNle-mNle-Glu-Cys-Gly-[(S)-propargylglycine]-Gly. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 97.7 mg, and its estimated purity by LCMS analysis was 99%. Analysis condition A: Retention time=1.39 min; ESI-MS(+) m/z 1046.9 (M+2H), most abundant ion; Analysis condition B: Retention time=2.05 min; ESI-MS(+) m/z 1046.8 (M+2H), most abundant ion; ESI-HRMS(+) m/z: Calculated: 1046.5091 (M+2H). Found: 1046.5058 (M+2H).

804
Preparation of INT-1400B

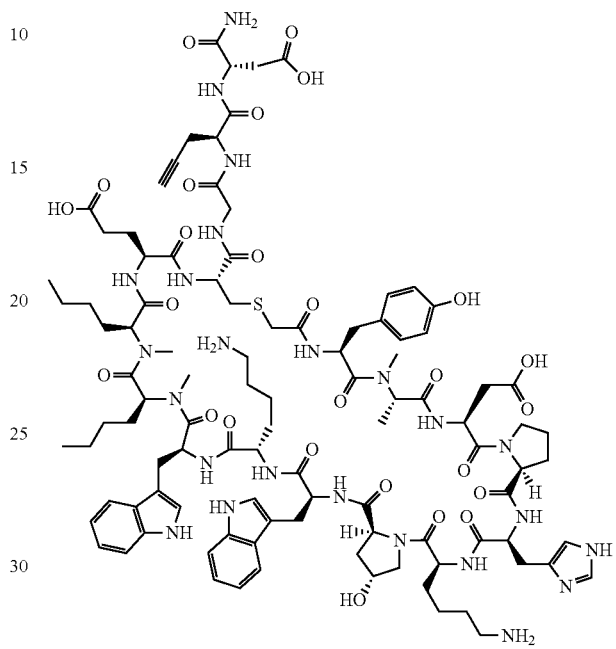

INTERMEDIATE 1400B

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-Trp-mNle-mNle-Glu-Cys-Gly-[(S)-propargylglycine]-Asp; After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 59.5 mg, and its estimated purity by LCMS analysis was 100%. Analysis condition A: Retention time=1.69 min; ESI-MS(+) m/z 1076.2 (M+2H), most abundant ion; Analysis condition B: Retention time=2.91 min; ESI-MS(+) m/z 1076.1 (M+2H), most abundant ion; ESI-HRMS(+) m/z: Calculated: 1075.5118 (M+2H). Found: 1075.5094 (M+2H).

Preparation of INT-1400C

INTERMEDIATE 1400C

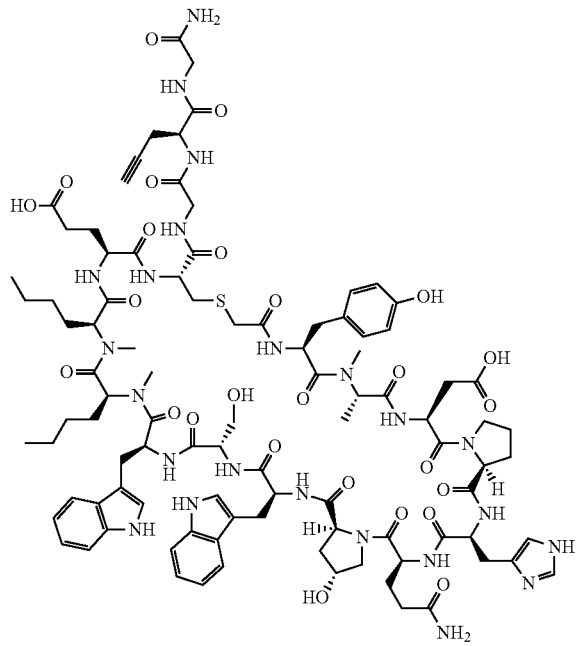

The following peptide was synthesized on a 0.1 mmol scale according to the procedures above. The underlined steps employed the double-coupling procedure. ClAc-Tyr-mAla-Asp-Pro-His-Gln-Hyp-Trp-Ser-Trp-mNle-mNle-Glu-Cys-Gly-[(S)-propargylglycine]-Gly. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation.

The yield of the product was 20.2 mg, and its estimated purity by LCMS analysis was 98%. Analysis condition A: Retention time=1.40 min; ESI-MS(+) m/z 1026.5 (M+2H), most abundant ion; Analysis condition B: Retention time=2.79 min; ESI-MS(+) m/z 1026.5 (M+2H), most abundant ion; ESI-HRMS(+) m/z:

Calculated: 1025.9594 (M+2H). Found: 1025.9591 (M+2H).

Preparation of INT-1400D

INTERMEDIATE 1400D

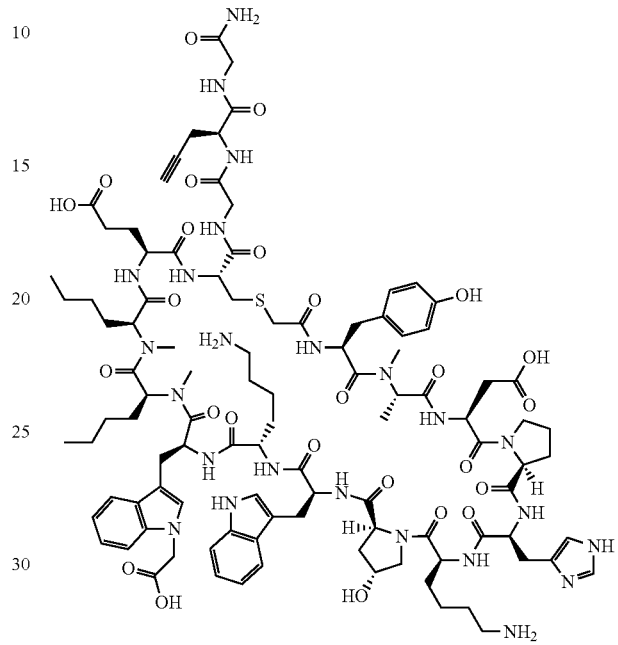

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-"Trp"-mNle-mNle-Glu-Cys-Gly-[(S)-propargylglycine]-Gly. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 6-minute hold at 100% B; Flow: 20 mL/min. Fractions containing the desired product were combined and dried via centrifugal evaporation. The yield of the product was 57.9 mgs, and its estimated purity by LCMS analysis was 100%. Analysis condition A: Retention time=1.16 min; ESI-MS(−) m/z 1076.6 (M+2H), most abundant ion; Analysis condition B: Retention time=2.23 min; ESI-MS(+) m/z 1076.3 (M+2H), most abundant ion; ESI-HRMS(+) m/z: Calculated: 1075.5118 (M+2H). Found: 1075.5086 (M+2H).

807
Preparation of INT-1400E

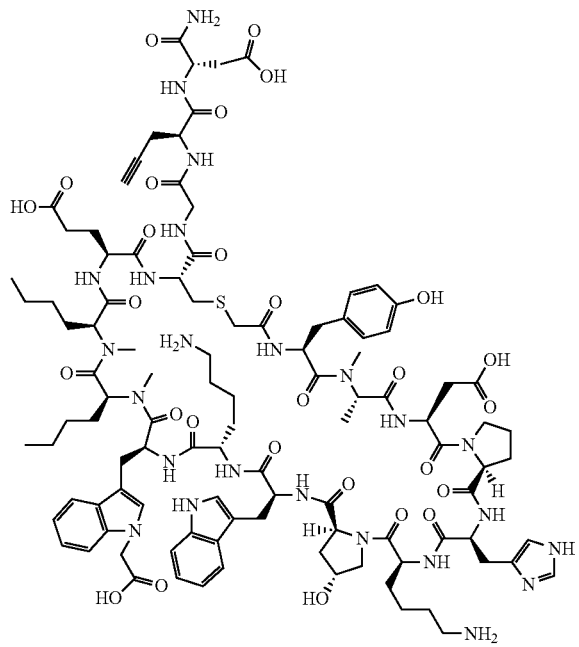

INTERMEDIATE 1400E

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-"Trp"-mNle-mNle-Glu-Cys-Gly-[(S)-propargylglycine]-Asp. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 30-75% B over 30 minutes, then a 6-minute hold at 100% B; Flow: 20 mL/min. Fractions containing the desired product were combined and dried via centrifugal evaporation. The yield of the product was 66.6 mgs, and its estimated purity by LCMS analysis was 94%. Analysis condition A: Retention time=1.12 min; ESI-MS(−) m/z 1105.5 (M+2H), most abundant ion; Analysis condition B: Retention time=2.19 min; ESI-MS(+) m/z 11055.4 (M+2H), most abundant ion; ESI-HRMS(+) m/z: Calculated: 1104.5146 (M+2H). Found: 1104.5115 (M+2H).

808
Preparation of INT-1400F

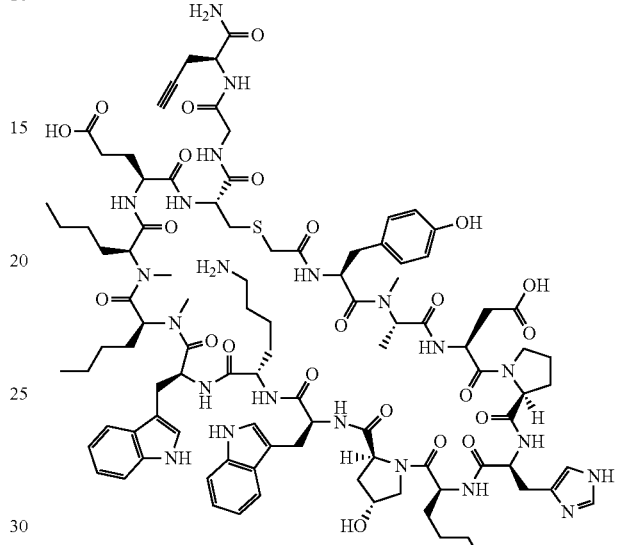

INTERMEDIATE 1400F

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-Trp-mNle-mNle-Glu-Cys-Gly-[(S)-propargylglycine]. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 87.3 mg, and its estimated purity by LCMS analysis was 99%. Analysis condition A: Retention time=1.39 min; ESI-MS(+) m/z 1019.0 (M+2H), most abundant ion; Analysis condition B: Retention time=2.53 min; ESI-MS(+) m/z 1018.9 (M+2H), most abundant ion;

ESI-HRMS(+) m/z: Calculated: 1017.9984 (M+2H). Found: 1017.9944 (M+2H).

Preparation of INT-1400G

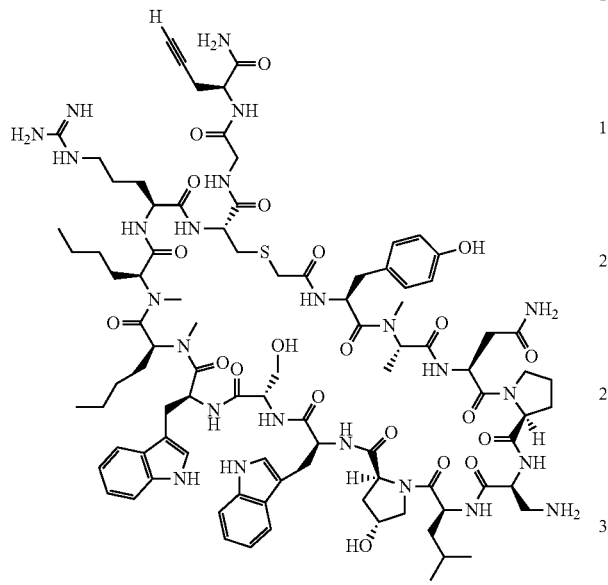

INTERMEDIATE 1400G

The following peptide was synthesized on a 0.2 mmol scale according to the procedures above. The underlined steps employed the double-coupling procedure. ClAc-Tyr-mAla-Asn-Pro-Dap-Leu-Hyp-Trp-Ser-Trp-mNle-mNle-Arg-Cys-Gly-[(S)-propargylglycine]. After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 44.2 mg, and its estimated purity by LCMS analysis was 98%. Analysis condition A: Retention time=1.62 min; ESI-MS(+) m/z 977.7 (M+2H), most abundant ion; Analysis condition B: Retention time=3.16 min; ESI-MS(+) m/z 977.7 (M+2H), most abundant ion; ESI-HRMS(+) m/z: Calculated: 977.4933 (M+2H). Found: 977.4906 (M+2H).

Preparation of INT-1400H

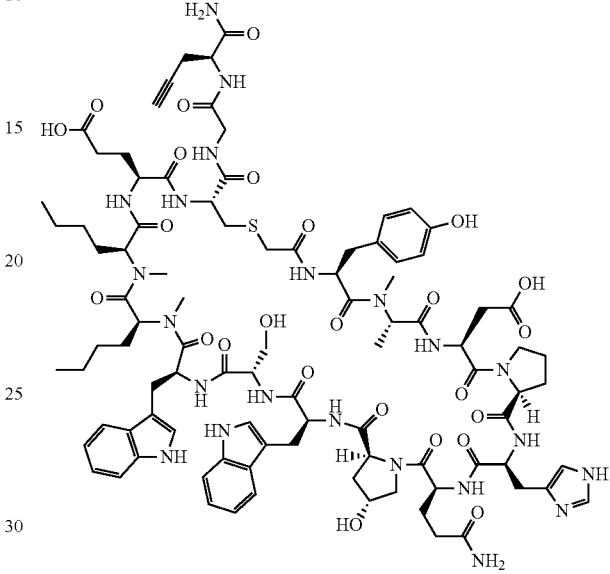

INTERMEDIATE 1400H

The following peptide was synthesized on a 0.2 mmol scale according to the procedures above. The underlined steps employed the double-coupling procedure. ClAc-Tyr-mAla-Asp-Pro-His-Gln-Hyp-Trp-Ser-Trp-mNle-mNle-Glu-Cys-Gly-[(S)-propargylglycine]; After deprotection and cyclization according to the procedures above, the compound was purified as follows: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 23.9 mg, and its estimated purity by LCMS analysis was 98%. Analysis condition A: Retention time=1.45 min; ESI-MS(+) m/z 997.5 (M+2H), most abundant ion; Analysis condition B: Retention time=2.87 min; ESI-MS(+) m/z 997.9 (M+2H), most abundant ion; ESI-HRMS(+) m/z: Calculated: 997.4487 (M+2H). Found: 997.4486 (M+2H).

Preparation of INT-1400I

INTERMEDIATE 1400I

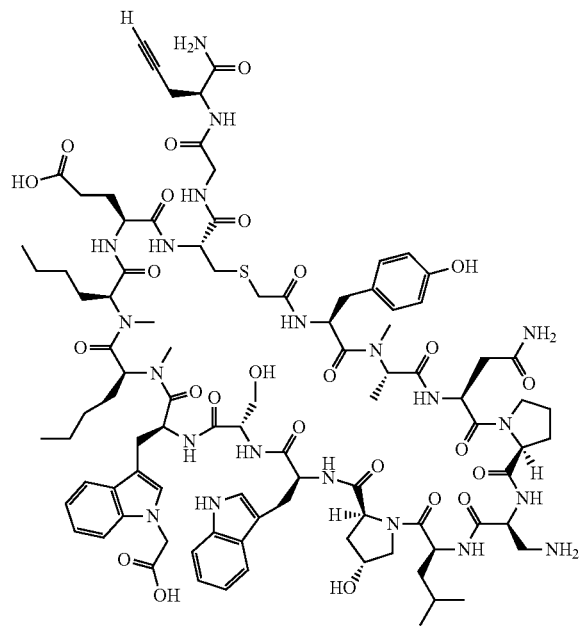

The following peptide was synthesized on a 0.1 mmol scale according to the procedures above. The underlined steps employed the double-coupling procedure. ClAc-Tyr-mAla-Asn-Pro-Dap-Leu-Hyp-Trp-Ser-[(S)-2-amino-3-(1-(carboxymethyl)-1H-indol-3-yl)propanoic acid]-mNle-mNle-E-Cys-Gly-[(S)-propargylglycine]. After deprotection and cyclization according to the procedures above, the compound was purified as follows: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-40% B over 20 minutes, then a 5-minute hold at 100% B; Flow: 20 mL/min. Fractions containing the desired product were combined and dried via centrifugal evaporation. The yield of the product was 42.1 mg, and its estimated purity by LCMS analysis was 98%. Analysis condition A: Retention time=1.26 min; ESI-MS(+) m/z 993.3 (M+2H), most abundant ion; Analysis condition B: Retention time=2.68 min; ESI-MS(+) m/z 993.3 (M+2H), most abundant ion; ESI-HRMS(+) m/z: Calculated: 992.9667 (M+2H). Found: 992.9660 (M+2H).

Preparation of INT-1400J

INTERMEDIATE 1400J

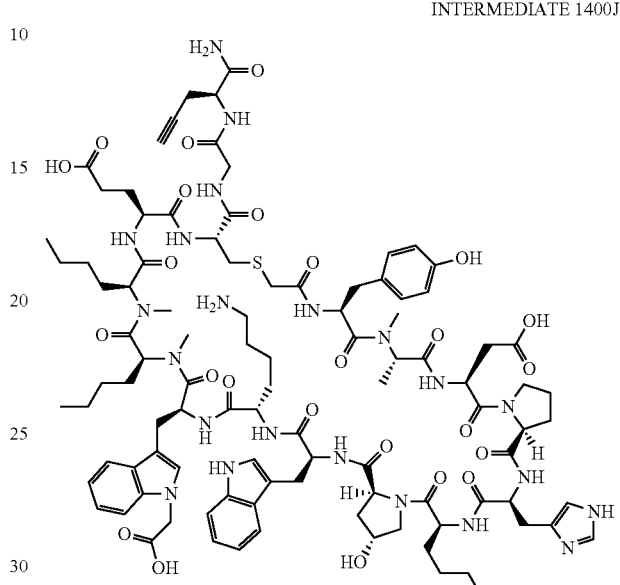

The following peptide was synthesized on a 0.2 mmol scale according to the procedures above. The underlined steps employed the double-coupling procedure. ClAc-Tyr-mAla-Asp-Pro-His-Lys-Hyp-Trp-Lys-[(S)-2-amino-3-(1-(carboxymethyl)-1H-indol-3-yl)propanoic acid]-mNle-mNle-Glu-Cys-Gly-[(S)-propargylglycine]; After deprotection and cyclization according to the procedures above, the compound was purified as follows: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 78.3 mg, and its estimated purity by LCMS analysis was 100%. Analysis condition A: Retention time=1.25 min; ESI-MS(+) m/z 1047.6 (M+2H), most abundant ion Analysis condition B: Retention time=2.65 min; ESI-MS(+) m/z 1047.4 (M+2H), most abundant ion ESI-HRMS(+) m/z: Calculated: 1047.0011 (M+2H).

Found: 1046.9960 (M+2H).

813
Preparation of INT-1400K

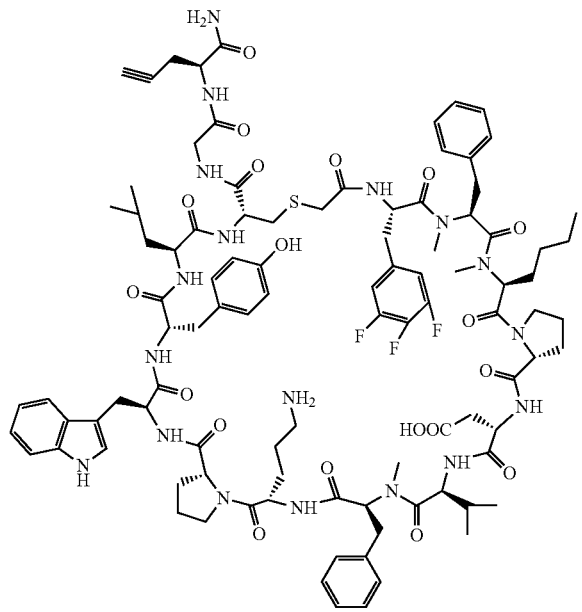

INTERMEDIATE 1400K

The following peptide was synthesized on a 0.1 mmol scale according to the procedures above. The underlined steps employed the double-coupling procedure. ClAc-F3Phe-mPhe-mNle-dPro-Asp-Val-mPhe-Orn-dPro-Trp-Tyr-Leu-Cys-Gly-[(S)-propargylglycine]. After deprotection and cyclization according to the procedures above, the compound was purified as follows: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation.

The yield of the product was 88.5 mg, and its estimated purity by LCMS analysis was 95%. Analysis condition A: Retention time=1.87 min; ESI-MS(+) m/z 975.7 (M+2H), most abundant ion. Analysis condition B: Retention time=3.25 min; ESI-MS(+) m/z 975.1 (M+2H), most abundant ion; ESI-HRMS(+) m/z: Calculated: 974.4593 (M+2H).

Found: 974.4571 (M+2H).

814
Preparation of INT-1400L

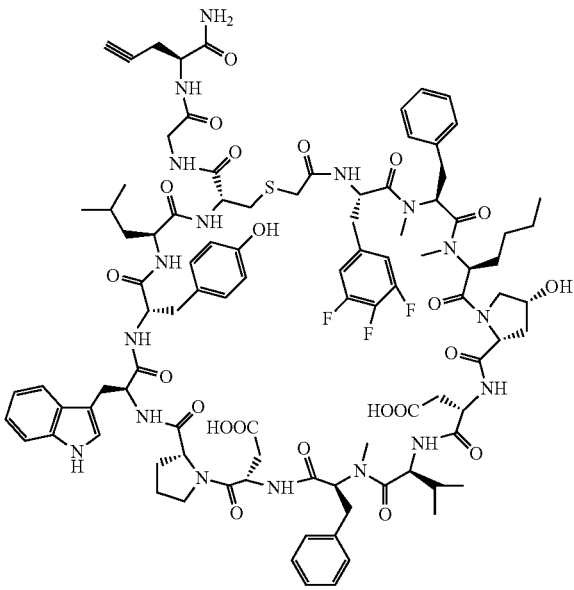

INTERMEDIATE 1400L

The following peptide was synthesized on a 0.1 mmol scale according to the procedures above. The underlined steps employed the double-coupling procedure. ClAc-F3Phe-mPhe-mNle-dHyp-Asp-Val-mPhe-Asp-dPro-Trp-Tyr-Leu-Cys-Gly-[(S)-propargylglycine]; After deprotection and cyclization according to the procedures above, the compound was purified as follows: The crude material was purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 70.7 mg, and its estimated purity by LCMS analysis was 100%. Analysis condition A: Retention time=1.47 min; ESI-MS(+) m/z 983.5 (M+2H), most abundant ion; Analysis condition B: Retention time=2.74 min; ESI-MS(+) m/z 983.7 (M+2H), most abundant ion; ESI-HRMS(+) m/z: Calculated: 982.9306 (M+2H). Found: 982.9300 (M+2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:
Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:
Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis Condition C:
Column: Waters Aquity UPLC BEH C18, 2.1×50 mm, 1.7-µm particles; Mobile Phase A: 100% Water: 0.05% TFA; Mobile Phase B: 100% Acetonitrile: 0.05% TFA; Temperature: 40° C.; Gradient: 2-98% B over 1.5 minutes, then a 0.5-minute hold at 100% B; Flow: 0.8 mL/min; Detection: UV at 220 nm.

Analysis Condition D:
Column: PHENOMENEX-LUNA 2.0×30 mm 3 um; Mobile Phase A: 90% Water-10% Methanol-0.1% TFA; Mobile Phase B: 10% Water-90% Methanol-0.1% TFA; Gradient: 0-100% B over 2 minutes, then a 1 to 4 minute hold at 100% B; Flow: 1 mL/min; Detection: UV at 220 nm.

Analysis Condition E:
Column: Xbridge Phenyl, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 5-100% B over 15 minutes; Flow: 0.5 mL/min; Detection: UV at 220 nm.

Analysis Condition F:
Column: XBridge C18, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 10-100% B over 30 minutes; Flow: 0.5 mL/min; Detection: UV at 220 nm.

Analysis Condition G:
Column: Waters CSH C18, 2.0×50 mm, 1.7-µm particles; Mobile Phase A: 5:95 acetonitrile:water with 0.1% TFA; Mobile Phase B: 95:5 acetonitrile:water with 0.1% TFA; Temperature: 50° C.; Gradient: 0% B, 0-100% B over 3 minutes, then a 0.5-minute hold at 100% B; Flow: 1 mL/min; Detection: UV at 220 nm.

Analysis Condition H:
Column: Xbridge C18, 3.0×150 mm, 3.5-µm particles; Mobile Phase A: 5:95 acetonitrile:water with 10 mM ammonium acetate; Mobile Phase B: 95:5 acetonitrile:water with 10 mM ammonium acetate; Gradient: 10-100% B over 18 minutes; Flow: 0.5 mL/min; Detection: UV at 220 nm.

Analysis Condition I:
Column: XSelectCSH C18, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 1.0 mL/min; Detection: UV at 220 nm.

Analysis Condition J:
Column: Zorbax Bonus RP, 3.0×150 mm, 3.5-µm particles; Mobile Phase A: 5:95 acetonitrile:water with 0.1% TFA; Mobile Phase B: 95:5 acetonitrile:water with 0.1% TFA; Gradient: 10-100% B over 15 minutes; Flow: 1.0 mL/min; Detection: UV at 220 nm.

Analysis Condition K:

Column: Waters Aquity UPLC BEH C18, 2.1×50 mm, 1.7-µm particles; Mobile Phase A: 100% Water: 0.05% TFA; Mobile Phase B: 100% Acetonitrile: 0.05% TFA; Temperature: 50° C.; Gradient: 2-98% B over 3.0 minutes, then a 0.5-minute hold at 100% B; Flow: 0.8 mL/min; Detection: UV at 220 nm.

Preparation of 14051

Example 14051

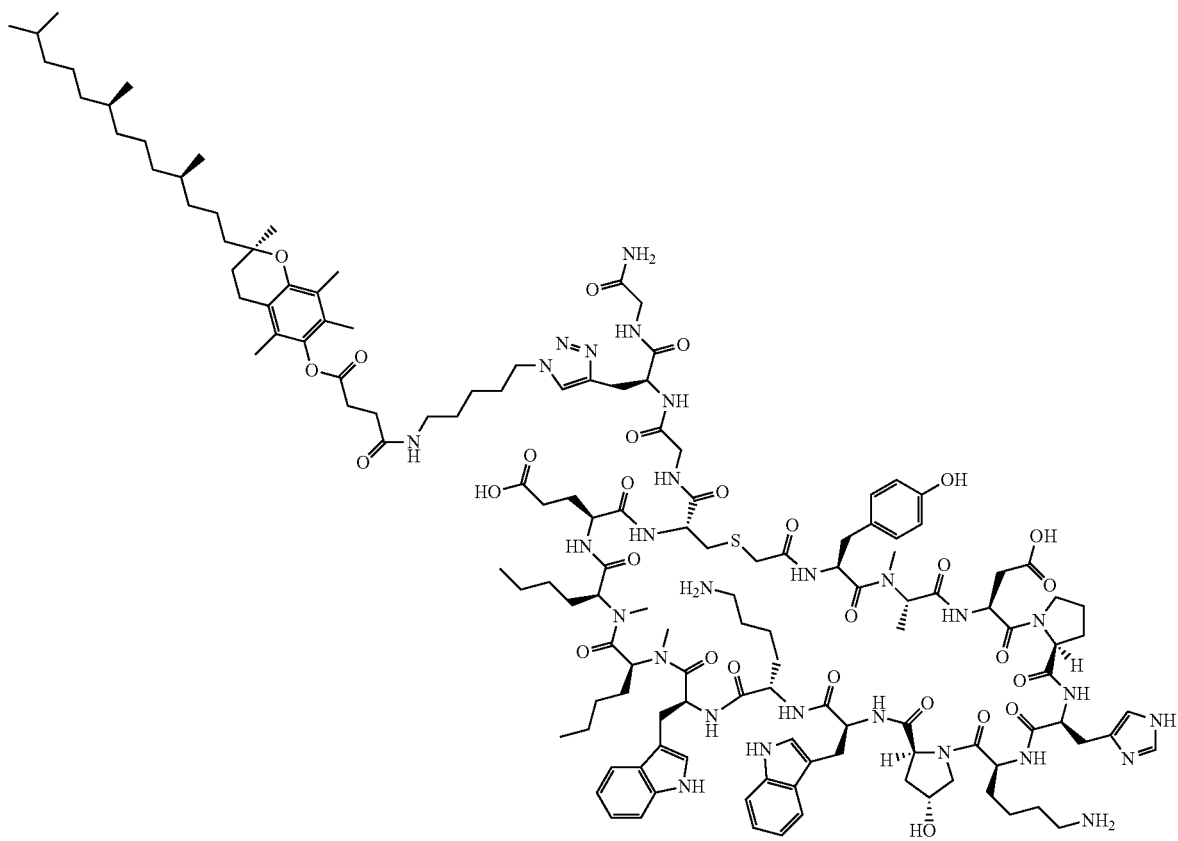

Intermediate 1400A (20 mg, 9.56 μmol) and (R)-2,5,7,8-tetramethyl-2-((4R,8R)-4,8,12-trimethyltridecyl)chroman-6-yl 4-((5-azidopentyl)amino)-4-oxobutanoate (18.38 mg, 0.029 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 55-100% B, 25 min, then a 6-minute hold at 100% B). Fractions containing the desired product were combined and dried via speed vacuum evaporation. The yield of the product was 7.22 mg, and its estimated purity by LCMS analysis was 90%. Analysis condition C: Retention time=1.64 min; ESI-MS(+) m/z 1367.8 (M+2H), most abundant ion. Analysis condition D: Retention time=2.48 min; ESI-MS(+) m/z 1367.4 (M+2H), most abundant ion.

Preparation of 14052

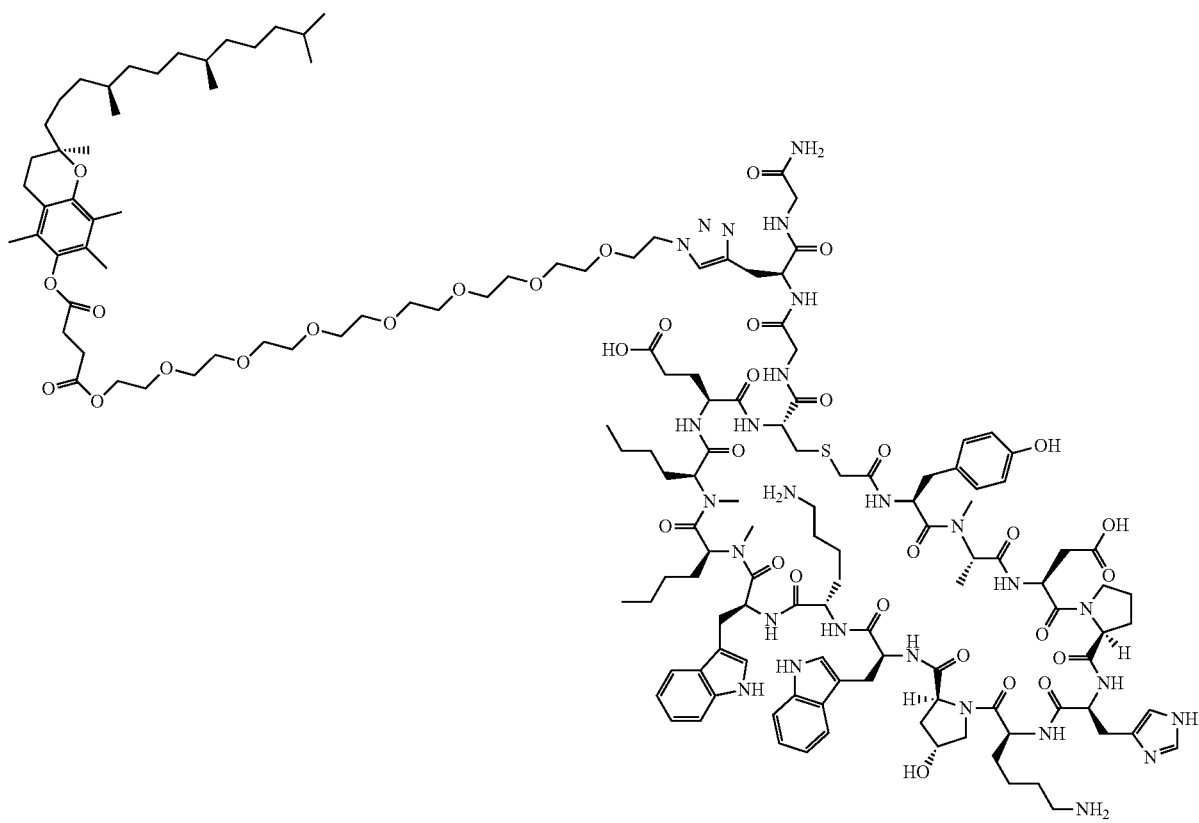

Example 14052

Intermediate 1400A (20 mg, 9.56 µmol) and 23-azido-3,6,9,12,15,18,21-heptaoxatricosyl((R)-2,5,7,8-tetramethyl-2-((4R,8R)-4,8,12-trimethyltridecyl)chroman-6-yl) succinate (26.0 mg, 0.029 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 25 min, then a 10-minute hold at 100% B). Fractions containing the desired product were combined and dried via speed vacuum evaporation. The yield of the product was 11 mg, and its estimated purity by LCMS analysis was 90%. Analysis condition C: Retention time=1.66 min; ESI-MS(+) m/z 1501.5 (M+2H), most abundant ion; Analysis condition D: Retention time=2.63 min; ESI-MS(+) m/z 1001.1 (M+3H), most abundant ion.

Preparation of 14053

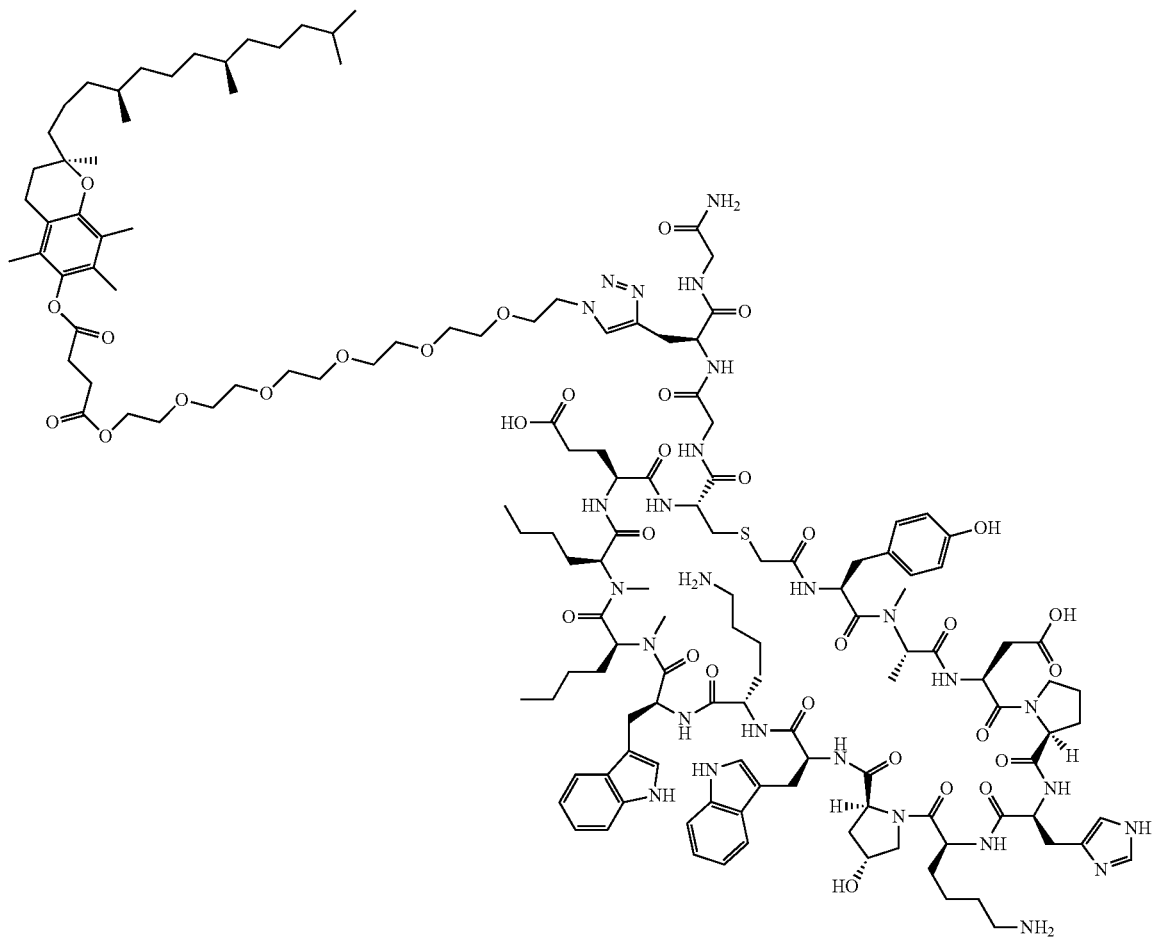

Example 14053

Intermediate 1400A (20 mg, 9.56 μmol) and 17-azido-3,6,9,12,15-pentaoxaheptadecyl ((R)-2,5,7,8-tetramethyl-2-((4R,8R)-4,8,12-trimethyltridecyl)chroman-6-yl) succinate (23.52 mg, 0.029 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 25 min, then a 7-minute hold at 100% B). Fractions containing the desired product were combined and dried via speed vacuum evaporation. The yield of the product was 5.3 mg, and its estimated purity by LCMS analysis was 90%. Analysis condition C: Retention time=1.66 min; ESI-MS(+) m/z 1457.4 (M+2H), most abundant ion; Analysis condition D: Retention time=3.22 min; ESI-MS(+) m/z 971.8 (M+3H), most abundant ion.

Preparation of 14054

Example 14054

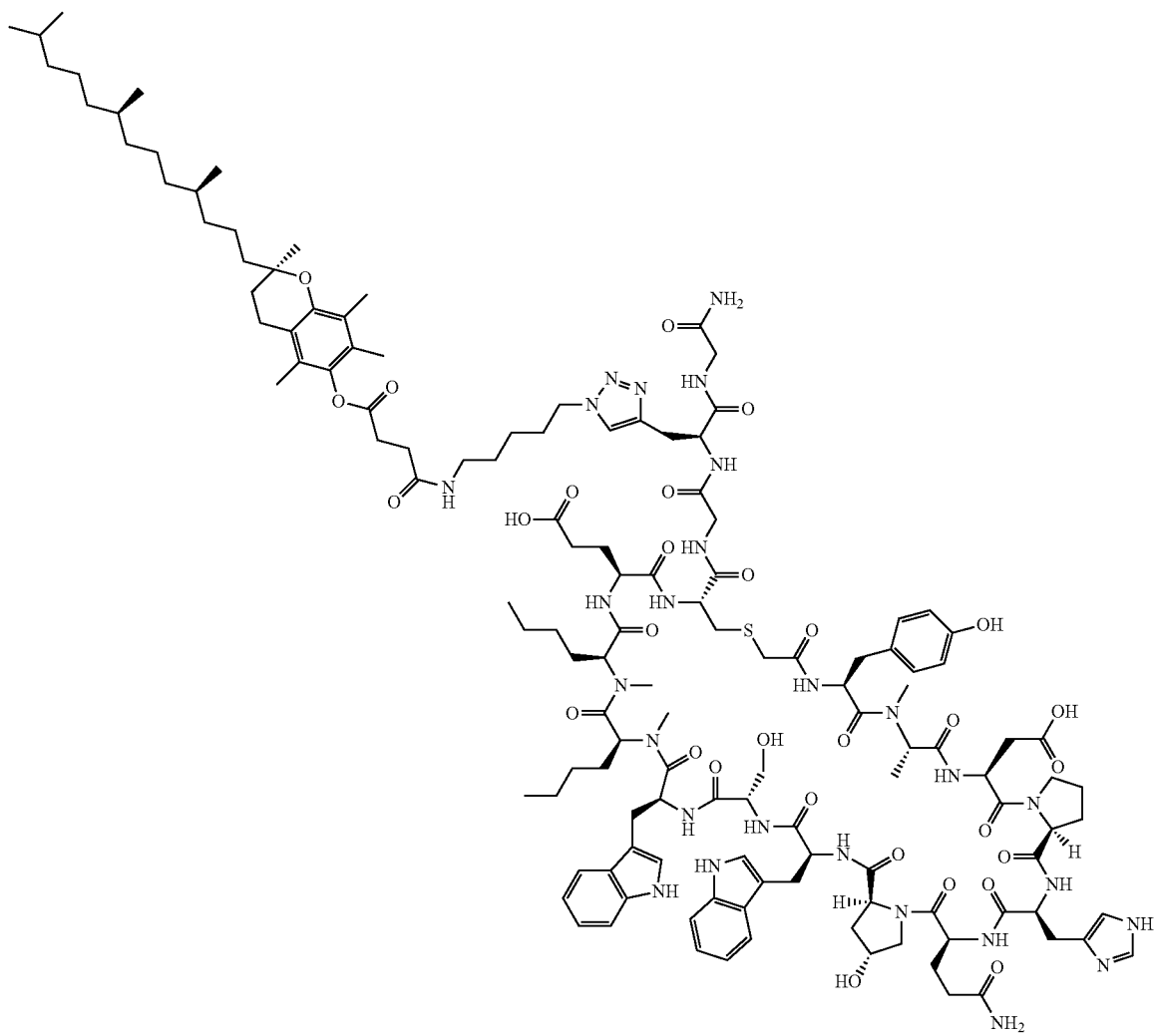

Intermediate 1400C (20 mg, 9.75 μmol) and (R)-2,5,7,8-tetramethyl-2-((4R,8R)-4,8,12-trimethyltridecyl)chroman-6-yl 4-((5-azidopentyl)amino)-4-oxobutanoate (18.38 mg, 0.029 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 55-100% B, 25 min, then a 10-minute hold at 100% B). Fractions containing the desired product were combined and dried via speed vacuum evaporation. The yield of the product was 8.2 mg, and its estimated purity by LCMS analysis was 90%. Analysis condition C: Retention time=1.76 min; ESI-MS(+) m/z 1347.3 (M+2H), most abundant ion. Analysis condition D: Retention time=2.79 min; ESI-MS(+) m/z 898.3 (M+3H), most abundant ion.

Preparation of 14055

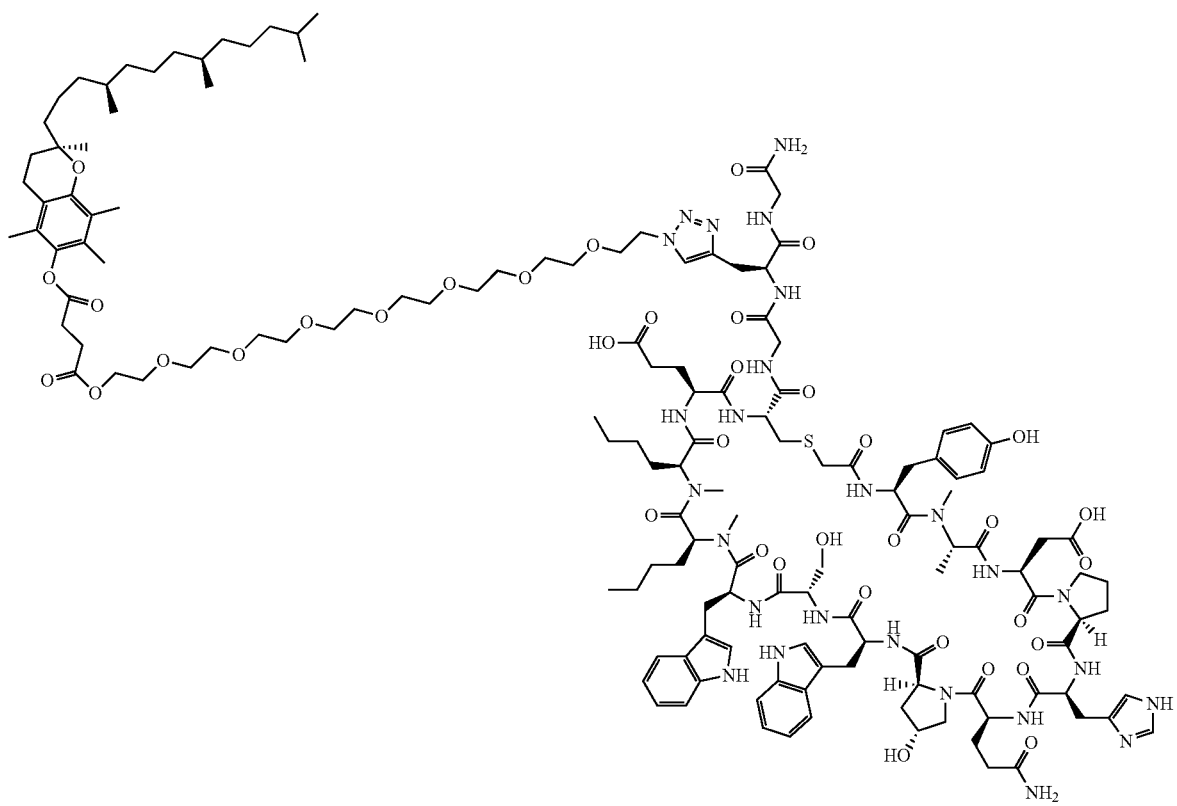

Example 14055

Intermediate 1400C (20 mg, 9.75 µmol) and 23-azido-3,6,9,12,15,18,21-heptaoxatricosyl((R)-2,5,7,8-tetramethyl-2-((4R,8R)-4,8,12-trimethyltridecyl)chroman-6-yl) succinate (26.6 mg, 0.029 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 55-100% B, 25 min, then a 15-minute hold at 100% B). Fractions containing the desired product were combined and dried via speed vacuum evaporation. The yield of the product was 9.0 mg, and its estimated purity by LCMS analysis was 90%. Analysis condition C: Retention time=1.82 min; ESI-MS(+) m/z 1480.9 (M+2H), most abundant ion; Analysis condition D: Retention time=2.99 min; ESI-MS(+) m/z 1480.9 (M+2H), most abundant ion.

Preparation of 14056

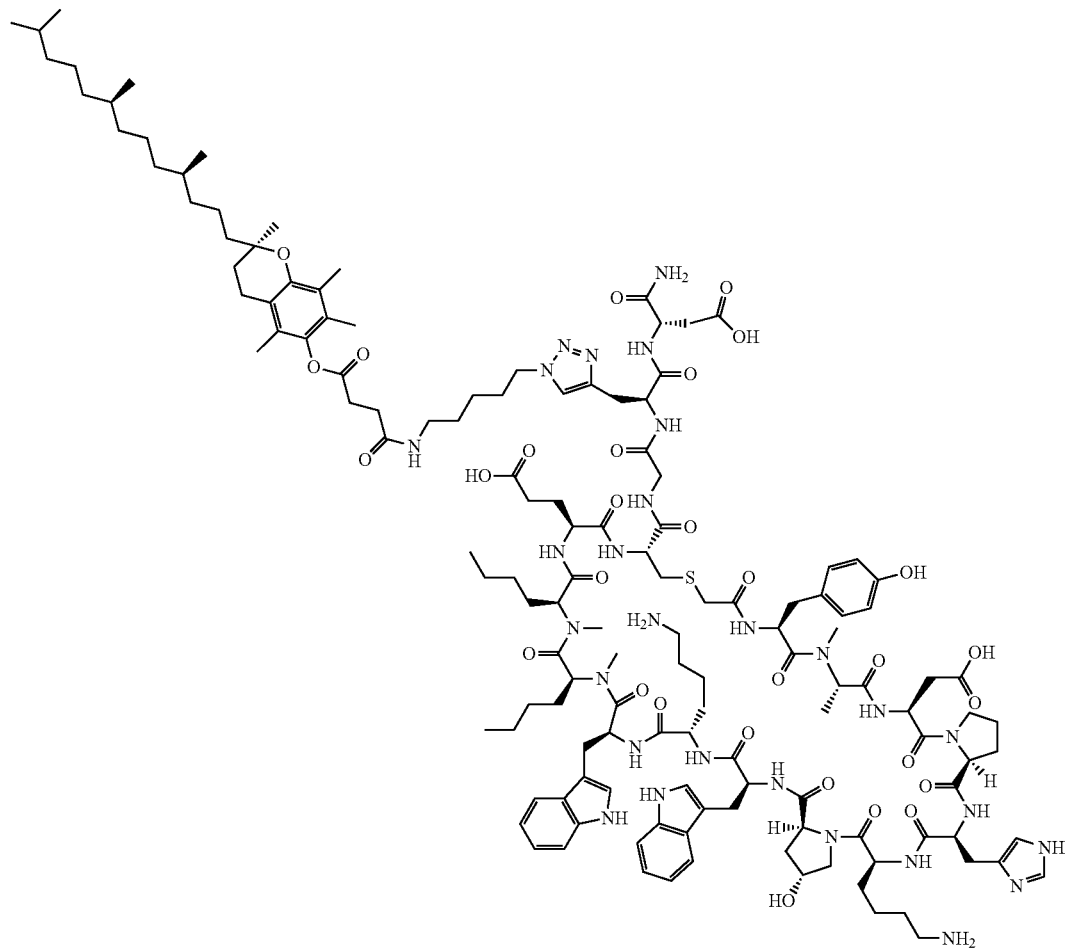

Example 14056

Intermediate 1400B (20 mg, 9.30 μmol) and (R)-2,5,7,8-tetramethyl-2-((4R,8R)-4,8,12-trimethyltridecyl)chroman-6-yl 4-((5-azidopentyl)amino)-4-oxobutanoate (17.88 mg, 0.028 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 25 min, then a 6-minute hold at 100% B). Fractions containing the desired product were combined and dried via speed vacuum evaporation. The yield of the product was 4.3 mg, and its estimated purity by LCMS analysis was 90%. Analysis condition D: Retention time=2.42 min; ESI-MS(+) m/z 931.4 (M+3H), most abundant ion.

Preparation of Example 14057

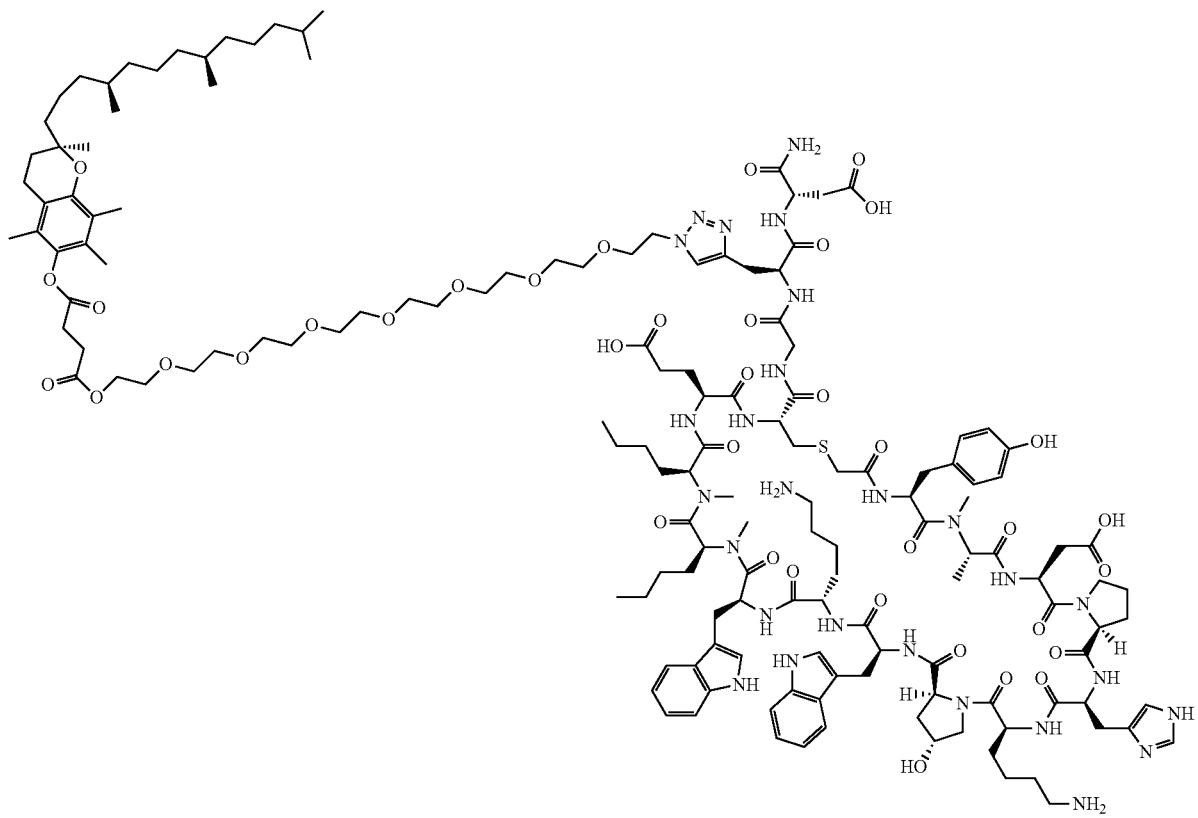

Example 14057

Intermediate 1400B (20 mg, 9.30 µmol) and 23-azido-3,6,9,12,15,18,21-heptaoxatricosyl((R)-2,5,7,8-tetramethyl-2-((4R,8R)-4,8,12-trimethyltridecyl)chroman-6-yl) succinate (25.3 mg, 0.028 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 25 min, then a 10-minute hold at 100% B). Fractions containing the desired product were combined and dried via speed vacuum evaporation The yield of the product was 4.3 mg, and its estimated purity by LCMS analysis was 90%. Analysis condition C: Retention time=1.44 min; ESI-MS(+) m/z 929.3 (M+2H); Analysis condition D: Retention time=2.66 min; ESI-MS(+) m/z 929.8 (M+2H), most abundant ion.

Preparation of Example 14058

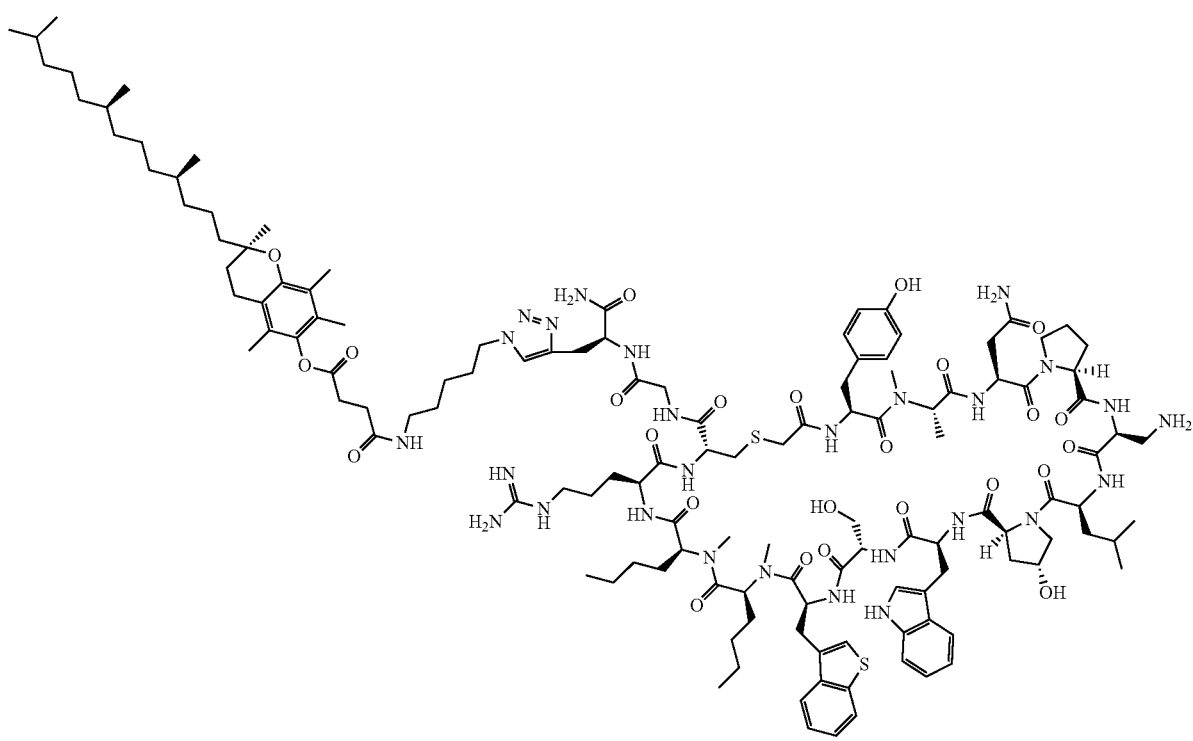

Example 14058

Intermediate 1300A (20 mg, 10.15 μmol) and (R)-2,5,7,8-tetramethyl-2-((4R,8R)-4,8,12-trimethyltridecyl)chroman-6-yl-4-((5-azidopentyl)amino-4-oxobutanoate (19.51 mg, 0.030 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1 TFA. Column: PHENOMENEX LUNA 30×100 mm, S10, Flow rate: 40 ml/min, 55-100% B, 25 min, then a 10-minute hold at 100% B). Fractions containing the desired product were combined and dried via speed vacuum evaporation. The yield of the product was 1.5 mg, and its estimated purity by LCMS analysis was 90%. Analysis condition D: Retention time=2.77 min; ESI-MS(+) m/z 1307.3 (M+2H).

Preparation of Example 14059

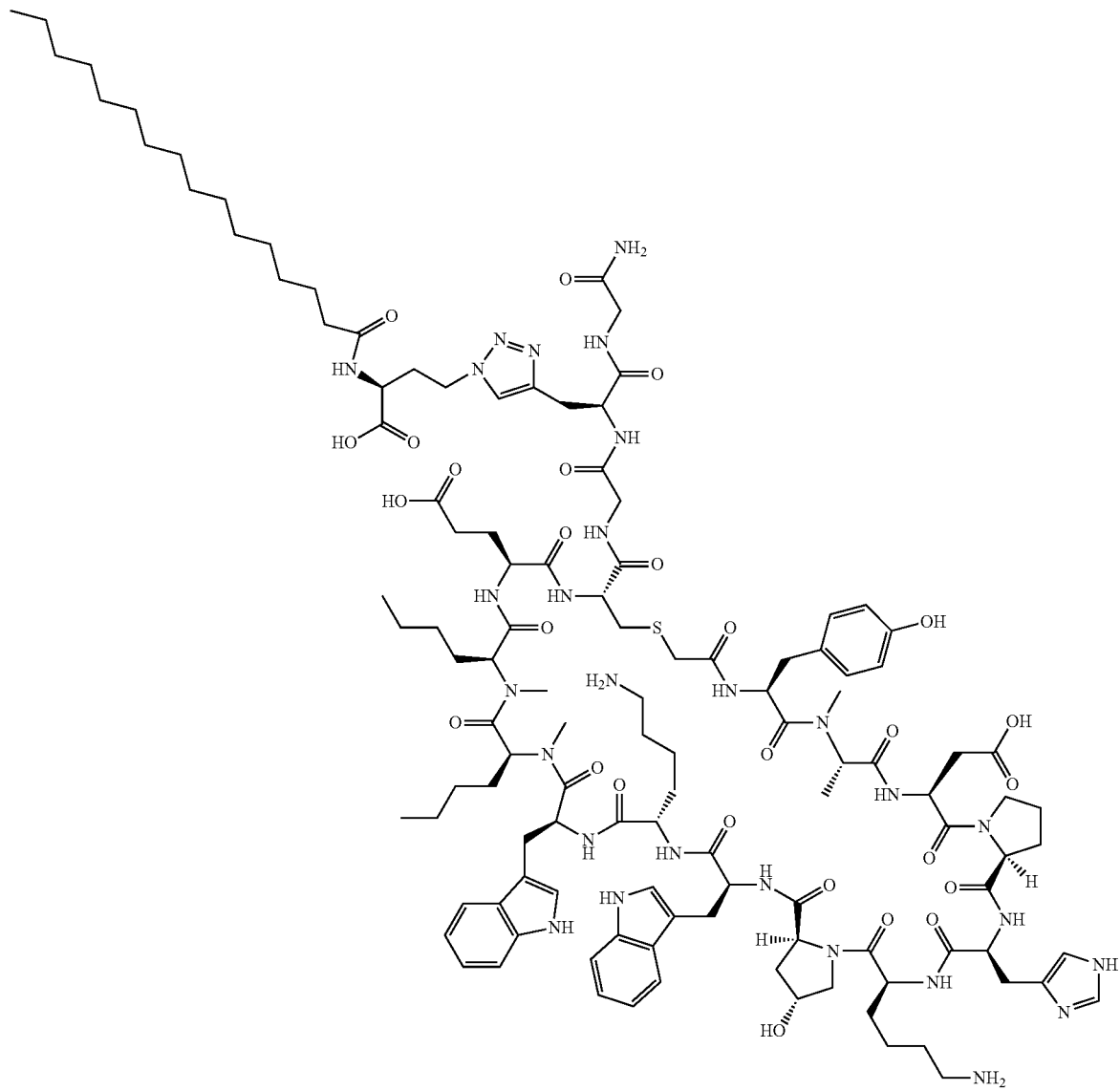

Example 14059

Intermediate 1400AB (25 mg, 0.012 μmol) and (S)-4-azido-2-palmitamidobutanoic acid (13.71 mg, 0.036 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 30 min). Fractions containing the desired product were combined and dried via speed vacuum evaporation. The yield of the product was 1.5 mg, and its estimated purity by LCMS analysis was 90%. Analysis condition D: Retention time=2.32 min; ESI-MS(+) m/z 1238.8 (M+2H).

Preparation of Example 14060

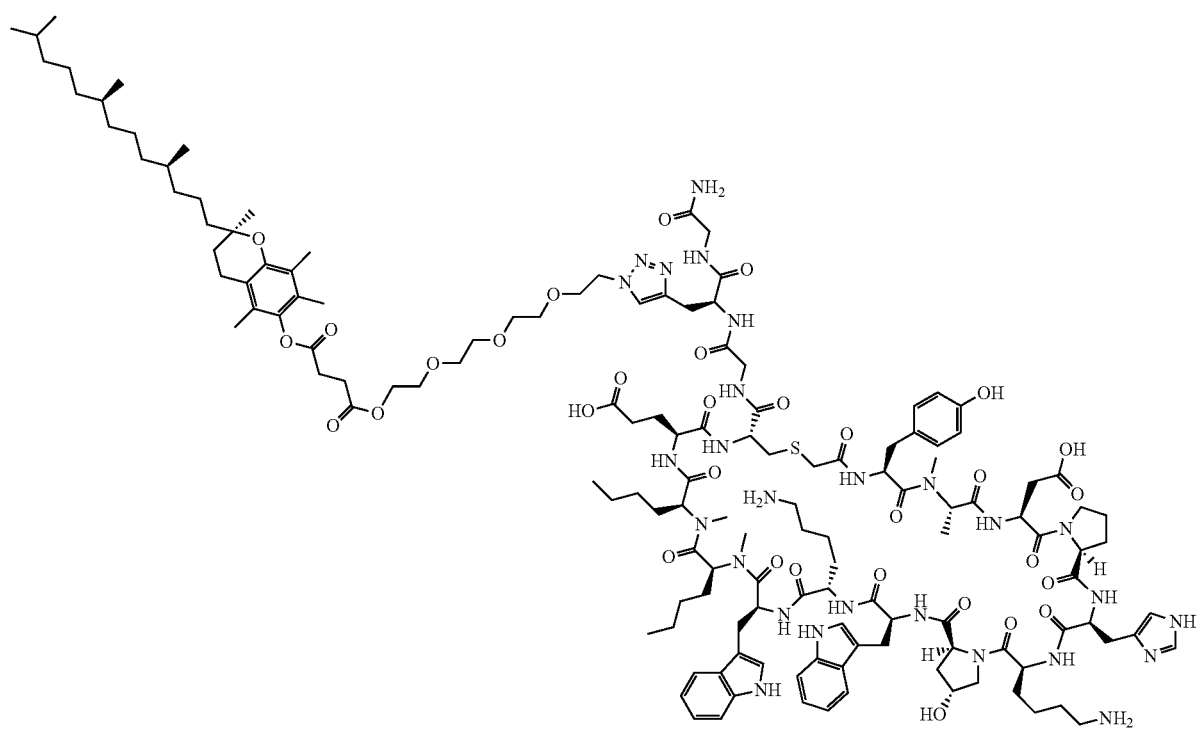

Example 14060

Intermediate 1400A (20 mg, 9.56 µmol) and 2-(2-(2-(2-azidoethoxy)ethoxy)ethoxy)ethyl((R)-2,5,7,8-tetramethyl-2-((4R,8R)-4,8,12-trimethyltridecyl)chroman-6-yl) succinate (20.99 mg, 0.029 mmol), were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 30 min, then a 3-minute hold at 100% B). Fractions containing the desired product were combined and dried via speed vacuum evaporation. The yield of the product was 1.5 mg, and its estimated purity by LCMS analysis was 90%. Analysis condition D: Retention time=2.52 min; ESI-MS(+) m/z 1413.1 (M+2H), most abundant ion.

Preparation of Example 14061

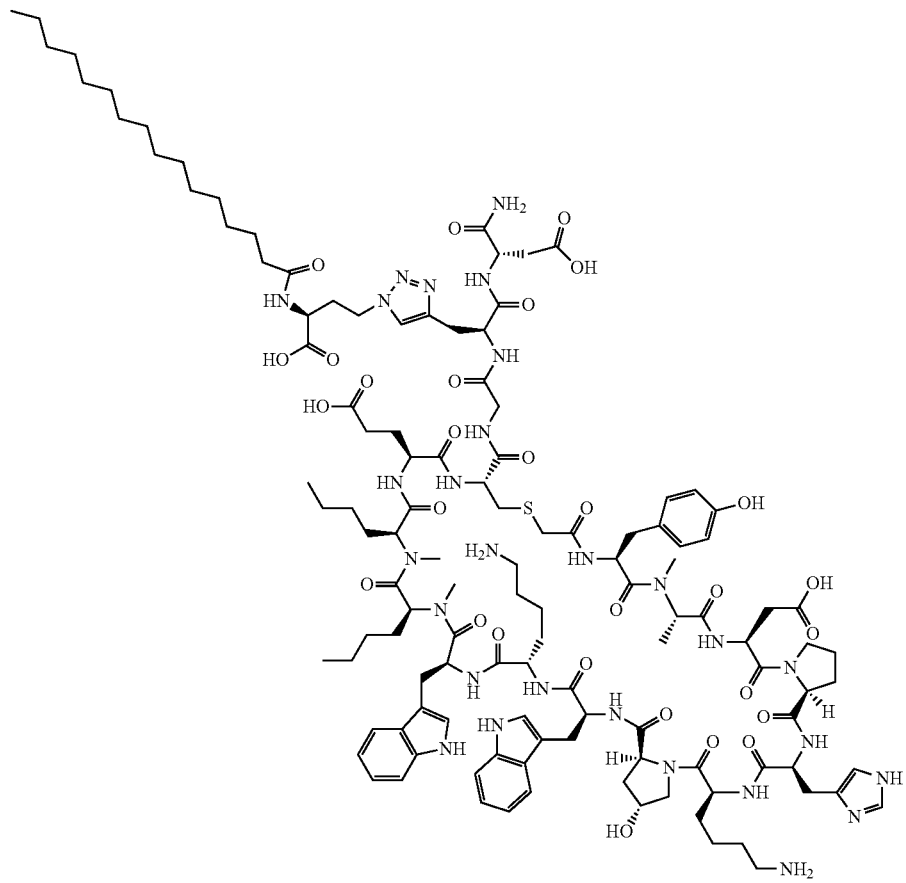

Example 14061

Intermediate 1400B (25 mg, 0.012 mmol) and (S)-4-azido-2-palmitamidobutanoic acid (13.34 mg, 0.035 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 55-100% B, 30 min). Fractions containing the desired product were combined and dried via speed vacuum evaporation The yield of the product was 9.0 mg, and its estimated purity by LCMS analysis was 90%. Analysis condition D: Retention time=2.31 min; ESI-MS(+) m/z 1267.7 (M+2H), most abundant ion.

Preparation of Example 14062

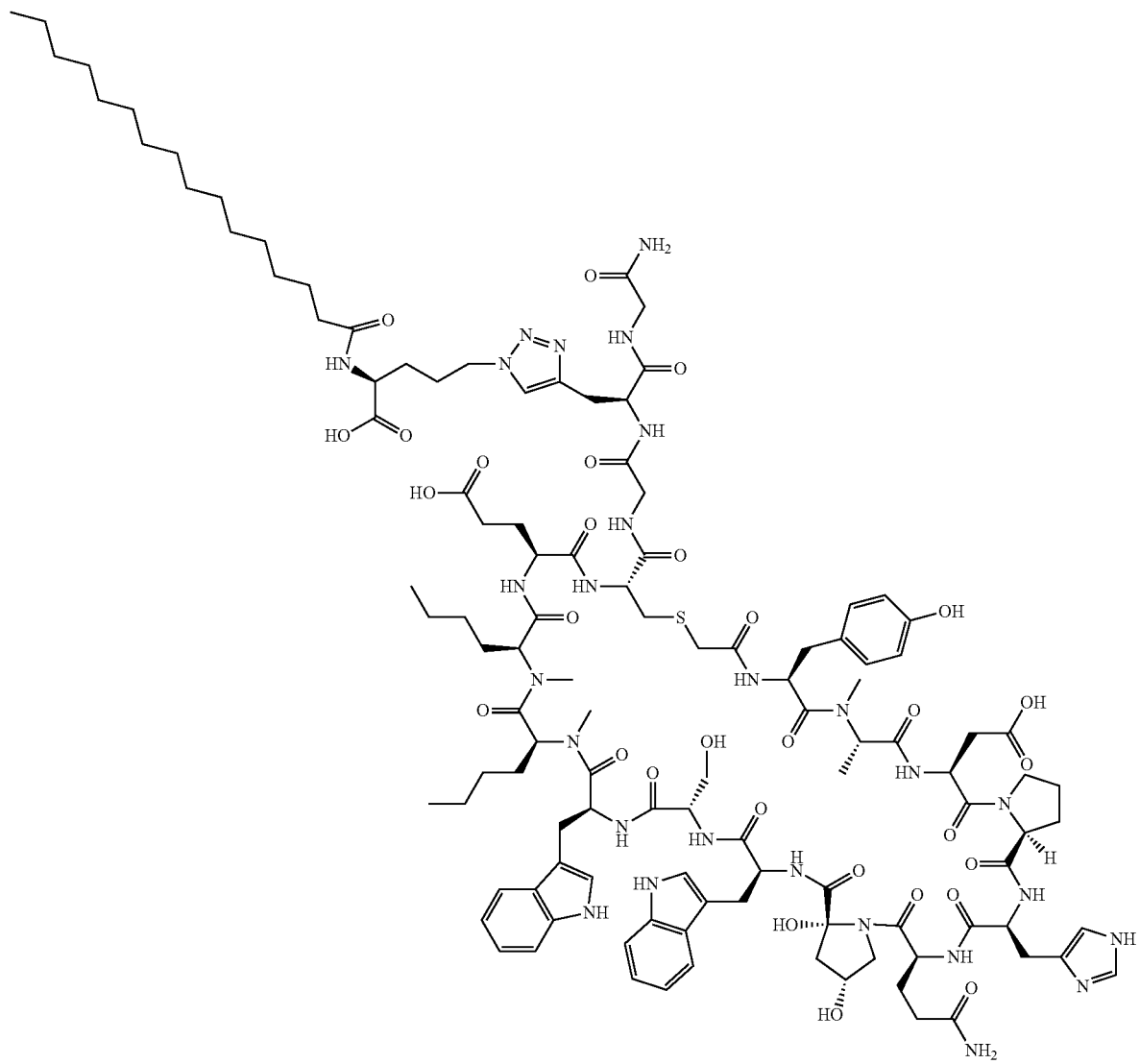

Example 14062

Intermediate 1400C (25 mg, 0.012 mmol) and (S)-4-azido-2-palmitamidobutanoic acid (13.99 mg, 0.037 mmol) were reacted as in the general triazole formation procedure above to afford crude product. The crude material was purified via Prep-HPLC (Solvent A=10% MeOH-90% H2O-0.1% TFA, purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 55-100% B, 30 min). Fractions containing the desired product were combined and dried via speed vacuum evaporation. The yield of the product was 10.0 mg, and its estimated purity by LCMS analysis was 90%. Analysis condition D: Retention time=2.47 min; ESI-MS(+) m/z 1217.9 (M+2H), most abundant ion.

Preparation of Example 14063

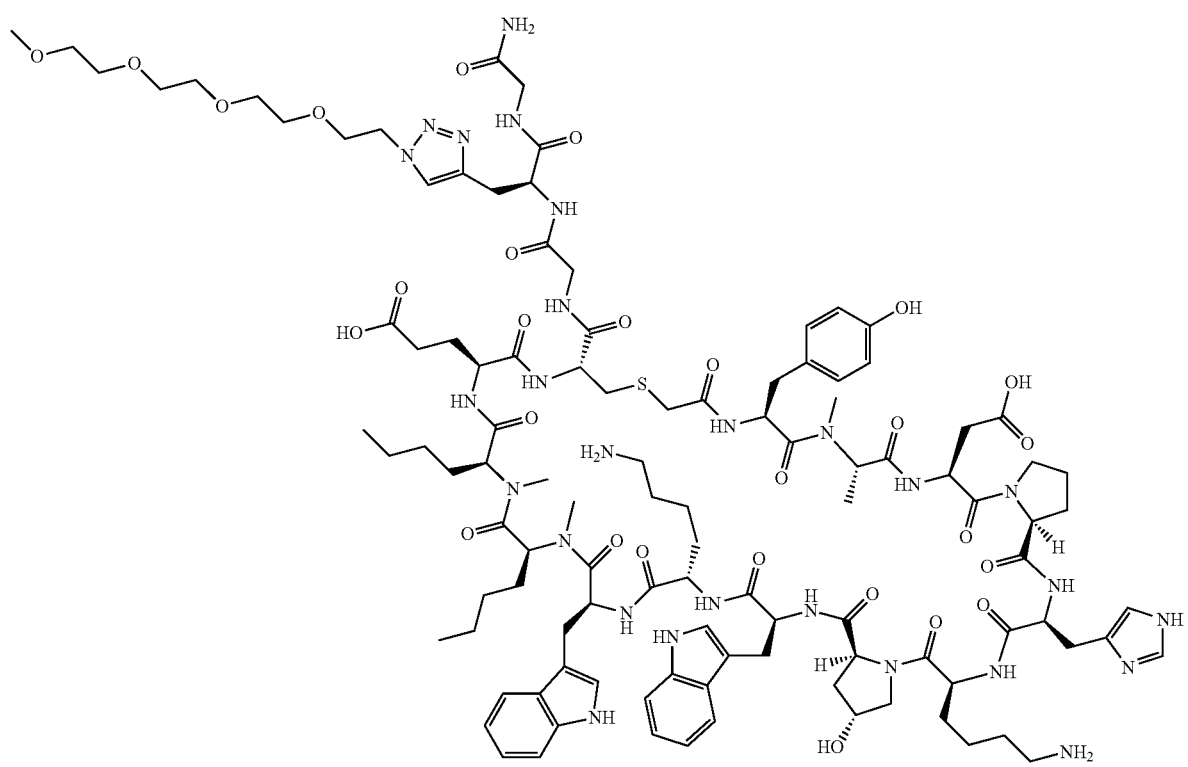

Example 14063

Intermediate 1400A (20 mg, 9.56 μmol) and 13-azido-2,5,8,11-tetraoxatridecane (6.69 mg, 0.029 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 35-100% B, 45 min). Fractions containing the desired product were combined and dried via speed vacuum evaporation. The yield of the product was 9.0 mg, and its estimated purity by LCMS analysis was 90%. Analysis condition D: Retention time=1.83 min; ESI-MS(+) m/z 1163.7 (M+2H), most abundant ion.

Preparation of Example 14064

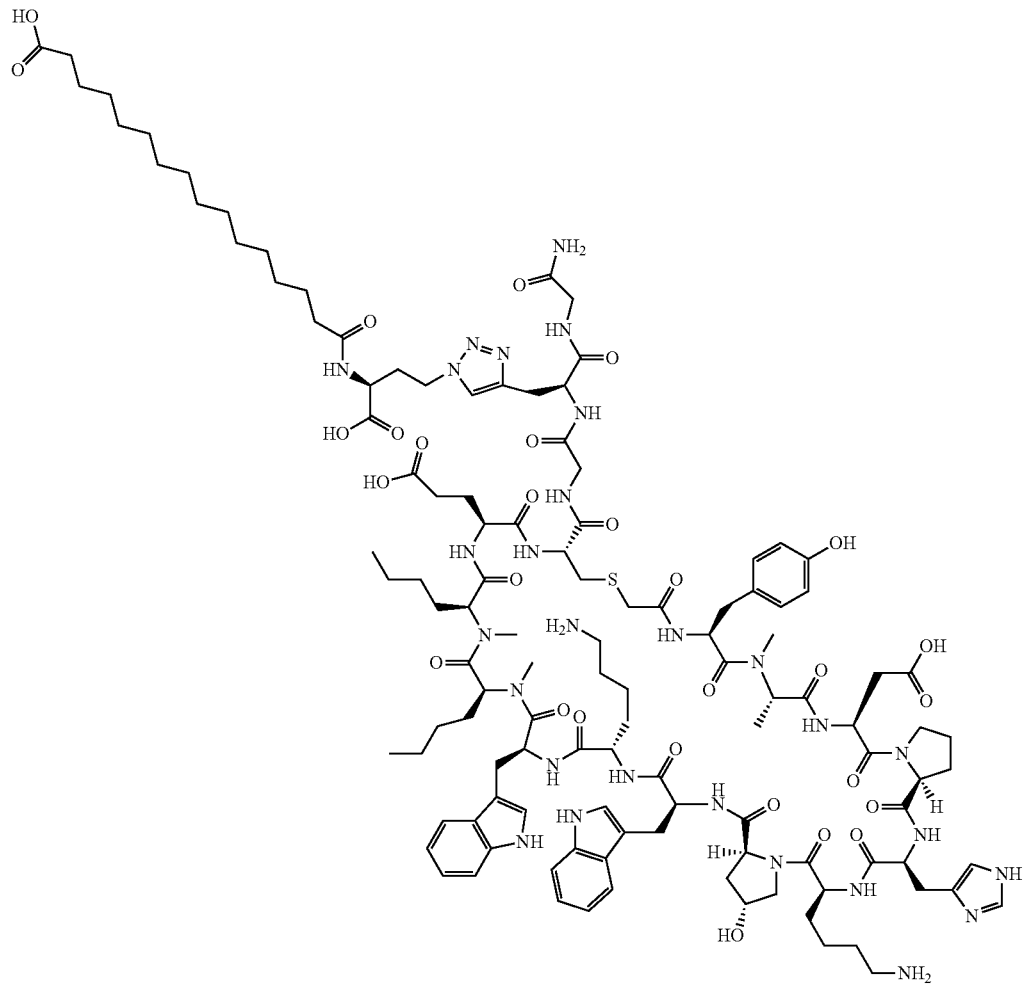

Example 14064

Intermediate 1400A (25 mg, 0.012 mmol) and (S)-16-((3-azido-1-carboxypropyl)amino)-16-oxohexadecanoic acid (14.79 mg, 0.036 mmol) were reacted as in the general triazole formation procedure above to afford crude product. The crude material was purified via Prep-HPLC (Solvent A=10% MeOH-90% $H_2O$-0.1% TFA, Solvent B=90% MeOH-10% $H_2O$-0.1% TFA. Column: PHENOMENEX LUNA 30×100 mm, S10, Flow rate: 40 ml/min, 45-100% B, 40 min, then a 5-minute hold at 100% B). Fractions containing the desired product were combined and dried via speed vacuum evaporation. The yield of the product was 20.0 mg, and its estimated purity by LCMS analysis was 90%. Analysis condition D: Retention time=2.09 min; ESI-MS(+) m/z 1253.6 (M+2H).

Preparation of Example 14065

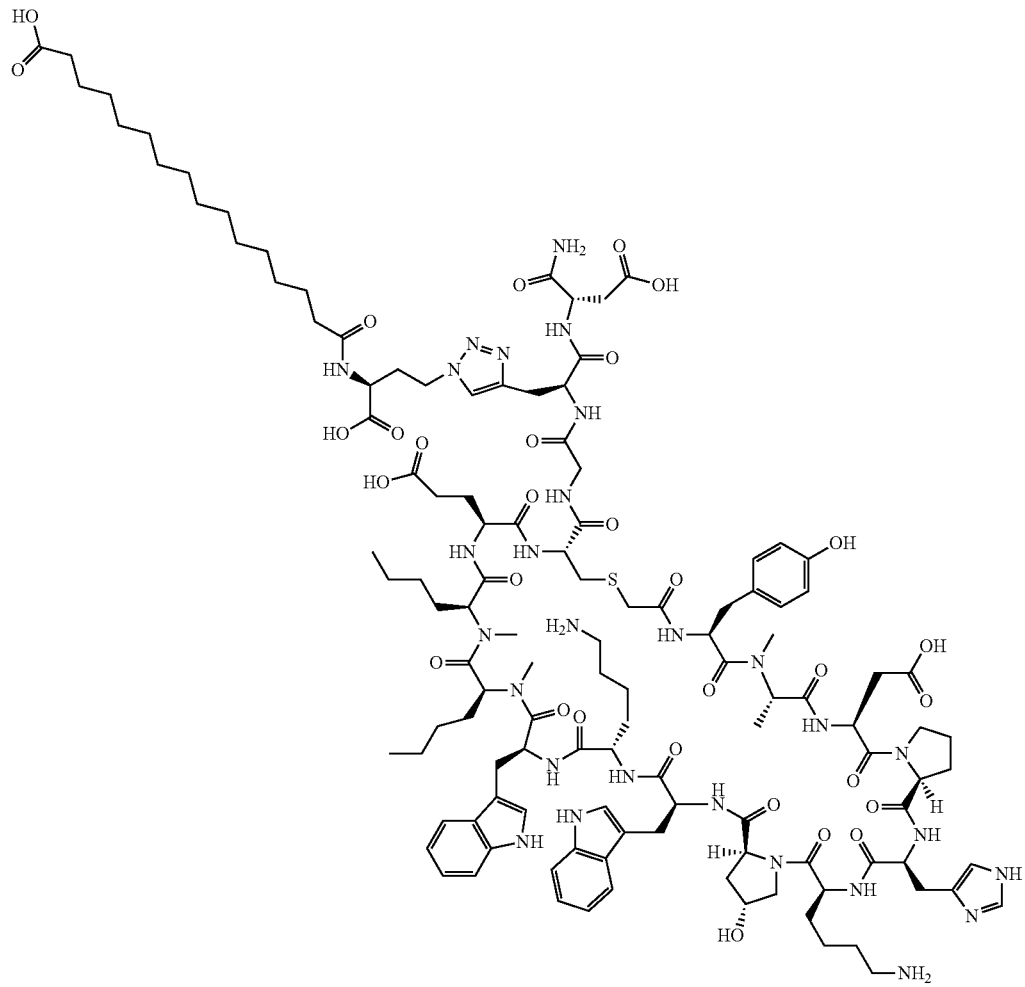

Example 14065

Intermediate 1400B (25 mg, 0.012 mmol) and (S)-16-((3-azido-1-carboxypropyl)amino)-16-oxohexadecanoic acid (14.39 mg, 0.035 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 50-100% B, 50 min). Fractions containing the desired product were combined and dried via speed vacuum evaporation.

The yield of the product was 13.0 mg, and its estimated purity by LCMS analysis was 90%. Analysis condition D: Retention time=2.15 min; ESI-MS(+) m/z 1282.5 (M+2H), most abundant ion.

Preparation of Example 14066

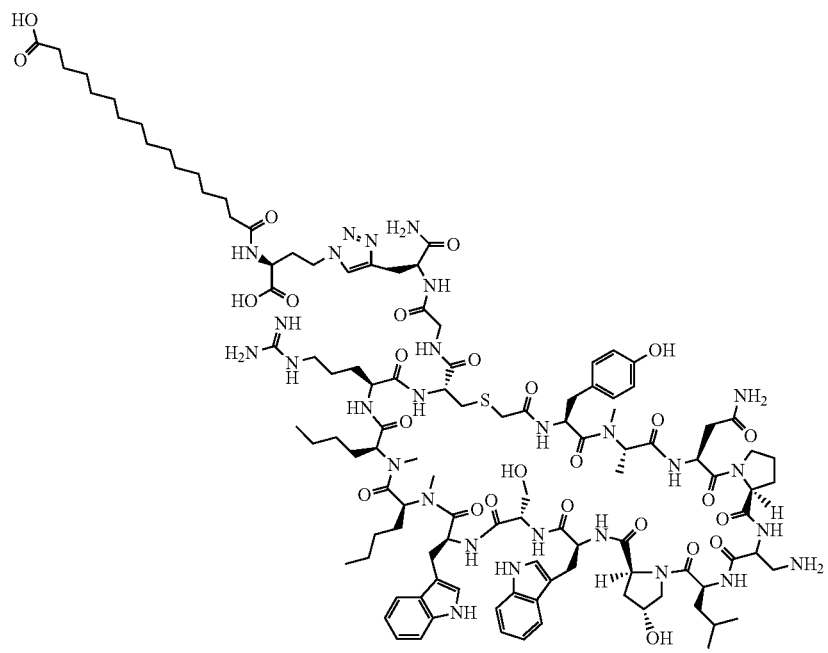

Example 14066

Intermediate 1400G (25 mg, 0.013 mmol) and (S)-16-((3-azido-1-carboxypropyl)amino)-16-oxohexadecanoic acid (6.33 mg, 0.015 mmol) were reacted as in the general triazole formation procedure above to afford crude product. The crude material was purified via Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 50-90% B, 60 min). Fractions containing the desired product were combined and dried via speed vacuum evaporation. The yield of the product was 10.0 mg, and its estimated purity by LCMS analysis was 90%. Analysis condition D: Retention time=2.18 min; ESI-MS(+) m/z 1184.6 (M+2H), most abundant ion.

Preparation of Example 14067

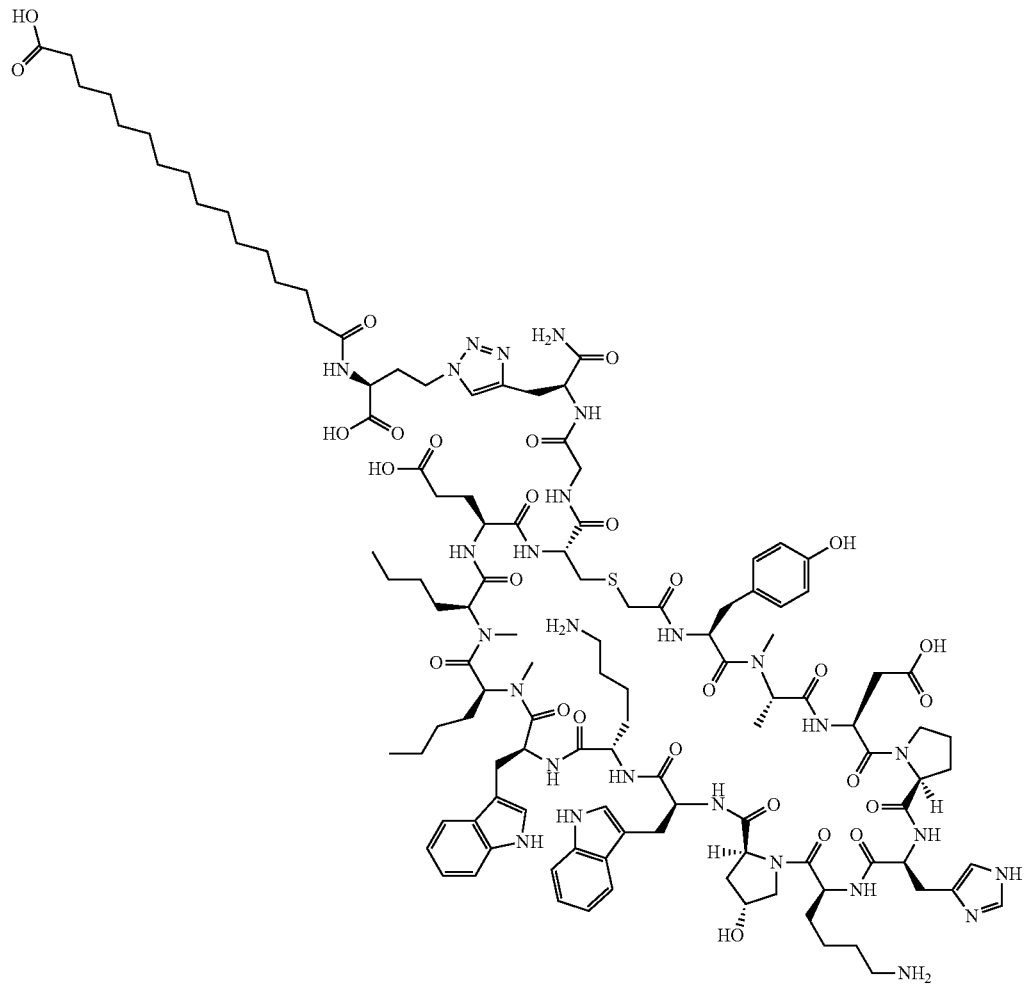

Example 14067

Intermediate 1400F (25 mg, 0.013 mmol) and (S)-16-((3-azido-1-carboxypropyl)amino)-16-oxohexadecanoic acid (7.60 mg, 0.018 mmol) were reacted as in the general triazole formation procedure above to afford crude product. The crude material was purified via Prep-HPLC (Solvent A=10% MeOH-90% H$_2$O—0.1% TFA, Solvent B=90% MeOH-10% H$_2$O-0.1% TFA. Column: PHENOMENEX LUNA 30×100 mm, S10, Flow rate: 40 ml/min, 55-90% B, 60 min). Fractions containing the desired product were combined and dried via speed vacuum evaporation. The yield of the product was 2.0 mg, and its estimated purity by LCMS analysis was 90%. Analysis condition D: Retention time=2.16 min; ESI-MS(+) m/z 1225.1 (M+2H), most abundant ion.

Preparation of Example 14068

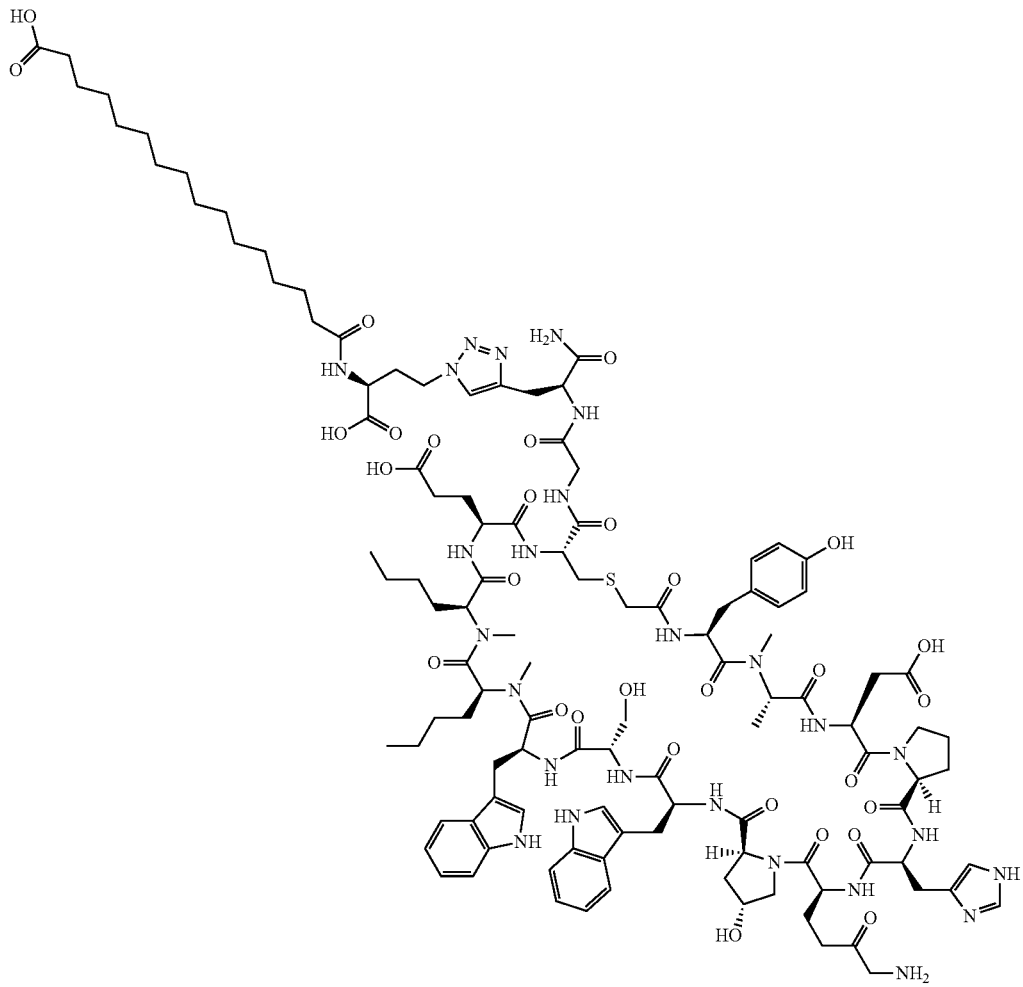

Example 14068

Intermediate 1400H (25 mg, 0.013 mmol) and (S)-16-((3-azido-1-carboxypropyl)amino)-16-oxohexadecanoic acid (6.21 mg, 0.015 mmol) were reacted as in the general triazole formation procedure above to afford crude product. The crude material was purified via preparative LC/MS with the following conditions: Column: XBridge Shield RP18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 15-minute hold at 100% B; Flow: 20 mL/min. Fractions containing the desired product were combined and dried via centrifugal evaporation. The yield of the product was 6.5 mg, and its estimated purity by LCMS analysis was 100%. Analysis condition B: Retention time=1.76 min; ESI-MS(+) m/z: 1204.3 (M+2H), most abundant ion. ESI-HRMS(+) m/z: Calculated: 1203.5830 (M+2H).

Found: 1203.5818 (M+2H).

Preparation of Example 14069

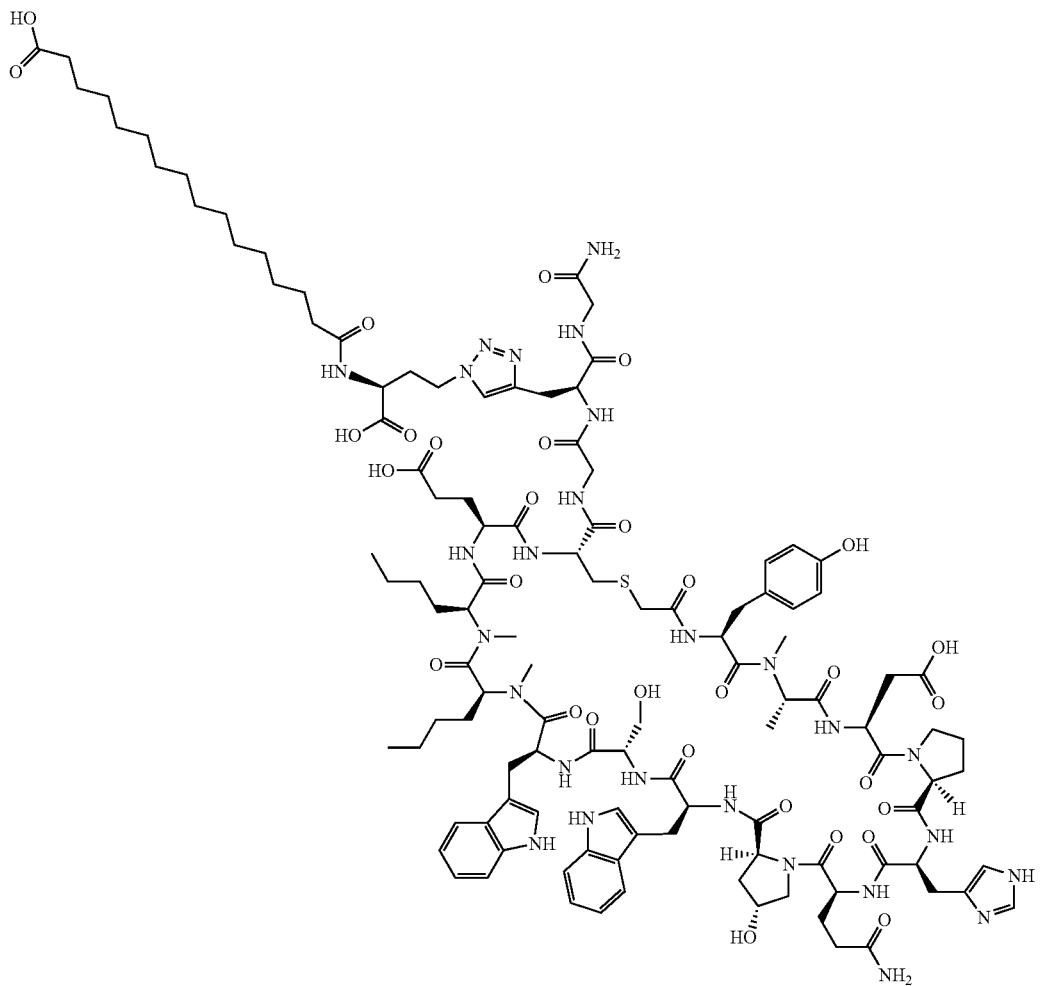

Example 14069

Intermediate 1400C (19.5 mg, 9.51 μmol) and (S)-16-((3-azido-1-carboxypropyl)amino)-16-oxohexadecanoic acid (4.71 mg, 0.011 mmol) were reacted as in the general triazole formation procedure above to afford crude product. The crude material was purified via preparative LC/MS with the following conditions: Column: XBridge Shield RP18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 5.2 mg, and its estimated purity by LCMS analysis was 96%. Analysis condition B: Retention time=1.75 min; ESI-MS(+) m/z: 1232.8 (M+2H), most abundant ion. ESI-HRMS(+) m/z: Calculated: 1232.0937 (M+2H).

Found: 1232.0902 (M+2H).

Preparation of Example 14070

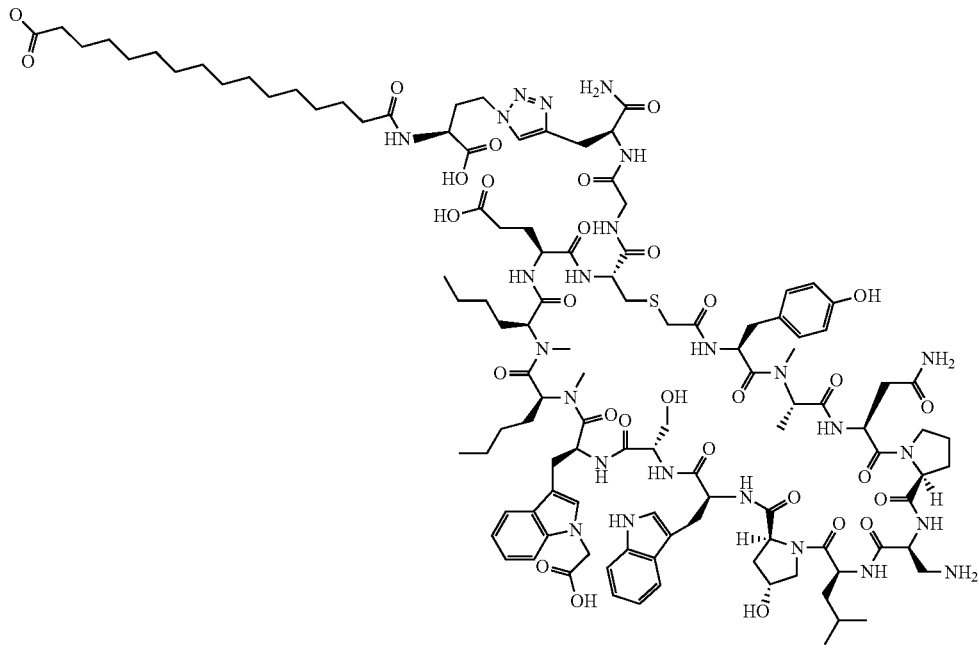

Example 14070

Intermediate 1400I (30 mg, 0.015 mmol) and (S)-16-((3-azido-1-carboxypropyl)amino)-16-oxohexadecanoic acid (7.48 mg, 0.018 mmol) were reacted as in the general triazole formation procedure above to afford crude product. The crude material was purity via preparative LC/MS with the following conditions: Column: XBridge C18, 19×200 mm, 5-μm particles; Mobile Phase A: 5:95 C18, 19×200 mm, 5-μm particles; Mobile Phase A: 5:95 acetonitrile:water with 10-Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 5-minute hold at 100% ESI-MS(+) B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 99%. Analysis condition A: Retention time=1.43 min; ESI-MS(+) m/z 1199.4 (M+2H), most abundant ion; Analysis condition B: Retention time=2.57 min; ESI-MS(+) m/z 1199.9 (M+2H), most abundant ion. ESI-HRMS(+) m/z: Calculated: 1199.1010 (M+2H). Found: 1199.1018 (M+2H).

Preparation of Example 14071

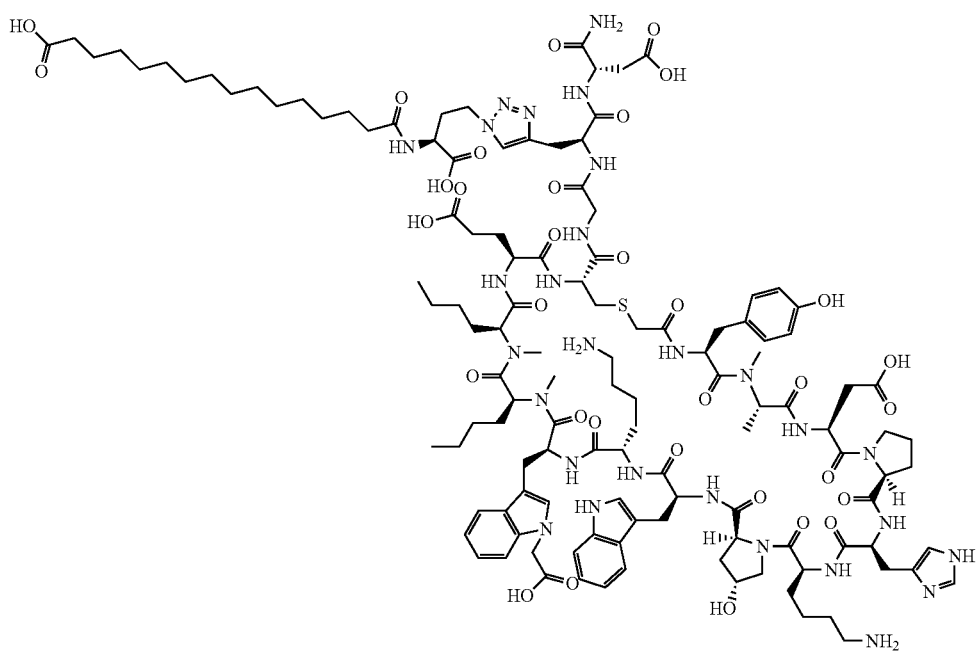

Example 14071

Intermediate 1400E (39 mg, 0.018 mmol) and (S)-16-((3-azido-1-carboxypropyl)amino)-16-oxohexadecanoic acid (8.74 mg, 0.021 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 97%. Analysis condition A: Retention time=1.32 min; ESI-MS(+) m/z 874.5 (M+3H); Analysis condition B: Retention time=2.71 min; ESI-MS(+) m/z 874.8 (M+3H); ESI-HRMS(+) m/z:

Calculated: 1310.6489 (M+2H). Found: 1310.6461 (M+2H).

Preparation of Example 14072

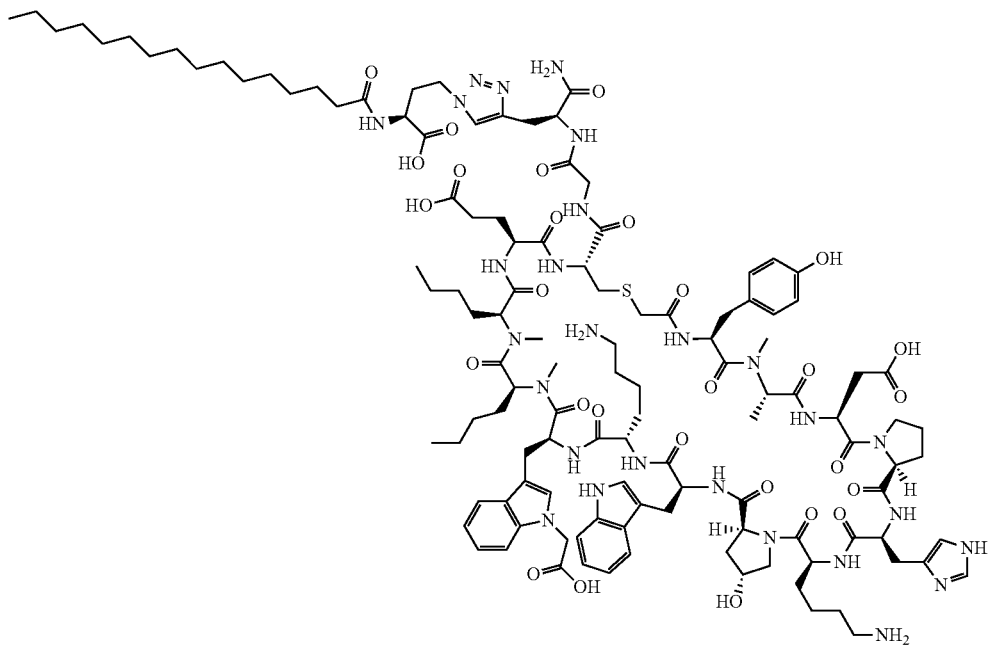

Example 14072

Intermediate 1400J (35 mg, 0.017 mmol) and (S)-4-azido-2-palmitamidobutanoic acid (7.68 mg, 0.020 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 9.0 mg, and its estimated purity by LCMS analysis was 97%. Analysis condition A: Retention time=1.80 min; ESI-MS(+) m/z 826.1 (M+3H), most abundant ion; Analysis condition B: Retention time=3.13 min; ESI-MS(+) m/z 1238.8 (M+2H).

ESI-HRMS(+) m/z: Calculated: 1238.1483 (M+2H). Found: 1238.1484 (M+2H).

Preparation of Example 14073

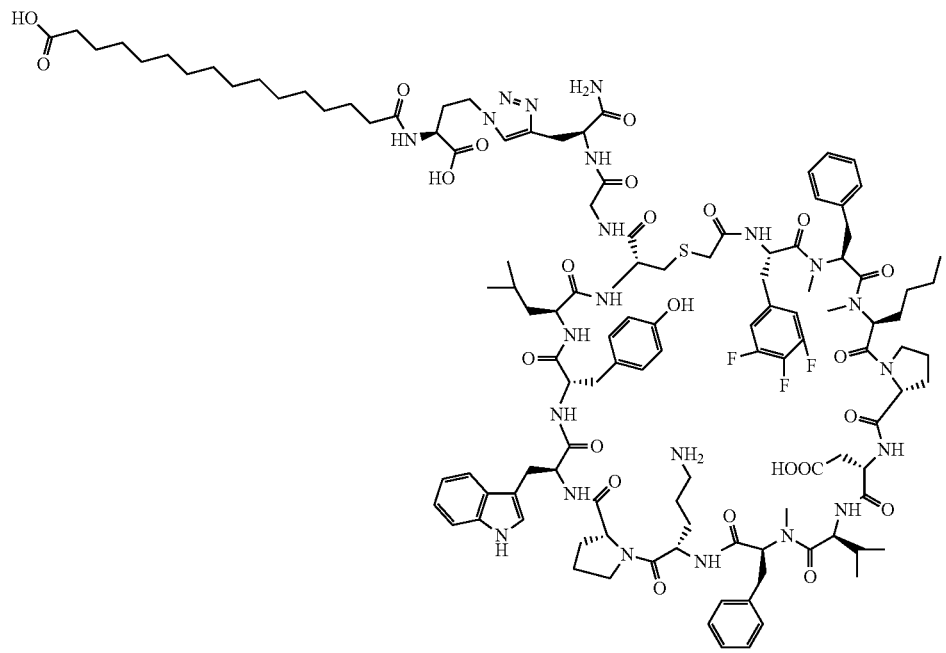

Example 14073

Intermediate 1400K (30 mg, 0.015 mmol) and (S)-16-((3-azido-1-carboxypropyl)amino)-16-oxohexadecanoic acid (7.62 mg, 0.018 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 12.0 mg, and its estimated purity by LCMS analysis was 100%. Analysis condition A: Retention time=1.92 min; ESI-MS(+) m/z 1181.0 (M+2H); Analysis condition B: Retention time=3.12 min; ESI-MS(+) m/z 1181.1 (M+2H), most abundant ion; ESI-HRMS(+) m/z: Calculated: 1180.5936 (M+2H). Found: 1180.5931 (M+2H).

Preparation of Example 14074

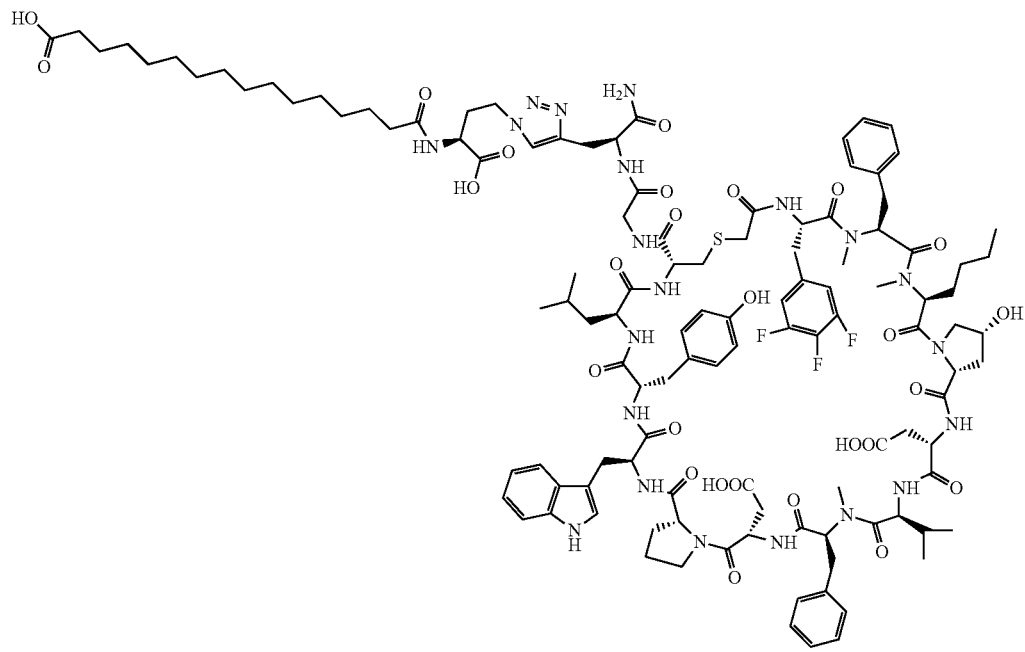

Example 14074

Intermediate 1400L (30 mg, 0.015 mmol) and (S)-16-((3-azido-1-carboxypropyl)amino)-16-oxohexadecanoic acid (7.56 mg, 0.018 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 100%. Analysis condition A: Retention time=1.68 min; ESI-MS(+) m/z 1189.5 (M+2H); Analysis condition B: Retention time=3.20 min; ESI-MS(+) m/z 1189.5 (M+2H); ESI-HRMS(+) m/z:

Calculated: 1189.0649 (M+2H). Found: 1189.0642 (M+2H).

Preparation of Example 14075

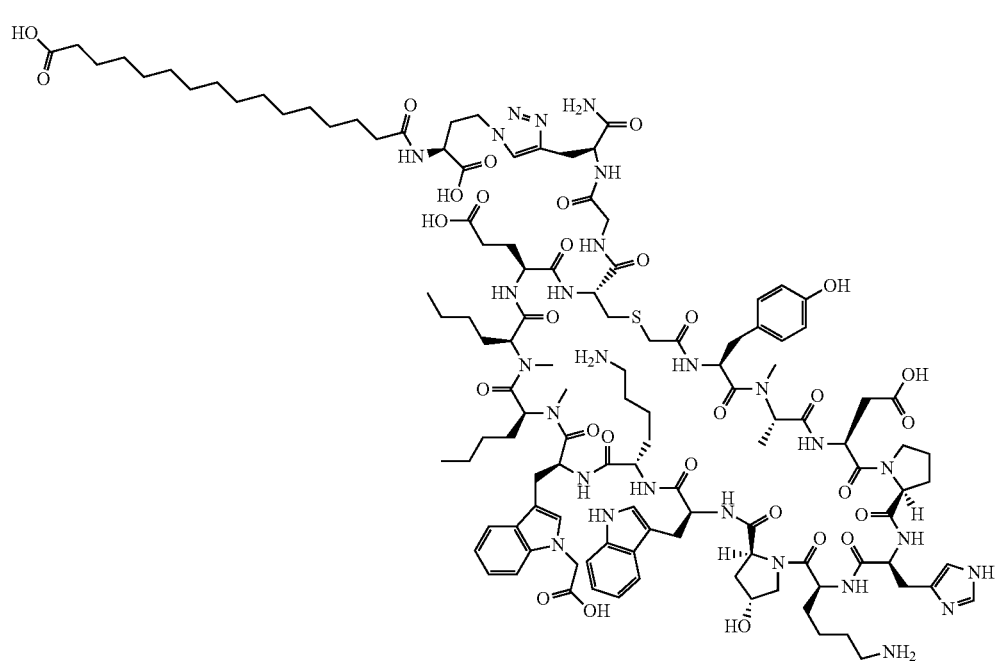

Example 14075

Intermediate 1400J (40 mg, 0.019 mmol) and (S)-16-((3-azido-1-carboxypropyl)amino)-16-oxohexadecanoic acid (9.46 mg, 0.023 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-35% B over 30 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 100%. Analysis condition A: Retention time=1.34 min; ESI-MS(+) m/z 936.2 (M+2H); Analysis condition B: Retention time=2.97 min; ESI-MS(+) m/z 936.2 (M+2H); ESI-HRMS(+) m/z: Calculated: 960.9769 (M+2H). Found: 960.9749 (M+2H).

Preparation of Example 14076

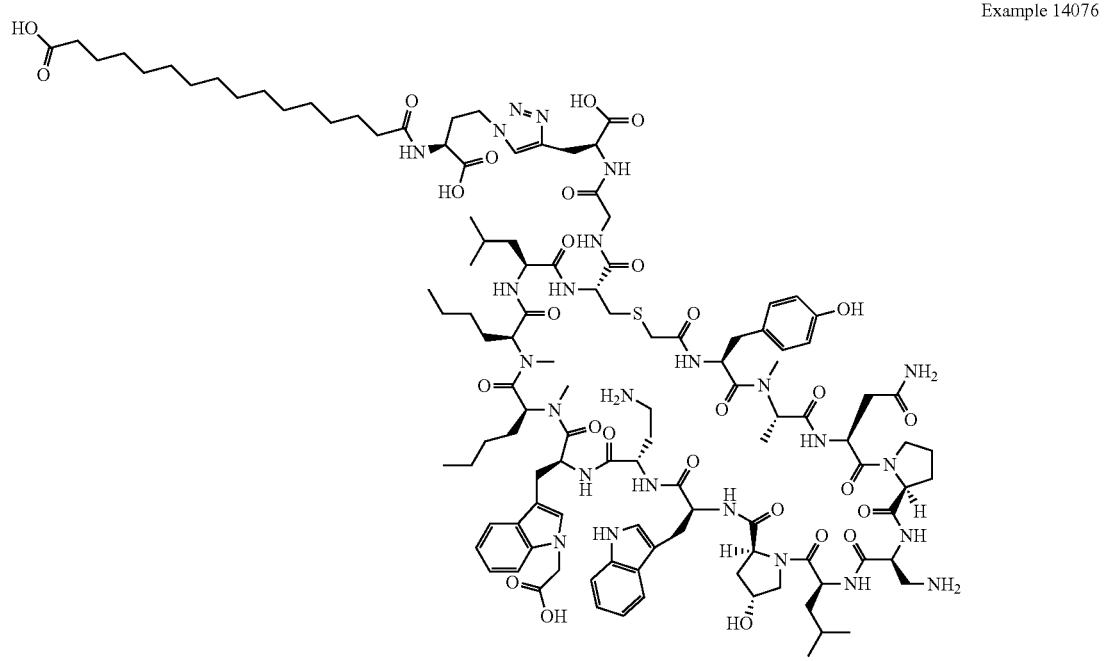 [SMILES: CCCC[C@H]1C(=O)N(C)[C@@H](CCCC)C(=O)N[C@@H](CC(C)C)C(=O)N[C@H](C(=O)NCC(=O)N[C@@H](C/C(=C/NCC[C@H](NC(=O)CCCCCCCCCCCCCCC(=O)O)C(=O)O)N=N)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 14076

Intermediate 1300V (30 mg, 0.015 mmol) and (S)-16-((3-azido-1-carboxypropyl)amino)-16-oxohexadecanoic acid (7.49 mg, 0.018 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 30 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 100%. Analysis condition A: Retention time=1.43 min; ESI-MS(+) m/z 1198.6 (M+2H), most abundant ion; Analysis condition B: Retention time=2.86 min; ESI-MS(+) m/z 1198.7 (M+2H), most abundant ion.

Preparation of Example 14077

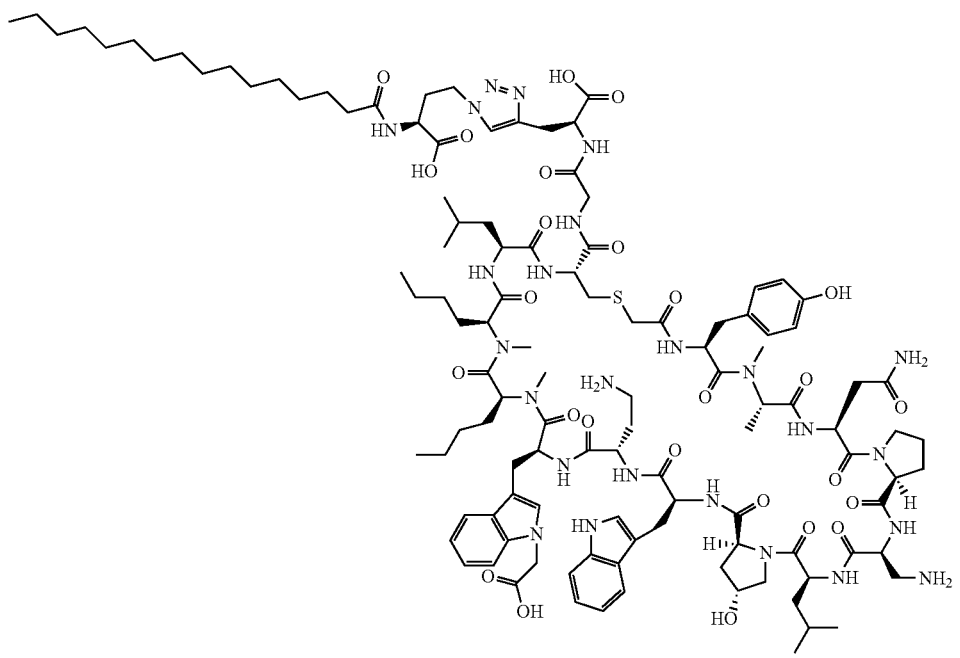

Example 14077

Intermediate 1300V (10 mg, 5.04 μmol) and (S)-4-azido-2-palmitamidobutanoic acid (2.32 mg, 6.05 μmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 100%. Analysis condition A: Retention time=1.85 min; ESI-MS(+) m/z 1184.2 (M+2H); ESI-HRMS(+) m/z: Calculated: 1003.5215 (M+2H). Found: 1003.5189 (M+2H).

Preparation of Example 14078

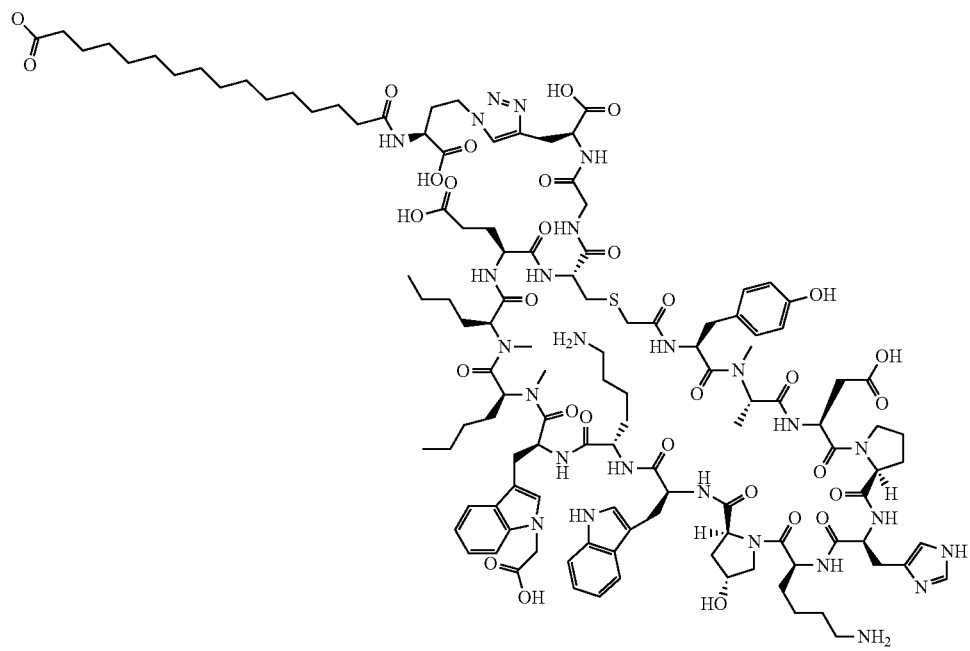

Example 14078

Intermediate 1300Y (30 mg, 0.014 mmol) and (S)-16-((3-azido-1-carboxypropyl)amino)-16-oxohexadecanoic acid (7.09 mg, 0.017 mmol) were reacted as in the general triazole formation procedure above to afford crude product. The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 96%. Analysis condition A: Retention time=1.28 min; ESI-MS(+) m/z 836.3 (M+3H), most abundant ion; Analysis condition B: Retention time=2.35 min; ESI-MS(+) m/z 836.8 (M+3H), most abundant ion.

Preparation of Example 14079

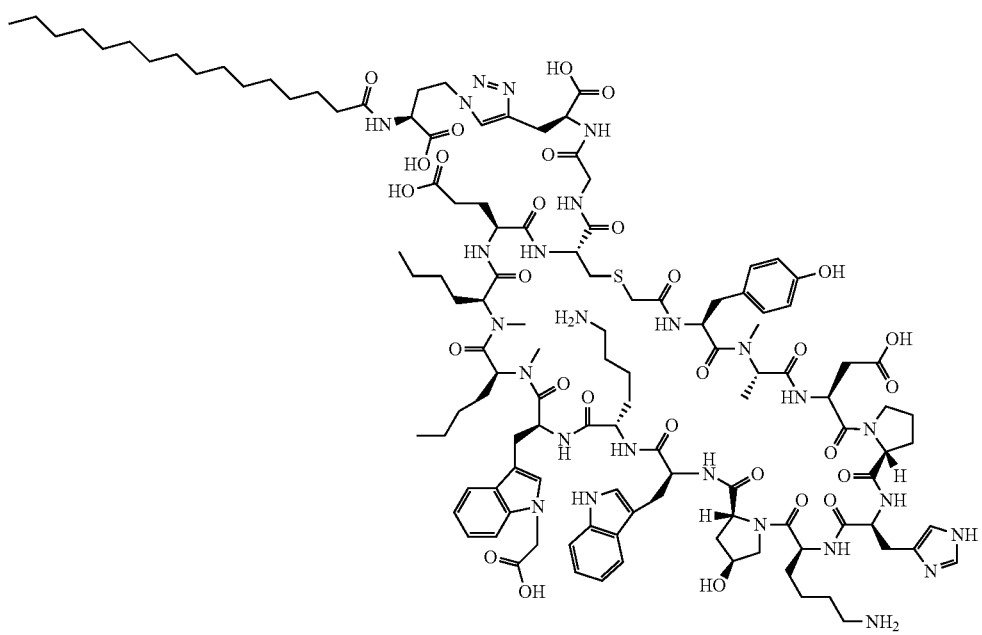

Example 14079

Intermediate 1300Y (10 mg, 4.77 μmol) and (S)-4-azido-2-palmitamidobutanoic acid (2.19 mg, 5.73 μmol) were reacted as in the general triazole formation procedure above to afford crude product. The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 2.5 mg, and its estimated purity by LCMS analysis was 96%. Analysis condition A: Retention time=1.50 min; ESI-MS(+) m/z 1239.5 (M+2H), most abundant ion.

Preparation of Example 14080

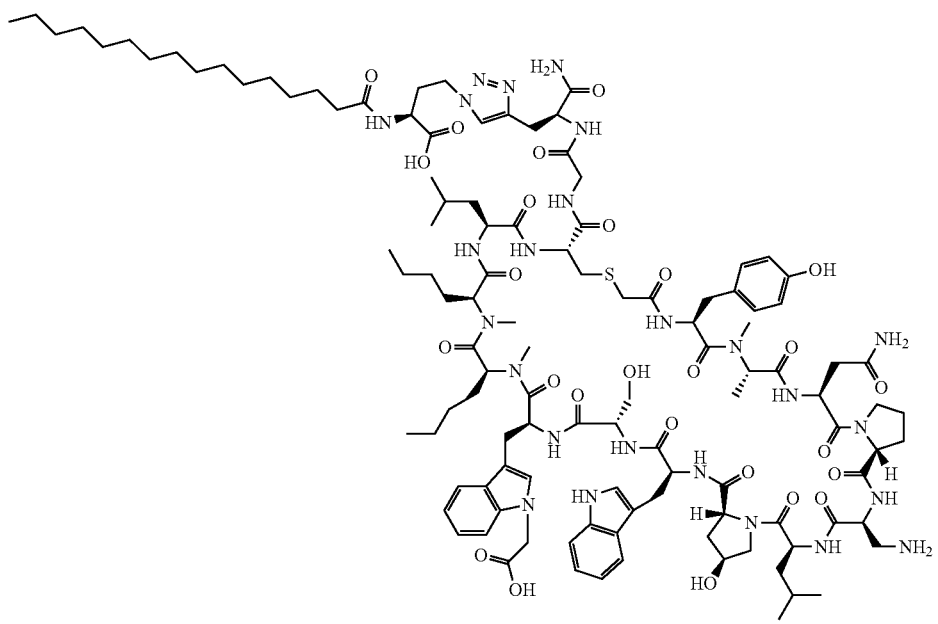

Example 14080

Intermediate 1300X (8 mg, 4.06 μmol) and (S)-4-azido-2-palmitamidobutanoic acid (1.87 mg, 4.87 μmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 96%. Analysis condition A: Retention time=2.12 min; ESI-MS(+) m/z 1176.7 (M+2H), most abundant ion.

Preparation of Example 14081

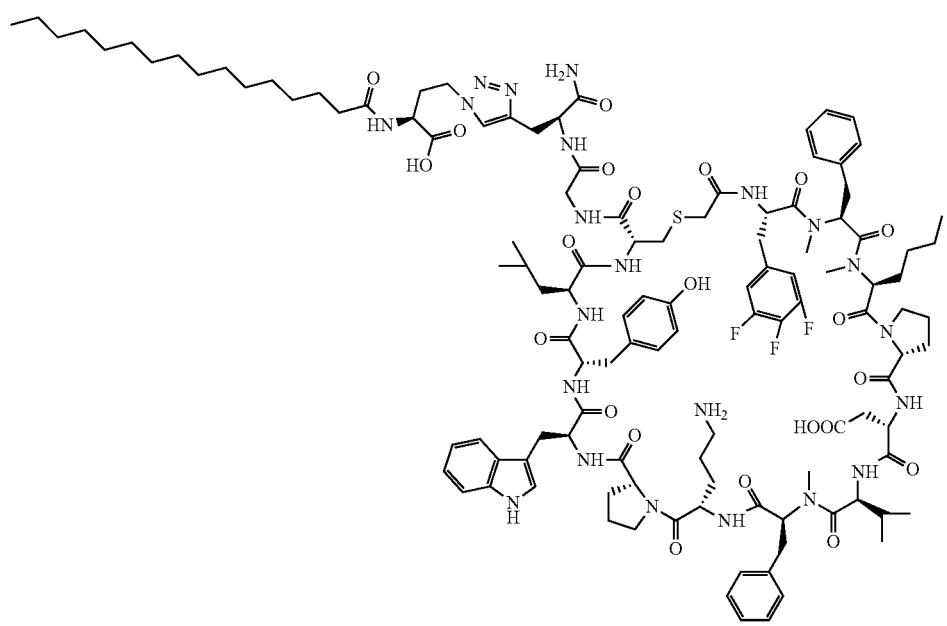

Example 14081

Intermediate 1400K (10 mg, 5.13 µmol) and (S)-4-azido-2-palmitamidobutanoic acid (2.36 mg, 6.16 µmol) were reacted as in the general triazole formation procedure above to afford crude product. The crude material was purified via preparative LC/MS with the following conditions: Column: waters xbridge c-18, 19×200 mm, 5-Lm particles; Mobile Phase A: 5:95 acetonitrile:water with 10-mM ammonium acetate; Mobile Phase B: 95:5 acetonitrile:water with 10-mM; ammonium acetate; Gradient: 35-75% B over 30 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 100%. Analysis condition A: Retention time=2.44 min; ESI-MS(+) m/z 1166.0 (M+2H), most abundant ion.

Preparation of Example 14082

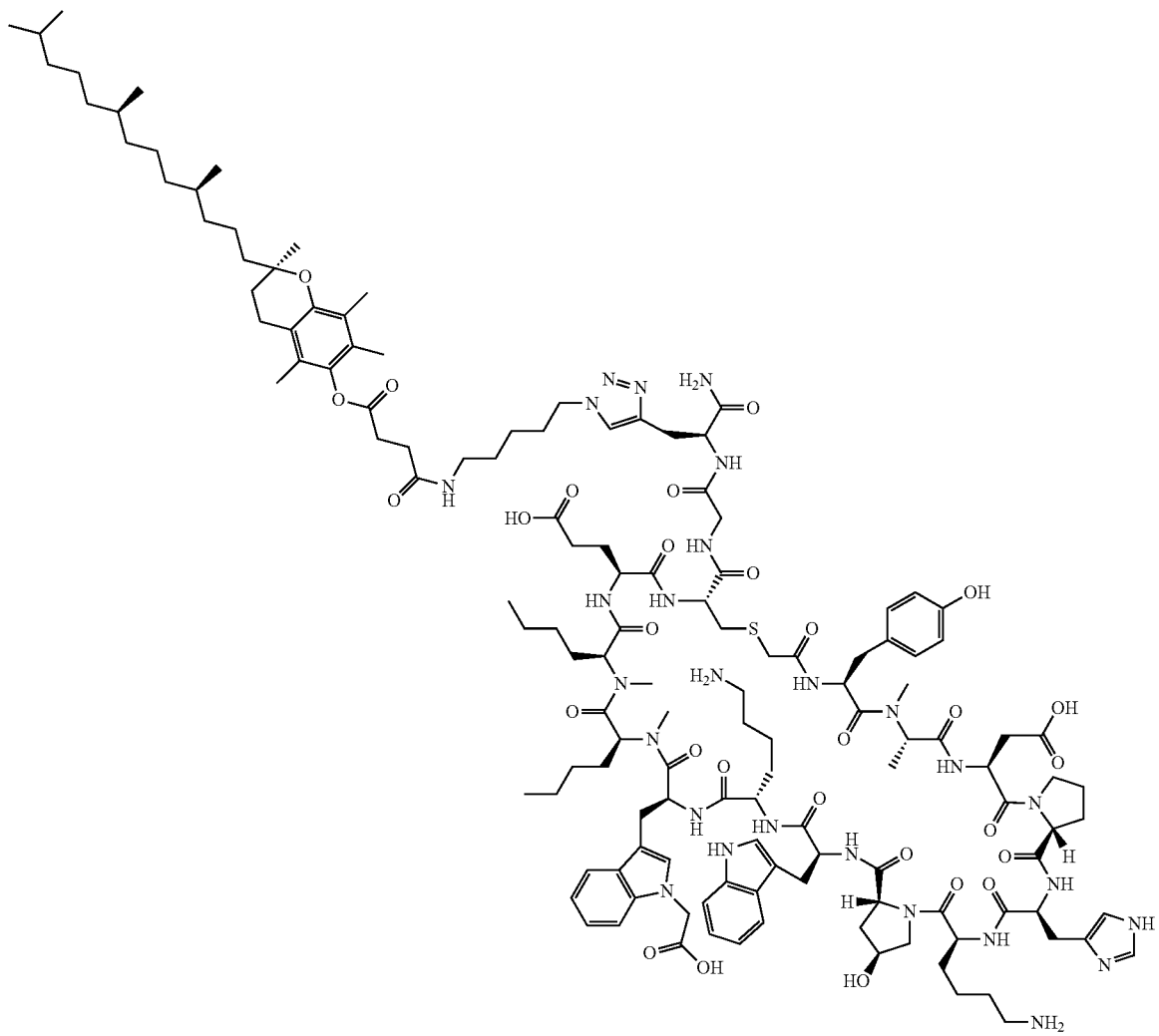

Example 14082

Intermediate 1400J (48 mg, 0.023 mmol) and (R)-2,5,7,8-tetramethyl-2-((4R,8R)-4,8,12-trimethyltridecyl)chroman-6-yl 4-((5-azidopentyl)amino)-4-oxobutanoate (17.64 mg, 0.028 mmol) were reacted as in the general triazole formation procedure above to afford crude product. The crude material was purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 60-100% B over 25 minutes, then a 10-minute hold at 100% B; Flow: 20 mL/min. Fractions containing the desired product were combined and dried via centrifugal evaporation. The material was further purified via preparative LC/MS with the following conditions: Column: XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 38-78% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 100%. Analysis condition C: Retention time=1.62 min; ESI-MS(+) m/z 912.8 (M+3H), most abundant ion.

Preparation of Example 14083

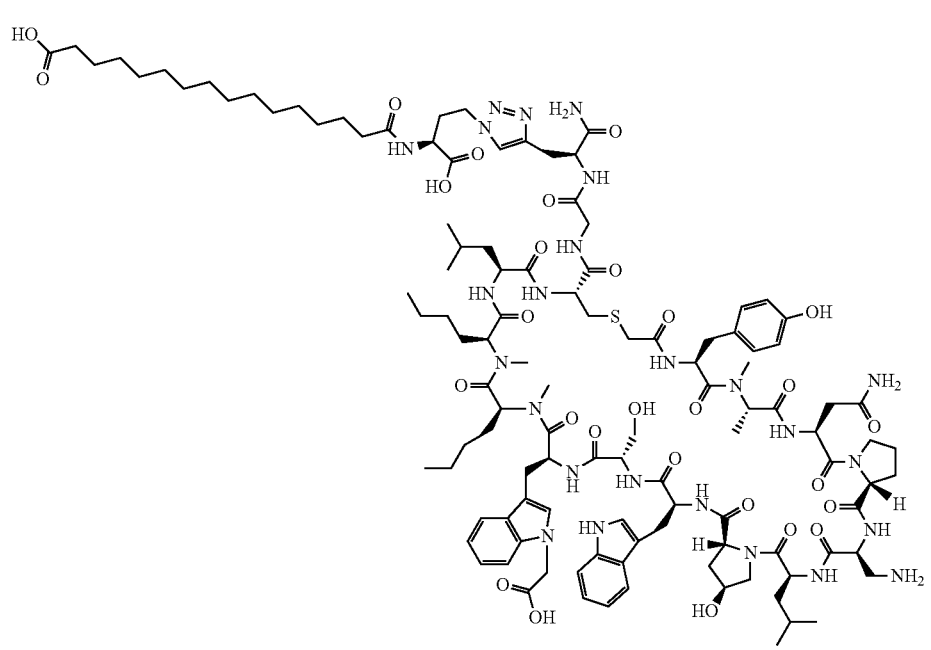

Example 14083

Intermediate 1300X (26 mg, 0.013 mmol) and (S)-16-((3-azido-1-carboxypropyl)amino)-16-oxohexadecanoic acid (6.54 mg, 0.016 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 100%. Analysis condition A: Retention time=1.42 min; ESI-MS(+) m/z 1191.8 (M+2H), most abundant ion. Analysis condition B: Retention time=2.86 min; ESI-MS(+) m/z 1191.6 (M+2H), most abundant ion.

Preparation of Example 14084

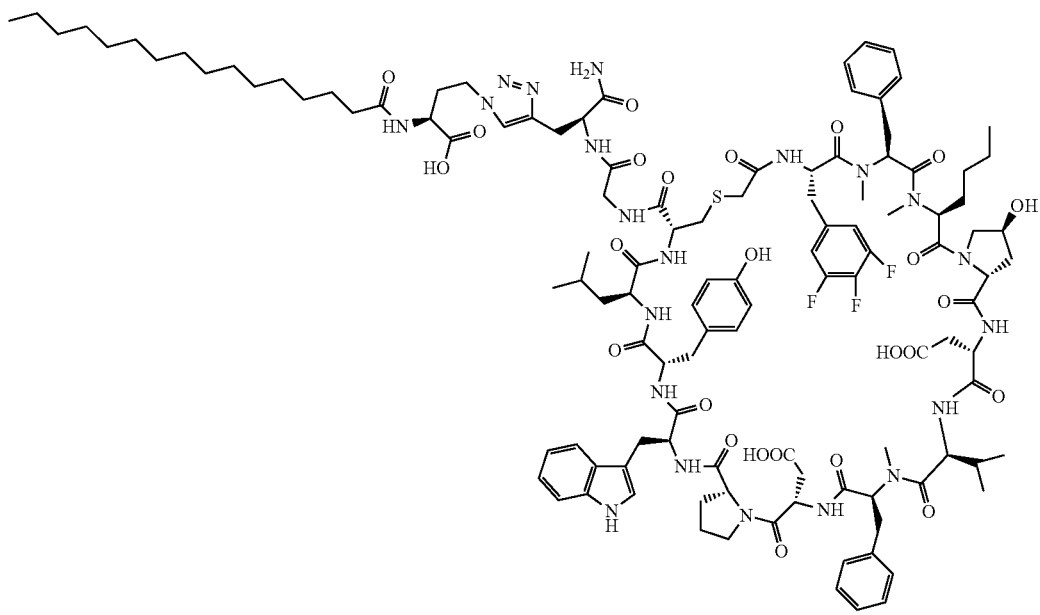

Example 14084

Intermediate 1400L (10 mg, 5.09 μmol) and (S)-4-azido-2-palmitamidobutanoic acid (2.34 mg, 6.11 μmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 100%. Analysis condition A: Retention time=1.87 min; ESI-MS(+) m/z 1175.3 (M+2H), most abundant ion; Analysis condition B: Retention time=3.10 min; ESI-MS(+) m/z 1175.7 (M+2H), most abundant ion.

Preparation of Example 14085

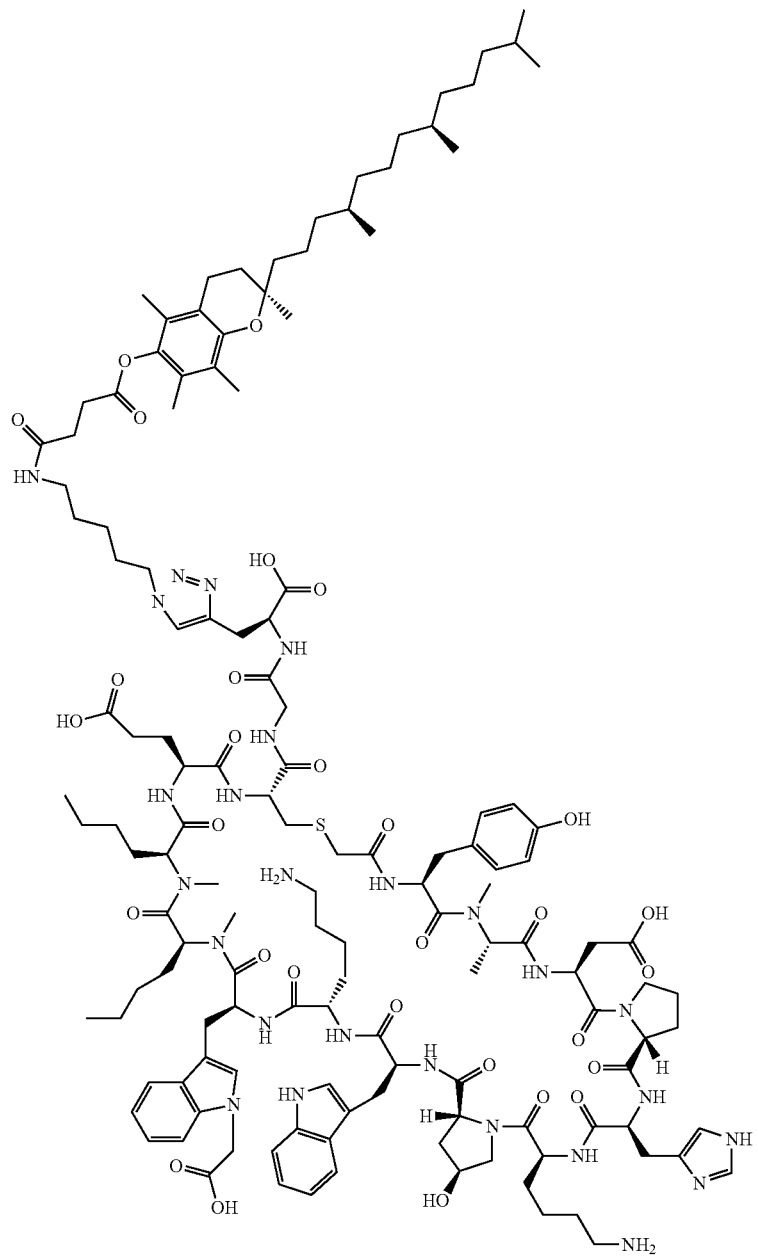

Example 14085

Intermediate 1300Y (54.8 mg, 0.026 mmol) and (R)-2,5,7,8-tetramethyl-2-((4R,8R)-4,8,12-trimethyltridecyl)chroman-6-yl 4-((5-azidopentyl)amino)-4-oxobutanoate (20.12 mg, 0.031 mmol) were reacted as in the general triazole formation procedure above to afford crude product. The crude material was purified via preparative LC/MS with the following conditions: Column: XBridge Phenyl, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-80% B over 30 minutes, then a 10-minute hold at 100% B; Flow: 20 mL/min. Fractions containing the desired product were combined and dried via centrifugal evaporation. The yield of the product was 15.2 mg, and its estimated purity by LCMS analysis was 100%. Analysis condition C: Retention time=1.87 min; ESI-MS(+) m/z 912.8 (M+3H), most abundant ion.

Preparation of Example 14086

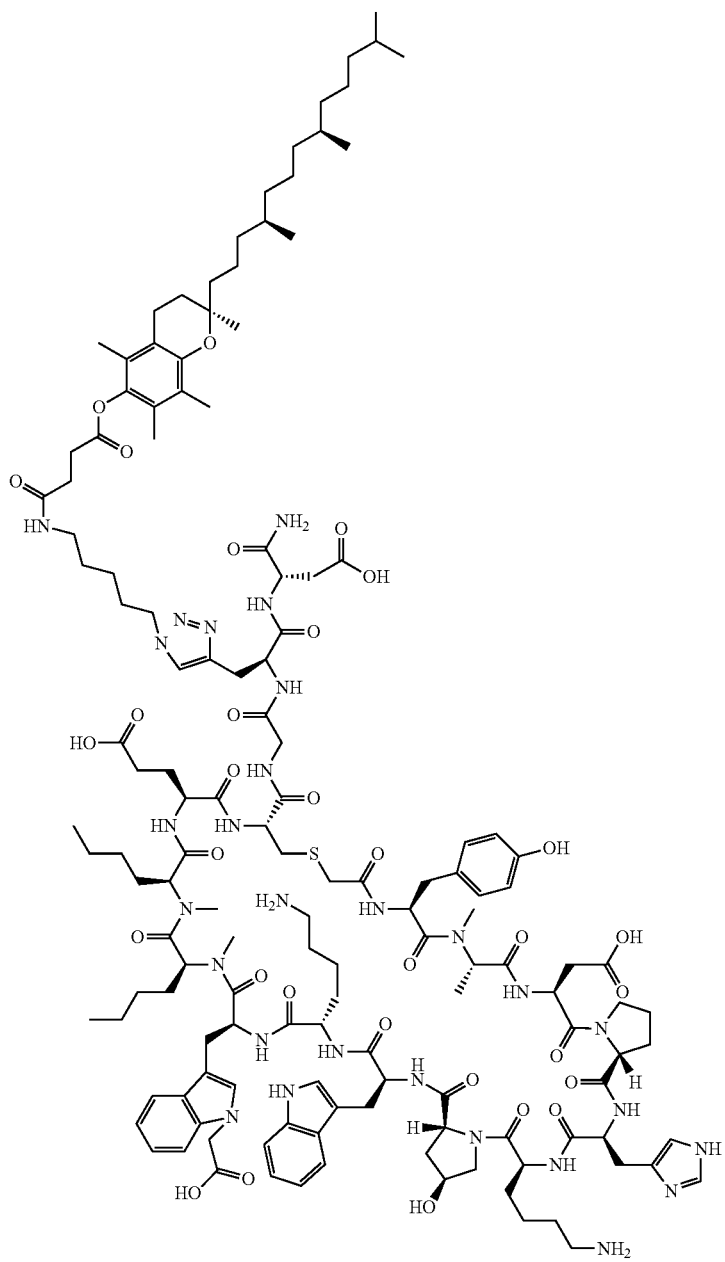

Example 14086

Intermediate 1400E (48.5 mg, 0.022 mmol) and (R)-2,5,7,8-tetramethyl-2-((4R,8R)-4,8,12-trimethyltridecyl)chroman-6-yl 4-((5-azidopentyl)amino)-4-oxobutanoate (16.89 mg, 0.026 mmol) were reacted as in the general triazole formation procedure above to afford crude product. The crude material was purified via preparative LC/MS with the following conditions: Column: XBridge Phenyl, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 30 minutes, then a 10-minute hold at 100% B; Flow: 20 mL/min. Fractions containing the desired product were combined and dried via centrifugal evaporation. The yield of the product was 18.3 mg, and its estimated purity by LCMS analysis was 100%. Analysis condition C: Retention time=2.90 min; ESI-MS(+) m/z 951.3 (M+3H), most abundant ion.

Preparation of Example 14087

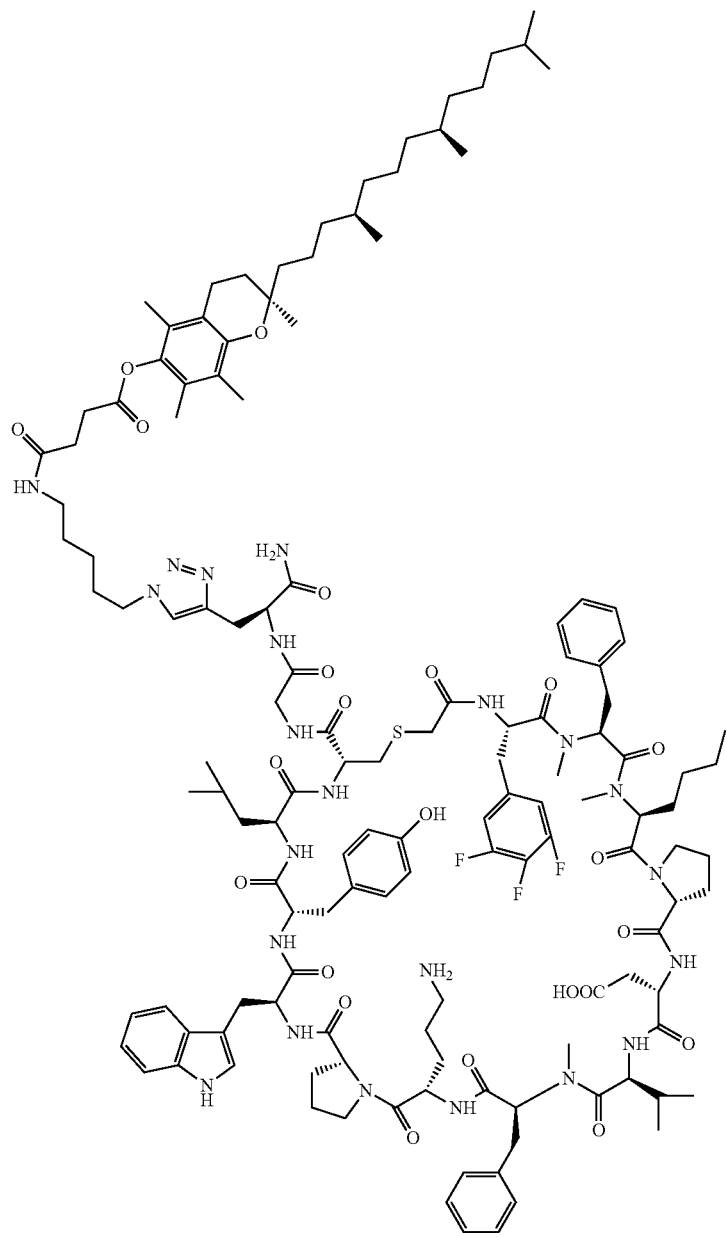

Example 14087

Intermediate 1400K (54 mg, 0.028 mmol) and (R)-2,5,7, 8-tetramethyl-2-((4R,8R)-4,8,12-trimethyltridecyl)chroman-6-yl 4-((5-azidopentyl)amino)-4-oxobutanoate (21.32 mg, 0.033 mmol) were reacted as in the general triazole formation procedure above to afford crude product. The crude material was purified via preparative LC/MS with the following conditions: Column: XBridge Phenyl, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 60-100% B over 30 minutes, then a 10-minute hold at 100% B; Flow: 20 mL/min. Fractions containing the desired product were combined and dried via centrifugal evaporation. The yield of the product was 35.9 mg, and its estimated purity by LCMS analysis was 100%. Analysis condition C: Retention time=3.23 min; ESI-MS(+) m/z 1295.2 (M+2H), most abundant ion.

Preparation of Example 14088

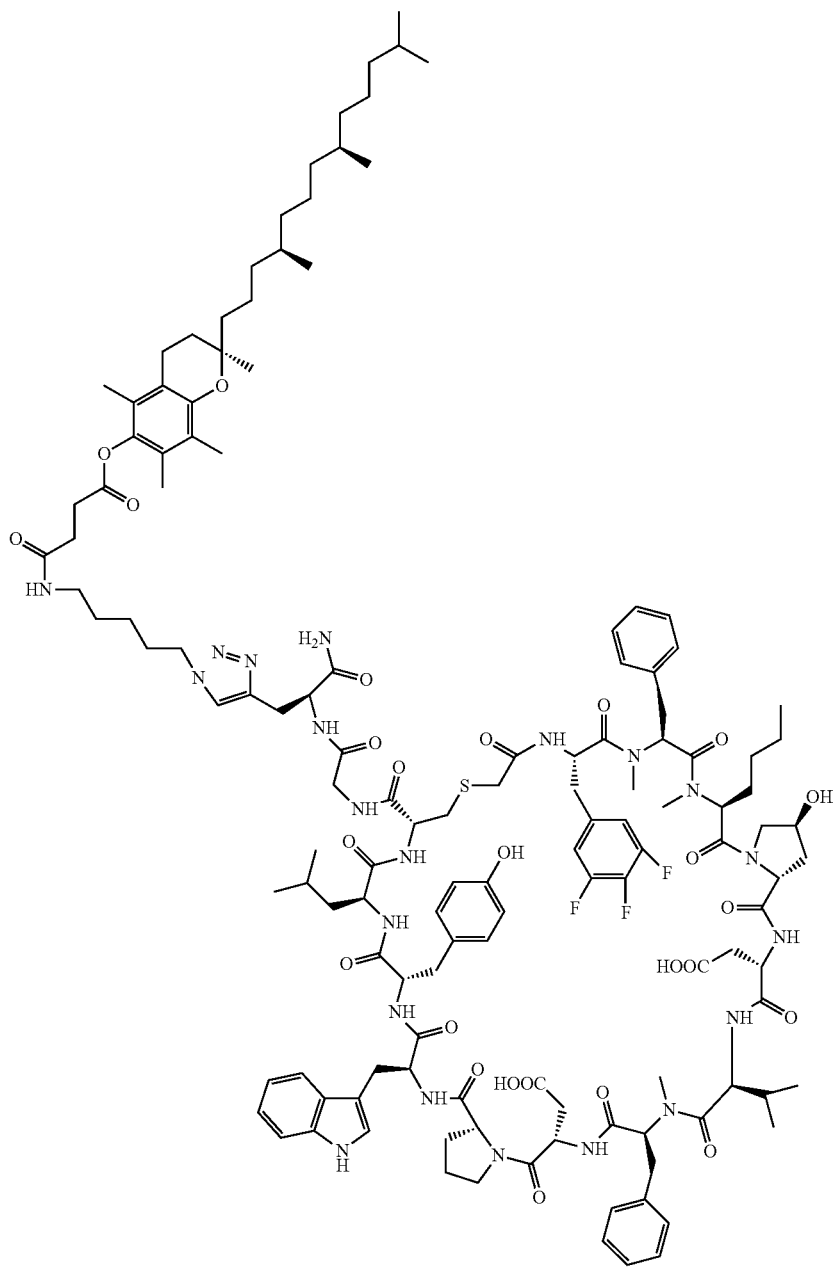

Exmaple 14088

Intermediate 1400L (54 mg, 0.027 mmol) and (R)-2,5,7,8-tetramethyl-2-((4R,8R)-4,8,12-trimethyltridecyl)chroman-6-yl 4-((5-azidopentyl)amino)-4-oxobutanoate (21.13 mg, 0.033 mmol) were reacted as in the general triazole formation procedure above to afford crude product. The crude material was purified via preparative LC/MS with the following conditions: Column: waters CSH c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 80-100% B over 30 minutes, then a 15-minute hold at 100% B; Flow: 20 mL/min. Fractions containing the desired product were combined and dried via centrifugal evaporation. The yield of the product was 29.2 mg, and its estimated purity by LCMS analysis was 100%. Analysis condition C: Retention time=2.91 min; ESI-MS(+) m/z 869.9 (M+3H), most abundant ion.

Preparation of Example 14089

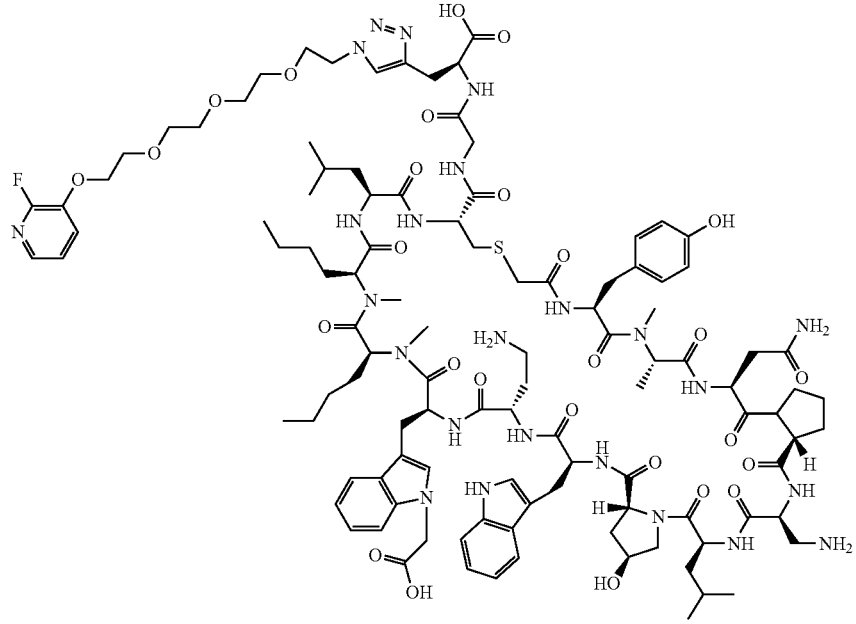

Example 14089

Intermediate 1300V (13 mg, 6.55 µmol) and 3-(2-(2-(2-(2-azidoethoxy)ethoxy)ethoxy)ethoxy)-2-fluoropyridine (2.060 mg, 6.55 µmol), were reacted as in the general triazole formation procedure above to afford crude product. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 1.0 mg, and its estimated purity by LCMS analysis was 100%. Analysis condition A: Retention time=1.60 min; ESI-MS(+) m/z 1149.3 (M+2H), most abundant ion; Analysis condition B: Retention time=3.13 min; ESI-MS(+) m/z 1149.4 (M+2H), most abundant ion; ESI-HRMS(+) m/z: Calculated: 1149.0648 (M+2H). Found: 1149.0635 (M+2H).

Preparation of Example 14090

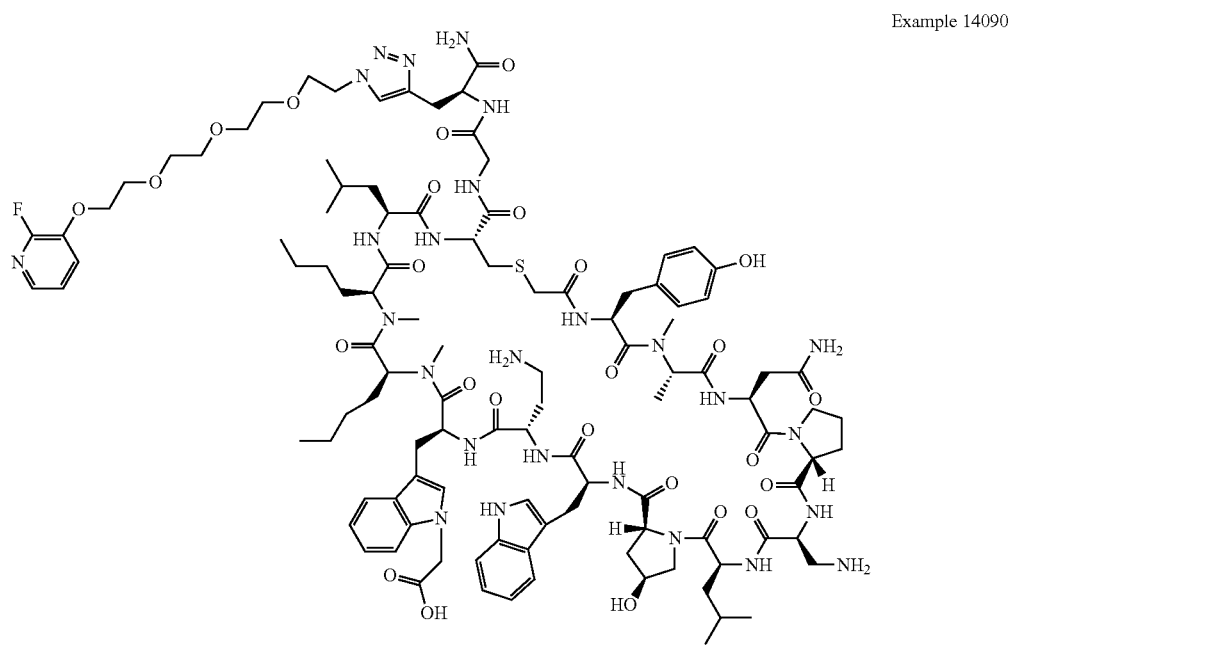 [SMILES: CCCC[C@H]1C(=O)N(C)[C@@H](CCCC)C(=O)N[C@@H](CC(C)C)C(=O)N[C@H](C(=O)NCC(=O)N[C@@H](C/C(=C/NCCOCCOCCOCCOc2cccnc2F)N=N)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 14090

Intermediate 1300W (12.7 mg, 6.41 μmol) and 3-(2-(2-(2-(2-azidoethoxy)ethoxy)ethoxy)ethoxy)-2-fluoropyridine (2.014 mg, 6.41 μmol), were reacted as in the general triazole formation procedure above to afford crude product. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 97%. Analysis condition A: Retention time=1.63 min; ESI-MS(+) m/z 1148.9 (M+2H), most abundant ion; Analysis condition B: Retention time=3.20 min; ESI-MS(+) m/z 1148.9 (M+2H), most abundant ion.

Preparation of Example 14092

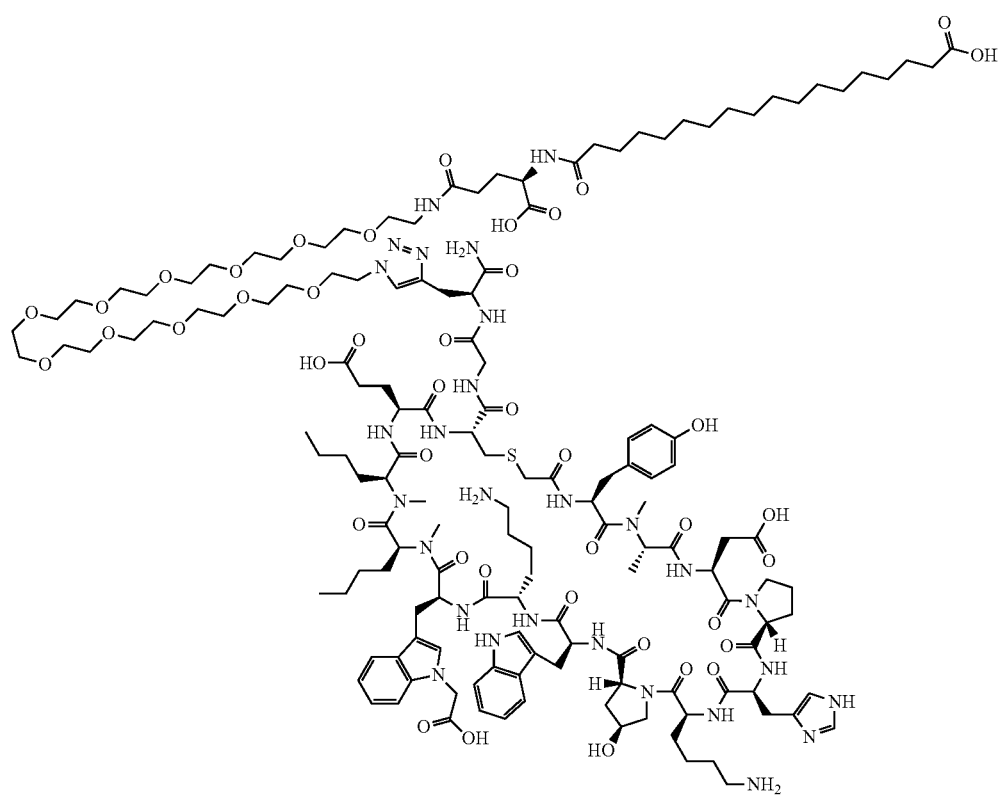

Example 14092

Intermediate 1400J (20 mg, 9.55 µmol) and (S)-1-azido-40-carboxy-37,42-dioxo-3,6,9,12,15,18,21,24,27,30,33-undecaoxa-36,41-diazanonapentacontan-59-oic acid (11.42 mg, 0.011 mmol) were reacted as in the general triazole formation procedure above to afford crude product. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile: water with 0.1% trifluoroacetic acid; Gradient: 20-60% B over 30 minutes, then a 10-minute hold at 100% B; Flow: 20 mL/min. Fractions containing the desired product were combined and dried via centrifugal evaporation. The yield of the product was 4.9 mg, and its estimated purity by LCMS analysis was 95%. Analysis condition A: Retention time=1.39 min; ESI-MS(+) m/z 1028.8 (M−3H), most abundant ion; Analysis condition B: Retention time=3.08 min; ESI-MS(+) m/z 1028.8 (M−3H), most abundant ion; ESI-HRMS(+) m/z: Calculated: 1544.8138 (M+2H). Found: 1544.8114 (M+2H).

Preparation of Example 14093

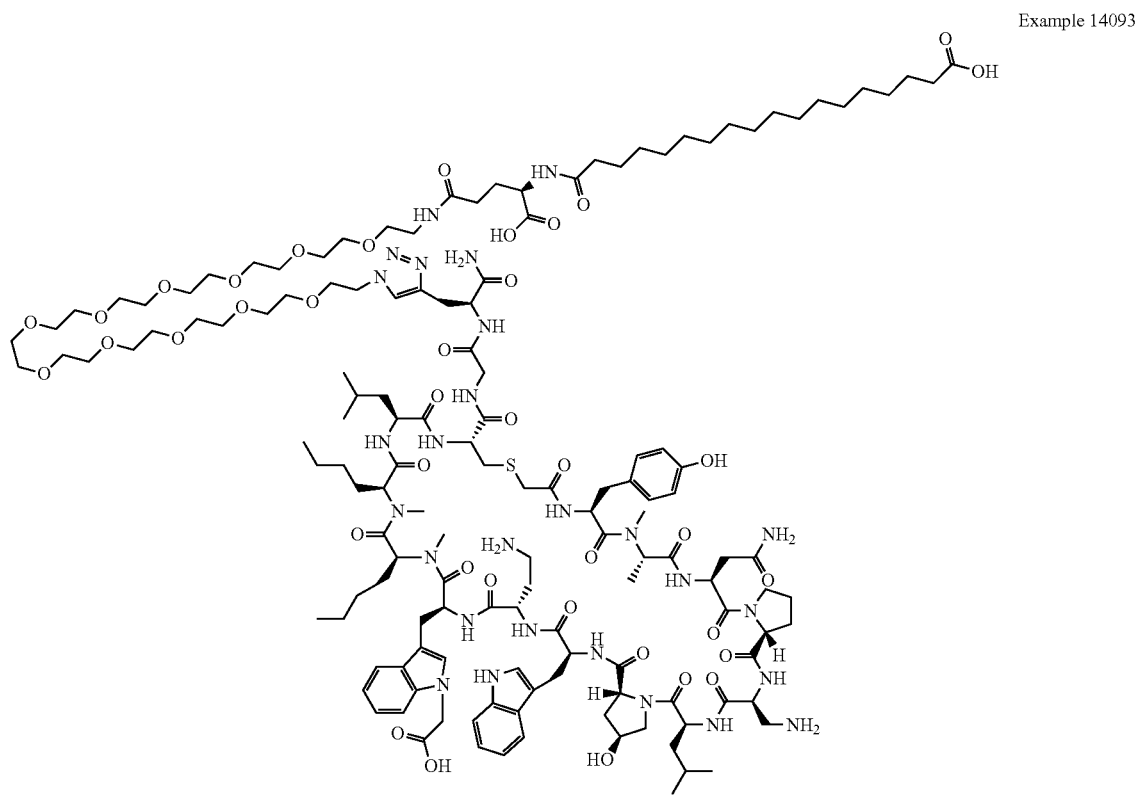 [SMILES: CCCC[C@H]1C(=O)N(C)[C@@H](CCCC)C(=O)N[C@@H](CC(C)C)C(=O)N[C@H](C(=O)NCC(=O)N[C@@H](C/C(=C/NCCOCCOCCOCCOCCOCCOCCOCCOCCOCCOCCOCCNC(=O)CC[C@@H](NC(=O)CCCCCCCCCCCCCCCCC(=O)O)C(=O)O)N=N)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 14093

Intermediate 1300V (30 mg, 15.0 μmol) and (S)-1-azido-40-carboxy-37,42-dioxo-3,6,9,12,15,18,21,24,27,30,33-undecaoxa-36,41-diazanonapentacontan-59-oic acid (18.08 mg, 0.018 mmol) were reacted as in the general triazole formation procedure above to afford crude product. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 35-75% B over 30 minutes, then a 7-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 100%. Analysis condition A: Retention time=1.96 min; ESI-MS(+) m/z 994.3 (M+3H), most abundant ion; ESI-HRMS(+) m/z:

Calculated: 1489.8080 (M+2H). Found: 1489.8043 (M+2H).

Preparation of Example 14095

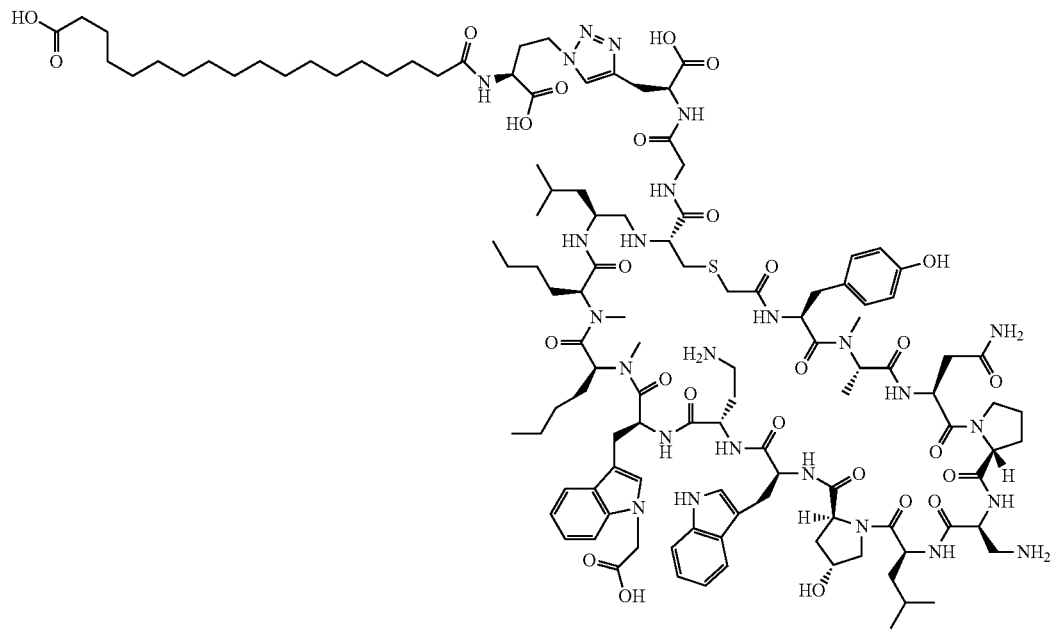

Example 14095

Intermediate 1300V (80 mg, 40.0 µmol) and (S)-18-((3-azido-1-carboxypropyl)amino)-18-oxooctadecanoic acid (17.77 mg, 0.040 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H2O/ACN, Solvent B=10 mM Ammonium Acetate in 5:95 H$_2$O/ACN. Flow rate: 40 ml/min, 15-50% B, 60 min, Sens=100%). The yield of the product was 24 mg, and its estimated purity by LCMS analysis was 90%. Analysis condition E: Retention time=2.51 min; ESI-MS(+) m/z 1213.12 (M+2H), most abundant ion; ESI-HRMS(+) m/z: Calculated: 1212.1452 (M+2H). Found: 1212.1405 (M+2H).

Preparation of Example 14096

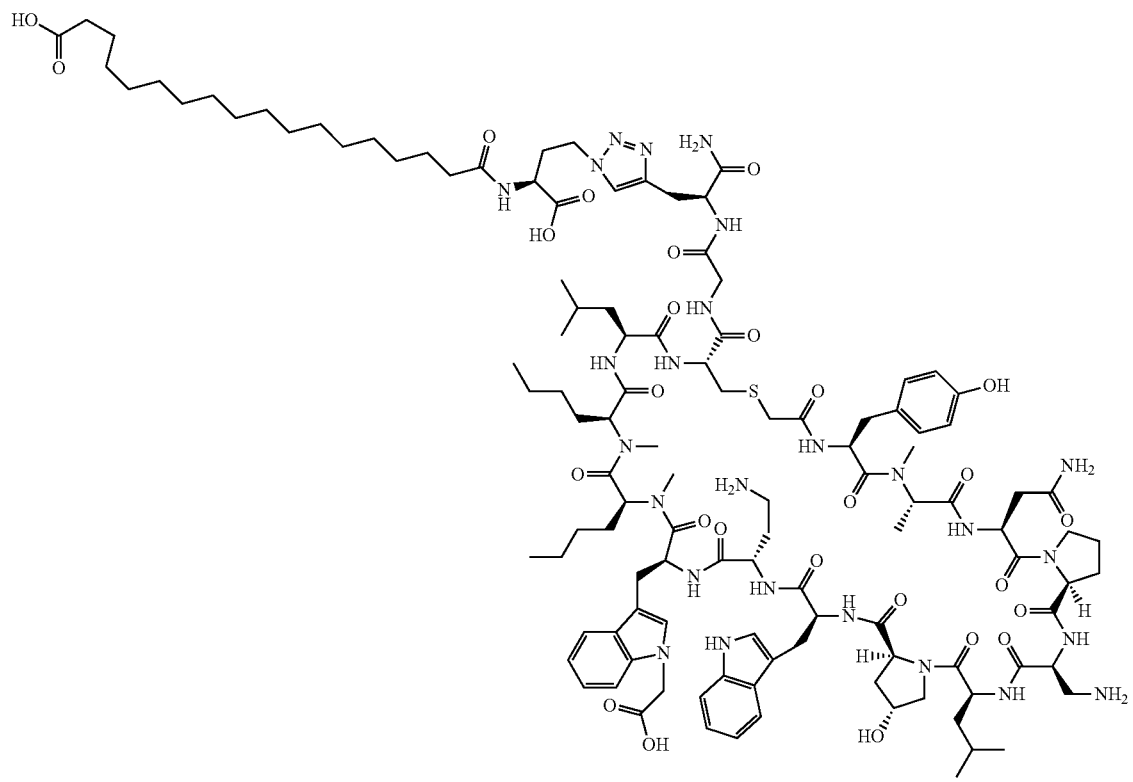

Example 14096

Intermediate 1300W (50 mg, 25.0 µmol) and (S)-18-((3-azido-1-carboxypropyl)amino)-18-oxooctadecanoic acid (11.11 mg, 0.025 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H2O/ACN, Solvent B=10 mM Ammonium Acetate in 5:95 H₂O/ACN. Flow rate: 40 ml/min, 15-50% B, 60 min, Sens=100%). The yield of the product was 14 mg, and its estimated purity by LCMS analysis was 90%. Analysis condition E: Retention time=2.62 min; ESI-MS(+) m/z 1212.31 (M+2H), most abundant ion; ESI-HRMS(+) m/z: Calculated: 1211.6532 (M+2H). Found: 1211.6525 (M+2H).

Preparation of Example 14097

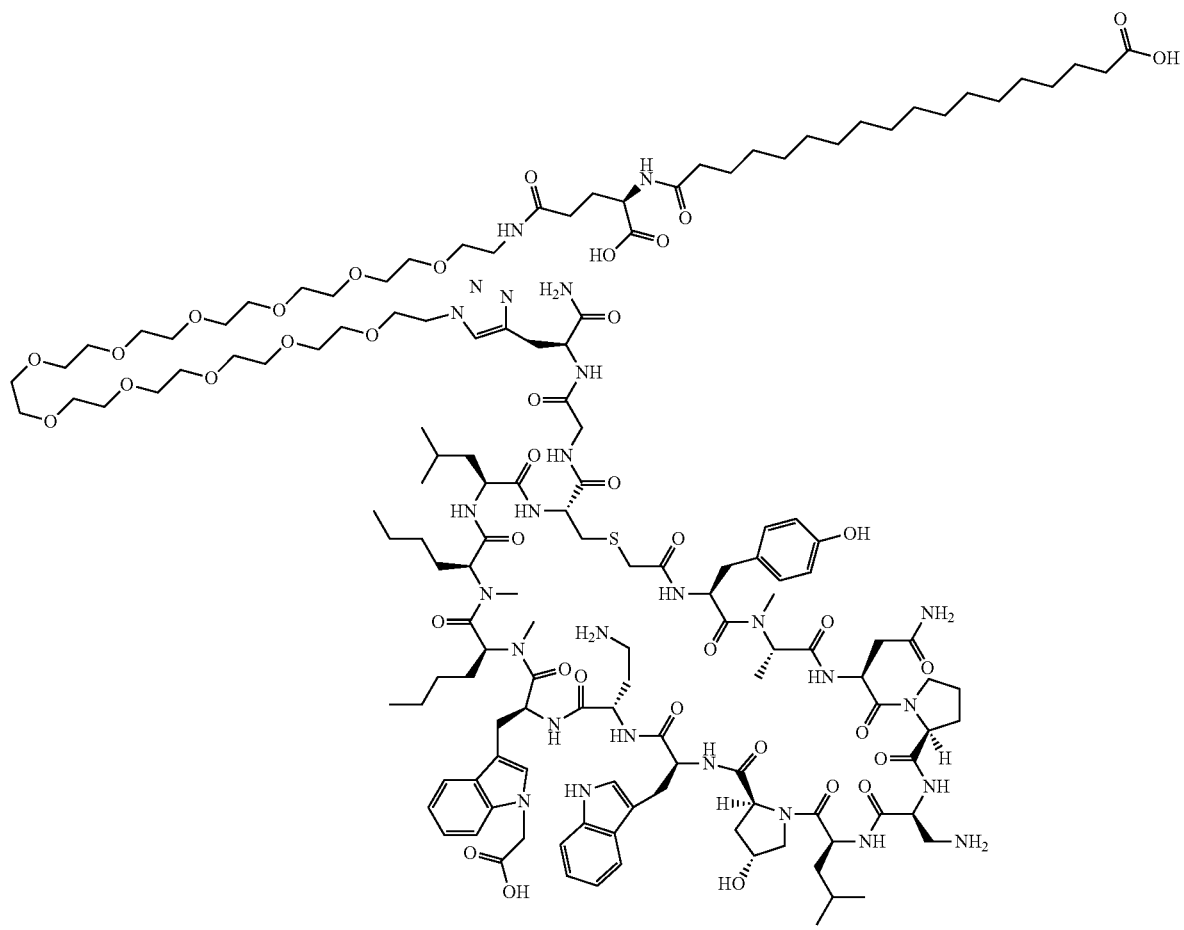

Example 14097

Intermediate 1300W (500 mg, 25.0 μmol) and (S)-1-azido-40-carboxy-37,42-dioxo-3,6,9,12,15,18,21,24,27,30,33-undecaoxa-36,41-diazanonapentacontan-59-oic acid (25.10 mg, 0.025 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H₂O/ACN, Solvent B=10 mM Ammonium Acetate in 5:95 H2O/ACN. Flow rate: 40 ml/min, 15-50% B, 60 min, Sens=100%). The yield of the product was 11 mg, and its estimated purity by LCMS analysis was 90%. Analysis condition E: Retention time=2.57 min; ESI-MS(+) m/z 1489.99 (M+2H), most abundant ion; ESI-HRMS(+) m/z: Calculated: 1489.3160 (M+2H).

Found: 1489.3155 (M+2H).

Preparation of Example 14098

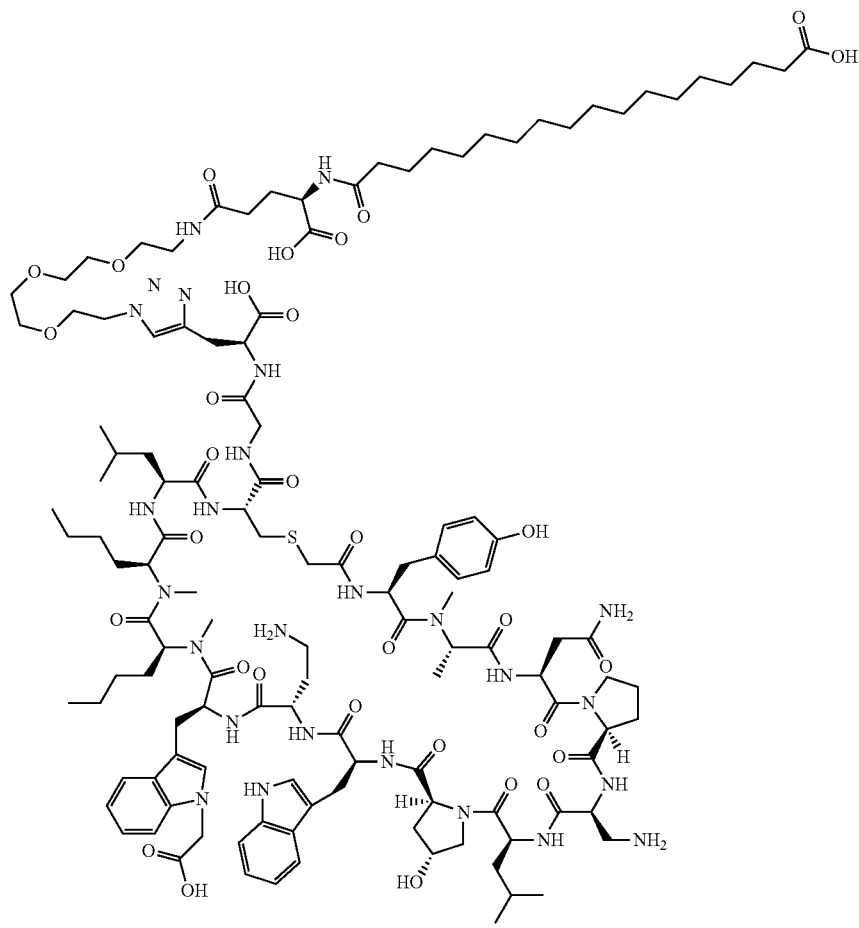

Example 14098

Intermediate 1300V (50 mg, 25.0 μmol) and (S)-1-azido-16-carboxy-13,18-dioxo-3,6,9-trioxa-12,17-diazapentatria-contan-35-oic acid (16.23 mg, 0.025 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H2O/ACN, Solvent B=10 mM Ammonium Acetate in 5:95 H2O/ACN. Flow rate: 40 ml/min, 15-50% B, 60 min, Sens=100%). The yield of the product was 29 mg, and its estimated purity by LCMS analysis was 90%. Analysis condition E: Retention time=2.50 min; ESI-MS(+) m/z 1314.37 (M+2H), most abundant ion ESI-HRMS(+) m/z: Calculated: 1313.7031 (M+2H). Found: 1313.7031 (M+2H).

Preparation of Example 14099

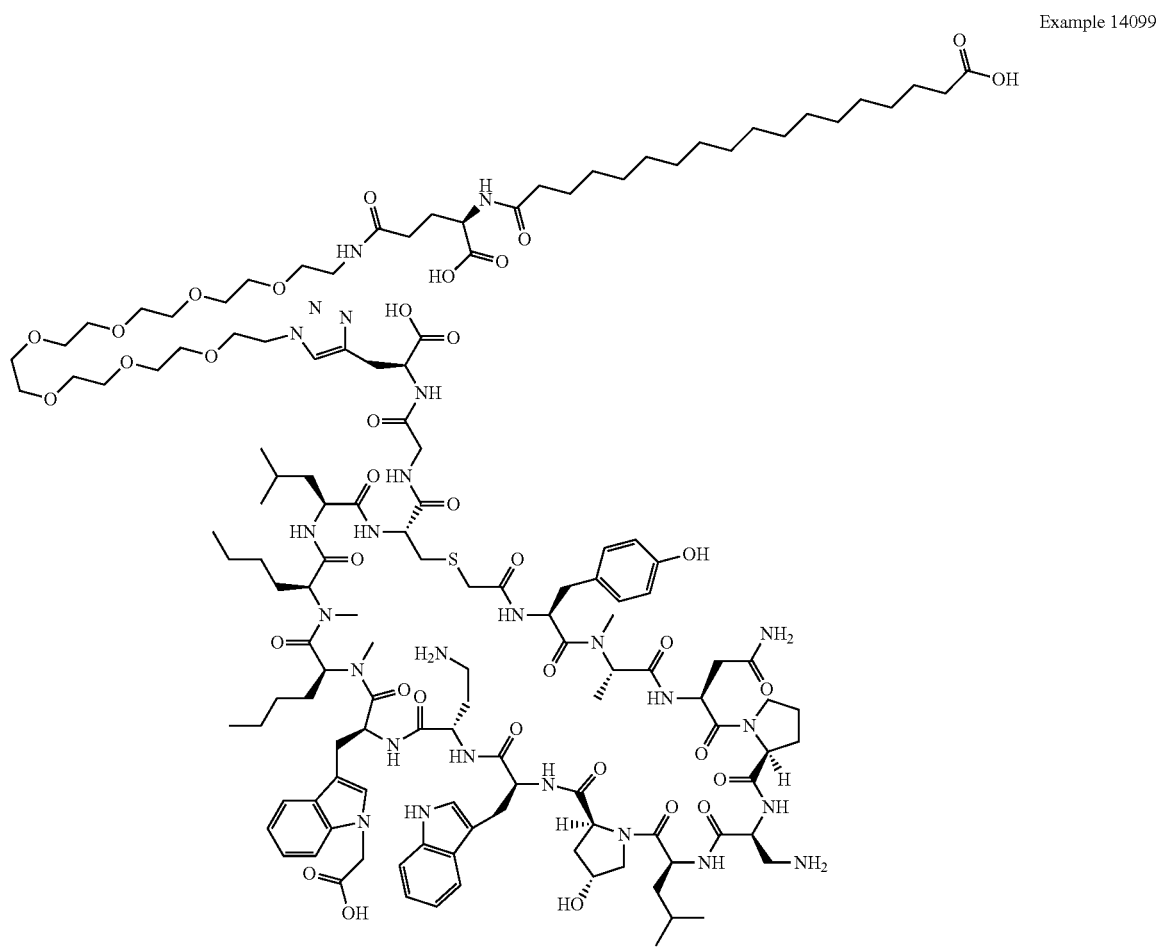

Example 14099

Intermediate 1300V (50 mg, 25.0 µmol) and (S)-1-azido-28-carboxy-25,30-dioxo-3,6,9,12,15,18,21-heptaoxa-24,29-diazaheptatetracontan-47-oic acid (20.67 mg, 0.025 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H2O/ACN, Solvent B=10 mM Ammonium Acetate in 5:95 H2O/ACN. Flow rate: 40 ml/min, 15-50% B, 60 min, Sens=100%). The yield of the product was 51 mg, and its estimated purity by LCMS analysis was 90%. Analysis condition E: Retention time=2.52 min; ESI-MS(+) m/z: 1402.83 (M+2H), most abundant ion ESI-HRMS(+) m/z: Calculated: 1401.7555 (M+2H). Found: 1401.7561 (M+2H).

Preparation of Example 14100

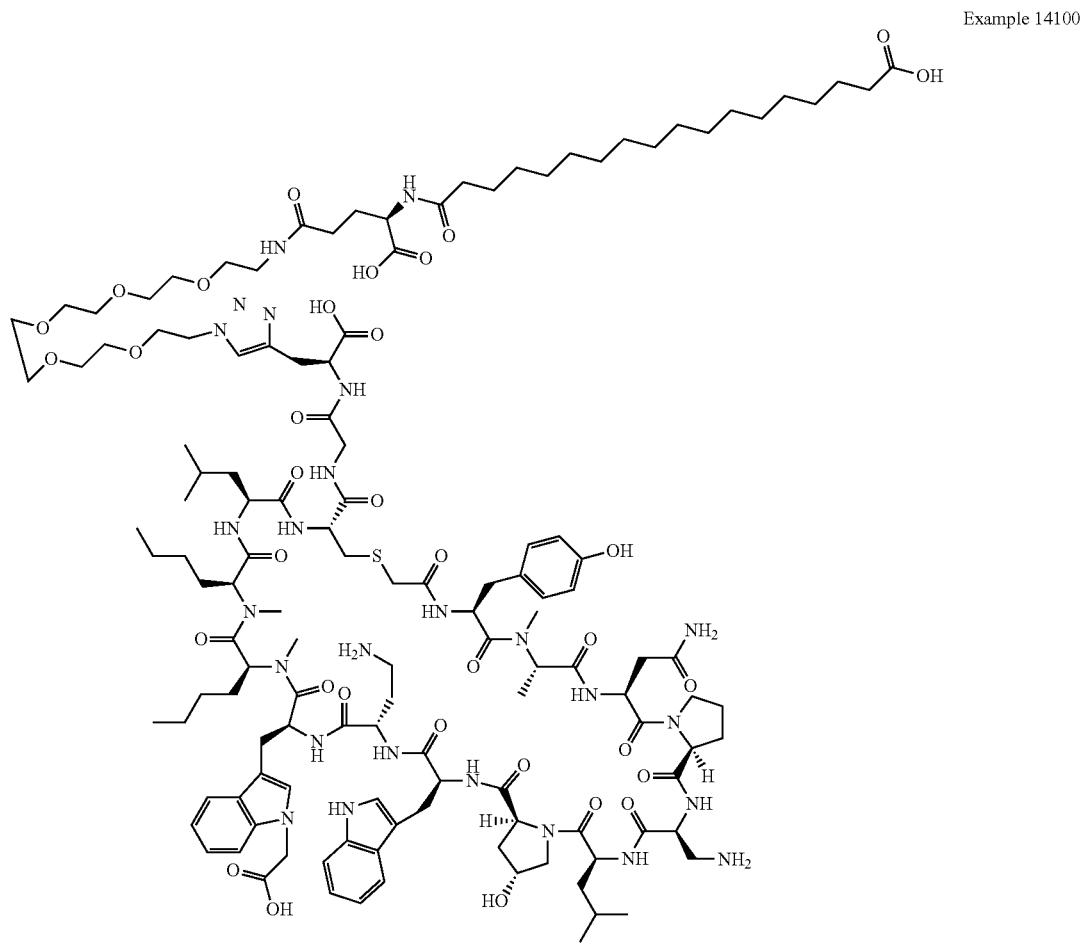

Example 14100

Intermediate 1300V (50 mg, 25.0 μmol) and (S)-1-azido-22-carboxy-19,24-dioxo-3,6,9,12,15-pentaoxa-18,23-diazahentetracontan-41-oic acid (18.45 mg, 0.025 mmol) were reacted as in the general triazole formation procedure above to afford crude product.

The crude product was purified by Prep-HPLC (Column: XBridge Prep C18 30×100 mm 5 um, Solvent A=10 mM Ammonium Acetate in 95:5 H$_2$O/ACN, Solvent B=10 mM Ammonium Acetate in 5:95 H$_2$O/ACN. Flow rate: 40 ml/min, 15-50% B, 60 min, Sens=100%). The yield of the product was 26 mg, and its estimated purity by LCMS analysis was 90%. Analysis condition D: Retention time=2.25 min; ESI-MS(+) m/z 1358.8 (M+2H), most abundant ion ESI-HRMS(+) m/z:

Calculated: 1357.7293 (M+2H). Found: 1357.7263 (M+2H).

Preparation of Example 14101

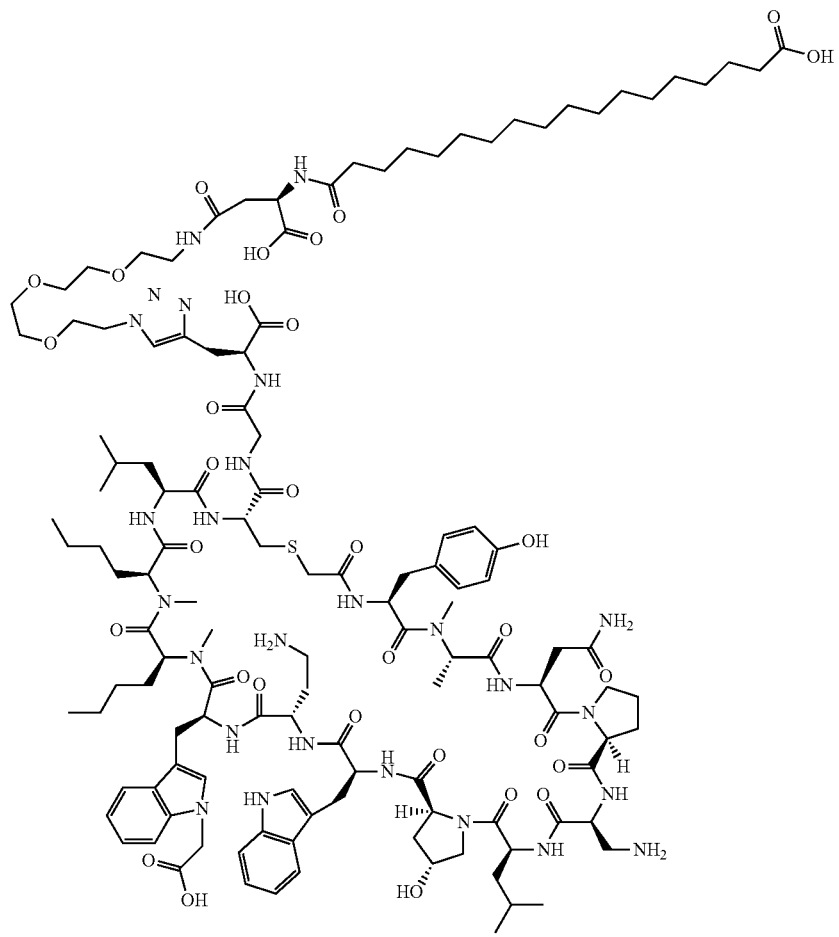

Example 14101

Intermediate 1300V (57 mg, 29.0 µmol) and (S)-1-azido-15-carboxy-13,17-dioxo-3,6,9-trioxa-12,16-diazatetratria-contan-34-oic acid (18.10 mg, 0.029 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H₂O/ACN, Solvent B=10 mM Ammonium Acetate in 5:95 H₂O/ACN. Flow rate: 40 ml/min, 15-50% B, 60 min, Sens=100%). The yield of the product was 15 mg, and its estimated purity by LCMS analysis was 90%. Analysis condition E: Retention time=2.50 min; ESI-MS(+) m/z 1307.4 (M+2H), most abundant ion; ESI-HRMS(+) m/z: Calculated: 1306.6953 (M+2H). Found: 1306.6927 (M+2H).

Preparation of Example 14102

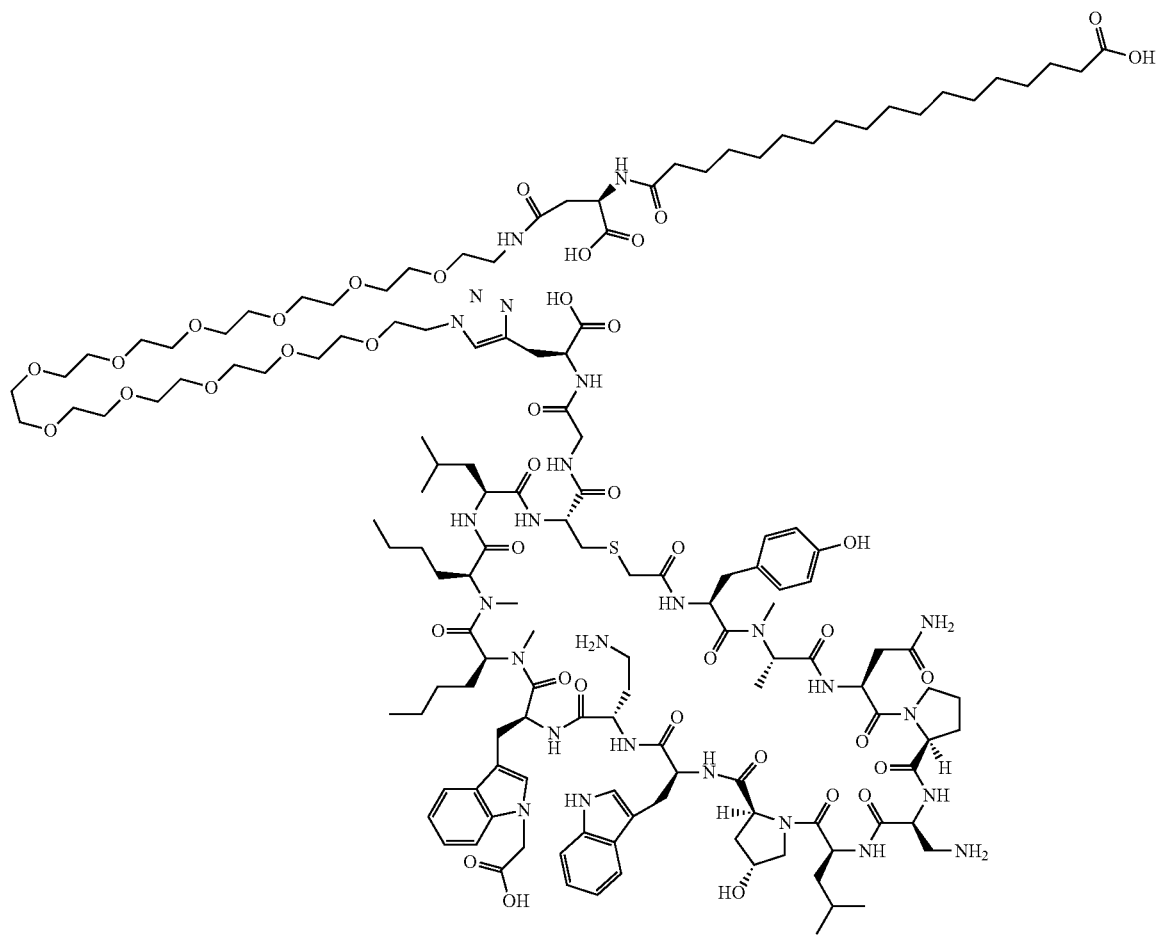

Example 14102

Intermediate 1300V (75 mg, 38.0 μmol) and (S)-1-azido-39-carboxy-37,41-dioxo-3,6,9,12,15,18,21,24,27,30,33-undecaoxa-36,40-diazaoctapentacontan-58-oic acid (37.1 mg, 0.038 mmol) were reacted as in the general triazole formation procedure above to afford crude product. The crude product was purified by Prep-HPLC (Column: XBridge Prep C18 30×100 mm 5 um, Solvent A=10 mM Ammonium Acetate in 95:5 H2O/ACN, Solvent B=10 mM Ammonium Acetate in 5:95 $H_2O$/ACN. Flow rate: 40 ml/min, 15-50% B, 60 min, Sens=100%). The yield of the product was 25 mg, and its estimated purity by LCMS analysis was 90%. Analysis condition D: Retention time=2.31 min; ESI-MS(+) m/z 1483.4 (M+2H), most abundant ion. ESI-HRMS(+) m/z: Calculated: 988.8692 (M+3H).

Found: 988.8696 (M+3H).

Preparation of Example 14103

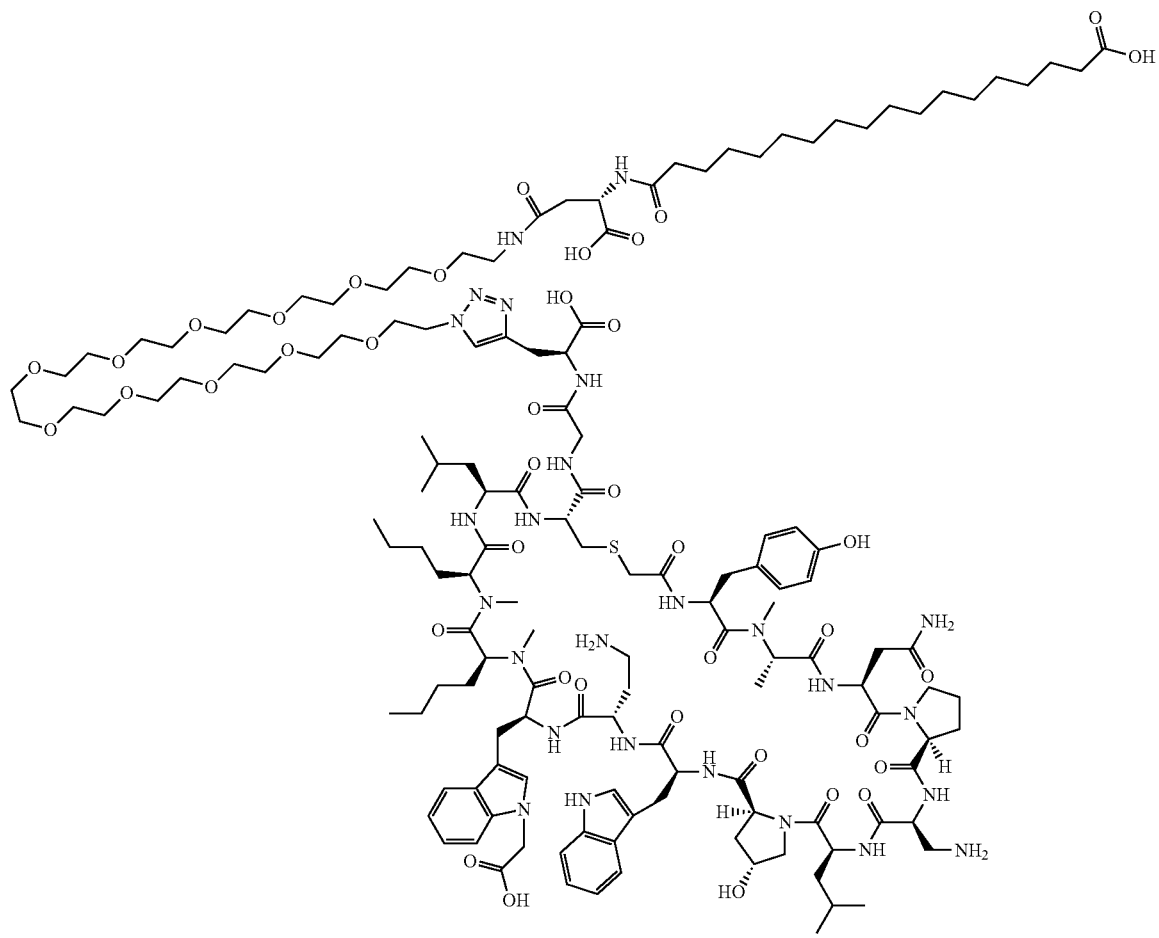

Example 14103

Intermediate 1300V (75 mg, 38.0 µmol) and (S)-1-azido-39-carboxy-37,41-dioxo-3,6,9,12,15,18,21,24,27,30,33-undecaoxa-36,40-diazaoctapentacontan-58-oic acid (37.1 mg, 0.038 mmol), were reacted as in the general triazole formation procedure above to afford crude product. The crude material was purified via preparative LC/MS with the following conditions: Column: Xbridge C18, 30×100 mm, 5-µm particles; Mobile Phase A: 10 mm Ammonium Acetate in 95:5 H$_2$O:ACN; Mobile Phase B: 10 mm Ammonium Acetate in 5:95 H$_2$O:ACN; Gradient: 15-50% B over 60 minutes, Flow: 40 mL/min, Sens: 100%. Fractions containing the desired product were combined and dried via centrifugal evaporation. The yield of the product was 25 mg, and its estimated purity by LCMS analysis was 90%. Analysis condition D: Retention time=2.243 min; ESI-MS(+) m/z 1483.4 (M+2H), most abundant ion; ESI-HRMS(+) m/z: Calculated: 1482.8001 (M+2H).

Found: 1482.7974 (M+2H).

Preparation of Example 14104

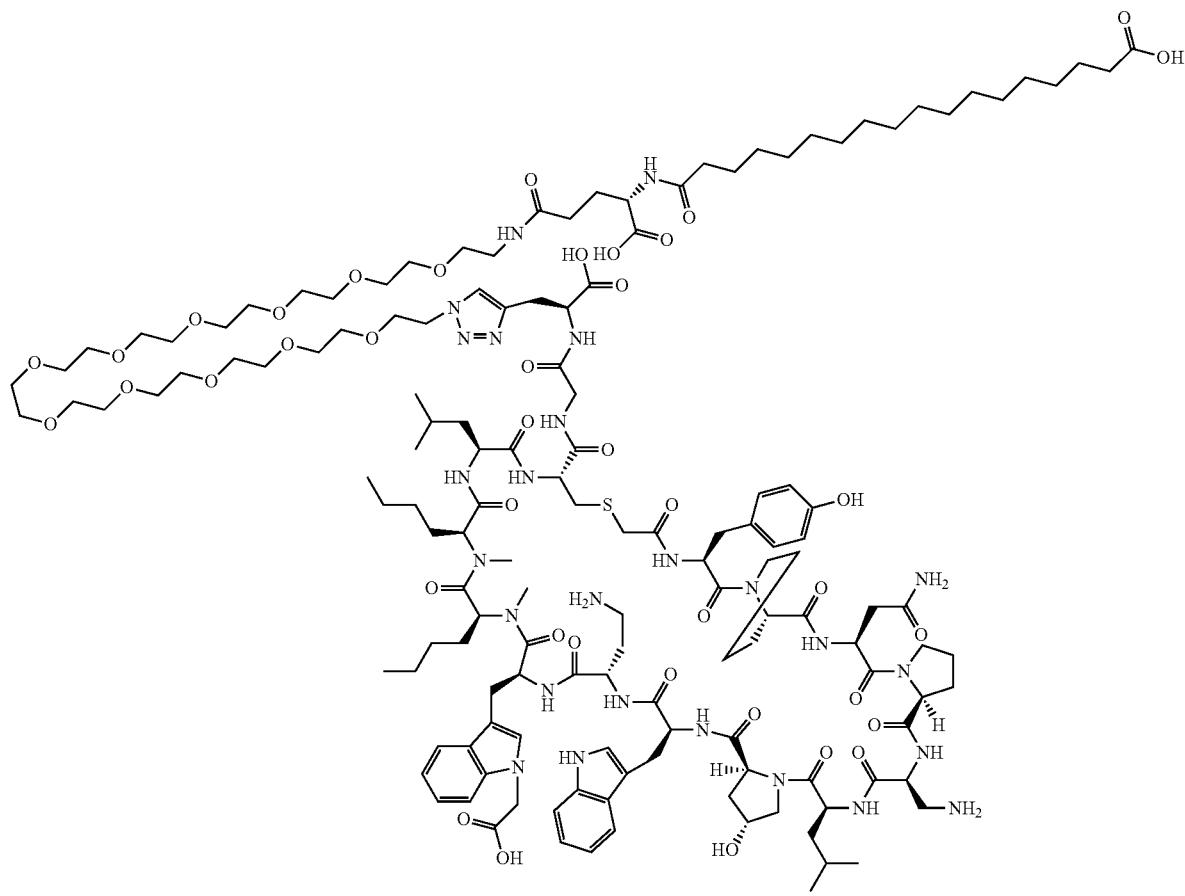

Intermediate 130AI (75 mg, 37.0 µmol) and (S)-1-azido-40-carboxy-37,42-dioxo-3,6,9,12,15,18,21,24,27,30,33-undecaoxa-36,41-diazanonapentacontan-59-oic acid (37.2 mg, 0.037 mmol), were reacted as in the general triazole formation procedure above to afford crude product. The crude material was purified via preparative LC/MS with the following conditions: Column: Xbridge C18, 30×100 mm, 5-µm particles; Mobile Phase A: 10 mm Ammonium Acetate in 95:5 $H_2O$:ACN; Mobile Phase B: 10 mm Ammonium Acetate in 5:95 $H_2O$:ACN; Gradient: 15-50% B over 60 minutes, Flow: 40 mL/min, Sens: 100%. Fractions containing the desired product were combined and dried via centrifugal evaporation. The yield of the product was 33 mg, and its estimated purity by LCMS analysis was 90%. Analysis condition D: Retention time=2.27 min; ESI-MS(+) m/z 1002.5 (M+3H), most abundant ion; ESI-HRMS(+) m/z: Calculated: 1502.8163 (M+2H).

Found: 1502.8137.

Preparation of Example 14105

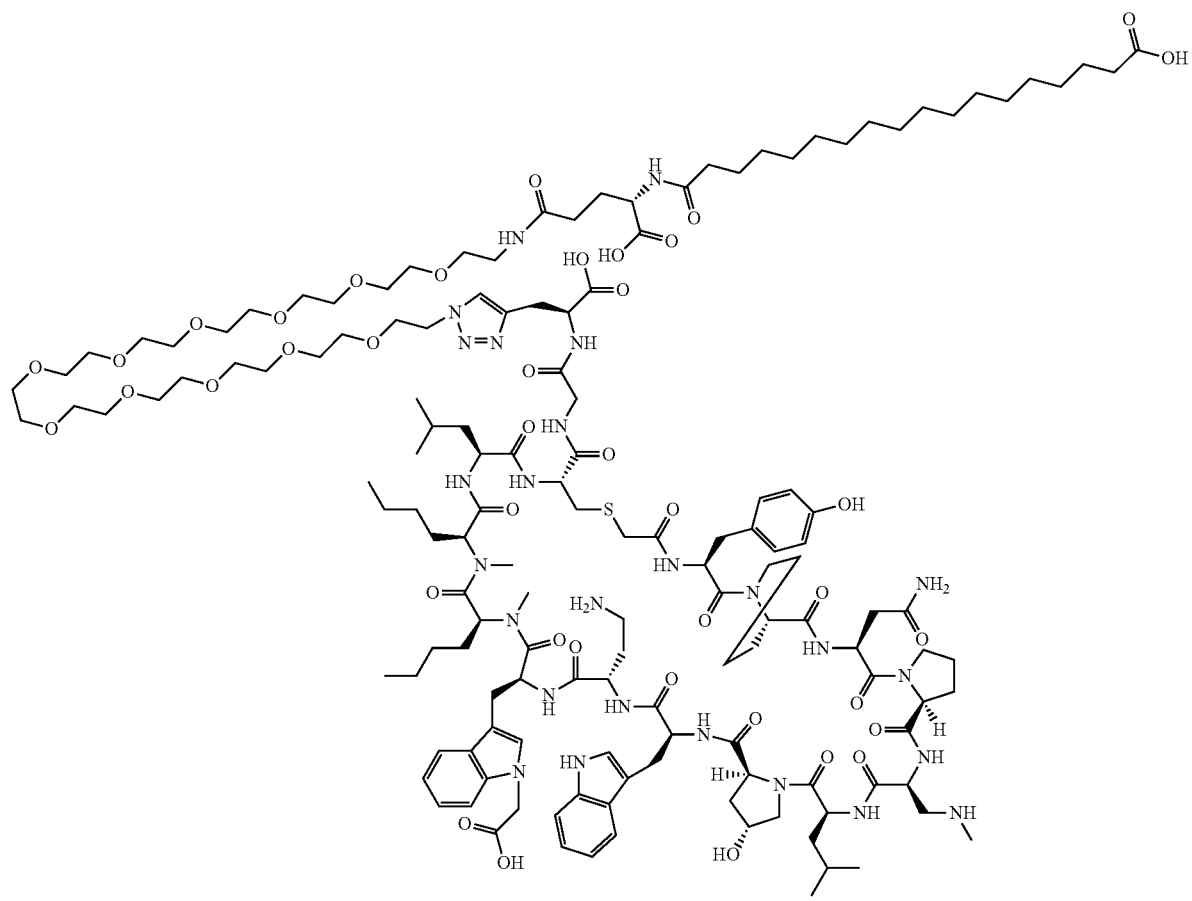

Intermediate 130AK (75 mg, 37.0 µmol) and (S)-1-azido-40-carboxy-37,42-dioxo-3,6,9,12,15,18,21,24,27,30,33-undecaoxa-36,41-diazanonapentacontan-59-oic acid (36.9 mg, 0.037 mmol), were reacted as in the general triazole formation procedure above to afford crude product. The crude material was purified via preparative LC/MS with the following conditions: Column: Xbridge C18, 30×100 mm, 5-µm particles; Mobile Phase A: 10 mm Ammonium Acetate in 95:5 $H_2O$:ACN; Mobile Phase B: 10 mm Ammonium Acetate in 5:95 $H_2O$:ACN; Gradient: 15-50% B over 60 minutes, Flow: 40 mL/min, Sens: 100%. Fractions containing the desired product were combined and dried via centrifugal evaporation. The yield of the product was 31 mg, and its estimated purity by LCMS analysis was 90%. Analysis condition D: Retention time=2.27 min; ESI-MS(+) m/z 1007.2 (M+3H), most abundant ion; ESI-HRMS(+) m/z: Calculated: 1509.8242 (M+2H).

Found: 1509.8224.

Preparation of Example 14106

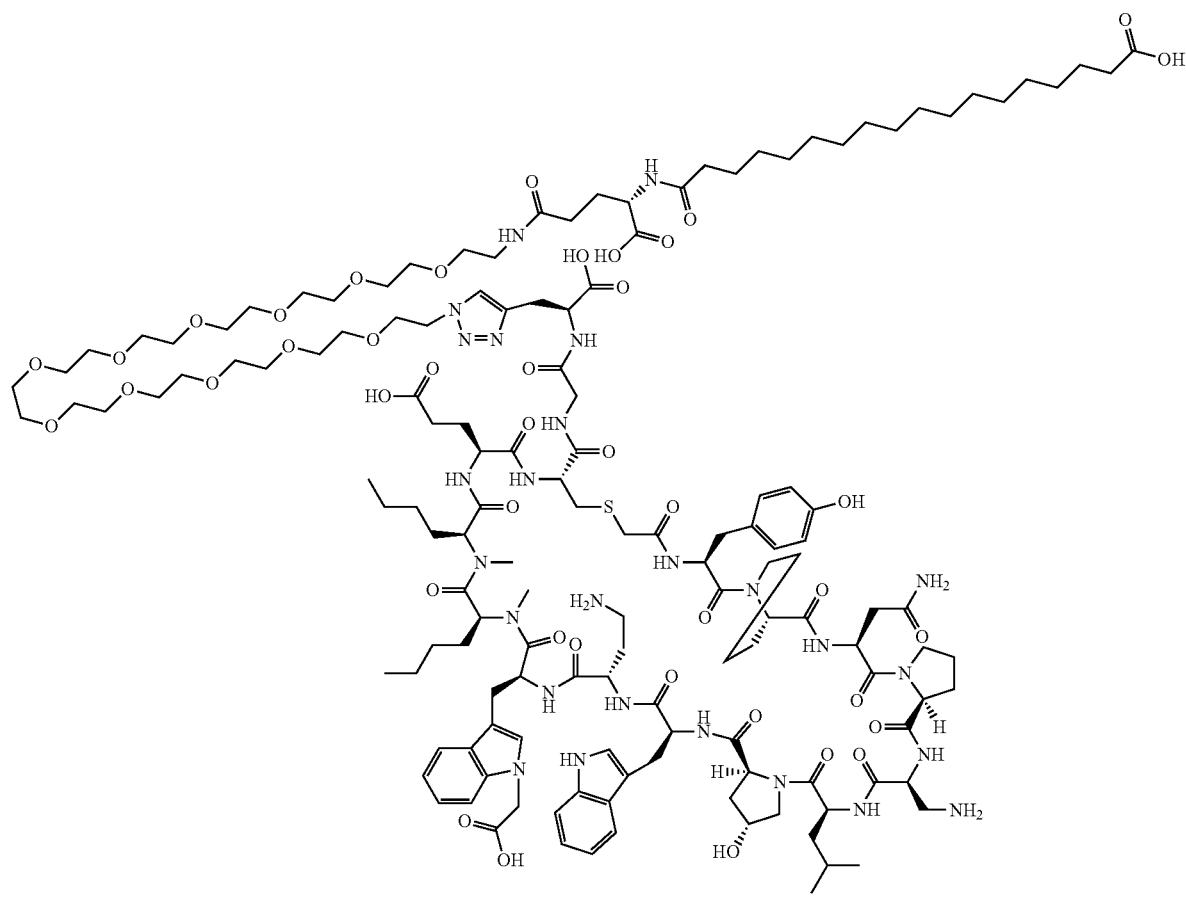

Intermediate 130AJ (75 mg, 37.0 μmol) and (S)-1-azido-40-carboxy-37,42-dioxo-3,6,9,12,15,18,21,24,27,30,33-undecaoxa-36,41-diazanonapentacontan-59-oic acid (36.9 mg, 0.037 mmol), were reacted as in the general triazole formation procedure above to afford crude product. The crude material was purified via preparative LC/MS with the following conditions: Column: Xbridge C18, 30×100 mm, 5-μm particles; Mobile Phase A: 10 mm Ammonium Acetate in 95:5 H$_2$O:ACN; Mobile Phase B: 10 mm Ammonium Acetate in 5:95 H$_2$O:ACN; Gradient: 15-50% B over 60 minutes, Flow: 40 mL/min, Sens: 100%. Fractions containing the desired product were combined and dried via centrifugal evaporation. The yield of the product was 26 mg, and its estimated purity by LCMS analysis was 90%. Analysis condition D: Retention time=2.24 min; ESI-MS(+) m/z 1007.8 (M+3H), most abundant ion; ESI-HRMS(+) m/z: Calculated: 1510.7956 (M+2H).
Found: 1510.7940.

Preparation of Example 14107

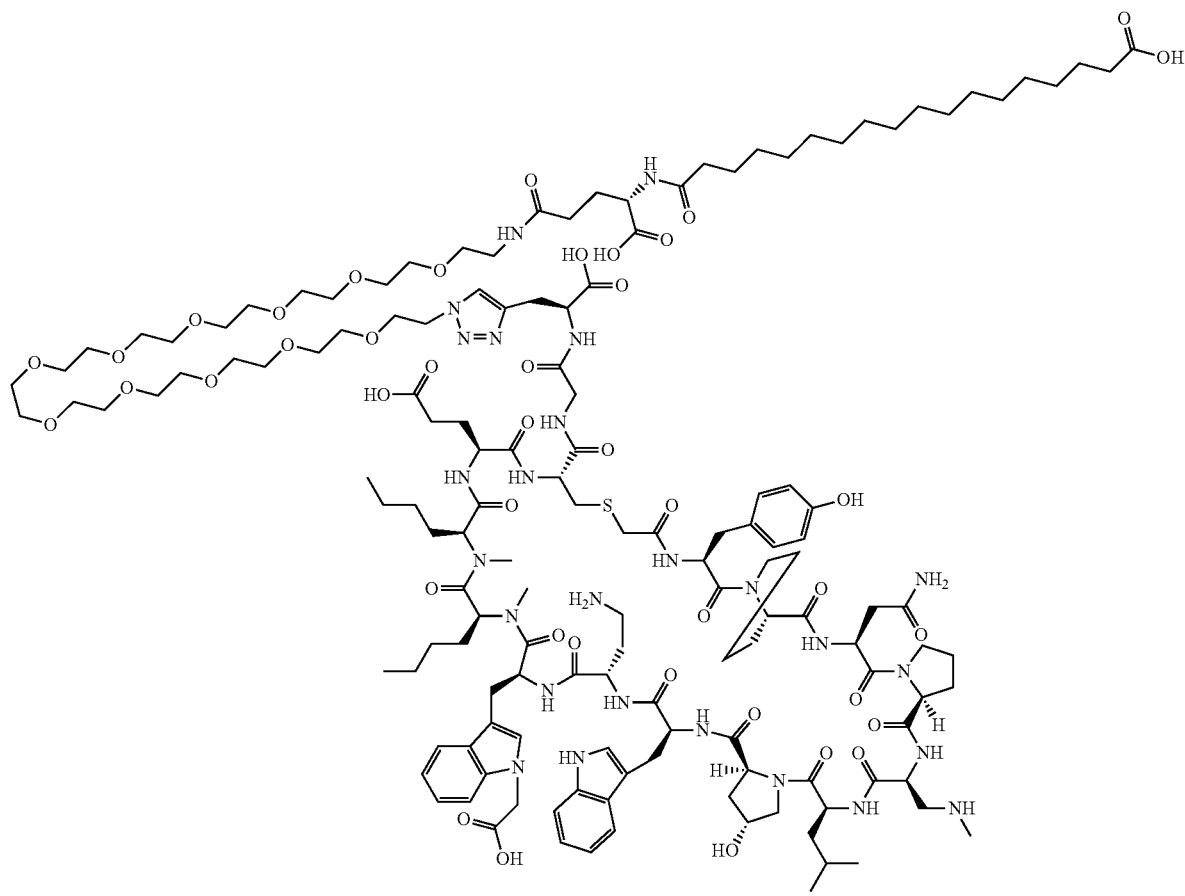

Intermediate 130AL (75 mg, 37.0 µmol) and (S)-1-azido-40-carboxy-37,42-dioxo-3,6,9,12,15,18,21,24,27,30,33-undecaoxa-36,41-diazanonapentacontan-59-oic acid (36.6 mg, 0.037 mmol), were reacted as in the general triazole formation procedure above to afford crude product. The crude material was purified via preparative LC/MS with the following conditions: Column: Xbridge C18, 30×100 mm, 5-µm particles; Mobile Phase A: 10 mm Ammonium Acetate in 95:5 $H_2O$:ACN; Mobile Phase B: 10 mm Ammonium Acetate in 5:95 H2O:ACN; Gradient: 15-50% B over 60 minutes, Flow: 40 mL/min, Sens: 100%. Fractions containing the desired product were combined and dried via centrifugal evaporation. The yield of the product was 29 mg, and its estimated purity by LCMS analysis was 90%. Analysis condition D: Retention time=2.23 min; ESI-MS(+) m/z 1012.5 (M+3H), most abundant ion; ESI-HRMS(+) m/z: Calculated: 1517.8034 (M+2H).

Found: 1517.8015.

927
Preparation of INT-1400M

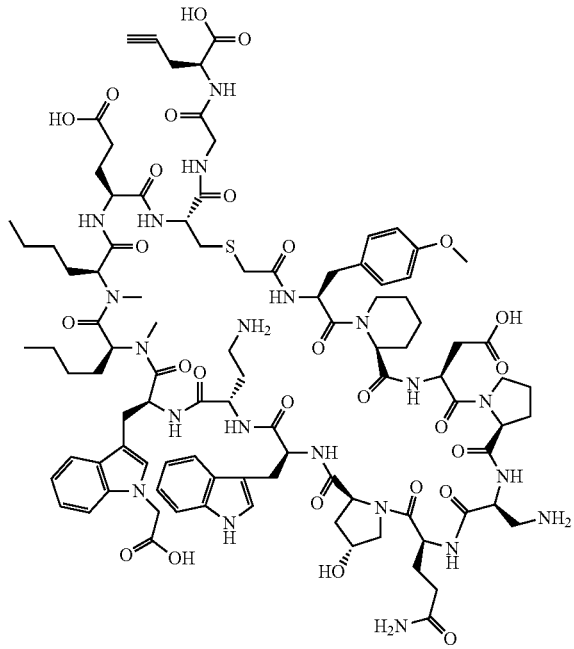

INTERMEDIATE 1400M

The above peptide was synthesized on a 1.0 mmol scale according to the procedures above. The underlined steps employed the double-coupling procedure. ClAc-Tyr(Me)-Pip-Asp-Pro-Dap-Gln-Hyp-Trp-Dab-Trp'-mNle-mNle-Glu-Cys-Gly-[(S)-propargylglycine]

After deprotection and cyclization according to the procedures above, the compound was purified as follows:

The crude material was purified via preparative LC/MS with the following conditions: Column: XBridge C18, 30×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 7-minute hold at 100% B; Flow: 50 mL/min. Fractions containing the desired product were combined and dried via centrifugal evaporation. The yield of the product was 30 mg, and its estimated purity by LCMS analysis was 66.9%.

Analysis condition E: Retention time=2.55 min; ESI-MS (−) m/z 1026.7 (M−2H), most abundant ion.

928
Preparation of INT-1400N

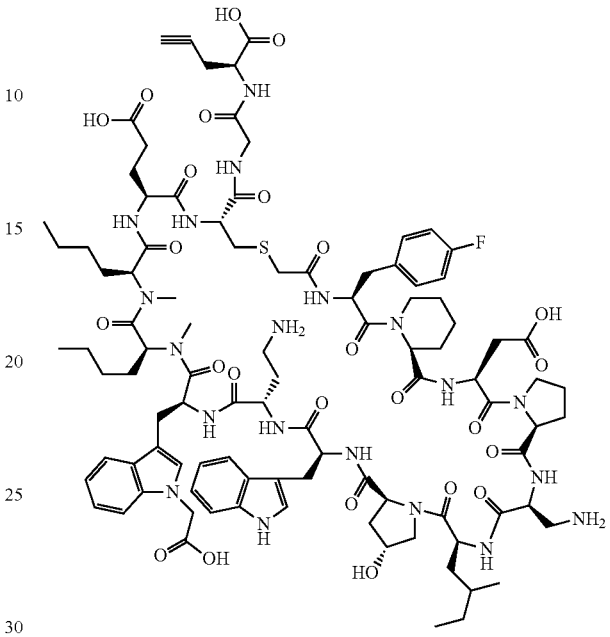

INTERMEDIATE 1400N

The above peptide was synthesized on a 1.8 mmol scale according to the procedures above. The underlined steps employed the double-coupling procedure. ClAc-Tyr(4-F)-Pip-Asp-Pro-Dap-Leu-Hyp-Trp-Dab-Trp'-mNle-mNle-Leu-Cys-Gly-[(S)-propargylglycine]

After deprotection and cyclization according to the procedures above, the compound was purified as follows: The crude material was purified via preparative LC/MS with the following conditions: Column: XBridge C18, 30×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 50 mL/min. Fractions containing the desired product were combined and dried via centrifugal evaporation.

The yield of the product was 90 mg, and its estimated purity by LCMS analysis was 52.5%. Analysis condition E: Retention time=1.73 min; ESI-MS(+) m/z 1007.0 (M+2H), most abundant ion.

Preparation of Example 14121

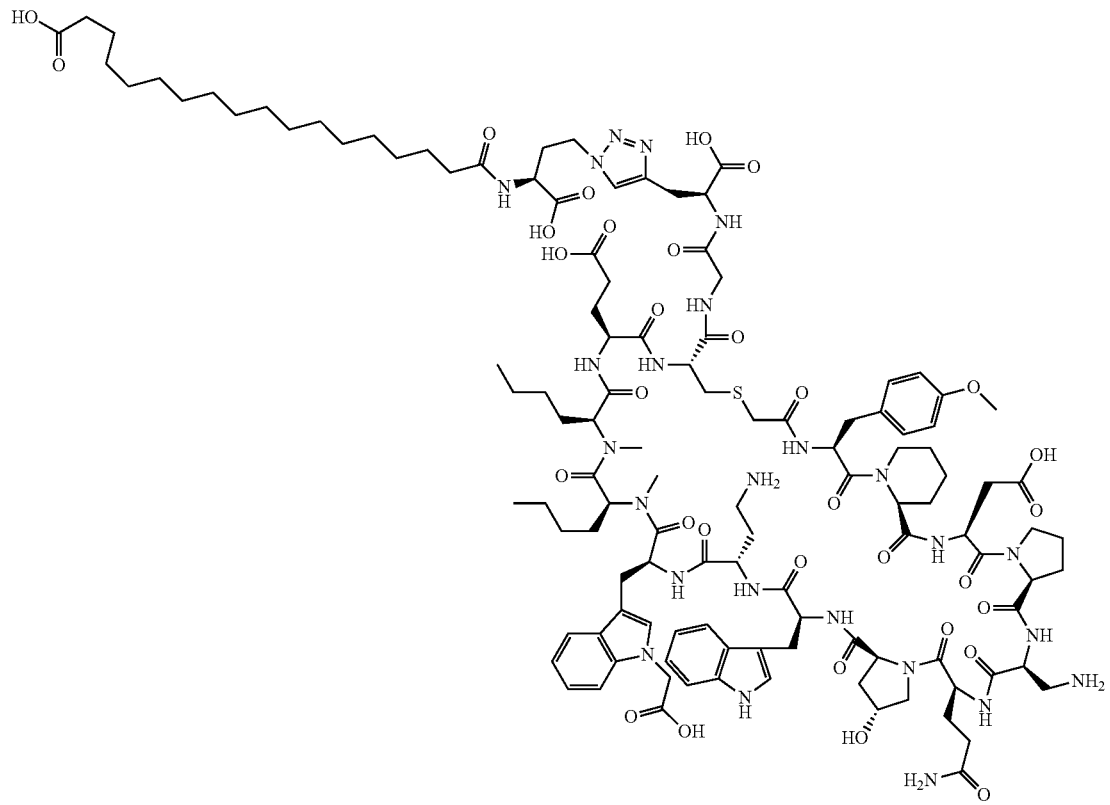

Example 14121

Intermediate 1400M (30 mg, 7.59 µmol) and (S)-18-((3-azido-1-carboxypropyl)amino)-18-oxooctadecanoic acid (3.34 mg, 7.59 µmol) were reacted as in the general triazole formation procedure to afford crude product. The crude material was purified via preparative LC/MS with the following conditions: (Column: XBridge Prep C18 30×100 mm 5 um, Solvent A=10 mM Ammonium Acetate in 95:5 $H_2O$/ACN, Solvent B=10 mM Ammonium Acetate in 5:95 $H_2O$/ACN. Flow rate: 40 ml/min, 15-50% B, 60 min). Fractions containing the desired product were combined and dried via centrifugal evaporation.

The yield of the product was 8.0 mg, and its estimated purity by LCMS analysis was 97%.

Analysis condition C: Retention time=1.15 min; ESI-MS (+) m/z 832.9 (M+3H).

Analysis condition D: Retention time=2.29 min; ESI-MS (+) m/z 1248.4 (M+2H).

Analysis condition E: Retention time=2.45 min; ESI-MS (−) m/z 830.0 (M−3H).

ESI-HRMS(+) m/z: Calculated: 1248.1194 (M+2H). Found: 1248.1185 (M+2H).

Preparation of Example 14122

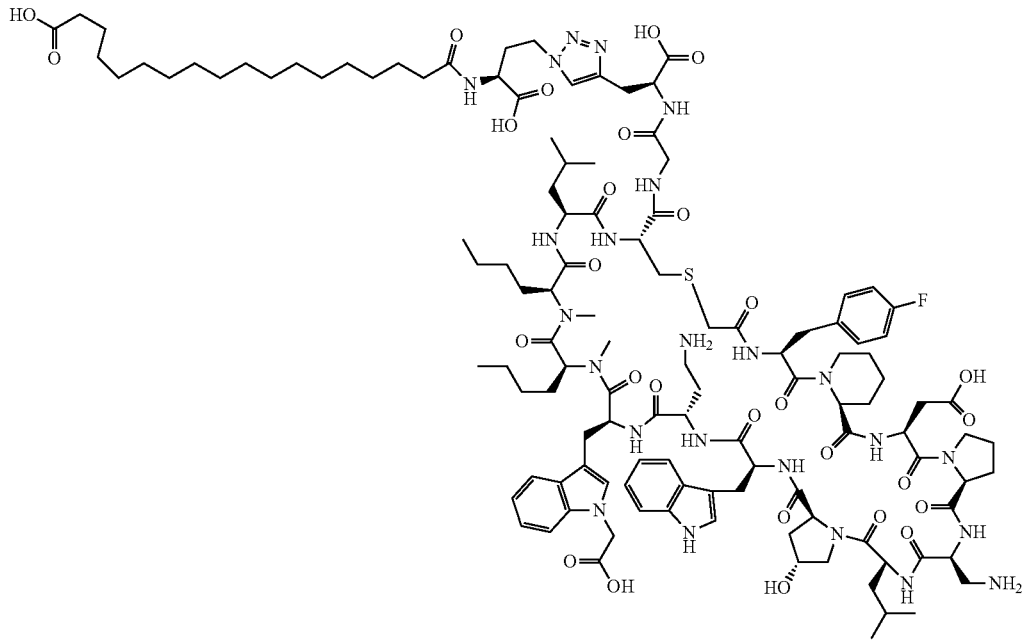

Example 14122

Intermediate 1400N (90 mg, 23 µmol) and (S)-18-((3-azido-1-carboxypropyl)amino)-18-oxooctadecanoic acid (10.34 mg, 23 µmol) were reacted as in the general triazole formation procedure to afford crude product. The crude material was purified via preparative LC/MS with the following conditions: (Column: XBridge Prep C18 30×100 mm 5 um, Solvent A=10 mM Ammonium Acetate in 95:5 H2O/ACN, Solvent B=10 mM Ammonium Acetate in 5:95 H$_2$O/ACN. Flow rate: 40 ml/min, 15-50% B, 60 min). Fractions containing the desired product were combined and dried via centrifugal evaporation.

The yield of the product was 12.0 mg, and its estimated purity by LCMS analysis was 97%.

Analysis condition D: Retention time=2.47 min; ESI-MS (+) m/z 1227.2 (M+2H).

Analysis condition E: Retention time=2.45 min; ESI-MS (+) m/z 1227.2 (M+2H).

ESI-HRMS(+) m/z: Calculated: 1226.6429 (M+2H). Found: 1226.6408 (M+2H).

Preparation of 1-tert-butyl 18-(perfluorophenyl)octadecanedioate

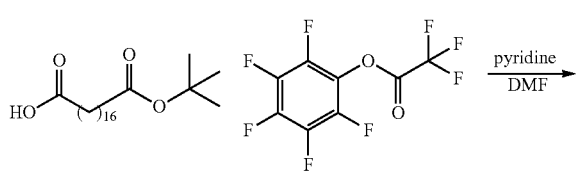

-continued

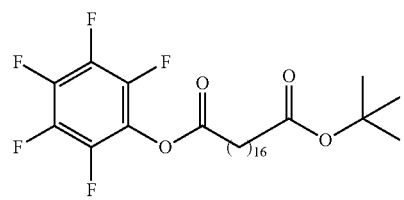

To a solution of 18-(tert-butoxy)-18-oxooctadecanoic acid (5.00 g, 13.49 mmol) in DMF (54.0 ml) was added pyridine (3.82 ml, 47.2 mmol), followed by pentafluorophenyl trifluoroacetate (5.81 ml, 33.7 mmol). A gel formed, and an additional stir bar was added to the reaction mixture. The mixture was stirred vigorously overnight. The reaction mixture was filtered (Buchner funnel/paper) to afford a white solid, which was washed with a small amount of DMF. A nitrogen-rich atmosphere was sucked through the filter cake for a few hours to provide 1-tert-butyl 18-(perfluorophenyl) octadecanedioate (6.50 g, 11.63 mmol, 90% yield). Analysis condition D: Retention time=4.12 min; ESI-MS(+) m/z 559.1 (M+Na).

Preparation of Preparation of (S)-5-(benzyloxy)-4-(18-(tert-butoxy)-18-oxooctadecanamido)-5-oxopentanoic acid

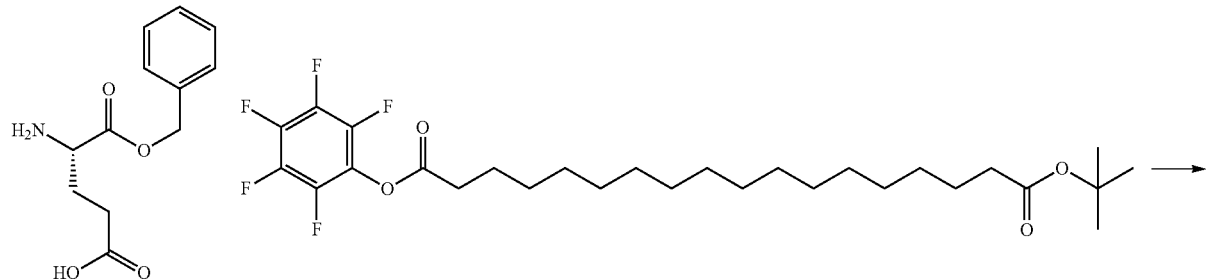

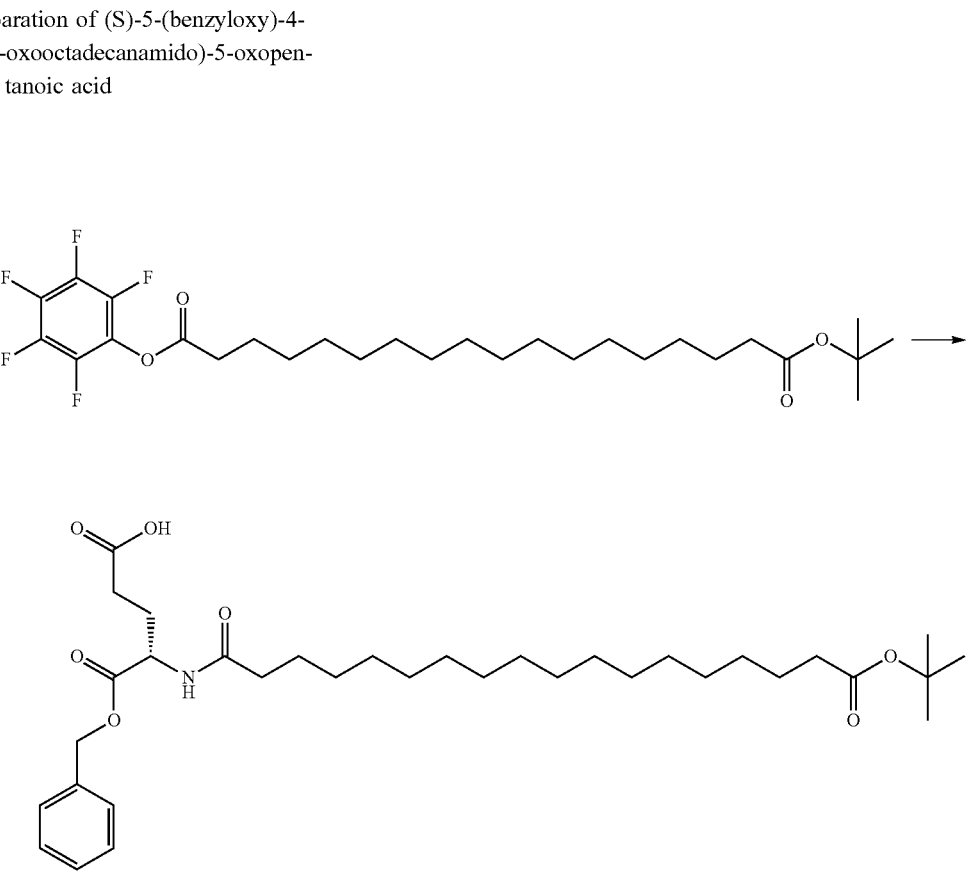

The mixture of (S)-4-amino-5-(benzyloxy)-5-oxopentanoic acid (1.1 g, 4.64 mmol), 1-tert-butyl 18-(perfluorophenyl)octadecanedioate (2.488 g, 4.64 mmol) and Hunig's Base (1.053 ml, 6.03 mmol) in DMF (15.45 ml) was stirred for 24 hr at rt. After 24 hr the reaction was homogeneous. The reaction mixture was poured into a saturated citric acid solution, and extracted with $CH_2Cl_2$ (3×50 ml). The organic fractions were combined, washed with brine, dried over $Na2SO_4$ and evaporated in vacuo. The resulting crude product was purified by Biotage (SG, 300 g, 0 to 25% acetone/$CH_2Cl_2$) to get (S)-5-(benzyloxy)-4-(18-(tert-butoxy)-18-oxooctadecanamido)-5-oxopentanoic acid (1.31 g, 2.221 mmol, 47.9% yield). Analysis condition D: Retention time=2.99 min; ESI-MS(+) m/z 591.2 (M+1); $^1H$ NMR (500 MHz, METHANOL-$d_4$) δ 7.41-7.28 (m, 5H), 5.22-5.14 (m, 2H), 4.49 (dd, J=9.2, 5.3 Hz, 1H), 2.42-2.35 (m, 2H), 2.27-2.19 (m, 4H), 2.19-2.13 (m, 1H), 1.96 (ddt, J=14.2, 9.0, 7.1 Hz, 1H), 1.65-1.52 (m, 4H), 1.48-1.41 (m, 9H), 1.37 (br. s., 1H), 1.33-1.26 (m, 24H).

Preparation of (S)-1-benzyl 5-(perfluorophenyl) 2-(18-(tert-butoxy)-18-oxooctadecanamido)pentanedioate

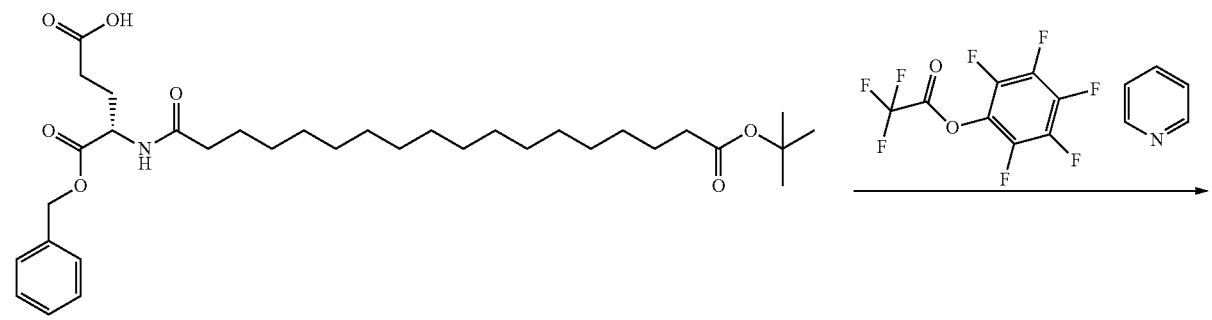

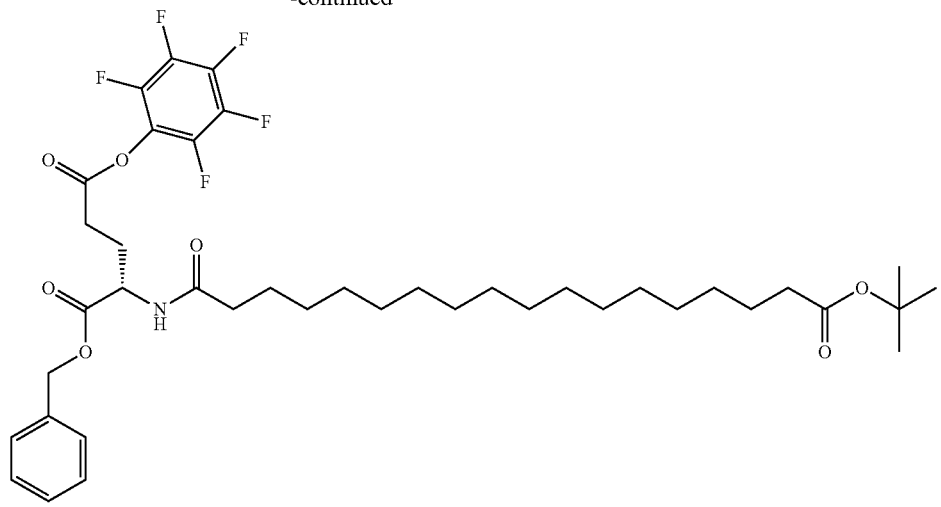

To a 100 ml RBF was added (S)-5-(benzyloxy)-4-(18-(tert-butoxy)-18-oxooctadecanamido)-5-oxopentanoic acid (1.31 g, 2.221 mmol), N,N-Dimethylformamide (7.40 ml), pyridine (0.387 g, 4.89 mmol), and perfluorophenyl 2,2,2-trifluoroacetate (1.244 g, 4.44 mmol). The reaction was allowed to stir for 24 hr at it. After 24 hr the reaction mixture was poured into a saturated citric acid solution, and extracted with CH$_2$Cl$_2$ (3×50 ml). The organic fractions were combined, washed with brine, dried over Na2SO$_4$ and evaporated in vacuo. The crude oil (S)-1-benzyl 5-(perfluorophenyl) 2-(18-(tert-butoxy)-18-oxooctadecanamido)pentanedioate was used as is in the next step. Analysis condition D: Retention time=3.60 min; ESI-MS(+) m/z 757.2 (M+1).

Preparation of (S)-tert-butyl 11-((benzyloxy)carbonyl)-1-(9H-fluoren-9-yl)-3,8,13-trioxo-2-oxa-4,7,12-triazatriacontan-30-oate

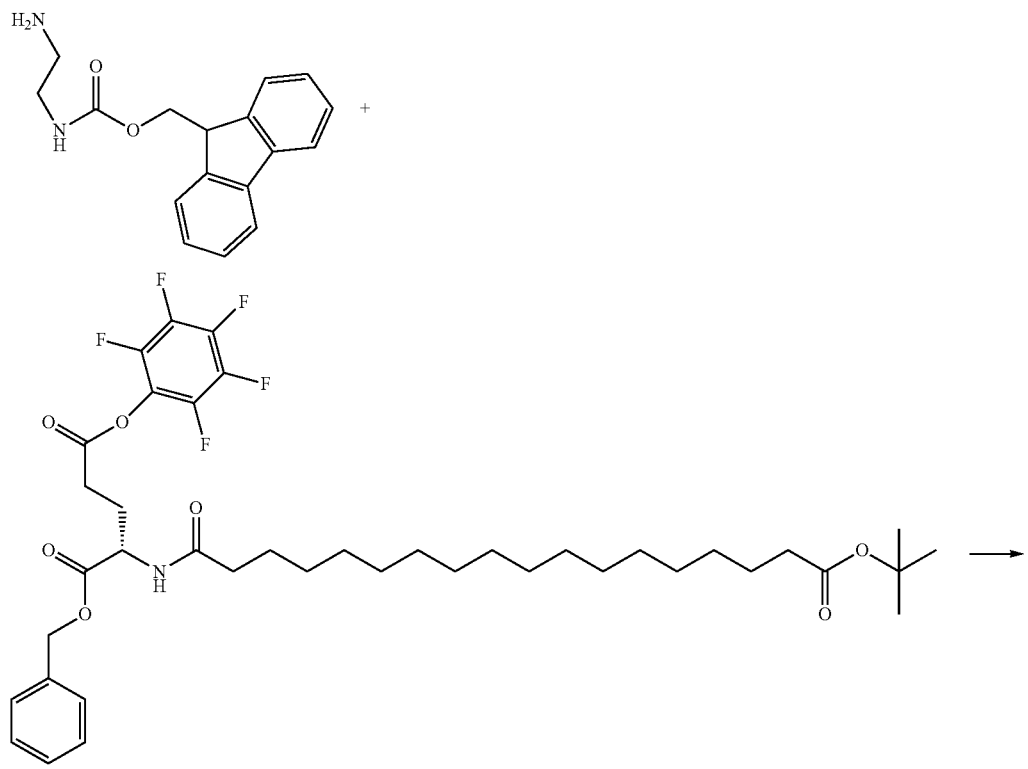

-continued

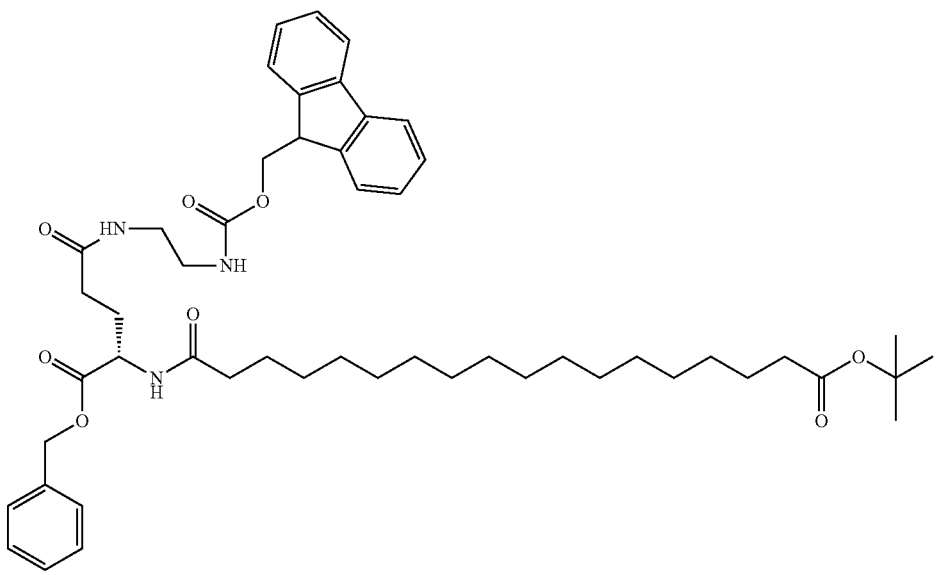

The mixture of (9H-fluoren-9-yl)methyl(2-aminoethyl) carbamate, HCl (0.850 g, 2.67 mmol), (S)-1-benzyl 5-(perfluorophenyl) 2-(18-(tert-butoxy)-18-oxooctadecanamido) pentanedioate (1.679 g, 2.221 mmol) and Hunig's Base (1.164 ml, 6.66 mmol) in DMF (10 ml) was stirred for 24 hr at rt. After 24 hr the reaction was homogeneous. The reaction mixture was poured into a saturated citric acid solution, and extracted with $CH_2Cl_2$ (3×50 ml). The organic fractions were combined, washed with brine, dried over $Na_2SO_4$ and evaporated in vacuo. The crude product was triturated with MeCN to get (S)-tert-butyl 11-((benzyloxy) carbonyl)-1-(9H-fluoren-9-yl)-3,8,13-trioxo-2-oxa-4,7,12-triazatriacontan-30-oate (1.448 g, 1.695 mmol, 76.3% yield).

Analysis condition D: Retention time=3.61 min; ESI-MS (+) m/z 855.5 (M+1) $^1$H NMR (500 MHz, METHANOL-$d_4$) δ 7.81 (d, J=7.6 Hz, 2H), 7.66 (d, J=7.5 Hz, 2H), 7.40 (t, J=7.5 Hz, 2H), 7.37-7.24 (m, 7H), 5.12 (d, J=2.3 Hz, 2H), 4.49-4.42 (m, 1H), 4.33 (dd, J=6.9, 4.4 Hz, 2H), 4.24-4.16 (m, 1H), 3.26-3.14 (m, 4H), 2.34-2.13 (m, 7H), 1.93 (dt, J=9.5, 6.9 Hz, 1H), 1.66-1.52 (m, 4H), 1.46 (s, 9H), 1.37-1.20 (m, 24H).

Preparation of (S)-5-(((2-aminoethyl)amino)-2-(18-(tert-butoxy)-18-oxooctadecanamido)-5-oxopentanoic acid

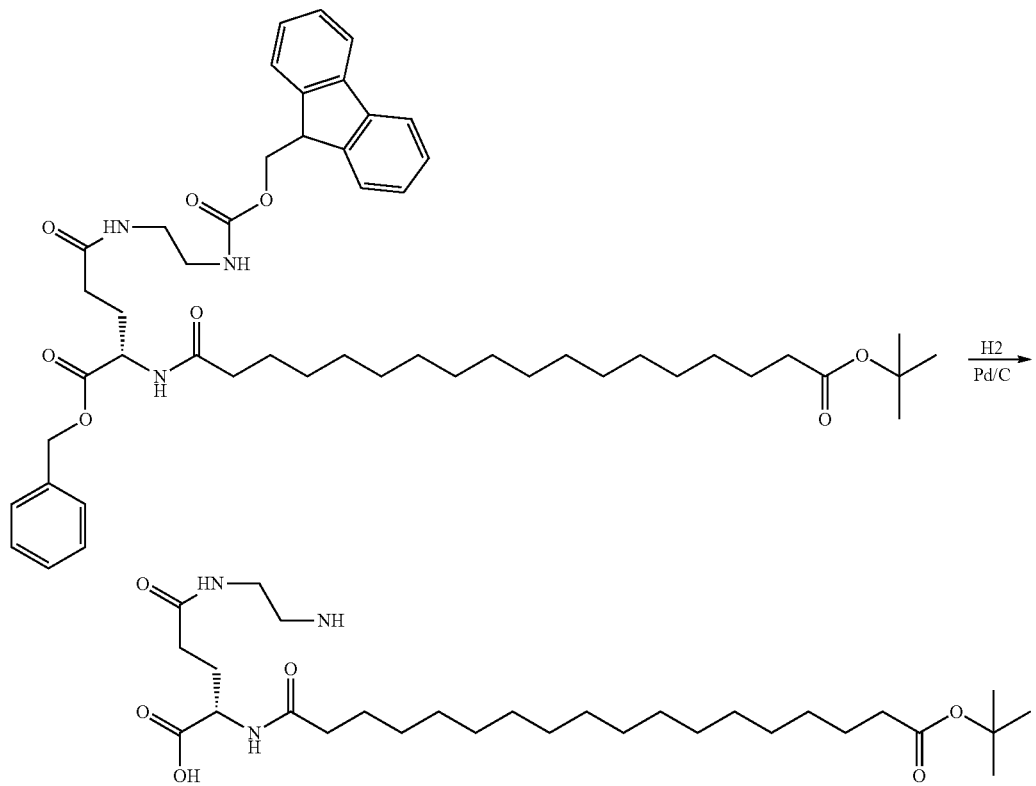

The mixture of (S)-tert-butyl 11-((benzyloxy)carbonyl)-1-(9H-fluoren-9-yl)-3,8,13-trioxo-2-oxa-4,7,12-triazatriacontan-30-oate (1.448 g, 1.695 mmol) in Methanol (28.3 ml) was added PALLADIUM ON CARBON (0.180 g, 0.170 mmol). The flask was sealed with a septum and charged with HYDROGEN via a balloon. The next day the reaction was filtered through celite to remove the catalyst and the the filtrate was evaporated in vacuo to afford (S)-5-((2-aminoethyl)amino)-2-(18-(tert-butoxy)-18-oxooctadecanamido)-5-oxopentanoic acid which is used as is. Analysis condition D: Retention time=2.44 min; ESI-MS(+) m/z 542.2 (M+1)

Preparation of (S)-5-((2-((((9H-fluoren-9-yl)methoxy)carbonyl)amino)ethyl)amino)-2-(18-(tert-butoxy)-18-oxooctadecanamido)-5-oxopentanoic acid

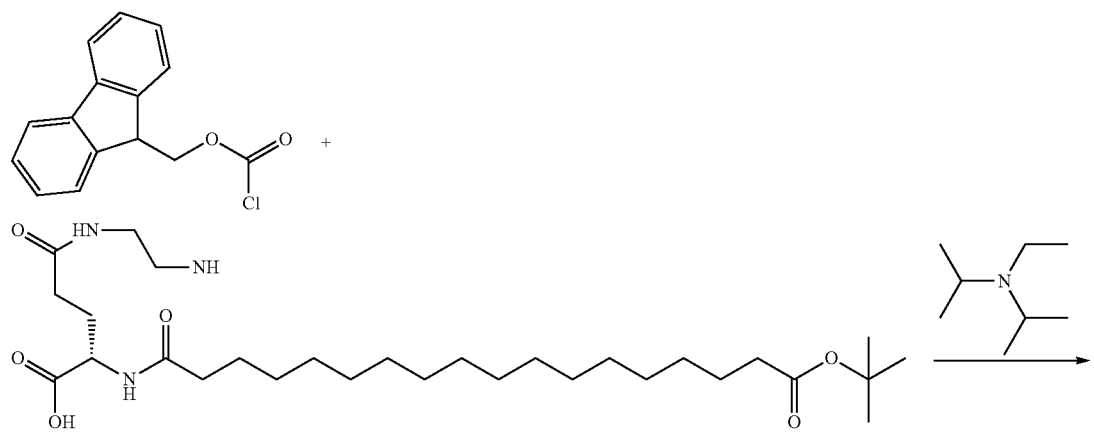

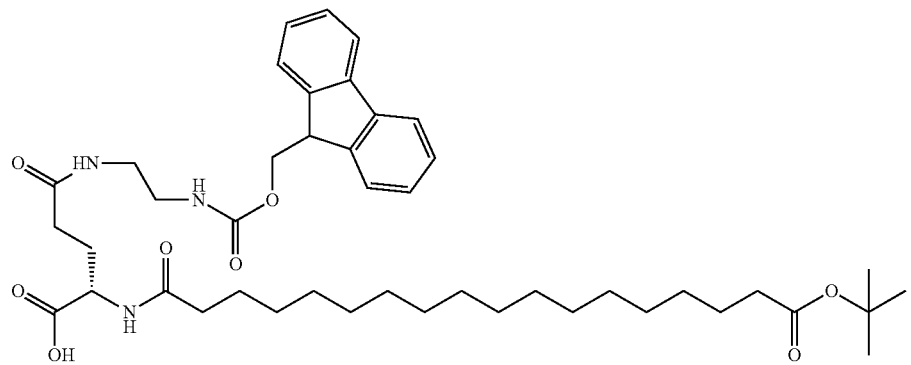

(S)-5-((2-aminoethyl)amino)-2-(18-(tert-butoxy)-18-oxooctadecanamido)-5-oxopentanoic acid (0.918 g, 1.694 mmol) in DCM (42.4 ml) at 0 OC was added DIEA (0.888 ml, 5.08 mmol) and 9-FLUORENYLMETHYL CHLOROFORMATE (0.482 g, 1.864 mmol). The resulting solution was allowed to warmed to rt stirred overnight. The crude product was purified by Prep-HPLC (Solvent A=10% Acetonitrile-90% H₂O-0.1% TFA, Solvent B=90% Acetonitrile-10% H2O-0.1% TFA. Column: waters-sunFire OBD30×100 mm, S10, Flow rate: 40 ml/min, 45-100% B, 10 min, additional 6 min after 100% B) to get (S)-5-((2-(((((9H-fluoren-9-yl)methoxy)carbonyl)amino)ethyl)amino)-2-(18-(tert-butoxy)-18-oxooctadecanamido)-5-oxopentanoic acid (443 mg, 0.580 mmol, 34.2% yield), 2 steps.

Analysis condition C: Retention time=1.84 min; ESI-MS (+) m/z 764.5 (M+1) ¹H NMR (500 MHz, METHANOL-d₄) δ 7.81 (d, J=7.5 Hz, 2H), 7.67 (d, J=7.5 Hz, 2H), 7.40 (t, J=7.5 Hz, 2H), 7.37-7.29 (m, 2H), 4.42 (dd, J=9.2, 4.8 Hz, 1H), 4.35 (dd, J=6.9, 4.0 Hz, 2H), 4.28-4.17 (m, 1H), 3.30-3.18 (m, 4H), 2.36-2.12 (m, 7H), 2.02-1.91 (m, 1H), 1.69-1.52 (m, 4H), 1.46 (s, 9H), 1.40-1.20 (m, 24H).

Preparation of Modified Chlorotrityl Resin 14A

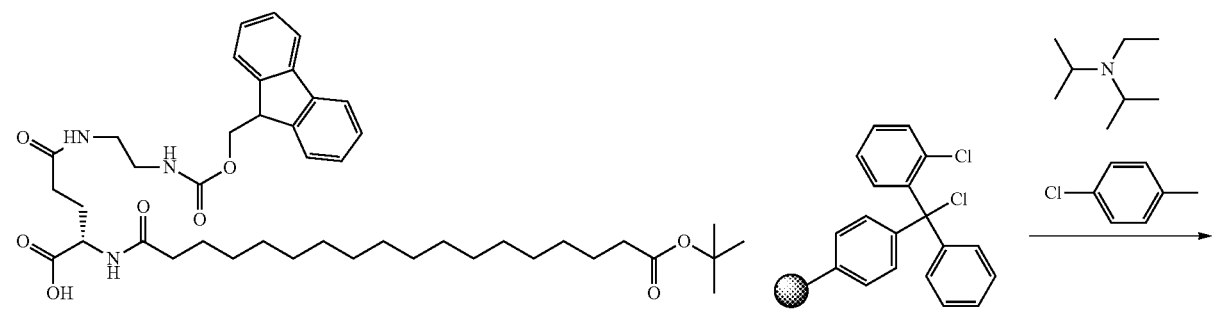

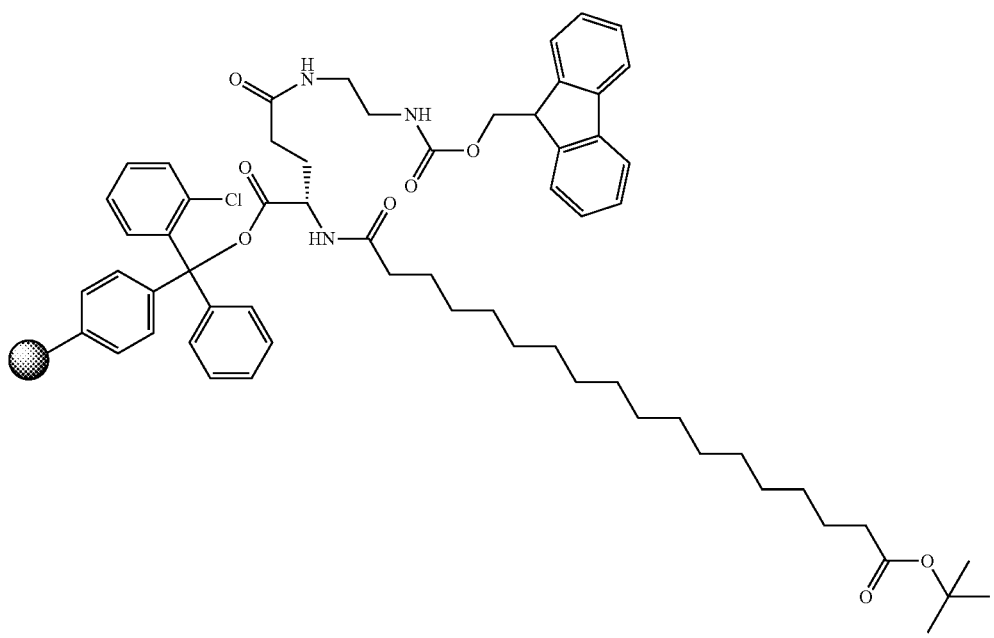

To a mixture of (S)-5-((2-(((((9H-fluoren-9-yl)methoxy)carbonyl)amino)ethyl)amino)-2-(18-(tert-butoxy)-18-oxooctadecanamido)-5-oxopentanoic acid (443 mg, 0.580 mmol) and Hunig's Base (658 µl, 3.77 mmol) dissolved in $CH_2Cl_2$ (5857 µl) was added 4-CHLOROTOLUENE (73.4 mg, 0.580 mmol). LC/MS of this mixture was taken as the standard. Swelled 1-chloro-2-(chloro(phenyl)(p-tolyl)methyl)benzene (1160 mg, 1.855 mmol) resin with $CH_2Cl_2$ (1.17E+04 µl) then add solution of acid and DIEA. Shaked the resin (monitor by taking aliquot out and taking LC/MS to compare to the standard LC/MS run) for 45 min. Added 25 mL of 9:1 MeOH/DIEA to the reaction vessel and immediately filtered the resin. The resin was rinsed 3 times with DCM (stirring for ~20 s in between washes). The resin was then shaken with ~20 mL DMF for 5 min, then filtered. This was repeated 2 more times with DMF, then 3 times with DCM. The resin was dried on the fritted funnel with N2 being passed through the resin.

Final weight: 1.5065 g, Theo. loading: 260 mg/0.1 mmol, Calc. loading: 371 mg/0.1 mmol (based on 70% yield).

Preparation of Example 14123

Example 14123

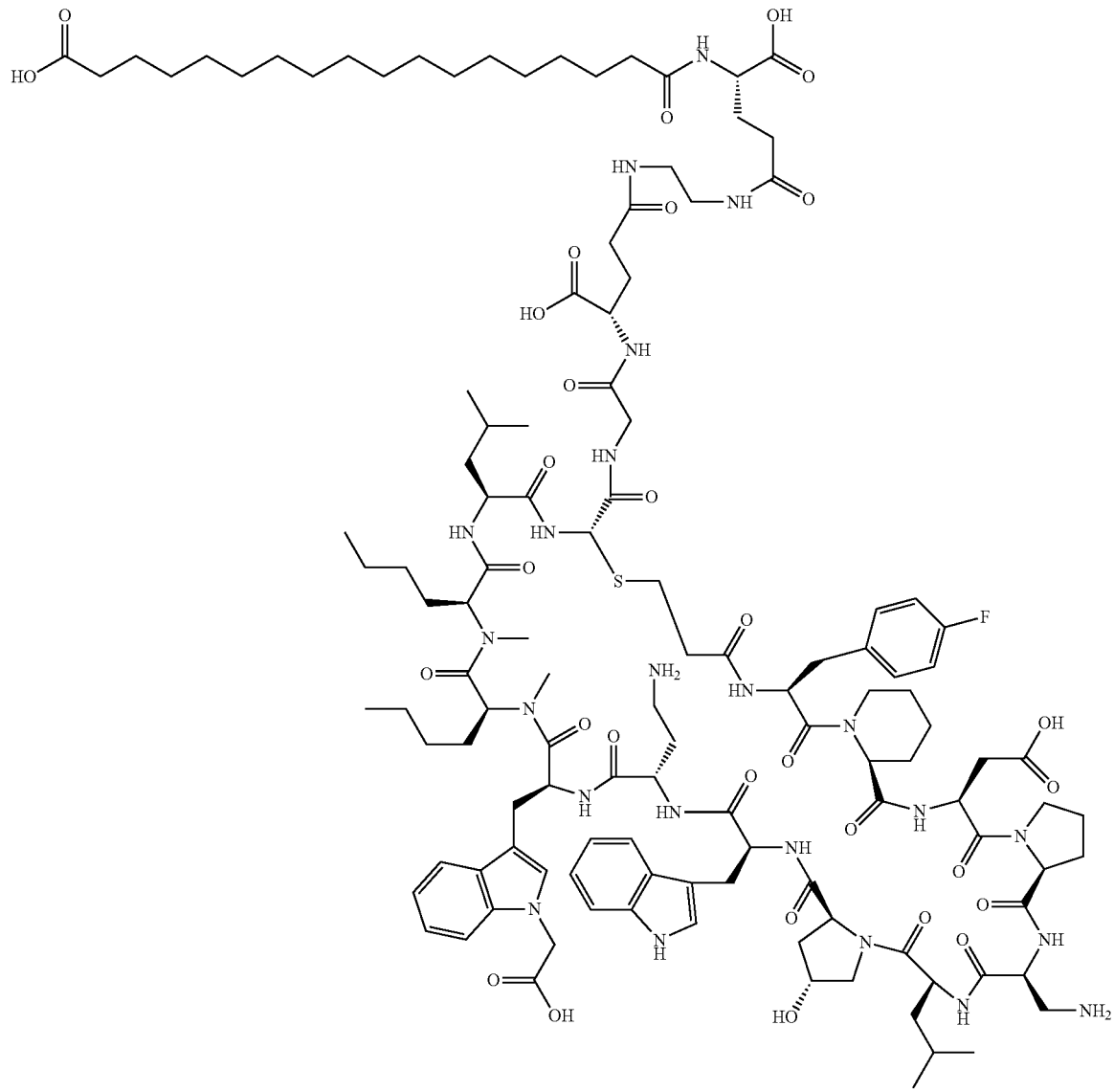

Example 14123 was synthesized on a 0.2 mmol scale according to the general procedures above, including chloroacetic acid coupling procedure A. The underlined steps employed the double-coupling procedure, and italicized residues were coupled with a 30 min single coupling. ClAc-Tyr(4-F)-Pip-Asp-Pro-Dap-Leu-Hyp-Trp-Dab-Trp'-mNle-mNle-Leu-Cys-Gly-((S)-4-((((9H-fluoren-9-yl)methoxy)carbonyl)amino)-5-(tert-butoxy)-5-oxopentanoic acid)-[Modified resin 14A]. After deprotection following Global Deprotection procedure B and cyclization according to Cyclization method B, the compound was purified as follows: The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 15 minutes, then a 5-minute hold at 100% B; Flow: 20 mL/min. Fractions containing the desired product were combined and dried via centrifugal evaporation.

The yield of the product was 1.4 mg, and its estimated purity by LCMS analysis was 96%.

Analysis condition C: Retention time=2.02 min; ESI-MS (+) m/z 838.7 (M+3) ESI-HRMS(+) m/z: Calculated: 1257.1564 (M+2H). Found: 1257.1641 (M+2H).

Preparation of Example 14124

Example 14124

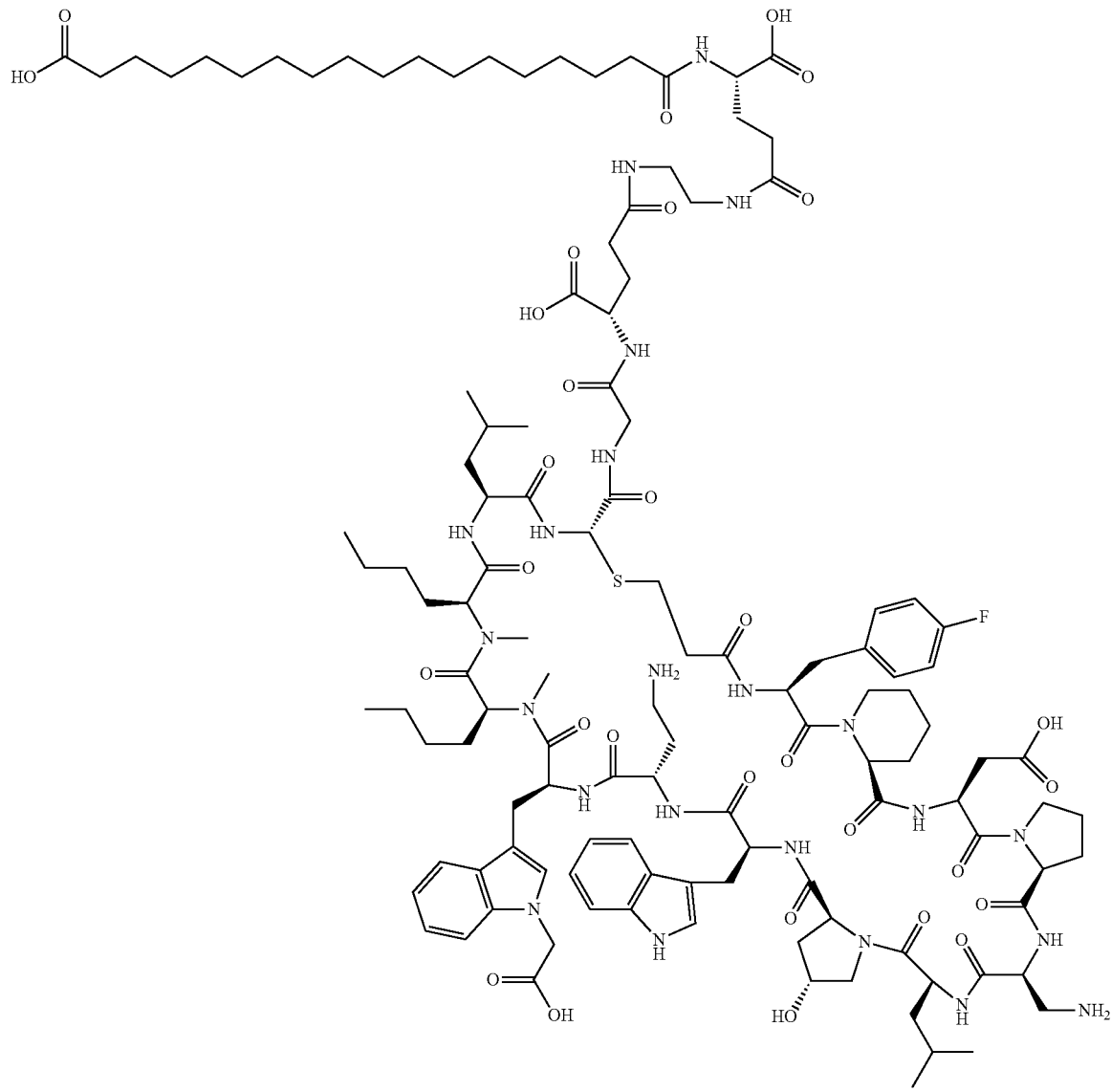

Example 14123 was synthesized on a 0.2 mmol scale according to the general procedures above, including chloroacetic acid coupling procedure A. The underlined steps employed the double-coupling procedure, and italicized residues were coupled with a 30 min single coupling. ClAc-Tyr(4-F)-Pip-Asp-Pro-Dap-Leu-Hyp-Trp-Dab-Trp'-mNle-mNle-Leu-Cys-Gly-((S)-3-((((9H-fluoren-9-yl)methoxy)carbonyl)amino)-4-(tert-butoxy)-4-oxobutanoic acid)-[Modified resin 14A]. After deprotection following Global Deprotection procedure B and cyclization according to Cyclization method B, the compound was purified as follows: The crude material was purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired product were combined and dried via centrifugal evaporation.

The yield of the product was 7.8 mg, and its estimated purity by LCMS analysis was 93%.

Analysis condition E: Retention time=1.90 min; ESI-MS (+) m/z 1250.9 (M+2) ESI-HRMS(+) m/z: Calculated: 1250.1486 (M+2H). Found: 1250.1547 (M+2H).

Preparation of
4-(18-(tert-butoxy)-18-oxooctadecanamido)butanoic
acid

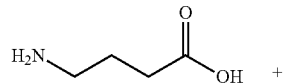
+

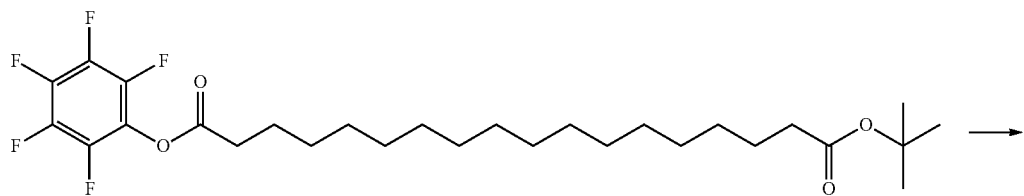
→

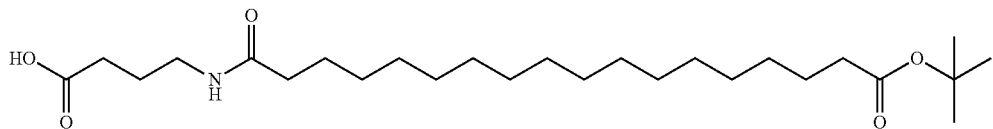

The mixture of 4-aminobutanoic acid (250 mg, 2.424 mmol), 1-tert-butyl 18-(perfluorophenyl)octadecanedioate (1301 mg, 2.424 mmol) and Hunig's Base (550 µl, 3.15 mmol) in DMF (8081 µl) was stirred for 24 hr at rt. After 24 hr the reaction was homogeneous. The reaction mixture was poured into a saturated citric acid solution, and extracted with $CH_2Cl_2$ (3×50 ml). The organic fractions were combined, washed with brine, dried over $Na_2SO_4$ and evaporated in vacuo. The crude product 4-(18-(tert-butoxy)-18-oxooctadecanamido)butanoic acid was used as is.

Analysis condition D: Retention time=2.02 min; ESI-MS (+) m/z 456.2 (M+1)

Preparation of tert-butyl 1-azido-37,42-dioxo-3,6,9,12,15,18,21,24,27,30,33-undecaoxa-36,41-diazanonapentacontan-59-oate

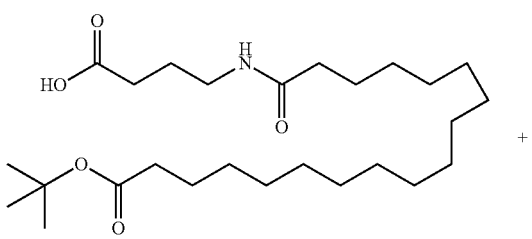
+

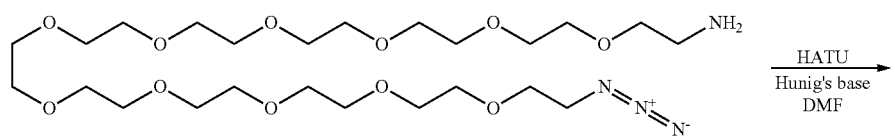

HATU
Hunig's base
DMF
→

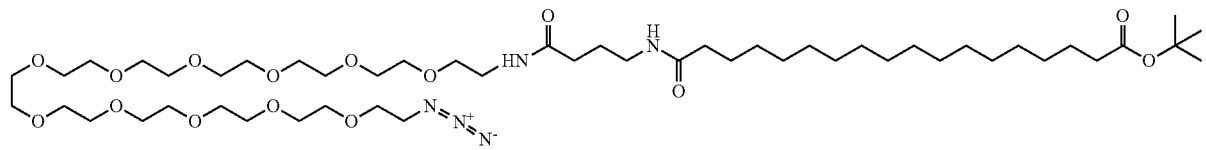

To a solution of 4-(18-(tert-butoxy)-18-oxooctadecanamido)butanoic acid (0.552 g, 1.212 mmol) in DMF (12.12 ml) was added Hunig's Base (0.635 ml, 3.64 mmol) and HATU (0.922 g, 2.424 mmol). 35-azido-3,6,9,12,15,18,21,24,27,30,33-undecaoxapentatriacontan-1-amine (0.692 g, 1.212 mmol) was then added, and the solution stirred at rt. The mixture was stirred overnight. The reaction mixture was poured into a saturated citric acid solution, and extracted with CH$_2$Cl$_2$ (3×50 ml). The organic fractions were combined, washed with brine, dried over Na2SO4 and evaporated in vacuo. The crude product tert-butyl 1-azido-37,42-dioxo-3,6,9,12,15,18,21,24,27,30,33-undecaoxa-36,41-diazanonapentacontan-59-oate was used as is.

Analysis condition D: Retention time=2.96 min; ESI-MS (+) m/z 1008.8 (M+1).

Preparation of 1-azido-37,42-dioxo-3,6,9,12,15,18,21,24,27,30,33-undecaoxa-36,41-diazanonapentacontan-59-oic acid The mixture of tert-butyl 1-azido-37,42-dioxo-3,6,9,12,15,18,21,24,27,30,33-undecaoxa-36,41-diazanonapentacontan-59-oate (1.222 g, 1.212 mmol) and TFA (3.0 ml, 38.9 mmol) in DCM (10 ml) was stirred at rt overnight. The reaction mixture was poured into a brine, and extracted with CH$_2$Cl$_2$ (3×50 ml). The organic fractions were combined and evaporated in vacuo. The resulting crude product was purified by Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 55-100% B, 10 min, stop at 13 min) to obtain 1-azido-37,42-dioxo-3,6,9,12,15,18,21,24,27,30,33-undecaoxa-36,41-diazanonapentacontan-59-oic acid (696 mg, 0.731 mmol, 60.3% yield), 3 steps. Analysis condition C: Retention time=1.24 min; ESI-MS(+) m/z 952.6 (M+1) $^1$H NMR (500 MHz, CHLOROFORM-d) δ 6.90 (t, J=5.0 Hz, 1H), 6.69-6.58 (m, 1H), 3.74-3.52 (m, 44H), 3.44 (q, J=5.2 Hz, 2H), 3.39 (t, J=5.1 Hz, 2H), 3.29 (q, J=6.0 Hz, 2H), 2.30 (dt, J=17.9, 7.2 Hz, 4H), 2.23-2.09 (m, 2H), 1.84 (quin, J=6.6 Hz, 2H), 1.61 (sxt, J=7.7 Hz, 4H), 1.39-1.17 (m, 24H).

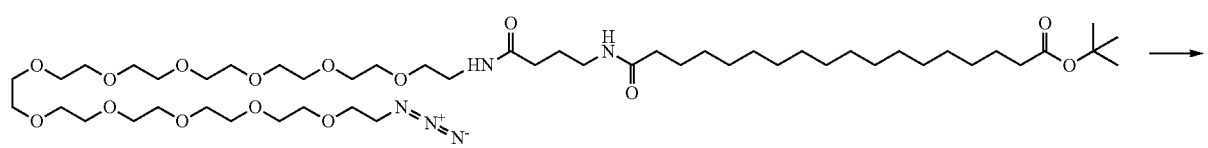

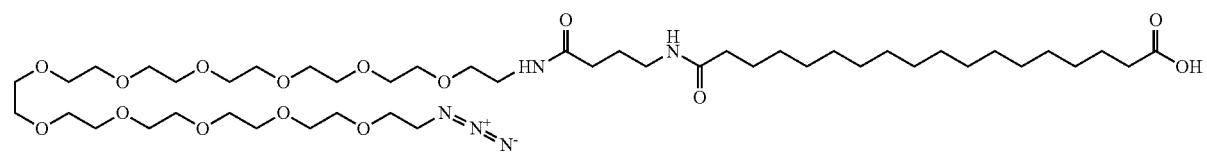

Preparation of Example 14125

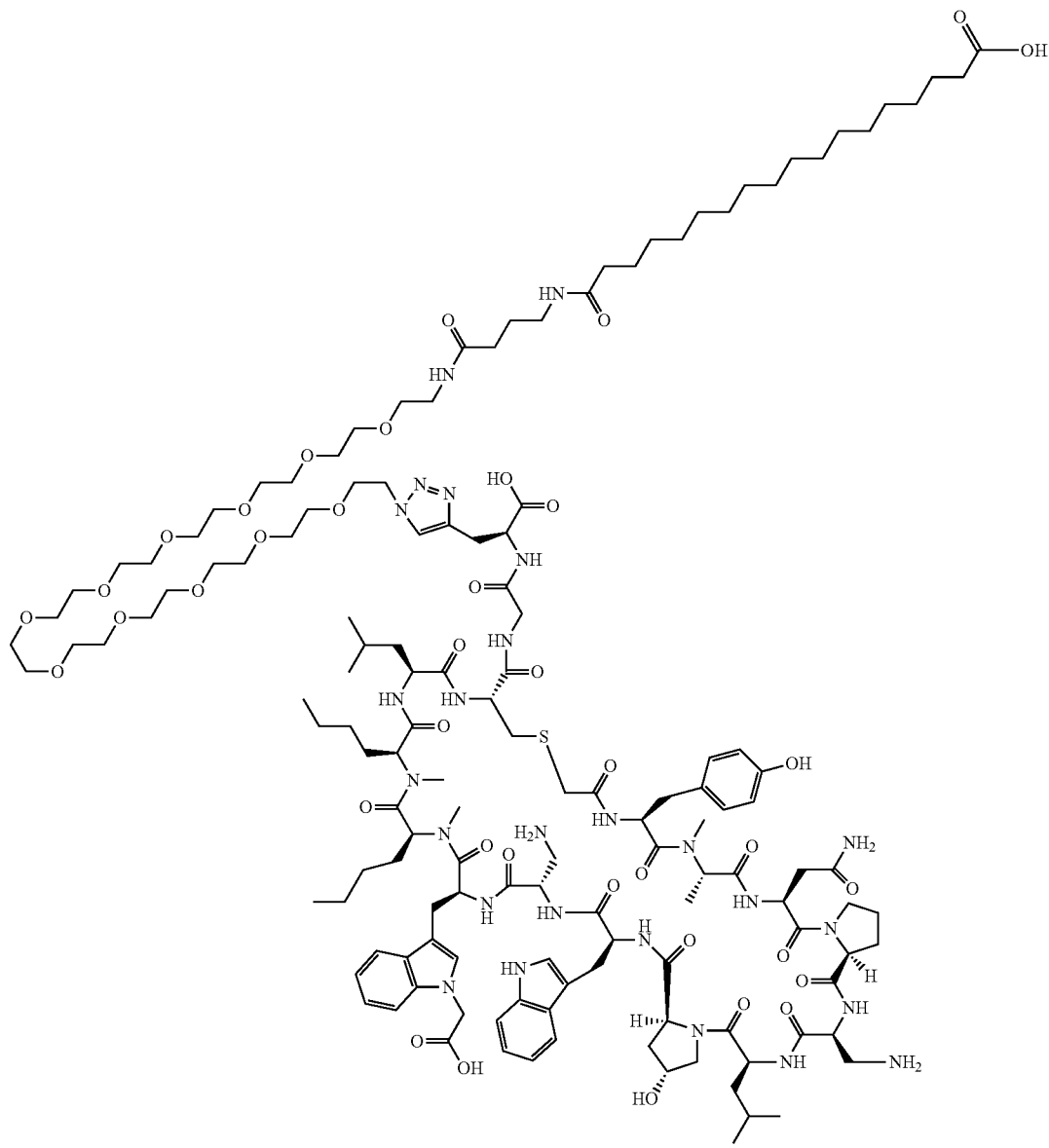

Example 14125

Intermediate 1300V (151 mg, 76 μmol) and 1H-azido-37,42-dioxo-3,6,9,12,15,18,21,24,27,30,33-undecaoxa-36,41-diazanonapentacontan-59-oic acid (72.5 mg, 76 μmol) were reacted as in the general triazole formation procedure to afford crude product. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-54% B over 14 minutes, then a 5-minute hold at 100% B; Flow: 20 mL/min. Fractions containing the desired product were combined and dried via centrifugal evaporation. The yield of the product was 45.8 mg, and its estimated purity by LCMS analysis was 95%.

Analysis condition D: Retention time=2.47 min; ESI-MS (+) m/z 979.5 (M+3H)

Analysis condition E: Retention time=2.01 min; ESI-MS (+) m/z 979.4 (M+3H)

ESI-HRMS(+) m/z: Calculated: 1467.8131 (M+2H). Found: 1467.8079 (M+2H).

Preparation of tert-butyl 18-((3-azidopropyl)amino)-18-oxooctadecanoate

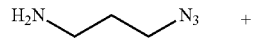
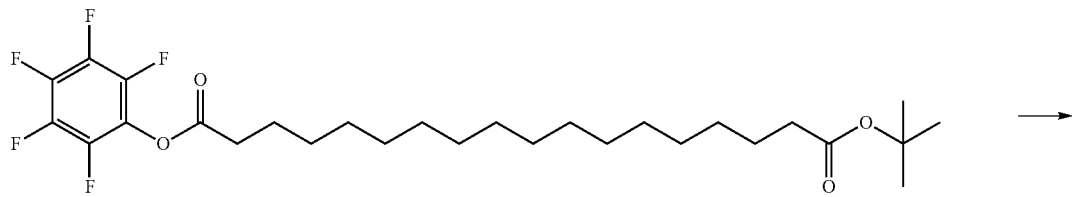
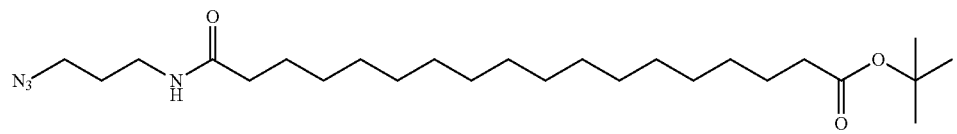

The mixture of 3-azidopropan-1-amine (250 mg, 2.497 mmol), 1-tert-butyl 18-(perfluorophenyl)octadecanedioate (1340 mg, 2.497 mmol) and Hunig's Base (567 µl, 3.25 mmol) in DMF (8323 µl) was stirred for 24 hr at rt. After 24 hr the reaction was homogeneous. The reaction mixture was poured into a saturated citric acid solution, and extracted with CH$_2$Cl$_2$ (3×50 ml). The organic fractions were combined, washed with brine, dried over Na2SO$_4$ and evaporated in vacuo. The crude product tert-butyl 18-((3-azidopropyl)amino)-18-oxooctadecanoate was used as is.

Analysis condition D: Retention time=2.76 min; ESI-MS (+) m/z 475.1 (M+Na).

Preparation of 18-((3-azidopropyl)amino)-18-oxooctadecanoic acid

The mixture of tert-butyl 18-((3-azidopropyl)amino)-18-oxooctadecanoate (750 mg, 1.657 mmol) and TFA (3.0 ml, 38.9 mmol) in DCM (10 ml) was stirred at rt for 2 h. The resulting crude product was purified by Prep-HPLC (Solvent A=10% MeOH-90% H$_2$O-0.1% TFA, Solvent B=90% MeOH-10% H$_2$O-0.1% TFA. Column: PHENOMENEX LUNA 30×100 mm, S10, Flow rate: 40 ml/min, 50-100% B, 10 min, stop at 13 min) to obtain 18-((3-azidopropyl)amino)-18-oxooctadecanoic acid (138 mg, 0.348 mmol, 21.00% yield), 2 steps. Analysis condition D: Retention time=2.67 min; ESI-MS(+) m/z 419.1 (M+Na)$^1$H NMR (500 MHz, CHLOROFORM-d) δ 7.28 (s, 1H), 3.47-3.28 (m, 4H), 2.40-2.27 (m, 2H), 2.24-2.14 (m, 2H), 1.87-1.76 (m, 2H), 1.65 (dq, J=14.9, 7.7 Hz, 4H), 1.40-1.18 (m, 24H).

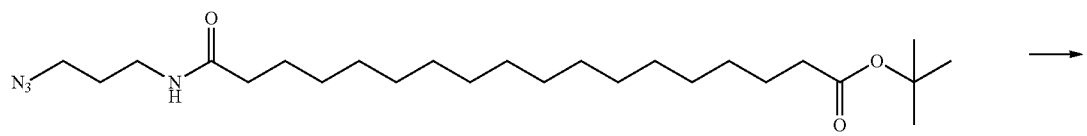
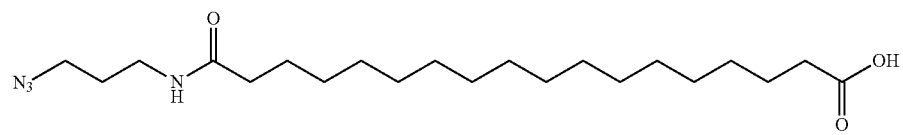

Preparation of Example 14126

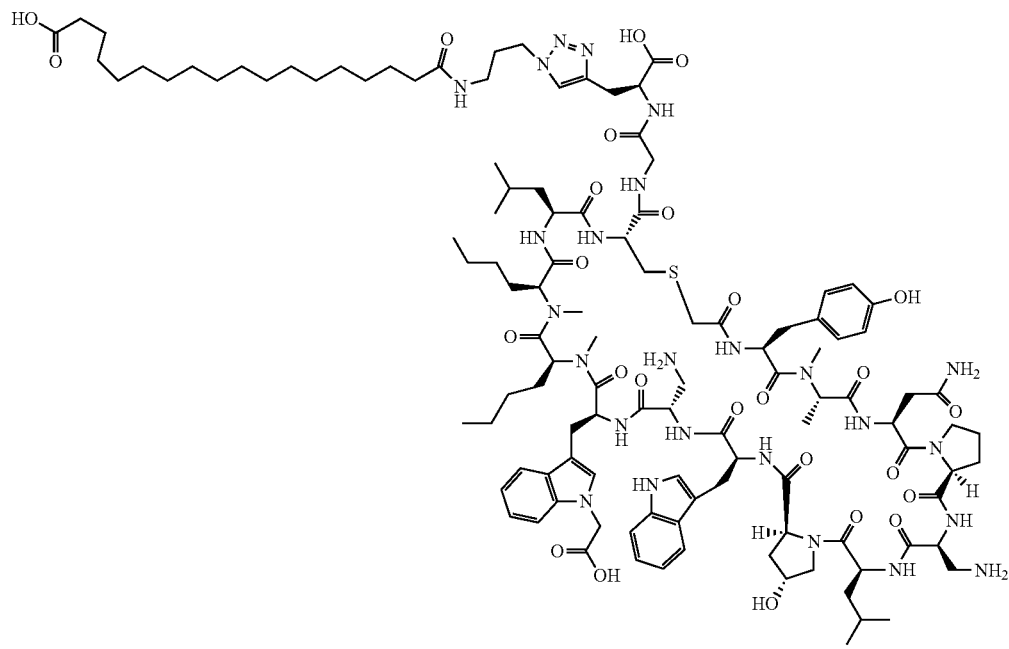

Example 14126

Intermediate 1300V (170 mg, 86 µmol) and 18-((3-azidopropyl)amino)-18-oxooctadecanoic acid (34 mg, 86 µmol) were reacted as in the general triazole formation procedure to afford crude product. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 28-56% B over 22 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 30 minutes, then a 5-minute hold at 100% B; Flow: 20 mL/min. Fractions containing the desired product were combined and dried via centrifugal evaporation.

The yield of the product was 20.3 mg, and its estimated purity by LCMS analysis was 97%.

Analysis condition D: Retention time=2.41 min; ESI-MS (+) m/z 1190.7 (M+2H).

Analysis condition E: Retention time=2.02 min; ESI-MS (+) m/z 1190.4 (M+2H).

ESI-HRMS(+) m/z: Calculated: 1190.1503 (M+2H). Found: 1190.1474 (M+2H).

Methods for Testing the Ability of Macrocyclic Peptides to Compete for the Binding of PD-1 to PD-L1 Using Homogenous Time-Resolved Fluorescence (HTRF) Binding Assays The ability of the macrocyclic peptides of the present disclosure to bind to PD-L1 was investigated using a PD-1/PD-L1 Homogenous Time-Resolved Fluorescence (HTRF) binding assay.

Methods

Homogenous Time-Resolved Fluorescence (HTRF) Assays of Binding of Soluble PD-1 to Soluble PD-L1. Soluble PD-1 and soluble PD-L1 refers to proteins with carboxyl-end truncations that remove the transmembrane-spanning regions and are fused to heterologous sequences, specifically the Fc portion of the human immunoglobuling G sequence (Ig) or the hexahistidine epitope tag (His). All binding studies were performed in an HTRF assay buffer consisting of dPBS supplemented with 0.1% (w/v) bovine serum albumin and 0.05% (v/v) Tween-20. For the PD-1-Ig/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. PD-L1 fusion proteins from either human, cynomologous macaques, mouse, or other species were used. HTRF detection was achieved using europium crypate-labeled anti-Ig monoclonal antibody (1 nM final) and allophycocyanin (APC) labeled anti-His monoclonal antibody (20 nM final). Antibodies were diluted in HTRF detection buffer and 5 µl was dispensed on top of binding reaction. The reaction was allowed to equilibrate for 30 minutes and signal (665 nm/620 nm ratio) was obtained using an EnVision fluorometer. Additional binding assays were established between PD-I-Ig/PD-L2-His (20 and 5 nM, respectively), CD80-His/PD-L1-Ig (100 and 10 nM, respectively) and CD80-His/CTLA4-Ig (10 and 5 nM, respectively). Binding/competition studies between biotinylated Compound No. 71 and human PD-L1-His were performed as follows. Macrocyclic peptide inhibitors were pre-incubated with PD-L1-His (10 nM final) for 60 minutes in 4 µl of assay buffer followed by addition of biotinylated Compound No. 71 (0.5 nM final) in 1 µl of assay buffer. Binding was allowed to equilibrate for 30 minutes followed by addition of europium crypated labeled Streptavidin (2.5 pM final) and APC-labeled anti-His (20 nM final) in 5 µl of HTRF buffer. The reaction was allowed to equilibrate for 30 m and signal (665 nm/620 nm ratio) was obtained using an EnVision fluorometer.

Recombinant Proteins. Carboxyl-truncated human PD-1 (amino acids 25-167) with a C-terminal human Ig epitope tag [hPD-1 (25-167)-3S-IG] and human PD-L1 (amino acids 18-239) with a C-terminal His epitope tag [hPD-L1(19-239)-tobacco vein mottling virus protease cleavage site (TVMV)-His] were expressed in HEK293T cells and purified sequentially by recombinant Protein A affinity chromatography and size exclusion chromatography. Human PD-L2-His (Sino Biologicals), CD80-His (Sino Biologicals), CTLA4-Ig (RnD Systems) were all obtained through commercial sources.

Sequence of Recombinant Human PD-1-Ig
hPD1(25-167)-3S-IG

```
  1 LDSPDRPWNP PTFSPALLVV TEGDNATFTC SFSNTSESFV LNWYRMSPSN
 51 QTDKLAAFPE DRSQPGQDCR FRVTQLPNGR DFHMSVVRAR RNDSGTYLCG
101 AISLAPKAQI KESLRAELRV TERRAEVPTA HPSPSPRPAG QFQGSPGGGG
151 GREPKSSDKT HTSPPSPAPE LLGGSSVFLF PPKPKDTLMI SRTPEVTCVV
201 VDVSHEDPEV KFNWYVDGVE VHNAKTKPRE EQYNSTYRVV SVLTVLHQDW
251 LNGKEYKCKV SNKALRAPIE KTISKAKGQP REPQVYTLPP SRDELTKNQV
301 SLTCLVKGFY PSDIAVEWES NGQPENNYKT TPPVLDSDGS FFLYSKLTVD
351 KSRWQQGNVF SCSVMHEALH NHYTQKSLSL SPGK
```

(SEQ ID NO:1)

Sequence of Recombinant Human PD-L1-TVMV-His (PD-L1-His)
hPiDL1(19-239)TVMV-His

```
  1 FTVTVPKDLY VVEYGSNMTI ECKFPVEKQL DLAALIVYWE MEDKNIIQFV
 51 HGEEDLKVQH SSYRQRARLL KDQLSLGNAA LQITDVKLQD AGVYRCMISY
101 GGADYKRITV KVNAPYNKIN QRILVVDPVT SEHELTCQAE GYPKAEVIWT
151 SSDHQVLSGK TTTTNSKREE KLFNVTSTLR INTTTNEIFY CTFRRLDPEE
201 NHTAELVIPE LPLAHPPNER TGSSETVRFQ GHHHHHH
```

(SEQ ID NO:2)

The results are shown in Table 1. As shown, the macrocyclic peptides of the present disclosure demonstrated potent inhibition of PD-1-Ig binding activity to PD-L1-TVMV-His (PD-L1-His). Ranges are as follows: A=0.10-1.6 µM; B=0.01-0.099 µM; C=0.0003-0.0099 µM.

TABLE 1

| Example Number | HTRF IC50 (µM) |
|---|---|
| INT 1300B | C |
| 14089 | C |
| 14090 | C |
| 3214 | C |
| 3619 | C |
| 3620 | 0.0090 |
| 3621 | B |
| 3622 | B |
| 3623 | C |
| 3624 | C |
| 3625 | 0.0063 |
| 3626 | C |
| INT 1300C | C |
| INT 1400K | C |
| INT 1400L | B |
| 11012 | B |
| 11032 | 0.2007 |
| 11033 | B |
| 11035 | B |
| 11036 | C |
| 11040 | C |
| 11041 | C |
| 11042 | 0.0049 |
| 11044 | B |
| 11045 | B |
| 11046 | B |
| 11047 | B |
| 11060 | A |
| 11061 | A |
| 11062 | 0.4558 |
| 11064 | C |
| 11066 | C |
| 11067 | B |
| 11073 | B |
| 11074 | C |
| 11075 | 0.0071 |
| 11076 | B |
| 11080 | 0.0127 |
| 11081 | B |
| 11082 | B |
| 11083 | B |
| 11085 | B |
| 11086 | 0.0190 |
| 11087 | B |
| 11088 | A |
| 11089 | B |
| 11090 | B |
| 11102 | 0.0130 |
| 11115 | A |
| 11119 | A |
| 11129 | B |
| 11130 | B |
| 11131 | B |
| 11132 | B |
| 11133 | 1.5710 |
| 11013 | B |
| 11015 | B |
| 11028 | B |
| 11029 | A |
| 11034 | C |
| 11038 | C |
| 11063 | 0.0092 |
| 11065 | B |
| 11068 | C |
| 11072 | C |
| 11077 | C |
| 11084 | B |

TABLE 1-continued

| Example Number | HTRF IC50 (µM) |
|---|---|
| 11112 | A |
| 11124 | A |
| 11125 | B |
| 11128 | B |
| 11017 | 0.2593 |
| 11018 | B |
| 11071 | C |
| 11078 | C |
| 11101 | 0.0041 |
| 11104 | A |
| 11107 | A |
| 11109 | A |
| 11069 | B |
| 11070 | C |
| 11079 | B |
| 11091 | C |
| 11092 | 0.0135 |
| 11093 | B |
| 11094 | 0.0188 |
| 11095 | C |
| 11096 | B |
| 11097 | B |
| 11098 | B |
| 11099 | C |
| 11100 | B |
| 11110 | 0.3140 |
| 11111 | A |
| 11108 | A |
| 11120 | A |
| INT 1300V | B |
| INT 1300W | B |
| INT 1300X | B |
| INT 1300Y | C |
| 11001 | 0.9522 |
| 11019 | A |
| INT 1300A | C |
| INT 1400A | C |
| INT 1400B | C |
| INT 1400C | C |
| INT 1400D | C |
| INT 1400E | C |
| INT 1400F | C |
| INT 1400G | C |
| INT 1400H | C |
| INT 1400I | B |
| INT 1400J | 0.0088 |
| 11002 | B |
| 11007 | B |
| 11008 | A |
| 11020 | A |
| 11031 | B |
| 11134 | B |
| 11005 | B |
| 11006 | B |
| 11009 | 0.0914 |
| 11010 | B |
| 11011 | B |
| 11016 | B |
| 11014 | A |
| 11030 | A |
| 11103 | B |
| 11116 | B |
| 11123 | B |
| 11126 | B |
| 11003 | 0.0546 |
| 11004 | B |
| 11021 | A |
| 11022 | A |
| 11023 | A |
| 11024 | A |
| 11025 | A |
| 11026 | A |
| 11027 | A |
| 11114 | A |
| 11135 | B |
| 11136 | B |
| 11137 | B |
| 11138 | B |

TABLE 1-continued

| Example Number | HTRF IC50 (μM) |
|---|---|
| 11139 | B |
| 11140 | B |
| 11141 | B |
| 11142 | B |
| 11143 | C |
| 11144 | B |
| 11145 | C |
| 11146 | B |
| 11147 | V |
| 11148 | V |
| 11149 | V |
| 11150 | B |
| 11151 | B |
| 11152 | A |
| 11153 | B |
| 11154 | C |
| 11155 | C |
| 11156 | C |
| 11157 | B |
| 11158 | B |
| 11159 | B |
| 11160 | A |
| 11161 | A |
| 11162 | A |
| 11163 | C |
| 11164 | C |
| 11165 | C |
| 11166 | A |
| 11167 | C |
| 11168 | C |
| 11169 | 0.0039 |
| 11170 | C |
| 11171 | C |
| 11172 | B |
| 11173 | A |
| 11174 | B |
| 11175 | B |
| 11176 | B |
| 11177 | A |
| 11178 | C |
| 11179 | 0.003 |
| 11180 | B |
| 11181 | A |
| 11182 | A |
| 11183 | A |
| 11184 | B |
| 11185 | B |
| 11186 | — |
| 11187 | B |
| 11188 | 0.28 |
| 11189 | A |
| 11190 | B |
| 11191 | B |
| 11192 | B |
| 11193 | B |
| 11194 | B |
| 11195 | B |
| 11196 | B |
| 11197 | B |
| 11198 | B |
| 11199 | B |
| 11200 | B |
| 11201 | B |
| 11202 | B |
| 11203 | B |
| 11204 | B |
| 11205 | 0.01 |
| 11206 | B |
| 11207 | B |
| 11208 | B |
| 11209 | B |
| 11210 | B |
| 11211 | C |
| 11212 | B |
| 11213 | B |
| 11214 | B |
| 11215 | B |
| 11216 | B |
| 11217 | B |
| 11218 | B |
| 11219 | B |
| 11220 | B |
| 11221 | B |
| 11222 | B |
| 11223 | B |
| 11224 | C |
| 11225 | C |
| 11226 | C |
| 11227 | C |
| 11228 | B |
| 11229 | B |
| 11230 | A |
| 11231 | B |
| 11232 | B |
| 11233 | C |
| 11234 | C |
| 11235 | B |
| 11236 | C |
| 11237 | B |
| 11238 | C |
| 11239 | B |
| 11240 | 0.01 |
| 11241 | B |
| 11242 | B |
| 11243 | A |
| 11244 | A |
| 11245 | B |
| 11246 | B |
| 11247 | B |
| 11248 | 0.22 |
| 11249 | C |
| 11250 | C |
| 11251 | B |
| 11252 | B |
| 11253 | C |
| 11254 | C |
| 11255 | C |
| 11256 | B |
| 14051 | A |
| 14052 | B |
| 14053 | A |
| 14054 | A |
| 14055 | 0.3880 |
| 14056 | A |
| 14057 | A |
| 14058 | A |
| 14060 | A |
| 14085 | B |
| 14086 | B |
| 14087 | A |
| 14088 | 0.7989 |
| 14082 | B |
| INT130AA | B |
| INT130AB | B |
| INT130AF | C |
| INT130AG | C |
| INT130AI | C |
| INT130AD | B |
| INT130AE | B |
| INT130AH | C |
| INT130AJ | C |
| INT130AK | C |
| INT130AL | C |
| 13051 | B |
| 13052 | B |
| 13122 | A |
| 13123 | 0.150 |
| 13124 | B |
| 13125 | B |
| 13126 | B |
| 13127 | B |
| 13128 | 0.013 |
| 13129 | B |
| 13130 | C |
| 13131 | B |
| 13132 | 0.0033 |

TABLE 1-continued

| Example Number | HTRF IC50 (µM) |
|---|---|
| 13133 | C |
| 14059 | B |
| 14061 | B |
| 14062 | B |
| 14063 | B |
| 14064 | C |
| 14065 | B |
| 14066 | C |
| 14067 | 0.0104 |
| 14068 | B |
| 14069 | B |
| 14070 | B |
| 14071 | B |
| 14072 | 0.0085 |
| 14073 | B |
| 14074 | B |
| 14075 | B |
| 14076 | C |
| 14077 | 0.0209 |
| 14078 | B |
| 14079 | B |
| 14080 | B |
| 14081 | A |
| 14083 | B |
| 14084 | 0.6270 |
| 14092 | C |
| 14093 | C |
| 14094 | B |
| 14095 | 0.014 |
| 14096 | 0.790 |
| 14068 | B |
| 14097 | 0.0072 |
| 14098 | C |
| 14099 | C |
| 14100 | C |
| 14101 | 0.0062 |
| 14069 | B |
| 14070 | B |
| 14071 | B |
| 14072 | 0.0085 |
| 14073 | B |
| 14074 | B |
| 14075 | B |
| 14076 | C |
| 14077 | B |
| 14078 | 0.0108 |
| 14079 | B |
| 14080 | B |
| 14081 | A |
| 14083 | B |
| 14084 | 0.6270 |
| 14092 | C |
| 14102/14103 | 0.014 |
| 14104 | A |
| 14105 | A |
| 14106 | A |
| 14107 | A |
| 14121 | B |
| 14122 | B |
| 13141 | A |
| 13142 | A |
| 13143 | A |
| 14123 | C |
| 13144 | B |
| 13145 | B |
| 14124 | B |
| 13146 | B |
| 13147 | A |
| 13148 | B |
| 13149 | B |
| 13150 | 0.0209 |
| 13151 | B |
| 13152 | C |
| 13153 | C |
| 13154 | C |
| 13155 | C |
| 13156 | C |
| 13157 | C |
| 13158 | C |
| 13159 | C |
| 13160 | C |
| 13161 | C |
| 13162 | 0.0038 |
| 13163 | C |
| 13164 | C |
| 14125 | C |
| 14126 | C |
| 11257 | C |
| 11258 | B |
| 11259 | C |
| 11260 | C |
| 11261 | C |
| 11262 | B |
| 11263 | C |
| 11264 | C |
| 11265 | B |
| 11266 | C |
| 11267 | B |
| 11268 | A |
| 11269 | ND |
| 11270 | ND |
| 11271 | ND |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

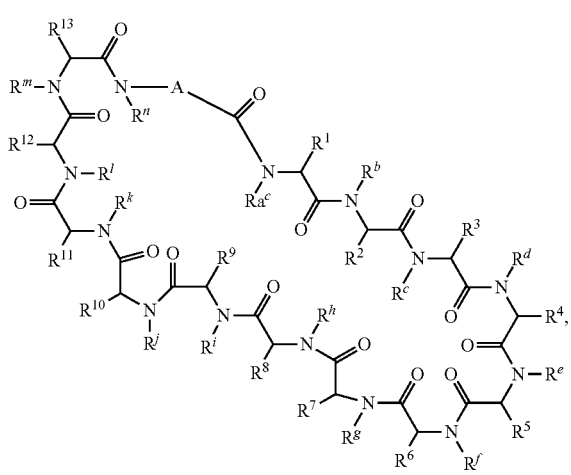

(I)

or a pharmaceutically acceptable salt thereof, wherein:

A is

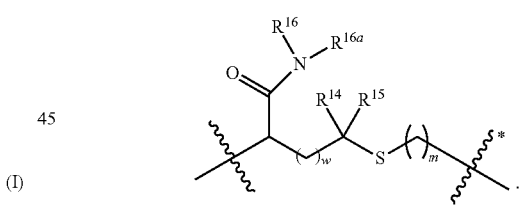

wherein:

denotes the point of attachment to the carbonyl group and $\sim\!\!*$ denotes the point of attachment to the nitrogen atom;

m is 1;
w is 0, 1, or 2;
$R^{14}$ and $R^{15}$ are hydrogen;
$R^{16a}$ is hydrogen;
$R^{16}$ is selected from
—$CH_2C(O)NHCH(R^{17})C(O)NH_2$;
—$CH_2C(O)NHCH(R^{17})C(O)NHCH(R^{17a})C(O)NH_2$; and
—$CH_2C(O)NHCH(R^{17})CO_2H$;
wherein:
X is selected from
—$(CH_2)_2CH(CO_2H)NHC(O)(CH_2)_p$;
—$(CH_2CH_2O)_q$; and —(CH$_2$CH$_2$O)$_q$CH$_2$CH$_2$NHC(O)CH$_2$CH$_2$CH(CO$_2$H)NHC(O)(CH$_2$)$_p$;
wherein q is 3, 4, 5, 6, 7, 8, 9, 10, or 11; and
wherein p is 14, 15, or 16;
each R$^{17a}$ is independently selected from hydrogen and —CH$_2$CO$_2$H,
each R$^{17}$ is —(CH$_2$)$_z$-triazolyl-X—R$^{35}$, wherein z is 1 and R$^{35}$ is selected from —CO$_2$H and CH$_3$,
R$^c$, R$^f$, R$^h$, R$^i$, R$^m$, and R$^n$ are hydrogen;
R$^a$, R$^e$, and R$^j$, are hydrogen;
R$^b$, R$^k$, and R$^l$ are methyl;
R$^1$ is phenylC$_1$-C$_3$alkyl wherein the phenyl part is optionally substituted with hydroxy, halo, or methoxy;
R$^2$ is C$_1$-C$_7$alkyl;
R$^3$ is amidoC$_1$-C$_3$alkyl or carboxyC$_1$-C$_3$alkyl;
R$^4$ and R$^d$, together with the atoms to which they are attached, form a pyrrolidine ring;

R$^5$ is selected from imidazolylC$_1$-C$_3$alkyl, aminoC$_1$-C$_3$alkyl, and aminobutyl;
R$^6$ is selected from amidoC$_1$-C$_3$alkyl, aminoC$_1$-C$_3$alkyl, aminobutyl, and C$_1$-C$_7$alkyl;
R$^7$ and R$^g$, together with the atoms to which they are attached, form a pyrrolidine ring optionally substituted with hydroxy;
R$^8$ and R$^{10}$ are indolylC$_1$-C$_3$alkyl optionally substituted with carboxyC$_1$-C$_3$alkyl;
R$^9$ is hydroxyC$_1$-C$_3$alkyl or aminoC$_1$-C$_3$alkyl;
R$^{11}$ is C$_1$-C$_7$alkyl;
R$^{12}$ is C$_1$-C$_7$alkyl; and
R$^{13}$ is selected from C$_1$-C$_7$alkyl, carboxyC$_1$-C$_3$alkyl, and —(CH$_2$)$_3$NHC(NH)NH$_2$.

2. A compound which is

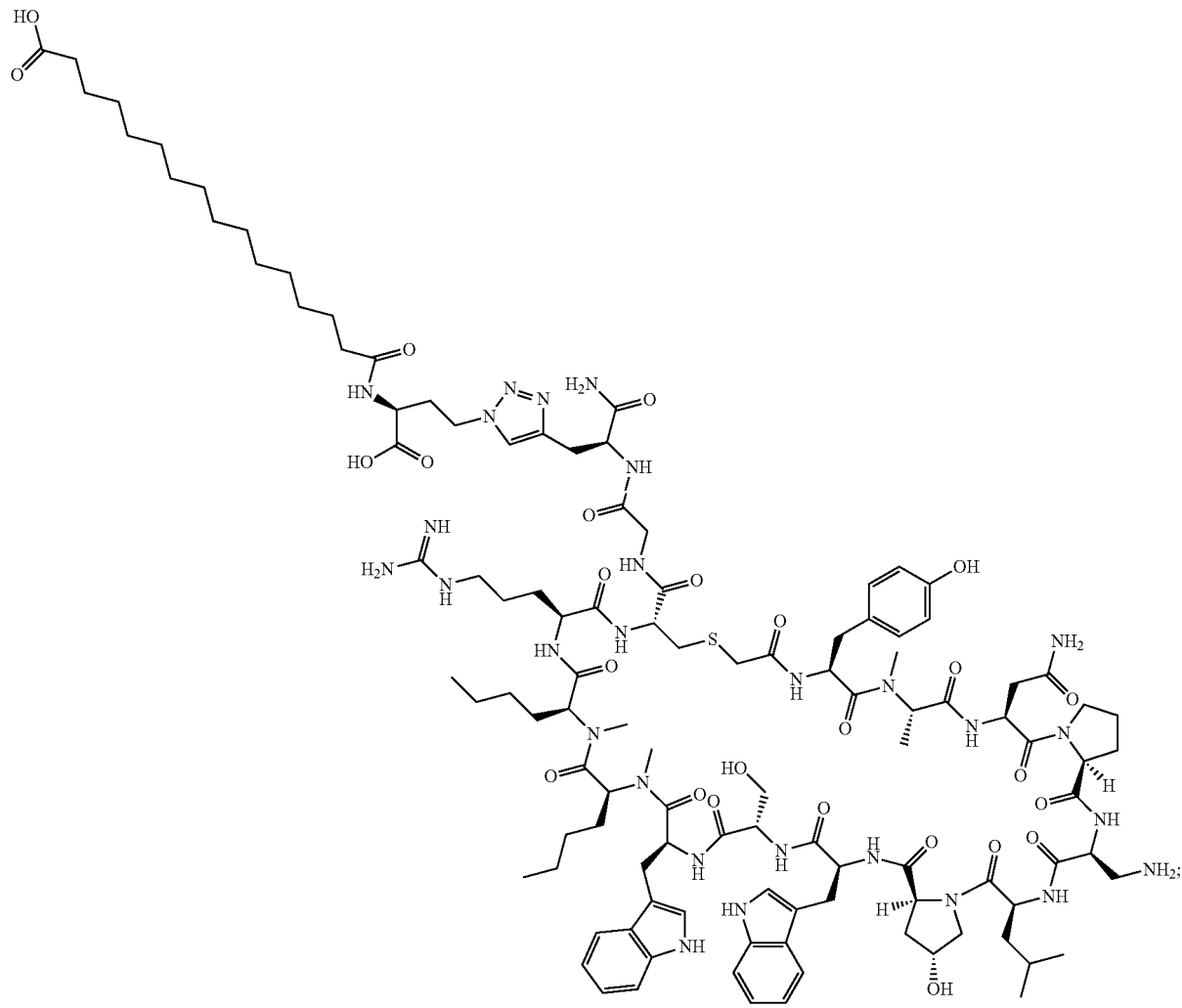 [SMILES: CCCC[C@H]1C(=O)N(C)[C@@H](CCCC)C(=O)N[C@@H](CCCNC(=N)N)C(=O)N[C@H](C(=O)NCC(=O)N[C@@H](Cc2cn(CC[C@H](NC(=O)CCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

or a pharmaceutically acceptable salt thereof.

3. A compound which is
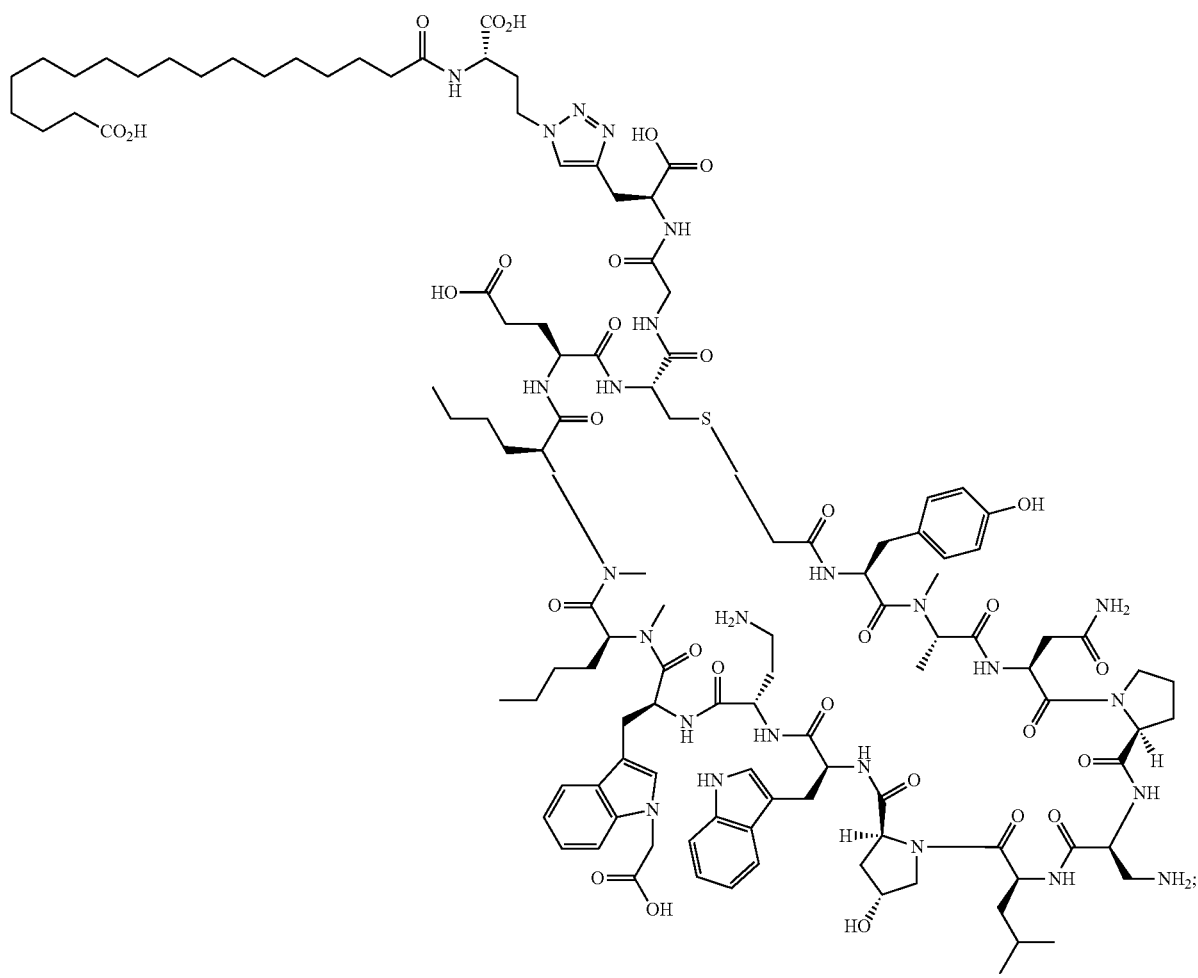 [SMILES: CCCC[C@H]1C(=O)N(C)[C@@H](CCCC)C(=O)N[C@@H](CCC(=O)O)C(=O)N[C@H](C(=O)NCC(=O)N[C@@H](Cc2cn(CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.
4. A compound which is
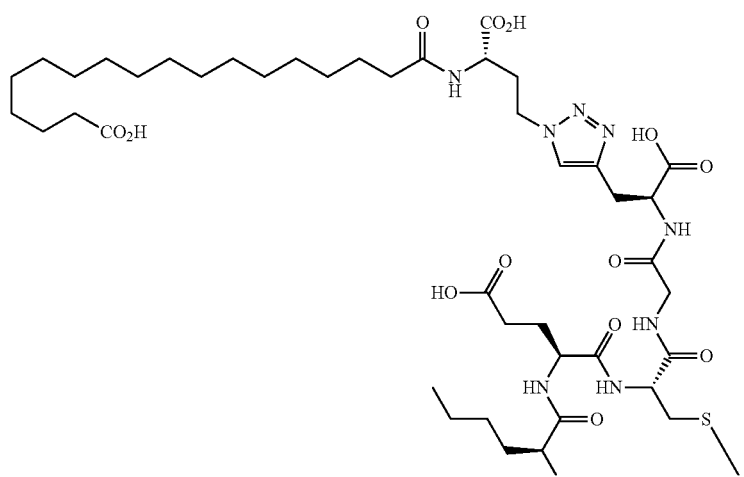

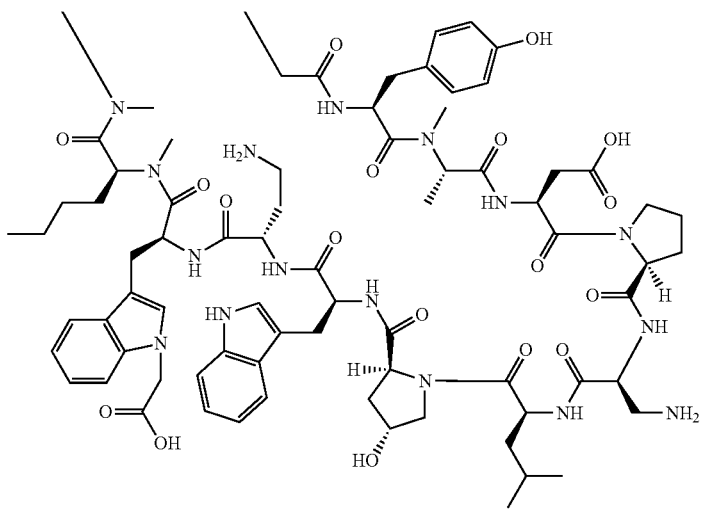
or a pharmaceutically acceptable salt thereof.
5. A compound which is
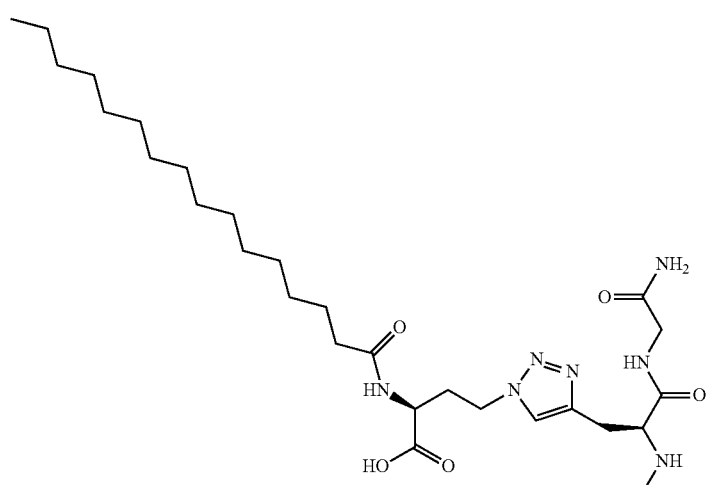

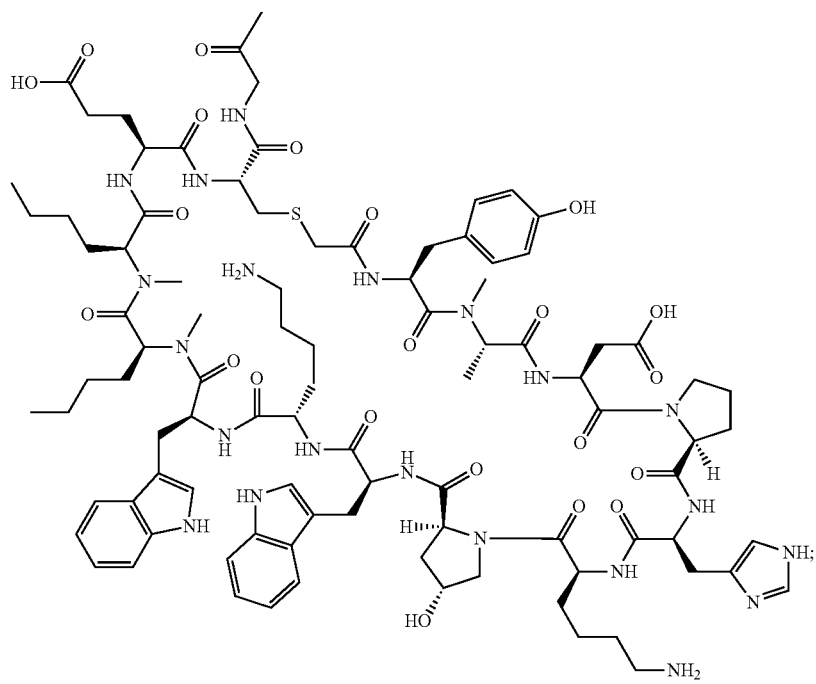
or a pharmaceutical acceptable salt thereof.
6. A compound which is
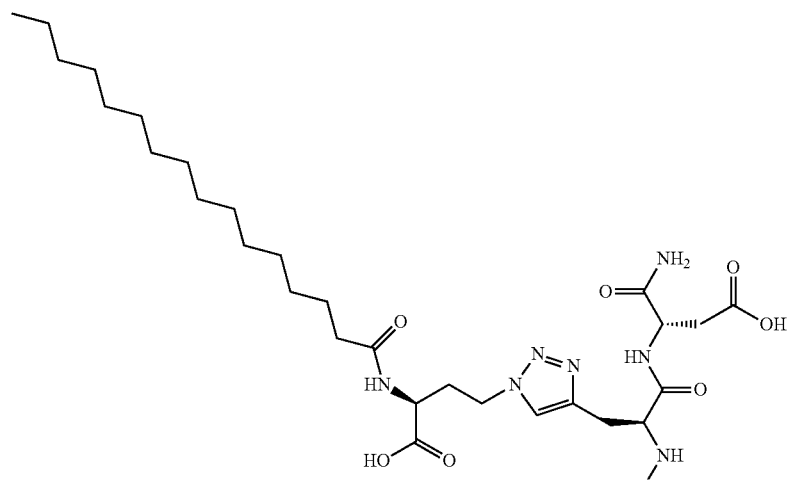

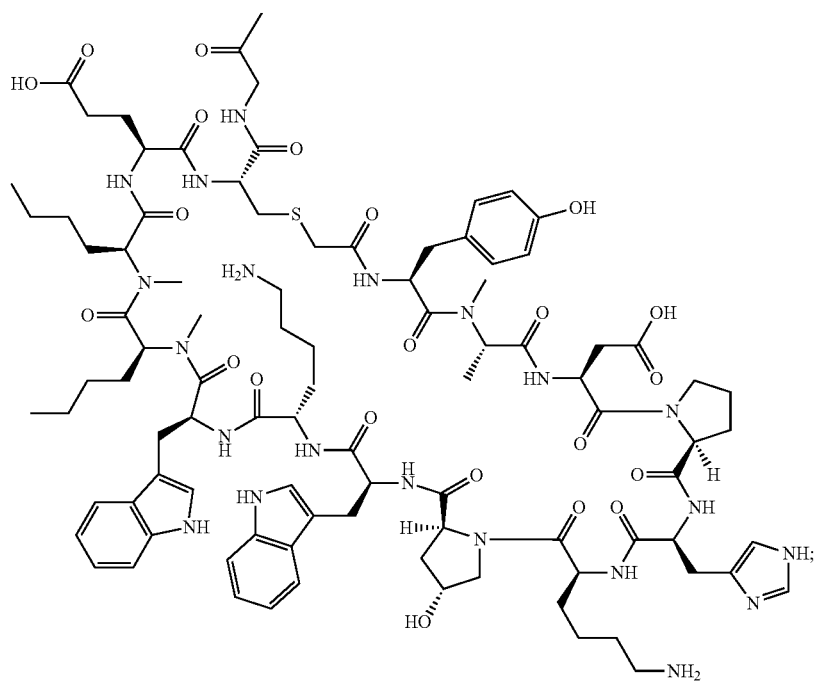
or a pharmaceutically acceptable salt thereof.
7. A compound which is
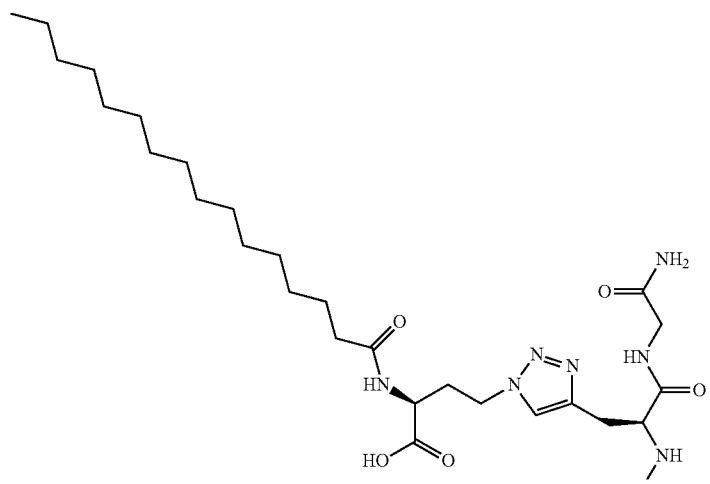

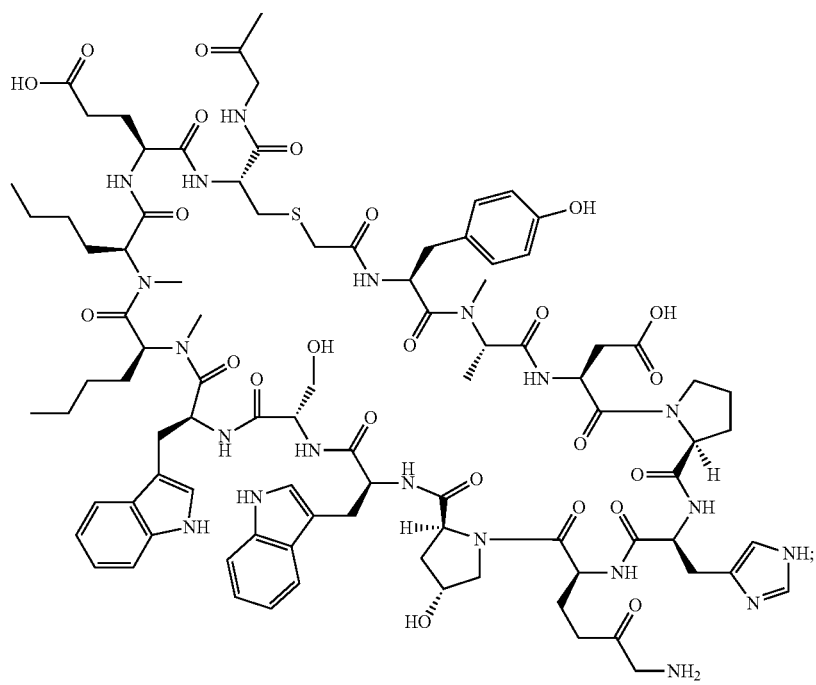
or a pharmaceutically acceptable salt thereof.
8. A compound which is
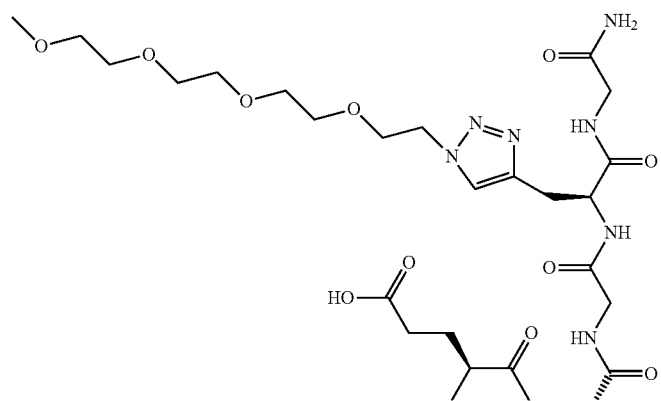

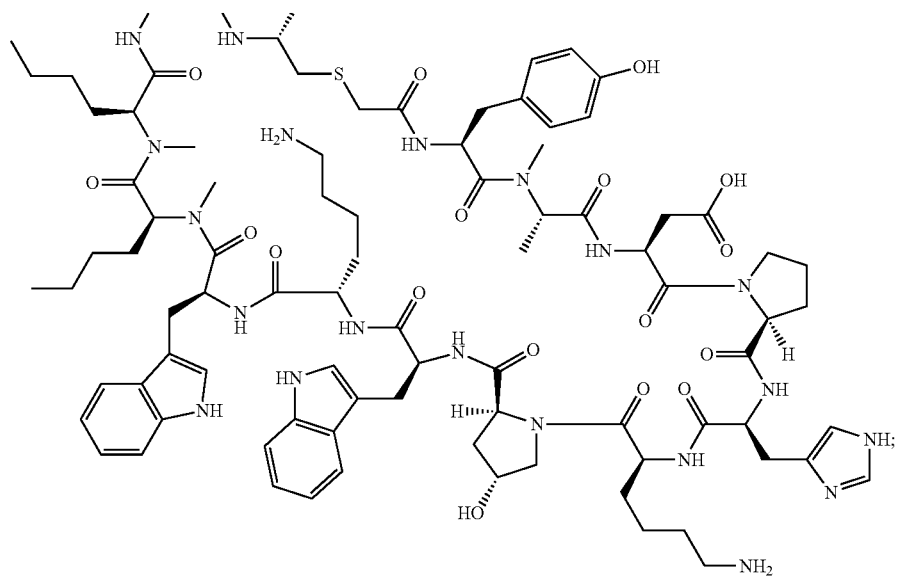
or a pharmaceutically acceptable salt thereof.
9. A compound which is
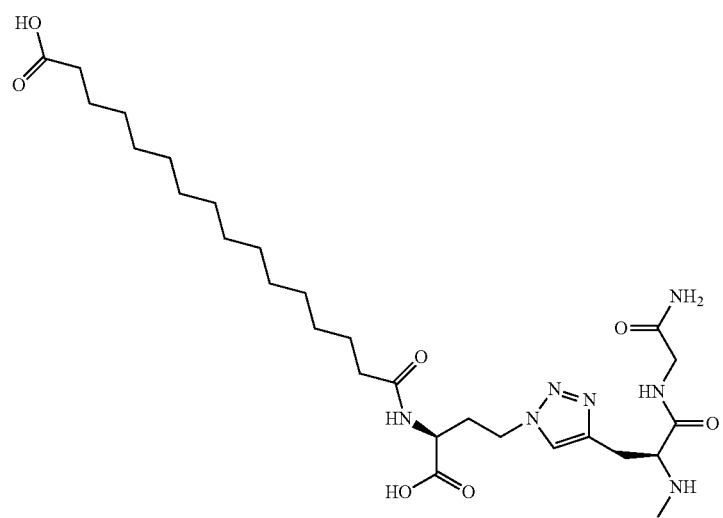

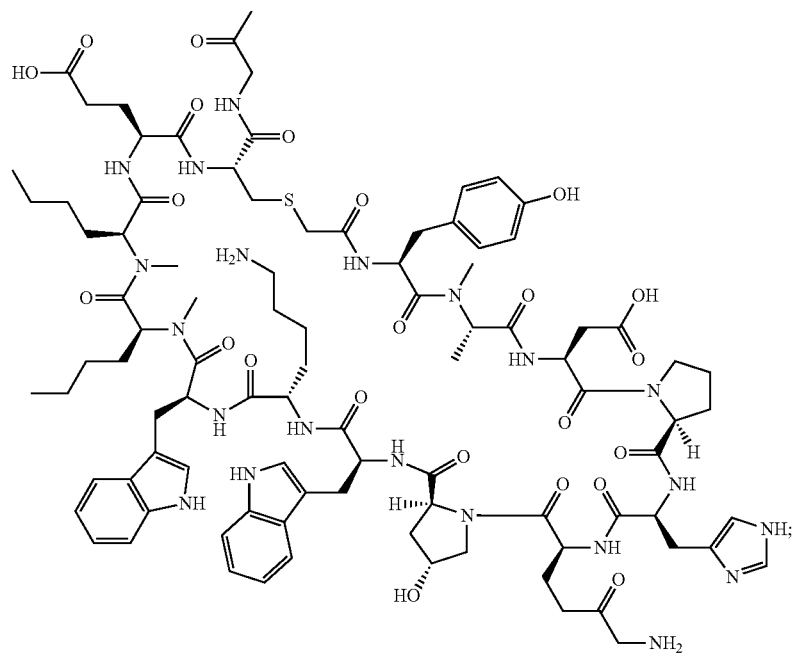
or a pharmaceutically acceptable salt thereof.
10. A compound which is
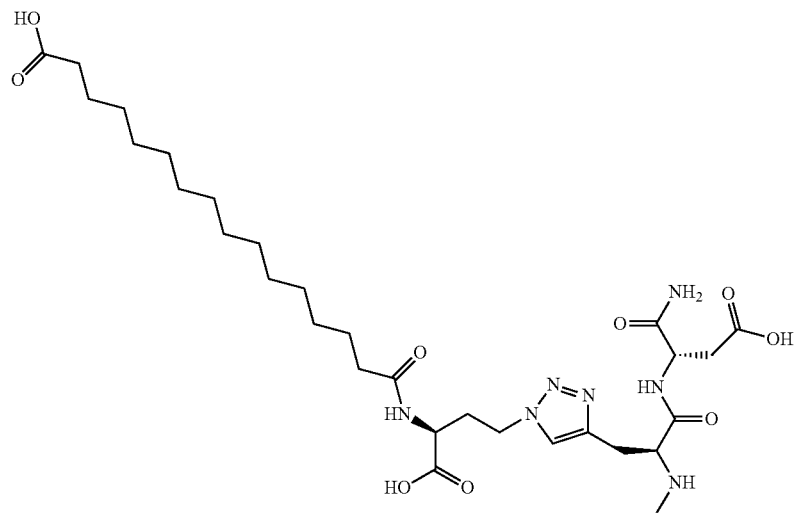

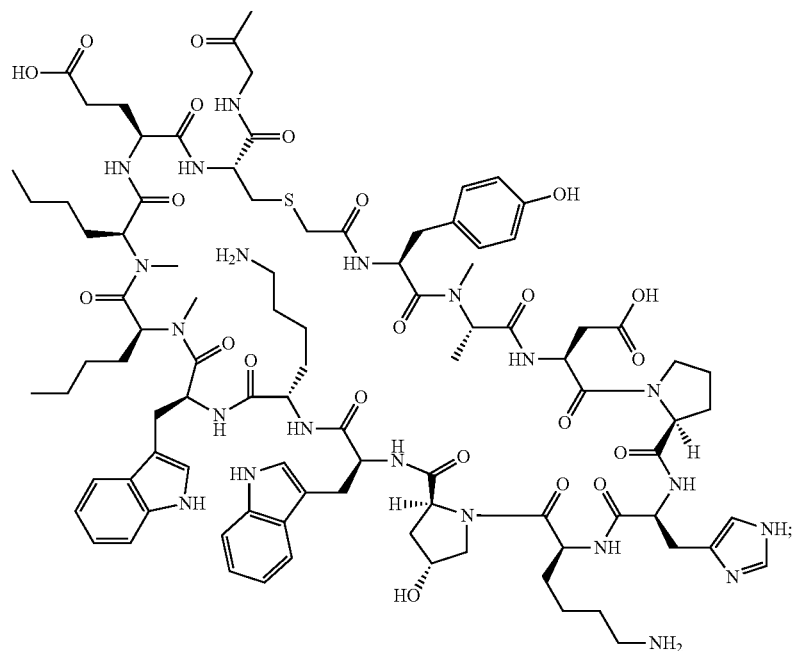
or a pharmaceutically acceptable salt thereof.
11. A compound which is
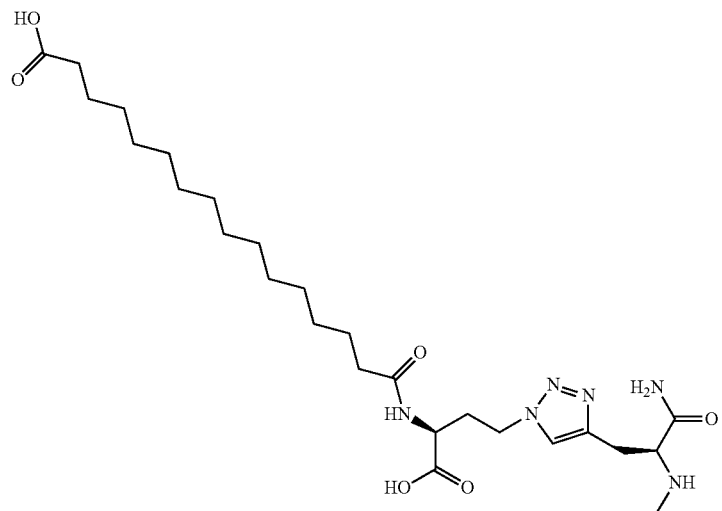

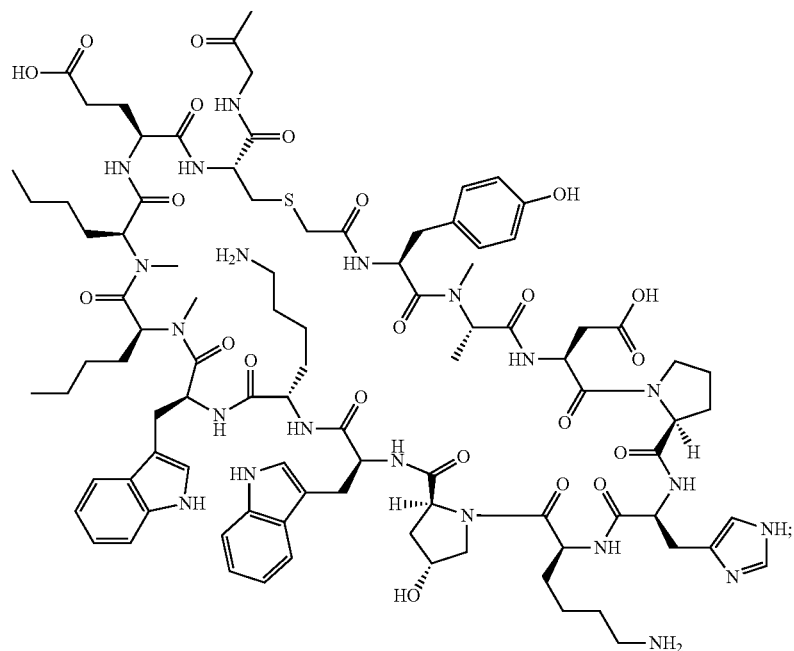
or a pharmaceutically acceptable salt thereof.
12. A compound which is
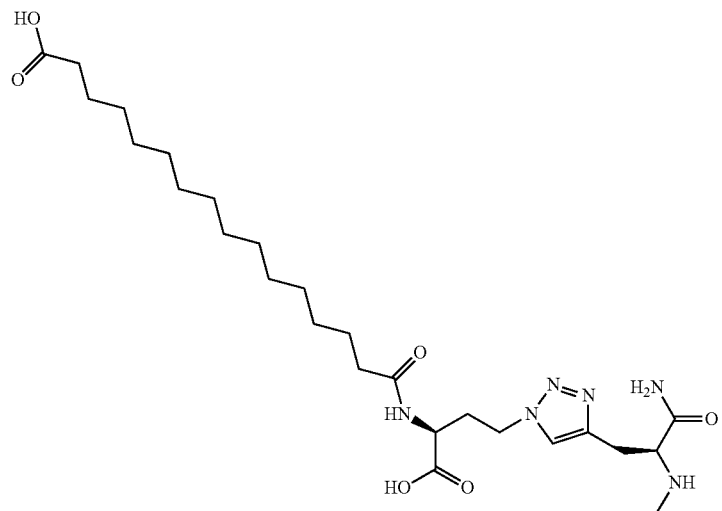

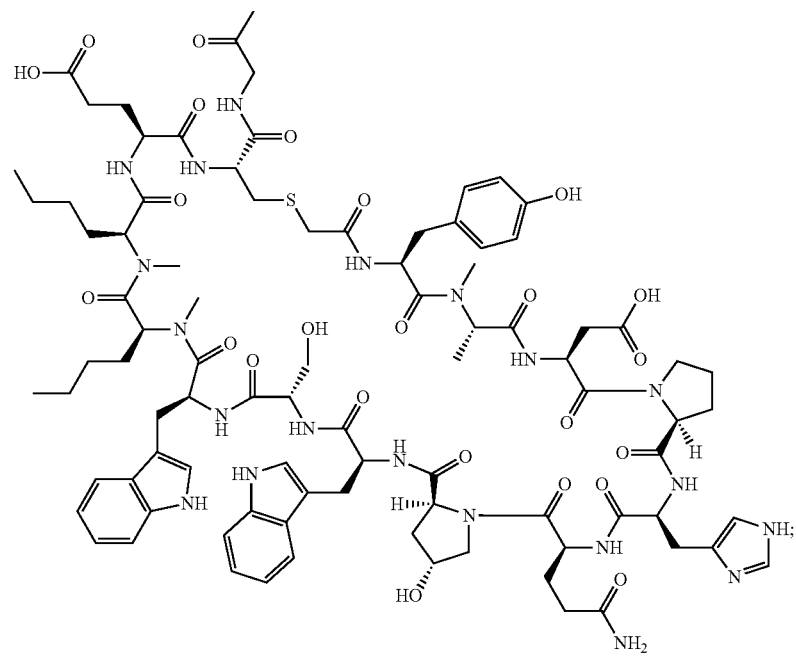
or a pharmaceutically acceptable salt thereof.
13. A compound which is
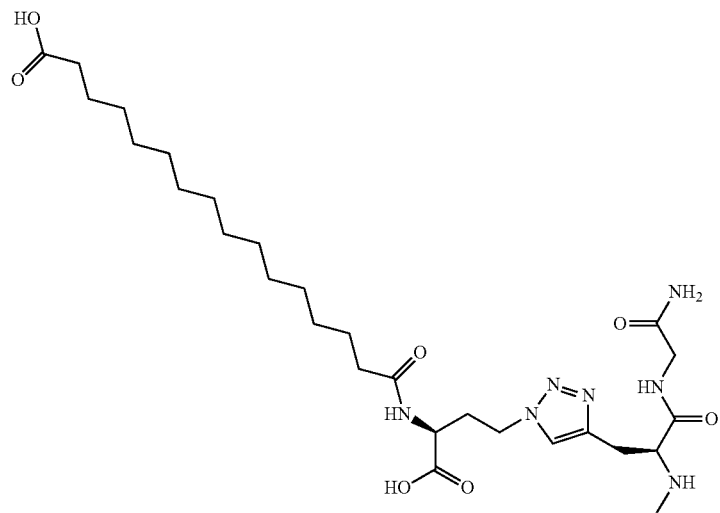

-continued
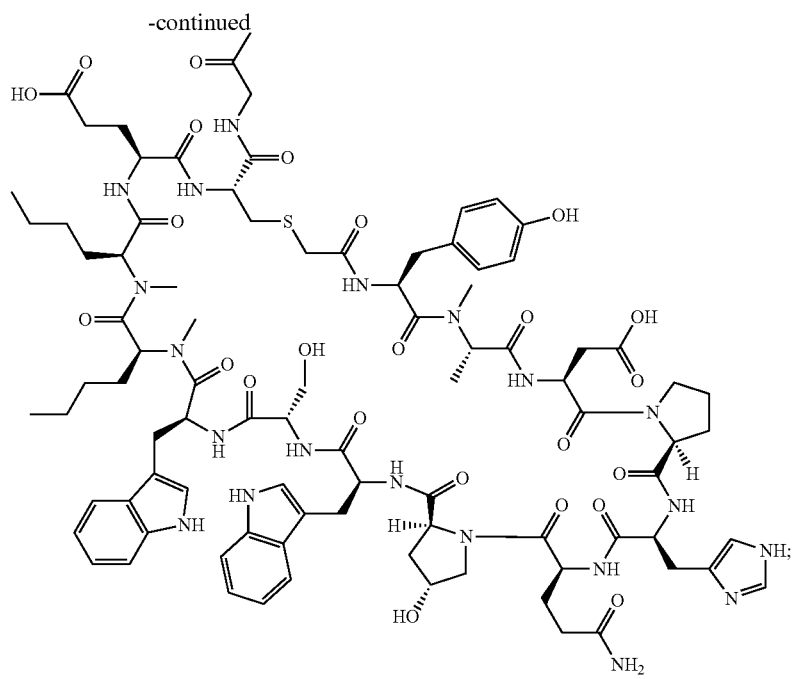
or a pharmaceutically acceptable salt thereof.
14. A compound which is
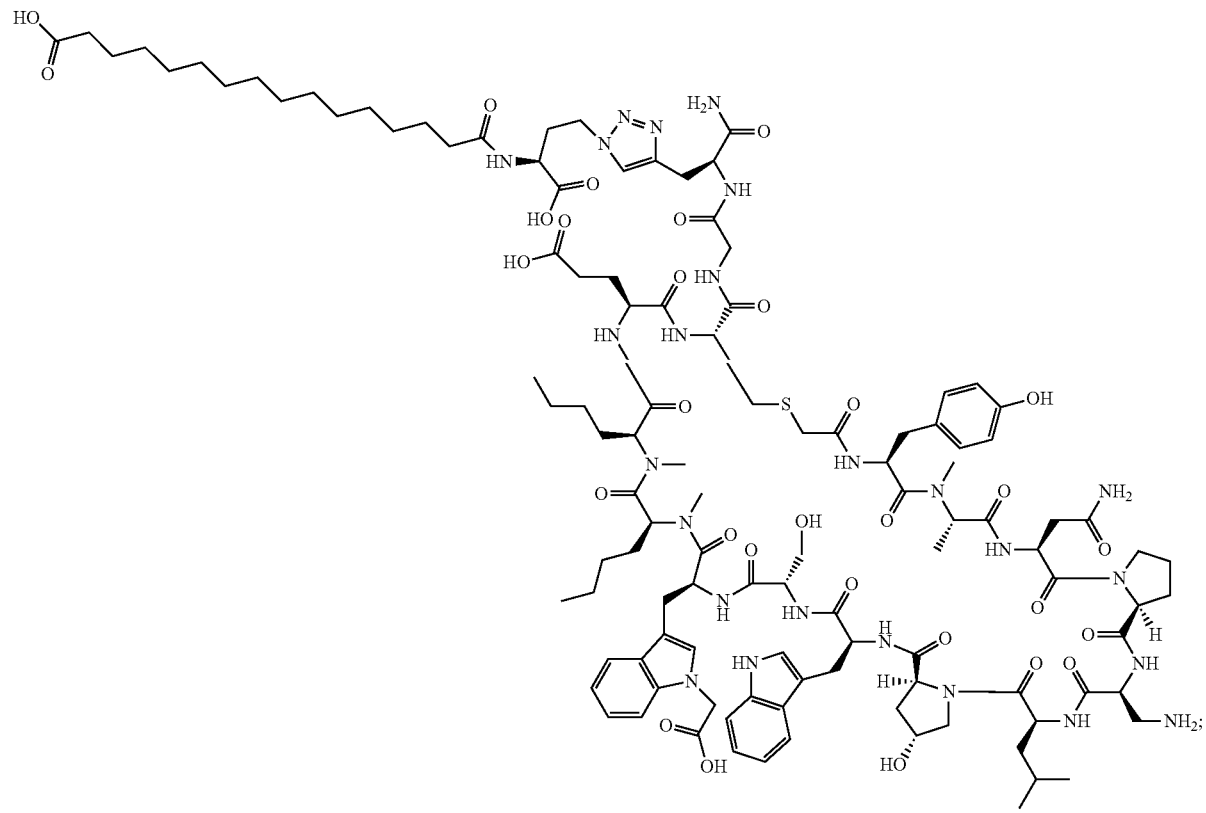 [SMILES: CCCC[C@H]1C(=O)N(C)[C@@H](CCCC)C(=O)N[C@@H](CCC(=O)O)C(=O)N[C@H](C(=O)NCC(=O)N[C@@H](Cc2cn(CC[C@H](NC(=O)CCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]
or a pharmaceutically acceptable salt thereof.

15. A compound which is
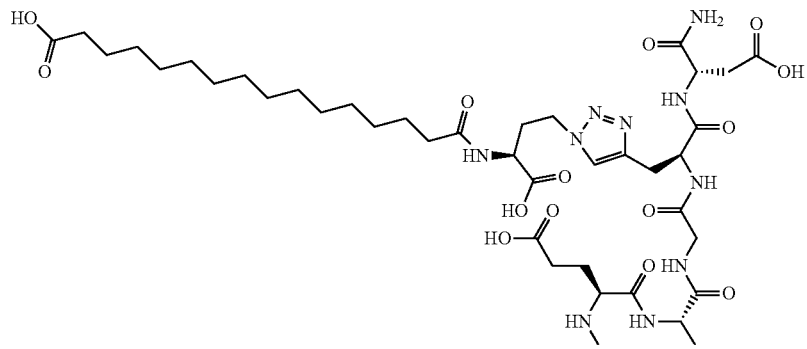
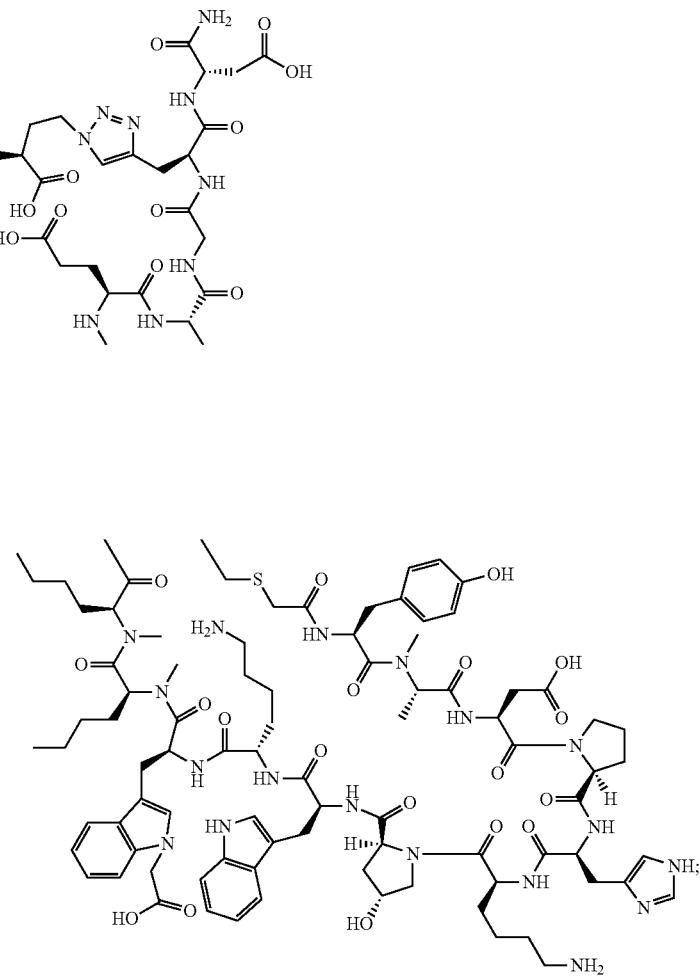
or a pharmaceutically acceptable salt thereof.
16. A compound which is
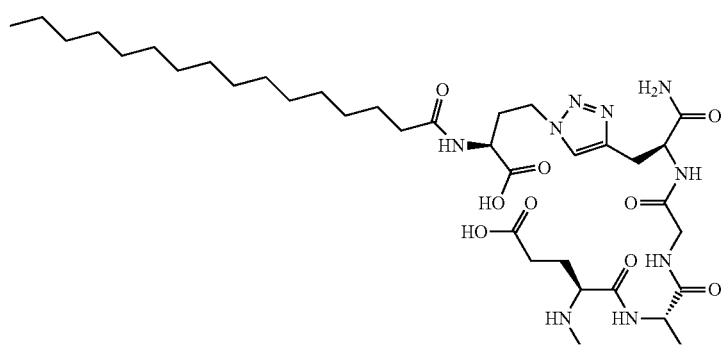

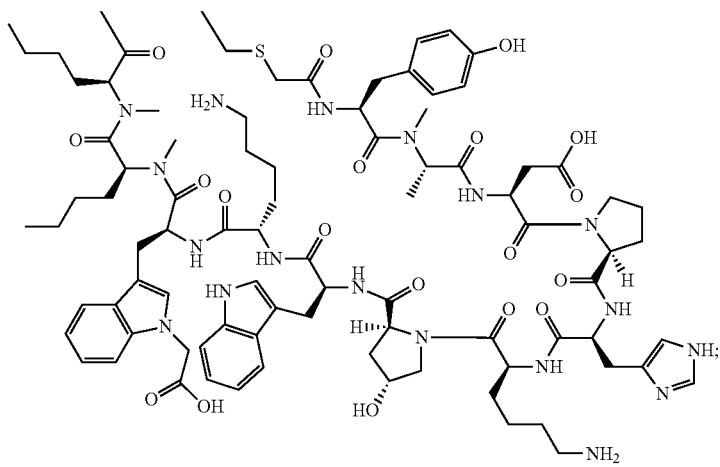
or a pharmaceutically acceptable salt thereof.
17. A compound which is
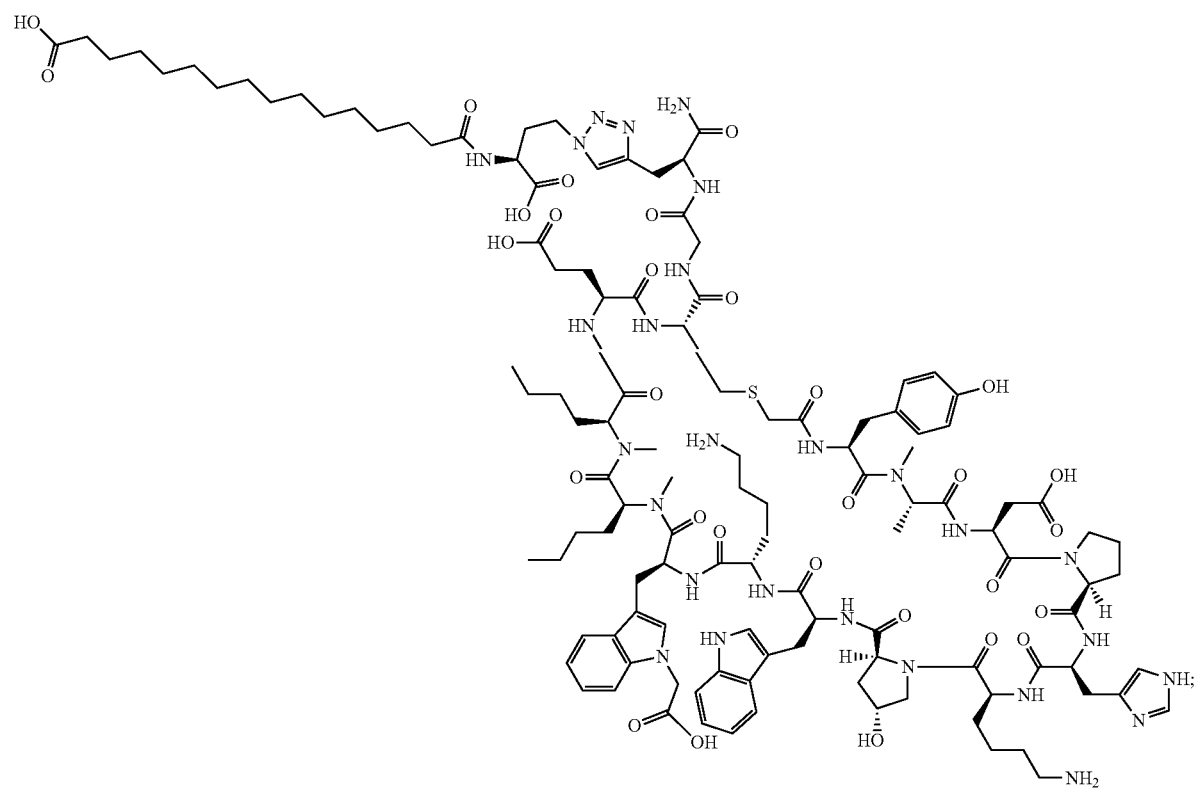 [SMILES: CCCC[C@H]1C(=O)N(C)[C@@H](CCCC)C(=O)N[C@@H](CCC(=O)O)C(=O)N[C@H](C(=O)NCC(=O)N[C@@H](Cc2cn(CC[C@H](NC(=O)CCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]
or a pharmaceutically acceptable salt thereof.

18. A compound which is
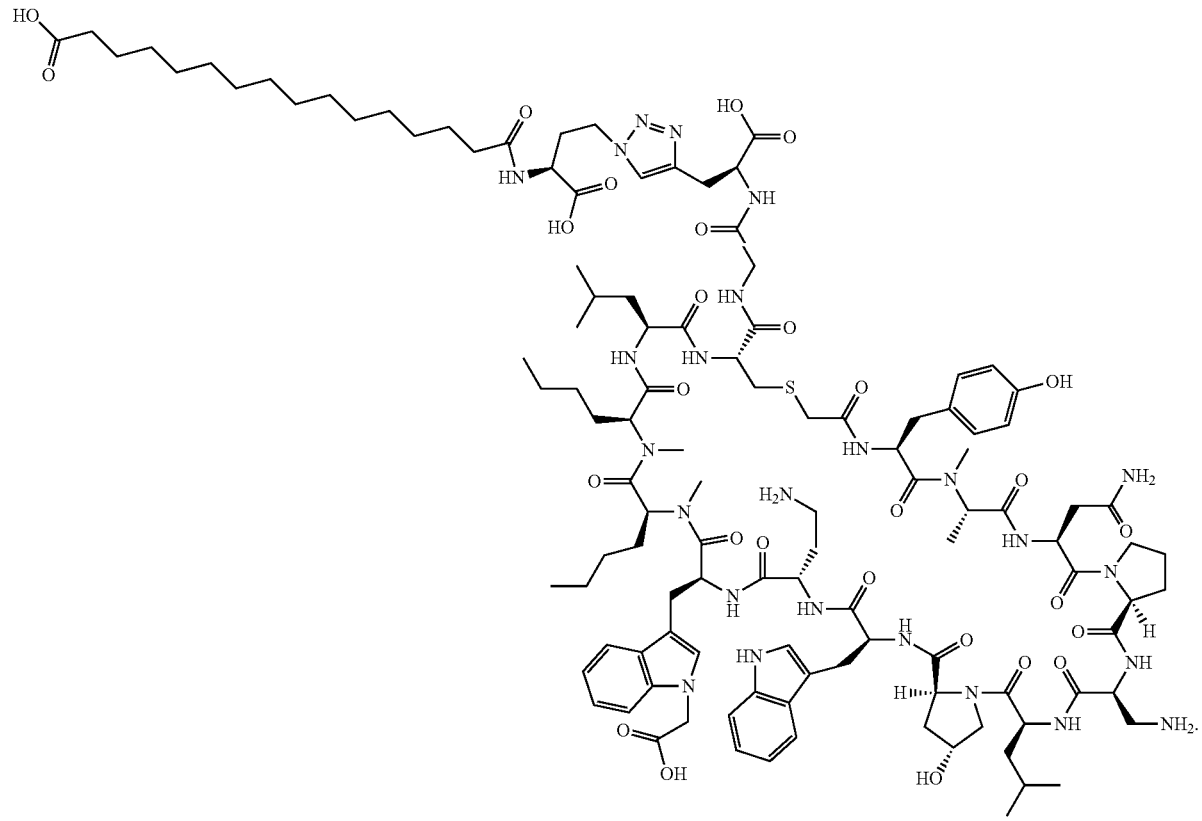 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CC[C@H](NC(=O)CCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.
19. A compound which is
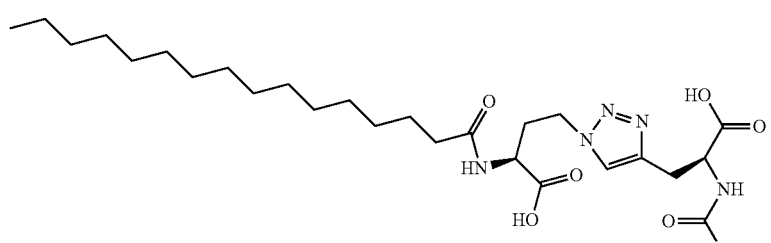

-continued
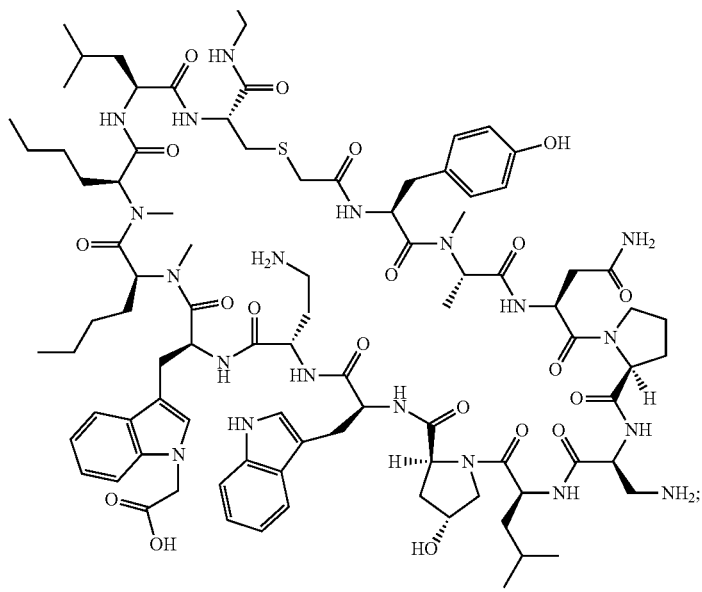
or a pharmaceutically acceptable salt thereof.
20. A compound which is
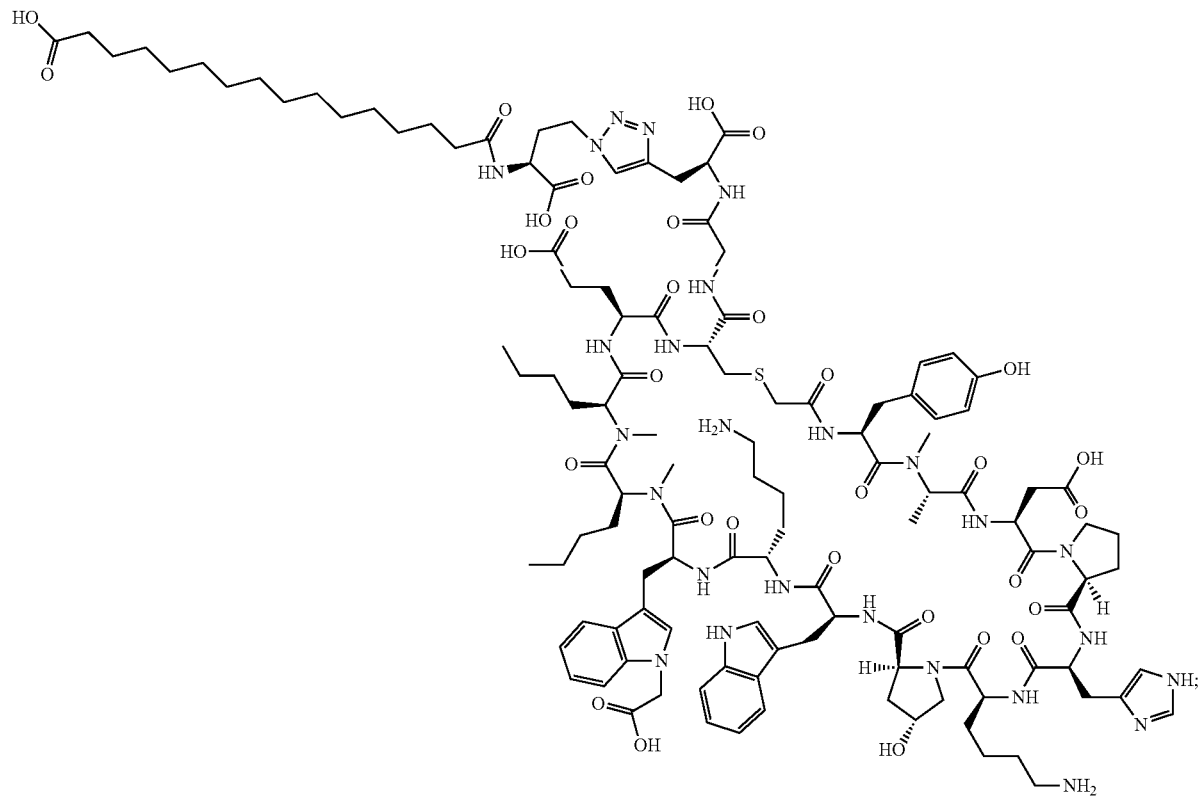 [SMILES: CCCC[C@H]1C(=O)N(C)[C@@H](CCCC)C(=O)N[C@@H](CCC(=O)O)C(=O)N[C@H](C(=O)NCC(=O)N[C@@H](Cc2cn(CC[C@H](NC(=O)CCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]
or a pharmaceutically acceptable salt thereof.

21. A compound which is
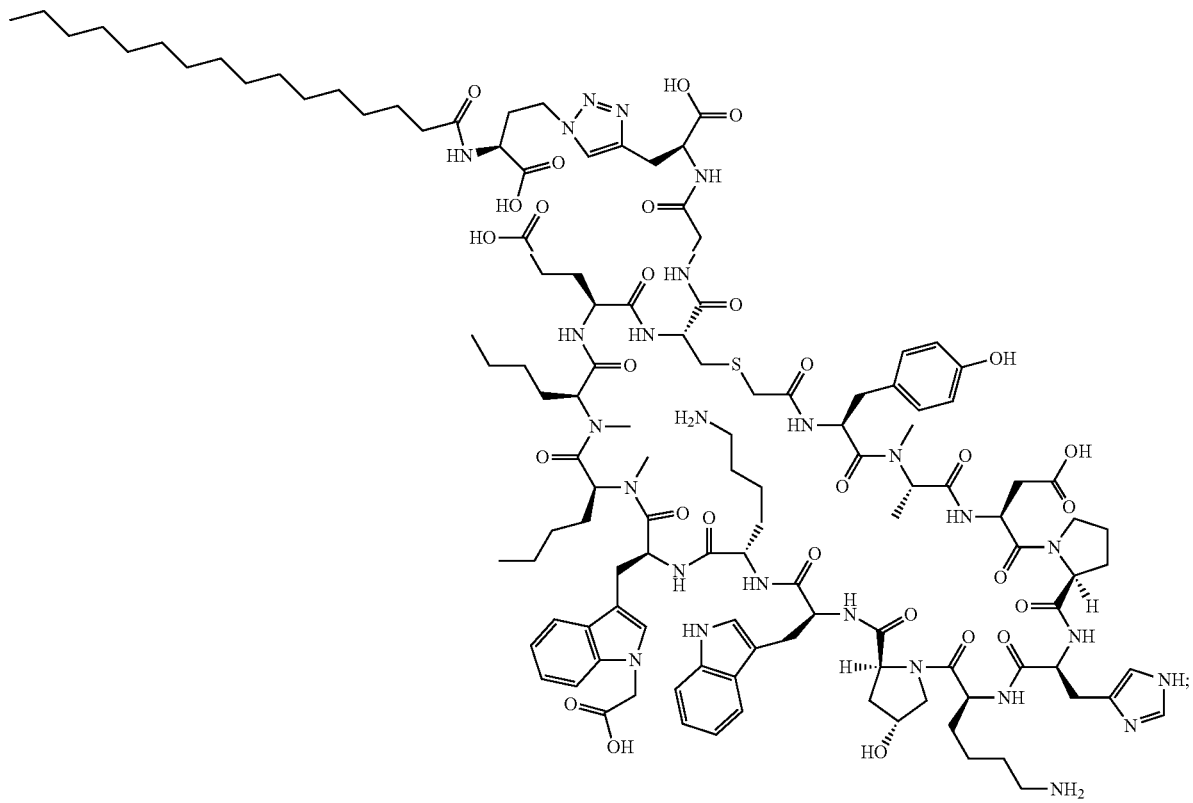 [SMILES: CCCCCCCCCCCCCCCC(=O)N[C@@H](CCn1cc(C[C@H](NC(=O)CNC(=O)[C@@H]2CSCC(=O)N[C@@H](Cc3ccc(O)cc3)C(=O)N(C)[C@@H](C)C(=O)N[C@@H](CC(=O)O)C(=O)N3CCC[C@H]3C(=O)N[C@@H](Cc3c[nH]cn3)C(=O)N[C@@H](CCCCN)C(=O)N3C[C@H](O)C[C@H]3C(=O)N[C@@H](Cc3c[nH]c4ccccc34)C(=O)N[C@@H](CCCCN)C(=O)N[C@@H](Cc3cn(CC(=O)O)c4ccccc34)C(=O)N(C)[C@@H](CCCC)C(=O)N(C)[C@@H](CCCC)C(=O)N[C@@H](CCC(=O)O)C(=O)N2)C(=O)O)nn1)C(=O)O]
or a pharmaceutically acceptable salt thereof.
22. A compound which is
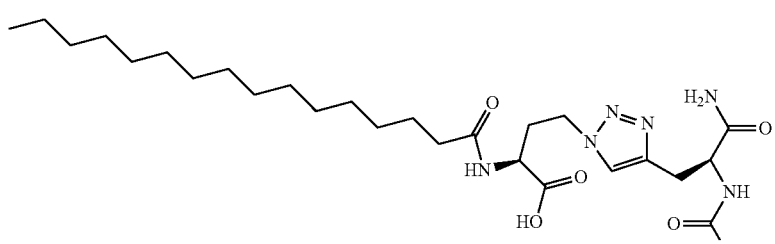

-continued
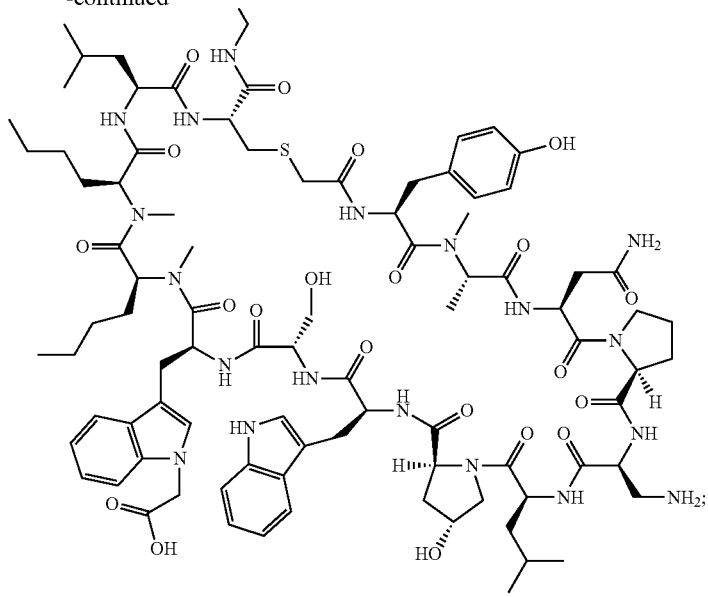
or a pharmaceutically acceptable salt thereof.
23. A compound which is
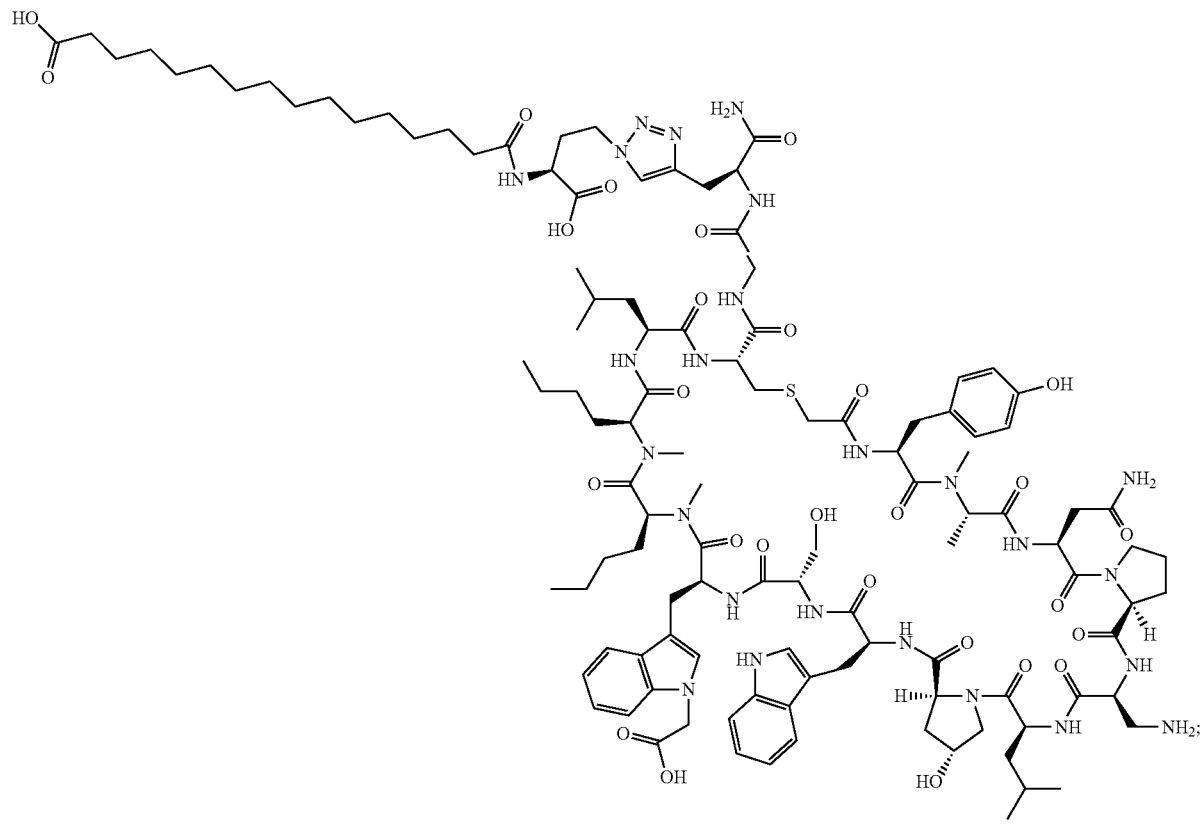 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CC[C@H](NC(=O)CCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]
or a pharmaceutically acceptable salt thereof.

24. A compound which is
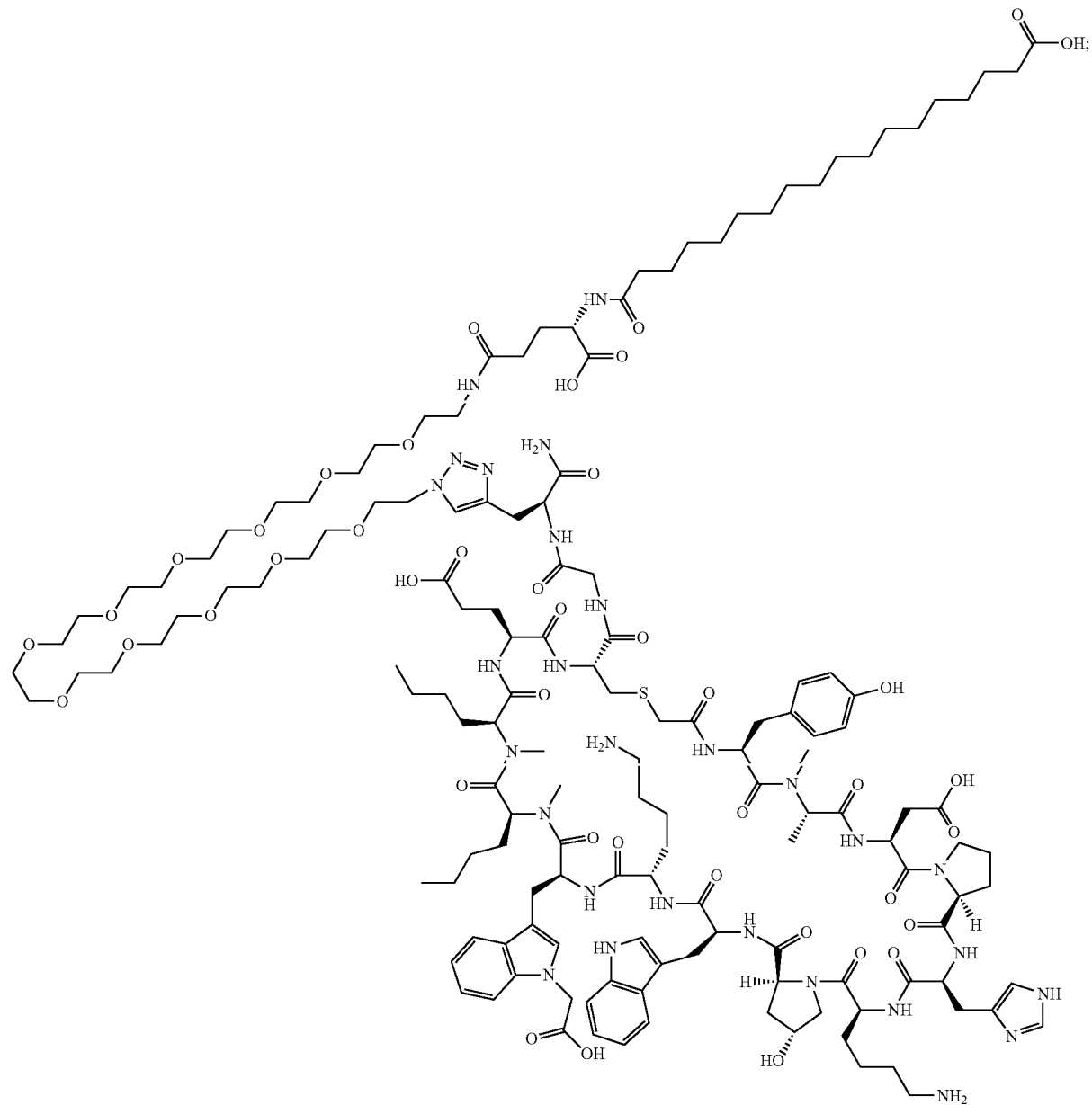 [SMILES: CCCC[C@H]1C(=O)N(C)[C@@H](CCCC)C(=O)N[C@@H](CCC(=O)O)C(=O)N[C@H](C(=O)NCC(=O)N[C@@H](Cc2cn(CCOCCOCCOCCOCCOCCOCCOCCOCCOCCOCCOCCNC(=O)CC[C@H](NC(=O)CCCCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]
or a pharmaceutically acceptable salt thereof.

25. A compound which is
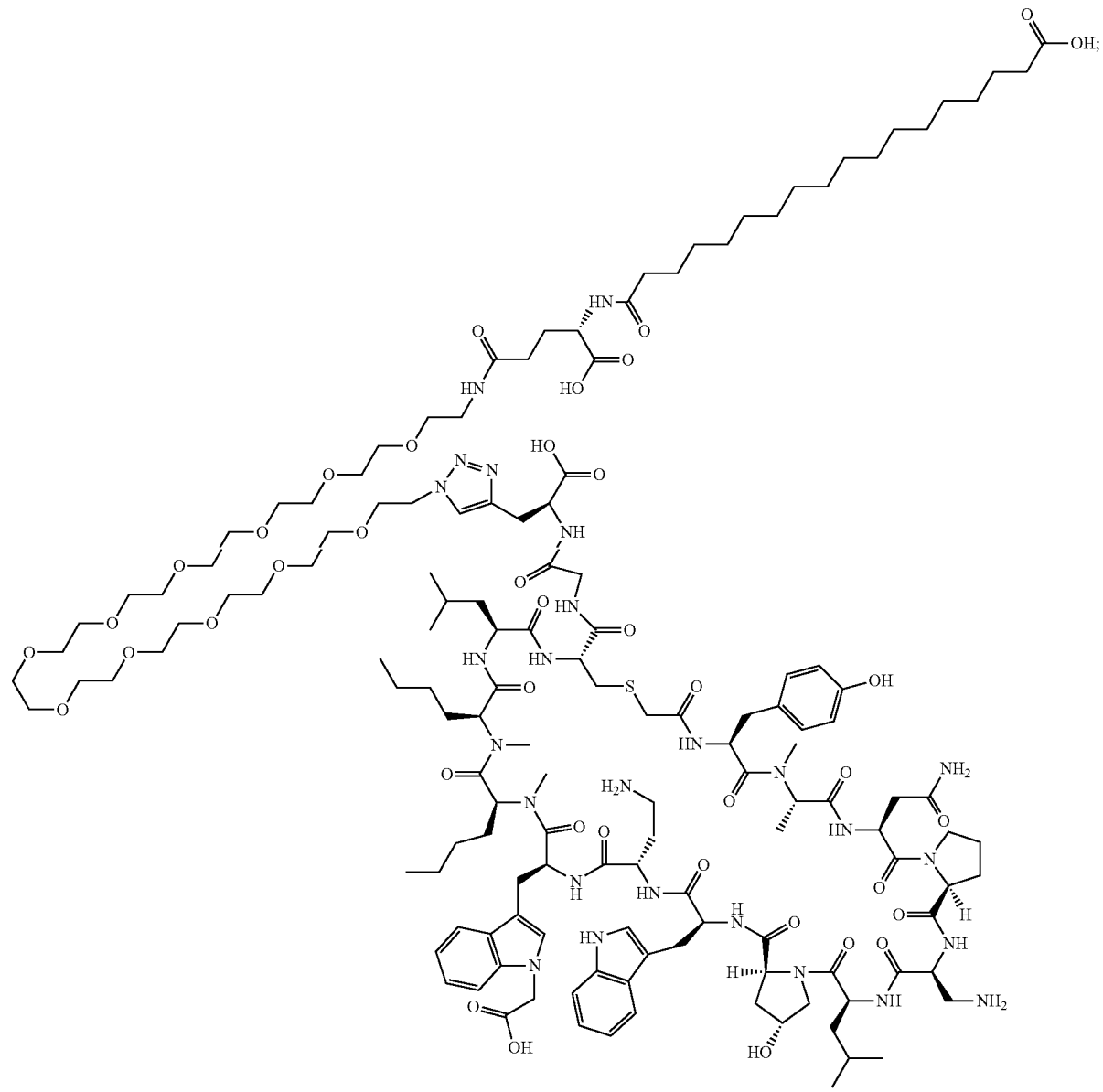 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOCCOCCOCCOCCOCCOCCOCCOCCNC(=O)CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.
26. A compound which is
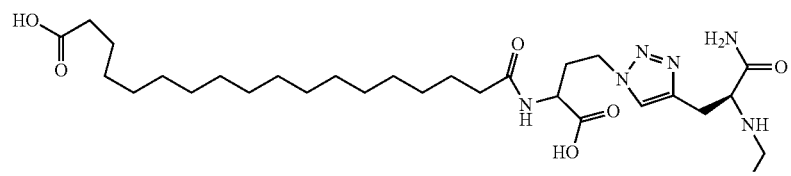

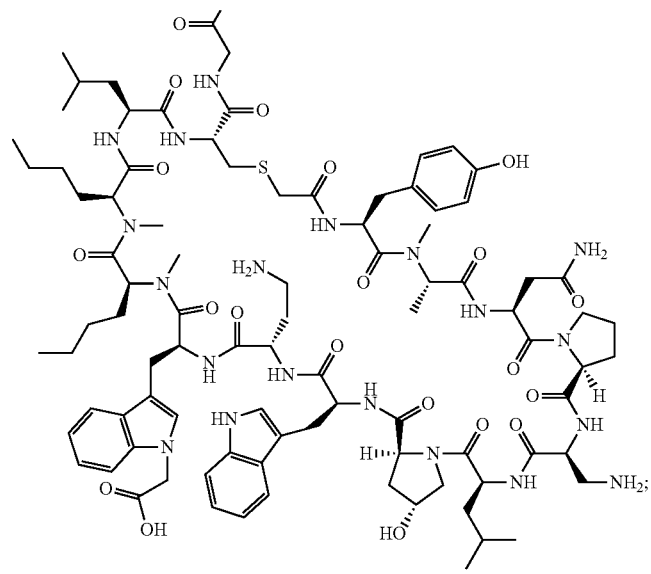
or a pharmaceutically acceptable salt thereof.
27. A compound which is
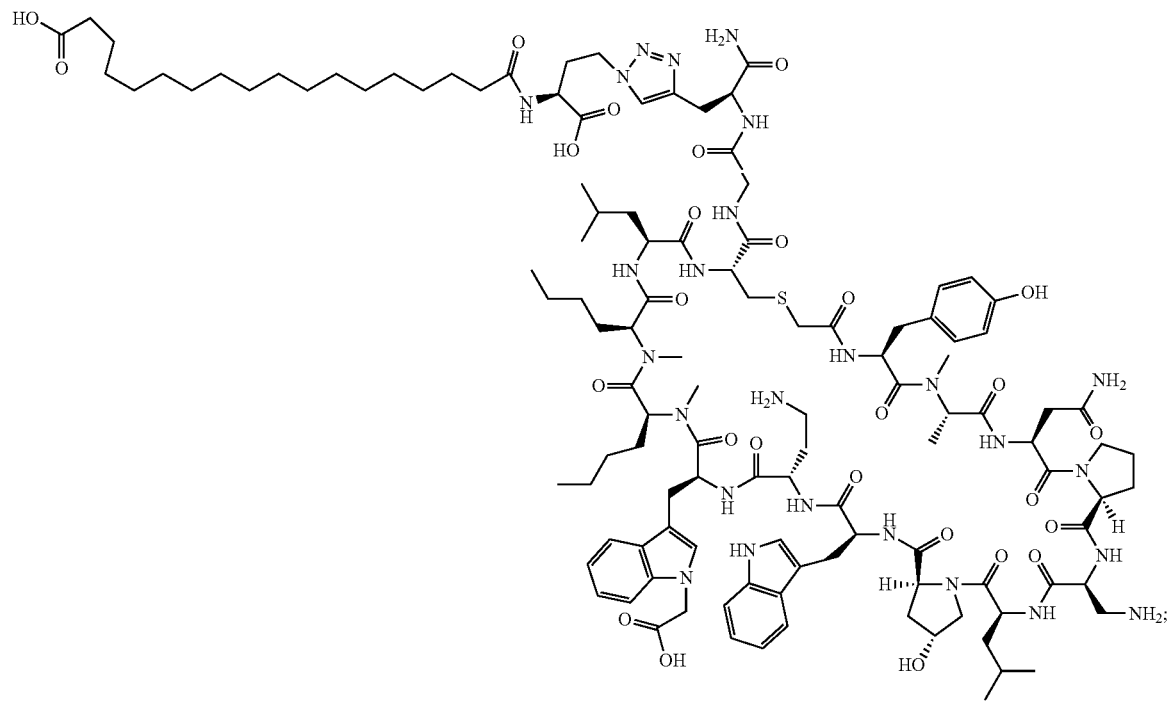 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CC[C@H](NC(=O)CCCCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.

28. A compound which is
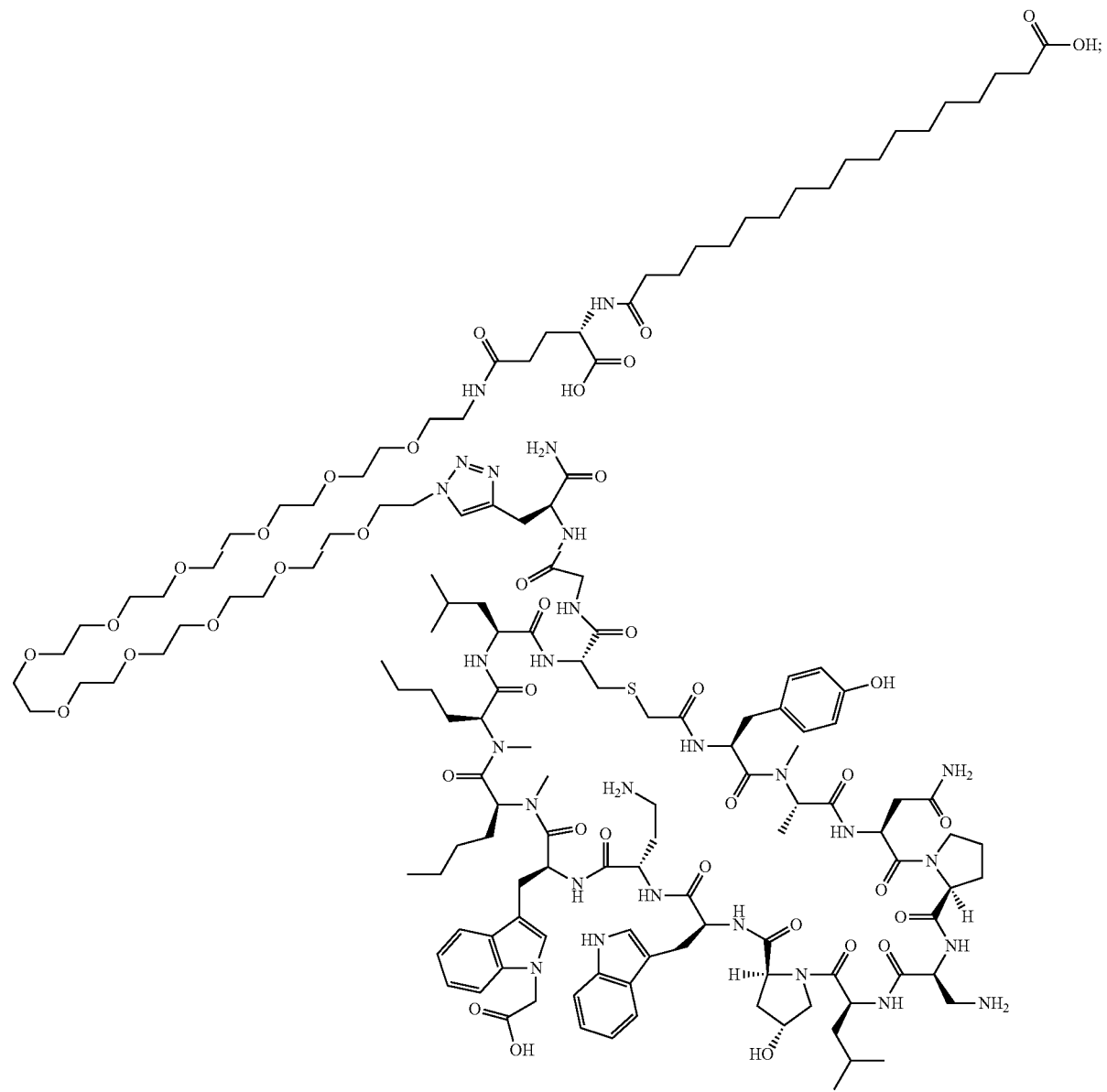 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOCCOCCOCCOCCOCCOCCOCCOCCNC(=O)CC[C@H](NC(=O)CCCCCCCCCCCCCCCCC(=O)O)C(=O)O)nn2)C(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.

29. A compound which is
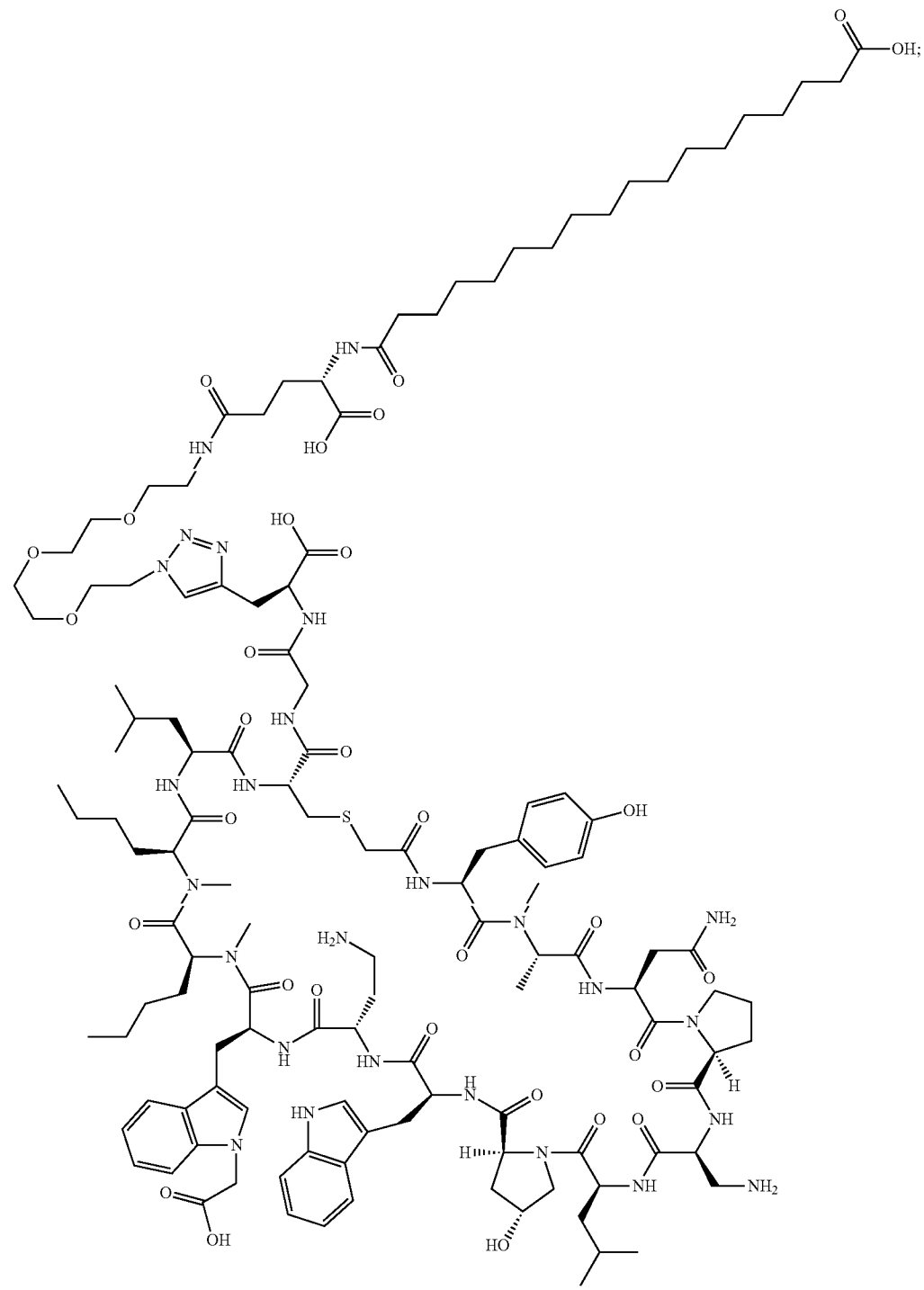 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCNC(=O)CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.

30. A compound which is
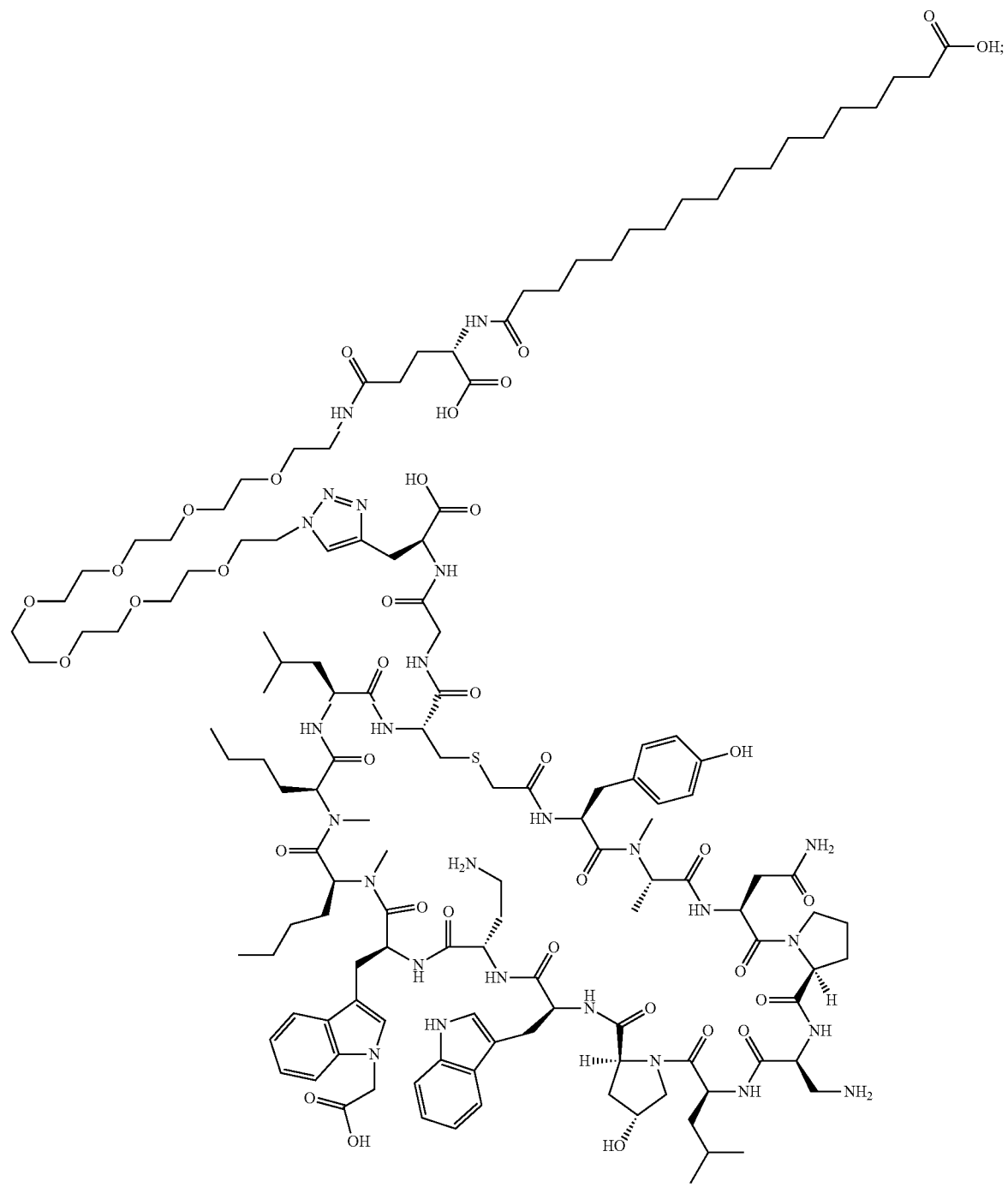 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOCCOCCOCCOCCNC(=O)CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.

31. A compound which is
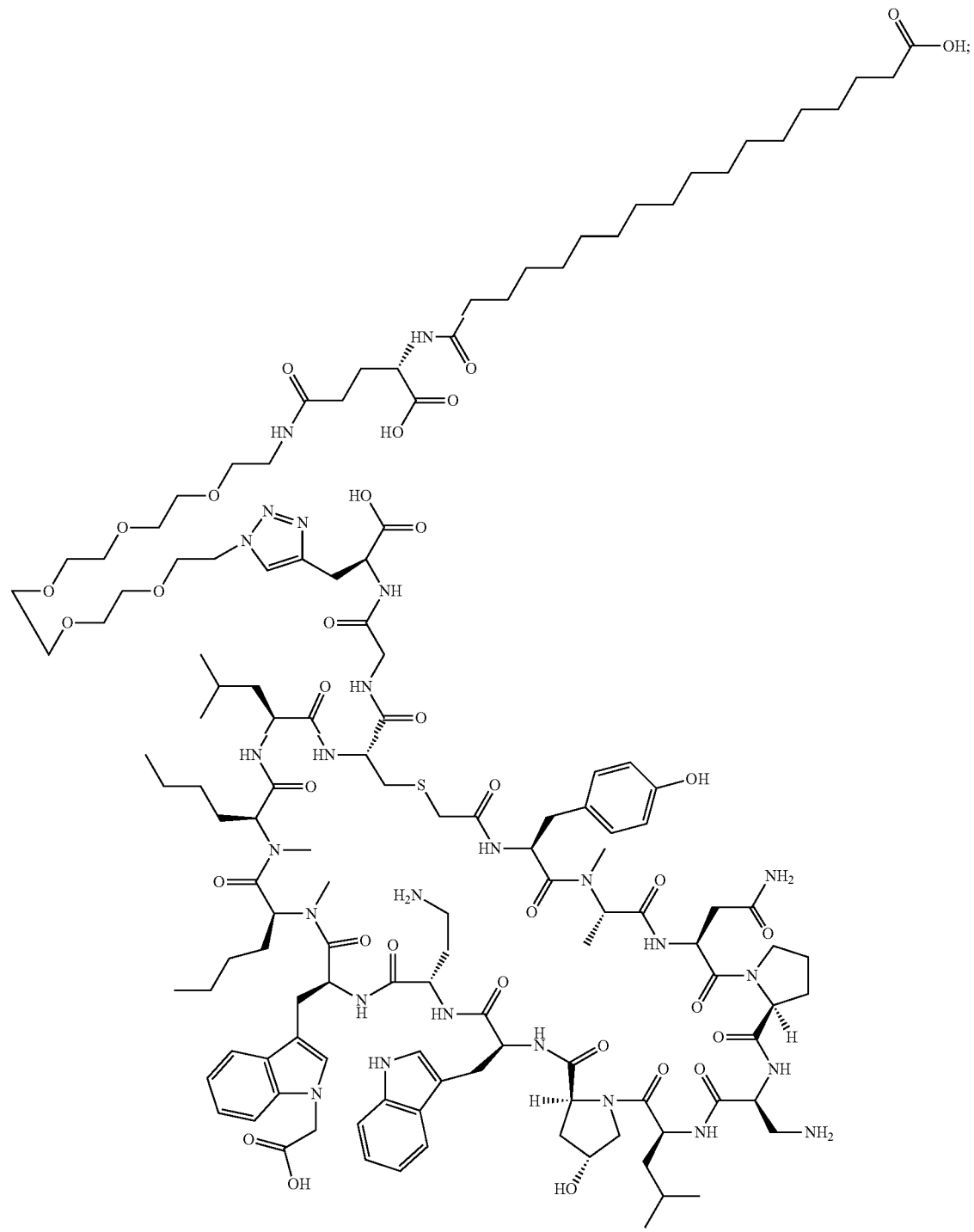 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCOCCOCCNC(=O)CC[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.

32. A compound which is
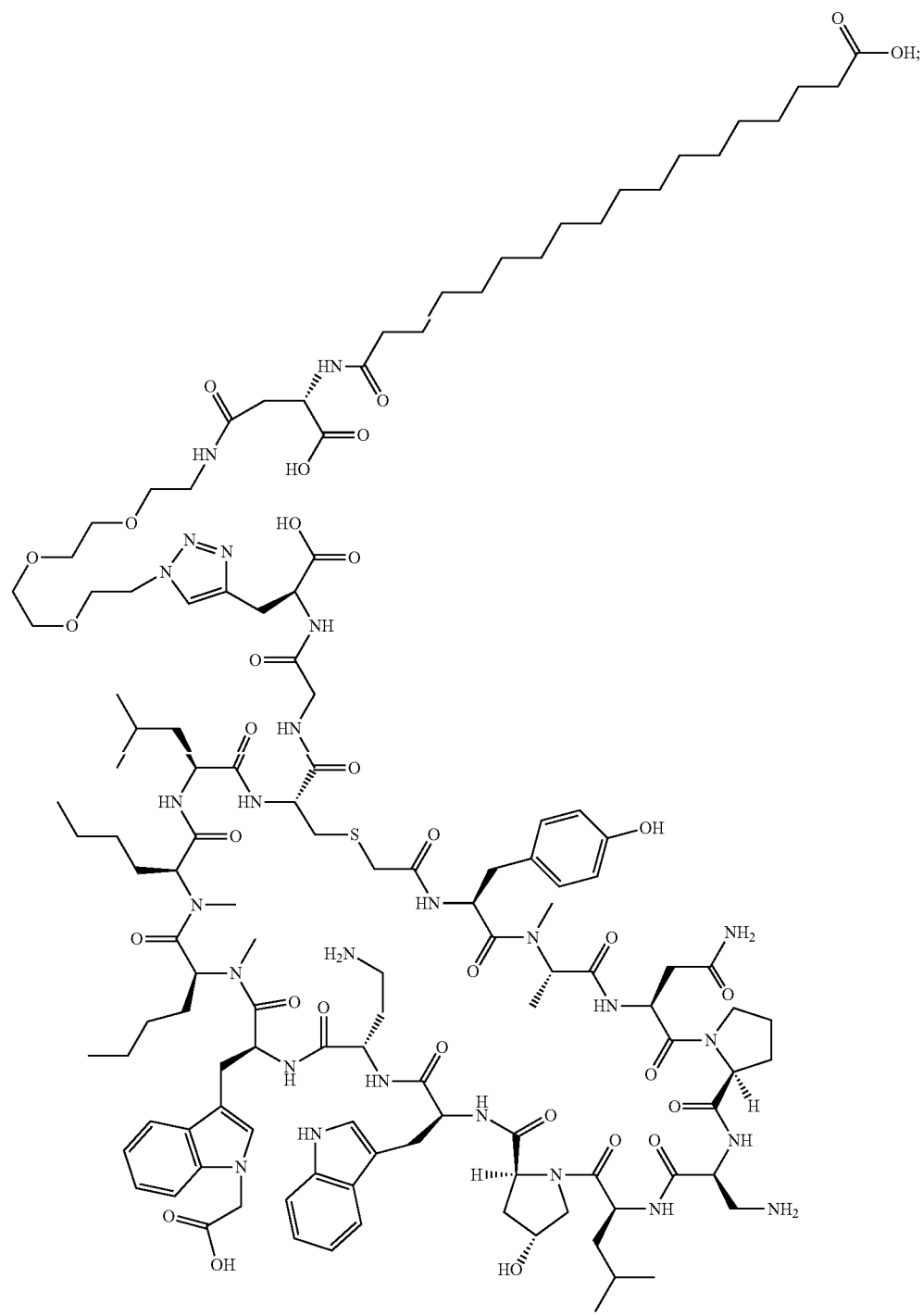 [SMILES: CCCC[C@H]1C(=O)N(C)[C@@H](CCCC)C(=O)N[C@@H](CC(C)C)C(=O)N[C@H](C(=O)NCC(=O)N[C@@H](Cc2cn(CCOCCOCCOCCNC(=O)C[C@H](NC(=O)CCCCCCCCCCCCCCCCC(=O)O)C(=O)O)nn2)C(=O)O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
or a pharmaceutically acceptable salt thereof.
* * * * *

UNITED STATES PATENT AND TRADEMARK OFFICE
CERTIFICATE OF CORRECTION

PATENT NO. : 9,856,292 B2
APPLICATION NO. : 14/938327
DATED : January 2, 2018
INVENTOR(S) : Gillman et al.

Page 1 of 3

It is certified that error appears in the above-identified patent and that said Letters Patent is hereby corrected as shown below:

In the Claims

Claim 1, Column 969, Lines 45-65:

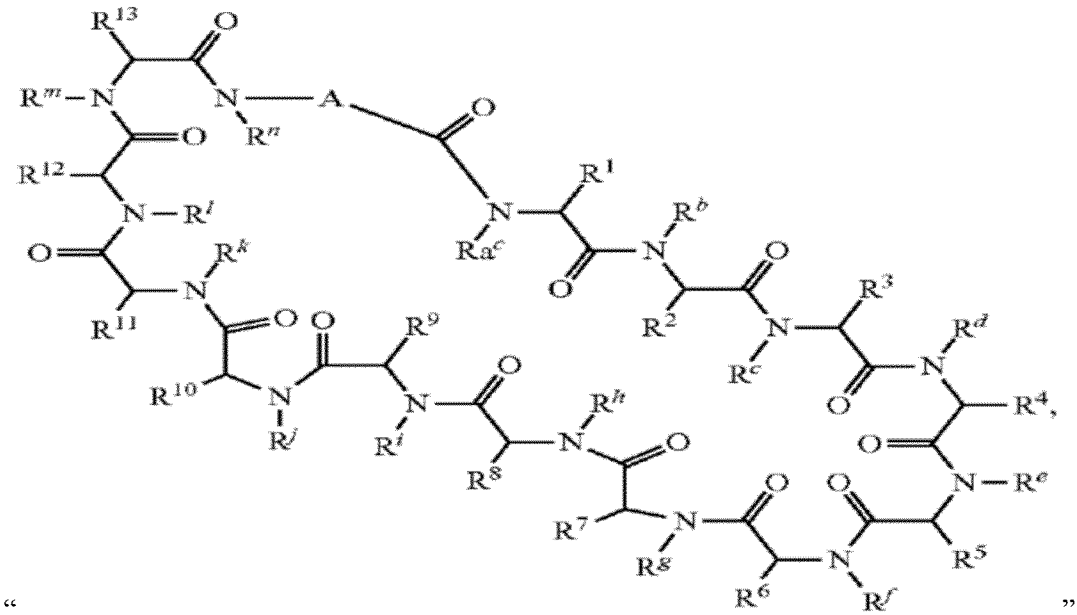

Delete " "

Signed and Sealed this
Eleventh Day of December, 2018

Andrei Iancu
*Director of the United States Patent and Trademark Office*

CERTIFICATE OF CORRECTION (continued)
U.S. Pat. No. 9,856,292 B2

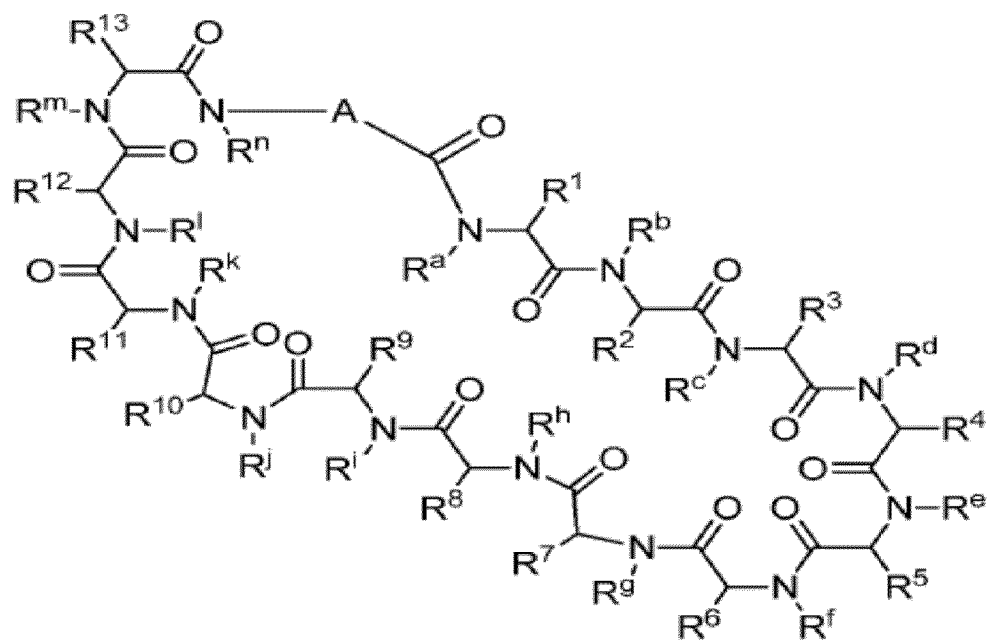

And insert --                                                                               ' --.

Claim 1, Column 970, Lines 42-48:

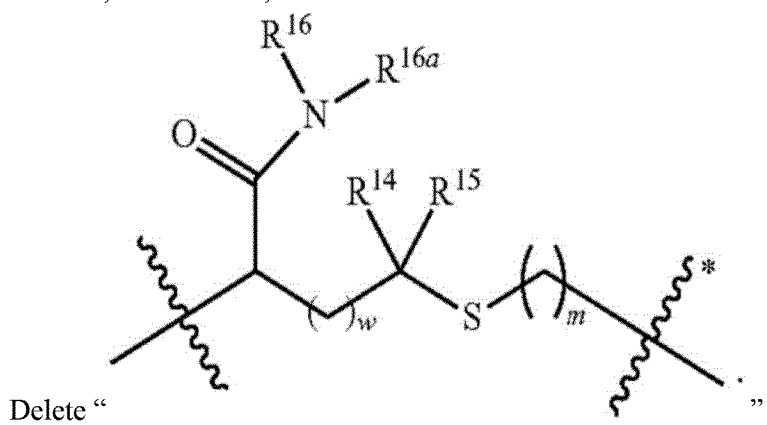

Delete "                                                                     "

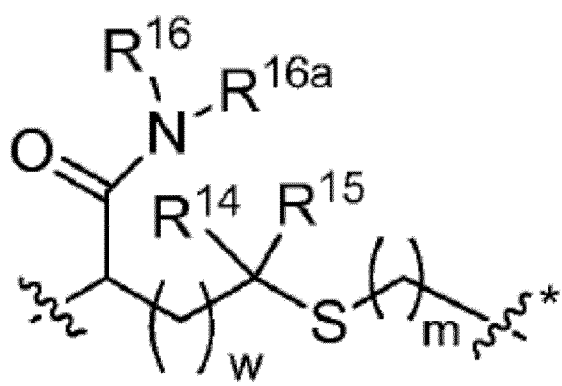

And insert --                               ' --.

Claim 26, Columns 1009-1010 and 1011-1012, Lines 59-61 (Columns 1009-1010) 1-30, (Columns 1011-1012):
Delete "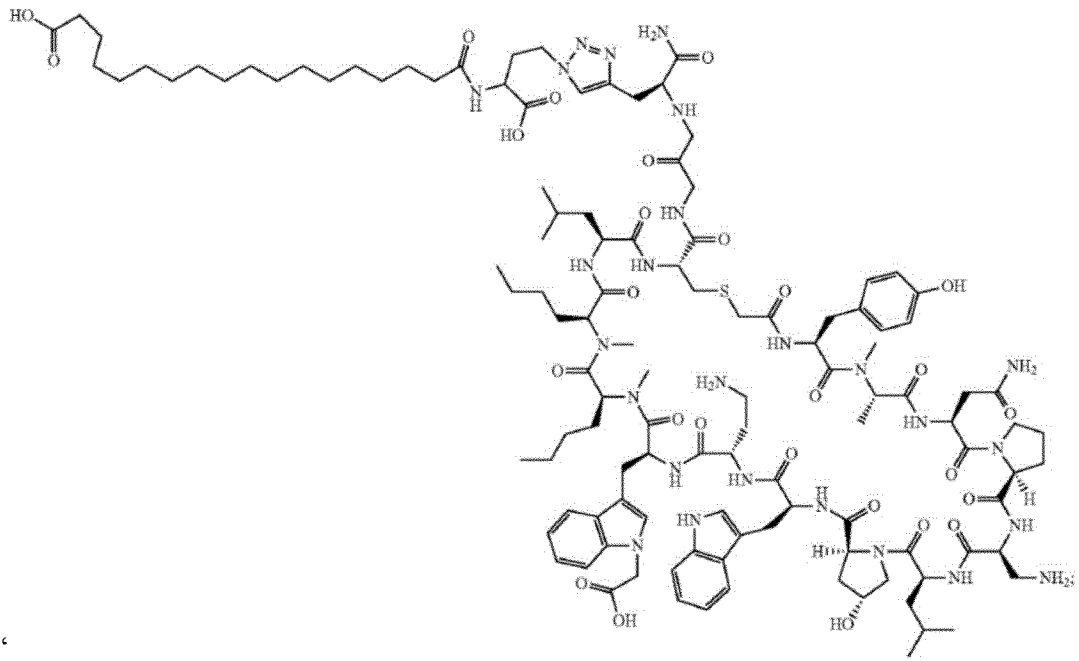"
And insert --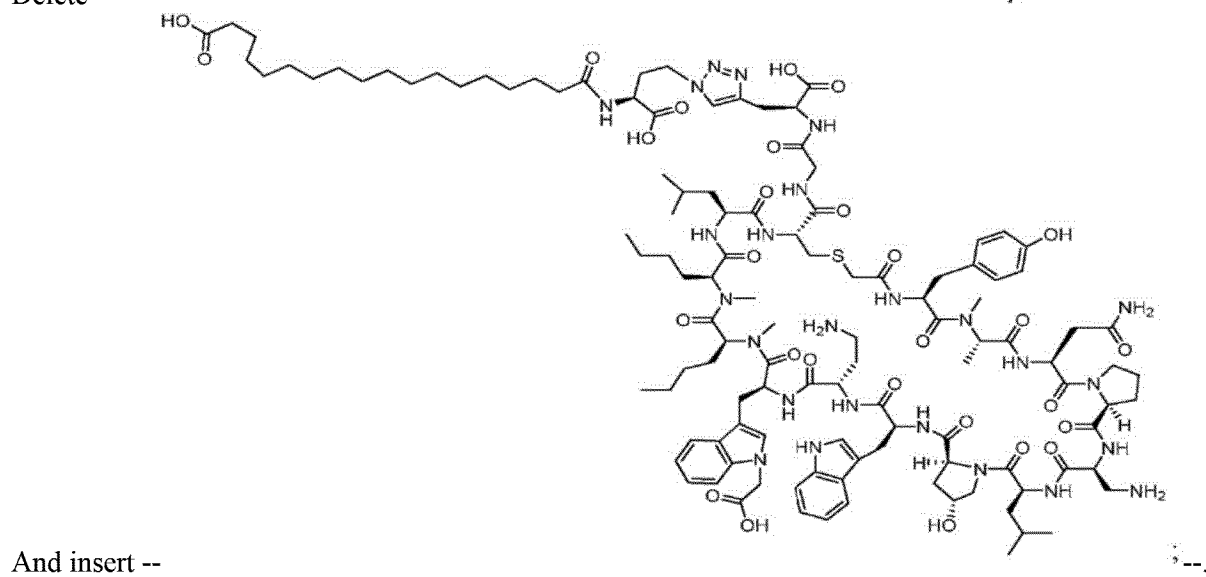;--.

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

Leu Asp Ser Pro Asp Arg Pro Trp Asn Pro Pro Thr Phe Ser Pro Ala
1               5                   10                  15

| | | | | | | | | | | | |
|---|---|---|---|---|---|---|---|---|---|---|---|
|Leu|Leu|Val|Val 20|Thr|Glu|Gly|Asp|Asn|Ala 25|Thr|Phe|Thr|Cys 30|Ser|Phe|

Ser Asn Thr Ser Glu Ser Phe Val Leu Asn Trp Tyr Arg Met Ser Pro
    35              40                  45

Ser Asn Gln Thr Asp Lys Leu Ala Ala Phe Pro Glu Asp Arg Ser Gln
50              55                  60

Pro Gly Gln Asp Cys Arg Phe Arg Val Thr Gln Leu Pro Asn Gly Arg
65              70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

```
Asn Met Thr Ile Glu Cys Lys Phe Pro Val Glu Lys Gln Leu Asp Leu
        20              25              30
Ala Ala Leu Ile Val Tyr Trp Glu Met Glu Asp Lys Asn Ile Ile Gln
        35              40              45
Phe Val His Gly Glu Glu Asp Leu Lys Val Gln His Ser Ser Tyr Arg
    50              55              60
Gln Arg Ala Arg Leu Leu Lys Asp Gln Leu Ser Leu Gly Asn Ala Ala
65              70              75              80
Leu Gln Ile Thr Asp Val Lys Leu Gln Asp Ala Gly Val Tyr Arg Cys
            85              90              95
Met Ile Ser Tyr Gly Gly Ala Asp Tyr Lys Arg Ile Thr Val Lys Val
        100             105             110
Asn Ala Pro Tyr Asn Lys Ile Asn Gln Arg Ile Leu Val Val Asp Pro
        115             120             125
Val Thr Ser Glu His Glu Leu Thr Cys Gln Ala Glu Gly Tyr Pro Lys
130             135             140
Ala Glu Val Ile Trp Thr Ser Ser Asp His Gln Val Leu Ser Gly Lys
145             150             155             160
Thr Thr Thr Thr Asn Ser Lys Arg Glu Glu Lys Leu Phe Asn Val Thr
                165             170             175
Ser Thr Leu Arg Ile Asn Thr Thr Thr Asn Glu Ile Phe Tyr Cys Thr
        180             185             190
Phe Arg Arg Leu Asp Pro Glu Glu Asn His Thr Ala Glu Leu Val Ile
        195             200             205
Pro Glu Leu Pro Leu Ala His Pro Pro Asn Glu Arg Thr Gly Ser Ser
        210             215             220
Glu Thr Val Arg Phe Gln Gly His His His His His His
225             230             235
```